United States Patent
Heemstra et al.

(10) Patent No.: US 10,258,045 B2
(45) Date of Patent: Apr. 16, 2019

(54) MOLECULES HAVING PESTICIDAL UTILITY AND INTERMEDIATES, COMPOSITIONS AND PROCESSES RELATED THERETO

(71) Applicant: Dow AgroSciences LLC, Indianapolis, IN (US)

(72) Inventors: Ronald J. Heemstra, Fishers, IN (US); Ronald Ross, Jr., Zionsville, IN (US); Timothy P. Martin, Noblesville, IN (US); Nicolaas Vermeulen, Indianapolis, IN (US); John F. Daeuble, Sr., Carmel, IN (US); Joseph D. Eckelbarger, Carmel, IN (US); Alex Nolan, Indianapolis, IN (US); Kaitlyn Gray, Indianapolis, IN (US); David A. Demeter, Fishers, IN (US); Ricky Hunter, Westfield, IN (US); Tony K. Trullinger, Westfield, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 15/727,878

(22) Filed: Oct. 9, 2017

(65) Prior Publication Data

US 2018/0098541 A1   Apr. 12, 2018

Related U.S. Application Data

(60) Provisional application No. 62/407,118, filed on Oct. 12, 2016, provisional application No. 62/407,092, filed on Oct. 12, 2016.

(51) Int. Cl.

| | | |
|---|---|---|
| *A01N 53/00* | (2006.01) |
| *C07C 237/52* | (2006.01) |
| *C07C 243/38* | (2006.01) |
| *C07C 255/46* | (2006.01) |
| *C07C 255/58* | (2006.01) |
| *C07C 271/18* | (2006.01) |
| *C07C 271/66* | (2006.01) |
| *C07C 311/21* | (2006.01) |
| *C07C 311/48* | (2006.01) |
| *C07C 317/24* | (2006.01) |

(Continued)

(52) U.S. Cl.
CPC ............ *A01N 53/00* (2013.01); *C07C 237/42* (2013.01); *C07C 237/52* (2013.01); *C07C 243/38* (2013.01); *C07C 255/19* (2013.01); *C07C 255/46* (2013.01); *C07C 255/58* (2013.01); *C07C 255/60* (2013.01); *C07C 271/18* (2013.01); *C07C 271/22* (2013.01); *C07C 271/28* (2013.01); *C07C 271/66* (2013.01); *C07C 281/02* (2013.01); *C07C 281/06* (2013.01); *C07C 311/09* (2013.01); *C07C 311/10* (2013.01); *C07C 311/21* (2013.01); *C07C 311/48* (2013.01); *C07C 317/24* (2013.01); *C07C 337/06* (2013.01); *C07C 381/00* (2013.01); *C07D 213/77* (2013.01); *C07D 213/81* (2013.01); *C07D 237/20* (2013.01); *C07D 239/42* (2013.01); *C07D 307/68* (2013.01); *C07D 333/38* (2013.01); *C07C 2601/02* (2017.05); *C07C 2601/04* (2017.05); *C07C 2601/08* (2017.05); *C07C 2601/16* (2017.05)

(58) Field of Classification Search
USPC ........................................................ 504/100
See application file for complete search history.

(56) References Cited

U.S. PATENT DOCUMENTS

| | | | |
|---|---|---|---|
| 7,754,717 B2 | 7/2010 | Dimauro et al. |
| 8,067,599 B2 | 11/2011 | Honold et al. |

(Continued)

FOREIGN PATENT DOCUMENTS

| | | | |
|---|---|---|---|
| WO | 9008126 A1 | 6/1990 |
| WO | 2016168056 A1 | 10/2016 |

(Continued)

OTHER PUBLICATIONS

International Search Report for PCTUS2016026409 aka WO2016168056.

(Continued)

*Primary Examiner* — Sreenivasan Padmanabhan
*Assistant Examiner* — Courtney A Brown

(57) ABSTRACT

This disclosure relates to the field of molecules having pesticidal utility against pests in Phyla Arthropoda, Mollusca, and Nematoda, processes to produce such molecules, intermediates used in such processes, pesticidal compositions containing such molecules, and processes of using such pesticidal compositions against such pests. These pesticidal compositions may be used, for example, as acaricides, insecticides, miticides, molluscicides, and nematicides. This document discloses molecules having the following formula ("Formula One").

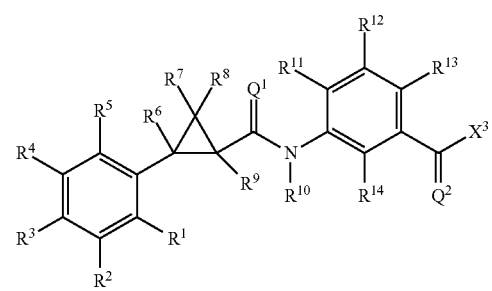

19 Claims, No Drawings

(51) Int. Cl.

| | | |
|---|---|---|
| C07C 381/00 | (2006.01) | |
| C07D 213/81 | (2006.01) | |
| C07D 307/68 | (2006.01) | |
| C07D 333/38 | (2006.01) | |
| C07C 255/60 | (2006.01) | |
| C07D 213/77 | (2006.01) | |
| C07C 271/22 | (2006.01) | |
| C07C 271/28 | (2006.01) | |
| C07C 281/02 | (2006.01) | |
| C07C 281/06 | (2006.01) | |
| C07C 311/09 | (2006.01) | |
| C07C 311/10 | (2006.01) | |
| C07C 337/06 | (2006.01) | |
| C07C 237/42 | (2006.01) | |
| C07C 255/19 | (2006.01) | |
| C07D 237/20 | (2006.01) | |
| C07D 239/42 | (2006.01) | |

(56) References Cited

U.S. PATENT DOCUMENTS

| | | |
|---|---|---|
| 8,492,404 B2 | 7/2013 | Martin et al. |
| 9,781,935 B2 | 10/2017 | Heemstra et al. |
| 9,795,139 B2 | 10/2017 | Eckelbarger et al. |
| 9,795,140 B2 | 10/2017 | Martin et al. |
| 2002/0068838 A1 | 6/2002 | Demassey et al. |
| 2014/0171308 A1 | 6/2014 | Lo et al. |
| 2017/0339961 A1 | 11/2017 | Heemstra et al. |
| 2018/0007911 A1 | 4/2018 | Martin et al. |
| 2018/0098541 A1 | 4/2018 | Heemstra et al. |
| 2018/0099919 A1 | 4/2018 | Choy et al. |

FOREIGN PATENT DOCUMENTS

| | | |
|---|---|---|
| WO | 2016168058 A1 | 10/2016 |
| WO | 2016168059 A1 | 10/2016 |
| WO | 2018071320 A1 | 4/2018 |
| WO | 2018071327 A1 | 4/2018 |

OTHER PUBLICATIONS

International Search Report for PCTUS2016026413 aka WO2016168058.
International Search Report for PCTUS2016026417 aka WO2016168059.
International Search Report for PCTUS2017055655 aka WO2018071320.
International Search Report for PCTUS2017055738 aka WO2018071327.
Sheshenev A E et al: "Generation and steroselective transformations of 3-phenylcyclopropene", Tetrahedron, Elsevier Science Publishers, Amsterdam, NL, vol. 65, No. 48, Sep. 30, 2009, pp. 100036-100046.
Sheshenev A E et al: "Stereo-and regiocontrol in ene-dimerisation and trimerisation of 1-trimethylsilyl-3-phenylcyclopropene", Tetrahedron, Elsevier Science Publishers, Amsterdam, NL, vol. 65, No. 51, Dec. 19, 2009, pp. 10552-10564.
Written Opinion of the International Search Authority for PCTUS2016026409 aka WO2016168056.
Written Opinion of the International Search Authority for PCTUS2016026413 aka WO2016168058.
Written Opinion of the International Search Authority for PCTUS2016026417 aka WO2016168059.
Written Opinion of the International Search Authority for PCTUS2017055655 aka WO2018071320.
Written Opinion of the International Search Authority for PCTUS2017055738 aka WO2018071327.
Yasukochi et al., "Practical, general, and systematic method for optical resolution of gem-dihalo- and monohalocyclopropanecarboxylic acids utilizing chiral 1,1'-binaphtholmonomethyl ethers: Application to the synthesis of three chiral pesticides," Org. Biomol. Chem., 2008, 6, 540-547. (Year:2008).
V. N. Kovalenko, et al.: "The resolution of trans-2,2-dichloro-3-methylcyclopropanecarboxylic acid via crystallization of its salts with (+)- and (−)-α-phenylethylamine, and the transformation of the resulting enantiomers into (R)- and (S)-dimethyl 2-methylsuccinates", Tetrahedron: Asymmetry, vol. 22, No. 1, Jan. 17, 2011, pp. 26 to 30, Elsevier Science Publishers, Amsterdam, NL.

MOLECULES HAVING PESTICIDAL UTILITY AND INTERMEDIATES, COMPOSITIONS AND PROCESSES RELATED THERETO

CROSS-REFERENCES TO RELATED APPLICATIONS

This Application claims the benefit of, and priority from, U.S. provisional application Ser. Nos. 62/407,092 and 62/407,118; all of which were filed on Oct. 12, 2016. The entire contents of all of the above-identified applications are hereby incorporated by reference into this Application.

FIELD OF THIS DISCLOSURE

This disclosure relates to the field of molecules having pesticidal utility against pests in Phyla Arthropoda, Mollusca, and Nematoda, processes to produce such molecules, intermediates used in such processes, pesticidal compositions containing such molecules, and processes of using such pesticidal compositions against such pests. These pesticidal compositions may be used, for example, as acaricides, insecticides, miticides, molluscicides, and nematicides.

BACKGROUND OF THIS DISCLOSURE

"Many of the most dangerous human diseases are transmitted by insect vectors" (Rivero et al.). "Historically, malaria, dengue, yellow fever, plague, filariasis, louse-borne typhus, trypanomiasis, leishmaniasis, and other vector borne diseases were responsible for more human disease and death in the $17^{th}$ through the early $20^{th}$ centuries than all other causes combined" (Gubler). Vector-borne diseases are responsible for about 17% of the global parasitic and infectious diseases. Malaria alone causes over 800,000 deaths a year, 85% of which occur in children under five years of age. Each year there are about 50 to about 100 million cases of dengue fever. A further 250,000 to 500,000 cases of dengue hemorrhagic fever occur each year (Matthews). Vector control plays a critical role in the prevention and control of infectious diseases. However, insecticide resistance, including resistance to multiple insecticides, has arisen in all insect species that are major vectors of human diseases (Rivero et al.). Recently, more than 550 arthropod species have developed resistance to at least one pesticide (Whalon et al.). Furthermore, the cases of insect resistance continue to exceed by far the number of cases of herbicide and fungicide resistance (Sparks et al.).

Each year insects, plant pathogens, and weeds, destroy more than 40% of all food production. This loss occurs despite the application of pesticides and the use of a wide array of non-chemical controls, such as, crop rotations, and biological controls. If just some of this food could be saved, it could be used to feed the more than three billion people in the world who are malnourished (Pimental).

Plant parasitic nematodes are among the most widespread pests, and are frequently one of the most insidious and costly. It has been estimated that losses attributable to nematodes are from about 9% in developed countries to about 15% in undeveloped countries. However, in the United States of America a survey of 35 States on various crops indicated nematode-derived losses of up to 25% (Nicol et al.).

It is noted that gastropods (slugs and snails) are pests of less economic importance than other arthropods or nematodes, but in certain places, they may reduce yields substantially, severely affecting the quality of harvested products, as well as, transmitting human, animal, and plant diseases. While only a few dozen species of gastropods are serious regional pests, a handful of species are important pests on a worldwide scale. In particular, gastropods affect a wide variety of agricultural and horticultural crops, such as, arable, pastoral, and fiber crops; vegetables; bush and tree fruits; herbs; and ornamentals (Speiser).

Termites cause damage to all types of private and public structures, as well as to agricultural and forestry resources. In 2005, it was estimated that termites cause over US$50 billion in damage worldwide each year (Korb).

Consequently, for many reasons, including those mentioned above, there is an on-going need for the costly (estimated to be about US$256 million per pesticide in 2010), time-consuming (on average about 10 years per pesticide), and difficult, development of new pesticides (CropLife America).

CERTAIN REFERENCES CITED IN THIS DISCLOSURE

CropLife America, The Cost of New Agrochemical Product Discovery, Development & Registration, and Research & Development predictions for the Future, 2010.

Drewes, M., Tietjen, K., Sparks, T. C., High-Throughput Screening in Agrochemical Research, *Modern Methods in Crop Protection Research*, Part I, *Methods for the Design and Optimization of New Active Ingredients*, Edited by Jeschke, P., Kramer, W., Schirmer, U., and Matthias W., p. 1-20, 2012.

Gubler, D., Resurgent Vector-Borne Diseases as a Global Health Problem, Emerging Infectious Diseases, Vol. 4, No. 3, p. 442-450, 1998.

Korb, J., Termites, *Current Biology*, Vol. 17, No. 23, 2007.

Matthews, G., Integrated Vector Management: Controlling Vectors of Malaria and Other Insect Vector Borne Diseases, Ch. 1, p. 1, 2011.

Nicol, J., Turner S., Coyne, L., den Nijs, L., Hocksland, L., Tahna-Maafi, Z., Current Nematode Threats to World Agriculture, *Genomic and Molecular Genetics of Plant—Nematode Interactions*, p. 21-43, 2011.

Pimental, D., Pest Control in World Agriculture, *Agricultural Sciences*—Vol. II, 2009.

Rivera, A., Vezilier, J., Weill, M., Read, A., Gander), S., Insect Control of Vector-Borne Diseases: When is Insect Resistance a Problem? *Public Library of Science Pathogens*, Vol. 6, No. 8, p. 1-9, 2010.

Sparks T. C., Nauen R., IRAC: Mode of action classification and insecticide resistance management, *Pesticide Biochemistry and Physiology* (2014) available online 4 Dec. 2014.

Speiser, B., Molluscicides, *Encyclopedia of Pest Management*, Ch. 219, p. 506-508, 2002.

Whalon, M., Mota-Sanchez, D., Hollingworth, R., Analysis of Global Pesticide Resistance in Arthropods, *Global Pesticide Resistance in Arthropods*, Ch. 1, p. 5-33, 2008.

Definitions Used in this Disclosure

The examples given in these definitions are generally non-exhaustive and must not be construed as limiting this disclosure. It is understood that a substituent should comply with chemical bonding rules and steric compatibility constraints in relation to the particular molecule to which it is attached. These definitions are only to be used for the purposes of this disclosure.

The phrase "active ingredient" means a material having activity useful in controlling pests, and/or that is useful in helping other materials have better activity in controlling pests, examples of such materials include, but are not limited to, acaricides, algicides, antifeedants, avicides, bactericides, bird repellents, chemosterilants, fungicides, herbicide safeners, herbicides, insect attractants, insect repellents, insecticides, mammal repellents, mating disrupters, molluscicides, nematicides, plant activators, plant growth regulators, rodenticides, synergists, and virucides (see alanwood.net). Specific examples of such materials include, but are not limited to, the materials listed in active ingredient group alpha.

The phrase "active ingredient group alpha" (hereafter "AIGA") means collectively the following materials:

(1) (3-ethoxypropyl)mercury bromide, 1,2-dibromoethane, 1,2-dichloroethane, 1,2-dichloropropane, 1,3-dichloropropene, 1-MCP, 1-methylcyclopropene, 1-naphthol, 2-(octylthio)ethanol, 2,3,3-TPA, 2,3,5-tri-iodobenzoic acid, 2,3,6-TBA, 2,4,5-T, 2,4,5-TB, 2,4,5-TP, 2,4-D, 2,4-DB, 2,4-DEB, 2,4-DEP, 2,4-DES, 2,4-DP, 2,4-MCPA, 2,4-MCPB, 2iP, 2-methoxyethylmercury chloride, 2-phenylphenol, 3,4-DA, 3,4-DB, 3,4-DP, 3,6-dichloropicolinic acid, 4-aminopyridine, 4-CPA, 4-CPB, 4-CPP, 4-hydroxyphenethyl alcohol, 8-hydroxyquinoline sulfate, 8-phenylmercurioxyquinoline, abamectin, abamectin-aminomethyl, abscisic acid, ACC, acephate, acequinocyl, acetamiprid, acethion, acetochlor, acetofenate, acetophos, acetoprole, acibenzolar, acifluorfen, aclonifen, ACN, acrep, acrinathrin, acrolein, acrylonitrile, acypetacs, afidopyropen, afoxolaner, alachlor, alanap, alanycarb, albendazole, aldicarb, aldicarb sulfone, aldimorph, aldoxycarb, aldrin, allethrin, allicin, allidochlor, allosamidin, alloxydim, allyl alcohol, allyxycarb, alorac, alpha-cypermethrin, alpha-endosulfan, alphamethrin, altretamine, aluminium phosphide, aluminum phosphide, ametoctradin, ametridione, ametryn, ametryne, amibuzin, amicarbazone, amicarthiazol, amidithion, amidoflumet, amidosulfuron, aminocarb, aminocyclopyrachlor, aminopyralid, aminotriazole, amiprofos-methyl, amiprophos, amiprophos-methyl, amisulbrom, amiton, amitraz, amitrole, ammonium sulfamate, amobam, amorphous silica gel, amorphous silicon dioxide, ampropylfos, AMS, anabasine, ancymidol, anilazine, anilofos, anisuron, anthraquinone, antu, apholate, aramite, arprocarb, arsenous oxide, asomate, aspirin, asulam, athidathion, atraton, atrazine, aureofungin, avermectin B1, AVG, aviglycine, azaconazole, azadirachtin, azafenidin, azamethiphos, azidithion, azimsulfuron, azinphosethyl, azinphos-ethyl, azinphosmethyl, azinphosmethyl, aziprotryn, aziprotryne, azithiram, azobenzene, azocyclotin, azothoate, azoxystrobin, bachmedesh, barban, barbanate, barium hexafluorosilicate, barium polysulfide, barium silicofluoride, barthrin, basic copper carbonate, basic copper chloride, basic copper sulfate, BCPC, beflubutamid, benalaxyl, benalaxyl-M, benazolin, bencarbazone, benclothiaz, bendaqingbingzhi, bendiocarb, bendioxide, benefin, benfluralin, benfuracarb, benfuresate, benmihuangcaoan, benodanil, benomyl, benoxacor, benoxafos, benquinox, bensulfuron, bensulide, bensultap, bentaluron, bentazon, bentazone, benthiavalicarb, benthiazole, benthiocarb, bentranil, benzadox, benzalkonium chloride, benzamacril, benzamizole, benzamorf, benzene hexachloride, benzfendizone, benzimine, benzipram, benzobicyclon, benzoepin, benzofenap, benzofluor, benzohydroxamic acid, benzomate, benzophosphate, benzothiadiazole, benzovindiflupyr, benzoximate, benzoylprop, benzthiazuron, benzuocaotong, benzyl benzoate, benzyladenine, berberine, beta-cyfluthrin, beta-cypermethrin, bethoxazin, BHC, bialaphos, bicyclopyrone, bifenazate, bifenox, bifenthrin, bifujunzhi, bilanafos, binapacryl, bingqingxiao, bioallethrin, bioethanomethrin, biopermethrin, bioresmethrin, biphenyl, bisazir, bismerthiazol, bismerthiazol-copper, bisphenylmercury methylenedi(x-naphthalene-y-sulphonate), bispyribac, bistrifluron, bisuitap, bitertanol, bithionol, bixafen, blasticidin-S, borax, Bordeaux mixture, boric acid, boscalid, BPPS, brassinolide, brassinolide-ethyl, brevicomin, brodifacoum, brofenprox, brofenvalerate, broflanilide, brofluthrinate, bromacil, bromadiolone, bromchlophos, bromethalin, bromethrin, bromfenvinfos, bromoacetamide, bromobonil, bromobutide, bromociclen, bromocyclen, bromo-DDT, bromofenoxim, bromofos, bromomethane, bromophos, bromophos-ethyl, bromopropylate, bromothalonil, bromoxynil, brompyrazon, bromuconazole, bronopol, BRP, BTH, bucarpolate, bufencarb, buminafos, bupirimate, buprofezin, Burgundy mixture, busulfan, busulphan, butacarb, butachlor, butafenacil, butam, butamifos, butane-fipronil, butathiofos, butenachlor, butene-fipronil, butethrin, buthidazole, buthiobate, buthiuron, butifos, butocarboxim, butonate, butopyronoxyl, butoxycarboxim, butralin, butrizol, butroxydim, buturon, butylamine, butylate, butylchlorophos, butylene-fipronil, cacodylic acid, cadusafos, cafenstrole, calciferol, calcium arsenate, calcium chlorote, calcium cyanamide, calcium cyanide, calcium polysulfide, calvinphos, cambendichlor, camphechlor, camphor, captafol, captan, carbam, carbamorph, carbanolate, carbaril, carbaryl, carbasulam, carbathion, carbendazim, carbendazol, carbetamide, carbofenotion, carbofuran, carbon disulfide, carbon tetrachloride, carbonyl sulfide, carbophenothion, carbophos, carbosulfan, carboxazole, carboxide, carboxin, carfentrazone, carpropamid, cartap, carvacrol, carvone, CAVP, CDAA, CDEA, CDEC, cellocidin, CEPC, ceralure, cerenox, cevadilla, Cheshunt mixture, chinalphos, chinalphos-methyl, chinomethionat, chinomethionate, chiralaxyl, chitosan, chlobenthiazone, chlomethoxyfen, chlorolose, chloromben, chloromine phosphorus, chloromphenicol, chloroniformethan, chloronil, chloronocryl, chlorontraniliprole, chlorozifop, chlorozine, chlorbenside, chlorbenzuron, chlorbicyclen, chlorbromuron, chlorbufam, chlordane, chlordecone, chlordimeform, chlorempenthrin, chloretazate, chlorethephon, chlorethoxyfos, chloreturon, chlorfenac, chlorfenapyr, chlorfenazole, chlorfenethol, chlorfenidim, chlorfenprop, chlorfenson, chlorfensulphide, chlorfenvinphos, chlorfenvinphos-methyl, chlorfluazuron, chlorflurazole, chlorflurecol, chlorfluren, chlorflurenol, chloridazon, chlorimuron, chlorinate, chlor-IPC, chlormephos, chlormequat, chlormesulone, chlormethoxynil, chlornidine, chlornitrofen, chloroacetic acid, chlorobenzilate, chlorodinitronaphthalenes, chlorofénizon, chloroform, chloromebuform, chloromethiuron, chloroneb, chlorophacinone, chlorophos, chloropicrin, chloropon, chloroprallethrin, chloropropylate, chlorothalonil, chlorotoluron, chloroxifenidim, chloroxuron, chloroxynil, chlorphonium, chlorphoxim, chlorprazophos, chlorprocarb, chlorpropham, chlorpyrifos, chlorpyrifos-methyl, chlorquinox, chlorsufuron, chlorthal, chlorthiamid, chlorthiophos, chlortoluron, chlozolinate, chltosan, cholecalciferol, choline chloride, chromafenozide, cicloheximide, cimectacarb, cimetacarb, cinerin I, cinerin II, cinerins, cinidon-ethyl, cinmethylin, cinosulfuron, cintofen, ciobutide, cisanilide, cismethrin, clacyfos, clefoxydim, clenpirin, clenpyrin, clethodim, climbazole, cliodinate, clodinafop, cloethocarb, clofencet, clofenotane, clofentezine, clofenvinfos, clofibric acid, clofop, clomazone, clomeprop, clonitralid, cloprop, cloproxydim, clopyralid, cloquintocet, cloransulam, closantel, clothianidin, clotrimazole, cloxyfonac, cloxylacon, clozylacon, CMA, CMMP, CMP, CMU, codlelure, colecalciferol, colophonate, copper 8-quinolinolate, copper acetate, copper acetoarsenite, copper arsenate, copper carbonate, basic, copper hydroxide, copper naphthenate, copper oleate, copper oxychloride, copper silicate, copper sulfate, copper sulfate, basic, copper zinc chromate, coumachlor, coumafène, coumafos, coumafuryl, coumaphos, coumatetralyl, coumethoxystrobin, coumithoate, coumoxystrobin, CPMC, CPMF, CPPC, credazine, cresol, cresylic acid, crimidine, crotamiton, crotoxyfos, crotoxyphos, crufomate, cryolite, cue-lure, cufraneb, cumyleron, cumyluron, cuprobam, cuprous oxide, curcumenol, CVMP, cyanamide, cyanatryn, cyanazine, cyanofenphos, cyanogen, cyanophos, cyanthoate, cyantraniliprole, cyanuric acid, cyazofamid, cybutryne, cyclafuramid, cyclanilide, cyclaniliprole, cyclethrin, cycloate, cycloheximide, cycloprate, cycloprothrin, cyclopyrimorate, cyclosulfamuron, cycloxydim, cycluron, cyenopyrafen, cyflufenamid, cyflumetofen, cyfluthrin, cyhalodiamide, cyhalofop, cyhalothrin, cyhexatin, cymiazole, cymoxanil, cyometrinil, cypendazole, cypermethrin, cyperquat, cyphenothrin, cyprazine, cyprazole, cyproconazole, cyprodinil, cyprofuram, cypromid, cyprosulfamide, cyromazine, cythioate, cytrex, daimuron, dalapon, daminozide, dayoutong, dazomet, DBCP, d-camphor, DCB, DCIP, DCPA (Japan), DCPA (USA), DCPTA, DCU, DDD, DDPP, DDT, DDVP, debacarb, decafentin, decamethrin, decarbofuran, deet, dehydroacetic acid, deiquat, delachlor, delnav, deltamethrin, demephion, demephion-O, demephion-S, demeton, demeton-methyl, demeton-O, demeton-O-methyl, demeton-S, demeton-S-methyl, demeton-S-methyl sulphone, demeton-S-methylsulphon, DEP, depalléthrine, derris, desmedipham, desmetryn, desmetryne, d-fanshiluquebingjuzhi, diafenthiuron, dialifor, dialifos, diallate, di-allate, diamidofos, dianat, diatomaceous earth, diatomite, diazinon, dibrom, dibutyl phthalate, dibutyl succinate, dicamba, dicapthon, dichlobenil, dichlobentiazox, dichlofenthion, dichlofluanid, dichlone, dichlorolurea, dichlorbenzuron, dichlorfenidim, dichlorflurecol, dichlorflurenol, dichlormate, dichlormid, dichloromethane, dichlorophen, dichlorprop, dichlorprop-P, dichlorvos, dichlozolin, dichlozoline, diclobutrazol, diclocymet, diclofop, diclomezine, dicloran, dicloromezotiaz, diclosulam, dicofol, dicophane, dicoumarol, dicresyl, dicrotophos, dicryl, dicumarol, dicyclanil, dicyclonon, dieldrin, dienochlor, diethamquat, diethatyl, diethion, diéthion, diethofencarb, dietholate, diéthon, diethyl pyrocarbonate, diethyltoluamide, difenacoum, difenoconazole, difenopenten, difenoxuron, difenzoquat, difethialone, diflovidazin, diflubenzuron, diflufenican, diflufenicanil, diflufenzopyr, diflumetorim, dikegulac, dilor, dimatif, dimefluthrin, dimefox, dimefuron, dimehypo, dimepiperate, dimetachlone, dimetan, dimethacarb, dimethachlone, dimethachlor, dimethametryn, dimethenamid, dimethenamid-P, dimethipin, dimethirimol, dimethoate, dimethomorph, dimethrin, dimethyl carbate, dimethyl disulfide, dimethyl phthalate, dimethylvinphos, dimetilan, dimexano, dimidazon, dimoxystrobin, dimpylate, dimuron, dinex, dingjunezuo, diniconazole, diniconazole-M, dinitramine, dinitrophenols, dinobuton, dinocap, dinocap-4, dinocap-6, dinocton, dinofenate, dinopenten, dinoprop, dinosam, dinoseb, dinosulfon, dinotefuran, dinoterb, dinoterbon, diofenolan, dioxabenzofos, dioxacarb, dioxathion, dioxation, diphacin, diphacinone, diphenadione, diphenamid, diphenamide, diphenyl sulfone, diphenylamine, diphenylsulphide, diprogulic acid, dipropalin, dipropetryn, dipterex, dipymetitrone, dipyrithione, diquat, disodium tetraborate, disosultap, disparlure, disugran, disul, disulfiram, disulfoton, ditalimfos, dithianon, dithicrofos, dithioether, dithiométon, dithiopyr, diuron, dixanthogen, d-limonene, DMDS, DMPA, DNOC, dodemorph, dodicin, dodine, dofenapyn, doguadine, dominicalure, doramectin, DPC, drazoxolon, DSMA, d-trans-allethrin, d-trans-resmethrin, dufulin, dymron, EBEP, EBP, ebufos, ecdysterone, echlomezol, EDB, EDC, EDDP, edifenphos, eglinazine, emamectin, EMPC, empenthrin, enadenine, endosulfan, endothal, endothall, endothion, endrin, enestroburin, enilconazole, enoxastrobin, ephirsulfonate, EPN, epocholeone, epofenonane, epoxiconazole, eprinomectin, epronaz, epsilon-metofluthrin, epsilon-momfluorothrin, EPTC, erbon, ergocalciferol, erlujixiancaoan, esdépalléthrine, esfenvalerate, ESP, esprocarb, etacelasil, etaconazole, etaphos, etem, ethaboxam, ethachlor, ethalfluralin, ethametsulfuron, ethaprochlor, ethephon, ethidimuron, ethiofencarb, ethiolate, ethion, ethiozin, ethiprole, ethirimol, ethoate-methyl, ethobenzanid, ethofumesate, ethohexadiol, ethoprop, ethoprophos, ethoxyfen, ethoxyquin, ethoxysulfuron, ethychlozate, ethyl formate, ethyl pyrophosphate, ethylan, ethyl-DDD, ethylene, ethylene dibromide, ethylene dichloride, ethylene oxide, ethylicin, ethylmercury 2,3-dihydroxypropyl mercaptide, ethylmercury acetate, ethylmercury bromide, ethylmercury chloride, ethylmercury phosphate, etinofen, ETM, etnipromid, etobenzanid, etofenprox, etoxazole, etridiazole, etrimfos, étrimphos, eugenol, EXD, famoxadone, famphur, fenac, fenamidone, fenaminosulf, fenaminstrobin, fenamiphos, fenapanil, fenarimol, fenasulam, fenazaflor, fenazaquin, fenbuconazole, fenbutatin oxide, fenchlorozole, fenchlorphos, fenclofos, fenclorim, fenethacarb, fenfluthrin, fenfuram, fenhexamid, fenidin, fenitropan, fenitrothion, fénizon, fenjuntong, fenobucarb, fenolovo, fenoprop, fenothiocarb, fenoxacrim, fenoxanil, fenoxaprop, fenoxaprop-P, fenoxasulfone, fenoxycarb, fenpicionil, fenpirithrin, fenpropathrin, fenpropidin, fenpropimorph, fenpyrazamine, fenpyroximate, fenquinotrione, fenridazon, fenson, fensulfothion, fenteracol, fenthiaprop, fenthion, fenthion-ethyl, fentiaprop, fentin, fentrazamide, fentrifanil, fenuron, fenuron-TCA, fenvalerate, ferbam, ferimzone, ferric phosphate, ferrous sulfate, fipronil, flamprop, flamprop-M, flazasulfuron, flocoumafen, flometoquin, flonicamid, florasulam, florpyrauxifen, fluacrypyrim, fluazaindolizine, fluazifop, fluazifop-P, fluazinam, fluazolate, fluazuron, flubendiamide, flubenzimine, flubrocythrinate, flucarbazone, flucetosulfuron, fluchloralin, flucofuron, flucycloxuron, flucythrinate, fludioxonil, fluénéthyl, fluenetil, fluensulfone, flufenacet, flufenerim, flufenican, flufenoxuron, flufenoxystrobin, flufenprox, flufenpyr, flufenzine, flufiprole, fluhexafon, flumethrin, flumetover, flumetralin, flumetsulam, flumezin, flumiclorac, flumioxazin, flumipropyn, flumorph, fluometuron, fluopicolide, fluopyram, fluorbenside, fluoridamid, fluoroacetamide, fluoroacetic acid, fluorochloridone, fluorodifen, fluoroglycofen, fluoroimide, fluoromide, fluoromidine, fluoronitrofen, fluoroxypyr, fluothiuron, fluotrimazole, fluoxastrobin, flupoxam, flupropacil, flupropadine, flupropanate, flupyradifurone, flupyrsulfuron, fluquinconazole, fluralaner, flurazole, flurecol, flurenol, fluridone, flurochloridone, fluromidine, fluroxypyr, flurprimidol, flursulamid, flurtamone, flusilazole, flusulfamide, flutenzine, fluthiacet, fluthiamide, flutianil, flutolanil, flutriafol, fluvalinate, fluxametamide, fluxapyroxad, fluxofenim, folpel, folpet, fomesafen, fonofos, foramsulfuron, forchlorfenuron, formaldehyde, formetanate, formothion, formparanate, fosamine, fosetyl, fosmethilan, fospirate, fosthiazate, fosthietan, frontalin, fthalide, fuberidazole, fucaojing, fucaomi, fujunmanzhi, fulumi, fumarin, funaihecaoling, fuphenthiourea, furalane, furalaxyl, furamethrin, furametpyr, furan tebufenozide, furathiocarb, furcarbanil, furconazole, furconazole-cis, furethrin, furfural, furilazole, furmecyclox, furophanate, furyloxyfen, gamma-BHC, gamma-cyhalothrin, gamma-HCH, genit, gibberellic acid, gibberellin A3, gibberellins, gliftor, glitor, glucochlorolose, glufosinate, glufosinate-P, glyodin, glyoxime, glyphosate, glyphosine, gossyplure, grandlure, griseofulvin, guanoctine, guazatine, halacrinate, halauxifen, halfenprox, halofenozide, halosafen, halosulfuron, haloxydine, haloxyfop, haloxyfop-P, haloxyfop-R, HCA, HCB, HCH, hemel, hempa, HEOD, heptachlor, heptafluthrin, heptenophos, heptopargil, herbimycin, herbimycin A, heterophos, hexachlor, hexachloran, hexachloroacetone, hexachlorobenzene, hexachlorobutadiene, hexachlorophene, hexaconazole, hexaflumuron, hexafluoromin, hexaflurate, hexalure, hexamide, hexazinone, hexylthiofos, hexythiazox, HHDN, holosulf, homobrassinolide, huancaiwo, huanchongjing, huangcaoling, huanjunzuo, hydramethylnon, hydrargaphen, hydrated lime, hydrogen cyanamide, hydrogen cyanide, hydroprene, hydroxyisoxazole, hymexazol, hyquincarb, IAA, IBA, IBP, icaridin, imazalil, imazamethabenz, imazamox, imazapic, imazapyr, imazaquin, mazethapyr, mazosulfuron, imibenconazole, imicyafos, imidacloprid, imidaclothiz, iminoctadine, imiprothrin, inabenfide, indanofan, indaziflam, indoxacarb, inezin, infusorial earth, iodobonil, iodocarb, iodofenphos, iodomethane, iodosulfuron, ofensulfuron, ioxynil, ipazine, IPC, ipconazole, ipfencarbazone, ipfentrifluconazole, iprobenfos, iprodione, iprovalicarb, iprymidam, ipsdienol, ipsenol, IPSP, IPX, isamidefos, isazofos, isobenzan, isocarbamid, isocarbamide, isocarbophos, isocil, isodrin, isofenphos, isofenphos-methyl, isofetamid, isolan, isomethiozin, isonoruron, isopamphos, isopolinate, isoprocarb, isoprocil, isopropalin, isopropazol, isoprothiolane, isoproturon, isopyrazam, isopyrimol, isothioate, isotianil, isouron, isovaledione, isoxaben, isoxachlortole, isoxadifen, isoxaflutole, isoxapyrifop, isoxathion, isuron, ivermectin, ixoxaben, izopamfos, izopamphos, japonilure, japothrins, jasmolin I, jasmolin II, jasmonic acid, jiahuangchongzong, jiajizengxiaolin, jiaxiangjunzhi, jiecaowan, jiecaoxi, Jinganmycin A, jodfenphos, juvenile hormone I, juvenile hormone II, juvenile hormone III, kadethrin, kappa-bifenthrin, kappa-tefluthrin, karbutilate, karetazan, kasugamycin, kejunlin, kelevan, ketospiradox, kieselguhr, kinetin, kinoprene, kiralaxyl, kresoxim-methyl, kulcaoxi, lactofen, lambda-cyhalothrin, lancotrione, latilure, lead arsenate, lenacil, lepimectin, leptophos, lianbenjingzhi, lime sulfur, lindane, lineatin, linuron, lirimfos, litlure, looplure, lufenuron, lüfuqingchongxianan, lüxiancaolin, lvdingjunzhi, lvfumijvzhi, lvxiancaolin, lythidathion, M-74, M-81, MAA, magnesium phosphide, malathion, maldison, maleic hydrazide, malonoben, maltodextrin, MAMA, mancopper, mancozeb, mandestrobin, mandipropamid, maneb, matrine, mazidox, MCC, MCP, MCPA, MCPA-thioethyl, MCPB, MCPP, mebenil, mecarbam, mecarbinzid, mecarphon, mecoprop, mecoprop-P, medimeform, medinoterb, medlure, mefenacet, mefenoxam, mefenpyr, mefentrifluconazole, mefluidide, megatomoic acid, melissyl alcohol, melitoxin, MEMC, menazon, MEP, mepanipyrim, meperfluthrin, mephenate, mephosfolan, mepiquat, mepronil, meptyldinocap, mercaptodimethur, mercaptophos, mercaptophos thiol, mercaptothion, mercuric chloride, mercuric oxide, mercurous chloride, merphos, merphos oxide, mesoprazine, mesosulfuron, mesotrione, mesulfen, mesulfenfos, mesulphen, metacresol, metaflumizone, metalaxyl, metalaxyl-M, metaldehyde, metam, metamifop, metamitron, metaphos, metaxon, metazachlor, metazosulfuron, metazoxolon, metconazole, metepa, metflurazon, methabenzthiazuron, methacrifos, methalpropalin, metham, methamidophos, methasulfocarb, methazole, methfuroxam, methibenzuron, methidathion, methiobencarb, methiocarb, methiopyrisulfuron, methiotepa, methiozolin, methiuron, methocrotophos, métholcarb, methometon, methomyl, methoprene, methoprotryn, methoprotryne, methoquin-butyl, methothrin, methoxychlor, methoxyfenozide, methoxyphenone, methyl apholate, methyl bromide, methyl eugenol, methyl iodide, methyl isothiocyanate, methyl parathion, methylacetophos, methylchloroform, methyldithiocarbamic acid, methyldymron, methylene chloride, methyl-isofenphos, methylmercaptophos, methylmercaptophos oxide, methylmercaptophos thiol, methylmercury benzoate, methylmercury dicyandiamide, methylmercury pentachlorophenoxide, methylneodecanamide, methylnitrophos, methyltriazothion, metiozolin, metiram, metiram-zinc, metobenzuron, metobromuron, metofluthrin, metolachlor, metolcarb, metometuron, metominostrobin, metosulam, metoxadiazone, metoxuron, metrafenone, metriam, metribuzin, metrifonate, metriphonate, metsulfovax, rnetsulfuron, mevinphos, mexacarbate, miechuwei, mieshuan, miewenjuzhi, milbemectin, milbemycin oxime, milneb, mimanan, mipafox, MIPC, mirex, MNAF, moguchun, molinate, molosultap, momfluorothrin, monalide, monisuron, monoamitraz, monochloroacetic acid, monocrotophos, monolinuron, monomehypo, monosulfiram, monosulfuron, monosultap, monuron, monuron-TCA, morfamquat, moroxydine, morphothion, morzid, moxidectin, MPMC, MSMA, MTMC, muscalure, myclobutanil, myclozolin, myricyl alcohol, N-(ethylmercury)-p-toluenesulphonanilide, NAA, NAAm, nabam, naftalofos, naled, naphthalene, naphthaleneacetamide, naphthalic anhydride, naphthalophos, naphthoxyacetic acids, naphthylacetic acids, naphthylindane-1,3-diones, naphthyloxyacetic acids, naproanilide, napropamide, napropamide-M, naptalam, natamycin, NBPOS, neburea, neburon, nendrin, neonicotine, nichlorfos, niclofen, niclosamide, nicobifen, nicosulfuron, nicotine, nicotine sulfate, nifluridide, nikkomycins, NIP, nipyraciofen, nipyralofen, nitenpyram, nithiazine, nitralin, nitrapyrin, nitrilacarb, nitrofen, nitrofluorfen, nitrostyrene, nitrothal-isopropyl, nobormide, nonanol, norbormide, norea, norflurazon, nornicotine, noruron, novaluron, noviflumuron, NPA, nuarimol, nuranone, OCH, octachlorodipropyl ether, octhilinone, o-dichlorobenzene, ofurace, ometheate, o-phenylphenol, orbencarb, orfralure, orthobencarb, ortho-dichlorobenzene, orthosulfamuron, oryctalure, orysastrobin, oryzalin, osthol, osthole, ostramone, ovatron, ovex, oxabetrinil, oxadiargyl, oxadiazon, oxadixyl, oxamate, oxamyl, oxapyrazon, oxapyrazone, oxasulfuron, oxathiapiprolin, oxaziclomefone, oxine-copper, oxine-Cu, oxolinic acid, oxpoconazole, oxycarboxin, oxydemeton-methyl, oxydeprofos, oxydisulfoton, oxyenadenine, oxyfluorfen, oxymatrine, oxytetracycline, oxythioquinox, PAC, paclobutrazol, paichongding, palléthrine, PAP, para-dichlorobenzene, parafluron, paraquat, parathion, parathion-methyl, parinol, Paris green, PCNB, PCP, PCP-Na, p-dichlorobenzene, PDJ, pebulate, pédinex, pefurazoate, pelargonic acid, penconazole, pencycuron, pendimethalin, penfenate, penflufen, penfluron, penoxalin, penoxsulam, pentachlorophenol, pentachlorophenyl laurate, pentanochlor, penthiopyrad, pentmethrin, pentoxazone, perchlordecone, perfluidone, permethrin, pethoxamid, PHC, phenamacril, phenamacril-ethyl, phénaminosulf, phenazine oxide, phenetacarbe, phenisopham, phenkapton, phenmedipham, phenmedipham-ethyl, phenobenzuron, phenothiel, phenothrin, phenproxide, phenthoate, phenylmercuriurea, phenylmercury acetate, phenylmercury chloride, phenylmercury derivative of pyrocatechol, phenylmercury nitrate, phenylmercury salicylate, phorate, phosacetim, phosalone, phosametine, phosazetin, phosazetin, phoscyclotin, phosdiphen, phosethyl, phosfolan, phosfolan-methyl, phosglycin, phosmet, phosnichlor, phosphamide, phosphamidon, phosphine, phosphinothricin, phosphocarb, phosphorus, phostin, phoxim, phoxim-methyl, phthalide, phthalophos, phthalthrin, picarbutrazox, picaridin, picloram, picolinafen, picoxystrobin, pimaricin, pindone, pinoxaden, piperalin, piperazine, piperonyl butoxide, piperonyl cyclonene, piperophos, piproctanly, piproctanyl, piprotal, pirimetaphos, pirimicarb, piriminil, pirimioxyphos, pirimiphos-ethyl, pirimiphos-methyl, pival, pivaldione, plifenate, PMA, PMP, polybutenes, polycarbamate, polychlorcamphene, polyethoxyquinoline, polyoxin D, polyoxins, polyoxorim, polythialan, potassium arsenite, potassium azide, potassium cyanate, potassium ethylxanthate, potassium naphthenate, potassium polysulfide, potassium thiocyanate, pp'-DDT, prallethrin, precocene I, precocene II, precocene III, pretilachlor, primidophos, primisulfuron, probenazole, prochloraz, proclonol, procyazine, procymidone, prodiamine, profenofos, profluazol, profluralin, profluthrin, profoxydim, profurite-aminium, proglinazine, prohexadione, prohydrojasmon, promacyl, promecarb, prometon, prometryn, prometryne, promurit, pronamide, propachlor, propafos, propamidine, propamocarb, propanil, propaphos, propaquizafop, propargite, proparthrin, propazine, propetamphos, propham, propiconazole, propidine, propineb, propisochlor, propoxur, propoxycarbazone, propyl isome, propyrisulfuron, propyzamide, proquinazid, prosuler, prosulfalin, prosulfocarb, prosulfuron, prothidathion, prothiocarb, prothioconazole, prothiofos, prothoate, protrifenbute, proxan, prymidophos, prynachlor, psoralen, psoralene, pydanon, pydiflumetofen, pyflubumide, pymetrozine, pyracarboiid, pyraclofos, pyraclonil, pyraclostrobin, pyraflufen, pyrafluprole, pyramat, pyrametostrobin, pyraoxystrobin, pyrasulfotole, pyrazflumid, pyrazolate, pyrazolynate, pyrazon, pyrazophos, pyrazosulfuron, pyrazothion, pyrazoxyfen, pyresmethrin, pyrethrin I, pyrethrin II, pyrethrins, pyribambenz-isopropyl, pyribambenz-propyl, pyribencarb, pyribenzoxim, pyributicarb, pyriclor, pyridaben, pyridafol, pyridalyl, pyridaphenthion, pyridaphenthione, pyridate, pyridinitril, pyrifenox, pyrifluquinazon, pyriftalid, pyrimétaphos, pyrimethanil, pyrimicarbe, pyrimidifen, pyriminobac, pyriminostrobin, pyrimiphos-éthyl, pyrimiphos-méthyl, pyrimisulfan, pyrimitate, pyrinuron, pyriofenone, pyriprole, pyripropanol, pyriproxyfen, pyrisoxazole, pyrithiobac, pyrolan, pyroquilon, pyroxasulfone, pyroxsulam, pyroxychlor, pyroxyfur, qincaosuan, qingkuling, quassia, quinacetol, quinalphos, quinalphos-methyl, quinazamid, quinclorac, quinconazole, quinmerac, quinoclamine, quinofumelin, quinomethionate, quinonamid, quinothion, quinoxyfen, quintiofos, quintozene, quizalofop, quizalolop-P, quwenzhi, quyingding, rabenzazole, rafoxanide, R-diniconazole, rebemide, regione, renriduron, rescalure, resmethrin, rhodethanil, rhodojaponin-III, ribavirin, rimsulfuron, rizazole, R-metalaxyl, rodéthanil, runnel, rotenone, ryania, sabadilla, saflufenacil, saijunmao, saisentong, salicylanilide, saliflufen, sanguinarine, santonin, S-bioallethrin, schradan, scilliroside, sebuthylazine, secbumeton, sedaxane, selamectin, semiamitraz, sesamex, sesamolin, sesone, sethoxydim, sevin, shuangjiaancaolin, shuangjianancaolin, S-hydroprene, siduron, sifumijvzhi, siglure, silafluofen, silatrane, silica aerogel, silica gel, silthiofam, silthiopham, silthiophan, silvex, simazine, simeconazole, simeton, simetryn, simetryne, sintofen, 5-kinoprene, slaked lime, SMA, S-methoprene, S-metolachlor, sodium arsenite, sodium azide, sodium chlorote, sodium cyanide, sodium fluoride, sodium fluoroacetate, sodium hexafluorosilicate, sodium naphthenate, sodium o-phenylphenoxide, sodium orthophenylphenoxide, sodium pentachlorophenate, sodium pentachlorophenoxide, sodium polysulfide, sodium silicofluoride, sodium tetrathiocarbohate, sodium thiocyanate, solan, sophamide, spinetoram, spinosad, spirodiclofen, spiromesifen, spirotetramat, spiroxamine, stirofos, streptomycin, strychnine, sulcatol, sulcofuron, sulcotrione, sulfallate, sulfentrazone, sulfiram, sulfluramid, sulfodiazole, sulfometuron, sulfosate, sulfosulfuron, sulfotep, sulfotepp, sulfoxaflor, sulfoxide, sulfoxime, sulfur, sulfuric acid, sulfuryl fluoride, sulglycapin, sulphosate, sulprofos, sultropen, swep, tau-fluvalinate, tavron, tazimcarb, TBTO, TBZ, TCA, TCBA, TCMTB, TCNB, TDE, tebuconazole, tebufenozide tebufenpyrad, tebufloquin, tebupirimfos, tebutam, tebuthiuron, tecloftalam, tecnazene, tecoram, tedion, teflubenzuron, tefluthrin, tefuryltrione, tembotrione, temefos, temephos, tepa, TEPP, tepraloxydim, teproloxydim, terallethrin, terbacil, terbucarb, terbuchlor, terbufos, terbumeton, terbuthylazine, terbutol, terbutryn, terbutryne, terraclor, terramicin, terramycin, tetcyclacis, tetrachloroethane, tetrachlorvinphos, tetraconazole, tetradifon, tetradisul, tetrafluron, tetramethrin, tetramethylfluthrin, tetramine, tetranactin, tetraniliprole, tetrapion, tetrasul, thallium sulfate, thallous sulfate, thenylchlor, theta-cypermethrin, thiabendazole, thiacloprid, thiadiazine, thiadifluor, thiamethoxam, thiameturon, thiapronil, thiazafluron, thiazfluron, thiazone, thiazopyr, thicrofos, thicyofen, thidiazimin, thidiazuron, thiencarbazone, thifensulfuron, thifluzamide, thimerosal, thimet, thiobencarb, thiocarboxime, thiochlorfenphim, thiochlorphenphime, thiocyanatodinitrobenzenes, thiocyclam, thiodan, thiodiazole-copper, thiodicarb, thiofanocarb, thiofanox, thiofluoximate, thiohempa, thiomersal, thiometon, thionazin, thiophanate, thiophanate-ethyl, thiophanate-methyl, thiophos, thioquinox, thiosemicarbazide, thiosultap, thiotepa, thioxamyl, thiram, thiuram, thuringiensin, tiabendazole, tiadinil, tiafenacil, tiaojiean, TIBA, tifatol, tiocarbazil, tioclorim, tioxazafen, tioxymid, tirpate, TMTD, tolclofosmethyl, tolfenpyrad, tolprocarb, tolpyralate, tolyfluanid, tolylfluanid, tolylmercury acetate, tomarin, topramezone, toxaphene, TPN, tralkoxydim, tralocythrin, tralomethrin, tralopyril, transfluthrin, transpermethrin, tretamine, triacontanol, triadimefon, triadimenol, triafamone, triallate, triallate, triamiphos, triapenthenol, triarathene, triarimol, triasulfuron, triazamate, triazbutil, triaziflam, triazophos, triazothion, triazoxide, tribasic copper chloride, tribasic copper sulfate, tribenuron, tribufos, tributyltin oxide, tricamba, trichlamide, trichlopyr, trichlorfon, trichlormetaphos-3, trichloronat, trichloronate, trichlorotrinitrobenzenes, trichlorphon, triclopyr, triclopyricarb, tricresol, tricyclazole, tricyclohexyltin hydroxide, tridemorph, tridiphane, trietazine, trifenmorph, trifenofos, trifloxystrobin, trifloxysulfuron, trifludimoxazin, triflumezopyrim, triflumizole, triflumuron, trifluralin, triflusulfuron, trifop, trifopsime, triforine, trihydroxytriazine, trimedlure, trimethacarb, trimeturon, trinexapac, triphenyltin, triprene, tripropindan, triptolide, tritac, trithialan, triticonazole, tritosulfuron, trunc-call, tuoyelin, uniconazole, uniconazole-P, urbacide, uredepa, valerate, validamycin, validamycin A, valifenalate, valone, vamidothion, vangard, vaniliprole, vernolate, vinclozolin, vitamin D3, warfarin, xiaochongliulin, xinjunan, xiwojunan, xiwojunzhi, XMC, xylachlor, xylenols, xylylcarb, xymiazole, yishijing, zarilamid, zeatin, zengxiaoan, zengxiaolin, zeta-cypermethrin, zinc naphthenate, zinc phosphide, zinc thiazole, zinc thiozole, zinc trichlorophenate, zinc trichlorophenoxide, zineb, ziram, zolaprofos, zoocoumarin, zoxamide, zuoanjunzhi, zuocaoan, zuojunzhi, zuomihuanglong, α-chlorohydrin, α-ecdysone, α-multistriatin, α-naphthaleneacetic acids, and β-ecdysone;

(2) the following molecules (a) N-(3-chloro-1-(pyridin-3-yl)-1H-pyrazol-4-yl)-N-ethyl-3-((3,3,3-trifluoropropyl)thio)propanamide (hereafter "AI-1")

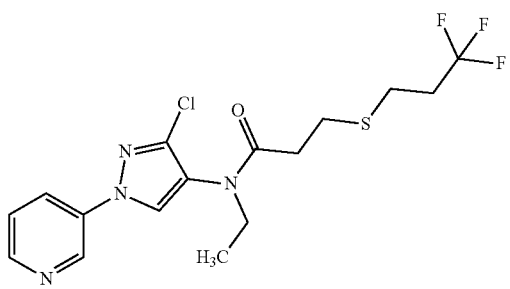 [SMILES: CCN(C(=O)CCSCCC(F)(F)F)c1cn(-c2cccnc2)nc1Cl]

(b) a molecule known as Lotilaner that has the following structure

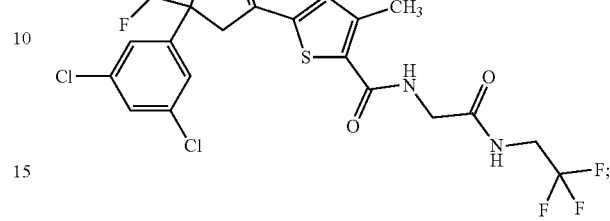

and (c) the following molecules in Table A

TABLE A

Structure of M# - active ingredients

| M# | Structure |
|---|---|
| M1 | R = CH, N<br>R₁ = H, Me |
| M2 | X = F, Cl<br>R = H, F |
| M3 | 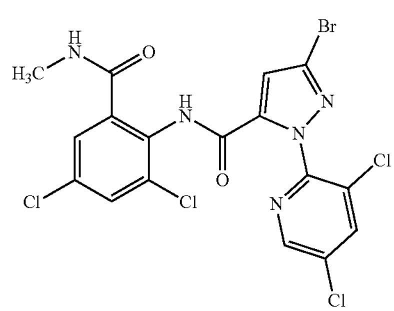 [SMILES: CNC(=O)c1cc(Cl)cc(Cl)c1NC(=O)c1cc(Br)nn1-c1ncc(Cl)cc1Cl] |

TABLE A-continued

Structure of M# - active ingredients

| M# | Structure |
|---|---|
| M4 | 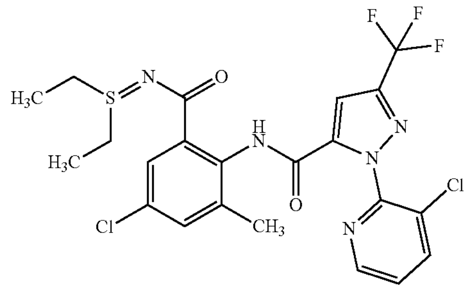 [SMILES: CCS(CC)=NC(=O)c1cc(Cl)cc(C)c1NC(=O)c1cc(C(F)(F)F)nn1-c1ncccc1Cl] |
| M5 | 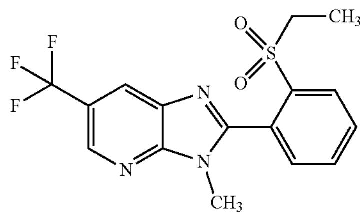 |
| M6 | 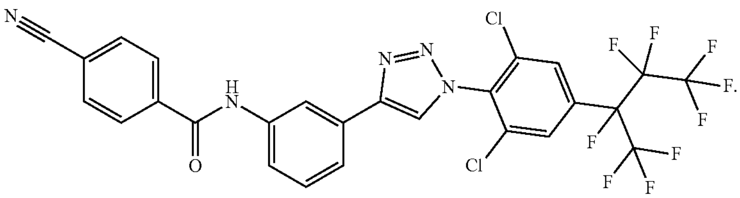 [SMILES: N#Cc1ccc(C(=O)Nc2cccc(-c3cn(-c4c(Cl)cc(C(F)(C(F)(F)F)C(F)(F)C(F)(F)F)cc4Cl)nn3)c2)cc1] |

As used in this disclosure, each of the above is an active ingredient. For more information consult the "Compendium of Pesticide Common Names" located at Alanwood.net and various editions, including the on-line edition, of "The Pesticide Manual" located at bcpcdata.com.

A particularly preferred selection of active ingredients are 1,3-dichloropropene, chlorpyrifos, hexaflumuron, methoxyfenozide, noviflumuron, spinetoram, spinosad, and sulfoxaflor (hereafter "AIGA-2").

Additionally, another particularly preferred selection of active ingredients are acequinocyl, acetamiprid, acetoprole, avermectin, azinphos-methyl, bifenazate, bifenthrin, carbaryl, carbofuran, chlorfenapyr, chlorfluazuron, chromafenozide, clothianidin, cyfluthrin, cypermethrin, deltamethrin, diafenthiuron, emamectin benzoate, endosulfan, esfenvalerate, ethiprole, etoxazole, fipronil, flonicamid, fluacrypyrim, gamma-cyhalothrin, halofenozide, indoxacarb, lambda-cyhalothrin, lufenuron, malathion, methomyl, novaluron, permethrin, pyridalyl, pyrimidifen, spirodiclofen, tebufenozide, thiacloprid, thiamethoxam, thiodicarb, tolfenpyrad, and zeta-cypermethrin (hereafter "AIGA-3").

The term "alkenyl" means an acyclic, unsaturated (at least one carbon-carbon double bond), branched or unbranched, substituent consisting of carbon and hydrogen, for example, vinyl, allyl, butenyl, pentenyl, and hexenyl.

The term "alkenyloxy" means an alkenyl further consisting of a carbon-oxygen single bond, for example, allyloxy, butenyloxy, pentenyloxy, hexenyloxy.

The term "alkoxy" means an alkyl further consisting of a carbon-oxygen single bond, for example, methoxy, ethoxy, propoxy, isopropoxy, butoxy, isobutoxy, and tert-butoxy.

The term "alkyl" means an acyclic, saturated, branched or unbranched, substituent consisting of carbon and hydrogen, for example, methyl, ethyl, propyl, isopropyl, butyl, and tert-butyl.

The term "alkynyl" means an acyclic, unsaturated (at least one carbon-carbon triple bond), branched or unbranched, substituent consisting of carbon and hydrogen, for example, ethynyl, propargyl, butynyl, and pentynyl.

The term "alkynyloxy" means an alkynyl further consisting of a carbon-oxygen single bond, for example, pentynyloxy, hexynyloxy, heptynyloxy, and octynyloxy.

The term "aryl" means a cyclic, aromatic substituent consisting of hydrogen and carbon, for example, phenyl, naphthyl, and biphenyl.

The term "biopesticide" means a microbial biological pest control agent that, in general, is applied in a similar manner to chemical pesticides. Commonly they are bacterial, but there are also examples of fungal control agents, including *Trichoderma* spp. and *Ampelomyces quisqualis*. One well-known biopesticide example is *Bacillus* species, a bacterial disease of Lepidoptera, Coleoptera, and Diptera. Biopesticides include products based on entomopathogenic fungi (e.g. *Metarhizium anisopliae*), entomopathogenic nematodes (e.g. *Steinernema feltiae*), and entomopathogenic viruses (e.g. *Cydia pomonella* granulovirus). Other examples of entomopathogenic organisms include, but are not limited to, baculoviruses, protozoa, and Microsporidia. For the avoidance of doubt, biopesticides are active ingredients.

The term "cycloalkenyl" means a monocyclic or polycyclic, unsaturated (at least one carbon-carbon double bond) substituent consisting of carbon and hydrogen, for example, cyclobutenyl, cyclopentenyl, cyclohexenyl, norbornenyl, bicyclo[2.2.2]octenyl tetrahydronaphthyl, hexahydronaphthyl, and octahydronaphthyl.

The term "cycloalkenyloxy" means a cycoalkenyl further consisting of a carbon-oxygen single bond, for example, cyclobutenyloxy, cyclopentenyloxy, norbornenyloxy, and bicyclo[2.2.2]octenyloxy.

The term "cycloalkyl" means a monocyclic or polycyclic, saturated substituent consisting of carbon and hydrogen, for example, cyclopropyl, cyclobutyl, cyclopentyl, norbornyl, bicyclo[2.2.2]octyl, and decahydronaphthyl.

The term "cycloalkoxy" means a cycloalkyl further consisting of a carbon-oxygen single bond, for example, cyclopropyloxy, cyclobutyloxy, cyclopentyloxy, norbornyloxy, and bicyclo[2.2.2]octyloxy.

The term "halo" means fluoro, chloro, bromo, and iodo.

The term "haloalkoxy" means an alkoxy further consisting of, from one to the maximum possible number of identical or different, halos, for example, fluoromethoxy, trifluoromethoxy, 2,2-difluoropropoxy, choromethoxy, trichloromethoxy, 1,1,2,2-tetrafluoroethoxy, and pentafluoroethoxy.

The term "haloalkyl" means an alkyl further consisting of, from one to the maximum possible number of, identical or different, halos, for example, fluoromethyl, trifluoromethyl, 2,2-difluoropropyl, chloromethyl, trichloromethyl, and 1,1, 2,2-tetrafluoroethyl.

The term "heterocyclyl" means a cyclic substituent that may be aromatic, fully saturated, or partially or fully unsaturated, where the cyclic structure contains at least one carbon and at least one heteroatom, where said heteroatom is nitrogen, sulfur, or oxygen. Examples are:

(1) aromatic heterocyclyl substituents include, but are not limited to, benzofuranyl, benzoisothiazolyl, benzoisoxazolyl, benzothienyl, benzothiazolyl, benzoxazolyl, cinnolinyl, furanyl, imidazolyl, indazolyl, indolyl, isoindolyl, isoquinolinyl, isothiazolyl, isoxazolyl, oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, tetrazolyl, thiazolinyl, thiazolyl, thienyl, triazinyl, and triazolyl;

(2) fully saturated heterocyclyl substituents include, but are not limited to, piperazinyl, piperidinyl, morpholinyl, pyrrolidinyl, tetrahydrofuranyl, and tetrahydropyranyl;

(3) partially or fully unsaturated heterocyclyl substituents include, but are not limited to, 4,5-dihydro-isoxazolyl, 4,5-dihydro-oxazolyl, 4,5-dihydro-1H-pyrazolyl, 2,3-dihydro-[1,3,4]-oxadiazolyl, and 1,2,3,4-tetrahydro-quinolinyl; and (4) Additional examples of heterocycyls include the following:

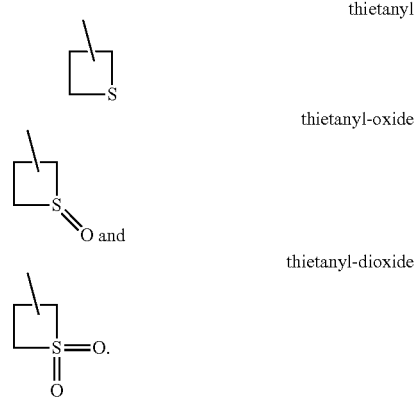

thietanyl thietanyl-oxide thietanyl-dioxide

The term "locus" means a habitat, breeding ground, plant, seed, soil, material, or environment, in which a pest is growing, may grow, or may traverse. For example, a locus may be: where crops, trees, fruits, cereals, fodder species, vines, turf, and/or ornamental plants, are growing; where domesticated animals are residing; the interior or exterior surfaces of buildings (such as places where grains are stored); the materials of construction used in buildings (such as impregnated wood); and the soil around buildings.

The phrase "MoA Material" means an active ingredient having a mode of action ("MoA") as indicated in IRAC MoA Classification v. 7.4, located at irac-online.org., which describes the following groups.

(1) Acetylcholinesterase (AChE) inhibitors, includes the following active ingredients acephate, alanycarb, aldicarb, azamethiphos, azinphos-ethyl, azinphos-methyl, bendiocarb, benfuracarb, butocarboxim, butoxycarboxim, cadusafos, carbaryl, carbofuran, carbosulfan, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethiofencarb, ethion, ethoprophos, famphur, fenamiphos, fenitrothion, fenobucarb, fenthion, formetanate, fosthiazate, furathiocarb, heptenophos, imicyafos, isofenphos, isoprocarb, isopropyl O-(methoxyaminothio-phosphoryl)salicylate, isoxathion, malathion, mecarbam, methamidophos, methidathion, methiocarb, methomyl, metolcarb, mevinphos, monocrotophos, Naled, omethoate, oxamyl, oxydemeton-methyl, parathion, parathion-methyl, phenthoate, phorate, phosalone, phosmet, phosphamidon, phoxim, pirimicarb, pirimiphos-methyl, profenofos, propetamphos, propoxur, prothiofos, pyraclofos, pyridaphenthion, quinalphos, sulfotep, tebupirimfos, temephos, terbufos, tetrachlorvinphos, thiodicarb, thiofanox, thiometon, triazamate, triazophos, trichlorfon, trimethacarb, vamidothion, XMC, and xylylcarb.

(2) GABA-gated chloride channel antagonists, includes the following active ingredients chlordane, endosulfan, ethiprole, and fipronil.

(3) Sodium channel modulators, includes the following active ingredients acrinathrin, allethrin, d-cis-trans allethrin, d-trans allethrin, bifenthrin, bioallethrin, bioallethrin S-cyclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans-isomers], deltamethrin, empenthrin [(EZ)-(1R)-isomers], esfenvalerate, etofenprox, fenpropathrin, fenvalerate, flucythrinate, flumethrin, tau-fluvalinate, halfenprox, imiprothrin, kadethrin, permethrin, phenothrin [(1R)-trans-isomer], prallethrin, pyrethrins (pyrethrum), resmethrin, silafluofen, tefluthrin, tetramethrin, tetramethrin [(1R)-isomers], tralomethrin, and transfluthrin, and methoxychlor.

(4) Nicotinic acetylcholine receptor (nAChR) agonists, includes the following active ingredients
  (4A) acetamiprid, clothianidin, dinotefuran, imidacloprid, nitenpyram, thiacloprid, thiamethoxam,
  (4B) nicotine,
  (4C) sulfoxaflor,
  (4D) flupyradifurone,
  (4E) triflumezopyrim and dicloromezotiaz.

(5) Nicotinic acetylcholine receptor (nAChR) allosteric activators, includes the following active ingredients spinetoram and spinosad.

(6) Chloride channel activators, includes the following active ingredients abamectin, emamectin benzoate, lepimectin, and milbemectin.

(7) Juvenile hormone mimics, includes the following active ingredients hydroprene, kinoprene, methoprene, fenoxycarb, and pyriproxyfen.

(8) Miscellaneous nonspecific (multi-site) inhibitors, includes the following active ingredients methyl bromide, chloropicrin, sulfuryl fluoride, borax, boric acid, disodium octaborate, sodium borate, sodium metaborate, tartar emetic, diazomet, and metam.

(9) Modulators of Chordotonal Organs, includes the following active ingredients pymetrozine and flonicamid.

(10) Mite growth inhibitors, includes the following active ingredients clofentezine, hexythiazox, diflovidazin, and etoxazole.

(11) Microbial disruptors of insect midgut membranes, includes the following active ingredients *Bacillus thuringiensis* subsp. *israelensis*, *Bacillus thuringiensis* subsp. *aizawai*, *Bacillus thuringiensis* subsp. *kurstaki*, *Bacillus thuringiensis* subsp. *tenebrionenis*, Bt crop proteins (Cry1Ab, Cry1Ac, Cry1Fa, Cry1A.105, Cry2Ab, Vip3A, mCry3A, Cry3Ab, Cry3Bb, Cry34Ab1/Cry35Ab1), and *Bacillus sphaericus*.

(12) Inhibitors of mitochondrial ATP synthase, includes the following active ingredients tetradifon, propargite, azocyclotin, cyhexatin, fenbutatin oxide, and diafenthiuron.

(13) Uncouplers of oxidative phosphorylation via disruption of the proton gradient, includes the following active ingredients chlorfenapyr, DNOC, and sulfluramid.

(14) Nicotinic acetylcholine receptor (nAChR) channel blockers, includes the following active ingredients bensultap, cartap hydrochloride, thiocyclam, and thiosultap-sodium.

(15) Inhibitors of chitin biosynthesis, type 0, includes the following active ingredients bistrifluron, chlorfluazuron, diflubenzuron, flucycloxuron, flufenoxuron, hexaflumuron, lufenuron, novaluron, noviflumuron, teflubenzuron, and triflumuron.

(16) Inhibitors of chitin biosynthesis, type 1, includes the following active ingredient buprofezin.

(17) Moulting disruptor, Dipteran, includes the following active ingredient cyromazine.

(18) Ecdysone receptor agonists, includes the following active ingredients chromafenozide, halofenozide, methoxyfenozide, and tebufenozide.

(19) Octopamine receptor agonists, includes the following active ingredient amitraz.

(20) Mitochondrial complex III electron transport inhibitors, includes the following active ingredients hydramethylnon, acequinocyl, and fluacrypyrim.

(21) Mitochondrial complex I electron transport inhibitors, includes the following active ingredients fenazaquin, fenpyroximate, pyrimidifen, pyridaben, tebufenpyrad, tolfenpyrad, and rotenone.

(22) Voltage-dependent sodium channel blockers, includes the following active ingredients indoxacarb and metaflumizone.

(23) Inhibitors of acetyl CoA carboxylase, includes the following active ingredients spirodiclofen, spiromesifen, and spirotetramat.

(24) Mitochondrial complex IV electron transport inhibitors, includes the following active ingredients, aluminium phosphide, calcium phosphide, phosphine, zinc phosphide, and cyanide.

(25) Mitochondrial complex II electron transport inhibitors, includes the following active ingredients cyenopyrafen, cyflumetofen, and pyflubumide, and

(28) Ryanodine receptor modulators, includes the following active ingredients chlorontraniliprole, cyantraniliprole, and flubendiamide.

Groups 26 and 27 are unassigned in this version of the classification scheme. Additionally, there is a Group UN that contains active ingredients of unknown or uncertain mode of action. This group includes the following active ingredients, azadirachtin, benzoximate, bifenazate, bromopropylate, chinomethionat, cryolite, dicofol, pyridalyl, and pyrifluquinazon.

The term "pest" means an organism that is detrimental to humans, or human concerns (such as, crops, food, livestock, etc.), where said organism is from Phyla Arthropoda, Mollusca, or Nematoda. Particular examples are ants, aphids, bed bugs, beetles, bristletails, caterpillars, cockroaches, crickets, earwigs, fleas, flies, grasshoppers, grubs, hornets, jassids, leafhoppers, lice, locusts, maggots, mealybugs, mites, moths, nematodes, plantbugs, planthoppers, psyllids, sawflies, scales, silverfish, slugs, snails, spiders, springtails, stink bugs, symphylans, termites, thrips, ticks, wasps, whiteflies, and wireworms.

Additional examples are pests in (1) Subphyla Chelicerata, Myriapoda, and Hexapoda.

(2) Classes of Arachnida, Symphyla, and Insecta.

(3) Order Anoplura. A non-exhaustive list of particular genera includes, but is not limited to, *Haematopinus* spp., *Hoplopleura* spp., *Linognathus* spp., *Pediculus* spp., *Polyplax* spp., *Solenopotes* spp., and *Neohaematopinis* spp. A non-exhaustive list of particular species includes, but is not limited to, *Haematopinus asini*, *Haematopinus suis*, *Linognathus setosus*, *Linognathus ovillus*, *Pediculus humanus capitis*, *Pediculus humanus humanus*, and *Pthirus pubis*.

(4) Order Coleoptera. A non-exhaustive list of particular genera includes, but is not limited to, *Acanthoscelides* spp., *Agriotes* spp., *Anthonomus* spp., *Apion* spp., *Apogonia* spp., *Araecerus* spp., *Aulacophora* spp., *Bruchus* spp., *Cerosterna* spp., *Cerotoma* spp., *Ceutorhynchus* spp., *Chaetocnema* spp., *Colaspis* spp., *Ctenicera* spp., *Curculio* spp., *Cyclocephala* spp., *Diabrotica* spp., *Dinoderus* spp., *Gnathocerus* spp., *Hemicoelus* spp., *Heterobostruchus* spp., *Hypera* spp., *Ips* spp., *Lyctus* spp., *Megascelis* spp., *Meligethes* spp., *Mezium* spp., *Niptus* spp., *Otiorhynchus* spp., *Pantomorus* spp., *Phyllophaga* spp., *Phyllotreta* spp., *Ptinus* spp., *Rhizotrogus* spp., *Rhynchites* spp., *Rhynchophorus* spp., *Scolytus* spp., *Sphenophorus* spp., *Sitophilus* spp., *Tenebrio* spp., and *Tribolium* spp. A non-exhaustive list of particular species includes, but is not limited to, *Acanthoscelides obtectus*, *Agrilus planipennis*, *Ahasverus advena*, *Alphitobius diaperinus*, *Anoplophora glabripennis*, *Anthonomus grandis*, *Anthrenus verbasci*, *Anthrenus falvipes*, *Ataenius spretulus*, *Atomaria linearis*, *Attagenus unicolor*, *Bothynoderes punctiventris*, *Bruchus pisorum*, *Callosobruchus maculatus*, *Carpophilus hemipterus*, *Cassida vittata*, *Cathartus quadricollis*, *Cerotoma trifurcate*, *Ceutorhynchus assimilis*, *Ceutorhynchus napi*, *Conoderus scalaris*, *Conoderus stigmosus*, *Conotrachelus nenuphar*, *Cotinis nitida*, *Crioceris asparagi*, *Cryptolestes ferrugineus*, *Cryptolestes pusillus*, *Cryptolestes turcicus*, *Cylindrocopturus adspersus*, *Deporaus marginatus*, *Dermestes lardarius*, *Dermestes maculatus*, *Epilachna varivestis*, *Euvrilletta peltata*, *Faustinus cubae*, *Hylobius pales*, *Hylotrupes bajulus*, *Hypera postica*, *Hypothenemus hampei*, *Lasioderma serricorne*, *Leptinotarsa decemlineata*, *Limonius canus*, *Liogenys fuscus*, *Liogenys suturalis*, *Lissorhoptrus oryzophilus*, *Lophocateres pusillus*, *Lyctus planicollis*, *Maecolaspis joliveti*, *Melanotus communis*, *Meligethes aeneus*, *Melolontha melolontha*, *Necrobia rufipes*, *Oberea brevis*, *Oberea lin-* earis, *Oryctes rhinoceros, Oryzaephilus mercator, Oryzaephilus surinamensis, Oulema melanopus, Oulema oryzae, Phyllophaga cuyabana, Polycaon stoutti, Popillia japonica, Prostephanus truncatus, Rhyzopertha dominica, Sitona lineatus, Sitophilus granarius, Sitophilus oryzae, Sitophilus zeamais, Stegobium paniceum, Tenebroides mauritanicus, Tribolium castaneum, Tribolium confusum, Trogoderma granarium, Trogoderma variabile, Xestobium rufovillosum,* and *Zabrus tenebrioides.*

(5) Order Dermaptera. A non-exhaustive list of particular species includes, but is not limited to, *Forficula auricularia.*

(6) Order Blattaria. A non-exhaustive list of particular species includes, but is not limited to, *Blattella germanica, Blattella asahinai, Blatta orientalis, Blatta lateralis, Parcoblatta pennsylvanica, Periplaneta americana, Periplaneta australasiae, Periplaneta brunnea, Periplaneta fuliginosa, Pycnoscelus surinamensis,* and *Supella longipalpa.*

(7) Order Diptera. A non-exhaustive list of particular genera includes, but is not limited to, *Aedes* spp., *Agromyza* spp., *Anastrepha* spp., *Anopheles* spp., *Bactrocera* spp., *Ceratitis* spp., *Chrysops* spp., *Cochliomyia* spp., *Contarinia* spp., *Culex* spp., *Culicoides* spp., *Dasineura* spp., *Delia* spp., *Drosophila* spp., *Fannia* spp., *Hylemya* spp., *Liriomyza* spp., *Musca* spp., *Phorbia* spp., *Pollenia* spp., *Psychoda* spp., *Simulium* spp., *Tabanus* spp., and *Tipula* spp. A non-exhaustive list of particular species includes, but is not limited to, *Agromyza frontella, Anastrepha suspensa, Anastrepha ludens, Anastrepha obliqua, Bactrocera cucurbitae, Bactrocera dorsalis, Bactrocera invadens, Bactrocera zonata, Ceratitis capitata, Dasineura brassicae, Delia platura, Fannia canicularis, Fannia scalaris, Gasterophilus intestinalis, Gracillia perseae, Haematobia irritans, Hypoderma lineatum, Liriomyza brassicae, Liriomyza sativa, Melophagus ovinus, Musca autumnalis, Musca domestica, Oestrus ovis, Oscinella frit, Pegomya betae, Piophila casei, Psila rosae, Rhagoletis cerasi, Rhagoletis pomonella, Rhagoletis mendax, Sitodiplosis mosellana,* and *Stomoxys calcitrans.*

(8) Order Hemiptera. A non-exhaustive list of particular Genera includes, but is not limited to, *Adelges* spp., *Aulacaspis* spp., *Aphrophora* spp., *Aphis* spp., *Bemisia* spp., *Ceroplastes* spp., *Chionaspis* spp., *Chrysomphalus* spp., *Coccus* spp., *Empoasca* spp., *Euschistus* spp., *Lepidosaphes* spp., *Lagynotomus* spp., *Lygus* spp., *Macrosiphum* spp., *Nephotettix* spp., *Nezara* spp., *Nilaparvata* spp., *Philaenus* spp., *Phytocoris* spp., *Piezodorus* spp., *Planococcus* spp., *Pseudococcus* spp., *Rhopalosiphum* spp., *Saissetia* spp., *Therioaphis* spp., *Toumeyella* spp., *Toxoptera* spp., *Trialeurodes* spp., *Triatoma* spp., and *Unaspis* spp. A non-exhaustive list of particular species includes, but is not limited to, *Acrosternum hilare, Acyrthosiphon pisum, Aleyrodes proletella, Aleurodicus dispersus, Aleurothrixus floccosus, Amrasca biguttula biguttula, Aonidiella aurantii, Aphis fabae, Aphis gossypii, Aphis glycines, Aphis pomi, Aulacorthum solani, Bactericera cockerelli, Bagrada hilaris, Bemisia argentifolii, Bemisia tabaci, Blissus leucopterus, Boisea trivittata, Brachycorynella asparagi, Brevennia rehi, Brevicoryne brassicae, Cacopsylla gyri, Cacopsylla pyricola, Calocoris norvegicus, Ceroplastes rubens, Cimex hemipterus, Cimex lectularius, Coccus pseudomagnoliarum, Dagbertus fasciatus, Dichelops furcatus, Diuraphis noxia, Diaphorina citri, Dysaphis plantaginea, Dysdercus suturellus, Edessa meditabunda, Empoasca vitis, Eriosoma lanigerum, Erythroneura elegantula, Eurygaster maura, Euschistus conspersus, Euschistus heros, Euschistus servus, Halyomorpha halys, Helopeltis antonii, Hyalopterus pruni, Helopeltis antonii, Helopeltis theivora, Icerya purchasi, Idioscopus nitidulus, Jacobiasca formosana, Laodelphax striatellus, Lecanium corni, Leptocorisa oratorius, Leptocorisa varicornis, Lygus hesperus, Maconellicoccus hirsutus, Macrosiphum euphorbiae, Macrosiphum granarium, Macrosiphum rosae, Macrosteles quadrilineatus, Mahanarva frimbiolata, Megacopta cribraria, Metopolophium dirhodum, Mictis longicornis, Myzus persicae, Nasonovia ribisnigri, Nephotettix cincticeps, Neurocolpus longirostris, Nezara viridula, Nilaparvata lugens, Paracoccus marginatus, Paratrioza cockerelli, Parlatoria pergandii, Parlatoria ziziphi, Peregrinus maidis, Phylloxera vitifoliae, Physokermes piceae, Phytocoris californicus, Phytocoris relativus, Piezodorus guildinii, Planococcus citri, Planococcus ficus, Poecilocapsus lineatus, Psallus vaccinicola, Pseudacysta perseae, Pseudococcus brevipes, Quadraspidiotus perniciosus, Rhopalosiphum maidis, Rhopalosiphum padi, Saissetia oleae, Scaptocoris castanea, Schizaphis graminum, Sitobion avenae, Sogatella furcifera, Trialeurodes vaporariorum, Trialeurodes abutiloneus, Unaspis yanonensis,* and *Zulia entrerriana.*

(9) Order Hymenoptera. A non-exhaustive list of particular genera includes, but is not limited to, *Acromyrmex* spp., *Atta* spp., *Camponotus* spp., *Diprion* spp., *Dolichovespula* spp., *Formica* spp., *Monomorium* spp., *Neodiprion* spp., *Paratrechina* spp., *Pheidole* spp., *Pogonomyrmex* spp., *Polistes* spp., *Solenopsis* spp., *Technomyrmex*, spp., *Tetramorium* spp., *Vespula* spp., *Vespa* spp., and *Xylocopa* spp. A non-exhaustive list of particular species includes, but is not limited to, *Athalia rosae, Atta texana, Caliroa cerasi, Cimbex americana, Iridomyrmex humilis, Linepithema humile, Mellifera Scutellata, Monomorium minimum, Monomorium pharaonis, Neodiprion sertifer, Solenopsis invicta, Solenopsis geminata, Solenopsis molesta, Solenopsis richtery, Solenopsis xyloni, Tapinoma sessile,* and *Wasmannia auropunctata.*

(10) Order Isoptera. A non-exhaustive list of particular genera includes, but is not limited to, *Coptotermes* spp., *Cornitermes* spp., *Cryptotermes* spp., *Heterotermes* spp., *Kalotermes* spp., *Incisitermes* spp., *Macrotermes* spp., *Marginitermes* spp., *Microcerotermes* spp., *Procornitermes* spp., *Reticulitermes* spp., *Schedorhinotermes* spp., and *Zootermopsis* spp. A non-exhaustive list of particular species includes, but is not limited to, *Coptotermes acinaciformis, Coptotermes curvignathus, Coptotermes frenchi, Coptotermes formosanus, Coptotermes gestroi, Cryptotermes brevis, Heterotermes aureus, Heterotermes tenuis, Incisitermes minor, Incisitermes snyderi, Microtermes obesi, Nasutitermes corniger, Odontotermes formosanus, Odontotermes obesus, Reticulitermes banyulensis, Reticulitermes grassei, Reticulitermes flavipes, Reticulitermes hageni, Reticulitermes hesperus, Reticulitermes santonensis, Reticulitermes speratus, Reticulitermes tibialis,* and *Reticulitermes virginicus.*

(11) Order Lepidopteran. A non-exhaustive list of particular genera includes, but is not limited to, *Adoxophyes* spp., *Agrotis* spp., *Argyrotaenia* spp., *Cacoecia* spp., *Caloptilia* spp., *Chilo* spp., *Chrysodeixis* spp., *Colias* spp., *Crambus* spp., *Diaphania* spp., *Diatraea* spp., *Earias* spp., *Ephestia* spp., *Epimecis* spp., *Feltia* spp., *Gortyna* spp., *Helicoverpa* spp., *Heliothis* spp., *Indarbela* spp., *Lithocolletis* spp., *Loxagrotis* spp., *Malacosoma* spp., *Nemapogon* spp., *Peridroma* spp., *Phyllonorycter* spp., *Pseudaletia* spp., *Plutella* spp., *Sesamia* spp., *Spodoptera* spp., *Synanthedon* spp., and *Yponomeuta* spp. A non-exhaustive list of particular species includes, but is not limited to, *Achaea janata, Adoxophyes orana, Agrotis ipsilon, Alabama argillacea, Amorbia cuneana, Amyelois transitella, Anacamptodes*

*defectaria, Anarsia lineatella, Anomis sabulifera, Anticarsia gemmatalis, Archips argyrospila, Archips rosana, Argyrotaenia citrana, Autographa gamma, Bonagota cranaodes, Borbo cinnara, Bucculatrix thurberiella, Capua reticulana, Carposina niponensis, Chlumetia transversa, Choristoneura rosaceana, Cnaphalocrocis medinalis, Conopomorpha cramerella, Corcyra cephalonica, Cossus cossus, Cydia caryana, Cydia funebrana, Cydia molesta, Cydia nigricana, Cydia pomonella, Darna diducta, Diaphania nitidalis, Diatraea saccharalis, Diatraea grandiosella, Earias insulana, Earias vittella, Ecdytolopha aurantianum, Elasmopalpus lignosellus, Ephestia cautella, Ephestia elutella, Ephestia kuehniella, Epinotia aporema, Epiphyas postvittana, Erionota thrax, Estigmene acrea, Eupoecilia ambiguella, Euxoa auxiliaris, Galleria mellonella, Grapholita molesta, Hedylepta indicata, Helicoverpa armigera, Helicoverpa zea, Heliothis virescens, Hellula undalis, Keiferia lycopersicella, Leucinodes orbonalis, Leucoptera coffeella, Leucoptera malifoliella, Lobesia botrana, Loxagrotis albicosta, Lymantria dispar, Lyonetia derkella, Mahasena corbetti, Mamestra brassicae, Manduca sexta, Maruca testulalis, Metisa plana, Mythimna unipuncta, Neoleucinodes elegantalis, Nymphula depunctalis, Operophtera brumata, Ostrinia nubilalis, Oxydia vesulia, Pandemis cerasana, Pandemis heparana, Papilio demodocus, Pectinophora gossypiella, Peridroma saucia, Perileucoptera coffeella, Phthorimaea operculella, Phyllocnistis citrella, Phyllonorycter blancardella, Pieris rapae, Plathypena scabra, Platynota idaeusalis, Plodia interpunctella, Plutella xylostella, Polychrosis viteana, Prays endocarpa, Prays oleae, Pseudaletia unipuncta, Pseudoplusia includens, Rachiplusia nu, Scirpophaga incertulas, Sesamia inferens, Sesamia nonagrioides, Setora nitens, Sitotroga cerealella, Sparganothis pilleriana, Spodoptera exigua, Spodoptera frugiperda, Spodoptera eridania, Thecla basilides, Tinea pellionella, Tineola bisselliella, Trichoplusia ni, Tuta absoluta, Zeuzera coffeae,* and *Zeuzea pyrina.*

(12) Order Mallophaga. A non-exhaustive list of particular genera includes, but is not limited to, *Anaticola* spp., *Bovicola* spp., *Chelopistes* spp., *Goniodes* spp., *Menacanthus* spp., and *Trichodectes* spp. A non-exhaustive list of particular species includes, but is not limited to, *Bovicola bovis, Bovicola caprae, Bovicola ovis, Chelopistes meleagridis, Goniodes dissimilis, Goniodes gigas, Menacanthus stramineus, Menopon gallinae,* and *Trichodectes canis.*

(13) Order Orthoptera. A non-exhaustive list of particular genera includes, but is not limited to, *Melanoplus* spp. and *Pterophylla* spp. A non-exhaustive list of particular species includes, but is not limited to, *Acheta domesticus, Anabrus simplex, Gryllotalpa africana, Gryllotalpa australis Gryllotalpa brachyptera, Gryllotalpa hexadactyla, Locusta migratoria, Microcentrum retinerve, Schistocerca gregaria,* and *Scudderia furcata.*

(14) Order Psocoptera. A non-exhaustive list of particular species includes, but is not limited to, *Liposcelis decolor, Liposcelis entomophila, Lachesilla quercus,* and *Trogium pulsatorium.*

(15) Order Siphonaptera. A non-exhaustive list of particular species includes, but is not limited to, *Ceratophyllus gallinae, Ceratophyllus niger, Ctenocephalides canis, Ctenocephalides fells,* and *Pulex irritans.*

(16) Order Thysanoptera. A non-exhaustive list of particular genera includes, but is not limited to, *Caliothrips* spp., *Frankliniella* spp., *Scirtothrips* spp., and *Thrips* spp. A non-exhaustive list of particular species includes, but is not limited to, *Caliothrips phaseoli, Frankliniella bispinosa, Frankliniella fusca, Frankliniella occidentalis, Frankliniella schultzei, Frankliniella tritici, Frankliniella williamsi, Heliothrips haemorrhoidalis, Rhipiphorothrips cruentatus, Scirtothrips citri, Scirtothrips dorsalis, Taeniothrips rhopalantennalis, Thrips hawaiiensis, Thrips nigropilosus, Thrips orientalis, Thrips palmi,* and *Thrips tabaci.*

(17) Order Thysanura. A non-exhaustive list of particular genera includes, but is not limited to, *Lepisma* spp. and *Thermobia* spp.

(18) Order Acarina. A non-exhaustive list of particular genera includes, but is not limited to, *Acarus* spp., *Aculops* spp., *Argus* spp., *Boophilus* spp., *Demodex* spp., *Dermacentor* spp., *Epitrimerus* spp., *Eriophyes* spp., *Ixodes* spp., *Oligonychus* spp., *Panonychus* spp., *Rhizoglyphus* spp., and *Tetranychus* spp. A non-exhaustive list of particular species includes, but is not limited to, *Acarapis woodi, Acarus siro, Aceria mangiferae, Aculops lycopersici, Aculus pelekassi, Aculus schlechtendali, Amblyomma americanum, Brevipalpus obovatus, Brevipalpus phoenicis, Dermacentor variabilis, Dermatophagoides pteronyssinus, Eotetranychus carpini, Liponyssoides sanguineus, Notoedres cati, Oligonychus coffeae, Oligonychus ilicis, Ornithonyssus bacoti, Panonychus citri, Panonychus ulmi, Phyllocoptruta oleivora, Polyphagotarsonemus latus, Rhipicephalus sanguineus, Sarcoptes scabiei, Tegolophus perseaflorae, Tetranychus urticae, Tyrophagus longior,* and *Varroa destructor.*

(19) Order Araneae. A non-exhaustive list of particular genera includes, but is not limited to, *Loxosceles* spp., *Latrodectus* spp., and *Atrax* spp. A non-exhaustive list of particular species includes, but is not limited to, *Loxosceles reclusa, Latrodectus mactans,* and *Atrax robustus.*

(20) Class Symphyla. A non-exhaustive list of particular species includes, but is not limited to, *Scutigerella immaculata.*

(21) Subclass Collembola. A non-exhaustive list of particular species includes, but is not limited to, *Bourletiella hortensis, Onychiurus armatus, Onychiurus fimetarius,* and *Sminthurus viridis.*

(22) Phylum Nematoda. A non-exhaustive list of particular genera includes, but is not limited to, *Aphelenchoides* spp., *Belonolaimus* spp., *Criconemella* spp., *Ditylenchus* spp., *Globodera* spp., *Heterodera* spp., *Hirschmanniella* spp., *Hoplolaimus* spp., *Meloidogyne* spp., *Pratylenchus* spp., and *Radopholus* spp. A non-exhaustive list of particular species includes, but is not limited to, *Dirofilaria immitis, Globodera pallida, Heterodera glycines, Heterodera zeae, Meloidogyne incognita, Meloidogyne javanica, Onchocerca volvulus, Pratylenchus penetrans, Radopholus similis,* and *Rotylenchulus reniformis.*

(23) Phylum Mollusca. A non-exhaustive list of particular species includes, but is not limited to, *Arion vulgaris, Cornu aspersum, Deroceras reticulatum, Limax flavus, Milax gagates,* and *Pomacea canaliculata.*

A particularly preferred pest group to control is sap-feeding pests. Sap-feeding pests, in general, have piercing and/or sucking mouthparts and feed on the sap and inner plant tissues of plants. Examples of sap-feeding pests of particular concern to agriculture include, but are not limited to, aphids, leafhoppers, moths, scales, thrips, psyllids, mealybugs, stinkbugs, and whiteflies. Specific examples of Orders that have sap-feeding pests of concern in agriculture include but are not limited to, Anoplura and Hemiptera. Specific examples of Hemiptera that are of concern in agriculture include, but are not limited to, *Aulacaspis* spp., *Aphrophora* spp., *Aphis* spp., *Bemisia* spp., *Coccus* spp., *Euschistus* spp., *Lygus* spp., *Macrosiphum* spp., *Nezara* spp., and *Rhopalosiphum* spp.

Another particularly preferred pest group to control is chewing pests. Chewing pests, in general, have mouthparts that allow them to chew on the plant tissue including roots, stems, leaves, buds, and reproductive tissues (including, but not limited to flowers, fruit, and seeds). Examples of chewing pests of particular concern to agriculture include, but are not limited to, caterpillars, beetles, grasshoppers, and locusts. Specific examples of Orders that have chewing pests of concern in agriculture include but are not limited to, Coleoptera and Lepidoptera. Specific examples of Coleoptera that are of concern in agriculture include, but are not limited to, *Anthonomus* spp., *Cerotoma* spp., *Chaetocnema* spp., *Colaspis* spp., *Cydocephala* spp., *Diabrotica* spp., *Hypera* spp., *Phyllophaga* spp., *Phyllotreta* spp., *Sphenophorus* spp., *Sitophilus* spp.

The phrase "pesticidally effective amount" means the amount of a pesticide needed to achieve an observable effect on a pest, for example, the effects of necrosis, death, retardation, prevention, removal, destruction, or otherwise diminishing the occurrence and/or activity of a pest in a locus. This effect may come about when pest populations are repulsed from a locus, pests are incapacitated in, or around, a locus, and/or pests are exterminated in, or around, a locus. Of course, a combination of these effects can occur. Generally, pest populations, activity, or both are desirably reduced more than fifty percent, preferably more than 90 percent, and most preferably more than 99 percent. In general, a pesticidally effective amount, for agricultural purposes, is from about 0.0001 grams per hectare to about 5000 grams per hectare, preferably from about 0.0001 grams per hectare to about 500 grams per hectare, and it is even more preferably from about 0.0001 grams per hectare to about 50 grams per hectare.

DETAILED DESCRIPTION OF THIS DISCLOSURE

This document discloses molecules of Formula One

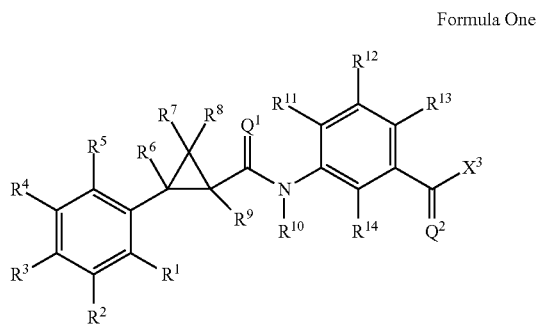

Formula One wherein:
(A) $R^1$ is selected from the group consisting of H, F, Cl, Br, I, CN, $NO_2$, $SF_5$, and $(C_1-C_3)$haloalkyl;
(B) $R^2$ is selected from the Group consisting of H, F, Cl, Br, I, CN, $NO_2$, $SF_5$, and $(C_1-C_3)$haloalkyl;
(C) $R^3$ is selected from the group consisting of H, F, Cl, Br, I, CN, $NO_2$, $SF_5$, and $(C_1-C_3)$haloalkyl;
(D) $R^4$ is selected from the group consisting of H, F, Cl, Br, I, CN, $NO_2$, $SF_5$, and $(C_1-C_3)$haloalkyl;
(E) $R^5$ is selected from the group consisting of H, F, Cl, Br, I, CN, $NO_2$, $SF_5$, and $(C_1-C_3)$haloalkyl;
(F) $R^6$ is H;
(G) $R^7$ is selected from the group consisting of F, Cl, and Br;
(H) $R^8$ is selected from the group consisting of F, Cl, and Br;
(I) $R^9$ is H;
(J) $Q^1$ is selected from the group consisting of O and S;
(K) $Q^2$ is selected from the group consisting of O and S;
(L) $R^{10}$ is selected from the group consisting of H, $(C_1-C_3)$ alkyl, $(C_2-C_3)$alkenyl, $(C_2-C_3)$alkynyl, $(C_1-C_3)$alkylO$(C_1-C_3)$alkyl, and $(C_1-C_3)$alkylOC(=O)$(C_1-C_3)$alkyl;
(M) $R^{11}$ is selected from the group consisting of H, F, Cl, Br, I, CN, $NO_2$, $(C_1-C_3)$alkyl, $(C_1-C_3)$haloalkyl, and $(C_1-C_3)$alkoxy;
(N) $R^{12}$ is selected from the group consisting of H, F, Cl, Br, I, CN, $NO_2$, $(C_1-C_3)$alkyl, $(C_1-C_3)$haloalkyl, and $(C_1-C_3)$alkoxy;
(O) $R^{13}$ is selected from the group consisting of H, F, Cl, Br, I, CN, $NO_2$, $(C_1-C_3)$alkyl, $(C_1-C_3)$haloalkyl, and $(C_1-C_3)$alkoxy;
(P) $R^{14}$ is selected from the group consisting of H, F, Cl, Br, I, CN, $NO_2$, $(C_1-C_3)$alkyl, $(C_1-C_3)$haloalkyl, and $(C_1-C_3)$alkoxy;
(Q) $X^3$ is:
  (1) $N(R^{15a})(R^{15b})$ wherein
    (a) said $R^{15a}$ is selected from the group consisting of H, $(C_1-C_3)$alkyl, $(C_2-C_3)$alkenyl, $(C_2-C_3)$alkynyl, $(C_1-C_3)$haloalkyl, $(C_1-C_3)$alkylphenyl, $(C_1-C_3)$alkylO$(C_1-C_3)$alkyl, $(C_1-C_3)$alkylOC(=O)$(C_1-C_3)$alkyl, and C(=O)$(C_1-C_3)$alkyl, and
    (b) said $R^{15b}$ is a substituted or unsubstituted phenyl, said substituted phenyl has one or more substituents selected from the group consisting of H, F, Cl, Br, I, CN, $NO_2$, $NH_2$, OH, $SF_5$, $(C_1-C_3)$alkyl, $(C_1-C_3)$haloalkyl, $(C_2-C_3)$alkenyl, $(C_2-C_3)$haloalkenyl, $(C_1-C_3)$alkoxy (C=O)O$(C_1-C_3)$alkyl, O(C=O)$(C_1-C_3)$alkyl, $N(R^{15c})_2$, $N=CHN(R^{15c})(X^4)$, $N(R^{15c})C(=O)O(X^4)$, $N(R^{15c})S(=O)_2(X^4)$, $N(S(=O)_2(C_1-C_3)$alkyl$)_2$, $N(R^{15c})C(=O)N(R^{15c})_2$, $N(R^{15c})C(=O)N(R^{15c})X^4$, $N(R^{15c})C(=S)N(R^{15c})_2$, $N(R^{15c})C(=S)N(R^{15c})X^4$, $N(R^{15c})(C_1-C_3)$alkyl$X^4$, $N(R^{15c})(CH(O(C_1-C_3)$alkyl$)_2)$, $N(R^{15c})((C_1-C_3)$alkylOC(=O)$(C_1-C_3)$alkyl), $N(R^{15c})((C_1-C_3)$alkylC(=O)N$(R^{15c})_2)$, $N(R^{15c})C(=O)(R^{15c})$, $N(R^{15c})C(=O)X^4$, $N(R^{15c})(C(=O))_2X^4$, $N(R^{15c})(C(=O))_2OX^4$, $N(R^{15c})(C(=O))_2N(R^{15c})X^4$, N(C(=O)O(C_1-C_6)$alkyl$)_2$, $N(R^{15c})C(=O)O(C_1-C_6)$alkyl, $N(R^{15c})C(=O)N(R^{15c})C(=O)O(R^{15c})$, $N(R^{15C})(C(=O)O(C_1-C_6)$alkyl), $N(R^{15c})(C(=O)O(C_1-C_6)$haloalkyl), $N((C_1-C_3)$alkylOC(=O)$(C_1-C_6)$alkyl)(C(=O)$(C_1-C_6)$alkyl), $N((C_1-C_3)$alkylO$(C_1-C_6)$alkyl)(C(=O)O$(C_1-C_6)$alkyl), and $N(R^{15c})C(=S)X^4$,
      (1) said $R^{15c}$ is each independently selected from the group consisting of H, $(C_1-C_3)$alkyl, $(C_2-C_3)$alkenyl, $(C_2-C_3)$alkynyl, $(C_1-C_3)$haloalkyl, $(C_2-C_3)$haloalkenyl, $(C_1-C_3)$alkylphenyl, $(C_1-C_3)$alkylO$(C_1-C_3)$alkyl, $(C_1-C_3)$alkylOC(=O)$(C_1-C_3)$alkyl, C(=O)$(C_1-C_3)$alkyl, and phenyl, optionally, for $N(R^{15c})_2$ said $N(R^{15c})_2$ is a heterohydrocarbyl ring containing one nitrogen ring atom and three to five carbon ring atoms, where said ring may be saturated or unsaturated,
      (2) said $X^4$ is selected from the group consisting of $(C_1-C_6)$alkyl, $(C_1-C_6)$haloalkyl, $(C_1-C_3)$alkylO ($C_1$-$C_3$)alkyl, O($C_1$-$C_6$)alkyl, ($C_3$-$C_6$)cycloalkyl, ($C_1$-$C_6$)alkylphenyl, phenyl, aryl, and heterocyclyl, each of which may be substituted with one or more of substituents selected from the group consisting of F, Cl, Br, I, CN, OH, $NO_2$, $NH_2$, oxo, ($C_1$-$C_3$)alkyl, ($C_1$-$C_3$)haloalkyl, NH($C_1$-$C_3$)alkyl, N(($C_1$-$C_3$)alkyl)$_2$, O($C_1$-$C_6$)alkyl, O($C_1$-$C_6$)haloalkyl, N($R^{15c}$)C(=O)O($C_1$-$C_6$)alkyl, N($R^{15c}$)S(=O)$_2$($R^{15c}$), S(=O)$_2$($R^{15c}$), ($C_1$-$C_3$)alkylO($C_1$-$C_3$)alkyl, ($C_3$-$C_6$)cycloalkyl, wherein (1)(a) and (1)(b) each said alkyl, alkenyl, alkynyl, cycloalkyl, phenyl, aryl, and heterocyclyl, may be substituted with one or more substituents selected from the group consisting of F, Cl, Br, I, CN, OH, $NO_2$, $NH_2$, NH($C_1$-$C_3$)alkyl, N(($C_1$-$C_3$)alkyl)$_2$, O($C_1$-$C_6$)alkyl, ($C_1$-$C_3$)alkylO($C_1$-$C_3$)alkyl, and ($C_3$-$C_6$)cycloalkyl;

(2) N($R^{16a}$)($R^{16b}$) wherein
  (a) said $R^{16a}$ is selected from the group consisting of H, ($C_1$-$C_3$)alkyl, ($C_2$-$C_3$)alkenyl, ($C_2$-$C_3$)alkynyl, ($C_1$-$C_3$)haloalkyl, ($C_1$-$C_3$)alkylO($C_1$-$C_3$)alkyl, ($C_1$-$C_3$)alkylOC(=O)($C_1$-$C_3$)alkyl, and C(=O)($C_1$-$C_3$)alkyl,
  (b) said $R^{16b}$ is a substituted or unsubstituted ($C_1$-$C_8$)alkyl, said substituted ($C_1$-$C_8$)alkyl has one or more substituents selected from the group consisting of F, Cl, Br, I, CN, $NO_2$, O($C_1$-$C_8$)alkyl, ($C_3$-$C_8$)cycloalkyl, ($C_1$-$C_8$)alkylphenyl, ($C_2$-$C_8$)alkenyl, ($C_2$-$C_8$)alkynyl, S($C_1$-$C_8$)alkyl, S(O)($C_1$-$C_8$)alkyl, S(O)$_2$($C_1$-$C_8$)alkyl, Ophenyl, O($C_2$-$C_8$)alkenyl, O($C_1$-$C_8$)alkyl($C_3$-$C_8$)cycloalkyl, O($C_1$-$C_8$)alkylphenyl, O($C_1$-$C_8$)alkyl($C_3$-$C_8$)cycloalkyl, O($C_1$-$C_8$)alkyl, C(=O)O($C_1$-$C_8$)alkyl, OC(=O)($C_1$-$C_8$)alkyl, C(=O)N($R^{16a}$)($C_1$-$C_8$)alkyl, N($R^{16a}$)C(=O)($C_1$-$C_8$)alkyl, S($C_1$-$C_8$)alkyl, S(O)($C_1$-$C_8$)alkyl, S(O)$_2$($C_1$-$C_8$)alkyl, S(O)$_2$$NH_2$, and N($R^{16a}$)S(O)$_2$($C_1$-$C_8$)alkyl,
  wherein (2)(a) and (2)(b) each alkyl, alkenyl, alkynyl, cycloalkyl, and phenyl, may be substituted with one or more substituents selected from the group consisting of F, Cl, Br, I, CN, OH, $NH_2$, $NO_2$, ($C_1$-$C_8$)alkyl, ($C_1$-$C_8$)alkoxy, ($C_1$-$C_8$)haloalkyl, N(($C_1$-$C_8$)alkyl)$_2$, and C(=O)O($C_1$-$C_8$)alkyl;

(3) N($R^{17a}$)(N($R^{17b}$)($R^{17c}$) wherein
  (a) said $R^{17a}$ is selected from the group consisting of H, ($C_1$-$C_3$)alkyl, ($C_2$-$C_3$)alkenyl, ($C_2$-$C_3$)alkynyl, ($C_1$-$C_3$)haloalkyl, ($C_1$-$C_3$)alkylO($C_1$-$C_3$)alkyl, ($C_1$-$C_3$)alkylOC(=O)($C_1$-$C_3$)alkyl, and C(=O)($C_1$-$C_3$)alkyl,
  (b) said $R^{17b}$ is selected from the group consisting of H, ($C_1$-$C_3$)alkyl, ($C_2$-$C_3$)alkenyl, ($C_2$-$C_3$)alkynyl, ($C_1$-$C_3$)haloalkyl, ($C_1$-$C_3$)alkylO($C_1$-$C_3$)alkyl, ($C_1$-$C_3$)alkylOC(=O)($C_1$-$C_3$)alkyl, and C(=O)($C_1$-$C_3$)alkyl,
  (c) said $R^{17c}$ is selected from the group consisting of H, substituted or unsubstituted phenyl, substituted or unsubstituted heterocyclyl, substituted or unsubstituted ($C_1$-$C_8$)alkyl, substituted or unsubstituted ($C_3$-$C_8$)cycloalkyl, C(=O)$X^5$, and C(=S)$X^5$,
    (1) said $X^5$ is selected from the group consisting of substituted or unsubstituted phenyl, substituted or unsubstituted heterocyclyl, substituted or unsubstituted ($C_1$-$C_8$)alkyl, O($C_1$-$C_8$)alkyl, O($C_1$-$C_8$)haloalkyl, O(substituted and unsubstituted)phenyl, N($R^{17a}$)($C_1$-$C_8$)alkyl, N($R^{17a}$)($C_1$-$C_8$)haloalkyl, N($R^{17a}$)($C_3$-$C_8$)cycloalkyl, N($R^{17a}$)(substituted and unsubstituted phenyl), and ($C_3$-$C_6$)cycloalkyl,
    (2) said substituted phenyl in (3)(c) has one or more substituents selected from the group consisting of F, Cl, Br, I, CN, $NO_2$, OH, ($C_1$-$C_3$)alkoxy, and ($C_1$-$C_3$)alkyl,
    (3) said substituted heterocyclyl in (3)(c) has one or more substituents selected from the group consisting of F, Cl, Br, I, CN, $NO_2$, OH, ($C_1$-$C_3$)alkoxy, and ($C_1$-$C_3$)alkyl,
    (4) said substituted ($C_1$-$C_8$)alkyl in (3)(c) has one or more substituents selected from the group consisting of F, Cl, Br, I, CN, OH, $NO_2$, $NH_2$, O($C_1$-$C_8$)alkyl, ($C_3$-$C_8$)cycloalkyl, phenyl, ($C_2$-$C_8$)alkenyl, ($C_2$-$C_8$)alkynyl, S($C_1$-$C_8$)alkyl, S(O)($C_1$-$C_8$)alkyl, S(O)$_2$($C_1$-$C_8$)alkyl, Ophenyl, O($C_2$-$C_8$)alkenyl, O($C_1$-$C_3$)alkyl($C_3$-$C_8$)cycloalkyl, O($C_1$-$C_8$)alkylphenyl, O($C_1$-$C_8$)alkyl($C_3$-$C_8$)cycloalkyl, C(=O)NH($C_1$-$C_8$)alkyl, NHC(=O)($C_1$-$C_8$)alkyl, S(O)$_2$$NH_2$, NH($C_1$-$C_3$)alkyl, N(($C_1$-$C_3$)alkyl)$_2$,
    (5) said substituted ($C_3$-$C_8$)cycloalkyl has one or more substituents selected from the group consisting of F, Cl, Br, I, CN, OH, ($C_1$-$C_3$)alkoxy, and ($C_1$-$C_3$)alkyl,
  wherein (2)(a), (2)(b), and (2)(c) each alkyl, alkenyl, alkynyl, cycloalkyl, haloalkyl, phenyl, and heterocyclyl, may be optionally substituted with one or more substituents selected from the group consisting of F, Cl, Br, I, CN, OH, $NH_2$, $NO_2$, ($C_1$-$C_8$)alkyl, ($C_1$-$C_8$)alkoxy ($C_1$-$C_8$)haloalkyl, N(($C_1$-$C_8$)alkyl)$_2$, and C(=O)O($C_1$-$C_8$)alkyl, optionally (N($R^{17b}$)($R^{17c}$)) is a heterohydrocarbyl ring containing one nitrogen ring atom and three to five carbon ring atoms, where said ring may be saturated or unsaturated;

(4) N($R^{18a}$)(N=C($R^{18b}$)($R^{18c}$)
  (a) said is selected from the group consisting of H, ($C_1$-$C_3$)alkyl, ($C_2$-$C_3$)alkenyl, ($C_2$-$C_3$)alkynyl, ($C_1$-$C_3$)alkylO($C_1$-$C_3$)alkyl, ($C_1$-$C_3$)alkylOC(=O)($C_1$-$C_3$)alkyl, and C(=O)($C_1$-$C_3$)alkyl,
  (b) said $R^{18b}$ is selected from the group consisting of H and ($C_1$-$C_3$)alkyl,
  (c) said $R^{18c}$ is selected from the group consisting of substituted or unsubstituted phenyl, substituted or unsubstituted heterocyclyl, substituted or unsubstituted ($C_1$-$C_8$)alkyl, substituted or unsubstituted ($C_3$-$C_8$)cycloalkyl,
    (1) said substituted phenyl in (4)(c) has one or more substituents selected from the group consisting of F, Cl, Br, I, CN, $NO_2$, OH, ($C_1$-$C_3$)alkoxy, ($C_1$-$C_3$)alkyl, ($C_1$-$C_3$)haloalkoxy, and ($C_1$-$C_3$)haloalkyl,
    (2) said substituted heterocyclyl in (4)(c) has one or more substituents selected from the group consisting of F, Cl, Br, I, CN, $NO_2$, OH, ($C_1$-$C_3$)alkoxy, ($C_1$-$C_3$)alkyl, ($C_1$-$C_3$)haloalkoxy, and ($C_1$-$C_3$)haloalkyl,
    (3) said substituted ($C_1$-$C_8$)alkyl has one or more substituents selected from the group consisting of F, Cl, Br, I, CN, $NO_2$, O($C_1$-$C_8$)alkyl, ($C_3$-$C_8$)cycloalkyl, phenyl, ($C_2$-$C_8$)alkenyl, ($C_2$-$C_8$)alkynyl, S($C_1$-$C_8$)alkyl, S(O)($C_1$-$C_8$)alkyl, S(O)$_2$($C_1$-$C_8$)alkyl, Ophenyl, O($C_2$-$C_8$)alkenyl, O($C_1$-$C_8$)alkyl($C_3$-$C_8$)cycloalkyl, O($C_1$-$C_8$)

alkylphenyl, O(C$_1$-C$_8$)alkyl(C$_3$-C$_8$)cycloalkyl, C(=O)NH(C$_1$-C$_8$)alkyl, NHC(=O)(C$_1$-C$_8$)alkyl, and S(O)$_2$NH$_2$, (4) said substituted (C$_3$-C$_8$)cycloalkyl has one or more substituents selected from the group consisting of F, Cl, Br, I, CN, OH, (C$_1$-C$_3$)alkoxy, and (C$_1$-C$_3$)alkyl, wherein (4)(a), (4)(b), and (4)(c) each alkyl, alkenyl, alkynyl, cycloalkyl, haloalkyl, phenyl, and heterocyclyl may be substituted with one or more substituents selected from the group consisting of F, Cl, Br, I, CN, OH, NH$_2$, NO$_2$, (C$_1$-C$_8$)alkyl, (C$_1$-C$_8$)alkoxy, (C$_1$-C$_8$)haloalkyl, N((C$_1$-C$_8$)alkyl)$_2$, and C(=O)O(C$_1$-C$_8$)alkyl, optionally C(R$^{18b}$)(R$^{18c}$) is a hydrocarbyl ring containing three to five carbon ring atoms, where said ring may be saturated or unsaturated, optionally, one or more of said carbon ring atoms may instead be nitrogen, oxygen, or sulfur atom;

and N-oxides, agriculturally acceptable acid addition salts, salt derivatives, solvates, ester derivatives, crystal polymorphs, isotopes, resolved stereoisomers, tautomers, pro-insecticides, of the molecules of Formula One.

In another embodiment a molecule according to Formula One wherein said molecule has the following formula Formula Two In another embodiment a molecule according to Formula One and Formula Two wherein R$^1$ is selected from the group consisting of H, F, Cl, Br, SF$_5$, and CF$_3$.

In another embodiment a molecule according to Formula One and Formula Two wherein R$^2$ is selected from the group consisting of H, F, Cl, Br, SF$_5$, and CF$_3$.

In another embodiment a molecule according to Formula One and Formula Two wherein R$^3$ is selected from the group consisting of H, F, Cl, Br, SF$_5$, and CF$_3$.

In another embodiment a molecule according to Formula One and Formula Two wherein R$^4$ is selected from the group consisting of H, F, Cl, Br, SF$_5$, and CF$_3$.

In another embodiment a molecule according to Formula One and Formula Two wherein R$^5$ is selected from the group consisting of H, F, Cl, Br, SF$_5$, and CF$_3$.

In another embodiment a molecule according to Formula One and Formula Two wherein at least one of R$^2$, R$^3$, and R$^4$, is SF$_5$.

In another embodiment a molecule according to Formula One and Formula Two wherein R$^7$ is Cl.

In another embodiment a molecule according to Formula One and Formula Two wherein R$^8$ is Cl.

In another embodiment a molecule according to Formula One and Formula Two wherein R$^7$, and R$^8$ are not the same.

In another embodiment a molecule according to Formula One and Formula Two wherein Q$^1$ is O.

In another embodiment a molecule according to Formula One and Formula Two wherein Q$^2$ is O.

In another embodiment a molecule according to Formula One and Formula Two wherein R$^{10}$ is H.

In another embodiment a molecule according to Formula One and Formula Two wherein R$^{11}$ is H.

In another embodiment a molecule according to Formula One and Formula Two wherein R$^{12}$ is selected from the group consisting of H, F, Cl, CH$_3$, and CF$_3$.

In another embodiment a molecule according to Formula One and Formula Two wherein R$^{13}$ is selected from the group consisting of F, Cl, CH$_3$, and OCH$_3$.

In another embodiment a molecule according to Formula One and Formula Two wherein R$^{14}$ is selected from the group consisting of H, F, and Cl.

In another embodiment a molecule according to Formula One and Formula Two wherein:

R$^1$ is selected from the group consisting of H, F, Cl, Br, SF$_5$, and CF$_3$;
R$^2$ is selected from the group consisting of H, F, Cl, Br, SF$_5$, and CF$_3$;
R$^3$ is selected from the group consisting of H, F, Cl, Br, SF$_5$, and CF$_3$;
R$^4$ is selected from the group consisting of H, F, Cl, Br, SF$_5$, and CF$_3$;
R$^5$ is selected from the group consisting of H, F, Cl, Br, SF$_5$, and CF$_3$;
R$^7$ is Cl;
R$^8$ is Cl;
Q$^1$ is O;
Q$^2$ is O;
R$^{10}$ is H;
R$^{11}$ is H;
R$^{12}$ is selected from the group consisting of H, F, Cl, CH$_3$, and CF$_3$;
R$^{13}$ is selected from the group consisting of F, Cl, CH$_3$, and OCH$_3$; and
R$^{14}$ is selected from the group consisting of H, F, and Cl.

In another embodiment a molecule according to Formula One and Formula Two wherein X$^3$ is N(R$^{15a}$)(R$^{15b}$).

In another embodiment a molecule according to Formula One and Formula Two wherein X$^3$ is N(R$^{15a}$)(R$^{15b}$) and said R$^{15b}$ is selected from the group consisting of N(R$^{15c}$)C(=O)(R$^{15c}$) and N(R$^{15c}$)C(=O)X$^4$, said R$^{15c}$ are each independently selected from the group consisting of (C$_1$-C$_3$)alkyl, (C$_2$-C$_3$)alkenyl, (C$_1$-C$_3$)haloalkyl, and (C$_1$-C$_3$)alkylO(C$_1$-C$_3$)alkyl, said X$^4$ is selected from the group consisting of (C$_1$-C$_6$)alkyl, (C$_1$-C$_6$)haloalkyl, and (C$_1$-C$_3$)alkylO(C$_1$-C$_3$)alkyl, and each said alkyl, haloalkyl, and alkenyl, may be substituted with one or more substituents selected from the group consisting of F, Cl, CN, and (C$_3$-C$_6$)cycloalkyl. For avoidance of doubt this includes, for example, substituting a haloalkyl, which includes the term "alkyl" with one or more substituents, for example CN or (C$_3$-C$_6$)cycloalkyl.

In another embodiment a molecule according to Formula One and Formula Two wherein X$^3$ is N(R$^{16a}$)(R$^{16b}$).

In another embodiment a molecule according to Formula One and Formula Two wherein X3 is N(R$^{17a}$)(N(R$^{17b}$)(R$^{17c}$)).

In another embodiment a molecule according to Formula One and Formula Two wherein X$^3$ is N(R$^{18a}$)(N=C(R$^{18b}$)(R$^{18c}$).

In another embodiment a molecule selected from Table 2, preferably a molecule selected from the group consisting of F1007, F1079, F1108, F1147, F1185, F1234, F1241, F1246, F1247, F1248, F1250, F1460, F1465, F1593, F1598, F1613, F1627, F1657, F1694, F1696, F1697, F1702, F1703, F1704, F1708, F1711, F1740, F2016, F2017, F2021, F2027, F2039, F2042, F2078, and F2081.

The molecules of Formula One may exist in different geometric or optical isomeric or different tautomeric forms. One or more centers of chirality may be present in which case molecules of Formula One may be present as pure enantiomers, mixtures of enantiomers, pure diastereomers or mixtures of diastereomers. It will be appreciated by those skilled in the art that one stereoisomer may be more active than the other stereoisomers. Individual stereoisomers may be obtained by known selective synthetic procedures, by conventional synthetic procedures using resolved starting materials, or by conventional resolution procedures. There may be double bonds present in the molecule, in which case compounds of Formula One may exist as single geometric isomers (cis or trans, E or Z) or mixtures of geometric isomers (cis and trans, E and Z). Centers of tautomerisation may be present. This disclosure covers all such isomers, tautomers, and mixtures thereof, in all proportions. The structures disclosed in the present disclosure maybe drawn in only one geometric form for clarity, but are intended to represent all geometric forms of the molecule.

Preparation of Molecules of Formula One
Preparation of Cyclopropyl Carboxylic Acids Stilbenes 1-1, wherein $R^1$, $R^2$, $R^3$, $R^4$, $R^5$, $R^6$, and $R^9$ are as previously disclosed, may be treated with a base such as sodium hydroxide in the presence of a carbene source such as chloroform or bromoform and a phase transfer catalyst such as N-benzyl-N,N-diethylethanaminium chloride in a polar protic solvent such as water at temperatures from about 0° C. to about 40° C. to provide diaryl cyclopropanes 1-2, wherein $R^1$, $R^2$, $R^3$, $R^4$, $R^5$, $R^6$, $R^7$, $R^8$, and $R^9$ are as previously disclosed (Scheme 1, step a). Alternatively, stilbenes 1-1, wherein $R^1$, $R^2$, $R^3$, $R^4$, $R^5$, $R^6$, and $R^9$ are previously disclosed, may be treated with a salt such as sodium iodide in the presence of a carbene source such as trimethyl(trifluoromethyl)silane in a polar aprotic solvent such as tetrahydrofuran at temperatures from about 80° C. to about 120° C. under microwave irradiation conditions to provide diaryl cyclopropanes 1-2, wherein $R^1$, $R^2$, $R^3$, $R^4$, $R^5$, $R^6$, $R^7$, $R^8$, and $R^9$ are as previously disclosed (Scheme 1, step a). Treatment of diaryl cyclopropanes 1-2 with a transition metal such as ruthenium(III) chloride in the presence of a stoichiometric oxidant such as sodium periodate in a solvent mixture preferably water, ethyl acetate, and acetonitrile at temperatures from about 0° C. to about 40° C. may provide cyclopropyl carboxylic acids 1-3, wherein $R^1$, $R^2$, $R^3$, $R^4$, $R^5$, $R^6$, $R^7$, $R^8$, and $R^9$ are as previously disclosed (Scheme 1, step b).

Scheme 1

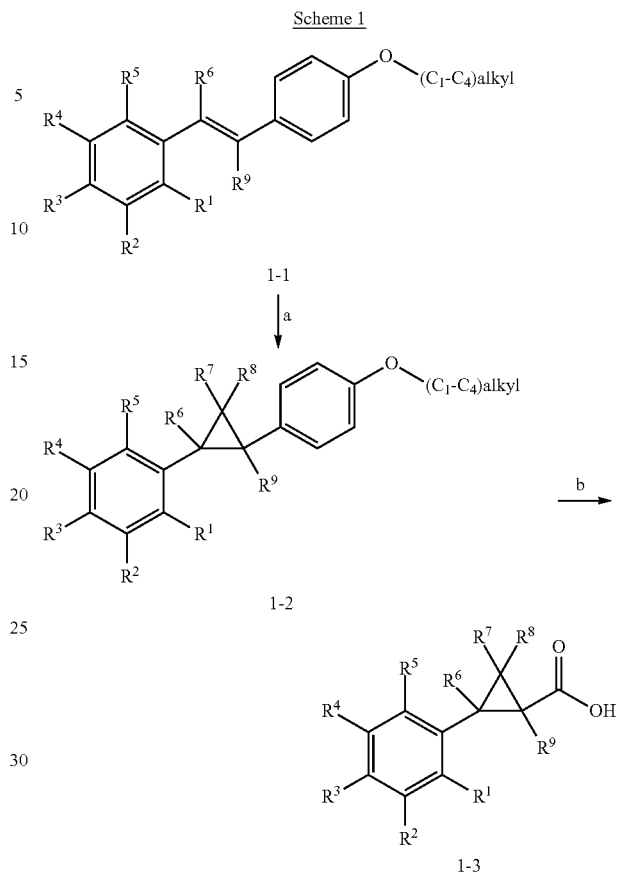

Preparation of Stilbenes

Stilbenes 1-1 may be prepared by several different methods as outlined in Scheme 2. Phenyl carbonyls 2-1, wherein $R^1$, $R^2$, $R^3$, $R^4$, $R^5$, and $R^6$ are as previously disclosed, may be treated with alkoxy benzyl phosphonates 2-2 in the presence of a base such as sodium methoxide in a polar aprotic solvent such as N,N-dimethylformamide at temperatures from about −10° C. to about 30° C. and subsequently heated to 40° C. to about 80° C. to provide stilbenes 1-1 (Scheme 2, step a). Aryl halides 2-3, wherein $R^1$, $R^2$, $R^3$, $R^4$, and $R^5$ are as previously disclosed, may be treated with vinylbenzenes 2-4, wherein $R^6$ and $R^9$ are as previously disclosed, in the presence of a transition metal catalyst such as palladium(II) acetate and a bisphosphine ligand such as 1,1'-bis(diphenylphosphino)ferrocene in a basic solvent such as triethylamine at temperatures from about 60° C. to about 100° C. to provide stilbenes 1-1 (Scheme 2, step b).

Scheme 2

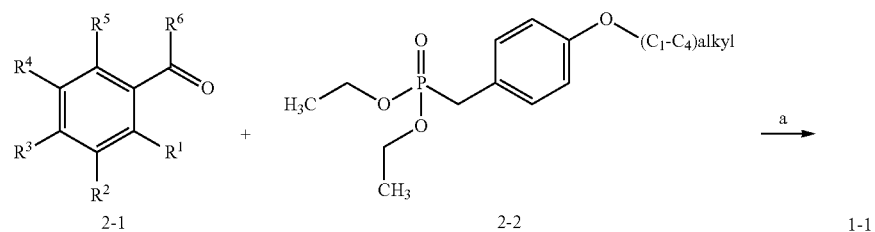

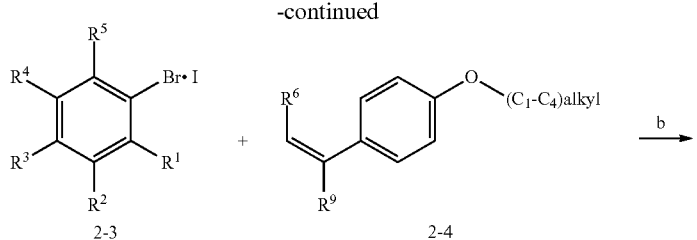

2-3     2-4

In yet another embodiment, stilbenes 1-1 may also be prepared by the Wittig olefination method (Chalal, M.; Vervandier-Fasseur, D.; Meunier, P.; Cattey, Hierso, J.-C. *Tetrahedron* 2012, 68, 3899-3907) as outlined in Scheme 2.5. Phenyl carbonyls 2-1, wherein $R^1$, $R^2$, $R^3$, $R^4$, and $R^5$ are as previously disclosed and $R^6$ is H, may be treated with alkoxy benzyl triphenylphosphonium chlorides 2.5-2 in the presence of a base such as n-butyl lithium in a polar aprotic solvent such as tetrahydrofuran at temperatures from about −78° C. to ambient temperature to provide stilbenes 1-1 (Scheme 2.5, step a).

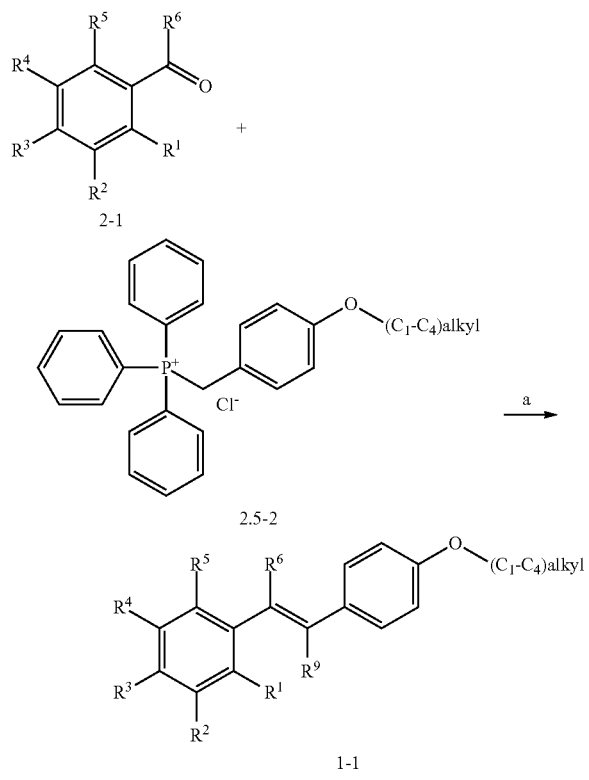

Scheme 2.5

Preparation of Cyclopropyl Amides

Cyclopropyl amides 3-3, wherein $Q^1$ is O, and $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $Q^2$, and $X^3$ are as previously disclosed, may be prepared by treatment with amines or amine salts 3-2, wherein $R^{10}$, $R^{11}$, $R^{12}$, $R^{13}$, $R^{14}$, $Q^2$, and $X^3$ are as previously disclosed, and activated carboxylic acids 3-1, wherein A is an activating group, and $R^1$, $R^2$, $R^3$, $R^4$, $R^5$, $R^6$, $R^7$, $R^8$, and $R^9$ are as previously disclosed, with a base, such as triethylamine, diisopropylethylamine, 4-methylmorpholine, or 4-dimethylaminopyridine in an anhydrous aprotic solvent such as dichloromethane, tetrahydrofuran, 1,2-dichloroethane, dimethylformamide, or any combination thereof, at temperatures between about 0° C. and about 120° C. (Scheme 3, step a).

Carboxylic acids 3-1, wherein A is an activating group, may be an acid halide, such as an acid chloride, an acid bromide, or an acid fluoride; a carboxylic ester, such as a para-nitrophenyl ester, a pentafluorophenyl ester, an ethyl (hydroxyimino)cyanoacetate ester, a methyl ester, an ethyl ester, a benzyl ester, an N-hydroxysuccinimidyl ester, a hydroxybenzotriazol-1-yl ester, or a hydroxypyridyltriazol-1-yl ester; an O-acylisourea; an acid anhydride; or a thioester. Acid chlorides may be prepared from the corresponding carboxylic acids by treatment with a dehydrating chlorinating reagent, such as oxalyl chloride or thionyl chloride. Activated carboxylic esters 3-1 may be prepared from carboxylic acids in situ with a uronium salt, such as 1-[bis(dimethylamino)methylene]-1H-1,2,3-triazolo[4,5-b]pyridinium 3-oxid hexafluorophosphate (HATU), O-(benzotriazol-1-yl)-N,N,N',N'-tetramethyluronium hexafluorophosphate (HBTU), or (1-cyano-2-ethoxy-2-oxoethylidenaminooxy)dimethylamino-morpholino-carbenium hexafluorophosphate (COMU). Activated carboxylic esters 3-1 may also be prepared from carboxylic acids in situ with a phosphonium salt such as benzotriazol-1-yl-oxytripyrrolidinophosphonium hexafluorophosphate (PyBop). Activated carboxylic esters 3-1 may also be prepared from carboxylic acids in situ with a coupling reagent such as 1-(3-dimethylamino propyl)-3-ethylcarbodiimide, or dicyclohexylcarbodiimide in the presence of a triazole such as hydroxybenzotriazole.monohydrate (HOBO or 1-hydroxy-7-azabenzotriazole (HOAt). O-Acylisoureas may be prepared with a dehydrating carbodimide such as 1-(3-dimethylamino propyl)-3-ethylcarbodiimide or dicyclohexylcarbodiimide. Activated carboxylic esters 3-1 may also be prepared from carboxylic acids in situ with a coupling reagent such as 2-chloro-1,3-dimethylimidazolidinium hexafluorophosphate (CIP) in the presence of a triazole such as 1-hydroxy-7-azabenzotriazole (HOAt). Activated carboxylic esters 3-1 may also be prepared from carboxylic acids in situ with a coupling reagent such as 2,4,6-tripropyl-1,3,5,2,4,6-trioxatriphosphinane 2,4,6-trioxide (T3P®) in the presence of a base such as pyridine.

Cyclopropyl amides 3-3, wherein $R^{15b}$ contains a sulfide and $R^{15a}$ is as previously disclosed, may be oxidized to the corresponding sulfoxide or sulfone by treatment with about one equivalent of meta-chloroperoxybenzoic acid in a polar aprotic solvent such as dichloromethane (sulfoxide) or about two equivalents of meta-chloroperoxybenzoic acid (sulfone) at temperatures between about 0° C. to about 40° C. Alternatively, cyclopropyl amides 3-3, wherein $R^{15b}$ contains a sulfide may be oxidized to the corresponding sulfoxide or sulfone by treatment with one equivalent of sodium perborate in a protic solvent such as acetic acid (sulfoxide) or two equivalents of sodium perborate (sulfone). Preferably, the oxidation will be performed at temperatures between about 40° C. to about 100° C. using about 1.5 equivalents of sodium perborate to provide chromatographically separable mixtures of sulfoxide and sulfone cyclopropyl amides 3-3. Alternatively, cyclopropyl amides 3-3 containing a sulfide may be oxidized to the corresponding sulfilimine by treating with about one equivalent of an amine such as cyanamide, about one equivalent of a base such as potassium tert-butoxide, and between one and two equivalents of an oxidant such as N-bromosuccinimide in a polar protic solvent such as methanol at temperatures between about 0° C. to about 40° C. The sulfilimine may be further oxidized to the corresponding sulfoximine by treatment with about one equivalent of meta-chloroperoxybenzoic acid and about two equivalents of potassium carbonate in a mixture of solvents such as 2:1:1 ethanol:dichloromethane:water at temperatures between about 0° C. to about 40° C.

Cyclopropyl amides 3-3, wherein $R^3$ is $NO_2$ may be reduced to the corresponding $NH_2$ by treatment with an acid source, such as ammonium chloride, and iron in a polar protic solvent, such as methanol, water, or any combination thereof, at temperatures from about 20° C. to about 60° C.

Amines or amine salts 3-2, wherein $Q^2$ is O may be treated directly with a source of sulfur, such as phosphorus pentasulfide or 2,4-bis(4-methoxyphenyl)-1,3,2,4-dithiadiphosphetane 2,4-disulfide (Lawesson's reagent) with or without additives such as 1,1,1,3,3,3-hexamethyldisoloxane, in an aprotic solvent chosen from tetrahydrofuran, dichloromethane, chloroform, toluene, or pyridine, at temperatures from about 40° C. to about 120° C. to provide amines or amine salts 3-2, wherein $Q^2$ is S.

tetrahydrofuran, 1,2-dichloroethane, dimethylformamide, or any combination thereof, at temperatures between about 0° C. and about 120° C. (Scheme 4, step a).

Activated carboxylic acids 4-1 may be an acid halide, such as an acid chloride, an acid bromide, or an acid fluoride; a carboxylic ester, such as a para-nitrophenyl ester, a pentafluorophenyl ester, an ethyl (hydroxyimino)cyanoacetate ester, a methyl ester, an ethyl ester, a benzyl ester, an N-hydroxysuccinimidyl ester, a hydroxybenzotriazol-1-yl ester, or a hydroxypyridyltriazol-1-yl ester; an O-acylisourea; an acid anhydride; or a thioester. Acid chlorides may be prepared from the corresponding carboxylic acids by treatment with a dehydrating chlorinating reagent, such as oxalyl chloride or thionyl chloride. Activated carboxylic esters 4-1 may be prepared from carboxylic acids in situ with a uronium salt, such as 1-[bis(dimethylamino)methylene]-1H-1,2,3-triazolo[4,5-b]pyridinium 3-oxid hexafluorophosphate (HATU), O-(benzotriazol-1-yl)-N,N,N'N'-tetramethyluronium hexafluorophosphate (HBTU), or (1-cyano-2-ethoxy-2-oxoethylidenaminooxy)dimethylamino-morpholino-carbenium hexafluorophosphate (COMU). Activated carboxylic esters 4-1 may also be prepared from carboxylic acids in situ with a phosphonium salt such as benzotriazol-1-yl-oxytripyrrolidinophosphonium hexafluorophosphate (PyBop). Activated carboxylic esters 4-1 may also be prepared from carboxylic acids in situ with a coupling reagent such as 1-(3-dimethylamino propyl)-3-ethylcarbodiimide, or dicyclohexylcarbodiimide in the presence of a triazole such as hydroxybenzotriazole.monohydrate (HOBt) or 1-hydroxy-7-azabenzotriazole (HOAt). O-Acylisoureas may be prepared with a dehydrating carbodimide such as 1-(3-dimethylamino propyl)-3-ethylcarbodiimide or dicyclohex- Scheme 3

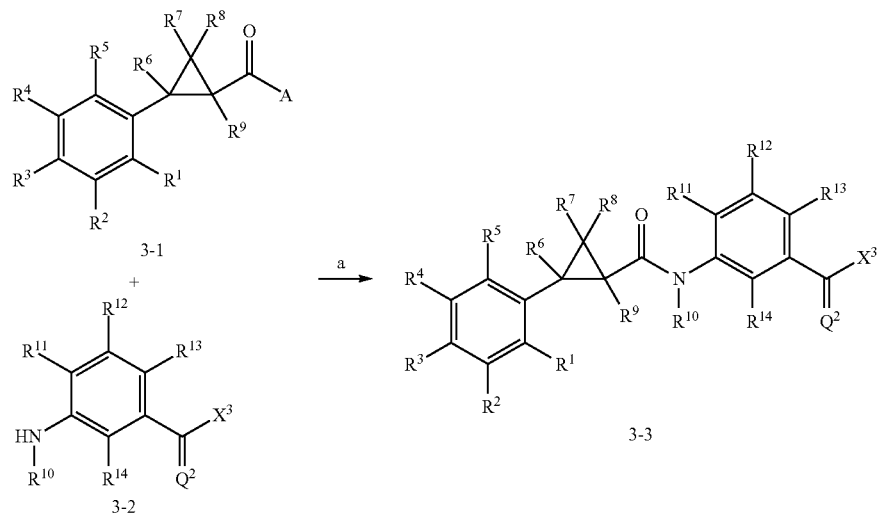

Cyclopropyl amides 4-3, wherein $Q^2$ is O, and $R^1$, $R^2$, $R^3$, $R^4$, $R^5$, $R^6$, $R^7$, $R^8$, $R^9$, $Q^1$, $R^{10}$, $R^{11}$, $R^{12}$, $R^{13}$, $R^{14}$, and $X^3$ are as previously disclosed, may be prepared by treatment with amines or amine salts 4-2, wherein $X^3$ is as previously disclosed, and activated carboxylic acids 4-1, wherein A is an activating group, and $R^1$, $R^2$, $R^3$, $R^4$, $R^5$, $R^6$, $R^7$, $R^8$, $R^9$, $Q^1$, $R^{10}$, $R^{11}$, $R^{12}$, $R^{13}$, and $R^{14}$ are as previously disclosed, with a base, such as triethylamine, diisopropylethylamine, 4-methylmorpholine, pyridine, or 4-dimethylaminopyridine in an anhydrous aprotic solvent such as dichloromethane, ylcarbodiimide. Activated carboxylic esters 4-1 may also be prepared from carboxylic acids in situ with a coupling reagent such as 2-chloro-1,3-dimethylimidazolidinium hexafluorophosphate (CIP) in the presence of a triazole such as 1-hydroxy-7-azabenzotriazole (HOAt). Activated carboxylic esters 4-1 may also be prepared from carboxylic acids in situ with a coupling reagent such as 2,4,6-tripropyl-1,3,5,2,4,6-trioxatriphosphinane 2,4,6-trioxide (T3P®) in the presence of a base such as pyridine.

Scheme 4

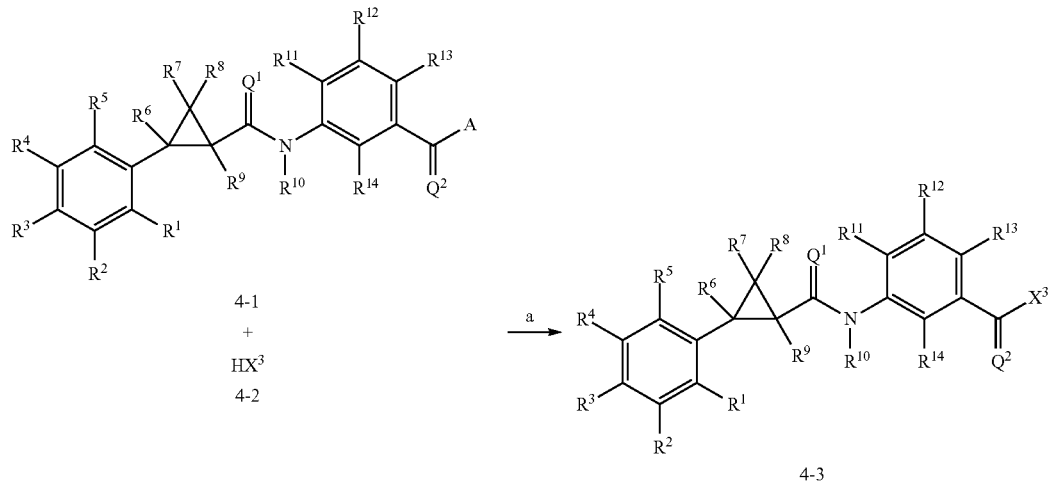

Cyclopropyl amides 5-2, wherein $X^3$ is $N(R^{15a})(R^{15b})$ and $R^{15b}$ is a substituted phenyl having one or more substituents including $N(R^{15c})_2$, wherein one of $R^{15c}$ is a $(C_1-C_3)$alkylphenyl; $Q^2$ is O, $R^1$, $R^2$, $R^3$, $R^4$, $R^5$, $R^6$, $R^7$, $R^8$, $R^9$, $Q^1$, $R^{10}$, $R^{11}$, $R^{12}$, $R^{13}$, $R^{14}$, and $R^{15a}$ are as previously disclosed, may be prepared by treatment of amines 5-1, wherein $X^3$ is $N(R^{15a})(R^{15b})$ and $R^{15b}$ is a substituted phenyl having one or more substituents including $N(R^{15c})_2$, wherein $R^{15c}$ is H; $Q^2$ is O, $R^1$, $R^2$, $R^3$, $R^4$, $R^5$, $R^6$, $R^7$, $R^8$, $R^9$, $Q^1$, $R^{10}$, $R^{11}$, $R^{12}$, $R^{13}$, $R^{14}$, $R^{15a}$ are as previously disclosed, with an aldehyde such as benzaldehyde in the presence of a reducing agent such as sodium cyanoborohydride in a solvent such as methanol, with or without an acid, such as acetic acid, at about room temperature (Scheme 5, step a).

Cyclopropyl amides 5-4, wherein $X^3$ is $N(R^{15a})(R^{15b})$ and $R^{15b}$ is a substituted phenyl having one or more substituents including $N(R^{15c})_2$, wherein one or more of $R^{15c}$ is $(C_1-C_3)$ alkyl; $Q^2$ is O, $R^1$, $R^2$, $R^3$, $R^4$, $R^5$, $R^6$, $R^7$, $R^8$, $R^9$, $Q^1$, $R^{10}$, $R^{11}$, $R^{12}$, $R^{13}$, $R^{14}$, and $R^{15a}$ are as previously disclosed, may be prepared by treatment of amines 5-1, wherein $X^3$ is $N(R^{15a})(R^{15b})$ and $R^{15b}$ is a substituted phenyl having one or more substituents including $N(R^{15c})_2$, wherein $R^{15c}$ is H; $Q^2$ is O, $R^1$, $R^2$, $R^3$, $R^4$, $R^5$, $R^6$, $R^7$, $R^8$, $R^9$, $Q^1$, $R^{10}$, $R^{11}$, $R^{12}$, $R^{13}$, $R^{14}$, and $R^{15a}$ are as previously disclosed, with an alkylating agent 5-3 such as an alkyl halide in the presence of a base, such as triethylamine, diisopropylethylamine, 4-methylmorpholine, 4-dimethylaminopyridine, or pyridine, in an anhydrous aprotic solvent such as dichloromethane, tetrahydrofuran, 1,2-dichloroethane, N,N-dimethylformamide, or any combination thereof, at temperatures between about 0° C. and about 120° C. (Scheme 5, step b).

Cyclopropyl amides 5-6, wherein $X^3$ is $N(R^{15a})(R^{15b})$ and $R^{15b}$ is a substituted phenyl having one or more substituents including $N(R^{15c})C(=O)X^4$; $Q^2$ is O, $R^1$, $R^2$, $R^3$, $R^4$, $R^5$, $R^6$, $R^7$, $R^8$, $R^9$, $Q^1$, $R^{10}$, $R^{11}$, $R^{12}$, $R^{13}$, $R^{14}$, and $R^{15a}$ are as previously disclosed, may be prepared by treatment of amines 5-1, wherein $X^3$ is $N(R^{15a})(R^{15b})$ and $R^{15b}$ is a substituted phenyl having one or more substituents including $N(R^{15c})_2$, wherein $R^{15c}$ is H; $Q^2$ is O, $R^1$, $R^2$, $R^3$, $R^4$, $R^5$, $R^6$, $R^7$, $R^8$, $R^9$, $Q^1$, $R^{10}$, $R^{11}$, $R^{12}$, $R^{13}$, $R^{14}$, and $R^{15a}$ are as previously disclosed, with an activated carboxylic acid 5-5 wherein A is an activating group and a base, such as triethylamine, diisopropylethylamine, 4-methylmorpholine, 4-dimethylaminopyridine, or pyridine, in an anhydrous aprotic solvent such as dichloromethane, tetrahydrofuran, 1,2-dichloroethane, N,N-dimethylformamide, or any combination thereof, at temperatures between about 0° C. and about 120° C. (Scheme 5, step c).

Activated carboxylic acids 5-5, may be an acid halide, such as an acid chloride, an acid bromide, an acid fluoride, or a chloroformate; a carboxylic ester, such as a p-nitrophenyl ester, a pentafluorophenyl ester, an ethyl (hydroxyimino)cyanoacetate ester, a methyl ester, an ethyl ester, a benzyl ester, an N-hydroxysuccinimidyl ester, a hydroxybenzotriazol-1-yl ester, or a hydroxypyridyltriazol-1-yl ester; an O-acylisourea; an acid anhydride; or a thioester. Acid chlorides may be prepared from the corresponding carboxylic acids by treatment with a dehydrating chlorinating reagent, such as oxalyl chloride or thionyl chloride. Activated carboxylic esters 5-5 may be prepared from carboxylic acids in situ with a uronium salt, such as 1-[bis (dimethylamino)methylene]-1H-1,2,3-triazolo[4,5-b]pyridinium 3-oxid hexafluorophosphate (HATU), O-(benzotriazol-1-yl)-N,N,N',N'-tetramethyluronium hexafluoro phosphate (HBTU), or (1-cyano-2-ethoxy-2-oxoethylidenaminooxy)dimethylamino-morpholino-carbenium hexafluorophosphate (COMU). Activated carboxylic esters 5-5 may also be prepared from carboxylic acids in situ with a phosphonium salt such as benzotriazol-1-yl-oxytripyrrolidinophosphonium hexafluorophosphate (PyBop). Activated carboxylic esters 5-5 may also be prepared from carboxylic acids in situ with a coupling reagent, such as 1-(3-dimethylamino propyl)-3-ethylcarbodiimide or dicyclohexylcarbodiimide, in the presence of a triazole such as hydroxybenzotriazole.monohydrate (HOBt) or 1-hydroxy-7-azabenzotriazole (HOAt). O-Acylisoureas may be prepared with a dehydrating carbodimide such as 1-(3-dimethylaminopropyl)-3-ethylcarbodiimide or dicyclohexylcarbodiimide. Activated carboxylic esters 5-5 may also be prepared from carboxylic acids in situ with a coupling reagent such as 2-chloro-1,3-dimethylimidazolidinium hexafluorophosphate (CIP) in the presence of a triazolol such as 1-hydroxy-7-azabenzotriazole (HOAt). Activated carboxylic esters 5-5 may also be prepared from carboxylic acids in situ with a coupling reagent such as 2,4,6-tripropyl-1,3,5,2,4,6-trioxatriphosphinane 2,4,6-trioxide (T3P®) in the presence of a base such as pyridine. In each 5-5 above, $X^4$, is as previously defined.

Scheme 5

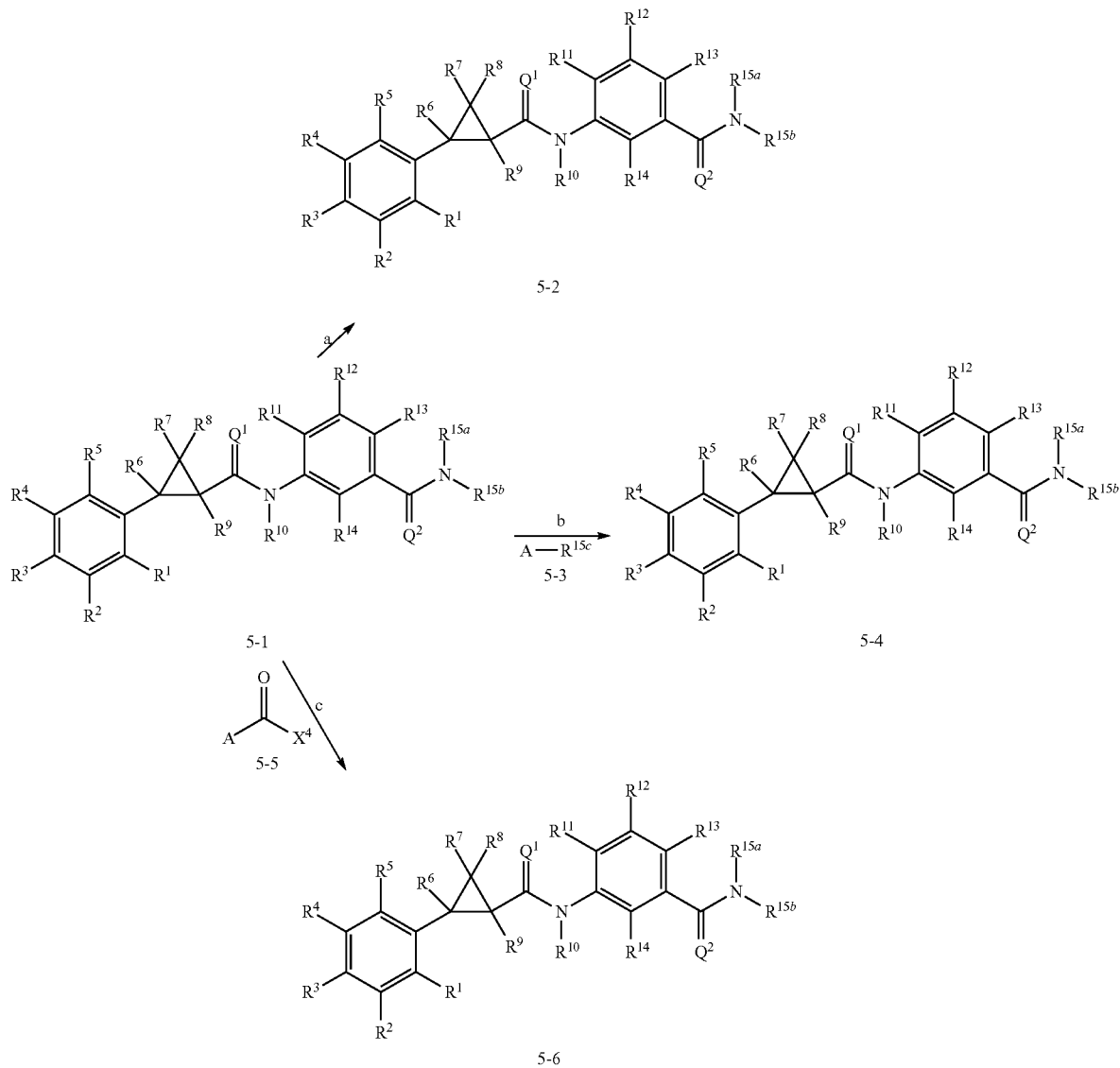

Cyclopropyl amides 6-4, wherein $X^3$ is $N(R^{15a})(R^{15b})$ and $R^{15b}$ is a substituted phenyl having one or more substituents including $N(R^{15c})_2$, wherein $R^{15c}$ is H; $Q^2$ is O, $R^1$, $R^2$, $R^3$, $R^4$, $R^5$, $R^6$, $R^7$, $R^8$, $R^9$, $Q^1$, $R^{10}$, $R^{11}$, $R^{12}$, $R^{13}$, $R^{14}$, and $R^{15a}$ are as previously disclosed, may be prepared by treatment of 6-1, wherein $X^3$ is $N(R^{15a})(R^{15b})$ and $R^{15b}$ is a substituted phenyl having one or more substituents including $NO_2$; $R^1$, $R^2$, $R^3$, $R^4$, $R^5$, $R^6$, $R^7$, $R^8$, $R^9$, $Q^1$, $R^{10}$, $R^{11}$, $R^{12}$, $R^{13}$, $R^{14}$, and $R^{15a}$ are as previously disclosed, with a metal such as palladium on carbon in the presence of a reducing agent such as hydrogen gas in a solvent such as ethyl acetate or with a metal such as iron in the presence of a reducing agent such as ammonium chloride in a solvent mixture such as methanol and water at a temperature of about 25° C. to about 60° C. (Scheme 6, step a).

Alternatively, cyclopropyl amides 6-4, wherein $X^3$ is $N(R^{15a})(R^{15b})$ and $R^{15b}$ is a substituted phenyl having one or more substituents including $N(R^{15c})_2$, wherein $R^{15c}$ is a $Q^2$ is O, $R^1$, $R^2$, $R^3$, $R^4$, $R^5$, $R^6$, $R^7$, $R^8$, $R^9$, $Q^1$, $R^{10}$, $R^{11}$, $R^{12}$, $R^{13}$, $R^{14}$, and $R^{15a}$ are as previously disclosed, may be prepared by treatment of 6-2, wherein $X^3$ is $N(R^{15a})(R^{15b})$ and $R^{15b}$ is a substituted phenyl having one or more substituents including $N(R^{15c})C(=O)O(C_1-C_6)$alkyl wherein $R^{15c}$ is H; $Q^2$ is O, $R^1$, $R^2$, $R^3$, $R^4$, $R^5$, $R^6$, $R^7$, $R^8$, $R^9$, $Q^1$, $R^{10}$, $R^{11}$, $R^{12}$, $R^{13}$, $R^{14}$, and $R^{15a}$ are as previously disclosed, with an anhydrous acid solution such as hydrochloric acid in 1,4-dioxane and dichloromethane at a temperature of about 25° C. (Scheme 6, step c).

Alternatively, cyclopropyl amides 6-4, wherein $X^3$ is $N(R^{15a})(R^{15b})$ and $R^{15b}$ is a substituted phenyl having one or more substituents including $N(R^{15c})_2$, wherein $R^{15c}$ is H; $Q^2$ is O, $R^1$, $R^2$, $R^3$, $R^4$, $R^5$, $R^6$, $R^7$, $R^8$, $R^9$, $Q^1$, $R^{10}$, $R^{11}$, $R^{12}$, $R^{13}$, $R^{14}$, and $R^{15a}$ are as previously disclosed, may be prepared by treatment of 6-3, wherein $X^3$ is $N(R^{15a})(R^{15b})$ and $R^{15b}$ is a substituted phenyl having one or more substituents including $N(C(=O)O(C_1-C_6)$alkyl$)_2$; $Q^2$ is O, $R^1$, $R^2$, $R^3$, $R^4$, $R^5$, $R^6$, $R^7$, $R^8$, $R^9$, $Q^1$, $R^{10}$, $R^{11}$, $R^{12}$, $R^{13}$, $R^{14}$, and $R^{15a}$ are as previously disclosed, with an anhydrous acid solution such as hydrochloric acid in 1,4-dioxane and dichloromethane at a temperature of about 25° C. (Scheme 6, step c).

Cyclopropyl amides 6-6, wherein $X^3$ is $N(R^{15a})(R^{15b})$ and $R^{15b}$ is a substituted phenyl having one or more substituents including $NH(R^{15c})$ wherein $R^{15c}$ is $(C_1-C_3)$alkyl; $Q^2$ is O, $R^1$, $R^2$, $R^3$, $R^4$, $R^5$, $R^6$, $R^7$, $R^8$, $R^9$, $Q^1$, $R^{10}$, $R^{11}$, $R^{12}$, $R^{13}$, $R^{14}$, and $R^{15a}$ are as previously disclosed, may be prepared by treatment of 6-5 wherein $X^3$ is $N(R^{15a})(R^{15b})$ and $R^{15b}$ is a substituted phenyl having one or more substituents including $N(R^{15c})C(=O)O(C_1-C_6)$alkyl wherein $R^{15c}$ is $(C_1-C_3)$ alkyl; $R^1$, $R^2$, $R^3$, $R^4$, $R^5$, $R^6$, $R^7$, $R^8$, $R^9$, $Q^1$, $R^{10}$, $R^{11}$, $R^{12}$, $R^{13}$, $R^{14}$, and $R^{15a}$ are as previously disclosed, with an anhydrous acid solution such as hydrochloric acid in 1,4-dioxane and dichloromethane at a temperature of about 25° C. (Scheme 6, step d).

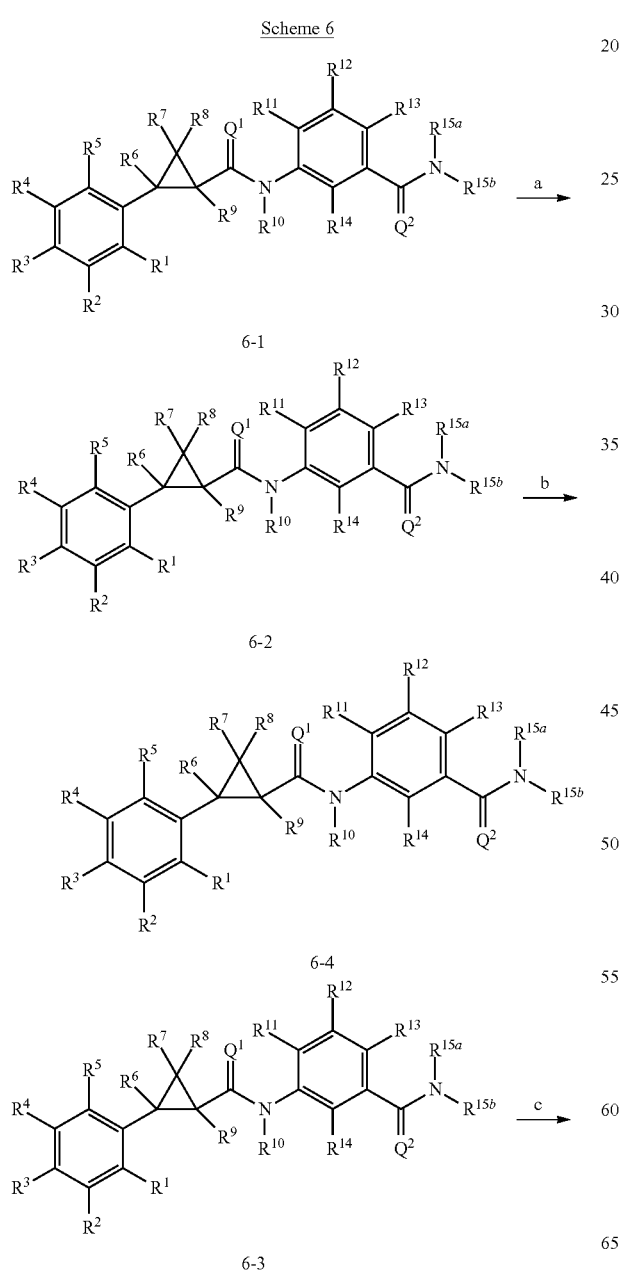

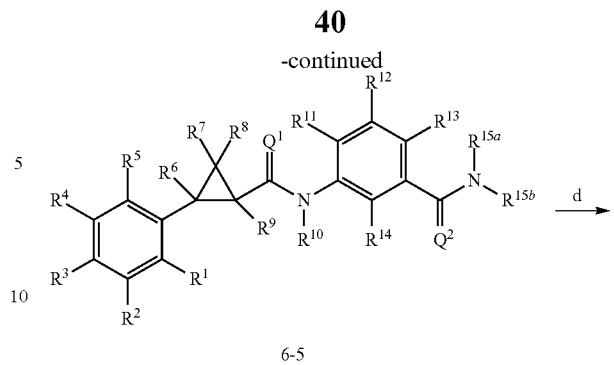

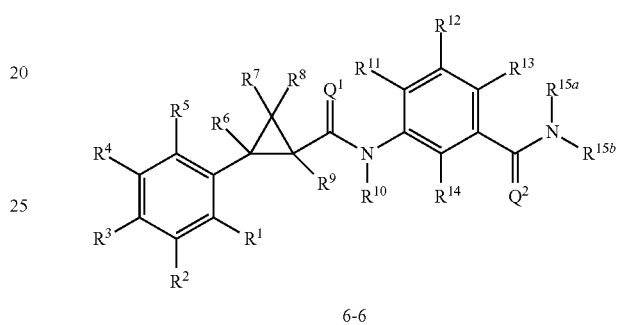

Cyclopropyl amides 7-2, wherein $X^3$ is $N(R^{15a})(R^{15b})$ and $R^{15b}$ is a substituted phenyl having one or more substituents including a $(C_2-C_3)$alkenyl or $(C_2-C_3)$haloalkenyl group; $Q^2$ is O; $R^1$, $R^2$, $R^3$, $R^4$, $R^5$, $R^6$, $R^7$, $R^8$, $R^9$, $Q^1$, $R^{10}$, $R^{11}$, $R^{12}$, $R^{13}$, $R^{14}$, and $R^{15a}$ are as previously disclosed, may be prepared by treatment of aryl halides 7-1, wherein $X^3$ is $N(R^{15a})(R^{15b})$ and $R^{15b}$ is a substituted phenyl having one or more substituents including Br or I; $Q^2$ is O; $R^1$, $R^2$, $R^3$, $R^4$, $R^5$, $R^6$, $R^7$, $R^8$, $R^9$, $Q^1$, $R^{10}$, $R^{11}$, $R^{12}$, $R^{13}$, $R^{14}$, and $R^{15a}$ are as previously disclosed, with a stannane such as 7-2, wherein $R^{15c}$ is a $(C_2-C_3)$alkenyl or $(C_2-C_3)$haloalkenyl group, in the presence of a metal catalyst such as bis(triphenylphosphine)palladium(II) dichloride in an aprotic solvent like 1,4-dioxane at a temperature of about 90° C. (Scheme 7, step a), thereby replacing the Br or I with the $(C_2-C_3)$alkenyl or $(C_2-C_3)$haloalkenyl group.

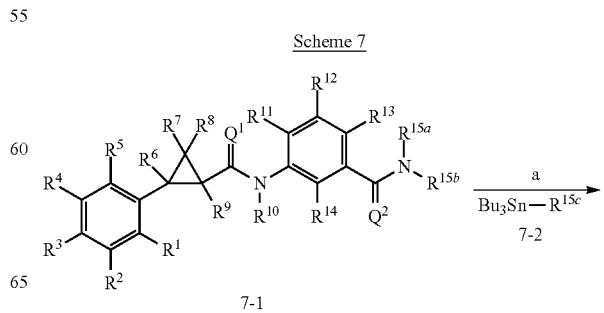

-continued

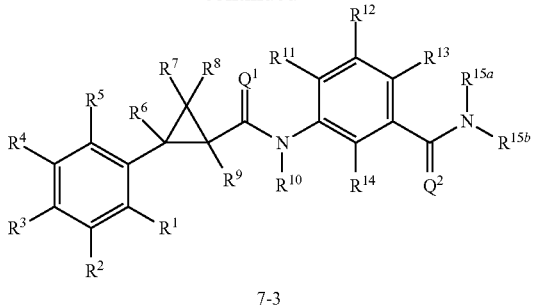

7-3

Cyclopropyl amides 8-3, wherein $Q^1$ is O, and $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $Q^2$, $R^{17a}$, $R^{17b}$, and $R^{17c}$ are as previously disclosed, may be prepared by treatment of amines or amine salts 8-2, wherein $R^{10}$, $R^{11}$, $R^{12}$, $R^{13}$, $R^{14}$, $Q^2$, $R^{17a}$, $R^{17b}$, and $R^{17c}$ are as previously disclosed, and activated carboxylic acids 8-1, wherein A is an activating group, and $R^1$, $R^2$, $R^3$, $R^4$, $R^5$, $R^6$, $R^7$, $R^8$, and $R^9$ are as previously disclosed, with a base, such as triethylamine, diisopropylethylamine, 4-methylmorpholine, or 4-dimethylaminopyridine in an anhydrous aprotic solvent such as dichloromethane, tetrahydrofuran, 1,2-dichloroethane, dimethylformamide, or any combination thereof, at temperatures between about 0° C. and about 120° C. (Scheme 8, step a).

Activated carboxylic acids 8-1 may be an acid halide, such as an acid chloride, an acid bromide, or an acid fluoride; a carboxylic ester, such as a para-nitrophenyl ester, a pentafluorophenyl ester, an ethyl (hydroxyimino)cyanoacetate ester, a methyl ester, an ethyl ester, a benzyl ester, an N-hydroxysuccinimidyl ester, a hydroxybenzotriazol-1-yl ester, or a hydroxypyridyltriazol-1-yl ester; an O-acylisourea; an acid anhydride; or a thioester. Acid chlorides may be prepared from the corresponding carboxylic acids by treatment with a dehydrating chlorinating reagent, such as oxalyl chloride or thionyl chloride. Activated carboxylic esters 8-1 may be prepared from carboxylic acids in situ with a uronium salt, such as 1-[bis(dimethylamino)methylene]-1H-1,2,3-triazolo[4,5-b]pyridinium 3-oxid hexafluorophosphate (HATU), O-(benzotriazol-1-yl)-N,N,N',N'-tetramethyluronium hexafluorophosphate (HBTU), or (1-cyano-2-ethoxy-2-oxoethylidenaminooxy)dimethylamino-morpholino-carbenium hexafluorophosphate (COMU). Activated carboxylic esters 8-1 may also be prepared from carboxylic acids in situ with a phosphonium salt such as benzotriazol-1-yl-oxytripyrrolidinophosphonium hexafluorophosphate (PyBop). Activated carboxylic esters 8-1 may also be prepared from carboxylic acids in situ with a coupling reagent such as 1-(3-dimethylamino propyl)-3-ethylcarbodiimide, or dicyclohexylcarbodiimide in the presence of a triazole such as hydroxybenzotriazole.monohydrate (HOBt) or 1-hydroxy-7-azabenzotriazole (HOAt). O-Acylisoureas may be prepared with a dehydrating carbodimide such as 1-(3-dimethylamino propyl)-3-ethylcarbodiimide or dicyclohexylcarbodiimide. Activated carboxylic esters 8-1 may also be prepared from carboxylic acids in situ with a coupling reagent such as 2-chloro-1,3-dimethylimidazolidinium hexafluorophosphate (CIP) in the presence of a triazole such as 1-hydroxy-7-azabenzotriazole (HOAt). Activated carboxylic esters 8-1 may also be prepared from carboxylic acids in situ with a coupling reagent such as 2,4,6-tripropyl-1,3,5,2,4,6-trioxatriphosphinane 2,4,6-trioxide (T3P®) in the presence of a base such as pyridine.

Scheme 8

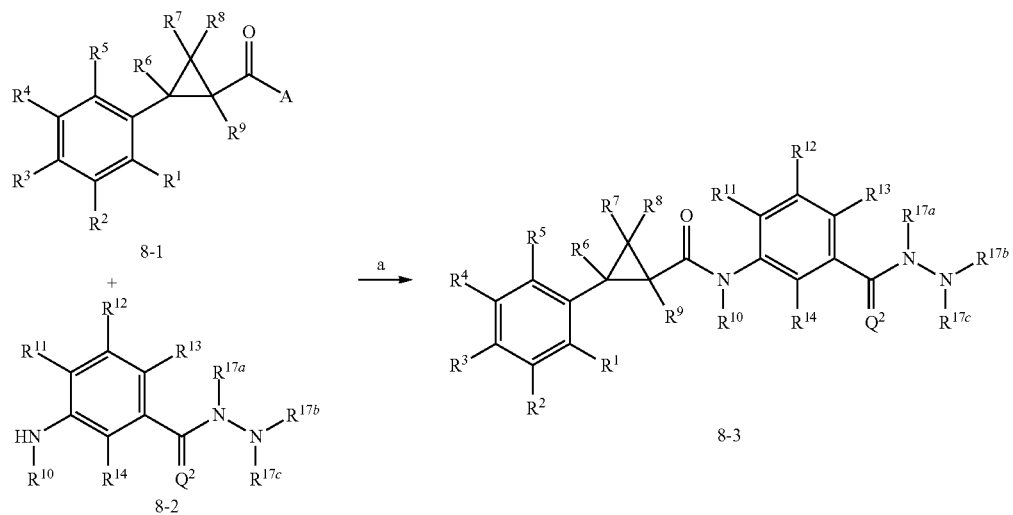

Cyclopropyl amides 9-3, wherein $Q^2$ is O, and $R^1$, $R^2$, $R^3$, $R^4$, $R^5$, $R^6$, $R^7$, $R^8$, $R^9$, $Q^1$, $R^{10}$, $R^{11}$, $R^{12}$, $R^{13}$, $R^{14}$, $R^{17a}$, $R^{17b}$, and $R^{17c}$ are as previously disclosed, may be prepared by treatment of hydrazines or hydrazine salts, 9-2, wherein $R^{17a}$, $R^{17b}$, and $R^{17c}$ are as previously disclosed, and activated carboxylic acids 9-1, wherein A is an activating group, and $R^1$, $R^2$, $R^3$, $R^4$, $R^5$, $R^6$, $R^7$, $R^8$, $R^9$, $Q^1$, $R^{10}$, $R^{11}$, $R^{12}$, $R^{13}$, and $R^{14}$ are as previously disclosed, with a base, such as triethylamine, diisopropylethylamine, 4-methylmorpholine, or 4-dimethylaminopyridine in an anhydrous aprotic solvent such as dichloromethane, tetrahydrofuran, 1,2-dichloroethane, dimethylformamide, or any combination thereof, at temperatures between about 0° C. and about 120° C. (Scheme 9, step a).

Activated carboxylic acids 9-1 may be an acid halide, such as an acid chloride, an acid bromide, or an acid fluoride; a carboxylic ester, such as a para-nitrophenyl ester, a pentafluorophenyl ester, an ethyl (hydroxyimino)cyanoacetate ester, a methyl ester, an ethyl ester, a benzyl ester, an N-hydroxysuccinimidyl ester, a hydroxybenzotriazol-1-yl ester, or a hydroxypyridyltriazol-1-yl ester; an O-acylisourea; an acid anhydride; or a thioester. Acid chlorides may be prepared from the corresponding carboxylic acids by treatment with a dehydrating chlorinating reagent, such as oxalyl chloride or thionyl chloride. Activated carboxylic esters 9-1 may be prepared from carboxylic acids in situ with a uronium salt, such as 1-[bis(dimethylamino)methylene]-1H-1,2,3-triazolo[4,5-b]pyridinium 3-oxid hexafluorophosphate (HATU), O-(benzotriazol-1-yl)-N,N,N',N'-tetramethyluronium hexafluorophosphate (HBTU), or (1-cyano-2-ethoxy-2-oxoethylidenaminooxy)dimethylamino-morpholino-carbenium hexafluorophosphate (COMU). Activated carboxylic esters 9-1 may also be prepared from carboxylic acids in situ with a phosphonium salt such as benzotriazol-1-yl-oxytripyrrolidinophosphonium hexafluorophosphate (PyBop). Activated carboxylic esters 9-1 may also be prepared from carboxylic acids in situ with a coupling reagent such as 1-(3-dimethylamino propyl)-3-ethylcarbodiimide, or dicyclohexylcarbodiimide in the presence of a triazole such as hydroxybenzotriazole.monohydrate (HOBt) or 1-hydroxy-7-azabenzotriazole (HOAt). O-Acylisoureas may be prepared with a dehydrating carbodimide such as 1-(3-dimethylamino propyl)-3-ethylcarbodiimide or dicyclohexylcarbodiimide. Activated carboxylic esters 9-1 may also be prepared from carboxylic acids in situ with a coupling reagent such as 2-chloro-1,3-dimethylimidazolidinium hexafluorophosphate (CIP) in the presence of a triazole such as 1-hydroxy-7-azabenzotriazole (HOAt). Activated carboxylic esters 9-1 may also be prepared from carboxylic acids in situ with a coupling reagent such as 2,4,6-tripropyl-1,3,5,2,4,6-trioxatriphosphinane 2,4,6-trioxide (T3P®) in the presence of a base such as pyridine.

acid solution such as hydrochloric acid in 1,4-dioxane and dichloromethane at a temperature of about 25° C. (Scheme 10, step a).

Cyclopropyl amides 10-4, wherein $Q^2$ is O, and $R^1$, $R^2$, $R^3$, $R^4$, $R^5$, $R^6$, $R^7$, $R^8$, $R^9$, $Q^1$, $R^{10}$, $R^{11}$, $R^{12}$, $R^{13}$, $R^{14}$, $R^{17a}$, and $R^{17b}$ are as previously disclosed, and $X^5$ is substituted or unsubstituted phenyl, substituted or unsubstituted heterocyclyl, substituted or unsubstituted $(C_1-C_8)$alkyl, $O(C_1-C_8)$alkyl, $O(C_1-C_8)$haloalkyl, $(C_3-C_6)$cycloalkyl, and O(substituted and unsubstituted)phenyl, may be prepared by treatment of cyclopropyl amides 10-2, wherein $Q^2$ is O, and $R^1$, $R^2$, $R^3$, $R^4$, $R^5$, $R^6$, $R^7$, $R^8$, $R^9$, $Q^1$, $R^{10}$, $R^{11}$, $R^{12}$, $R^{13}$, $R^{14}$, $R^{17a}$, and $R^{17b}$ are as previously disclosed, and an activated carboxylic acid or chloroformate 10-3, wherein A is an activating group, and $X^5$ is disclosed above, with a base, such as triethylamine, diisopropylethylamine, 4-methylmorpholine, 4-dimethylaminopyridine, or pyridine, in an anhydrous aprotic solvent such as dichloromethane, tetrahydrofuran, 1,2-dichloroethane, N,N-dimethylformamide, or any combination thereof, at temperatures between about 0° C. and about 120° C. (Scheme 10, step b).

Activated carboxylic acids 10-3 may be an acid halide, such as an acid chloride, an acid bromide, or an acid fluoride; a carboxylic ester, such as a p-nitrophenyl ester, a pentafluorophenyl ester, an ethyl (hydroxyimino)cyanoacetate ester, a methyl ester, an ethyl ester, a benzyl ester, an N-hydroxysuccinimidyl ester, a hydroxybenzotriazol-1-yl ester, or a hydroxypyridyltriazol-1-yl ester; an O-acylisourea; an acid anhydride; or a thioester. Acid chlorides may be prepared from the corresponding carboxylic acids by treatment with a dehydrating chlorinating reagent, such as oxalyl chloride or thionyl chloride. Activated carboxylic esters 10-3 may be prepared from carboxylic acids in situ with a uronium salt, such as 1-[bis(dimethylamino)methylene]-1H-1,2,3-triazolo[4,5-b]pyridinium 3-oxid hexafluorophosphate Scheme 9

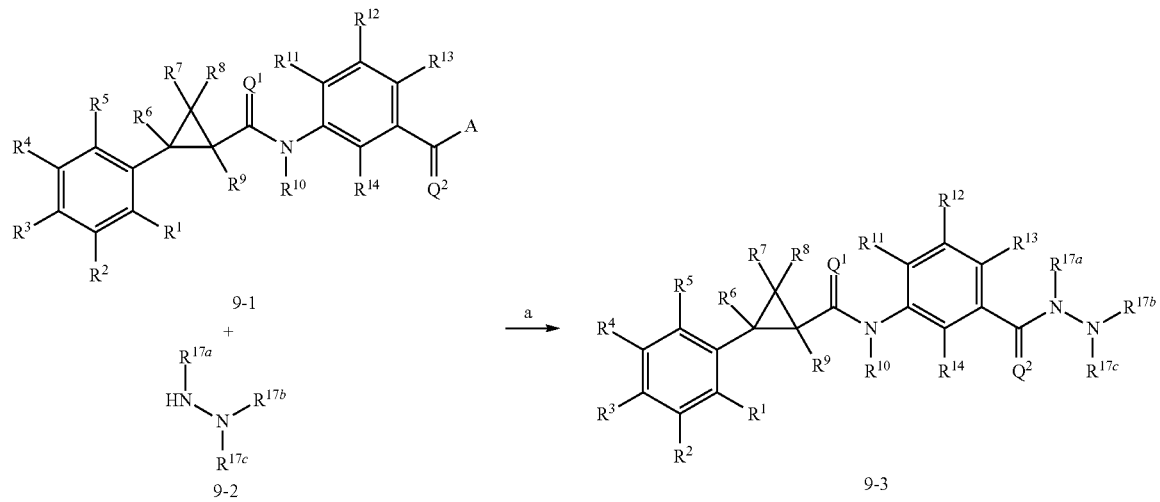

Cyclopropyl amides 10-2, wherein $Q^2$ is O, $R^{17a}$ and $R^{17b}$ are H, $(C_1-C_3)$alkyl, $(C_2-C_6)$alkenyl, $(C_2-C_6)$alkynyl, or $(C_1-C_6)$haloalkyl, and $R^1$, $R^2$, $R^3$, $R^4$, $R^5$, $R^6$, $R^7$, $R^8$, $R^9$, $Q^1$, $R^{10}$, $R^{11}$, $R^{12}$, $R^{13}$, and $R^{14}$, are as previously disclosed, may be prepared by treatment of 10-1 wherein $Q^2$ is O, $R^{17a}$, $R^{17b}$, $R^1$, $R^2$, $R^3$, $R^4$, $R^5$, $R^6$, $R^7$, $R^8$, $R^9$, $Q^1$, $R^{10}$, $R^{11}$, $R^{12}$, $R^{13}$, and $R^{14}$ are as previously disclosed, with an anhydrous (HATU), O-(benzotriazol-1-yl)-N,N,N',N'-tetramethyluronium hexafluorophosphate (HBTU), or (1-cyano-2-ethoxy-2-oxoethylidenaminooxy)dimethylamino-morpholino-carbenium hexafluorophosphate (COMU). Activated carboxylic esters 10-3 may also be prepared from carboxylic acids in situ with a phosphonium salt such as benzotriazol-1-yl-oxytripyrrolidinophosphonium hexafluorophosphate (PyBop). Activated carboxylic esters 10-3 may also be prepared from carboxylic acids in situ with a coupling reagent, such as 1-(3-dimethylamino propyl)-3-ethylcarbodiimide or dicyclohexylcarbodiimide, in the presence of a triazole such as hydroxybenzotriazole.monohydrate (HOBt) or 1-hydroxy-7-azabenzotriazole (HOAt). O-Acylisoureas may be prepared with a dehydrating carbodimide such as 1-(3-dimethylaminopropyl)-3-ethylcarbodiimide or dicyclohexylcarbodiimide. Activated carboxylic esters 10-3 may also be prepared from carboxylic acids in situ with a coupling reagent such as 2-chloro-1,3-dimethylimidazolidinium hexafluorophosphate (CIP) in the presence of a triazolol such as 1-hydroxy-7-azabenzotriazole (HOAt). Activated carboxylic esters 10-3 may also be prepared from carboxylic acids in situ with a coupling reagent such as 2,4,6-tripropyl-1,3,5,2,4,6-trioxatriphosphinane 2,4,6-trioxide (T3P®) in the presence of a base such as pyridine.

Cyclopropyl amides 10-6, wherein $Q^2$ is O, and $R^1$, $R^2$, $R^3$, $R^4$, $R^5$, $R^6$, $R^7$, $R^8$, $R^9$, $Q^1$, $R^{10}$, $R^{11}$, $R^{12}$, $R^{13}$, $R^{14}$, $R^{17a}$, and $R^{17b}$ are as previously disclosed, and $X^5$ is N($R^{17a}$)($C_1$-$C_8$)alkyl, N($R^{17a}$)($C_1$-$C_8$)haloalkyl, N($R^{17a}$)($C_3$-$C_8$)cycloalkyl, and N($R^{17a}$) (substituted and unsubstituted phenyl), may be prepared by treatment of cyclopropyl amides 10-2, wherein $Q^2$ is O, and $R^1$, $R^2$, $R^3$, $R^4$, $R^5$, $R^6$, $R^7$, $R^8$, $R^9$, $Q^1$, $R^{10}$, $R^{11}$, $R^{12}$, $R^{13}$, $R^{14}$, $R^{17a}$, and $R^{17b}$ are as previously disclosed, with an isocyanate or isothiocyanate 10-5, wherein $Q^4$ is O or S, respectively, and $X^5$ is as disclosed above, in an anhydrous solvent such as tetrahydrofuran or ethanol, at temperatures between about 0° C. and about 80° C. (Scheme 10, step c).

Cyclopropyl amides 10-7, wherein $Q^2$ is O, $R^{17b}$ is H, $R^{17c}$ is substituted or unsubstituted heterocyclyl, substituted or unsubstituted ($C_1$-$C_8$)alkyl, and ($C_3$-$C_8$)cycloalkyl, and $R^1$, $R^2$, $R^3$, $R^4$, $R^5$, $R^6$, $R^7$, $R^8$, $R^9$, $Q^1$, $R^{10}$, $R^{11}$, $R^{12}$, $R^{13}$, $R^{14}$, and $R^{17a}$ are as previously disclosed, may be prepared by treatment of cyclopropyl amides 10-2 wherein $Q^2$ is O, $R^{17b}$ is H, and $R^1$, $R^2$, $R^3$, $R^4$, $R^5$, $R^6$, $R^7$, $R^8$, $R^9$, $Q^1$, $R^{10}$, $R^{11}$, $R^{12}$, $R^{13}$, $R^{14}$, are as previously disclosed, with an aldehyde of ketone, wherein $R^{17c}$ is as disclosed above, in the presence of an acid, such as acetic acid, and a reducing agent, such as sodium cyanoborohydride, in a polar aprotic solvent, such as ethanol, at temperatures between about 0° C. and about 80° C. (Scheme 10, step b).

Scheme 10

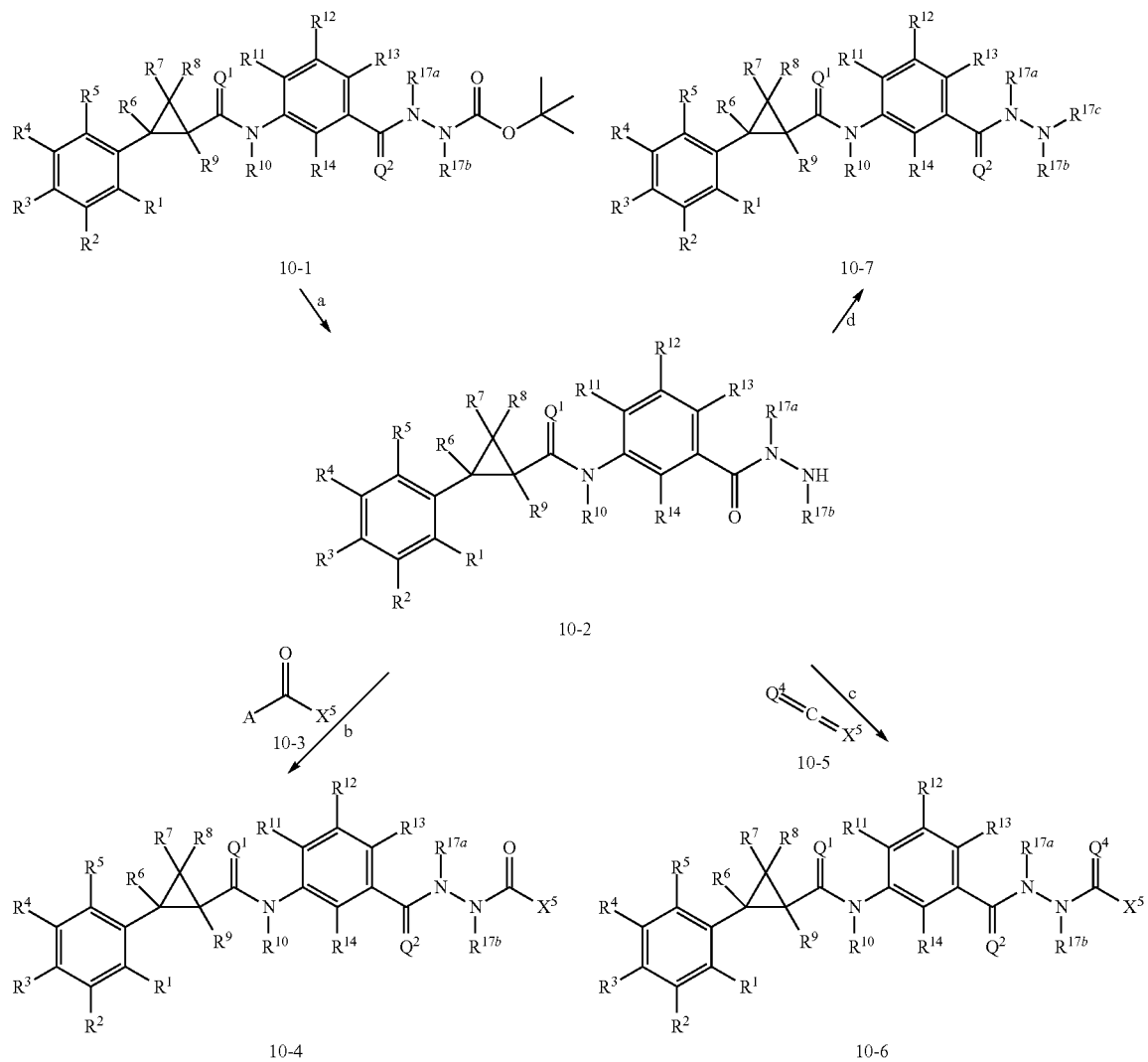

Cyclopropyl amides 11-3, wherein $Q^2$ is O, and $R^1$, $R^2$, $R^3$, $R^4$, $R^5$, $R^6$, $R^7$, $R^8$, $R^9$, $Q^1$, $R^{10}$, $R^{11}$, $R^{12}$, $R^{13}$, $R^{14}$, $R^{18a}$, and $R^{18c}$ are as previously disclosed, may be prepared by treatment of hydrazide 11-1 wherein $Q^2$ is O, and $R^1$, $R^2$, $R^3$, $R^4$, $R^5$, $R^6$, $R^7$, $R^8$, $R^9$, $Q^1$, $R^{10}$, $R^{11}$, $R^{12}$, $R^{13}$, $R^{14}$, and $R^{18a}$ are as previously disclosed, with aldehydes or ketones 11-2, wherein $R^{18b}$ and $R^{18c}$ are as previously disclosed, with or without an acid, such as acetic acid, in a polar aprotic solvent such as ethanol, at temperatures between about 0° C. and about 80° C. (Scheme 18, step a).

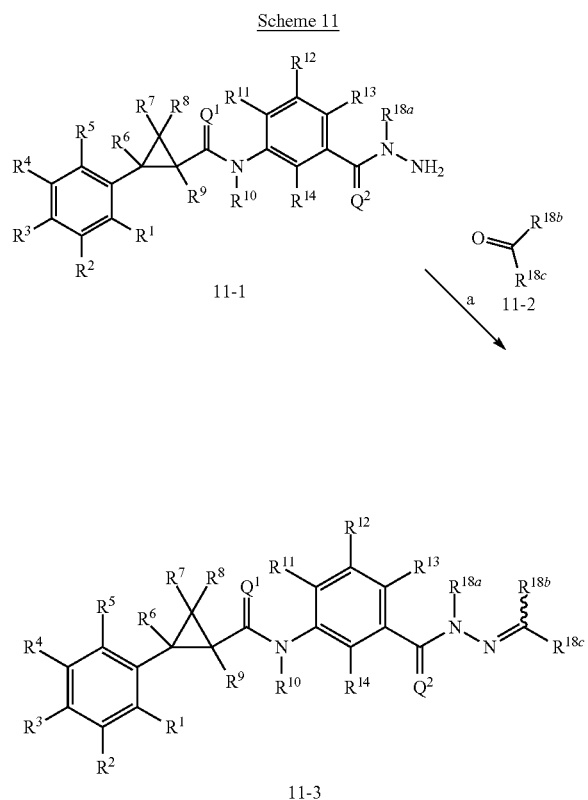

In some embodiments, 1-3 may be prepared from the α,β-unsaturated aldehyde 12-1, wherein $R^1$, $R^2$, $R^3$, $R^4$, $R^5$, $R^6$, and $R^9$ are as previously. It will be understood by one skilled in the art that compound 12-1 may be synthesized via Aldol condensation (see Yoshikawa, M.; Kemei, T. PCT Int. Appl. 2010123006, 2010) of an appropriately substituted, commercially available aldehyde and acetaldehyde. Treatment of 12-1 with a $(C_1-C_6)$alkyl orthoformate, in the presence of an acid whose pH is 0-5 such as hydrobromic acid, N-bromosuccinimide, hydrochloric acid, N-chlorosuccinimide, and pyridinium p-toluenesulfonate (PPTS), in a $(C_1-C_6)$alkanol solvent, at a temperature from 0° C. to ambient and under ambient pressure provides the acetal 12-2, wherein $R^1$, $R^2$, $R^3$, $R^4$, $R^5$, $R^6$, and $R^9$ are as previously disclosed and $R^a$ is a $(C_1-C_6)$alkyl or $R^a$ and $R^a$ taken together can form a cyclic acetal (Scheme 12, step a). The acetal 12-2 may be converted to the cyclopropyl acetal 12-3, wherein $R^1$, $R^2$, $R^3$, $R^4$, $R^5$, $R^6$, $R^7$, $R^8$, $R^9$, and $R^a$ are as previously disclosed, by treatment with a carbene source such as a haloform, for example, bromoform or chloroform, in the presence of an inorganic base, such as sodium or potassium hydroxide or sodium or potassium carbonate, and a phase-transfer catalyst such as benzyl triethylammonium chloride, (−)-N-dodecyl-N-methylephedrinium bromide, tetramethylammonium bromide, tetrapropylammonium bromide, tetrabutylammonium tetrafluoroborate, tetramethylammonium chloride or tetrabutylammonium hexafluorophosphate at a temperature from about ambient temperature up to below the boiling point of the haloform (Scheme 12, step b). Caution: Step B is an exothermic reaction and careful control of the exotherm should be exercised when conducting this reaction. The cyclopropyl acetal 12-3 may be transformed into the aldehyde 12-4, wherein $R^1$, $R^2$, $R^3$, $R^4$, $R^5$, $R^6$, $R^7$, $R^8$, and $R^9$ are as previously disclosed, in a polar solvent selected from the group consisting of acetone, acetonitrile, methanol, ethanol, nitromethane, N,N-dimethylformamide, dimethyl sulfoxide, ethyl acetate, tetrahydrofuran and 1,4-dioxane, in the presence of an aqueous mineral acid selected from the group consisting of nitric acid, hydrochloric acid, hydrobromic acid, and sulfuric acid (Scheme 12, step c) at ambient temperature. The cyclopropyl acid 1-3, wherein $R^1$, $R^2$, $R^3$, $R^4$, $R^5$, $R^6$, $R^7$, $R^8$, and $R^9$ are as previously disclosed, may be obtained by oxidation of the aldehyde 12-4 with oxidants such sodium permanganate or potassium permanganate, or under Pinnick oxidation conditions in a polar aprotic solvent selected from the group consisting of acetone, acetonitrile, N,N-dimethylformamide, dimethyl sulfoxide, ethyl acetate, tetrahydrofuran and 1,4-dioxane at a temperature from about 0° C. to about ambient temperature (Scheme 12, step d). Standard safety precautions should be exercised because an exotherm may occur when conducting this reaction.

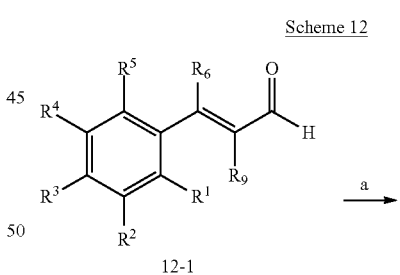

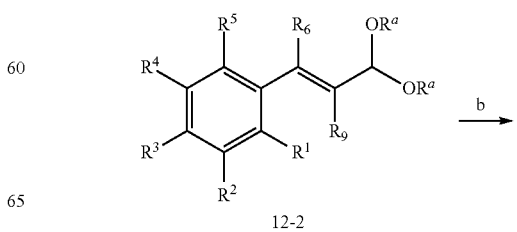

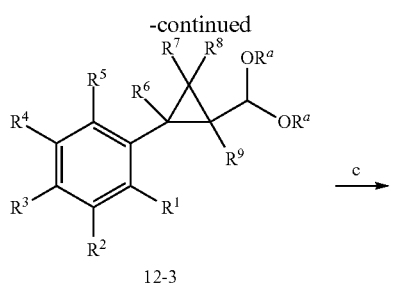

It will be understood by those skilled in the art that, in some embodiments, the cyclopropyl acid 1-3, wherein $R^1$, $R^2$, $R^3$, $R^4$, $R^5$, $R^6$, $R^7$, $R^8$, and $R^9$ are as previously disclosed, may be resolved into its (R,R) and (S,S) enantiomers via a method such as that in Kovalenko V. N., Kulinkovich O. G. *Tetrahedron: Asymmetry* 2011, 22, 26 (Scheme 13, step a).

Scheme 13

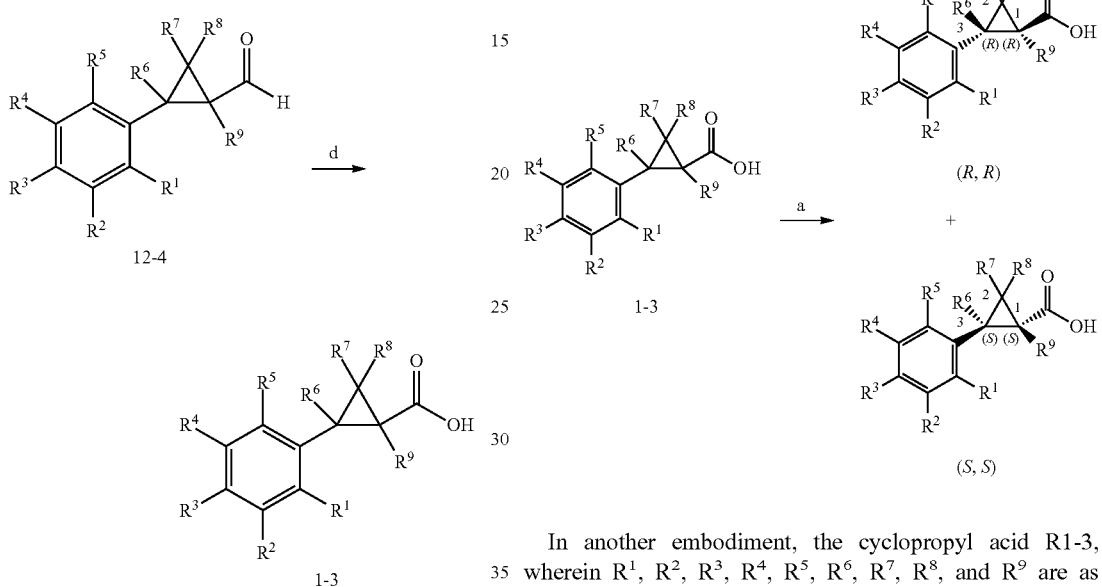

In another embodiment, the cyclopropyl acid R1-3, wherein $R^1$, $R^2$, $R^3$, $R^4$, $R^5$, $R^6$, $R^7$, $R^8$, and $R^9$ are as previously disclosed, may be resolved into its (R,R) and (S,S) enantiomers via a method in Scheme R1.

Scheme R1

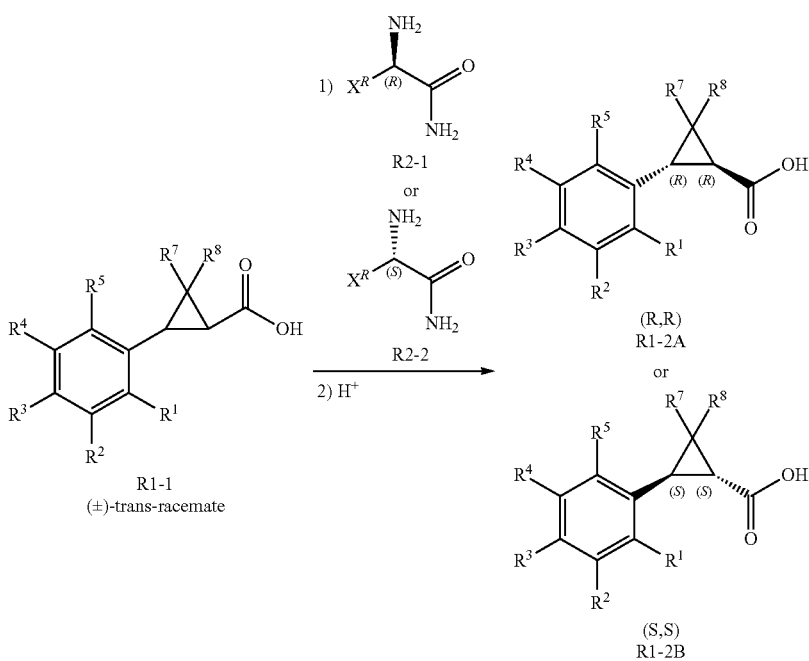

wherein: $X^R$ is selected from the group consisting of $C_1$-$C_4$ alkyl or benzyl.

In Scheme R1, the (±)-trans-racemate of Formula R1-1 (i.e., the mixture of (R,R) and (S,S) enantiomers of a trans-2,2-dichloro-3-(substituted phenyl)cyclopropane-carboxylic acid) is combined with a resolving agent that is either the enantiomeric amine of Formula R2-1 or Formula R2-2, in a suitable solvent, to provide the diastereomeric amine salts of Formula R3-1A or Formula R3-1B,

R3-1A

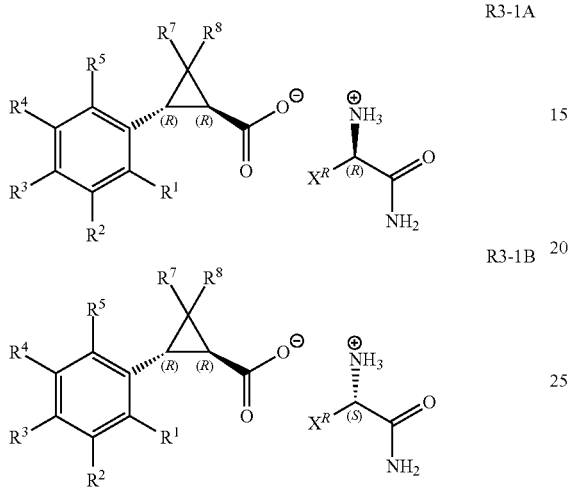

R3-1B or of Formula R3-2A or Formula R3-2B,

R3-2A

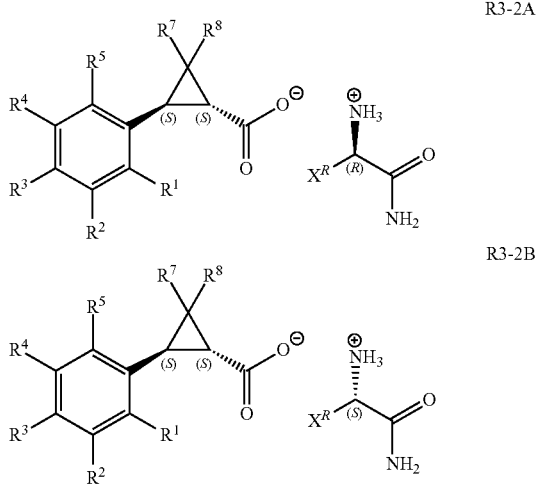

R3-2B that selectively crystallize or precipitate out of the resulting mixture. The diastereomeric amine salt of Formula R3-1A or Formula R3-1B, or of Formula R3-2A or Formula R3-2B, can then be isolated from the mixture and treated with an acid to provide the (1R,3R)- or the (1S,3S)-2,2-dihalo-3-(substituted phenyl)cyclopropanecarboxylic acid of Formula R1-2A or Formula R1-2B, respectively.

EXAMPLES

These examples are for illustration purposes and are not to be construed as limiting this disclosure to only the embodiments disclosed in these examples.

Starting materials, reagents, and solvents that were obtained from commercial sources were used without further purification. Anhydrous solvents were purchased as Sure/Seal™ from Aldrich and were used as received. Melting points were obtained on a Thomas Hoover Unimelt capillary melting point apparatus or an OptiMelt Automated Melting Point System from Stanford Research Systems and are uncorrected. Examples using "room temperature" were conducted in climate controlled laboratories with temperatures ranging from about 20° C. to about 24° C. Molecules are given their known names, named according to naming programs within ISIS Draw, ChemDraw, or ACD Name Pro. If such programs are unable to name a molecule, such molecule is named using conventional naming rules. $^1$H NMR spectral data are in ppm (δ) and were recorded at 300, 400, 500, or 600 MHz; $^{13}$C NMR spectral data are in ppm (δ) and were recorded at 75, 100, or 150 MHz; and $^{19}$F NMR spectral data are in ppm (δ) and were recorded at 376 MHz, unless otherwise stated.

Example 1: Preparation of trans-2-Chloro-5-(2,2-dichloro-3-(3,4-dichlorophenyl)cyclopropane-1-carboxamido)-N-(2-methyl-4-(2,2,2-trifluoroacetamido)phenyl)benzamide (F1061)

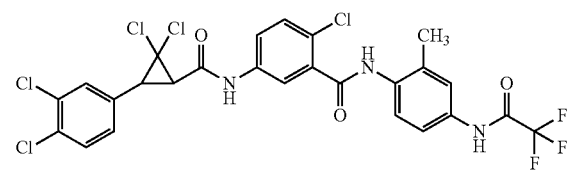 [SMILES: Cc1cc(NC(=O)C(F)(F)F)ccc1NC(=O)c1cc(NC(=O)C2C(c3ccc(Cl)c(Cl)c3)C2(Cl)Cl)ccc1Cl]

To a solution of trans-N-(4-amino-2-methylphenyl)-2-chloro-5-(2,2-dichloro-3-(3,4-dichlorophenyl)cyclopropane-1-carboxamido)benzamide (DP1) (0.100 g, 0.179 mmol) and triethylamine (0.037 mL, 0.269 mmol) in dichloromethane (2.0 mL) was added trifluoroacetic anhydride (0.030 mL, 0.215 mmol). The reaction mixture was stirred at room temperature for 18 hours. The reaction mixture was directly loaded onto a Celite® cartridge. Purification by flash column chromatography using 0-40% ethyl acetate/hexanes as eluent afforded the title compound as a white solid (0.080 g, 68%).

The following compounds were prepared in like manner to the procedure outlined in Example 1:

trans-2-Chloro-5-(2,2-dichloro-3-(3,4-dichlorophenyl)cyclopropane-1-carboxamido)-N-(4-(2,2-difluoroacetamido)-2-methylphenyl)benzamide (F1062)

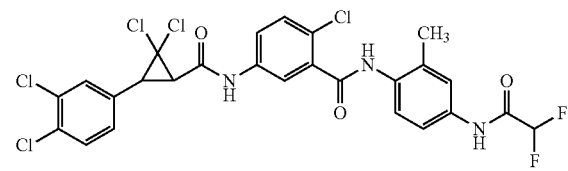 [SMILES: Cc1cc(NC(=O)C(F)F)ccc1NC(=O)c1cc(NC(=O)C2C(c3ccc(Cl)c(Cl)c3)C2(Cl)Cl)ccc1Cl]

Isolated as a white solid (0.109 g, 95%).

2-Chloro-5-((1R,3R)-2,2-dichloro-3-(3,4-dichlorophenyl)cyclopropane-1-carboxamido)-N-(2,4-difluoro-3-(2,2,2-trifluoroacetamido)phenyl)benzamide (F1064)

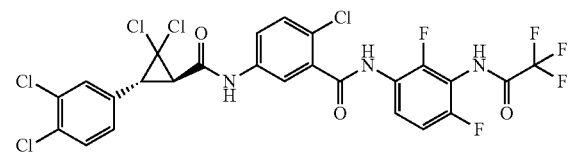

Isolated as a light yellow solid (0.103 g, 89%).

2-Chloro-5-((1R,3R)-2,2-dichloro-3-(3,4-dichloro-
phenyl)cyclopropane-1-carboxamido)-N-(3-(2,2-
difluoroacetamido)-2,4-difluorophenyl)benzamide
(F1065)

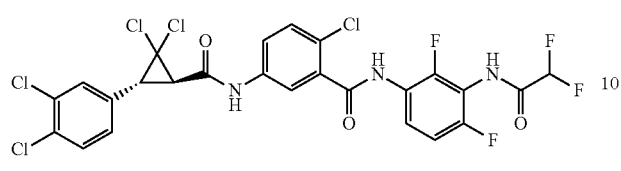

Isolated as a white solid (0.088 g, 77%).

trans-2-Chloro-5-(2,2-dichloro-3-(3,4-dichlorophe-
nyl)cyclopropane-1-carboxamido)-N-(3,5-difluoro-
4-(2,2,2-trifluoroacetamido)phenyl)benzamide
(F1120)

Isolated as an off-white solid (0.096 g, 82%).

trans-2-Chloro-5-(2,2-dichloro-3-(3,4-dichlorophe-
nyl)cyclopropane-1-carboxamido)-N-(4-fluoro-2-(2,
2,2-trifluoroacetamido)phenyl)benzamide (F1121)

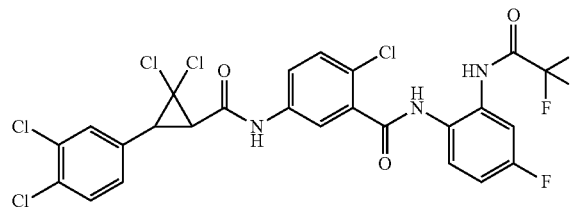

Isolated as a light yellow solid (0.111 g, 85%).

trans-2-Chloro-5-(2,2-dichloro-3-(3,4-dichlorophe-
nyl)cyclopropane-1-carboxamido)-N-(4-(2,2-difluo-
roacetamido)-3,5-difluorophenyl)benzamide (F1122)

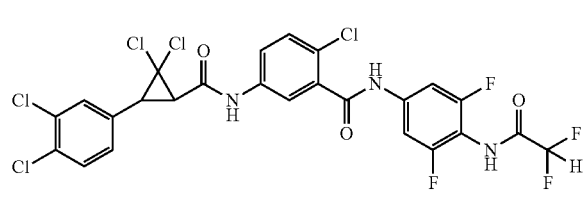 [SMILES: O=C(Nc1cc(F)c(NC(=O)C(F)(F)F)c(F)c1)c1cc(NC(=O)C2C(c3ccc(Cl)c(Cl)c3)C2(Cl)Cl)ccc1Cl]

Isolated as an off-white solid (0.066 g, 58%).

trans-2-Chloro-5-(2,2-dichloro-3-(3,4-dichlorophe-
nyl)cyclopropane-1-carboxamido)-N-(2-(2,2-difluo-
roacetamido)-4-fluorophenyl)benzamide (F1123)

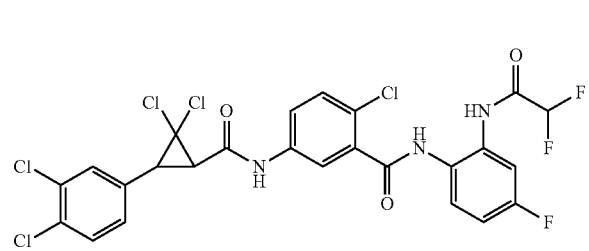 [SMILES: O=C(Nc1ccc(F)cc1NC(=O)C(F)F)c1cc(NC(=O)C2C(c3ccc(Cl)c(Cl)c3)C2(Cl)Cl)ccc1Cl]

Isolated as an off-white solid (0.0885 g, 74%).

2-Chloro-5-((1R,3R)-2,2-dichloro-3-(3,4-dichloro-
phenyl)cyclopropane-1-carboxamido)-N-(2,6-dif-
luoro-4-(2,2,2-trifluoroacetamido)phenyl)benzamide
(F1261)

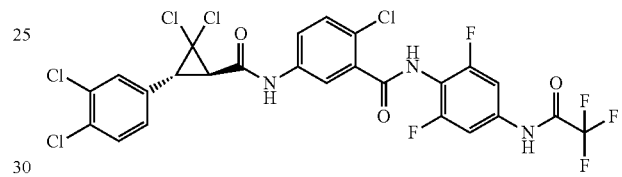

Isolated as a light yellow foam (0.065 g, 69%).

2-Chloro-5-((1R,3R)-2,2-dichloro-3-(3,5-dichloro-
phenyl)cyclopropane-1-carboxamido)-N-(2,4-dif-
luoro-3-(2,2,2-trifluoroacetamido)phenyl)-3-fluo-
robenzamide (F1330)

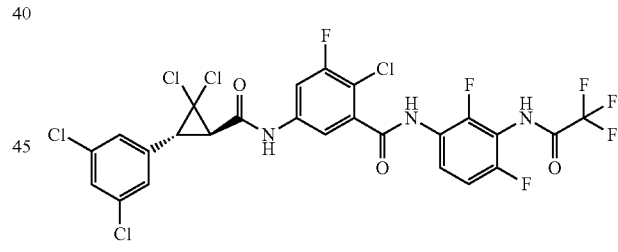

Isolated as a white powder (0.068 g, 98%).

2-Chloro-5-((1R,3R)-2,2-dichloro-3-(3,5-dichloro-
phenyl)cyclopropane-1-carboxamido)-N-(3-(2,2-
difluoroacetamido)-2,4-difluorophenyl)-3-fluoroben-
zamide (F1333)

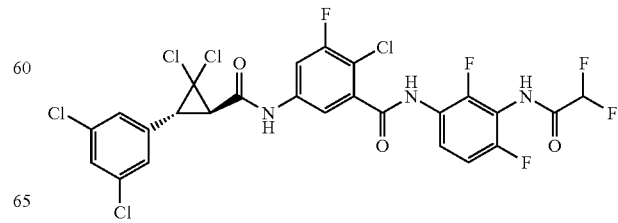

Isolated as an off-white powder (0.069 g, 100%).

2-Chloro-5-((1R,3R)-2,2-dichloro-3-(3,4,5-trichloro-phenyl)cyclopropane-1-carboxamido)-N-(2,4-difluoro-3-(2,2,2-trifluoroacetamido)phenyl)-3-fluorobenzamide (F1334)

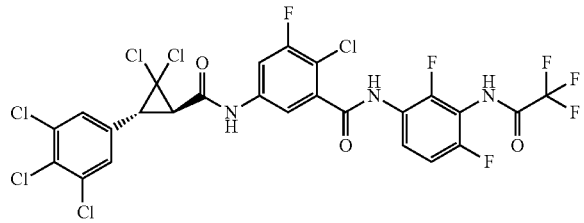 [SMILES: O=C(Nc1ccc(F)c(NC(=O)C(F)(F)F)c1F)c1cc(NC(=O)[C@H]2[C@H](c3cc(Cl)c(Cl)c(Cl)c3)C2(Cl)Cl)cc(F)c1Cl]

Isolated as an off-white powder (0.062 g, 100%).

2-Chloro-5-((1R,3R)-2,2-dichloro-3-(3,4,5-trichloro-phenyl)cyclopropane-1-carboxamido)-N-(3-(2,2-difluoroacetamido)-2,4-difluorophenyl)-3-fluorobenzamide (F1335)

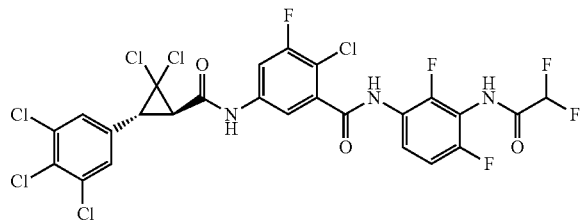 [SMILES: O=C(Nc1ccc(F)c(NC(=O)C(F)F)c1F)c1cc(NC(=O)[C@H]2[C@H](c3cc(Cl)c(Cl)c(Cl)c3)C2(Cl)Cl)cc(F)c1Cl]

Isolated as a light yellow powder (0.057 g, 99%).

trans-2-Chloro-5-(2,2-dichloro-3-(3,4-dichlorophenyl)cyclopropane-1-carboxamido)-N-(3,5-difluoro-4-(2,2,2-trichloroacetamido)phenyl)benzamide (F1146)

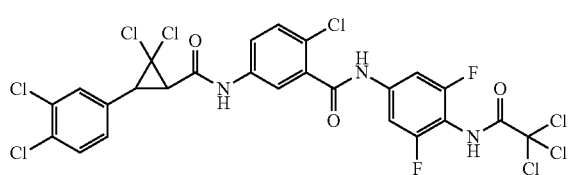 [SMILES: O=C(Nc1cc(F)c(NC(=O)C(Cl)(Cl)Cl)c(F)c1)c1cc(NC(=O)C2C(c3ccc(Cl)c(Cl)c3)C2(Cl)Cl)ccc1Cl]

Isolated as an off-white solid (0.046 g, 37%).

2-Chloro-5-((1R,3R)-2,2-dichloro-3-(3-chloro-4-fluorophenyl)cyclopropane-1-carboxamido)-N-(3-(2,2-difluoroacetamido)-2,4-difluorophenyl)-3-fluorobenzamide (F1256)

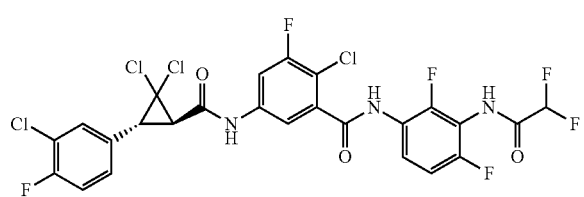 [SMILES: O=C(Nc1ccc(F)c(NC(=O)C(F)F)c1F)c1cc(NC(=O)[C@H]2[C@H](c3ccc(F)c(Cl)c3)C2(Cl)Cl)cc(F)c1Cl]

Isolated as a light tan foam (0.184 g, 56%).

2-Chloro-5-((1R,3R)-2,2-dichloro-3-(3,4-dichloro-phenyl)cyclopropane-1-carboxamido)-N-(3-(2,2-difluoroacetamido)-2,4-difluorophenyl)-3-fluorobenzamide (F1287)

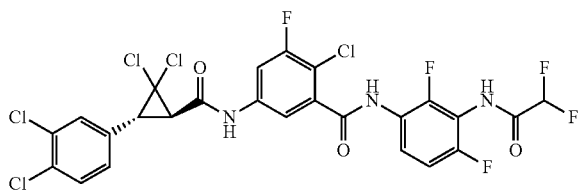 [SMILES: O=C(Nc1ccc(F)c(NC(=O)C(F)F)c1F)c1cc(NC(=O)[C@H]2[C@H](c3ccc(Cl)c(Cl)c3)C2(Cl)Cl)cc(F)c1Cl]

Isolated as a white solid (0.064 g, 90%).

2-Chloro-5-((1R,3R)-2,2-dichloro-3-(3,4-dichloro-phenyl)cyclopropane-1-carboxamido)-N-(2,4-difluoro-3-(2,2,2-trifluoroacetamido)phenyl)-3-fluorobenzamide (F1288)

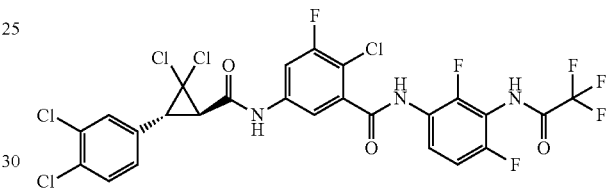

Isolated as a white solid (0.068 g, 93%).

2-Chloro-5-((1R,3R)-2,2-dichloro-3-(4-fluoro-3-(trifluoromethyl)phenyl)-cyclopropane-1-carboxamido)-N-(3-(2,2-difluoroacetamido)-2,4-difluorophenyl)-3-fluorobenzamide (F1289)

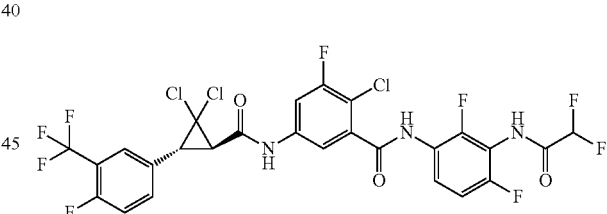

Isolated as a white solid (0.065 g, 91%).

2-Chloro-5-((1R,3R)-2,2-dichloro-3-(4-fluoro-3-(trifluoromethyl)phenyl)cyclopropane-1-carboxamido)-N-(2,4-difluoro-3-(2,2,2-trifluoroacetamido)phenyl)-3-fluorobenzamide (F1290)

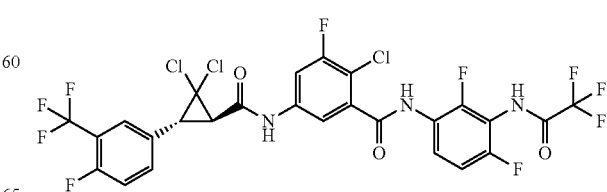

Isolated as a white solid (0.068 g, 93%).

2-Chloro-5-((1R,3R)-2,2-dichloro-3-(3-chloro-4-fluorophenyl)cyclopropane-1-carboxamido)-N-(2,4-difluoro-3-(2,2,2-trifluoroacetamido)phenyl)-3-fluorobenzamide (F1291)

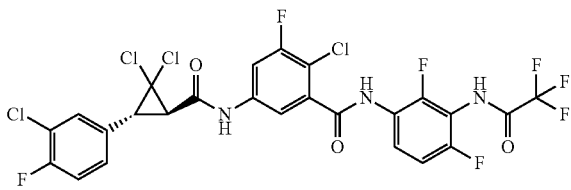

Isolated as a white solid (0.062 g, 95%).

Example 2: Preparation of N-(3-acetamido-2,4-difluorophenyl)-2-chloro-5-((1R,3R)-2,2-dichloro-3-(3,4-dichlorophenyl)cyclopropane-1-carboxamido)benzamide (F1083)

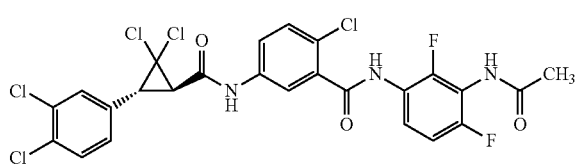

To a solution of N-(3-amino-2,4-difluorophenyl)-2-chloro-5-((1R,3R)-2,2-dichloro-3-(3,4-dichlorophenyl)cyclopropane-1-carboxamido)benzamide (DP2) (0.06 g, 0.104 mmol) in pyridine (0.30 mL, 3.71 mmol) stirred at room temperature was added acetic anhydride (9.77 µl, 0.104 mmol). The reaction mixture was stirred at room temperature for 18 hours, was quenched with water (3 mL), and was extracted with ethyl acetate (10 mL). The organic layer was washed with hydrochloric acid (1 N) and brine before being poured through a phase separator. The organic layer was concentrated under reduced pressure to give a residue. Purification by column chromatography using 0-30% ethyl acetate/hexanes as eluent afforded the title compound as a white solid (0.043 g, 67%).

The following compounds were prepared in like manner to the procedure outlined in Example 2:

2-Chloro-N-(3-(2-chloro-2,2-difluoroacetamido)-2,4-difluorophenyl)-5-((1R,3R)-2,2-dichloro-3-(3,4-dichlorophenyl)cyclopropane-1-carboxamido)benzamide (F1248)

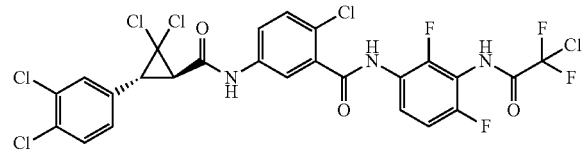

Isolated as a white solid (0.039 g, 74%).

2-Chloro-5-((1R,3R)-2,2-dichloro-3-(3,4-dichlorophenyl)cyclopropane-1-carboxamido)-N-(2,4-difluoro-3-(2,2,3,3,3-pentafluoropropanamido)phenyl)benzamide (F1251)

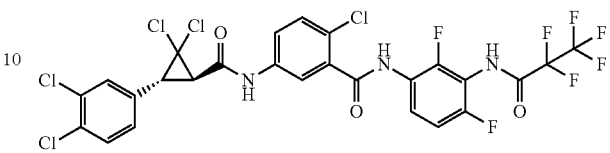

Isolated as a white solid (0.072 g, 57%).

2-Chloro-5-((1R,3R)-2,2-dichloro-3-(3,4-dichlorophenyl)cyclopropane-1-carboxamido)-N-(3-(2,2-dichloroacetamido)-2,4-difluorophenyl)benzamide (F1252)

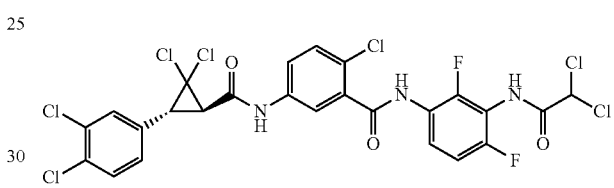

Isolated as a white solid (0.068 g, 57%).

N-(4-Acetamido-2,6-difluorophenyl)-2-chloro-5-((1R,3R)-2,2-dichloro-3-(3,4-dichlorophenyl)cyclopropane-1-carboxamido)benzamide (F1262)

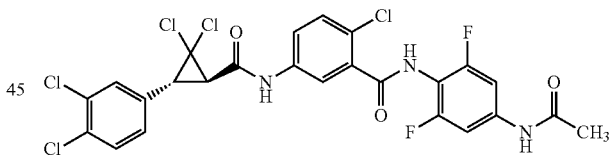

Isolated as a white solid (0.022 g, 26%).

2-Chloro-5-((1R,3R)-2,2-dichloro-3-(3,4-dichlorophenyl)cyclopropane-1-carboxamido)-N-(4-(2,2-dichloroacetamido)-2,6-difluorophenyl)benzamide (F1272)

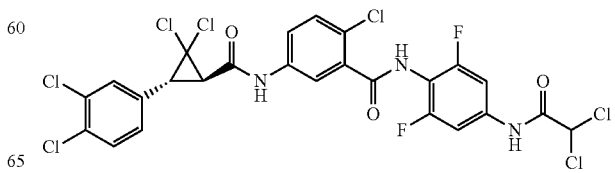

Isolated as a white solid (0.028 g, 29%).

2-Chloro-5-((1R,3R)-2,2-dichloro-3-(3-chloro-4-
fluorophenyl)cyclopropane-1-carboxamido)-N-(3-(2,
2-difluoroacetamido)-2,6-difluorophenyl)benzamide
(F1234)

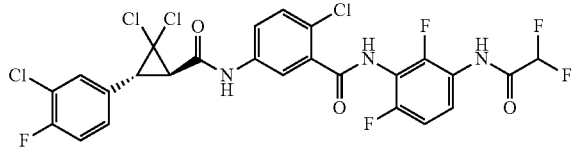 [SMILES: O=C(Nc1c(F)ccc(NC(=O)C(F)F)c1F)c1cc(NC(=O)[C@H]2[C@H](c3ccc(F)c(Cl)c3)C2(Cl)Cl)ccc1Cl]

Isolated as a white foamy solid (0.083 g, 66%).

2-Chloro-5-((1R,3R)-2,2-dichloro-3-(3,4,5-trichloro-
phenyl)cyclopropane-1-carboxamido)-N-(3-(2,2-
difluoroacetamido)-2,6-difluorophenyl)benzamide
(F1238)

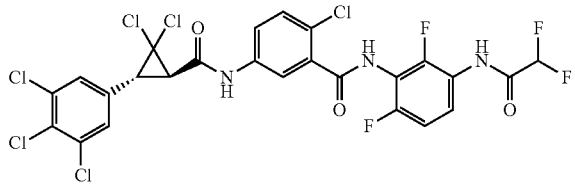 [SMILES: O=C(Nc1c(F)ccc(NC(=O)C(F)F)c1F)c1cc(NC(=O)[C@H]2[C@H](c3cc(Cl)c(Cl)c(Cl)c3)C2(Cl)Cl)ccc1Cl]

Isolated as an off-white foamy solid (0.090 g, 72%).

2-Chloro-5-((1R,3R)-2,2-dichloro-3-(3,4-dichloro-
phenyl)cyclopropane-1-carboxamido)-N-(3-(2,2-
difluoroacetamido)-2,6-difluorophenyl)benzamide
(F1240)

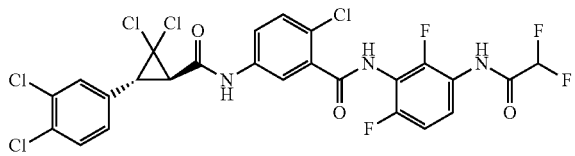 [SMILES: O=C(Nc1c(F)ccc(NC(=O)C(F)F)c1F)c1cc(NC(=O)[C@H]2[C@H](c3ccc(Cl)c(Cl)c3)C2(Cl)Cl)ccc1Cl]

Isolated as a white foamy solid (0.100 g, 84%).

2-Chloro-5-((1R,3R)-2,2-dichloro-3-(3,5-dichloro-
phenyl)cyclopropane-1-carboxamido)-N-(3-(2,2-
difluoroacetamido)-2,6-difluorophenyl)benzamide
(F1241)

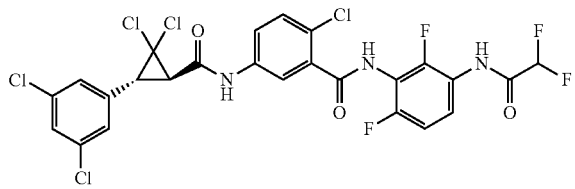 [SMILES: O=C(Nc1c(F)ccc(NC(=O)C(F)F)c1F)c1cc(NC(=O)[C@H]2[C@H](c3cc(Cl)cc(Cl)c3)C2(Cl)Cl)ccc1Cl]

Isolated as a white foamy solid (0.086 g, 68%).

2-Chloro-5-((1R,3R)-2,2-dichloro-3-(3,4-dichloro-
phenyl)cyclopropane-1-carboxamido)-N-(5-(2,2-
difluoroacetamido)-2,4-difluorophenyl)benzamide
(F1242)

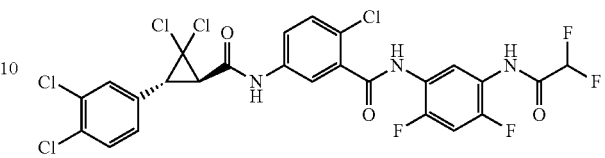

Isolated as a glassy solid (0.074 g, 59%).

2-Chloro-N-(5-(2-chloro-2,2-difluoroacetamido)-2,
4-difluorophenyl)-5-((1R,3R)-2,2-dichloro-3-(3,4-
dichlorophenyl)cyclopropane-1-carboxamido)benz-
amide (F1243)

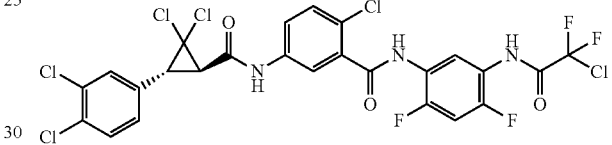

Isolated as a white foamy solid (0.065 g, 49%).

2-Chloro-5-((1R,3R)-2,2-dichloro-3-(3,4-dichloro-
phenyl)cyclopropane-1-carboxamido)-N-(5-(2,2-
dichloroacetamido)-2,4-difluorophenyl)benzamide
(F1244)

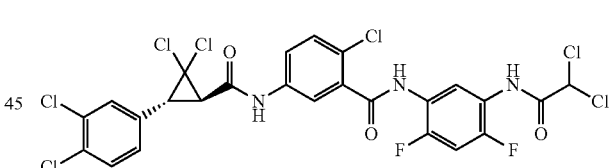

Isolated as an off-white foamy solid (0.035 g, 28%).

2-Chloro-5-((1R,3R)-2,2-dichloro-3-(3,4-dichloro-
phenyl)cyclopropane-1-carboxamido)-N-(2,4-dif-
luoro-5-(2,2,2-trifluoroacetamido)phenyl)benzamide
(F1245)

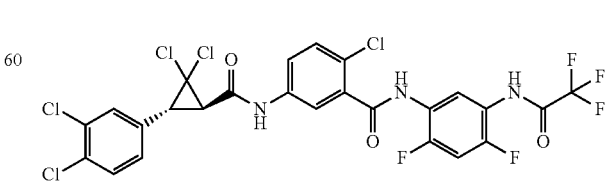

Isolated as a white foamy solid (0.080 g, 65%).

N-(5-Acetamido-2,4-difluorophenyl)-2-chloro-5-((1R,3R)-2,2-dichloro-3-(3,4-dichlorophenyl)cyclopropane-1-carboxamido)benzamide (F1246)

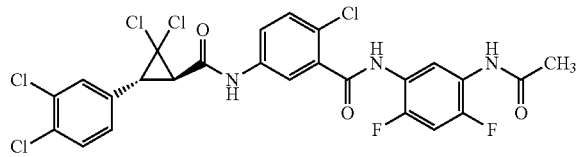 [SMILES: CC(=O)Nc1cc(NC(=O)c2cc(NC(=O)[C@H]3[C@H](c4ccc(Cl)c(Cl)c4)C3(Cl)Cl)ccc2Cl)c(F)cc1F]

Isolated as an off-white foamy solid (0.080 g, 71%).

trans-N-(4-Acetamido-3,5-difluorophenyl)-2-chloro-5-(2,2-dichloro-3-(3,4-dichlorophenyl)cyclopropane-1-carboxamido)benzamide (F1124)

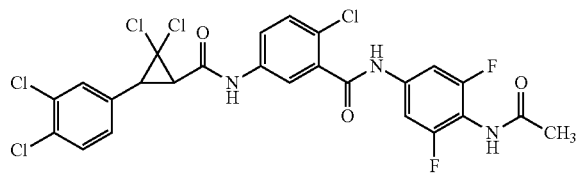 [SMILES: CC(=O)Nc1c(F)cc(NC(=O)c2cc(NC(=O)C3C(c4ccc(Cl)c(Cl)c4)C3(Cl)Cl)ccc2Cl)cc1F]

Isolated as an off-white solid (0.042 g, 39%).

trans-N-(2-Acetamido-4-fluorophenyl)-2-chloro-5-(2,2-dichloro-3-(3,4-dichlorophenyl)cyclopropane-1-carboxamido)benzamide (F1125)

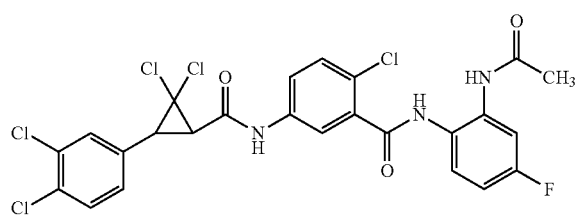 [SMILES: CC(=O)Nc1cc(F)ccc1NC(=O)c1cc(NC(=O)C2C(c3ccc(Cl)c(Cl)c3)C2(Cl)Cl)ccc1Cl]

Isolated as an off-white solid (0.039 g, 33%).

trans-2-Chloro-5-(2,2-dichloro-3-(3,4-dichlorophenyl)cyclopropane-1-carboxamido)-N-(4-fluoro-2-(2,2,2-trichloroacetamido)phenyl)benzamide (F1126)

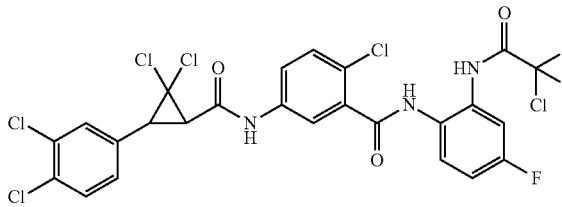

Isolated as a light yellow solid (0.078 g, 59%).

Example 3: Preparation of 2-chloro-5-((1R,3R)-2,2-dichloro-3-(4-fluoro-3-(trifluoromethyl)phenyl)cyclopropane-1-carboxamido)-N-(2,4-difluoro-3-(2,2,2-trifluoroacetamido)phenyl)benzamide (F1169)

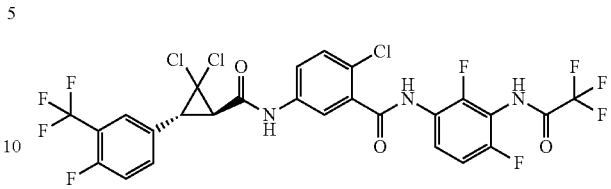

Trifluoroacetic anhydride (0.035 g, 0.251 mmol) was added dropwise to a stirred solution of N-(3-amino-2,4-difluorophenyl)-2-chloro-5-((1R,3R)-2,2-dichloro-3-(4-fluoro-3-(trifluoromethyl)phenyl)cyclopropane-1-carboxamido)benzamide (DP9) (0.100 g, 168 mmol), and triethylamine (0.051 g, 0.503 mmol) in anhydrous dichloromethane (3 mL). The solution was stirred for 12 hours at 23° C. and concentrated. Purification by silica gel flash chromatography gave the title compound as a white foam (0.084 g, 69%).

The following compounds were prepared in like manner to the procedure outlined in Example 3:

2-Chloro-N-(3-(2-chloro-2,2-difluoroacetamido)-2,4-difluorophenyl)-5-((1R,3R)-2,2-dichloro-3-(4-fluoro-3-(trifluoromethyl)phenyl)cyclopropane-1-carboxamido)benzamide (F1170)

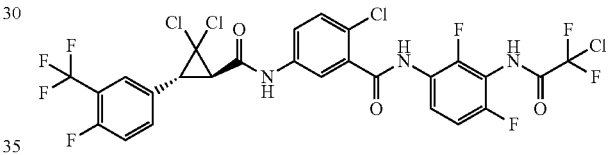

Isolated as a white solid (0.089 g, 71%).

2-Chloro-5-((1R,3R)-2,2-dichloro-3-(4-fluoro-3-(trifluoromethyl)phenyl)cyclopropane-1-carboxamido)-N-(3-(2,2-dichloroacetamido)-2,4-difluorophenyl)benzamide (F1174)

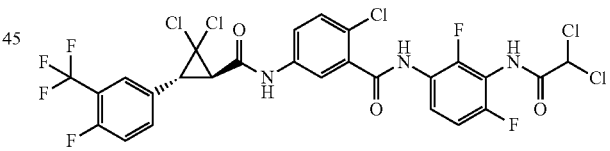

Isolated as a white foam (0.058 g, 46%).

2-Chloro-5-((1R,3R)-2,2-dichloro-3-(4-fluoro-3-(trifluoromethyl)phenyl)cyclopropane-1-carboxamido)-N-(3-(2,2-difluoroacetamido)-2,4-difluorophenyl)benzamide (F1175)

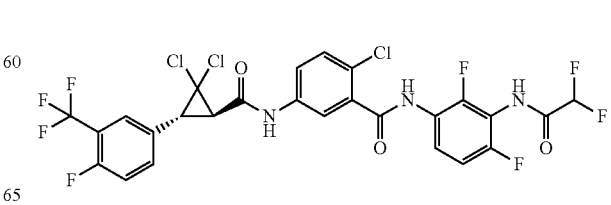

Isolated as a white solid (0.283 g, 70%).

N-(3-Benzamido-2,4-difluorophenyl)-2-chloro-5-
((1R,3R)-2,2-dichloro-3-(4-fluoro-3-(trifluorom-
ethyl)phenyl)cyclopropane-1-carboxamido)benz-
amide (F1179)

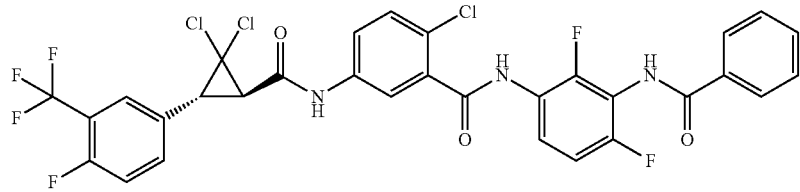 [SMILES: O=C(Nc1c(F)ccc(NC(=O)c2cc(NC(=O)[C@H]3[C@H](c4ccc(F)c(C(F)(F)F)c4)C3(Cl)Cl)ccc2Cl)c1F)c1ccccc1]

Isolated as a white foam (0.015 g, 12%).

N-(3-(2-Bromo-2,2-difluoroacetamido)-2,4-difluoro-
phenyl)-2-chloro-5-((1R,3R)-2,2-dichloro-3-(4-
fluoro-3-(trifluoromethyl)phenyl)cyclopropane-1-
carboxamido)benzamide (F1276)

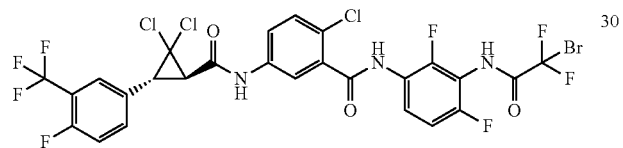

Isolated as a white solid (0.078 g, 59%).

trans-2-Chloro-5-(2,2-dichloro-3-(3,5-dichloro-4-
fluorophenyl)cyclopropane-1-carboxamido)-N-(3-(2,
2-difluoroacetamido)-2,4-difluorophenyl)benzamide
(F1331)

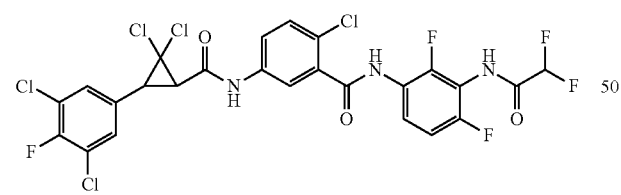

Isolated as a white foam (0.037 g, 62%).

trans-2-Chloro-5-(2,2-dichloro-3-(3,5-dichloro-4-
fluorophenyl)cyclopropane-1-carboxamido)-N-(2,4-
difluoro-3-(2,2,2-trifluoroacetamido)phenyl)benz-
amide (F1332)

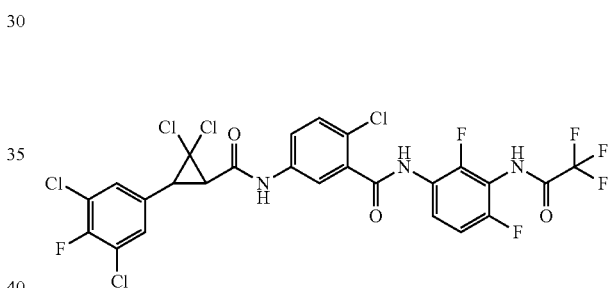

Isolated as a white solid (0.031 g, 51%).

Example 4: Preparation of tert-butyl (4-((3-(2-
chloro-5-((1R,3R)-2,2-dichloro-3-(3,4-dichlorophe-
nyl)cyclopropane-1-carboxamido)benzamido)-2,6-
difluorophenyl)amino)-4-oxobutyl)carbamate
(F1199)

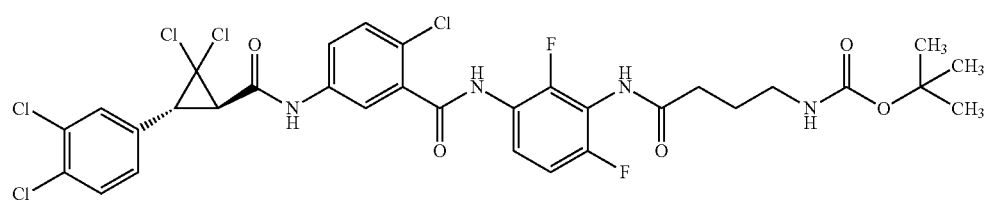 [SMILES: CC(C)(C)OC(=O)NCCCC(=O)Nc1c(F)ccc(NC(=O)c2cc(NC(=O)[C@H]3[C@H](c4ccc(Cl)c(Cl)c4)C3(Cl)Cl)ccc2Cl)c1F]

To a solution of N-(3-amino-2,4-difluorophenyl)-2-chloro-5-((1R,3R)-2,2-dichloro-3-(3,4-dichlorophenyl)cyclopropane-1-carboxamido)benzamide (DP2) (0.100 g, 0.173 mmol) in ethyl acetate (2 mL) stirred at room temperature were added 4-((tert-butoxycarbonyl)amino)butanoic acid (0.035 g, 0.173 mmol) and pyridine (0.028 mL, 0.345 mmol). 2,4,6-Tripropyl-1,3,5,2,4,6-trioxatriphosphinane 2,4,6-trioxide (T3P®; 165 mg, 0.259 mmol was added a 50% solution in ethyl acetate. The reaction mixture was warmed to 50° C. for 18 hours then cooled to room temperature and concentrated under a stream of nitrogen. Purification by column chromatography using 0-80% ethyl acetate/hexanes as eluent afforded the title compound as a white solid (0.111 g, 84%).

The following compounds were prepared in like manner to the procedure outlined in Example 4:

trans-tert-Butyl (4-((4-(2-chloro-5-(2,2-dichloro-3-(3,4-dichlorophenyl)-cyclopropane-1-carboxamido)benzamido)-3-methylphenyl)amino)-4-oxobutyl)carbamate (F1200)

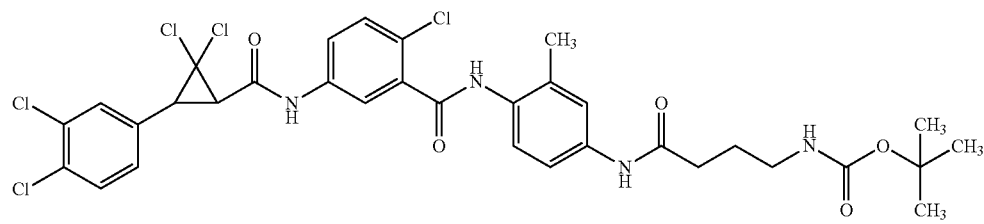 [SMILES: Cc1cc(NC(=O)CCCNC(=O)OC(C)(C)C)ccc1NC(=O)c1cc(NC(=O)C2C(c3ccc(Cl)c(Cl)c3)C2(Cl)Cl)ccc1Cl]

Isolated as a white solid (0.097 g, 72%).

2-Chloro-5-((1R,3R)-2,2-dichloro-3-(3,4-dichlorophenyl)cyclopropane-1-carboxamido)-N-(3-(2,2-difluoropropanamido)-2,4-difluorophenyl)benzamide (F1249)

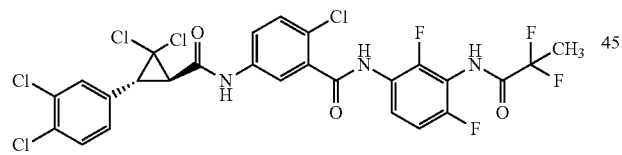

Isolated as a white solid (0.097 g, 83%).

N-(3-Benzamido-2,4-difluorophenyl)-2-chloro-5-((1R,3R)-2,2-dichloro-3-(3,4-dichlorophenyl)cyclopropane-1-carboxamido)benzamide (F1253)

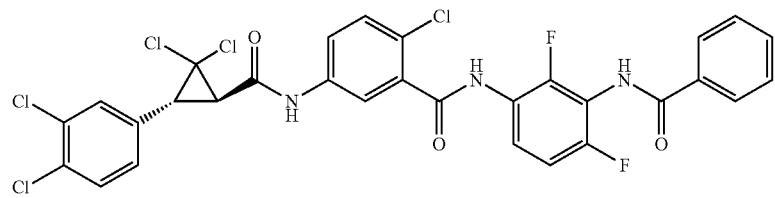 [SMILES: O=C(Nc1c(F)ccc(NC(=O)c2cc(NC(=O)[C@H]3[C@H](c4ccc(Cl)c(Cl)c4)C3(Cl)Cl)ccc2Cl)c1F)c1ccccc1]

Isolated as a light brown solid (0.076 g, 64%).

Example 5: Preparation of trans-N-(3-acetamido-2-chloro-4-fluorophenyl)-2-chloro-5-(2,2-dichloro-3-(3,5-dichlorophenyl)cyclopropane-1-carboxamido)benzamide (F1160)

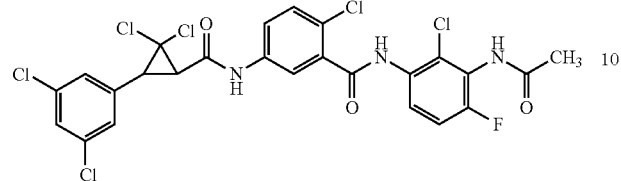

2,4,6-Tripropyl-1,3,5,2,4,6-trioxatriphosphinane 2,4,6-trioxide (T3P®, 50% solution in ethyl acetate; 0.281 g, 0.441 mmol) was added dropwise to a stirred solution of trans-2-chloro-5-(2,2-dichloro-3-(3,5-dichlorophenyl)cyclopropane-1-carboxamido)benzoic acid (C12) (0.100 g, 220 mmol), N-(3-amino-2-chloro-6-fluorophenyl)acetamide (C194) (0.048 g, 0.220 mmol), and pyridine (0.053 g, 0.661 mmol) in anhydrous ethyl acetate (3 mL). The solution was stirred for 12 hours at 23° C. and concentrated. Purification by silica gel flash chromatography gave the title compound as a white foam (0.105 g, 71%).

The following compounds were prepared in like manner to the procedure outlined in Example 5:

N-(3-Acetamido-2-chloro-4-fluorophenyl)-2-chloro-5-((1R,3R)-2,2-dichloro-3-(4-fluoro-3-(trifluoromethyl)phenyl)cyclopropane-1-carboxamido)benzamide (F1161)

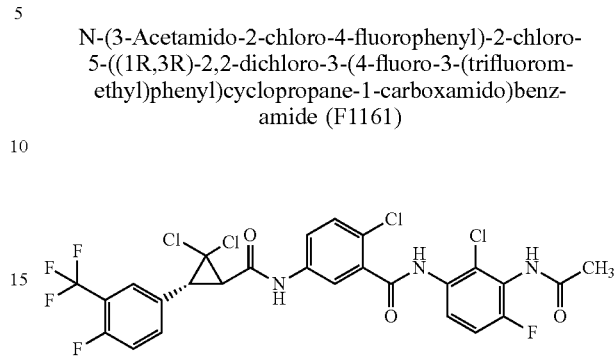

Isolated as a white foam (0.052 g, 71%).

Example 6: Preparation of 2-chloro-5-((1R,3R)-2,2-dichloro-3-(4-fluoro-3-(trifluoromethyl)phenyl)cyclopropane-1-carboxamido)-N-(2,4-difluoro-3-(4-fluorobenzamido)phenyl)benzamide (F1204)

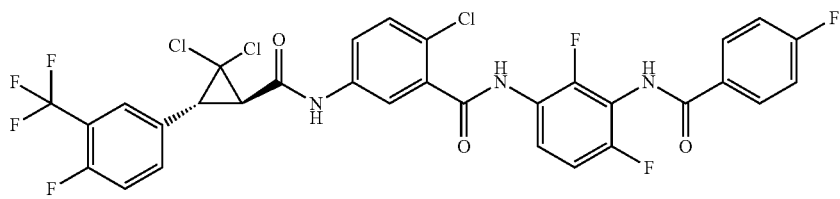 [SMILES: O=C(Nc1c(F)ccc(NC(=O)c2cc(NC(=O)[C@H]3[C@H](c4ccc(F)c(C(F)(F)F)c4)C3(Cl)Cl)ccc2Cl)c1F)c1ccc(F)cc1]

2,4,6-Tripropyl-1,3,5,2,4,6-trioxatriphosphinane 2,4,6-trioxide (T3P®, 50% solution in ethyl acetate; 0.213 g, 0.335 mmol) was added dropwise to a stirred solution of N-(3-amino-2,4-difluorophenyl)-2-chloro-5-((1R,3R)-2,2-dichloro-3-(4-fluoro-3-(trifluoromethyl)phenyl)cyclopropane-1-carboxamido)benzamide (DP9) (0.100 g, 0.168 mmol), 4-fluorobenzoic acid (0.028 g, 0.201 mmol), and pyridine (0.040 g, 0.503 mmol) in anhydrous ethyl acetate (3 mL). The solution was stirred for 12 hours at 50° C. and concentrated. Purification by silica gel flash chromatography gave the title compound as a white foam (0.029 g, 23%).

The following compounds were prepared in like manner to the procedure outlined in Example 6:

2-Chloro-5-((1R,3R)-2,2-dichloro-3-(4-fluoro-3-(trifluoromethyl)phenyl)cyclopropane-1-carboxamido)-N-(2,4-difluoro-3-(4-methoxybenzamido)phenyl)benzamide (F1205)

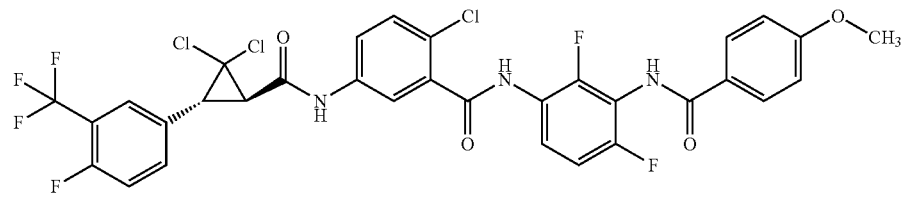 [SMILES: COc1ccc(C(=O)Nc2c(F)ccc(NC(=O)c3cc(NC(=O)[C@H]4[C@H](c5ccc(F)c(C(F)(F)F)c5)C4(Cl)Cl)ccc3Cl)c2F)cc1]

Isolated as a white solid (0.020 g, 16%).

N-(3-(2-Chloro-5-(((1R,3R)-2,2-dichloro-3-(4-fluoro-3-(trifluoromethyl)phenyl)cyclopropane-1-carboxamido)benzamido)-2,6-difluorophenyl)nicotinamide (F1206)

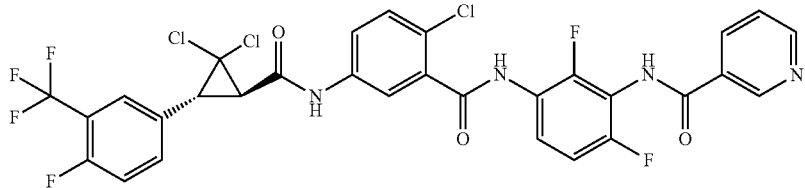 [SMILES: O=C(Nc1c(F)ccc(NC(=O)c2cc(NC(=O)[C@H]3[C@H](c4ccc(F)c(C(F)(F)F)c4)C3(Cl)Cl)ccc2Cl)c1F)c1cccnc1]

Isolated as a white solid (0.041 g, 33%).

N-(3-Acetamido-2,4-difluorophenyl)-2-chloro-5-((1R,3R)-2,2-dichloro-3-(4-fluoro-3-(trifluoromethyl)phenyl)cyclopropane-1-carboxamido)benzamide (F1231)

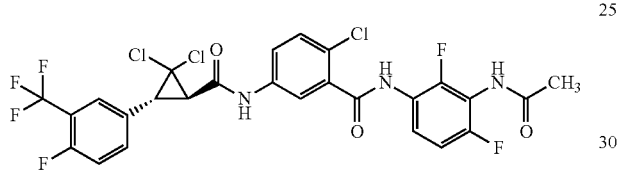
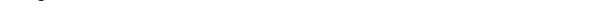

Isolated as a white solid (0.029 g, 26%).

N-(3-(2-Chloro-5-(((1R,3R)-2,2-dichloro-3-(4-fluoro-3-(trifluoromethyl)phenyl)cyclopropane-1-carboxamido)benzamido)-2,6-difluorophenyl)-6-fluoronicotinamide (F1258)

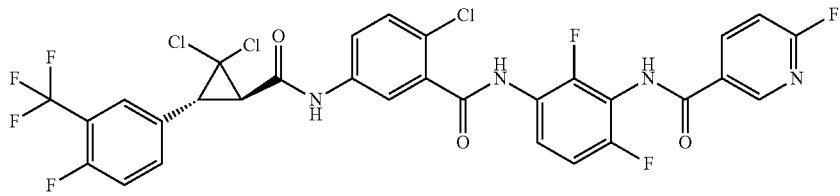 [SMILES: O=C(Nc1c(F)ccc(NC(=O)c2cc(NC(=O)[C@H]3[C@H](c4ccc(F)c(C(F)(F)F)c4)C3(Cl)Cl)ccc2Cl)c1F)c1ccc(F)nc1]

Isolated as a white solid (0.019 g, 15%).

2-Chloro-N-(3-(1-cyanocyclopropane-1-carboxamido)-2,4-difluorophenyl)-5-((1R,3R)-2,2-dichloro-3-(4-fluoro-3-(trifluoromethyl)phenyl)cyclopropane-1-carboxamido)benzamide (F1263)

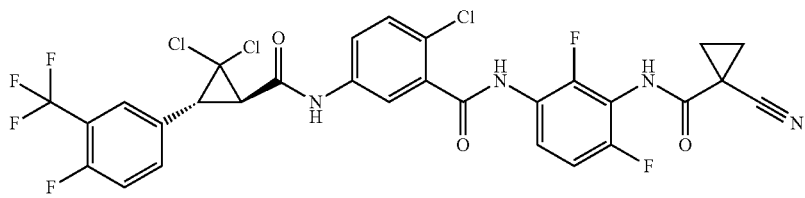 [SMILES: N#CC1(C(=O)Nc2c(F)ccc(NC(=O)c3cc(NC(=O)[C@H]4[C@H](c5ccc(F)c(C(F)(F)F)c5)C4(Cl)Cl)ccc3Cl)c2F)CC1]

Isolated as a white foam (0.078 g, 64%).

2-Chloro-N-(3-(cyclopropanecarboxamido)-2,4-difluorophenyl)-5-((1R,3R)-2,2-dichloro-3-(4-fluoro-3-(trifluoromethyl)phenyl)cyclopropane-1-carboxamido)benzamide (F1264)

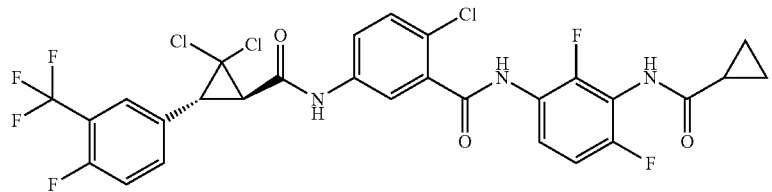 [SMILES: O=C(Nc1ccc(F)c(NC(=O)C2CC2)c1F)c1cc(NC(=O)[C@H]2[C@H](c3ccc(F)c(C(F)(F)F)c3)C2(Cl)Cl)ccc1Cl]

Isolated as a white foam (0.100 g, 85%).

2-Chloro-N-(3-(2,2-dichloro-1-methylcyclopropane-1-carboxamido)-2,4-difluorophenyl)-5-((1R,3R)-2,2-dichloro-3-(4-fluoro-3-(trifluoromethyl)phenyl)cyclopropane-1-carboxamido)benzamide (F1273)

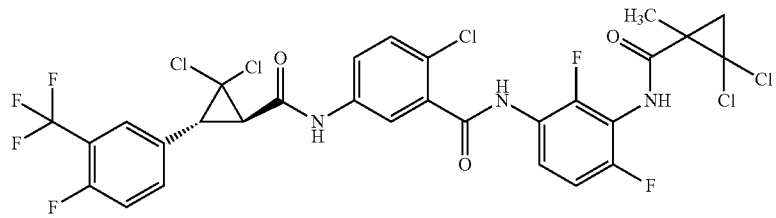 [SMILES: CC1(C(=O)Nc2c(F)ccc(NC(=O)c3cc(NC(=O)[C@H]4[C@H](c5ccc(F)c(C(F)(F)F)c5)C4(Cl)Cl)ccc3Cl)c2F)CC1(Cl)Cl]

Isolated as a white solid (0.078 g, 30%).

2-Chloro-5-((1R,3R)-2,2-dichloro-3-(4-fluoro-3-(trifluoromethyl)phenyl)cyclopropane-1-carboxamido)-N-(2,4-difluoro-3-pivalamidophenyl)benzamide (F1274)

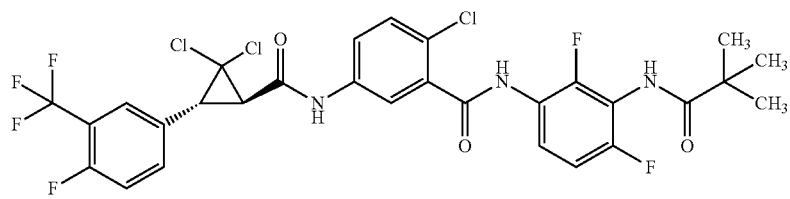 [SMILES: CC(C)(C)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white solid (0.014 g, 12%).

2-Chloro-5-((1R,3R)-2,2-dichloro-3-(4-fluoro-3-(trifluoromethyl)phenyl)cyclopropane-1-carboxamido)-N-(3-(2,2-difluorocyclopropane-1-carboxamido)-2,4-difluorophenyl)benzamide (F1275)

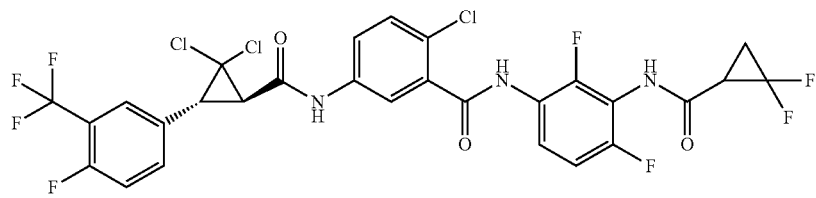 [SMILES: O=C(Nc1ccc(F)c(NC(=O)C2CC2(F)F)c1F)c1cc(NC(=O)[C@H]2[C@H](c3ccc(F)c(C(F)(F)F)c3)C2(Cl)Cl)ccc1Cl]

Isolated as a white solid (0.135 g, 73%).

2-Chloro-N-(3-(cyclohex-3-ene-1-carboxamido)-2,4-difluorophenyl)-5-((1R,3R)-2,2-dichloro-3-(4-fluoro-3-(trifluoromethyl)phenyl)cyclopropane-1-carboxamido)benzamide (F1297)

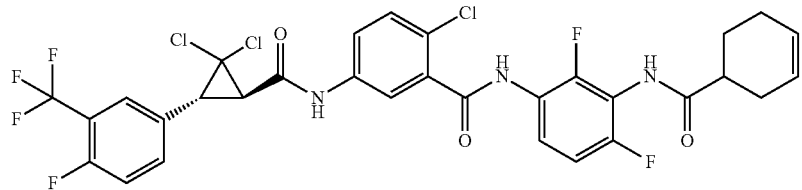 [SMILES: O=C(Nc1ccc(F)c(NC(=O)C2CC=CCC2)c1F)c1cc(NC(=O)[C@H]2[C@H](c3ccc(F)c(C(F)(F)F)c3)C2(Cl)Cl)ccc1Cl]

Isolated as a white solid (0.119 g, 96%).

2-Chloro-5-((1R,3R)-2,2-dichloro-3-(4-fluoro-3-(trifluoromethyl)phenyl)cyclopropane-1-carboxamido)-N-(2,4-difluoro-3-(2-oxo-2-phenylacetamido)phenyl)benzamide (F1298)

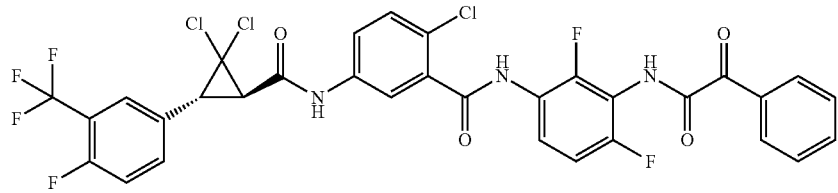 [SMILES: O=C(Nc1c(F)ccc(NC(=O)c2cc(NC(=O)[C@H]3[C@H](c4ccc(F)c(C(F)(F)F)c4)C3(Cl)Cl)ccc2Cl)c1F)C(=O)c1ccccc1]

Isolated as a clear colorless oil (0.087 g, 68%).

2-Chloro-5-((1R,3R)-2,2-dichloro-3-(4-fluoro-3-(trifluoromethyl)phenyl)cyclopropane-1-carboxamido)-N-(2,4-difluoro-3-(2-(methylsulfonyl)acetamido)phenyl)benzamide (F1299)

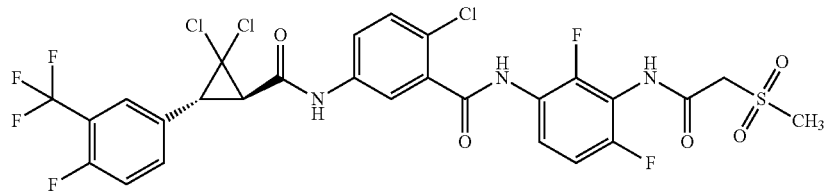 [SMILES: CS(=O)(=O)CC(=O)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white foam (0.111 g, 88%).

N-(3-(2-Chloro-5-((1R,3R)-2,2-dichloro-3-(4-fluoro-3-(trifluoromethyl)phenyl)cyclopropane-1-carboxamido)benzamido)-2,6-difluorophenyl)furan-2-carboxamide (F1300)

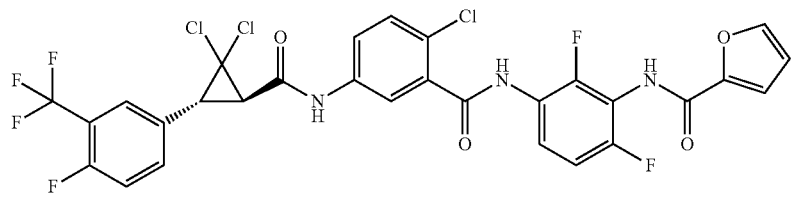 [SMILES: O=C(Nc1c(F)ccc(NC(=O)c2cc(NC(=O)[C@H]3[C@H](c4ccc(F)c(C(F)(F)F)c4)C3(Cl)Cl)ccc2Cl)c1F)c1ccco1]

Isolated as a white solid (0.035 g, 70%).

2-Chloro-5-((1R,3R)-2,2-dichloro-3-(4-fluoro-3-(trifluoromethyl)phenyl)cyclopropane-1-carboxamido)-N-(2,4-difluoro-3-(2,2,3,3-tetrafluoropropanamido)phenyl)benzamide (F1301)

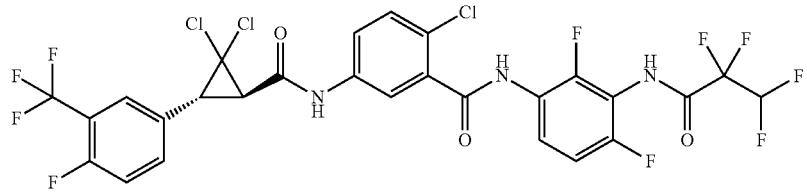 [SMILES: O=C(Nc1ccc(F)c(NC(=O)C(F)(F)C(F)F)c1F)c1cc(NC(=O)[C@H]2[C@H](c3ccc(F)c(C(F)(F)F)c3)C2(Cl)Cl)ccc1Cl]

Isolated as a white foam (0.103 g, 81%).

N-(3-(2-Chloro-5-((1R,3R)-2,2-dichloro-3-(4-fluoro-3-(trifluoromethyl)phenyl)cyclopropane-1-carboxamido)benzamido)-2,6-difluorophenyl)-5-methylthiophene-2-carboxamide (F1302)

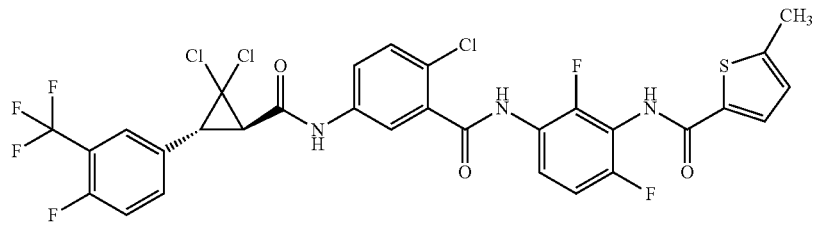 [SMILES: Cc1ccc(C(=O)Nc2c(F)ccc(NC(=O)c3cc(NC(=O)[C@H]4[C@H](c5ccc(F)c(C(F)(F)F)c5)C4(Cl)Cl)ccc3Cl)c2F)s1]

Isolated as a white solid (0.035 g, 28%).

2-Chloro-5-((1R,3R)-2,2-dichloro-3-(4-fluoro-3-(trifluoromethyl)phenyl)cyclopropane-1-carboxamido)-N-(2,4-difluoro-3-(3-oxocyclobutane-1-carboxamido)phenyl)benzamide (F1303)

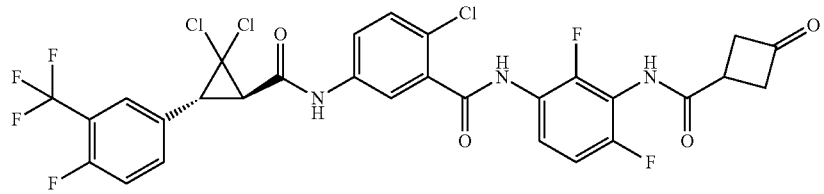 [SMILES: O=C1CC(C(=O)Nc2c(F)ccc(NC(=O)c3cc(NC(=O)[C@H]4[C@H](c5ccc(F)c(C(F)(F)F)c5)C4(Cl)Cl)ccc3Cl)c2F)C1]

Isolated as a white solid (0.093 g, 76%).

Example 7: Preparation of trans-N-(4-Acetamido-2-methylphenyl)-2-chloro-5-(2,2-dichloro-3-(3,4-dichlorophenyl)cyclopropane-1-carboxamido)benzamide (F1059)

To a solution of trans-N-(4-amino-2-methylphenyl)-2-chloro-5-(2,2-dichloro-3-(3,4-dichlorophenyl)cyclopropane-1-carboxamido)benzamide (DP1) (0.100 g, 0.179 mmol) and triethylamine (0.037 mL, 0.269 mmol) in dichloromethane (2.0 mL) was added acetyl chloride (0.015 g, 0.197 mmol). The reaction mixture was stirred at room temperature for 18 hours. The reaction mixture was diluted with ethyl acetate and washed with hydrochloric acid (1 N; 2×) and brine. Celite® was added to the organic layer, and the mixture was concentrated under reduced pressure. Purification by flash column chromatography using 0-40% ethyl acetate/hexanes as eluent afforded the title compound as an off-white solid (0.079 g, 73%).

The following compounds were prepared in like manner to the procedure outlined in Example 7:

trans-2-Chloro-5-(2,2-dichloro-3-(3,4-dichlorophenyl)cyclopropane-1-carboxamido)-N-(2-methyl-4-(2,2,2-trichloroacetamido)phenyl)benzamide (F1060)

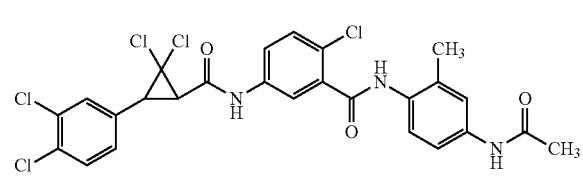 [SMILES: CC(=O)Nc1ccc(NC(=O)c2cc(NC(=O)C3C(c4ccc(Cl)c(Cl)c4)C3(Cl)Cl)ccc2Cl)c(C)c1]

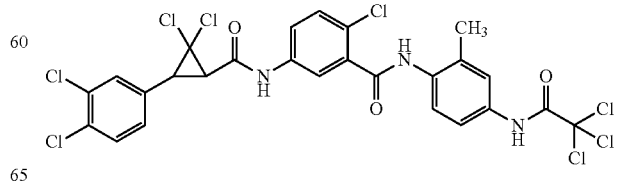

Isolated as a white solid (0.060 g, 47%).

2-Chloro-5-((1R,3R)-2,2-dichloro-3-(3,4-dichlorophenyl)cyclopropane-1-carboxamido)-N-(2,4-difluoro-3-(2,2,2-trichloroacetamido)phenyl)benzamide (F1063)

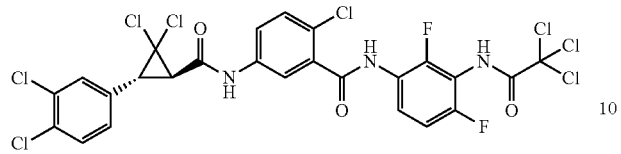

Isolated as a white solid (0.039 g, 34%).

2-Chloro-5-((1R,3R)-2,2-dichloro-3-(3,4-dichlorophenyl)cyclopropane-1-carboxamido)-N-(2,4-difluoro-3-(2-methoxyacetamido)phenyl)benzamide (F1254)

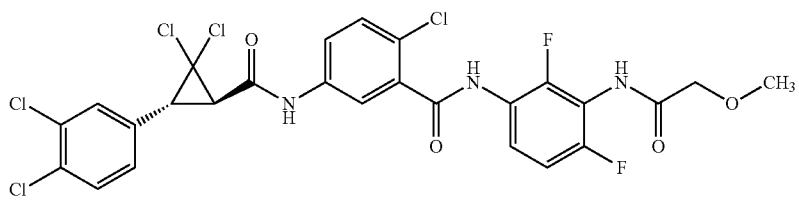

Isolated as a white solid (0.072 g, 64%).

Example 8: Preparation of 2-chloro-5-((1R,3R)-2,2-dichloro-3-(4-fluoro-3-(trifluoromethyl)phenyl)cyclopropane-1-carboxamido)-N-(2,4-difluoro-3-(N-(methylsulfonyl)methylsulfonamido)phenyl)benzamide (F1277)

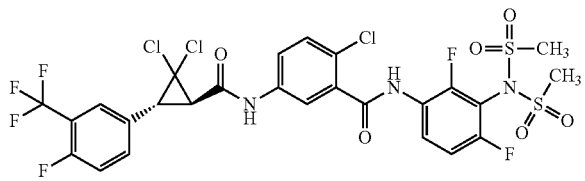 [SMILES: CS(=O)(=O)N(c1c(F)ccc(NC(=O)c2cc(NC(=O)[C@H]3[C@H](c4ccc(F)c(C(F)(F)F)c4)C3(Cl)Cl)ccc2Cl)c1F)S(C)(=O)=O]

Methanesulfonyl chloride (0.029 g, 0.251 mmol) was added dropwise to a stirred solution of N-(3-amino-2,4-difluorophenyl)-2-chloro-5-((1R,3R)-2,2-dichloro-3-(4-fluoro-3-(trifluoromethyl)phenyl)cyclopropane-1-carboxamido)benzamide (DP9) (0.100 g, 168 mmol) and triethylamine (0.051 g, 0.503 mmol) in anhydrous dichloromethane (3 mL). The solution was stirred for 12 hours at 23° C. and concentrated. Purification by silica gel flash chromatography gave the title compound as a white foam (0.044 g, 33%).

Example 9: Preparation of 2-chloro-5-((1R,3R)-2,2-dichloro-3-(4-fluoro-3-(trifluoromethyl)phenyl)cyclopropane-1-carboxamido)-N-(2,4-difluoro-3-(phenylsulfonamido)phenyl)benzamide (F1295)

Benzenesulfonyl chloride (0.044 g, 0.251 mmol) was added to a stirred solution of N-(3-amino-2,4-difluorophenyl)-2-chloro-5-((1R,3R)-2,2-dichloro-3-(4-fluoro-3-(trifluoromethyl)phenyl)cyclopropane-1-carboxamido)benzamide (DP9) (0.100 g, 168 mmol) in acetonitrile (3 mL). The solution was stirred for 36 hours at 70° C. and concentrated. Purification by silica gel flash chromatography provided the title compound as a pink solid (0.112 g, 86%).

Example 10: Preparation of trans-2-chloro-N-(4-((4-chlorobenzyl)amino)-2-methylphenyl)-5-(2,2-dichloro-3-(3,5-dichlorophenyl)cyclopropane-1-carboxamido)benzamide (F1010)

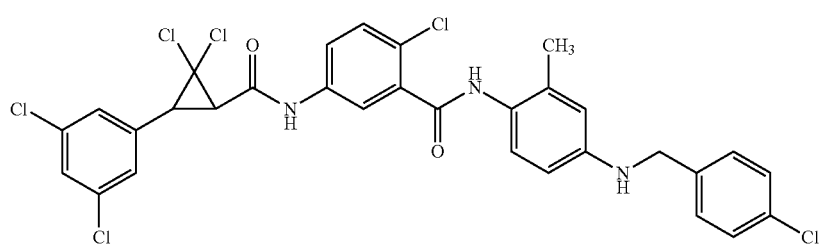 [SMILES: Cc1cc(NCc2ccc(Cl)cc2)ccc1NC(=O)c1cc(NC(=O)C2C(c3cc(Cl)cc(Cl)c3)C2(Cl)Cl)ccc1Cl]

4-Chlorobenzaldehyde (0.0252 g, 0.179 mmol) was added to a stirred suspension of trans-N-(4-amino-2-methylphenyl)-2-chloro-5-(2,2-dichloro-3-(3,5-dichlorophenyl)cyclopropane-1-carboxamido)benzamide (DP4) (0.100 g, 0.179 mmol) and sodium acetate (29.4 mg, 0.359 mmol) in methanol (20 mL), water (15 mL) and acetic acid (3 mL). The resulting heterogeneous mixture was stirred at 25° C. for 3 hours. Sodium cyanoborohydride (0.0158 g, 0.251 mmol) was added in one portion. The resulting colorless solution was stirred at ambient temperature for another 4 hours. The reaction mixture was quenched with water (50 mL) and extracted with diethyl ether (3×50 mL). The organic extracts were washed successively with water and saturated aqueous sodium chloride solution, dried over anhydrous magnesium sulfate, and concentrated under vacuum on a rotary evaporator. Purification by silica gel flash chromatography provided the title compound as a yellow foam (0.087 g, 68%).

The following compounds were prepared in like manner to the procedure outlined in Example 10:

trans-2-Chloro-5-(2,2-dichloro-3-(3,5-dichlorophenyl)cyclopropane-1-carboxamido)-N-(4-((4-methoxybenzyl)amino)-2-methylphenyl)benzamide (F1035)

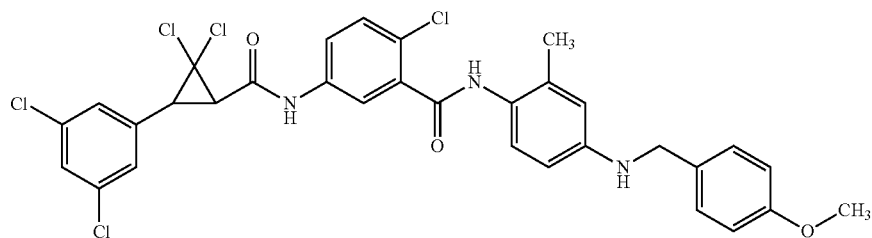 [SMILES: COc1ccc(CNc2ccc(NC(=O)c3cc(NC(=O)C4C(c5cc(Cl)cc(Cl)c5)C4(Cl)Cl)ccc3Cl)c(C)c2)cc1]

Isolated as a yellow foam (0.095 g, 74%).

trans-2-Chloro-N-(4-((4-cyanobenzyl)amino)-2-methylphenyl)-5-(2,2-dichloro-3-(3,5-dichlorophenyl)cyclopropane-1-carboxamido)benzamide (F1040)

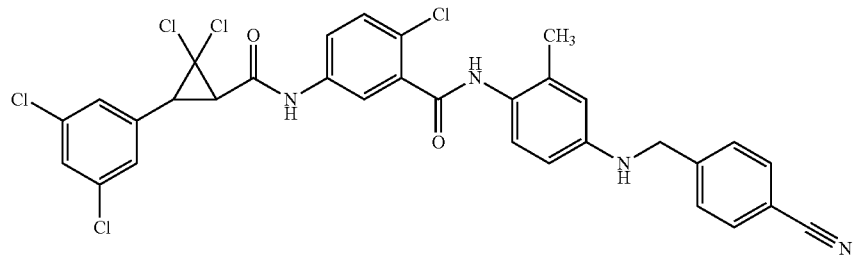 [SMILES: Cc1cc(NCc2ccc(C#N)cc2)ccc1NC(=O)c1cc(NC(=O)C2C(c3cc(Cl)cc(Cl)c3)C2(Cl)Cl)ccc1Cl]

Isolated as a yellow solid (0.097 g, 76%).

trans-2-Chloro-5-(2,2-dichloro-3-(3,5-dichlorophenyl)cyclopropane-1-carboxamido)-N-(2-methyl-4-((4-methylbenzyl)amino)phenyl)benzamide (F1041)

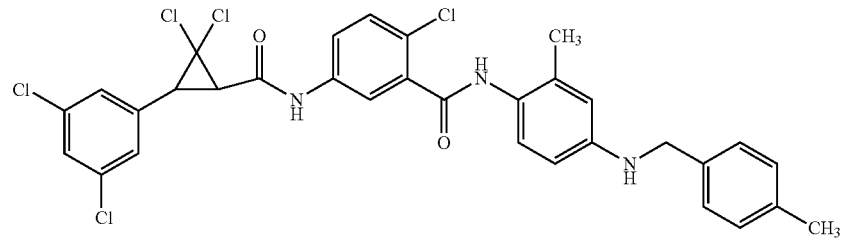 [SMILES: Cc1ccc(CNc2ccc(NC(=O)c3cc(NC(=O)C4C(c5cc(Cl)cc(Cl)c5)C4(Cl)Cl)ccc3Cl)c(C)c2)cc1]

Isolated as a yellow solid (0.081 g, 65%).

trans-2-Chloro-5-(2,2-dichloro-3-(4-fluoro-3-(trifluoromethyl)phenyl)cyclopropane-1-carboxamido)-N-(2,4-difluoro-3-((4-methoxybenzyl)amino)phenyl)benzamide (F1096)

Isolated as a white foam (0.059 g, 47%).

trans-2-Chloro-5-(2,2-dichloro-3-(3,5-dichlorophenyl)cyclopropane-1-carboxamido)-N-(2-methyl-4-((4-(trifluoromethoxy)benzyl)amino)phenyl)benzamide (F1.117)

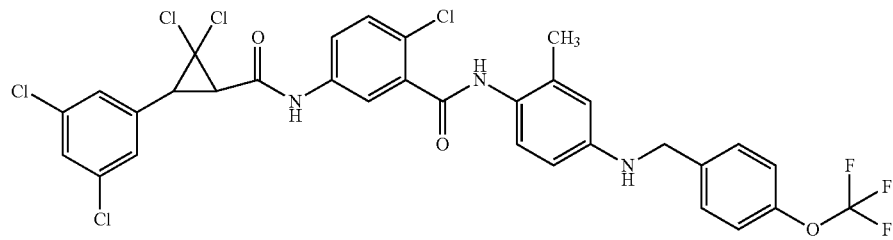 [SMILES: Cc1cc(NCc2ccc(OC(F)(F)F)cc2)ccc1NC(=O)c1cc(NC(=O)C2C(c3cc(Cl)cc(Cl)c3)C2(Cl)Cl)ccc1Cl]

Isolated as a yellow solid (0.113 g, 82%).

trans-2-Chloro-5-(2,2-dichloro-3-(3,5-dichlorophenyl)cyclopropane-1-carboxamido)-N-(2-methyl-4-((4-nitrobenzyl)amino)phenyl)benzamide (F1166)

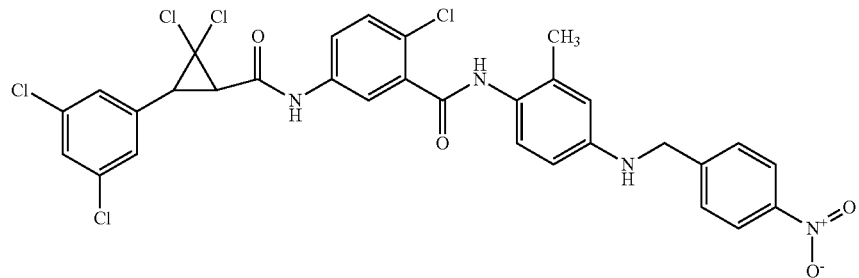 [SMILES: Cc1cc(NCc2ccc([N+](=O)[O-])cc2)ccc1NC(=O)c1cc(NC(=O)C2C(c3cc(Cl)cc(Cl)c3)C2(Cl)Cl)ccc1Cl]

Isolated as a yellow oil (0.076 g, 77%).

trans-2-Chloro-5-(2,2-dichloro-3-(3,5-dichlorophenyl)cyclopropane-1-carboxamido)-N-(2-methyl-4-((4-(trifluoromethyl)benzyl)amino)phenyl)benzamide (F1165)

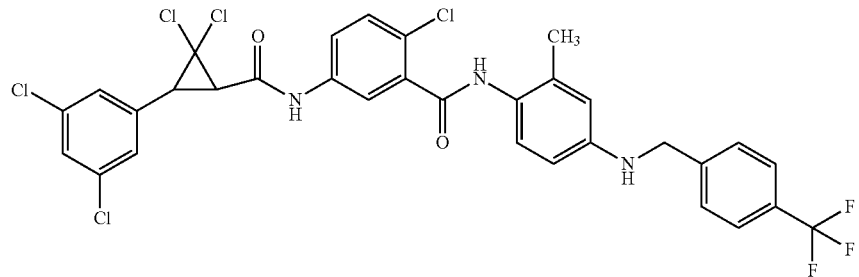 [SMILES: Cc1cc(NCc2ccc(C(F)(F)F)cc2)ccc1NC(=O)c1cc(NC(=O)C2C(c3cc(Cl)cc(Cl)c3)C2(Cl)Cl)ccc1Cl]

Isolated as a pale yellow solid (0.055 g, 54%).

trans-N-(4-(Benzylamino)-2-methylphenyl)-2-chloro-5-(2,2-dichloro-3-(3,5-dichlorophenyl)cyclopropane-1-carboxamido)benzamide (F1176)

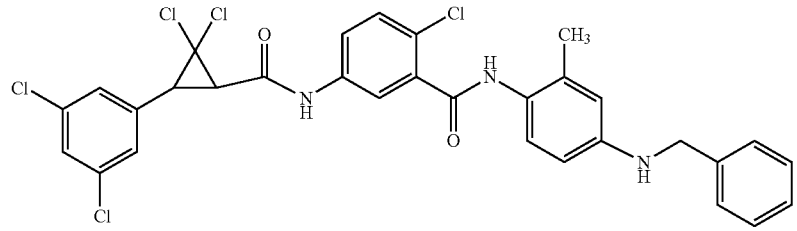 [SMILES: Cc1cc(NCc2ccccc2)ccc1NC(=O)c1cc(NC(=O)C2C(c3cc(Cl)cc(Cl)c3)C2(Cl)Cl)ccc1Cl]

Isolated as a pale yellow loam (0.039 g, 42%).

trans-2-Chloro-5-(2,2-dichloro-3-(3,5-dichlorophenyl)cyclopropane-1-carboxamido)-N-(2-methyl-4-(phenethylamino)phenyl)benzamide (F1177)

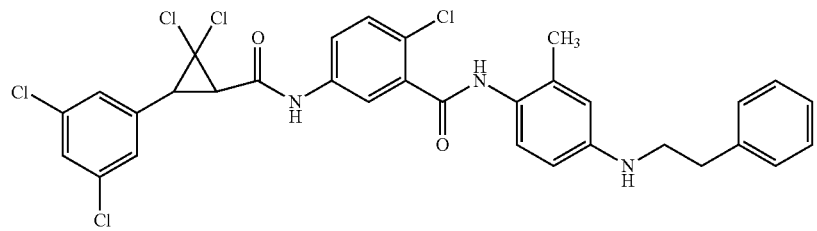 [SMILES: Cc1cc(NCCc2ccccc2)ccc1NC(=O)c1cc(NC(=O)C2C(c3cc(Cl)cc(Cl)c3)C2(Cl)Cl)ccc1Cl]

Isolated as a pale yellow foam (0.025 g, 27%).

trans-2-Chloro-5-(2,2-dichloro-3-(3,5-dichlorophenyl)cyclopropane-1-carboxamido)-N-(2-methyl-4-((2-phenylpropyl)amino)phenyl)benzamide (F1178)

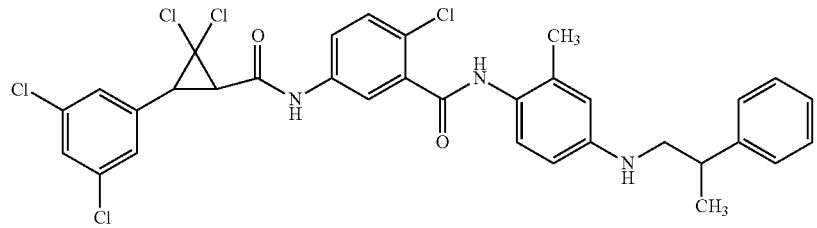

Isolated as a pale yellow foam (0.055 g, 58%).

2-Chloro-5-(((1R,3R)-2,2-dichloro-3-(4-fluoro-3-(trifluoromethyl)phenyl)cyclopropane-1-carboxamido)-N-(2,4-difluoro-3-((4-nitrobenzyl)amino)phenyl)benzamide (F1296)

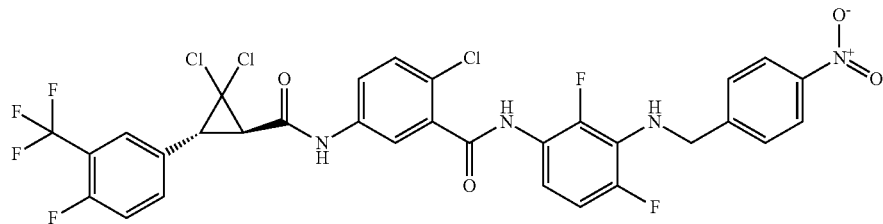 [SMILES: O=C(Nc1ccc(F)c(NCc2ccc([N+](=O)[O-])cc2)c1F)c1cc(NC(=O)[C@H]2[C@H](c3ccc(F)c(C(F)(F)F)c3)C2(Cl)Cl)ccc1Cl]

Isolated as a yellow oil (0.008 g, 4%).

Example 11: Preparation of trans-2-chloro-5-(2,2-dichloro-3-(3,5-dichlorophenyl)cyclopropane-1-carboxamido)-N-(4-fluoro-3-vinylphenyl)benzamide (F1311)

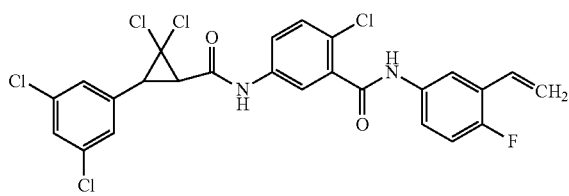 [SMILES: C=Cc1cc(NC(=O)c2cc(NC(=O)C3C(c4cc(Cl)cc(Cl)c4)C3(Cl)Cl)ccc2Cl)ccc1F]

To a solution of trans-N-(3-bromo-4-fluorophenyl)-2-chloro-5-(2,2-dichloro-3-(3,5-dichlorophenyl)cyclopropane-1-carboxamido)benzamide (F1304) (0.4 g, 0.64 mmol) in 1,4-dioxane (7 mL) degassed with argon were added tributylvinyltin (0.26 mL, 0.89 mmol) and bis(triphenylphosphine)palladium(II) dichloride (0.044 g, 0.064 mmol), and the reaction mixture was irradiated in a microwave at 90° C. for 1 hours. The reaction mixture was cooled to room temperature, diluted with water and extracted with ethyl acetate (2×10 mL). The organic layer was dried over anhydrous sodium sulfate, filtered and concentrated under reduced pressure. Purification by column chromatography using 15-20% ethyl acetate/petroleum ether as eluent afforded the title compound as an off-white solid (0.11 g, 40%).

The following compounds were prepared in like manner to the procedure outlined in Example 11:

trans-2-Chloro-5-(2,2-dichloro-3-(3,5-dichlorophenyl)cyclopropane-1-carboxamido)-N-(4-fluoro-2-vinylphenyl)benzamide (F1312)

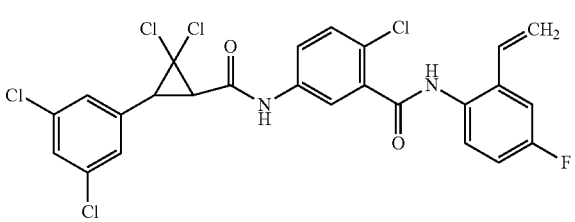 [SMILES: C=Cc1cc(F)ccc1NC(=O)c1cc(NC(=O)C2C(c3cc(Cl)cc(Cl)c3)C2(Cl)Cl)ccc1Cl]

Isolated as an off-white solid (0.12 g, 44%).

trans-2-Chloro-5-(2,2-dichloro-3-(3,5-dichlorophenyl)cyclopropane-1-carboxamido)-N-(2-fluoro-4-vinylphenyl)benzamide (F1313)

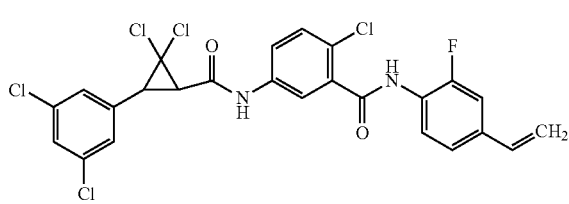 [SMILES: C=Cc1ccc(NC(=O)c2cc(NC(=O)C3C(c4cc(Cl)cc(Cl)c4)C3(Cl)Cl)ccc2Cl)c(F)c1]

Isolated as an off-white solid (0.18 g, 49%).

trans-2-Chloro-5-(2,2-dichloro-3-(3,5-dichlorophenyl)cyclopropane-1-carboxamido)-N-(2,4-difluoro-3-vinylphenyl)benzamide (F1314)


Isolated as an off-white solid (0.07 g, 26%).

trans-2-Chloro-5-(2,2-dichloro-3-(3,5-dichlorophenyl)cyclopropane-1-carboxamido)-N-(2,4-difluoro-5-vinylphenyl)benzamide (F1315)

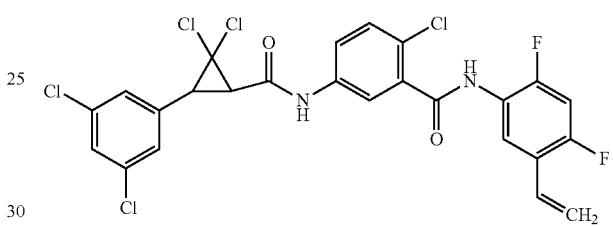

Isolated as an off-white solid (0.13 g, 48%).

trans-2-Chloro-5-(2,2-dichloro-3-(3,5-dichlorophenyl)cyclopropane-1-carboxamido)-N-(2,4-difluoro-6-vinylphenyl)benzamide (F1316)


Isolated as an off-white solid (0.12 g, 44%).

trans-2-Chloro-5-(2,2-dichloro-3-(3,5-dichlorophenyl)cyclopropane-1-carboxamido)-N-(3,4-difluoro-5-vinylphenyl)benzamide (F1317)


Isolated as an off-white solid (0.10 g, 37%).

trans-2-Chloro-5-(2,2-dichloro-3-(3,5-dichlorophenyl)cyclopropane-1-carboxamido)-N-(4-fluoro-3-(1-fluorovinyl)phenyl)benzamide (F1318)

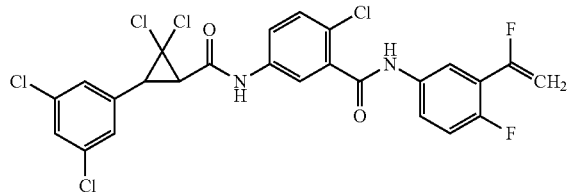 [SMILES: C=C(F)c1cc(NC(=O)c2cc(NC(=O)C3C(c4cc(Cl)cc(Cl)c4)C3(Cl)Cl)ccc2Cl)ccc1F]

Isolated as an off-write solid (0.15 g, 55%).

trans-2-Chloro-5-(2,2-dichloro-3-(3,5-dichlorophenyl)cyclopropane-1-carboxamido)-N-(4-fluoro-2-(1-fluorovinyl)phenyl)benzamide (F1319)

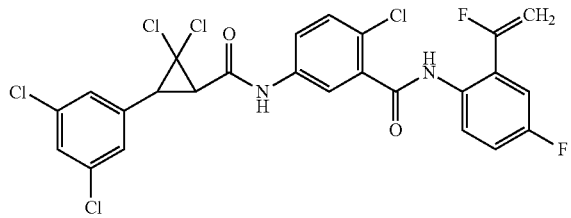 [SMILES: C=C(F)c1cc(F)ccc1NC(=O)c1cc(NC(=O)C2C(c3cc(Cl)cc(Cl)c3)C2(Cl)Cl)ccc1Cl]

Isolated as an off-white solid (0.17 g, 70%).

trans-2-Chloro-5-(2,2-dichloro-3-(3,5-dichlorophenyl)cyclopropane-1-carboxamido)-N-(2-fluoro-4-(1-fluorovinyl)phenyl)benzamide (F1320)

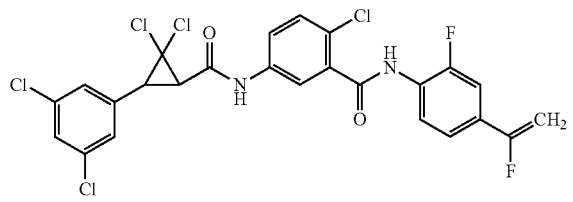 [SMILES: C=C(F)c1ccc(NC(=O)c2cc(NC(=O)C3C(c4cc(Cl)cc(Cl)c4)C3(Cl)Cl)ccc2Cl)c(F)c1]

Isolated as an off-white solid (0.15 g, 62%).

trans-2-Chloro-5-(2,2-dichloro-3-(3,5-dichlorophenyl)cyclopropane-1-carboxamido)-N-(2,4-difluoro-3-(1-fluorovinyl)phenyl)benzamide (F1321)

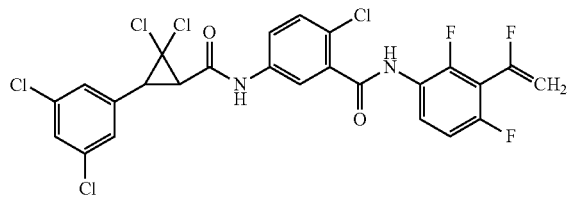 [SMILES: C=C(F)c1c(F)ccc(NC(=O)c2cc(NC(=O)C3C(c4cc(Cl)cc(Cl)c4)C3(Cl)Cl)ccc2Cl)c1F]

Isolated as an off-white solid (0.12 g, 63%).

trans-2-Chloro-5-(2,2-dichloro-3-(3,5-dichlorophenyl)cyclopropane-1-carboxamido)-N-(2,4-difluoro-6-(1-fluorovinyl)phenyl)benzamide (F1322)

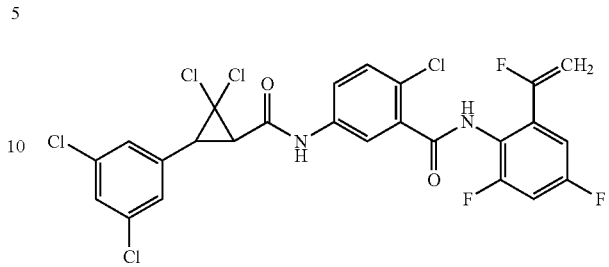

Isolated as an off-white solid (0.09 g, 50%).

trans-2-Chloro-5-(2,2-dichloro-3-(3,5-dichlorophenyl)cyclopropane-1-carboxamido)-N-(3,4-difluoro-5-(1-fluorovinyl)phenyl)benzamide (F1323)

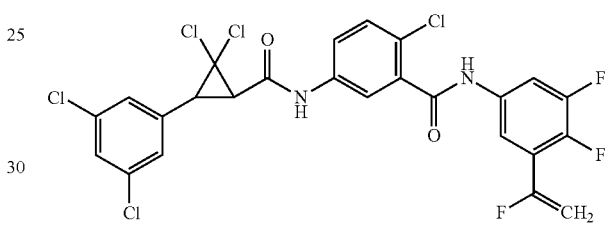

Isolated as an off-white solid (0.11 g, 58%).

Example 12: Preparation of trans-2-chloro-5-(2,2-dichloro-3-(3,5-dichlorophenyl)cyclopropane-1-carboxamido)-N-(4-((2-hydroxyethyl)amino)-2-methylphenyl)benzamide (F1130)

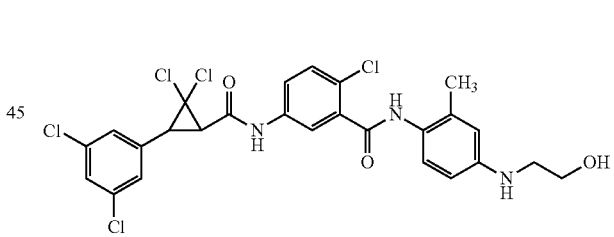

4 M Hydrogen chloride in 1,4-dioxane (0.370 mL, 1.479 mmol) was added dropwise to a stirred solution of trans-2-((tert-butoxycarbonyl)(4-(2-chloro-5-(2,2-dichloro-3-(3,5-dichlorophenyl)cyclopropane-1-carboxamido)benzamido)-3-methylphenyl)amino)ethyl acetate (F1129) (0.110 g, 0.148 mmol) in dichloromethane (5 mL). The resulting suspension of solid was stirred for 12 hours at 23° C. and then quenched with saturated aqueous sodium bicarbonate (5 mL). The aqueous mixture was extracted with ethyl acetate (3×5 mL) and the organic extract was washed with saturated aqueous sodium chloride solution (5 mL) and concentrated under vacuum on a rotary evaporator. Purification by silica gel flash chromatography gave the title compound as a pale yellow foam (0.050 g, 53%).

The following compounds were prepared in like manner to the procedure outlined in Example 12:

2-((4-(2-Chloro-5-((1R,3R)-2,2-dichloro-3-(4-fluoro-3-(trifluoromethyl)phenyl)cyclopropane-1-carboxamido)benzamido)-3-methylphenyl)amino)ethyl acetate (F1144)

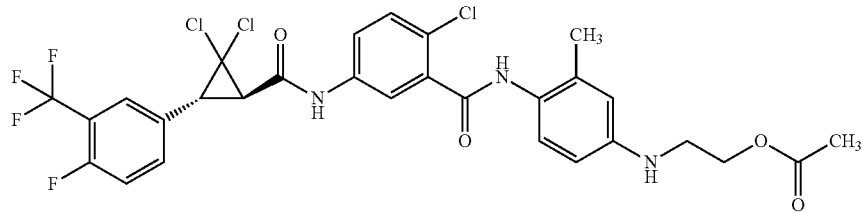 [SMILES: CC(=O)OCCNc1ccc(NC(=O)c2cc(NC(=O)[C@H]3[C@H](c4ccc(F)c(C(F)(F)F)c4)C3(Cl)Cl)ccc2Cl)c(C)c1]

Isolated as a clear colorless oil (0.043 g, 31%).

2-Chloro-5-((1R,3R)-2,2-dichloro-3-(4-fluoro-3-(trifluoromethyl)phenyl)cyclopropane-1-carboxamido)-N-(4-((2-hydroxyethyl)amino)-2-methylphenyl)benzamide (F1145)

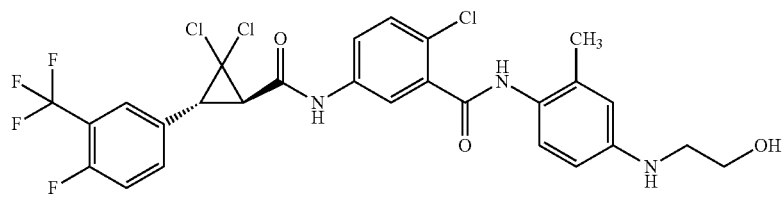 [SMILES: Cc1cc(NCCO)ccc1NC(=O)c1cc(NC(=O)[C@H]2[C@H](c3ccc(F)c(C(F)(F)F)c3)C2(Cl)Cl)ccc1Cl]

Isolated as a pale yellow foam (0.040 g, 31%).

trans-N-(4-((3-Amino-3-oxopropyl)amino)-2-methylphenyl)-2-chloro-5-(2,2-dichloro-3-(3,5-dichlorophenyl)cyclopropane-1-carboxamido)benzamide (F1158)

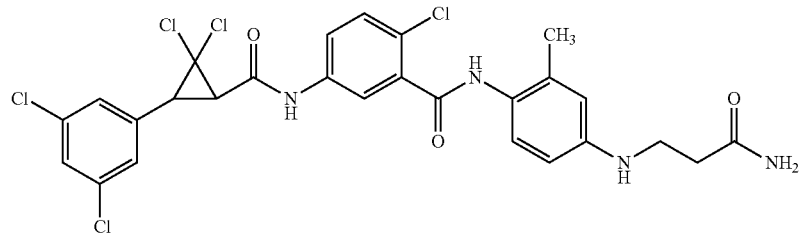 [SMILES: Cc1cc(NCCC(N)=O)ccc1NC(=O)c1cc(NC(=O)C2C(c3cc(Cl)cc(Cl)c3)C2(Cl)Cl)ccc1Cl]

Isolated as a grey solid (0.013 g, 16%).

trans-2-Chloro-5-(2,2-dichloro-3-(3,5-dichlorophenyl)cyclopropane-1-carboxamido)-N-(4-((2-methoxyethyl)amino)-2-methylphenyl)benzamide (F1162)

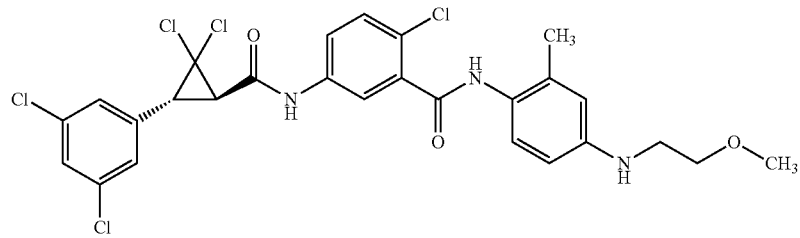 [SMILES: COCCNc1ccc(NC(=O)c2cc(NC(=O)[C@H]3[C@H](c4cc(Cl)cc(Cl)c4)C3(Cl)Cl)ccc2Cl)c(C)c1]

Isolated as a pale yellow foam (0.062 g, 86%).

Example 13: Preparation of N-(3-amino-2,4-difluorophenyl)-2-chloro-5-((1R,3R)-2,2-dichloro-3-(3-chloro-4-fluorophenyl)cyclopropane-1-carboxamido)-3-fluorobenzamide (F1255)

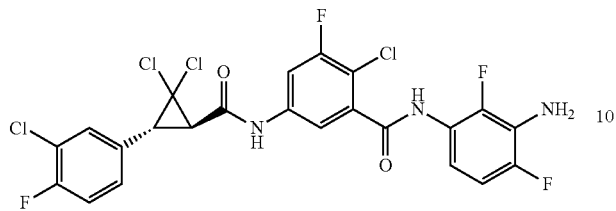

To a solution of tert-butyl-N-tert-butoxycarbonyl-N-[3-[[2-chloro-5-[[(1R,3R)-2,2-dichloro-3-(3-chloro-4-fluorophenyl)cyclopropane-carbonyl]amino]-3-fluorobenzoyl]amino]-2,6-difluorophenyl]carbamate (F1239) (0.166 g, 0.21 mmol) in dioxane (1 mL) was added a 4 molar solution of hydrogen chloride in dioxane (0.53 mL, 2.12 mmol), and the colorless solution was stirred at room temperature for 16 hours. The light-yellow solution was concentrated and the residue was partitioned between ethyl acetate (5 mL) and saturated aqueous sodium bicarbonate (5 mL). The phases were separated and the aqueous phase was extracted with additional ethyl acetate (2×2.5 mL). The combined organic extracts were washed with brine (3 mL), dried over sodium sulfate, filtered, and concentrated to an amber residue. The residue was dissolved in minimal ethyl acetate and adsorbed to Celite®. Purification by automated flash chromatography using a gradient of 0-40% ethyl acetate in hexanes as eluent provided the title compound as a white solid (0.111 g, 88%).

The following compounds were prepared in like manner to the procedure outlined in Example 13:

N-(3-Amino-2,4-difluorophenyl)-5-(2,2-dichloro-3-(3-chloro-4-fluorophenyl)cyclopropane-1-carboxamido)-2-fluoro-3-methylbenzamide (F1151)

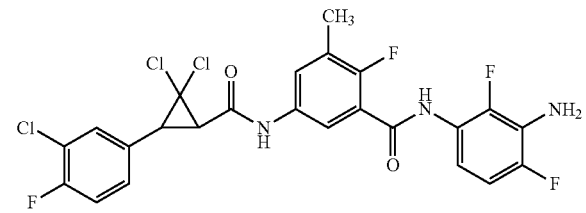 [SMILES: Cc1cc(NC(=O)C2C(c3ccc(F)c(Cl)c3)C2(Cl)Cl)cc(C(=O)Nc2ccc(F)c(N)c2F)c1F]

Isolated as a white solid (0.056 g, 74%).

N-(3-(4-Aminobutanamido)-2,4-difluorophenyl)-2-chloro-5-((1R,3R)-2,2-dichloro-3-(3,4-dichlorophenyl)cyclopropane-1-carboxamido)benzamide (F1201)

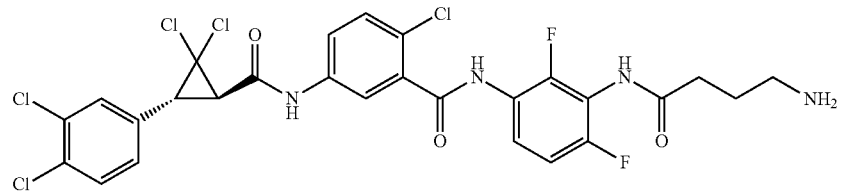 [SMILES: NCCCC(=O)Nc1c(F)ccc(NC(=O)c2cc(NC(=O)[C@H]3[C@H](c4ccc(Cl)c(Cl)c4)C3(Cl)Cl)ccc2Cl)c1F]

Isolated as a white foam (0.077 g, 81%).

trans-N-(4-(4-Aminobutanamido)-2-methylphenyl)-2-chloro-5-(2,2-dichloro-3-(3,4-dichlorophenyl)cyclopropane-1-carboxamido)benzamide (F1202)

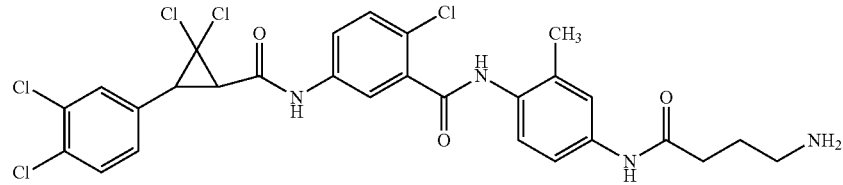 [SMILES: Cc1cc(NC(=O)CCCN)ccc1NC(=O)c1cc(NC(=O)C2C(c3ccc(Cl)c(Cl)c3)C2(Cl)Cl)ccc1Cl]

Isolated as a white solid (0.035 g, 42%).

N-(3-Amino-2,6-difluorophenyl)-2-chloro-5-((1R,3R)-2,2-dichloro-3-(3,5-dichlorophenyl)cyclopropane-1-carboxamido)benzamide (F1227)

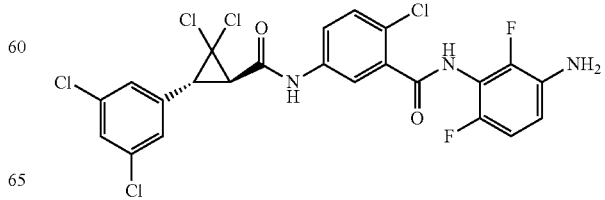

Isolated as a brown foamy solid (0.225 g, 95%).

N-(3-Amino-2,6-difluorophenyl)-2-chloro-5-((1R,3R)-2,2-dichloro-3-(3,4,5-trichlorophenyl)cyclopropane-1-carboxamido)benzamide (F1228)

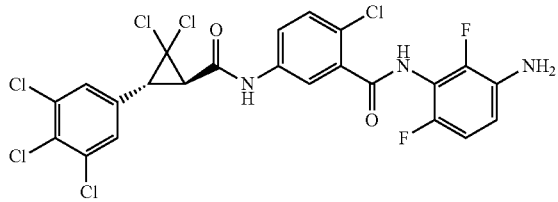 [SMILES: Nc1ccc(F)c(NC(=O)c2cc(NC(=O)[C@H]3[C@H](c4cc(Cl)c(Cl)c(Cl)c4)C3(Cl)Cl)ccc2Cl)c1F]

Isolated as an off-white foam (0.216 g, 97%).

N-(3-Amino-2,6-difluorophenyl)-2-chloro-5-((1R,3R)-2,2-dichloro-3-(3-chloro-4-fluorophenyl)cyclopropane-1-carboxamido)benzamide (F1247)

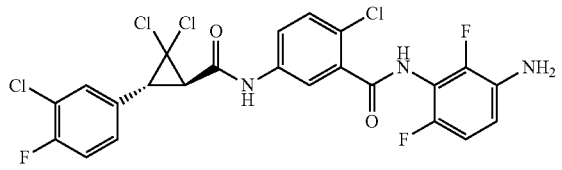 [SMILES: Nc1ccc(F)c(NC(=O)c2cc(NC(=O)[C@H]3[C@H](c4ccc(F)c(Cl)c4)C3(Cl)Cl)ccc2Cl)c1F]

Isolated as a white foamy solid (0.195 g, 92%).

N-(3-Amino-2,6-difluorophenyl)-2-chloro-5-((1R,3R)-2,2-dichloro-3-(3,4-dichlorophenyl)cyclopropane-1-carboxamido)benzamide (F1250)

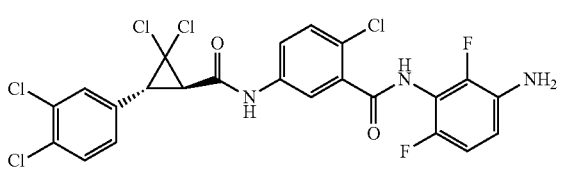 [SMILES: Nc1ccc(F)c(NC(=O)c2cc(NC(=O)[C@H]3[C@H](c4ccc(Cl)c(Cl)c4)C3(Cl)Cl)ccc2Cl)c1F]

Isolated as a white foamy solid (0.225 g, 97%).

N-(3-Amino-2,4-difluorophenyl)-2-chloro-5-((1R,3R)-2,2-dichloro-3-(3,4-dichlorophenyl)cyclopropane-1-carboxamido)-N-methylbenzamide (F1056)

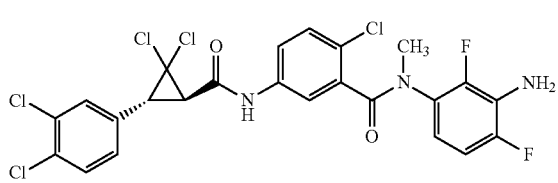 [SMILES: CN(C(=O)c1cc(NC(=O)[C@H]2[C@H](c3ccc(Cl)c(Cl)c3)C2(Cl)Cl)ccc1Cl)c1ccc(F)c(N)c1F]

Isolated as a beige foam (0.1 g, 85%).

trans-N-(3-Amino-2,4-difluorophenyl)-2-chloro-5-(3-(3,5-dichlorophenyl)-2,2-difluorocyclopropane-1-carboxamido)benzamide (F1080)

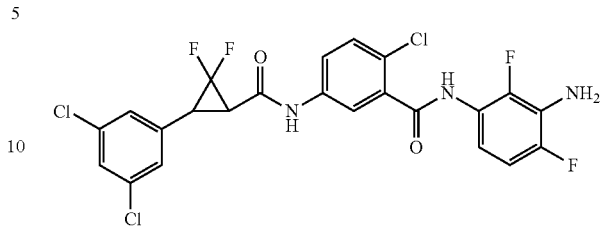

Isolated as an off-white powder (0.94 g, 94%).

N-(3-Amino-2,4-difluorophenyl)-2-chloro-5-((1R,3R)-2,2-dichloro-3-(3,5-dichlorophenyl)cyclopropane-1-carboxamido)-3-fluorobenzamide (F1324)

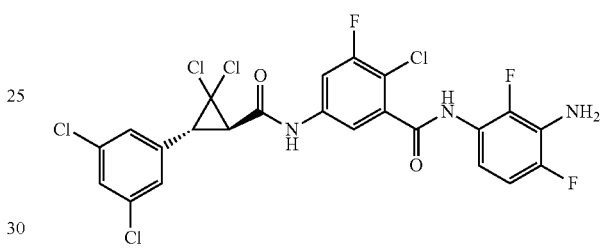

Isolated as a light yellow solid 0.195 g, 75%).

N-(3-Amino-2,4-difluorophenyl)-2-chloro-5-((1R,3R)-2,2-dichloro-3-(3,4,5-trichlorophenyl)cyclopropane-1-carboxamido)-3-fluorobenzamide (F1325)

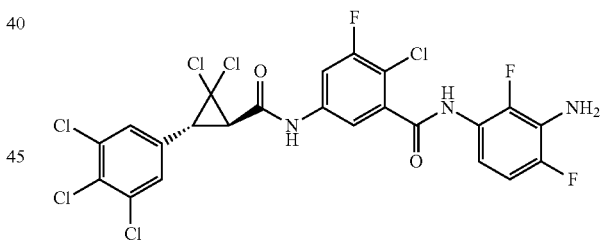

Isolated as an off-white solid (0.130 g, 46%).

N-(3-Amino-2,6-difluorophenyl)-2-chloro-5-((1R,3R)-2,2-dichloro-3-(3,5-dichlorophenyl)cyclopropane-1-carboxamido)-3-fluorobenzamide (F1336)

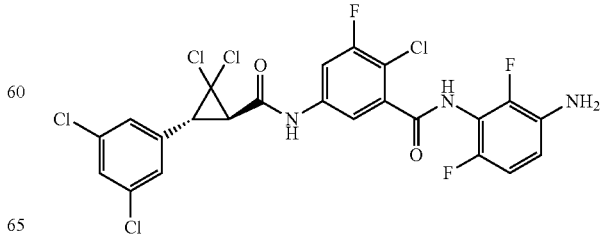

Isolated as a tan powder (0.160 g, 81%).

trans-N-(3-Amino-2,4-difluorophenyl)-2,6-dichloro-3-(2,2-dichloro-3-(3-chloro-4-fluorophenyl)cyclopropane-1-carboxamido)benzamide (F1110)

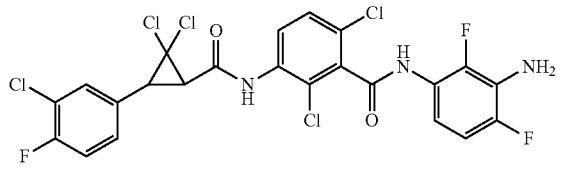 [SMILES: Nc1c(F)ccc(NC(=O)c2c(Cl)ccc(NC(=O)C3C(c4ccc(F)c(Cl)c4)C3(Cl)Cl)c2Cl)c1F]

Isolated as a light-tan solid (0.034 g, 76%).

trans-N-(3-Amino-2,4-difluorophenyl)-3-(2,2-dichloro-3-(3-chloro-4-fluorophenyl)cyclopropane-1-carboxamido)-2,6-difluorobenzamide (F1111)

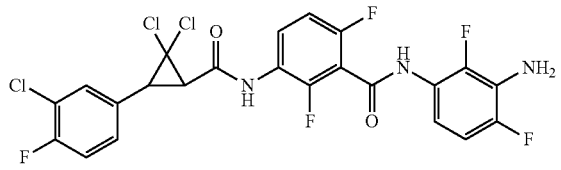 [SMILES: Nc1c(F)ccc(NC(=O)c2c(F)ccc(NC(=O)C3C(c4ccc(F)c(Cl)c4)C3(Cl)Cl)c2F)c1F]

Isolated as a tan solid (0.044 g, 80%).

trans-N-(4-Amino-3,5-difluorophenyl)-2-chloro-5-(2,2-dichloro-3-(3,4-dichlorophenyl)cyclopropane-1-carboxamido)benzamide (DP3)

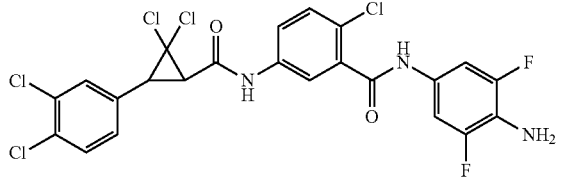 [SMILES: Nc1c(F)cc(NC(=O)c2cc(NC(=O)C3C(c4ccc(Cl)c(Cl)c4)C3(Cl)Cl)ccc2Cl)cc1F]

Isolated as a light brown foam (1.59 g, 93%).

trans-N-(3-Amino-2,4-difluorophenyl)-5-(2,2-dichloro-3-(3-chloro-4-fluorophenyl)cyclopropane-1-carboxamido)-2-fluoro-3-methylbenzamide (F1151)

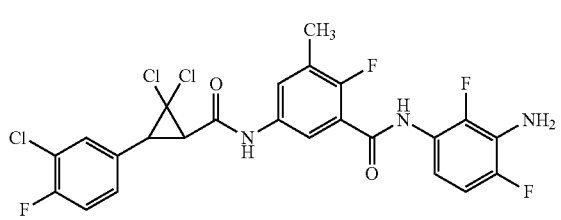 [SMILES: Cc1cc(NC(=O)C2C(c3ccc(F)c(Cl)c3)C2(Cl)Cl)cc(C(=O)Nc2ccc(F)c(N)c2F)c1F]

Isolated as a white solid (0.056 g, 74%).

trans-N-(3-Amino-2,4-difluorophenyl)-2-chloro-5-(2,2-dichloro-3-(3-chloro-4-fluorophenyl)cyclopropane-1-carboxamido)-3-fluorobenzamide (F1156)

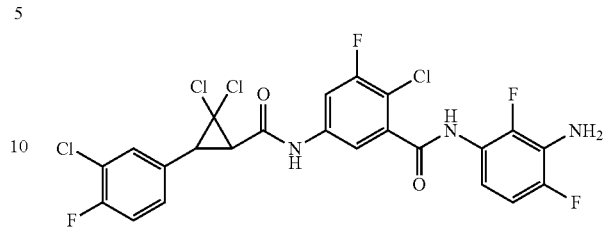

Isolated as a tan solid (0.100 g, 86%).

trans-N-(3-Amino-2,4-difluorophenyl)-2-chloro-5-(2,2-dichloro-3-(3-chloro-4-fluorophenyl)cyclopropane-1-carboxamido)-3-methylbenzamide (F1222)

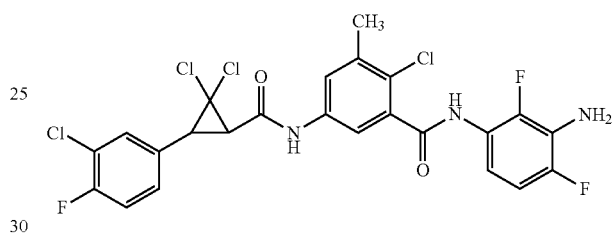

Isolated as a tan solid (0.054 g, 46%).

trans-N-(3-Amino-2,4-difluorophenyl)-3-chloro-5-(2,2-dichloro-3-(3-chloro-4-fluorophenyl)cyclopropane-1-carboxamido)-2-methylbenzamide (F1223)

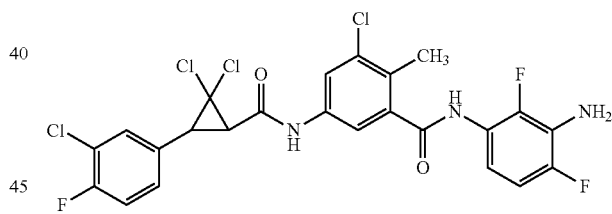

Isolated as a tan foam (0.052 g, 46%).

trans-N-(3-Amino-2,4-difluorophenyl)-2-chloro-5-(2,2-dichloro-3-(3-chloro-4-fluorophenyl)cyclopropane-1-carboxamido)-3-(trifluoromethyl)benzamide (F1225)

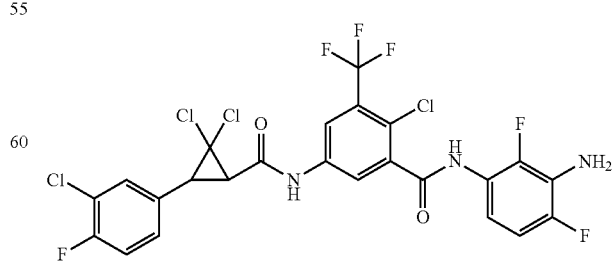

Isolated as a white solid (0.052 g, 83%).

trans-N-(3-Amino-2,4-difluorophenyl)-5-(2,2-di-
chloro-3-(3-chloro-4-fluoro-phenyl)cyclopropane-1-
carboxamido)-3-fluoro-2-methoxybenzamide
(F1226)

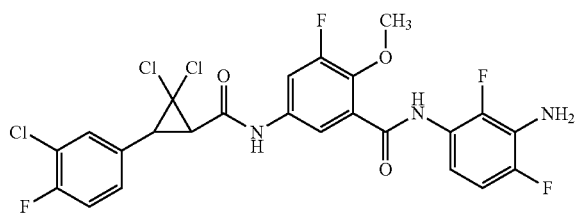 [SMILES: COc1c(F)cc(NC(=O)C2C(c3ccc(F)c(Cl)c3)C2(Cl)Cl)cc1C(=O)Nc1ccc(F)c(N)c1F]

Isolated as a white solid (0.053 g, 81%).

N-(3-Amino-2,4-difluorophenyl)-2-chloro-5-((1R,
3R)-2,2-dichloro-3-(3,4-dichlorophenyl)cyclopro-
pane-1-carboxamido)-3-fluorobenzamide (F1284)

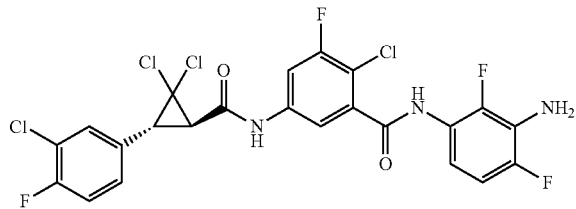 [SMILES: Nc1c(F)ccc(NC(=O)c2cc(NC(=O)[C@H]3[C@H](c4ccc(F)c(Cl)c4)C3(Cl)Cl)cc(F)c2Cl)c1F]

Isolated as a white solid (0.193 g, 91%).

N-(3-Amino-2,4-difluorophenyl)-2-chloro-5-((1R,
3R)-2,2-dichloro-3-(4-fluoro-3-(trifluoromethyl)
phenyl)cyclopropane-1-carboxamido)-3-fluorobenz-
amide (F1285)

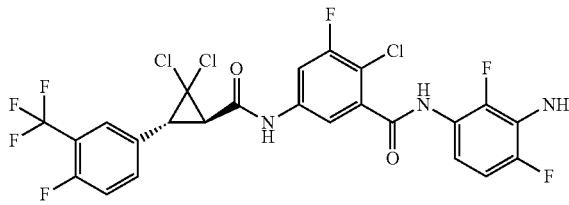

Isolated as a white solid (0.208 g, 93%).

trans-N-(3-Amino-2,4-difluorophenyl)-5-(2,2-di-
chloro-3-(3-chloro-4-fluorophenyl)cyclopropane-1-
carboxamido)-3-fluoro-2-methylbenzamide (F1286)

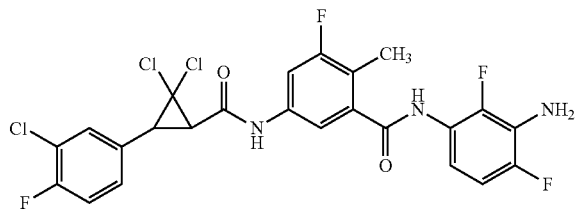 [SMILES: Cc1c(F)cc(NC(=O)C2C(c3ccc(F)c(Cl)c3)C2(Cl)Cl)cc1C(=O)Nc1ccc(F)c(N)c1F]

Isolated as a white solid (0.062 g, 89%).

trans-N-(4-Amino-2-methylphenyl)-2-chloro-5-(2,2-
dichloro-3-(3,5-dichlorophenyl)cyclopropane-1-
carboxamido)benzamide (DP4)

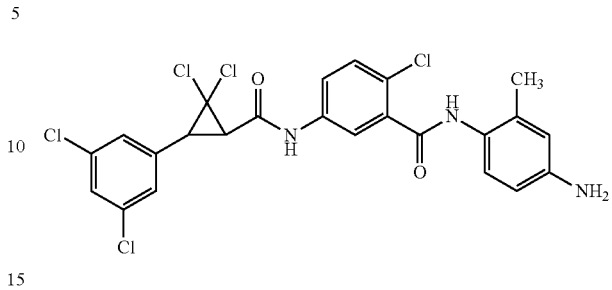

Isolated as a white solid (0.053 g, 83%).

N-(3-Amino-2,4-difluorophenyl)-2-chloro-5-((1R,
3R)-2,2-dichloro-3-(3,4-dichlorophenyl)cyclopro-
pane-1-carboxamido)benzamide (DP2)

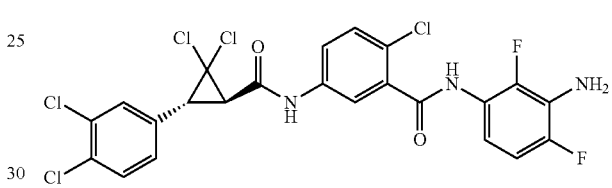

Isolated as a white solid (0.115 g, 89%).

N-(5-Amino-2,4-difluorophenyl)-2-chloro-5-((1R,
3R)-2,2-dichloro-3-(3,4-dichlorophenyl)cyclopro-
pane-1-carboxamido)benzamide (DP5)

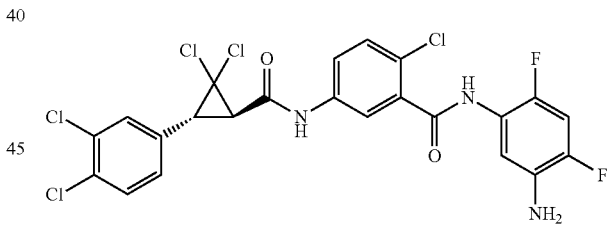

Isolated as a white solid (0.107 g, 96%).

Example 14: Preparation of trans-N-(2-amino-4-
fluorophenyl)-2-chloro-5-(2,2-dichloro-3-(3,4-di-
chlorophenyl)cyclopropane-1-carboxamido)benz-
amide (DP6)

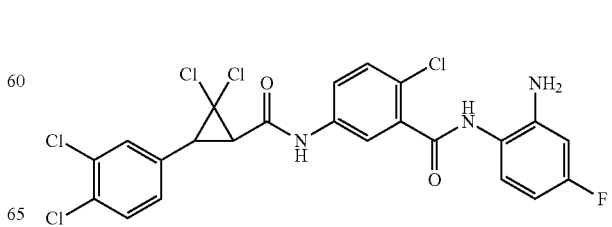

To a slurry of trans-2-chloro-5-(2,2-dichloro-3-(3,4-dichlorophenyl)cyclopropane-1-carboxamido)-N-(4-fluoro-2-nitrophenyl)benzamide (DP13) (0.880 g, 1.49 mmol) in a 4:1 mixture of methanol (14 mL) and water (4.7 mL) were added iron powder (0.415 g, 7.44 mmol) and ammonium chloride (0.239 g, 4.46 mmol), and the mixture was warmed to 55° C. and stirred for 21 hours. The reaction mixture was filtered through a pad of Celite®, washing with ethyl acetate. The filtrate was concentrated under reduced pressure, and the residue was partitioned between ethyl acetate (100 mL) and water (60 mL). The phases were separated and the organic phase was dried over magnesium sulfate, filtered, and concentrated to give a dark residue. The residue was dissolved in minimal ethyl acetate and adsorbed to Celite®. Purification by automated flash chromatography using a gradient of 0-40% ethyl acetate in hexanes as eluent gave the title compound as a yellow foam (0.66 g, 75%).

The following compounds were prepared in like manner to the procedure outlined in Example 14:

N-(2-Amino-3-fluorophenyl)-2-chloro-5-((1R,3R)-2,2-dichloro-3-(3-chloro-4-fluorophenyl)cyclopropane-1-carboxamido)benzamide (F1133)

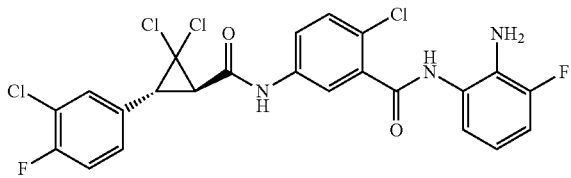 [SMILES: Nc1c(F)cccc1NC(=O)c1cc(NC(=O)[C@H]2[C@H](c3ccc(F)c(Cl)c3)C2(Cl)Cl)ccc1Cl]

Isolated as a light brown powder (0.030 g, 80%).

N-(2-Amino-4,5-difluorophenyl)-2-chloro-5-((1R,3R)-2,2-dichloro-3-(3-chloro-4-fluorophenyl)cyclopropane-1-carboxamido)benzamide (F1134)

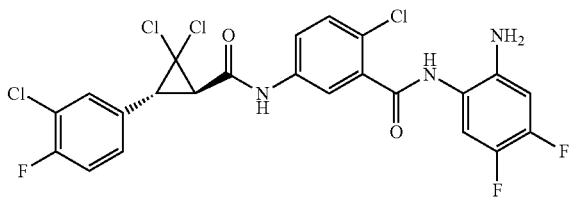 [SMILES: Nc1cc(F)c(F)cc1NC(=O)c1cc(NC(=O)[C@H]2[C@H](c3ccc(F)c(Cl)c3)C2(Cl)Cl)ccc1Cl]

Isolated as a light brown film (0.016 g, 34%).

N-(5-Amino-2-fluoro-4-methylphenyl)-2-chloro-5-((1R,3R)-2,2-dichloro-3-(3-chloro-4-fluorophenyl)cyclopropane-1-carboxamido)benzamide (F1135)

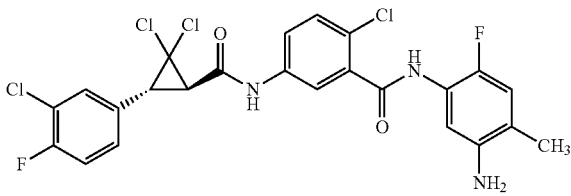

Isolated as a light blue solid (0.050 g, 59%).

Example 15: Preparation of trans-N-(4-amino-2,3-dimethylphenyl)-2-chloro-5-(2,2-dichloro-3-(3,5-dichlorophenyl)cyclopropane-1-carboxamido)benzamide (F1229)

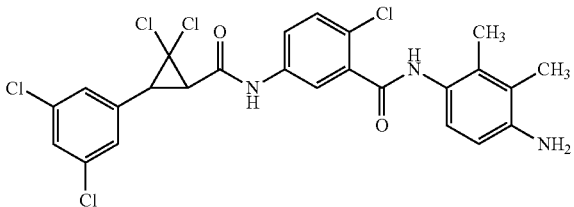 [SMILES: Cc1c(N)ccc(NC(=O)c2cc(NC(=O)C3C(c4cc(Cl)cc(Cl)c4)C3(Cl)Cl)ccc2Cl)c1C]

Iron powder (325 mesh; 0.065 g, 1.163 mmol) was added to a stirred solution of ethanol (10 mL) and concentrated HCl (0.01 mL, 0.116 mmol). The suspension was heated at 65° C. for 1 hour and then cooled to 55° C. A solution of ammonium chloride (0.045 g, 0.838 mmol) in water (3 mL) was added, followed by trans-2-chloro-5-(2,2-dichloro-3-(3,5-dichlorophenyl)cyclopropane-1-carboxamido)-N-(2,3-dimethyl-4-nitrophenyl)benzamide (F1180) (0.140 g, 0.233 mmol). The reaction mixture was heated to 60° C. for 2 hours, cooled, and filtered through a pad of Celite®. The filtrate was extracted with ethyl acetate (3×20 mL). The combined organic extracts were washed with water and brine, dried over anhydrous magnesium sulfate, filtered, and concentrated under reduced pressure on a rotary evaporator. Purification of the crude product by silica gel flash chromatography afforded the title compound as a tan solid (0.032 g, 23%)

The following compounds were prepared in like manner to the procedure outlined in Example 15:

trans-N-(4-Amino-2,5-dimethylphenyl)-2-chloro-5-(2,2-dichloro-3-(3,5-dichlorophenyl)cyclopropane-1-carboxamido)benzamide (F1257)

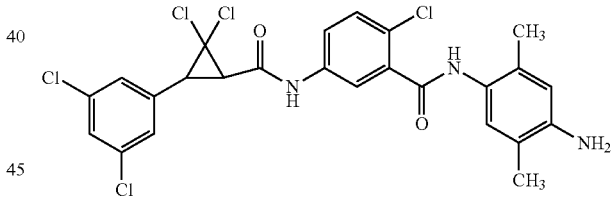

Isolated as a gold roam (0.047 g, 36%).

Example 16: Preparation of trans-2-chloro-5-(2,2-dichloro-3-(3,5-dichlorophenyl)cyclopropane-1-carboxamido)-N-(2,4-difluoro-3-hydroxyphenyl)benzamide (F1203)

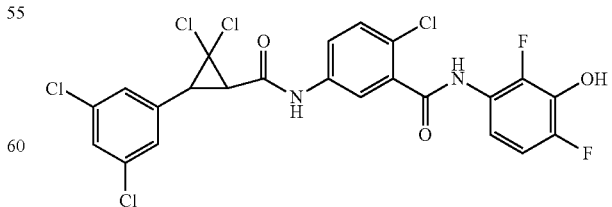

trans-3-(2-Chloro-5-(2,2-dichloro-3-(3,5-dichlorophenyl)cyclopropane-1-carboxamido)benzamido)-2,6-difluorophenyl acetate (F1193) (0.067 g, 0.108 mmol) was dissolved in methanol (2.2 mL) and treated with saturated sodium hydrogen carbonate solution (0.5 mL) with stirring at room temperature. Analysis of the reaction mixture after 1 hour by thin layer chromatography (2:1 hexanes-ethyl acetate) indicated that the reaction was complete. The reaction mixture was partitioned between ethyl acetate and 1N aqueous hydrochloric acid, the layers were separated, and the organic layer was dried over sodium sulfate. Purification by preparative thin layer chromatography (20×20×0.2 cm plate, 3:1 hexanes-ethyl acetate) gave the title compound as a tan foam (0.06 g, 96%).

Example 17: Preparation of tert-butyl-N-tert-butoxycarbonyl-N-[3-[2-chloro-[5-[[(1R,3R)-2,2-dichloro-3-(3,5-dichlorophenyl)cyclopropanecarbonyl]amino]-3-fluorobenzoyl]amino]-2,6-difluorophenyl]carbamate (F1292)

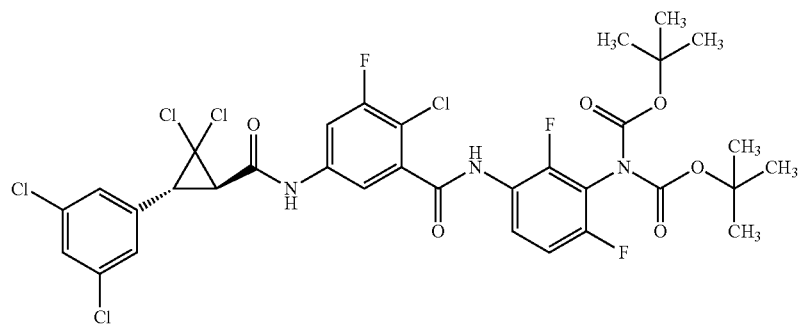 [SMILES: CC(C)(C)OC(=O)N(C(=O)OC(C)(C)C)c1c(F)ccc(NC(=O)c2cc(NC(=O)[C@H]3[C@H](c4cc(Cl)cc(Cl)c4)C3(Cl)Cl)cc(F)c2Cl)c1F]

(1R,3R)-2,2-Dichloro-3-(3,5-dichlorophenyl)cyclopropane-1-carboxylic acid (C91) (0.131 g, 0.436 mmol) as a slurry in toluene (4 mL) was treated with oxalyl chloride (0.382 mL, 4.36 mmol) and a single drop of N,N-dimethyl formamide with stirring at room temperature. After the mixture became homogeneous and gas evolution ceased, the solution was concentrated to a clear oil. tert-Butyl-N-tert-butoxycarbonyl-N-(3-(5-amino-2-chloro-3-fluorobenzamido)-2,6-difluorophenyl)carbamate (C108) (0.225 g, 0.436 mmol) and sodium bicarbonate (0.110 g, 1.31 mmol) were added to the flask as solids followed by ethyl acetate (4 mL), and the cloudy mixture was allowed to stir at room temperature for 18 hours. Analysis of an aliquot by liquid chromatography/mass spectroscopy indicated complete conversion to the desired compound. The reaction mixture was partitioned between ethyl acetate and an aqueous mixture of sodium hydrogen carbonate and sodium chloride. The layers were separated and the organic layer was dried over sodium sulfate, filtered and concentrated to an oil. Trituration with hexanes and drying yielded the title compound as an off-white solid (0.347 g, 100%).

The following compounds were prepared in like manner to the procedure outlined in Example 17:

tert-Butyl-N-tert-butoxycarbonyl-N-(3-(2-chloro-5-((1R,3R)-2,2-dichloro-3-(3,4,5-trichlorophenyl)cyclopropane-1-carboxamido)-3-fluorobenzamido)-2,6-difluorophenyl)carbamate (F1294)

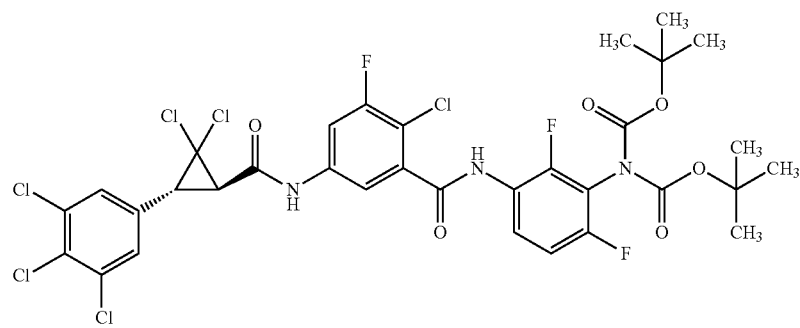 [SMILES: CC(C)(C)OC(=O)N(C(=O)OC(C)(C)C)c1c(F)ccc(NC(=O)c2cc(NC(=O)[C@H]3[C@H](c4cc(Cl)c(Cl)c(Cl)c4)C3(Cl)Cl)cc(F)c2Cl)c1F]

Isolated as an off-white solid (0.367 g, 100%).

tert-Butyl (3-(2-chloro-5-((1R,3R)-2,2-dichloro-3-(3,5-dichlorophenyl)cyclopropane-1-carboxamido)-3-fluorobenzamido)-2,6-difluorophenyl)carbamate (F1326)

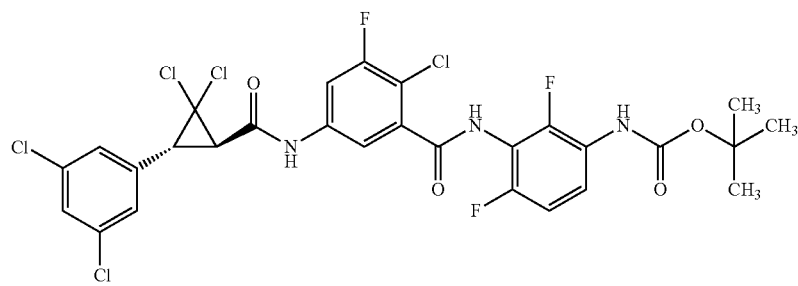 [SMILES: CC(C)(C)OC(=O)Nc1ccc(F)c(NC(=O)c2cc(NC(=O)[C@H]3[C@H](c4cc(Cl)cc(Cl)c4)C3(Cl)Cl)cc(F)c2Cl)c1F]

Isolated as a yellow glass (0.257 g, 100%).

tert-Butyl (3-(2-chloro-5-((1R,3R)-2,2-dichloro-3-(3,4,5-trichlorophenyl)cyclopropane-1-carboxamido)-3-fluorobenzamido)-2,4-difluorophenyl)carbamate (F1327)

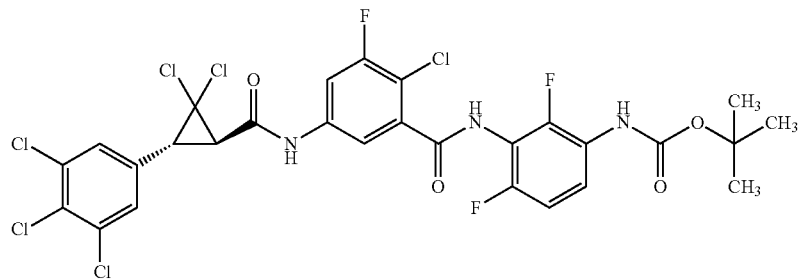 [SMILES: CC(C)(C)OC(=O)Nc1ccc(F)c(NC(=O)c2cc(NC(=O)[C@H]3[C@H](c4cc(Cl)c(Cl)c(Cl)c4)C3(Cl)Cl)cc(F)c2Cl)c1F]

Isolated as a yellow glass (0.240 g, 99%).

tert-Butyl (3-(2-chloro-5-((1R,3R)-2,2-dichloro-3-(3,4-dichlorophenyl)cyclopropane-1-carboxamido)-3-fluorobenzamido)-2,4-difluorophenyl)carbamate (F1328)

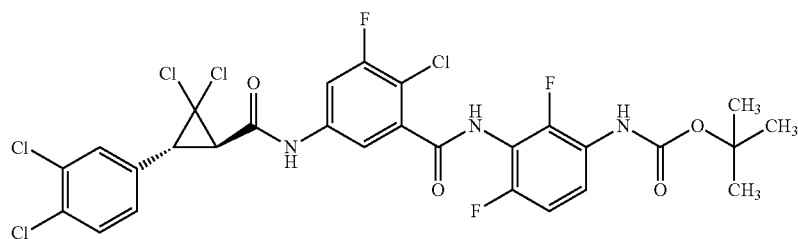 [SMILES: CC(C)(C)OC(=O)Nc1ccc(F)c(NC(=O)c2cc(NC(=O)[C@H]3[C@H](c4ccc(Cl)c(Cl)c4)C3(Cl)Cl)cc(F)c2Cl)c1F]

Isolated as a yellow glass (0.245 g, 100%).

tert-Butyl (3-(2-chloro-5-(((1R,3R)-2,2-dichloro-3-(4-fluoro-3-(trifluoromethyl)phenyl)cyclopropane-1-carboxamido)-3-fluorobenzamido)-2,4-difluorophenyl)carbamate (F1329)

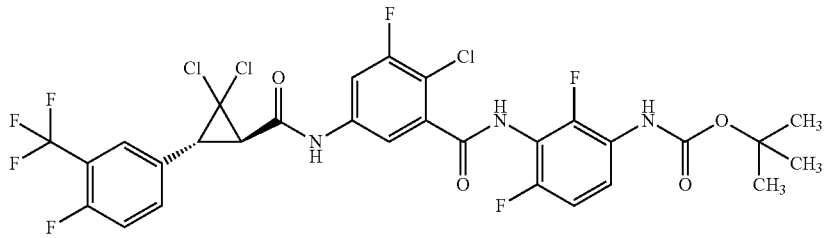 [SMILES: CC(C)(C)OC(=O)Nc1ccc(F)c(NC(=O)c2cc(NC(=O)[C@H]3[C@H](c4ccc(F)c(C(F)(F)F)c4)C3(Cl)Cl)cc(F)c2Cl)c1F]

Isolated as a light yellow glass (0.242 g, 100%).

Example 18: Preparation of trans-5-(3-(3-bromo-4,5-dichlorophenyl)-2,2-dichlorocyclopropane-1-carboxamido)-2-chloro-N-(4-fluorophenyl)benzamide (F1005)

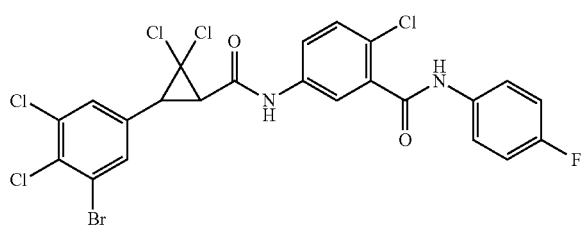 [SMILES: O=C(Nc1ccc(F)cc1)c1cc(NC(=O)C2C(c3cc(Cl)c(Cl)c(Br)c3)C2(Cl)Cl)ccc1Cl]

Dichloromethane (2 mL) was added to a 20 mL glass vial containing 5-amino-2-chloro-N-(4-fluorophenyl)benzamide (C98) (0.105 g, 0.396 mmol), 4-dimethylaminopyridine (0.053 g, 0.436 mmol), trans-3-(3-bromo-4,5-dichlorophenyl)-2,2-dichlorocyclopropane-1-carboxylic acid (C29) (0.150 g, 0.396 mmol) and 1-ethyl-3-(3-dimethylaminopropyl)carbodiimide hydrochloride (0.114 g, 0.594 mmol) at room temperature. The reaction mixture was stirred at room temperature for 72 hours, concentrated, and purified by silica gel flash column chromatography using 0-100% ethyl acetate/hexanes as eluent to give the title compound as a yellow foam (0.118 g, 45%).

The following compounds were prepared in like manner to the procedure outlined in Example 18:

trans-2-Chloro-5-(2,2-dichloro-3-(2-chloro-5-(trifluoromethyl)phenyl)cyclopropane-1-carboxamido)-N-(2,4-difluorophenyl)benzamide (F1004)

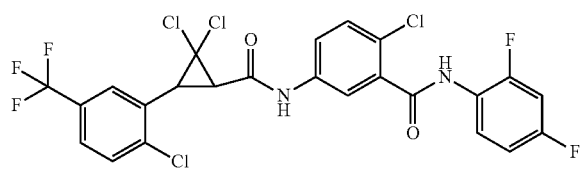 [SMILES: O=C(Nc1ccc(F)cc1F)c1cc(NC(=O)C2C(c3cc(C(F)(F)F)ccc3Cl)C2(Cl)Cl)ccc1Cl]

Isolated as a white foam (0.056 g, 61%).

trans-5-(3-(3-Bromo-4,5-dichlorophenyl)-2,2-dichlorocyclopropane-1-carboxamido)-2-chloro-N-(4-fluorophenyl)benzamide (F1005)

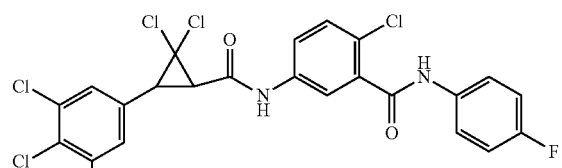

Isolated as a yellow foam (0.1182 g, 45%).

trans-5-(3-(4-Bromo-3,5-dichlorophenyl)-2,2-dichlorocyclopropane-1-carboxamido)-2-chloro-N-(2,4-difluorophenyl)benzamide (F1006)

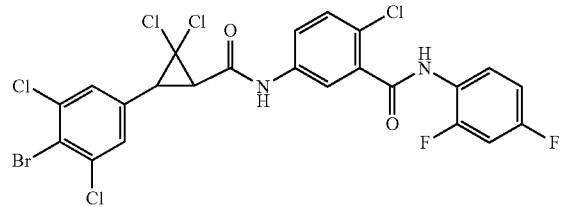

Isolated as a yellow foam (0.0959 g, 77%).

trans-5-(3-(3-Bromo-4,5-dichlorophenyl)-2,2-dichlorocyclopropane-1-carboxamido)-2-chloro-N-(2,4-difluorophenyl)benzamide (F1007)

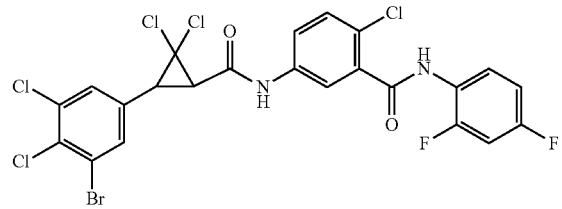 [SMILES: O=C(Nc1ccc(F)cc1F)c1cc(NC(=O)C2C(c3cc(Cl)c(Cl)c(Br)c3)C2(Cl)Cl)ccc1Cl]

Isolated as a yellow foam (0.0878 g, 70%).

trans-2-Chloro-5-(2,2-dichloro-3-(perfluorophenyl)cyclopropane-1-carboxamido)-N-(2,4-difluorophenyl)benzamide (F1009)

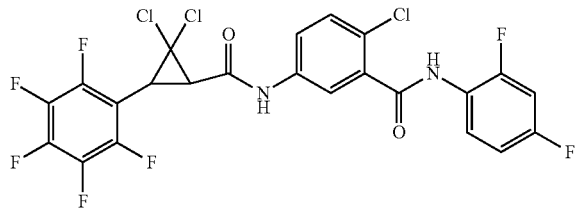 [SMILES: O=C(Nc1ccc(F)cc1F)c1cc(NC(=O)C2C(c3c(F)c(F)c(F)c(F)c3F)C2(Cl)Cl)ccc1Cl]

Isolated as a white foam (0.068 g, 71%).

trans-5-(3-(3-Bromo-4,5-difluorophenyl)-2,2-dichlorocyclopropane-1-carboxamido)-2-chloro-N-(2,4-difluorophenyl)benzamide (F1011)

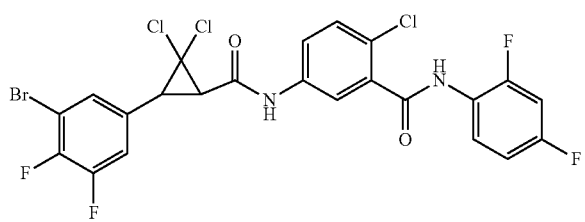 [SMILES: O=C(Nc1ccc(F)cc1F)c1cc(NC(=O)C2C(c3cc(F)c(F)c(Br)c3)C2(Cl)Cl)ccc1Cl]

Isolated as a white foam (0.060 g, 43%).

cis-5-(3-(3-Bromo-4,5-difluorophenyl)-2,2-dichlorocyclopropane-1-carboxamido)-2-chloro-N-(2,4-difluorophenyl)benzamide (F1012)

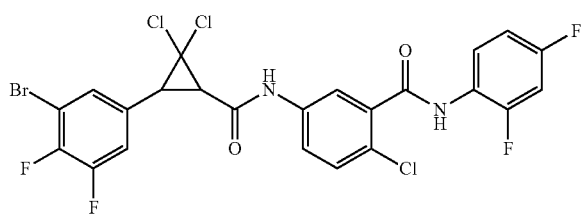

Isolated as a white foam (0.031 g, 22%).

trans-2-Chloro-5-(2,2-dichloro-3-(3,4-dichloro-5-fluorophenyl)cyclopropane-1-carboxamido)-N-(2,4-difluorophenyl)benzamide (F1024)

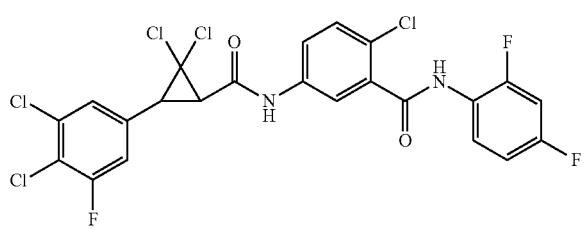

Isolated as a white foam (0.071 g, 49%).

cis-2-Chloro-5-(2,2-dichloro-3-(3,4-dichloro-5-fluorophenyl)cyclopropane-1-carboxamido)-N-(2,4-difluorophenyl)benzamide (F1025)

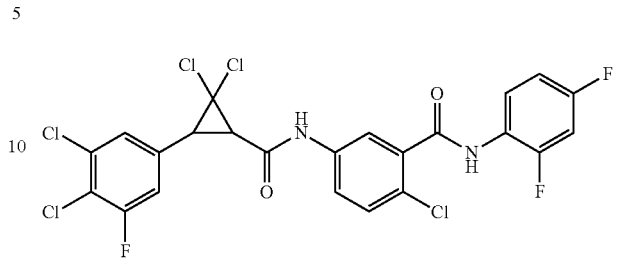

Isolated as a white solid (0.023 g, 16%).

trans-5-(3-(3-Bromo-5-(pentafluoro-$\lambda^6$-sulfanyl)phenyl)-2,2-dichlorocyclopropane-1-carboxamido)-2-chloro-N-(2,4-difluorophenyl)benzamide (F1031)

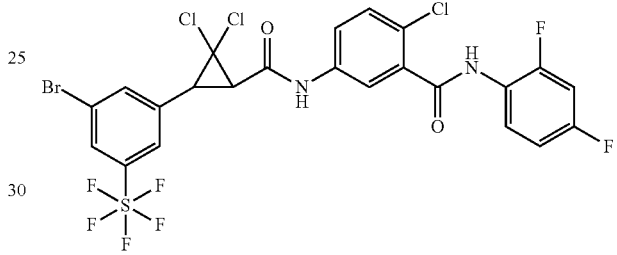

Isolated as a white foam (0.066 g, 52%).

cis-5-(3-(3-Bromo-5-(pentafluoro-$\lambda^6$-sulfanyl)phenyl)-2,2-dichlorocyclopropane-1-carboxamido)-2-chloro-N-(2,4-difluorophenyl)benzamide (F1032)

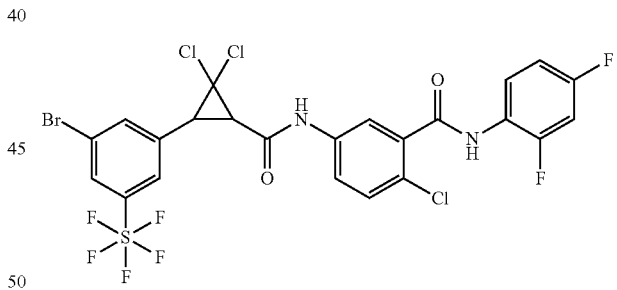

Isolated as a clear colorless oil (0.031 g, 24%).

cis-2-Chloro-5-(2,2-dichloro-3-(3-chloro-2,4-difluorophenyl)cyclopropane-1-carboxamido)-N-(2,4-difluorophenyl)benzamide (F1033)

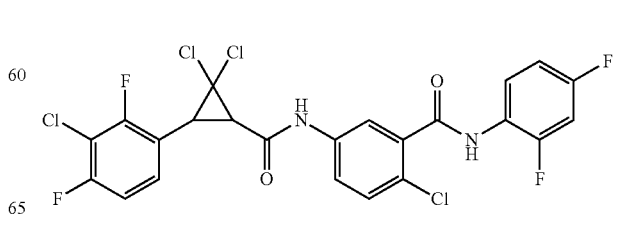

Isolated as a white foam (0.043 g, 29%).

109 trans-2-Chloro-5-(2,2-dichloro-3-(3-chloro-2,4-difluorophenyl)cyclopropane-1-carboxamido)-N-(2,4-difluorophenyl)benzamide (F1034)

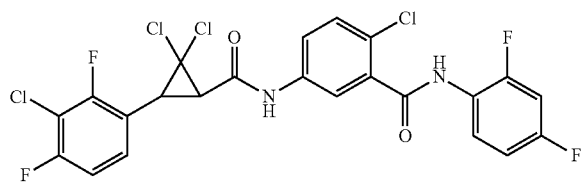 [SMILES: O=C(Nc1ccc(F)cc1F)c1cc(NC(=O)C2C(c3ccc(F)c(Cl)c3F)C2(Cl)Cl)ccc1Cl]

Isolated as a white foam (0.033 g, 22%).

trans-2-Cyano-5-(2,2-dichloro-3-(3,5-dichlorophenyl)cyclopropane-1-carboxamido)-N-(2,4-difluorophenyl)-N-methylbenzamide (F1039)

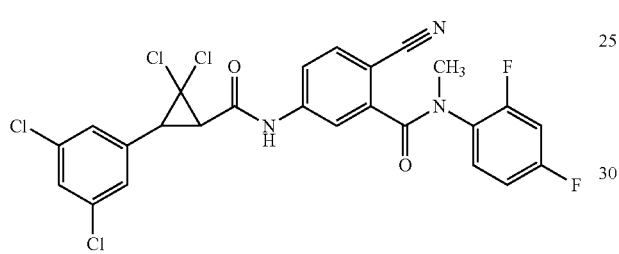

Isolated as a white foam (0.043 g, 38%).

trans-N-Allyl-2-chloro-N-(2-cyano-4-fluorophenyl)-5-(2,2-dichloro-3-(3,5-dichlorophenyl)cyclopropane-1-carboxamido)benzamide (F1055)

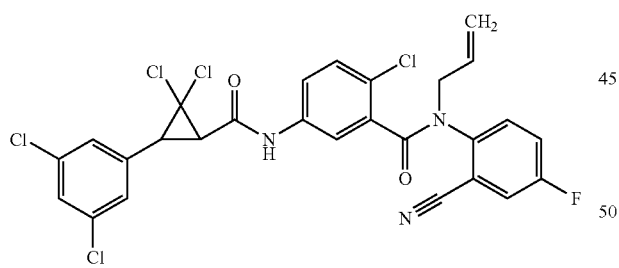

Isolated as an orange foam (0.144 g, 47%).

110 trans-2-Chloro-5-(3-(3,5-dichlorophenyl)-2,2-difluorocyclopropane-1-carboxamido)-N-(4-fluorophenyl)benzamide (F1057)

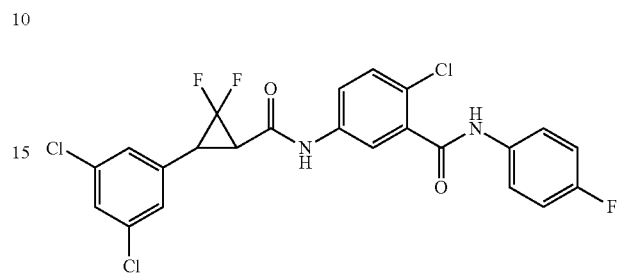

Isolated as an off-white solid (0.128 g, 84%).

trans-2-Chloro-5-(3-(3,5-dichlorophenyl)-2,2-difluorocyclopropane-1-carboxamido)-N-(2,4-difluorophenyl)benzamide (F1058)

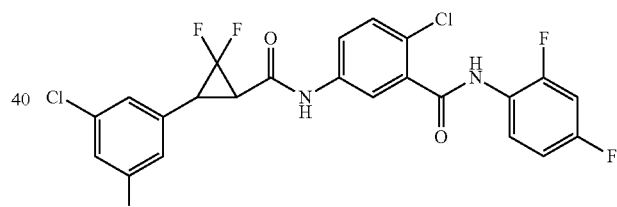

Isolated as a white powder (0.127 g, 80%).

trans-tert-Butyl (3-(2-chloro-5-(3-(3,5-dichlorophenyl)-2,2-difluorocyclopropane-1-carboxamido)benzamido)-2,6-difluorophenyl)carbamate (F1070)

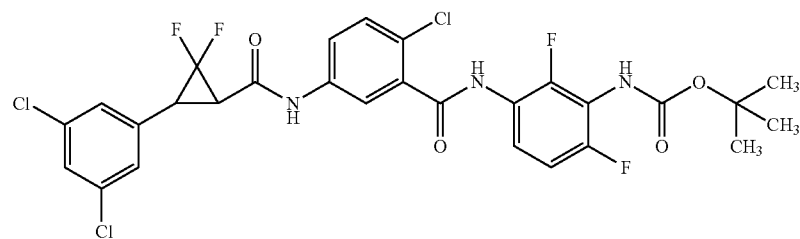 [SMILES: CC(C)(C)OC(=O)Nc1c(F)ccc(NC(=O)c2cc(NC(=O)C3C(c4cc(Cl)cc(Cl)c4)C3(F)F)ccc2Cl)c1F]

Isolated as a white powder (0.150 g, 83%).

111 trans-2-Chloro-5-(2,2-dichloro-3-(3,4-dichlorophenyl)cyclopropane-1-carboxamido)-N-(2,4-difluoro-3-(methylamino)phenyl)-N-methylbenzamide (F1071)

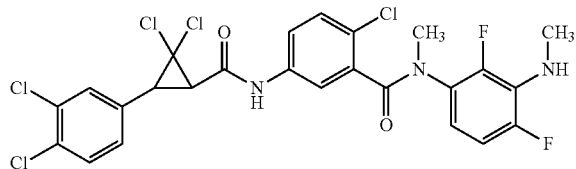 [SMILES: CNc1c(F)ccc(N(C)C(=O)c2cc(NC(=O)C3C(c4ccc(Cl)c(Cl)c4)C3(Cl)Cl)ccc2Cl)c1F]

Isolated as a beige foam (0.061 g, 95%).

trans-2-Chloro-N-(2-cyano-4-fluorophenyl)-5-(2,2-dichloro-3-(3,5-dichlorophenyl)cyclopropane-1-carboxamido)-N-(prop-2-yn-1-yl)benzamide (F1072)

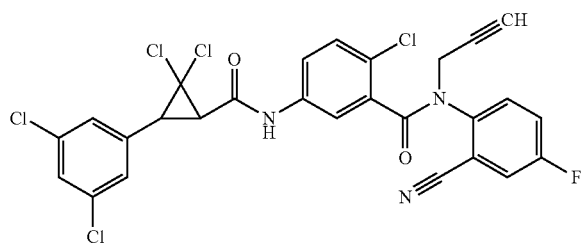 [SMILES: C#CCN(C(=O)c1cc(NC(=O)C2C(c3cc(Cl)cc(Cl)c3)C2(Cl)Cl)ccc1Cl)c1ccc(F)cc1C#N]

Isolated as a yellow foam (0.066 g, 50%).

trans-(2-Chloro-N-(2-cyano-4-fluorophenyl)-5-(2,2-dichloro-3-(3,5-dichlorophenyl)cyclopropane-1-carboxamido)benzamido)methyl acetate (F1084)

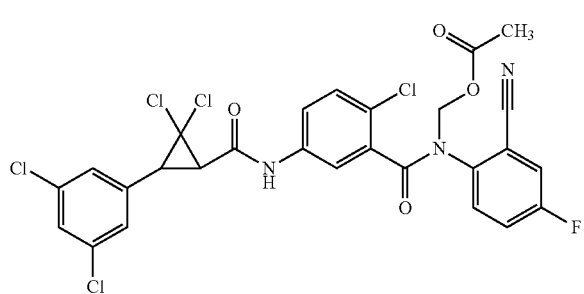 [SMILES: CC(=O)OCN(C(=O)c1cc(NC(=O)C2C(c3cc(Cl)cc(Cl)c3)C2(Cl)Cl)ccc1Cl)c1ccc(F)cc1C#N]

Isolated as a yellow film (0.026 g, 22%).

trans-2-Chloro-5-(2,2-dichloro-3-(4-iodophenyl)cyclopropane-1-carboxamido)-N-(2,4-difluorophenyl)benzamide (F1087)

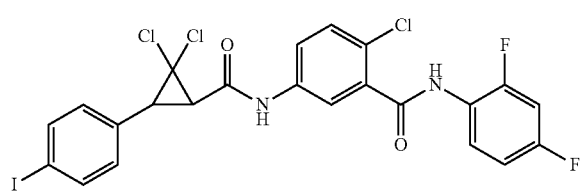 [SMILES: O=C(Nc1ccc(F)cc1F)c1cc(NC(=O)C2C(c3ccc(I)cc3)C2(Cl)Cl)ccc1Cl]

Isolated as an off-white powder (0.14 g, 72%).

112 trans-2-Chloro-5-(2,2-dichloro-3-(3-iodophenyl)cyclopropane-1-carboxamido)-N-(2,4-difluorophenyl)benzamide (F1088)

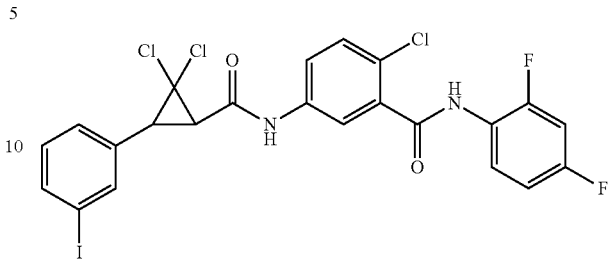

Isolated as a brown semisolid (0.14 g, 68%).

trans-2-Chloro-5-(2,2-dichloro-3-(4-(pentafluoro-$\lambda^6$-sulfanyl)phenyl)cyclopropane-1-carboxamido)-N-(2,4-difluorophenyl)benzamide (F1089)

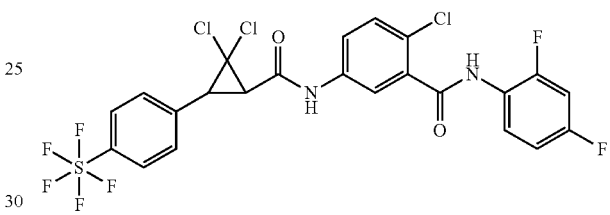

Isolated as a white foam (0.14 g, 72%).

trans-2-Chloro-5-(2,2-dichloro-3-(3-(pentafluoro-$\lambda^6$-sulfanyl)phenyl)cyclopropane-1-carboxamido)-N-(2,4-difluorophenyl)benzamide (F1090)

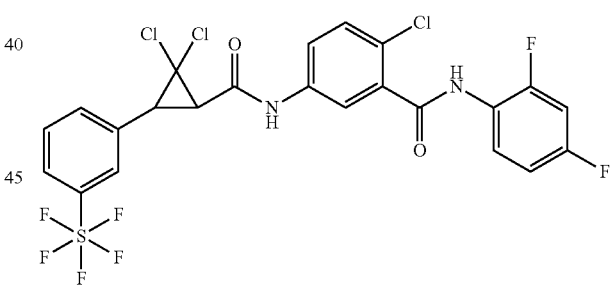

Isolated as a brown semisolid (0.15 g, 73%).

trans-2-Chloro-N-(2-cyano-4-fluorophenyl)-5-(2,2-dichloro-3-(3,5-dichlorophenyl)cyclopropane-1-carboxamido)-N-ethylbenzamide (F1091)

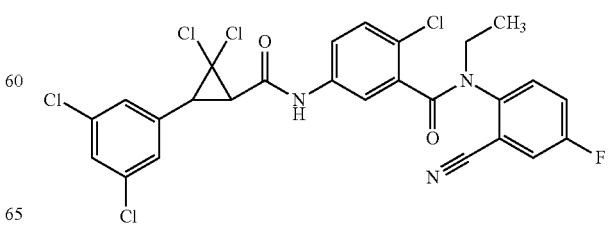

Isolated as a colorless film (0.083 g, 43%).

113 trans-N-Benzyl-2-chloro-N-(2-cyano-4-fluorophenyl)-5-(2,2-dichloro-3-(3,5-dichlorophenyl)cyclopropane-1-carboxamido)benzamide (F1099)

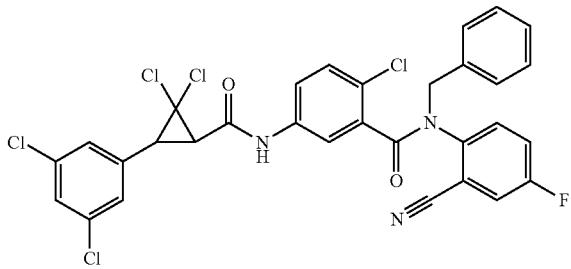 [SMILES: N#Cc1cc(F)ccc1N(Cc1ccccc1)C(=O)c1cc(NC(=O)C2C(c3cc(Cl)cc(Cl)c3)C2(Cl)Cl)ccc1Cl]

Isolated as a yellow foam (0.228 g, 60%).

trans-N-(3-Amino-2,4-difluorophenyl)-2-chloro-5-(2,2-dichloro-3-(4-iodophenyl)cyclopropane-1-carboxamido)benzamide (F1140)

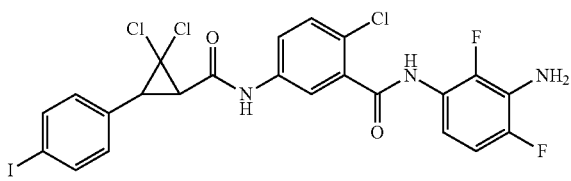 [SMILES: Nc1c(F)ccc(NC(=O)c2cc(NC(=O)C3C(c4ccc(I)cc4)C3(Cl)Cl)ccc2Cl)c1F]

Isolated as an off-white powder (0.087 g, 42%).

trans-N-(3-Amino-2,4-difluorophenyl)-2-chloro-5-(2,2-dichloro-3-(3-iodophenyl)cyclopropane-1-carboxamido)benzamide (F1141)

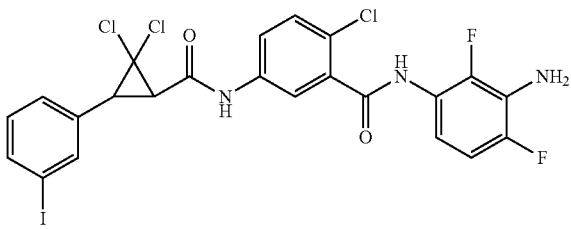 [SMILES: Nc1c(F)ccc(NC(=O)c2cc(NC(=O)C3C(c4cccc(I)c4)C3(Cl)Cl)ccc2Cl)c1F]

Isolated as a gray foam (0.081 g, 40%).

trans-N-(3-Amino-2,4-difluorophenyl)-2-chloro-5-(2,2-dichloro-3-(4-(pentafluoro-$\lambda^6$-sulfanyl)phenyl)cyclopropane-1-carboxamido)benzamide (F1142)

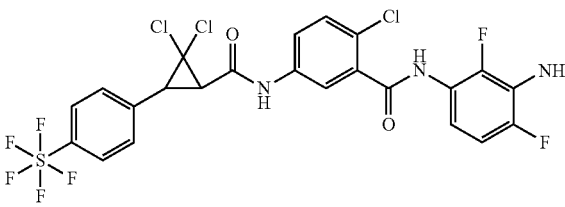

Isolated as a white powder (0.073 g, 36%).

114 trans-N-(3-Amino-2,4-difluorophenyl)-2-chloro-5-(2,2-dichloro-3-(3-(pentafluoro-$\lambda^6$-sulfanyl)phenyl)cyclopropane-1-carboxamido)benzamide (F1143)

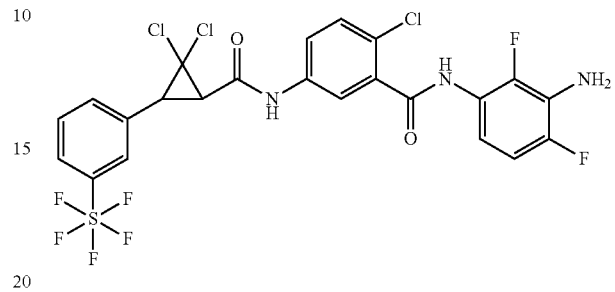

Isolated as an off-white foam (0.074 g, 36%).

trans-2-chloro-5-(2,2-dichloro-3-(3-iodophenyl)cyclopropane-1-carboxamido)-N-(3-(2,2-difluoroacetamido)-2,4-difluorophenyl)benzamide (F1281)

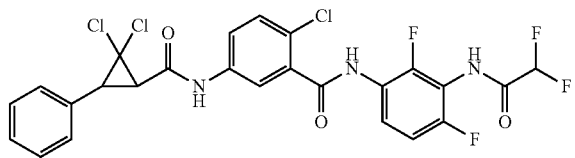

Isolated as a tan powder (0.078 g, 49%).

trans-2-Chloro-5-(2,2-dichloro-3-(3-(pentafluoro-$\lambda^6$-sulfanyl)phenyl)cyclopropane-1-carboxamido)-N-(3-(2,2-difluoroacetamido)-2,4-difluorophenyl)benzamide (F1293)

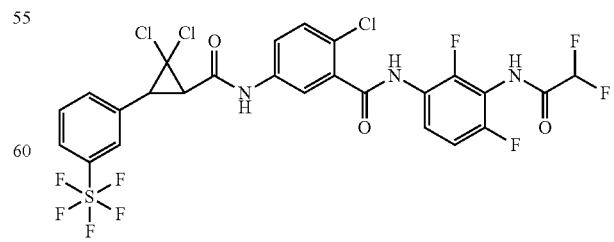

Isolated as a pale yellow foam (0.046 g, 29%).

tert-butyl N-tert-butoxycarbonyl-N-[3-[[2-chloro-5-[[(1R,3R)-2,2-dichloro-3-(3,4-dichlorophenyl)cyclopropanecarbonyl]amino]benzoyl]-methyl-amino]-2,6-difluoro-phenyl]carbamate (CF1)

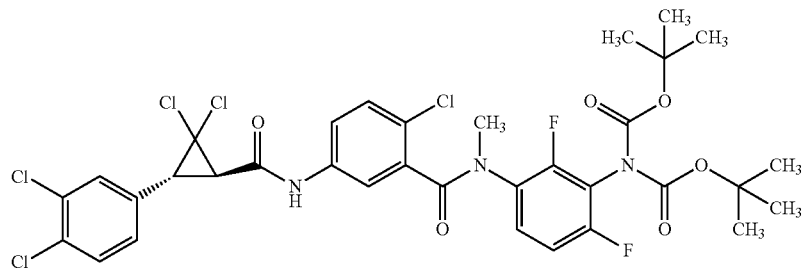 [SMILES: CN(C(=O)c1cc(NC(=O)[C@H]2[C@H](c3ccc(Cl)c(Cl)c3)C2(Cl)Cl)ccc1Cl)c1ccc(F)c(N(C(=O)OC(C)(C)C)C(=O)OC(C)(C)C)c1F]

Isolated as a white foam (0.149 g, 65%): $^1$H NMR (500 MHz, Methanol-d$_4$) δ 7.92 (s, 0H), 7.84-7.59 (m, 2H), 7.59-7.42 (m, 4H), 7.28 (ddd, J=15.3, 8.4, 2.1 Hz, 1H), 7.22 (d, J=8.9 Hz, 1H), 7.00 (t, J=9.2 Hz, 1H), 3.55 (dd, J=16.9, 8.3 Hz, 1H), 3.41 (s, 3H), 3.25-3.19 (m, 1H), 3.13 (d, J=8.3 Hz, 1H), 1.41 (s, 8H), 1.34-1.22 (m, 9H); $^{19}$F NMR (471 MHz, Methanol-d$_4$) δ −119.20, −120.57, −121.26 (dt, J=9.4, 4.8 Hz), −124.91, −125.98; ESIMS m/z 792 ([M−H]$^−$).

trans tert-Butyl (3-(2-chloro-5-(2,2-dichloro-3-(3,4-dichlorophenyl)cyclopropane-1-carboxamido)-N-methylbenzamido)-2,6-difluorophenyl)(methyl)carbamate (CF2)

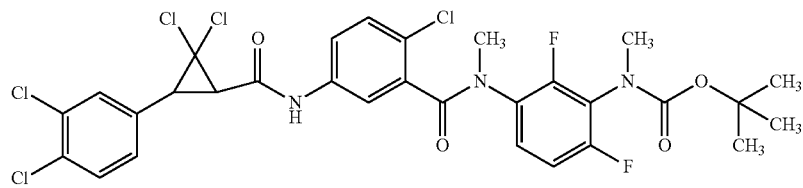 [SMILES: CN(C(=O)c1cc(NC(=O)C2C(c3ccc(Cl)c(Cl)c3)C2(Cl)Cl)ccc1Cl)c1ccc(F)c(N(C)C(=O)OC(C)(C)C)c1F]

Isolated as a white foam (0.081 g, 40.6%): $^1$H NMR (500 MHz, Methanol-d$_4$) δ 7.90 (d, J=24.5 Hz, 1H), 7.71 (d, J=13.8 Hz, 1H), 7.56-7.44 (m, 3H), 7.38 (s, 1H), 7.31-7.25 (m, 1H), 7.22 (dd, J=8.9, 1.8 Hz, 1H), 6.93 (t, J=9.1 Hz, 1H), 3.55 (dd, J=22.7, 8.3 Hz, 1H), 3.42 (d, J=1.7 Hz, 3H), 3.22 (q, J=3.3 Hz, 1H), 3.18 (s, 0H), 3.14 (d, J=8.1 Hz, 1H), 3.09 (s, 1H), 2.93 (s, 2H), 1.53-1.45 (m, 2H), 1.39-1.27 (m, 6H), 1.26-1.15 (m, 3H); $^{19}$F NMR (471 MHz, Methanol-d$_4$) δ −118.58 (d, J=165.0 Hz), −119.80, −120.43, −124.14 (d, J=231.2 Hz), −126.04 (d, J=428.3 Hz); ESIMS m/z 730 ([M+Na]$^+$).

tert-Butyl-N-((tert-butoxy)carbonyl)-N-(3-(2-chloro-5-((1R,3R)-2,2-dichloro-3-(3,4-dichlorophenyl)cyclopropane-1-carboxamido)benzamido)-2,6-difluorophenyl)carbamate (DP7)

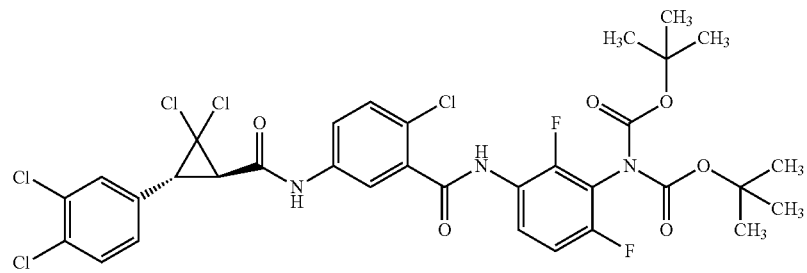 [SMILES: CC(C)(C)OC(=O)N(C(=O)OC(C)(C)C)c1c(F)ccc(NC(=O)c2cc(NC(=O)[C@H]3[C@H](c4ccc(Cl)c(Cl)c4)C3(Cl)Cl)ccc2Cl)c1F]

Isolated as a white solid (0.174 g, 67%).

trans-tert-Butyl (4-(2-chloro-5-(2,2-dichloro-3-(3,4-dichlorophenyl)cyclopropane-1-carboxamido)benzamido)-3-methylphenyl)carbamate (DP14)

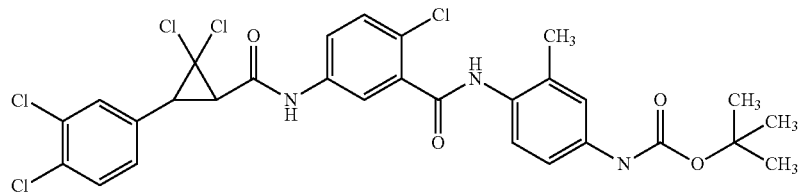 [SMILES: Cc1cc(NC(=O)OC(C)(C)C)ccc1NC(=O)c1cc(NC(=O)C2C(c3ccc(Cl)c(Cl)c3)C2(Cl)Cl)ccc1Cl]

Isolated as a white solid (2.75 g, 78%).

(1R,3R)-2,2-Dichloro-N-(4-chloro-3-(1,2-dimethyl-2-phenylhydrazine-1-carbonyl)phenyl)-3-(3,4-dichlorophenyl)cyclopropane-1-carboxamide (F2544)

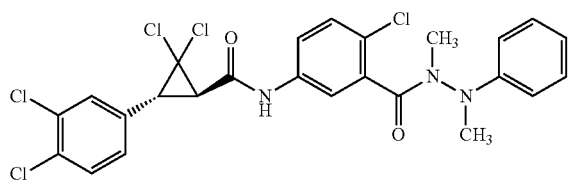 [SMILES: CN(C(=O)c1cc(NC(=O)[C@H]2[C@H](c3ccc(Cl)c(Cl)c3)C2(Cl)Cl)ccc1Cl)N(C)c1ccccc1]

Isolated as a pale orange foam (0.266 g, 66%).

Example 19: Preparation of trans-N-(3-amino-2,4-difluorophenyl)-2-chloro-5-(2,2-dichloro-3-(4-fluoro-3-(trifluoromethyl)phenyl)cyclopropane-1-carboxamido)-N-methylbenzamide (F1112)

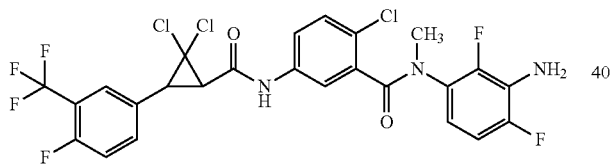

Step 1: tert-Butyl N-tert-butoxycarbonyl-N-[3-[(2-chloro-5-nitro-benzoyl)-methyl-amino]-2,6-difluoro-phenyl]carbamate (C144) (0.138 g, 0.225 mmol), ammonium chloride (0.0409 g, 0.764 mmol), and iron powder (0.0711 g, 1.273 mmol) were taken up in methanol (2.4 mL) and water (0.8 mL) to give a black suspension. The reaction mixture was heated to 60° C. for 5 hours. The reaction mixture was filtered and the filtrate was washed with ethyl acetate. The combined organic layers were washed with water, dried over magnesium sulfate, and evaporated to give the crude material as an orange oil, which was used without purification.

Step 2: The crude aniline was dissolved in dichloromethane (2422 µL) to give an orange solution. 4.0 M Hydrogen chloride in 1,4-dioxane (606 µL, 2.422 mmol) was added and the reaction mixture was stirred at room temperature overnight. The volatiles were removed. To the residue was added trans-2,2-dichloro-3-(4-fluoro-3-(trifluoromethyl)phenyl)cyclopropane-1-carboxylic acid (C76) (0.077 g, 0.242 mmol) and N,N-dimethylpyridin-4-amine (0.0592 g, 0.484 mmol) in dichloromethane (2422 µL) to give a yellow suspension. N-(3-Dimethylaminopropyl)-N'-ethylcarbodiimide hydrochloride (69.6 mg, 0.363 mmol) was added and everything went into solution, and the reaction mixture darkened to a deep blue color. The reaction mixture was stirred at room temperature for 3 hours. The volatiles were removed. Purification by flash column chromatography using 0-100% ethyl acetate/hexanes as eluent provided the title compound as a pale yellow foam (0.061 g, 39%).

The following compounds were prepared in like manner to the procedure outlined in Example 19:

trans-N-Allyl-N-(3-amino-2,4-difluorophenyl)-2-chloro-5-(2,2-dichloro-3-(4-fluoro-3-(trifluoromethyl)phenyl)cyclopropene-1-carboxamido)benzamide (F1113)

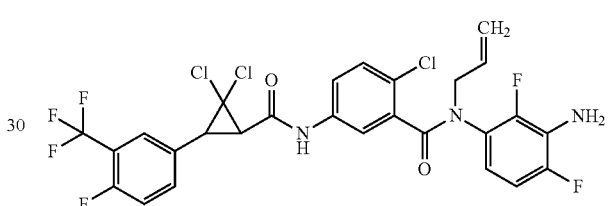

Isolated as a yellow foam (0.042 g, 49%).

trans-N-(3-Amino-2,4-difluorophenyl)-2-chloro-5-(2,2-dichloro-3-(4-fluoro-3-(trifluoromethyl)phenyl)cyclopropane-1-carboxamido)-N-(prop-2-yn-1-yl)benzamide (F1114)

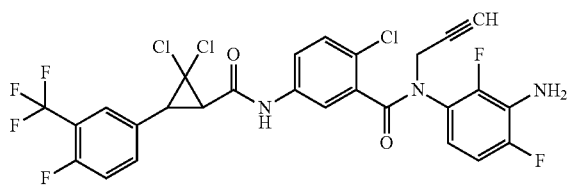 [SMILES: C#CCN(C(=O)c1cc(NC(=O)C2C(c3ccc(F)c(C(F)(F)F)c3)C2(Cl)Cl)ccc1Cl)c1ccc(F)c(N)c1F]

Isolated as a yellow foam (0.054 g, 35%).

Example 20: Preparation of trans-2,6-dichloro-3-(2,2-dichloro-3-(3-chloro-4-fluorophenyl)cyclopropane-1-carboxamido)-N-(2,4-difluorophenyl)benzamide (F1105)

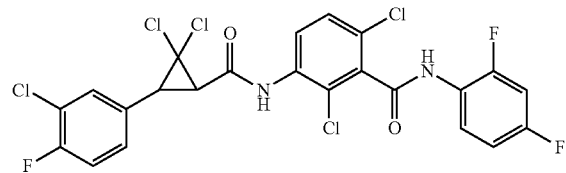 [SMILES: O=C(Nc1ccc(F)cc1F)c1c(Cl)ccc(NC(=O)C2C(c3ccc(F)c(Cl)c3)C2(Cl)Cl)c1Cl]

To a solution of trans-2,2-dichloro-3-(3-chloro-4-fluorophenyl)cyclopropane-1-carboxylic acid (C40) (0.040 g, 0.14 mmol), 3-amino-2,6-dichloro-N-(2,4-difluorophenyl)benzamide (C129), (0.045 g, 0.14 mmol), and pyridine (0.034 g, 0.43 mmol) in ethyl acetate (4 mL) was added a 50% solution of 2,4,6-tripropyl-1,3,5,2,4,6-trioxatriphosphinane 2,4,6-trioxide (0.17 mL, 0.28 mmol) in ethyl acetate. The resulting colorless solution was stirred at 50° C. for 16 hours and cooled to room temperature. The reaction mixture was adsorbed to Celite® (~1.5 g) and purified by automated flash chromatography using a gradient of 0-55% ethyl acetate in Hexanes as eluent to give the title compound as a white solid (0.083 g, 100%).

The following compounds were prepared in like manner to the procedure outlined in Example 20:

tert-Butyl-(3-(2-chloro-5-((1R,3R)-2,2-dichloro-3-(4-fluoro-3-(trifluoromethyl)phenyl)cyclopropane-1-carboxamido)benzamido)-2,6-difluorophenyl)carbamate (F1053)

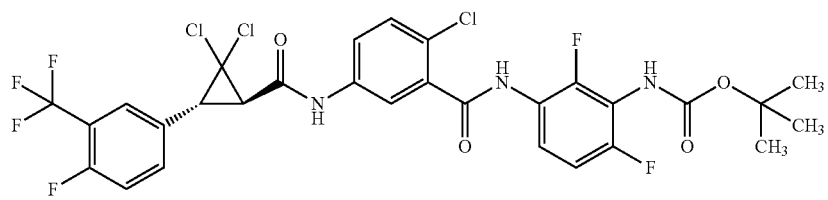 [SMILES: CC(C)(C)OC(=O)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white foam (2.43 g, 89%).

trans-2-Chloro-5-(2,2-dichloro-3-(4-fluoro-3-methyl-5-(trifluoromethyl)phenyl)cyclopropane-1-carboxamido)-N-(2,4-difluorophenyl)benzamide (F1066)

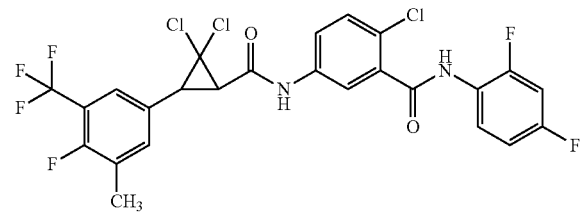 [SMILES: Cc1cc(C2C(C(=O)Nc3ccc(Cl)c(C(=O)Nc4ccc(F)cc4F)c3)C2(Cl)Cl)cc(C(F)(F)F)c1F]

Isolated as a white foam (0.059 g, 31%).

cis-2-Chloro-5-(2,2-dichloro-3-(4-fluoro-3-methyl-5-(trifluoromethyl)phenyl)cyclopropane-1-carboxamido)-N-(2,4-difluorophenyl)benzamide (F1067)

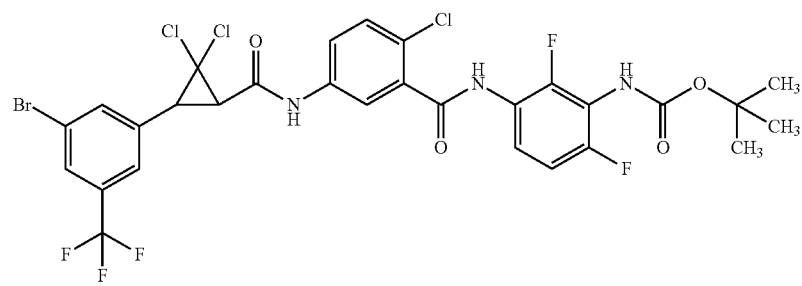 [SMILES: CC(C)(C)OC(=O)Nc1c(F)ccc(NC(=O)c2cc(NC(=O)C3C(c4cc(Br)cc(C(F)(F)F)c4)C3(Cl)Cl)ccc2Cl)c1F]

Isolated as a white foam (0.050 g, 26%).

trans-tert-Butyl-(3-(5-(3-(3-bromo-5-(trifluoromethyl)phenyl)-2,2-dichlorocyclopropane-1-carboxamido)-2-chlorobenzamido)-2,6-difluorophenyl)carbamate (F1073)

Isolated as a white solid (0.129 g, 82%).

tert-Butyl-(3-(2-chloro-5-(((1S,3S)-2,2-dichloro-3-(4-fluoro-3-(trifluoromethyl)phenyl)cyclopropane-1-carboxamido)benzamido)-2,6-difluorophenyl)carbamate (F1074)

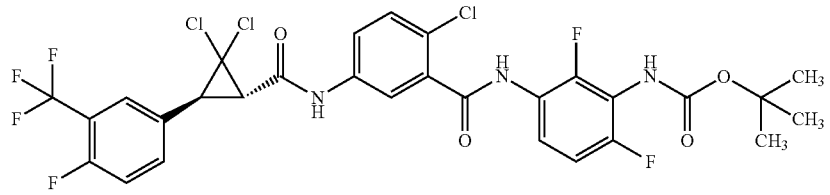 [SMILES: CC(C)(C)OC(=O)Nc1c(F)ccc(NC(=O)c2cc(NC(=O)[C@@H]3[C@@H](c4ccc(F)c(C(F)(F)F)c4)C3(Cl)Cl)ccc2Cl)c1F]

Isolated as a white solid (0.542 g, 73%).

trans-tert-Butyl-(3-(2-chloro-5-(2,2-dichloro-3-(4-chloro-3-(trifluoromethyl)phenyl)cyclopropane-1-carboxamido)benzamido)-2,6-difluorophenyl)carbamate (F1077)

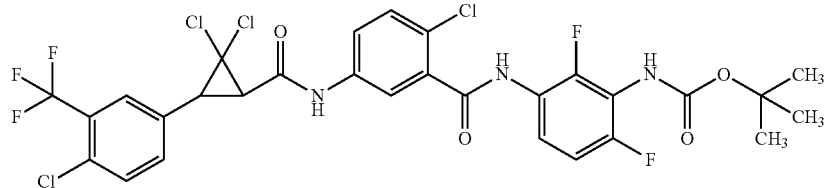 [SMILES: CC(C)(C)OC(=O)Nc1c(F)ccc(NC(=O)c2cc(NC(=O)C3C(c4ccc(Cl)c(C(F)(F)F)c4)C3(Cl)Cl)ccc2Cl)c1F]

Isolated as a white solid (0.143 g, 85%).

trans-tert-Butyl-(3-(2-chloro-5-(2,2-dichloro-3-(4-fluoro-3-(trifluoromethyl)phenyl)cyclopropane-1-carboxamido)benzamido)-2,6-difluorophenyl)carbamate (F1078)

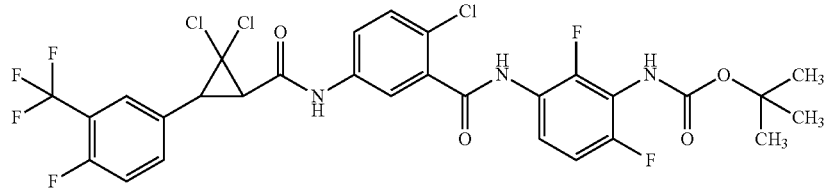 [SMILES: CC(C)(C)OC(=O)Nc1c(F)ccc(NC(=O)c2cc(NC(=O)C3C(c4ccc(F)c(C(F)(F)F)c4)C3(Cl)Cl)ccc2Cl)c1F]

Isolated as a white solid (0.984 g, 85%).

trans-3-(2,2-Dichloro-3-(3-chloro-4-fluorophenyl)cyclopropane-1-carboxamido)-N-(2,4-difluorophenyl)-2,6-difluorobenzamide (F1086)


Isolated as a white solid (0.047 g, 68%).

trans-tert-Butyl-(3-(2-chloro-5-(2,2-dichloro-3-(3-fluoro-5-(trifluoromethyl)phenyl)cyclopropane-1-carboxamido)benzamido)-2,6-difluorophenyl)carbamate (F1092)

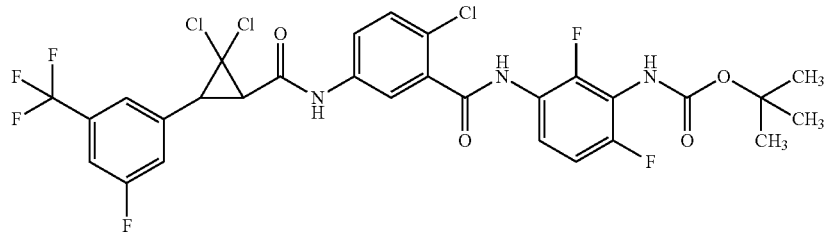

Isolated as a white solid (0.199 g, 86%).

trans-5-(3-(3-bromo-2,5-difluorophenyl)-2,2-dichlorocyclopropane-1-carboxamido)-2-chloro-N-(2,4-difluorophenyl)benzamide (F1093)

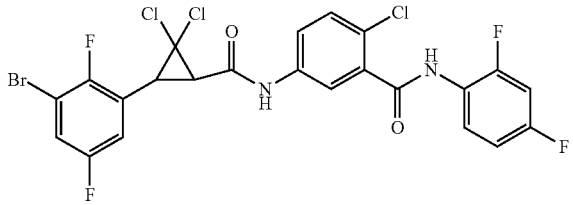 [SMILES: O=C(Nc1ccc(F)cc1F)c1cc(NC(=O)C2C(c3cc(F)cc(Br)c3F)C2(Cl)Cl)ccc1Cl]

Isolated as a white foam (0.033 g, 30%).

cis-5-(3-(3-Bromo-2,5-difluorophenyl)-2,2-dichlorocyclopropane-1-carboxamido)-2-chloro-N-(2,4-difluorophenyl)benzamide (F1094)

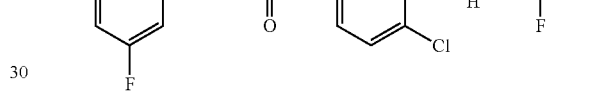

Isolated as a clear colorless oil (0.042 g, 38%).

trans-tert-Butyl-(3-(5-(3-(3-bromo-2,5-difluorophenyl)-2,2-dichlorocyclopropane-1-carboxamido)-2-chlorobenzamido)-2,6-difluorophenyl)carbamate (F1095)

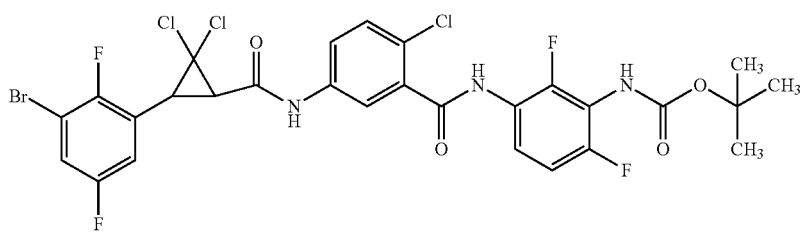 [SMILES: CC(C)(C)OC(=O)Nc1c(F)ccc(NC(=O)c2cc(NC(=O)C3C(c4cc(F)cc(Br)c4F)C3(Cl)Cl)ccc2Cl)c1F]

Isolated as a white solid (0.058 g, 26%).

trans-3-(2,2-Dichloro-3-(3-chloro-4-fluorophenyl)cyclopropane-1-carboxamido)-2,6-difluoro-N-(4-fluorophenyl)benzamide (F1100)

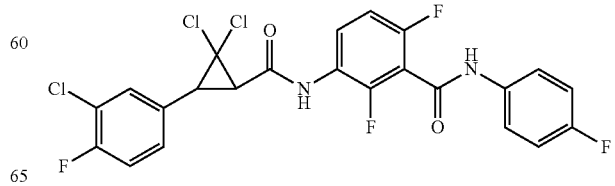

Isolated as a white solid (0.074 g, 91%).

125 trans-N-(4-Acetamidophenyl)-3-(2,2-dichloro-3-(3-chloro-4-fluorophenyl)cyclopropane-1-carboxamido)-2,6-difluorobenzamide (F1101)

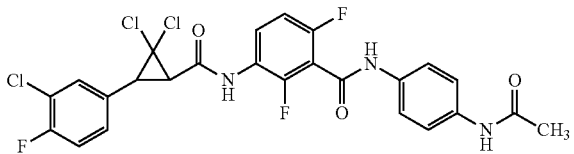 [SMILES: CC(=O)Nc1ccc(NC(=O)c2c(F)ccc(NC(=O)C3C(c4ccc(F)c(Cl)c4)C3(Cl)Cl)c2F)cc1]

Isolated as a white solid (0.030 g, 90%).

trans-N-(4-Acetamidophenyl)-2,6-dichloro-3-(2,2-dichloro-3-(3-chloro-4-fluorophenyl)cyclopropane-1-carboxamido)benzamide (F1102)

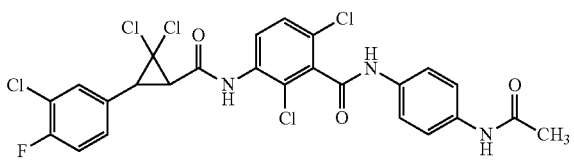 [SMILES: CC(=O)Nc1ccc(NC(=O)c2c(Cl)ccc(NC(=O)C3C(c4ccc(F)c(Cl)c4)C3(Cl)Cl)c2Cl)cc1]

Isolated as a white solid (0.032 g, 71%).

trans-2,6-Dichloro-3-(2,2-dichloro-3-(3-chloro-4-fluorophenyl)cyclopropane-1-carboxamido)-N-(4-fluorophenyl)benzamide (F1103)

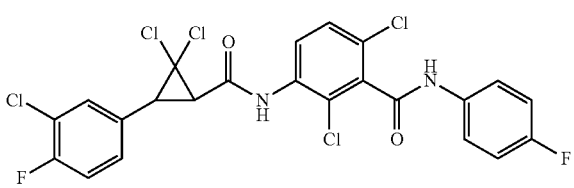

Isolated as a white solid (0.068 g, 88%).

126 trans-2,6-Dichloro-3-(2,2-dichloro-3-(3-chloro-4-fluorophenyl)cyclopropane-1-carboxamido)-N-phenylbenzamide (F1104)

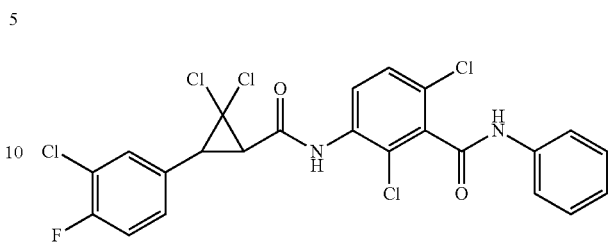

Isolated as a white solid (0.075 g, 94%).

trans-N-(4-Aminophenyl)-2,6-dichloro-3-(2,2-dichloro-3-(3-chloro-4-fluorophenyl)cyclopropane-1-carboxamido)-N-methylbenzamide (F1106)

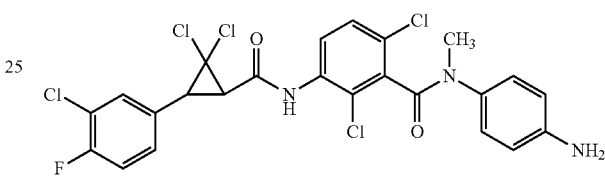

Isolated as a tan solid (0.038 g, 53%).

trans-tert-Butyl-N-tert-butoxycarbonyl-N-[3-[[2,6-dichloro-3-[[2,2-dichloro-3-(3-chloro-4-fluorophenyl)cyclopropanecarbonyl]amino]benzoyl]amino]-2,6-difluoro-phenyl]carbamate (F1107)

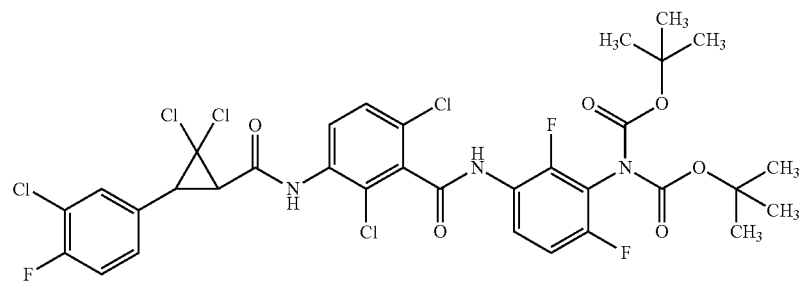

Isolated as a white solid (0.086 g, 80%).

trans-3-(2,2-Dichloro-3-(3-chloro-4-fluorophenyl)cyclopropane-1-carboxamido)-2,6-difluoro-N-phenylbenzamide (F1108)

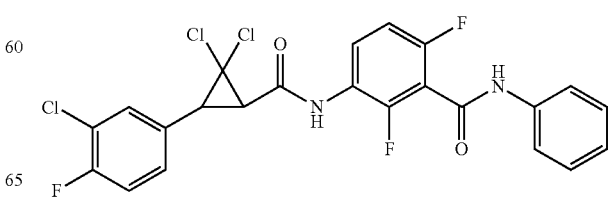

Isolated as a tan solid (0.082 g, 96%).

trans-tert-Butyl-N-tert-butoxycarbonyl-N-[3-[[3-[[2,2-dichloro-3-(3-chloro-4-fluorophenyl)cyclopropanecarbonyl]amino]-2,6-difluorobenzoyl]amino]-2,6-difluorophenyl]carbamate (F1109)

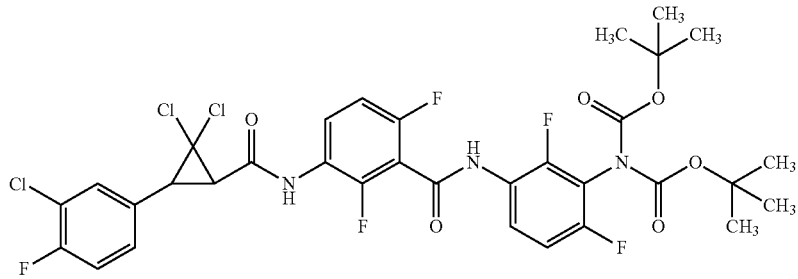 [SMILES: CC(C)(C)OC(=O)N(C(=O)OC(C)(C)C)c1c(F)ccc(NC(=O)c2c(F)ccc(NC(=O)C3C(c4ccc(F)c(Cl)c4)C3(Cl)Cl)c2F)c1F]

Isolated as a tan solid (0.101 g, 73%).

trans-tert-Butyl-(3-(5-(3-(4-bromo-3-(trifluoromethyl)phenyl)-2,2-dichlorocyclopropane-1-carboxamido)-2-chlorobenzamido)-2,6-difluorophenyl)carbamate (F1115)

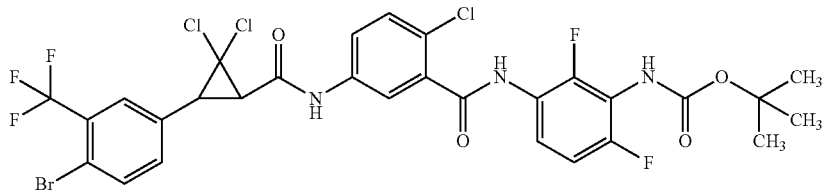

Isolated as a white foam (0.179 g, 85%).

trans-2-Chloro-5-(2,2-dichloro-3-(3-chloro-5-(trifluoromethyl)phenyl)cyclopropane-1-carboxamido)-N-(2,4-difluorophenyl)benzamide (F1118)

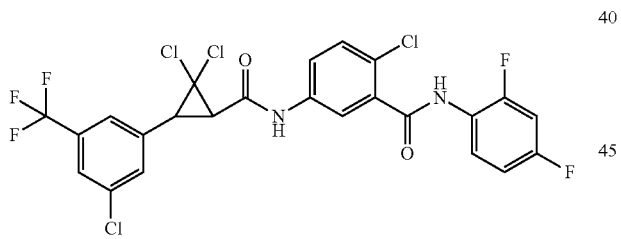

Isolated as a white foam (0.078 g, 83%).

trans-tert-Butyl-(3-(2-chloro-5-(2,2-dichloro-3-(3-chloro-5-(trifluoromethyl)phenyl)cyclopropane-1-carboxamido)benzamido)-2,6-difluorophenyl)carbamate (F1119)

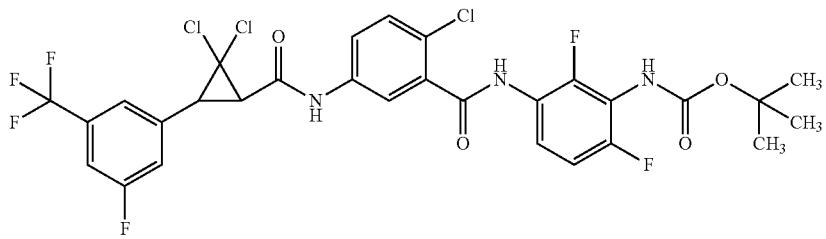

Isolated as a white solid (0.197 g, 88%).

trans-2-Chloro-5-(2,2-dichloro-3-(3,4-dichloro-5-(trifluoromethyl)phenyl)cyclopropane-1-carboxamido)-N-(2,4-difluorophenyl)benzamide (F1147)

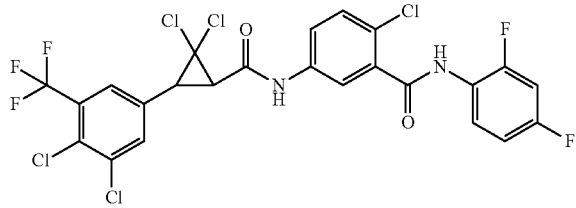 [SMILES: O=C(Nc1ccc(F)cc1F)c1cc(NC(=O)C2C(c3cc(Cl)c(Cl)c(C(F)(F)F)c3)C2(Cl)Cl)ccc1Cl]

Isolated as a pale yellow foam (0.094 g, 52%).

cis-2-Chloro-5-(2,2-dichloro-3-(3,4-dichloro-5-(trifluoromethyl)phenyl)cyclopropane-1-carboxamido)-N-(2,4-difluorophenyl)benzamide (F1148)

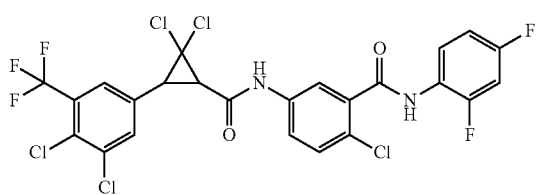

Isolated as a clear, colorless oil (0.028 g, 15%).

trans-2-Chloro-5-(2,2-dichloro-3-(4-chloro-3-fluoro-5-(trifluoromethyl)phenyl)cyclopropane-4-carboxamido)-N-(2,4-difluorophenyl)benzamide (F1163)

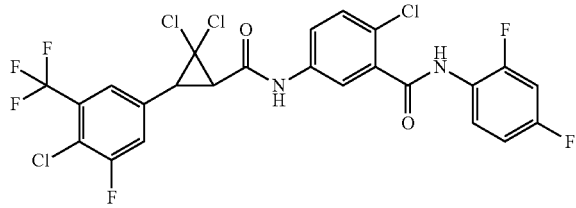

Isolated as a clear, colorless oil (0.115 g, 62%).

cis-2-Chloro-5-(2,2-dichloro-3-(4-chloro-3-fluoro-5-(trifluoromethyl)phenyl)cyclopropane-1-carboxamido)-N-(2,4-difluorophenyl)benzamide (F1164)

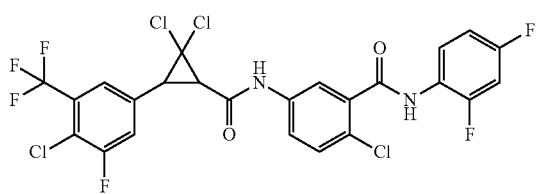 [SMILES: O=C(Nc1ccc(F)cc1F)c1cc(NC(=O)C2C(c3cc(Cl)c(Cl)c(C(F)(F)F)c3)C2(Cl)Cl)ccc1Cl]

Isolated as a white foam (0.040 g, 22%).

trans-2-Chloro-5-(2,2-dichloro-3-(3,5-dichloro-4-fluorophenyl)cyclopropane-1-carboxamido)-N-(2,4-difluorophenyl)benzamide (F1172)

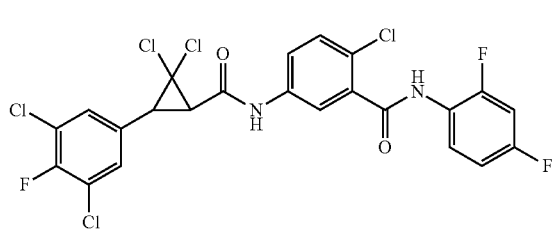 [SMILES: O=C(Nc1ccc(F)cc1F)c1cc(NC(=O)C2C(c3cc(Cl)c(F)c(Cl)c3)C2(Cl)Cl)ccc1Cl]

Isolated as a white foam (0.076 g, 39%).

cis-2-Chloro-5-(2,2-dichloro-3-(3,5-dichloro-4-fluorophenyl)cyclopropane-1-carboxamido)-N-(2,4-difluorophenyl)benzamide (F1173)

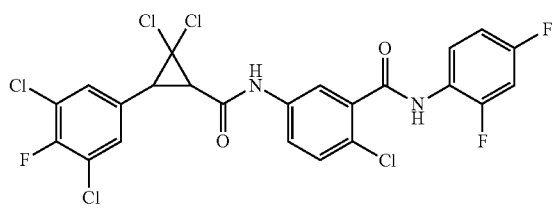 [SMILES: O=C(Nc1ccc(F)cc1F)c1cc(NC(=O)C2C(c3cc(Cl)c(F)c(Cl)c3)C2(Cl)Cl)ccc1Cl]

Isolated as a white foam (0.032 g, 17%).

trans-2-chloro-5-(2,2-dichloro-3-(3-chloro-5-(pentafluoro-$\lambda^6$-sulfanyl)phenyl)cyclopropane-1-carboxamido)-N-(2,4-difluorophenyl)benzamide (F1232)

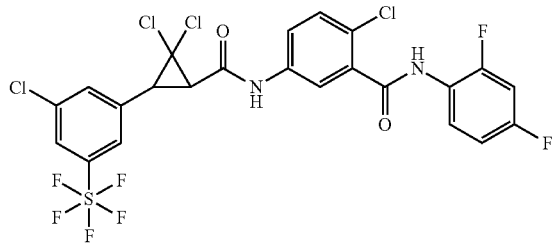 [SMILES: O=C(Nc1ccc(F)cc1F)c1cc(NC(=O)C2C(c3cc(Cl)cc(S(F)(F)(F)(F)F)c3)C2(Cl)Cl)ccc1Cl]

Isolated as a white foam (0.088 g, 50%).

cis-2-Chloro-5-(2,2-dichloro-3-(3-chloro-5-(pentafluoro-$\lambda^6$-sulfanyl)phenyl)cyclopropane-1-carboxamido)-I-(2,4-difluorophenyl)benzamide (F1233)

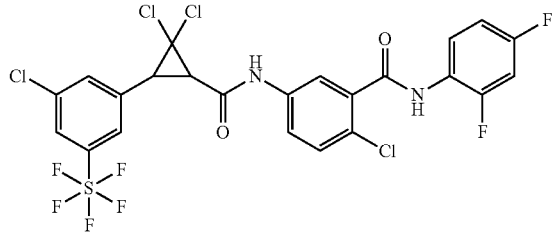 [SMILES: O=C(Nc1ccc(F)cc1F)c1cc(NC(=O)C2C(c3cc(Cl)cc(S(F)(F)(F)(F)F)c3)C2(Cl)Cl)ccc1Cl]

Isolated as a clear, colorless oil (0.035 g, 20%).

tert-Butyl-N-tert-butoxycarbonyl-N-[3-[[2-chloro-5-[[(1R,3R)-2,2-dichloro-3-(3,4-dichlorophenyl)cyclopropanecarbonyl]amino]-3-fluorobenzoyl]amino]-2,6-difluorophenyl]carbamate (F1282)

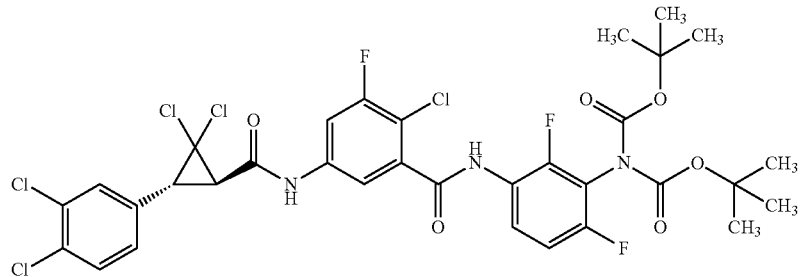 [SMILES: CC(C)(C)OC(=O)N(C(=O)OC(C)(C)C)c1c(F)ccc(NC(=O)c2cc(NC(=O)[C@H]3[C@H](c4ccc(Cl)c(Cl)c4)C3(Cl)Cl)cc(F)c2Cl)c1F]

Isolated as a white solid (0.284 g, 80%).

tert-Butyl-N-tert-butoxycarbonyl-N-[3-[[2-chloro-5-[[(1R,3R)-2,2-dichloro-3-[4-fluoro-3-(trifluoromethyl)phenyl]cyclopropanecarbonyl]amino]-3-fluoro-benzoyl]amino]-2,6-difluorophenyl]carbamate (F1283)

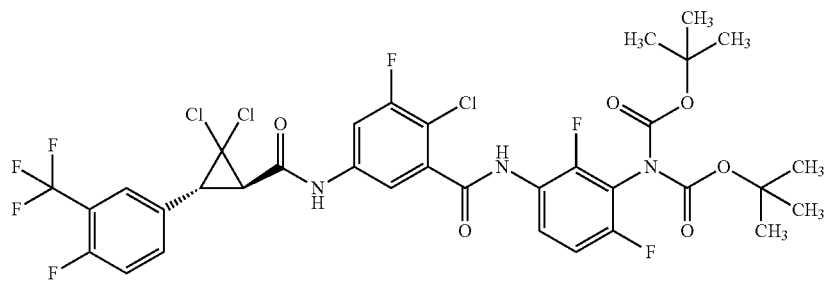 [SMILES: CC(C)(C)OC(=O)N(C(=O)OC(C)(C)C)c1c(F)ccc(NC(=O)c2cc(NC(=O)[C@H]3[C@H](c4ccc(F)c(C(F)(F)F)c4)C3(Cl)Cl)cc(F)c2Cl)c1F]

Isolated as a white solid (0.298 g, 83%).

trans-2-Chloro-5-(2,2-dichloro-3-(2-chloro-5-(trifluoromethyl)phenyl)-cyclopropane-1-carboxamido)-N-(2,2,2-trifluoroethyl)benzamide (F2001)

trans-2-Chloro-5-(2,2-dichloro-3-(perfluorophenyl)cyclopropane-1-carboxamido)-N-(2,2,2-trifluoroethyl)benzamide (F2002)

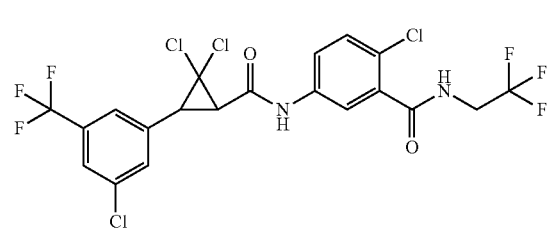 [SMILES: O=C(NCC(F)(F)F)c1cc(NC(=O)C2C(c3cc(Cl)cc(C(F)(F)F)c3)C2(Cl)Cl)ccc1Cl]

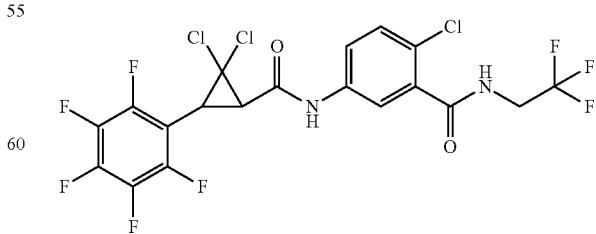

Isolated as a white foam (0.047 g, 52%).

Isolated as a white solid (0.069 g, 76%).

trans-5-(3-(3-Bromo-4,5-difluorophenyl)-2,2-dichlorocyclopropane-1-carboxamido)-2-chloro-N-(2,2,2-trifluoroethyl)benzamide (F2003)

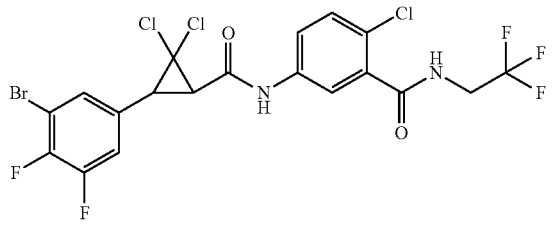 [SMILES: O=C(NCC(F)(F)F)c1cc(NC(=O)C2C(c3cc(F)c(F)c(Br)c3)C2(Cl)Cl)ccc1Cl]

Isolated as a white foam (0.067 g, 51%).

cis-5-(3-(3-Bromo-4,5-difluorophenyl)-2,2-dichlorocyclopropane-1-carboxamido)-2-chloro-N-(2,2,2-trifluoroethyl)benzamide (F2004)

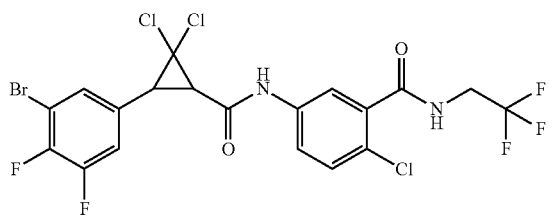 [SMILES: O=C(NCC(F)(F)F)c1cc(NC(=O)C2C(c3cc(F)c(F)c(Br)c3)C2(Cl)Cl)ccc1Cl]

Isolated as a white foam (0.029 g, 22%).

trans-2,6-Dichloro-3-(2,2-dichloro-3-(3-chloro-4-fluorophenyl)cyclopropane-1-carboxamido)-N-(2,2,3,3,3-pentafluoropropyl)benzamide (F2005)

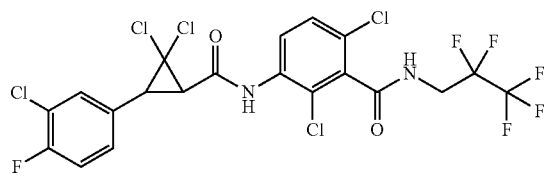 [SMILES: O=C(NCC(F)(F)C(F)(F)F)c1c(Cl)ccc(NC(=O)C2C(c3ccc(F)c(Cl)c3)C2(Cl)Cl)c1Cl]

Isolated as a white solid (0.068 g, 93%).

trans-2-Chloro-5-(2,2-dichloro-3-(3,4-dichloro-5-fluorophenyl)cyclopropane-1-carboxamido)-N-(2,2,2-trifluoroethyl)benzamide (F2006)

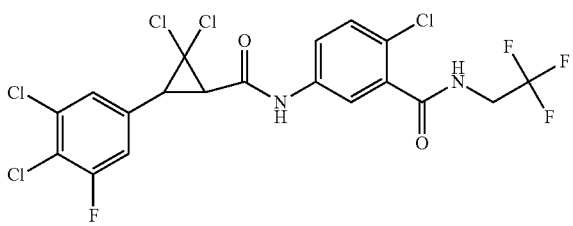 [SMILES: O=C(NCC(F)(F)F)c1cc(NC(=O)C2C(c3cc(F)c(Cl)c(Cl)c3)C2(Cl)Cl)ccc1Cl]

Isolated as a clear colorless oil (0.077 g, 56%).

cis-2-Chloro-5-(2,2-dichloro-3-(3,4-dichloro-5-fluorophenyl)cyclopropane-1-carboxamido)-N-(2,2,2-trifluoroethyl)benzamide (F2007)

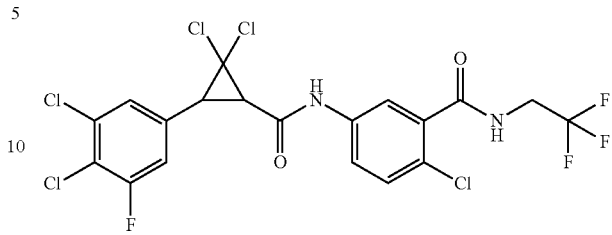

Isolated as a clear colorless oil (0.022 g, 16%).

trans-5-(3-(3-Bromo-5-(pentafluoro-$\lambda^6$-sulfanyl)phenyl)-2,2-dichlorocyclopropane-1-carboxamido)-2-chloro-N-(2,2,2-trifluoroethyl)benzamide (F2008)

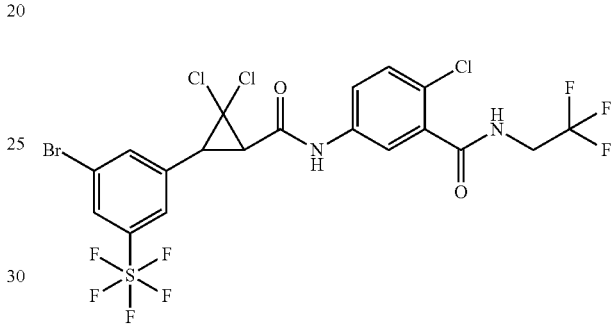

Isolated as a white foam (0.065 g, 54%).

cis-5-(3-(3-Bromo-5-(pentafluoro-$\lambda^6$-sulfanyl)phenyl)-2,2-dichlorocyclopropane-1-carboxamido)-2-chloro-N-(2,2,2-trifluoroethyl)benzamide (F2009)

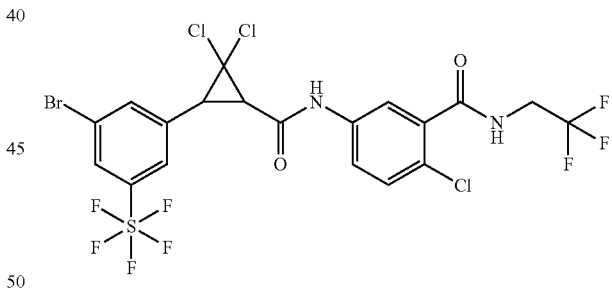

Isolated as a clear colorless oil (0.028 g, 23%).

cis-2-Chloro-5-(2,2-dichloro-3-(3-chloro-2,4-difluorophenyl)cyclopropane-1-carboxamido)-N-(2,2,2-trifluoroethyl)benzamide (F2010)

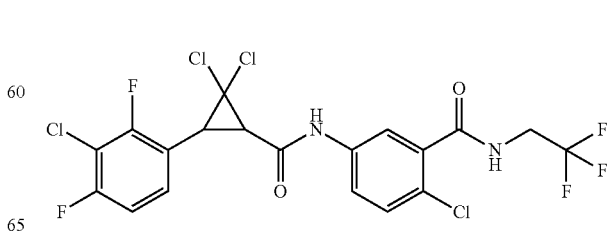

Isolated as a white foam (0.039 g, 28%).

trans-2-Chloro-5-(2,2-dichloro-3-(3-chloro-2,4-difluorophenyl)cyclopropane-1-carboxamido)-N-(2,2,2-trifluoroethyl)benzamide (F2011)

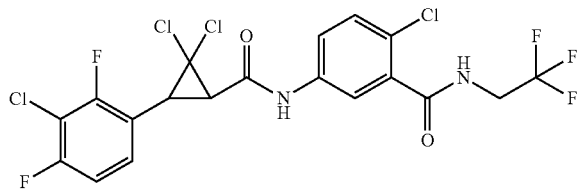 [SMILES: O=C(NCC(F)(F)F)c1cc(NC(=O)C2C(c3ccc(F)c(Cl)c3F)C2(Cl)Cl)ccc1Cl]

Isolated as a clear colorless oil (0.037 g, 26%).

trans-2-Chloro-5-(2,2-dichloro-3-(3-chloro-2-fluoro-5-(trifluoromethyl)phenyl)cyclopropane-1-carboxamido)-N-(2,2,2-trifluoroethyl)benzamide (F2012)

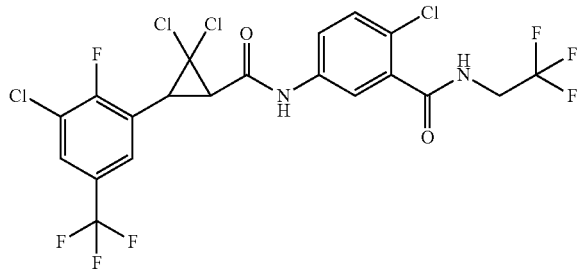 [SMILES: O=C(NCC(F)(F)F)c1cc(NC(=O)C2C(c3cc(C(F)(F)F)cc(Cl)c3F)C2(Cl)Cl)ccc1Cl]

Isolated as a clear colorless oil (0.041 g, 31%).

cis-2-Chloro-5-(2,2-dichloro-3-(3-chloro-2-fluoro-5-(trifluoromethyl)phenyl)cyclopropane-1-carboxamido)-N-(2,2,2-trifluoroethyl)benzamide (F2013)

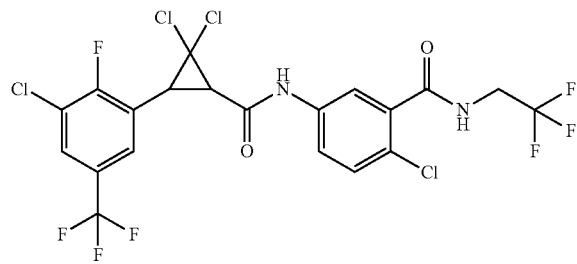 [SMILES: O=C(NCC(F)(F)F)c1cc(NC(=O)C2C(c3cc(C(F)(F)F)cc(Cl)c3F)C2(Cl)Cl)ccc1Cl]

Isolated as a white foam (0.055 g, 42%).

trans-2-Chloro-5-(2,2-dichloro-3-(4-fluoro-3-methyl-5-(trifluoromethyl)phenyl)-cyclopropane-1-carboxamido)-N-(2,2,2-trifluoroethyl)benzamide (F2014)

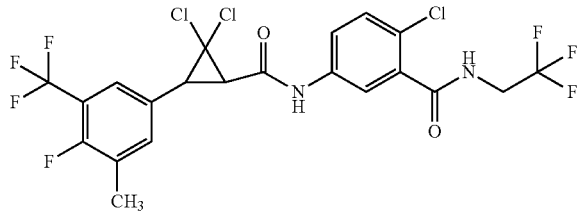 [SMILES: Cc1cc(C2C(C(=O)Nc3ccc(Cl)c(C(=O)NCC(F)(F)F)c3)C2(Cl)Cl)cc(C(F)(F)F)c1F]

Isolated as a white foam (0.068 g, 38%).

cis-2-Chloro-5-(2,2-dichloro-3-(4-fluoro-3-methyl-5-(trifluoromethyl)phenyl)-cyclopropane-1-carboxamido)-N-(2,2,2-trifluoroethyl)benzamide (F2015)

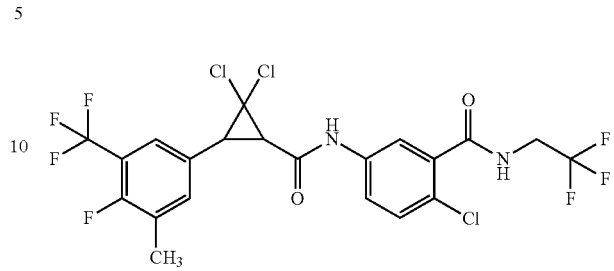

Isolated as a gold oil (0.045 g, 25%).

trans-3-(2,2-Dichloro-3-(3-chloro-4-fluorophenyl)cyclopropane-1-carboxamido)-N-ethyl-2,6-difluorobenzamide (F2016)


Isolated as a white solid (0.068 g, 91%).

trans-3-(2,2-Dichloro-3-(3-chloro-4-fluorophenyl)cyclopropane-1-carboxamido)-2,6-difluoro-N-(2,2,2-trifluoroethyl)benzamide (F2017)

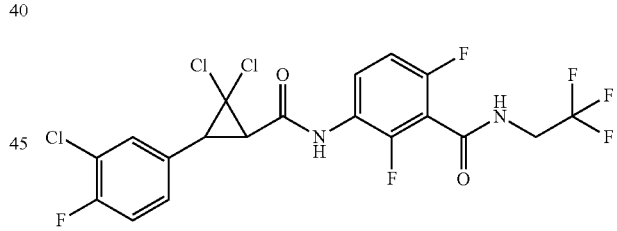

Isolated as a white solid (0.081 g, 96%).

trans-3-(2,2-Dichloro-3-(3-chloro-4-fluorophenyl)cyclopropane-1-carboxamido)-2,6-difluoro-N-(2,2,3,3,3-pentafluoropropyl)benzamide (F2018)

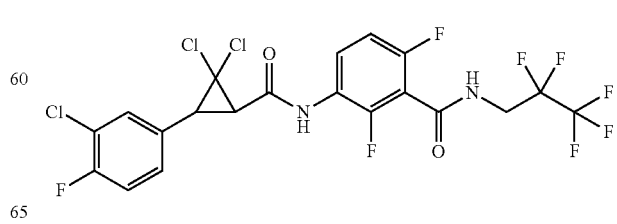

Isolated as a white solid (0.068 g, 94%).

trans-2,6-Dichloro-3-(2,2-dichloro-3-(3-chloro-4-fluorophenyl)cyclopropane-1-carboxamido)-N-ethylbenzamide (F2019)

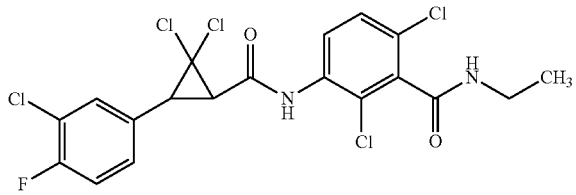 [SMILES: CCNC(=O)c1c(F)ccc(NC(=O)C2C(c3ccc(F)c(Cl)c3)C2(Cl)Cl)c1F]

Isolated as a white solid (0.077 g, 88%).

trans-2,6-Dichloro-3-(2,2-dichloro-3-(3-chloro-4-fluorophenyl)cyclopropane-1-carboxamido)-N-(2,2,2-trifluoroethyl)benzamide (F2020)

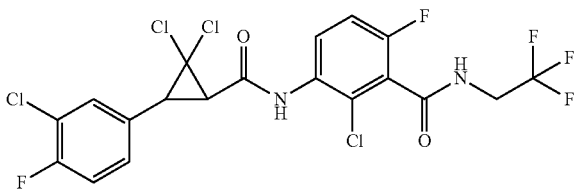 [SMILES: O=C(NCC(F)(F)F)c1c(F)ccc(NC(=O)C2C(c3ccc(F)c(Cl)c3)C2(Cl)Cl)c1Cl]

Isolated as a white solid (0.052 g, 66%).

trans-3-(2,2-Dichloro-3-(3-chloro-4-fluorophenyl)cyclopropane-1-carboxamido)-2,6-difluoro-N-propylbenzamide (F2021)

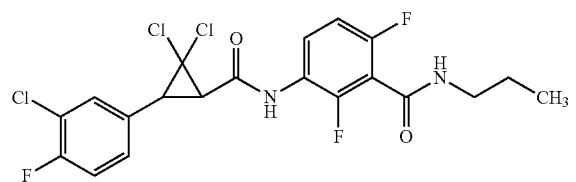 [SMILES: CCCNC(=O)c1c(F)ccc(NC(=O)C2C(c3ccc(F)c(Cl)c3)C2(Cl)Cl)c1F]

Isolated as a white foam (0.084 g, 91%).

trans-2,6-Dichloro-3-(2,2-dichloro-3-(3-chloro-4-fluorophenyl)cyclopropane-1-carboxamido)-N-propylbenzamide (F2022)

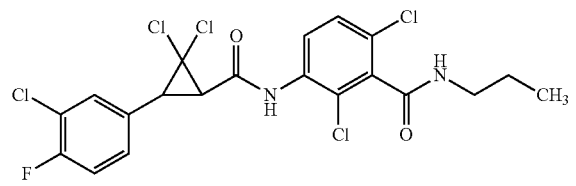

Isolated as a white solid (0.077 g, 90%).

trans-3-(2,2-Dichloro-3-(3-chloro-4-fluorophenyl)cyclopropane-1-carboxamido)-2,6-difluoro-N-(3,3,3-trifluoropropyl)benzamide (F2023)

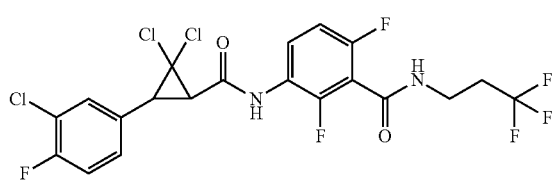 [SMILES: O=C(NCCC(F)(F)F)c1c(F)ccc(NC(=O)C2C(c3ccc(F)c(Cl)c3)C2(Cl)Cl)c1F]

Isolated as a white solid 0.067 g, 82%).

trans-2,6-Dichloro-3-(2,2-dichloro-3-(3-chloro-4-fluorophenyl)cyclopropane-1-carboxamido)-N-(3,3,3-trifluoropropyl)benzamide (F2024)

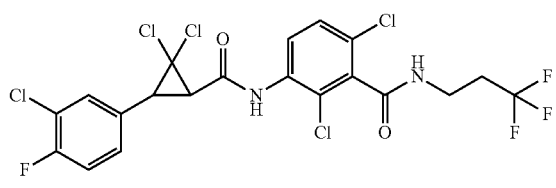 [SMILES: O=C(NCCC(F)(F)F)c1c(Cl)ccc(NC(=O)C2C(c3ccc(F)c(Cl)c3)C2(Cl)Cl)c1Cl]

Isolated as a white solid (0.071 g, 92%).

trans-2,6-Dichloro-3-(2,2-dichloro-3-(3-chloro-4-fluorophenyl)cyclopropane-1-carboxamido)-N-(2-fluoroethyl)benzamide (F2025)

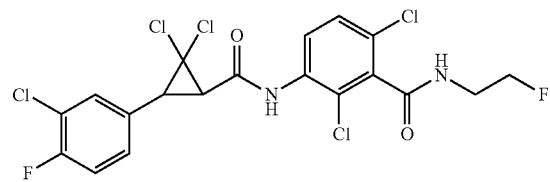

Isolated as a white solid (0.070 g, 84%).

trans-2,6-Dichloro-N-(3-chloropropyl)-3-(2,2-dichloro-3-(3-chloro-4-fluorophenyl)cyclopropane-1-carboxamido)benzamide (F2026)

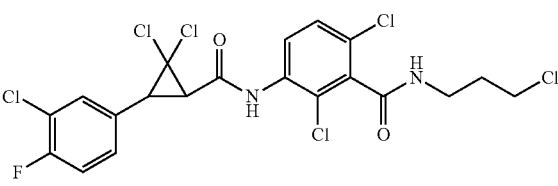 [SMILES: O=C(NCCCCl)c1c(Cl)ccc(NC(=O)C2C(c3ccc(F)c(Cl)c3)C2(Cl)Cl)c1Cl]

Isolated as a white solid (0.070 g, 88%).

trans-3-(2,2-Dichloro-3-(3-chloro-4-fluorophenyl)
cyclopropane-1-carboxamido)-2,6-difluoro-N-(2-
fluoroethyl)benzamide (F2027)

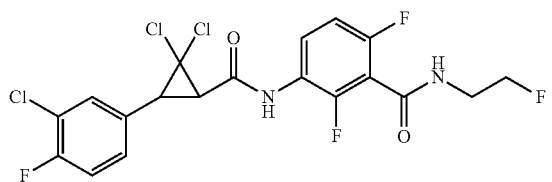 [SMILES: O=C(NCCF)c1c(F)ccc(NC(=O)C2C(c3ccc(F)c(Cl)c3)C2(Cl)Cl)c1F]

Isolated as a white solid (0.088 g, 96%).

trans-N-(3-Chloropropyl)-3-(2,2-dichloro-3-(3-
chloro-4-fluorophenyl)cyclopropane-1-carbox-
amido)-2,6-difluorobenzamide (F2028)

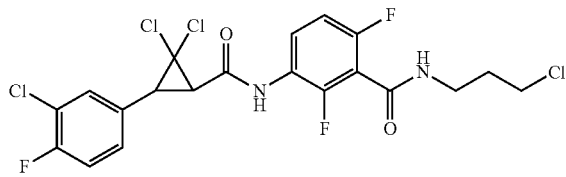 [SMILES: O=C(NCCCCl)c1c(F)ccc(NC(=O)C2C(c3ccc(F)c(Cl)c3)C2(Cl)Cl)c1F]

Isolated as a white solid (0.083 g, 98%).

Example 21: Preparation of trans-N-(3-amino-2,4-
difluorophenyl)-2-chloro-5-(2,2-dichloro-3-(4-
fluoro-3-(trifluoromethyl)phenyl)cyclopropane-1-
carboxamido)benzamide (DP8)

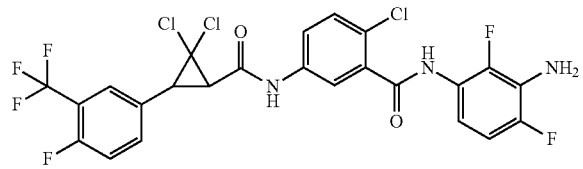 [SMILES: Nc1c(F)ccc(NC(=O)c2cc(NC(=O)C3C(c4ccc(F)c(C(F)(F)F)c4)C3(Cl)Cl)ccc2Cl)c1F]

Step 1: Preparation of trans-tert-butyl-N-tert-bu-
toxycarbonyl-N-[3-(5-(3-(4-fluoro 3-trifluoromethyl)
phenyl)-2,2-dichlorocyclopropane-1-carboxamido)-
2-chlorobenzamido)-2,6-difluorophenyl]carbamate Anhydrous ethyl acetate (3 mL) was added to a 10 mL glass tube containing trans-2,2-dichloro-3-(4-fluoro-3-(trifluoromethyl)phenyl)cyclopropane-1-carboxylic acid (C76) (0.05 g, 0.158 mmol), and tert-butyl-N-((tert-butoxy)carbonyl)-N-(3-(5-amino-2-chlorobenzamido)-2,6-difluorophenyl)carbamate (C135) (0.079 g, 0.158 mmol) at room temperature. To the resulting solution were then added pyridine (0.0374 g, 0.473 mmol) and 2,4,6-tripropyl-1,3,5,2,4,6-tri-oxatriphosphinane 2,4,6-trioxide (T3P®, 50% solution in ethyl acetate; 0.201 g, 0.315 mmol). The solution was stirred at 24° C. for 12 hours, concentrated to dryness, and purified by silica gel flash column chromatography using 0-50% ethyl acetate/hexanes as eluent to give trans-tert-butyl-N-tert-butoxycarbonyl-N-[3-(5-(4-fluoro-3-(trifluoromethyl) phenyl)-2,2-dichlorocyclopropane-1-carboxamido)-2-chlorobenzamido)-2,6-difluorophenyl]carbamate as a white solid. (0.114 g, 86%).

Step 2: Preparation of trans-N-(3-amino-2,4-difluo-
rophenyl)-2-chloro-5-(2,2-dichloro-3-(4-fluoro-3-
(trifluoromethyl)phenyl)cyclopropane-1-carbox-
amido)benzamide Anhydrous hydrogen chloride solution (4.0 M in dioxane; 0.326 mL, 1.305 mmol) was added to a suspension of trans-tert-butyl-N-tert-butoxycarbonyl-N-[3-(5-(3-(4-fluoro 3-trifluoromethyl)phenyl)-2,2-dichlorocyclopropane-1-carboxamido)-2-chlorobenzamido)-2,6-difluorophenyl]carbamate (0.104 g, 0.130 mmol). The suspension was stirred at 24° C. for 12 hours. The dichloromethane was then removed under a stream of nitrogen and the sample was dissolved in ethyl acetate (20 mL) and washed with saturated aqueous sodium bicarbonate (5 mL) and saturated aqueous sodium chloride solution (5 mL). The ethyl acetate solution was dried over anhydrous magnesium sulfate, filtered and concentrated under vacuum on a rotary evaporator. Purification of the residue with silica gel flash chromatography using 0-50% ethyl acetate/hexanes as eluent provided the title compound as a white foam (0.043 g, 53%).

The following compounds were prepared in like manner to the procedure outlined in Example 21:

trans-N-(3-Amino-2,4-difluorophenyl)-5-(3-(3-
bromo-5-(pentafluoro-$\lambda^6$-sulfanyl)phenyl)-2,2-di-
chlorocyclopropane-1-carboxamido)-2-chlorobenz-
amide (F1042)

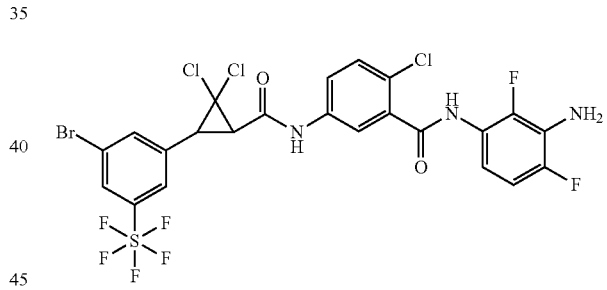

Isolated as a white foam (0.079 g, 74%).

cis-N-(3-Amino-2,4-difluorophenyl)-5-(3-(3-bromo-
5-(pentafluoro-$\lambda^6$-sulfanyl)phenyl)-2,2-dichlorocy-
clopropane-1-carboxamido)-2-chlorobenzamide
(F1043)

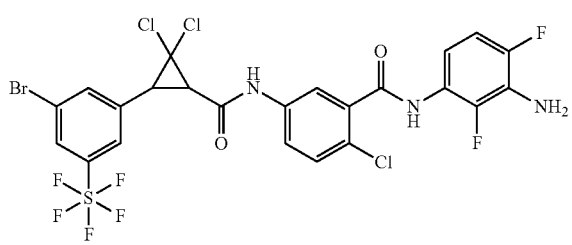

Isolated as a clear, colorless oil (0.028 g, 56%).

141 trans-N-(3-Amino-2,4-difluorophenyl)-5-(3-(3-bromo-4,5-difluorophenyl)-2,2-dichlorocyclopropane-1-carboxamido)-2-chlorobenzamide (F1044)

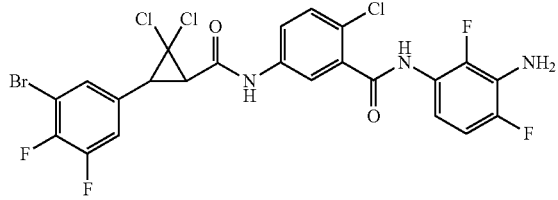

Isolated as a clear, colorless oil (0.062 g, 56%).

cis-N-(3-Amino-2,4-difluorophenyl)-5-(3-(3-bromo-4,5-difluorophenyl)-2,2-dichlorocyclopropane-1-carboxamido)-2-chlorobenzamide (F1045)

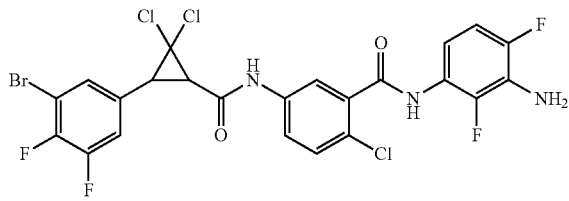 [SMILES: Nc1c(F)ccc(NC(=O)c2cc(NC(=O)C3C(c4cc(F)c(F)c(Br)c4)C3(Cl)Cl)ccc2Cl)c1F]

Isolated as a clear, colorless oil (0.032 g, 53%).

trans-N-(3-Amino-2,4-difluorophenyl)-2-chloro-5-(2,2-dichloro-3-(3,4-dichloro-5-fluorophenyl)cyclopropane-1-carboxamido)benzamide (F1046)

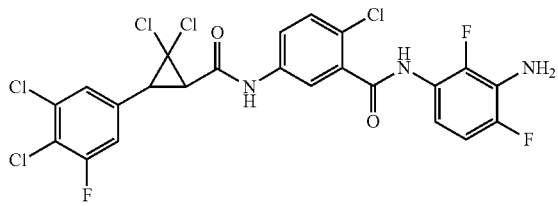 [SMILES: Nc1c(F)ccc(NC(=O)c2cc(NC(=O)C3C(c4cc(F)c(Cl)c(Cl)c4)C3(Cl)Cl)ccc2Cl)c1F]

Isolated as a white foam (0.085 g, 65%).

cis-N-(3-Amino-2,4-difluorophenyl)-2-chloro-5-(2,2-dichloro-3-(3,4-dichloro-5-fluorophenyl)cyclopropane-1-carboxamido)benzamide (F1047)

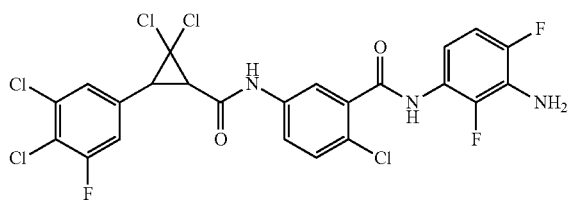 [SMILES: Nc1c(F)ccc(NC(=O)c2cc(NC(=O)C3C(c4cc(F)c(Cl)c(Cl)c4)C3(Cl)Cl)ccc2Cl)c1F]

Isolated as a clear colorless oil (0.026 g, 82%).

142

N-(3-amino-2,4-difluorophenyl)-2-chloro-5-((cis)-2,2-dichloro-3-(3-chloro-2,4-difluorophenyl)cyclopropane-1-carboxamido)benzamide (F1048)

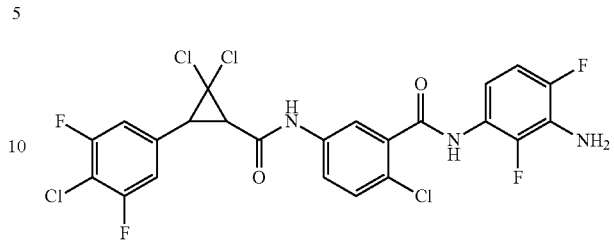

Isolated as a white foam (0.053 g, 60%).

trans-N-(3-Amino-2,4-difluorophenyl)-2-chloro-5-(2,2-dichloro-3-(3-chloro-2,4-difluorophenyl)cyclopropane-1-carboxamido)benzamide (F1049)

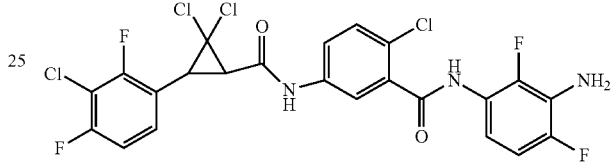

Isolated as a white solid (0.041 g, 63%).

trans-2-Chloro-5-(2,2-dichloro-3-(3-chloro-2-fluoro-5-(trifluoromethyl)phenyl)cyclopropane-1-carboxamido)-N-(2,4-difluorophenyl)benzamide (F1050)

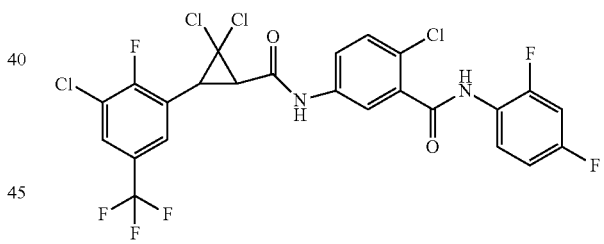

Isolated as a white foam (0.042 g, 30%).

cis-2-Chloro-5-(2,2-dichloro-3-(3-chloro-2-fluoro-5-(trifluoromethyl)phenyl)cyclopropane-1-carboxamido)-N-(2,4-difluorophenyl)benzamide (F1051)

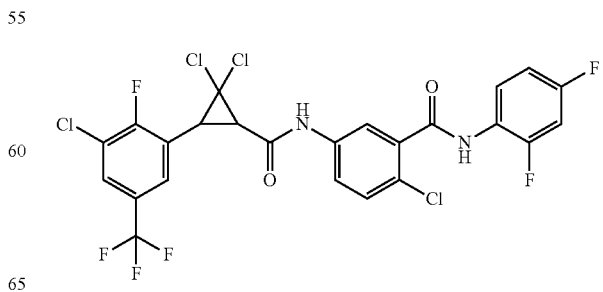

Isolated as a white foam (0.063 g, 46%).

N-(3-Amino-2,4-difluorophenyl)-2-chloro-5-((1R,3R)-2,2-dichloro-3-(4-fluoro-3-(trifluoromethyl)phenyl)cyclopropane-1-carboxamido)benzamide (DP9)

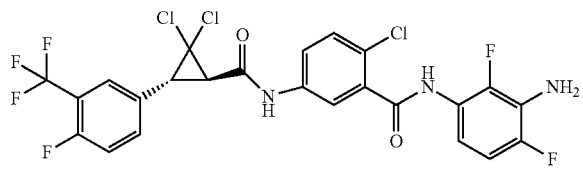 [SMILES: Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white solid (1.5 g, 69%).

trans-N-(3-Amino-2,4-difluorophenyl)-2-chloro-5-(2,2-dichloro-3-(4-fluoro-3-methyl-5-(trifluoromethyl)phenyl)cyclopropane-1-carboxamido)benzamide (F1068)

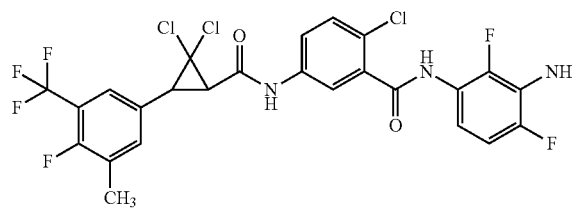

Isolated as a white foam (0.042 g, 44%).

cis-N-(3-Amino-2,4-difluorophenyl)-2-chloro-5-((cis)-2,2-dichloro-3-(4-fluoro-3-methyl-5-(trifluoromethyl)phenyl)cyclopropane-1-carboxamido)benzamide (F1069)

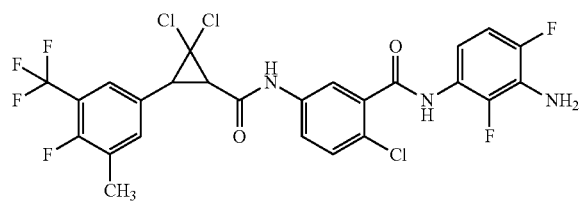 [SMILES: Cc1cc(C2C(C(=O)Nc3ccc(Cl)c(C(=O)Nc4ccc(F)c(N)c4F)c3)C2(Cl)Cl)cc(C(F)(F)F)c1F]

Isolated as a white foam (0.032 g, 51%).

trans-N-(3-Amino-2,4-difluorophenyl)-5-(3-(3-bromo-5-(trifluoromethyl)phenyl)-2,2-dichlorocyclopropane-1-carboxamido)-2-chlorobenzamide (F1075)

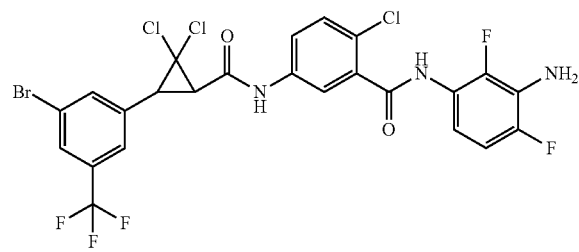 [SMILES: Nc1c(F)ccc(NC(=O)c2cc(NC(=O)C3C(c4cc(Br)cc(C(F)(F)F)c4)C3(Cl)Cl)ccc2Cl)c1F]

Isolated as a clear, colorless oil (0.062 g, 66%).

trans-N-(3-Amino-2,4-difluorophenyl)-2-chloro-5-(2,2-dichloro-3-(4-chloro-3-(trifluoromethyl)phenyl)cyclopropane-1-carboxamido)benzamide (F1079)

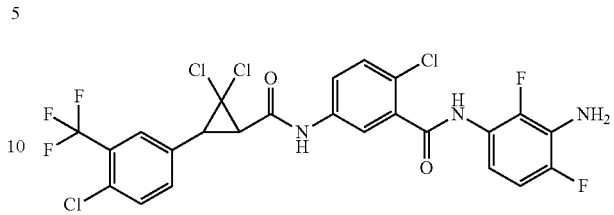

Isolated as a white foam (0.068 g, 68%).

cis-(3-Amino-2,4-difluorophenyl)-5-(3-(3-bromo-2,5-difluorophenyl)-2,2-dichlorocyclopropane-1-carboxamido)-2-chlorobenzamide (F1097)

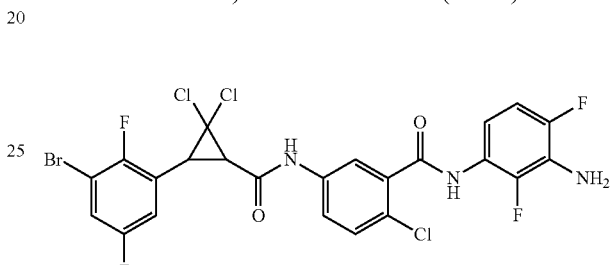

Isolated as a clear, colorless oil (0.019 g, 58%).

trans-N-(3-Amino-2,4-difluorophenyl)-5-(3-(3-bromo-2,5-difluorophenyl)-2,2-dichlorocyclopropane-1-carboxamido)-2-chlorobenzamide (F1098)

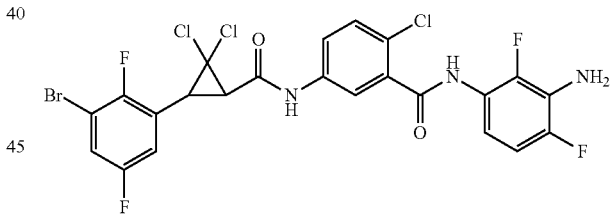

Isolated as a clear, colorless oil (0.014 g, 32%).

trans-N-(3-Amino-2,4-difluorophenyl)-5-(3-(4-bromo-3-(trifluoromethyl)phenyl)-2,2-dichlorocyclopropane-1-carboxamido)-2-chlorobenzamide (F1116)

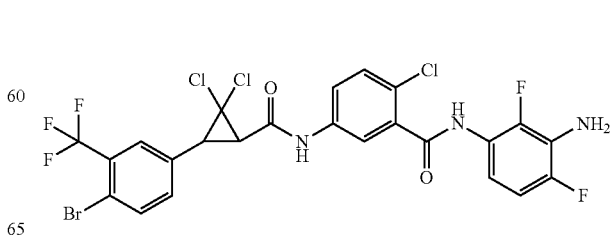

Isolated as a white foam (0.140 g, 86%).

trans-N-(3-Amino-2,4-difluorophenyl)-2-chloro-5-(2,2-dichloro-3-(3-chloro-5-(trifluoromethyl)phenyl)cyclopropane-1-carboxamido)benzamide (F1127)

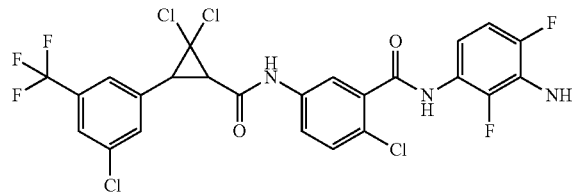

Isolated as a clear, colorless of (0.085 g, 61%).

trans-N-(3-Amino-2,4-difluorophenyl)-2-chloro-5-(2,2-dichloro-3-(3,4-dichloro-5-(trifluoromethyl)phenyl)cyclopropane-1-carboxamido)benzamide (F1149)

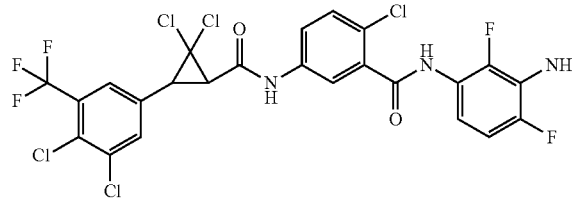

Isolated as a white foam (0.083 g, 81%).

cis-N-(3-Amino-2,4-difluorophenyl)-2-chloro-5-(2,2-dichloro-3-(3,4-dichloro-5-(trifluoromethyl)phenyl)cyclopropane-1-carboxamido)benzamide (F1150)

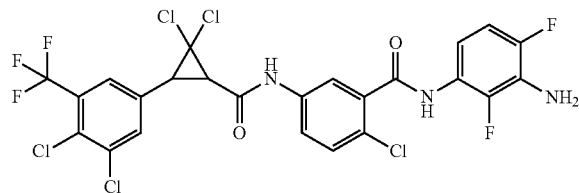 [SMILES: Nc1c(F)ccc(NC(=O)c2cc(NC(=O)C3C(c4cc(Cl)c(Cl)c(C(F)(F)F)c4)C3(Cl)Cl)ccc2Cl)c1F]

Isolated as a clear, colorless oil (0.037 g, 70%).

trans-N-(3-Amino-2,4-difluorophenyl)-2-chloro-5-(2,2-dichloro-3-(4-chloro-3-fluoro-5-(trifluoromethyl)phenyl)cyclopropane-1-carboxamido)benzamide (F1167)

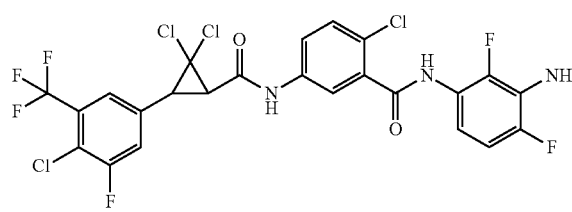

Isolated as a white foam (0.072 g, 64%).

cis-N-(3-Amino-2,4-difluorophenyl)-2-chloro-5-(2,2-dichloro-3-(4-chloro-3-fluoro-5-(trifluoromethyl)phenyl)cyclopropane-1-carboxamido)benzamide (F1168)

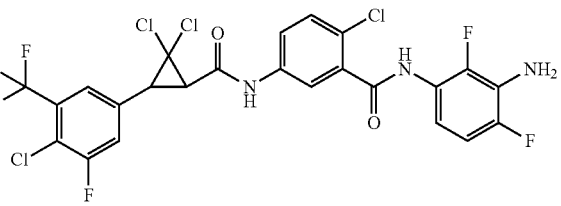

Isolated as a clear, colorless oil (0.024 g, 63%).

trans-N-(3-Amino-2,4-difluorophenyl)-2-chloro-5-(2,2-dichloro-3-(3,5-dichloro-4-fluorophenyl)cyclopropane-1-carboxamido)benzamide (F1181)

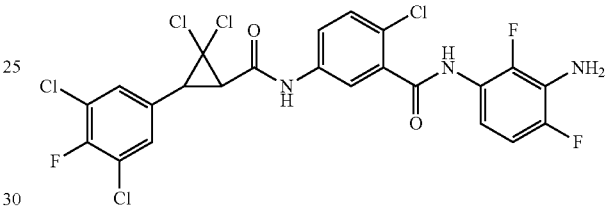

Isolated as a white foam (0.099 g, 68%).

cis-N-(3-Amino-2,4-difluorophenyl)-2-chloro-5-(2,2-dichloro-3-(3,5-dichloro-4-fluorophenyl)cyclopropane-1-carboxamido)benzamide (F1182)

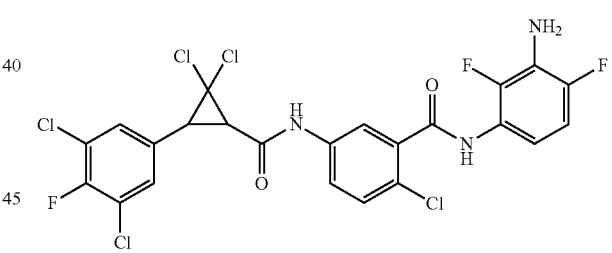

Isolated as a white foam (0.038 g, 77%).

trans-N-(3-Amino-2,4-difluorophenyl)-2-chloro-5-(2,2-dichloro-3-(3-chloro-5-(pentafluoro-$\lambda^6$-sulfanyl)phenyl)cyclopropane-1-carboxamido)benzamide (F1259)

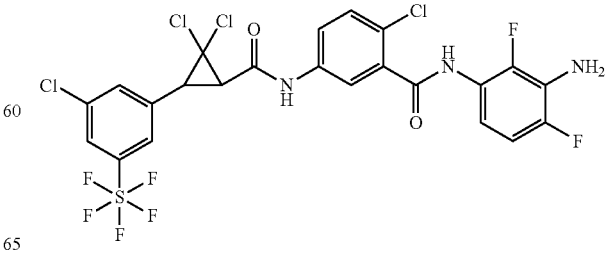

Isolated as a clear, colorless oil (0.071 g, 70%).

cis-N-(3-Amino-2,4-difluorophenyl)-2-chloro-5-(2,2-dichloro-3-(3-chloro-5-(pentafluoro-λ⁶-sulfanyl)phenyl)cyclopropane-1-carboxamido)benzamide (F1260)

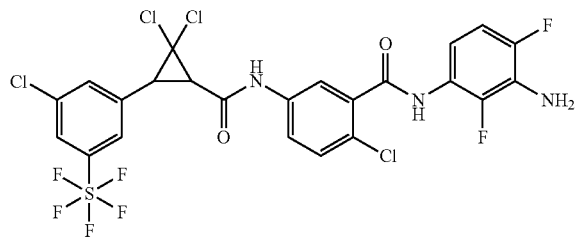 [SMILES: Nc1c(F)ccc(NC(=O)c2cc(NC(=O)C3C(c4cc(Cl)cc(S(F)(F)(F)(F)F)c4)C3(Cl)Cl)ccc2Cl)c1F]

Isolated as a clear, colorless oil (0.032 g, 67%).

Example 22: Preparation of trans-2-chloro-5-(2,2-dichloro-3-(3,5-dichlorophenyl)cyclopropane-1-carboxamido)-N-(2,4-difluoro-3-methoxyphenyl)benzamide (F1171)

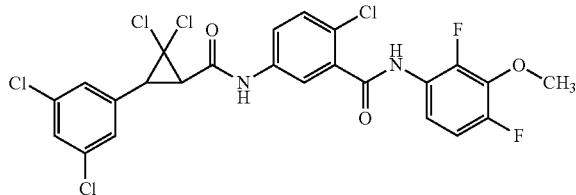 [SMILES: COc1c(F)ccc(NC(=O)c2cc(NC(=O)C3C(c4cc(Cl)cc(Cl)c4)C3(Cl)Cl)ccc2Cl)c1F]

trans-2-Chloro-5-(2,2-dichloro-3-(3,5-dichlorophenyl)cyclopropane-1-carboxamido)benzoic acid (C12) (0.1 g, 0.22 mmol) as a slurry in toluene (2 mL) was treated with oxalyl chloride (0.0.097 mL. 1.1 mmol) and a single drop of N,N-dimethylformamide with stirring at room temperature. After the mixture became homogeneous and gas evolution ceased, the solution was concentrated to a clear oil and then cooled in an ice bath under nitrogen. 2,4-Difluoro-3-methoxyaniline (0.035 g, 0.22 mmol) was added as a solution in pyridine (2 mL) with stirring and the reaction mixture was allowed to warm to room temperature and stir overnight. An aliquot was removed and diluted with dimethyl sulfoxide and examined by liquid chromatography/mass spectroscopy which indicated a mixture of the desired product and starting carboxylic acid. The reaction mixture was partitioned between ethyl acetate and aqueous hydrochloric acid (1 N), the layers were separated, and the organic phase was dried over sodium sulfate. Purification by flash silica gel chromatography (3:1 hexane-ethyl acetate) gave the title compound as a green-tinted solid (0.075 g, 57%).

The following compounds were prepared in like manner to the procedure outlined in Example 22:

trans-3-(2-Chloro-5-(2,2-dichloro-3-(3,5-dichlorophenyl)cyclopropane-1-carboxamido)benzamido)-2,6-difluorophenyl acetate (F1193)

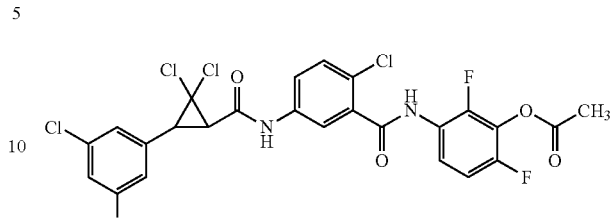

Isolated as a light yellow foam (0.105 g, 52%).

trans-Methyl 3-(2-chloro-5-(2,2-dichloro-3-(3,5-dichlorophenyl)cyclopropane-1-carboxamido)benzamido)-2,6-difluorobenzoate (F1265)

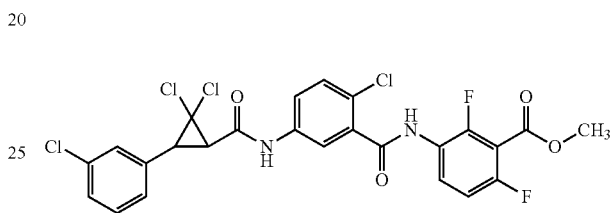

Isolated as a white foam (0.060 g, 44%).

Example 23: Preparation of trans-2-chloro-5-(2,2-dichloro-3-(3,5-dichlorophenyl)cyclopropane-1-carboxamido)-N-(4-hydroxy-2-methylphenyl)benzamide (F1224)

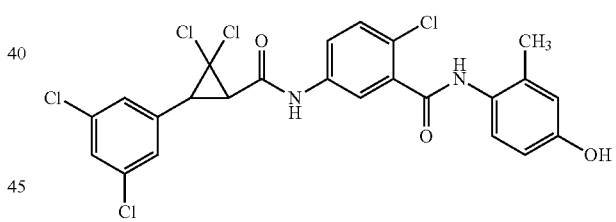

trans-2-Chloro-5-(2,2-dichloro-3-(3,5-dichlorophenyl)cyclopropane-1-carboxamido)benzoic acid (C12) (0.221 g, 0.487 mmol), 4-amino-3-methylphenol (0.072 g, 0.59 mmol) and 4-dimethylaminopyridine (0.071 g, 0.59 mmol) were weighed into a round bottomed flask. N,N-Dimethylformamide (2 mL) was added via syringe and -ethyl-3-(3-dimethylaminopropyl)carbodiimide hydrochloride (0.19 g, 0.97 mmol) was added with stirring at room temperature. After 64 hours, an aliquot was removed, diluted with dimethyl sulfoxide and analyzed by liquid chromatography/mass spectroscopy which indicated multiple products. After 120 hours, the reaction mixture was partitioned between ethyl acetate and brine, the layers were separated and the organic phase was dried over sodium sulfate. Purification by reverse phase chromatography gave, in order of elution, trans-2-chloro-5-(2,2-dichloro-3-(3,5-dichlorophenyl)cyclopropane-1-carboxamido)-N-(4-hydroxy-2-methylphenyl)benzamide, isolated as an off-white solid (0.022 g, 8%) and trans-4-amino-3-methylphenyl 2-chloro-5-(2,2-dichloro-3-(3,5-dichlorophenyl)cyclopropane-1-carboxamido)benzoate, isolated as an off-white solid (0.064 g, 24%): $^1$H NMR (400 MHz, Acetone-$d_6$) δ 10.25 (br s, 1H), 8.40 (d, J=2.6 Hz, 1H), 7.96 (dd, J=8.8, 2.7 Hz, 1H), 7.57 (d, J=8.8 Hz, 1H), 7.50 (s, 3H), 6.92 (d, J=2.6 Hz, 1H), 6.87 (dd, J=8.5, 2.7 Hz, 1H), 6.74 (d, J=8.5 Hz, 1H), 4.47 (ad, J=10.7 Hz, 2H), 3.67 (d, J=8.3 Hz, 1H), 3.46 (d, J=8.4 Hz, 1H), 2.17 (s, 3H); $^{13}$C NMR (101 MHz, Acetone-d$_6$) δ 163.94, 162.59, 144.40, 141.76, 137.93, 137.41, 134.71, 131.46, 130.64, 127.85, 127.38, 123.60, 122.74, 122.46, 121.84, 119.33, 114.40, 61.91, 39.23, 37.55, 16.70; ESIMS m/z 559 ([M+H]$^+$).

Example 24: Preparation of trans-tert-butyl-(4-(2-chloro-5-(2,2-dichloro-3-(3,5-dichlorophenyl)cyclopropane-1-carboxamido)benzamido)-3-methylphenyl)carbamate (DP10)

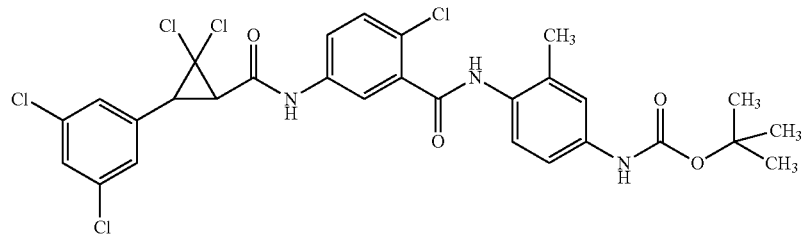 [SMILES: Cc1cc(NC(=O)OC(C)(C)C)ccc1NC(=O)c1cc(NC(=O)C2C(c3cc(Cl)cc(Cl)c3)C2(Cl)Cl)ccc1Cl]

To a solution of tert-butyl (4-amino-3-methylphenyl)carbamate (C184) (0.052 g, 0.233 mmol) in dichloromethane (2 mL) was added 3-(((ethylimino)methylene)amino)-N,N-dimethylpropan-1-amine hydrochloride (0.045 g, 0.233 mmol), N,N-dimethylpyridin-4-amine (0.021 g, 0.171 mmol), and trans-2-chloro-5-(2,2-dichloro-3-(3,5-dichlorophenyl)cyclopropane-1-carboxamido)benzoic acid (C12) (0.075 g, 0.155 mmol). The reaction was stirred at room temperature for 14 hours. The reaction was directly loaded onto a Celite loading column and purified by flash column chromatography using a gradient of 0-30% ethyl acetate/hexanes as eluent to afford the title compound as a white solid (0.056 g, 55%): $^1$H NMR (300 MHz, DMSO-d$_6$) δ 10.91 (s, 1H), 9.90 (s, 1H), 9.32 (s, 1H), 7.90 (d, J=2.6 Hz, 1H), 7.74 (dd, J=8.8, 2.6 Hz, 1H), 7.63 (t, J=1.8 Hz, 1H), 7.60-7.51 (m, 3H), 7.38 (s, 1H), 7.25 (q, J=8.9 Hz, 2H), 3.64 (d, J=8.5 Hz, 1H), 3.52 (d, J=8.5 Hz, 1H), 2.23 (s, 3H), 1.48 (s, 9H); (thin film) 3277, 2980, 1684, 1655, 1539 cm$^{-1}$; ESIMS 656 ([M−H]$^-$).

Example 25: Preparation of tert-butyl-N-tert-butoxycarbonyl-N-[3-[[2-chloro-5-[[(1R,3R)-2,2-dichloro-3-(3-chloro-4-fluorophenyl)cyclopropanecarbonyl]amino]-3-fluorobenzoyl]amino]-2,6-difluorophenyl]carbamate (F1239)

To a solution of 2-chloro-5-((1R,3R)-2,2-dichloro-3-(3-chloro-4-fluorophenyl)cyclopropane-1-carboxamido)-3-fluorobenzoic acid (C1) (0.360 g, 0.79 mmol) in ethyl acetate (2.5 mL) were added tert-butyl N-(3-amino-2,6-difluoro-phenyl)-N-tert-butoxycarbonylcarbamate (C182) (0.327 g, 0.95 mmol), and pyridine (0.188 g, 0.191 mL, 2.37 mmol) followed by a 50% solution of 2,4,6-tripropyl-1,3,5,2,4,6-trioxatriphosphinane 2,4,6-trioxide (0.94 mL, 1.58 mmol) in ethyl acetate, and the resulting gold solution was warmed to 45° C. and stirred for 68 hours. The reaction mixture was concentrated and the viscous, amber residue was dissolve in minimal methylene chloride (~3 mL) and adsorbed to Celite®. The adsorbed material was purified by automated flash chromatography using a gradient of 0-25% ethyl acetate in hexanes as eluent to give the title compound (0.166 g, 87%) as a white solid.

The following compounds were prepared in like manner to the procedure outlined in Example 25:

2-Chloro-5-((1R,3R)-2,2-dichloro-3-(3-chloro-4-fluorophenyl)cyclopropane-1-carboxamido)-N-(3-fluoro-2-nitrophenyl)benzamide (F1081)

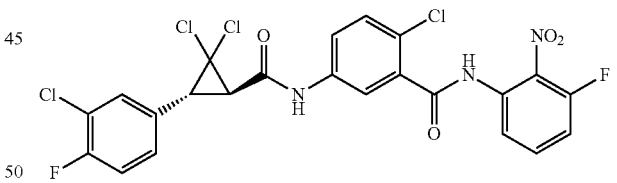

Isolated as a yellow solid (0.056 g, 43%).

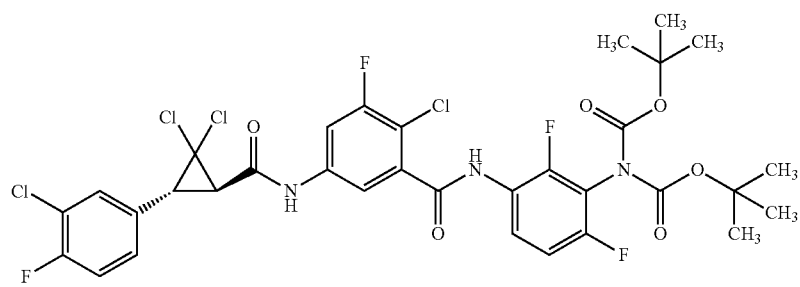 [SMILES: CC(C)(C)OC(=O)N(C(=O)OC(C)(C)C)c1c(F)ccc(NC(=O)c2cc(NC(=O)[C@H]3[C@H](c4ccc(F)c(Cl)c4)C3(Cl)Cl)cc(F)c2Cl)c1F]

151

2-Chloro-5-((1R,3R)-2,2-dichloro-3-(3-chloro-4-fluorophenyl)cyclopropane-1-carboxamido)-N-(2-fluoro-4-methyl-5-nitrophenyl)benzamide (F1082)


Isolated as an off-white foam (0.109 g, 81%).

2-Chloro-5-((1R,3R)-2,2-dichloro-3-(3-chloro-4-fluorophenyl)cyclopropane-1-carboxamido)-N-(4,5-difluoro-2-nitrophenyl)benzamide (F1085)

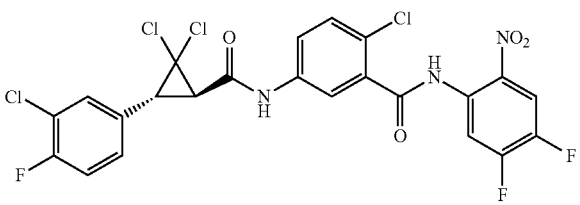

Isolated as a yellow film (0.039 g, 28%).

2-Chloro-5-((1R,3R)-2,2-dichloro-3-(3,5-dichlorophenyl)cyclopropane-1-carboxamido)-N-(3-(2,2-difluoroacetamido)-2,4-difluorophenyl)benzamide (F1268)

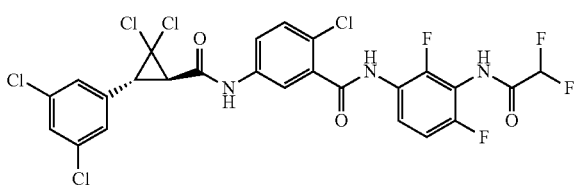 [SMILES: O=C(Nc1ccc(F)c(NC(=O)C(F)F)c1F)c1cc(NC(=O)[C@H]2[C@H](c3cc(Cl)cc(Cl)c3)C2(Cl)Cl)ccc1Cl]

Isolated as a white powder (0.049 g, 34%).

2-Chloro-5-((1R,3R)-2,2-dichloro-3-(3,4,5-trichlorophenyl)cyclopropane-1-carboxamido)-N-(3-(2,2-difluoroacetamido)-2,4-difluorophenyl)benzamide (F1269)

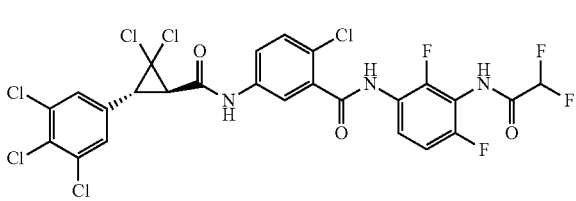 [SMILES: O=C(Nc1ccc(F)c(NC(=O)C(F)F)c1F)c1cc(NC(=O)[C@H]2[C@H](c3cc(Cl)c(Cl)c(Cl)c3)C2(Cl)Cl)ccc1Cl]

Isolated as a white solid (0.078 g, 55%).

152

2-Chloro-5-((1R,3R)-2,2-dichloro-3-(3-chloro-4-fluorophenyl)cyclopropane-1-carboxamido)-N-(3-(2,2-difluoroacetamido)-2,4-difluorophenyl)benzamide (F1270)

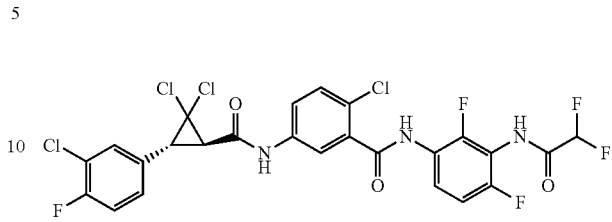

Isolated as a white foam (0.084 g, 58%).

2-Chloro-5-((1R,3R)-2,2-dichloro-3-(3,4-dichlorophenyl)cyclopropane-1-carboxamido)-N-(3-(2,2-difluoro-N-methylacetamido)-2,4-difluorophenyl)benzamide (F1271)

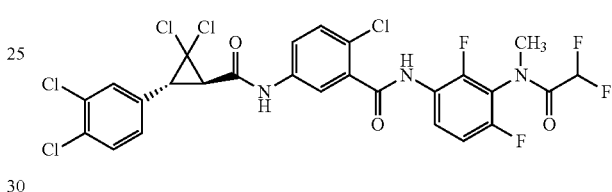

Isolated as a white foam (0.090 g, 61%).

trans-N-(3-Bromo-4-fluorophenyl)-2-chloro-5-(2,2-dichloro-3-(3,5-dichlorophenyl)cyclopropane-1-carboxamido)benzamide (F1304)

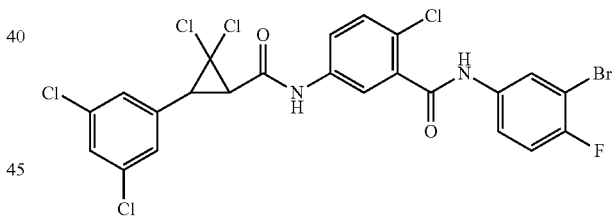

Isolated as an off-white solid (0.18 g, 33%).

trans-N-(2-Bromo-4-fluorophenyl)-2-chloro-5-(2,2-dichloro-3-(3,5-dichlorophenyl)cyclopropane-1-carboxamido)benzamide (F1305)

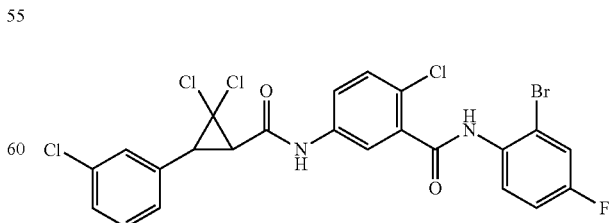

Isolated as an off-white solid (0.18 g, 37%).

153 trans-N-(4-Bromo-2-fluorophenyl)-2-chloro-5-(2,2-dichloro-3-(3,5-dichlorophenyl)cyclopropane-1-carboxamido)benzamide (F1306)

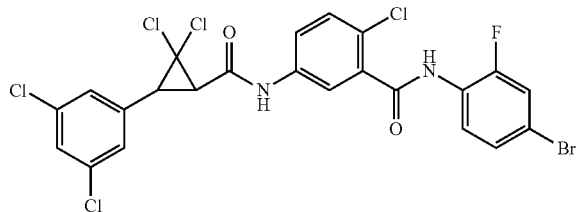 [SMILES: O=C(Nc1ccc(Br)cc1F)c1cc(NC(=O)C2C(c3cc(Cl)cc(Cl)c3)C2(Cl)Cl)ccc1Cl]

Isolated as an off-white solid (0.18 g, 37%).

trans-N-(3-Bromo-2,4-difluorophenyl)-2-chloro-5-(2,2-dichloro-3-(3,5-dichlorophenyl)cyclopropane-1-carboxamido)benzamide (F1307)

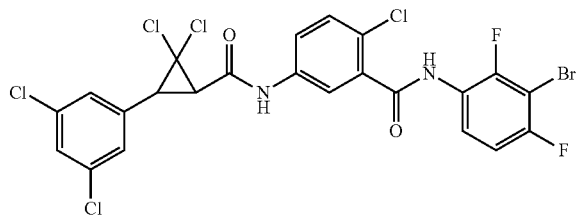 [SMILES: O=C(Nc1ccc(F)c(Br)c1F)c1cc(NC(=O)C2C(c3cc(Cl)cc(Cl)c3)C2(Cl)Cl)ccc1Cl]

Isolated as an off-white solid (0.33 g, 39%).

trans-N-(5-Bromo-2,4-difluorophenyl)-2-chloro-5-(2,2-dichloro-3-(3,5-dichlorophenyl)cyclopropane-1-carboxamido)benzamide (F1308)

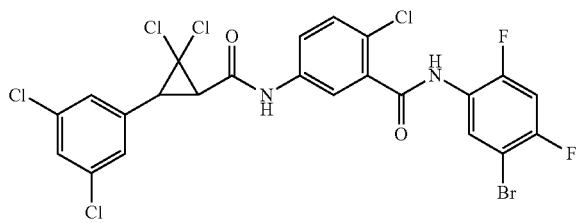 [SMILES: O=C(Nc1cc(Br)c(F)cc1F)c1cc(NC(=O)C2C(c3cc(Cl)cc(Cl)c3)C2(Cl)Cl)ccc1Cl]

Isolated as an off-white solid (0.48 g, 34%).

trans-N-(2-Bromo-4,6-difluorophenyl)-2-chloro-5-(2,2-dichloro-3-(3,5-dichlorophenyl)cyclopropane-1-carboxamido)benzamide (F1309)

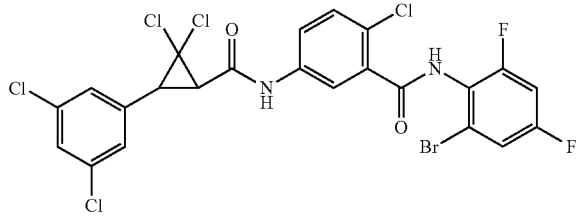 [SMILES: O=C(Nc1c(F)cc(F)cc1Br)c1cc(NC(=O)C2C(c3cc(Cl)cc(Cl)c3)C2(Cl)Cl)ccc1Cl]

Isolated as an off-white solid (0.24 g, 28%).

154 trans-N-(3-Bromo-4,5-difluorophenyl)-2-chloro-5-(2,2-dichloro-3-(3,5-dichlorophenyl)cyclopropane-1-carboxamido)benzamide (DP11)

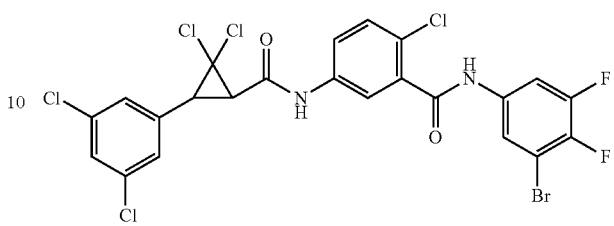

Isolated as an off-white solid (0.62 g, 44%).

trans-N-(3-Amino-2,4,5,6-tetrafluorophenyl)-2-chloro-5-(2,2-dichloro-3-(3,5-dichlorophenyl)cyclopropane-1-carboxamido)benzamide (F1022)

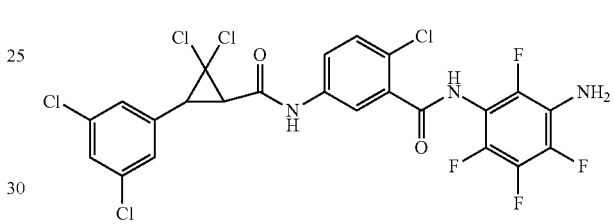

Isolated as a white foam (0.012 g, 8%).

trans-tert-Butyl-(3-(2-chloro-5-(2,2-dichloro-3-(3,5-dichlorophenyl)cyclopropane-1-carboxamido)benzamido)-2,4-difluorophenyl)carbamate (F1023)

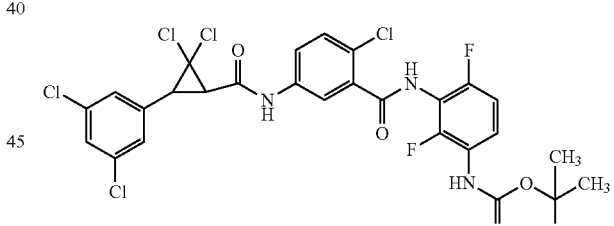

Isolated as a white foam (0.088 g, 56%).

trans-N-(3-Acetamido-2,4-dimethylphenyl)-2-chloro-5-(2,2-dichloro-3-(3,5-dichlorophenyl)cyclopropane-1-carboxamido)benzamide (F1128)

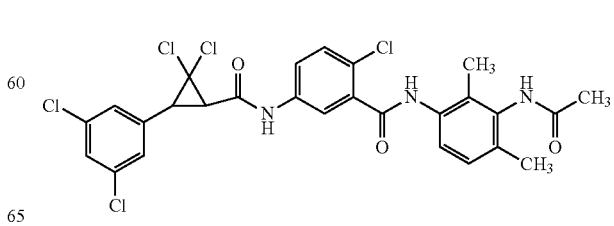

Isolated as a white solid (0.094 g, 66%).

155 trans-2-Chloro-5-(2,2-dichloro-3-(3,5-dichlorophenyl)cyclopropane-1-carboxamido)-N-(2,3-dimethyl-4-nitrophenyl)benzamide (F1180)

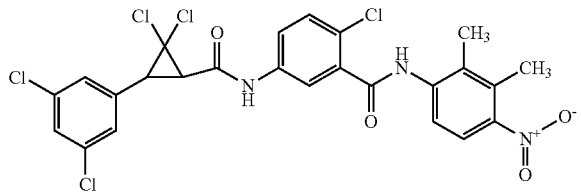 [SMILES: Cc1c(NC(=O)c2cc(NC(=O)C3C(c4cc(Cl)cc(Cl)c4)C3(Cl)Cl)ccc2Cl)ccc([N+](=O)[O-])c1C]

Isolated as a yellow solid (0.246 g, 70%).

trans-2-Chloro-5-(2,2-dichloro-3-(3,5-dichlorophenyl)cyclopropane-1-carboxamido)-N-(2,5-dimethyl-4-nitrophenyl)benzamide (F1230)

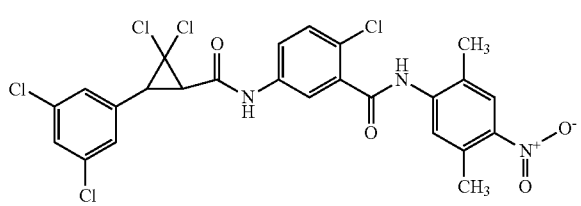 [SMILES: Cc1cc([N+](=O)[O-])c(C)cc1NC(=O)c1cc(NC(=O)C2C(c3cc(Cl)cc(Cl)c3)C2(Cl)Cl)ccc1Cl]

Isolated as a white solid (0.041 g, 12%).

trans-N-(4-Bromo-2-methylphenyl)-2-chloro-5-(2,2-dichloro-3-(3,5-dichlorophenyl)cyclopropane-1-carboxamido)benzamide (F1054)

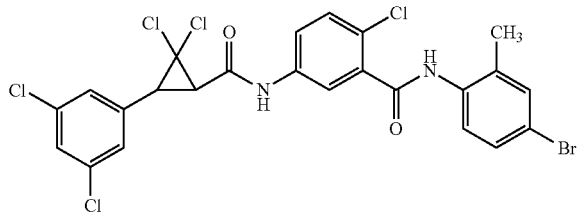 [SMILES: Cc1cc(Br)ccc1NC(=O)c1cc(NC(=O)C2C(c3cc(Cl)cc(Cl)c3)C2(Cl)Cl)ccc1Cl]

Isolated as a white powder (0.46 g, 84%).

156 trans-2-Chloro-5-(2,2-dichloro-3-(3-chloro-4-fluorophenyl)cyclopropane-1-carboxamido)-3-fluoro-N-(4-fluorophenyl)benzamide (F1152)

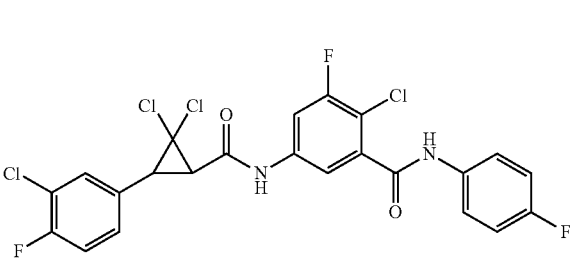

Isolated as a pale-yellow solid (0.065 g, 88%).

trans-2-Chloro-5-(2,2-dichloro-3-(3-chloro-4-fluorophenyl)cyclopropane-1-carboxamido)-N-(2,4-difluorophenyl)-3-fluorobenzamide (F1153)

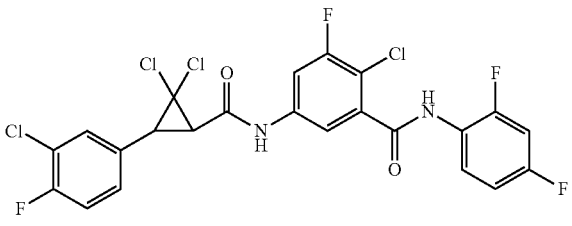 [SMILES: O=C(Nc1ccc(F)cc1)c1cc(NC(=O)C2C(c3ccc(F)c(Cl)c3)C2(Cl)Cl)cc(F)c1Cl]

Isolated as a pale-yellow solid (0.071 g, 93%).

trans-N-(4-Acetamidophenyl)-2-chloro-5-(2,2-dichloro-3-(3-chloro-4-fluorophenyl)cyclopropane-1-carboxamido)-3-fluorobenzamide (F1154)

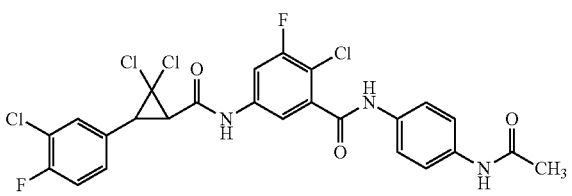 [SMILES: CC(=O)Nc1ccc(NC(=O)c2cc(NC(=O)C3C(c4ccc(F)c(Cl)c4)C3(Cl)Cl)cc(F)c2Cl)cc1]

Isolated as a white solid (0.077 g, 97%).

trans-tert-Butyl-N-tert-butoxycarbonyl-N-[3-[[2-chloro-5-[[2,2-dichloro-3-(3-chloro-4-fluorophenyl)cyclopropanecarbonyl]amino]-3-fluorobenzoyl]amino]-2,6-difluorophenyl]carbamate (F1155)

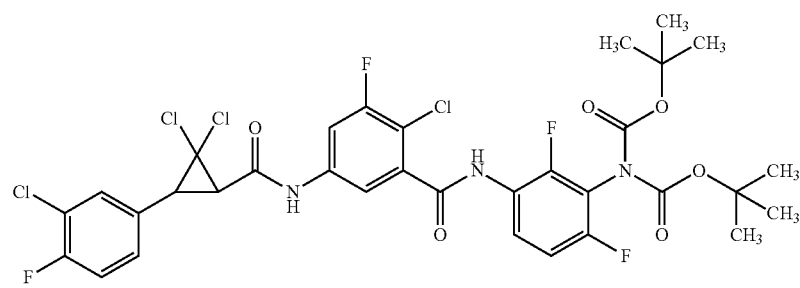

Isolated as a light-yellow-solid (0.0185 g, 85%).

157 trans-2-Chloro-5-(2,2-dichloro-3-(3-chloro-4-fluoro-phenyl)cyclopropane-1-carboxamido)-3-methyl-N-phenylbenzamide (F1183)

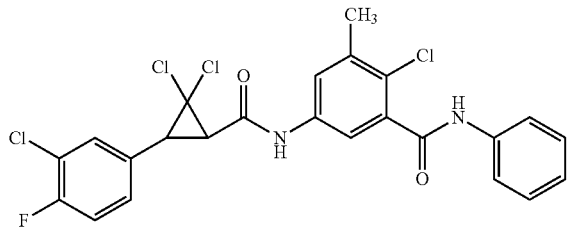

Isolated as a white solid (0.072 g, 89%).

trans-2-Chloro-5-(2,2-dichloro-3-(3-chloro-4-fluoro-phenyl)cyclopropane-1-carboxamido)-N-(4-fluoro-phenyl)-3-methylbenzamide (F1184)

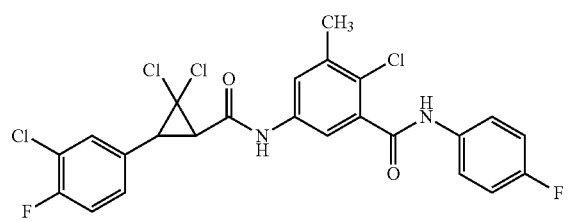

Isolated as a tan solid (0.071 g, 86%).

158 trans-2-Chloro-5-(2,2-dichloro-3-(3-chloro-4-fluoro-phenyl)cyclopropane-1-carboxamido)-N-(2,4-difluoro-phenyl)-3-methylbenzamide (F1185)

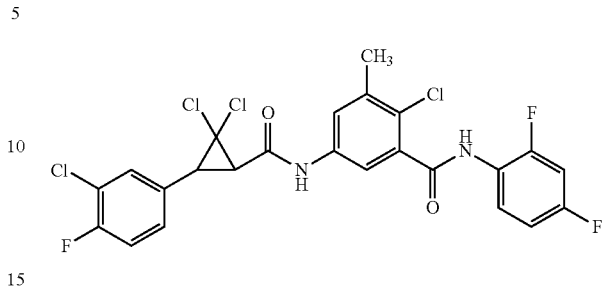

Isolated as a white solid (0.070 g, 84%).

trans-N-(4-Acetamidophenyl)-2-chloro-5-(2,2-di-chloro-3-(3-chloro-4-fluorophenyl)cyclopropane-1-carboxamido)-3-methylbenzamide (F1186)

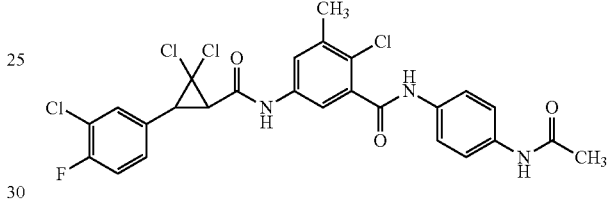

Isolated as a light pink solid (0.067 g, 74%).

trans-tert-Butyl-N-tert-butoxycarbonyl-N-[3-[[2-chloro-5-[[2,2-dichloro-3-(3-chloro-4-fluorophenyl)cyclopropanecarbonyl]amino]-3-methylbenzoyl]amino]-2,6-difluorophenyl]carbamate (F1187)

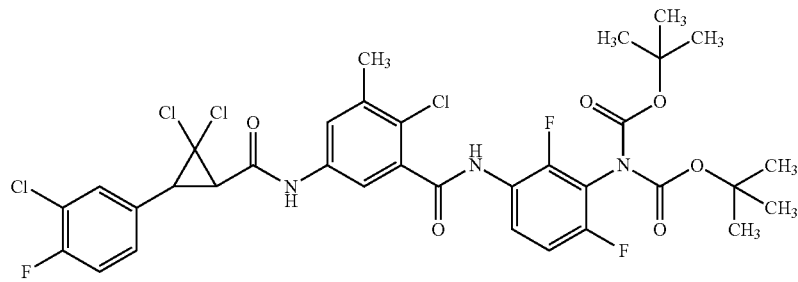

Isolated as a light tan solid (0.109 g, 88%).

trans-3-Chloro-5-(2,2-dichloro-3-(3-chloro-4-fluoro-phenyl)cyclopropane-1-carboxamido)-2-methyl-N-phenylbenzamide (F1188)

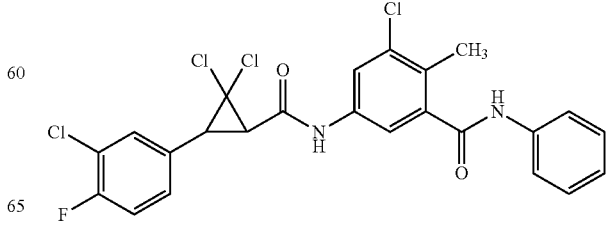

Isolated as a white solid (0.073 g, 93%).

159 trans-3-Chloro-5-(2,2-dichloro-3-(3-chloro-4-fluoro-phenyl)cyclopropane-1-carboxamido)-N-(4-fluoro-phenyl)-2-methylbenzamide (F1189)

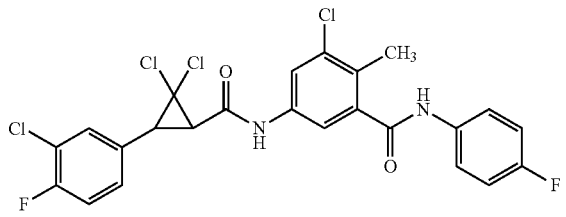

Isolated as a light tan solid (0.072 g, 89%).

trans-3-Chloro-5-(2,2-dichloro-3-(3-chloro-4-fluoro-phenyl)cyclopropane-1-carboxamido)-N-(2,4-difluo-rophenyl)-2-methylbenzamide (F1190)

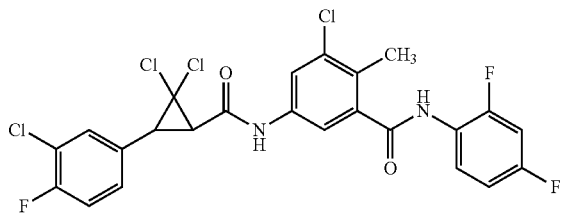

Isolated as a light-tan solid (0.073 g, 90%).

160 trans-N-(4-Acetamidophenyl)-3-chloro-5-(2,2-di-chloro-3-(3-chloro-4-fluorophenyl)cyclopropane-1-carboxamido)-2-methylbenzamide (F1191)

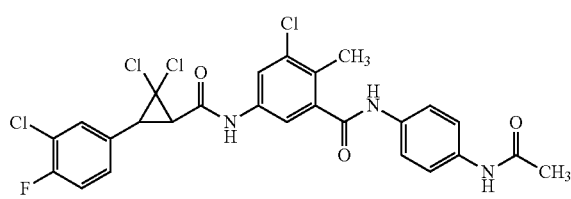 [SMILES: CC(=O)Nc1ccc(NC(=O)c2cc(NC(=O)C3C(c4ccc(F)c(Cl)c4)C3(Cl)Cl)cc(Cl)c2C)cc1]

Isolated as a white solid (0.081 g, 93%).

trans-tert-Butyl-N-tert-butoxycarbonyl-N-[3-[[3-chloro-5-[[2,2-dichloro-3-(3-chloro-4-fluorophenyl)cyclopropanecarbonyl]amino]-2-methylbenzoyl]amino]-2,6-difluorophenyl]carbamate (F1192)

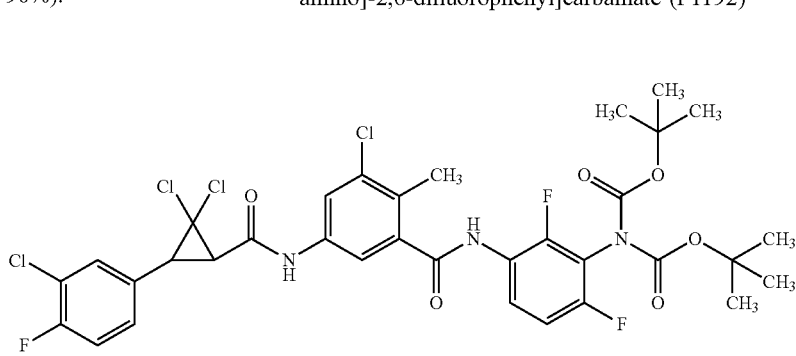

Isolated as a white solid (0.131 g, 99%).

trans-3-Chloro-5-(2,2-dichloro-3-(3-chloro-4-fluoro-phenyl)cyclopropane-1-carboxamido)-2-fluoro-N-phenylbenzamide (F1194)

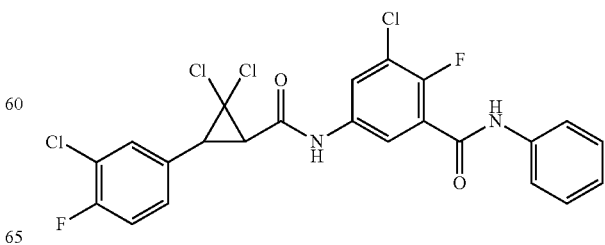

Isolated as an off-white solid (0.043 g, 44%).

161 trans-3-Chloro-5-(2,2-dichloro-3-(3-chloro-4-fluorophenyl)cyclopropane-1-carboxamido)-2-fluoro-N-(4-fluorophenyl)benzamide (F1195)

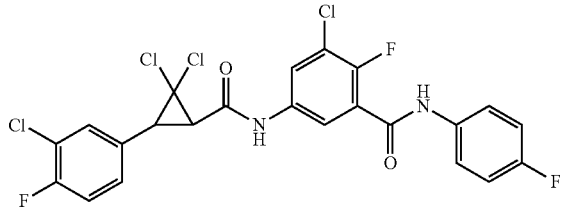 [SMILES: O=C(Nc1ccc(F)cc1)c1cc(NC(=O)C2C(c3ccc(F)c(Cl)c3)C2(Cl)Cl)cc(F)c1F]

Isolated as an off-white solid (0.072 g, 71%).

trans-3-Chloro-5-(2,2-dichloro-3-(3-chloro-4-fluorophenyl)cyclopropane-1-carboxamido)-N-(2,4-difluorophenyl)-2-fluorobenzamide (F1196)

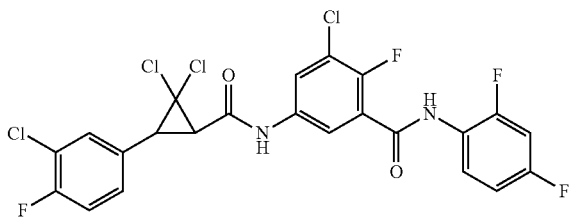

Isolated as an off-white solid (0.064 g, 61%).

162 trans-N-(4-Acetamidophenyl)-3-chloro-5-(2,2-dichloro-3-(3-chloro-4-fluorophenyl)cyclopropane-1-carboxamido)-2-fluorobenzamide (F1197)

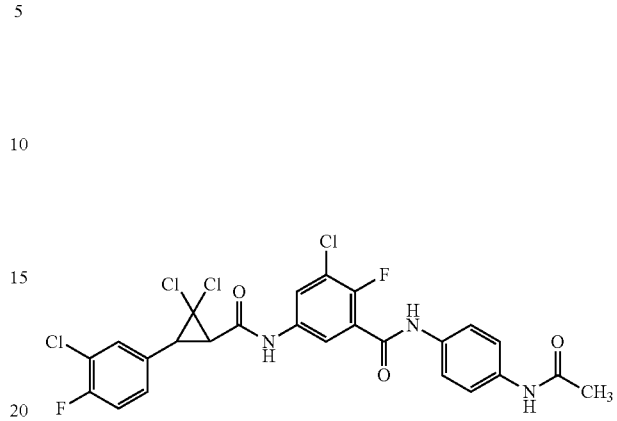

Isolated as a white solid (0.044 g, 40%).

trans-tert-Butyl-N-tert-butoxycarbonyl-N-[3-[[3-chloro-5-[[2,2-dichloro-3-(3-chloro-4-fluorophenyl)cyclopropanecarbonyl]amino]-2-fluorobenzoyl]amino]-2,6-difluorophenyl]carbamate (F1198)

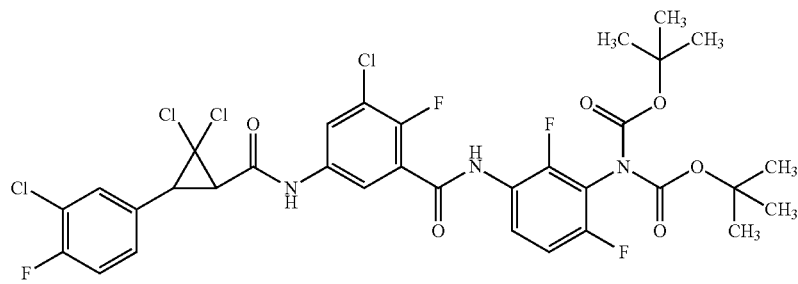

Isolated as an off-white solid (0.099 g, 65%).

trans-5-(2,2-Dichloro-3-(3-chloro-4-fluorophenyl)cyclopropane-1-carboxamido)-2,3-difluoro-N-phenylbenzamide (F1207)

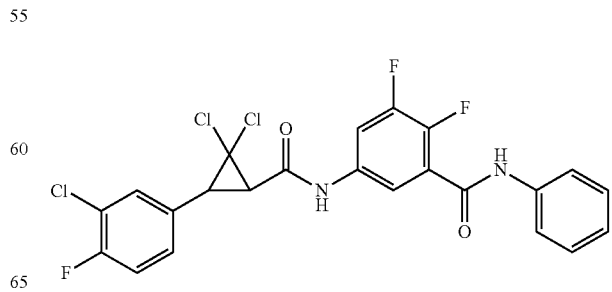

Isolated as an off-white solid (0.066 g, 67%).

163 trans-5-(2,2-Dichloro-3-(3-chloro-4-fluorophenyl)cyclopropane-1-carboxamido)-2,3-difluoro-N-(4-fluorophenyl)benzamide (F1208)

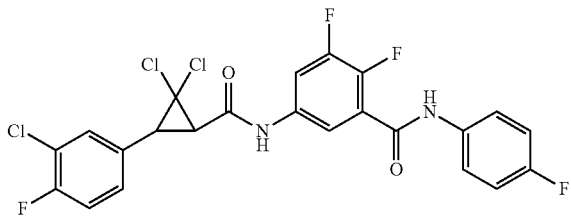

Isolated as a white solid (0.079 g, 77%).

trans-5-(2,2-Dichloro-3-(3-chloro-4-fluorophenyl)cyclopropane-1-carboxamido)-N-(2,4-difluorophenyl)-2,3-difluorobenzamide (F1209)

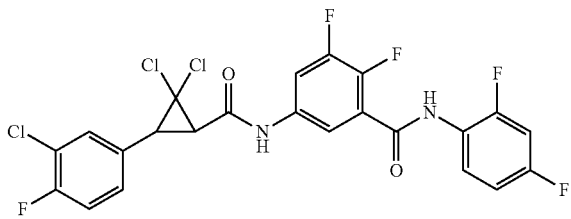 [SMILES: O=C(Nc1ccc(F)cc1F)c1cc(NC(=O)C2C(c3ccc(F)c(Cl)c3)C2(Cl)Cl)cc(F)c1F]

Isolated as a white solid (0.039 g, 84%).

164 trans-N-(4-Acetamidophenyl)-5-(2,2-dichloro-3-(3-chloro-4-fluorophenyl)cyclopropane-1-carboxamido)-2,3-difluorobenzamide (F1210)

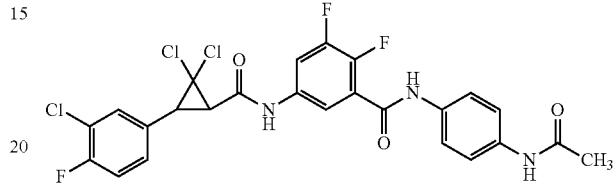

Isolated as a white solid (0.086 g, 78%).

trans-tert-Butyl-N-tert-butoxycarbonyl-N-[3-[[5-[[2,2-dichloro-3-(3-chloro-4-fluorophenyl)cyclopropanecarbonyl]amino]-2,3-difluorobenzoyl]amino]-2,6-difluorophenyl]carbamate (F1211)

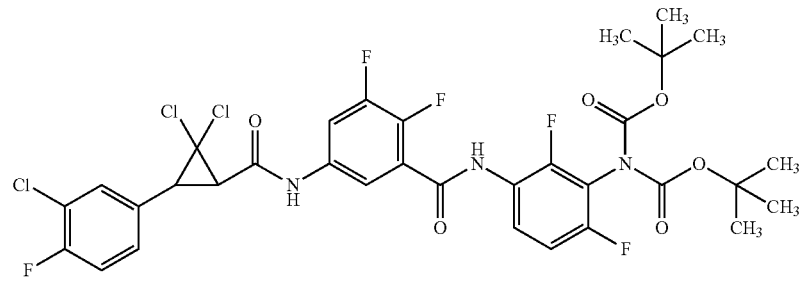 [SMILES: CC(C)(C)OC(=O)N(C(=O)OC(C)(C)C)c1c(F)ccc(NC(=O)c2cc(NC(=O)C3C(c4ccc(F)c(Cl)c4)C3(Cl)Cl)cc(F)c2F)c1F]

Isolated as a light yellow solid (0.130 g, 89%).

trans-2-Chloro-5-(2,2-dichloro-3-(3-chloro-4-fluorophenyl)cyclopropane-1-carboxamido)-N-phenyl-3-(trifluoromethyl)benzamide (F1212)

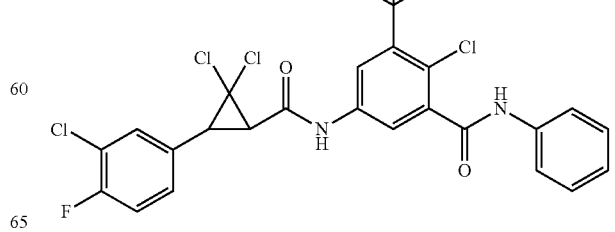

Isolated as a tan solid (0.060 g, 76%).

165 trans-5-(2,2-Dichloro-3-(3-chloro-4-fluorophenyl)
cyclopropane-1-carboxamido)-3-fluoro-2-methoxy-
N-phenylbenzamide (F1213)

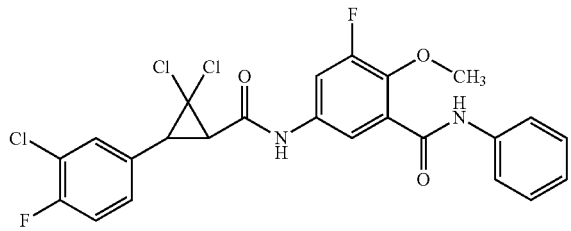 [SMILES: COc1c(F)cc(NC(=O)C2C(c3ccc(F)c(Cl)c3)C2(Cl)Cl)cc1C(=O)Nc1ccccc1]

Isolated as a tan solid (0.067 g, 86%).

trans-2-Chloro-5-(2,2-dichloro-3-(3-chloro-4-fluoro-
phenyl)cyclopropane-1-carboxamido)-N-(4-fluoro-
phenyl)-3-(trifluoromethyl)benzamide (F1214)

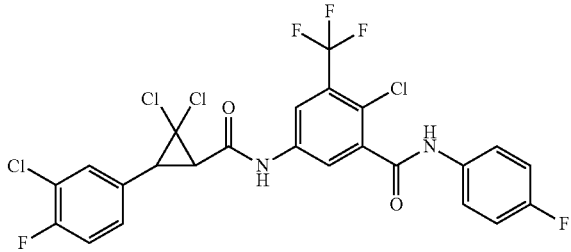 [SMILES: O=C(Nc1ccc(F)cc1)c1cc(NC(=O)C2C(c3ccc(F)c(Cl)c3)C2(Cl)Cl)cc(C(F)(F)F)c1Cl]

Isolated as a tan solid (0.066 g, 83%).

166 trans-2-Chloro-5-(2,2-dichloro-3-(3-chloro-4-fluoro-
phenyl)cyclopropane-1-carboxamido)-N-(2,4-difluo-
rophenyl)-3-(trifluoromethyl)benzamide (F1215)

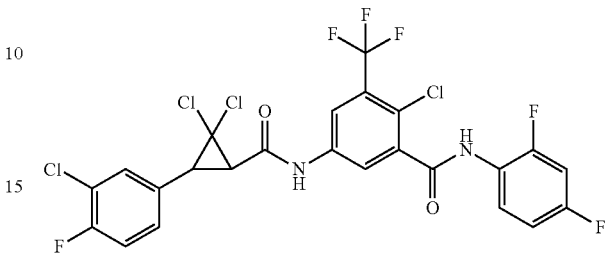

Isolated as a tan foam (0.072 g, 88%).

trans-N-(4-Acetamidophenyl)-2-chloro-5-(2,2-di-
chloro-3-(3-chloro-4-fluorophenyl)cyclopropane-1-
carboxamido)-3-(trifluoromethyl)benzamide (F1216)

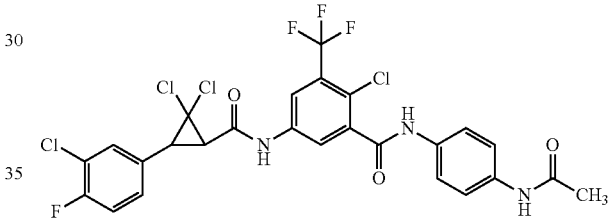

Isolated as a tan solid (0.072 g, 83%).

trans-tert-Butyl-N-tert-butoxycarbonyl-N-[3-[[2-
chloro-5-[[2,2-dichloro-3-(3-chloro-4-fluoro-phenyl)
cyclopropanecarbonyl]amino]-3-(trifluoromethyl)-
benzoyl]amino]-2,6-difluorophenyl]carbamate
(F1217)

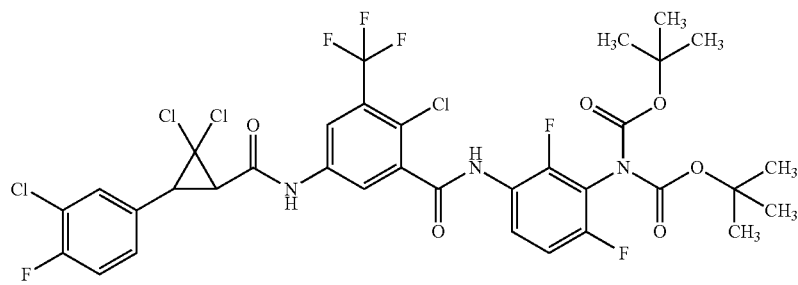 [SMILES: CC(C)(C)OC(=O)N(C(=O)OC(C)(C)C)c1c(F)ccc(NC(=O)c2cc(NC(=O)C3C(c4ccc(F)c(Cl)c4)C3(Cl)Cl)cc(C(F)(F)F)c2Cl)c1F]

Isolated as a light-yellow solid (0.098 g, 86%).

167 trans-5-(2,2-Dichloro-3-(3-chloro-4-fluorophenyl)cyclopropane-1-carboxamido)-3-fluoro-N-(4-fluorophenyl)-2-methoxybenzamide (F1218)

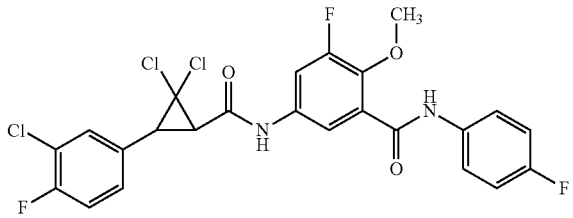 [SMILES: COc1c(F)cc(NC(=O)C2C(c3ccc(F)c(Cl)c3)C2(Cl)Cl)cc1C(=O)Nc1ccc(F)cc1]

Isolated as a tan foam (0.072 g, 89%).

trans-5-(2,2-Dichloro-3-(3-chloro-4-fluorophenyl)cyclopropane-1-carboxamido)-N-(2,4-difluorophenyl)-3-fluoro-2-methoxybenzamide (F1219)

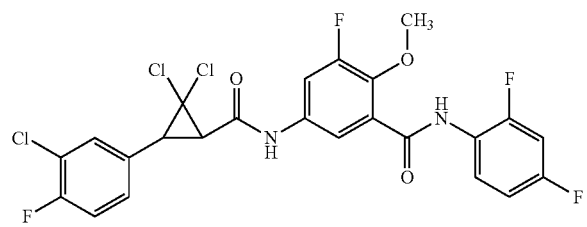

Isolated as a white solid (0.065 g, 79%).

168 trans-N-(4-Acetamidophenyl)-5-(2,2-dichloro-3-(3-chloro-4-fluorophenyl)-cyclopropane-1-carboxamido)-3-fluoro-2-methoxybenzamide (F1220)

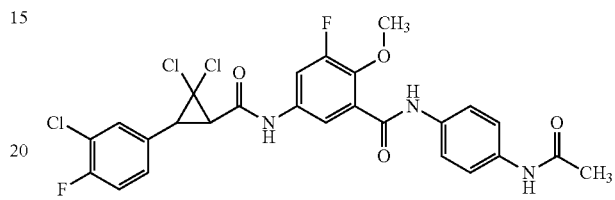

Isolated as a light-yellow solid (0.075 g, 87%).

trans-tert-Butyl-N-tert-butoxycarbonyl-N-[3-[[5-[[2,2-dichloro-3-(3-chloro-4-fluorophenyl)cyclopropanecarbonyl]amino]-3-fluoro-2-methoxybenzoyl]amino]-2,6-difluorophenyl]carbamate (F1221)

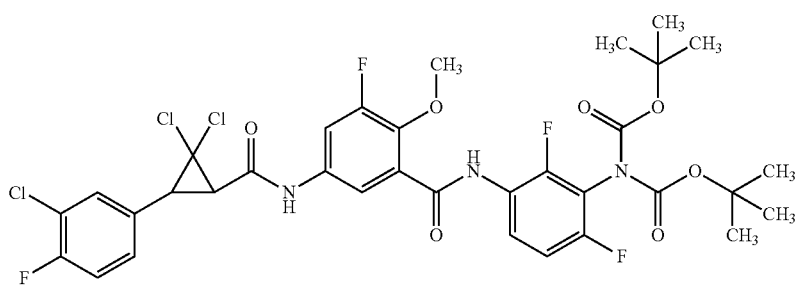

Isolated as a light-yellow solid (0.109 g, 94%).

trans-tert-Butyl-N-tert-butoxycarbonyl-N-[4-[[2-chloro-5-[[2,2-dichloro-3-(3,4-dichlorophenyl)cyclopropanecarbonyl]amino]benzoyl]amino]-2,6-difluoro-phenyl]carbamate (F1266)

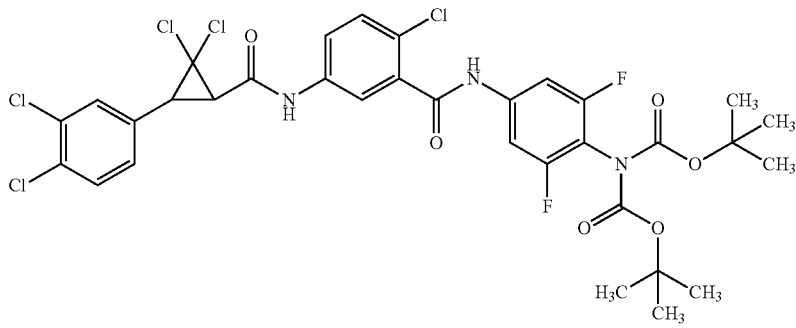 [SMILES: CC(C)(C)OC(=O)N(C(=O)OC(C)(C)C)c1c(F)cc(NC(=O)c2cc(NC(=O)C3C(c4ccc(Cl)c(Cl)c4)C3(Cl)Cl)ccc2Cl)cc1F]

Isolated as a light brown solid (2.06 g, 79%).

169 tert-Butyl-N-((tert-butoxy)carbonyl)-N-(5-(2-chloro-5-((1R,3R)-2,2-dichloro-3-(3,4-dichlorophenyl)cyclopropane-1-carboxamido)benzamido)-2,4-difluorophenyl)carbamate (DP12)

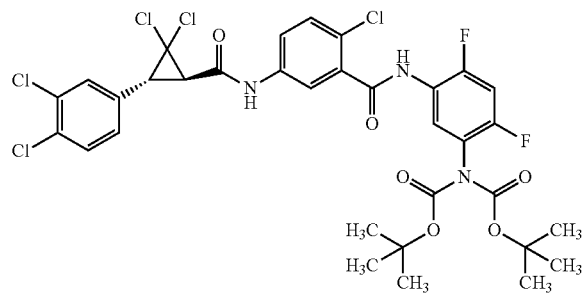 [SMILES: CC(C)(C)OC(=O)N(C(=O)OC(C)(C)C)c1cc(NC(=O)c2cc(NC(=O)[C@H]3[C@H](c4ccc(Cl)c(Cl)c4)C3(Cl)Cl)ccc2Cl)c(F)cc1F]

Isolated as a white solid (0.154 g, 90%).

trans-2-Chloro-5-(2,2-dichloro-3-(3,4-dichlorophenyl)cyclopropane-1-carboxamido)-N-(4-fluoro-2-nitrophenyl)benzamide (DP13)

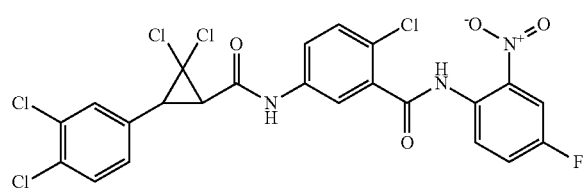

Isolated as a yellow solid (0.8 g, 42%).

170 trans-5-(2,2-Dichloro-3-(3-chloro-4-fluorophenyl)cyclopropane-1-carboxamido)-3-fluoro-N-(4-fluorophenyl)-2-methylbenzamide (F1278)

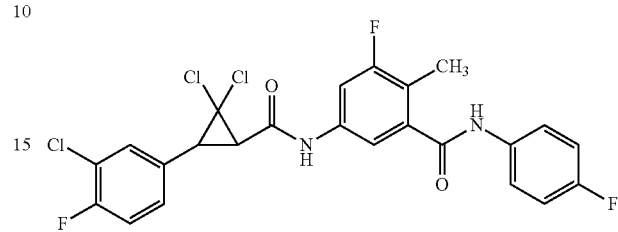

Isolated as a light-tan solid (0.058 g, 85%).

trans-5-(2,2-Dichloro-3-(3-chloro-4-fluorophenyl)cyclopropane-1-carboxamido)-N-(2,4-difluorophenyl)-3-fluoro-2-methylbenzamide (F1279)

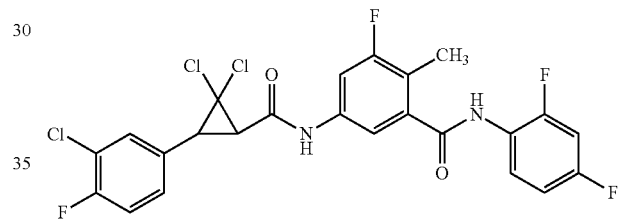

Isolated as a light-tan solid (0.059 g, 84%).

trans-tert-Butyl-N-tert-butoxycarbonyl-N-[3-[[5-[[2,2-dichloro-3-(3-chloro-4-fluorophenyl)cyclopropanecarbonyl]amino]-3-fluoro-2-methylbenzoyl]amino]-2,6-difluorophenyl]carbamate (F1280)

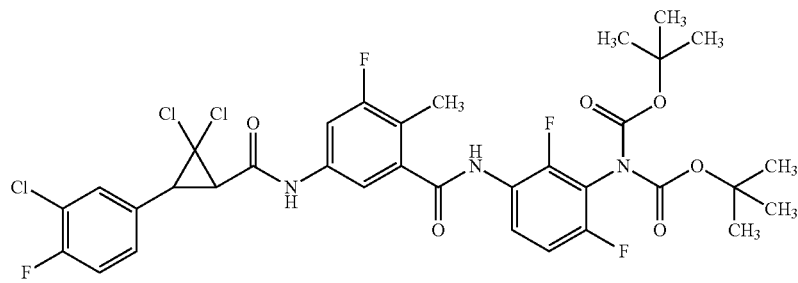

Isolated as a white solid (0.099 g, 100%).

171 trans-5-(2,2-Dichloro-3-(3-chloro-4-fluorophenyl)
cyclopropane-1-carboxamido)-N-ethyl-2-fluoro-3-
methylbenzamide (F2029)

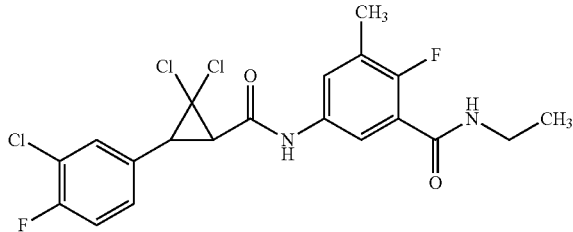

Isolated as a white solid (0.068 g, 83%).

trans-5-(2,2-Dichloro-3-(3-chloro-4-fluorophenyl)
cyclopropane-1-carboxamido)-2-fluoro-3-methyl-N-
(2,2,2-trifluoroethyl)benzamide (F2030)

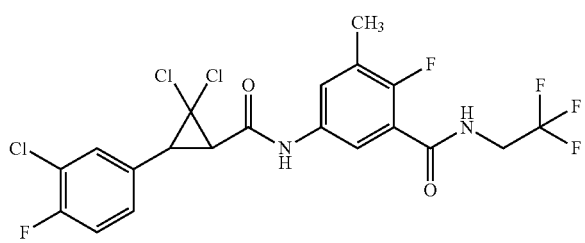 [SMILES: Cc1cc(NC(=O)C2C(c3ccc(F)c(Cl)c3)C2(Cl)Cl)cc(C(=O)NCC(F)(F)F)c1F]

Isolated as a white solid (0.077 g, 84%).

trans-5-(2,2-Dichloro-3-(3-chloro-4-fluorophenyl)
cyclopropane-1-carboxamido)-2-fluoro-3-methyl-N-
(2,2,3,3,3-pentafluoropropyl)benzamide (F2031)

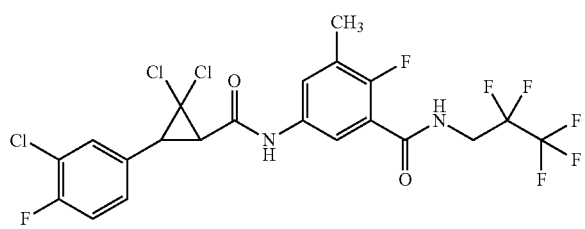

Isolated as a white solid (0.083 g, 82%).

trans-N-(3-Chloropropyl)-5-(2,2-dichloro-3-(3-
chloro-4-fluorophenyl)-cyclopropane-1-carbox-
amido)-2-fluoro-3-methylbenzamide (F2032)

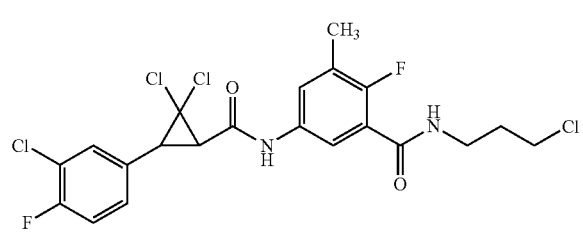 [SMILES: Cc1cc(NC(=O)C2C(c3ccc(F)c(Cl)c3)C2(Cl)Cl)cc(C(=O)NCCCCl)c1F]

Isolated as a white solid (0.069 g, 78%).

172 trans-2-Chloro-5-(2,2-dichloro-3-(3-chloro-4-fluoro-
phenyl)cyclopropane-1-carboxamido)-N-ethyl-3-
fluorobenzamide (F2033)

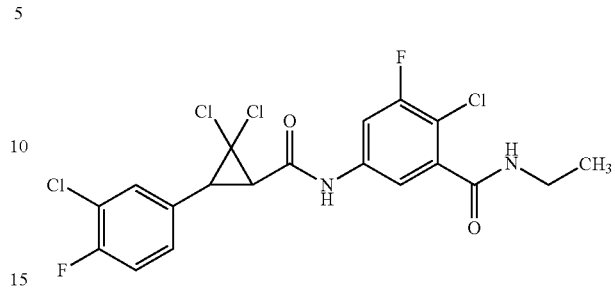

Isolated as a white solid (0.046 g, 71%).

trans-2-Chloro-5-(2,2-dichloro-3-(3-chloro-4-fluoro-
phenyl)cyclopropane-1-carboxamido)-3-fluoro-N-(2,
2,2-trifluoroethyl)benzamide (F2034)

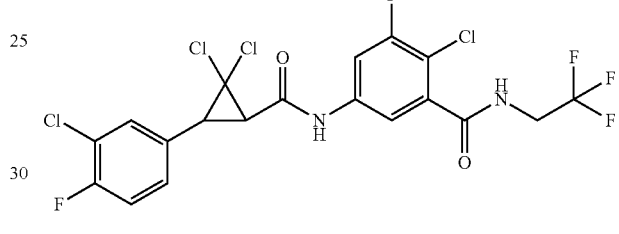

Isolated as a white solid (0.061 g, 85%).

trans-2-Chloro-5-(2,2-dichloro-3-(3-chloro-4-fluoro-
phenyl)cyclopropane-1-carboxamido)-3-fluoro-N-(2,
2,3,3,3-pentafluoropropyl)benzamide (F2035)

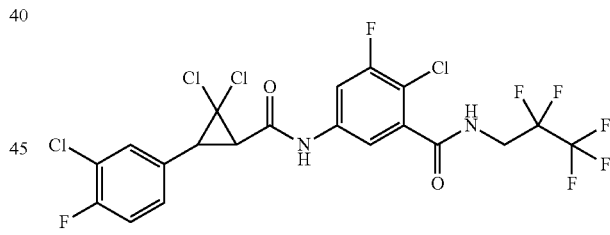

Isolated as a white solid (0.070 g, 89%).

trans-2-Chloro-N-(3-chloropropyl)-5-(2,2-dichloro-
3-(3-chloro-4-fluorophenyl)cyclopropane-1-carbox-
amido)-3-fluorobenzamide (F2036)

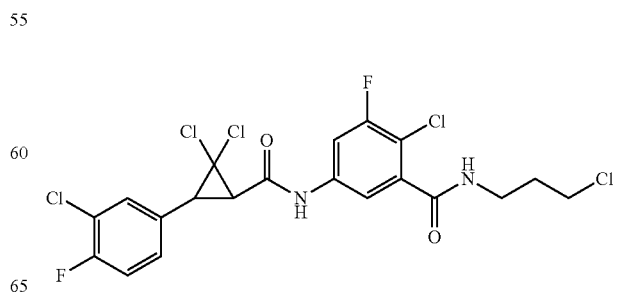

Isolated as a white solid (0.063 g, 87%).

trans-2-Chloro-5-(2,2-dichloro-3-(3-chloro-4-fluoro-phenyl)cyclopropane-1-carboxamido)-N-ethyl-3-methylbenzamide (F2037)

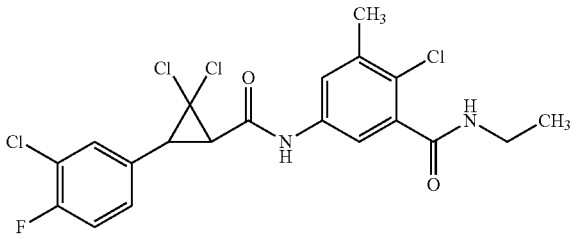

Isolated as a white solid (0.055 g, 77%).

trans-2-Chloro-5-(2,2-dichloro-3-(3-chloro-4-fluoro-phenyl)cyclopropane-1-carboxamido)-3-methyl-N-(2,2,2-trifluoroethyl)benzamide (F2038)

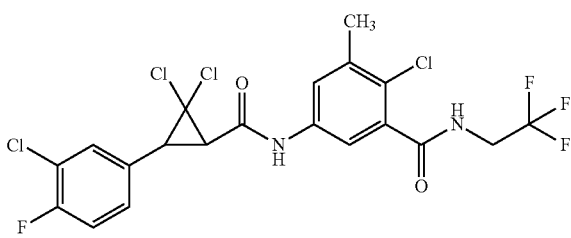 [SMILES: Cc1cc(NC(=O)C2C(c3ccc(F)c(Cl)c3)C2(Cl)Cl)cc(C(=O)NCC(F)(F)F)c1Cl]

Isolated as a tan solid (0.052 g, 66%).

trans-2-Chloro-5-(2,2-dichloro-3-(3-chloro-4-fluoro-phenyl)cyclopropane-1-carboxamido)-3-methyl-N-(2,2,3,3,3-pentafluoropropyl)benzamide (F2039)

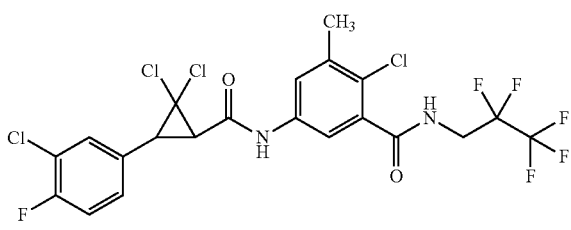 [SMILES: Cc1cc(NC(=O)C2C(c3ccc(F)c(Cl)c3)C2(Cl)Cl)cc(C(=O)NCC(F)(F)C(F)(F)F)c1Cl]

Isolated as a white solid (0.080 g, 93%).

trans-2-Chloro-N-(3-chloropropyl)-5-(2,2-dichloro-3-(3-chloro-4-fluorophenyl)cyclopropane-1-carboxamido)-3-methylbenzamide (F2040)

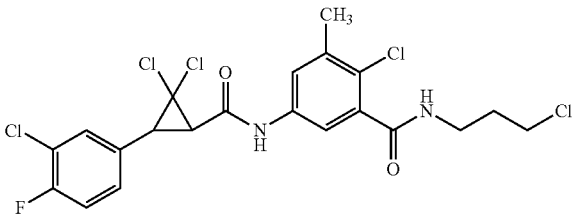

Isolated as a white solid (0.054 g, 69%).

trans-3-Chloro-5-(2,2-dichloro-3-(3-chloro-4-fluoro-phenyl)cyclopropane-1-carboxamido)-N-ethyl-2-methylbenzamide (F2041)

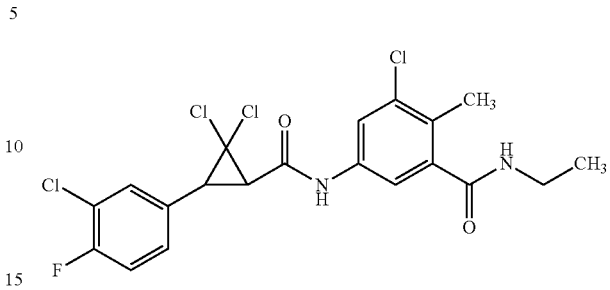

Isolated as a white solid (0.031 g, 44%).

trans-3-Chloro-5-(2,2-dichloro-3-(3-chloro-4-fluoro-phenyl)cyclopropane-1-carboxamido)-2-methyl-N-(2,2,2-trifluoroethyl)benzamide (F2042)


Isolated as a white solid (0.066 g, 83%).

trans-3-Chloro-5-(2,2-dichloro-3-(3-chloro-4-fluoro-phenyl)cyclopropane-1-carboxamido)-2-methyl-N-(2,2,3,3,3-pentafluoropropyl)benzamide (F2043)


Isolated as a white solid (0.071 g, 82%).

trans-3-Chloro-N-(3-chloropropyl)-5-(2,2-dichloro-3-(3-chloro-4-fluorophenyl)cyclopropane-1-carboxamido)-2-methylbenzamide (F2044)

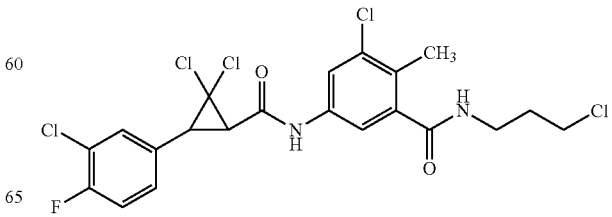

Isolated as a tan solid (0.050 g, 64%).

175 trans-3-Chloro-5-(2,2-dichloro-3-(3-chloro-4-fluoro-phenyl)cyclopropane-1-carboxamido)-2-fluoro-N-(2,2,2-trifluoroethyl)benzamide (F2045)

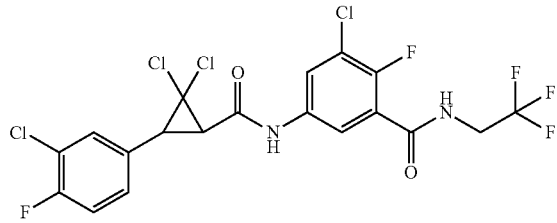

Isolated as a white solid (0.047 g, 47%).

trans-3-Chloro-5-(2,2-dichloro-3-(3-chloro-4-fluoro-phenyl)cyclopropane-1-carboxamido)-2-fluoro-N-(2,2,3,3,3-pentafluoropropyl)benzamide (F2046)

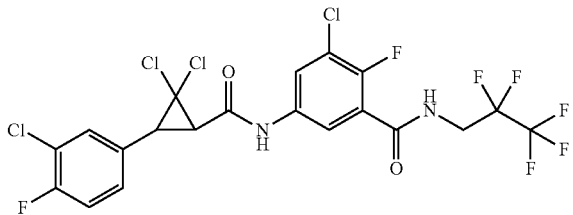 [SMILES: O=C(NCC(F)(F)C(F)(F)F)c1cc(NC(=O)C2C(c3ccc(F)c(Cl)c3)C2(Cl)Cl)cc(Cl)c1F]

Isolated as an off-white solid (0.074 g, 68%).

trans-3-Chloro-5-(2,2-dichloro-3-(3-chloro-4-fluoro-phenyl)cyclopropane-1-carboxamido)-N-ethyl-2-fluorobenzamide (F2047)

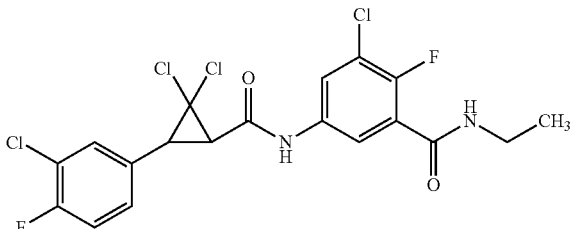

Isolated as an off-white solid (0.062 g, 70%).

trans-3-Chloro-N-(3-chloropropyl)-5-(2,2-dichloro-3-(3-chloro-4-fluorophenyl)cyclopropane-1-carboxamido)-2-fluorobenzamide (F2048)

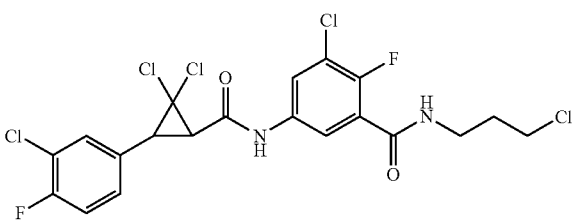 [SMILES: O=C(NCCCCl)c1cc(NC(=O)C2C(c3ccc(F)c(Cl)c3)C2(Cl)Cl)cc(F)c1F]

Isolated as an off-white solid (0.062 g, 63%).

176 trans-5-(2,2-Dichloro-3-(3-chloro-4-fluorophenyl)cyclopropane-1-carboxamido)-2,3-difluoro-N-(2,2,2-trifluoroethyl)benzamide (F2049)

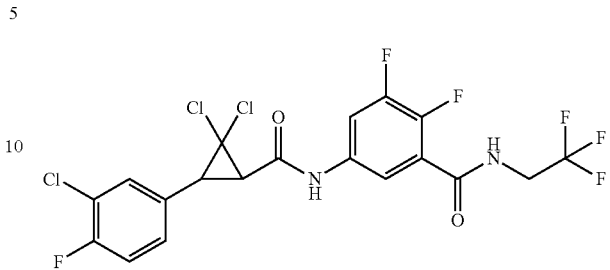

Isolated as a white solid (0.079 g, 79%).

trans-5-(2,2-Dichloro-3-(3-chloro-4-fluorophenyl)cyclopropane-1-carboxamido)-2,3-difluoro-N-(2,2,3,3,3-pentafluoropropyl)benzamide (F2050)

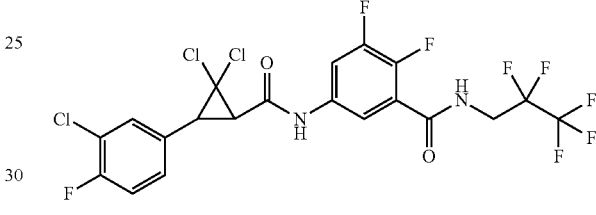

Isolated as a white solid (0.092 g, 84%).

trans-5-(2,2-Dichloro-3-(3-chloro-4-fluorophenyl)cyclopropane-1-carboxamido)-N-ethyl-2,3-difluorobenzamide (F2051)

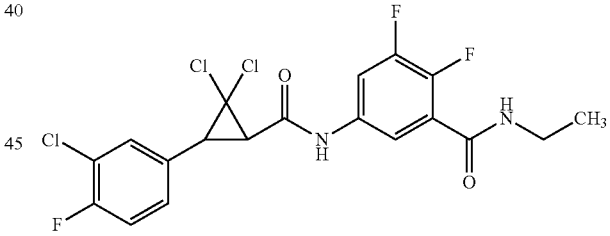

Isolated as a white solid (0.073 g, 82%).

trans-N-(3-Chloropropyl)-5-(2,2-dichloro-3-(3-chloro-4-fluorophenyl)cyclopropane-1-carboxamido)-2,3-difluorobenzamide (F2052)

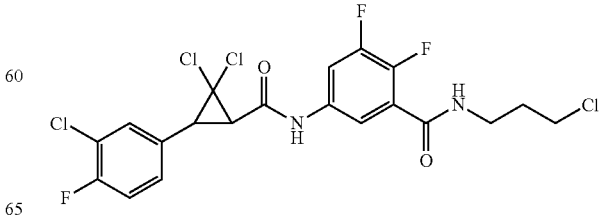

Isolated as a white solid (0.075 g, 76%).

trans-2-Chloro-5-(2,2-dichloro-3-(3-chloro-4-fluoro-
phenyl)cyclopropane-1-carboxamido)-N-ethyl-3-
(trifluoromethyl)benzamide (F2053)

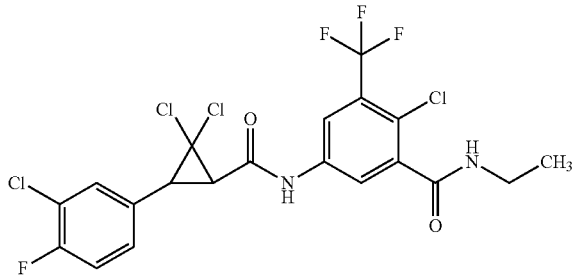 [SMILES: CCNC(=O)c1cc(NC(=O)C2C(c3ccc(F)c(Cl)c3)C2(Cl)Cl)cc(C(F)(F)F)c1Cl]

Isolated as a pale-yellow solid (0.045 g, 64%).

trans-2-Chloro-5-(2,2-dichloro-3-(3-chloro-4-fluoro-
phenyl)cyclopropane-1-carboxamido)-N-(2,2,2-trif-
luoroethyl)-3-(trifluoromethyl)benzamide (F2054)

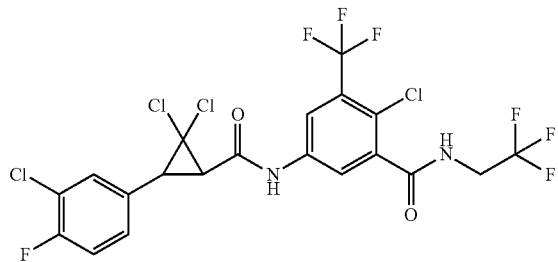 [SMILES: O=C(NCC(F)(F)F)c1cc(NC(=O)C2C(c3ccc(F)c(Cl)c3)C2(Cl)Cl)cc(C(F)(F)F)c1Cl]

Isolated as a white foam (0.062 g, 80%).

trans-2-Chloro-5-(2,2-dichloro-3-(3-chloro-4-fluoro-
phenyl)cyclopropane-1-carboxamido)-3-(trifluorom-
ethyl)-N-(3,3,3-trifluoropropyl)benzamide (F2055)

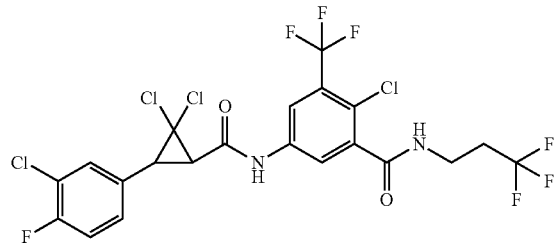 [SMILES: O=C(NCCC(F)(F)F)c1cc(NC(=O)C2C(c3ccc(F)c(Cl)c3)C2(Cl)Cl)cc(C(F)(F)F)c1Cl]

Isolated as a white solid (0.063 g, 79%).

trans-2-Chloro-5-(2,2-dichloro-3-(3-chloro-4-fluoro-
phenyl)cyclopropane-1-carboxamido)-N-(2,2,3,3,3-
pentafluoropropyl)-3-(trifluoromethyl)benzamide
(F2056)

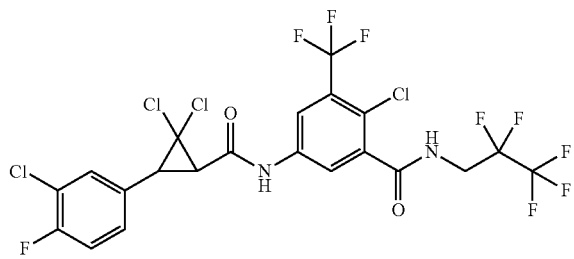 [SMILES: O=C(NCC(F)(F)C(F)(F)F)c1cc(NC(=O)C2C(c3ccc(F)c(Cl)c3)C2(Cl)Cl)cc(C(F)(F)F)c1Cl]

Isolated as a white foam (0.053 g, 62%).

trans-5-(2,2-Dichloro-3-(3-chloro-4-fluorophenyl)
cyclopropane-1-carboxamido)-N-ethyl-3-fluoro-2-
methoxybenzamide (F2057)

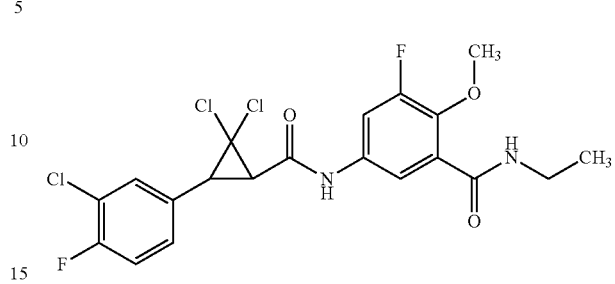

Isolated as a white foam (0.054 g, 76%).

trans-5-(2,2-Dichloro-3-(3-chloro-4-fluorophenyl)
cyclopropane-1-carboxamido)-3-fluoro-2-methoxy-
N-(2,2,2-trifluoroethyl)benzamide (F2058)

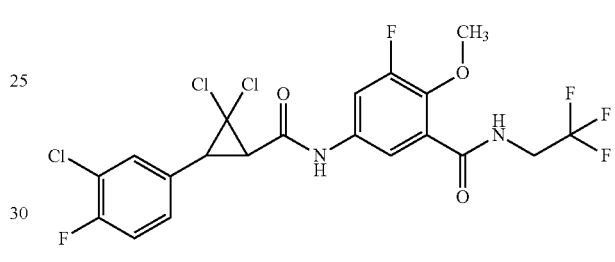

Isolated as a white foam (0.069 g, 86%).

trans-5-(2,2-Dichloro-3-(3-chloro-4-fluorophenyl)
cyclopropane-1-carboxamido)-3-fluoro-2-methoxy-
N-(3,3,3-trifluoropropyl)benzamide (F2059)

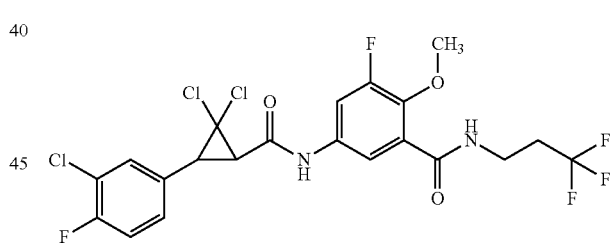

Isolated as a white foam (0.070 g, 86%).

trans-5-(2,2-Dichloro-3-(3-chloro-4-fluorophenyl)
cyclopropane-1-carboxamido)-3-fluoro-2-methoxy-
N-(2,2,3,3,3-pentafluoropropyl)benzamide (F2060)

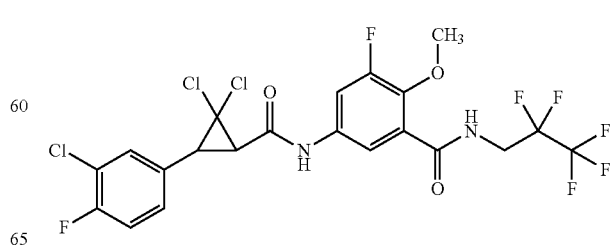

Isolated as a white foam (0.069 g, 81%).

trans-3-Chloro-5-(2,2-dichloro-3-(3-chloro-4-fluoro-
phenyl)cyclopropane-1-carboxamido)-2-methoxy-N-
(2,2,2-trifluoroethyl)benzamide (F2061)

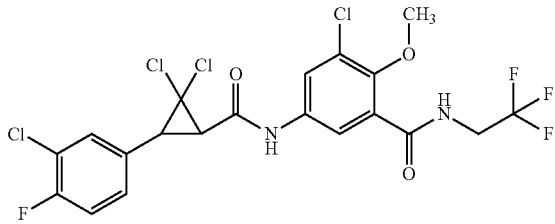 [SMILES: COc1c(F)cc(NC(=O)C2C(c3ccc(F)c(Cl)c3)C2(Cl)Cl)cc1C(=O)NCC(F)(F)F]

Isolated as a white solid (0.060 g, 77%).

trans-3-Chloro-5-(2,2-dichloro-3-(3-chloro-4-fluoro-
phenyl)cyclopropane-1-carboxamido)-2-methoxy-N-
(2,2,3,3,3-pentafluoropropyl)benzamide (F2062)

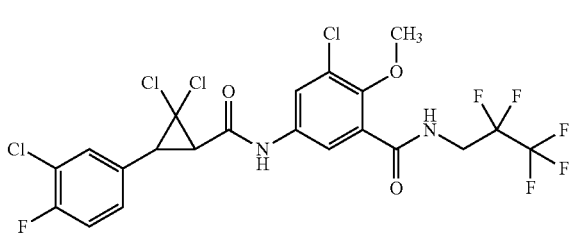 [SMILES: COc1c(Cl)cc(NC(=O)C2C(c3ccc(F)c(Cl)c3)C2(Cl)Cl)cc1C(=O)NCC(F)(F)C(F)(F)F]

Isolated as a white solid (0.075 g, 88%).

trans-5-(2,2-Dichloro-3-(3-chloro-4-fluorophenyl)
cyclopropane-1-carboxamido)-3-fluoro-2-methyl-N-
(2,2,2-trifluoroethyl)benzamide (F2063)

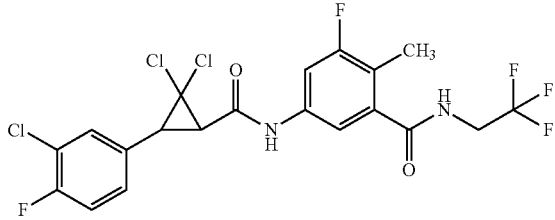 [SMILES: Cc1c(F)cc(NC(=O)C2C(c3ccc(F)c(Cl)c3)C2(Cl)Cl)cc1C(=O)NCC(F)(F)F]

Isolated as a white solid (0.063 g, 96%).

trans-5-(2,2-Dichloro-3-(3-chloro-4-fluorophenyl)
cyclopropane-1-carboxamido)-3-fluoro-2-methyl-N-
(2,2,3,3,3-pentafluoropropyl)benzamide (F2064)

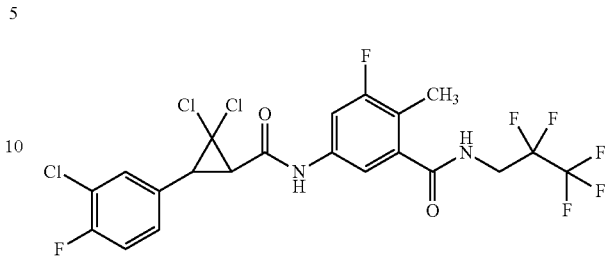

Isolated as a white solid (0.059 g, 81%).

trans-5-(2,2-Dichloro-3-(3-chloro-4-fluorophenyl)
cyclopropane-1-carboxamido)-2-fluoro-N-(4-fluoro-
phenyl)-3-methylbenzamide (F1136)

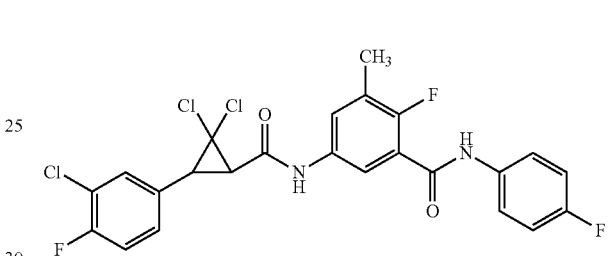

Isolated as a tan solid (0.078 g, 81%).

trans-5-(2,2-Dichloro-3-(3-chloro-4-fluorophenyl)
cyclopropane-1-carboxamido)-N-(2,4-difluorophe-
nyl)-2-fluoro-3-methylbenzamide (F1137)

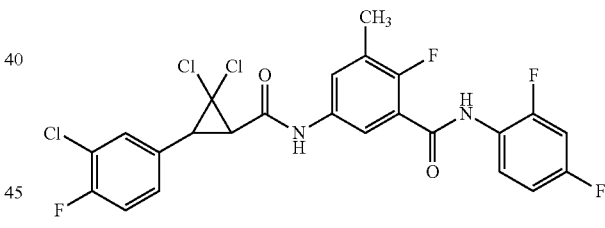

Isolated as a tan foam (0.082 g, 87%).

trans-tert-Butyl-N-tert-butoxycarbonyl-N-[3-[[5-[[2,
2-dichloro-3-(3-chloro-4-fluorophenyl)cyclopropan-
ecarbonyl]amino]-2-fluoro-3-methylbenzoyl]amino]-
2,6-difluorophenyl]carbamate (F1138)

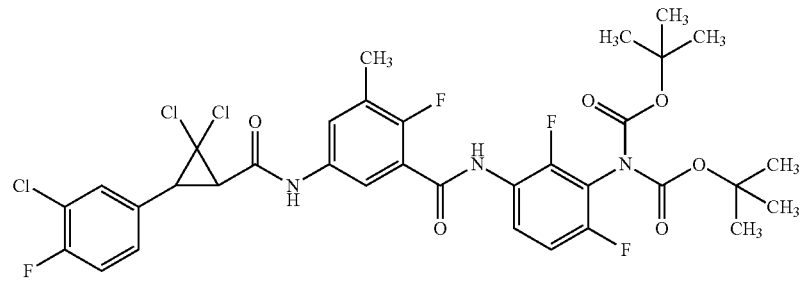 [SMILES: Cc1cc(NC(=O)C2C(c3ccc(F)c(Cl)c3)C2(Cl)Cl)cc(C(=O)Nc2ccc(F)c(N(C(=O)OC(C)(C)C)C(=O)OC(C)(C)C)c2F)c1F]

Isolated as a white solid (0.149 g, 83%).

181 trans-N-(4-Acetamidophenyl)-5-(2,2-dichloro-3-(3-chloro-4-fluorophenyl)-cyclopropane-1-carboxamido)-2-fluoro-3-methylbenzamide (F1139)

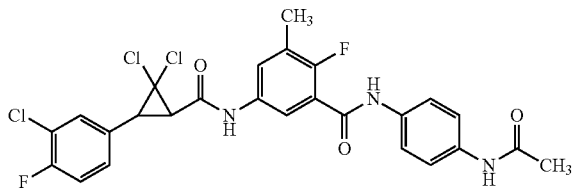 [SMILES: CC(=O)Nc1ccc(NC(=O)c2cc(NC(=O)C3C(c4ccc(F)c(Cl)c4)C3(Cl)Cl)cc(C)c2F)cc1]

Isolated as a white solid (0.088 g, 85%).

trans-3-Chloro-5-(2,2-dichloro-3-(3-chloro-4-fluorophenyl)cyclopropane-1-carboxamido)-N-(4-fluorophenyl)-2-methoxybenzamide (F1235)

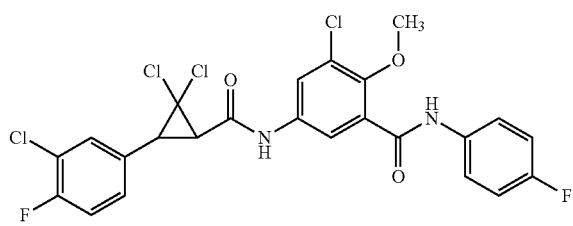 [SMILES: COc1c(Cl)cc(NC(=O)C2C(c3ccc(F)c(Cl)c3)C2(Cl)Cl)cc1C(=O)Nc1ccc(F)cc1]

Isolated as a white solid (0.048 g, 60%).

182 trans-3-Chloro-5-(2,2-dichloro-3-(3-chloro-4-fluorophenyl)cyclopropane-1-carboxamido)-N-(2,4-difluorophenyl)-2-methoxybenzamide (F1236)

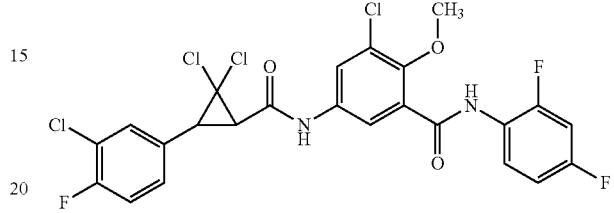

Isolated as a white solid (0.059 g, 72%).

trans-tert-Butyl-N-tert-butoxycarbonyl-N-[3-[[3-chloro-5-[[2,2-dichloro-3-(3-chloro-4-fluorophenyl)cyclopropanecarbonyl]amino]-2-methoxybenzoyl]amino]-2,6-difluorophenyl]carbamate (F1237)

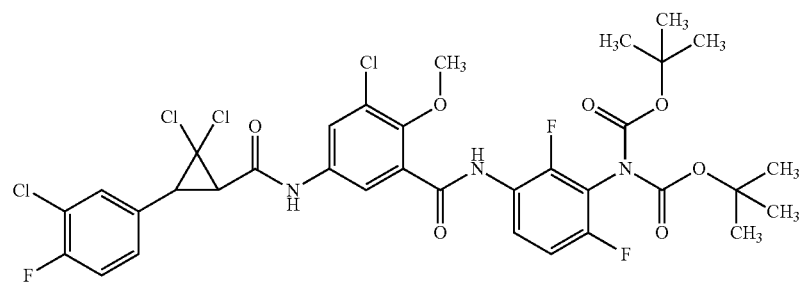 [SMILES: COc1c(Cl)cc(NC(=O)C2C(c3ccc(F)c(Cl)c3)C2(Cl)Cl)cc1C(=O)Nc1ccc(F)c(N(C(=O)OC(C)(C)C)C(=O)OC(C)(C)C)c1F]

Isolated as an off-white solid (0.059 g, 52%).

Example 26: Preparation of trans-2-((tert-butoxycarbonyl)(4-(2-chloro-5-(2,2-dichloro-3-(3,5-dichlorophenyl)cyclopropane-1-carboxamido)benzamido)-3-methylphenyl)amino)ethyl acetate (F1129)

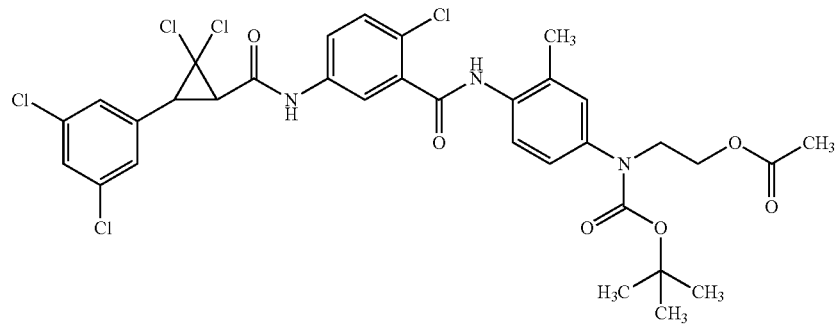 [SMILES: CC(=O)OCCN(C(=O)OC(C)(C)C)c1ccc(NC(=O)c2cc(NC(=O)C3C(c4cc(Cl)cc(Cl)c4)C3(Cl)Cl)ccc2Cl)c(C)c1]

Step 1: Preparation of 2-((tert-butoxycarbonyl)(3-methyl-4-nitrophenyl)amino)ethyl acetate tert-Butyl (3-methyl-4-nitrophenyl)carbamate (C223) (1.0 g, 3.96 mmol) dissolved in anhydrous N,N-dimethylformamide (5 mL) was added dropwise to a stirred suspension of sodium hydride (60% oil dispersion, 0.206 g, 5.15 mmol) in anhydrous N,N-dimethylformamide (50 mL) at a rate that maintained the temperature below 30° C. Upon completion of the addition, the resulting orange solution was stirred at room temperature for 30 minutes followed by the dropwise addition of 2-bromoethyl acetate (0.662 g, 3.96 mmol). The resulting solution was stirred at room temperature for 12 hours, then carefully quenched with water (100 mL), and extracted with ethyl acetate (3×50 mL). The organic extracts were washed successively with water and saturated aqueous sodium chloride solution, dried over anhydrous magnesium sulfate, and concentrated under vacuum on a rotary evaporator. Purification by silica gel flash chromatography provided the title compound as a yellow oil (0658 g, 47%): $^1$H NMR (400 MHz, CDCl$_3$) δ 8.04-7.97 (m, 1H), 7.26 (m, 2H), 4.31-4.23 (m, 2H), 3.93 (t, J=5.6 Hz, 2H), 2.62 (s, 3H), 1.97 (s, 3H), 1.48 (s, 9H); $^{13}$C NMR (101 MHz, CDCl$_3$) δ 170.72, 170.58, 153.57, 146.91, 145.94, 134.81, 129.85, 125.53, 124.40, 81.83, 77.37, 77.05, 76.73, 62.16, 62.08, 48.76, 28.21, 20.86, 20.76, 20.70; ESIMS m/z 339 ([M+H]+).

Step 2: Preparation of 2-((4-amino-3-methylphenyl)(tert-butoxycarbonyl)amino)ethyl acetate Palladium hydroxide (10% w/w; 0.135 g, 0.096 mmol) was added to a stirred solution of 2-((tert-butoxycarbonyl)(3-methyl-4-nitrophenyl)amino)ethyl acetate (0.650 g, 1.92 mmol) dissolved in ethyl acetate (50 mL). The flask was evacuated and filled with hydrogen via a balloon adapter, and the resulting black suspension was stirred for 13 hours at room temperature. The reaction mixture was filtered through a pad of Celite® and concentrated under vacuum on a rotary evaporator to give the title compound as a brown solid (0.527 g, 85%); $^1$H NMR (400 MHz, CDCl$_3$) δ 6.85 (s, 2H), 6.61 (d, J=8.2 Hz, 1H), 4.18 (t, J=5.8 Hz, 2H), 3.79 (t, J=5.8 Hz, 2H), 3.60 (s, 2H), 2.14 (s, 3H), 2.00 (s, 3H), 1.40 (s, 9H); ESIMS m/z 309 ([M+H]$^+$).

Step 3: Preparation of trans-2-((tert-butoxycarbonyl)(4-(2-chloro-5-(2,2-dichloro-3-(3,5-dichlorophenyl)cyclopropane-1-carboxamido)benzamido)-3-methylphenyl)amino)ethyl acetate (F1129)

2,4,6-Tripropyl-1,3,5,2,4,6-trioxatriphosphinane 2,4,6-trioxide (T3P®, 50% solution in ethyl acetate; 0.281 g, 0.441 mmol) was added dropwise to a stirred solution of trans-2-chloro-5-(2,2-dichloro-3-(3,5-dichlorophenyl)cyclopropane-1-carboxamido)benzoic acid (C12) (0.100 g, 220 mmol), 2-((4-amino-3-methylphenyl)(tert-butoxycarbonyl)amino)ethyl acetate (0.068 g, 0.220 mmol), and pyridine (0.053 g, 0.661 mmol) in anhydrous ethyl acetate (3 mL). The solution was stirred for 12 hours at 23° C. and concentrated. Purification by silica gel flash chromatography gave the title compound as a white foam (0.149 g, 86%).

The following compounds were prepared in like manner to the procedure outlined in Example 26:

trans-tert-Butyl-(4-(2-chloro-5-(2,2-dichloro-3-(3,5-dichlorophenyl)cyclopropane-1-carboxamido)benzamido)-3-methylphenyl)(2-cyanoethyl)carbamate (F1157)

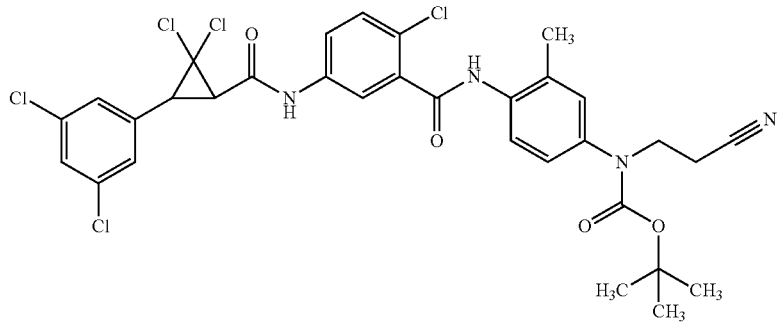 [SMILES: Cc1cc(N(CCC#N)C(=O)OC(C)(C)C)ccc1NC(=O)c1cc(NC(=O)C2C(c3cc(Cl)cc(Cl)c3)C2(Cl)Cl)ccc1Cl]

Isolated as a white solid (0.134 g, 81%).

trans-tert-Butyl-(4-(2-chloro-5-(2,2-dichloro-3-(3,5-dichlorophenyl)cyclopropane-1-carboxamido)benzamido)-3-ethylphenyl)(2-methoxyethyl)carbamate (F1159)

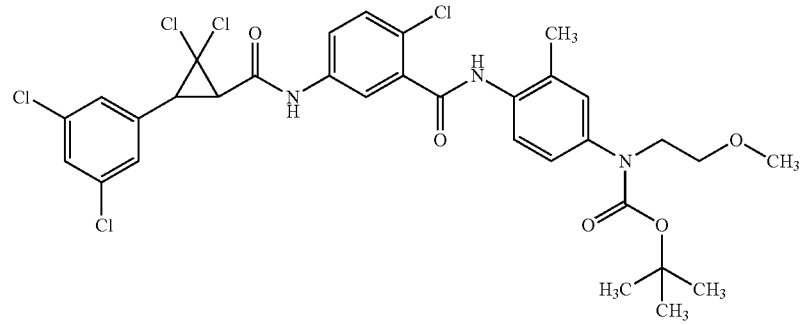 [SMILES: COCCN(C(=O)OC(C)(C)C)c1ccc(NC(=O)c2cc(NC(=O)C3C(c4cc(Cl)cc(Cl)c4)C3(Cl)Cl)ccc2Cl)c(C)c1]

Isolated as a clear colorless oil (0.121 g, 73%).

Example 27: Preparation of N-(4-Amino-2,6-difluorophenyl)-2-chloro-5-((1R,3R)-2,2-dichloro-3-(3,5-dichlorophenyl)cyclopropane-1-carboxamido)benzamide (F1027)

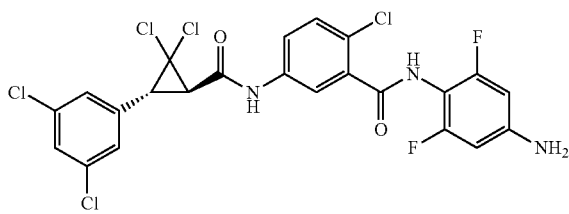 [SMILES: Nc1cc(F)c(NC(=O)c2cc(NC(=O)[C@H]3[C@H](c4cc(Cl)cc(Cl)c4)C3(Cl)Cl)ccc2Cl)c(F)c1]

To a solution of 2-chloro-5-((1R,3R)-2,2-dichloro-3-(3,5-dichlorophenyl)cyclopropane-1-carboxamido)benzoic acid (C13) (0.100 g, 0.220 mmol) and tert-butyl-N-((tert-butoxy)carbonyl)-N-(4-amino-3,5-difluorophenyl)carbamate (C181) (0.076 g, 0.220 mmol) in ethyl acetate (2 mL) were added pyridine (0.036 mL, 0.441 mmol) and 2,4,6-tripropyl-1,3,5,2,4,6-trioxatriphosphinane 2,4,6-trioxide (T3P®) as a 50% solution in ethyl acetate (0.210 g, 0.331 mmol). The mixture was warmed to 45° C. for 48 hours. The reaction mixture was cooled to room temperature and concentrated under a stream of nitrogen. The residue was purified by flash column chromatography using 0-30% ethyl acetate/hexanes as eluent. Product fractions were combined and concentrated under reduced pressure. The resulting residue was dissolved in dichloromethane (2 mL), and a 4 M solution of hydrogen chloride in dioxane (0.545 mL, 2.18 mmol) was added. The reaction mixture was stirred at room temperature for 18 hours. The solvent was evaporated under a stream of nitrogen. The residue was partitioned between ethyl acetate and saturated aqueous sodium bicarbonate. The phases were separated, the organic layer was washed with saturated aqueous sodium bicarbonate and brine and then passed through a phase separator to dry, and the solvent was concentrated. Purification by flash column chromatography using 0-30% ethyl acetate/hexanes as eluent afforded the title compound as a white solid (0.025 g, 19%).

The following compounds were prepared in like manner to the procedure outlined in Example 27:

N-(4-Amino-2,6-difluorophenyl)-2-chloro-5-((1R,3R)-2,2-dichloro-3-(3,4-dichlorophenyl)cyclopropane-1-carboxamido)benzamide (F1028)

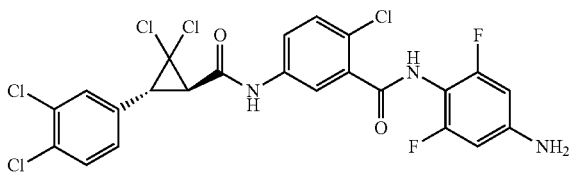

Isolated as a white solid (0.019 g, 15%).

N-(4-Amino-2,6-difluorophenyl)-2-chloro-5-((1R,3R)-2,2-dichloro-3-(3,4,5-trichlorophenyl)cyclopropane-1-carboxamido)benzamide (F1029)

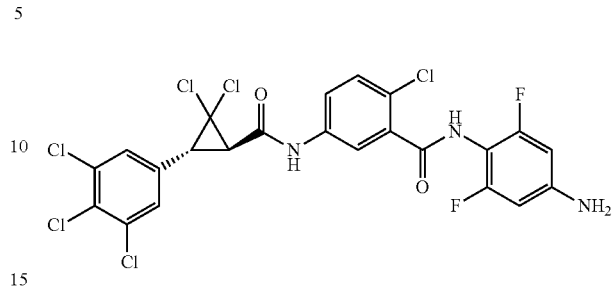

Isolated as a white solid (0.022 g, 17%).

N-(4-Amino-2,6-difluorophenyl)-2-chloro-5-((1R,3R)-2,2-dichloro-3-(3-chloro-4-fluorophenyl)cyclopropane-1-carboxamido)benzamide (F1030)

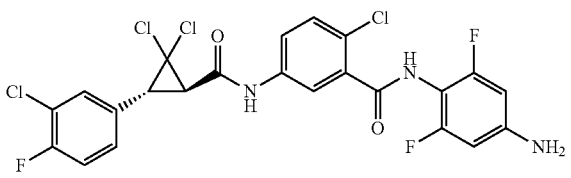 [SMILES: Nc1cc(F)c(NC(=O)c2cc(NC(=O)[C@H]3[C@H](c4ccc(Cl)c(Cl)c4)C3(Cl)Cl)ccc2Cl)c(F)c1]

Isolated as a white solid (0.019 g, 14%).

trans-N-(3-Amino-2,4-difluorophenyl)-2-chloro-5-(2,2-dichloro-3-(3-(difluoromethyl)-4-fluorophenyl)cyclopropane-1-carboxamido)benzamide (F1036)

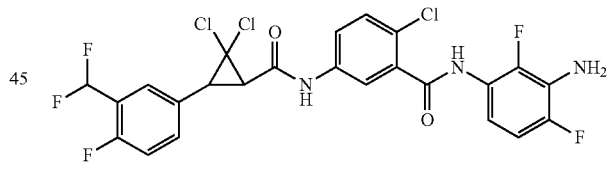

Isolated as a white solid (0.080 g, 42%).

trans-N-(3-Amino-2,4-difluorophenyl)-2-chloro-5-(2,2-dichloro-3-(4-chloro-3-(difluoromethyl)phenyl)cyclopropane-1-carboxamido)benzamide (F1037)

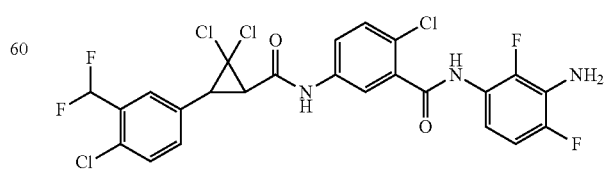

Isolated as a white solid (0.086 g, 46%).

trans-N-(3-Amino-2,4-difluorophenyl)-2-chloro-5-(2,2-dichloro-3-(3-chloro-5-(difluoromethyl)phenyl)cyclopropane-1-carboxamido)benzamide (F1038)

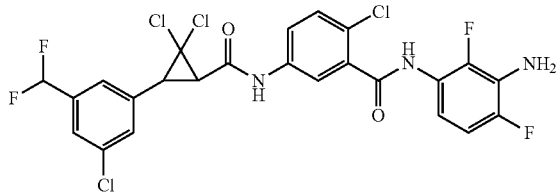 [SMILES: Nc1c(F)ccc(NC(=O)c2cc(NC(=O)C3C(c4cc(Cl)cc(C(F)F)c4)C3(Cl)Cl)ccc2Cl)c1F]

Isolated as a light yellow foam (0.079 g, 42%).

trans-N-(3-Amino-2,6-difluorophenyl)-2-chloro-5-(2,2-dichloro-3-(3,5-dichlorophenyl)cyclopropane-1-carboxamido)benzamide (F1026)

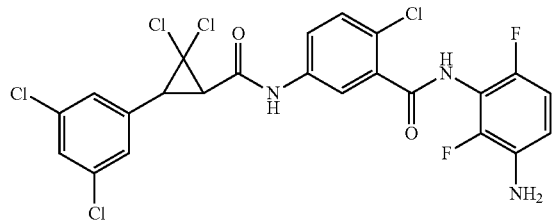 [SMILES: Nc1ccc(F)c(NC(=O)c2cc(NC(=O)C3C(c4cc(Cl)cc(Cl)c4)C3(Cl)Cl)ccc2Cl)c1F]

Isolated as a white foam (0.037 g, 76%).

trans-N-(4-Amino-2-methylphenyl)-2-chloro-5-(2,2-dichloro-3-(3,4-dichlorophenyl)cyclopropane-1-carboxamido)benzamide (DP1)

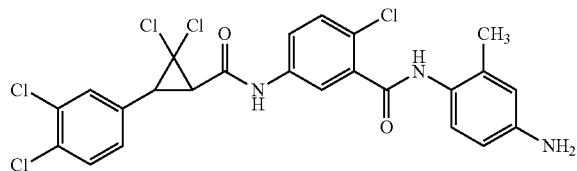 [SMILES: Cc1cc(N)ccc1NC(=O)c1cc(NC(=O)C2C(c3ccc(Cl)c(Cl)c3)C2(Cl)Cl)ccc1Cl]

Isolated as a white foam (0.838 g, 99%).

Example 28: Preparation of trans-2,2-dichloro-N-(4-chloro-3-(2-(pyridin-2-yl)hydrazine-1-carbonyl)phenyl)-3-(3,5-dichlorophenyl)cyclopropane-1-carboxamide (F2502)

To a solution of trans-2-chloro-5-(2,2-dichloro-3-(3,5-dichlorophenyl)cyclopropane-1-carboxamido)benzoic acid (C12) (0.080 g, 0.176 mmol) and 2-(1-methylhydrazinyl)pyridine (0.033 g, 0.265 mmol) in ethyl acetate (2 mL) at room temperature were added sequentially diisopropylethylamine (0.123 mL, 0.706 mmol) and 2,4,6-tripropyl-1,3,5,2,4,6-trioxatriphosphinane 2,4,6-trioxide (T3P®; 0.225 g, 0.353 mmol) as a 50% solution in ethyl acetate. The reaction mixture was stirred for 18 hours at room temperature and then concentrated under a stream of nitrogen. Purification by column chromatography using 0-100% ethyl acetate; hexanes as eluent afforded the title compound as a yellow solid (0.019 g, 20%).

The following compounds were prepared in like manner to the procedure outlined in Example 28:

trans-2,2-dichloro-N-(4-chloro-3-(2-(4-chloro-3-(trifluoromethyl)phenyl)hydrazine-1-carbonyl)phenyl)-3-(3,5-dichlorophenyl)cyclopropane-1-carboxamide (F2501)

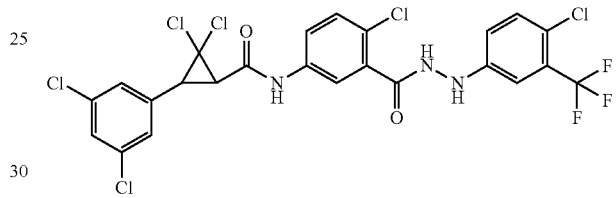

Isolated as a light yellow foam (0.058 g, 44%).

trans-2,2-Dichloro-N-(4-chloro-3-(2-methyl-2-(pyridin-2-yl)hydrazine-1-carbonyl)phenyl)-3-(3,5-dichlorophenyl)cyclopropane-1-carboxamide (F2503)

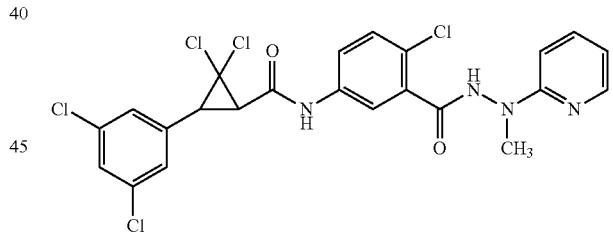

Isolated as a yellow solid (0.046 g, 47%).

trans-2,2-Dichloro-N-(4-chloro-3-(2-(5-chloropyridin-2-yl)hydrazine-1-carbonyl)phenyl)-3-(3,5-dichlorophenyl)cyclopropane-1-carboxamide (F2504)

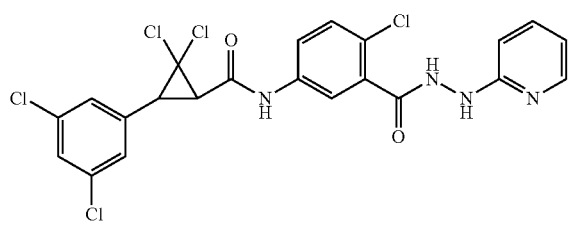 [SMILES: O=C(NNc1ccccn1)c1cc(NC(=O)C2C(c3cc(Cl)cc(Cl)c3)C2(Cl)Cl)ccc1Cl]

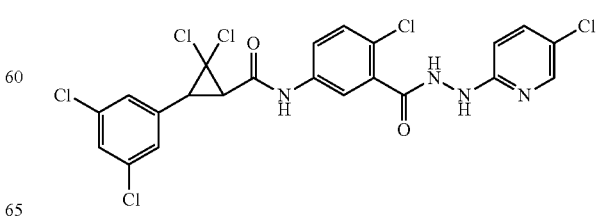

Isolated as an off-white solid (0.045 g, 44%).

trans-2,2-Dichloro-N-(4-chloro-3-(2-(3-chloropyri-
din-2-yl)hydrazine-1-carbonyl)phenyl)-3-(3,5-di-
chlorophenyl)cyclopropane-1-carboxamide (F2505)

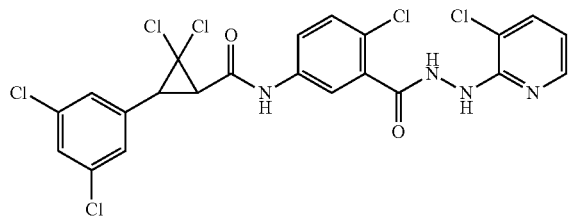 [SMILES: O=C(NNc1ncccc1Cl)c1cc(NC(=O)C2C(c3cc(Cl)cc(Cl)c3)C2(Cl)Cl)ccc1Cl]

Isolated as an off-white solid (0.036 g, 35%).

trans-2,2-Dichloro-N-(4-chloro-3-(2-(6-chloro-
pyridazin-3-yl)hydrazine-1-carbonyl)phenyl)-3-(3,5-
dichlorophenyl)cyclopropane-1-carboxamide
(F2506)

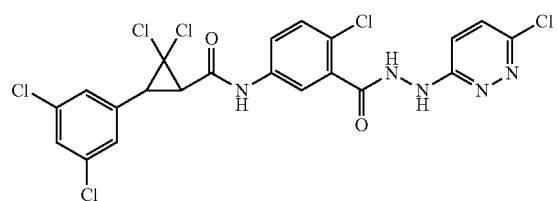 [SMILES: O=C(NNc1ccc(Cl)nn1)c1cc(NC(=O)C2C(c3cc(Cl)cc(Cl)c3)C2(Cl)Cl)ccc1Cl]

Isolated as a light yellow solid (0.070 g, 69%).

trans-2,2-Dichloro-N-(4-chloro-3-(2-methyl-2-(4-
(trifluoromethyl)pyridin-2-yl)hydrazine-1-carbonyl)
phenyl)-3-(3,5-dichlorophenyl)cyclopropane-1-car-
boxamide (F2507)

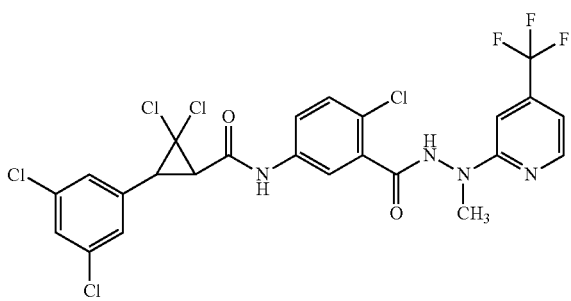 [SMILES: CN(NC(=O)c1cc(NC(=O)C2C(c3cc(Cl)cc(Cl)c3)C2(Cl)Cl)ccc1Cl)c1cc(C(F)(F)F)ccn1]

Isolated as a white solid (0.096 g, 86%).

trans-2,2-Dichloro-N-(4-chloro-3-(2-(pyrimidin-2-
yl)hydrazine-1-carbonyl)phenyl)-3-(3,5-dichlorophe-
nyl)cyclopropane-1-carboxamide (F2508)

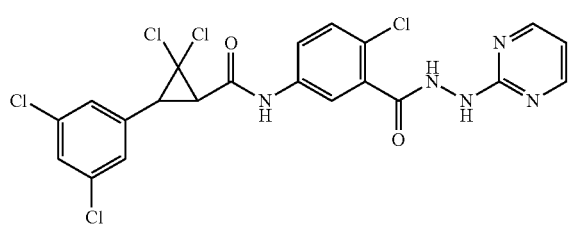 [SMILES: O=C(NNc1ncccn1)c1cc(NC(=O)C2C(c3cc(Cl)cc(Cl)c3)C2(Cl)Cl)ccc1Cl]

Isolated as a white solid (0.027 g, 28%).

trans-2,2-Dichloro-N-(4-chloro-3-(2-(pyrimidin-4-
yl)hydrazine-1-carbonyl)phenyl)-3-(3,5-dichlorophe-
nyl)cyclopropane-1-carboxamide (F2509)

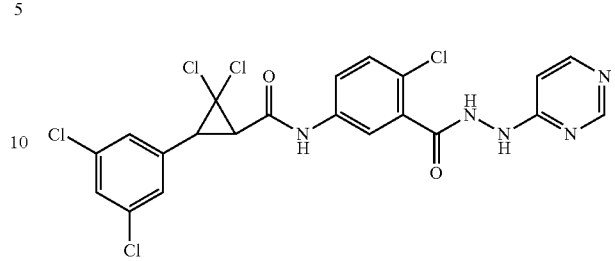

Isolated as a white solid (0.016 g, 17%).

(1R,3R)-2,2-Dichloro-N-(4-chloro-3-(2-methyl-2-
phenylhydrazine-1-carbonyl)phenyl)-3-(3,5-dichlo-
rophenyl)cyclopropane-1-carboxamide (F2510)


Isolated as a white solid (0.045 g, 37%).

(1R,3R)-2,2-Dichloro-N-(4-chloro-3-(2-methyl-2-
phenylhydrazine-1-carbonyl)phenyl)-3-(3,4,5-
trichlorophenyl)cyclopropane-1-carboxamide
(F2511)


Isolated as a white solid (0.048 g, 40%).

(1R,3R)-2,2-Dichloro-N-(4-chloro-3-(2-methyl-2-
phenylhydrazine-1-carbonyl)phenyl)-3-(3-chloro-4-
fluorophenyl)cyclopropane-1-carboxamide (F2512)

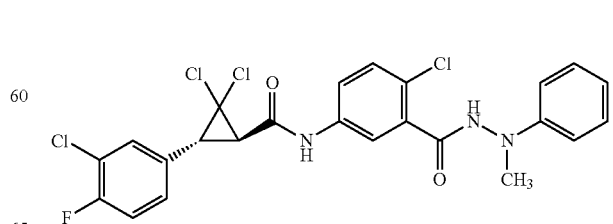

Isolated as a white solid (0.041 g, 33%).

191

(1R,3R)-2,2-Dichloro-N-(4-chloro-3-(2-methyl-2-phenylhydrazine-1-carbonyl)phenyl)-3-(3,4-dichlorophenyl)cyclopropane-1-carboxamide (F2513)

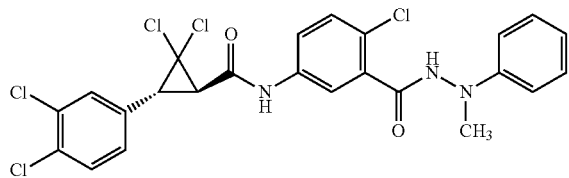 [SMILES: CN(NC(=O)c1cc(NC(=O)[C@H]2[C@H](c3ccc(Cl)c(Cl)c3)C2(Cl)Cl)ccc1Cl)c1ccccc1]

Isolated as a white solid (0.057 g, 46%).

trans-2,2-Dichloro-N-(4-chloro-3-(2-(4-fluorophenyl)hydrazine-1-carbonyl)phenyl)-3-(3,5-dichlorophenyl)cyclopropane-1-carboxamide (F2553)

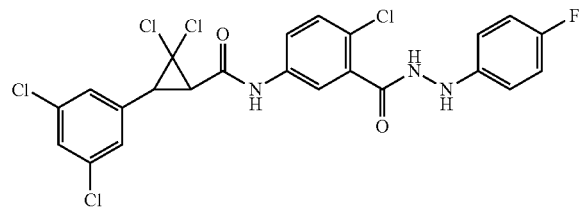 [SMILES: O=C(NNc1ccc(F)cc1)c1cc(NC(=O)C2C(c3cc(Cl)cc(Cl)c3)C2(Cl)Cl)ccc1Cl]

Isolated as a yellow foam (0.036 g, 31%).

trans-2,2-Dichloro-N-(4-chloro-3-(2-(4-cyanophenyl)hydrazine-1-carbonyl)phenyl)-3-(3,5-dichlorophenyl)cyclopropane-1-carboxamide (F2554)

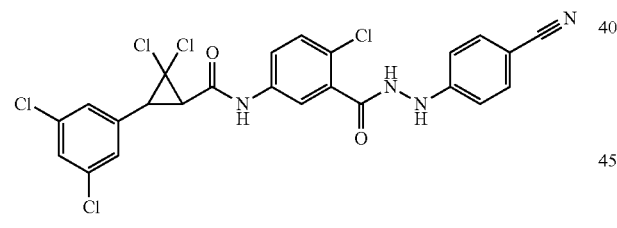

Isolated as a light foam (0.070 g, 63%).

trans-2,2-Dichloro-N-(4-chloro-3-(2-(4-nitrophenyl)hydrazine-1-carbonyl)phenyl)-3-(3,5-dichlorophenyl)cyclopropane-1-carboxamide (F2555)

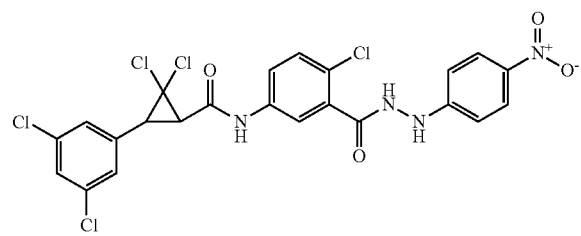 [SMILES: O=C(NNc1ccc([N+](=O)[O-])cc1)c1cc(NC(=O)C2C(c3cc(Cl)cc(Cl)c3)C2(Cl)Cl)ccc1Cl]

Isolated as an orange solid (0.146 g, 66%).

192 trans-2,2-Dichloro-N-(4-chloro-3-(2-phenylhydrazine-1-carbonyl)phenyl)-3-(3,5-dichlorophenyl)cyclopropane-1-carboxamide (F2556)

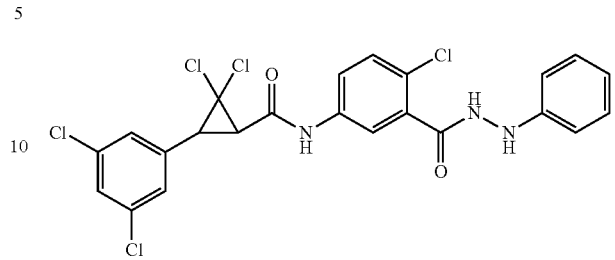

Isolated as an off-white foam (0.0911 g, 82%).

trans-2,2-Dichloro-N-(4-chloro-3-(2-methyl-2-phenylhydrazine-1-carbonyl)phenyl)-3-(3,5-dichlorophenyl)cyclopropane-1-carboxamide (F2557)

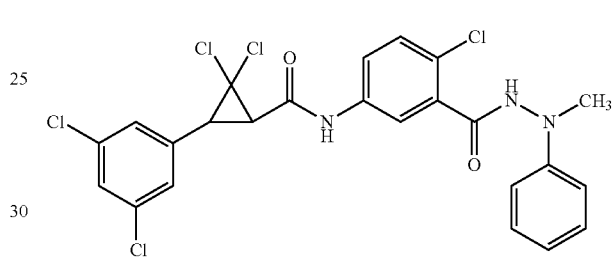

Isolated as an off-white foam (0.094 g, 85%).

trans-2,2-Dichloro-N-(4-chloro-3-(2-(2,5-difluorophenyl)hydrazine-1-carbonyl)phenyl)-3-(3,5-dichlorophenyl)cyclopropane-1-carboxamide (F2558)

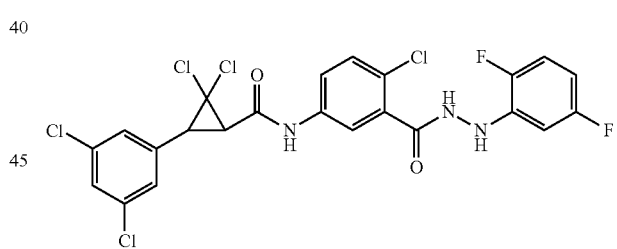

Isolated as an off-white foam (0.0796 g, 72%).

trans-2,2-Dichloro-N-(4-chloro-3-(2-(2,4-difluorophenyl)hydrazine-1-carbonyl)phenyl)-3-(3,5-dichlorophenyl)cyclopropane-1-carboxamide (F2559)

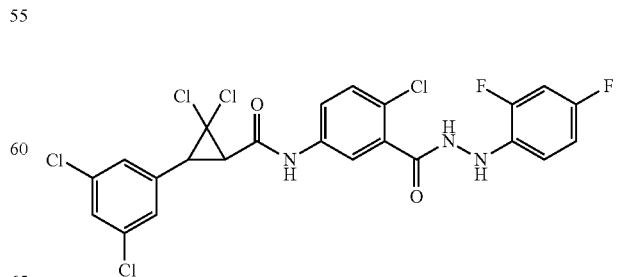

Isolated as an off-white foam (0.089 g, 80%).

193 trans-2,2-Dichloro-N-(4-chloro-3-(2-(3,4-dichlorophenyl)hydrazine-1-carbonyl)phenyl)-3-(3,5-dichlorophenyl)cyclopropane-1-carboxamide (F2560)

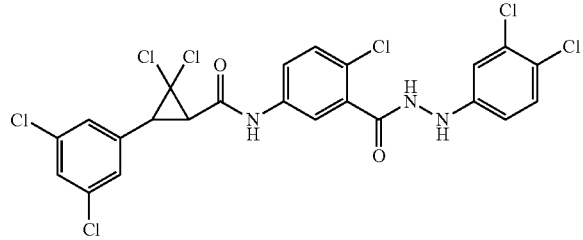 [SMILES: O=C(NNc1ccc(Cl)c(Cl)c1)c1cc(NC(=O)C2C(c3cc(Cl)cc(Cl)c3)C2(Cl)Cl)ccc1Cl]

Isolated as a light brown foam (0.072 g, 60%).

trans-2,2-Dichloro-N-(4-chloro-3-(2-(2,5-dichlorophenyl)hydrazine-1-carbonyl)phenyl)-3-(3,5-dichlorophenyl)cyclopropane-1-carboxamide (F2561)

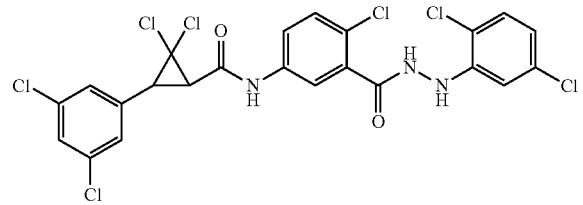 [SMILES: O=C(NNc1cc(Cl)ccc1Cl)c1cc(NC(=O)C2C(c3cc(Cl)cc(Cl)c3)C2(Cl)Cl)ccc1Cl]

Isolated as a light brown foam (0.095 g, 79%).

trans-2,2-Dichloro-N-(4-chloro-3-(2-(4-fluoro-2-methylphenyl)hydrazine-1-carbonyl)phenyl)-3-(3,5-dichlorophenyl)cyclopropane-1-carboxamide (F2562)

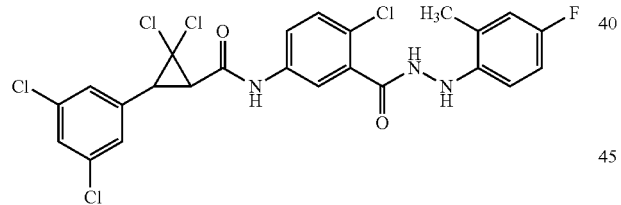

Isolated as a light brown foam (0.080 g, 71%).

trans-2,2-Dichloro-N-(4-chloro-3-(2-(4-methoxyphenyl)hydrazine-1-carbonyl)phenyl)-3-(3,5-dichlorophenyl)cyclopropane-1-carboxamide (F2563)

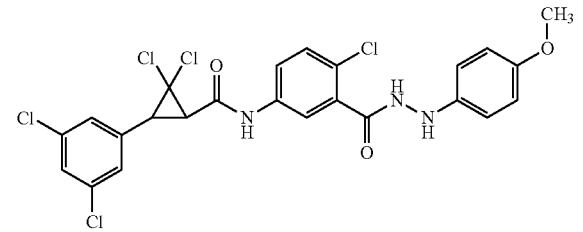 [SMILES: COc1ccc(NNC(=O)c2cc(NC(=O)C3C(c4cc(Cl)cc(Cl)c4)C3(Cl)Cl)ccc2Cl)cc1]

Isolated as a light brown foam (0.039 g, 35%).

194 trans-2,2-Dichloro-N-(4-chloro-3-(2-(4-(trifluoromethoxy)phenyl)hydrazine-1-carbonyl)phenyl)-3-(3,5-dichlorophenyl)cyclopropane-1-carboxamide (F2564)

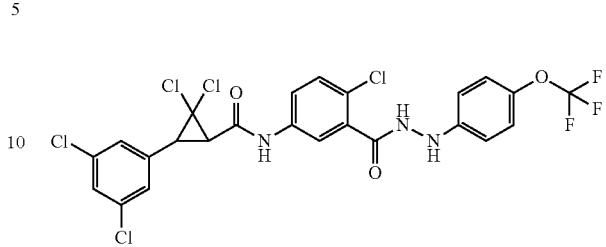

Isolated as a light brown foam (0.082 g, 63%).

trans-2,2-Dichloro-N-(4-chloro-3-(2-(4-(perfluoroethoxy)phenyl)hydrazine-1-carbonyl)phenyl)-3-(3,5-dichlorophenyl)cyclopropane-1-carboxamide (F2565)

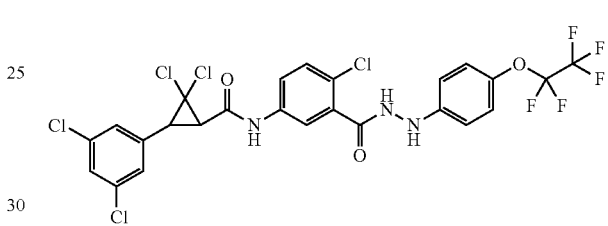

Isolated as a light brown foam (0.105 g, 79%).

trans-2,2-Dichloro-N-(4-chloro-3-(2-(4-(trifluoromethyl)phenyl)hydrazine-1-carbonyl)phenyl)-3-(3,5-dichlorophenyl)cyclopropane-1-carboxamide (F2571)


Isolated as an off-white foam (0.048 g, 38%).

trans-2,2-Dichloro-N-(4-chloro-3-(2-(3-(trifluoromethyl)phenyl)hydrazine-1-carbonyl)phenyl)-3-(3,5-dichlorophenyl)cyclopropane-1-carboxamide (F2572)

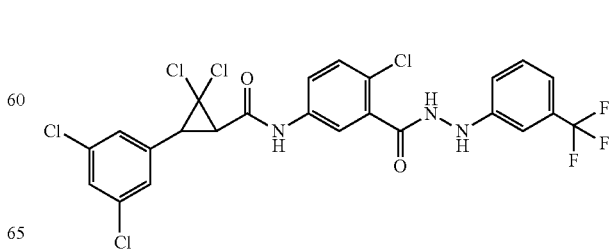

Isolated as a light brown foam (0.054 g, 43%).

trans-2,2-Dichloro-N-(4-chloro-3-(2-(2-(trifluoromethyl)phenyl)hydrazine-1-carbonyl)phenyl)-3-(3,5-dichlorophenyl)cyclopropane-1-carboxamide (F2573)

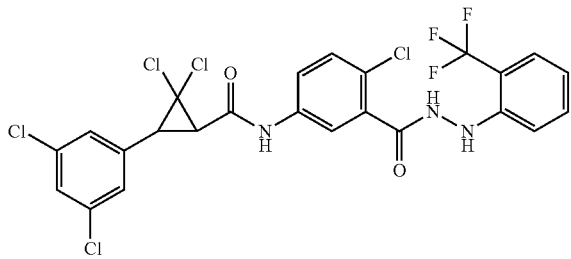 [SMILES: O=C(NNc1ccccc1C(F)(F)F)c1cc(NC(=O)C2C(c3cc(Cl)cc(Cl)c3)C2(Cl)Cl)ccc1Cl]

Isolated as a light brown foam (0.107 g, 86%).

trans-2,2-Dichloro-N-(4-chloro-3-(2-methyl-2-(m-tolyl)hydrazine-1-carbonyl)phenyl)-3-(3,5-dichlorophenyl)cyclopropane-1-carboxamide (F2574)

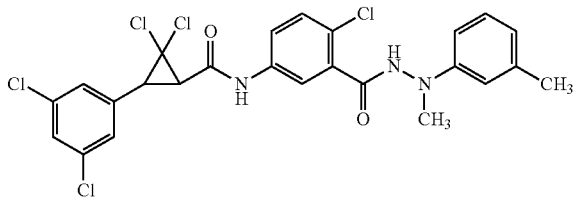 [SMILES: Cc1cccc(N(C)NC(=O)c2cc(NC(=O)C3C(c4cc(Cl)cc(Cl)c4)C3(Cl)Cl)ccc2Cl)c1]

Isolated as an off-white foam (0.103 g, 88%).

trans-2,2-Dichloro-N-(4-chloro-3-(2-(p-tolyl)hydrazine-1-carbonyl)phenyl)-3-(3,5-dichlorophenyl)cyclopropane-1-carboxamide (F2575)

Isolated as a light brown foam (0.030 g, 26%).

trans-2,2-Dichloro-N-(4-chloro-3-(2-(2-cyanophenyl)hydrazine-1-carbonyl)phenyl)-3-(3,5-dichlorophenyl)cyclopropane-1-carboxamide (F2576)

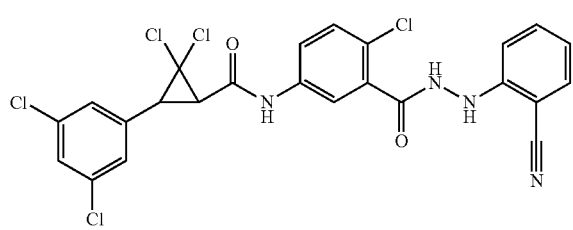 [SMILES: N#Cc1ccccc1NNC(=O)c1cc(NC(=O)C2C(c3cc(Cl)cc(Cl)c3)C2(Cl)Cl)ccc1Cl]

Isolated as a light yellow foam (0.058 g, 50%).

Example 29: Preparation of trans-N-(3-(2-acetylhydrazine-1-carbonyl)-4-chlorophenyl)-2,2-dichloro-3-(3,5-dichlorophenyl)cyclopropane-1-carboxamide (F2514)

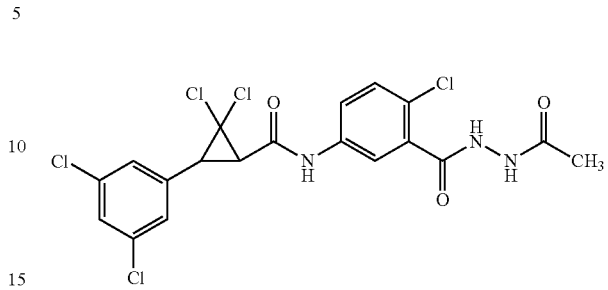

To a solution of trans-2,2-dichloro-N-(4-chloro-3-(hydrazinecarbonyl)phenyl)-3-(3,5-dichlorophenyl)cyclopropane-1-carboxamide hydrochloride (F2567) (0.25 g, 0.498 mmol) in tetrahydrofuran (5 mL) was added triethylamine (0.15 g, 1.49 mmol) and acetic anhydride (0.061 g, 0.598 mmol) at 0° C. The reaction mixture was stirred at room temperature for 16 hours. The reaction mixture was concentrated under reduced pressure, and the residue was dissolved in ethyl acetate (20 mL) and washed with water (2×10 mL) and brine (5 mL). The organic layer was dried over anhydrous sodium sulfate, filtered, and concentrated under reduced pressure. Purification by column chromatography eluting with 40-60% ethyl acetate/petroleum ether afforded the title compound as a white solid (0.08 g, 32%).

The following compounds were prepared in like manner to the procedure outlined in Example 29:

trans-2,2-Dichloro-N-(4-chloro-3-(2-(2,2,2-trifluoroacetyl)hydrazine-1-carbonyl)phenyl)-3-(3,5-dichlorophenyl)cyclopropane-1-carboxamide (F2515)

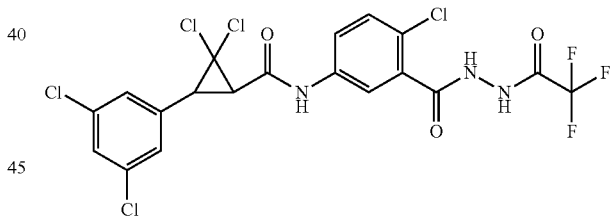

Isolated as a white solid (0.06 g, 21%).

trans-2,2-Dichloro-N-(4-chloro-3-(2-(3,3,3-trifluoropropanoyl)hydrazine-1-carbonyl)phenyl)-3-(3,5-dichlorophenyl)cyclopropane-1-carboxamide (F2516)

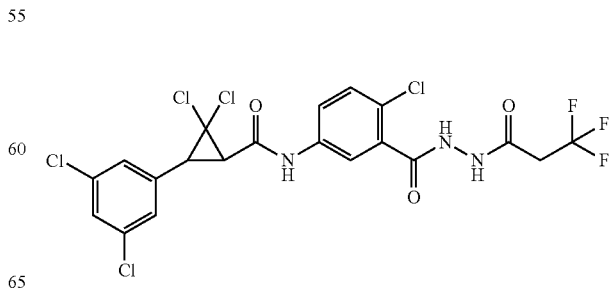

Isolated as a white solid (0.06 g, 26%).

trans-2,2-Dichloro-N-(4-chloro-3-(2-(2,2-difluorocyclopropane-1-carbonyl)hydrazine-1-carbonyl)phenyl)-3-(3,5-dichlorophenyl)cyclopropane-1-carboxamide (F2517)

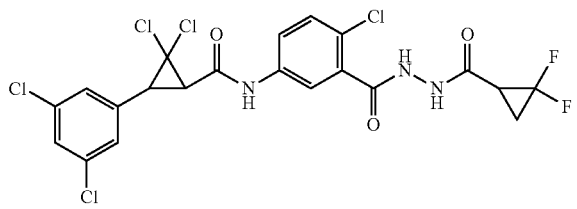 [SMILES: O=C(NNC(=O)C1CC1(F)F)c1cc(NC(=O)C2C(c3cc(Cl)cc(Cl)c3)C2(Cl)Cl)ccc1Cl]

Isolated as a white solid (0.07 g, 31%).

trans-2,2-Dichloro-N-(4-chloro-3-(2-(1-cyanocyclopropane-1-carbonyl)hydrazine-1-carbonyl)phenyl)-3-(3,5-dichlorophenyl)cyclopropane-1-carboxamide (F2518)

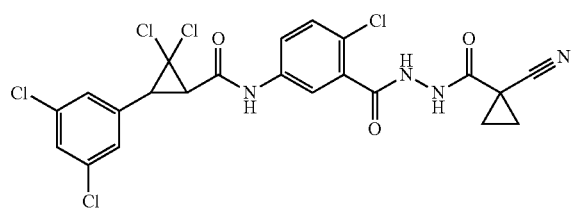 [SMILES: N#CC1(C(=O)NNC(=O)c2cc(NC(=O)C3C(c4cc(Cl)cc(Cl)c4)C3(Cl)Cl)ccc2Cl)CC1]

Isolated as a white solid (0.07 g, 31%).

trans-N-(3-(2-Benzoylhydrazine-1-carbonyl)-4-chlorophenyl)-2,2-dichloro-3-(3,5-dichlorophenyl)cyclopropane-1-carboxamide (F2519)

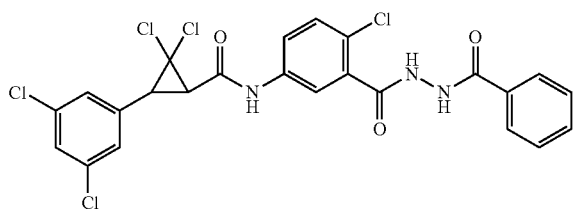 [SMILES: O=C(NNC(=O)c1cc(NC(=O)C2C(c3cc(Cl)cc(Cl)c3)C2(Cl)Cl)ccc1Cl)c1ccccc1]

Isolated as a white solid (0.15 g, 68%).

trans-N-(3-(2-Acetyl-2-methylhydrazine-1-carbonyl)-4-chlorophenyl)-2,2-dichloro-3-(3,5-dichlorophenyl)cyclopropane-1-carboxamide (F2522)

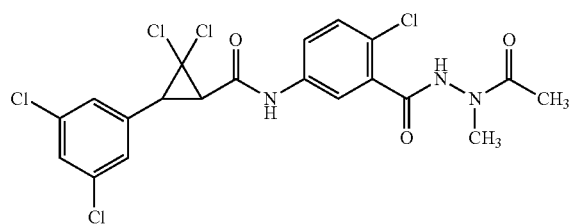 [SMILES: CC(=O)N(C)NC(=O)c1cc(NC(=O)C2C(c3cc(Cl)cc(Cl)c3)C2(Cl)Cl)ccc1Cl]

Isolated as an off-white sod (0.02 g, 10%).

trans-2,2-Dichloro-N-(4-chloro-3-(2-methyl-2-(2,2,2-trifluoroacetyl)hydrazine-1-carbonyl)phenyl)-3-(3,5-dichlorophenyl)cyclopropane-1-carboxamide (F2523)

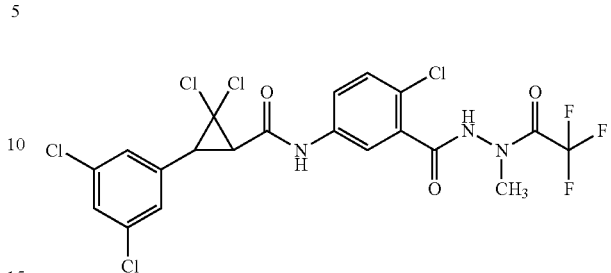

Isolated as an off-white solid (0.085 g, 38%).

trans-2,2-Dichloro-N-(4-chloro-3-(2-(2-cyclopropylacetyl)-2-methylhydrazine-1-carbonyl)phenyl)-3-(3,5-dichlorophenyl)cyclopropane-1-carboxamide (F2524)

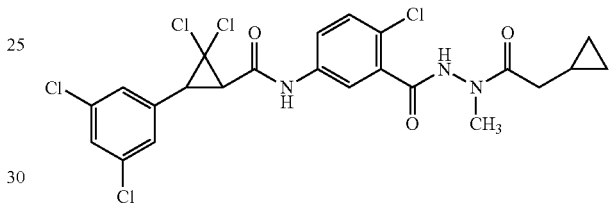

Isolated as an off-white solid 0.04 g, 18%).

trans-2,2-Dichloro-N-(4-chloro-3-(2-(1-cyanocyclopropane-1-carbonyl)-2-methylhydrazine-1-carbonyl)phenyl)-3-(3,5-dichlorophenyl)cyclopropane-1-carboxamide (F2525)

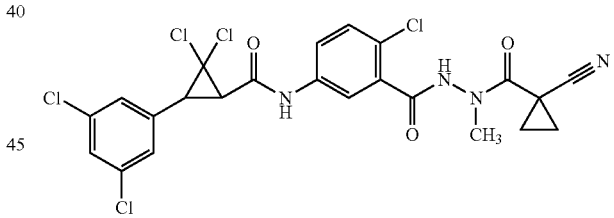

Isolated as an off-white solid 0.11 g, 50%).

trans-2,2-Dichloro-N-(4-chloro-3-(2-(dimethylglycyl)-2-methylhydrazine-1-carbonyl)phenyl)-3-(3,5-dichlorophenyl)cyclopropane-1-carboxamide (F2526)

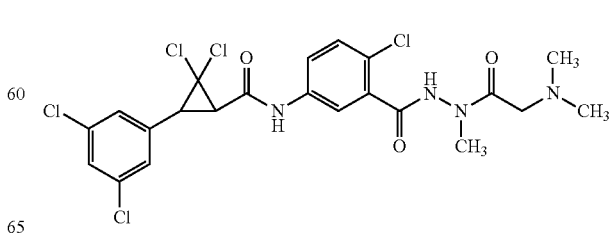

Isolated as an off-white solid (0.11 g, 50%).

trans-N-(3-(2-Benzoyl-2-methylhydrazine-1-carbonyl)-4-chlorophenyl)-2,2-dichloro-3-(3,5-dichlorophenyl)cyclopropane-1-carboxamide (F2527)

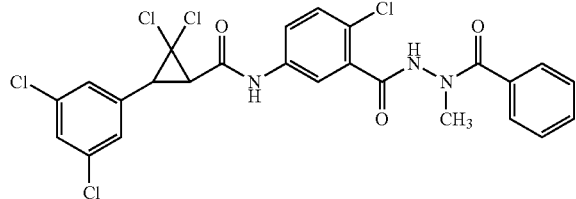

Isolated as an off-white solid (0.12 g, 48%).

trans-2,2-Dichloro-N-(4-chloro-3-(2-(2-cyclopropylacetyl)hydrazine-1-carbonyl)phenyl)-3-(3,5-dichlorophenyl)cyclopropane-1-carboxamide (F2528)

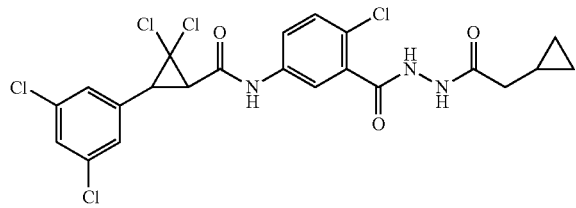 [SMILES: O=C(CC1CC1)NNC(=O)c1cc(NC(=O)C2C(c3cc(Cl)cc(Cl)c3)C2(Cl)Cl)ccc1Cl]

Isolated as a white solid (0.11 g, 50%).

trans-2,2-Dichloro-N-(4-chloro-3-(2-(2-methoxyacetyl)hydrazine-1-carbonyl)phenyl)-3-(3,5-dichlorophenyl)cyclopropane-1-carboxamide (F2529)

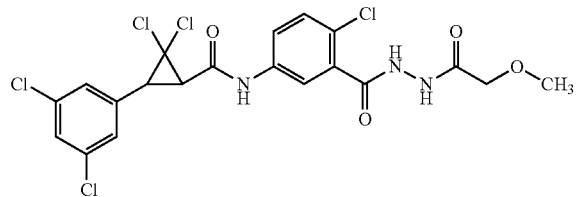 [SMILES: COCC(=O)NNC(=O)c1cc(NC(=O)C2C(c3cc(Cl)cc(Cl)c3)C2(Cl)Cl)ccc1Cl]

Isolated as an off-white solid (0.09 g, 42%).

trans-2,2-Dichloro-N-(4-chloro-3-(2-(dimethylglycyl)hydrazine-1-carbonyl)phenyl)-3-(3,5-dichlorophenyl)cyclopropane-1-carboxamide (F2530)

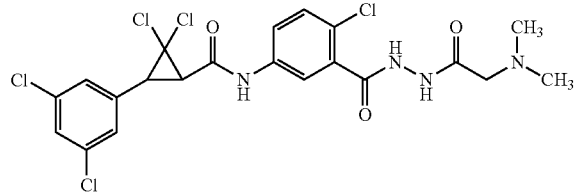 [SMILES: CN(C)CC(=O)NNC(=O)c1cc(NC(=O)C2C(c3cc(Cl)cc(Cl)c3)C2(Cl)Cl)ccc1Cl]

Isolated as an off-white foam (0.06 g, 25%).

trans-2,2-Dichloro-N-(4-chloro-3-(2-picolinoylhydrazine-1-carbonyl)phenyl)-3-(3,5-dichlorophenyl)cyclopropane-1-carboxamide (F2531)

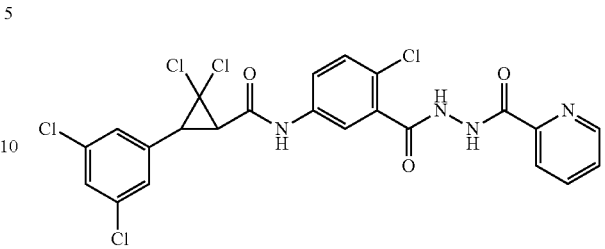

Isolated as an off-white solid (0.055 g, 26%).

trans-2,2-Dichloro-N-(4-chloro-3-(2-(3,3,3-trifluoro-2-(trifluoromethyl)propanoyl)hydrazine-1-carbonyl)phenyl)-3-(3,5-dichlorophenyl)cyclopropane-1-carboxamide (F2532)

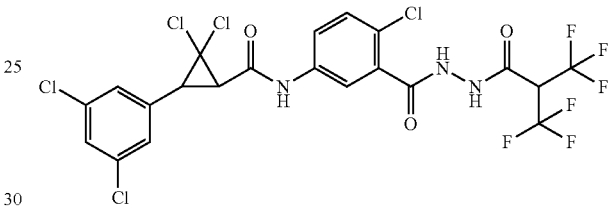

Isolated as an off-white solid 0.04 g, 16%).

trans-2,2-Dichloro-N-(4-chloro-3-(2-methyl-2-(3,3,3-trifluoropropanoyl)hydrazine-1-carbonyl)phenyl)-3-(3,5-dichlorophenyl)cyclopropane-1-carboxamide (F2533)

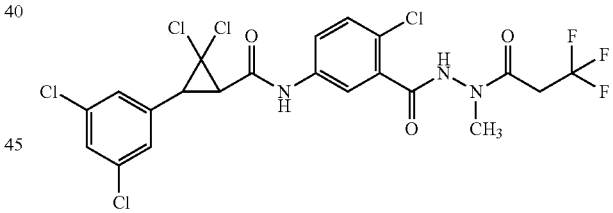

Isolated as an off-white solid (0.085 g, 38%).

trans-2,2-Dichloro-N-(4-chloro-3-(2-(2,2-difluorocyclopropane-1-carbonyl)-2-methylhydrazine-1-carbonyl)phenyl)-3-(3,5-dichlorophenyl)cyclopropane-1-carboxamide (F2534)

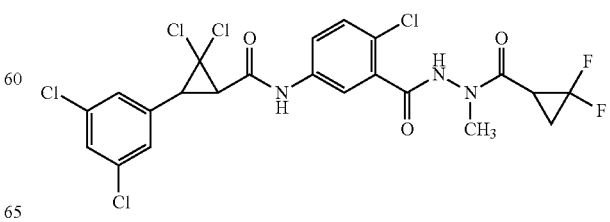

Isolated as an off-white solid (0.065 g, 29%).

Example 30: Preparation of trans-2-(2-chloro-5-(2,2-dichloro-3-(3,5-dichlorophenyl)cyclopropane-1-carboxamido)benzoyl)-N-(2,2,2-trifluoroethyl)hydrazine-1-carboxamide (F2535)

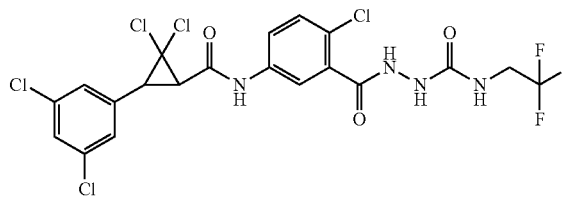

To a solution of trans-2,2-dichloro-N-(4-chloro-3-(hydrazinecarbonyl)phenyl)-3-(3,5-dichlorophenyl)cyclopropane-1-carboxamide hydrochloride (F2567) (0.175 g, 0.347 mmol) in tetrahydrofuran (4 mL) were added triethylamine (0.105 g, 1.04 mmol) and 1,1,1-trifluoro-2-isocyanatoethane (0.052 g, 0.417 mmol) at 0° C. The reaction mixture was stirred at room temperature for 16 hours. The reaction mixture was concentrated under reduced pressure, and the residue was dissolved in ethyl acetate (20 mL) and washed with water (2×10 mL) and brine (5 mL). The organic layer was dried over anhydrous sodium sulfate, filtered, and concentrated under reduced pressure. Purification by column chromatography eluting with 40-60% ethyl acetate/petroleum ether afforded the title compound as an off-white solid (0.10 g, 48%).

The following compounds were prepared in like manner to the procedure outlined in Example 30:

trans-2-(2-Chloro-5-(2,2-dichloro-3-(3,5-dichlorophenyl)cyclopropane-1-carboxamido)benzoyl)-N-isopropylhydrazine-1-carboxamide (F2536)

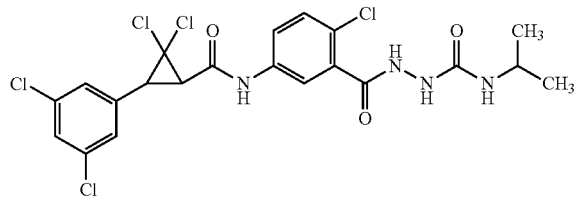 [SMILES: CC(C)NC(=O)NNC(=O)c1cc(NC(=O)C2C(c3cc(Cl)cc(Cl)c3)C2(Cl)Cl)ccc1Cl]

Isolated as an off-white solid (0.13 g, 61%).

trans-2-(2-Chloro-5-(2,2-dichloro-3-(3,5-dichlorophenyl)cyclopropane-1-carboxamido)benzoyl)-N-phenylhydrazine-1-carboxamide (F2537)

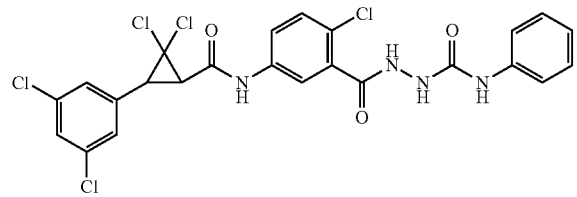 [SMILES: O=C(NNC(=O)c1cc(NC(=O)C2C(c3cc(Cl)cc(Cl)c3)C2(Cl)Cl)ccc1Cl)Nc1ccccc1]

Isolated as an off-white solid (0.06 g, 26%).

trans-2-(2-Chloro-5-(2,2-dichloro-3-(3,5-dichlorophenyl)cyclopropane-1-carboxamido)benzoyl)-N-(cyclopropylmethyl)hydrazine-1-carboxamide (F2538)

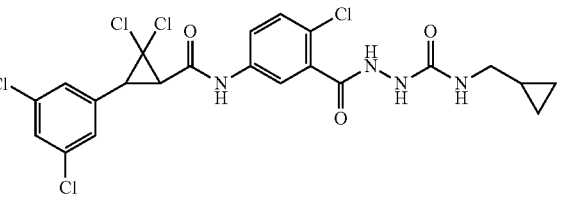

Isolated as an off-white solid (0.11 g, 50%).

Example 31: Preparation of trans-2,2-dichloro-N-(4-chloro-3-(2-((2,2,2-trifluoroethyl)carbamothioyl)hydrazine-1-carbonyl)phenyl)-3-(3,5-dichlorophenyl)cyclopropane-1-carboxamide (F2539)

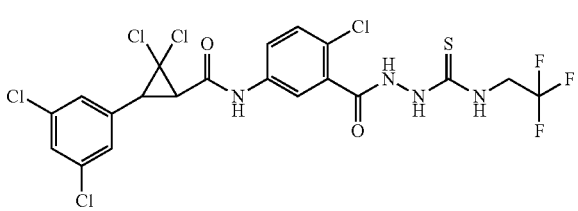 [SMILES: O=C(NNC(=S)NCC(F)(F)F)c1cc(NC(=O)C2C(c3cc(Cl)cc(Cl)c3)C2(Cl)Cl)ccc1Cl]

To a solution of trans-2,2-dichloro-N-(4-chloro-3-(hydrazinecarbonyl)phenyl)-3-(3,5-dichlorophenyl)cyclopropane-1-carboxamide hydrochloride (F2567) (0.190 g, 0.377 mmol) in tetrahydrofuran (4 mL) were added triethylamine (0.114 g, 1.13 mmol) and 1,1,1-trifluoro-2-isothiocyanatoethane (0.064 g, 0.452 mmol) at 0° C. The reaction mixture was stirred at room temperature for 16 hours. The reaction mixture was concentrated under reduced pressure, and the residue was dissolved in ethyl acetate (20 mL) and washed with water (2×10 mL) and brine (5 mL). The organic layer was dried over anhydrous sodium sulfate, filtered, and concentrated under reduced pressure. Purification by column chromatography eluting with 40-60% ethyl acetate/petroleum ether afforded the title compound as an off-white solid (0.08 g, 35%).

The following compounds were prepared in like manner to the procedure outlined in Example 31:

trans-2,2-Dichloro-N-(4-chloro-3-(2-(isopropylcarbamothioyl)hydrazine-1-carbonyl)phenyl)-3-(3,5-dichlorophenyl)cyclopropane-1-carboxamide (F2540)

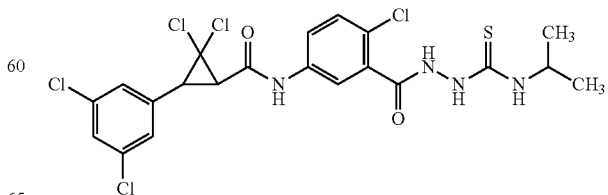

Isolated as an off-white solid (0.06 g, 27%).

trans-2,2-Dichloro-N-(4-chloro-3-(2-(phenylcarbamothioyl)hydrazine-1-carbonyl)phenyl)-3-(3,5-dichlorophenyl)cyclopropane-1-carboxamide (F2541)

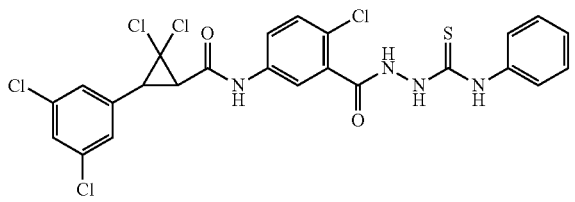

Isolated as an off-white solid (0.07 g, 26%).

Example 32: Preparation of trans-ethyl 2-(2-chloro-5-(2,2-dichloro-3-(3,5-dichlorophenyl)cyclopropane-1-carboxamido)benzoyl)hydrazine-1-carboxylate (F2542)

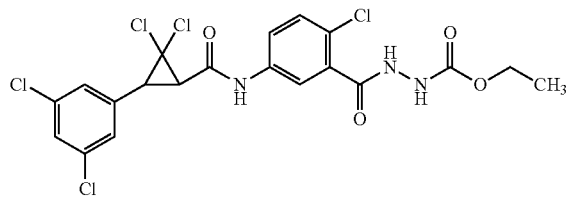 [SMILES: CCOC(=O)NNC(=O)c1cc(NC(=O)C2C(c3cc(Cl)cc(Cl)c3)C2(Cl)Cl)ccc1Cl]

To a solution of trans-2,2-dichloro-N-(4-chloro-3-(hydrazinecarbonyl)phenyl)-3-(3,5-dichlorophenyl)cyclopropane-1-carboxamide hydrochloride (F2567) (0.175 g, 0.347 mmol) in tetrahydrofuran (4 mL) were added triethylamine (0.114 g, 1.13 mmol) and ethyl chloroformate (0.049 g, 0.452 mmol) at 0° C. The reaction mixture was stirred at room temperature for 16 hours. The reaction mixture was concentrated under reduced pressure, and the residue was dissolved in ethyl acetate (20 mL) and washed with water (2×10 mL) and brine (5 mL). The organic layer was dried over anhydrous sodium sulfate, filtered, and concentrated under reduced pressure. Purification by column chromatography eluting with 40-60% ethyl acetate/petroleum ether afforded the title compound as an off-white solid (0.04 g, 19%).

The following compounds were prepared in like manner to the procedure outlined in Example 32:

trans-Trifluoromethyl 2-(2-chloro-5-(2,2-dichloro-3-(3,5-dichlorophenyl)cyclopropane-1-carboxamido)benzoyl)hydrazine-1-carboxylate (F2543)

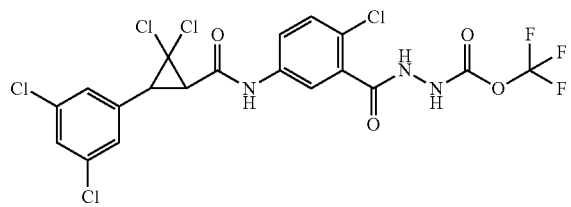 [SMILES: O=C(NNC(=O)c1cc(NC(=O)C2C(c3cc(Cl)cc(Cl)c3)C2(Cl)Cl)ccc1Cl)OC(F)(F)F]

Isolated as an off-white solid (0.05 g, 21%).

Example 33: Preparation of trans-2,2-dichloro-N-(4-chloro-3-(2-(4-fluorobenzyl)hydrazine-1-carbonyl)phenyl)-3-(3,5-dichlorophenyl)cyclopropane-1-carboxamide (F2570)

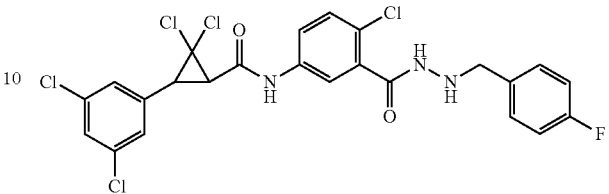

To a 50 mL flask were added trans-2,2-dichloro-N-(4-chloro-3-(hydrazinecarbonyl)phenyl)-3-(3,5-dichlorophenyl)cyclopropane-1-carboxamide (F2567) (0.10 g, 0.214 mmol), methanol (3 mL) and 4-fluorobenzaldehyde (0.023 mL, 0.214 mmol). The reaction mixture was stirred at room temperature overnight. The solution was concentrated and the residue purified by column chromatography using 0-100% ethyl acetate/hexanes as gradient to afford the imine product as a colorless foam. The foam was dissolved in methanol (3 mL) and to the solution were added sequentially sodium borohydride (0.081 g, 1.283 mmol) and acetic acid (0.024 mL, 0.428 mmol). The reaction mixture was stirred overnight at room temperature. Saturated aqueous sodium bicarbonate solution (5 mL) was added carefully to the reaction mixture, and the mixture was extracted with ethyl acetate (10 mL). The organic layer was dried over sodium sulfate, filtered, and concentrated to afford the title compound as a colorless foam (0.065 g, 48%).

The following compounds were prepared in like manner to the procedure outlined in Example 33:

trans-2,2-dichloro-N-(4-chloro-3-(2-(4,4-difluorocyclohexyl)hydrazine-1-carbonyl)phenyl)-3-(3,5-dichlorophenyl)cyclopropane-1-carboxamide (F2569)

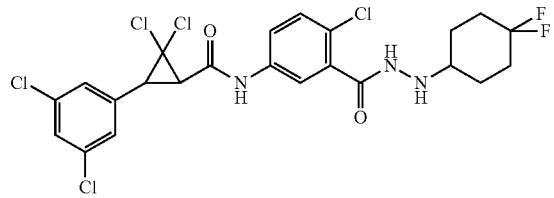 [SMILES: O=C(NNC1CCC(F)(F)CC1)c1cc(NC(=O)C2C(c3cc(Cl)cc(Cl)c3)C2(Cl)Cl)ccc1Cl]

Isolated as an off-white foam (0.030 g, 22%).

Example 34: Preparation of trans-2,2-dichloro-N-(4-chloro-3-(2-(2,4-difluorobenzyl)hydrazine-1-carbonyl)phenyl)-3-(3,5-dichlorophenyl)cyclopropane-1-carboxamide (F2547)

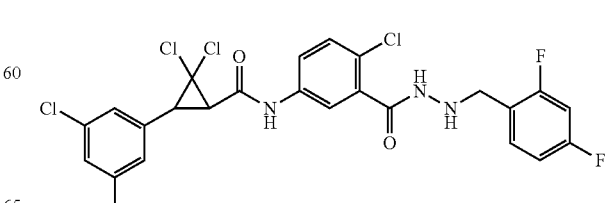

To a solution of trans-2,2-dichloro-N-(4-chloro-3-(2-(2,4-difluorobenzylidene)hydrazine-1-carbonyl)phenyl)-3-(3,5-dichlorophenyl)cyclopropane-1-carboxamide (F3004) (0.20 g, 0.34 mmol) in ethanol (6 mL) were added acetic acid (0.1 mL) and sodium cyanoborohydride (0.107 g, 1.7 mmol) at 0° C. and the reaction mixture was stirred at room temperature for 16 hours. The reaction mixture was poured into water (10 mL) and extracted with ethyl acetate (2×10 mL). The organic layer was dried over anhydrous sodium sulfate, filtered, and concentrated under reduced pressure. Purification by column chromatography using 20-40% ethyl acetate/petroleum ether as eluent afforded the title compound as an off-white solid (0.155 g, 77%).

The following compounds were prepared in like manner to the procedure outlined in Example 34:

trans-2,2-Dichloro-N-(4-chloro-3-(2-(1-phenylethyl)hydrazine-1-carbonyl)phenyl)-3-(3,5-dichlorophenyl)cyclopropane-1-carboxamide (F2548)

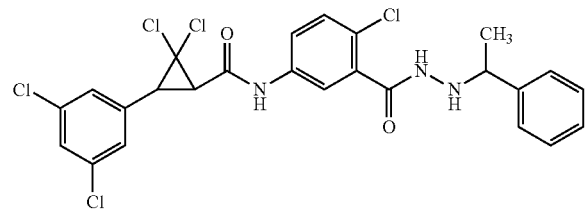 [SMILES: CC(NNC(=O)c1cc(NC(=O)C2C(c3cc(Cl)cc(Cl)c3)C2(Cl)Cl)ccc1Cl)c1ccccc1]

Isolated as an off-white solid (0.175 g, 70%).

trans-2,2-Dichloro-N-(4-chloro-3-(2-(cyclopropylmethyl)hydrazine-1-carbonyl)phenyl)-3-(3,5-dichlorophenyl)cyclopropane-1-carboxamide (F2549)

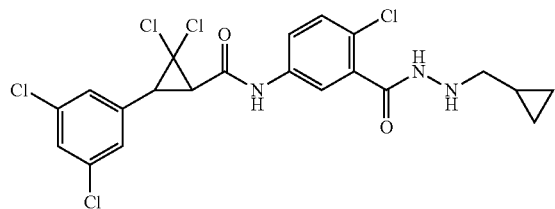 [SMILES: O=C(NNCC1CC1)c1cc(NC(=O)C2C(c3cc(Cl)cc(Cl)c3)C2(Cl)Cl)ccc1Cl]

Isolated as an off-white solid (0.085 g, 40%).

trans-2,2-Dichloro-N-(4-chloro-3-(2-(3,3,3-trifluoropropyl)hydrazine-1-carbonyl)phenyl)-3-(3,5-dichlorophenyl)cyclopropane-1-carboxamide (F2550)

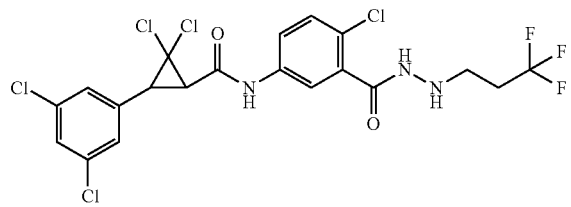 [SMILES: O=C(NNCCC(F)(F)F)c1cc(NC(=O)C2C(c3cc(Cl)cc(Cl)c3)C2(Cl)Cl)ccc1Cl]

Isolated as an off-white solid (0.080 g, 35%).

trans-2,2-Dichloro-N-(4-chloro-3-(2-(1-methoxypropan-2-yl)hydrazine-1-carbonyl)phenyl)-3-(3,5-dichlorophenyl)cyclopropane-1-carboxamide (F2551)

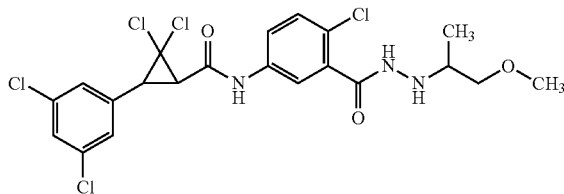 [SMILES: COCC(C)NNC(=O)c1cc(NC(=O)C2C(c3cc(Cl)cc(Cl)c3)C2(Cl)Cl)ccc1Cl]

Isolated as an off-white solid (0.085 g, 33%).

trans-2,2-Dichloro-N-(4-chloro-3-(1-methyl-2-(3,3,3-trifluoropropyl)hydrazine-1-carbonyl)phenyl)-3-(3,5-dichlorophenyl)cyclopropane-1-carboxamide (F2552)

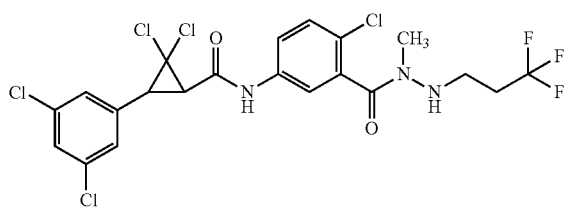 [SMILES: CN(NCCC(F)(F)F)C(=O)c1cc(NC(=O)C2C(c3cc(Cl)cc(Cl)c3)C2(Cl)Cl)ccc1Cl]

Isolated as an off-white solid (0.10 g, 55%).

trans-N-(3-(2-Benzylhydrazine-1-carbonyl)-4-chlorophenyl)-2,2-dichloro-3-(3,5-dichlorophenyl)cyclopropane-1-carboxamide (F2545)

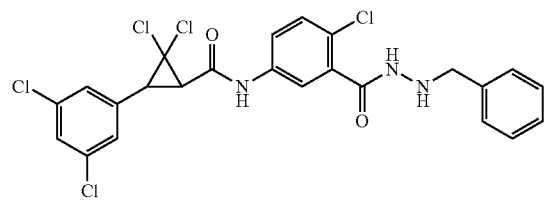 [SMILES: O=C(NNCc1ccccc1)c1cc(NC(=O)C2C(c3cc(Cl)cc(Cl)c3)C2(Cl)Cl)ccc1Cl]

Isolated as an off-white solid (0.100 g, 28%).

trans-2,2-Dichloro-N-(4-chloro-3-(2-(2,5-difluorobenzyl)hydrazine-1-carbonyl)phenyl)-3-(3,5-dichlorophenyl)cyclopropane-1-carboxamide (F2546)

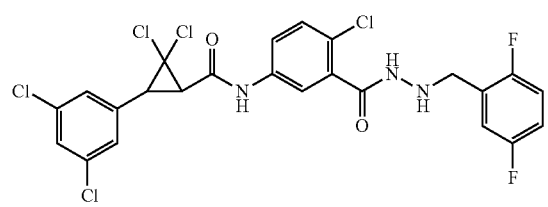 [SMILES: O=C(NNCc1cc(F)ccc1F)c1cc(NC(=O)C2C(c3cc(Cl)cc(Cl)c3)C2(Cl)Cl)ccc1Cl]

Isolated as an off-white solid (0.04 g, 32%).

Example 35: Preparation of trans-N-(3-(2-Benzylldenehydrazine-1-carbonyl)-4-chlorophenyl)-2,2-dichloro-3-(3,5-dichlorophenyl)cyclopropane-1-carboxamide (F3001)

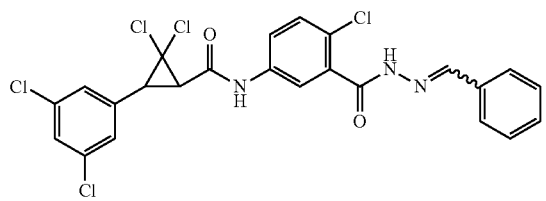 [SMILES: O=C(NN=Cc1ccccc1)c1cc(NC(=O)C2C(c3cc(Cl)cc(Cl)c3)C2(Cl)Cl)ccc1Cl]

To a solution of trans-2,2-dichloro-N-(4-chloro-3-(hydrazinecarbonyl)phenyl)-3-(3,5-dichlorophenyl)cyclopropane-1-carboxamide hydrochloride (F2567) (0.300 g, 0.60 mmol) in ethanol (8.0 mL) was added sodium acetate trihydrate (0.099 g, 1.2 mmol) at room temperature and the mixture was stirred for 15 min. Benzaldehyde (0.19 g, 1.8 mmol) was added followed by acetic acid (0.1 mL), and the reaction mixture was stirred at room temperature for 16 hours. The reaction mixture was poured into water (10 mL) and extracted with ethyl acetate (2×10 mL). The organic layer was dried over anhydrous sodium sulfate, filtered and concentrated under reduced pressure. Purification by column chromatography using 20-40% ethyl acetate/petroleum ether as eluent afforded the title compound as a pale brown solid (0.110 g, 35%).

The following compounds were prepared in like manner to the procedure outlined in Example 35:

trans-2,2-Dichloro-N-(4-chloro-3-(2-(pyridin-2-ylmethylene)hydrazine-1-carbonyl)phenyl)-3-(3,5-dichlorophenyl)cyclopropane-1-carboxamide (F3002)

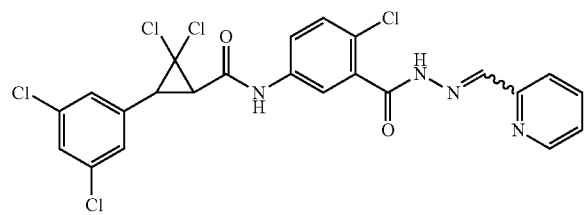 [SMILES: O=C(NN=Cc1ccccn1)c1cc(NC(=O)C2C(c3cc(Cl)cc(Cl)c3)C2(Cl)Cl)ccc1Cl]

Isolated as an off-white solid (0.125 g, 33%).

trans-2,2-Dichloro-N-(4-chloro-3-(2-(2,5-difluorobenzylidene)hydrazine-1-carbonyl)phenyl)-3-(3,5-dichlorophenyl)cyclopropane-1-carboxamide (F3003)

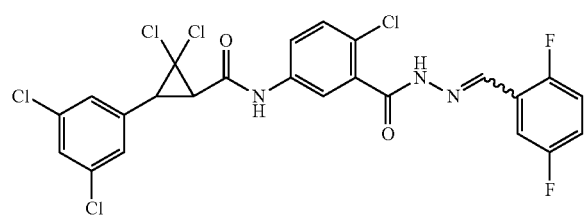 [SMILES: O=C(NN=Cc1cc(F)ccc1F)c1cc(NC(=O)C2C(c3cc(Cl)cc(Cl)c3)C2(Cl)Cl)ccc1Cl]

Isolated as an off-white solid (0.13 g, 34%).

trans-2,2-Dichloro-N-(4-chloro-3-(2-(2,4-difluorobenzylidene)hydrazine-1-carbonyl)phenyl)-3-(3,5-dichlorophenyl)cyclopropane-1-carboxamide (F3004)

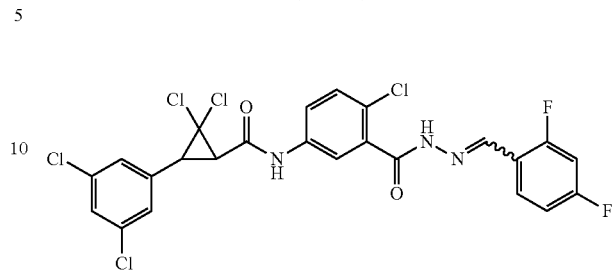

Isolated as an off-white solid (0.105 g, 32%).

trans-2,2-Dichloro-N-(4-chloro-3-(2-(1-phenylethylidene)hydrazine-1-carbonyl)phenyl)-3-(3,5-dichlorophenyl)cyclopropane-1-carboxamide (F3005)

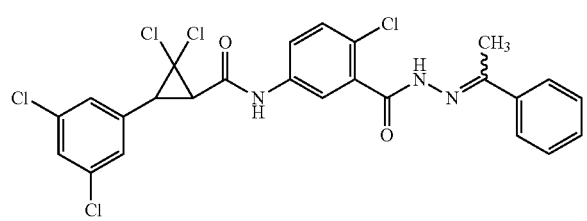

Isolated as an off-white solid (0.100 g, 38%).

trans-2,2-Dichloro-N-(4-chloro-3-(2-(thiazol-2-ylmethylene)hydrazine-1-carbonyl)phenyl)-3-(3,5-dichlorophenyl)cyclopropane-1-carboxamide (F3006)

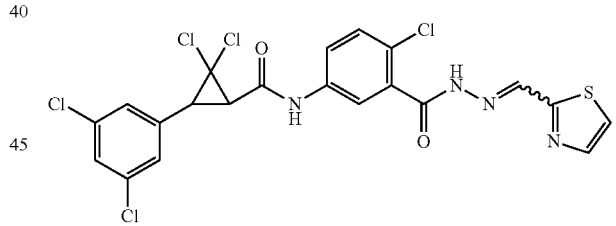

Isolated as a pale yellow solid (0.080 g, 30%).

trans-2,2-Dichloro-N-(4-chloro-3-(2-(cyclopropylmethylene)hydrazine-1-carbonyl)phenyl)-3-(3,5-dichlorophenyl)cyclopropane-1-carboxamide (F3007)

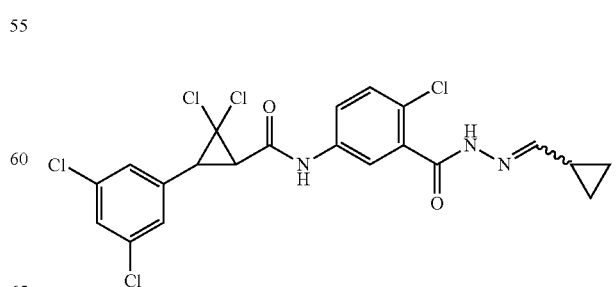

Isolated as a pale yellow solid (0.100 g, 30%).

trans-2,2-Dichloro-N-(4-chloro-3-(2-(3,3,3-trifluoro-propylidene)hydrazine-1-carbonyl)phenyl)-3-(3,5-dichlorophenyl)cyclopropane-1-carboxamide (F3008)

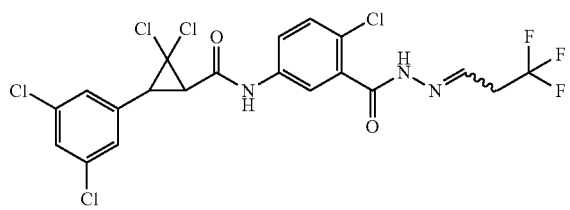 [SMILES: O=C(NN=CCC(F)(F)F)c1cc(NC(=O)C2C(c3cc(Cl)cc(Cl)c3)C2(Cl)Cl)ccc1Cl]

Isolated as an off-white solid (0.300 g, 40%).

trans-2,2-Dichloro-N-(4-chloro-3-(2-(propan-2-ylidene)hydrazine-1-carbonyl)phenyl)-3-(3,5-dichlorophenyl)cyclopropane-1-carboxamide (F3010)

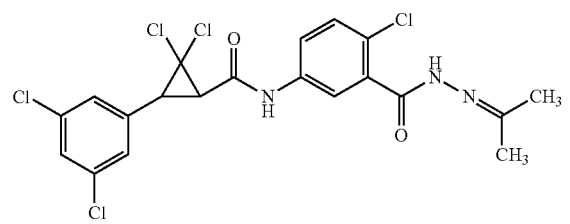 [SMILES: CC(C)=NNC(=O)c1cc(NC(=O)C2C(c3cc(Cl)cc(Cl)c3)C2(Cl)Cl)ccc1Cl]

Isolated as an off-white foam (0.05 g, 41%).

Example 36: Preparation of trans-2,2-dichloro-N-(4-chloro-3-(1-methyl-2-(3,3,3-trifluoropropylidene)hydrazine-1-carbonyl)phenyl)-3-(3,5-dichlorophenyl)cyclopropane-1-carboxamide (F3009)

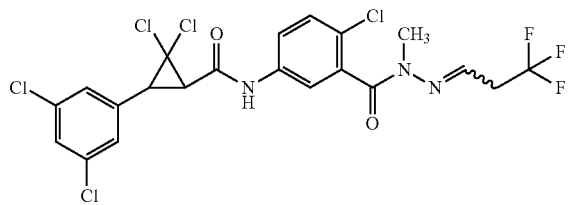 [SMILES: CN(N=CCC(F)(F)F)C(=O)c1cc(NC(=O)C2C(c3cc(Cl)cc(Cl)c3)C2(Cl)Cl)ccc1Cl]

To a solution of trans-2-chloro-5-(2,2-dichloro-3-(3,5-dichlorophenyl)cyclopropane-1-carboxamido)benzoic acid (C12) (0.50 g, 1.10 mmol) in dichloromethane (10 mL) were added sequentially N,N-dimethylformamide (3 drops) and oxalyl chloride (0.14 mL, 1.66 mmol) at 0° C., and the reaction mixture was stirred at room temperature for 3 hours. The reaction mixture was then concentrated under reduced pressure (bath temperature was maintained at 30-35° C.). The acid chloride was dissolved in dichloromethane (6 mL) and was added to a solution of 1-methyl-2-(3,3,3-trifluoropropylidene)hydrazine (C220) (0.600 g (crude)) and triethylamine (0.46 mL, 3.3 mmol) in dichloromethane (10 mL) at 0° C. The reaction mixture was stirred at room temperature for 10 hours. The reaction mixture was diluted with dichloromethane (20 mL) and washed with water. The organic layer was dried over anhydrous sodium sulfate, filtered, and concentrated under reduced pressure. Purification by column chromatography using 20-40% ethyl acetate/petroleum ether as eluent afforded the title compound as a pink solid (0.320 g, 50%).

Example 37: Preparation of trans-2,2-dichloro-N-(4-chloro-3-(hydrazinecarbonyl)phenyl)-3-(3,5-dichlorophenyl)cyclopropane-1-carboxamide hydrochloride (F2567)

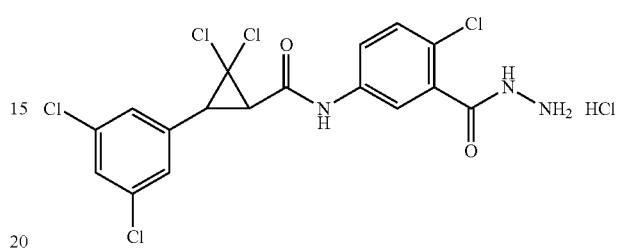

To a solution of trans-tert-butyl 2-(2-chloro-5-(2,2-dichloro-3-(3,5-dichlorophenyl)cyclopropane-1-carboxamido)benzoyl)hydrazine-1-carboxylate (F2566) (1.00 g, 1.77 mmol) in dichloromethane (10 mL) was added 4 M HCl in 1,4-dioxane (5 mL) at 0° C. and the reaction mixture was stirred at 20° C. for 16 hours. The reaction mixture was concentrated under reduced pressure. The residue was triturated with diethyl ether. and the resulting solid was filtered and dried under vacuum. The title compound was isolated as an off-white solid (0.600 g, 68%).

The following compounds were prepared in like manner to the procedure outlined in Example 37:

trans-2,2-Dichloro-N-(4-chloro-3-(2-methylhydrazine-1-carbonyl)phenyl)-3-(3,5-dichlorophenyl)cyclopropane-1-carboxamide hydrochloride (F2521)

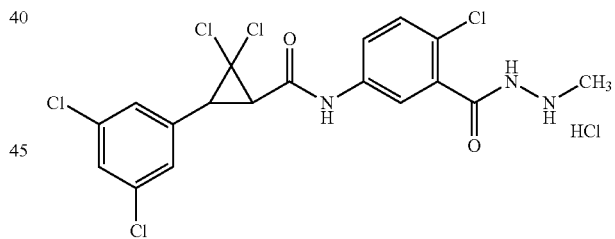

Isolated as a white solid (2.6 g, 78%).

Example 38: Preparation of trans-tert-butyl 2-(2-chloro-5-(2,2-dichloro-3-(3,5-dichlorophenyl)cyclopropane-1-carboxamido)benzoyl)hydrazine-1-carboxylate (F2566)

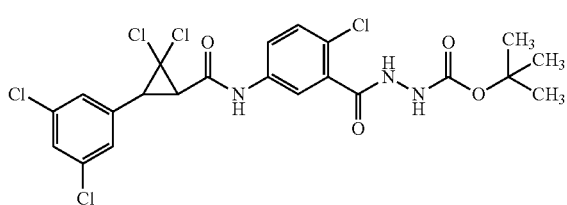 [SMILES: CC(C)(C)OC(=O)NNC(=O)c1cc(NC(=O)C2C(c3cc(Cl)cc(Cl)c3)C2(Cl)Cl)ccc1Cl]

To a solution of trans-2-chloro-5-(2,2-dichloro-3-(3,5-dichlorophenyl)cyclopropane-1-carboxamido)benzoic acid (C12) (7.60 g, 16.9 mmol) in dichloromethane (200 mL) was added tert-butyl hydrazine carboxylate (2.20 g, 16.9 mmol) and 3-(((ethylimino)methylene) amino)-N,N-dimethylpropan-1-amine hydrochloride (EDC; 3.20 g, 16.9 mmol). The reaction mixture was stirred at room temperature for 16 hours. The reaction mixture was concentrated under reduced pressure and the residue was taken up in water and extracted with ethyl acetate (2×200 mL). The organic layer was washed with saturated aqueous sodium bicarbonate solution (50 mL), dried over anhydrous sodium sulfate, filtered and concentrated under reduced pressure. Purification by column chromatography eluting with 10% ethyl acetate in petroleum ether afforded the title compound as an off-white solid (1.20 g, 22%).

The following compounds were prepared in like manner to the procedure outlined in Example 38:

trans-tert-Butyl 2-(2-chloro-5-(2,2-dichloro-3-(3,5-dichlorophenyl)cyclopropane-1-carboxamido)benzoyl)-1-methylhydrazine-1-carboxylate (F2520)

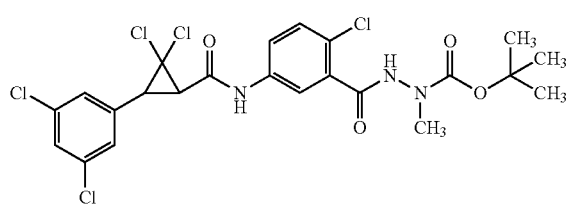 [SMILES: CN(NC(=O)c1cc(NC(=O)C2C(c3cc(Cl)cc(Cl)c3)C2(Cl)Cl)ccc1Cl)C(=O)OC(C)(C)C]

Isolated as an off-white solid (2.6 g, 78%).

Example 39: Preparation of 2-chloro-5-((1R,3R)-2,2-dichloro-3-(3-chloro-4-fluorophenyl)cyclopropane-1-carboxamido)-3-fluorobenzoic acid (C1)

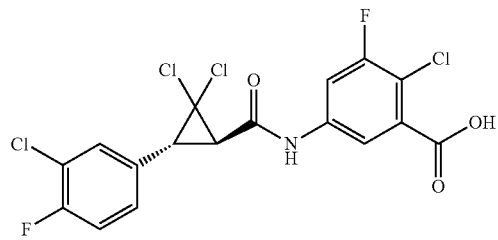 [SMILES: O=C(O)c1cc(NC(=O)[C@H]2[C@H](c3ccc(F)c(Cl)c3)C2(Cl)Cl)cc(F)c1Cl]

Step 1: To a suspension of (1R,3R)-2,2-dichloro-3-(3-chloro-4-fluorophenyl)cyclopropane-1-carboxylic acid (C93) (0.445 g, 1.57 mmol) in 1,2-dichloroethane (10 mL) were added two drops of N,N-dimethylformamide followed by the dropwise addition of oxalyl dichloride (1.992 g, 15.7 mmol), and the resulting light-yellow mixture was stirred at room temperature for 16 hours. The solvent and excess oxalyl dichloride were evaporated under reduced pressure, and the resulting gold oil was dissolved in 1,2-dichloroethane (10 mL) and concentrated (repeated 2×) to give the intermediate acid chloride as a gold oil which was used without purification.

Step 2: To a mixture of 5-amino-2-chloro-3-fluorobenzoic acid (C196) (0.357 g, 1.88 mmol) and triethylamine (0.334 g, 3.30 mmol) in 1,2-dichloroethane (15 mL) was added a solution of the freshly prepared acid chloride, (1R,3R)-2,2-dichloro-3-(3-chloro-4-fluorophenyl)cyclopropane-1-carbonyl chloride (0.474 g, 1.57 mmol), dropwise at 0° C., and the resulting green solution was stirred under nitrogen while warming to room temperature over a 1-hour period, and then stirred at room temperature for 3 hours. The reaction mixture was concentrated to a dark oil, and the oil was partitioned between ethyl acetate (100 mL) and 1 normal aqueous hydrogen chloride (25 mL). The phases were separated and the aqueous layer was extracted with additional ethyl acetate (25 mL). The combined organic extracts were washed with brine (50 mL), dried over sodium sulfate, filtered, and concentrated to an amber oil. The oil was dissolved in minimal ethyl acetate and adsorbed to Celite®. The adsorbed material was purified by reverse-phase, automated flash chromatography using a gradient of 10-100% acetonitrile in water as eluent to give the title compound as a light tan solid (0.398 g, 55%): mp 205-208° C.; $^1$H NMR (400 MHz, DMSO-$d_6$) δ 13.78 (s, 1H), 11.12 (s, 1H), 7.92 (d, J=10.8 Hz, 2H), 7.71 (dd, J=7.1, 1.8 Hz, 1H), 7.54-7.39 (m, 2H), 3.59 (d, J=8.4 Hz, 1H), 3.43 (d, J=8.4 Hz, 1H); $^{19}$F NMR (376 MHz, DMSO-$d_6$) δ −111.57, −117.24; HRMS-ESI (m/z) [M$^+$]$^+$ calcd for $C_{17}H_9Cl_4F_2NO_3$, 452.9305; found, 452.9303.

The following compounds were prepared in like manner to the procedure outlined in Example 39:

trans-2-Chloro-5-(2,2-dichloro-3-(3-chloro-4-fluorophenyl)cyclopropane-1-carboxamido)-3-fluorobenzoic acid (C2)

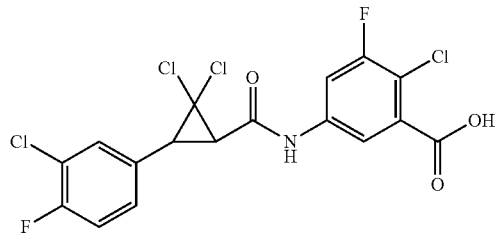

Isolated as a light tan solid (0.740 g, 50%): mp 186-189° C.; $^1$H NMR (400 MHz, DMSO-$d_6$) δ 13.78 (s, 1H), 11.12 (s, 1H), 7.92 (d, J=10.6 Hz, 2H), 7.71 (d, J=7.1 Hz, 1H), 7.57-7.38 (m, 2H), 3.59 (d, J=8.4 Hz, 1H), 3.43 (d, J=8.5 Hz, 1H); $^{19}$F NMR (376 MHz, DMSO-$d_6$) δ −111.54, −117.23; ESIMS m/z 454 ([M−H]$^-$).

trans-5-(2,2-Dichloro-3-(3-chloro-4-fluorophenyl)cyclopropane-1-carboxamido)-2-fluoro-3-methylbenzoic acid (C3)

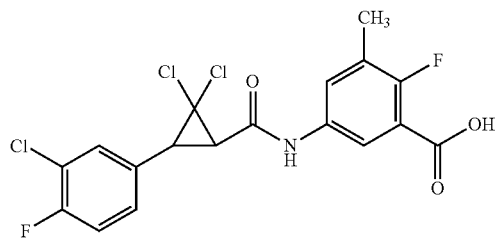

Isolated as a tan solid (1.229 g, 87%): mp 228-235° C.; $^1$H NMR (400 MHz, DMSO-d$_6$) δ 13.25 (s, 1H), 10.76 (s, 1H), 7.99 (dd, J=6.1, 2.8 Hz, 1H), 7.75 (dd, J=6.2, 2.8 Hz, 1H), 7.70 (dd, J=7.1, 2.0 Hz, 1H), 7.53-7.40 (m, 2H), 3.56 (d, J=8.4 Hz, 1H), 339 (d, J=8.5 Hz, 1H), 2.27 (d, J=2.1 Hz, 3H); $^{19}$F NMR (376 MHz, DMSO-d$_6$) δ −117.31, −120.17; ESIMS m/z 434 ([M−H]$^−$).

trans-2-Chloro-5-(2,2-dichloro-3-(3-chloro-4-fluorophenyl)cyclopropane-1-carboxamido)-3-methylbenzoic acid (C4)

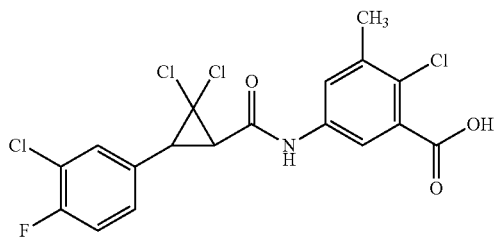 [SMILES: Cc1cc(NC(=O)C2C(c3ccc(F)c(Cl)c3)C2(Cl)Cl)cc(C(=O)O)c1Cl]

Isolated as a light-tan solid (0.875 g, 69%): mp 218-222° C.; $^1$H NMR (400 MHz, DMSO-d$_6$) δ 13.42 (s, 1H), 10.84 (s, 1H), 7.90 (d, J=2.6 Hz, 1H), 7.80-7.63 (m, 2H), 7.59-7.33 (m, 2H), 3.56 (d, J=8.4 Hz, 1H), 3.41 (d, J=8.4 Hz, 1H), 2.38 (s, 3H); $^{19}$F NMR (376 MHz, DMSO-d$_6$) δ −117.29; ESIMS m/z 450 ([M−H]$^−$).

trans-3-Chloro-5-(2,2-dichloro-3-(3-chloro-4-fluorophenyl)cyclopropane-1-carboxamido)-2-methylbenzoic acid (C5)

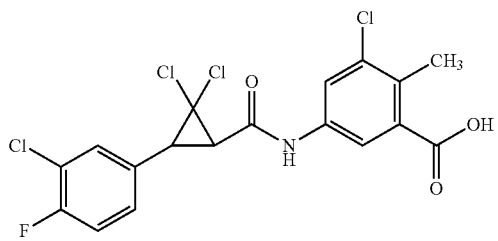 [SMILES: Cc1c(Cl)cc(NC(=O)C2C(c3ccc(F)c(Cl)c3)C2(Cl)Cl)cc1C(=O)O]

Isolated as a tan solid (0.780 g, 63%): mp 219-225° C.; $^1$H NMR (400 MHz, DMSO-d$_6$) δ 13.34 (s, 1H), 10.90 (s, 1H), 8.02 (d, J=2.3 Hz, 1H), 7.96 (d, J=2.3 Hz, 1H), 7.71 (dd, J=7.1, 1.9 Hz, 1H), 7.52-7.40 (m, 2H), 3.57 (d, J=8.4 Hz, 1H), 3.40 (d, J=8.5 Hz, 1H), 2.49 (s, 3H); $^{19}$F NMR (376 MHz, DMSO-d$_6$) δ −117.29; ESIMS m/z 450 ([M−H]$^−$).

trans-2-Chloro-5-(2,2-dichloro-3-(3-chloro-4-fluorophenyl)cyclopropane-1-carboxamido)-3-(trifluoromethyl)benzoic acid (C6)

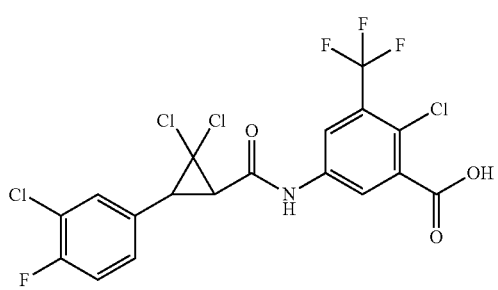 [SMILES: O=C(O)c1cc(NC(=O)C2C(c3ccc(F)c(Cl)c3)C2(Cl)Cl)cc(C(F)(F)F)c1Cl]

Isolated as an off-white solid (0.800 g, 47%): mp 216-219° C.; $^1$H NMR (400 MHz, DMSO-d$_6$) δ 14.00 (s, 1H), 11.23 (s, 1H), 8.33-8.23 (m, 2H), 7.72 (dd, J=7.1, 1.9 Hz, 1H), 7.56-7.39 (m, 2H), 3.60 (d, J=8.4 Hz, 1H), 3.44 (d, J=8.5 Hz, 1H); $^{19}$F NMR (376 MHz, DMSO-d$_6$) δ −61.39, −117.21; ESIMS m/z 503 ([M−2H]$^−$).

trans-5-(2,2-Dichloro-3-(3-chloro-4-fluorophenyl)cyclopropane-1-carboxamido)-3-fluoro-2-methoxybenzoic acid (C7)

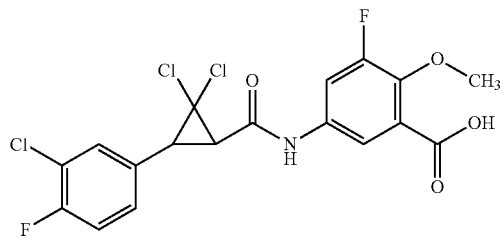 [SMILES: COc1c(F)cc(NC(=O)C2C(c3ccc(F)c(Cl)c3)C2(Cl)Cl)cc1C(=O)O]

Isolated as a tan solid (0.760 g, 50%): mp 183-186° C.; $^1$H NMR (400 MHz, DMSO-d$_6$) δ 13.28 (s, 1H), 10.91 (s, 1H), 7.93-7.78 (m, 1H), 7.78-7.66 (m, 2H), 7.47 (d, J=9.0 Hz, 2H), 3.83 (s, 3H), 3.57 (d, J=8.4 Hz, 1H), 3.40 (d, J=8.5 Hz, 1H); $^{19}$F NMR (376 MHz, DMSO-d$_6$) δ −117.29, −128.27; ESIMS m/z 450 ([M−H]$^−$).

trans-3-Chloro-5-(2,2-dichloro-3-(3-chloro-4-fluorophenyl)cyclopropane-1-carboxamido)-2-fluorobenzoic acid (C8)

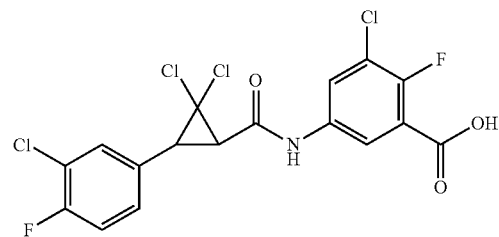

Isolated as a tan solid (0.82 g, 48%): mp 217-224° C.; $^1$H NMR (400 MHz, DMSO-d$_6$) δ 13.70 (s, 1H), 11.01 (s, 1H), 8.13 (dd, J=6.1, 2.8 Hz, 1H), 8.06 (dd, J=5.8, 2.7 Hz, 1H), 7.71 (dd, J=7.2, 1.9 Hz, 1H), 7.54-7.38 (m, 2H), 3.59 (d, J=8.4 Hz, 1H), 3.41 (d, J=8.5 Hz, 1H); $^{19}$F NMR (376 MHz, DMSO-d$_6$) δ −117.25, −119.42; ESIMS m/z 453 ([M−H]$^−$).

trans-5-(2,2-Dichloro-3-(3-chloro-4-fluorophenyl)cyclopropane-1-carboxamido)-2,3-difluorobenzoic acid (C9)

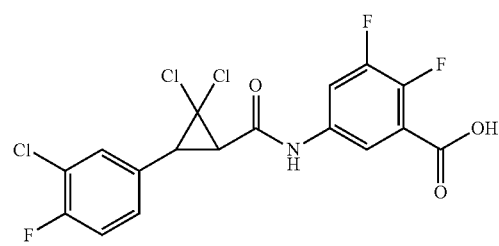

Isolated as a white solid (0.93 g, 57%): mp 222-226° C.; $^1$H NMR (400 MHz, DMSO-$d_6$) δ 11.03 (s, 1H), 8.05-7.87 (m, 2H), 7.71 (dd, J=7.1, 1.9 Hz, 1H), 7.46 (dd, J=8.0, 4.1 Hz, 2H), 3.58 (d, J=8.4 Hz, 1H), 3.41 (d, J=8.5 Hz, 1H); $^{19}$F NMR (376 MHz, DMSO-$d_6$) δ −117.26, −135.55 (d, J=22.4 Hz), −142.67 (d, J=22.4 Hz); ESIMS m/z 437 ([M−H]$^-$).

trans-3-Chloro-5-(2,2-dichloro-3-(3-chloro-4-fluorophenyl)cyclopropane-1-carboxamido)-2-methoxybenzoic acid (C10)

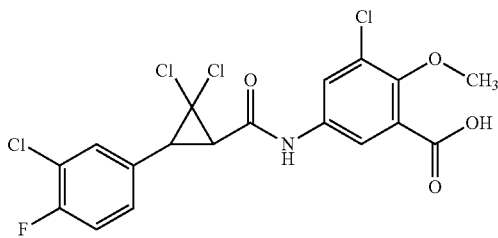 [SMILES: COc1c(Cl)cc(NC(=O)C2C(c3ccc(F)c(Cl)c3)C2(Cl)Cl)cc1C(=O)O]

Isolated as a light tan solid (0.380 g, 22%): $^1$H NMR (400 MHz, DMSO-$d_6$) δ 13.38 (s, 1H), 10.91 (s, 1H), 8.03 (d, J=2.7 Hz, 1H), 7.90 (d, J=2.7 Hz, 1H), 7.70 (dd, J=7.1, 2.0 Hz, 1H), 7.54-7.38 (m, 2H), 3.81 (s, 3H), 3.57 (d, J=8.4 Hz, 1H), 3.40 (d, J=8.5 Hz, 1H); $^{19}$F NMR (376 MHz, DMSO-$d_6$) δ −117.28; ESIMS m/z 466 ([M−H]$^-$).

trans-5-(2,2-Dichloro-3-(3-chloro-4-fluorophenyl)cyclopropane-1-carboxamido)-3-fluoro-2-methylbenzoic acid (C11)

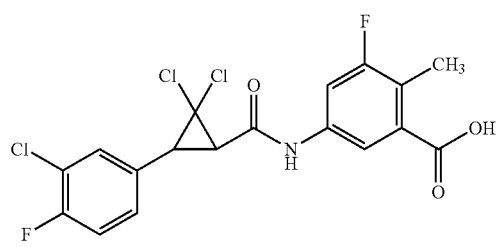 [SMILES: Cc1c(F)cc(NC(=O)C2C(c3ccc(F)c(Cl)c3)C2(Cl)Cl)cc1C(=O)O]

Isolated as a white solid (0.304 g, 53%): mp 210-212° C.; $^1$H NMR (400 MHz, DMSO-$d_6$) δ 13.26 (s, 1H), 10.94 (s, 1H), 7.88 (d, J=2.2 Hz, 1H), 7.77 (dd, J=11.8, 2.1 Hz, 1H), 7.70 (dd, J=7.1, 1.9 Hz, 1H), 7.46 (dd, J=7.8, 4.3 Hz, 2H), 3.57 (d, J=8.4 Hz, 1H), 3.41 (d, J=8.4 Hz, 1H), 2.38 (d, J=2.0 Hz, 3H); $^{19}$F NMR (376 MHz, DMSO-$d_6$) δ −114.04, −117.29; HRMS-ESI (m/z) [M$^+$]$^+$ calcd for $C_{18}H_{12}Cl_3F_2NO_3$, 432.9851; found, 432.9856.

trans-2-chloro-5-(2,2-dichloro-3-(3,5-dichlorophenyl)cyclopropane-1-carboxamido)benzoic acid (C12)

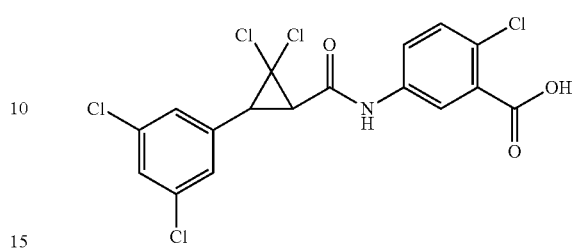

Isolated as a light brown solid (0.421 g, 93%): mp 234-236° C.; $^1$H NMR (400 MHz, DMSO-$d_6$) δ 13.47 (s, 1H), 10.90 (s, 1H), 8.16 (d, J=2.3 Hz, 1H), 7.78 (dd, J=8.7, 2.4 Hz, 1H), 7.59 (m, 4H), 3.56 (dd, J=49.8, 8.5 Hz, 2H), 1.09 (m, 1H); $^{13}$C NMR (101 MHz, DMSO-$d_6$) δ 166.26, 165.77, 162.61, 137.57, 137.27, 134.04, 132.18, 131.44, 131.22, 127.88, 127.66, 126.40, 125.92, 122.88, 121.17, 102.37, 62.11, 38.41, 36.83; ESIMS m/z 454 ([M+H]$^+$).

2-Chloro-5-((1R,3R)-2,2-dichloro-3-(3,5-dichlorophenyl)cyclopropane-1-carboxamido)benzoic acid (C13)

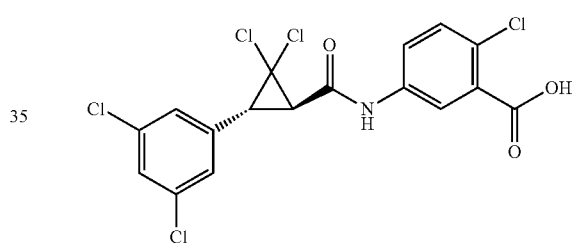

Isolated as a grey solid (3.80 g, 96%): $^1$H NMR (300 MHz, DMSO-$d_6$) δ 13.48 (s, 1H), 10.90 (s, 1H), 8.15 (d, J=2.6 Hz, 1H), 7.78 (dd, J=8.8, 2.7 Hz, 1H), 7.63 (t, J=1.9 Hz, 1H), 7.57-7.50 (m, 3H), 3.62 (d, J=8.5 Hz, 1H), 3.49 (d, J=8.5 Hz, 1H); ESIMS m/z 454 ([M+H]$^+$).

2-Chloro-5-((1R,3R)-2,2-dichloro-3-(3,4-dichlorophenyl)cyclopropane-1-carboxamido)benzoic acid (C14)

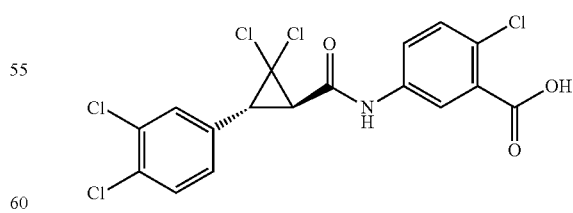

Isolated as a grey solid (3.70 g, 98%): $^1$H NMR (300 MHz, DMSO-$d_6$) δ 13.47 (s, 1H), 10.95 (s, 1H), 8.16 (d, J=2.7 Hz, 1H), 7.82-7.73 (m, 2H), 7.69 (d, J=8.3 Hz, 1H), 7.53 (d, J=8.7 Hz, 1H), 7.43 (dd, J=8.5, 2.1 Hz, 1H), 3.60 (d, J=8.5 Hz, 1H), 3.45 (d, J=8.5 Hz, 1H); ESIMS m/z 454 ([M+H]$^+$).

2-Chloro-5-((1R,3R)-2,2-dichloro-3-(3,4,5-trichlorophenyl)cyclopropane-1-carboxamido)benzoic acid (C15)

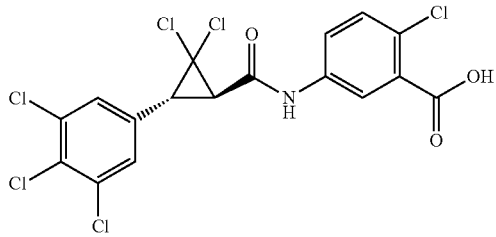 [SMILES: O=C(O)c1cc(NC(=O)[C@H]2[C@H](c3cc(Cl)c(Cl)c(Cl)c3)C2(Cl)Cl)ccc1Cl]

Isolated as a grey solid (3.60 g, 99%): $^1$H NMR (400 MHz, DMSO-$d_6$) δ 13.44 (s, 1H), 10.91 (s, 1H), 8.16 (d, J=2.7 Hz, 1H), 7.80-7.76 (m, 3H), 7.54 (d, J=8.7 Hz, 1H), 3.63 (dt, J=8.5, 0.7 Hz, 1H), 3.52 (d, J=8.5 Hz, 1H); ESIMS m/z 488 ([M+H]$^+$).

2-Chloro-5-((1R,3R)-2,2-dichloro-3-(3-chloro-4-fluorophenyl)cyclopropane-1-carboxamido)benzoic acid (C16)

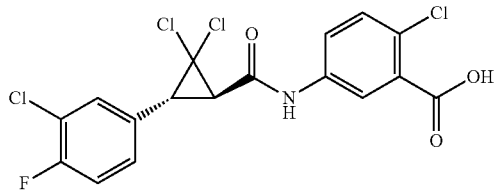 [SMILES: O=C(O)c1cc(NC(=O)[C@H]2[C@H](c3ccc(F)c(Cl)c3)C2(Cl)Cl)ccc1Cl]

Isolated as a grey solid (3.80 g, 99%): $^1$H NMR (400 MHz, DMSO-$d_6$) δ 13.48 (s, 1H), 10.93 (s, 1H), 8.16 (d, J=2.6 Hz, 1H), 7.78 (dd, J=8.8, 2.7 Hz, 1H), 7.71 (dd, J=7.2, 2.0 Hz, 1H), 7.53 (d, J=8.7 Hz, 1H), 7.50-7.42 (m, 2H), 3.58 (d, J=8.4 Hz, 1H), 3.42 (d, J=8.5 Hz, 1H); $^{19}$F NMR (376 MHz, DMSO-$d_6$) δ −117.29; ESIMS m/z 438 ([M+H]$^+$).

Example 40: Preparation of cis/trans-3-(3-bromo-4,5-difluorophenyl)-2,2-dichlorocyclopropane-1-carboxylic acid (C17)

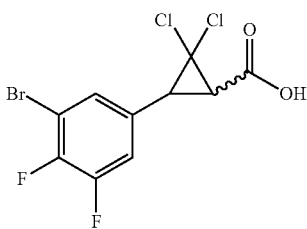

Step 1: Preparation of (E/Z)-1-bromo-2,3-difluoro-5-(4-methoxystyryl)benzene

N-Butyllithium (2.5 Molar (M) in hexane) (3.62 mL, 9.05 mmol) was added to a stirred suspension of (4-methoxybenzyl)triphenylphosphonium chloride (3.79 g, 9.05 mmol) in dry tetrahydrofuran (50 mL) at −30° C. The resulting heterogeneous dark red mixture was stirred at −25-−30° C. for 30 minutes, followed by the dropwise addition of a solution of 3-bromo-4,5-difluorobenzaldehyde (2 g, 9.05 mmol) in anhydrous tetrahydrofuran (5 mL). The resulting suspension of white solid was stirred at −30° C. for another 2 hours, then allowed to warm to ambient temperature and stirred for another 12 hours. The reaction mixture was quenched with water (100 mL) and extracted with diethyl ether (3×50 mL). The organic extracts were washed successively with water and saturated aqueous sodium chloride solution, dried over anhydrous magnesium sulfate, and concentrated under vacuum on a rotary evaporator. Purification by silica gel flash chromatography provided the title compound as a clear colorless oil (1.6 g, 54%, approx. 1:1 mixture of E- and Z-stilbenes): EMS m/z 325.

Step 2: Preparation of 1-bromo-5-(2,2-dichloro-3-(4-methoxyphenyl)cyclopropyl)-2,3-difluorobenzene To a stirred solution of (E/Z)-1-bromo-2,3-difluoro-5-(4-methoxystyryl)benzene (1.165 g, 3.58 mmol) and tetrabutylammonium hexafluorophosphate(V) (0.139 g, 0.358 mmol) in chloroform (28.7 mL) were added sodium hydroxide powder (1.433 g, 35.8 mmol) and water (200 μL) at 23° C. The resulting mixture was vigorously stirred at 50-55° C. for 16 hours. The reaction mixture was diluted with water and extracted with dichloromethane. The combined organic layers were dried over sodium sulfate, filtered, and concentrated. Purification by silica gel flash column chromatography provided the title compound as a pale yellow oil (1.7 g, 63%, approx. 2:1 cis- to trans-cyclopropanes): EIMS m/z 325

Step 3. Preparation of cis/trans-3-(3-bromo-4,5-difluorophenyl)-2,2-dichlorocyclopropane-1-carboxylic acid Ruthenium(III) chloride hydrate (0.047 g, 0.207 mmol) was added to a stirred mixture of crude cis/trans-3-(3-bromo-4,5-difluorophenyl)-2,2-dichlorocyclopropane-1-carboxylic acid (1.69 g, 4.14 mmol) in water:ethyl acetate:acetonitrile (2.5:1:1, 90 mL) at 23° C. Sodium periodate (13.29 g, 62.1 mmol) was carefully added portionwise at a rate to maintain the temperature below 50° C. The resulting biphasic brown mixture was vigorously stirred at 23° C. for 2 hours. The reaction mixture was diluted with water (200 mL) and extracted with ethyl acetate (3×50 mL). The combined organic layers were dried over magnesium sulfate, filtered, and concentrated. The residue was dissolved in minimal acetonitrile and purified by C-18 flash chromatography to give the title compound as a grey solid (0.665 g, 44% approx. 2:1 mixture of trans/cis cyclopropanes): $^1$H NMR (400 MHz, CDCl$_3$CDCl$_3$) δ 8.90 (s, 1H), 7.42-7.21 (m, 1H), 7.10 (dddd, J=26.8, 9.3, 6.6, 2.1 Hz, 1H), 3.35 (dd, J=49.0, 9.6 Hz, 1H), 3.01-2.77 (m, 1H); $^{19}$F NMR (376 MHz, CDCl$_3$) δ −129.47, −129.53, −130.16, −130.21, −132.59, −132.64, −133.35, −133.41; ESIMS m/z 345 ([M−H]$^-$).

The following compounds were prepared in like manner to the procedure outlined in Example 40:

cis/trans-2,2-Dichloro-3-(3,4-dichloro-5-fluorophenyl)cyclopropane-1-carboxylic acid (C18)

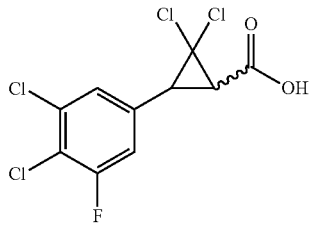 [SMILES: O=C(O)C1C(c2cc(F)c(Cl)c(Cl)c2)C1(Cl)Cl]

Isolated as a grey solid (0.459 g, 44%, approx. 3:1 trans/cis): $^1$H NMR (400 MHz, CDCl$_3$CDCl$_3$) δ 8.73 (s, 1H), 7.20 (d, J=1.7 Hz, 1H), 7.14-6.91 (m, 1H), 3.36 (dd, J=51.9, 9.6 Hz, 1H), 2.91 (dd, J=47.1, 9.6 Hz, 1H); $^{19}$F NMR (376 MHz, CDCl$_3$) δ −108.55, −109.27; ESIMS m/z 317 ([M−H]$^-$).

cis/trans-3-(3-Bromo-5-(pentafluoro-λ$^6$-sulfanyl)phenyl)-2,2-dichlorocyclopropane-1-carboxylic acid (C19)

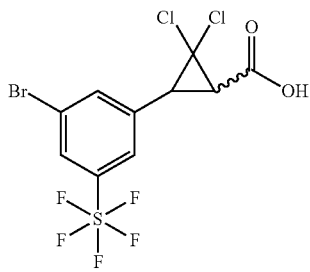

Isolated as a grey solid (0.260 g, 40%, approx. 2:1 trans/cis): $^1$H NMR (400 MHz, CDCl$_3$CDCl$_3$) δ 10.43 (s, 1H), 7.88 (dt, J=13.2, 1.9 Hz, 1H), 7.75-7.48 (m, 2H), 3.61-3.29 (m, 1H), 2.96 (dd, J=38.3, 9.6 Hz, 1H); ESIMS m/z 435 ([M−H]$^-$).

cis/trans-2,2-Dichloro-3-(3-chloro-2,4-difluorophenyl)cyclopropane-1-carboxylic acid (C20)

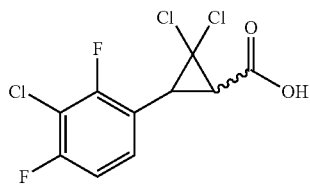 [SMILES: O=C(O)C1C(c2ccc(F)c(Cl)c2F)C1(Cl)Cl]

Isolated as a grey solid (0.656 g, 35%, approx. 1:1 trans/cis): $^1$H NMR (400 MHz, CDCl$_3$CDCl$_3$) δ 9.27 (s, 1H), 7.35 (q, J=7.5 Hz, 1H), 7.11-6.90 (m, 1H), 3.33 (dd, J=104.1, 9.5 Hz, 1H), 3.06-2.77 (m, 1H); $^{19}$F NMR (376 MHz, CDCl$_3$) δ −111.34, −111.35, −111.40, −111.41, −112.05, −112.06, −113.13, −113.14; ESIMS m/z 300 ([M−H]$^-$).

cis/trans-2,2-Dichloro-3-(3-chloro-2-fluoro-5-(trifluoromethyl)phenyl)cyclopropane-1-carboxylic acid (C21)

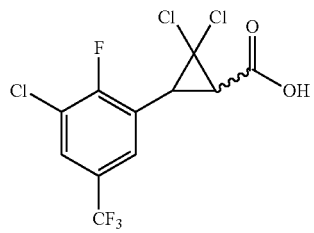 [SMILES: O=C(O)C1C(c2cc(C(F)(F)F)cc(Cl)c2F)C1(Cl)Cl]

Isolated as a grey solid (0.485 g, 31%, approx. 2:1 trans/cis): $^1$H NMR (400 MHz, CDCl$_3$CDCl$_3$) δ 9.02 (s, 1H), 7.87-7.61 (m, 1H), 7.39-7.23 (m, 1H), 3.60-3.19 (m, 1H), 3.14-2.85 (m, 1H); $^{19}$F NMR (376 MHz, CDCl$_3$) δ −62.32, −108.88, −110.51; ESIMS m/z 350 ([M−H]$^-$).

cis/trans-2,2-Dichloro-3-(4-fluoro-3-methyl-5-(trifluoromethyl)phenyl)cyclopropane-1-carboxylic acid (C22)

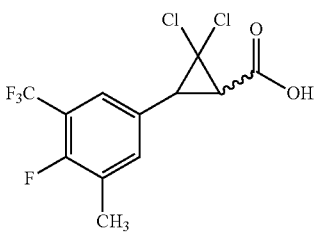 [SMILES: Cc1cc(C2C(C(=O)O)C2(Cl)Cl)cc(C(F)(F)F)c1F]

Isolated as a green oil (1.42 g, 66%, approx. 3:1 trans/cis): $^1$H NMR (400 MHz, CDCl$_3$CDCl$_3$) δ 7.33 (dd, J=21.3, 6.3 Hz, 2H), 6.82 (s, 1H), 3.38 (dd, J=50.6, 9.7 Hz, 1H), 3.04-2.82 (m, 1H), 2.34 (dd, J=10.0, 2.3 Hz, 3H); $^{19}$F NMR (376 MHz, CDCl$_3$) δ −61.53, −118.49, −119.16; ESIMS m/z 330 ([M−H]$^-$).

cis/trans-3-(3-Bromo-2,5-difluorophenyl)-2,2-dichlorocyclopropane-1-carboxylic acid (C23)

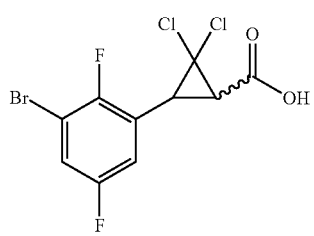 [SMILES: O=C(O)C1C(c2cc(F)cc(Br)c2F)C1(Cl)Cl]

Isolated as a grey solid (0.545 g, 51%, approx. 1:1 trans/cis): $^1$H NMR (400 MHz, CDCl$_3$CDCl$_3$) δ 9.97 (s, 1H), 7.29 (dtt, J=7.1, 4.4, 2.3 Hz, 1H), 7.00 (dddd, J=137.6, 8.2, 5.3, 3.5 Hz, 1H), 3.52-3.10 (m, 1H), 3.07-2.74 (m, 1H); $^{19}$F NMR (376 MHz, CDCl$_3$) δ −112.49, −112.53, −114.36, −114.40, −115.73, −115.77, −116.17, −116.21; ESIMS m/z 345 ([M−H]$^-$).

221 cis/trans-2,2-Dichloro-3-(3,4-dichloro-5-(trifluoromethyl)phenyl)cyclopropane-1-carboxylic acid (C24)

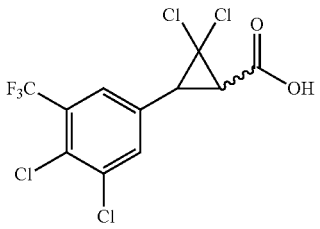 [SMILES: O=C(O)C1C(c2cc(Cl)c(Cl)c(C(F)(F)F)c2)C1(Cl)Cl]

Isolated as a tan solid (0.295 g, 25%, approx. 2:1 trans/cis): $^1$H NMR (400 MHz, CDCl$_3$CDCl$_3$) δ 7.71-7.45 (m, 2H), 6.48 (s, 1H), 3.38 (dd, J=62.2, 9.6 Hz, 1H), 2.95 (dd, J=41.0, 9.6 Hz, 1H); $^{19}$F NMR (376 MHz, CDCl$_3$) δ -63.01; ESIMS m/z 366 ([M-H]$^-$).

cis/trans-2,2-Dichloro-3-(4-chloro-3-fluoro-5-(trifluoromethyl)phenyl)cyclopropane-1-carboxylic acid (C25)

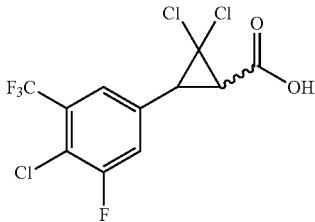 [SMILES: O=C(O)C1C(c2cc(F)c(Cl)c(C(F)(F)F)c2)C1(Cl)Cl]

Isolated as a grey solid (0.392 g, 33%, approx. 3:1 trans/cis): $^1$H NMR (400 MHz, CDCl$_3$CDCl$_3$) δ 9.56 (s, 1H), 7.55-7.36 (m, 1H), 7.28 (dd, J=8.8, 2.0 Hz, 1H), 3.41 (dd, J=59.6, 9.6 Hz, 1H), 2.95 (dd, J=46.2, 9.6 Hz, 1H); $^{19}$F NMR (376 MHz, CDCl$_3$) δ -62.50, -109.97, -110.78; ESIMS m/z 350 ([M-H]$^-$).

cis/trans-2,2-Dichloro-3-(3,5-dichloro-4-fluorophenyl)cyclopropane-1-carboxylic acid (C26)

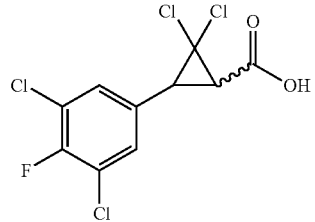 [SMILES: O=C(O)C1C(c2cc(Cl)c(F)c(Cl)c2)C1(Cl)Cl]

Isolated as a grey solid (0.889 g, 48%, approx. 2:1 trans/cis): $^1$H NMR (400 MHz, CDCl$_3$CDCl$_3$) δ 9.83 (s, 1H), 7.54-6.93 (m, 2H), 3.34 (dd, J=50.9, 9.6 Hz, 1H), 2.89 (dd, J=46.6, 9.6 Hz, 1H); $^{19}$F NMR (376 MHz, CDCl$_3$) δ -115.34, -115.98; ESIMS m/z 317 ([M-H]$^-$).

222 cis/trans-2,2-Dichloro-3-(3-chloro-5-(pentafluoro-λ$^6$-sulfanyl)phenyl)cyclopropane-1-carboxylic acid (C27)

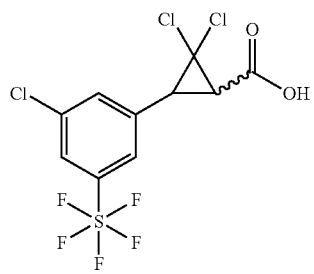 [SMILES: O=C(O)C1C(c2cc(Cl)cc(S(F)(F)(F)(F)F)c2)C1(Cl)Cl]

Isolated as a grey solid (0.412 g, 35%, approx. 3:1 trans/cis): $^1$H NMR (400 MHz, CDCl$_3$CDCl$_3$) δ 7.81-7.69 (m, 1H), 7.63-7.38 (m, 2H), 5.95 (s, 1H), 3.61-3.31 (m, 1H), 3.11-2.87 (m, 1H); ESIMS m/z 390 ([M-H]$^-$).

cis/trans-2,2-Dichloro-3-(perfluorophenyl)cyclopropane-1-carboxylic acid (C28)

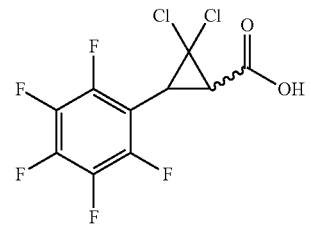 [SMILES: O=C(O)C1C(c2c(F)c(F)c(F)c(F)c2F)C1(Cl)Cl]

Isolated as a white solid (1.44 g, 67%): $^1$H NMR (400 MHz, CDCl$_3$) δ 10.19 (s, 1H), 3.30 (d, J=8.2 Hz, 1H), 3.09 (d, J=8.3 Hz, 1H); $^{19}$F NMR (376 MHz, CDCl$_3$) δ -140.52, -140.54, -140.58, -140.60, -152.14, -152.20, -152.25, -160.82, -160.84, -160.87, -160.89, -160.93, -160.95; ESIMS m/z 320 ([M-H]$^-$).

trans-3-(3-Bromo-4,5-dichlorophenyl)-2,2-dichlorocyclopropane-1-carboxylic acid (C29)

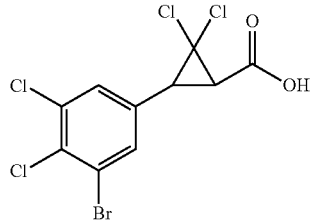 [SMILES: O=C(O)C1C(c2cc(Cl)c(Cl)c(Br)c2)C1(Cl)Cl]

Isolated as a white foam (1.3 g, 54%): $^1$H NMR (400 MHz, CDCl$_3$) δ 7.53 7.42 (m, 1H), 7.35 (d, J=2.0 Hz, 1H), 3.41 (d, J=8.3 Hz, 1H), 2.86 (d, J=8.2 Hz, 1H). ESIMS m/z 376 ([M-H]$^-$).

trans-3-(4-Bromo-3,5-dichlorophenyl)-2,2-dichloro-cyclopropane-1-carboxylic acid (C30)

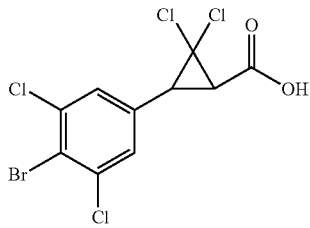

Isolated as a white foam (0.6 g, 29%): $^1$H NMR (400 MHz, CDCl$_3$) δ 7.29 (d, J=0.7 Hz, 2H), 3.39 (d, J=8.2 Hz, 1H), 2.87 (d, J=8.3 Hz, 1H), ESIMS m/z 376 ([M−H]$^−$).

Example 41: Preparation of trans-2,2-dichloro-3-(3-(pentafluoro-λ$^6$-sulfanyl)phenyl)cyclopropane-1-carboxylic acid (C31)

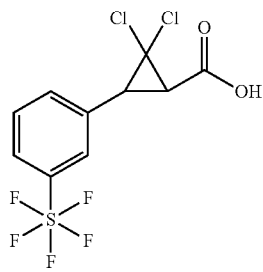

To a round-bottom flask equipped with a magnetic stir bar were added sodium periodate (37.0 g, 0.174 mol), and water (250 mL). Nitrogen was bubbled into the solution for 15 minutes. (3-((1R,3R)-2,2-Dichloro-3-(4-methoxyphenyl)cyclopropyl)phenyl)pentafluoro-λ$^6$-sulfane (C44) (3.7 g, 0.0109 mol) was dissolved in a mixture of ethyl acetate (30 mL)/acetonitrile (30 mL) and added to the flask followed by ruthenium chloride (0.150 g, 0.00067 mol). The mixture was stirred for 16 hours. The mixture was diluted with dichloromethane (250 mL), filtered through Celite®, and the solid filter cake was rinsed with dichloromethane. The filtrate was transferred to a separatory funnel. The organic layer was separated and the aqueous phase was extracted with dichloromethane (4×100 mL). The combined organic layers were dried over anhydrous sodium sulfate, and concentrated under reduced pressure. Purification by reverse-phase medium performance liquid chromatography (RP-MPLC) using 10-80% acetonitrile/water as eluent afforded the title compound as a (2.0 g, 51%): $^1$H NMR (400 MHz, CDCl$_3$) δ 7.76 (d, J=8.5 Hz, 1H), 7.65 (s, 1H), 7.51 (t, J=8.0 Hz, 1H), 7.44 (d, J=7.8 Hz, 1H), 3.55 (d, J=8.3 Hz, 1H), 2.93 (d, J=8.3 Hz, 1H); ESIMS m/z 358 ([M+H]$^+$).

The following compounds were prepared in like manner to the procedure outlined in Example 41:

trans-2,2-Dichloro-3-(4-(pentafluoro-λ$^6$-sulfanyl)phenyl)cyclopropane-1-carboxylic acid (C32)

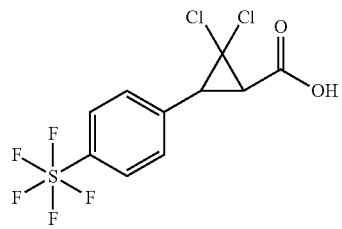 [SMILES: O=C(O)C1C(c2ccc(S(F)(F)(F)(F)F)cc2)C1(Cl)Cl]

Isolated as a white powder (2.2 g): $^1$H NMR (400 MHz, CDCl$_3$) δ 7.78 (d, J=8.7 Hz, 2H), 7.38 (d, J=8.4 Hz, 2H), 3.53 (d, J=8.3 Hz, 1H), 2.93 (d, J=8.3 Hz, 1H); ESIMS m/z 358 ([M+H]$^+$).

trans-2,2-Dichloro-3-(3-iodophenyl)cyclopropane-1-carboxylic acid (C33)

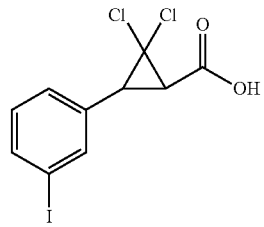 [SMILES: O=C(O)C1C(c2cccc(I)c2)C1(Cl)Cl]

Isolated as a white powder (0.700 g): $^1$H NMR (400 MHz, CDCl$_3$) δ 7.69 (d, J=7.9 Hz, 1H), 7.62 (s, 1H), 7.29-7.21 (m, 1H), 7.12 (t, J=7.8 Hz, 1H), 3.44 (d, J=8.3 Hz, 1H), 2.87 (d, J=8.3 Hz, 1H); ESIMS m/z 358 ([M+H]$^+$).

trans-2,2-Dichloro-3-(4-iodophenyl)cyclopropane-1-carboxylic acid (C34)

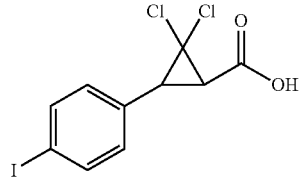 [SMILES: O=C(O)C1C(c2ccc(I)cc2)C1(Cl)Cl]

Isolated as a white powder (1.2 g): $^1$H NMR (400 MHz, CDCl$_3$) δ 7.72 (d, J=8.4 Hz, 2H), 7.01 (d, J=8.2 Hz, 2H), 3.43 (d, J=8.3 Hz, 1H), 2.85 (d, J=8.3 Hz, 1H); ESIMS m/z 358 ([M+H]$^+$).

trans-3-(3,5-Dichlorophenyl)-2,2-difluorocyclopropane-1-carboxylic acid (C35)

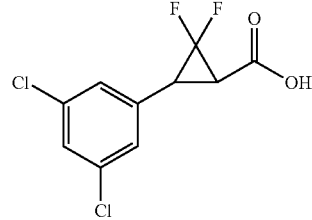 [SMILES: O=C(O)C1C(c2cc(Cl)cc(Cl)c2)C1(F)F]

Isolated as an off-white solid (0.640 g, 44%): mp 138-142° C.; $^1$H NMR (400 MHz, CDCl$_3$) δ 7.34 (t, J=1.9 Hz, 1H), 7.16 (d, J=1.8 Hz, 2H), 3.47 (ddd, J=11.9, 7.8, 4.1 Hz, 1H), 2.75 (ddd, J=11.1, 7.9, 1.7 Hz, 1H); $^{13}$C NMR (101

MHz, CDCl$_3$) δ 170.91, 135.50, 133.88, 128.56, 126.74, 109.91 (dd, J=295.1, 289.3 Hz), 32.62 (dd, J=11.3, 9.2 Hz), 32.07 (t, J=11.5 Hz); $^{19}$F NMR (376 MHz, CDCl$_3$) δ −132.28 (d, J=152.7 Hz), −132.84 (d, J=152.8 Hz); ESIMS m/z 267 ([M−H]$^-$).

Example 42: Preparation of trans-2,2-dichloro-3-(3,5-dichlorophenyl)cyclopropanecarboxylic acid (C36)

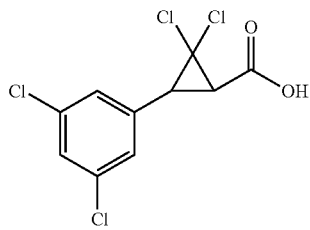 [SMILES: O=C(O)C1C(c2cc(Cl)cc(Cl)c2)C1(Cl)Cl]

Ruthenium(III) chloride (0.080 g, 0.39 mmol) was added to a stirred mixture of trans-1,3-dichloro-5-(-2,2-dichloro-3-(4-methoxyphenyl)cyclopropyl)benzene (C48) (2.8 g, 7.7 mmol) and sodium periodate (33 g, 160 mmol) in water:ethyl acetate:acetonitrile (8:1:1, 155 mL) at 23° C. The resulting biphasic brown mixture was vigorously stirred at 23° C. for 5 hours. The reaction mixture was diluted with water (1000 mL) and extracted with dichloromethane (4×200 mL). The combined organic layers were dried over magnesium sulfate, filtered, and concentrated. The residue was diluted with a sodium hydroxide solution (1 M, 100 mL) and washed with diethyl ether (4×50 mL). The aqueous layer was adjusted to pH 2, using concentrated hydrochloric acid, and extracted with dichloromethane (3×50 mL). The combined organic layers were dried over magnesium sulfate, filtered, and concentrated to afford the title product as a light brown powder (0.78 g, 34%): mp 117-120° C.; $^1$H NMR (400 MHz, DMSO-d$_6$) δ 13.38 (br s, 1H), 7.52-7.65 (m, 3H), 3.57 (d, J=8.5 Hz, 1H), 3.50 (d, J=8.5 Hz, 1H); IR (thin film) 3083 (s), 3011 (s), 1731 (s), 1590 (w), 1566 (s), 1448 (w), 1431 (m), 1416 (m) cm$^{-1}$.

The following compounds were prepared in like manner to the procedure outlined in Example 42:

trans-2,2-Dichloro-3-(3,4,5-trichlorophenyl)cyclopropanecarboxylic acid (C37)

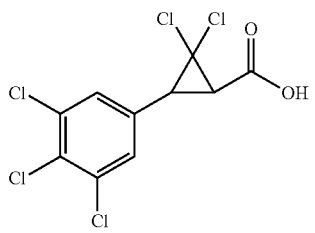 [SMILES: O=C(O)C1C(c2cc(Cl)c(Cl)c(Cl)c2)C1(Cl)Cl]

Isolated as a yellow powder (1.5 g, 39%): $^1$H NMR (400 MHz, CDCl$_3$) δ 7.31 (d, J=0.7 Hz, 2H), 3.40 (d, J=8.2 Hz, 1H), 2.86 (d, J=8.3 Hz, 1H); $^{13}$C NMR (101 MHz, CDCl$_3$) δ 171.05, 134.55, 132.44, 131.75, 128.89, 61.18, 39.26, 37.14; ESIMS m/z 333 ([M−H]$^-$).

trans-2,2-Dichloro-3-(3,4-dichlorophenyl)cyclopropanecarboxylic acid (C38)

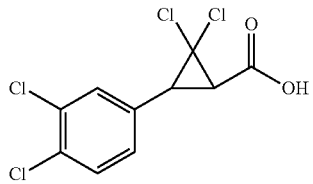 [SMILES: O=C(O)C1C(c2ccc(Cl)c(Cl)c2)C1(Cl)Cl]

Isolated as a pale yellow solid (3.2 g, 51%): $^1$H NMR (400 MHz, CDCl$_3$) δ 7.47 (d, J=8.3 Hz, 1H), 7.37 (d, J=1.6 Hz, 1H), 7.12 (ddd, J=8.3, 2.1, 0.6 Hz, 1H), 3.43 (d, J=8.3 Hz, 1H), 2.86 (d, J=8.3 Hz, 1H); $^{13}$C NMR (101 MHz, CDCl$_3$) δ 171.52, 132.91, 132.76, 132.29, 130.66, 130.62, 128.02, 61.48, 39.65, 37.13; ESIMS m/z 298 ([M−H]$^-$).

trans-2,2-Dichloro-3-(3-chloro-5-(trifluoromethyl)phenyl)cyclopropanecarboxylic acid (C39)

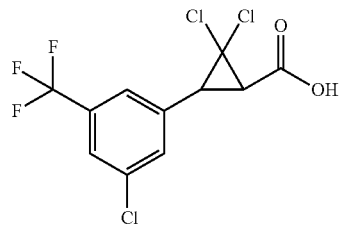 [SMILES: O=C(O)C1C(c2cc(Cl)cc(C(F)(F)F)c2)C1(Cl)Cl]

Isolated as an off-white solid (0.73 g, 28%): mp 113-115° C.; $^1$H NMR (400 MHz, DMSO-d$_6$) δ 13.39 (br s, 1H), 7.91 (s, 1H), 7.86 (s, 1H), 7.84 (s, 1H), 3.69-3.60 (m, 2H); ESIMS m/z 333 ([M−H]$^-$).

trans-2,2-Dichloro-3-(3-chloro-4-fluorophenyl)cyclopropanecarboxylic acid (C40)

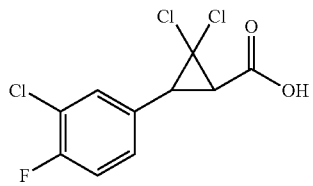

Isolated as an off-white solid (1.0 g, 53%): mp 121-123° C.; $^1$H NMR (400 MHz, DMSO-d$_6$) δ 13.35 (br s, 1H), 7.71 (dd, J=2.0, 7.2 Hz, 1H), 7.53-7.35 (m, 2H), 3.50-3.41 (m, 2H); ESIMS m/z 281 ([M−H]$^-$).

trans-2, 2-Dichloro-3-(3-chloro-5-(difluoromethyl)phenyl)cyclopropane-1-carboxylic acid (C41)

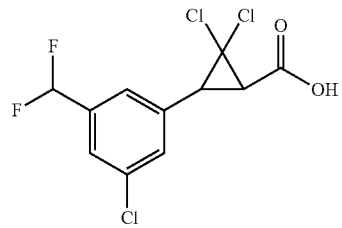

Isolated as an off-white solid (2.6 g, 63%); $^1$H NMR (300 MHz, CDCl$_3$) missing COOH signal δ 7.49 (s, 1H), 7.38 (s, 1H), 7.30 (s, 1H), 6.63 (t, J=56.0 Hz, 1H), 3.50 (d, J=8.4 Hz, 1H), 2.91 (d, J=8.0 Hz, 1H); $^{19}$F NMR (282.2 MHz, CDCl$_3$) δ −112.04; ESIMS m/z 313 ([M−H]$^-$).

trans-2,2-Dichloro-3-(4-chloro-3-(difluoromethyl)phenyl)cyclopropane-1-carboxylic acid (C42)

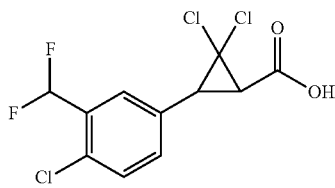

Isolated as an off-white solid (6.2 g, 69%): $^1$H NMR (400 MHz, CDCl$_3$) δ 10.5 (br s, 1H), 7.55 (s, 1H), 7.46 (d, J=8.0 Hz, 1H), 7.34 (d, J=8.4 Hz, 1H), 6.95 (t, J=54.8 Hz, 1H), 3.50 (d, J=8.4 Hz, 1H), 2.91 (d, J=8.4 Hz, 1H); $^{19}$F NMR (376.2 MHz, CDCl$_3$) δ −115.52; ESIMS m/z 313 ([M−H]$^-$).

trans-2,2-Dichloro-3-(3-(difluoromethyl)-4-fluorophenyl)cyclopropane-1-carboxylic acid (C43)

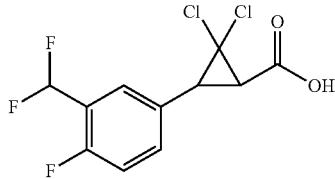

Isolated as an off-white solid (6.0 g, 77%): $^1$H NMR (400 MHz, CDCl$_3$) missing COOH signal δ 7.49 (d, J=6.0 Hz, 1H), 7.40 (br s, 1H), 7.17 (t, J=9.2 Hz, 1H), 6.90 (t, J=54.8 Hz, 1H), 3.49 (d, J=8.0 Hz, 1H), 2.89 (d, J=8.4 Hz, 1H); $^{19}$F NMR (376.2 MHz, CDCl$_3$) δ −114.47, −119.69; ESIMS m/z 297 ([M−H]$^-$).

Example 43: Preparation of trans-(3-(2,2-dichloro-3-(4-methoxyphenyl)cyclopropyl)phenyl)pentafluoro-λ$^6$-sulfane (C44)

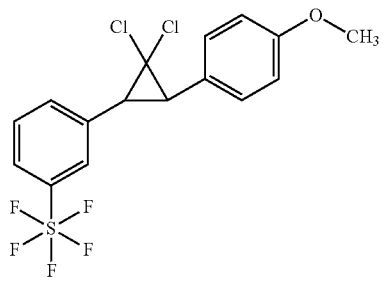 [SMILES: COc1ccc(C2C(c3cccc(S(F)(F)(F)(F)F)c3)C2(Cl)Cl)cc1]

To a round-bottom flask equipped with a magnetic stir bar were added (E)-pentafluoro(3-(4-methoxystyryl)phenyl)-λ$^6$-sulfane (C57) (4.13 g, 0.0123 mol) and benzyl triethylammonium chloride (0.6 g, 0.00264 mol). Chloroform (150 mL) was added followed by an ice-cold aqueous solution of sodium hydroxide (20 g, 0.5 mol) dissolved in water (34 mL). The biphasic mixture was stirred at 40° C. 16 hours. The reaction mixture was cooled to 23° C., water (100 mL) was added, and the reaction mixture was transferred to a separatory funnel. The organic layer was separated and the aqueous phase was extracted with chloroform (2×50 mL). The combined organic layers were washed with brine (50 mL), dried over anhydrous sodium sulfate and concentrated under reduced pressure. Purification by flash chromatography using 0-15% ethyl acetate/hexane as eluent gave the title compound as a (3.8 g, 75%): $^1$H NMR (400 MHz, CDCl$_3$) δ 7.75 (m, 2H), 7.58-7.46 (m, 2H), 7.30 (d, J=8.6 Hz, 2H), 6.95 (d, J=8.7 Hz, 2H), 3.84 (s, 3H), 3.20 (s, 2H); ESIMS m/z 419 ([M+H]$^+$).

The following compounds were prepared in like manner to the procedure outlined in Example 43:

trans-(4-(2,2-Dichloro-3-(4-methoxyphenyl)cyclopropyl)phenyl pentafluoro-λ$^6$-sulfane (C45)

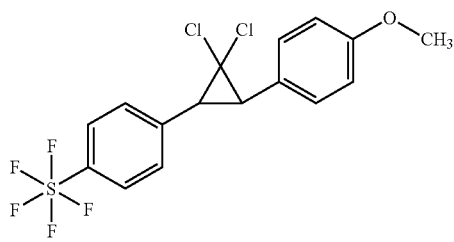

Isolated as a white powder (4.0 g): $^1$H NMR (400 MHz, CDCl$_3$) δ 7.75 (d, J=8.8 Hz, 2H), 7.44 (d, J=8.4 Hz, 2H), 7.30-7.23 (m, 2H), 6.91 (d, J=8.7 Hz, 2H), 3.81 (s, 3H), 3.21-3.08 (m, 2H); ESIMS m/z 419 ([M+H]$^+$).

trans-1-(2,2-Dichloro-3-(4-methoxyphenyl)cyclopropyl)-3-iodobenzene (C46)

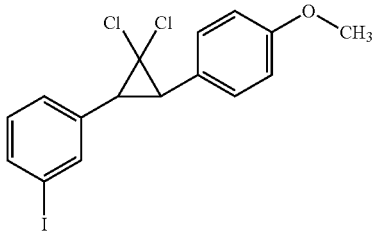 [SMILES: COc1ccc(C2C(c3cccc(I)c3)C2(Cl)Cl)cc1]

Isolated as a white powder (5.7 g): $^1$H NMR (400 MHz, CDCl$_3$) δ 7.73 (s, 1H), 7.68 (d, J=7.9 Hz, 1H), 7.35 (d, J=7.7 Hz, 1H), 7.31-7.25 (m, 2H), 7.13 (t, J=7.8 Hz, 1H), 6.94 (d, J=8.7 Hz, 2H), 3.84 (s, 3H), 3.13 (m, 2H); ESIMS m/z 419 ([M+H]$^+$).

trans-1-(2,2-Dichloro-3-(4-iodophenyl)cyclopropyl)-4-methoxybenzene (C47)

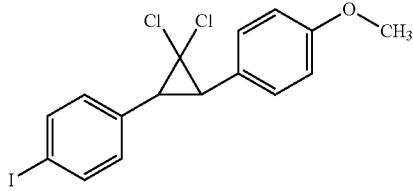 [SMILES: COc1ccc(C2C(c3ccc(I)cc3)C2(Cl)Cl)cc1]

Isolated as a white powder (4.0 g): $^1$H NMR (400 MHz, CDCl$_3$) δ 7.72 (d, J=8.4 Hz, 2H), 7.29 (m, 2H), 7.12 (d, J=8.1 Hz, 2H), 6.93 (d, J=8.8 Hz, 2H), 3.83 (s, 3H), 3.11 (m, 2H); ESIMS m/z 419 ([M+H]$^+$).

Example 44: Preparation of trans-1,3-dichloro-5-(2,2-dichloro-3-(4-methoxyphenyl)cyclopropyl)benzene (C48)

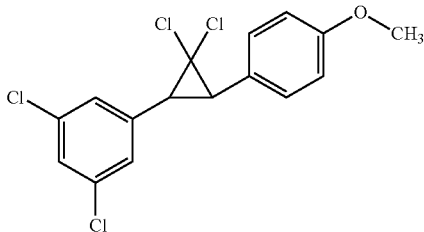 [SMILES: COc1ccc(C2C(c3cc(Cl)cc(Cl)c3)C2(Cl)Cl)cc1]

Aqueous sodium hydroxide (50%, 6.8 mL, 130 mmol) was added to a stirred solution of (E)-1,3-dichloro-5-(4-methoxystyryl)benzene (C61) (2.4 g, 8.6 mmol) and N-benzyl-N,N-diethylethanaminium chloride (0.20 g, 0.86 mmol) in chloroform (14 mL, 170 mmol) at 23° C. The resulting biphasic, dark brown mixture was vigorously stirred at 23° C. for 24 hours. The reaction mixture was diluted with water (200 mL) and extracted with dichloromethane (2×100 mL). The combined organic layers were dried over magnesium sulfate, filtered, and concentrated to afford the title product as a brown oil (2.8 g, 90%): $^1$H NMR (400 MHz, CDCl$_3$) δ 7.34 (t, J=1.8 Hz, 1H), 7.21-7.30 (m, 4H), 6.93 (m, 2H), 3.83 (s, 3H), 3.14 (d, J=8.5 Hz, 1H), 3.08 (d, J=8.5 Hz, 1H); IR (thin film) 3075 (w), 2934 (w), 2836 (w), 1724 (w), 1640 (w), 1609 (m), 1584 (m), 1568 (s), 1513 (s) cm$^{-1}$.

The following compounds were prepared in like manner to the procedure outlined in Example 44:

trans-1,2,3-Trichloro-5-(2,2-dichloro-3-(4-methoxyphenyl)cyclopropyl)benzene (C49)

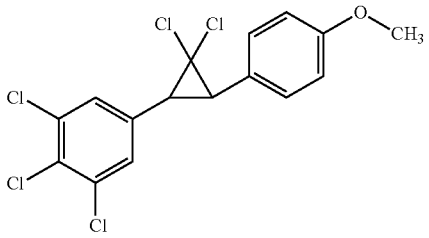 [SMILES: COc1ccc(C2C(c3cc(Cl)c(Cl)c(Cl)c3)C2(Cl)Cl)cc1]

Isolated as a dark foam (4.7 g, 100%): $^1$H NMR (400 MHz, CDCl$_3$) δ 7.40 (d, J=0.6 Hz, 2H), 7.29-7.22 (m, 2H), 6.96-6.89 (m, 2H), 3.83 (s, 3H), 3.12 (d, J=8.8 Hz, 1H), 3.06 (d, J=8.7 Hz, 1H); $^{13}$C NMR (101 MHz, CDCl$_3$) δ 159.46, 135.08, 134.23, 130.91, 129.85, 129.16, 125.42, 114.02, 64.67, 55.32, 39.62, 38.48.

trans-1,2-Dichloro-4-(2,2-dichloro-3-(4-methoxyphenyl)cyclopropyl)benzene (C50)

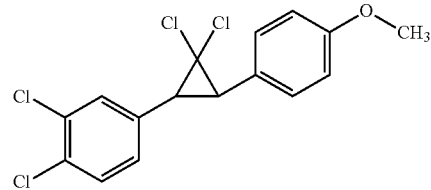

Isolated as an orange-red oil (7.6 g, 99%); $^1$H NMR (400 MHz, CDCl$_3$) δ 7.47 (d, J=4.9 Hz, 1H), 7.45 (bs, 1H), 7.30-7.23 (m, 2H), 7.21 (dd, J=8.2, 1.9 Hz, 1H), 6.96-6.90 (m, 2H), 3.83 (s, 3H), 3.11 (app. q, J=8.8 Hz, 2H); $^{13}$C NMR (101 MHz, CDCl$_3$) δ 159.39, 134.90, 132.62, 131.99, 130.90, 130.40, 129.90, 128.33, 125.81, 113.98, 64.94, 55.33, 39.52, 38.75.

trans-1-Chloro-3-(2,2-dichloro-3-(4-methoxyphenyl)cyclopropyl)-5-(difluoromethyl)benzene (C51)

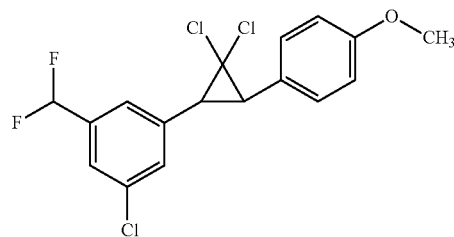 [SMILES: COc1ccc(C2C(c3cc(Cl)cc(C(F)F)c3)C2(Cl)Cl)cc1]

Isolated as a yellow liquid (11.5 g, 69%): $^1$H NMR (300 MHz, CDCl$_3$): δ 7.47 (s, 2H), 7.39 (s, 1H), 7.28 (d, J=8.7 Hz, 2H), 6.93 (d, J=8.7 Hz, 2H), 6.64 (t, J=56.1 Hz, 1H), 3.83 (s, 3H), 3.16 (q, J=8.7 Hz, 2H).

trans-1-Chloro-4-(2,2-dichloro-3-(4-methoxyphenyl)cyclopropyl)-2-(difluoromethyl) benzene (C52)

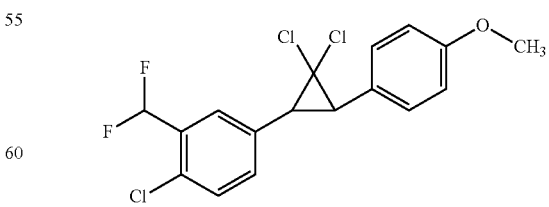

Isolated as a pale yellow solid (10.7 g, 83%): $^1$H NMR (400 MHz, CDCl$_3$) δ 7.65 (s, 1H), 7.46-7.41 (m, 2H), 7.28 (d, J=8.4 Hz, 2H), 7.10-6.83 (m, 3H), 3.83 (s, 3H), 3.18-3.13 (m, 2H).

trans-4-(2,2-Dichloro-3-(4-methoxyphenyl)cyclopropyl)-2-(difluoromethyl)-1-fluorobenzene (C53)

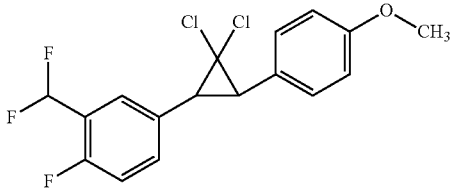 [SMILES: COc1ccc(C2C(c3ccc(F)c(C(F)F)c3)C2(Cl)Cl)cc1]

Isolated as an off-white solid (10.0 g, 55%): ESIMS m/z 374 ([M+H]$^+$).

trans-1-Chloro-3-(2,2-dichloro-3-(4-methoxyphenyl)cyclopropyl)-5-(trifluoromethyl)benzene (C54)

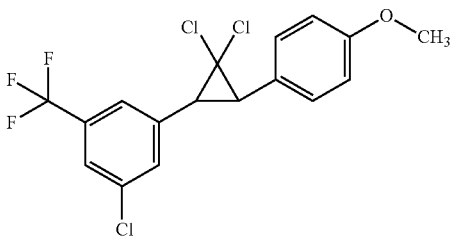 [SMILES: COc1ccc(C2C(c3cc(Cl)cc(C(F)(F)F)c3)C2(Cl)Cl)cc1]

Isolated as a brown solid (4.0 g, 74%): $^1$H NMR (300 MHz, CDCl$_3$) δ 7.64 (s, 1H), 7.45 (s, 1H), 7.42 (s, 1H), 7.26 (d, J=9.0 Hz, 2H), 6.93 (d, J=9.0 Hz, 1H), 3.83 (s, 3H), 3.15-3.05 (m, 2H); ESIMS m/z 395 ([M+H]$^+$).

trans-2-Chloro-4-(2,2-dichloro-3-(4-methoxyphenyl)cyclopropyl)-1-fluorobenzene (C55)

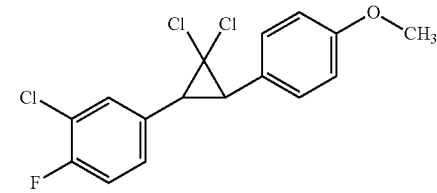 [SMILES: COc1ccc(C2C(c3ccc(F)c(Cl)c3)C2(Cl)Cl)cc1]

Isolated as a brown liquid (2.0 g, 58%): ESIMS m/z 345 ([M+H]$^+$).

Example 45: Preparation of trans-1,3-dichloro-5-(2,2-difluoro-3-(4-methoxyphenyl)cyclopropyl)benzene (C56)

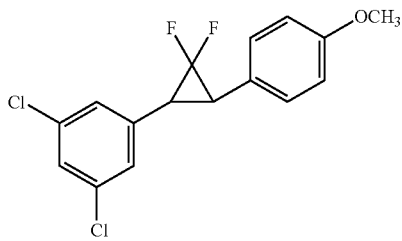 [SMILES: COc1ccc(C2C(c3cc(Cl)cc(Cl)c3)C2(F)F)cc1]

(E)-1,3-Dichloro-5-(4-methoxystyryl)benzene (C61) (1.5 g, 5.4 mmol) was dissolved in tetrahydrofuran (10 mL) in a 25 mL microwave vial. Trimethyl(trifluoromethyl)silane (3.8 g, 26.9 mmol) and sodium iodide (0.81 g, 5.4 mmol) were added and the capped vial was heated in the microwave at 85° C. for 1 hour. The vial was vented with a needle and analysis of an aliquot by $^1$H NMR spectroscopy indicated approximately 20% conversion. Additional trimethyl(trifluoromethyl)silane (7.2 g, 54 mmol) and sodium iodide (0.56 g, 3.8 mmol) were added, and the mixture was heated in the microwave at 110° C. for 8 hours. Further analysis of an aliquot by $^1$H NMR spectroscopy indicated complete conversion with some decomposition. The reaction mixture was partitioned between ethyl acetate and saturated sodium chloride solution, the layers were separated, and the organic phase was dried over sodium sulfate. Filtration and concentration gave the product as a brown oil (1.8 g, 100%): $^1$H NMR (400 MHz, CDCl$_3$) δ 7.30 (t, J=1.9 Hz, 1H), 7.25-7.19 (m, 4H), 6.93-6.88 (m, 2H), 3.82 (s, 3H), 2.97 (q, J=7.8 Hz, 1H), 2.88 (q, J=7.6 Hz, 1H); $^{19}$F NMR (376 MHz, CDCl$_3$) δ −133.89; EIMS m/z 329.

Example 46: Preparation of (E)-pentafluoro(3-(4-methoxystyryl)phenyl)-λ$^6$-sulfane (C57)

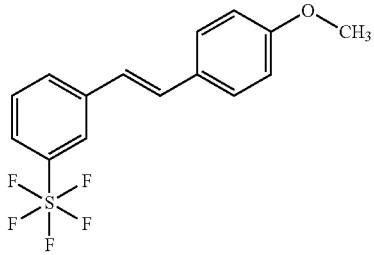 [SMILES: COc1ccc(/C=C/c2cccc(S(F)(F)(F)(F)F)c2)cc1]

A flame-dried round-bottom flask equipped with a magnetic stir bar was purged with nitrogen. Potassium tert-butoxide (0.55 g, 0.0049 mol), 18-crown-6 (0.2 g, 0.00076 mol) and tetrahydrofuran (20 mL) were added. The suspension was cooled to 5° C. 3-(Pentafluorothio) benzaldehyde (0.8, 0.00345 mol) and diethyl (4-methoxybenzyl)phosphonate (1.16 g, 0.00449 mol) were dissolved in tetrahydrofuran (4 mL) and added to the above suspension over 15 minutes. The internal temperature did not exceed 8° C. during the addition. The reaction mixture was warmed to 23° C. over 30 minutes and then heated at 50° C. for 4 hours. The reaction was concentrated under reduced pressure. Water (100 mL) and methyl tort-butyl ether (MTBE; 100 mL) were added. The organic layer was separated and the aqueous phase was extracted with MTBE (2×75 mL). The combined organic layers were washed with brine (75 mL), dried over anhydrous sodium sulfate, and concentrated under reduced pressure. Purification by flash chromatography using 0-15% ethyl acetate/hexane as eluent provided the title compound as an off-white solid (0.85 g, 73%): $^1$H NMR (400 MHz, CDCl$_3$) δ 7.84 (s, 1H), 7.64-7.56 (m, 2H), 7.47 (d, J=8.7 Hz, 2H), 7.42 (t, J=8.0 Hz, 1H), 7.11 (d, J=16.3 Hz, 1H), 7.02-6.86 (m, 3H), 3.84 (s, 3H); ESIMS m/z 337 ([M+H]$^+$).

The following compounds were prepared in like manner to the procedure outlined in Example 46:

(E)-Pentafluoro(4-(4-methoxystyryl)phenyl)-$\lambda^6$-sulfane (C58)

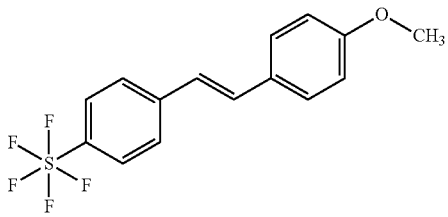 [SMILES: COc1ccc(/C=C/c2ccc(S(F)(F)(F)(F)F)cc2)cc1]

Isolated as a white powder (3.7 g 70%): $^1$H NMR (400 MHz, CDCl$_3$) δ 7.71 (d, J=8.8 Hz, 2H), 7.53 (d, J=8.5 Hz, 2H), 7.48 (d, J=8.7 Hz, 2H), 7.14 (d, J=16.3 Hz, 1H), 7.01-6.87 (m, 3H), 3.85 (s, 3H); ESIMS m/z 337 ([M+H]$^+$).

(E)-1-Iodo-3-(4-methoxystyryl)benzene (C59)

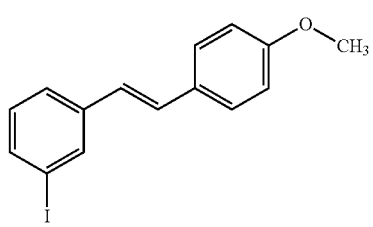 [SMILES: COc1ccc(/C=C/c2cccc(I)c2)cc1]

Isolated as a white powder (5.3 g 91%): $^1$H NMR (400 MHz, CDCl$_3$) δ 7.85 (s, 1H), 7.55 (d, J=7.8 Hz, 1H), 7.45-7.41 (m, 3H), 7.09-7.02 (m, 2H), 6.91 (d, J=8.8 Hz, 2H), 6.85 (d, J=16.3 Hz, 1H), 3.84 (s, 3H); ESIMS m/z 337 ([M+H]$^+$).

(E)-1-Iodo-4-(4-methoxystyryl)benzene (C60)

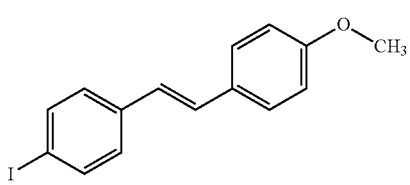 [SMILES: COc1ccc(/C=C/c2ccc(I)cc2)cc1]

Isolated as a white powder (3.3 g 94%): $^1$H NMR (400 MHz, CDCl$_3$) δ 7.66 (d, J=8.4 Hz, 2H), 7.44 (d, J=8.7 Hz, 2H), 7.22 (d, J=8.4 Hz, 2H), 7.06 (d, J=16.3 Hz, 1H), 6.94-6.83 (m, 3H), 3.83 (s, 3H); ESIMS m/z 337 ([M+H]$^+$).

Example 47: Preparation of (E)-1,3-dichloro-5-(4-methoxystyryl)benzene (C61)

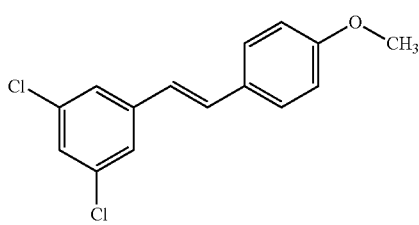 [SMILES: COc1ccc(/C=C/c2cc(Cl)cc(Cl)c2)cc1]

Sodium methoxide powder (98%, 0.63 g, 11 mmol) was added to a stirred solution of 3,5-dichlorobenzaldehyde (2.0 g, 11 mmol) and diethyl 4-methoxybenzylphosphonate (2.0 mL, 11 mmol) in dry N,N-dimethylformamide (38 mL) at 23° C. The resulting heterogeneous dark blue mixture was heated to 80° C., resulting in a dark brown mixture, and stirred for 24 hours. The cooled reaction mixture was diluted with water (500 mL) and extracted with diethyl ether (3×100 mL). The combined organic layers were diluted with hexane (150 mL) and washed with water (300 mL). The organic layer was dried over magnesium sulfate, filtered, and concentrated to afford the title product as a light brown oil (2.4 g, 75%): $^1$H NMR (400 MHz, CDCl$_3$) δ 7.44 (m, 2H), 7.34 (d, J=2 Hz, 2H), 7.20 (t, J=2 Hz, 1H), 7.06 (d, J=16.5 Hz, 1H), 6.91 (m, 2H), 6.82 (d, J=16.5 Hz, 1H), 3.84 (s, 3H); IR (thin film) 2934 (w), 2835 (w), 1724 (w), 1637 (w), 1605 (m), 1581 (m), 1558 (m), 1511 (s) cm$^{-1}$.

The following compounds were prepared in like manner to the procedure outlined in Example 47:

(E)-1,2,3-Trichloro-5-(4-methoxystyryl)benzene (C62)

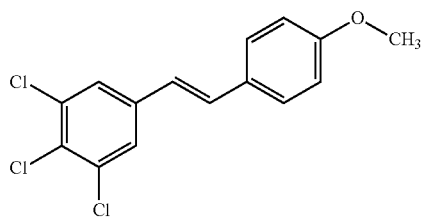 [SMILES: COc1ccc(/C=C/c2cc(Cl)c(Cl)c(Cl)c2)cc1]

Isolated as an off-white solid (3.7 g, 31%): $^1$H NMR (400 MHz, CDCl$_3$) δ 7.49-7.46 (m, 2H), 7.47-7.39 (m, 2H), 7.04 (d, J=16.3 Hz, 1H), 6.93-6.89 (m, 2H), 6.78 (d, J=16.3 Hz, 1H), 3.84 (s, 3H); $^{13}$C NMR (101 MHz, CDCl$_3$) δ 159.46, 135.08, 134.23, 130.91, 129.85, 129.16, 125.42, 114.02, 64.67, 55.32, 39.62, 38.48; EMS m/z 313 ([M]$^+$).

(E)-1,2-Dichloro-4-(4-methoxystyryl)benzene (C63)

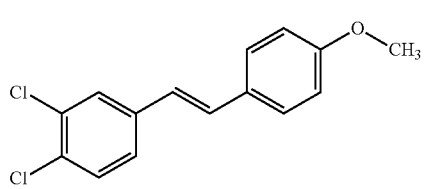 [SMILES: COc1ccc(/C=C/c2ccc(Cl)c(Cl)c2)cc1]

Isolated as an off-white solid (6.0 g, 53%): mp 91-94° C.; $^1$H NMR (400 MHz, CDCl$_3$) δ 7.56 (d, J=2.0 Hz, 1H), 7.46-7.42 (m, 2H), 7.39 (d, J=8.4 Hz, 1H), 7.29 (dd, J=8.4, 2.1 Hz, 1H), 7.04 (d, J=16.2 Hz, 1H), 6.93-6.88 (m, 2H), 6.85 (d, J=16.3 Hz, 1H), 3.84 (s, 3H); $^{13}$C NMR (101 MHz, CDCl$_3$) δ 159.75, 137.86, 132.72, 130.58, 130.49, 130.12, 129.33, 127.96, 127.77, 125.37, 123.98, 114.24, 55.35; EIMS m/z 279 ([M]$^+$).

(E)-1-Chloro-3-(4-methoxystyryl)-5-(trifluoromethyl)benzene (C64)

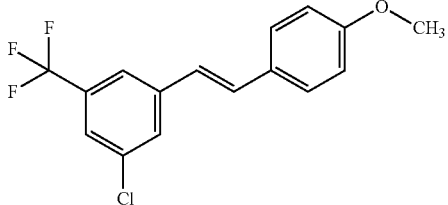 [SMILES: COc1ccc(/C=C/c2cc(Cl)cc(C(F)(F)F)c2)cc1]

Isolated as an off-white solid (4.3 g, 58%): $^1$H NMR (300 MHz, CDCl$_3$) δ 7.62 (s, 1H), 7.58 (s, 1H), 7.48-7.42 (m, 3H), 7.12 (d, J=16.2 Hz, 1H), 6.95-6.85 (m, 3H), 3.84 (s, 3H); ESIMS m/z 313 ([M+H]$^+$).

(E)-2-Bromo-1,3-dichloro-5-(4-methoxystyryl)benzene (C65)

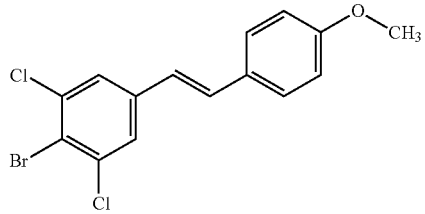 [SMILES: COc1ccc(/C=C/c2cc(Cl)c(Br)c(Cl)c2)cc1]

Isolated as an off-white solid (2.8 g, 40%): $^1$H NMR (300 MHz, CDCl$_3$) δ 7.46 (s, 2H), 7.43 (d, J=9.0 Hz, 2H), 7.07 (d, J=13.5 Hz, 1H), 6.90 (d, J=9.0 Hz, 1H), 6.73 (d, J=13.5 Hz, 1H), 3.84 (s, 3H); ESIMS m/z 358 ([M+H]$^+$).

(E)-2-Chloro-1-fluoro-4-(4-methoxystyryl)benzene (C66)

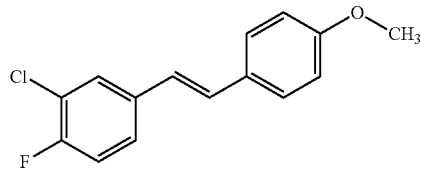

Isolated as an off-white solid (6.0 g, 72%): ESIMS m/z 263 ([M+H]$^+$).

Example 48: Preparation of (E)-1,3-dichloro-2-fluoro-5-(4-methoxystyryl)benzene (C67)

A stirred mixture of 5-bromo-1,3-dichloro-2-fluorobenzene (2.00 g, 8.20 mmol), 1-methoxy-4-vinylbenzene (1.32 g, 9.80 mmol), and triethylamine (20 mL) under argon was degassed for 5 minutes. Palladium(II) acetate (0.0368 g, 0.164 mmol) and 1,1'-bis(diphenylphosphino)ferrocene (0.181 g, 0.328 mmol) were added and the reaction was heated to 90° C. for 16 hours. The reaction mixture was poured into water and extracted with ethyl acetate. The combined organic layers were dried over sodium sulfate, filtered, and concentrated. Purification by flash column chromatography provided the title compound as an off-white solid (1.60 g, 67%): $^1$H NMR (300 MHz, CDCl$_3$) δ 7.41 (d, J=8.8 Hz, 2H), 7.31 (s, 1H), 7.37 (s, 1H), 6.96 (d, J=16.0 Hz, 1H), 6.89 (d, J=8.8 Hz, 2H), 6.76 (d, J=16.0 Hz, 1H), 3.84 (s, 3H); ESIMS m/z 297 ([M+H]$^+$).

Example 49: Preparation of (E)-3-chloro-5-(4-methoxystyryl) benzaldehyde (C68)

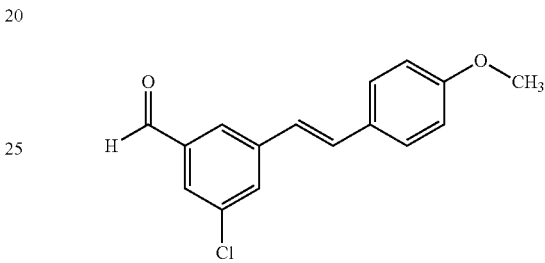

To a stirred solution of 3-bromo-5-chlorobenzaldehyde (20.0 g, 91.32 mmol) in dimethylacetamide, 1-methoxy-4-vinylbenzene (18.3 g, 136.9 mmol) and triethylamine (50 mL, 273.96 mmol) were added, and the reaction mixture was degassed with argon for 5 minutes. Palladium(II) acetate (410 mg, 1.83 mmol) and tri-o-tolylphosphine (1.11 g, 3.65 mmol) were added, and the resulting reaction mixture was heated to 100° C. for 16 hours. The reaction mixture was poured into water and extracted with ethyl acetate. The combined organic layer was dried over sodium sulfate and concentrated under reduced pressure. The resulting crude material was purified by flash column chromatography using 5-10% ethyl acetate in petroleum ether as the eluent to afford the title compound as a yellow solid (13.5 g, 54%); $^1$H NMR (300 MHz, CDCl$_3$) δ 9.99 (s, 1H), 7.85 (s, 1H), 7.69 (s, 2H), 7.47 (d, J=8.4 Hz, 2H), 7.16 (d, J=16.2 Hz, 1H), 6.94 (t, J=8.4 Hz, 3H), 3.84 (s, 3H); ESIMS m/z 273 ([M+H]$^+$).

The following compounds were prepared in like manner to the procedure outlined in Example 49:

(E)-2-Chloro-5-(4-methoxystyryl)benzaldehyde (C69)

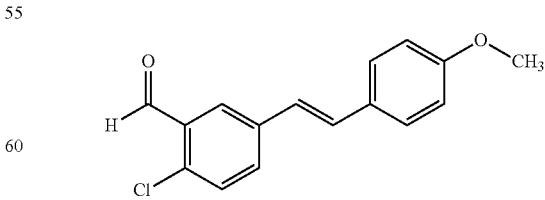

Isolated as a pale yellow solid (11.8 g, 27%): $^1$H NMR (300 MHz, CDCl$_3$) δ 10.45 (s, 1H), 8.02 (s, 1H), 7.62 (d, J=6.4 Hz, 1H), 7.46-7.40 (m, 3H), 7.12 (d, J=16.4 Hz, 1H), 6.95-6.90 (m, 3H), 3.95 (s, 3H); ESIMS m/z 273 ([M+H]$^+$).

(E)-2-Fluoro-5-(4-methoxystyryl)benzaldehyde (C70)

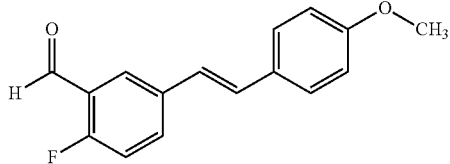

Isolated as an off-white solid (0.25 g, 20%): $^1$H NMR (400 MHz, CDCl$_3$) δ 10.43 (s, 1H), 7.90 (d, J=8.4 Hz, 1H), 7.54-7.46 (m, 4H), 7.20 (d, J=16.0 Hz, 1H), 6.94-6.90 (m, 3H), 3.85 (s, 3H); ESIMS m/z 274 ([M+H]$^+$).

Example 50: Preparation of (E)-1-chloro-3-(difluoromethyl)-5-(4-methoxy-styryl)benzene (C71)

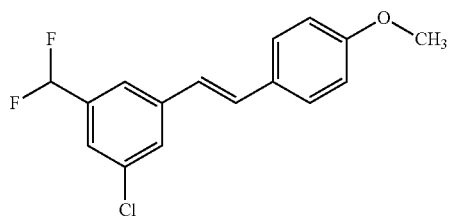 [SMILES: COc1ccc(/C=C/c2cc(Cl)cc(C(F)F)c2)cc1]

To a stirred solution of (E)-3-chloro-5-(4-methoxystyryl)benzaldehyde (C68) (13 g, 47.79 mmol) in dichloromethane (130 mL) was added diethylaminosulfur trifluoride (31.5 mL, 238.97 mmol) at −78° C. The resulting solution was stirred for 20 hours at room temperature. The reaction mixture was cooled to 0° C., and a solution of saturated aqueous sodium bicarbonate was added dropwise. The layers were separated and the aqueous layer was extracted with dichloromethane (3×75 mL). The combined organic layer was washed with water and brine, dried over sodium sulfate, and concentrated. The crude material was purified by flash column chromatography using 10-20% ethyl acetate in hexanes as the eluent to afford the title compound as a pale yellow oil (13.1 g, 94%): $^1$H NMR (400 MHz, CDCl$_3$) δ 7.55 (s, 1H), 7.45 (d, J=8.8 Hz, 3H), 7.34 (s, 1H), 7.10 (d, J=16 Hz, 1H), 6.90 (t, J=8.4 Hz, 3H), 6.61 (t, J=56.4 Hz, 1H), 3.80 (s, 3H); $^{19}$F NMR (376 MHz, CDCl$_3$) δ −111.72.

The following compounds were prepared in like manner to the procedure outlined in Example 50:

(E)-1-Chloro-2-(difluoromethyl)-4-(4-methoxystyryl)benzene (C72)

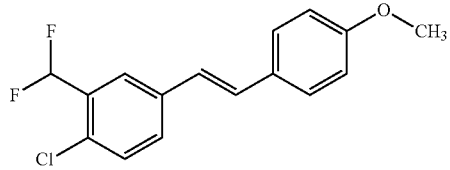 [SMILES: COc1ccc(/C=C/c2ccc(Cl)c(C(F)F)c2)cc1]

Isolated as an off-white solid (12 g, 94%): $^1$H NMR (300 MHz, CDCl$_3$) δ 7.75 (s, 1H), 7.51-7.44 (m, 3H), 7.37 (d, J=8.4 Hz, 1H), 7.13 (d, J=6.6 Hz, 1H), 7.06 (s, 1H), 6.95-6.89 (m, 3H), 3.95 (s, 3H); $^{19}$F NMR (282 MHz, CDCl$_3$) δ −115.31; ESIMS m/z 295 ([M+H]$^+$).

(E)-2-(Difluoromethyl)-1-fluoro-4-(4-methoxystyryl)benzene (C73)

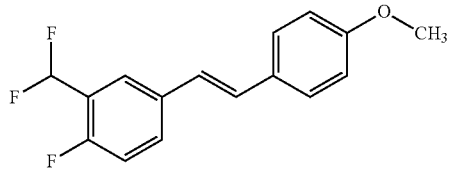

Isolated as an off-white solid (14.0 g, 70%): $^1$H NMR (300 MHz, CDCl$_3$) δ 7.69 (d, J=9.0 Hz, 1H), 7.57-7.53 (m, 1H), 7.45 (d, J=9.9 Hz, 2H), 7.13-7.06 (m, 2H), 7.00-6.89 (m, 4H), 3.85 (s, 3H); ESIMS m/z 279 ([M+H]$^+$).

Example 51: Preparation of trans-2,2-dichloro-3-(3,5-dichlorophenyl)cyclopropane carboxylic acid (C36)

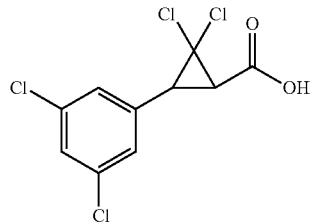 [SMILES: O=C(O)C1C(c2cc(Cl)cc(Cl)c2)C1(Cl)Cl]

Sodium permanganate (40% aqueous) (84 g, 236 mmol) was added dropwise to a stirred mixture of trans-2,2-dichloro-3-(3,5-dichlorophenyl)cyclopropane-1-carbaldehyde (C79) (58.7 g, 196 mmol) in acetone (982 mL) at 15° C. The resulting mixture was stirred at 20° C. for 2 hours. The reaction mixture was diluted with isopropyl alcohol (20 mL) and concentrated to remove the acetone. Celite® and aqueous hydrochloric acid (1 N, 295 mL, 295 mmol) were added to the brown residue. The resulting mixture was diluted with ethyl acetate (500 mL) and filtered through Celite®. The filtrate was washed with brine (200 mL). The organic layer was dried over sodium sulfate, filtered and concentrated. The resulting slurry was diluted with heptane (~200 mL) and allowed to solidify at 20° C. The solid was collected, washed with heptane and dried to afford the title product as a white solid (54.68 g, 91%): $^1$H NMR (300 MHz, CDCl$_3$) δ 7.36 (t, J=1.9 Hz, 1H), 7.17 (dd, J=1.9, 0.7 Hz, 2H), 3.48-3.37 (m, 1H), 2.87 (d, J=8.3 Hz, 1H); $^{13}$C NMR (400 MHz, CDCl$_3$) δ 135.44, 135.28, 128.66, 127.30, 39.68, 36.88; ESIMS m/z=298.9 ([M−H])$^−$.

The following compounds were prepared in like manner to the procedure outlined in Example 51:

trans-2,2-Dichloro-3-(3,4,5-trichlorophenyl)cyclopropane-1-carboxylic acid (C37)

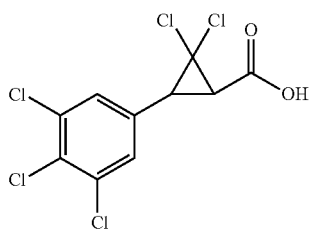

Isolated as a white solid (2.78 g, 95%): $^1$H NMR (400 MHz, DMSO-$d_6$) δ 13.41 (s, 1H), 7.81 (d, J=0.6 Hz, 2H), 3.62 (d, J=8.6 Hz, 1H), 3.52 (d, J=8.6 Hz, 1H); ESIMS m/z 332 ([M−H]$^−$).

trans-2,2-Dichloro-3-(3,4-dichlorophenyl)cyclopropane-1-carboxylic acid (C38)

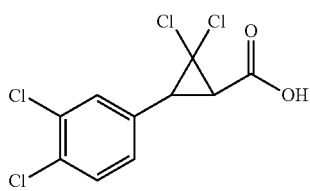

Isolated as a white solid (124 g, 82%): mp 133-135° C.: $^1$H NMR (500 MHz, DMSO-$d_6$) δ 13.39 (s, 1H), 7.76 (d, J=2.0 Hz, 1H), 7.64 (d, J=8.3 Hz, 1H), 7.44 (dd, J=8.4, 2.1 Hz, 1H), 3.49 (s, 2H). $^{13}$C NMR (126 MHz, DMSO-$d_6$) δ 166.34, 133.35, 130.47, 130.33, 130.09, 129.77, 128.81, 61.43, 37.00, 36.06.

trans-2,2-Dichloro-3-(3-chloro-4-fluorophenyl)cyclopropane-1-carboxylic acid (C40)

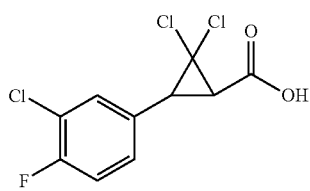

Isolated as a white solid (165 g, 71%): $^1$H NMR (400 MHz, CDCl$_3$) δ 11.57 (s, 1H), 7.42 (dd, J=8.2, 7.6 Hz, 1H), 7.11-6.98 (m, 2H), 3.46 (d, J=8.2 Hz, 1H), 2.85 (d, J=8.3 Hz, 1H); $^{19}$F NMR (376 MHz, CDCl$_3$) δ −114.07; ESIMS m/z 282 ([M−H]$^−$).

In another preparation, isolated as a white powder (10.385 g, 77%): 119-121° C.; $^1$H NMR (400 MHz, CDCl$_3$) δ 11.83 (s, 1H), 7.32 (d, J=6.9 Hz, 1H), 7.16 (d, J=6.7 Hz, 2H), 3.45 (d, J=8.3 Hz, 1H), 2.85 (d, J=8.3 Hz, 1H); $^{13}$C NMR (101 MHz, CDCl$_3$) δ 172.18, 159.26, 156.77, 130.95, 129.26, 129.22, 128.57, 128.50, 121.52, 121.34, 116.94, 116.73, 61.59, 39.64, 37.30; $^{19}$F NMR (376 MHz, CDCl$_3$) δ −115.16; ESIMS m/z 281 [(M−H)$^−$).

trans-3-(4-Bromo-3-(trifluoromethyl)phenyl)-2,2-dichlorocyclopropane-1-carboxylic acid (C74)

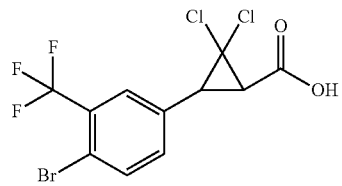

Isolated as a white solid (1.21 g, 51%): $^1$H NMR (400 MHz, CDCl$_3$) δ 10.87 (s, 1H), 7.74 (d, J=8.3 Hz, 1H), 7.58 (d, J=2.2 Hz, 1H), 7.30 (dd, J=8.3, 2.2 Hz, 1H), 3.49 (d, J=8.3 Hz, 1H), 2.91 (d, J=8.3 Hz, 1H); $^{19}$F NMR (376 MHz, CDCl$_3$) δ −62.77, −62.78; ESIMS m/z 377 ([M−H]$^−$).

trans-2,2-Dichloro-3-(4-chloro-3-(trifluoromethyl)phenyl)cyclopropane-1-carboxylic acid (C75)

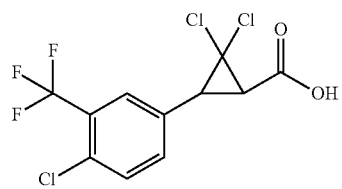

Isolated as a white solid (2.02 g, 43%): $^1$H NMR (400 MHz, CDCl$_3$) δ 7.96-7.51 (m, 3H), 7.39 (dd, J=8.3, 2.2 Hz, 1H), 3.50 (d, J=8.3 Hz, 1H), 2.90 (d, J=8.3 Hz, 1H); $^{19}$F NMR (376 MHz, CDCl$_3$) δ −62.75, −62.75; ESIMS m/z 332 ([M−H]$^−$).

trans-2,2-Dichloro-3-(4-fluoro-3-(trifluoromethyl)phenyl)cyclopropane-1-carboxylic acid (C76)

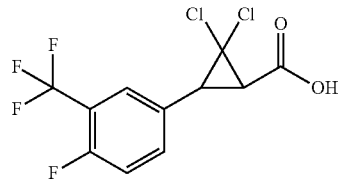

Isolated as a white solid (3.08 g, 67%): $^1$H NMR (400 MHz, CDCl$_3$) δ 8.18 (s, 1H), 7.64-7.39 (m, 2H), 7.24 (t, J=9.3 Hz, 1H), 3.50 (dd, J=8.4, 1.0 Hz, 1H), 2.89 (d, J=8.3 Hz, 1H); $^{19}$F NMR (376 MHz, CDCl$_3$) δ −61.48, −61.51, −114.23, −114.26, −114.29; ESIMS m/z 316 ([M−H]$^−$).

trans-2,2-Dichloro-3-(3-fluoro-5-(trifluoromethyl)phenyl)cyclopropane-1-carboxylic acid (C77)

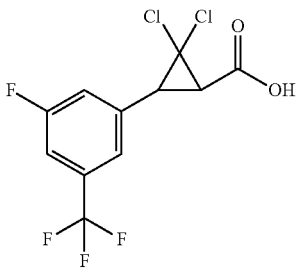 [SMILES: O=C(O)C1C(c2cc(F)cc(C(F)(F)F)c2)C1(Cl)Cl]

Isolated as a white solid (3.7 g, 55%): ¹H NMR (400 MHz, CDCl₃) δ 11.40 (s, 1H), 7.42-7.27 (m, 2H), 7.20 (dt, J=8.9, 2.0 Hz, 1H), 3.53 (d, J=8.3 Hz, 1H), 2.93 (d, J=8.3 Hz, 1H); ¹⁹F NMR (376 MHz, CDCl₃) δ −62.86, −109.49; ESIMS m/z 316 ([M−H]⁻).

trans-3-(3-Bromo-5-(trifluoromethyl)phenyl)-2,2-dichlorocyclopropane-1-carboxylic acid (C78)

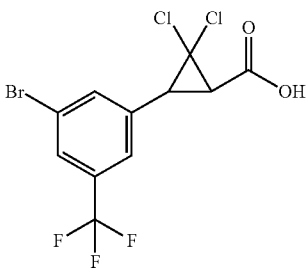 [SMILES: O=C(O)C1C(c2cc(Br)cc(C(F)(F)F)c2)C1(Cl)Cl]

Isolated as a tan solid (0.375 g, 31%): ¹H NMR (400 MHz, CDCl₃) δ 10.52 (s, 1H), 7.77 (s, 1H), 7.62 (d, J=1.8 Hz, 1H), 7.46 (s, 1H), 3.52 (d, J=8.2 Hz, 1H), 2.93 (d, J=8.3 Hz, 1H); ¹⁹F NMR (376 MHz, CDCl₃) δ −62.84; ESIMS m/z 377 ([M−H]⁻).

Example 52: Preparation of trans-2,2-dichloro-3-(3,5-dichlorophenyl)cyclopropane-1-carbaldehyde (C79)

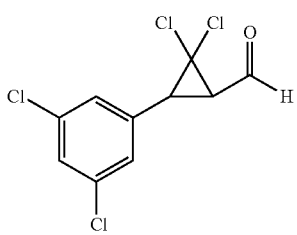 [SMILES: O=CC1C(c2cc(Cl)cc(Cl)c2)C1(Cl)Cl]

Aqueous hydrochloric acid (2 N, 237 mL) was added to a stirred solution of 1,3-dichloro-5-((trans-2,2-dichloro-3-(diethoxymethyl)cyclopropyl)benzene (C83) (85.7 g, 227 mmol) in acetonitrile (1184 mL). The mixture was stirred at 20° C. for 16 hours. The resulting mixture was diluted with water (200 mL) and concentrated to remove the acetonitrile. The resulting aqueous mixture was extracted with hexanes (600 mL). The organic layer was washed water (300 mL), dried over anhydrous sodium sulfate, filtered and concentrated. The crude product was purified by flash column chromatography using 0-20% ethyl acetate/hexanes as eluent to afford the title product as a yellow oil (58.7 g, 86%, purity 95%): ¹H NMR (400 MHz, CDCl₃) δ 9.54 (d, J=4.0 Hz, 1H), 7.46-7.09 (m, 3H), 3.51 (d, J=8.0 Hz, 1H), 2.92 (dd, J=8.0, 4.0 Hz, 1H); ¹³C NMR (126 MHz, CDCl₃) δ 193.41, 135.33, 135.09, 128.78, 127.34, 42.89, 39.31; IR (thin film) 3078, 2847, 1714, 1590, 1566, 1417, 1387.

The following compounds were prepared in like manner to the procedure outlined in Example 52:

trans-2,2-Dichloro-3-(3,4-dichlorophenyl)cyclopropane-1-carbaldehyde (C80)

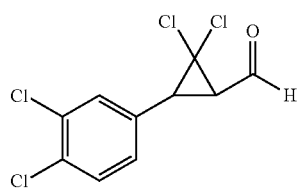 [SMILES: O=CC1C(c2ccc(Cl)c(Cl)c2)C1(Cl)Cl]

Isolated as orange oil (143 g, 98%): ¹H NMR (400 MHz, CDCl₃) δ 9.53 (d, J=4.1 Hz, 1H), 7.47 (d, J=8.3 Hz, 1H), 7.37 (dd, J=2.2, 0.7 Hz, 1H), 7.12 (ddd, J=8.3, 2.2, 0.7 Hz, 1H), 3.51 (dd, J=7.9, 0.8 Hz, 1H), 2.90 (dd, J=8.0, 4.1 Hz, 1H).

trans-2,2-Dichloro-3-(3,4,5-trichlorophenyl)cyclopropane-1-carbaldehyde (C81)

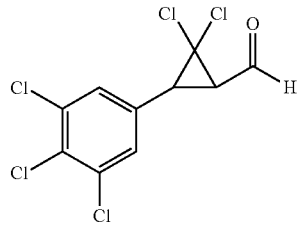 [SMILES: O=CC1C(c2cc(Cl)c(Cl)c(Cl)c2)C1(Cl)Cl]

Isolated as a yellow solid (2.8 g, 69%): ¹H NMR (400 MHz, CDCl₃) δ 9.55 (d, J=3.9 Hz, 1H), 7.30 (d, J=0.7 Hz, 2H), 3.48 (dt, J=8.0, 0.8 Hz, 1H), 2.92 (dd, J=7.9, 3.9 Hz, 1H).

trans-2,2-Dichloro-3-(3-chloro-4-fluorophenyl)cyclopropane-1-carbaldehyde (C82)

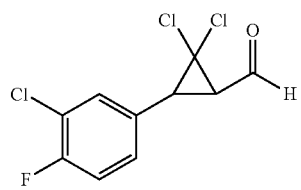 [SMILES: O=CC1C(c2ccc(F)c(Cl)c2)C1(Cl)Cl]

Isolated as orange oil (230 g, 97%): $^1$H NMR (300 MHz, CDCl$_3$) δ 9.52 (d, J=4.2 Hz, 1H), 7.36-7.30 (m, 1H), 7.19-7.16 (m, 1H), 7.15 (d, J=1.2 Hz, 1H), 3.51 (dt, J=7.9, 0.7 Hz, 1H), 2.88 (dd, J=7.9, 4.2 Hz, 1H).

In another preparation, isolated as a yellow oil (12.496 g, 71%): $^1$H NMR (400 MHz, CDCl$_3$) δ 9.52 (d, J=4.1 Hz, 1H), 7.33 (d, J=7.2 Hz, 1H), 7.16 (dd, J=6.8, 1.0 Hz, 2H), 3.53 (d, J=7.9 Hz, 1H), 2.90 (dd, J=7.9, 4.1 Hz, 1H); $^{13}$C NMR (101 MHz, CDCl$_3$) δ 193.77, 159.27, 156.78, 131.03, 129.04, 129.00, 128.66, 128.59, 121.49, 121.31, 116.95, 116.74, 61.68, 43.10, 39.25; $^{19}$F NMR (376 MHz, CDCl$_3$) δ −115.01; EIMS m/z 266.

Example 53: Preparation of 1,3-dichloro-5-(trans-2, 2-dichloro-3-(diethoxy-methyl)cyclopropyl)benzene (C83)

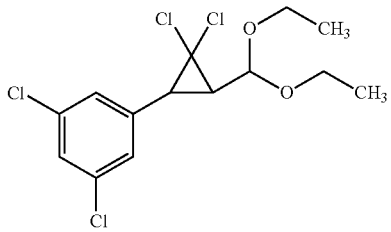 [SMILES: CCOC(OCC)C1C(c2cc(Cl)cc(Cl)c2)C1(Cl)Cl]

A 1 L 4-neck flask equipped with a mechanical stirrer, condenser, temperature probe and nitrogen inlet was charged with (E)-1,3-dichloro-5-(3,3-diethoxyprop-1-en-1-yl)benzene (C87) (40 g, 138 mmol) and CHCl$_3$ (447 mL). Tetrabutylammonium hexafluorophosphate(V) (1.081 g, 2.76 mmol) was added. The light yellow solution was heated to 45° C. With vigorous stirring (~400 rpm), aqueous sodium hydroxide (50%, 182 mL) was added dropwise via addition funnel (over 1 hour). After 20 hours, the mixture was allowed to cool. The mixture was diluted with hexane (200 mL). The organic top layer was decanted (off the aqueous lower suspension) through Celite®, washing the filtercake with hexane (200 mL). The filtrate was washed with brine (~200 mL), dried over sodium sulfate, filtered and concentrated to provide the title compound as a brown oil (50.2 g, 97%, purity 95%): $^1$H NMR (300 MHz, CDCl$_3$) δ 7.31 (t, J=1.9 Hz, 1H), 7.15 (dd, J=1.9, 0.7 Hz, 2H), 4.59 (d, J=6.2 Hz, 1H), 3.80-3.57 (m, 4H), 2.77 (d, J=8.5 Hz, 1H), 2.25 (dd, J=8.5, 6.2 Hz, 1H), 1.30 (t, J=7.0 Hz, 3H), 1.20 (t, J=7.1 Hz, 3H).

The following compounds were prepared in like manner to the procedure outlined in Example 53:

1,2-Dichloro-4-(trans-2,2-dichloro-3-(diethoxymethyl)cyclopropyl)benzene (C84)

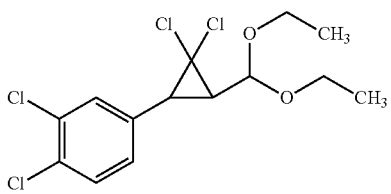

Isolated as a brown oil (184 g, 99%): $^1$H NMR (400 MHz, CDCl$_3$) δ 7.43 (d, J=8.2 Hz, 1H), 7.36 (dd, J=2.2, 0.7 Hz, 1H), 7.10 (ddd, J=8.3, 2.1, 0.7 Hz, 1H), 4.59 (d, J=6.2 Hz, 1H), 3.82-3.55 (m, 4H), 2.77 (d, J=8.5 Hz, 1H), 2.24 (dd, J=8.5, 6.3 Hz, 1H), 1.30 (t, J=7.0 Hz, 3H), 1.20 (t, J=7.1 Hz, 3H).

1,2,3-Trichloro-5-(trans-2,2-dichloro-3-(diethoxymethyl)cyclopropyl)benzene (C85)

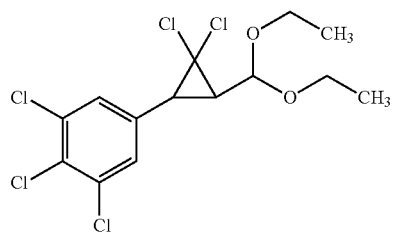 [SMILES: CCOC(OCC)C1C(c2cc(Cl)c(Cl)c(Cl)c2)C1(Cl)Cl]

Isolated as a brown oil (146 g, 93%); $^1$H NMR (400 MHz, CDCl$_3$) δ 7.29 (d, J=0.7 Hz, 2H), 4.59 (d, J=6.1 Hz, 1H), 3.82-3.54 (m, 4H), 2.75 (d, J=8.5 Hz, 1H), 2.23 (dd, J=8.5, 6.1 Hz, 1H), 1.30 (t, J=7.0 Hz, 3H), 1.20 (t, J=7.0 Hz, 3H).

2-Chloro-4-(trans-2,2-dichloro-3-(diethoxymethyl)cyclopropyl)-1-fluorobenzene (C86)

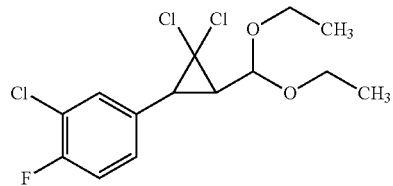 [SMILES: CCOC(OCC)C1C(c2ccc(F)c(Cl)c2)C1(Cl)Cl]

Isolated as a brown oil (63 g, 96%): $^1$H NMR (400 MHz, CDCl$_3$) δ 7.44 (dd, J=7.0, 2.2 Hz, 1H), 7.29-7.22 (m, 1H), 7.09 (t, J=8.7 Hz, 1H), 6.62 (dd, J=16.1, 1.2 Hz, 1H), 6.14 (dd, J=16.1, 5.0 Hz, 1H), 5.05 (dd, J=4.9, 1.2 Hz, 1H), 3.70 (dq, J=9.3, 7.0 Hz, 2H), 3.56 (dq, J=9.4, 7.1 Hz, 2H), 1.25 (t, J=7.1 Hz, 6H); $^{13}$C NMR (101 MHz, CDCl$_3$) δ 158.91, 156.42, 133.65, 133.62, 130.47, 128.65, 128.07, 128.05, 126.39, 126.32, 121.26, 121.08, 116.72, 116.51, 100.93, 61.17, 15.24; $^{19}$F NMR (376 MHz, CDCl$_3$) δ −116.36.

In another preparation, isolated as an amber oil (22.38 g, 88%): $^1$H NMR (400 MHz, CDCl$_3$) δ 7.31 (m, 1H), 7.13 (m, 2H), 4.59 (d, J=6.3 Hz, 1H), 3.69 (m, 4H), 2.78 (d, J=8.5 Hz, 1H), 2.23 (dd, J=8.5, 6.3 Hz, 1H), 1.30 (t, J=7.1 Hz, 3H), 1.20 (t, J=7.1 Hz, 3H); $^{19}$F NMR (376 MHz, CDCl$_3$) δ −116.48; EMS m/z 295 [M-OEt].

Example 54: Preparation of (E)-1,3-dichloro-5-(3,3-diethoxyprop-1-en-1-yl)benzene (C87)

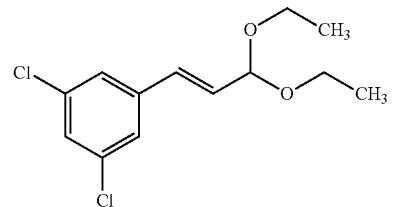 [SMILES: CCOC(/C=C/c1cc(Cl)cc(Cl)c1)OCC]

Step 1a: Acetaldehyde (120 g, 2688 mmol) was added to a stirred mixture of 3,5-dichlorobenzaldehyde (96 g, 538 mmol) in toluene (400 mL) at 0° C. A solution of potassium hydroxide (3.35 g, 53.8 mmol) in methyl alcohol (10 mL) was added dropwise via addition funnel. The resulting mixture was stirred at 0° C. for 4 hours until ail of the 3,5-dichlorobenzaldehyde was consumed by thin layer chromatography. Step 1b: Ethyl acetate (500 mL) and concentrated hydrochloric acid (37% aqueous, 44.1 mL, 538 mmol) were added to the reaction mixture. The resulting mixture was heated at 80° C., and a colorless liquid was allowed to distill (200 mL). The reaction mixture was diluted with water (500 mL) and extracted with ethyl acetate. The organic layer was washed with brine, dried over sodium sulfate, filtered, and concentrated to afford (E)-3-(3,5-dichlorophenyl) acrylaldehyde as a light yellow solid (115 g) which was used directly without further purification: $^1$H NMR (300 MHz, CDCl$_3$) δ 9.72 (dd, J=7.4, 0.5 Hz, 1H), 7.43 (q, J=1.8 Hz, 3H), 7.35 (d, J=16.0 Hz, 1H), 6.69 (dd, J=16.0, 7.4 Hz, 1H).

Step 2: Triethoxymethane (31.4 g, 208 mmol) and pyridin-1-ium 4-methylbenzenesulfonate (0.528 g, 2.079 mmol) were added to a stirred solution of (E)-3-(3,5-dichlorophenyl) acrylaldehyde (44 g, 208 mmol) in ethanol (416 mL). The resulting mixture was stirred at 20° C. for 20 hours. A solution of saturated aqueous sodium carbonate (50 mL) was added to the reaction mixture. The resulting mixture was concentrated at 45° C. to remove the ethanol. The concentrate was diluted with water and extracted with hexane. The organic layer was washed with brine, dried over sodium sulfate, filtered and concentrated to afford the title product as a light yellow oil (56.13 g, 93%): $^1$H NMR (400 MHz, CDCl$_3$) δ 7.25 (dt, J=10.6, 1.9 Hz, 3H), 6.61 (dd, J=16.1, 1.1 Hz, 1H), 6.22 (dd, J=16.1, 4.7 Hz, 1H), 5.17 (s, 1H), 5.14-5.00 (m, 1H), 3.78-3.49 (m, 4H), 1.24 (q, J=7.2 Hz, 6H); $^{13}$C NMR (101 MHz, CDCl$_3$) δ 139.34, 135.14, 130.27, 129.88, 127.71, 125.08, 100.60, 61.20, 15.25.

The following compounds were prepared in like manner to the procedure outlined in Example 54:

(E)-1,2-Dichloro-4-(3,3-diethoxyprop-1-en-1-yl)benzene(C88)

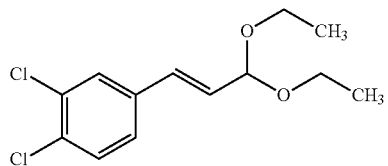 [SMILES: CCOC(/C=C/c1ccc(Cl)c(Cl)c1)OCC]

Isolated as an orange oil (142 g, 91%): $^1$H NMR (300 MHz, CDCl$_3$) δ 7.48 (d, J=2.0 Hz, 1H), 7.39 (dd, J=8.3, 0.8 Hz, 1H), 6.62 (d, J=16.1 Hz, 1H), 6.20 (ddd, J=16.1, 4.9, 0.8 Hz, 1H), 5.06 (dt, J=4.9, 1.0 Hz, 1H), 3.78-3.48 (m, 4H), 1.25 (td, J=7.1, 0.8 Hz, 6H).

(E)-1,2,3-Trichloro-5-(3,3-diethoxyprop-1-en-1-yl)benzene(C89)

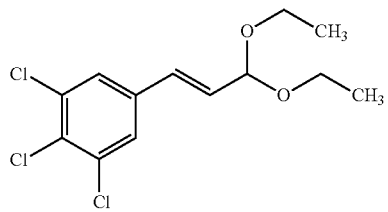 [SMILES: CCOC(/C=C/c1cc(Cl)c(Cl)c(Cl)c1)OCC]

Isolated as an orange oil (40 g, 91%): $^1$H NMR (400 MHz, CDCl$_3$) δ 7.41 (s, 2H), 6.58 (dd, J=16.1, 1.2 Hz, 1H), 6.21 (dd, J=16.1, 4.6 Hz, 1H), 5.06 (dd, J=4.7, 1.2 Hz, 1H), 3.69 (dq, J=9.3, 7.1 Hz, 2H), 3.55 (dq, J=9.5, 7.0 Hz, 2H), 1.25 (t, J=7.1 Hz, 6H).

(E)-2-Chloro-4-(3,3-diethoxyprop-1-en-1-yl)-1-fluorobenzene (C90)

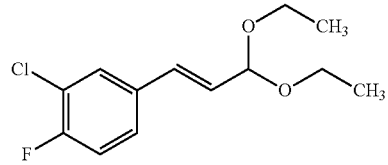 [SMILES: CCOC(/C=C/c1ccc(F)c(Cl)c1)OCC]

Isolated as an orange oil (283 g, 84%): $^1$H NMR (400 MHz, CDCl$_3$) δ 7.44 (dd, J=7.0, 2.2 Hz, 1H), 7.29-7.22 (m, 1H), 7.09 (t, J=8.7 Hz, 1H), 6.62 (dd, J=16.1, 1.2 Hz, 1H), 6.14 (dd, J=16.1, 5.0 Hz, 1H), 5.05 (dd, J=4.9, 1.2 Hz, 1H), 3.70 (dq, J=9.3, 7.0 Hz, 2H), 3.56 (dq, J=9.4, 7.1 Hz, 2H), 1.25 (t, J=7.1 Hz, 6H); $^{13}$C NMR (101 MHz, CDCl$_3$) δ 158.91, 156.42, 133.65, 133.62, 130.47, 128.65, 128.07, 128.05, 126.39, 126.32, 121.26, 121.08, 116.72, 116.51, 100.93, 61.17, 15.24; $^{19}$F NMR (376 MHz, CDCl$_3$) δ −116.36.

In another preparation, isolated as a colorless oil (16.75 g, 64%); $^1$H NMR (400 MHz, CDCl$_3$) δ 7.43 (dd, J=7.0, 2.2 Hz, 1H), 7.25 (m, 1H), 7.07 (t, J=8.7 Hz, 1H), 6.62 (d, J=16.1 Hz, 1H), 6.13 (dd, J=16.1, 4.9 Hz, 1H), 5.05 (dd, J=4.9, 1.0 Hz, 1H), 3.70 (dq, J=9.4, 7.1 Hz, 2H), 3.56 (dq, J=9.4, 7.0 Hz, 2H), 1.25 (t, J=7.1 Hz, 6H); $^{13}$C NMR (101 MHz, CDCl$_3$) δ 158.91, 156.42, 133.65, 133.62, 130.47, 128.65, 128.07, 128.05, 126.39, 126.32, 121.26, 121.08, 116.72, 116.51, 100.93, 61.17, 15.24; $^{19}$F NMR (376 MHz, CDCl$_3$) δ −116.36; EIMS m/z 258.

Example 55: Preparation of (1R,3R)-2,2-dichloro-3-(3,5-dichlorophenyl)cyclopropane-1-carboxylic acid (C91)

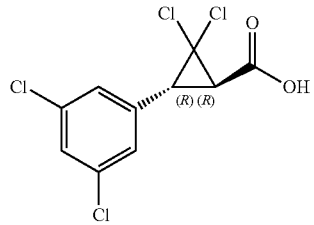 [SMILES: O=C(O)[C@H]1[C@H](c2cc(Cl)cc(Cl)c2)C1(Cl)Cl]

1$^{st}$ resolution: (R)-1-Phenylethanamine (6.49 g, 53.0 mmol) was slowly added to a stirred solution of rac-2,2-dichloro-3-(3,5-dichlorophenyl)cyclopropane-carboxylic acid) (32.45 g, 106 mmol) in acetone (106 mL). The resulting solution was stirred at 45° C. After a solid began to deposit, the mixture was placed at 5° C. for 4 hours. The solid was collected, washed with minimal cold acetone and dried. The white solid salt was diluted with ethyl acetate (100 mL) and washed with aqueous hydrochloric acid (1 N, 10 mL) and brine (30 mL). The organic layer was dried over sodium sulfate, filtered and concentrated to afford the title product as a white solid (10.33 g, 88% enantiomeric excess "ee").

2$^{nd}$ resolution: (R)-1-Phenylethanamine (3.4 g, 28 mmol) was slowly added to a stirred solution of rac-2,2-dichloro-3-(3,5-dichlorophenyl)cyclopropane-carboxylic acid) (10.33 g, 88% ee) in acetone (100 mL). After 2 hours, a solid was collected, washed with minimal cold acetone and dried. The solid was treated with aqueous hydrochloric acid to afford the title compound as a white solid (7.84 g, 97% ee, 24.2%): Specific Rotation: +47.4 (10 mg/mL in acetonitrile, 589 nm, 25.2° C.); $^1$H NMR (300 MHz, CDCl$_3$) δ 7.36 (t, J=1.9 Hz, 1H), 7.17 (dd, J=1.9, 0.7 Hz, 2H), 3.48-3.37 (m, 1H), 2.87 (d, J=8.3 Hz, 1H); $^{13}$C NMR (400 MHz, DMSO-d$_6$) δ 166.28, 136.40, 133.39, 127.27, 127.04, 61.36, 37.10, 35.98; ESIMS m/z 298.9 ([M−H]$^-$).

Enantiomeric excess values (ee %) was determined by Chiral HPLC method as follows: Column: CHIRALPAK© ZWIX(+), particle size 3 μm, dimension 3 mm×150 mm, DAIC 511584; Mobile phase which is a mixture of 500 mL acetonitrile, 500 mL methanol, 20 mL water, 1.9 mL formic acid, and 2.6 mL diethylamine; Flow rate: 0.5 mL/min; Time: 9 min; Temperature: 25° C.

The following compounds were prepared in like manner to the procedure outlined in Example 55:

(1R,3R)-2,2-Dichloro-3-(3,4-dichlorophenyl)cyclopropane-1-carboxylic acid (C92)

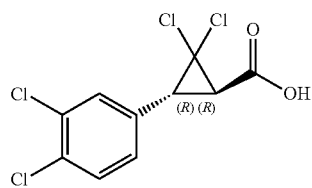 [SMILES: O=C(O)[C@H]1[C@H](c2ccc(Cl)c(Cl)c2)C1(Cl)Cl]

Isolated as a white solid (6.7 g, 30%, 96% ee). Analytical data are consistent with racemic acid C38.

(1R,3R)-2,2-Dichloro-3-(3-chloro-4-fluorophenyl)cyclopropane-1-carboxylic acid (C93)

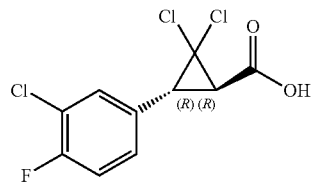

Isolated as a white solid (0.5 g, 13%, 99% ee). Analytical data are consistent with racemic acid C40.

(1R,3R)-2,2-Dichloro-3-(3,4,5-trichlorophenyl)cyclopropane-1-carboxylic acid (C94)

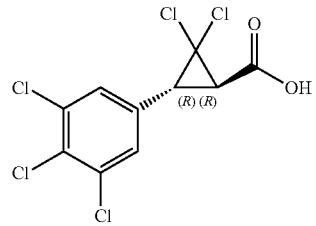 [SMILES: O=C(O)[C@H]1[C@H](c2cc(Cl)c(Cl)c(Cl)c2)C1(Cl)Cl]

Isolated as a white solid (2 g, 29%, 99% ee). Analytical data are consistent with racemic acid C37.

(1R,3R)-2,2-Dichloro-3-(4-fluoro-3-(trifluoromethyl)phenyl)cyclopropane-1-carboxylic acid (C95)

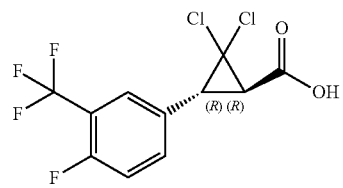

Isolated as a clear colorless oil (0.11 g, 14%, 80% ee). Analytical data are consistent with racemic acid C76.

Example 56: Preparation of 3,4,5-trichlorobenzaldehyde (C96)

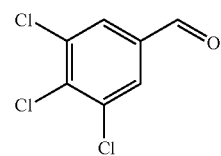 [SMILES: O=Cc1cc(Cl)c(Cl)c(Cl)c1]

In an oven dried, nitrogen flushed, 500 mL round-bottomed flask equipped with a pressure equalizing addition funnel, 5-bromo-1,2,3-trichlorobenzene (10.0 g, 38.4 mmol) was dissolved in tetrahydrofuran (100 mL), and the resulting solution was cooled in an ice bath under nitrogen. isoPropyl magnesium chloride (2 M solution tetrahydrofuran, 21.1 mL, 42.3 mmol) was added dropwise with good stirring over 15 minutes via the addition funnel. After 0.5 hours, N,N-dimethylformamide (3.72 mL, 48.0 mmol) was added to the dark solution with stirring. After an additional 0.5 hours, hydrochloric acid (1 N, 100 mL) was added with stirring. The layers were separated, and the organic layer was washed with brine. The combined aqueous layers were extracted with ether, and the combined organics were dried over sodium sulfate, filtered, and concentrated to afford the title compound as a white solid (10:1 mixture of title compound to 1,2,3-trichlorobenzene, 7.96 g, 99%): $^1$H NMR (CDCl$_3$) δ 9.91 (s, 1H), 7.88 (s, 2H); EIMS m/z 209 ([M]$^+$).

Example 57: Preparation of 5-amino-2-cyano-N-(2,4-difluorophenyl)-N-methylbenzamide (C97)

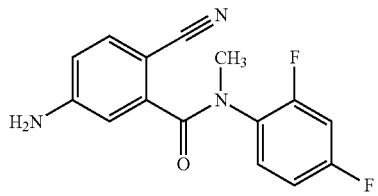

To a solution of 2-cyano-N-(2,4-difluorophenyl)-N-methyl-5-nitrobenzamide (C138) (0.051 g, 0.16 mmol) in methanol (1.5 mL) and water (0.5 mL) was added iron powder (0.045 g, 0.80 mmol) and ammonium chloride (0.026 g, 0.48 mmol). The reaction mixture was heated at 60° C. for 2 hours. The reaction mixture was filtered through Celite®, and the filtrate was diluted with ethyl acetate and washed with water. The combined organic phases were dried over magnesium sulfate, filtered, and concentrated to provide the title compound as a colorless oil (0.054 g, 99%): Major isomer—$^1$H NMR (500 MHz, CDCl$_3$) δ 7.37 (td, J=8.8, 5.8 Hz, 1H), 7.22 (d, J=8.5 Hz, 1H), 6.82-6.70 (m, 2H), 6.53 (t, J=1.9 Hz, 1H), 6.47 (dd, J=8.5, 2.4 Hz, 1H), 4.27 (s, 2H), 3.41 (s, 3H); $^{19}$F NMR (471 MHz, CDCl$_3$) δ −107.99 (p, J=7.8 Hz), −115.44 (q, J=8.8 Hz); ESIMS m/z 288 ([M+H]$^+$).

The following compounds were prepared in like manner to the procedure outlined in Example 57:

Preparation of 5-amino-2-chloro-N-(4-fluorophenyl)benzamide (C98)

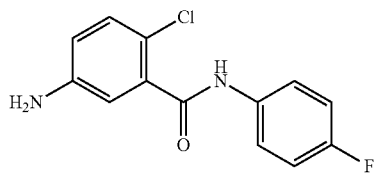 [SMILES: Nc1ccc(Cl)c(C(=O)Nc2ccc(F)cc2)c1]

Isolated as a white solid (1.75 g, 54%).

5-Amino-2-chloro-N-(2,4-difluorophenyl)benzamide (C99)

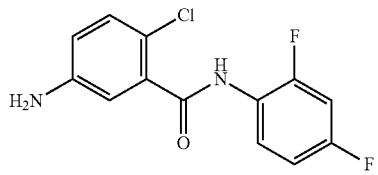 [SMILES: Nc1ccc(Cl)c(C(=O)Nc2ccc(F)cc2F)c1]

Isolated as a purple solid (0.37 g, 28%): $^1$H NMR (400 MHz, CDCl$_3$) δ 8.42 (tdd, J=9.7, 6.0, 3.6 Hz, 1H), 8.25 (s, 1H), 7.21 (d, J=8.5 Hz, 1H), 7.13 (d, J=2.9 Hz, 1H), 6.97-6.88 (m, 2H), 6.73 (dd, J=8.5, 2.9 Hz, 1H), 3.84 (s, 2H); $^{19}$F NMR (376 MHz, CDCl$_3$) δ −114.57 (d, J=4.6 Hz), −125.78 (d, J=4.6 Hz); ESIMS m/z 283 ([M+H]$^+$).

N-Allyl-5-amino-2-chloro-N-(2-cyano-4-fluorophenyl)benzamide (C100)

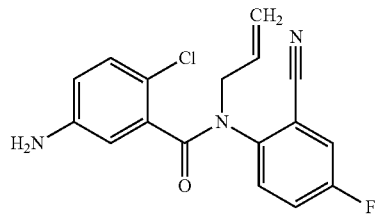 [SMILES: C=CCN(C(=O)c1cc(N)ccc1Cl)c1ccc(F)cc1C#N]

A mixture of amide rotamers was isolated as a gold oil (0.156 g, quant.): Major isomer—$^1$H NMR (500 MHz, CDCl$_3$) δ 7.53-7.34 (m, 2H), 7.27-7.11 (m, 2H), 6.90 (d, J=8.6 Hz, 1H), 6.44 (dd, J=8.6, 2.8 Hz, 1H), 5.97 (ddq, J=16.9, 10.1, 6.8 Hz, 1H), 5.29-5.04 (m, 1H), 4.94 (dq, J=16.6, 1.2 Hz, 1H), 4.37-4.16 (m, 2H), 3.88 (s, 2H); $^{19}$F NMR (471 MHz, CDCl$_3$) δ −110.82 (q, J=7.5 Hz); ESIMS m/z 330 ([M+H]$^+$).

5-Amino-2-chloro-N-(2-cyano-4-fluorophenyl)-N-(prop-2-yn-1-yl)benzamide (C101)

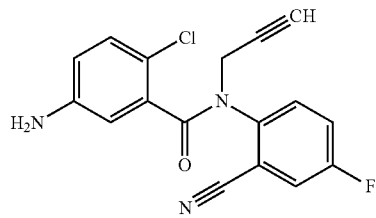 [SMILES: C#CCN(C(=O)c1cc(N)ccc1Cl)c1ccc(F)cc1C#N]

A mixture of amide rotamers was isolated as a colorless oil (0.067 g, 62%): $^1$H NMR (500 MHz, CDCl$_3$) δ 7.70-7.40 (m, 2H), 7.26-7.15 (m, 1H), 7.01-6.64 (m, 2H), 6.46 (dd, J=8.6, 2.8 Hz, 1H), 5.20-4.29 (m, 3H), 3.81 (d, J=80.7 Hz, 1H), 2.29 (dt, J=11.8, 2.4 Hz, 1H); $^{19}$F NMR (471 MHz, CDCl$_3$) δ −110.08 (q, J=7.2 Hz); ESIMS m/z 328 ([M+H]$^+$).

(5-Amino-2-chloro-N-(2-cyano-4-fluorophenyl)benzamido)methyl acetate (C102)

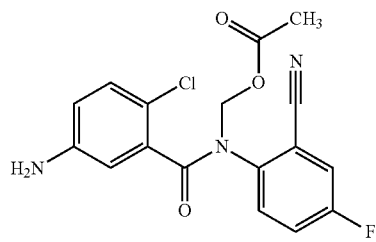

A mixture of amide rotamers was isolated as a colorless oil (0.063 g, 97%): $^1$H NMR (500 MHz, CDCl$_3$) δ 7.58-7.34 (m, 2H), 7.31-7.14 (m, 2H), 6.94-6.62 (m, 2H), 6.49-6.37 (m, 1H), 4.98-4.45 (m, 1H), 4.24 (s, 1H), 3.80 (d, J=77.8 Hz, 2H), 1.26 (td, J=7.2, 1.9 Hz, 3H); $^{19}$F NMR (471 MHz, CDCl$_3$) δ −109.28−−109.86 (m); ESIMS m/z 383 ([M+H]$^+$).

2-Chloro-N-(2-cyano-4-fluorophenyl)-N-ethyl-5-nitrobenzamide (C103)

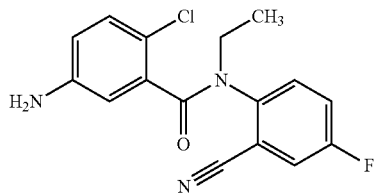

A mixture of amide rotamers was isolated as a white solid (0.110 g, 64%): $^1$H NMR (500 MHz, CDCl$_3$) δ 7.58-7.34 (m, 2H), 7.31-7.14 (m, 2H), 6.94-6.62 (m, 2H), 6.49-6.37 (m, 1H), 4.98-4.45 (m, 1H), 4.24 (s, 1H), 3.80 (m, 2H), 1.26 (td, J=7.2, 1.9 Hz, 3H); $^{19}$F NMR (471 MHz, CDCl$_3$) δ −108.27 (s), −109.81 (q, J=6.7 Hz); ESIMS m/z 348 ([M+H]$^+$).

5-Amino-N-benzyl-2-chloro-N-(2-cyano-4-fluorophenyl)benzamide (C104)

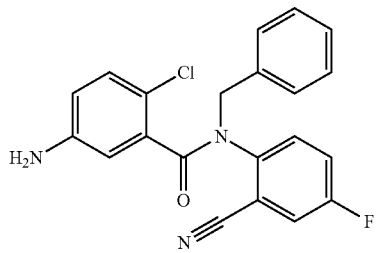 [SMILES: N#Cc1cc(F)ccc1N(Cc1ccccc1)C(=O)c1cc(N)ccc1Cl]

A mixture of amide rotamers was isolated as a white foam (0.206 g, 98%): $^1$H NMR (500 MHz, CDCl$_3$) δ 738-7.17 (m, 7H), 7.15-6.92 (m, 2H), 6.92-6.84 (m, 1H), 6.68 (dd, J=8.8, 2.8 Hz, 1H), 6.41 (dd, J=8.6, 2.8 Hz, 1H), 5.76 (d, J=14.5 Hz, 1H), 4.69-4.41 (m, 1H), 3.85 (m, 2H); $^{19}$F NMR (471 MHz, CDCl$_3$) δ −108.73-−110.02 (m); ESIMS m/z 380 ([M+H]$^+$).

tert-Butyl N-[3-[(5-amino-2-chloro-benzoyl)-methyl-amino]-2,6-difluoro-phenyl]-N-tert-butoxycarbonyl-carbamate (C105)

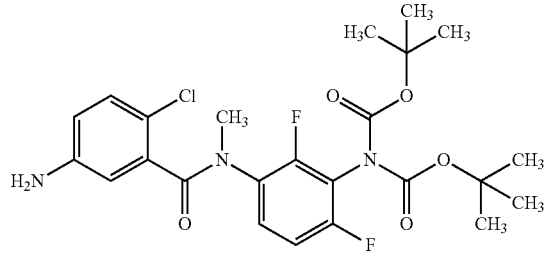 [SMILES: CN(C(=O)c1cc(N)ccc1Cl)c1ccc(F)c(N(C(=O)OC(C)(C)C)C(=O)OC(C)(C)C)c1F]

A mixture of amide rotamers was isolated as a colorless oil (0.140 g, 63%): $^1$H NMR (500 MHz, CDCl$_3$) δ 7.23-7.09 (m, 1H), 7.04-6.86 (m, 1H), 6.79-6.64 (m, 1H), 6.50-6.34 (m, 2H), 3.77 (s, 2H), 3.39 (s, 3H), 1.43 (d, J=13.3 Hz, 18H); $^{19}$F NMR (471 MHz, CDCl$_3$) δ −116.85-−118.50 (m), −123.55 (s); ESIMS m/z 534 ([M+Na]$^+$).

tert-Butyl N-[3-[(5-amino-2-chloro-benzoyl)-methyl-amino]-2,6-difluoro-phenyl]-N-methyl-carbamate (C106)

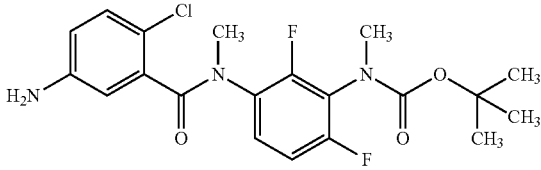 [SMILES: CN(C(=O)c1cc(N)ccc1Cl)c1ccc(F)c(N(C)C(=O)OC(C)(C)C)c1F]

A mixture of amide rotamers was isolated as a pale yellow foam (0.114 g, 92%): $^1$H NMR (500 MHz, CDCl$_3$) δ 7.25-6.86 (m, 2H), 6.85-6.28 (m, 3H), 4.50 (dd, J=72.3, 40.3 Hz, 1H), 3.41 (s, 3H), 3.23-2.99 (m, 3H), 1.56 (s, 1H), 1.55-1.30 (m, 9H); $^{19}$F NMR (471 MHz, CDCl$_3$) δ −118.27 (dt, J=10.7, 5.6 Hz), −122.00-−124.47 (m); ESIMS m/z 448 ([M+Na]$^+$).

5-Amino-2-chloro-N,N'-dimethyl-N'-phenylbenzohydrazide (C107)

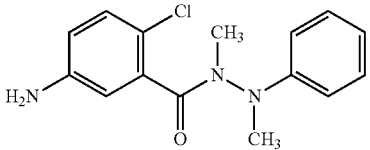

Isolated as a yellow solid (0.203 g, 80%): $^1$H NMR (400 MHz, DMSO-d$_6$) δ 7.32-7.22 (m, 2H), 6.99 (d, J=8.4 Hz, 1H), 6.87 (t, J=7.1 Hz, 1H), 6.83-6.75 (m, 2H), 6.48 (q, J=2.6 Hz, 2H), 5.24 (s, 2H), 3.04 (s, 3H), 2.98 (s, 3H); ESIMS m/z 273 ([M+H]$^+$).

tert-Butyl-N-[3-[(5-amino-2-chloro-3-fluorobenzoyl)amino]-2,6-difluorophenyl]-N-tert-butoxycarbonyl-carbamate (C108)

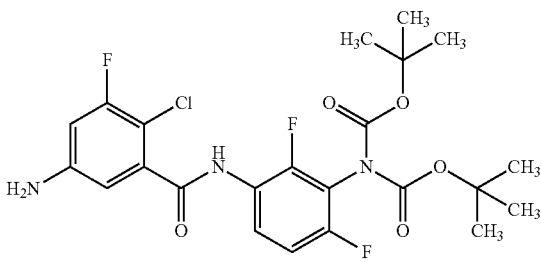 [SMILES: CC(C)(C)OC(=O)N(C(=O)OC(C)(C)C)c1c(F)ccc(NC(=O)c2cc(N)cc(F)c2Cl)c1F]

Isolated as a light-tan solid (0.864 g, 71%): mp 150-153° C.; $^1$H NMR (400 MHz, DMSO-d$_5$) δ 10.39 (s, 1H), 7.68 (td, J=8.8, 5.8 Hz, 1H), 7.25 (td, J=9.2, 1.7 Hz, 1H), 6.59 (ddd, J=7.0, 5.5, 2.5 Hz, 2H), 5.82 (s, 2H), 1.40 (s, 18H); $^{19}$F NMR (376 MHz, DMSO-d$_5$) δ −115.54, −123.59, −126.30; HRMS-ESI (m/z) [M$^+$]$^+$ calcd for C$_{23}$H$_{25}$ClF$_3$N$_3$O$_5$, 515.1435; found, 515.1431.

3-Amino-2,6-dichloro-N-(2,2,3,3,3-pentafluoropropyl)benzamide (C109)

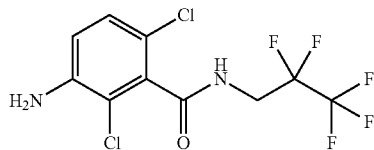

Isolated as a tan solid (0.057 g, 82%): mp 116-128° C.; $^1$H NMR (400 MHz, CDCl$_3$) δ 7.10 (d, J=8.7 Hz, 1H), 6.74 (d, J=8.7 Hz, 1H), 6.04 (s, 1H), 4.18 (td, J=15.1, 6.5 Hz, 3H); $^{19}$F NMR (376 MHz, CDCl$_3$) δ −84.15, −121.50; EIMS m/z 336.

3-Amino-N-ethyl-2,6-difluorobenzamide (C110)

Isolated as a cream-colored solid (0.036 g, 44%): mp 123-126° C.; $^1$H NMR (400 MHz, DMSO-d$_6$) δ 8.56 (t, J=5.6 Hz, 1H), 6.92-6.69 (m, 2H), 5.09 (s, 2H), 3.23 (qd, J=7.2, 5.5 Hz, 2H), 1.08 (t, J=7.2 Hz, 3H); $^{19}$F NMR (376 MHz, DMSO-d$_6$) δ −131.96, −131.96, −135.48, −135.49; ESIMS m/z 201 ([M+H]$^+$).

3-Amino-2,6-difluoro-N-(2,2,2-trifluoroethyl)benzamide (C111)

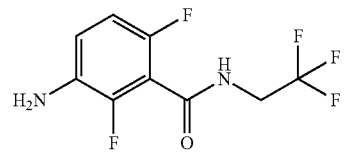

Isolated as a yellow solid (0.106 g, 68%): mp 133-136° C.; $^1$H NMR (400 MHz, DMSO-d$_6$) δ 9.30 (t, J=6.3 Hz, 1H), 6.93-6.74 (m, 2H), 5.17 (s, 2H), 4.07 (qd, J=9.7, 6.3 Hz, 2H); $^{19}$F NMR (376 MHz, DMSO-d$_6$) δ −70.67, −131.95, −131.95, −135.20, −135.21; ESIMS m/z 255 ([M+H]$^+$).

3-Amino-2,6-difluoro-N-(2,2,3,3,3-pentafluoropropyl)benzamide (C112)

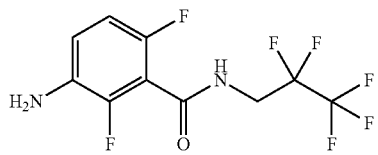 [SMILES: Nc1ccc(F)c(C(=O)NCC(F)(F)C(F)(F)F)c1F]

Isolated as a light-brown solid (0.090 g, 59%): mp 82-85° C.; $^1$H NMR (400 MHz, DMSO-d$_6$) δ 9.31 (t, J=6.3 Hz, 1H), 6.93-6.72 (m, 2H), 5.17 (s, 2H), 4.12 (td, J=15.5, 6.4 Hz, 2H); $^{19}$F NMR (376 MHz, DMSO-d$_6$) δ −83.42, −120.11, −131.86, −135.12; ESIMS m/z 305 ([M+H]$^+$).

3-Amino-2,6-dichloro-N-ethylbenzamide (C113)

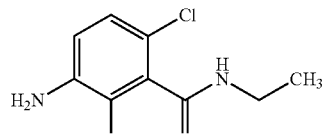

Isolated as a peach-colored solid (0.058 g, 68%): mp 179-182° C.; $^1$H NMR (400 MHz, DMSO-d$_6$) δ 8.45 (t, J=5.7 Hz, 1H), 7.10 (d, J=8.7 Hz, 1H), 6.77 (d, J=8.8 Hz, 1H), 5.61 (s, 2H), 3.22 (qd, J=7.2, 5.6 Hz, 2H), 1.09 (t, J=7.3 Hz, 3H); ESIMS m/z 233 ([M+H]$^+$).

3-Amino-2,6-dichloro-N-(2,2,2-trifluoroethyl)benzamide (C114)

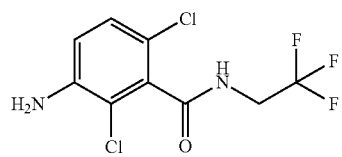

Isolated as an orange solid (0.125 g, 77%): mp 178-181° C.; $^1$H NMR (400 MHz, DMSO-d$_6$) δ 9.23 (t, J=6.4 Hz, 1H), 7.13 (d, J=8.8 Hz, 1H), 6.81 (d, J=8.8 Hz, 1H), 5.68 (s, 2H), 4.05 (qd, J=9.7, 6.3 Hz, 2H); $^{19}$F NMR (376 MHz, DMSO-d$_6$) δ −70.05; ESIMS m/z 287 ([M+H]$^+$).

3-Amino-2,6-difluoro-N-propylbenzamide (C115)

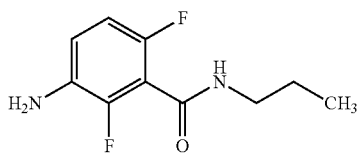

Isolated as a light-orange oil (0.080 g, 62%): $^1$H NMR (400 MHz, DMSO-d$_6$) δ 8.54 (t, J=5.7 Hz, 1H), 6.90-6.65 (m, 2H), 5.09 (s, 2H), 3.17 (td, J=6.8, 5.7 Hz, 2H), 1.48 (h, J=7.2 Hz, 2H), 0.89 (t, J=7.4 Hz, 3H); $^{19}$F NMR (376 MHz, DMSO-d$_6$) δ −131.92, −131.93, −135.41, −135.41; ESIMS m/z 215 ([M+H]$^+$).

3-Amino-2,6-dichloro-N-propylbenzamide (C116)

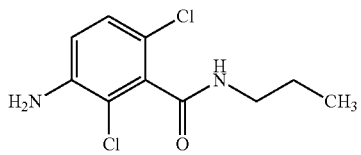

Isolated as a tan solid (0.089 g, 72%): mp 165-168° C.; $^1$H NMR (400 MHz, DMSO-$d_6$) δ 8.47 (t, J=5.7 Hz, 1H), 7.10 (d, J=8.8 Hz, 1H), 6.77 (d, J=8.7 Hz, 1H), 3.16 (td, J=6.8, 5.6 Hz, 2H), 1.50 (h, J=7.2 Hz, 2H), 0.91 (t, J=7.4 Hz, 3H); ESIMS m/z 247 ([M+H]$^+$).

3-Amino-2,6-difluoro-N-(3,3,3-trifluoropropyl)benzamide (C117)

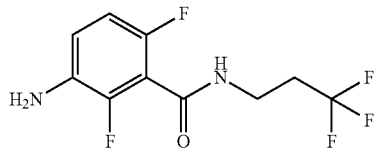 [SMILES: Nc1ccc(F)c(C(=O)NCCC(F)(F)F)c1F]

Isolated as an orange solid (0.104 g, 67%): mp 71-74° C.; $^1$H NMR (400 MHz, DMSO-$d_6$) δ 8.81 (t, J=5.7 Hz, 1H), 6.92-6.69 (m, 2H), 5.13 (s, 2H), 3.45 (q, J=6.5 Hz, 2H), 2.57-2.43 (m, 2H); $^{19}$F NMR (376 MHz, DMSO-$d_6$) δ −63.90, −131.90, −135.35; ESIMS m/z 269 ([M+H]$^+$).

3-Amino-2,6-dichloro-N-(3,3,3-trifluoropropyl)benzamide (C118)

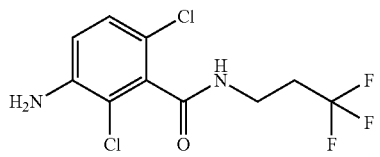 [SMILES: Nc1ccc(Cl)c(C(=O)NCCC(F)(F)F)c1Cl]

Isolated as a peach-colored solid (0.129 g, 80%): mp 144-147° C.; $^1$H NMR (400 MHz, DMSO-$d_6$) δ 8.77 (t, J=5.7 Hz, 1H), 7.11 (d, J=8.7 Hz, 1H), 6.79 (d, J=8.8 Hz, 1H), 5.65 (s, 2H), 3.43 (td, J=6.9, 5.7 Hz, 2H), 2.58-2.44 (m, 2H); $^{19}$F NMR (376 MHz, DMSO-$d_6$) δ −64.00; ESIMS m/z 301 ([M+H]$^+$).

3-Amino-2,6-dichloro-N-(2-fluoroethyl)benzamide (C119)

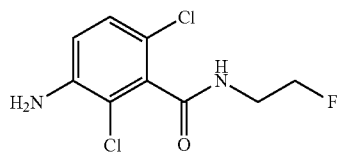

Isolated as a peach-colored solid (0.092 g, 74%): mp 170-172° C.; $^1$H NMR (400 MHz, DMSO-$d_6$) δ 8.78 (t, J=5.6 Hz, 1H), 7.11 (d, J=8.7 Hz, 1H), 6.78 (d, J=8.8 Hz, 1H), 5.63 (s, 2H), 4.50 (dt, J=47.4, 5.1 Hz, 2H), 3.51 (dq, J=26.6, 5.3 Hz, 2H); $^{19}$F NMR (376 MHz, DMSO-$d_6$) δ 16.09; ESIMS m/z 251 ([M+H]$^+$).

3-Amino-2,6-dichloro-N-(3-chloropropyl)benzamide (C120)

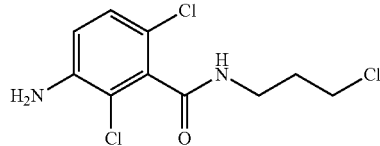

Isolated as a peach solid (0.128 g, 84%): mp 124-127° C.; $^1$H NMR (400 MHz, DMSO-$d_6$) δ 8.59 (t, J=5.7 Hz, 1H), 7.11 (d, J=8.7 Hz, 1H), 6.78 (d, J=8.8 Hz, 1H), 5.64 (s, 2H), 3.71 (t, J=6.6 Hz, 2H), 3.33 (d, J=5.8 Hz, 5H), 1.95 (p, J=6.7 Hz, 2H); ESIMS m/z 281 ([M+H]$^+$).

3-Amino-2,6-difluoro-N-(2-fluoroethyl)benzamide (C121)

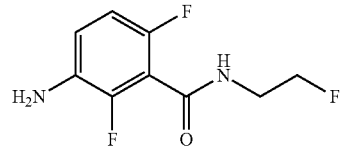 [SMILES: Nc1ccc(F)c(C(=O)NCCF)c1F]

Isolated as a purple solid (0.079 g, 74%): mp 97-99° C.; $^1$H NMR (400 MHz, DMSO-$d_6$) δ 8.83 (t, J=5.6 Hz, 1H), 6.89-6.71 (m, 2H), 5.11 (s, 2H), 4.49 (dt, J=47.5, 5.0 Hz, 2H), 3.52 (dq, J=27.0, 5.2 Hz, 2H); $^{19}$F NMR (376 MHz, DMSO-$d_6$) δ 15.42, −131.81, −131.82, −135.24, −135.25; ESIMS m/z 219 ([M+H]$^+$).

3-Amino-N-(3-chloropropyl)-2,6-difluorobenzamide (C122)

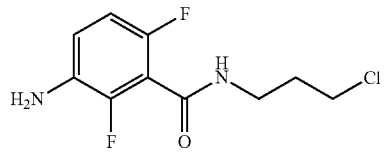 [SMILES: Nc1ccc(F)c(C(=O)NCCCCl)c1F]

Isolated as an amber oil (0.083 g, 73%): $^1$H NMR (400 MHz, DMSO-$d_6$) δ 8.67 (t, J=5.7 Hz, 1H), 6.93-6.66 (m, 2H), 5.12 (s, 2H), 3.68 (t, J=6.6 Hz, 2H), 3.34 (q, J=6.4 Hz, 2H), 1.93 (p, J=6.6 Hz, 2H); $^{19}$F NMR (376 MHz, DMSO-$d_6$) δ −132.00, −132.00, −135.48, −135.48; ESIMS m/z 249 ([M+H]$^+$).

3-Amino-N-(2,4-difluorophenyl)-2,6-difluorobenzamide (C123)

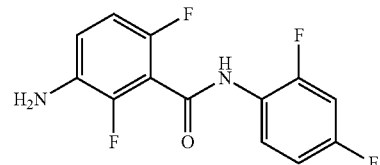

Isolated as a peach-colored solid (0.077 g, 46%): mp 147-150° C.; $^1$H NMR (400 MHz, DMSO-d$_6$) δ 10.51 (s, 1H), 7.75 (td, J=8.9, 6.1 Hz, 1H), 7.37 (ddd, J=11.4, 9.2, 2.8 Hz, 1H), 7.12 (tt, J=8.7, 1.9 Hz, 1H), 6.95-6.77 (m, 2H), 5.20 (s, 2H); $^{19}$F NMR (376 MHz, DMSO-d$_6$) δ −113.26, −113.28, −117.37, −117.39, −131.64, −131.65, −134.94, −134.95; ESIMS m/z 285 ([M+H]$^+$).

3-Amino-2,6-difluoro-N-(4-fluorophenyl)benzamide (C124)

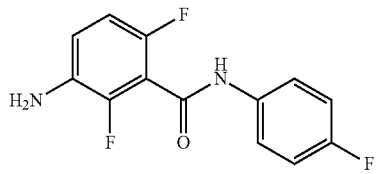

Isolated as a light-orange solid (0.114 g, 77%): mp 164-167° C.; $^1$H NMR (400 MHz, DMSO-d$_6$) δ 10.74 (s, 1H), 7.82-7.62 (m, 2H), 7.20 (t, J=8.9 Hz, 2H), 7.04-6.68 (m, 2H), 5.22 (s, 2H); $^{19}$F NMR (376 MHz, DMSO-d$_6$) δ −118.34, −118.36, −131.90, −131.90, −135.32, −135.33; ESIMS m/z 267 ([M+H]$^+$).

N-(4-Acetamidophenyl)-3-amino-2,6-difluorobenzamide (C125)

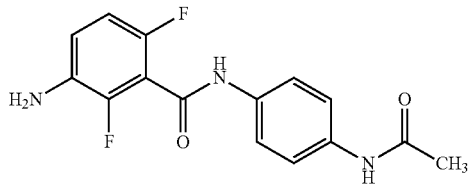

Isolated as a white solid (0.017 g, 54%): mp 210-213° C.; $^1$H NMR (400 MHz, DMSO-d$_6$) δ 10.59 (s, 1H), 9.92 (s, 1H), 7.60 (d, J=9.0 Hz, 2H), 7.54 (d, J=9.0 Hz, 2H), 6.94-6.77 (m, 2H), 5.19 (s, 2H), 2.03 (s, 3H); $^{19}$F NMR (376 MHz, DMSO-d$_6$) δ −131.84, −131.85, −135.29, −135.30; ESIMS m/z 306 ([M+H]$^+$).

N-(4-Acetamidophenyl)-3-amino-2,6-dichlorobenzamide (C126)

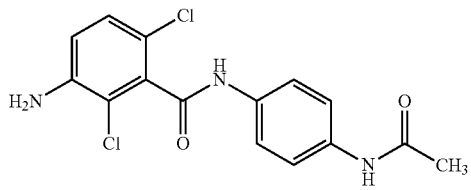

Isolated as a gray solid (0.029 g, 25%): mp 215-278° C.; $^1$H NMR (400 MHz, DMSO-d$_6$) δ 10.50 (s, 1H), 9.91 (s, 1H), 7.62-7.56 (m, 2H), 7.56-7.50 (m, 2H), 7.17 (d, J=8.8 Hz, 1H), 6.84 (d, J=8.8 Hz, 1H), 5.70 (s, 2H), 2.02 (s, 3H); ESIMS m/z 338 ([M+H]$^+$).

3-Amino-2,6-dichloro-N-(4-fluorophenyl)benzamide (C127)

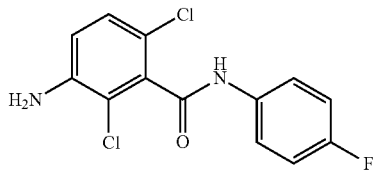

Isolated as a white solid (0.093 g, 81%): mp 204-207° C.; $^1$H NMR (400 MHz, DMSO-d$_6$) δ 10.65 (s, 1H), 7.75-7.66 (m, 2H), 7.24-7.14 (m, 3H), 6.85 (d, J=8.8 Hz, 1H), 5.73 (s, 2H); $^{19}$F NMR (376 MHz, DMSO-d$_6$) δ −118.56; ESIMS m/z 299 ([M+H]$^+$).

3-Amino-2,6-dichloro-N-phenylbenzamide (C128)

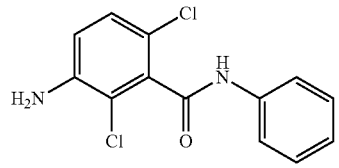 [SMILES: Nc1ccc(Cl)c(C(=O)Nc2ccccc2)c1Cl]

Isolated as a white solid (0.129 g, 91%): mp 172-175; $^1$H NMR (400 MHz, DMSO-d$_6$) δ 10.58 (s, 1H), 7.73-7.63 (m, 2H), 7.41-7.27 (m, 2H), 7.18 (d, J=8.8 Hz, 1H), 7.14-7.06 (m, 1H), 6.85 (d, J=8.8 Hz, 1H), 5.72 (s, 2H), ESIMS m/z 281 ([M+H]$^+$).

3-Amino-2,6-dichloro-N-(2,4-difluorophenyl)benzamide (C129)

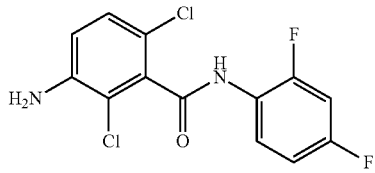 [SMILES: Nc1ccc(Cl)c(C(=O)Nc2ccc(F)cc2F)c1Cl]

Isolated as a white solid (0.127 g, 87%): mp 187-189° C.; $^1$H NMR (400 MHz, DMSO-d$_6$) δ 10.47 (s, 1H), 7.76 (td, J=8.9, 6.2 Hz, 1H), 7.35 (ddd, J=10.7, 9.1, 2.9 Hz, 1H), 7.23-7.08 (m, 2H), 6.84 (d, J=8.8 Hz, 1H), 5.71 (s, 2H); $^{19}$F NMR (376 MHz, DMSO-d$_6$) δ −113.48, −113.50, −117.40, −117.41; ESIMS m/z 317 ([M+H]$^+$).

3-Amino-N-(4-aminophenyl)-2,6-dichloro-N-methylbenzamide (C130)

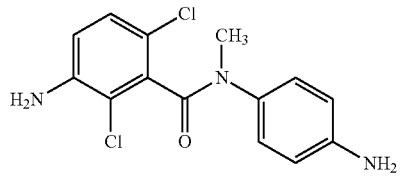 [SMILES: CN(C(=O)c1c(Cl)ccc(N)c1Cl)c1ccc(N)cc1]

Isolated as a waxy gray solid (0.052 g, 80%): $^1$H NMR (400 MHz, DMSO-$d_6$) δ 7.03-6.89 (m, 3H), 6.58 (d, J=8.7 Hz, 1H), 6.38-6.31 (m, 2H), 5.47 (s, 2H), 5.10 (s, 2H), 3.24 (s, 3H); ESIMS m/z 310 ([M+H]$^+$).

tert-Butyl-N-[3-[(3-amino-2,6-dichlorobenzoyl)amino]-2,6-difluorophenyl]-N-tert-butoxycarbonyl-carbamate (C131)

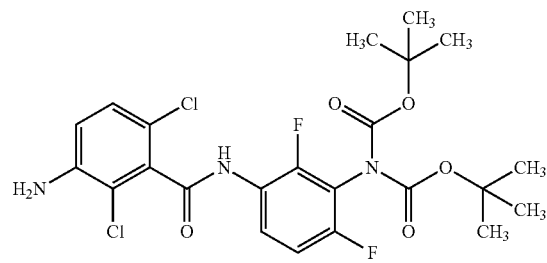

Isolated as a waxy white solid (0.166 g, 61%): mp 84-89° C.; $^1$H NMR (400 MHz, DMSO-$d_6$) δ 10.58 (s, 1H), 7.76 (td, J=8.8, 5.8 Hz, 1H), 7.26 (td, J=9.2, 1.7 Hz, 1H), 7.18 (d, J=8.7 Hz, 1H), 6.85 (d, J=8.8 Hz, 1H), 5.73 (s, 2H), 1.40 (s, 18H); $^{19}$F NMR (376 MHz, DMSO-$d_6$) δ -123.71, -126.64; ESIMS m/z 530 ([M-H]$^-$).

3-Amino-2,6-difluoro-N-phenylbenzamide (C132)

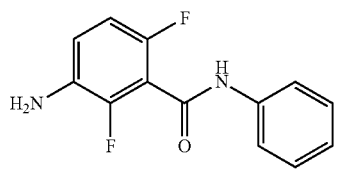 [SMILES: Nc1ccc(F)c(C(=O)Nc2ccccc2)c1F]

Isolated as a tan solid (0.109 g, 85%): mp 173-176° C.; $^1$H NMR (400 MHz, DMSO-$d_6$) δ 10.67 (s, 1H), 7.75-7.64 (m, 2H), 7.41-7.30 (m, 2H), 7.19-7.07 (m, 1H), 6.98-6.77 (m, 2H), 5.21 (s, 2H); $^{19}$F NMR (376 MHz, DMSO-$d_6$) δ -131.91, -131.92, -135.34, -135.35; ESIMS m/z 249 ([M+H]$^+$).

tert-Butyl-N-[3-[(3-amino-2,6-difluorobenzoyl)amino]-2,6-difluorophenyl]-N-tert-butoxycarbonyl-carbamate (C133)

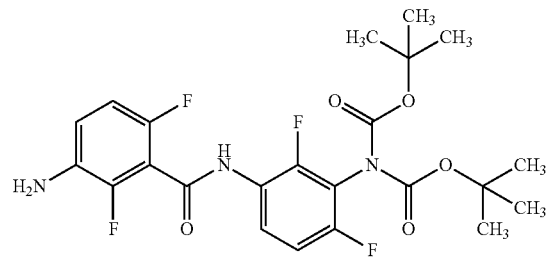 [SMILES: CC(C)(C)OC(=O)N(C(=O)OC(C)(C)C)c1c(F)ccc(NC(=O)c2c(F)ccc(N)c2F)c1F]

Isolated as an orange solid (0.086 g, 61%): mp 148-151° C.; $^1$H NMR (400 MHz, DMSO-$d_6$) δ 10.62 (s, 1H), 7.75 (td, J=8.8, 5.8 Hz, 1H), 7.26 (td, J=9.3, 1.7 Hz, 1H), 6.99-6.78 (m, 2H), 5.22 (s, 2H), 1.40 (s, 18H); $^{19}$F NMR (376 MHz, DMSO-$d_6$) δ -123.58, -126.68, -131.69, -131.70, -134.99, -135.00; ESIMS m/z 498 ([M-H]$^-$).

Example 58: Preparation of tert-Butyl (4-(5-amino-2-chlorobenzamido)-3-methylphenyl)carbamate (C134)

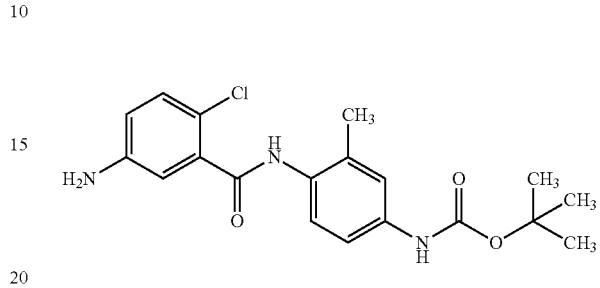

To a solution of tert-butyl (4-(2-chloro-5-nitrobenzamido)-3-methylphenyl)carbamate (C153) (2.2 g, 5.42 mmol) in ethyl acetate (54 ml) under N$_2$ was added Pd/C (0.95 g, 0.445 mmol). The reaction mixture was placed under approx. one atmosphere of hydrogen (balloon) and stirred overnight at room temperature. The reaction mixture was filtered through a plug of Celite® and concentrated under reduced pressure to afford the title compound as a brown foam (2.09 g, 92%): $^1$H NMR (400 MHz, DMSO-$d_6$) δ 9.68 (s, 1H), 9.28 (s, 1H), 7.35 (d, J=2.2 Hz, 1H), 7.26 (dd, J=8.6, 2.4 Hz, 1H), 7.18 (d, J=8.6 Hz, 1H), 7.12 (d, J=8.6 Hz, 1H), 6.75 (d, J=2.7 Hz, 1H), 6.64 (dd, J=8.6, 2.7 Hz, 1H), 5.64 (s, 2H), 2.21 (s, 3H), 1.48 (s, 9H); $^{13}$C NMR (101 MHz, DMSO-$d_6$) δ 165.69, 152.77, 147.30, 137.32, 137.27, 133.57, 130.14, 129.79, 126.41, 119.77, 115.93, 115.55, 113.84, 78.91, 54.86, 28.13, 18.21; ESIMS m/z 374 ([M-H]$^-$).

The following compounds were prepared in like manner to the procedure outlined in Example 58:

tert-Butyl-N-((tert-butoxy)carbonyl)-N-(3-(5-amino-2-chlorobenzamido)-2,6-difluorophenyl)carbamate (C135)

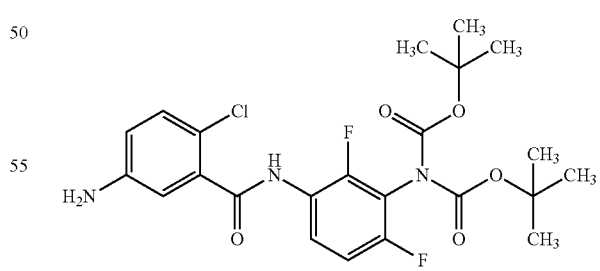

Isolated as a white solid (2.89 g, 59%): $^1$H NMR (400 MHz, DMSO-$d_6$) δ 10.28 (s, 1H), 7.67 (td, J=8.8, 5.8 Hz, 1H), 7.24 (td, J=9.3, 1.7 Hz, 1H), 7.13 (d, J=8.6 Hz, 1H), 6.73 (d, J=2.7 Hz, 1H), 6.65 (dd, J=8.6, 2.8 Hz, 1H), 5.48 (s, 2H), 1.40 (s, 18H); $^{19}$F NMR (376 MHz, DMSO-$d_6$) δ -123.86, -126.24; ESIMS m/z 496 ([M-H]$^-$).

5-Amino-2-chloro-N-(3-(2,2-difluoroacetamido)-2,4-difluorophenyl)benzamide (C136)

Example 60: Preparation of 2-cyano-N-(2,4-difluorophenyl)-N-methyl-5-nitrobenzamide (C138)

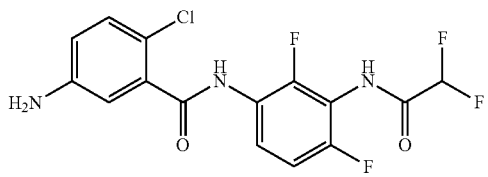

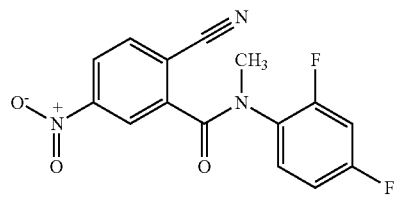

Isolated as a brown foam (0.485 g, 97%): ESIMS m/z 376 ([M+H]+), $^1$H NMR (400 MHz, DMSO-$d_6$) δ 10.77 (s, 1H), 10.28 (s, 1H), 7.73-7.54 (m, 1H), 7.31-7.18 (m, 1H), 7.13 (d, J=8.6 Hz, 1H), 6.73 (d, J=2.8 Hz, 1H), 6.70-6.27 (m, 2H), 5.49 (s, 2H). $^{19}$F NMR (376 MHz, DMSO-$d_6$) δ −120.94 (d, J=2.6 Hz), −124.00 (d, J=2.7 Hz), −125.80.

Example 59: Preparation of tert-butyl-N-((tert-butoxyl)carbonyl)-N-(5-(5-amino-2-chlorobenzamido)-2,4-difluorophenyl)carbamate (C137)

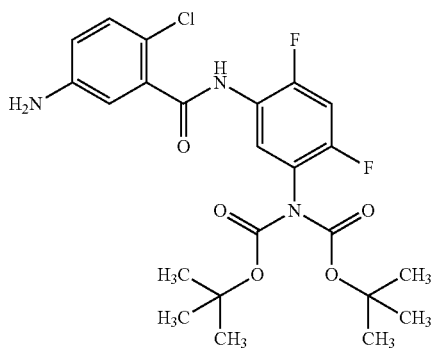 [SMILES: CC(C)(C)OC(=O)N(C(=O)OC(C)(C)C)c1cc(NC(=O)c2cc(N)ccc2Cl)c(F)cc1F]

To a vial containing tert-butyl-N-((tert-butoxy)carbonyl)-N-(5-amino-2,4-difluorophenyl)carbamate (C183) (0.4 g, 1.16 mmol) were added 2-chloro-5-nitrobenzoic acid (0.23 g, 1.16 mmol), 4-dimethylaminopyridine (0.15 g, 1.28 mmol), 1-ethyl-3-(3-dimethylaminopropyl)carbodiimide (0.33 g, 1.74 mmol), and dichloromethane (6 mL). The reaction mixture was stirred at room temperature for 18 h then was directly loaded onto a prepacked Celite® cartridge and flushed through a silica gel column with ethyl acetate/hexanes. The resulting yellow foam was dissolved in ethyl acetate (2 mL) and 10% palladium on carbon (10 mg, 0.009 mmol) was added. The slurry was stirred under an atmosphere of hydrogen gas (balloon) for 7 hours. The slurry was filtered through a pad of Celite® with ethyl acetate and concentrated. Purification by flash column chromatography gave the title compound as a white foam (0.1479 g, 25%): $^1$H NMR (400 MHz, DMSO-$d_6$) δ 10.27 (s, 1H), 7.67 (t, J=8.1 Hz, 1H), 7.50 (t, J=10.1 Hz, 1H), 7.12 (d, J=8.6 Hz, 1H), 6.73 (d, J=2.7 Hz, 1H), 6.65 (dd, J=8.6, 2.7 Hz, 1H), 5.48 (s, 2H), 1.40 (s, 18H); $^{19}$F NMR (376 MHz, DMSO-$d_6$) δ −117.30 (d, J=6.4 Hz), −122.18 (d, J=6.4 Hz); ESIMS m/z 495.6 [(M−H)−].

To a solution of 2-bromo-N-(2,4-difluorophenyl)-N-methyl-5-nitrobenzamide (0.120 g, 0.323 mmol) (C149) in N,N-dimethylformamide (1.6 mL) was added copper(I) cyanide (0.145 g, 1.62 mmol). The reaction mixture was degassed under vacuum, backfilled with nitrogen, capped in a 2-mL microwave vial, and heated at 160° C. for 20 minutes in a Biotage Initiator® microwave reactor with external IR-sensor temperature monitoring from the side of the vessel. The reaction mixture was diluted with ethyl acetate while stirring vigorously and then filtered through Celite® washing with ethyl acetate. The filtrate was washed with brine. The organic phase was dried over magnesium sulfate, filtered, and concentrated. Purification by flash column chromatography using 0-25% ethyl acetate/hexanes as eluent provided the title compound as a mixture of amide rotamers as a beige solid (0.051 g, 47%): $^1$H NMR (500 MHz, CDCl$_3$) δ 8.20 (d, J=8.1 Hz, 2H), 7.81-7.72 (m, 1H), 7.39 (td, J=8.8, 5.7 Hz, 1H), 6.86 (dddd, J=8.9, 7.5, 2.8, 1.5 Hz, 1H), 6.76 (ddd, J=10.6, 8.3, 2.8 Hz, 1H), 3.50 (s, 3H); $^{19}$F NMR (471 MHz, CDCl$_3$) δ −106.15 (h, J=8.1 Hz), −115.12 (q, J=8.9 Hz); ESIMS m/z 318 ([M+H]$^+$).

Example 61: Preparation of N-allyl-2-chloro-N-(2-cyano-4-fluorophenyl)-5-nitrobenzamide (C139)

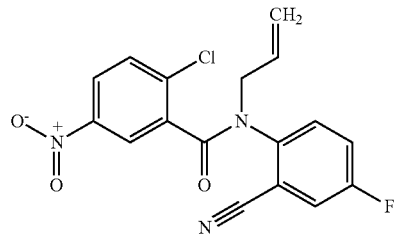

To a solution of 2-chloro-N-(2-cyano-4-fluorophenyl)-5-nitrobenzamide (C152) (0.200 g, 0.626 mmol) in tetrahydrofuran (6.3 mL) cooled in an ice bath was added sodium hydride (60% oil immersion, 0.030 g, 0.75 mmol). The slurry was stirred for 30 minutes, and allyl bromide (0.081 mL, 0.94 mmol) was added. The reaction mixture was stirred for 18 hours. The reaction was quenched by the slow addition of water (10 mL) and diluted with ethyl acetate (10 mL). The organic layer was dried over magnesium sulfate, filtered, and concentrated. Purification by flash column chromatography using 0-25% ethyl acetate/hexanes as eluent provided the title compound as a mixture of amide rotamers as an off-white solid (0.162 g, 68%): Major isomer—$^1$H NMR (500 MHz, CDCl$_3$) δ 8.31 (d, J=2.7 Hz, 1H), 8.05 (dd, J=8.8, 2.7 Hz, 1H), 7.42 (d, J=8.8 Hz, 1H), 7.40 (s, 1H), 7.30 (dd, J=7.4, 2.9 Hz, 1H), 7.20 (ddd, J=8.9, 7.5, 3.0

Hz, 1H), 5.99 (ddt, J=17.0, 10.1, 6.7 Hz, 1H), 5.30-5.17 (m, 2H), 4.89 (dd, J=14.6, 6.0 Hz, 1H), 4.29 (dd, J=14.6, 7.5 Hz, 1H); $^{19}$F NMR (471 MHz, CDCl$_3$) δ −108.13 (q, J=6.9 Hz); ESIMS m/z 360 ([M+H]$^+$).

The following compounds were prepared in like manner to the procedure outlined in Example 61:

2-Chloro-N-(2-cyano-4-fluorophenyl)-5-nitro-N-(prop-2-yn-1-yl)benzamide (C140)

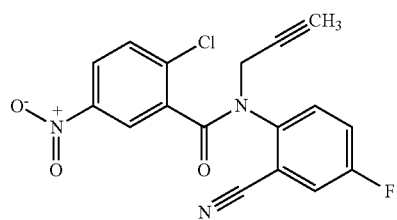

A mixture of amide rotamers was isolated as a white foam (0.128 g, quant.): Major isomer—$^1$H NMR (500 MHz, CDCl$_3$) δ 8.30 (d, J=2.6 Hz, 1H), 8.07 (dd, J=8.8, 2.6 Hz, 1H), 7.54 (dt, J=6.7, 3.4 Hz, 1H), 7.43 (d, J=8.8 Hz, 1H), 7.33 (dd, J=7.3, 2.9 Hz, 1H), 7.23 (ddd, J=8.9, 7.5, 3.0 Hz, 1H), 5.21 (dd, J=17.4, 2.5 Hz, 1H), 4.41 (m, 1H), 2.34 (t, J=2.5 Hz, 1H); $^{19}$F NMR (471 MHz, CDCl$_3$) δ −107.37 (q, J=6.8 Hz); ESIMS m/z 358 ([M+H]$^+$).

(2-Chloro-N-(2-cyano-4-fluorophenyl)-5-nitrobenzamido)methyl acetate (C141)

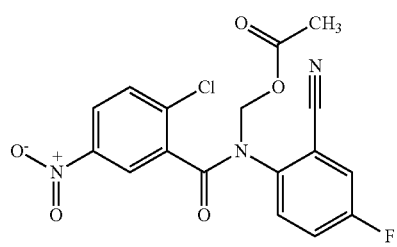

A mixture of amide rotamers was isolated as a yellow oil (0.067 g, 52%): $^1$H NMR (500 MHz, CDCl$_3$) δ 8.50-8.34 (m, 1H), 8.35-8.04 (m, 1H), 7.73-7.39 (m, 3H), 7.34-7.19 (m, 1H), 5.99-5.80 (m, 1H), 5.56-5.28 (m, 1H), 2.14 (d, J=4.0 Hz, 3H); $^{19}$F NMR (471 MHz, CDCl$_3$) δ −108.78 (q, J=7.0 Hz); ESIMS m/z 392 ([M+H]$^+$).

2-Chloro-N-(2-cyano-4-fluorophenyl)-N-ethyl-5-nitrobenzamide (C142)

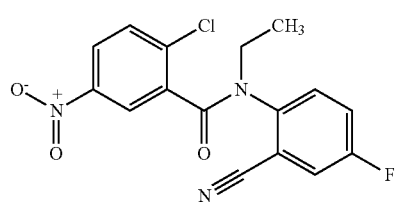

A mixture of amide rotamers was isolated as a white solid (0.110 g, 64%): Major isomer—$^1$H NMR (500 MHz, CDCl$_3$) δ 8.32-8.28 (m, 1H), 8.04 (dd, J=8.8, 2.7 Hz, 1H), 7.40 (dd, J=8.9, 5.2 Hz, 2H), 7.32 (dd, J=7.4, 2.9 Hz, 1H), 7.22 (ddd, J=8.9, 7.4, 2.9 Hz, 1H), 4.27 (dq, J=14.2, 7.2 Hz, 1H), 3.84 (dq, J=14.1, 7.1 Hz, 1H), 1.31 (t, J=7.2 Hz, 3H); $^{19}$F NMR (471 MHz, CDCl$_3$) δ −108.27 (s); ESIMS m/z 348 ([M+H]$^+$).

N-Benzyl-2-chloro-N-(2-cyano-4-fluorophenyl)-5-nitrobenzamide (C143)

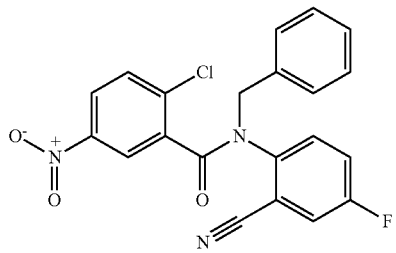

A mixture of amide rotamers was isolated as a white foam (0.216 g, 80%): $^1$H NMR (500 MHz, CDCl$_3$) δ 8.32-8.27 (m, 1H), 8.03 (dd, J=8.8, 2.6 Hz, 1H), 7.40 (d, J=8.8 Hz, 1H), 7.33-7.24 (m, 6H), 7.02-6.92 (m, 2H), 5.77 (m, 1H), 4.60 (m, 1H); $^{19}$F NMR (471 MHz, CDCl$_3$) δ −107.79-−108.26 (m); ESIMS m/z 410 ([M+H]$^+$).

tert-Butyl N-tert-butoxycarbonyl-N-[3-[(2-chloro-5-nitro-benzoyl)-methyl-amino]-2,6-difluoro-phenyl]carbamate (C144)

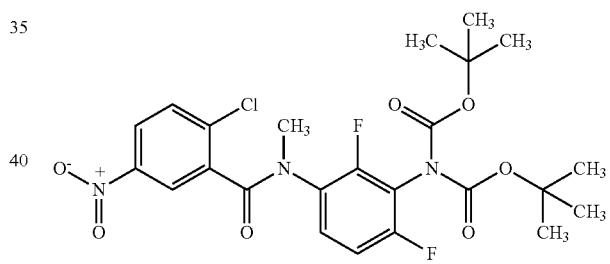

A mixture of amide rotamers was isolated as a pale yellow oil (0.179 g, 55%): $^1$H NMR (500 MHz, CDCl$_3$) δ 8.15 (dd, J=2.6, 1.5 Hz, 1H), 8.03 (dd, J=8.8, 2.7 Hz, 1H), 7.36 (d, J=8.8 Hz, 1H), 7.29-7.23 (m, 1H), 6.81 (td, J=8.8, 1.9 Hz, 1H), 3.45 (s, 3H), 1.41 (dd, J=39.8, 7.5 Hz, 18H); $^{19}$F NMR (471 MHz, CDCl$_3$) δ −115.52 (s), −120.91-−123.25 (m); ESIMS m/z 541 ([M+H]$^+$).

tert-Butyl N-[3-[allyl-(2-chloro-5-nitro-benzoyl)amino]-2,6-difluoro-phenyl]-N-tert-butoxycarbonyl-carbamate (C145)

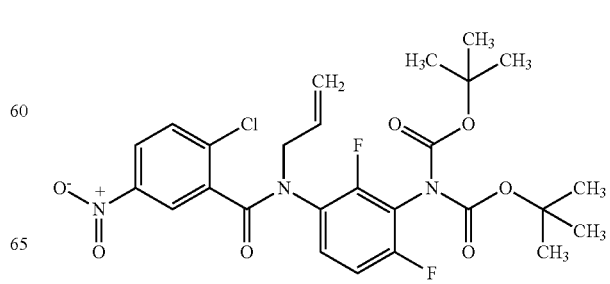

A mixture of amide rotamers was isolated as a colorless oil (0.068 g, 38%): $^1$H NMR (500 MHz, CDCl$_3$) δ 8.16 (t, J=2.2 Hz, 1H), 8.03 (dd, J=8.8, 2.7 Hz, 1H), 7.36 (d, J=8.8 Hz, 1H), 7.31-7.22 (m, 1H), 6.81 (td, J=8.8, 1.8 Hz, 1H), 5.95 (ddt, J=16.9, 10.2, 6.6 Hz, 1H), 5.26-5.16 (m, 2H), 4.61 (dd, J=14.9, 6.3 Hz, 1H), 4.34 (dd, J=14.7, 6.9 Hz, 1H), 1.46-1.32 (m, 18H); $^{19}$F NMR (471 MHz, CDCl$_3$) δ −114.18−−116.23 (m), −121.37 (s); ESIMS m/z 590 ([M+Na]$^+$).

tert-Butyl N-tert-butoxycarbonyl-N-[3-[(2-chloro-5-nitro-benzoyl)-prop-2-ynyl-amino]-2,6-difluoro-phenyl]carbamate (C146)

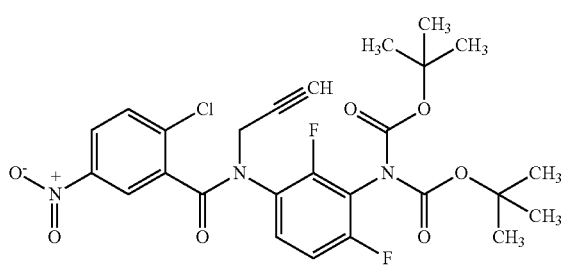

A mixture of amide rotamers was isolated as a beige sticky solid (0.144 g, 85%): $^1$H NMR (500 MHz, CDCl$_3$) δ 8.17 (t, J=2.2 Hz, 1H), 8.04 (dd, J=8.8, 2.7 Hz, 1H), 7.47-7.40 (m, 1H), 7.37 (d, J=8.8 Hz, 1H), 6.84 (td, J=8.8, 1.8 Hz, 1H), 4.99 (d, J=17.4 Hz, 1H), 4.43-4.31 (m, 1H), 2.29 (t, J=2.5 Hz, 1H), 1.40 (dd, J=31.4, 3.8 Hz, 18H); $^{19}$F NMR (471 MHz, CDCl$_3$) δ −114.79 (s), −121.53 (s); ESIMS m/z 588 ([M+Na]$^+$).

tert-Butyl (3-(2-chloro-N-methyl-5-nitrobenzamido)-2,6-difluorophenyl)(methyl)carbamate (C147)

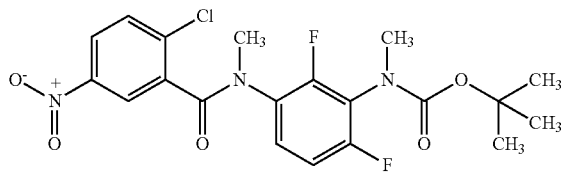

A mixture of amide rotamers was isolated as a colorless oil (0.071 g, 26%): $^1$H NMR (500 MHz, CDCl$_3$) δ 8.16 (d, J=51.3 Hz, 1H), 8.03 (ddd, J=9.6, 6.8, 2.6 Hz, 1H), 7.42 (d, J=8.7 Hz, 1H), 7.21-6.98 (m, 1H), 6.86-6.57 (m, 1H), 3.65-3.43 (m, 3H), 3.22-2.92 (m, 3H), 1.40 (m, 9H); $^{19}$F NMR (471 MHz, CDCl$_3$) δ −115.40 (s), −122.10 (s); ESIMS m/z 455 ([M+H]$^+$).

Example 62: Preparation of N-(2,6-difluoro-3-nitrophenyl)-2,2-difluoro-N-methylacetamide (C148)

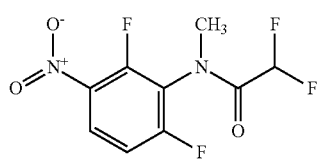 [SMILES: CN(C(=O)C(F)F)c1c(F)ccc([N+](=O)[O-])c1F]

To a solution of N-(2,6-difluoro-3-nitrophenyl)-2,2-difluoroacetamide (C193) (0.400 g, 1.59 mmol) in dry N,N-dimethylformamide (12 mL) cooled in an ice bath was added sodium hydride (60% oil dispersion, 0.076 g, 1.90 mmol). The slurry was stirred for 5 minutes in the ice bath. The bath was removed and the reaction was stirred an additional 40 minutes. Iodomethane (0.099 mL, 1.59 mmol) was added. The reaction mixture was stirred at room temperature overnight. The reaction was quenched with water (15 mL) and diluted with ethyl acetate (40 mL). The phases were separated, and the organic layer was washed with 1:1 brine/water (4×20 mL). The organic layer was poured through a phase separator to dry and then concentrated under reduced pressure to afford the title compound as a yellow oil (0.30 g, 71%): $^1$H NMR (400 MHz, DMSO-d$_6$) δ rotamers 8.45 (ddd, J=9.5, 8.5, 5.7 Hz, 0.65H), 8.36 (ddd, J=9.5, 8.4, 5.5 Hz, 0.35H), 7.69-7.52 (m, 1H), 7.05 (t, J=52.1 Hz, 0.35H), 6.43 (t, J=51.6 Hz, 0.65H), 3.43 (d, J=1.2 Hz, 1H), 3.25 (s, 2H); $^{19}$F NMR (376 MHz, DMSO-d$_6$) δ rotamers −106.63 (d, J=10.3 Hz), −106.82−−107.10 (m), −120.60−−120.78 (m), −120.98 (d, J=10.4 Hz), −124.26−−124.99 (m), −124.80−−125.41 (m), −126.78 (d, J=3.4 Hz); EIMS m/z 266.

Example 63: Preparation of 2-bromo-N-(2,4-difluorophenyl)-N-methyl-5-nitrobenzamide (C149)

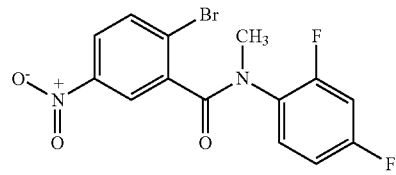

2-Bromo-5-nitrobenzoic acid (0.500 g, 2.03 mmol) and 4-dimethylaminopyridine (0.273 g, 2.24 mmol) were sequentially added to a stirred mixture of 2,4-difluoro-N-methylamine (0.349 mL, 2.44 mmol) and 1-ethyl-3-(3-dimethylaminopropyl)carbodiimide hydrochloride (0.584 g, 3.05 mmol) in dichloromethane (13.5 mL) at room temperature. The reaction was stirred at room temperature for 20 hours. The reaction mixture was diluted with dichloromethane and washed with saturated aqueous sodium bicarbonate followed by hydrochloric acid (1 N). The organic phase was dried over magnesium sulfate, filtered, and concentrated. Purification by flash column chromatography using 0-25% ethyl acetate/hexanes as eluent provided the title compound as a beige solid (0.149 g, 19%): $^1$HNMR (500 MHz, CDCl$_3$) δ 8.29 (d, J=2.7 Hz, 0H), 8.21-8.14 (m, 0H), 8.07 (dd, J=2.7, 1.4 Hz, 1H), 7.93 (dd, J=8.8, 2.7 Hz, 1H), 7.86 (dd, J=8.7, 6.2 Hz, 0H), 7.61 (d, J=8.8 Hz, 1H), 7.47-7.39 (m, 0H), 7.30 (dt, J=9.0, 4.5 Hz, 1H), 7.04-6.97 (m, 0H), 6.83-6.72 (m, 2H), 3.45 (s, 4H), 3.19 (s, 1H); 19F NMR (471 MHz, CDCl$_3$) δ −106.76, −108.81 (dt, J=14.9, 7.9 Hz), −114.38, −115.36 (q, J=8.6 Hz); ESIMS m/z 373 ([M+H]$^+$).

Example 64: Preparation of 2-chloro-N-(4-fluorophenyl)-5-nitrobenzamide (C150)

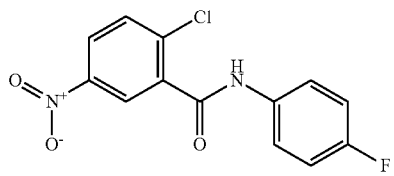 [SMILES: O=C(Nc1ccc(F)cc1)c1cc([N+](=O)[O-])ccc1Cl]

2-Chloro-5-nitrobenzoic acid (0.250 g, 1.24 mmol) and 4-dimethylaminopyridine (0.197 g, 1.61 mmol) were sequentially added to a stirred mixture of 4-fluoroaniline (0.141 mL, 1.49 mmol) and 1-ethyl-3-(3-dimethylaminopropyl)carbodiimide hydrochloride (0.357 g, 1.86 mmol) in 1,2-dichloroethane (12.4 mL) at room temperature. The reaction was stirred at room temperature for 20 hours. The reaction mixture was diluted with dichloromethane and washed with saturated aqueous sodium bicarbonate followed by hydrochloric acid (1 N) to provide the title compound as a light brown solid (0.188 g, 49%): $^1$H NMR (400 MHz, CDCl$_3$) δ 8.59 (d, J=2.7 Hz, 1H), 8.26 (dd, J=8.8, 2.8 Hz, 1H), 7.90 (s, 1H), 7.66 (d, J=8.8 Hz, 1H), 7.64-7.57 (m, 2H), 7.15-7.05 (m, 2H); $^{19}$F NMR (376 MHz, CDCl$_3$) δ −116.03; ESIMS m/z 295 ([M+H]$^+$).

The following compounds were prepared in like manner to the procedure outlined in Example 64:

2-Chloro-N-(2,4-difluorophenyl)-5-nitrobenzamide (C151)

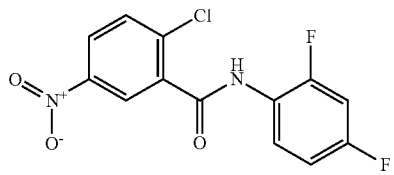 [SMILES: O=C(Nc1ccc(F)cc1F)c1cc([N+](=O)[O-])ccc1Cl]

Isolated as a light purple solid (1.48 g, 64%): $^1$H NMR (400 MHz, CDCl$_3$) δ 8.68 (d, J=2.7 Hz, 1H), 8.40 (td, J=9.1, 6.7 Hz, 1H), 8.30 (dd, J=8.8, 2.7 Hz, 1H), 8.09 (s, 1H), 7.69 (d, J=8.8 Hz, 1H), 7.04-6.89 (m, 2H); $^{19}$F NMR (376 MHz, CDCl$_3$) δ −113.04 (d, J=5.0 Hz), −125.45 (d, J=5.1 Hz); ESIMS m/z 313 ([M+H]$^+$).

2-Chloro-N-(2-cyano-4-fluorophenyl)-5-nitrobenzamide (C152)

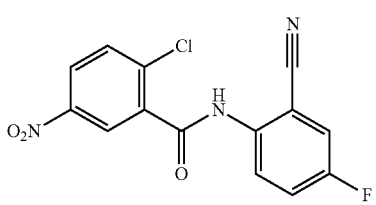 [SMILES: N#Cc1cc(F)ccc1NC(=O)c1cc([N+](=O)[O-])ccc1Cl]

Isolated as a white solid (0.439 g, 55%): $^1$H NMR (400 MHz, DMSO-d$_6$) δ 11.06 (s, 1H), 8.52 (d, J=2.8 Hz, 1H), 8.38 (dd, J=8.8, 2.8 Hz, 1H), 8.02-7.86 (m, 2H), 7.83-7.61 (m, 2H); $^{19}$F NMR (376 MHz, DMSO-d$_6$) δ −113.90; ESIMS m/z 320 ([M+H]$^+$).

tert-Butyl (4-(2-chloro-5-nitrobenzamido)-3-methylphenyl)carbamate (C153)

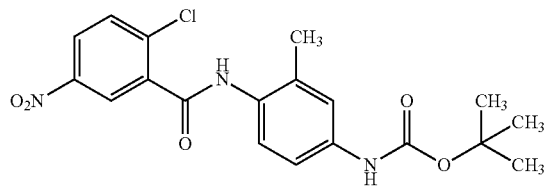 [SMILES: Cc1cc(NC(=O)OC(C)(C)C)ccc1NC(=O)c1cc([N+](=O)[O-])ccc1Cl]

Isolated as a yellow solid (2.19 g, 67%): mp 195-200° C.; $^1$H NMR (300 MHz, DMSO-d$_6$) δ 10.06 (s, 1H), 9.34 (s, 1H), 8.45 (d, J=2.7 Hz, 1H), 8.33 (dd, J=8.8, 2.8 Hz, 1H), 7.88 (d, J=8.8 Hz, 1H), 7.43-7.24 (m, 3H), 2.24 (s, 3H), 1.48 (s, 9H); ESIMS m/z 404 ([M−H]$^-$).

tert-Butyl-N-((tert-butoxy)carbonyl)-N-(3-(2-chloro-5-nitrobenzamido)-2,4-difluorophenyl)carbamate (C154)

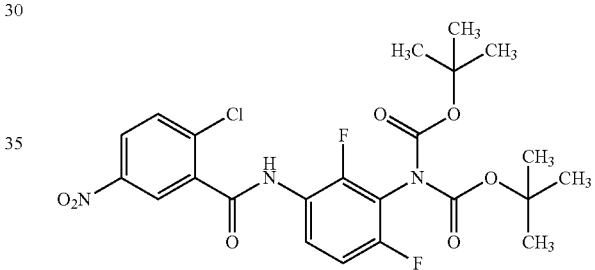

Isolated as a yellow oil (5.2 g, 66%): $^1$H NMR (400 MHz, DMSO-d$_6$) δ 10.69 (s, 1H), 8.51 (d, J=2.7 Hz, 1H), 8.35 (dd, J=8.8, 2.8 Hz, 1H), 7.97-7.79 (m, 2H), 7.30 (td, J=9.3, 1.7 Hz, 1H), 1.41 (s, 18H); $^{19}$F NMR (376 MHz, DMSO-d$_6$) δ −123.43, −127.02 (d, J=2.0 Hz); ESIMS m/z 526 ([M−H]$^-$).

Example 65: Preparation of tert-Butyl-N-tert-butoxycarbonyl-N-[3-[(2-chloro-3-fluoro-5-nitrobenzoyl)amino]-2,6-difluorophenyl]carbamate (C155)

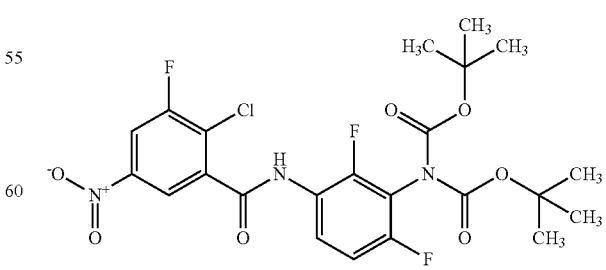

To a solution of 2-chloro-3-fluoro-5-nitrobenzoic acid (C206) (1.81 g, 8.25 mmol) and tert-butyl N-(5-amino-2,6-difluorophenyl)-N-tert-butoxycarbonyl carbamate (C182)

(2.84 g, 8.25 mmol) in ethyl acetate (41 mL) were added pyridine (1.96 g, 24.7 mmol) followed by a 50% solution of 2,4,6-tripropyl-1,3,5,2,4,6-trioxatriphosphinane 2,4,6-trioxide (9.82 mL, 16.5 mmol) in ethyl acetate, and the resulting gold solution was warmed to 48° C. and stirred for 12 hours. The reaction mixture was concentrated under reduced pressure to give a viscous, gold oil. The oil was dissolved in minimal dichloromethane (~8 mL) and adsorbed to Celite®. The adsorbed material was purified by automated flash chromatography using a gradient of 0-40% ethyl acetate in hexanes to give the title compound as a white solid (2.095 g, 83%): mp 167-169° C.; $^1$H NMR (400 MHz, DMSO-$d_6$) δ 10.76 (s, 1H), 8.52 (dd, J=8.8, 2.6 Hz, 1H), 8.43 (dd, J=2.6, 1.4 Hz, 1H), 7.89 (td, J=8.9, 5.8 Hz, 1H), 7.31 (td, J=9.3, 1.8 Hz, 1H), 1.41 (s, 18H); $^{19}$F NMR (376 MHz, DMSO-$d_6$) δ −109.64, −123.26, −127.07, −127.08; HRMS-ESI (m/z) [M+]$^+$ calcd for $C_{23}H_{23}ClF_3N_3O_7$, 545.1177; found, 545.1172.

Example 66: Preparation of 2,6-dichloro-N-(2,4-difluorophenyl)-3-nitrobenzamide (C156)

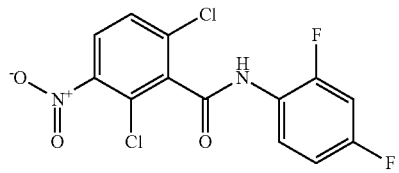

Step 1: To a suspension of 2,6-dichloro-3-nitrobenzoic acid (0.15 g, 0.64 mmol) in 1,2-dichloroethane (10 mL) were added two drops of N,N-dimethylformamide followed by the dropwise addition of oxalyl dichloride (0.40 g, 0.27 mL, 3.2 mmol), and the resulting light-yellow solution was stirred at room temperature for 16 hours. The solvent and excess oxalyl dichloride were evaporated under reduced pressure, and the resulting gold oil was dissolved in 1,2-dichloroethane (10 mL) and concentrated (repeated 2×) to give the intermediate acid chloride as a gold oil which was used without purification.

Step 2: To a solution of 2,4-difluoroaniline (0.082 g, 0.64 mmol) and N-ethyl-N-isopropylpropan-2-amine (0.17 g, 1.34 mmol) in 1,2-dichloroethane (1 mL) was added a solution of the freshly prepared acid chloride, 2,6-dichloro-3-nitrobenzoyl chloride (0.162 g, 0.64 mmol) in 1,2-dichloroethane (1 mL) dropwise at 0° C. The resulting light-orange solution was warmed to 50° C. and stirred for 8 hours. The reaction mixture was adsorbed to Celite® and purified by automated flash chromatography using a gradient of 0-60% ethyl acetate in hexanes as eluent to give the title compound as a tan solid (0.171 g, 75%): mp 199-202° C.; $^1$H NMR (500 MHz, DMSO-$d_6$) δ 10.83 (s, 1H), 8.21 (d, J=8.8 Hz, 1H), 7.94 (td, J=8.9, 6.1 Hz, 1H), 7.88 (d, J=8.8 Hz, 1H), 7.41 (ddd, J=10.9, 9.0, 2.9 Hz, 1H), 7.17 (dddd, J=9.5, 8.4, 2.9, 1.4 Hz, 1H); $^{19}$F NMR (471 MHz, DMSO-$d_6$) δ −112.94, −112.95, −112.96, −112.96, −112.97, −112.97, −112.98, −112.99, −113.00, −118.60, −118.62, −118.62, −118.64, −118.64, −118.66; ESIMS m/z 347 ([M+H]$^+$).

The following compounds were prepared in like manner to the procedure outlined in Example 66:

N-(4-Acetamidophenyl)-2,6-dichloro-3-nitrobenzamide (C157)

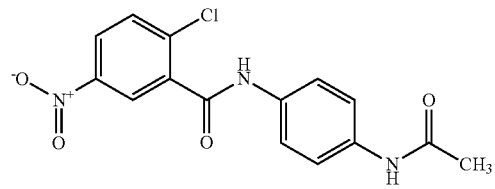

Isolated as a light-yellow solid (0.153 g, 63%): mp 268-270° C.; $^1$H NMR (400 MHz, DMSO-$d_6$) δ 10.82 (s, 1H), 9.97 (s, 1H), 8.20 (d, J=8.8 Hz, 1H), 7.89 (d, J=8.8 Hz, 1H), 7.58 (s, 4H), 2.04 (s, 3H); IR (thin film) 3640, 3250, 3054, 1656, 1527, 1310, 827, 706 cm$^{-1}$; ESIMS m/z 366 ([M−2H]$^-$).

2,6-Dichloro-N-(4-fluorophenyl)-3-nitrobenzamide (C158)

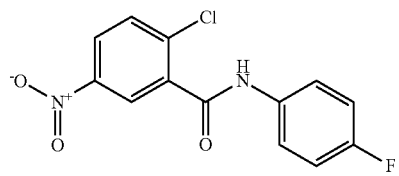

Isolated as a light-orange solid (0.148 g, 70%): mp 211-214° C.; $^1$H NMR (400 MHz, DMSO-$d_6$) δ 10.98 (s, 1H), 8.22 (d, J=8.8 Hz, 1H), 7.90 (d, J=8.8 Hz, 1H), 7.77-7.63 (m, 2H), 7.34-7.11 (m, 2H); $^{19}$F NMR (376 MHz, DMSO-$d_6$) δ −117.60; ESIMS m/z 329 ([M+H]$^+$).

2,6-Dichloro-3-nitro-N-phenylbenzamide (C159)

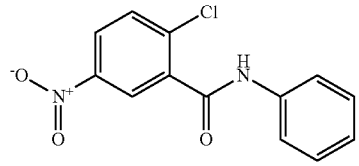

Isolated as a light-orange solid (0.173 g, 86%): mp 180-183° C.; NMR (500 MHz, DMSO-$d_6$) δ 10.90 (s, 1H), 8.22 (d, J=8.7 Hz, 1H), 7.90 (d, J=8.7 Hz, 1H), 7.70-7.64 (m, 2H), 7.42-7.34 (m, 2H), 7.22-7.08 (m, 1H); ESIMS m/z 311 ([M+H]$^+$).

N-(4-Aminophenyl)-2,6-dichloro-N-methyl-3-nitrobenzamide (C160)

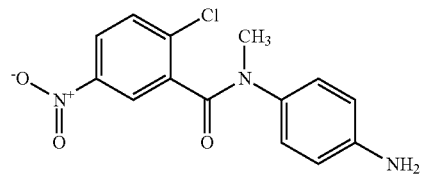

Isolated as a green solid (0.085 g, 36%): mp 176-180° C.; $^1$H NMR (500 MHz, DMSO-d$_6$) δ 7.93 (d, J=8.8 Hz, 1H), 7.63 (d, J=8.7 Hz, 1H), 7.02-6.97 (m, 2H), 6.41-6.35 (m, 2H), 5.23 (s, 2H), 3.30 (s, 3H); ESIMS m/z 340 ([M+H]$^+$).

tert-Butyl-N-tert-butoxycarbonyl-N-[3-[(2,6-dichloro-3-nitrobenzoyl)amino]-2,6-difluorophenyl] carbamate (C161)

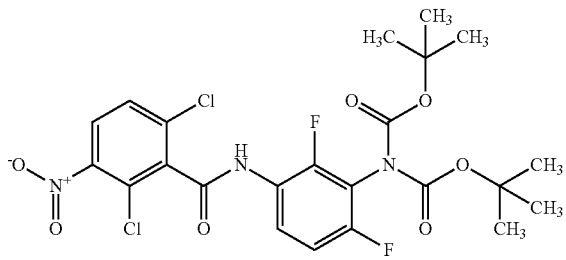

Isolated as a light-orange solid (0.302 g, 78%): mp 164-167° C.; $^1$H NMR (500 MHz, DMSO-d$_6$) δ 10.93 (s, 1H), 8.23 (d, J=8.8 Hz, 1H), 7.97-7.84 (m, 2H), 7.31 (td, J=9.3, 1.7 Hz, 1H), 1.40 (s, 18H); $^{19}$F NMR (471 MHz, DMSO-d$_6$) δ −123.11, −123.12, −123.14, −127.55, −127.57; ESIMS m/z 560 ([M−H]$^−$).

2,6-Difluoro-3-nitro-N-phenylbenzamide (C162)

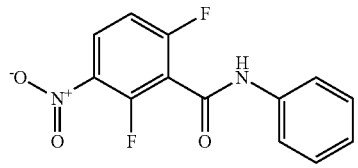

Isolated as a yellow solid (0.161 g, 90%): mp 161-163° C.; $^1$H NMR (500 MHz, DMSO-d$_6$) δ 10.98 (s, 1H), 8.42 (td, J=9.0, 5.6 Hz, 1H), 7.71-7.63 (m, 2H), 7.56 (ddd, J=9.4, 7.9, 1.5 Hz, 1H), 7.44-7.35 (m, 2H), 7.24-7.14 (m, 1H); $^{19}$F NMR (471 MHz, DMSO-d$_6$) δ −102.54, −102.56, −102.56, −102.57, −102.58, −102.60, −117.46, −117.48, −117.51; ESIMS m/z 279 ([M+H]$^+$).

2,6-Difluoro-N-(4-fluorophenyl)-3-nitrobenzamide (C163)

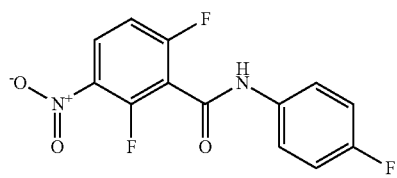

Isolated as a light-orange solid (0.178 g, 93%); mp 158-160° C.; $^1$H NMR (500 MHz, DMSO-d$_6$) δ 11.05 (s, 1H), 8.43 (td, J=9.0, 5.6 Hz, 1H), 7.76-7.65 (m, 2H), 7.56 (ddd, J=9.5, 8.0, 1.5 Hz, 1H), 7.25 (t, J=8.9 Hz, 2H); $^{19}$F NMR (471 MHz, DMSO-d$_6$) δ −102.47, −102.48, −102.49, −102.50, −102.50, −102.52, −117.37, −117.39, −117.40, −117.41, −117.42, −117.43, −117.44; ESIMS m/z 297 ([M+H]$^+$).

N-(4-Acetamidophenyl)-2,6-difluoro-3-nitrobenzamide (C164)

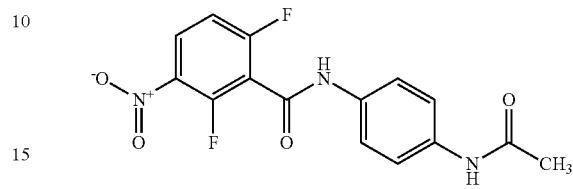

Isolated as a white solid (0.041 g, 19%): mp 251-255° C.; $^1$H NMR (500 MHz, DMSO-d$_6$) δ 10.90 (s, 1H), 9.97 (s, 1H), 8.41 (td, J=9.0, 5.6 Hz, 1H), 7.59 (s, 4H), 7.54 (ddd, J=9.3, 7.9, 1.4 Hz, 1H), 2.04 (s, 3H); $^{19}$F NMR (471 MHz, DMSO-d$_6$) δ −102.50, −102.52, −102.54, −102.55, −117.45, −117.47, −117.49; ESIMS m/z 336 ([M+H]$^+$).

tert-Butyl-N-tert-butoxycarbonyl-N-[3-[(2,6-difluoro-3-nitrobenzoyl)amino]-2,6-difluorophenyl] carbamate (C165)

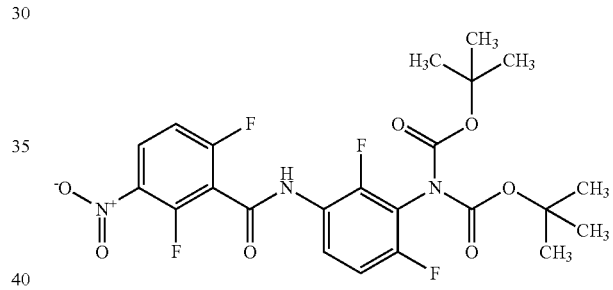

Isolated as a pale-yellow solid (0.165 g, 48%): mp 163-165° C.; $^1$H NMR (500 MHz, DMSO-d$_6$) δ 10.98 (s, 1H), 8.43 (td, J=9.0, 5.6 Hz, 1H), 7.87 (td, J=8.8, 5.7 Hz, 1H), 7.55 (ddd, J=9.4, 8.0, 1.4 Hz, 1H), 7.31 (td, J=9.2, 1.7 Hz, 1H), 1.40 (s, 18H); $^{19}$F NMR (471 MHz, DMSO-d$_6$) δ −102.41, −102.43, −102.45, −102.46, −117.12, −117.14, −117.16, −122.89, −122.91, −122.93, −127.37, −127.39; ESIMS m/z 528 ([M−H]$^−$).

2,6-Dichloro-3-nitro-N-(2,2,3,3,3-pentafluoropropyl) benzamide (C166)

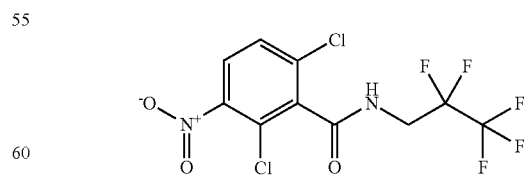

Isolated as a white solid (0.095 g, 64%): mp 139-142° C.; $^1$H NMR (400 MHz, CDCl$_3$) δ 7.85 (d, J=8.8 Hz, 1H), 7.50 (d, J=8.8 Hz, 1H), 6.29 (s, 1H), 4.18 (td, J=14.9, 6.4 Hz, 2H); $^{19}$F NMR (376 MHz, CDCl$_3$) δ −84.17, −121.45; ESIMS m/z 367 ([M+H]$^+$).

2,6-Dichloro-N-ethyl-3-nitrobenzamide (C167)

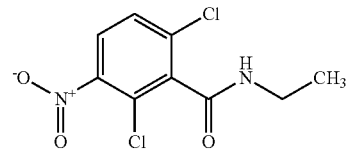

Isolated as a yellow solid (0.108 g, 61%): mp 104-108° C.; $^1$H NMR (400 MHz, CDCl$_3$) δ 7.80 (d, J=8.7 Hz, 1H), 7.47 (d, J=8.8 Hz, 1H), 5.91 (s, 1H), 3.54 (qd, J=7.3, 5.8 Hz, 2H), 1.29 (t, J=7.3 Hz, 3H); IR (thin film) 3253, 3086, 2980, 1819, 1645, 1564, 1518, 1344, 928, 698 cm$^{-1}$; ESIMS m/z 261 ([M–H]$^-$).

N-Ethyl-2,6-difluoro-3-nitrobenzamide (C168)

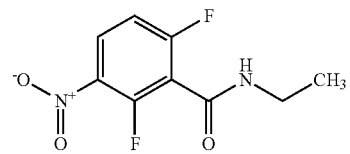

Isolated as a yellow solid (0.108 g, 62%): mp 104-108° C.; $^1$H NMR (400 MHz, CDCl$_3$) δ 8.16 (ddd, J=9.3, 8.2, 5.5 Hz, 1H), 7.10 (ddd, J=9.4, 7.7, 1.8 Hz, 1H), 6.08 (s, 1H), 3.52 (qd, J=7.3, 5.7 Hz, 2H), 1.27 (t, J=7.3 Hz, 3H); $^{19}$F NMR (376 MHz, CDCl$_3$) δ −100.08, −100.10, −114.72, −114.75; IR (thin film) 3240, 3087, 2996, 1713, 1620, 1531, 1347, 1298, 1028, 843 cm$^{-1}$; ESIMS m/z 231 ([M+H]$^+$).

2,6-Dichloro-3-nitro-N-propylbenzamide (C169)

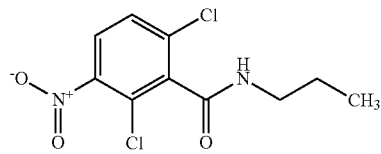

Isolated as a yellow solid (0.158 g, 88%): mp 126-129° C.; $^1$H NMR (400 MHz, DMSO-d$_6$) δ 8.82 (t, J=5.8 Hz, 1H), 8.12 (d, J=8.8 Hz, 1H), 7.81 (d, J=8.8 Hz, 1H), 3.23 (td, J=6.9, 5.7 Hz, 2H), 1.54 (h, J=7.2 Hz, 2H), 0.93 (t, J=7.4 Hz, 3H); ESIMS m/z 277 ([M+H]$^+$).

2,6-Dichloro-N-(2-fluoroethyl)-3-nitrobenzamide (C170)

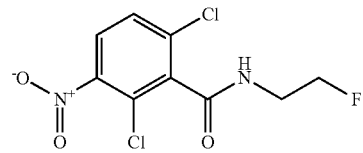

Isolated as a cream-colored solid (0.154 g, 84%): mp 148-150° C.; $^1$H NMR (500 MHz, DMSO-d$_6$) δ 9.14 (t, J=5.7 Hz, 1H), 8.14 (d, J=8.8 Hz, 1H), 7.82 (d, J=8.7 Hz, 1H), 4.55 (dt, J=47.4, 4.9 Hz, 2H), 3.65-3.53 (m, 2H); $^{19}$F NMR (471 MHz, DMSO-d$_6$) δ 20.28, 20.23, 20.18, 20.12, 20.07, 20.06, 20.02, 19.96; ESIMS m/z 281 ([M+H]$^+$).

2,6-Dichloro-3-nitro-N-(2,2,2-trifluoroethyl)benzamide (C171)

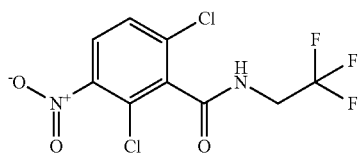

Isolated as a pale-yellow solid (0.182 g, 88%): mp 182-184° C.; $^1$H NMR (500 MHz, DMSO-d$_6$) δ 9.57 (t, J=6.3 Hz, 1H), 8.18 (d, J=8.7 Hz, 1H), 7.85 (d, J=8.8 Hz, 1H), 4.17 (qd, J=9.7, 6.3 Hz, 2H); $^{19}$F NMR (471 MHz, DMSO-d$_6$) δ −70.07, −70.09, −70.11; ESIMS m/z 315 ([M–H]$^-$).

2,6-Dichloro-3-nitro-N-(3,3,3-trifluoropropyl)benzamide (C172)

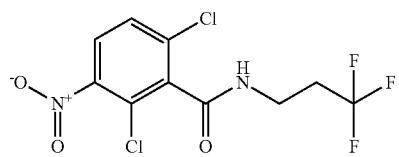

Isolated as a pale-yellow solid (0.186 g, 86%): mp 128-130° C.; $^1$H NMR (500 MHz, DMSO-d$_6$) δ 9.14 (t, J=5.8 Hz, 1H), 8.15 (d, J=8.7 Hz, 1H), 7.82 (d, J=8.8 Hz, 1H), 3.51 (td, J=6.8, 5.7 Hz, 2H), 2.61-2.52 (m, 2H); $^{19}$F NMR (471 MHz, DMSO-d$_6$) δ −63.89, −63.91, −63.94; ESIMS m/z 331 ([M+H]$^+$).

2,6-Dichloro-N-(3-chloropropyl)-3-nitrobenzamide (C173)

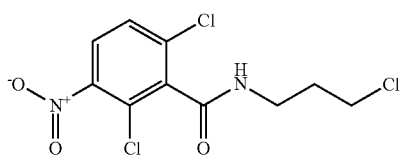

Isolated as a yellow solid (0.180 g, 89%): mp 116-120° C.; $^1$H NMR (500 MHz, DMSO-d$_6$) δ 8.94 (t, J=5.7 Hz, 1H), 8.14 (d, J=8.7 Hz, 1H), 7.82 (d, J=8.7 Hz, 1H), 3.72 (t, J=6.5 Hz, 2H), 3.40 (q, J=6.4 Hz, 2H), 1.98 (p, J=6.6 Hz, 2H); ESIMS m/z 311 ([M+H]$^+$).

2,6-Difluoro-3-nitro-N-propylbenzamide (C174)

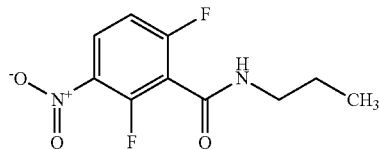

Isolated as a light-yellow solid (0.149 g, 95%): mp 85-88° C.; $^1$H NMR (500 MHz, DMSO-$d_6$) δ 8.93-8.83 (m, 1H), 8.33 (td, J=9.0, 5.6 Hz, 1H), 7.46 (ddd, J=9.4, 8.0, 1.5 Hz, 1H), 3.24 (td, J=6.8, 5.6 Hz, 2H), 1.52 (h, J=7.2 Hz, 2H), 0.91 (t, J=7.4 Hz, 3H); $^{19}$F NMR (471 MHz, DMSO-$d_6$) δ −102.84, −102.85, −102.87, −102.88, −102.89, −117.84, −117.86, −117.88; ESIMS m/z 245 ([M+H]$^+$).

2,6-Difluoro-N-(2-fluoroethyl)-3-nitrobenzamide (C175)

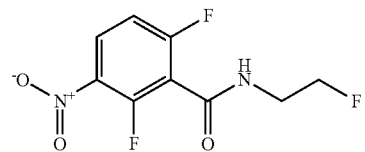

Isolated as a yellow solid (0.135 g, 82%): mp 95-99° C.; $^1$H NMR (500 MHz, DMSO-$d_6$) δ 9.20 (t, J=5.6 Hz, 1H), 8.35 (td, J=9.0, 5.6 Hz, 1H), 7.47 (ddd, J=9.4, 8.0, 1.6 Hz, 1H), 4.54 (dt, J=47.5, 4.9 Hz, 2H), 3.66-3.54 (m, 2H); $^{19}$F NMR (471 MHz, DMSO-$d_6$) δ 19.65, 19.59, 19.55, 19.53, 19.49, 19.45, 19.43, 19.39, 19.33, −102.68, −102.70, −102.71, −102.71, −102.72, −102.74, −117.56, −117.58, −117.60; ESIMS m/z 249 ([M+H]$^+$).

2,6-Difluoro-3-nitro-N-(2,2,2-trifluoroethyl)benzamide (C176)

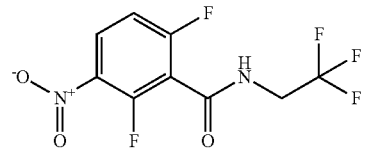

Isolated as a white solid (0.175 g, 97%): mp 137-139° C.; $^1$H NMR (500 MHz, DMSO-$d_6$) δ 9.64 (t, J=6.3 Hz, 1H), 8.39 (td, J=9.0, 5.6 Hz, 1H), 7.50 (ddd, J=9.5, 8.0, 1.5 Hz, 1H), 4.19 (qd, J=9.6, 6.3 Hz, 2H); $^{19}$F NMR (471 MHz, DMSO-$d_6$) δ −70.70, −70.72, −70.74, −102.73, −102.74, −102.75, −102.75, −102.76, −102.76, −102.77, −102.78, −117.46, −117.48, −117.50; ESIMS m/z 283 ([M−H]$^-$).

2,6-Difluoro-3-nitro-N-(3,3,3-trifluoropropyl)benzamide (C177)

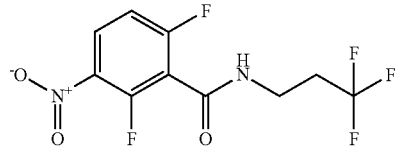

Isolated as a pale-yellow solid (0.167 g, 87%): mp 108-110° C.; $^1$H NMR (500 MHz, DMSO-$d_6$) δ 9.18 (t, J=5.8 Hz, 1H), 8.35 (td, J=9.0, 5.6 Hz, 1H), 7.47 (ddd, J=9.5, 8.1, 1.5 Hz, 1H), 3.53 (td, J=6.6, 5.6 Hz, 2H), 2.60-2.51 (m, 2H); $^{19}$F NMR (471 MHz, DMSO-$d_6$) δ −63.83, −63.86, −63.88, −102.67, −102.69, −102.70, −102.72, −117.59, −117.61, −117.63; ESIMS m/z 299 ([M+H]$^+$).

2,6-Difluoro-3-nitro-N-(2,2,3,3,3-pentafluoropropyl)benzamide (C178)

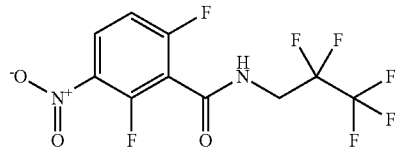

Isolated as a white solid (0.177 g, 83%): mp 143-145° C.; $^1$H NMR (500 MHz, DMSO-$d_6$) δ 9.66 (t, J=6.3 Hz, 1H), 8.39 (td, J=9.0, 5.6 Hz, 1H), 7.50 (ddd, J=9.5, 8.1, 1.6 Hz, 1H), 4.24 (td, J=15.2, 6.3 Hz, 2H); $^{19}$F NMR (471 MHz, DMSO-$d_6$) δ −83.41, −102.65, −102.66, −102.68, −102.70, −117.38, −117.40, −117.42, −120.07, −120.10, −120.14; IR (thin film) 3282, 3100, 2973, 1677, 1541, 1224, 1033, 730 cm$^{-1}$; ESIMS m/z 333 ([M−H]$^-$).

N-(3-Chloropropyl)-2,6-difluoro-3-nitrobenzamide (C179)

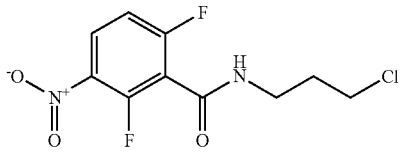

Isolated as a yellow solid (0.137 g, 77%): mp 84-87° C.; $^1$H NMR (500 MHz, DMSO-$d_6$) δ 9.00 (t, J=5.7 Hz, 1H), 8.35 (td, J=9.0, 5.6 Hz, 1H), 7.47 (ddd, J=9.5, 8.0, 1.5 Hz, 1H), 3.70 (t, J=6.5 Hz, 2H), 3.41 (td, J=6.7, 5.5 Hz, 2H), 1.97 (p, J=6.6 Hz, 2H); $^{19}$F NMR (471 MHz, DMSO-$d_6$) δ −102.82, −102.82, −102.83, −102.84, −102.85, −117.76, −117.78, −117.81; ESIMS m/z 279 ([M+H]$^+$).

tert-Butyl (3-(2-chloro-3-fluoro-5-nitrobenzamido)-2,4-difluorophenyl)carbamate (C180)

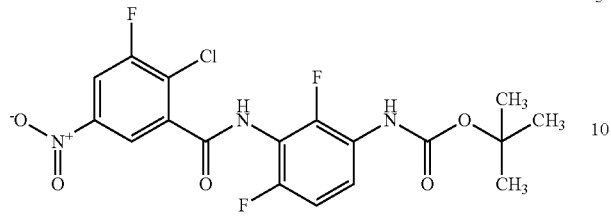

Isolated as an off-white solid (0.590 g, 100%): mp=202-204° C. (dec); ¹H NMR (400 MHz, DMSO-d₆) δ 10.63 (s, 1H), 9.06 (s, 1H), 8.51 (dd, J=8.8, 2.6 Hz, 1H), 8.40 (dd, J=2.6, 1.4 Hz, 1H), 8.07 (t, J=8.3 Hz, 1H), 7.42 (t, J=10.4 Hz, 1H), 1.46 (s, 9H); ¹⁹F NMR (376 MHz, DMSO-d₆) δ −109.72, −122.28, −123.56; ESIMS m/z 544 ([M−H]⁻).

Example 67: Preparation of tert-butyl-N-((tert-butoxy)carbonyl)-N-(4-amino-3,5-difluorophenyl)carbamate (C181)

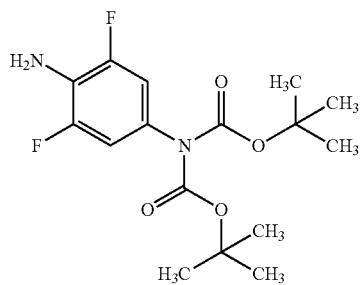 [SMILES: CC(C)(C)OC(=O)N(C(=O)OC(C)(C)C)c1cc(F)c(N)c(F)c1]

To a solution of tert-butyl-N-((tert-butoxy)carbonyl)-(3,5-difluoro-4-nitrophenyl)carbamate (C189) (1.75 g, 4.67 mmol) in ethyl acetate (30 mL) was added 5% palladium on carbon (0.498 g, 0.234 mmol). The reaction mixture was stirred vigorously overnight at room temperature under a balloon of hydrogen. The reaction mixture was filtered through a pad of Celite® and washed with ethyl acetate. The filtrates were concentrated under reduced pressure to afford the title compound as an off-white solid (1.57 g, 98%): ¹H NMR (400 MHz, DMSO-d₆) δ 7.07 (ddd, J=11.4, 8.9, 2.8 Hz, 1H), 6.79 (dd, J=9.3, 2.4 Hz, 1H), 4.87 (s, 2H), 1.36 (s, 18H); ¹⁹F NMR (376 MHz, DMSO-d₆) δ −128.55, −129.75.

The following compounds were prepared in like manner to the procedure outlined in Example 67:

tert-Butyl N-(3-amino-2,6-difluoro-phenyl)-N-tert-butoxycarbonyl-carbamate (C182)

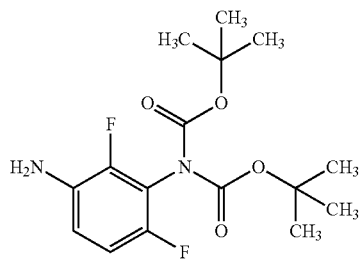

Isolated as a white solid (5.06 g, 100%); ¹H NMR (400 MHz, DMSO-d₆) δ 6.87 (td, J=9.3, 1.7 Hz, 1H), 6.74 (td, J=9.4, 5.7 Hz, 1H), 5.12 (s, 2H), 1.39 (s, 18H); ¹⁹F NMR (376 MHz, DMSO-d₆) δ −137.96 (d, J=3.7 Hz), −141.10 (d, J=3.7 Hz); ESIMS m/z 244 ([M-BOC]⁻).

tert-Butyl-N-((tert-butoxy)carbonyl)-N-(5-amino-2,4-difluorophenyl)carbamate (C183)

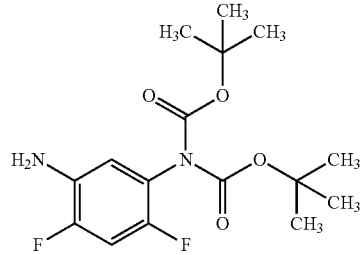

Isolated as a cream colored solid (1.05 g, 88%): ¹H NMR (400 MHz, CDCl₃) δ 6.82 (dd, J=10.5, 9.3 Hz, 1H), 6.60 (dd, J=9.1, 7.5 Hz, 1H), 3.59 (s, 2H), 1.43 (s, 18H); ¹⁹F NMR (376 MHz, CDCl₃) δ −131.04 (t, J=2.2 Hz), −131.38 (d, J=2.0 Hz); ESIMS m/z 245 ([M-C₅H₉O₂+H]⁺).

tert-Butyl (4-amino-3-methylphenyl)carbamate (C184)

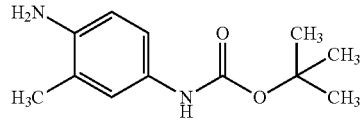

Isolated as a light pink solid (12.4 g, 87%): ¹H NMR (400 MHz, DMSO-d₆) δ 8.72 (s, 1H), 7.01 (s, 1H), 6.93 (d, J=8.5 Hz, 1H), 6.49 (d, J=8.4 Hz, 1H), 4.49 (s, 2H), 2.00 (s, 3H), 1.44 (s, 9H); ESIMS m/z 223 ([M+H]⁺).

tert-Butyl-N-((tert-butoxy)carbonyl (4-amino-2,6-difluorophenyl)carbamate (C185)

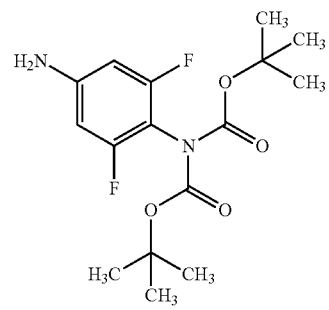

Isolated as an off-white solid (1.5 g, 73%): ¹H NMR (400 MHz, DMSO-d₆) δ 6.28-6.18 (m, 2H), 5.83 (s, 2H), 1.37 (s, 18H); ¹⁹F NMR (376 MHz, DMSO-d₆) δ −122.91; ESIMS m/z 345 ([M+H]⁺).

N-(3-Amino-2,6-difluorophenyl)-2,2-difluoroacetamide (C186)

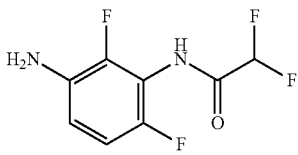

Isolated as a light brown solid (0.91 g, 98%): $^1$H NMR (400 MHz, DMSO-$d_6$) δ 10.50 (s, 1H), 6.88 (td, J=9.3, 1.9 Hz, 1H), 6.72 (td, J=9.3, 5.5 Hz, 1H), 6.49 (t, J=53.2 Hz, 1H), 5.58 (s, 2H); $^{19}$F NMR (376 MHz, DMSO-$d_6$) δ −125.61, −135.65 (d, J=3.4 Hz), −138.69 (d, J=3.5 Hz); EIMS m/z 222.

N-(3-Amino-2,6-difluorophenyl)-2,2-difluoro-N-methylacetamide (C187)

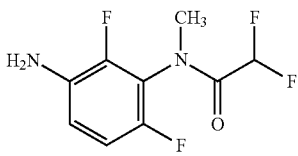 [SMILES: CN(C(=O)C(F)F)c1c(F)ccc(N)c1F]

Isolated as a light yellow oil (0.26 g, 96%): $^1$H NMR (400 MHz, DMSO-$d_6$) δ rotamers 7.00 (td, J=9.3, 1.7 Hz, 1H), 6.85 (td, J=9.4, 5.7 Hz, 1H), 6.24 (t, J=52.1 Hz, 1H), 5.32 (s, 2H), 3.33 (d, J=2.7 Hz, 3H); $^{19}$F NMR (376 MHz, DMSO-$d_6$) δ rotamers −124.15 (dd, J=16.1, 2.9 Hz), −137.89-−138.92 (m), −140.84-−141.99 (m); EIMS m/z 236.

tert-Butyl (3-(5-amino-2-chloro-3-fluorobenzamido)-2,4-difluorophenyl)carbamate (C188)

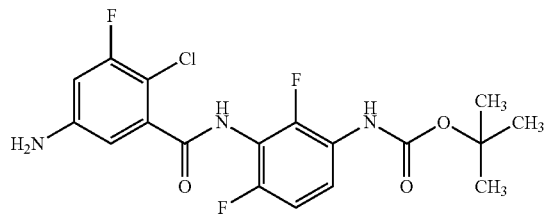 [SMILES: CC(C)(C)OC(=O)Nc1ccc(F)c(NC(=O)c2cc(N)cc(F)c2Cl)c1F]

Isolated as a tan powder (0.563 g, 100%): $^1$H NMR (400 MHz, CDCl$_3$) δ 8.99 (t, J=8.5 Hz, 1H), 8.08 (br s, 1H), 6.97-6.89 (m, 2H), 6.59 (dd, J=10.4, 2.7 Hz, 1H), 6.55 (br s, 1H), 3.98 (br s, 2H), 1.54 (s, 9H); $^{19}$F NMR (376 MHz, CDCl$_3$) δ −112.06, −131.58, −132.13; ESIMS m/z 414 ([M−H]$^−$).

Example 68: Preparation of tert-Butyl-N-((tert-butoxy)carbonyl)-(3,5-difluoro-4-nitrophenyl)carbamate (C189)

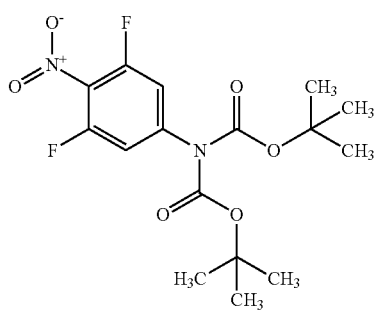 [SMILES: CC(C)(C)OC(=O)N(C(=O)OC(C)(C)C)c1cc(F)c([N+](=O)[O-])c(F)c1]

To a solution of 3,5-difluoro-4-nitroaniline (1.0 g, 5.74 mmol) in dichloromethane (25.0 mL) was added di-tert-butyl dicarbonate (2.63 g, 12.1 mmol) followed by 4-dimethylaminopyridine (0.070 g, 0.574 mmol). The reaction mixture was stirred for 48 hours at room temperature. The reaction mixture was quenched with water and poured through a phase separator. The organic layer was concentrated. Purification by flash column chromatography using 0-20% ethyl acetate/hexanes as eluent afforded the title compound as a yellow solid (1.79 g, 83%): $^1$H NMR (400 MHz, CDCl$_3$) δ 7.04 (ddd, J=9.7, 8.0, 2.7 Hz, 1H), 6.90 (ddd, J=8.2, 2.7, 1.9 Hz, 1H), 1.43 (s, 18H); $^{19}$F NMR (376 MHz, CDCl$_3$) δ −133.35 (d, J=23.5 Hz), −137.44 (d, J=23.4 Hz); ESIMS m/z 375 ([M+H]$^+$).

The following compounds were prepared in like manner to the procedure outlined in Example 68:

tert-Butyl-N-((tert-butoxy)carbonyl)-N-(2,6-difluoro-3-nitrophenyl)carbamate (C190)

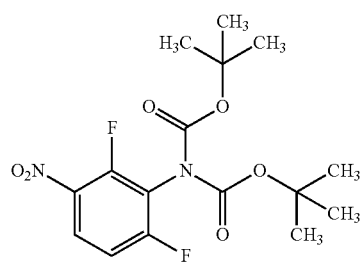 [SMILES: CC(C)(C)OC(=O)N(C(=O)OC(C)(C)C)c1c(F)ccc([N+](=O)[O-])c1F]

Isolated as a white foam (5.2 g, 69%): $^1$H NMR (300 MHz, CDCl$_3$) δ 8.14 (ddd, J=9.2, 8.1, 5.5 Hz, 1H), 7.10 (ddd, J=9.7, 8.0, 2.0 Hz, 1H), 1.45 (s, 18H); $^{19}$F NMR (376 MHz, CDCl$_3$) δ −105.95 (dd, J=10.9, 2.7 Hz), −119.53 (d, J=10.6 Hz); ESIMS m/z 397 ([M+Na]$^+$).

tert-Butyl-N-((tert-butoxy)carbonyl)-N-(2,4-difluoro-5-nitrophenyl)carbamate (C191)

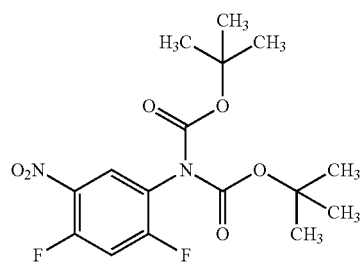 [SMILES: CC(C)(C)OC(=O)N(C(=O)OC(C)(C)C)c1cc([N+](=O)[O-])c(F)cc1F]

Isolated as a white solid (1.2 g, 56%): $^1$H NMR (400 MHz, CDCl$_3$) δ 8.05 (t, J=7.7 Hz, 1H), 7.11 (dd, J=10.2, 8.9 Hz, 1H), 1.46 (s, 18H); $^{19}$F NMR (376 MHz, CDCl$_3$) δ −105.08 (dd, J=14.8, 2.2 Hz), −111.35 (dd, J=14.6, 2.3 Hz); ESIMS m/z 397 ([M+Na]$^+$).

tert-Butyl-N-((tert-butoxy)carbonyl)-(2,6-difluoro-4-nitrophenyl)carbamate (C192)

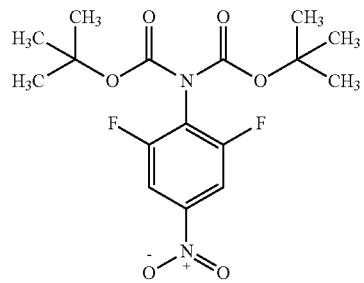

Isolated as a light yellow solid (2.0 g, 84%): $^1$H NMR (400 MHz, DMSO-$d_6$) δ 8.33-8.24 (m, 2H), 1.40 (s, 18 H); $^{19}$F NMR (376 MHz, DMSO-$d_6$) δ −115.68; ESIMS m/z 374 ([M−H]$^-$).

Example 69: Preparation of N-(2,6-difluoro-3-nitrophenyl)-2,2-difluoroacetamide (C193)

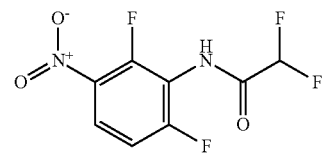 [SMILES: O=C(Nc1c(F)ccc([N+](=O)[O-])c1F)C(F)F]

To a solution of 2,6-difluoro-3-nitroaniline (1.00 g, 5.74 mmol) in dichloromethane (2.0 mL) stirred at room temperature was added triethylamine (1.20 mL, 8.62 mmol) and 2,2-difluoroacetic anhydride (1.30 g, 7.47 mmol). The reaction mixture was stirred at room temperature for 18 hours. The mixture was then loaded onto a Celite® cartridge and purified by column chromatography using 0-40% ethyl acetate/hexanes as eluent to afford the title compound as a white solid (1.50 g, 100% yield): $^1$H NMR (400 MHz, DMSO-$d_6$) δ 11.07 (s, 1H), 8.29 (ddd, J=9.5, 8.4, 5.5 Hz, 1H), 7.53 (td, J=9.2, 1.9 Hz, 1H), 6.59 (t, J=53.0 Hz, 1H); $^{19}$F NMR (376 MHz, DMSO-$d_6$) δ −105.42 (d, J=10.7 Hz), −120.10 (d, J=10.6 Hz), −125.98; EIMS m/z 252.

Example 70: Preparation of N-(3-amino-2-chloro-6-fluorophenyl)acetamide (C194)

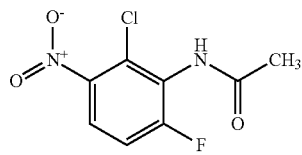

Step 1: Preparation of N-(2-chloro-6-fluorophenyl)acetamide

Acetic anhydride (10 g, 99 mmol) was added dropwise to a stirred solution of 2-chloro-6-fluoroaniline (12.5 g, 86 mmol), in glacial acetic acid (50 mL). The resulting gold solution was heated at 90° C. for 2 hours, then cooled and quenched with water (500 mL). The resulting solid was collected by vacuum filtration, washed with water (100 mL) and hexanes (100 mL) and dried in vacuo at 40° C. to a constant weight to give the title compound as a tan solid (14.87 g, 88%): $^1$H NMR (400 MHz, CDCl$_3$) δ 7.86 (s, 1H), 7.05 (dt, J=63.2, 8.4 Hz, 3H), 2.13 (s, 3H); ESIMS m/z 188 ([M+H]$^+$).

Step 2: Preparation of N-(2-chloro-6-fluoro-3-nitrophenyl)acetamide

Sodium nitrate (4.53 g, 53.3 mmol) dissolved in water (5 mL) was added dropwise to a stirred solution of N-(2-chloro-6-fluorophenyl)acetamide (5 g, 26.7 mmol), in concentrated sulfuric acid (10 mL) at −10° C. Upon completion of the addition, the resulting yellow solution was stirred at 0° C. for 30 minutes, then warmed to and stirred at room temperature for another 12 hours. The reaction mixture was poured into water (~250 mL) and the resulting solid was collected by vacuum filtration. Recrystallization from acetonitrile gave the title compound as a light tan solid (3.2 g, 49%): $^1$H NMR (400 MHz, DMSO-$d_6$) δ 10.07 (s, 1H), 8.12 (dd, J=9.2, 5.0 Hz, 1H), 7.70-7.55 (m, 1H), 2.12 (s, 3H); ESIMS m/z 233 ([M+H]$^+$).

Step 3: Preparation of N-(3-amino-2-chloro-6-fluorophenyl)acetamide

Iron powder (325 mesh; 2.16 g, 38.7 mmol) was added to a stirred solution of ethanol (50 mL) and concentrated hydrochloric acid (0.37 mL, 3.87 mmol). The suspension was heated at 65° C. for 1 hour and then cooled to 55° C. A solution of ammonium chloride (1.49 g, 27.0 mmol) in water (5 mL) was added, followed by N-(2-chloro-6-fluoro-3-nitrophenyl)acetamide (1.8 g, 7.74 mmol). The reaction mixture was heated to 60° C. for 8 hours, cooled, and filtered through a pad of Celite®. The filtrate was extracted with ethyl acetate (3×50 mL). The combined organic extracts were washed with water and brine, dried over anhydrous magnesium sulfate, filtered, and concentrated under reduced pressure on a rotary evaporator. Purification by silica gel flash chromatography gave the title compound as a tan solid (1.2 g, 72%): $^1$H NMR (400 MHz, DMSO-$d_6$) δ 9.51 (s, 1H), 6.96 (t, J=9.2 Hz, 1H), 6.71 (dd, J=9.0, 5.1 Hz, 1H), 5.23 (s, 2H), 2.03 (s, 3H); ESIMS m/z 203 ([M+H]$^+$).

Example 71: Preparation of 3-amino-2,6-difluorophenyl acetate (C195)

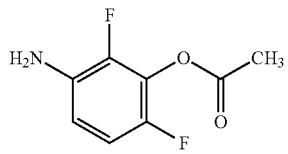

3-Amino-2,6-difluorophenol (0.074 g, 0.51 mmol) and 4-dimethylaminopyridine (0.005 g, 0.042 mmol) were dissolved in methylene chloride (2 mL) and the resulting solution was cooled in an ice bath under nitrogen. Acetic anhydride (0.042 mL, 0.446 mmol) and triethylamine (0.062 mL, 0.446 mmol) were added via syringe with stirring. After three hours, analysis by thin layer chromatography (1:1 hexanes-ethyl acetate) indicated complete conversion. The reaction mixture was concentrated, loaded directly onto a flash silica gel column and eluted with 4:1 hexanes-ethyl acetate to give the title compound as a sticky orange solid (0.071 g, 89%): $^1$H NMR (400 MHz, CDCl$_3$) δ 6.78 (td, J=9.2, 2.2 Hz, 1H), 6.58 (td, J=9.1, 5.0 Hz, 1H), 3.63 (br s, 2H), 2.37 (s, 3H); $^{19}$F NMR (376 MHz, CDCl$_3$) δ −140.23 (d, J=1.6 Hz), −146.77 (d, J=1.9 Hz); EIMS m/z 187.

Example 72: Preparation of 5-amino-2-chloro-3-fluorobenzoic acid (C196)

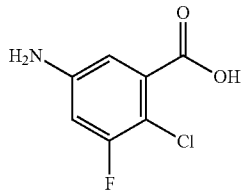

To a solution of 2-chloro-3-fluoro-5-nitrobenzoic acid (C206) (5 g, 22.8 mmol) in ethyl acetate (150 mL) was added 5% platinum on carbon (0.5 g, 10% w/w) and the reaction mixture was stirred under hydrogen gas (15 psi) for 24 hours. The reaction mixture was carefully filtered through a pad of Celite®, the pad washed with 50% ethyl acetate in methanol, and the filtrate concentrated under reduced pressure. The crude product was triturated with diethyl ether to afford the title compound as a pale yellow solid (2.1 g, 50%): mp 187-189° C.; $^1$H NMR (400 MHz, DMSO-d$_6$) δ 13.28 (br s, 1H), 6.81 (dd, J=1.2, 2.4 Hz, 1H), 6.61 (dd, J=2.4, 12.0 Hz, 1H), 5.77 (br s, 2H); $^{19}$F NMR (376 MHz, DMSO-d$_6$) δ −114.65; ESIMS m/z 190 ([M+H]$^+$).

The following compounds were prepared in like manner to the procedure outlined in Example 72:

5-Amino-2-chloro-3-(trifluoromethyl)benzoic acid (C197)

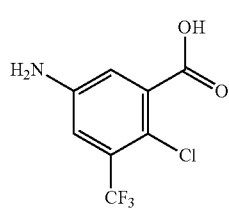 [SMILES: Nc1cc(C(=O)O)c(Cl)c(C(F)(F)F)c1]

Isolated as a brown solid (3.2 g, 68%): mp 195-197° C.; $^1$H NMR (400 MHz, DMSO-d$_6$) δ 7.18-7.08 (m, 1H), 7.06-7.02 (m, 1H); $^{19}$F NMR (376 MHz, DMSO-d$_6$) δ −61.21; ESIMS m/z 240 ([M+H]$^+$).

5-Amino-2-chloro-3-methylbenzoic acid (C198)

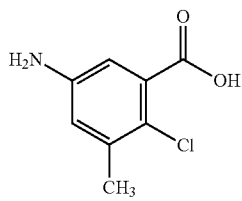

Isolated as a brown solid (3.2 g, 72%): mp 190-192° C.; $^1$H NMR (400 MHz, DMSO-d$_6$) δ 12.82 (br s, 1H), 6.76 (d, J=2.4 Hz, 1H), 6.67 (d, J=2.4, 1H), 2.22 (s, 3H); ESIMS m/z 186 ([M+H]$^+$).

5-Amino-2,3-difluorobenzoic acid (C199)

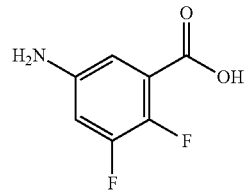

Isolated as a brown solid (2.5 g, 60%): mp 211-213° C.; $^1$H NMR (400 MHz, DMSO-d$_6$) δ 13.20 (br s, 1H), 6.84-6.78 (m, 1H), 6.74-6.64 (m, 1H), 5.46 (br s, 2H); $^{19}$F NMR (376 MHz, DMSO-d$_6$) δ −138.22, −155.42; ESIMS m/z 174 ([M+H]$^+$).

5-Amino-3-chloro-2-fluorobenzoic acid (C200)

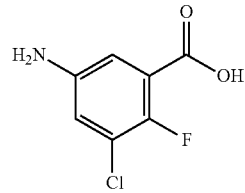

Isolated as a brown solid (4.0 g, 66%): mp 205-207° C.; $^1$H NMR (300 MHz, DMSO-d$_6$) δ 13.40 (br s, 1H), 7.02-6.94 (m, 1H), 6.92-6.84 (m, 1H), 5.48 (br s, 2H); $^{19}$F NMR (376 MHz, DMSO-d$_6$) δ −132.31; ESIMS m/z 190 ([M+H]$^+$).

5-Amino-2-fluoro-3-methylbenzoic acid (C201)

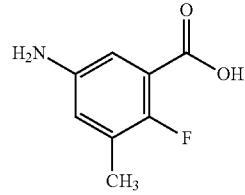

Isolated as a brown solid (5.2 g, 76%): mp 206-208° C.; $^1$H NMR (300 MHz, DMSO-d$_6$) δ 12.82 (br s, 1H), 6.88-6.80 (m, 1H), 6.68-6.58 (m, 1H), 5.28 (br s, 2H), 2.12 (s, 3H); $^{19}$F NMR (282 MHz, DMSO-d$_6$) δ −132.24; ESIMS m/z 170 ([M+H]$^+$).

5-Amino-3-chloro-2-methylbenzoic acid (C202)

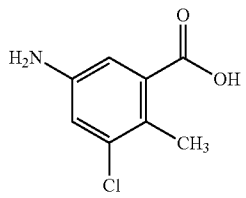

Isolated as an off-white solid (1.3 g, 65%): mp 192-194° C.; $^1$H NMR (400 MHz, DMSO-d$_6$) δ 12.82 (br s, 1H), 6.93 (d, J=2.1 Hz, 1H), 6.78 (d, J=2.4 Hz, 1H), 5.37 (br s, 2H), 2.31 (s, 3H); ESIMS m/z 186 ([M+H]$^+$).

5-Amino-3-fluoro-2-methylbenzoic acid (C203)

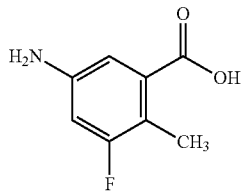

Isolated as a brown solid (0.3 g, 55%): mp 164-166° C.; $^1$H NMR (400 MHz, DMSO-d$_6$) δ 12.82 (br s, 1H), 6.87 (d, J=2.0 Hz, 1H), 6.48 (dd, J=2.0, 8.0 Hz, 1H), 5.36 (br s, 2H), 2.19 (s, 3H); $^{19}$F NMR (376 MHz, DMSO-d$_6$) δ −116.94; ESIMS m/z 170 ([M+H]$^+$).

5-Amino-3-chloro-2-methoxybenzoic acid (C204)

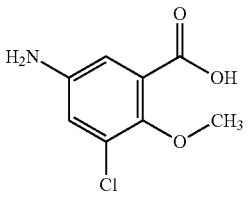

Isolated as a brown solid (2.5 g, 75%): mp 173-175° C.; $^1$H NMR (400 MHz, DMSO-d$_6$) δ 12.8 (br s, 1H), 6.84 (d, J=2.8 Hz, 1H), 6.79 (d, J=2.8 Hz, 1H), 5.62 (br s, 2H), 3.68 (s, 3H); ESIMS m/z 202 ([M+H]$^+$).

5-Amino-3-fluoro-2-methoxybenzoic acid (C205)

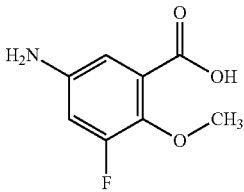

Isolated as a pale yellow solid (6.01 g, 85%): mp 148-150° C.; $^1$H NMR (400 MHz, DMSO-d$_6$) δ 12.82 (br s, 1H), 6.72-6.66 (m, 1H), 6.55 (dd, J=2.0, 13.6 Hz, 1H), 5.40 (br s, 2H), 3.69 (s, 3H); $^{19}$F NMR (376 MHz, DMSO-d$_6$) δ −131.02; ESIMS m/z 186 ([M+H]$^+$).

Example 73: Preparation of 2-chloro-3-fluoro-5-nitrobenzoic acid (C206)

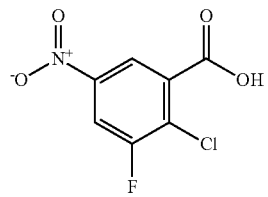

To a suspension of 2-chloro-3-fluorobenzoic acid (10 g, 57.5 mmol) in concentrated sulfuric acid (62 mL, 1149.5 mmol) was added concentrated nitric acid (4 mL, 86.2 mmol) dropwise at −10° C. and the reaction mixture was stirred between −10° C. and 0° C. for 3 hours. The reaction mixture was slowly poured into a beaker of crushed ice (~1 L), and the resulting precipitated solid was filtered and washed with water (100 mL). The crude product was recrystallized from hot water to afford the title compound as an off-white solid (7.5 g, 60%): mp 163-165° C.; $^1$H NMR (400 MHz, DMSO-d$_6$) δ 14.60-13.92 (br s, 1H), 8.53 (dd, J=2.8, 8.8 Hz, 1H), 8.44-8.41 (m, 1H); $^{19}$F NMR (376 MHz, DMSO-d$_6$) δ −108.50; ESIMS m/z 218 ([M−H]$^−$).

The following compounds were prepared in like manner to the procedure outlined in Example 73:

2-Chloro-5-nitro-3-(trifluoromethyl)benzoic acid (C207)

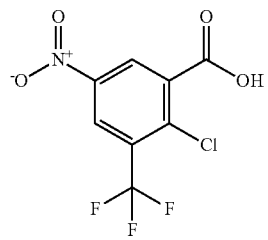

The title compound was recrystallized from hot water to give a brown solid (9 g, 80%): mp 165-167° C.; $^1$H NMR (400 MHz, DMSO-d$_6$) δ 8.77 (d, J=2.8 Hz, 1H), 8.61 (d, J=2.8 Hz, 1H); $^{19}$F NMR (376 MHz, DMSO-d$_6$) δ −61.72; ESIMS m/z 268 ([M−H]$^−$).

2-Chloro-3-methyl-5-nitrobenzoic acid (C208)

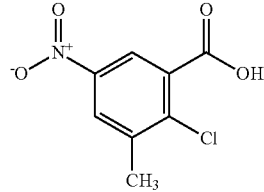

The title compound was precipitated from a diethyl ether solution with n-pentane to give an off-white solid (8.2 g, 65%): mp 205-207° C.; $^1$H NMR (300 MHz, DMSO-d$_6$) δ 8.41 (d, J=2.4 Hz, 1H), 8.34 (d, J=3.0 Hz, 1H), 2.24 (s, 3H); ESIMS m/z 214 ([M–H]$^-$).

2,3-Difluoro-5-nitrobenzoic acid (C209)

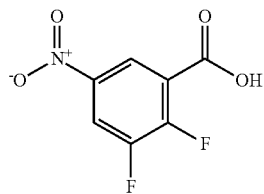

The title compound was recrystallized from hot water to give an off-white solid (5.2 g, 40%): mp 132-134° C.; $^1$H NMR (300 MHz, DMSO-d$_6$) δ 14.60-13.80 (br s, 1H), 8.74-8.62 (m, 1H), 8.52-8.40 (m, 1H); $^{19}$F NMR (282 MHz, DMSO-d$_6$) δ –125.36, –132.16; ESIMS m/z 202 ([M–H]$^-$).

3-Chloro-2-fluoro-5-nitrobenzoic acid (C210)

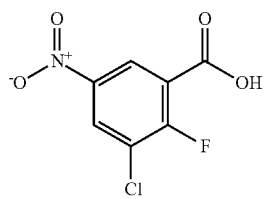

The title compound was recrystallized from hot water to give an off-white solid (6.9 g, 55%): mp 186-188° C.; $^1$H NMR (400 MHz, DMSO-d$_6$) δ 14.40-13.80 (br s, 1H), 8.78-8.70 (m, 1H), 8.58-8.48 (m, 1H); $^{19}$F NMR (376 MHz, DMSO-d$_6$) δ –102.78; ESIMS m/z 218 ([M–H]$^-$).

2-Fluoro-3-methyl-5-nitrobenzoic acid (C211)

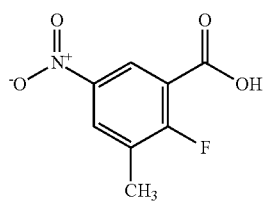

The title compound was precipitated from a methanol solution with water to give a pale brown solid (7.5 g, 58%): mp 168-170° C.; $^1$H NMR (300 MHz, DMSO-d$_6$) δ 13.88 (br s, 1H) 8.48-8.40 (m, 2H), 2.41 (s, 3H); $^{19}$F NMR (376 MHz, DMSO-d$_6$) δ –106.64; ESIMS m/z 198 ([M–H]$^-$).

3-Chloro-2-methoxy-5-nitrobenzoic acid (C212)

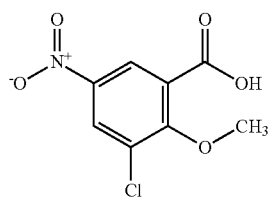

Note: The reaction solvent used was a mixture of sulfuric acid and acetic acid (1:1), and the title compound was recrystallized from hot water and isolated as an off-white solid (9.3 g, 75%): mp 155-157° C.; $^1$H NMR (300 MHz, DMSO-d$_6$) δ 8.54 (d, J=2.4 Hz, 1H), 8.42 (d, J=2.4 Hz, 1H), 3.96 (s, 3H); ESIMS m/z 232 ([M–H]$^-$).

3-Fluoro-2-methoxy-5-nitrobenzoic acid (C213)

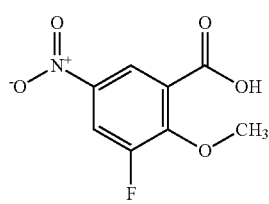

Note: The reaction solvent used was a mixture of sulfuric acid and acetic acid (1:1), and the title compound was recrystallized from hot water and isolated as an off-white solid (9.1 g, 70%): mp 106-108° C.; $^1$H NMR (400 MHz, DMSO-d$_6$) δ 13.62 (br s, 1H), 8.40 (dd, J=2.8, 10.8 Hz, 1H), 8.32-8.28 (m, 1H), 4.04 (s, 3H); $^{19}$F NMR (376 MHz, DMSO-d$_6$) δ –125.26; ESIMS m/z 216 ([M+H]$^+$).

Example 74: Preparation of methyl 3-chloro-2-methyl-5-nitrobenzoate (C214)

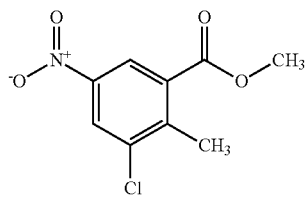

Step 1: Preparation of 3-chloro-2-methyl-5-nitrobenzoic acid

To a suspension of 3-chloro-2-methylbenzoic acid (10 g, 57.5 mmol) in concentrated sulfuric acid (48 mL, 867 mmol) was added concentrated nitric acid (2.5 mL, 68.4 mmol) dropwise at –10° C. and the reaction mixture was stirred between –10° C. and 0° C. for 3 hours. The reaction mixture was slowly poured into a beaker of crushed ice (~1 L), and the precipitated solid was collected by filtration and washed with water (100 mL). The crude product was recrystallized from hot water to give a mixture of 3-chloro-2-methyl-5/6- nitrobenzoic acid as a brown solid (7.5 g), which was used without any purification: ESIMS m/z 214 ([M−H]⁻).

Step 2: Preparation of methyl 3-chloro-2-methyl-5-nitrobenzoate

To a stirred solution of 3-chloro-2-methyl-5/6-nitrobenzoic acid (6 g, 28 mmol) in methanol (100 mL) was added thionyl chloride at ambient temperature, and the reaction mixture was stirred at 80° C. for 4 hours. The reaction mixture was concentrated under reduced pressure. Purification by silica gel column chromatography using 20-30% ethyl acetate in petroleum ether as eluent gave the title compound (1.5 g; 12% yield over two steps) as a pale-yellow said: $^1$H NMR (400 MHz, CDCl$_3$) δ 8.58 (d, J=2.4 Hz, 1H), 8.37 (d, J=2.4 Hz, 1H), 3.97 (s, 3H), 2.72 (s, 3H); ESIMS m/z 228 ([M−H]⁻).

The following compounds were prepared in like manner to the procedure outlined in Example 74:

Methyl 3-fluoro-2-methyl-5-nitrobenzoate (C215)

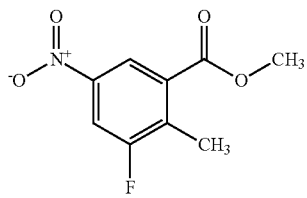

Isolated as a pale-yellow solid (1 g, 10% yield over two steps): $^1$H NMR (300 MHz, CDCl$_3$) δ 8.58 (s, 1H), 8.04 (dd, J=2.4, 9.0 Hz, 1H), 3.97 (s, 3H), 2.61 (d, J=2.4, 3H); ESIMS m/z 214 ([M+H]⁺).

Example 75: Preparation of 3-chloro-2-methyl-5-nitrobenzoic acid (C216)

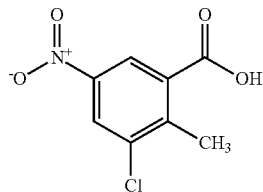

To a stirred solution of methyl 3-chloro-2-methyl-5-nitrobenzoate (C214) (1.5 g, 6.5 mmol) in a mixture of tetrahydrofuran, methanol, and water (2:1:2; 20 mL total) was added lithium hydroxide-monohydrate (0.820 g, 19.5 mmol), and the reaction mixture was stirred at ambient temperature for 16 hours. The reaction mixture was concentrated under reduced pressure, and the residue was dissolved in water (20 mL) and acidified with 2 N hydrochloric acid (10 mL; pH=1-2). The resulting precipitated solid was collected by filtration, washed with water (50 mL), and dried under vacuum to afford the title compound (1 g, 71%) as an off-white solid: mp 176-178° C.; $^1$H NMR (300 MHz, DMSO-d$_6$) δ 13.9 (br s, 1H), 8.43 (s, 2H), 2.64 (s, 3H); ESIMS m/z 214 ([M−H]⁻).

The following compounds were prepared in like manner to the procedure outlined in Example 75:

3-Fluoro-2-methyl-5-nitrobenzoic acid (C217)

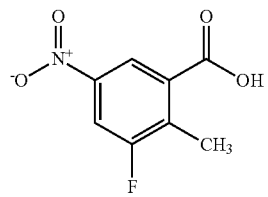

Isolated as an off-white solid (0.800 g, 86%): mp 146-148° C.; $^1$H NMR (300 MHz, DMSO-d$_6$) δ 13.92 (br s, 1H), 8.37 (s, 1H), 8.25 (dd, J=2.4, 9.3 Hz, 1H), 2.50 (d, J=2.1 Hz, 1H); $^{19}$F NMR (376 MHz, DMSO-d$_6$) δ −110.64; ESIMS m/z 198 ([M−H]⁻).

Example 76: Preparation of 2-chloro-N,N'-dimethyl-5-nitro-N'-phenylbenzohydrazide (C218)

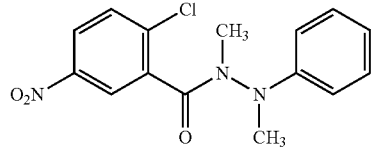 [SMILES: CN(C(=O)c1cc([N+](=O)[O-])ccc1Cl)N(C)c1ccccc1]

To a solution of 2-chloro-N'-methyl-5-nitro-N'-phenylbenzohydrazide (C219) (0.273 g, 0.893 mmol) in N,N-dimethylformamide (8.5 mL) cooled to 0° C. was added sodium hydride (60% oil immersion, 0.045 g, 1.116 mmol). The reaction mixture was allowed to stir at 0° C. for 15 minutes and then methyl iodide (0.070 mL, 1.116 mmol) was added. The reaction mixture was allowed to warm to room temperature and was stirred for 3 hours. The reaction was quenched with water (10 mL) and extracted with ethyl acetate (25 mL). The organic layer was washed with water (3×15 mL) and brine (15 mL) and then concentrated under reduced pressure to afford the title compound as a yellow solid (0.283 g, 98%): $^1$H NMR (400 MHz, CDCl$_3$) δ 8.13 (d, J=2.6 Hz, 1H), 8.08 (dd, J=8.8, 2.6 Hz, 1H), 7.53 (d, J=8.8 Hz, 1H), 7.32 (dd, J=8.9, 7.3 Hz, 2H), 6.95 (tt, J=7.3, 1.1 Hz, 1H), 6.75 (dt, J=7.9, 1.1 Hz, 2H), 3.20 (s, 3H), 3.11 (s, 3H); IR (thin film) 3074, 2925, 1662, 1524, 1494, 1345, 869, 741 cm$^{-1}$; ESIMS m/z 320 ([M+H]⁺).

Example 77: Preparation of 2-chloro-N'-methyl-5-nitro-N'-phenylbenzohydrazide (C219)

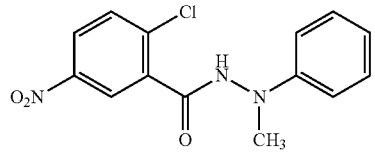 [SMILES: CN(NC(=O)c1cc([N+](=O)[O-])ccc1Cl)c1ccccc1]

To a solution of 2-chloro-5-nitrobenzoic acid (0.300 g, 1.49 mmol) and 1-methyl-1-phenylhydrazine (0.282 g, 2.31 mmol) in ethyl acetate (5.0 mL) stirred at room temperature were added pyridine (0.235 g, 2.98 mmol) and 2,4,6-tripropyl-1,3,5,2,4,6-trioxatriphosphinane 2,4,6-trioxide (T3P®)

as a 50% solution in ethyl acetate (1.421 g, 2.23 mmol). The reaction mixture was stirred at room temperature for 48 hours. The reaction mixture was diluted with ethyl acetate (20 mL). The organic phase was washed with 1 M aqueous hydrochloric acid (15 mL), water (2×10 mL), and brine (10 mL) and was concentrated under reduced pressure. Purification by column chromatography using 0-35% ethyl acetate/hexanes as eluent afforded the title compound as a pale yellow solid (0.273 g, 60%): $^1$H NMR (400 MHz, CDCl$_3$) $^1$H NMR (400 MHz, DMSO-d$_6$) δ 10.71 (s, 1H), 8.47 (d, J=2.8 Hz, 1H), 8.34 (dd, J=8.8, 2.8 Hz, 1H), 7.89 (d, J=8.8 Hz, 1H), 7.41-7.17 (m, 2H), 6.94 (dt, J=7.7, 1.0 Hz, 2H), 6.87-6.52 (m, 1H), 3.24 (s, 3H); IR (thin film) 3207, 3064, 2967, 2807, 1670, 1538, 1351, 737 cm$^{-1}$; ESIMS m/z 306 ([M+H]$^+$).

Example 78: Preparation of 1-methyl-2-(3,3,3-trifluoropropylidene)hydrazine (C220)

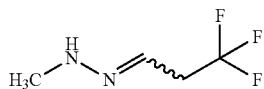

To a solution of 3,3,3-trifluoropropanal (0.600 g, 5.4 mmol) in ethanol (12 mL) was added methyl hydrazine (0.493 g, 10.8 mmol) and acetic acid (0.1 mL) at 0° C. The reaction mixture was stirred at room temperature for 16 hours. The reaction mixture was poured into water (20 mL) and extracted with diethyl ether (2×20 mL). The organic layer was dried over anhydrous sodium sulfate, filtered, and concentrated under reduced pressure to afford the title compound (crude) as a brown liquid (0.600 g): $^1$H NMR (300 MHz, CDCl$_3$) δ 6.67 (t, J=5.6 Hz, 1H), 5.34-5.30 (m, 1H), 3.10-2.96 (m, 2H), 2.83 (s, 3H).

Example 79: Preparation of 5-amino-N-(3-amino-2,4-difluorophenyl)-2-chlorobenzamide hydrochloride (C221)

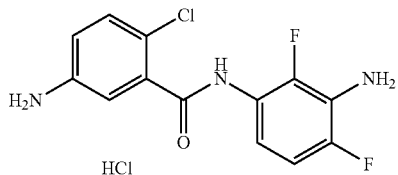 [SMILES: Nc1ccc(Cl)c(C(=O)Nc2ccc(F)c(N)c2F)c1 ; Cl]

A 4 M solution of hydrochloric acid in 1,4-dioxane (4.5 mL, 18 mmol) was added to a stirred solution of tert-butyl-N-((tert-butoxy)carbonyl)-N-(3-(5-amino-2-chlorobenzamido)-2,6-difluorophenyl)carbamate (C135) in dichloromethane (18 mL) at 23° C. The resulting thick off-white mixture was stirred at 23° C. for 18 hours. The reaction mixture was concentrated by rotary evaporation to afford the title compound as an off-white powder (0.660 g, 99% crude yield): $^1$H NMR (400 MHz, DMSO-d$_6$) δ 10.16 (s, 1H), 7.47 (d, J=8.5 Hz, 1H), 7.23 (br s, 1H), 7.17 (br d, J=8.5 Hz, 1H), 6.90 (td, J=10, 1.2 Hz, 1H), 6.80 (m, 1H); ESIMS m/z 298 ([M+H]$^+$).

Example 80: Preparation of 2-chloro-N-(3-(2,2-difluoroacetamido)-2,4-difluorophenyl)-5-nitrobenzamide (C222)

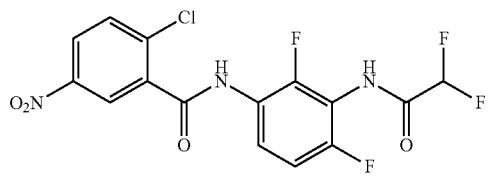 [SMILES: O=C(Nc1ccc(F)c(NC(=O)C(F)F)c1F)c1cc([N+](=O)[O-])ccc1Cl]

To a solution of N-(3-amino-2,6-difluorophenyl)-2,2-difluoroacetamide (C186) (0.455 g, 2.05 mmol) in ethyl acetate (7 mL) was added sodium bicarbonate (0.344 g, 4.10 mmol) and 2-chloro-5-nitrobenzoyl chloride (0.451 mg, 2.05 mmol). The reaction mixture was stirred for 3 hours at room temperature. The reaction mixture was diluted with ethyl acetate and washed with water (15 mL). The organic layer was passed through a phase separator to dry and concentrated to afford the title compound as a white solid (0.55 g, 66%): $^1$H NMR (400 MHz, DMSO-d$_6$) δ 10.80 (s, 1H), 10.69 (s, 1H), 8.50 (d, J=2.7 Hz, 1H), 8.35 (dd, J=8.8, 2.8 Hz, 1H), 7.94-7.80 (m, 2H), 7.31 (td, J=9.3, 1.8 Hz, 1H), 6.55 (t, J=53.2 Hz, 1H); $^{19}$F NMR (376 MHz, DMSO-d$_6$) δ −120.61 (d, J=2.6 Hz), −124.72 (d, J=2.7 Hz), −125.81; ESIMS m/z 406 ([M+H]$^+$).

Example 81: Preparation of tert-butyl (3-methyl-4-nitrophenyl)carbamate (C223)

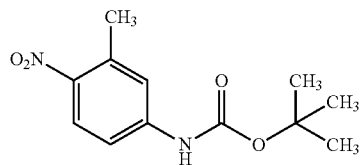 [SMILES: Cc1cc(NC(=O)OC(C)(C)C)ccc1[N+](=O)[O-]]

N,N-Dimethylpyridin-4-amine (2.41 g, 19.72 mmol) was added portionwise to a stirring solution of 3-methyl-4-nitroaniline (15 g, 99 mmol) and di-tert-butyl dicarbonate (25.8 g, 118 mmol) in dichloromethane (200 mL). The resulting yellow solution was stirred at 24° C. for 18 hours and concentrated under vacuum on a rotary evaporator. Purification by silica gel flash chromatography with a gradient of ethyl acetate in hexane to give the title compound as a pale yellow solid (11.5 g, 44%). $^1$H NMR (400 MHz, CDCl$_3$) δ 8.04 (d, J=9.0 Hz, 1H), 7.41 (d, J=2.4 Hz, 1H), 7.30 (dd, J=9.0, 2.5 Hz, 1H), 6.80 (s, 1H), 2.62 (s, 3H), 1.53 (s, 9H); $^{13}$C NMR (101 MHz, CDCl3) δ 151.96, 142.97, 136.22, 126.70, 120.79, 115.55, 81.75, 28.22, 21.45; ESIMS m/z 253 ([M+H]$^+$).

Example R1 Resolution of racemic trans-2,2-dichloro-3-(3,5-dichlorophenyl)cyclopropane-1-carboxylic acid with (L)-leucinamide to provide (1R,3R)-2,2-dichloro-3-(3,5-dichlorophenyl)cyclopropane-1-carboxylic acid Example R2 Resolution of racemic trans-2,2-dichloro-3-(3-chloro-4-fluorophenyl)cyclopropane-1-carboxylic acid with (L)-leucinamide to provide (R,R)-trans-2,2-dichloro-3-(3-chloro-4-fluorophenyl)cyclopropane-1-carboxylic acid

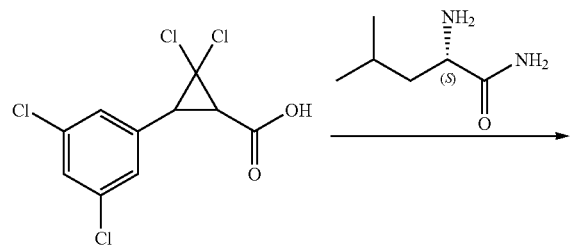

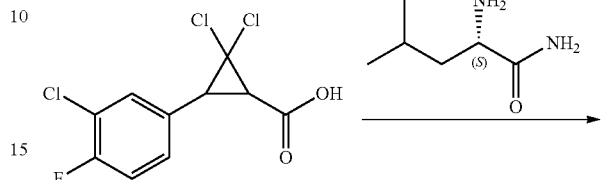

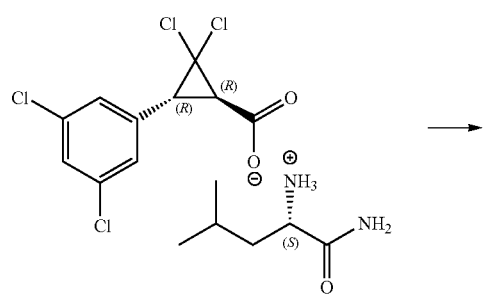

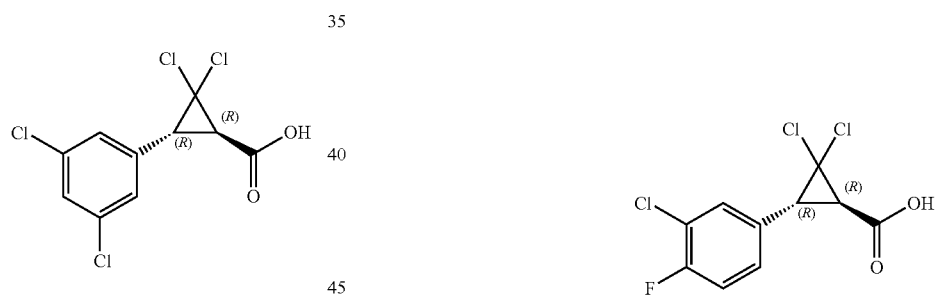

A mixture of (L)-leucinamide (163 mg, 1.25 mmol) and racemic trans-2,2-dichloro-3-(3,5-dichlorophenyl)cyclopropane-carboxylic acid) (750 mg, 2.5 mmol) in acetonitrile (20 mL) was stirred at 60° C. for 0.5 hours. After a solid began to deposit, the mixture placed at room temperature for 4 hours. The white solid was collected, washed with minimal acetonitrile and dried: $^1$H NMR (400 MHz, DMSO-d$^6$) δ 7.81 (s, 1H), 7.53 (t, J=1.9 Hz, 1H), 7.43 (d, J=1.9 Hz, 2H), 7.31 (s, 1H), 3.58-3.44 (m, 1H), 3.27 (d, J=8.6 Hz, 1H), 3.08 (d, J=8.6 Hz, 1H), 1.68 (dt, J=13.3, 6.6 Hz, 1H), 1.49 (dt, J=10.1, 6.8 Hz, 2H), 0.89 (t, J=6.7 Hz, 6H).

The white solid salt was diluted with EtOAc and washed with 1N HCl and brine solution. The organic layer was dried over Na$_2$SO$_4$, filtered and concentrated to afford the title product as a white solid: (0.202 g, 91% ee, 27% yield); $^1$H NMR (300 MHz, CDCl$_3$) δ 7.36 (t, J=1.9 Hz, 1H), 7.17 (dd, J=1.9, 0.7 Hz, 2H), 3.48-3.37 (m, 1H), 2.87 (d, J=8.3 Hz, 1H). $^{13}$C NMR (400 MHz, DMSO-d$^6$) δ 166.28, 136.40, 133.39, 127.27, 127.04, 61.36, 37.10, 35.98. LCMS m/z=298.9 [M+H].

A mixture of (L)-leucinamide (0.45 g, 3.5 mmol) and racemic trans-2,2-dichloro-3-(3-chloro-4-fluorophenyl)cyclopropane-carboxylic acid) (1.41 g, 5 mmol) in acetonitrile (20 mL) was stirred at 60° C. for 0.5 hours. After a solid began to deposit, the mixture was placed at room temperature for 4 hours. The white solid was collected, washed with minimal acetonitrile and dried: 1H NMR (400 MHz, DMSO-d6) δ 7.81 (s, 1H), 7.53 (t, J=1.9 Hz, 1H), 7.43 (d, J=1.9 Hz, 2H), 7.31 (s, 1H), 3.58-3.44 (m, 1H), 3.27 (d, J=8.6 Hz, 1H), 3.08 (d, J=8.6 Hz, 1H), 1.68 (dt, J=13.3, 6.6 Hz, 1H), 1.49 (dt, J=10.1, 6.8 Hz, 2H), 0.89 (t, J=6.7 Hz, 6H).

The white solid salt was diluted with EtOAc and washed with 1N HCl and brine solution. The organic layer was dried over Na$_2$SO$_4$, filtered and concentrated to afford the title product as a white solid: (0.64 g, 91% ee, 45% yield); 1H NMR (400 MHz, DMSO-d6) δ 13.29 (s, 1H), 7.72 (dd, J=7.1, 2.1 Hz, 1H), 7.56-7.32 (m, 2H), 3.46 (d, J=1.0 Hz, 2H); 19F NMR (376 MHz, DMSO-d6) δ −117.35.

Example R3 Resolution of racemic trans-2,2-dichloro-3-(3,4-dichlorophenyl)cyclopropane-1-carboxylic acid with (L)-leucinamide to provide (R,R)-trans-2,2-dichloro-3-(3,4-dichlorophenyl)cyclopropane-1-carboxylic acid Example R4 Resolution of racemic trans-2,2-dichloro-3-(3-trifluoromethyl-4-fluorophenyl)cyclopropane-1-carboxylic acid with (L)-leucinamide to provide (1R,3R)-2,2-dichloro-3-(3-trifluoromethyl-4-fluorophenyl)cyclopropane-1-carboxylic acid

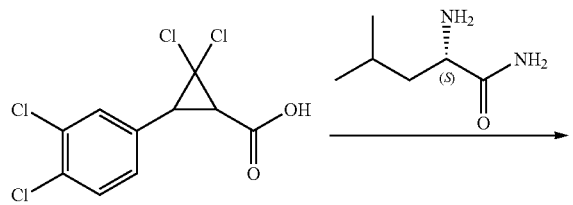

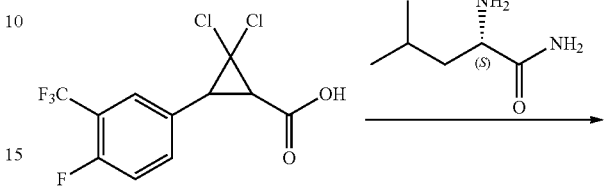

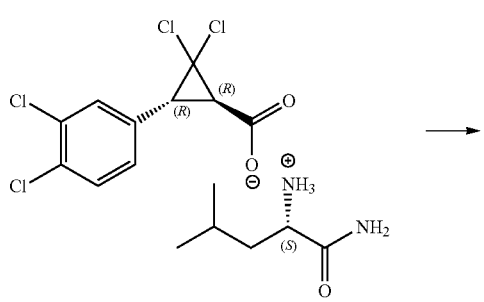

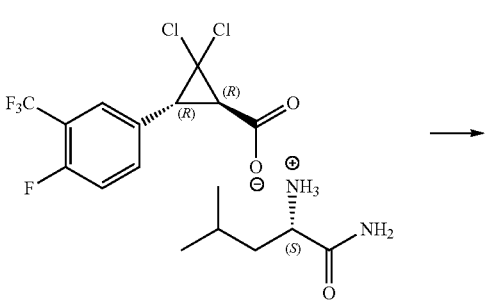

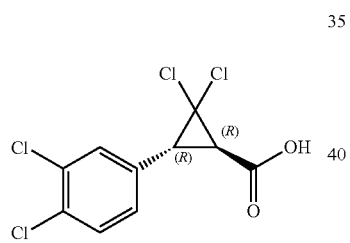

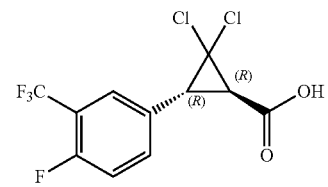

A mixture of (L)-leucinamide (326 mg, 2.5 mmol) and racemic trans-2,2-dichloro-3-(3,4-dichlorophenyl)cyclopropane-carboxylic acid) (1.5 g, 5 mmol) in acetonitrile (20 mL) was stirred at 60° C. for 0.5 hours. After a solid began to deposit, the mixture was placed at room temperature for 4 hours. The solid was collected, washed with minimal acetonitrile and dried: $^1$H NMR (400 MHz, DMSO-d$^6$) δ 7.72 (s, 1H), 7.64 (d, J=2.1 Hz, 1H), 7.60 (d, J=8.3 Hz, 1H), 7.34 (dd, J=8.4, 2.1 Hz, 1H), 7.31-7.26 (m, 1H), 3.48 (dd, J=8.2, 6.2 Hz, 1H), 3.26 (d, J=8.6 Hz, 1H), 3.03 (d, J=8.7 Hz, 1H), 1.74-1.57 (m, 1H), 1.47 (ddd, J=14.6, 7.7, 6.1 Hz, 2H), 0.89 (t, J=6.9 Hz, 6H).

The white solid salt was diluted with EtOAc and washed with 1N HCl and brine solution. The organic layer was dried over Na$_2$SO$_4$, filtered and concentrated to afford the title product as a white solid: (0.56 g, 96% ee, 36% yield); $^1$H NMR (500 MHz, DMSO-d$^6$) δ 13.39 (s, 1H), 7.76 (d, J=2.1 Hz, 1H), 7.64 (d, J=8.3 Hz, 1H), 7.44 (dd, J=8.4, 2.1 Hz, 1H), 3.49 (s, 2H). $^{13}$C NMR (126 MHz, DMSO) δ 166.34, 133.35, 130.47, 130.33, 130.09, 129.77, 128.81, 61.43, 37.00, 36.06. LCMS m/z=298.9 [M+H].

A mixture of (L)-leucinamide (15.6 g, 120 mmol) and racemic trans-2,2-dichloro-3-(3-trifluoromethyl-4-fluorophenyl)cyclopropane-1-carboxylic acid (63.4 g, 200 mmol) in acetonitrile (800 mL) was stirred at 60° C. for 1 hr. After a solid began to deposit, the mixture was placed at room temperature for 4 hours. The solid was collected, washed with minimal acetonitrile and dried to afford the salt of (L)-leucinamide and trans-(1R,3R)-2,2-dichloro-3-(4-fluoro-3-(trifluoromethyl)phenyl)cyclopropane-1-carboxylate as a white solid: (38.9 g, 95% ee, 43%); $^1$H NMR (400 MHz, DMSO-d$^6$) δ 7.80 (s, 1H), 7.73 (m, Hz, 2H), 7.49 (dd, J=10.7, 8.6 Hz, 1H), 7.31 (s, 1H), 3.53 (dd, J=7.9, 6.4 Hz, 1H), 3.34 (d, J=8.6 Hz, 1H), 3.07 (d, J=8.6 Hz, 1H), 1.77-1.60 (m, 1H), 1.60-1.40 (m, 2H), 0.89 (t, J=6.7 Hz, 6H); $^{19}$F NMR (376 MHz, DMSO) δ -59.88, -117.93.

The white solid salt was diluted with EtOAc and washed with 1.5N HCl and water. The organic layer was dried over Na$_2$SO$_4$, filtered and concentrated to afford the title product as a white solid (27.3 g, 95% ee, 43% yield). $^1$H NMR (400 MHz, DMSO-d$^6$) δ 13.24 (s, 1H), 8.03-7.71 (m, 2H), 7.54 (dd, J=10.6, 8.7 Hz, 1H), 3.65-3.51 (m, 2H); $^{19}$F NMR (376 MHz, DMSO-d$^6$) δ -59.93, -117.06; LCMS m/z=316 [M−H].

Example R5 Resolution of racemic trans-2,2-dichloro-3-(4-fluoro-3-(trifluoromethyl)phenyl)cyclopropane-1-carboxylic acid with (R)-2-amino-3-phenylpropanamide ((D)-phenylalanine) to provide (R)-2-amino-3-phenylpropanamide (1R,3R)-2,2-dichloro-3-(4-fluoro-3-(trifluoromethyl)phenyl)cyclopropane-1-carboxylate Example R6 Resolution of racemic trans-2,2-dichloro-3-(4-fluoro-3-(trifluoromethyl)phenyl)cyclopropane-1-carboxylic acid with (S)-2-amino-3-phenylpropanamide to provide (S)-2-amino-3-phenylpropanamide (1S,3S)-2,2-dichloro-3-(4-fluoro-3-(trifluoromethyl)phenyl)cyclopropane-1-carboxylate

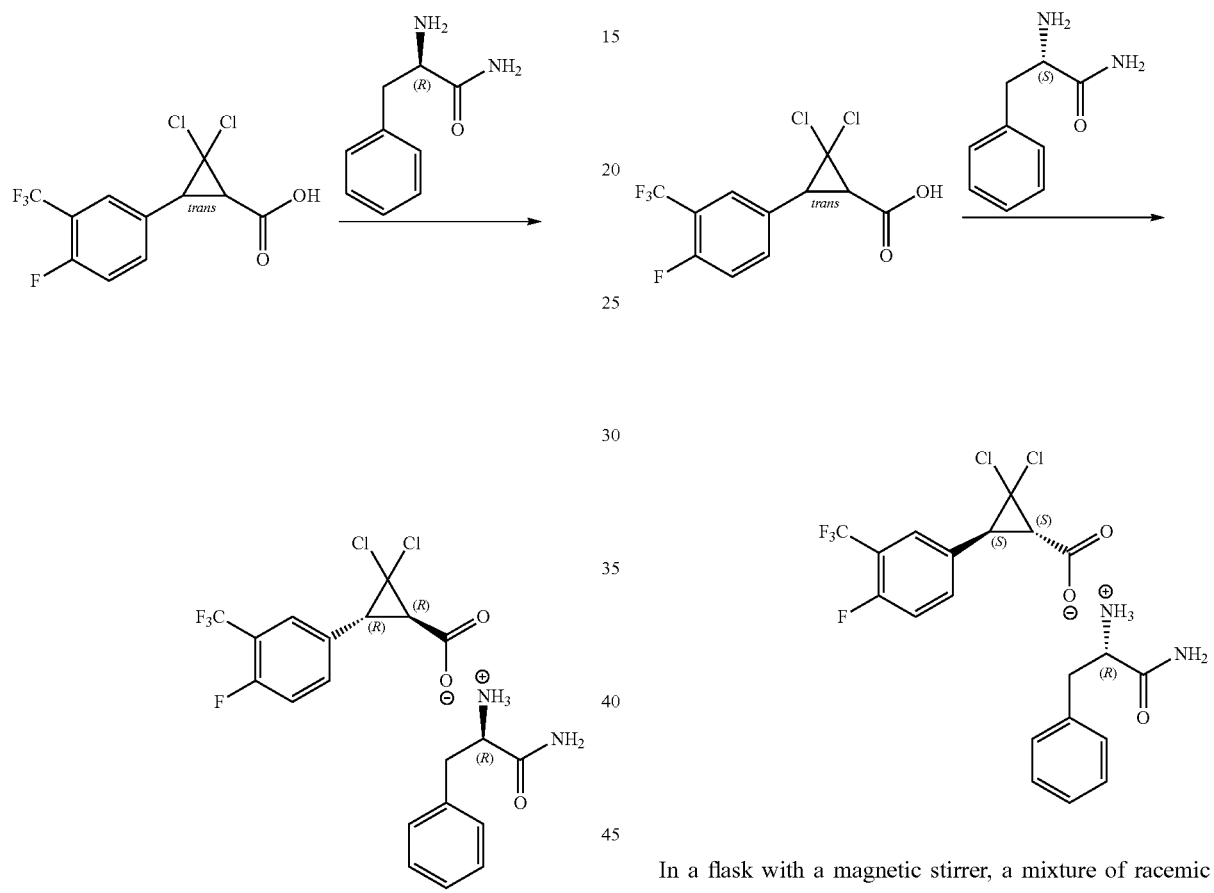

In a flask with a magnetic stirrer, a mixture of 2,2-dichloro-3-(4-fluoro-3-(trifluoromethyl)phenyl)cyclopropane-1-carboxylic acid (1.58 g, 5.0 mmol) and (R)-2-amino-3-phenylpropanamide (411 mg, 2.5 mmol) in acetonitrile (20 mL) was heated to 60° C. The resulting suspension was stirred at 60° C. for 10 min, then cooled to RT. The mixture was stirred overnight. The product was filtered and washed with acetonitrile, then dried in air and at 35° C. in a vacuum oven to give (R)-2-amino-3-phenylpropanamide (1R,3R)-2,2-dichloro-3-(4-fluoro-3-(trifluoromethyl)phenyl)cyclopropane-1-carboxylate (710 mg, 1.475 mmol, 29.5% yield) as a white solid. Chiral HPLC analysis indicated the ratio of SS/RR was 6/93 (86% ee).

In a flask with a magnetic stirrer, a mixture of racemic 2,2-dichloro-3-(4-fluoro-3-(trifluoromethyl)phenyl)cyclopropane-1-carboxylic acid (1.58 g, 5.0 mmol) and (S)-2-amino-3-phenylpropanamide (411 mg, 2.5 mmol) in acetonitrile (ACN, 20 mL) was heated to 60° C. The resulting suspension was stirred at 60° C. for 10 min, then cooled to rt. The mixture was stirred overnight. The product was filtered and washed with ACN, then dried in air and at 35° C. in a vacuum oven to give (S)-2-amino-3-phenylpropanamide (1S,3S)-2,2-dichloro-3-(4-fluoro-3-(trifluoromethyl)phenyl)cyclopropane-1-carboxylate (0.669 g, 1.390 mmol, 27.8% yield) as a white solid. The chiral HPLC indicated the ratio of SS/RR was 96/3 (93% ee).

The following compounds were prepared in like manner to the procedure outlined in Example 1:

trans-5-(3-(3-Bromo-4-chlorophenyl)-2,2-dichloro-
cyclopropane-1-carboxamido)-2-chloro-N-(2,4-dif-
luoro-3-(2,2,2-trifluoroacetamido)phenyl)benzamide
(F1358)

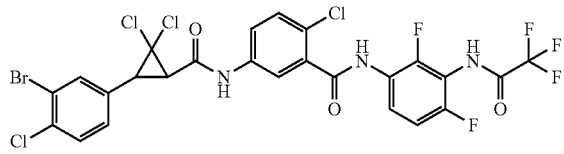

Isolated as a white solid (0.140 g, 63%).

trans-5-(3-(3-Bromo-4-chlorophenyl)-2,2-dichloro-
cyclopropane-1-carboxamido)-2-chloro-N-(3-(2,2-
difluoroacetamido)-2,4-difluorophenyl)benzamide
(F1359)

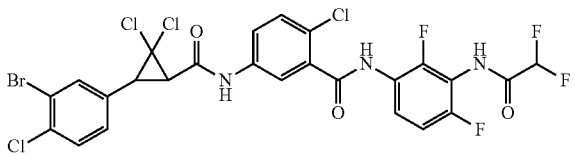 [SMILES: O=C(Nc1ccc(F)c(NC(=O)C(F)F)c1F)c1cc(NC(=O)C2C(c3ccc(Cl)c(Br)c3)C2(Cl)Cl)ccc1Cl]

Isolated as a white solid (0.098 g, 56%).

trans-2-Chloro-N-(4-chloro-3-(2,2,2-trifluoroacet-
amido)phenyl)-5-(2,2-dichloro-3-(3-chloro-4-fluoro-
phenyl)cyclopropane-1-carboxamido)benzamide
(F1366)

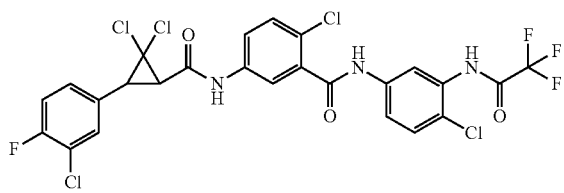 [SMILES: O=C(Nc1ccc(Cl)c(NC(=O)C(F)(F)F)c1)c1cc(NC(=O)C2C(c3ccc(F)c(Cl)c3)C2(Cl)Cl)ccc1Cl]

Isolated as a white solid (0.076 g, 80%).

trans-2-Chloro-5-(2,2-dichloro-3-(3-chloro-4-fluoro-
phenyl)cyclopropane-1-carboxamido)-N-(3,5-di-
chloro-4-(2,2,2-trifluoroacetamido)phenyl)benz-
amide (F1368)

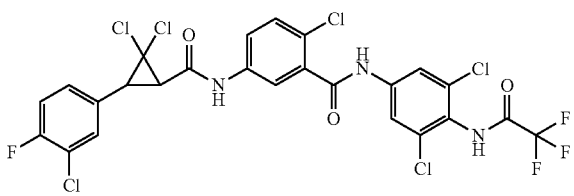 [SMILES: O=C(Nc1cc(Cl)c(NC(=O)C(F)(F)F)c(Cl)c1)c1cc(NC(=O)C2C(c3ccc(F)c(Cl)c3)C2(Cl)Cl)ccc1Cl]

Isolated as a white solid (0.069 g, 76%).

trans-2-Chloro-N-(3-chloro-4-(2,2,2-trifluoroacet-
amido)phenyl)-5-(2,2-dichloro-3-(3-chloro-4-fluoro-
phenyl)cyclopropane-1-carboxamido)benzamide
(F1384)

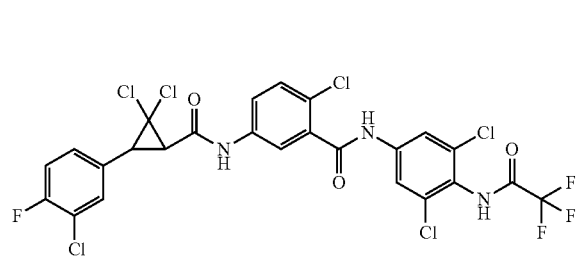 [SMILES: O=C(Nc1cc(Cl)c(NC(=O)C(F)(F)F)c(Cl)c1)c1cc(NC(=O)C2C(c3ccc(F)c(Cl)c3)C2(Cl)Cl)ccc1Cl]

Isolated as a white solid (0.093 g, 70%).

trans-2-Chloro-N-(3-cyano-4-(2,2,2-trifluoroacet-
amido)phenyl)-5-(2,2-dichloro-3-(3-chloro-4-fluoro-
phenyl)cyclopropane-1-carboxamido)benzamide
(F1388)

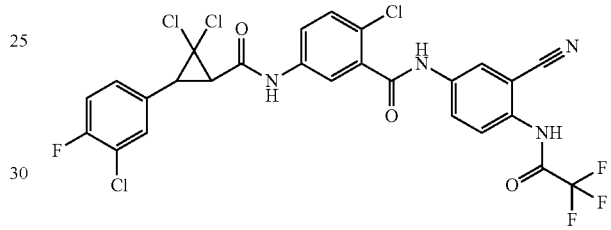

Isolated as a yellow foam (0.039 g, 72%).

2-Chloro-5-((1R,3R)-2,2-dichloro-3-(4-fluoro-3-
(trifluoromethyl)phenyl)cyclopropane-1-carbox-
amido)-N-(2,3-dimethyl-4-(2,2,2-trifluoroacetamido)
phenyl)benzamide (F1392)

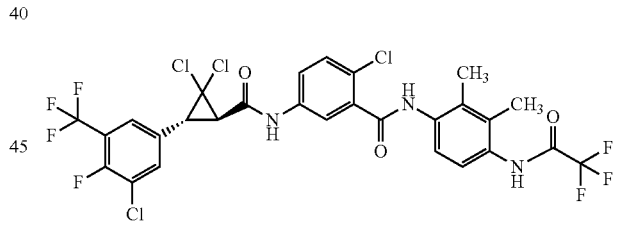

Isolated as a white foam (0.055 g, 80%).

trans-2-Chloro-5-(2,2-dichloro-3-(3-chloro-4-fluoro-
phenyl)cyclopropane-1-carboxamido)-N-(4-(2,2,2-
trifluoroacetamido)-3-(trifluoromethyl)phenyl)benz-
amide (F1393)

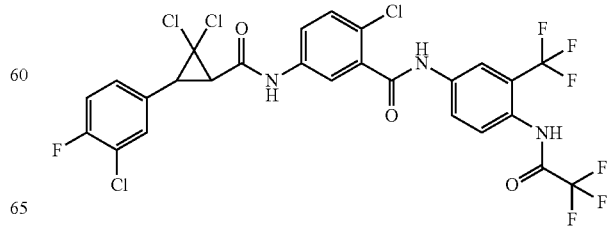

Isolated as a white foam (0.078 g, 75%).

301

2-Chloro-5-((1R,3R)-2,2-dichloro-3-(4-fluoro-3-(trifluoromethyl)phenyl)cyclopropane-1-carboxamido)-N-(3-(2,2-difluoroacetamido)-2,6-difluorophenyl)benzamide (F1394)

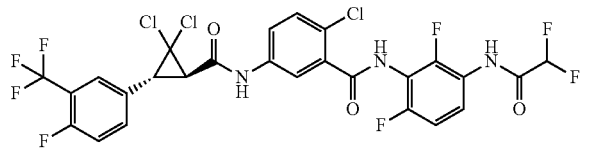 [SMILES: O=C(Nc1c(F)ccc(NC(=O)C(F)F)c1F)c1cc(NC(=O)[C@H]2[C@H](c3ccc(F)c(C(F)(F)F)c3)C2(Cl)Cl)ccc1Cl]

Isolated as a white foam (0.078 g, 75%).

2-Chloro-5-((1R,3R)-2,2-dichloro-3-(4-fluoro-3-(trifluoromethyl)phenyl)cyclopropane-1-carboxamido)-N-(2-methyl-3-(2,2,2-trifluoroacetamido)phenyl)benzamide (F1451)

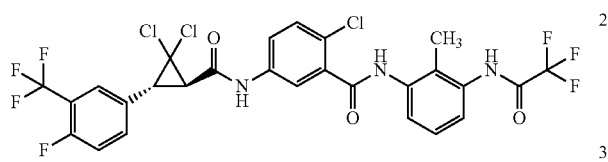

Isolated as a white solid (0.087 g, 75%).

5-((1R,3R)-2,2-Dichloro-3-(3,4-dichlorophenyl)cyclopropane-1-carboxamido)-N-(3-(2,2-difluoroacetamido)-2,4-difluorophenyl)-2-fluorobenzamide (F1491)

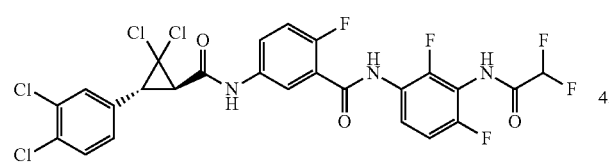

Isolated as a white solid (0.086 g, 76%).

5-((1R,3R)-2,2-Dichloro-3-(3,4-dichlorophenyl)cyclopropane-1-carboxamido)-N-(2,4-difluoro-3-(2,2,2-trifluoroacetamido)phenyl)-2-fluorobenzamide (F1492)

Isolated as a white solid (0.102 g, 87%).

302

5-((1R,3R)-2,2-Dichloro-3-(3,4-dichlorophenyl)cyclopropane-1-carboxamido)-N-(5-(2,2-difluoroacetamido)-2,4-difluorophenyl)-2-fluorobenzamide (F1509)

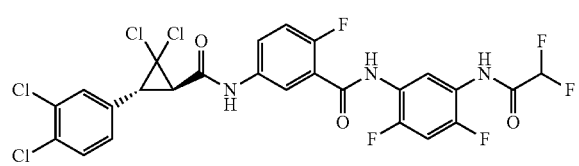 [SMILES: O=C(Nc1cc(NC(=O)C(F)F)c(F)cc1F)c1cc(NC(=O)[C@H]2[C@H](c3ccc(Cl)c(Cl)c3)C2(Cl)Cl)ccc1F]

Isolated as a white foam (0.059 g, 51.9%).

5-((1R,3R)-2,2-Dichloro-3-(3,4-dichlorophenyl)cyclopropane-1-carboxamido)-N-(2,4-difluoro-5-(2,2,2-trifluoroacetamido)phenyl)-2-fluorobenzamide (F1510)

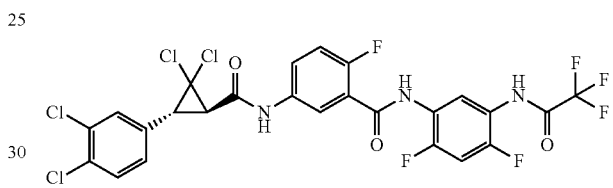

Isolated as a tan solid (0.119 g, 85%).

trans-5-(3-(4-Bromophenyl)-2,2-dichlorocyclopropane-1-carboxamido)-2-chloro-N-(3-(2,2-difluoroacetamido)-2,4-difluorophenyl)benzamide (F1597)

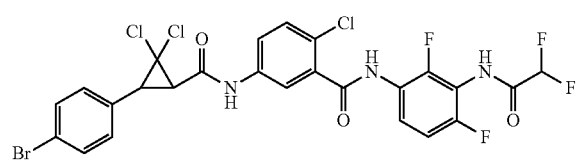

Isolated as a clear, colorless oil (0.050 g, 86%).

trans-2-Chloro-5-(2,2-dichloro-3-(4-fluorophenyl)cyclopropane-1-carboxamido)-N-(3-(2,2-difluoroacetamido)-2,4-difluorophenyl)benzamide (F1598)

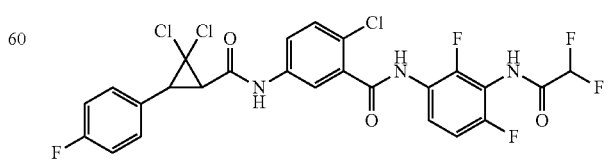

Isolated as a clear, colorless oil (0.052 g, 78%).

303 trans-2-Chloro-5-(2,2-dichloro-3-(4-chlorophenyl)
cyclopropane-1-carboxamido)-N-(3-(2,2-difluoroac-
etamido)-2,4-difluorophenyl)benzamide (F1599)

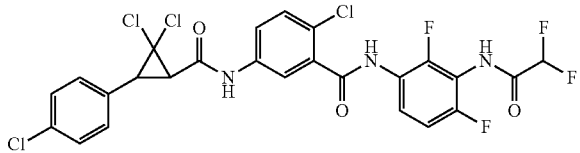 [SMILES: O=C(Nc1ccc(F)c(NC(=O)C(F)F)c1F)c1cc(NC(=O)C2C(c3ccc(Cl)cc3)C2(Cl)Cl)ccc1Cl]

Isolated as a white foam (0.101 g, 87%).

trans-5-(3-(3-Bromophenyl)-2,2-dichlorocyclopro-
pane-1-carboxamido)-2-chloro-N-(3-(2,2-difluoroac-
etamido)-2,4-difluorophenyl)benzamide (F1600)

Isolated as a clear, colorless oil (0.057 g, 80%).

trans-2-Chloro-5-(2,2-dichloro-3-(3-chlorophenyl)
cyclopropane-1-carboxamido)-N-(3-(2,2-difluoroac-
etamido)-2,4-difluorophenyl)benzamide (F1601)

Isolated as a white foam (0.076 g, 75%).

304 trans-2-Chloro-5-(2,2-dichloro-3-(3-fluorophenyl)
cyclopropane-1-carboxamido)-N-(3-(2,2-difluoroac-
etamido)-2,4-difluorophenyl)benzamide (F1602)

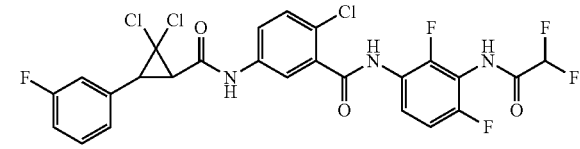

Isolated as a white foam (0.103 g, 83%).

2-Chloro-5-((1R,3R)-2,2-dichloro-3-(3,4-dichloro-
phenyl)cyclopropane-1-carboxamido)-N-(2,4-dif-
luoro-3-(2,2,2-trifluoro-N-methylacetamido)phenyl)
benzamide (F1614)

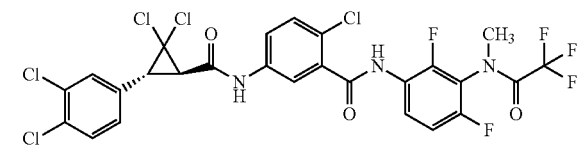

Isolated as a white foam (0.109 g, 93%).

2-Chloro-5-((1R,3R)-2,2-dichloro-3-(3,4-dichloro-
phenyl)cyclopropane-1-carboxamido)-N-(2,4-dif-
luoro-3-(2,2,3,3,3-pentafluoro-N-methylpropana-
mido)phenyl)benzamide (F1615)

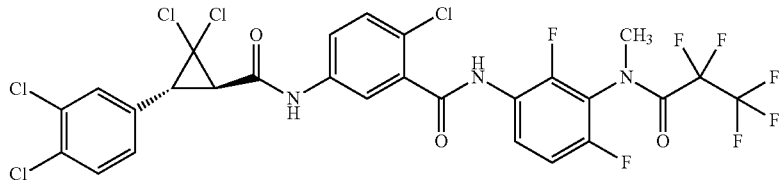 [SMILES: CN(C(=O)C(F)(F)C(F)(F)F)c1c(F)ccc(NC(=O)c2cc(NC(=O)[C@H]3[C@H](c4ccc(Cl)c(Cl)c4)C3(Cl)Cl)ccc2Cl)c1F]

Isolated as a white foam (0.123 g, 98%).

trans-5-(3-(3-Bromo-4,5-dichlorophenyl)-2,2-dichlo-
rocyclopropane-1-carboxamido)-2-chloro-N-(3-(2,2-
difluoroacetamido)-2,4-difluorophenyl)benzamide
(F1623)

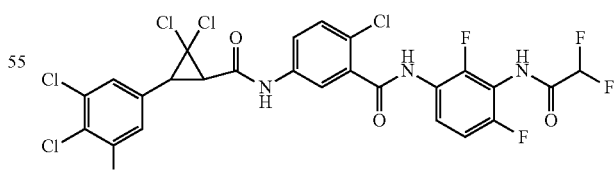

Isolated as a white foam (0.061 g, 68%). The title compound was prepared from N-(3-amino-2,4-difluorophenyl)-5-(3-(3-bromo-4,5-dichlorophenyl)-2,2-dichlorocyclopropane-1-carboxamido)-2-chlorobenzamide which was prepared via methods described in U.S. Patent Application Publication US20160304522A1 (F621).

305 trans-2-Chloro-5-(2,2-dichloro-3-(4-fluoro-3-iodo-phenyl)cyclopropane-1-carboxamido)-N-(3-(2,2-difluoroacetamido)-2,4-difluorophenyl)benzamide (F1624)

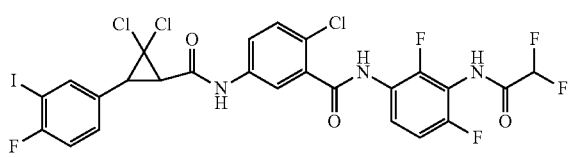 [SMILES: O=C(Nc1ccc(F)c(NC(=O)C(F)F)c1F)c1cc(NC(=O)C2C(c3ccc(F)c(I)c3)C2(Cl)Cl)ccc1Cl]

Isolated as a white solid (0.066 g, 74%).

2-Chloro-5-((1R,3R)-2,2-dichloro-3-(4-chloro-3-(trifluoromethyl)phenyl)cyclopropane-1-carboxamido)-N-(2,4-difluoro-3-(2,2,2-trifluoroacetamido)phenyl)benzamide (F1656)

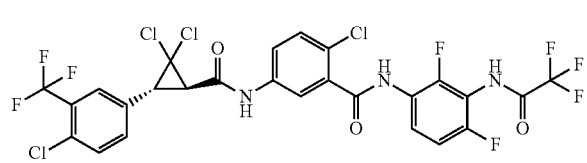 [SMILES: O=C(Nc1ccc(F)c(NC(=O)C(F)(F)F)c1F)c1cc(NC(=O)[C@H]2[C@H](c3ccc(Cl)c(C(F)(F)F)c3)C2(Cl)Cl)ccc1Cl]

Isolated as a white foam (0.077 g, 84%).

2-Chloro-5-((1R,3R)-2,2-dichloro-3-(4-chloro-3-(trifluoromethyl)phenyl)cyclopropane-1-carboxamido)-N-(3-(2,2-difluoroacetamido)-2,4-difluorophenyl)benzamide (F1657)

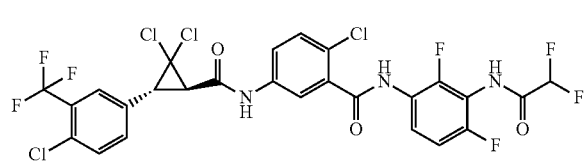 [SMILES: O=C(Nc1ccc(F)c(NC(=O)C(F)F)c1F)c1cc(NC(=O)[C@H]2[C@H](c3ccc(Cl)c(C(F)(F)F)c3)C2(Cl)Cl)ccc1Cl]

Isolated as a white foam (0.082 g, 91%).

306

2-Chloro-5-((1R,3R)-2,2-dichloro-3-(3-(trifluoromethyl)phenyl)cyclopropane-1-carboxamido)-N-(3-(2,2-difluoroacetamido)-2,4-difluorophenyl)benzamide (F1675)

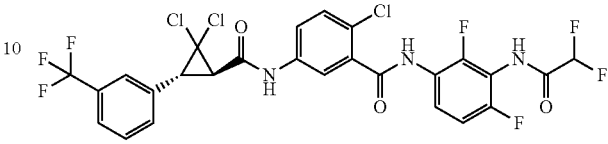

Isolated as a white solid (0.077 g, 86%).

2-Chloro-5-((1R,3R)-2,2-dichloro-3-(4-fluoro-3-(trifluoromethyl)phenyl)cyclopropane-1-carboxamido)-N-(5-(2,2-difluoroacetamido)-2,4-difluoro-3-methylphenyl)benzamide (F1680)

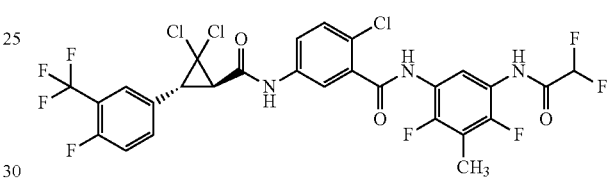

Isolated as a white foam (0.048 g, 71%).

2-Chloro-5-((1R,3R)-2,2-dichloro-3-(3-chloro-4-fluorophenyl)cyclopropane-1-carboxamido)-N-(2,4-difluoro-3-(2,2,2-trifluoroacetamido)phenyl)benzamide (F1695)

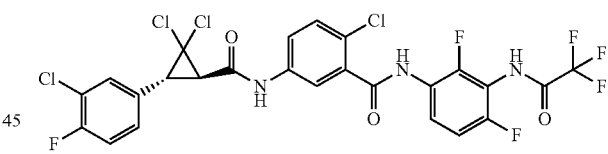

Isolated as a yellow foam (0.094 g, 80%).

2-Chloro-5-((1R,3R)-2,2-dichloro-3-(3-chloro-4-fluorophenyl)cyclopropane-1-carboxamido)-N-(2,4-difluoro-3-(2,2,3,3,3-pentafluoropropanamido)phenyl)benzamide (F1696)

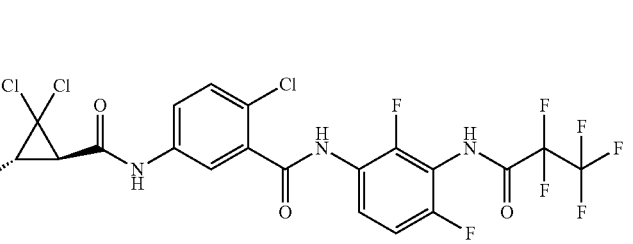

Isolated as a white foam (0.089 g, 71%).

307

2-Chloro-5-((1R,3R)-2,2-dichloro-3-(3-fluoro-5-(trifluoromethyl)phenyl)cyclopropane-1-carboxamido)-N-(3-(2,2-difluoroacetamido)-2,4-difluorophenyl)benzamide (F1711)

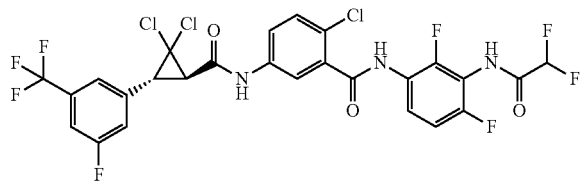 [SMILES: O=C(Nc1ccc(F)c(NC(=O)C(F)F)c1F)c1cc(NC(=O)[C@H]2[C@H](c3cc(F)cc(C(F)(F)F)c3)C2(Cl)Cl)ccc1Cl]

Isolated as a white solid (0.075 g, 84%).

2-Chloro-5-((1R,3R)-2,2-dichloro-3-(4-fluoro-3-(trifluoromethyl)phenyl)cyclopropane-1-carboxamido)-N-(5-(2,2-difluoroacetamido)-2,3,4-trifluorophenyl)benzamide (F1744)

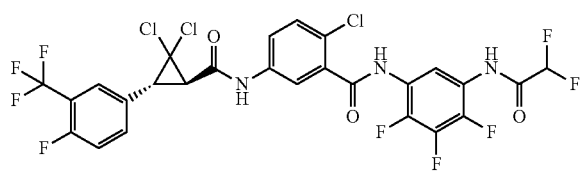 [SMILES: O=C(Nc1cc(NC(=O)C(F)F)c(F)c(F)c1F)c1cc(NC(=O)[C@H]2[C@H](c3ccc(F)c(C(F)(F)F)c3)C2(Cl)Cl)ccc1Cl]

Isolated as a clear, colorless oil (0.117 g, 99%).

2-Chloro-5-((1R,3R)-2,2-dichloro-3-(3,4-dichlorophenyl)cyclopropane-1-carboxamido)-N-(2,4-difluoro-3-(2,2,2-trifluoroacetamido)phenyl)-N-methylbenzamide (F1792)

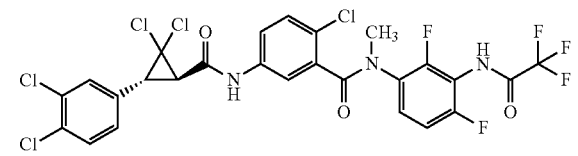 [SMILES: CN(C(=O)c1cc(NC(=O)[C@H]2[C@H](c3ccc(Cl)c(Cl)c3)C2(Cl)Cl)ccc1Cl)c1ccc(F)c(NC(=O)C(F)(F)F)c1F]

Isolated as a white foam (0.082 g, 70%).

2-Chloro-5-((1R,3R)-2,2-dichloro-3-(4-fluoro-3-(trifluoromethyl)phenyl)cyclopropane-1-carboxamido)-N-(2,4-difluoro-3-(2,2,2-trifluoroacetamido)phenyl)-N-methylbenzamide (F1795)

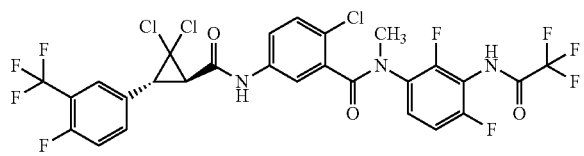 [SMILES: CN(C(=O)c1cc(NC(=O)[C@H]2[C@H](c3ccc(F)c(C(F)(F)F)c3)C2(Cl)Cl)ccc1Cl)c1ccc(F)c(NC(=O)C(F)(F)F)c1F]

Isolated as a light yellow oil (0.091 g, 79%).

308 trans-5-(3-(3,5-bis(Trifluoromethyl)phenyl)-2,2-dichlorocyclopropane-1-carboxamido)-2-chloro-N-(2,4-difluoro-3-(2,2,2-trifluoroacetamido)phenyl)benzamide (F1801)

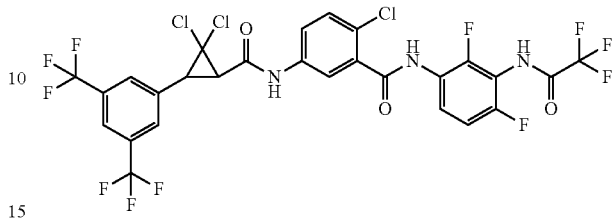

Isolated as a white solid (0.098 g, 86%).

trans-5-(3-(3,5-bis(Trifluoromethyl)phenyl)-2,2-dichlorocyclopropane-1-carboxamido)-2-chloro-N-(3-(2,2-difluoroacetamido)-2,4-difluorophenyl)benzamide (F1802)

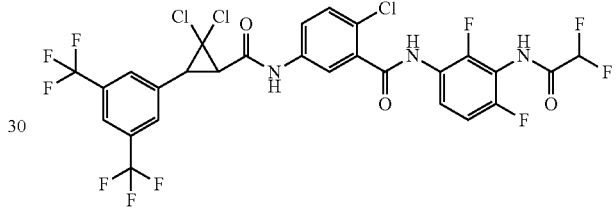

Isolated as a white solid (0.096 g, 86%).

The following compounds were prepared in like manner to the procedure outlined in Example 2:

N-(3-Acetamido-2,4-difluorophenyl)-5-((1R,3R)-2,2-dichloro-3-(3,4-dichlorophenyl)cyclopropane-1-carboxamido)-2-fluorobenzamide (F1493)

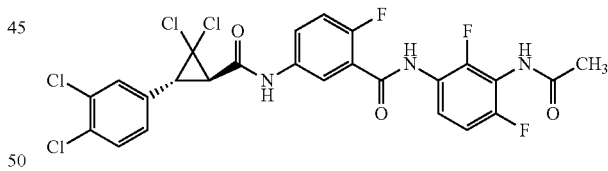

Isolated as a tan solid (0.100 g, 66%).

N-(5-Acetamido-2,4-difluorophenyl)-5-((1R,3R)-2,2-dichloro-3-(3,4-dichlorophenyl)cyclopropane-1-carboxamido)-2-fluorobenzamide (F1511)

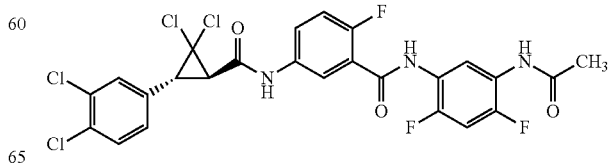

Isolated as a white foam (0.108 g, 84%).

N-(3-Acetamido-2,4-difluorophenyl)-2-chloro-5-((1R,3R)-2,2-dichloro-3-(4-chloro-3-(trifluoromethyl)phenyl)cyclopropane-1-carboxamido)benzamide (F1658)

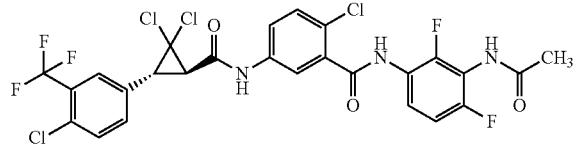

Isolated as a white solid (0.061 g, 72%).

N-(3-Acetamido-2,4-difluorophenyl)-2-chloro-5-((1R,3R)-2,2-dichloro-3-(3-chloro-4-fluorophenyl)cyclopropane-1-carboxamido)benzamide (F1694)

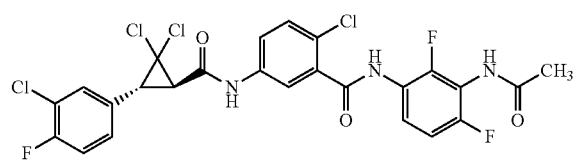 [SMILES: CC(=O)Nc1c(F)ccc(NC(=O)c2cc(NC(=O)[C@H]3[C@H](c4ccc(Cl)c(Cl)c4)C3(Cl)Cl)ccc2F)c1F]

Isolated as a white foam (0.094 g, 88%). The title compound was prepared from N-(3-amino-2,4-difluorophenyl)-2-chloro-5-((1R,3R)-2,2-dichloro-3-(3-chloro-4-fluorophenyl)cyclopropane-1-carboxamido)benzamide which was prepared using methods described in U.S. Patent Application Publication US20160304522A1 (F317).

N-(3-Acetamido-2,4-difluorophenyl)-2-chloro-5-((1R,3R)-2,2-dichloro-3-(4-fluoro-3-(trifluoromethyl)phenyl)cyclopropane-1-carboxamido)-N-methylbenzamide (F1799)

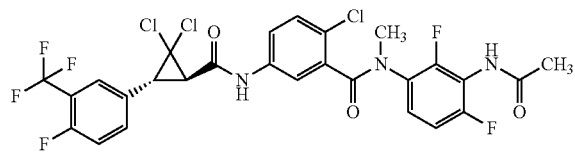 [SMILES: CC(=O)Nc1c(F)ccc(N(C)C(=O)c2cc(NC(=O)[C@H]3[C@H](c4ccc(F)c(C(F)(F)F)c4)C3(Cl)Cl)ccc2Cl)c1F]

Isolated as a white foam (0.070 g, 65%).

trans-N-(3-Acetamido-2,4-difluorophenyl)-5-(3-(3,5-bis(trifluoromethyl)phenyl)-2,2-dichlorocyclopropane-1-carboxamido)-2-chlorobenzamide (F1803)

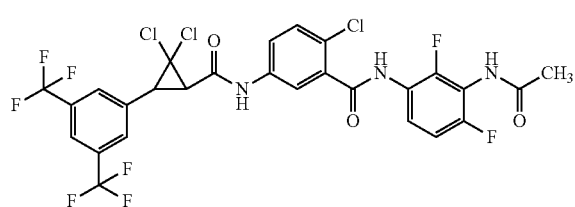 [SMILES: CC(=O)Nc1c(F)ccc(NC(=O)c2cc(NC(=O)C3C(c4cc(C(F)(F)F)cc(C(F)(F)F)c4)C3(Cl)Cl)ccc2Cl)c1F]

Isolated as a white foam (0.062 g, 58%).

The following compounds were prepared in like manner to the procedure outlined in Example 3:

2-Chloro-5-((1R,3R)-2,2-dichloro-3-(3,5-dichlorophenyl)cyclopropane-1-carboxamido)-N-(2,6-difluoro-3-(2,2,2-trifluoroacetamido)phenyl)-3-fluorobenzamide (F1340)

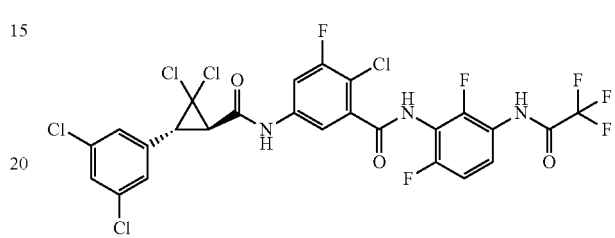

Isolated as a white solid (0.050 g, 96%).

2-Chloro-5-((1R,3R)-2,2-dichloro-3-(3,5-dichlorophenyl)cyclopropane-1-carboxamido)-N-(3-(2,2-difluoroacetamido)-2,6-difluorophenyl)-3-fluorobenzamide (F1341)

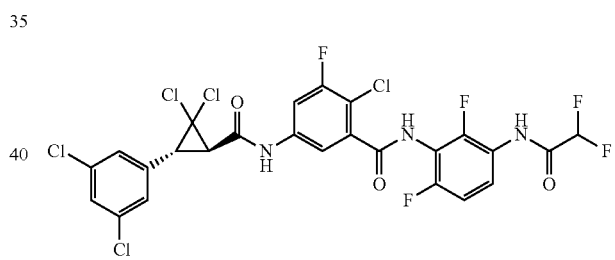

Isolated as a yellow solid (0.052 g, 100%).

2-Chloro-5-((1R,3R)-2,2-dichloro-3-(3,4,5-trichlorophenyl)cyclopropane-1-carboxamido)-N-(2,6-difluoro-3-(2,2,2-trifluoroacetamido)phenyl)-3-fluorobenzamide (F1342)

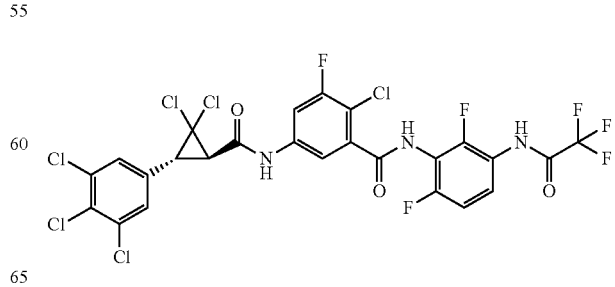

Isolated as a white solid (0.051 g, 98%).

311

2-Chloro-5-((1R,3R)-2,2-dichloro-3-(3,4,5-trichlorophenyl)cyclopropane-1-carboxamido)-N-(3-(2,2-difluoroacetamido)-2,6-difluorophenyl)-3-fluorobenzamide (F1343)

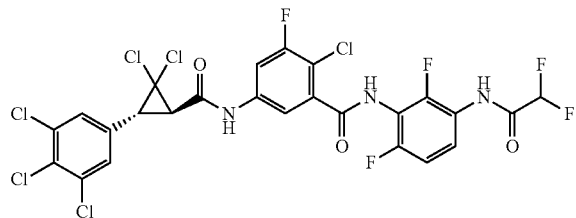 [SMILES: O=C(Nc1c(F)ccc(NC(=O)C(F)F)c1F)c1cc(NC(=O)[C@H]2[C@H](c3cc(Cl)c(Cl)c(Cl)c3)C2(Cl)Cl)cc(F)c1Cl]

Isolated as an off-white solid (0.050 g, 99%).

2-Chloro-5-((1R,3R)-2,2-dichloro-3-(3,4-dichlorophenyl)cyclopropane-1-carboxamido)-N-(2,6-difluoro-3-(2,2,2-trifluoroacetamido)phenyl)-3-fluorobenzamide (F1344)

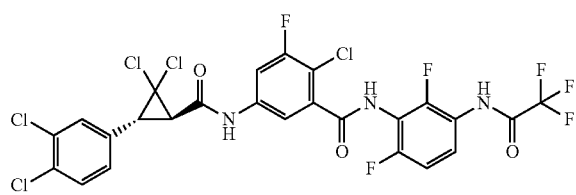 [SMILES: O=C(Nc1c(F)ccc(NC(=O)C(F)(F)F)c1F)c1cc(NC(=O)[C@H]2[C@H](c3ccc(Cl)c(Cl)c3)C2(Cl)Cl)cc(F)c1Cl]

Isolated as a white solid (0.049 g, 100%).

2-Chloro-5-((1R,3R)-2,2-dichloro-3-(3,4-dichlorophenyl)cyclopropane-1-carboxamido)-N-(3-(2,2-difluoroacetamido)-2,6-difluorophenyl)-3-fluorobenzamide (F1345)

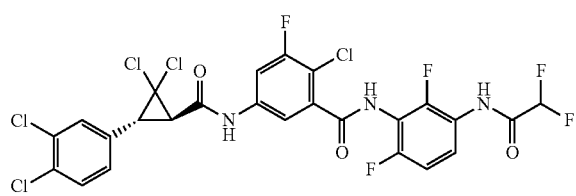 [SMILES: O=C(Nc1c(F)ccc(NC(=O)C(F)F)c1F)c1cc(NC(=O)[C@H]2[C@H](c3ccc(Cl)c(Cl)c3)C2(Cl)Cl)cc(F)c1Cl]

Isolated as a white solid (0.047 g, 99%).

2-Chloro-5-((1R,3R)-2,2-dichloro-3-(4-fluoro-3-(trifluoromethyl)phenyl)cyclopropane-1-carboxamido)-N-(2,6-difluoro-3-(2,2,2-trifluoroacetamido)phenyl)-3-fluorobenzamide (F1346)

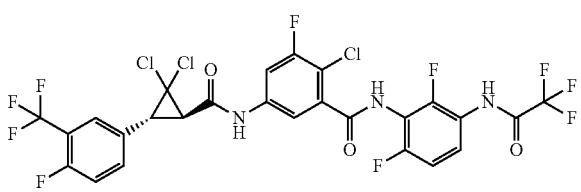 [SMILES: O=C(Nc1c(F)ccc(NC(=O)C(F)(F)F)c1F)c1cc(NC(=O)[C@H]2[C@H](c3ccc(F)c(C(F)(F)F)c3)C2(Cl)Cl)cc(F)c1Cl]

Isolated as a white solid (0.046 g, 99%).

312

2-Chloro-5-((1R,3R)-2,2-dichloro-3-(4-fluoro-3-(trifluoromethyl)phenyl)cyclopropane-1-carboxamido)-N-(3-(2,2-difluoroacetamido)-2,6-difluorophenyl)-3-fluorobenzamide (F1347)

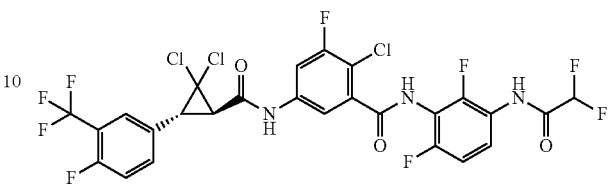

Isolated as an off white solid (0.045 g, 100%).

N-(3-(2-Bromo-2,2-difluoroacetamido)-2,6-difluorophenyl)-2-chloro-5-((1R,3R)-2,2-dichloro-3-(4-fluoro-3-(trifluoromethyl)phenyl)cyclopropane-1-carboxamido)-3-fluorobenzamide (F1356)

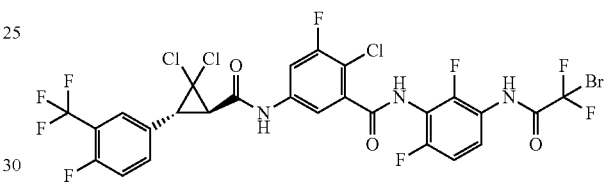

Isolated as an off white solid (0.048 g, 96%).

2-Chloro-5-((1R,3R)-2,2-dichloro-3-(3-chloro-4-fluorophenyl)cyclopropane-1-carboxamido)-N-(5-(2,2-difluoroacetamido)-2,4-difluorophenyl)-3-fluorobenzamide (F1400)

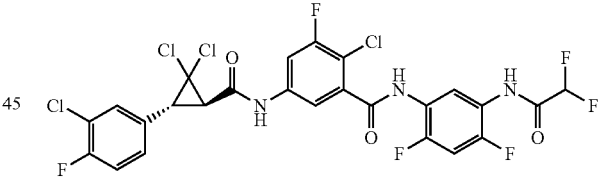

Isolated as a tan solid (0.086 g, 90%).

2-Chloro-5-((1R,3R)-2,2-dichloro-3-(3-chloro-4-fluorophenyl)cyclopropane-1-carboxamido)-N-(2,4-difluoro-5-(2,2,2-trifluoroacetamido)phenyl)-3-fluorobenzamide (F1401)

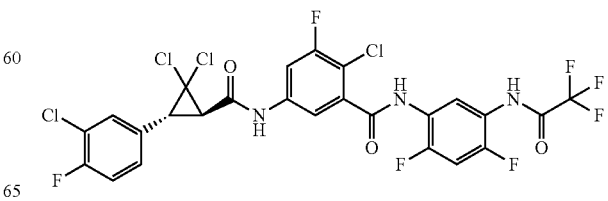

Isolated as a white solid (0.087 g, 89%).

313

2-Chloro-5-((1R,3R)-2,2-dichloro-3-(3,4-dichlorophenyl)cyclopropane-1-carboxamido)-N-(5-(2,2-difluoroacetamido)-2,4-difluorophenyl)-3-fluorobenzamide (F1402)

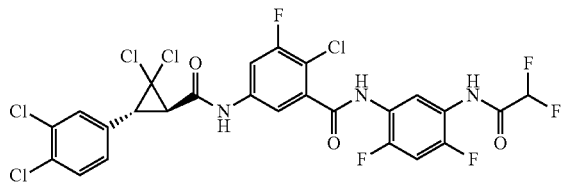 [SMILES: O=C(Nc1cc(NC(=O)C(F)F)c(F)cc1F)c1cc(NC(=O)[C@H]2[C@H](c3ccc(Cl)c(Cl)c3)C2(Cl)Cl)cc(F)c1Cl]

Isolated as a tan solid (0.078 g, 83%).

2-Chloro-5-((1R,3R)-2,2-dichloro-3-(3,4-dichlorophenyl)cyclopropane-1-carboxamido)-N-(2,4-difluoro-5-(2,2,2-trifluoroacetamido)phenyl)-3-fluorobenzamide (F1403)

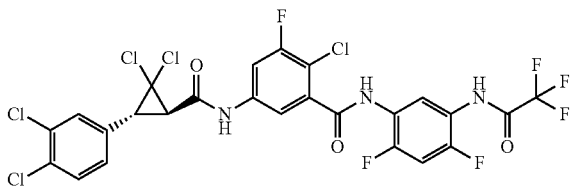 [SMILES: O=C(Nc1cc(NC(=O)C(F)(F)F)c(F)cc1F)c1cc(NC(=O)[C@H]2[C@H](c3ccc(Cl)c(Cl)c3)C2(Cl)Cl)cc(F)c1Cl]

Isolated as a light-tan solid (0.090 g, 93%).

2-Chloro-5-((1R,3R)-2,2-dichloro-3-(3,4,5-trichlorophenyl)cyclopropane-1-carboxamido)-N-(5-(2,2-difluoroacetamido)-2,4-difluorophenyl)-3-fluorobenzamide (F1404)

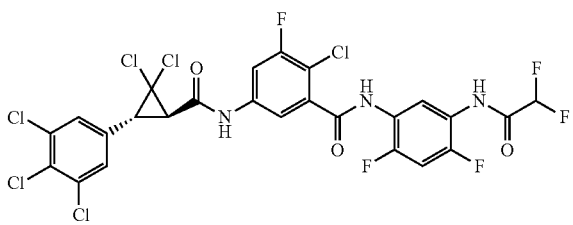 [SMILES: O=C(Nc1cc(NC(=O)C(F)F)c(F)cc1F)c1cc(NC(=O)[C@H]2[C@H](c3cc(Cl)c(Cl)c(Cl)c3)C2(Cl)Cl)cc(F)c1Cl]

Isolated as a light-tan solid (0.085 g, 91%).

2-Chloro-5-((1R,3R)-2,2-dichloro-3-(3,4,5-trichlorophenyl)cyclopropane-1-carboxamido)-N-(2,4-difluoro-5-(2,2,2-trifluoroacetamido)phenyl)-3-fluorobenzamide (F1405)

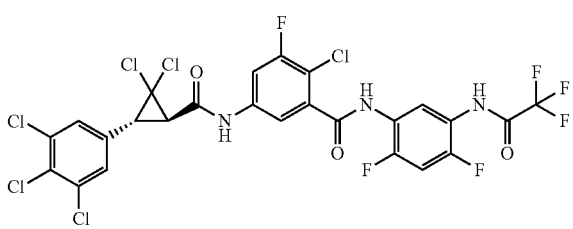 [SMILES: O=C(Nc1cc(NC(=O)C(F)(F)F)c(F)cc1F)c1cc(NC(=O)[C@H]2[C@H](c3cc(Cl)c(Cl)c(Cl)c3)C2(Cl)Cl)cc(F)c1Cl]

Isolated as a white solid (0.085 g, 88%).

314

2-Chloro-5-((1R,3R)-2,2-dichloro-3-(4-fluoro-3-(trifluoromethyl)phenyl)cyclopropane-1-carboxamido)-N-(5-(2,2-difluoroacetamido)-2,4-difluorophenyl)-3-fluorobenzamide (F1406)

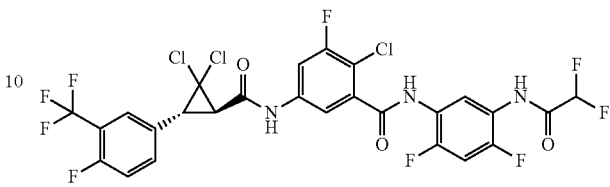

Isolated as a light-tan solid (0.087 g, 94%).

2-Chloro-5-((1R,3R)-2,2-dichloro-3-(4-fluoro-3-(trifluoromethyl)phenyl)cyclopropane-1-carboxamido)-N-(2,4-difluoro-5-(2,2,2-trifluoroacetamido)phenyl)-3-fluorobenzamide (F1407)

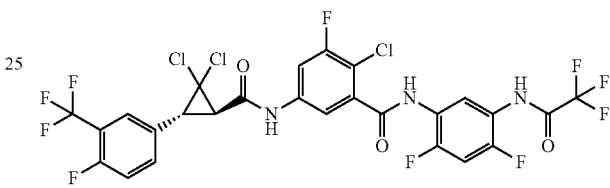

Isolated as a white solid (0.086 g, 89%).

2-Chloro-5-((1R,3R)-2,2-dichloro-3-(3,5-dichlorophenyl)cyclopropane-1-carboxamido)-N-(5-(2,2-difluoroacetamido)-2,4-difluorophenyl)-3-fluorobenzamide (F1408)

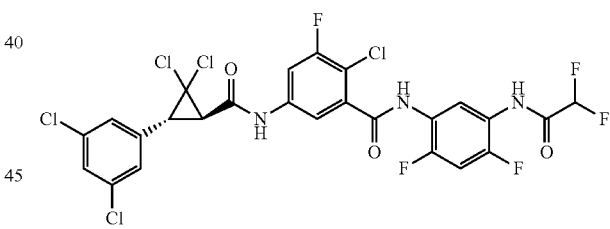

Isolated as a light-tan solid (0.084 g, 88%).

2-Chloro-5-((1R,3R)-2,2-dichloro-3-(3,5-dichlorophenyl)cyclopropane-1-carboxamido)-N-(2,4-difluoro-5-(2,2,2-trifluoroacetamido)phenyl)-3-fluorobenzamide (F1409)

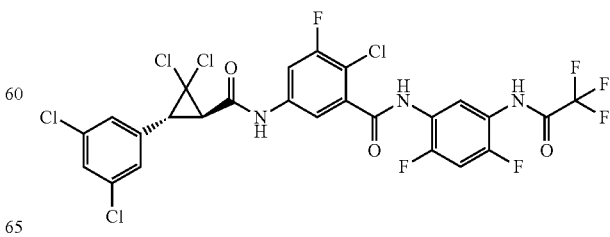

Isolated as a white solid (0.087 g, 89%).

315

2-Chloro-5-((1R,3R)-2,2-dichloro-3-(3,4-dichloro-phenyl)cyclopropane-1-carboxamido)-N-(3-(2,2-difluoroacetamido)-2,6-difluorophenyl)-3-methyl-benzamide (F1429)

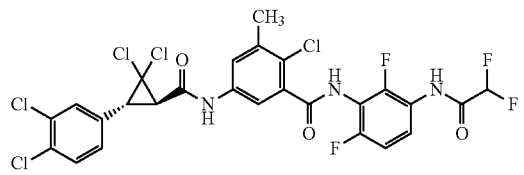 [SMILES: Cc1cc(NC(=O)[C@H]2[C@H](c3ccc(Cl)c(Cl)c3)C2(Cl)Cl)cc(C(=O)Nc2c(F)ccc(NC(=O)C(F)F)c2F)c1Cl]

Isolated as a white solid (0.056 g, 99%).

2-Chloro-5-((1R,3R)-2,2-dichloro-3-(3,4-dichloro-phenyl)cyclopropane-1-carboxamido)-N-(2,6-difluoro-3-(2,2,2-trifluoroacetamido)phenyl)-3-methyl-benzamide (F1430)

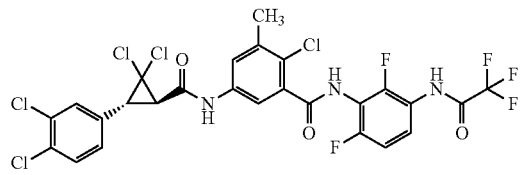 [SMILES: Cc1cc(NC(=O)[C@H]2[C@H](c3ccc(Cl)c(Cl)c3)C2(Cl)Cl)cc(C(=O)Nc2c(F)ccc(NC(=O)C(F)(F)F)c2F)c1Cl]

Isolated as a tan solid (0.057 g, 98%).

2-Chloro-5-((1R,3R)-2,2-dichloro-3-(3,4,5-trichloro-phenyl)cyclopropane-1-carboxamido)-N-(3-(2,2-difluoroacetamido)-2,6-difluorophenyl)-3-methyl-benzamide (F1431)

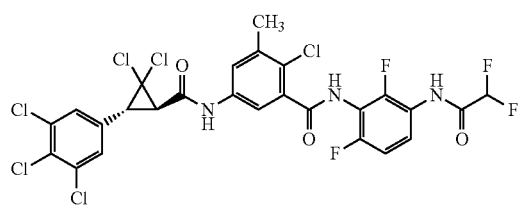 [SMILES: Cc1cc(NC(=O)[C@H]2[C@H](c3cc(Cl)c(Cl)c(Cl)c3)C2(Cl)Cl)cc(C(=O)Nc2c(F)ccc(NC(=O)C(F)F)c2F)c1Cl]

Isolated as a tan solid (0.058 g, 94%).

2-Chloro-5-((1R,3R)-2,2-dichloro-3-(3,4,5-trichloro-phenyl)cyclopropane-1-carboxamido)-N-(2,6-difluoro-3-(2,2,2-trifluoroacetamido)phenyl)-3-methyl-benzamide (F1432)

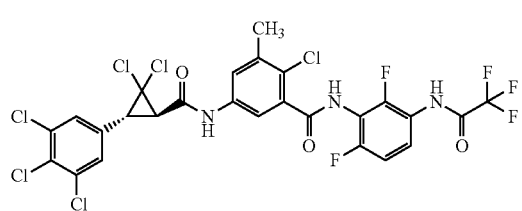 [SMILES: Cc1cc(NC(=O)[C@H]2[C@H](c3cc(Cl)c(Cl)c(Cl)c3)C2(Cl)Cl)cc(C(=O)Nc2c(F)ccc(NC(=O)C(F)(F)F)c2F)c1Cl]

Isolated as a white solid (0.060 g, 95%).

316

2-Chloro-5-((1R,3R)-2,2-dichloro-3-(4-fluoro-3-(trifluoromethyl)phenyl)cyclopropane-1-carboxamido)-N-(3-(2,2-difluoroacetamido)-2,6-difluorophenyl)-3-methylbenzamide (F1468)

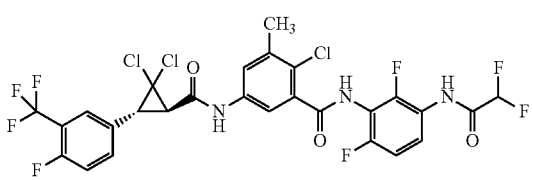 [SMILES: Cc1cc(NC(=O)[C@H]2[C@H](c3ccc(F)c(C(F)(F)F)c3)C2(Cl)Cl)cc(C(=O)Nc2c(F)ccc(NC(=O)C(F)F)c2F)c1Cl]

Isolated as a white solid (0.056 g, 99%).

2-Chloro-5-((1R,3R)-2,2-dichloro-3-(4-fluoro-3-(trifluoromethyl)phenyl)cyclopropane-1-carboxamido)-N-(2,6-difluoro-3-(2,2,2-trifluoroacetamido)phenyl)-3-methylbenzamide (F1469)

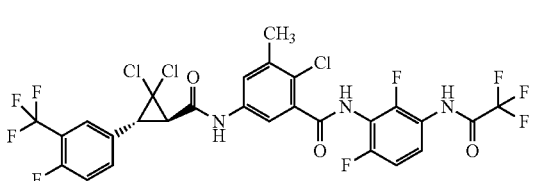

Isolated as a white solid (0.058 g, 100%).

2-Chloro-5-((1R,3R)-2,2-dichloro-3-(3,4-dichloro-phenyl)cyclopropane-1-carboxamido)-N-(3-(2,2-difluoroacetamido)-2,4-difluorophenyl)-3-methyl-benzamide (F1484)

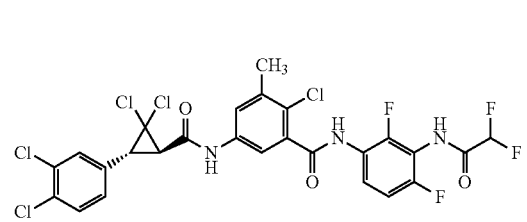 [SMILES: Cc1cc(NC(=O)[C@H]2[C@H](c3ccc(Cl)c(Cl)c3)C2(Cl)Cl)cc(C(=O)Nc2ccc(F)c(NC(=O)C(F)F)c2F)c1Cl]

Isolated as a tan powder (0.057 g, 100%).

2-Chloro-5-((1R,3R)-2,2-dichloro-3-(3,4-dichloro-phenyl)cyclopropane-1-carboxamido)-N-(2,4-difluoro-3-(2,2,2-trifluoroacetamido)phenyl)-3-methyl-benzamide (F1485)

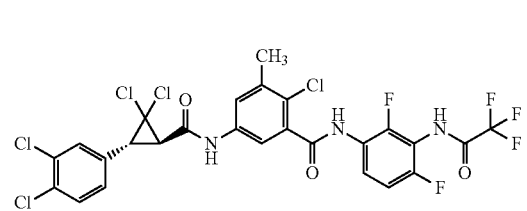 [SMILES: Cc1cc(NC(=O)[C@H]2[C@H](c3ccc(Cl)c(Cl)c3)C2(Cl)Cl)cc(C(=O)Nc2ccc(F)c(NC(=O)C(F)(F)F)c2F)c1Cl]

Isolated as a tan powder (0.058 g, 100%).

317

2-Chloro-5-((1R,3R)-2,2-dichloro-3-(3,4,5-trichlorophenyl)cyclopropane-1-carboxamido)-N-(3-(2,2-difluoroacetamido)-2,4-difluorophenyl)-3-methylbenzamide (F1486)

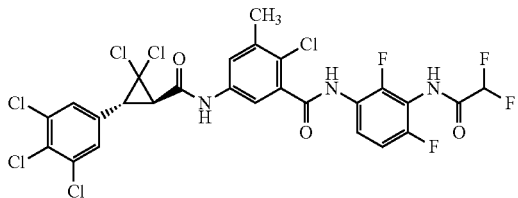 [SMILES: Cc1cc(NC(=O)[C@H]2[C@H](c3cc(Cl)c(Cl)c(Cl)c3)C2(Cl)Cl)cc(C(=O)Nc2ccc(F)c(NC(=O)C(F)F)c2F)c1Cl]

Isolated as a tan powder (0.062 g, 100%).

2-Chloro-5-((1R,3R)-2,2-dichloro-3-(3,4,5-trichlorophenyl)cyclopropane-1-carboxamido)-N-(2,4-difluoro-3-(2,2,2-trifluoroacetamido)phenyl)-3-methylbenzamide (F1487)

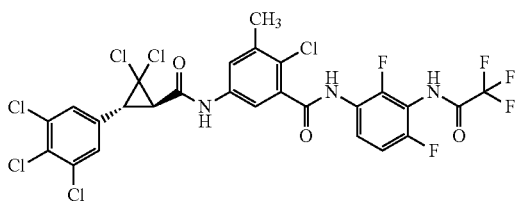 [SMILES: Cc1cc(NC(=O)[C@H]2[C@H](c3cc(Cl)c(Cl)c(Cl)c3)C2(Cl)Cl)cc(C(=O)Nc2ccc(F)c(NC(=O)C(F)(F)F)c2F)c1Cl]

Isolated as a tan powder (0.060 g, 95%).

2-Chloro-5-((1R,3R)-2,2-dichloro-3-(4-fluoro-3-(trifluoromethyl)phenyl)cyclopropane-1-carboxamido)-N-(3-(2,2-difluoroacetamido)-2,4-difluorophenyl)-3-methylbenzamide (F1494)

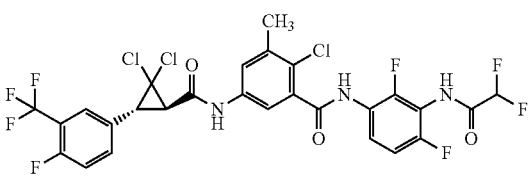 [SMILES: Cc1cc(NC(=O)[C@H]2[C@H](c3ccc(F)c(C(F)(F)F)c3)C2(Cl)Cl)cc(C(=O)Nc2ccc(F)c(NC(=O)C(F)F)c2F)c1Cl]

Isolated as a tan powder (0.047 g, 99%).

2-Chloro-5-((1R,3R)-2,2-dichloro-3-(4-fluoro-3-(trifluoromethyl)phenyl)cyclopropane-1-carboxamido)-N-(2,4-difluoro-3-(2,2,2-trifluoroacetamido)phenyl)-3-methylbenzamide (F1495)

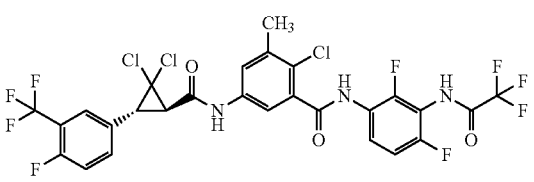 [SMILES: Cc1cc(NC(=O)[C@H]2[C@H](c3ccc(F)c(C(F)(F)F)c3)C2(Cl)Cl)cc(C(=O)Nc2ccc(F)c(NC(=O)C(F)(F)F)c2F)c1Cl]

Isolated as a tan powder (0.049 g, 99%).

318

2-Chloro-5-((1R,3R)-2,2-dichloro-3-(3,4-dichlorophenyl)cyclopropane-1-carboxamido)-N-(5-(2,2-difluoroacetamido)-2,4-difluorophenyl)-3-methylbenzamide (F1496)

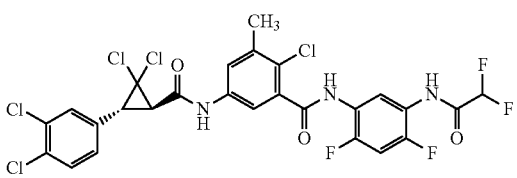 [SMILES: Cc1cc(NC(=O)[C@H]2[C@H](c3ccc(Cl)c(Cl)c3)C2(Cl)Cl)cc(C(=O)Nc2cc(NC(=O)C(F)F)c(F)cc2F)c1Cl]

Isolated as a tan powder (0.055 g, 90%).

2-Chloro-5-((1R,3R)-2,2-dichloro-3-(3,4-dichlorophenyl)cyclopropane-1-carboxamido)-N-(2,4-difluoro-5-(2,2,2-trifluoroacetamido)phenyl)-3-methylbenzamide (F1497)

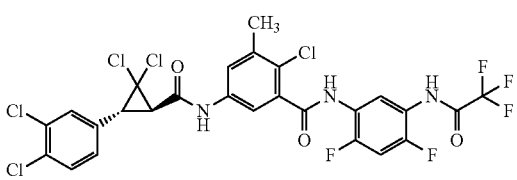 [SMILES: Cc1cc(NC(=O)[C@H]2[C@H](c3ccc(Cl)c(Cl)c3)C2(Cl)Cl)cc(C(=O)Nc2cc(NC(=O)C(F)(F)F)c(F)cc2F)c1Cl]

Isolated as a tan powder (0.063 g, 100%).

2-Chloro-5-((1R,3R)-2,2-dichloro-3-(3,4,5-trichlorophenyl)cyclopropane-1-carboxamido)-N-(5-(2,2-difluoroacetamido)-2,4-difluorophenyl)-3-methylbenzamide (F1498)

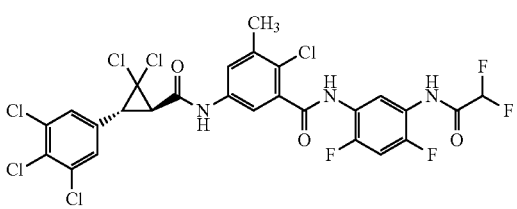 [SMILES: Cc1cc(NC(=O)[C@H]2[C@H](c3cc(Cl)c(Cl)c(Cl)c3)C2(Cl)Cl)cc(C(=O)Nc2cc(NC(=O)C(F)F)c(F)cc2F)c1Cl]

Isolated as a tan powder (0.067 g, 99%).

2-Chloro-5-((1R,3R)-2,2-dichloro-3-(3,4,5-trichlorophenyl)cyclopropane-1-carboxamido)-N-(2,4-difluoro-5-(2,2,2-trifluoroacetamido)phenyl)-3-methylbenzamide (F1499)

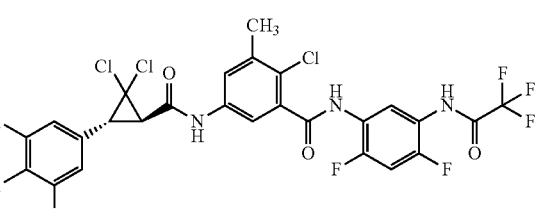

Isolated as a tan powder (0.066 g, 95%).

2-Chloro-5-((1R,3R)-2,2-dichloro-3-(4-fluoro-3-
(trifluoromethyl)phenyl)cyclopropane-1-carbox-
amido)-N-(5-(2,2-difluoroacetamido)-2,4-difluoro-
phenyl)-3-methylbenzamide (F1500)

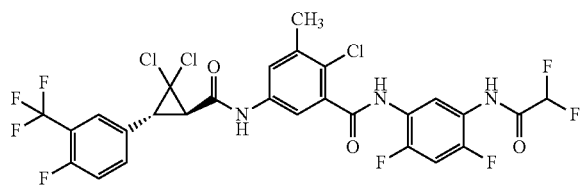 [SMILES: Cc1cc(NC(=O)[C@H]2[C@H](c3ccc(F)c(C(F)(F)F)c3)C2(Cl)Cl)cc(C(=O)Nc2cc(NC(=O)C(F)F)c(F)cc2F)c1Cl]

Isolated as a tan powder (0.056 g, 99%).

2-Chloro-5-((1R,3R)-2,2-dichloro-3-(4-fluoro-3-
(trifluoromethyl)phenyl)cyclopropane-1-carbox-
amido)-N-(2,4-difluoro-5-(2,2,2-trifluoroacetamido)
phenyl)-3-methylbenzamide (F1501)

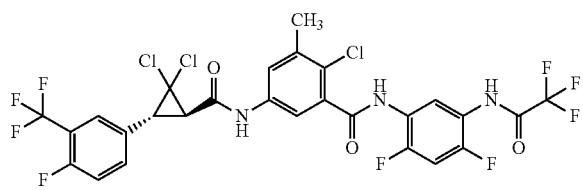 [SMILES: Cc1cc(NC(=O)[C@H]2[C@H](c3ccc(F)c(C(F)(F)F)c3)C2(Cl)Cl)cc(C(=O)Nc2cc(NC(=O)C(F)(F)F)c(F)cc2F)c1Cl]

Isolated as a tan powder (0.057 g, 99%).

N-(3-Acetamido-2,4-difluorophenyl)-2-chloro-5-
((1R,3R)-2,2-dichloro-3-(3,5-dichlorophenyl)cyclo-
propane-1-carboxamido)-3-fluorobenzamide
(F1502)

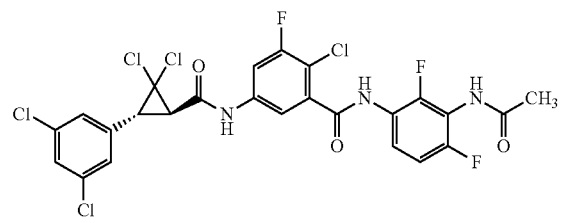 [SMILES: CC(=O)Nc1c(F)ccc(NC(=O)c2cc(NC(=O)[C@H]3[C@H](c4cc(Cl)cc(Cl)c4)C3(Cl)Cl)cc(F)c2Cl)c1F]

Isolated as a tan powder (0.039 g, 52%).

N-(3-Acetamido-2,4-difluorophenyl)-2-chloro-5-
((1R,3R)-2,2-dichloro-3-(3,4,5-trichlorophenyl)cy-
clopropane-1-carboxamido)-3-fluorobenzamide
(F1504)

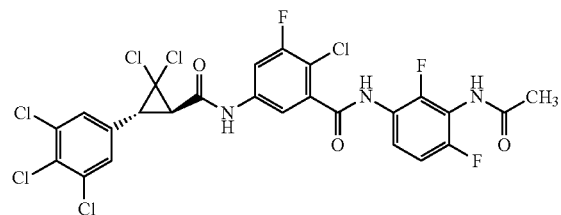 [SMILES: CC(=O)Nc1c(F)ccc(NC(=O)c2cc(NC(=O)[C@H]3[C@H](c4cc(Cl)c(Cl)c(Cl)c4)C3(Cl)Cl)cc(F)c2Cl)c1F]

Isolated as a tan powder (0.071 g, 44%).

The following compounds were prepared in like manner
to the procedure outlined in Example 4:

2-Chloro-5-((1R,3R)-2,2-dichloro-3-(3,4-dichloro-
phenyl)cyclopropane-1-carboxamido)-N-(2,4-dif-
luoro-3-(2,2,3,3-tetrafluoropropanamido)phenyl)
benzamide (F1414)

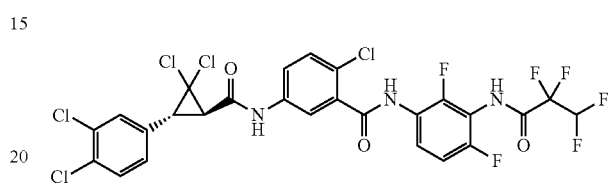

Isolated as a white foam (0.104 g, 85%).

2-Chloro-N-(2,4-dichloro-3-(2-cyanoacetamido)
phenyl)-5-((1R,3R)-2,2-dichloro-3-(3,4-dichlorophe-
nyl)cyclopropane-1-carboxamido)benzamide
(F1415)

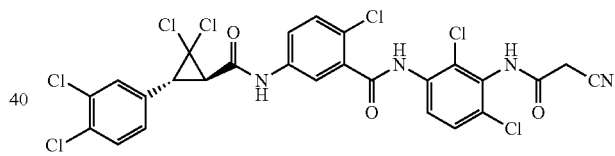

Isolated as a white solid (0.110 g, 98%).

N-(3-(2-Chloro-5-((1R,3R)-2,2-dichloro-3-(3,4-di-
chlorophenyl)cyclopropane-1-carboxamido)ben-
zamido)-2,6-difluorophenyl)furan-2-carboxamide
(F1416)

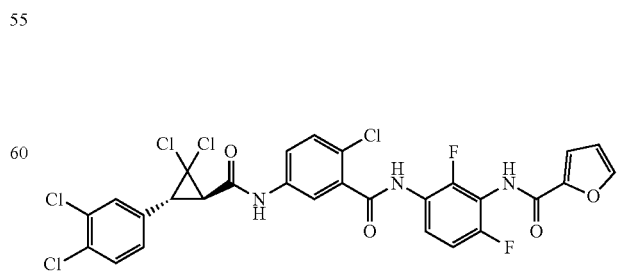

Isolated as a white solid (0.089 g, 76%).

2-Chloro-N-(3-(2-cyclopropylacetamido)-2,4-difluorophenyl)-5-((1R,3R)-2,2-dichloro-3-(3,4-dichlorophenyl)cyclopropane-1-carboxamido)benzamide (F1417)

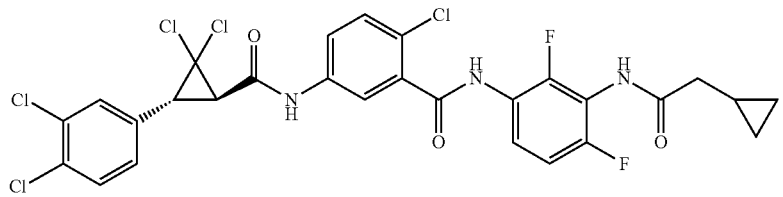 [SMILES: O=C(CC1CC1)Nc1c(F)ccc(NC(=O)c2cc(NC(=O)[C@H]3[C@H](c4ccc(Cl)c(Cl)c4)C3(Cl)Cl)ccc2Cl)c1F]

Isolated as a white solid (0.104 g, 91%).

2-Chloro-5-((1R,3R)-2,2-dichloro-3-(3,4-dichlorophenyl)cyclopropane-1-carboxamido)-N-(2,4-difluoro-3-(3,3,3-trifluoropropanamido)phenyl)benzamide (F1418)

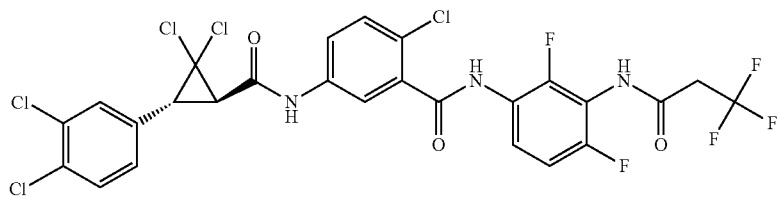 [SMILES: O=C(CC(F)(F)F)Nc1c(F)ccc(NC(=O)c2cc(NC(=O)[C@H]3[C@H](c4ccc(Cl)c(Cl)c4)C3(Cl)Cl)ccc2Cl)c1F]

Isolated as a white solid (0.103 g, 87%).

2-Chloro-5-((1R,3R)-2,2-dichloro-3-(3,4-dichlorophenyl)cyclopropane-1-carboxamido)-N-(3-(3-ethoxypropanamido)-2,4-difluorophenyl)benzamide (F1419)

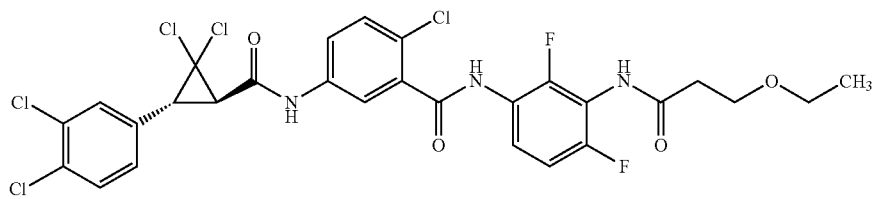 [SMILES: CCOCCC(=O)Nc1c(F)ccc(NC(=O)c2cc(NC(=O)[C@H]3[C@H](c4ccc(Cl)c(Cl)c4)C3(Cl)Cl)ccc2Cl)c1F]

Isolated as a white foam (0.098 g, 84%).

2-Chloro-5-((1R,3R)-2,2-dichloro-3-(3,4-dichlorophenyl)cyclopropane-1-carboxamido)-N-(2,4-difluoro-3-(2,2,3,3,4,4,4-heptafluorobutanamido)phenyl)benzamide (F1463)

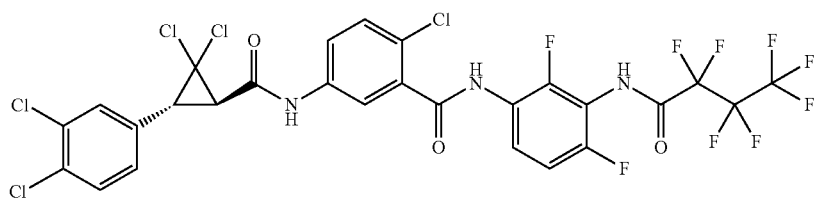 [SMILES: O=C(Nc1ccc(F)c(NC(=O)C(F)(F)C(F)(F)C(F)(F)F)c1F)c1cc(NC(=O)[C@H]2[C@H](c3ccc(Cl)c(Cl)c3)C2(Cl)Cl)ccc1Cl]

Isolated as a white foam (0.087 g, 65%).

2-Chloro-5-((1R,3R)-2,2-dichloro-3-(3,4-dichlorophenyl)cyclopropane-1-carboxamido)-N-(3-(2,2-difluoro-2-phenylacetamido)-2,4-difluorophenyl)benzamide (F1471)

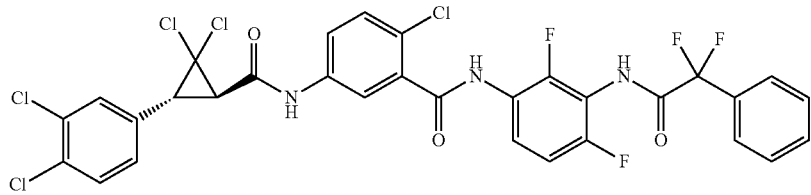 [SMILES: O=C(Nc1ccc(F)c(NC(=O)C(F)(F)c2ccccc2)c1F)c1cc(NC(=O)[C@H]2[C@H](c3ccc(Cl)c(Cl)c3)C2(Cl)Cl)ccc1Cl]

Isolated as a light yellow foam (0.086 g, 68%).

2-Chloro-5-((1R,3R)-2,2-dichloro-3-(3,4-dichlorophenyl)cyclopropane-1-carboxamido)-N-(2,4-difluoro-3-propionamidophenyl)benzamide (F1472)

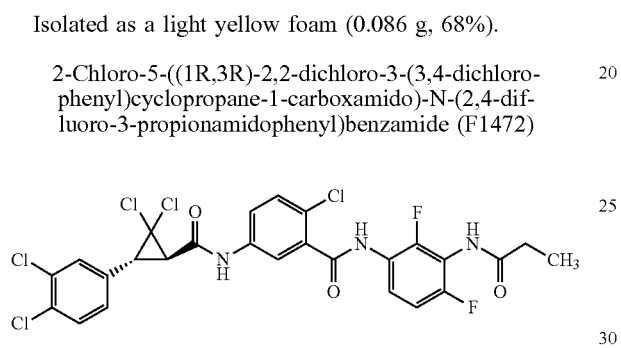

Isolated as a white solid (0.074 g, 67%).

N-(3-Butyramido-2,4-difluorophenyl)-2-chloro-5-((1R,3R)-2,2-dichloro-3-(3,4-dichlorophenyl)cyclopropane-1-carboxamido)benzamide (F1473)

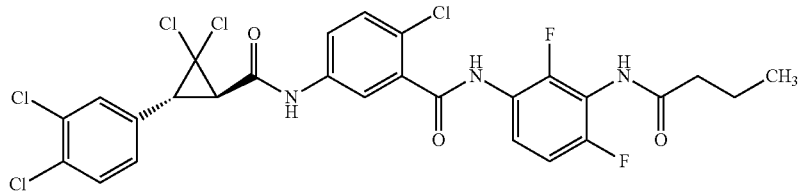 [SMILES: CCCC(=O)Nc1c(F)ccc(NC(=O)c2cc(NC(=O)[C@H]3[C@H](c4ccc(Cl)c(Cl)c4)C3(Cl)Cl)ccc2Cl)c1F]

Isolated as a white solid (0.088 g, 79%).

2-Chloro-5-((1R,3R)-2,2-dichloro-3-(3,4-dichlorophenyl)cyclopropane-1-carboxamido)-N-(2,4-difluoro-3-pentanamidophenyl)benzamide (F1474)

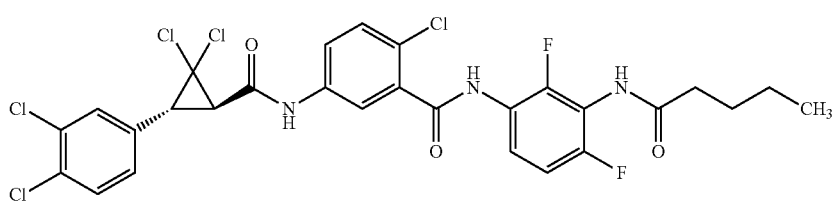

Isolated as a white solid (0.092 g, 80%).

2-Chloro-5-((1R,3R)-2,2-dichloro-3-(3,4-dichloro-
phenyl)cyclopropane-1-carboxamido)-N-(2,4-dif-
luoro-3-(3-oxocyclobutane-1-carboxamido)phenyl)
benzamide (F1475)

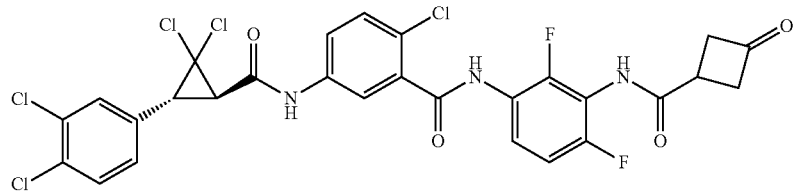 [SMILES: O=C1CC(C(=O)Nc2c(F)ccc(NC(=O)c3cc(NC(=O)[C@H]4[C@H](c5ccc(Cl)c(Cl)c5)C4(Cl)Cl)ccc3Cl)c2F)C1]

Isolated as a white foam (0.106 g, 91%).

2-Chloro-5-((1R,3R)-2,2-dichloro-3-(3,4,5-trichloro-
phenyl)cyclopropane-1-carboxamido)-N-(2,6-dif-
luoro-3-(2,2,3,3-tetrafluoropropanamido)phenyl)
benzamide (F1534)

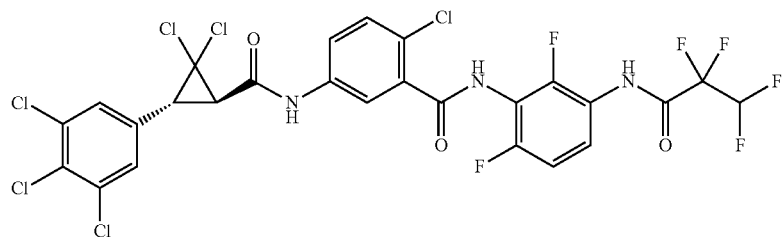 [SMILES: O=C(Nc1c(F)ccc(NC(=O)C(F)(F)C(F)F)c1F)c1cc(NC(=O)[C@H]2[C@H](c3cc(Cl)c(Cl)c(Cl)c3)C2(Cl)Cl)ccc1Cl]

Isolated as a white solid (0.037 g, 65%).

2-Chloro-5-((1R,3R)-2,2-dichloro-3-(3,4-dichloro-
phenyl)cyclopropane-1-carboxamido)-N-(2,6-dif-
luoro-3-(2,2,3,3-tetrafluoropropanamido)phenyl)
benzamide (F1535)

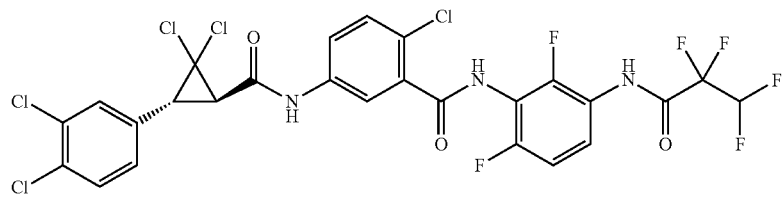 [SMILES: O=C(Nc1c(F)ccc(NC(=O)C(F)(F)C(F)F)c1F)c1cc(NC(=O)[C@H]2[C@H](c3ccc(Cl)c(Cl)c3)C2(Cl)Cl)ccc1Cl]

Isolated as a white solid (0.039 g, 67%).

2-Chloro-5-((1R,3R)-2,2-dichloro-3-(4-fluoro-3-
(trifluoromethyl)phenyl)cyclopropane-1-carbox-
amido)-N-(2,6-difluoro-3-(2,2,3,3-tetrafluoropro-
panamido)phenyl)benzamide (F1564)

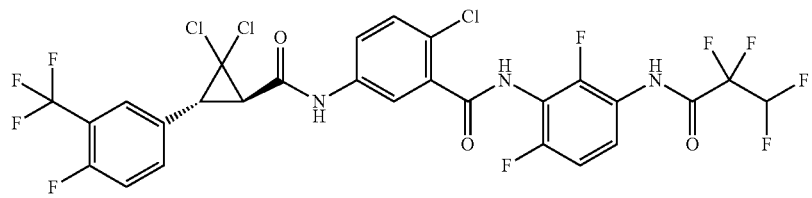 [SMILES: O=C(Nc1c(F)ccc(NC(=O)C(F)(F)C(F)F)c1F)c1cc(NC(=O)[C@H]2[C@H](c3ccc(F)c(C(F)(F)F)c3)C2(Cl)Cl)ccc1Cl]

Isolated as a white solid (0.104 g, 76%).

2-Chloro-5-((1R,3R)-2,2-dichloro-3-(3,4-dichloro-
phenyl)cyclopropane-1-carboxamido)-N-(2,4-dif-
luoro-5-(2,2,3,3-tetrafluoropropanamido)phenyl)
benzamide (F1565)

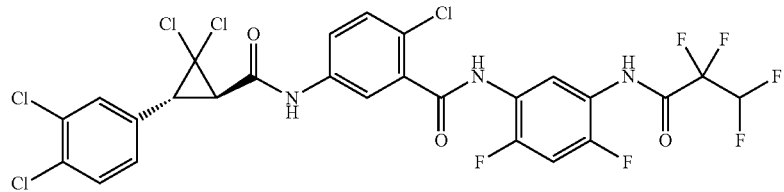 [SMILES: O=C(Nc1cc(NC(=O)C(F)(F)C(F)F)c(F)cc1F)c1cc(NC(=O)[C@H]2[C@H](c3ccc(Cl)c(Cl)c3)C2(Cl)Cl)ccc1Cl]

Isolated as a white solid (0.043 g, 58%).

2-Chloro-5-((1R,3R)-2,2-dichloro-3-(3,4,5-trichloro-
phenyl)cyclopropane-1-carboxamido)-N-(2,4-dif-
luoro-3-(2,2,3,3-tetrafluoropropanamido)phenyl)
benzamide (F1567)

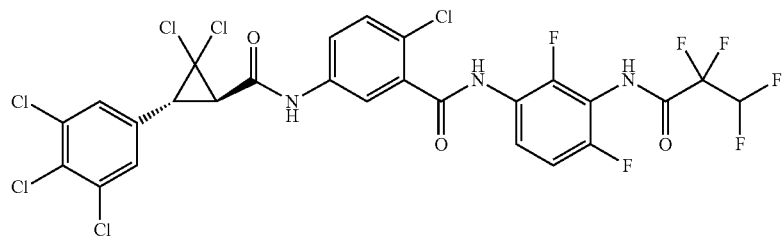 [SMILES: O=C(Nc1ccc(F)c(NC(=O)C(F)(F)C(F)F)c1F)c1cc(NC(=O)[C@H]2[C@H](c3cc(Cl)c(Cl)c(Cl)c3)C2(Cl)Cl)ccc1Cl]

Isolated as a white solid (0.107 g, 87%).

2-Chloro-5-((1R,3R)-2,2-dichloro-3-(3,4,5-trichloro-
phenyl)cyclopropane-1-carboxamido)-N-(2,4-dif-
luoro-5-(2,2,3,3-tetrafluoropropanamido)phenyl)
benzamide (F1568)

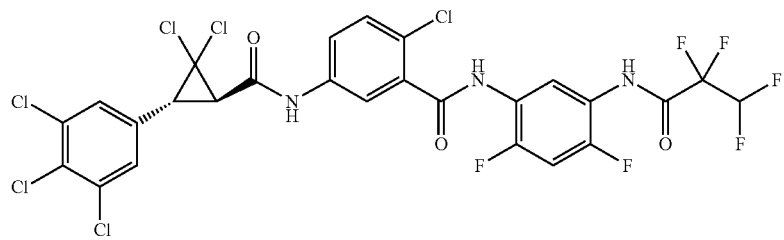 [SMILES: O=C(Nc1cc(NC(=O)C(F)(F)C(F)F)c(F)cc1F)c1cc(NC(=O)[C@H]2[C@H](c3cc(Cl)c(Cl)c(Cl)c3)C2(Cl)Cl)ccc1Cl]

Isolated as a white solid (0.096 g, 78%).

2-Chloro-5-((1R,3R)-2,2-dichloro-3-(4-fluoro-3-
(trifluoromethyl)phenyl)cyclopropane-1-carbox-
amido)-N-(2,4-difluoro-5-(2,2,3,3-tetrafluoropro-
panamido)phenyl)benzamide (F1569)

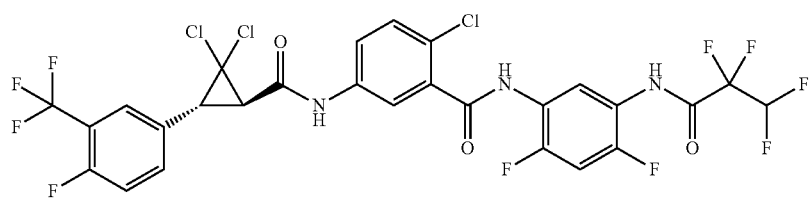 [SMILES: O=C(Nc1cc(NC(=O)C(F)(F)C(F)F)c(F)cc1F)c1cc(NC(=O)[C@H]2[C@H](c3ccc(F)c(C(F)(F)F)c3)C2(Cl)Cl)ccc1Cl]

Isolated as a white solid (0.099 g, 80%).

2-Chloro-5-((1R,3R)-2,2-dichloro-3-(3,4-dichloro-
phenyl)cyclopropane-1-carboxamido)-N-(3-(2-
ethoxypropanamido)-2,4-difluorophenyl)benzamide
(F1604)

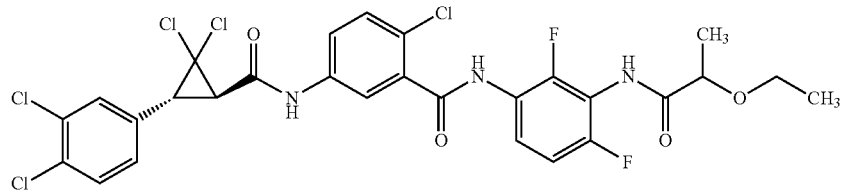 [SMILES: CCOC(C)C(=O)Nc1c(F)ccc(NC(=O)c2cc(NC(=O)[C@H]3[C@H](c4ccc(Cl)c(Cl)c4)C3(Cl)Cl)ccc2Cl)c1F]

Isolated as a white solid (0.093 g, 79%).

2-Chloro-5-((1R,3R)-2,2-dichloro-3-(3,4-dichloro-
phenyl)cyclopropane-1-carboxamido)-N-(3-(2-
ethoxy-2-methylpropanamido)-2,4-difluorophenyl)
benzamide (F1605)

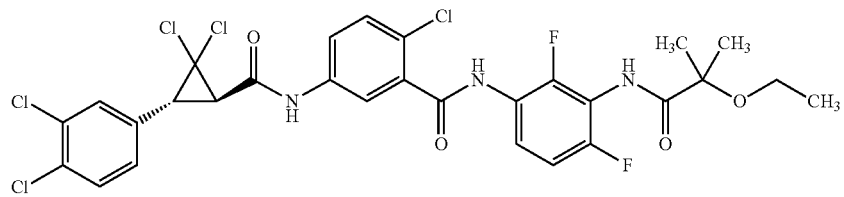 [SMILES: CCOC(C)(C)C(=O)Nc1c(F)ccc(NC(=O)c2cc(NC(=O)[C@H]3[C@H](c4ccc(Cl)c(Cl)c4)C3(Cl)Cl)ccc2Cl)c1F]

Isolated as a white foam (0.097 g, 81%).

2-Chloro-5-((1R,3R)-2,2-dichloro-3-(3,4-dichloro-
phenyl)cyclopropane-1-carboxamido)-N-(2,4-dif-
luoro-3-isobutyramidophenyl)benzamide (F1606)

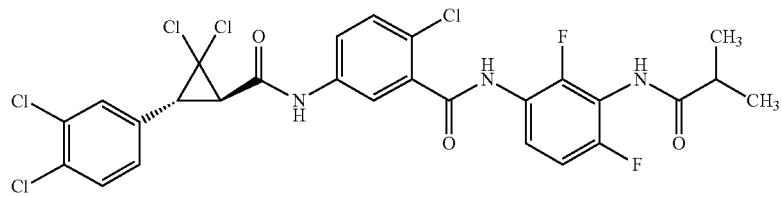 [SMILES: CC(C)C(=O)Nc1c(F)ccc(NC(=O)c2cc(NC(=O)[C@H]3[C@H](c4ccc(Cl)c(Cl)c4)C3(Cl)Cl)ccc2Cl)c1F]

Isolated as a white solid (0.084 g, 75%).

2-Chloro-5-((1R,3R)-2,2-dichloro-3-(3,4-dichloro-
phenyl)cyclopropane-1-carboxamido)-N-(2,4-dif-
luoro-3-(3,3,3-trifluoro-2-(trifluoromethyl)propana-
mido)phenyl)benzamide (F1607)

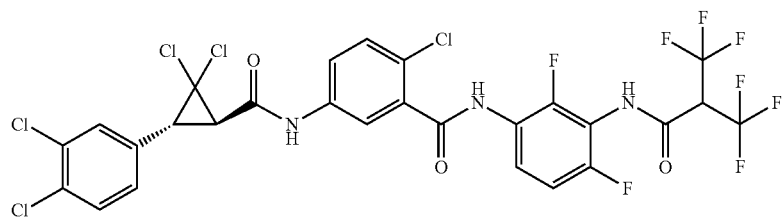 [SMILES: O=C(Nc1ccc(F)c(NC(=O)C(C(F)(F)F)C(F)(F)F)c1F)c1cc(NC(=O)[C@H]2[C@H](c3ccc(Cl)c(Cl)c3)C2(Cl)Cl)ccc1Cl]

Isolated as a white solid (0.115 g, 88%).

2-Chloro-5-((1R,3R)-2,2-dichloro-3-(3,4-dichloro-phenyl)cyclopropane-1-carboxamido)-N-(3-(2,2-difluorocyclopropane-1-carboxamido)-2,4-difluoro-phenyl)benzamide (F1608)

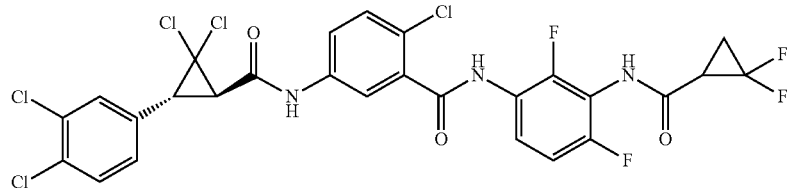 [SMILES: O=C(Nc1ccc(F)c(NC(=O)C2CC2(F)F)c1F)c1cc(NC(=O)[C@H]2[C@H](c3ccc(Cl)c(Cl)c3)C2(Cl)Cl)ccc1Cl]

Isolated as a white solid (0.102 g, 87%).

2-Chloro-N-(3-(1-cyanocyclopropane-1-carbox-amido)-2,4-difluorophenyl)-5-((1R,3R)-2,2-di-chloro-3-(3,4-dichlorophenyl)cyclopropane-1-car-boxamido)benzamide (F1609)

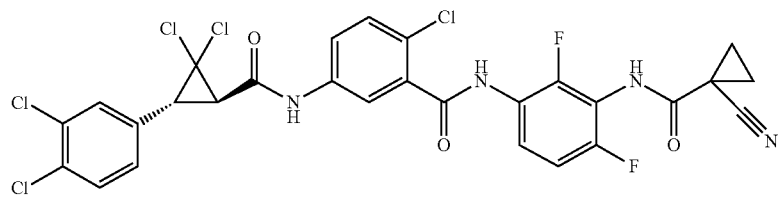 [SMILES: N#CC1(C(=O)Nc2c(F)ccc(NC(=O)c3cc(NC(=O)[C@H]4[C@H](c5ccc(Cl)c(Cl)c5)C4(Cl)Cl)ccc3Cl)c2F)CC1]

Isolated as a white foam (0.090 g, 77%).

N-(3-(2-Chloro-5-((1R,3R)-2,2-dichloro-3-(3,4-di-chlorophenyl)cyclopropane-1-carboxamido)ben-zamido)-2,6-difluorophenyl)tetrahydrofuran-3-car-boxamide (F1610)

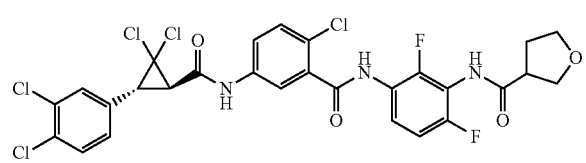 [SMILES: O=C(Nc1ccc(F)c(NC(=O)C2CCOC2)c1F)c1cc(NC(=O)[C@H]2[C@H](c3ccc(Cl)c(Cl)c3)C2(Cl)Cl)ccc1Cl]

Isolated as a white foam (0.111 g, 95%).

N-(3-(2-Chloro-5-((1R,3R)-2,2-dichloro-3-(3,4-di-chlorophenyl)cyclopropane-1-carboxamido)ben-zamido)-2,6-difluorophenyl)tetrahydrofuran-2-car-boxamide (F1611)

Isolated as a white foam (0.066 g, 56%).

2-Chloro-5-((1R,3R)-2,2-dichloro-3-(3,4-dichloro-phenyl)cyclopropane-1-carboxamido)-N-(3-(2-ethoxy-N-methylpropanamido)-2,4-difluorophenyl)benzamide (F1616)

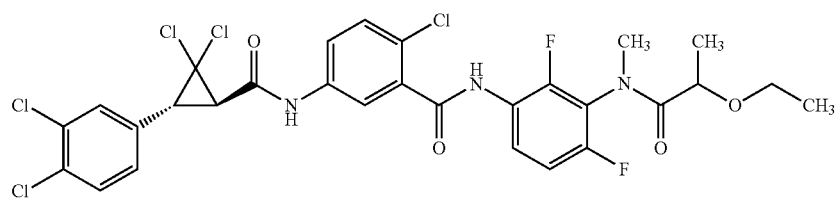 [SMILES: CCOC(C)C(=O)N(C)c1c(F)ccc(NC(=O)c2cc(NC(=O)[C@H]3[C@H](c4ccc(Cl)c(Cl)c4)C3(Cl)Cl)ccc2Cl)c1F]

Isolated as a white foam (0.093 g, 79%).

2-Chloro-N-(3-(2-cyano-N-methylacetamido)-2,4-difluorophenyl)-5-((1R,3R)-2,2-dichloro-3-(3,4-dichlorophenyl)cyclopropane-1-carboxamido)benzamide (F1617)

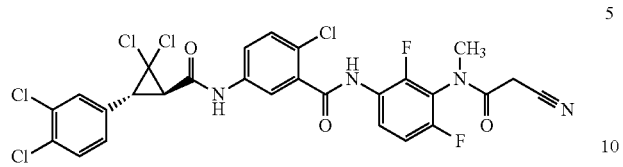

Isolated as a white foam (0.096 g, 86%).

2-Chloro-5-((1R,3R)-2,2-dichloro-3-(3,4-dichlorophenyl)cyclopropane-1-carboxamido)-N-(2,4-difluoro-3-(2-methoxy-N-methylacetamido)phenyl)benzamide (F1630)

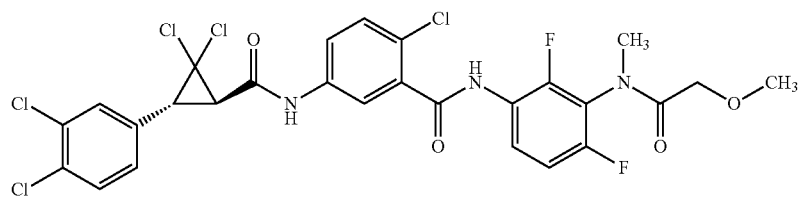 [SMILES: COCC(=O)N(C)c1c(F)ccc(NC(=O)c2cc(NC(=O)[C@H]3[C@H](c4ccc(Cl)c(Cl)c4)C3(Cl)Cl)ccc2Cl)c1F]

Isolated as a white foam (0.082 g, 92%).

2-Chloro-5-((1R,3R)-2,2-dichloro-3-(3,4,5-trichlorophenyl)cyclopropane-1-carboxamido)-N-(3-(2-ethoxypropanamido)-2,4-difluorophenyl)benzamide (F1645)

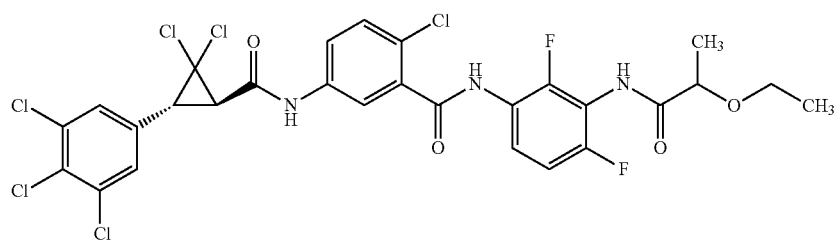 [SMILES: CCOC(C)C(=O)Nc1c(F)ccc(NC(=O)c2cc(NC(=O)[C@H]3[C@H](c4cc(Cl)c(Cl)c(Cl)c4)C3(Cl)Cl)ccc2Cl)c1F]

Isolated as a white solid (0.079 g, 68%). The title compound was prepared from N-(3-amino-2,4-difluorophenyl)-2-chloro-5-((1R,3R)-2,2-dichloro-3-(3,4,5-trichlorophenyl)cyclopropane-1-carboxamido)benzamide which was prepared via methods described in U.S. Patent Application Publication US20160304522A1 (F315).

2-Chloro-5-((1R,3R)-2,2-dichloro-3-(3,4,5-trichlorophenyl)cyclopropane-1-carboxamido)-N-(2,4-difluoro-3-(2-methoxyacetamido)phenyl)benzamide (F1646)

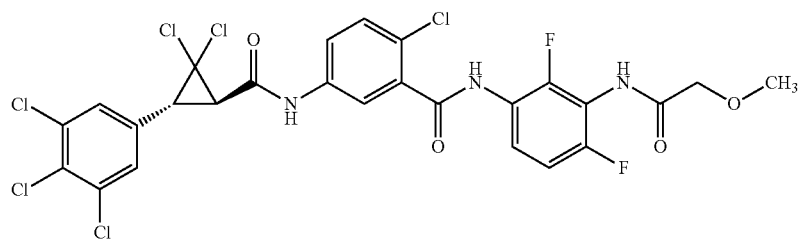 [SMILES: COCC(=O)Nc1c(F)ccc(NC(=O)c2cc(NC(=O)[C@H]3[C@H](c4cc(Cl)c(Cl)c(Cl)c4)C3(Cl)Cl)ccc2Cl)c1F]

Isolated as a white solid (0.087 g, 78%).

N-(3-(2-Chloro-5-(((1R,3R)-2,2-dichloro-3-(3,4,5-trichlorophenyl)cyclopropane-1-carboxamido)benzamido)-2,6-difluorophenyl)tetrahydrofuran-2-carboxamide (F1647)


Isolated as a white foam (0.071 g, 77%).

N-(3-(2-Chloro-5-(((1R,3R)-2,2-dichloro-3-(3,4,5-trichlorophenyl)cyclopropane-1-carboxamido)benzamido)-2,6-difluorophenyl)furan-2-carboxamide (F1648)

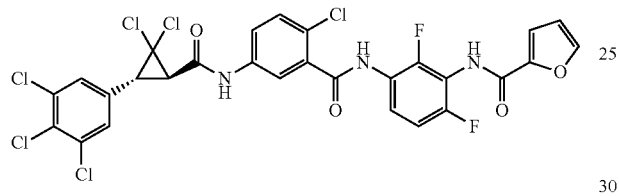

Isolated as a white foam (0.072 g, 62%).

2-Chloro-5-(((1R,3R)-2,2-dichloro-3-(3,4,5-trichlorophenyl)cyclopropane-1-carboxamido)-N-(2,4-difluoro-3-(3-oxocyclobutane-1-carboxamido)phenyl)benzamide (F1649)

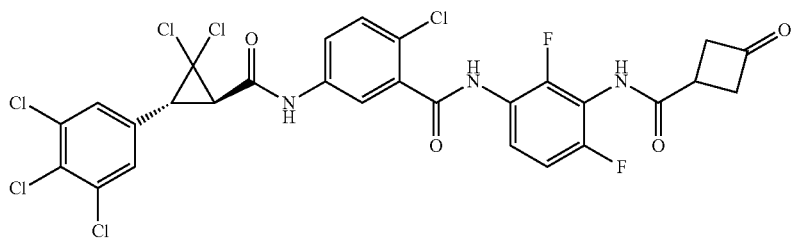 [SMILES: O=C1CC(C(=O)Nc2c(F)ccc(NC(=O)c3cc(NC(=O)[C@H]4[C@H](c5cc(Cl)c(Cl)c(Cl)c5)C4(Cl)Cl)ccc3Cl)c2F)C1]

Isolated as a white foam (0.040 g, 35%).

2-Chloro-N-(3-(2-cyanoacetamido)-2,4-difluorophenyl)-5-(((1R,3R)-2,2-dichloro-3-(3,4,5-trichlorophenyl)cyclopropane-1-carboxamido)benzamide (F1650)

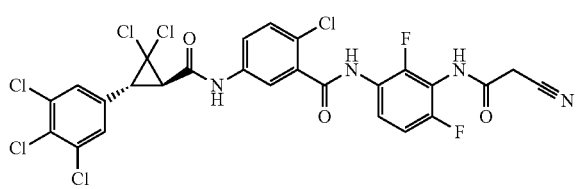 [SMILES: N#CCC(=O)Nc1c(F)ccc(NC(=O)c2cc(NC(=O)[C@H]3[C@H](c4cc(Cl)c(Cl)c(Cl)c4)C3(Cl)Cl)ccc2Cl)c1F]

Isolated as a yellow foam (0.062 g, 56%).

2-Chloro-5-(((1R,3R)-2,2-dichloro-3-(3,4,5-trichlorophenyl)cyclopropane-1-carboxamido)-N-(2,4-difluoro-3-(3,3,3-trifluoropropanamido)phenyl)benzamide (F1651)

Isolated as a white foam (0.074 g, 63%).

2-Chloro-5-((1R,3R)-2,2-dichloro-3-(3,4,5-trichloro-
phenyl)cyclopropane-1-carboxamido)-N-(2,4-dif-
luoro-3-(2,2,3,3,4,4,4-heptafluoropropanamido)phe-
nyl)benzamide (F1652)

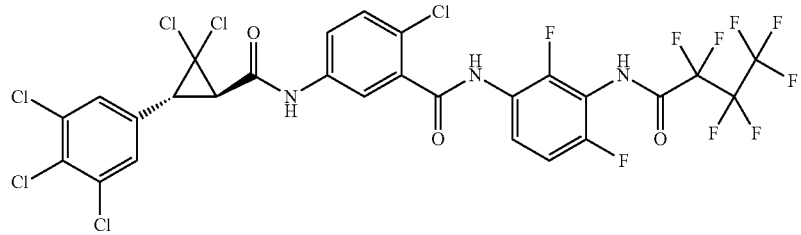 [SMILES: O=C(Nc1ccc(F)c(NC(=O)C(F)(F)C(F)(F)C(F)(F)F)c1F)c1cc(NC(=O)[C@H]2[C@H](c3cc(Cl)c(Cl)c(Cl)c3)C2(Cl)Cl)ccc1Cl]

Isolated as a white foam (0.052 g, 39%).

2-Chloro-N-(3-(2-cyclopropylacetamido)-2,4-difluo-
rophenyl)-5-((1R,3R)-2,2-dichloro-3-(3,4,5-trichlo-
rophenyl)cyclopropane-1-carboxamido)benzamide
(F1653)

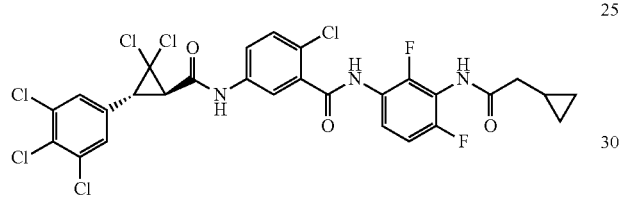

Isolated as a white foam (0.099 g, 88%).

2-Chloro-5-((1R,3R)-2,2-dichloro-3-(3,4,5-trichloro-
phenyl)cyclopropane-1-carboxamido)-N-(2,4-dif-
luoro-3-propionamidophenyl)benzamide (F1654)

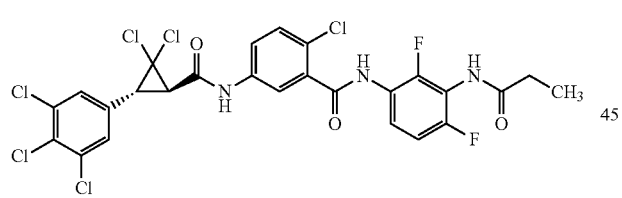

Isolated as a white foam (0.099 g, 90%).

N-(3-Butyramido-2,4-difluorophenyl)-2-chloro-5-
((1R,3R)-2,2-dichloro-3-(3,4,5-trichlorophenyl)cy-
clopropane-1-carboxamido)benzamide (F1655)

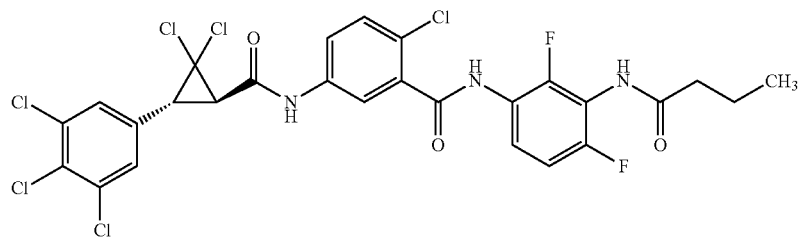 [SMILES: CCCC(=O)Nc1c(F)ccc(NC(=O)c2cc(NC(=O)[C@H]3[C@H](c4cc(Cl)c(Cl)c(Cl)c4)C3(Cl)Cl)ccc2Cl)c1F]

Isolated as a white foam (0.095 g, 85%).

N-(3-Butyramido-2,4-difluorophenyl)-2-chloro-5-((1R,3R)-2,2-dichloro-3-(4-chloro-3-(trifluoromethyl)phenyl)cyclopropane-1-carboxamido)benzamide (F1659)

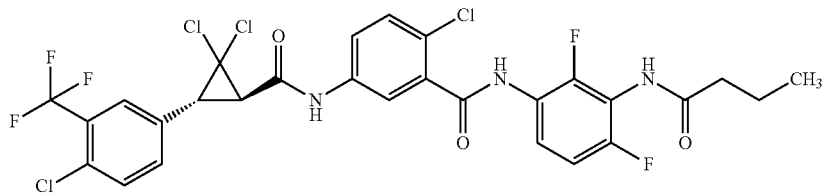 [SMILES: CCCC(=O)Nc1c(F)ccc(NC(=O)c2cc(NC(=O)[C@H]3[C@H](c4ccc(Cl)c(C(F)(F)F)c4)C3(Cl)Cl)ccc2Cl)c1F]

Isolated as a white foam (0.067 g, 75%).

2-Chloro-5-((1R,3R)-2,2-dichloro-3-(4-chloro-3-(trifluoromethyl)phenyl)cyclopropane-1-carboxamido)-N-(3-(2-ethoxypropanamido)-2,4-difluorophenyl)benzamide (F1660)

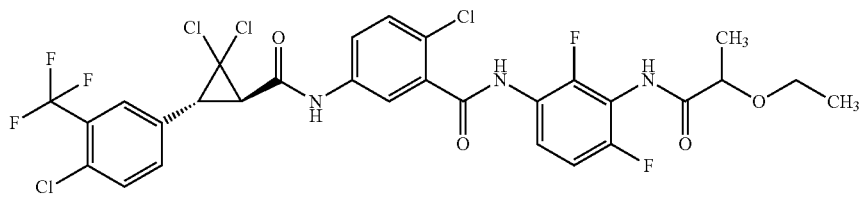 [SMILES: CCOC(C)C(=O)Nc1c(F)ccc(NC(=O)c2cc(NC(=O)[C@H]3[C@H](c4ccc(Cl)c(C(F)(F)F)c4)C3(Cl)Cl)ccc2Cl)c1F]

Isolated as a white solid (0.071 g, 77%).

N-(3-(2-Chloro-5-((1R,3R)-2,2-dichloro-3-(4-chloro-3-(trifluoromethyl)phenyl)cyclopropane-1-carboxamido)benzamido)-2,6-difluorophenyl)tetrahydrofuran-2-carboxamide (F1661)

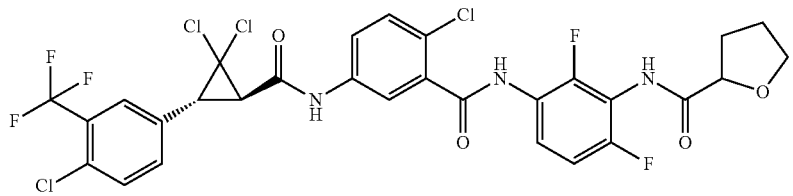 [SMILES: O=C(Nc1ccc(F)c(NC(=O)C2CCCO2)c1F)c1cc(NC(=O)[C@H]2[C@H](c3ccc(Cl)c(C(F)(F)F)c3)C2(Cl)Cl)ccc1Cl]

Isolated as a white solid (0.069 g, 75%).

2-Chloro-5-((1R,3R)-2,2-dichloro-3-(3,4-dichlorophenyl)cyclopropane-1-carboxamido)-N-(2,4-difluoro-3-(1-(trifluoromethyl)cyclopropane-1-carboxamido)phenyl)benzamide (F1662)

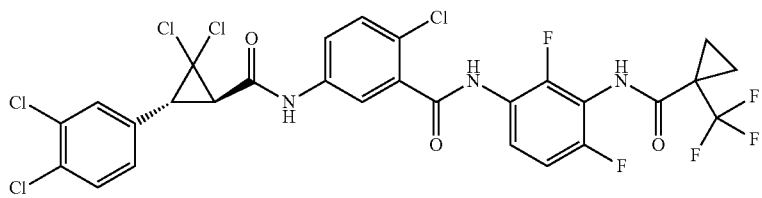 [SMILES: O=C(Nc1ccc(F)c(NC(=O)C2(C(F)(F)F)CC2)c1F)c1cc(NC(=O)[C@H]2[C@H](c3ccc(Cl)c(Cl)c3)C2(Cl)Cl)ccc1Cl]

Isolated as a white foam (0.033, 27%).

341

(R)—N-(3-(2-Chloro-5-((1R,3R)-2,2-dichloro-3-(3,4-dichlorophenyl)cyclopropane-1-carboxamido)benzamido)-2,6-difluorophenyl)pyrrolidine-2-carboxamide (F1663)

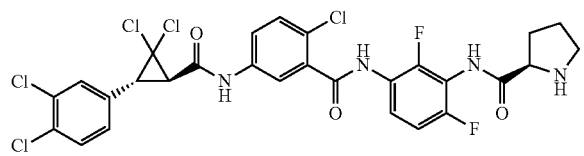

Isolated as a white foam (0.044 g, 38%).

(S)—N-(3-(2-chloro-5-((1R,3R)-2,2-dichloro-3-(3,4-dichlorophenyl)cyclopropane-1-carboxamido)benzamido)-2,6-difluorophenyl)pyrrolidine-2-carboxamide (F1664)

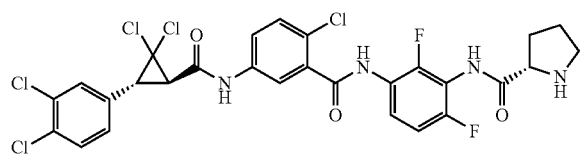

Isolated as a white foam (0.039 g, 33%).

N-(3-(2-Chloro-5-((1R,3R)-2,2-dichloro-3-(3,4-dichlorophenyl)cyclopropane-1-carboxamido)benzamido)-2,6-difluorophenyl)isoxazole-5-carboxamide (F1671)

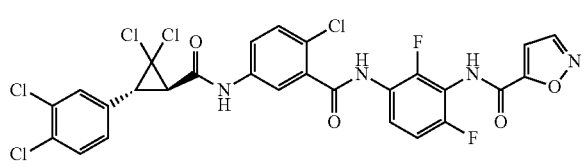 [SMILES: O=C(Nc1c(F)ccc(NC(=O)c2cc(NC(=O)[C@H]3[C@H](c4ccc(Cl)c(Cl)c4)C3(Cl)Cl)ccc2Cl)c1F)c1ccno1]

Isolated as a white foam (0.069 g, 70%).

342

N-(3-(2-Chloro-5-((1R,3R)-2,2-dichloro-3-(3,4-dichlorophenyl)cyclopropane-1-carboxamido)benzamido)-2,6-difluorophenyl)isothiazole-5-carboxamide (F1672)

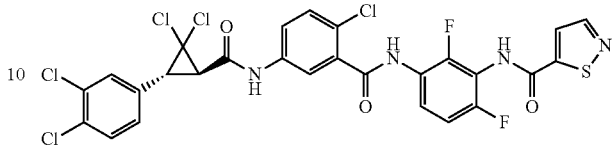

Isolated as a white foam (0.059 g, 58%).

2-Chloro-5-((1R,3R)-2,2-dichloro-3-(3,4-dichlorophenyl)cyclopropane-1-carboxamido)-N-(2,4-difluoro-3-(2-phenylacetamido)phenyl)benzamide (F1673)

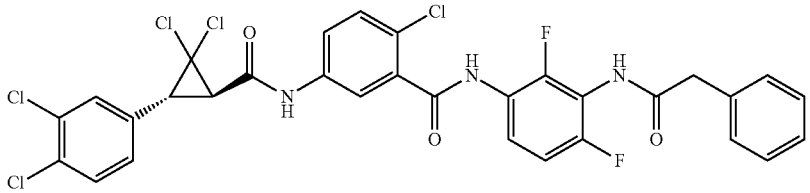 [SMILES: O=C(Cc1ccccc1)Nc1c(F)ccc(NC(=O)c2cc(NC(=O)[C@H]3[C@H](c4ccc(Cl)c(Cl)c4)C3(Cl)Cl)ccc2Cl)c1F]

Isolated as a white foam (0.073 g, 72%).

2-Chloro-5-((1R,3R)-2,2-dichloro-3-(3,4,5-trichlorophenyl)cyclopropane-1-carboxamido)-N-(3-(2,2-dichloroacetamido)-2,4-difluorophenyl)benzamide (F1685)

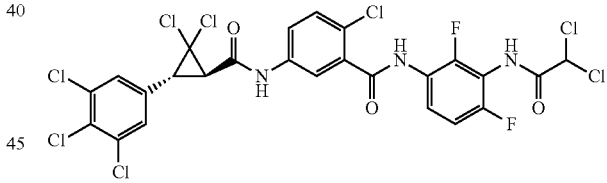

Isolated as a white foam (0.104 g, 88%).

2-Chloro-N-(3-(2-chloro-2,2-difluoroacetamido)-2,4-difluorophenyl)-5-((1R,3R)-2,2-dichloro-3-(3,4,5-trichlorophenyl)cyclopropane-1-carboxamido)benzamide (F1686)

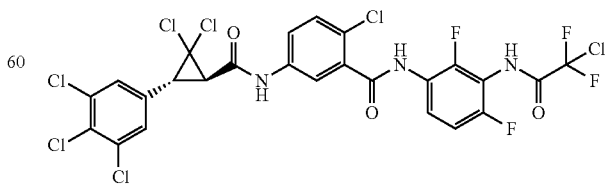

Isolated as a white foam (0.097 g, 82%).

2-Chloro-N-(3-(2-chloro-2,2-difluoroacetamido)-2,4-difluorophenyl)-5-((1R,3R)-2,2-dichloro-3-(3-chloro-4-fluorophenyl)cyclopropane-1-carboxamido)benzamide (F1697)

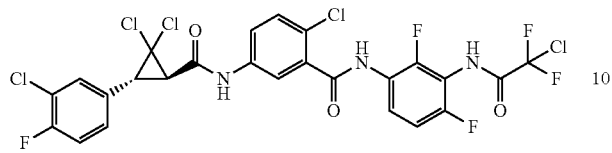

Isolated as a white foam (0.104 g, 87%).

2-Chloro-5-((1R,3R)-2,2-dichloro-3-(3-chloro-4-fluorophenyl)cyclopropane-1-carboxamido)-N-(3-(2-ethoxypropanamido)-2,4-difluorophenyl)benzamide (F1698)

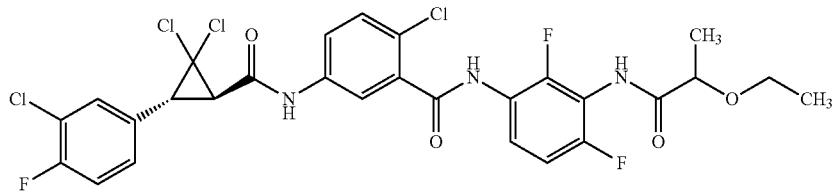 [SMILES: CCOC(C)C(=O)Nc1c(F)ccc(NC(=O)c2cc(NC(=O)[C@H]3[C@H](c4ccc(F)c(Cl)c4)C3(Cl)Cl)ccc2Cl)c1F]

Isolated as a white solid (0.098 g, 83%).

N-(3-(2-Chloro-5-((1R,3R)-2,2-dichloro-3-(3-chloro-4-fluorophenyl)cyclopropane-1-carboxamido)benzamido)-2,6-difluorophenyl)tetrahydrofuran-2-carboxamide (F1699)

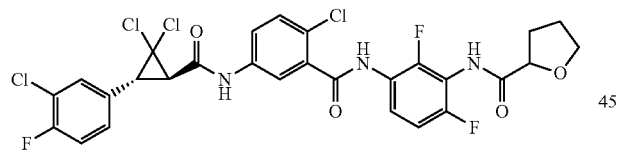

Isolated as a white foam (0.107 g, 91%).

2-Chloro-N-(3-(2-cyanoacetamido)-2,4-difluorophenyl)-5-((1R,3R)-2,2-dichloro-3-(3-chloro-4-fluorophenyl)cyclopropane-1-carboxamido)benzamide (F1700)

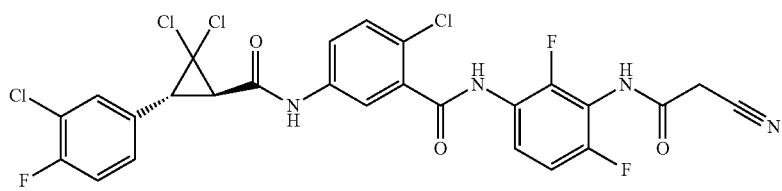 [SMILES: N#CCC(=O)Nc1c(F)ccc(NC(=O)c2cc(NC(=O)[C@H]3[C@H](c4ccc(F)c(Cl)c4)C3(Cl)Cl)ccc2Cl)c1F]

Isolated as a white foam (0.089 g, 80%).

2-Chloro-5-((1R,3R)-2,2-dichloro-3-(3-chloro-4-fluorophenyl)cyclopropane-1-carboxamido)-N-(2,4-difluoro-3-(3,3,3-trifluoropropanamido)phenyl)benzamide (F1701)

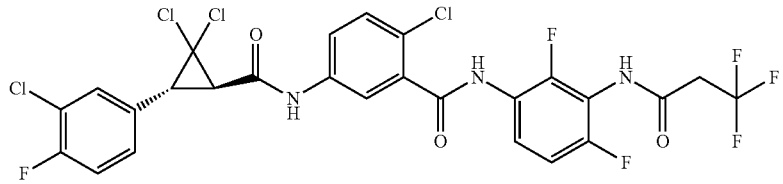 [SMILES: O=C(CC(F)(F)F)Nc1c(F)ccc(NC(=O)c2cc(NC(=O)[C@H]3[C@H](c4ccc(F)c(Cl)c4)C3(Cl)Cl)ccc2Cl)c1F]

Isolated as a white foam (0.098 g, 82%).

2-Chloro-N-(3-(2-cyclopropylacetamido)-2,4-difluorophenyl)-5-((1R,3R)-2,2-dichloro-3-(3-chloro-4-fluorophenyl)cyclopropane-1-carboxamido)benzamide (F1702)

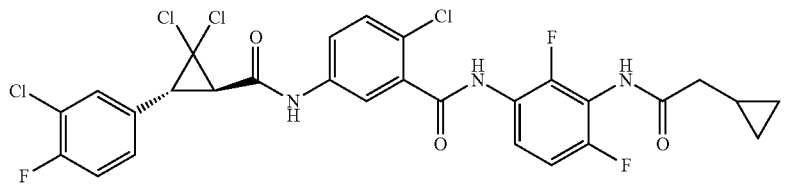 [SMILES: O=C(CC1CC1)Nc1c(F)ccc(NC(=O)c2cc(NC(=O)[C@H]3[C@H](c4ccc(F)c(Cl)c4)C3(Cl)Cl)ccc2Cl)c1F]

Isolated as a white solid (0.094 g, 82%).

2-Chloro-5-((1R,3R)-2,2-dichloro-3-(3-chloro-4-fluorophenyl)cyclopropane-1-carboxamido)-N-(2,4-difluoro-3-(2,2,3,3-tetrafluoropropanamido)phenyl)benzamide (F1703)

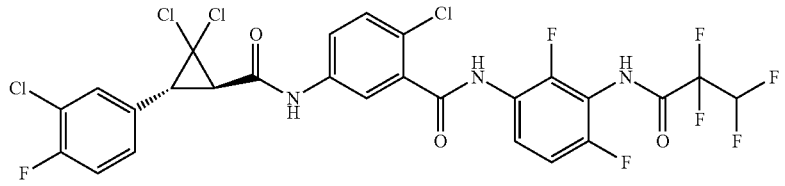 [SMILES: O=C(Nc1ccc(F)c(NC(=O)C(F)(F)C(F)F)c1F)c1cc(NC(=O)[C@H]2[C@H](c3ccc(F)c(Cl)c3)C2(Cl)Cl)ccc1Cl]

Isolated as a white foam (0.110 g, 89%).

2-Chloro-5-((1R,3R)-2,2-dichloro-3-(3-chloro-4-fluorophenyl)cyclopropane-1-carboxamido)-N-(2,4-difluoro-3-propionamidophenyl)benzamide (F1704)

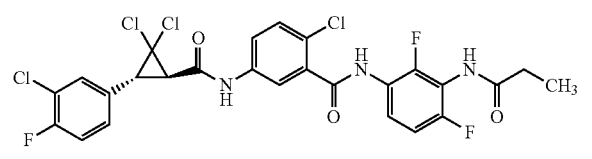 [SMILES: CCC(=O)Nc1c(F)ccc(NC(=O)c2cc(NC(=O)[C@H]3[C@H](c4ccc(F)c(Cl)c4)C3(Cl)Cl)ccc2Cl)c1F]

Isolated as a white foam (0.103 g, 94%).

N-(3-Butyramido-2,4-difluorophenyl)-2-chloro-5-((1R,3R)-2,2-dichloro-3-(3-chloro-4-fluorophenyl)cyclopropane-1-carboxamido)benzamide (F1705)

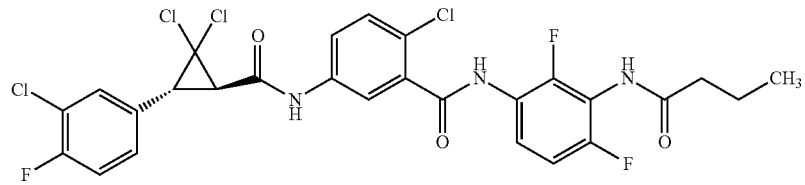

Isolated as a white solid (0.99 g, 88%).

2-Chloro-N-(3-(2-chloro-2,2-difluoroacetamido)-2,4-difluorophenyl)-5-((1R,3R)-2,2-dichloro-3-(4-chloro-3-(trifluoromethyl)phenyl)cyclopropane-1-carboxamido)benzamide (F1719)

Isolated as a white foam (0.54 g, 76%).

2-Chloro-5-((1R,3R)-2,2-dichloro-3-(4-fluoro-3-(trifluoromethyl)phenyl)cyclopropane-1-carboxamido)-N-(3-((S)-2-ethoxypropanamido)-2,4-difluorophenyl)benzamide (F1731)

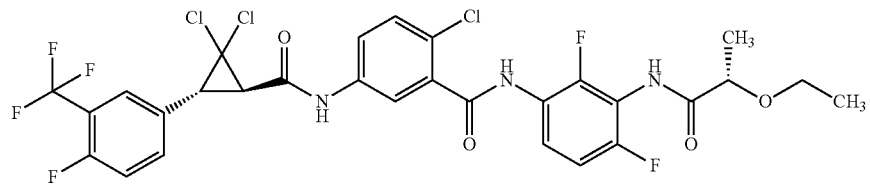 [SMILES: CCO[C@@H](C)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white foam (0.080 g, 69%).

2-Chloro-5-((1R,3R)-2,2-dichloro-3-(4-fluoro-3-(trifluoromethyl)phenyl)cyclopropane-1-carboxamido)-N-(3-((R)-2-ethoxypropanamido)-2,4-difluorophenyl)benzamide (F1732)

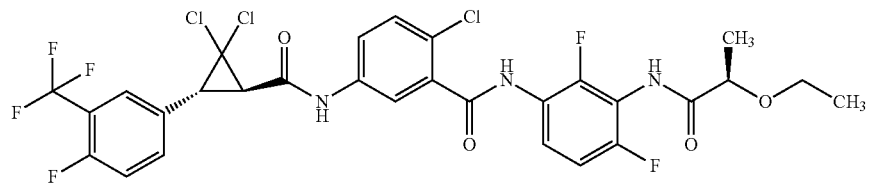 [SMILES: CCO[C@H](C)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white foam (0.097 g, 83%).

2-Chloro-5-((1R,3R)-2,2-dichloro-3-(3,4-dichloro-
phenyl)cyclopropane-1-carboxamido)-N-(3-((S)-2-
ethoxypropanamido)-2,4-difluorophenyl)benzamide
(F1733)

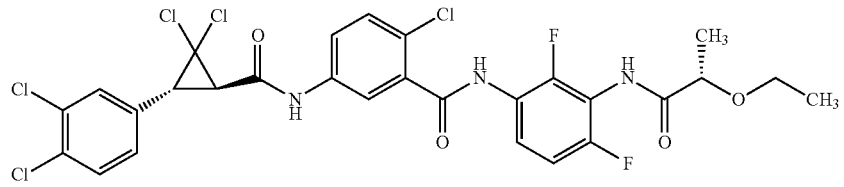 [SMILES: CCO[C@@H](C)C(=O)Nc1c(F)ccc(NC(=O)c2cc(NC(=O)[C@H]3[C@H](c4ccc(Cl)c(Cl)c4)C3(Cl)Cl)ccc2Cl)c1F]

Isolated as a white foam (0.068 g, 58%).

2-Chloro-5-((1R,3R)-2,2-dichloro-3-(3,4-dichloro-
phenyl)cyclopropane-1-carboxamido)-N-(3-((R)-2-
ethoxypropanamido)-2,4-difluorophenyl)benzamide
(F1734)

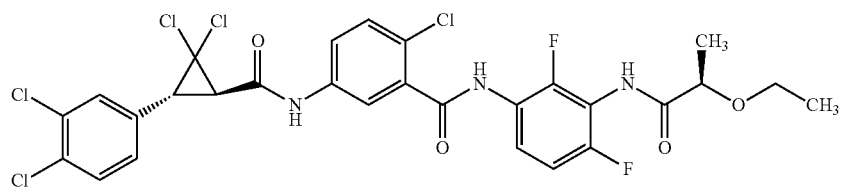 [SMILES: CCO[C@H](C)C(=O)Nc1c(F)ccc(NC(=O)c2cc(NC(=O)[C@H]3[C@H](c4ccc(Cl)c(Cl)c4)C3(Cl)Cl)ccc2Cl)c1F]

Isolated as a white foam (0.081 g, 69%).

2-Chloro-5-((1R,3R)-2,2-dichloro-3-(3-chloro-4-
fluorophenyl)cyclopropane-1-carboxamido)-N-(2,4-
difluoro-3-(2,2,3,3,4,4,4-heptafluorobutanamido)
phenyl)benzamide (F1741)

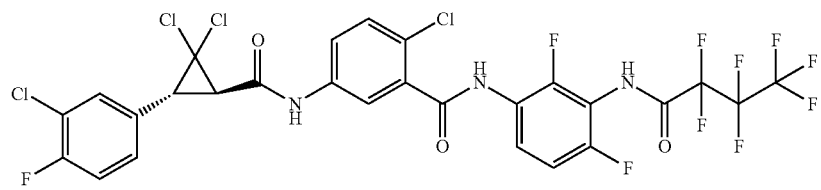 [SMILES: O=C(Nc1ccc(F)c(NC(=O)C(F)(F)C(F)(F)C(F)(F)F)c1F)c1cc(NC(=O)[C@H]2[C@H](c3ccc(F)c(Cl)c3)C2(Cl)Cl)ccc1Cl]

Isolated as a white solid (0.051 g, 38%).

2-Chloro-5-((1R,3R)-2,2-dichloro-3-(4-fluoro-3-
(trifluoromethyl)phenyl)cyclopropane-1-carbox-
amido)-N-(2,4-difluoro-3-(2-(trifluoromethoxy)acet-
amido)phenyl)benzamide (F1742)

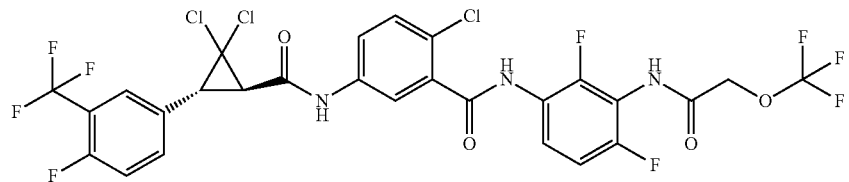

Isolated as a white solid (0.104 g, 86%).

2-Chloro-5-((1R,3R)-2,2-dichloro-3-(4-fluoro-3-(trifluoromethyl)phenyl)cyclopropane-1-carboxamido)-N-(2,4-difluoro-3-(2-oxopropanamido)phenyl)benzamide (F1754)

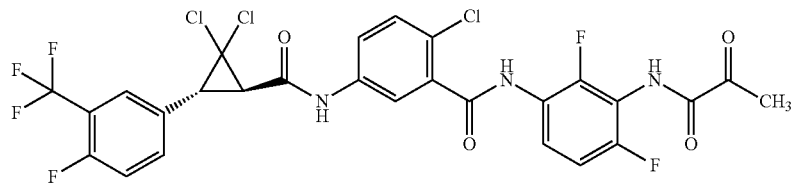 [SMILES: CC(=O)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white solid (0.035 g, 40%).

2-Chloro-5-((1R,3R)-2,2-dichloro-3-(4-fluoro-3-(trifluoromethyl)phenyl)cyclopropane-1-carboxamido)-N-(2,4-difluoro-3-(4,4,4-trifluoro-3-methylbutanamido)phenyl)benzamide (F1760)

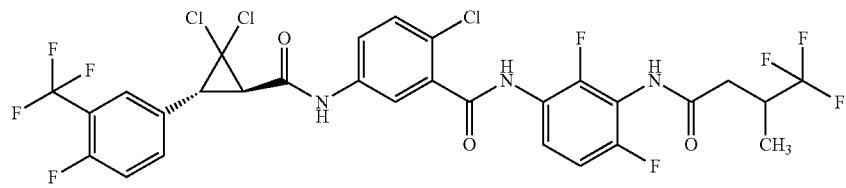 [SMILES: CC(CC(=O)Nc1c(F)ccc(NC(=O)c2cc(NC(=O)[C@H]3[C@H](c4ccc(F)c(C(F)(F)F)c4)C3(Cl)Cl)ccc2Cl)c1F)C(F)(F)F]

Isolated as a white foam (0.101 g, 82%).

2-Chloro-5-((1R,3R)-2,2-dichloro-3-(3,4-dichlorophenyl)cyclopropane-1-carboxamido)-N-(2,4-difluoro-3-(2-(trifluoromethoxy)acetamido)phenyl)benzamide (F1766)

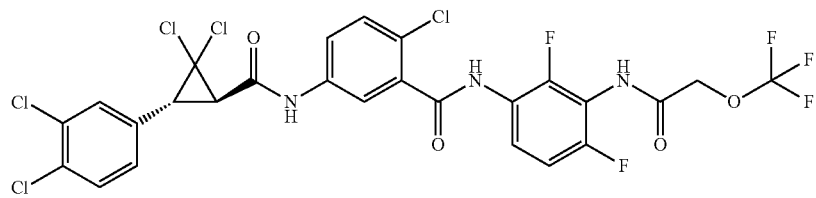 [SMILES: O=C(COC(F)(F)F)Nc1c(F)ccc(NC(=O)c2cc(NC(=O)[C@H]3[C@H](c4ccc(Cl)c(Cl)c4)C3(Cl)Cl)ccc2Cl)c1F]

Isolated as a white foam (0.100 g, 82%).

2-Chloro-5-((1R,3R)-2,2-dichloro-3-(3,4-dichlorophenyl)cyclopropane-1-carboxamido)-N-(2,4-difluoro-3-(2-(trifluoromethoxy)propanamido)phenyl)benzamide (F1767)

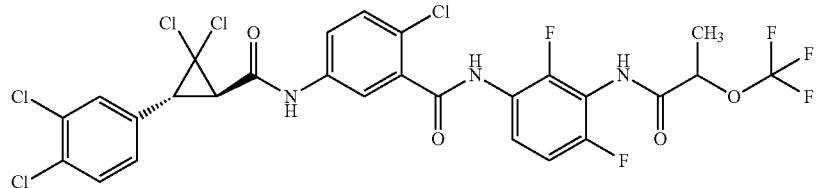

Isolated as a white foam (0.096 g, 78%).

2-Chloro-5-((1R,3R)-2,2-dichloro-3-(3-chloro-4-fluorophenyl)cyclopropane-1-carboxamido)-N-(2,4-difluoro-3-(2-(trifluoromethoxy)acetamido)phenyl)benzamide (F1768)

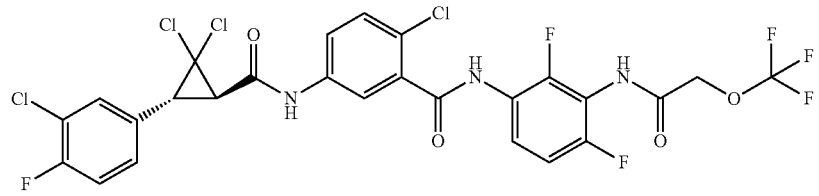

Isolated as a white foam (0.101 g, 83%).

2-Chloro-5-((1R,3R)-2,2-dichloro-3-(3-chloro-4-fluorophenyl)cyclopropane-1-carboxamido)-N-(2,4-difluoro-3-(2-(trifluoromethoxy)propanamido)phenyl)benzamide (F1769)

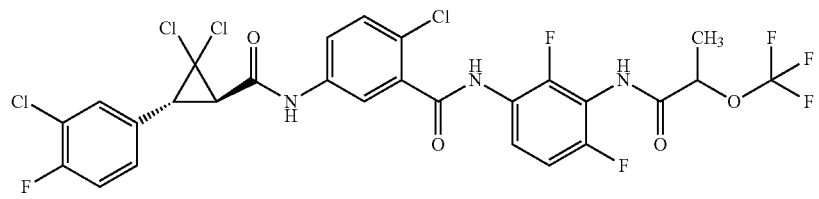

Isolated as a white foam (0.109 g, 87%).

5-((1R,3R)-2,2-Dichloro-3-(3,4,5-trichlorophenyl)cyclopropane-1-carboxamido)-N-(2,6-difluoro-3-(2-(trifluoromethoxy)acetamido)phenyl)-2,3-difluorobenzamide (F1777)

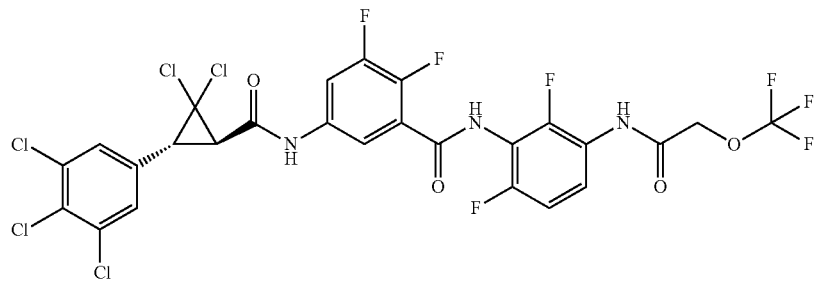 [SMILES: O=C(COC(F)(F)F)Nc1ccc(F)c(NC(=O)c2cc(NC(=O)[C@H]3[C@H](c4cc(Cl)c(Cl)c(Cl)c4)C3(Cl)Cl)cc(F)c2F)c1F]

Isolated as a white foam (0.058 g, 83%).

N-(3-(5-((1R,3R)-2,2-Dichloro-3-(3,4,5-trichlorophenyl)cyclopropane-1-carboxamido)-2,3-difluorobenzamido)-2,4-difluorophenyl)tetrahydrofuran-2-carboxamide (F1778)

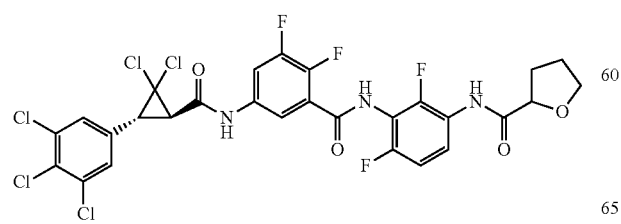

Isolated as a white foam (0.046 g, 68%).

5-((1R,3R)-2,2-Dichloro-3-(3,4,5-trichlorophenyl)
cyclopropane-1-carboxamido)-N-(2,6-difluoro-3-(2,
2,3,3,4,4,4-heptafluorobutanamido)phenyl)-2,3-dif-
luorobenzamide (F1779)

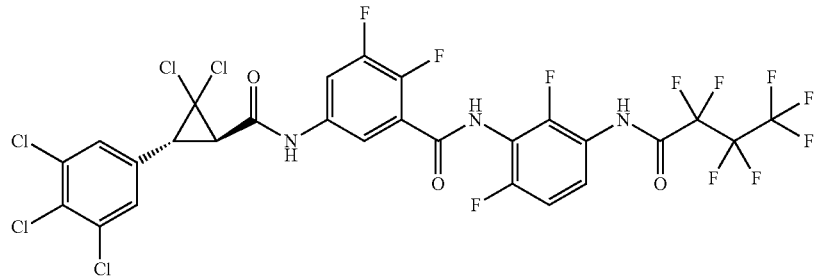 [SMILES: O=C(Nc1c(F)ccc(NC(=O)C(F)(F)C(F)(F)C(F)(F)F)c1F)c1cc(NC(=O)[C@H]2[C@H](c3cc(Cl)c(Cl)c(Cl)c3)C2(Cl)Cl)cc(F)c1F]

Isolated as a white foam (0.053 g, 70%).

2-Chloro-5-((1R,3R)-2,2-dichloro-3-(3,4-dichloro-
phenyl)cyclopropane-1-carboxamido)-N-(2,4-dif-
luoro-3-(2-(trifluoromethoxy)acetamido)phenyl)-N-
methylbenzamide (F1793)

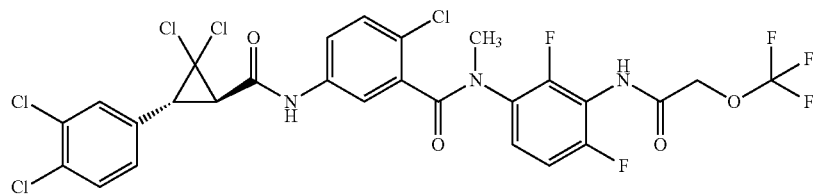 [SMILES: CN(C(=O)c1cc(NC(=O)[C@H]2[C@H](c3ccc(Cl)c(Cl)c3)C2(Cl)Cl)ccc1Cl)c1ccc(F)c(NC(=O)COC(F)(F)F)c1F]

Isolated as a white foam (0.107 g, 88%).

2-Chloro-5-((1R,3R)-2,2-dichloro-3-(3,4-dichloro-
phenyl)cyclopropane-1-carboxamido)-N-(3-(2-
ethoxypropanamido)-2,4-difluorophenyl)-N-methyl-
benzamide (F1794)

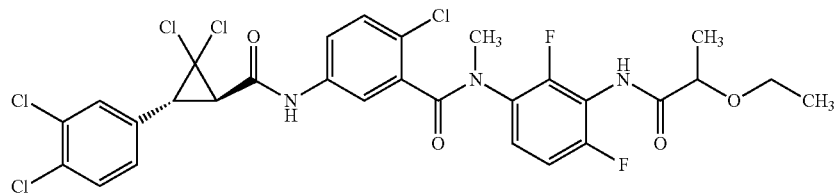 [SMILES: CCOC(C)C(=O)Nc1c(F)ccc(N(C)C(=O)c2cc(NC(=O)[C@H]3[C@H](c4ccc(Cl)c(Cl)c4)C3(Cl)Cl)ccc2Cl)c1F]

Isolated as a white foam (0.088 g, 75%).

2-Chloro-5-((1R,3R)-2,2-dichloro-3-(4-fluoro-3-
(trifluoromethyl)phenyl)cyclopropane-1-carbox-
amido)-N-(2,4-difluoro-3-(2-(trifluoromethoxy)acet-
amido)phenyl)-N-methylbenzamide (F1796)

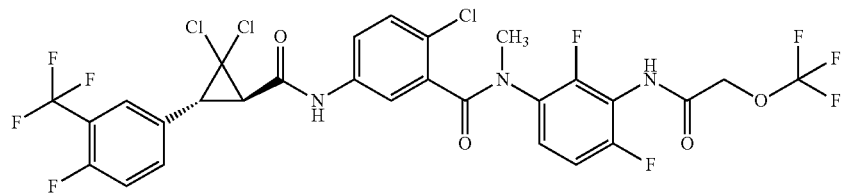 [SMILES: CN(C(=O)c1cc(NC(=O)[C@H]2[C@H](c3ccc(F)c(C(F)(F)F)c3)C2(Cl)Cl)ccc1Cl)c1ccc(F)c(NC(=O)COC(F)(F)F)c1F]

Isolated as a white foam (0.095 g, 79%).

2-Chloro-5-(((1R,3R)-2,2-dichloro-3-(4-fluoro-3-(trifluoromethyl)phenyl)cyclopropane-1-carboxamido)-N-(3-(2-ethoxypropanamido)-2,4-difluorophenyl)-N-methylbenzamide (F1797)

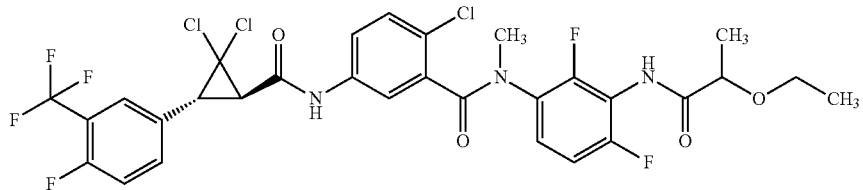 [SMILES: CCOC(C)C(=O)Nc1c(F)ccc(N(C)C(=O)c2cc(NC(=O)[C@H]3[C@H](c4ccc(F)c(C(F)(F)F)c4)C3(Cl)Cl)ccc2Cl)c1F]

Isolated as a white foam (0.092 g, 79%).

N-(3-(2-Chloro-5-(((1R,3R)-2,2-Dichloro-3-(4-fluoro-3-(trifluoromethyl)phenyl)cyclopropane-1-carboxamido)-N-methylbenzamido)-2,6-difluorophenyl)tetrahydrofuran-2-carboxamide (F1798)

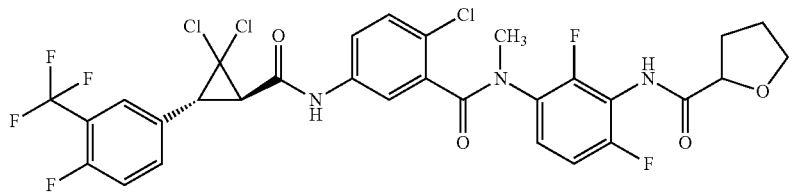 [SMILES: CN(C(=O)c1cc(NC(=O)[C@H]2[C@H](c3ccc(F)c(C(F)(F)F)c3)C2(Cl)Cl)ccc1Cl)c1ccc(F)c(NC(=O)C2CCCO2)c1F]

Isolated as a white foam (0.098 g, 84%).

2-Chloro-5-(((1R,3R)-2,2-dichloro-3-(4-fluoro-3-(trifluoromethyl)phenyl)cyclopropane-1-carboxamido)-N-(2,4-difluoro-3-(4,4,4-trifluorobutanamido)phenyl)benzamide (F1800)

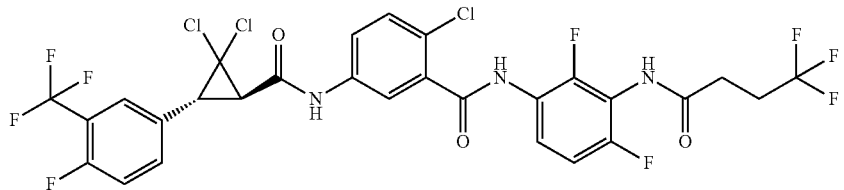 [SMILES: O=C(CCC(F)(F)F)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white foam (0.11 g, 92%).

trans-5-(3-(3,5-bis(Trifluoromethyl)phenyl)-2,2-dichlorocyclopropane-1-carboxamido)-2-chloro-N-(2,4-difluoro-3-(2-(trifluoromethoxy)acetamido)phenyl)benzamide (F1804)

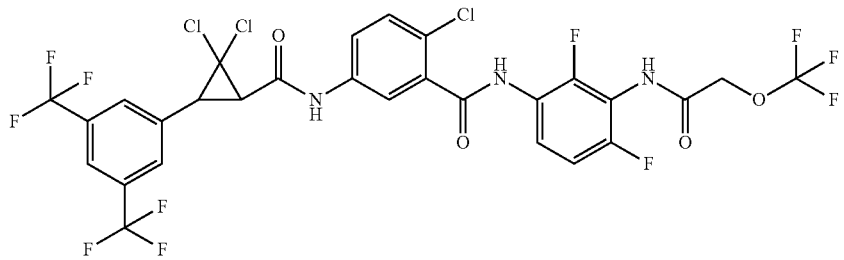 [SMILES: O=C(COC(F)(F)F)Nc1c(F)ccc(NC(=O)c2cc(NC(=O)C3C(c4cc(C(F)(F)F)cc(C(F)(F)F)c4)C3(Cl)Cl)ccc2Cl)c1F]

Isolated as a white foam (0.106 g, 89%).

trans-N-(3-(5-(3-(3,5-bis(Trifluoromethyl)phenyl)-2,
2-dichlorocyclopropane-1-carboxamido)-2-chlo-
robenzamido)-2,6-difluorophenyl)tetrahydrofuran-2-
carboxamide (F1805)

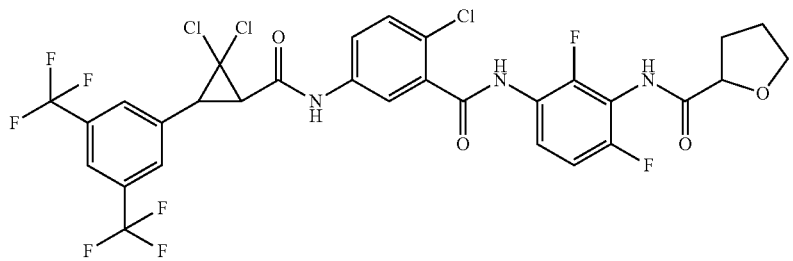 [SMILES: O=C(Nc1ccc(F)c(NC(=O)C2CCCO2)c1F)c1cc(NC(=O)C2C(c3cc(C(F)(F)F)cc(C(F)(F)F)c3)C2(Cl)Cl)ccc1Cl]

Isolated as a white foam (0.105 g, 91%).

trans-5-(3-(3,5-bis(Trifluoromethyl)phenyl)-2,2-
dichlorocyclopropane-1-carboxamido)-N-(3-bu-
tyramido-2,4-difluorophenyl)-2-chlorobenzamide
(F1806)

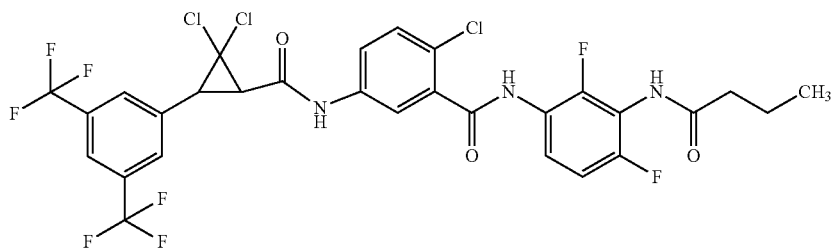 [SMILES: CCCC(=O)Nc1c(F)ccc(NC(=O)c2cc(NC(=O)C3C(c4cc(C(F)(F)F)cc(C(F)(F)F)c4)C3(Cl)Cl)ccc2Cl)c1F]

Isolated as a white foam (0.098 g, 89%).

N-(3-(2-Chloro-5-((1R,3R)-2,2-dichloro-3-(4-fluoro-
3-(trifluoromethyl)phenyl)cyclopropane-1-carbox-
amido)benzamido)-2,6-difluorophenyl)isoxazole-5-
carboxamide (F1816)

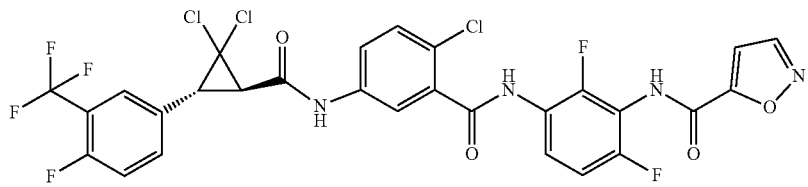 [SMILES: O=C(Nc1c(F)ccc(NC(=O)c2cc(NC(=O)[C@H]3[C@H](c4ccc(F)c(C(F)(F)F)c4)C3(Cl)Cl)ccc2Cl)c1F)c1ccno1]

Isolated as a white foam (0.078 g, 84%).

N-(3-(2-Chloro-5-((1R,3R)-2,2-dichloro-3-(4-fluoro-
3-(trifluoromethyl)phenyl)cyclopropane-1-carbox-
amido)benzamido)-2,6-difluorophenyl)isothiazole-5-
carboxamide (F1817)

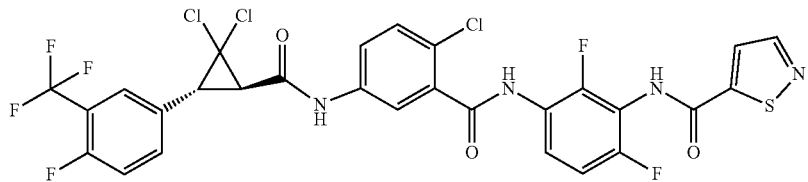 [SMILES: O=C(Nc1c(F)ccc(NC(=O)c2cc(NC(=O)[C@H]3[C@H](c4ccc(F)c(C(F)(F)F)c4)C3(Cl)Cl)ccc2Cl)c1F)c1ccns1]

Isolated as a white foam (0.036 g, 38%).

N-(3-(2-Chloro-5-((1R,3R)-2,2-dichloro-3-(4-fluoro-3-(trifluoromethyl)phenyl)cyclopropane-1-carboxamido)benzamido)-2,6-difluorophenyl)isoxazole-3-carboxamide (F1818)

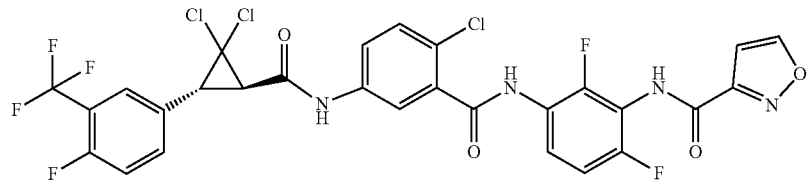 [SMILES: O=C(Nc1c(F)ccc(NC(=O)c2cc(NC(=O)[C@H]3[C@H](c4ccc(F)c(C(F)(F)F)c4)C3(Cl)Cl)ccc2Cl)c1F)c1ccon1]

Isolated as a white foam (0.067 g, 72%).

N-(3-(2-Chloro-5-((1R,3R)-2,2-dichloro-3-(4-fluoro-3-(trifluoromethyl)phenyl)cyclopropane-1-carboxamido)benzamido)-2,6-difluorophenyl)-1-(2,2,2-trifluoroethyl)-1H-pyrazole-3-carboxamide (F1819)

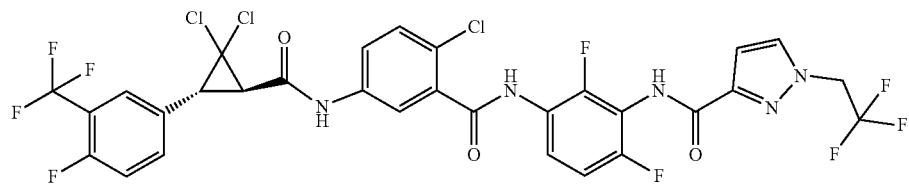 [SMILES: O=C(Nc1c(F)ccc(NC(=O)c2cc(NC(=O)[C@H]3[C@H](c4ccc(F)c(C(F)(F)F)c4)C3(Cl)Cl)ccc2Cl)c1F)c1ccn(CC(F)(F)F)n1]

Isolated as a white foam (0.070 g, 67%).

N-(3-(2-Chloro-5-((1R,3R)-2,2-dichloro-3-(4-fluoro-3-(trifluoromethyl)phenyl)cyclopropane-1-carboxamido)benzamido)-2,6-difluorophenyl)-1,2,3-thiadiazole-5-carboxamide (F1820)

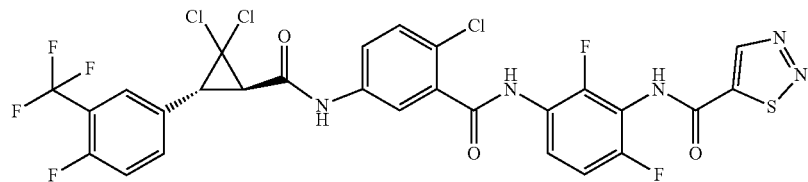 [SMILES: O=C(Nc1c(F)ccc(NC(=O)c2cc(NC(=O)[C@H]3[C@H](c4ccc(F)c(C(F)(F)F)c4)C3(Cl)Cl)ccc2Cl)c1F)c1cnns1]

Isolated as a white foam (0.040 g, 42%).

N-(3-(2-Chloro-5-((1R,3R)-2,2-dichloro-3-(4-fluoro-3-(trifluoromethyl)phenyl)cyclopropane-1-carboxamido)benzamido)-2,6-difluorophenyl)-3-(trifluoromethyl)isoxazole-5-carboxamide (F1824)

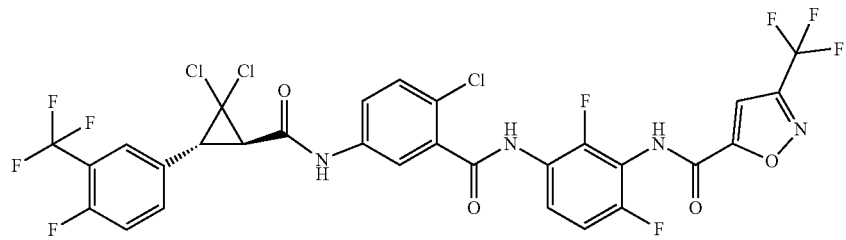 [SMILES: O=C(Nc1c(F)ccc(NC(=O)c2cc(NC(=O)[C@H]3[C@H](c4ccc(F)c(C(F)(F)F)c4)C3(Cl)Cl)ccc2Cl)c1F)c1cc(C(F)(F)F)no1]

Isolated as a white foam (0.024 g, 24%).

trans-5-(3-(3,5-bis(Trifluoromethyl)phenyl)-2,2-dichlorocyclopropane-1-carboxamido)-2-chloro-N-(2,4-difluoro-3-(2,2,3,3,4,4,4-heptafluorobutanamido)phenyl)benzamide (F1825)

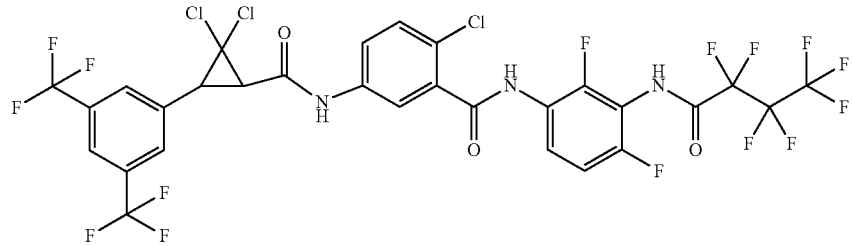 [SMILES: O=C(Nc1ccc(F)c(NC(=O)C(F)(F)C(F)(F)C(F)(F)F)c1F)c1cc(NC(=O)C2C(c3cc(C(F)(F)F)cc(C(F)(F)F)c3)C2(Cl)Cl)ccc1Cl]

Isolated as a white foam (0.105 g, 80%).

2-Chloro-5-((1R,3R)-2,2-dichloro-3-(4-fluoro-3-(trifluoromethyl)phenyl)cyclopropane-1-carboxamido)-N-(2,4-difluoro-3-(4,4,4-trifluoro-3-(trifluoromethyl)butanamido)phenyl)benzamide (F1833)

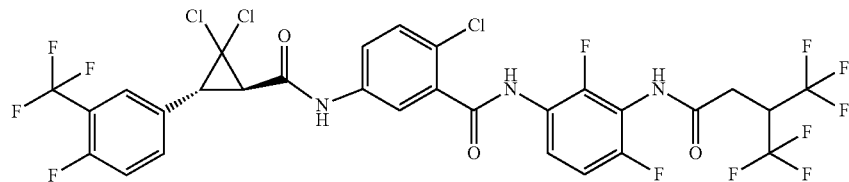 [SMILES: O=C(CC(C(F)(F)F)C(F)(F)F)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white foam (0.114 g, 86%).

2-Chloro-5-((1R,3R)-2,2-dichloro-3-(4-fluoro-3-(trifluoromethyl)phenyl)cyclopropane-1-carboxamido)-N-(3-(4,4-difluoropentanamido)-2,4-difluorophenyl)benzamide (F1843)

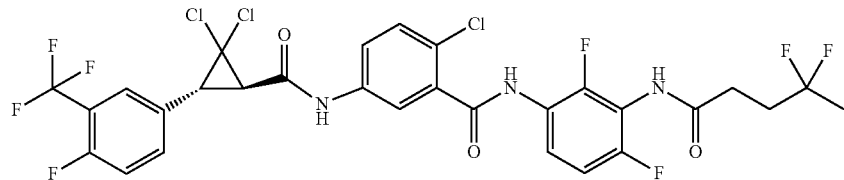 [SMILES: CC(F)(F)CCC(=O)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white foam (0.100 g, 84%).

2-Chloro-5-((1R,3R)-2,2-dichloro-3-(4-fluoro-3-(trifluoromethyl)phenyl)cyclopropane-1-carboxamido)-N-(2,4-difluoro-3-(4,4,5,5,5-pentafluoropentanamido)phenyl)benzamide (F1844)

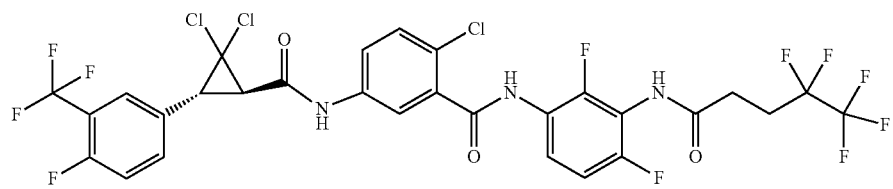 [SMILES: O=C(CCC(F)(F)C(F)(F)F)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white foam (0.113 g, 88%).

2-Chloro-5-((1R,3R)-2,2-dichloro-3-(4-fluoro-3-(trifluoromethyl)phenyl)cyclopropane-1-carboxamido)-N-(2,4-difluoro-3-(3-methylbutanamido)phenyl)benzamide (F1845)

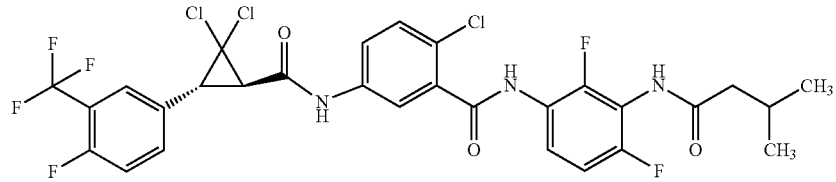 [SMILES: CC(C)CC(=O)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white foam (0.101 g, 88%).

2-Chloro-5-((1R,3R)-2,2-dichloro-3-(4-fluoro-3-(trifluoromethyl)phenyl)cyclopropane-1-carboxamido)-N-(2,4-difluoro-3-(2-(2,2,2-trifluoroethoxy)acetamido)phenyl)benzamide (F1846)

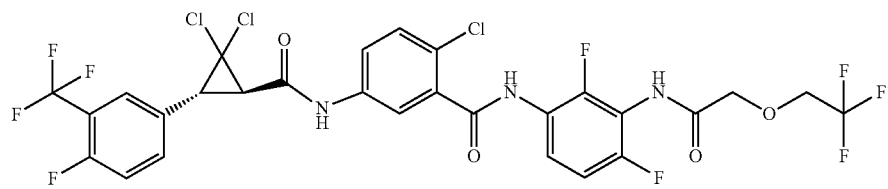 [SMILES: O=C(COCC(F)(F)F)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white foam (0.119 g, 80%).

2-Chloro-5-((1R,3R)-2,2-dichloro-3-(3,4-dichlorophenyl)cyclopropane-1-carboxamido)-N-(2,4-difluoro-3-(4,4,4-trifluorobutanamido)phenyl)benzamide (F1847)

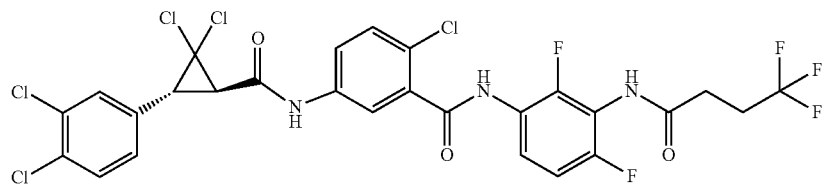 [SMILES: O=C(CCC(F)(F)F)Nc1c(F)ccc(NC(=O)c2cc(NC(=O)[C@H]3[C@H](c4ccc(Cl)c(Cl)c4)C3(Cl)Cl)ccc2Cl)c1F]

Isolated as a white foam (0.105 g, 86%).

2-Chloro-5-((1R,3R)-2,2-dichloro-3-(3-chloro-4-fluorophenyl)cyclopropane-1-carboxamido)-N-(2,4-difluoro-3-(4,4,4-trifluorobutanamido)phenyl)benzamide (F1848)

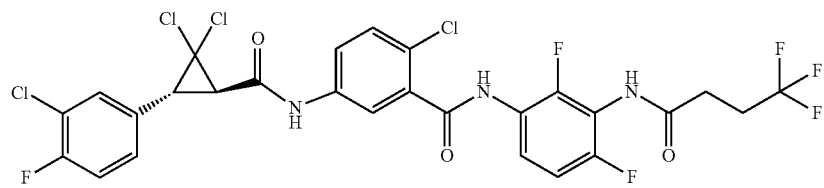 [SMILES: O=C(CCC(F)(F)F)Nc1c(F)ccc(NC(=O)c2cc(NC(=O)[C@H]3[C@H](c4ccc(F)c(Cl)c4)C3(Cl)Cl)ccc2Cl)c1F]

Isolated as a white foam (0.101 g, 83%).

N-(3-(1-Acetylcyclopropane-1-carboxamido)-2,4-difluorophenyl)-2-chloro-5-((1R,3R)-2,2-dichloro-3-(4-fluoro-3-(trifluoromethyl)phenyl)cyclopropane-1-carboxamido)benzamide (F1850)

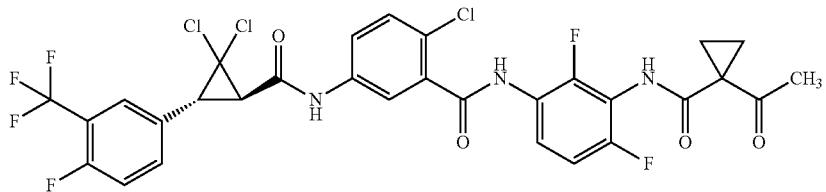 [SMILES: CC(=O)C1(C(=O)Nc2c(F)ccc(NC(=O)c3cc(NC(=O)[C@H]4[C@H](c5ccc(F)c(C(F)(F)F)c5)C4(Cl)Cl)ccc3Cl)c2F)CC1]

Isolated as a white solid (0.044 g, 42%).

2-Chloro-5-((1R,3R)-2,2-dichloro-3-(3,4-dichlorophenyl)cyclopropane-1-carboxamido)-N-(3-(4,4-difluoropentanamido)-2,4-difluorophenyl)benzamide (F1860)

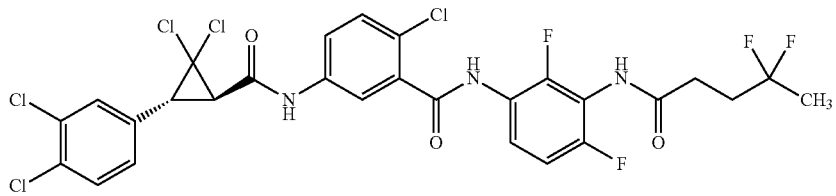

Isolated as a white solid (0.103 g, 85%).

2-Chloro-5-((1R,3R)-2,2-dichloro-3-(3,4-dichlorophenyl)cyclopropane-1-carboxamido)-N-(2,4-difluoro-3-(4,4,5,5,5-pentafluoropentanamido)phenyl)benzamide (F1861)

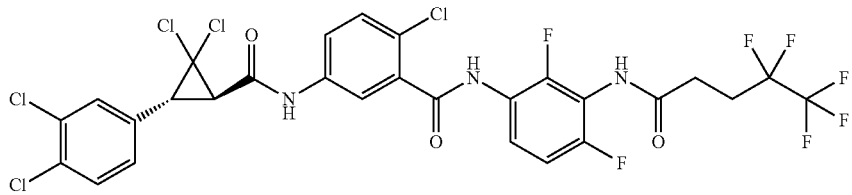 [SMILES: O=C(CCC(F)(F)C(F)(F)F)Nc1c(F)ccc(NC(=O)c2cc(NC(=O)[C@H]3[C@H](c4ccc(Cl)c(Cl)c4)C3(Cl)Cl)ccc2Cl)c1F]

Isolated as a white foam (0.119 g, 92%).

2-Chloro-5-((1R,3R)-2,2-dichloro-3-(3,4-dichlorophenyl)cyclopropane-1-carboxamido)-N-(2,4-difluoro-3-(4,4,4-trifluoro-2-methylbutanamido)phenyl)benzamide (F1862)

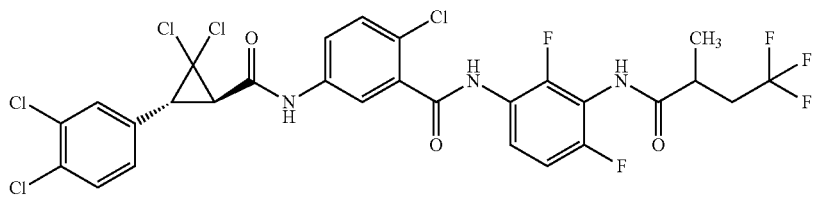 [SMILES: CC(CC(F)(F)F)C(=O)Nc1c(F)ccc(NC(=O)c2cc(NC(=O)[C@H]3[C@H](c4ccc(Cl)c(Cl)c4)C3(Cl)Cl)ccc2Cl)c1F]

Isolated as a white foam (0.047 g, 38%).

2-Chloro-5-((1R,3R)-2,2-dichloro-3-(3,4-dichloro-phenyl)cyclopropane-1-carboxamido)-N-(2,4-difluoro-3-(2-(2,2,2-trifluoroethoxy)acetamido)phenyl) benzamide (F1863)

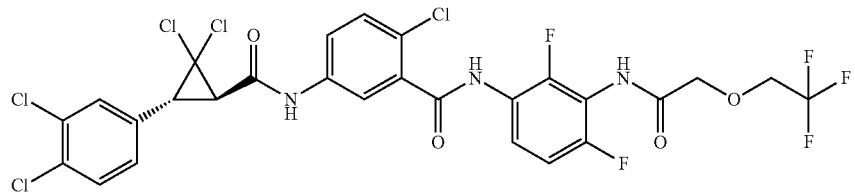 [SMILES: O=C(COCC(F)(F)F)Nc1c(F)ccc(NC(=O)c2cc(NC(=O)[C@H]3[C@H](c4ccc(Cl)c(Cl)c4)C3(Cl)Cl)ccc2Cl)c1F]

Isolated as a white foam (0.109 g, 88%).

2-Chloro-5-((1R,3R)-2,2-dichloro-3-(3-chloro-4-fluorophenyl)cyclopropane-1-carboxamido)-N-(3-(4,4-difluoropentanamido)-2,4-difluorophenyl)benzamide (F1864)

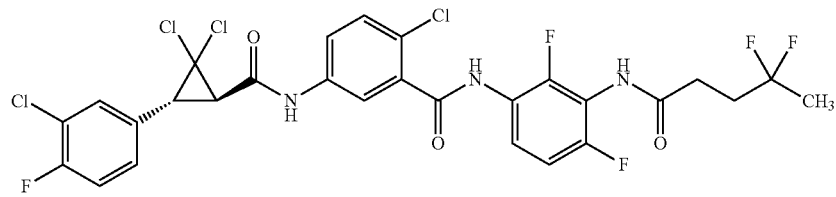

Isolated as a white foam (0.100 g, 83%).

2-Chloro-5-((1R,3R)-2,2-dichloro-3-(3-chloro-4-fluorophenyl)cyclopropane-1-carboxamido)-N-(2,4-difluoro-3-(4,4,5,5,5-pentafluoropentanamido)phenyl) benzamide (F1865)

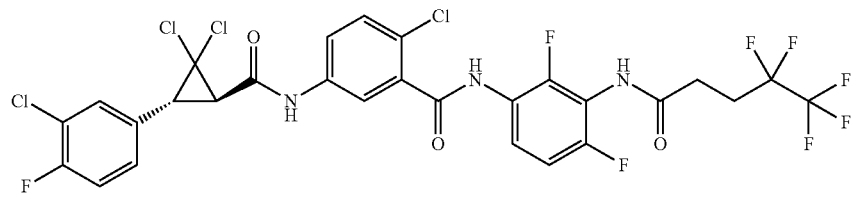 [SMILES: O=C(CCC(F)(F)C(F)(F)F)Nc1c(F)ccc(NC(=O)c2cc(NC(=O)[C@H]3[C@H](c4ccc(F)c(Cl)c4)C3(Cl)Cl)ccc2Cl)c1F]

Isolated as a white foam (0.113 g, 86%).

2-Chloro-5-((1R,3R)-2,2-dichloro-3-(3-chloro-4-fluorophenyl)cyclopropane-1-carboxamido)-N-(2,4-difluoro-3-(4,4,4-trifluoro-2-methylbutanamido) phenyl) benzamide (F1866)

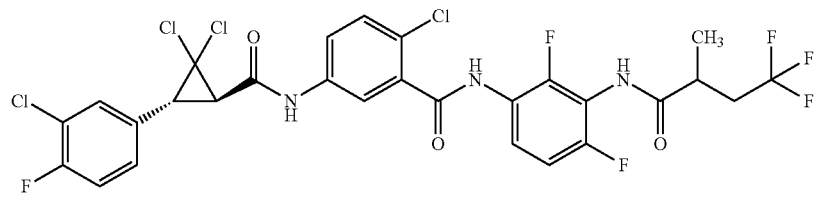 [SMILES: CC(CC(F)(F)F)C(=O)Nc1c(F)ccc(NC(=O)c2cc(NC(=O)[C@H]3[C@H](c4ccc(F)c(Cl)c4)C3(Cl)Cl)ccc2Cl)c1F]

Isolated as a white foam (0.094 g, 75%).

2-Chloro-5-((1R,3R)-2,2-dichloro-3-(3-chloro-4-fluorophenyl)cyclopropane-1-carboxamido)-N-(2,4-difluoro-3-(2-(2,2,2-trifluoroethoxy)acetamido)phenyl) benzamide (F1867)

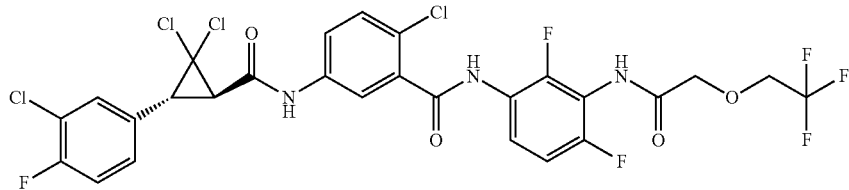

Isolated as a white foam (0.115 g, 92%).

2-Chloro-5-((1R,3R)-2,2-dichloro-3-(3,4-dichlorophenyl)cyclopropane-1-carboxamido)-N-(2,4-difluoro-3-(2-fluoroacrylamido)phenyl)benzamide (F1871)

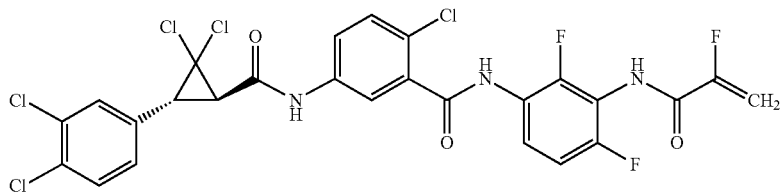 [SMILES: C=C(F)C(=O)Nc1c(F)ccc(NC(=O)c2cc(NC(=O)[C@H]3[C@H](c4ccc(Cl)c(Cl)c4)C3(Cl)Cl)ccc2Cl)c1F]

Isolated as a white foam (0.047 mg, 42%).

2-Chloro-5-((1R,3R)-2,2-dichloro-3-(3,4,5-trichlorophenyl)cyclopropane-1-carboxamido)-N-(2,4-difluoro-3-(2-fluoroacrylamido)phenyl)benzamide (F1872)

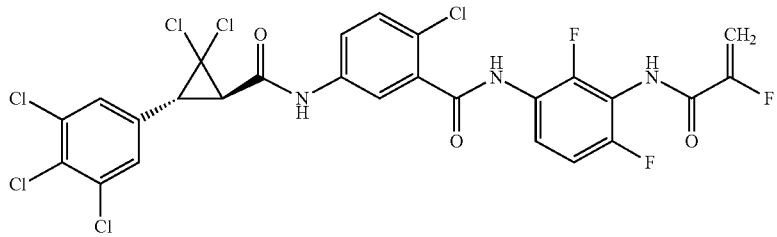 [SMILES: C=C(F)C(=O)Nc1c(F)ccc(NC(=O)c2cc(NC(=O)[C@H]3[C@H](c4cc(Cl)c(Cl)c(Cl)c4)C3(Cl)Cl)ccc2Cl)c1F]

Isolated as an off-white foam (0.053 g, 47%).

N-(3-(But-3-enamido)-2,4-difluorophenyl)-2-chloro-5-((1R,3R)-2,2-dichloro-3-(3,4-dichlorophenyl)cyclopropane-1-carboxamido)benzamide (F1873)

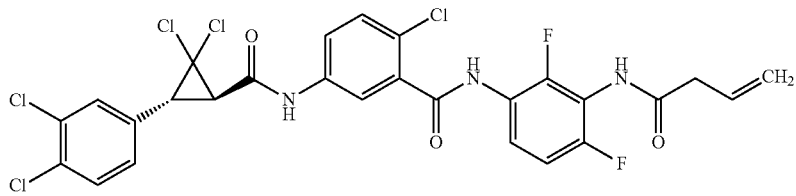 [SMILES: C=CCC(=O)Nc1c(F)ccc(NC(=O)c2cc(NC(=O)[C@H]3[C@H](c4ccc(Cl)c(Cl)c4)C3(Cl)Cl)ccc2Cl)c1F]

Isolated as a white foam (0.065 g, 69%).

N-(3-(But-3-enamido)-2,4-difluorophenyl)-2-chloro-5-((1R,3R)-2,2-dichloro-3-(4-fluoro-3-(trifluoromethyl)phenyl)cyclopropane-1-carboxamido)benzamide (F1874)

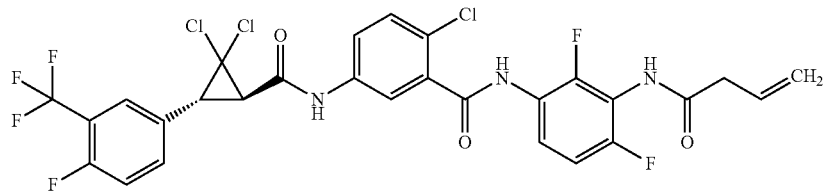 [SMILES: C=CCC(=O)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white foam (0.097 g, 87%).

N-(3-(But-3-enamido)-2,6-difluorophenyl)-5-((1R,3R)-2,2-dichloro-3-(3,4,5-trichlorophenyl)cyclopropane-1-carboxamido)-2,3-difluorobenzamide (F1875)

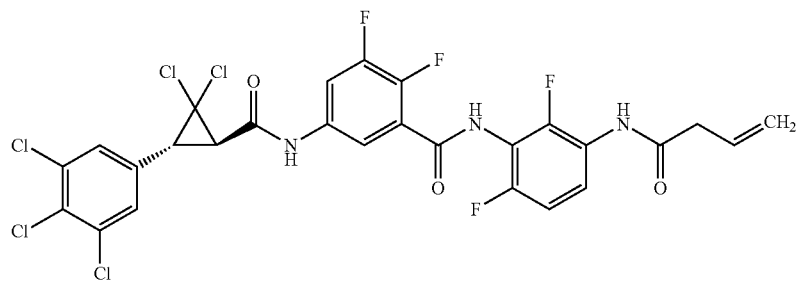 [SMILES: C=CCC(=O)Nc1ccc(F)c(NC(=O)c2cc(NC(=O)[C@H]3[C@H](c4cc(Cl)c(Cl)c(Cl)c4)C3(Cl)Cl)cc(F)c2F)c1F]

Isolated as a white foam (0.054 g, 84%).

N-(3-(But-3-enamido)-2,4-difluorophenyl)-2-chloro-5-((1R,3R)-2,2-dichloro-3-(3-chloro-4-fluorophenyl)cyclopropane-1-carboxamido)benzamide (F1876)

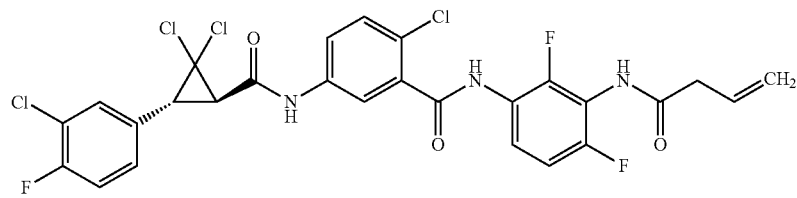 [SMILES: C=CCC(=O)Nc1c(F)ccc(NC(=O)c2cc(NC(=O)[C@H]3[C@H](c4ccc(F)c(Cl)c4)C3(Cl)Cl)ccc2Cl)c1F]

Isolated as a white foam (0.074 g, 66%).

N-(3-Acrylamido-2,4-difluorophenyl)-2-chloro-5-((1R,3R)-2,2-dichloro-3-(4-fluoro-3-(trifluoromethyl)phenyl)cyclopropane-1-carboxamido)benzamide (F1877)

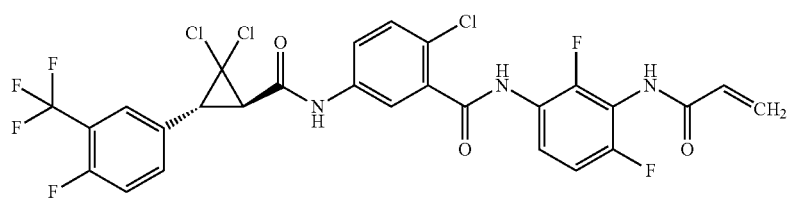 [SMILES: C=CC(=O)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white solid (0.041 g, 21%).

The following compounds were prepared in like manner to the procedure outlined in Example 5:

N-(3-Acetamido-2,4-dichlorophenyl)-2-chloro-5-((1R,3R)-2,2-dichloro-3-(4-fluoro-3-(trifluoromethyl)phenyl)cyclopropane-1-carboxamido)benzamide (F1412)

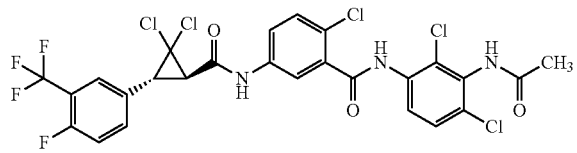 [SMILES: CC(=O)Nc1c(Cl)ccc(NC(=O)c2cc(NC(=O)[C@H]3[C@H](c4ccc(F)c(C(F)(F)F)c4)C3(Cl)Cl)ccc2Cl)c1Cl]

Isolated as a white solid (0.043 g, 29%).

N-(3-Acetamido-2,4-difluorophenyl)-5-((1R,3R)-2,2-dichloro-3-(3,4,5-trichlorophenyl)cyclopropane-1-carboxamido)-2,3-difluorobenzamide (F1433)

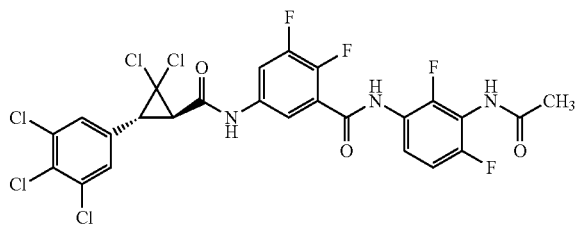 [SMILES: CC(=O)Nc1c(F)ccc(NC(=O)c2cc(NC(=O)[C@H]3[C@H](c4cc(Cl)c(Cl)c(Cl)c4)C3(Cl)Cl)cc(F)c2F)c1F]

The title compound was synthesized with a reaction time of 24-48 hours and isolated as a glassy oil (0.086 g, 76%).

tert-Butyl (3-(2-chloro-5-((1R,3R)-2,2-dichloro-3-(3,5-dichlorophenyl)cyclopropane-1-carboxamido)benzamido)-2,4-difluorophenyl)carbamate (F1434)

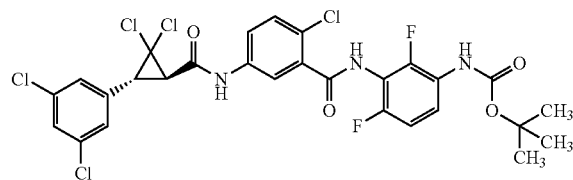 [SMILES: CC(C)(C)OC(=O)Nc1ccc(F)c(NC(=O)c2cc(NC(=O)[C@H]3[C@H](c4cc(Cl)cc(Cl)c4)C3(Cl)Cl)ccc2Cl)c1F]

The title compound was synthesized with a reaction time of 24-48 hours and isolated as a white solid (0.330 g, 88%).

tert-Butyl (3-(2-chloro-5-((1R,3R)-2,2-dichloro-3-(3,4-dichlorophenyl)cyclopropane-1-carboxamido)benzamido)-2,4-difluorophenyl)carbamate (F1435)

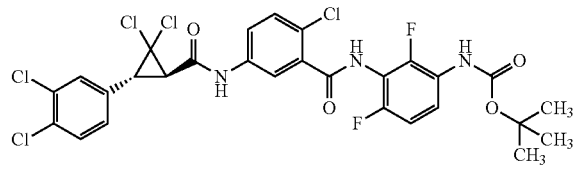 [SMILES: CC(C)(C)OC(=O)Nc1ccc(F)c(NC(=O)c2cc(NC(=O)[C@H]3[C@H](c4ccc(Cl)c(Cl)c4)C3(Cl)Cl)ccc2Cl)c1F]

The title compound was synthesized with a reaction time of 24-48 hours and isolated as a white solid (0.270 g, 76%).

tert-Butyl (3-(2-chloro-5-((1R,3R)-2,2-dichloro-3-(3,4,5-trichlorophenyl)cyclopropane-1-carboxamido)benzamido)-2,4-difluorophenyl)carbamate (F1436)

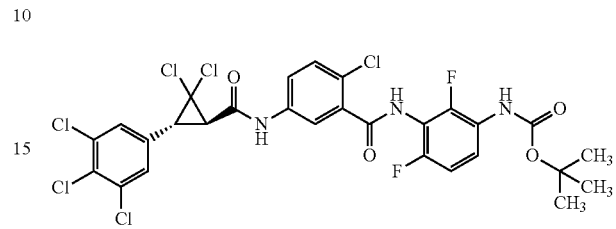

The title compound was synthesized with a reaction time of 24-48 hours and isolated as a white foam (0.320 g, 81%).

5-((1R,3R)-2,2-Dichloro-3-(3,4,5-trichlorophenyl)cyclopropane-1-carboxamido)-N-(3-(2,2-difluoroacetamido)-2,4-difluorophenyl)-2,3-difluorobenzamide (F1437)

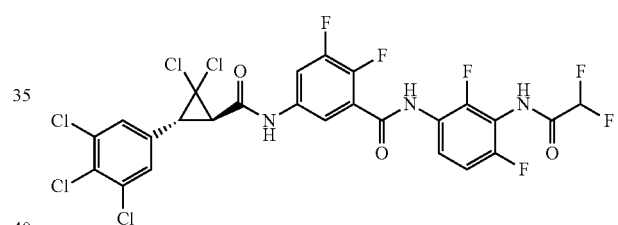

The title compound was synthesized with a reaction time of 24-48 hours and isolated as a brown powder (0.050 g, 38%).

5-((1R,3R)-2,2-Dichloro-3-(3,4,5-trichlorophenyl)cyclopropane-1-carboxamido)-N-(2,4-difluoro-3-(2,2,2-trifluoroacetamido)phenyl)-2,3-difluorobenzamide (F1438)

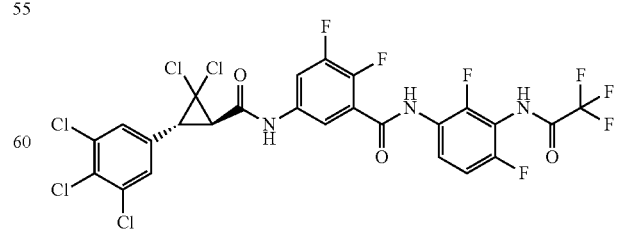

The title compound was synthesized with a reaction time of 24-48 hours and isolated as a glassy solid (0.058 g, 48%).

N-(3-Acetamido-2,4-difluorophenyl)-5-((1R,3R)-2,2-dichloro-3-(3,5-dichlorophenyl)cyclopropane-1-carboxamido)-2,3-difluorobenzamide (F1439)

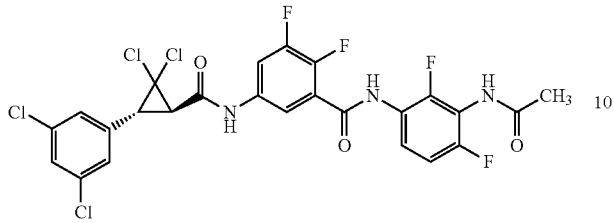

The title compound was synthesized with a reaction time of 24-48 hours and isolated as a glassy oil (0.024 g, 21%).

5-((1R,3R)-2,2-Dichloro-3-(3,5-dichlorophenyl)cyclopropane-1-carboxamido)-N-(3-(2,2-difluoroacetamido)-2,4-difluorophenyl)-2,3-difluorobenzamide (F1440)

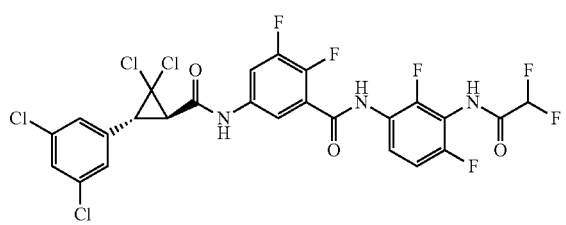 [SMILES: O=C(Nc1ccc(F)c(NC(=O)C(F)F)c1F)c1cc(NC(=O)[C@H]2[C@H](c3cc(Cl)cc(Cl)c3)C2(Cl)Cl)cc(F)c1F]

The title compound was synthesized with a reaction time of 24-48 hours and isolated s a glassy oil (0.040 g, 32%).

5-((1R,3R)-2,2-Dichloro-3-(3,5-dichlorophenyl)cyclopropane-1-carboxamido)-N-(2,4-difluoro-3-(2,2,2-trifluoroacetamido)phenyl)-2,3-difluorobenzamide (F1441)

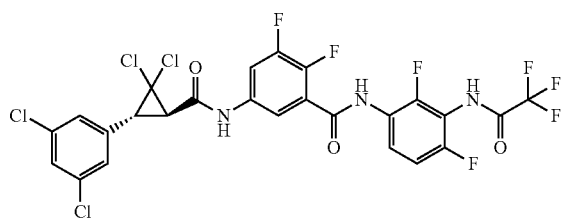 [SMILES: O=C(Nc1ccc(F)c(NC(=O)C(F)(F)F)c1F)c1cc(NC(=O)[C@H]2[C@H](c3cc(Cl)cc(Cl)c3)C2(Cl)Cl)cc(F)c1F]

The title compound was synthesized with a reaction time of 24-48 hours and isolated as a glassy oil (0.028 g, 22%).

N-(3-Acetamido-2,4-difluorophenyl)-5-((1R,3R)-2,2-dichloro-3-(3,4-dichlorophenyl)cyclopropane-1-carboxamido)-2,3-difluorobenzamide (F1442)

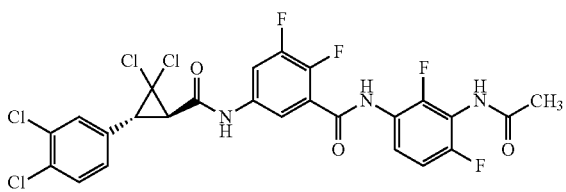 [SMILES: CC(=O)Nc1c(F)ccc(NC(=O)c2cc(NC(=O)[C@H]3[C@H](c4ccc(Cl)c(Cl)c4)C3(Cl)Cl)cc(F)c2F)c1F]

The title compound was synthesized with a reaction time of 24-48 hours and isolated as a pale solid (0.100 g, 84%).

5-((1R,3R)-2,2-Dichloro-3-(3,4-dichlorophenyl)cyclopropane-1-carboxamido)-N-(3-(2,2-difluoroacetamido)-2,4-difluorophenyl)-2,3-difluorobenzamide (F1443)

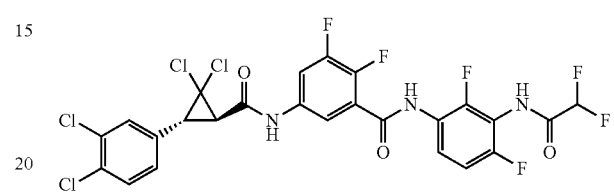

The title compound was synthesized with a reaction time of 24-48 hours and isolated as a glassy oil (0.085 g, 67%).

5-((1R,3R)-2,2-Dichloro-3-(3,4-dichlorophenyl)cyclopropane-1-carboxamido)-N-(2,4-difluoro-3-(2,2,2-trifluoroacetamido)phenyl)-2,3-difluorobenzamide (F1444)

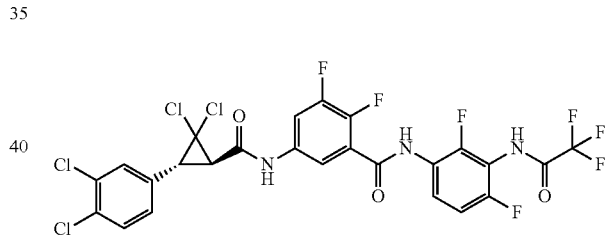

The title compound was synthesized with a reaction time of 24-48 hours and isolated as a glassy solid (0.058 g, 45%).

tert-Butyl (3-(2-chloro-5-((1R,3R)-2,2-dichloro-3-(3-chloro-4-fluorophenyl)cyclopropane-1-carboxamido)benzamido)-2,4-difluorophenyl)carbamate (F1445)

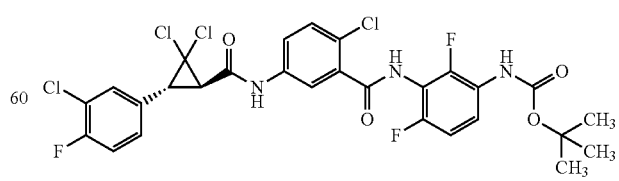

The title compound was synthesized with a reaction time of 24-48 hours and isolated as a foamy solid (0.325 g, 98%).

2-Chloro-5-((1R,3R)-2,2-dichloro-3-(4-fluoro-3-(trifluoromethyl)phenyl)cyclopropane-1-carboxamido)-N-(3-(N-ethyl-2,2-difluoroacetamido)-2,4-difluorophenyl)benzamide (F1452)

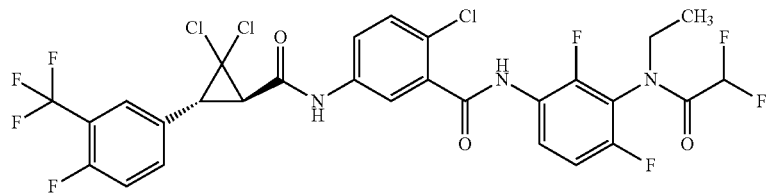 [SMILES: CCN(C(=O)C(F)F)c1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white foam (0.148 g, 94%).

tert-Butyl-N-((tert-butoxy)carbonyl)-N-[3-[[5-[[(1R,3R)-2,2-dichloro-3-(3,4-dichlorophenyl)cyclopropanecarbonyl]amino]-2-fluoro-benzoyl]amino]-2,6-difluoro-phenyl]carbamate (F1453)

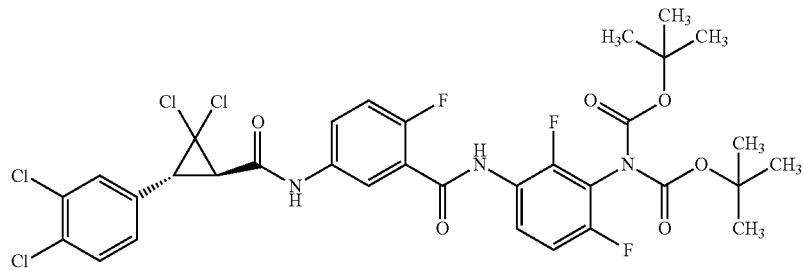 [SMILES: CC(C)(C)OC(=O)N(C(=O)OC(C)(C)C)c1c(F)ccc(NC(=O)c2cc(NC(=O)[C@H]3[C@H](c4ccc(Cl)c(Cl)c4)C3(Cl)Cl)ccc2F)c1F]

Isolated as a colorless oil (0.661 g, 76%).

2-Chloro-5-((1R,3R)-2,2-dichloro-3-(3-chloro-4-fluorophenyl)cyclopropane-1-carboxamido)-N-(3-(2,2-difluoro-N-methylacetamido)-2,4-difluorophenyl)benzamide (F1460)

Isolated as a white foam (0.117 g, 78%).

2-Chloro-5-((1R,3R)-2,2-dichloro-3-(3,4,5-trichlorophenyl)cyclopropane-1-carboxamido)-N-(3-(2,2-difluoro-N-methylacetamido)-2,4-difluorophenyl)benzamide (F1461)

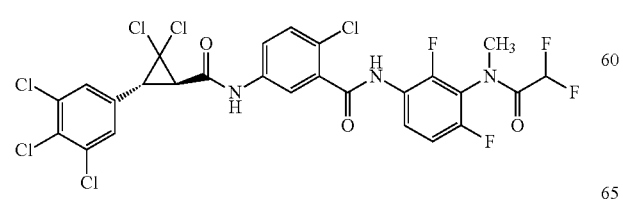

Isolated as a white foam (0.119 g, 82%).

2-Chloro-5-((1R,3R)-2,2-dichloro-3-(3,5-dichlorophenyl)cyclopropane-1-carboxamido)-N-(3-(2,2-difluoro-N-methylacetamido)-2,4-difluorophenyl)benzamide (F1462)

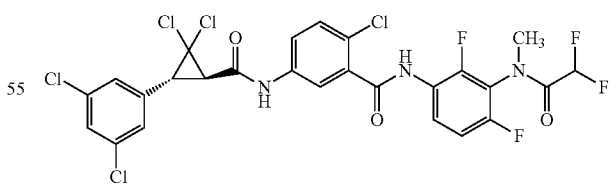

Isolated as a white foam (0.111 g, 75%).

N-(3-(N-Allyl-2,2-difluoroacetamido)-2,4-difluorophenyl)-2-chloro-5-((1R,3R)-2,2-dichloro-3-(4-fluoro-3-(trifluoromethyl)phenyl)cyclopropane-1-carboxamido)benzamide (F1482)

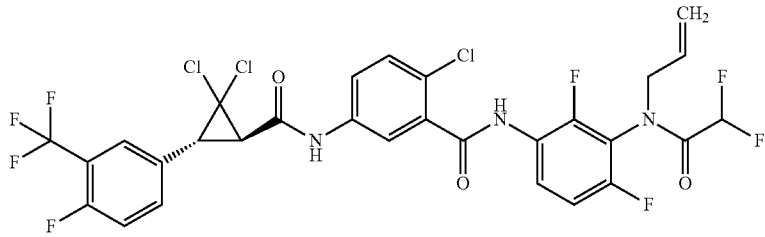 [SMILES: C=CCN(C(=O)C(F)F)c1c(F)ccc(NC(=O)c2cc(NC(=O)[C@H]3[C@H](c4ccc(F)c(C(F)(F)F)c4)C3(Cl)Cl)ccc2Cl)c1F]

Isolated as a clear, colorless oil (0.052 g, 33%).

2-Chloro-5-((1R,3R)-2,2-dichloro-3-(4-fluoro-3-(trifluoromethyl)phenyl)cyclopropane-1-carboxamido)-N-(2,4-difluoro-3-(N-methylacetamido)phenyl)benzamide (F1506)

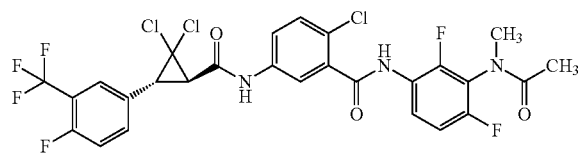

Isolated as a white foam (0.057 g, 39%).

5-((1R,3R)-2,2-Dichloro-3-(3,4-dichlorophenyl)cyclopropane-1-carboxamido)-N-(3-(2,2-difluoroacetamido)-2,6-difluorophenyl)-2-fluorobenzamide (F1512)

Isolated as a white solid (0.068 g, 46%).

5-((1R,3R)-2,2-Dichloro-3-(3,4-dichlorophenyl)cyclopropane-1-carboxamido)-N-(2,6-difluoro-3-(2,2,2-trifluoroacetamido)phenyl)-2-fluorobenzamide (F1513)

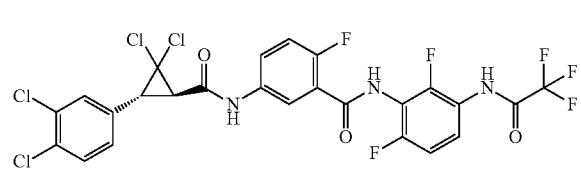 [SMILES: O=C(Nc1c(F)ccc(NC(=O)C(F)(F)F)c1F)c1cc(NC(=O)[C@H]2[C@H](c3ccc(Cl)c(Cl)c3)C2(Cl)Cl)ccc1F]

Isolated as a white solid (0.064 g, 42%).

N-(3-Acetamido-2,6-difluorophenyl)-5-((1R,3R)-2,2-dichloro-3-(3,4-dichlorophenyl)cyclopropane-1-carboxamido)-2-fluorobenzamide (F1514)

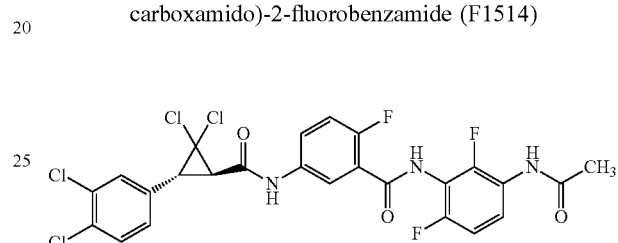

Isolated as a white foam (0.031 g, 24%).

5-((1R,3R)-2,2-Dichloro-3-(3,4,5-trichlorophenyl)cyclopropane-1-carboxamido)-N-(2,4-difluoro-3-(2,2,2-trifluoroacetamido)phenyl)-2-fluorobenzamide (F1526)

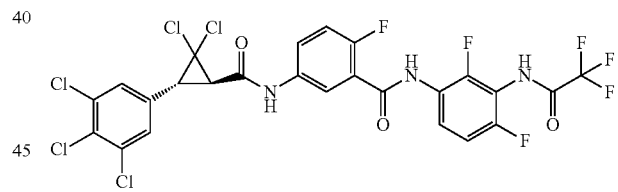

Isolated as a white solid (0.083 g, 56%).

5-((1R,3R)-2,2-Dichloro-3-(3,4,5-trichlorophenyl)cyclopropane-1-carboxamido)-N-(3-(2,2-difluoroacetamido)-2,4-difluorophenyl)-2-fluorobenzamide (F1527)

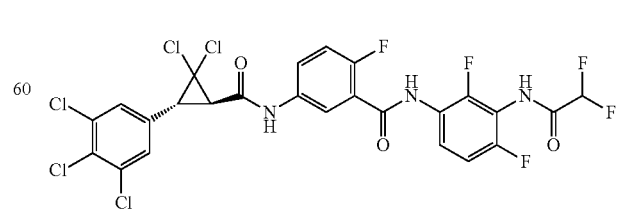

Isolated as a white solid (0.065 g, 46%).

383

N-(3-Acetamido-2,4-difluorophenyl)-5-((1R,3R)-2,2-dichloro-3-(3,4,5-trichlorophenyl)cyclopropane-1-carboxamido)-2-fluorobenzamide (F1528)

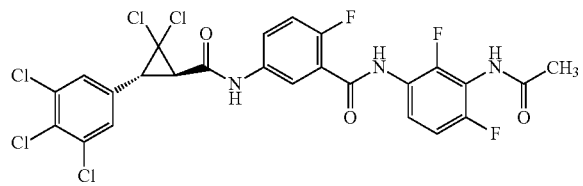

Isolated as a brown solid (0.088 g, 65%).

5-((1R,3R)-2,2-Dichloro-3-(4-fluoro-3-(trifluoromethyl)phenyl)cyclopropane-1-carboxamido)-N-(2,4-difluoro-3-(2,2,2-trifluoroacetamido)phenyl)-2-fluorobenzamide (F1529)

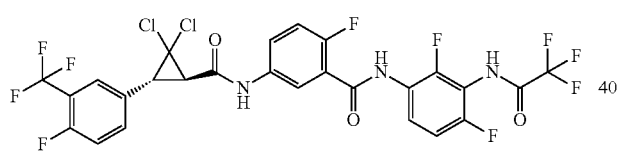

Isolated as a white solid (0.100 g, 67%).

384

5-((1R,3R)-2,2-Dichloro-3-(4-fluoro-3-(trifluoromethyl)phenyl)cyclopropane-1-carboxamido)-N-(3-(2,2-difluoroacetamido)-2,4-difluorophenyl)-2-fluorobenzamide (F1530)

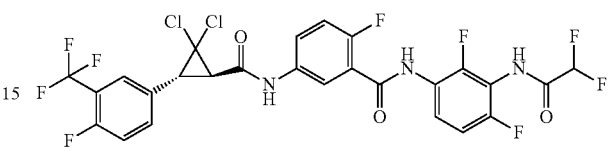

Isolated as a white solid (0.095 g, 66%).

N-(3-acetamido-2,4-difluorophenyl)-5-((1R,3R)-2,2-dichloro-3-(4-fluoro-3-(trifluoromethyl)phenyl)cyclopropane-1-carboxamido)-2-fluorobenzamide (F1531)

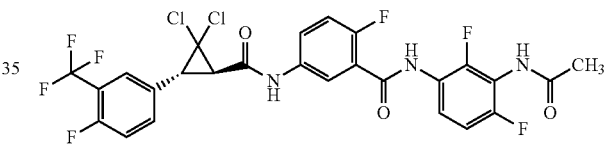

Isolated as a brown solid (0.117 g, 85%).

tert-Butyl (3-(2-chloro-5-((1R,3R)-2,2-dichloro-3-(3,4-dichlorophenyl)cyclopropane-1-carboxamido)benzamido)-2,6-difluorophenyl)(methyl)carbamate (F1549)

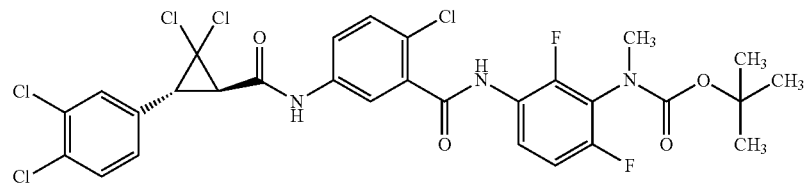 [SMILES: CN(C(=O)OC(C)(C)C)c1c(F)ccc(NC(=O)c2cc(NC(=O)[C@H]3[C@H](c4ccc(Cl)c(Cl)c4)C3(Cl)Cl)ccc2Cl)c1F]

Isolated as a colorless glass (1.05 g, 98%).

385

5-((1R,3R)-2,2-Dichloro-3-(3,4,5-trichlorophenyl)cyclopropane-1-carboxamido)-N-(2,4-difluoro-5-(2,2,2-trifluoroacetamido)phenyl)-2-fluorobenzamide (F1551)

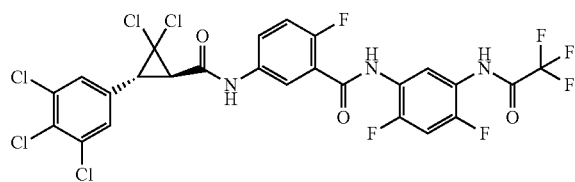 [SMILES: O=C(Nc1cc(NC(=O)C(F)(F)F)c(F)cc1F)c1cc(NC(=O)[C@H]2[C@H](c3cc(Cl)c(Cl)c(Cl)c3)C2(Cl)Cl)ccc1F]

Isolated as a yellow foam (0.087 g, 59%).

5-((1R,3R)-2,2-Dichloro-3-(3,4,5-trichlorophenyl)cyclopropane-1-carboxamido)-N-(5-(2,2-difluoroacetamido)-2,4-difluorophenyl)-2-fluorobenzamide (F1552)

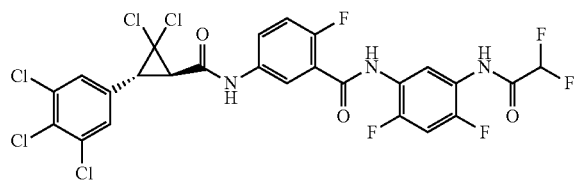 [SMILES: O=C(Nc1cc(NC(=O)C(F)F)c(F)cc1F)c1cc(NC(=O)[C@H]2[C@H](c3cc(Cl)c(Cl)c(Cl)c3)C2(Cl)Cl)ccc1F]

Isolated as a yellow foam (0.073 g, 51%).

N-(5-Acetamido-2,4-difluorophenyl)-5-((1R,3R)-2,2-dichloro-3-(3,4,5-trichlorophenyl)cyclopropane-1-carboxamido)-2-fluorobenzamide (F1553)

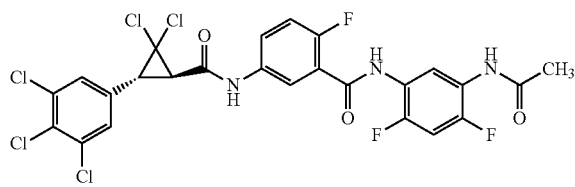 [SMILES: CC(=O)Nc1cc(NC(=O)c2cc(NC(=O)[C@H]3[C@H](c4cc(Cl)c(Cl)c(Cl)c4)C3(Cl)Cl)ccc2F)c(F)cc1F]

Isolated as a white foam (0.081 g, 60%).

386

5-((1R,3R)-2,2-Dichloro-3-(3,4,5-trichlorophenyl)cyclopropane-1-carboxamido)-N-(2,6-difluoro-3-(2,2,2-trifluoroacetamido)phenyl)-2-fluorobenzamide (F1554)

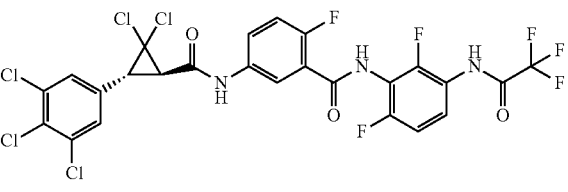 [SMILES: O=C(Nc1c(F)ccc(NC(=O)C(F)(F)F)c1F)c1cc(NC(=O)[C@H]2[C@H](c3cc(Cl)c(Cl)c(Cl)c3)C2(Cl)Cl)ccc1F]

Isolated as a white foam (0.092 g, 63%).

5-((1R,3R)-2,2-Dichloro-3-(3,4,5-trichlorophenyl)cyclopropane-1-carboxamido)-N-(3-(2,2-difluoroacetamido)-2,6-difluorophenyl)-2-fluorobenzamide (F1555)

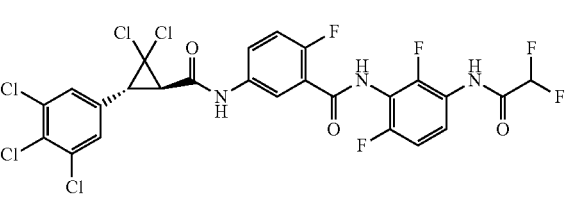 [SMILES: O=C(Nc1c(F)ccc(NC(=O)C(F)F)c1F)c1cc(NC(=O)[C@H]2[C@H](c3cc(Cl)c(Cl)c(Cl)c3)C2(Cl)Cl)ccc1F]

Isolated as a white foam (0.073 g, 51%).

N-(3-Acetamido-2,6-difluorophenyl)-5-((1R,3R)-2,2-dichloro-3-(3,4,5-trichlorophenyl)cyclopropane-1-carboxamido)-2-fluorobenzamide (F1556)

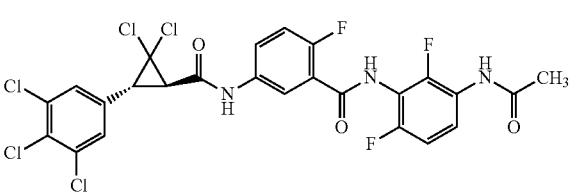 [SMILES: CC(=O)Nc1ccc(F)c(NC(=O)c2cc(NC(=O)[C@H]3[C@H](c4cc(Cl)c(Cl)c(Cl)c4)C3(Cl)Cl)ccc2F)c1F]

Isolated as a white solid (0.083 g, 61%).

5-((1R,3R)-2,2-Dichloro-3-(4-fluoro-3-(trifluoromethyl)phenyl)cyclopropane-1-carboxamido)-N-(2,4-difluoro-5-(2,2,2-trifluoroacetamido)phenyl)-2-fluorobenzamide (F1557)

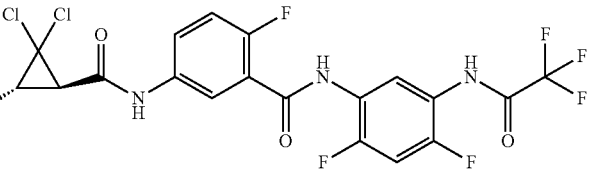

Isolated as a white foam (0.114 g, 76%).

5-((1R,3R)-2,2-Dichloro-3-(4-fluoro-3-(trifluoromethyl)phenyl)cyclopropane-1-carboxamido)-N-(5-(2,2-difluoroacetamido)-2,4-difluorophenyl)-2-fluorobenzamide (F1558)

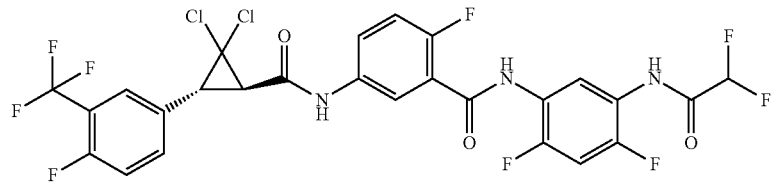 [SMILES: O=C(Nc1cc(NC(=O)C(F)F)c(F)cc1F)c1cc(NC(=O)[C@H]2[C@H](c3ccc(F)c(C(F)(F)F)c3)C2(Cl)Cl)ccc1F]

Isolated as a yellow foam (0.112 g, 77%).

N-(5-Acetamido-2,4-difluorophenyl)-5-((1R,3R)-2,2-dichloro-3-(4-fluoro-3-(trifluoromethyl)phenyl)cyclopropane-1-carboxamido)-2-fluorobenzamide (F1559)

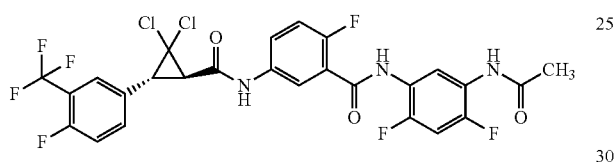

Isolated as a white foam (0.122 g, 89%).

5-((1R,3R)-2,2-Dichloro-3-(4-fluoro-3-(trifluoromethyl)phenyl)cyclopropane-1-carboxamido)-N-(2,6-difluoro-3-(2,2,2-trifluoroacetamido)phenyl)-2-fluorobenzamide (F1560)

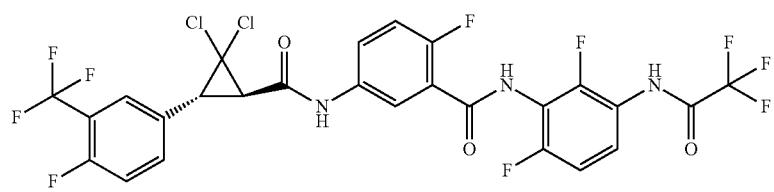 [SMILES: O=C(Nc1c(F)ccc(NC(=O)C(F)(F)F)c1F)c1cc(NC(=O)[C@H]2[C@H](c3ccc(F)c(C(F)(F)F)c3)C2(Cl)Cl)ccc1F]

Isolated as a white foam (0.128 g, 86%).

5-((1R,3R)-2,2-Dichloro-3-(4-fluoro-3-(trifluoromethyl)phenyl)cyclopropane-1-carboxamido)-N-(3-(2,2-difluoroacetamido)-2,6-difluorophenyl)-2-fluorobenzamide (F1561)

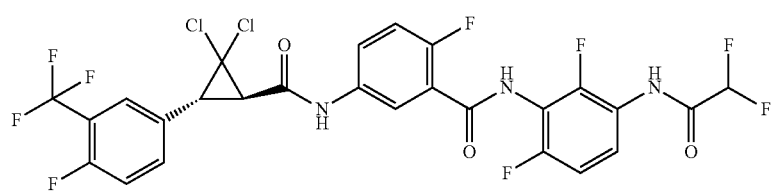 [SMILES: O=C(Nc1c(F)ccc(NC(=O)C(F)F)c1F)c1cc(NC(=O)[C@H]2[C@H](c3ccc(F)c(C(F)(F)F)c3)C2(Cl)Cl)ccc1F]

Isolated as a white foam (0.101 g, 70%).

N-(3-Acetamido-2,6-difluorophenyl)-5-((1R,3R)-2,
2-dichloro-3-(4-fluoro-3-(trifluoromethyl)phenyl)
cyclopropane-1-carboxamido)-2-fluorobenzamide
(F1562)

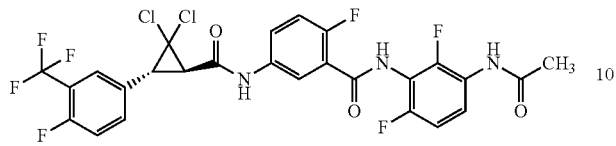

Isolated as a white solid (0.108 g, 79%).

N-(3-Acetamido-2,4-difluorophenyl)-5-((1R,3R)-2,
2-dichloro-3-(4-fluoro-3-(trifluoromethyl)phenyl)
cyclopropane-1-carboxamido)-2,3-difluorobenz-
amide (F1570)

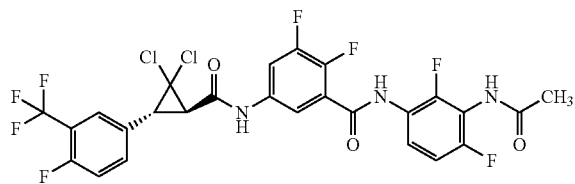 [SMILES: CC(=O)Nc1c(F)ccc(NC(=O)c2cc(NC(=O)[C@H]3[C@H](c4ccc(F)c(C(F)(F)F)c4)C3(Cl)Cl)cc(F)c2F)c1F]

The title compound was synthesized with a reaction time of 24-48 hours and isolated as a glassy solid (0.046 g, 61%).

5-((1R,3R)-2,2-Dichloro-3-(4-fluoro-3-(trifluorom-
ethyl)phenyl)cyclopropane-1-carboxamido)-N-(3-(2,
2-difluoroacetamido)-2,4-difluorophenyl)-2,3-difluo-
robenzamide (F1571)

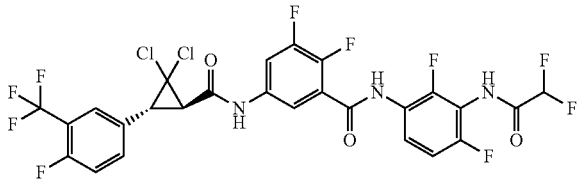 [SMILES: O=C(Nc1ccc(F)c(NC(=O)C(F)F)c1F)c1cc(NC(=O)[C@H]2[C@H](c3ccc(F)c(C(F)(F)F)c3)C2(Cl)Cl)cc(F)c1F]

The title compound was synthesized with a reaction time of 24-48 hours and isolated as a glassy white solid (0.054 g, 68%).

5-((1R,3R)-2,2-Dichloro-3-(4-fluoro-3-(trifluorom-
ethyl)phenyl)cyclopropane-1-carboxamido)-N-(2,4-
difluoro-3-(2,2,2-trifluoroacetamido)phenyl)-2,3-
difluorobenzamide (F1572)

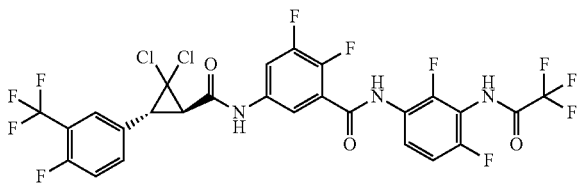 [SMILES: O=C(Nc1ccc(F)c(NC(=O)C(F)(F)F)c1F)c1cc(NC(=O)[C@H]2[C@H](c3ccc(F)c(C(F)(F)F)c3)C2(Cl)Cl)cc(F)c1F]

The title compound was synthesized with a reaction time of 24-48 hours and isolated as a glassy solid (0.057 g, 70%).

5-((1R,3R)-2,2-Dichloro-3-(4-fluoro-3-(trifluorom-
ethyl)phenyl)cyclopropane-1-carboxamido)-N-(3-(2,
2-difluoroacetamido)-2,6-difluorophenyl)-2,3-difluo-
robenzamide (F1573)

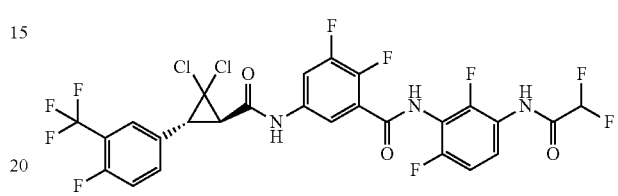

The title compound was synthesized with a reaction time of 24-48 hours and isolated as a glassy solid (0.024 g, 29%).

5-((1R,3R)-2,2-Dichloro-3-(4-fluoro-3-(trifluorom-
ethyl)phenyl)cyclopropane-1-carboxamido)-N-(2,6-
difluoro-3-(2,2,2-trifluoroacetamido)phenyl)-2,3-
difluorobenzamide (F1574)

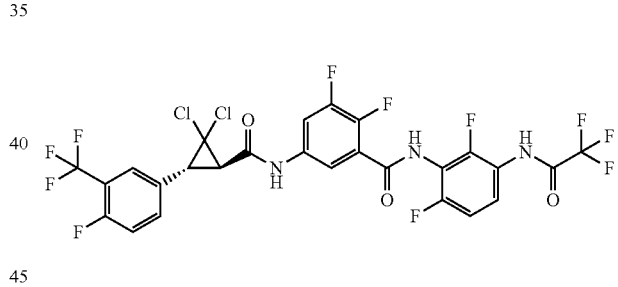

The title compound was synthesized with a reaction time of 24-48 hours and isolated as a glassy solid (0.060 g, 73%).

N-(3-Acetamido-2,6-difluorophenyl)-5-((1R,3R)-2,
2-dichloro-3-(3,4-dichlorophenyl)cyclopropane-1-
carboxamido)-2,3-difluorobenzamide (F1575)

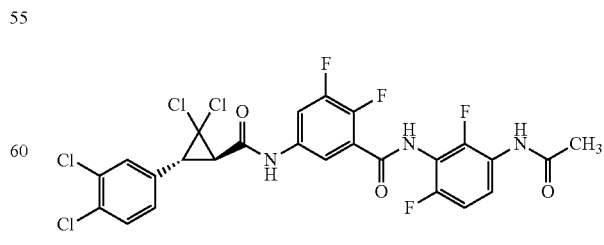

The title compound was synthesized with a reaction time of 24-48 hours and isolated as a glassy solid (0.062 g, 91%).

391

N-(3-Acetamido-2,6-difluorophenyl)-5-((1R,3R)-2,2-dichloro-3-(4-fluoro-3-(trifluoromethyl)phenyl)cyclopropane-1-carboxamido)-2,3-difluorobenzamide (F1576)

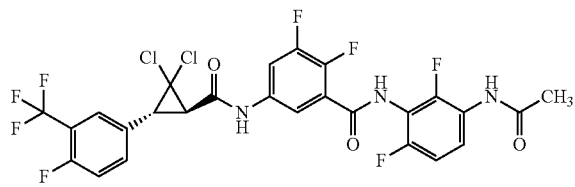 [SMILES: CC(=O)Nc1ccc(F)c(NC(=O)c2cc(NC(=O)[C@H]3[C@H](c4ccc(F)c(C(F)(F)F)c4)C3(Cl)Cl)cc(F)c2F)c1F]

The title compound was synthesized with a reaction time of 24-48 hours and isolated as a glassy solid (0.055 g, 73%).

5-((1R,3R)-2,2-Dichloro-3-(3,4-dichlorophenyl)cyclopropane-1-carboxamido)-N-(3-(2,2-difluoroacetamido)-2,6-difluorophenyl)-2,3-difluorobenzamide (F1577)

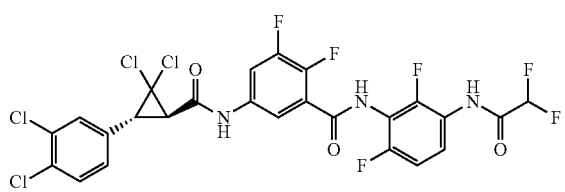 [SMILES: O=C(Nc1c(F)ccc(NC(=O)C(F)F)c1F)c1cc(NC(=O)[C@H]2[C@H](c3ccc(Cl)c(Cl)c3)C2(Cl)Cl)cc(F)c1F]

The title compound was synthesized with a reaction time of 24-48 hours and isolated as a glassy solid (0.058 g, 72%).

5-((1R,3R)-2,2-Dichloro-3-(3,4-dichlorophenyl)cyclopropane-1-carboxamido)-N-(2,6-difluoro-3-(2,2,2-trifluoroacetamido)phenyl)-2,3-difluorobenzamide (F1578)

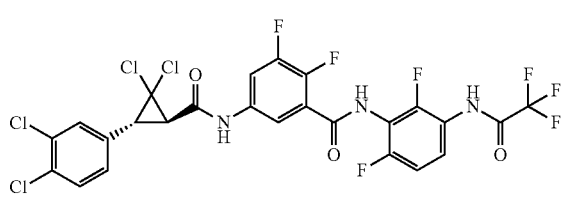 [SMILES: O=C(Nc1c(F)ccc(NC(=O)C(F)(F)F)c1F)c1cc(NC(=O)[C@H]2[C@H](c3ccc(Cl)c(Cl)c3)C2(Cl)Cl)cc(F)c1F]

The title compound was synthesized with a reaction time of 24-48 hours and isolated as a glassy solid (0.048 g, 65%).

5-((1R,3R)-2,2-Dichloro-3-(3,4,5-trichlorophenyl)cyclopropane-1-carboxamido)-N-(2,4-difluoro-5-(2,2,2-trifluoroacetamido)phenyl)-2,3-difluorobenzamide (F1579)

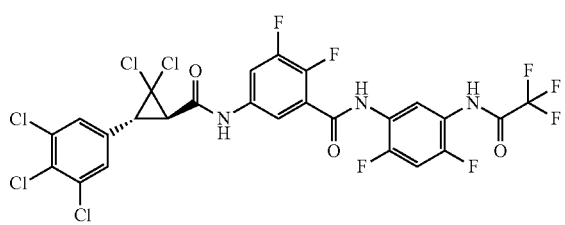 [SMILES: O=C(Nc1cc(NC(=O)C(F)(F)F)c(F)cc1F)c1cc(NC(=O)[C@H]2[C@H](c3cc(Cl)c(Cl)c(Cl)c3)C2(Cl)Cl)cc(F)c1F]

392

The title compound was synthesized with a reaction time of 24-48 hours and isolated as a glassy solid (0.055 g, 68%).

5-((1R,3R)-2,2-Dichloro-3-(3,4,5-trichlorophenyl)cyclopropane-1-carboxamido)-N-(5-(2,2-difluoroacetamido)-2,4-difluorophenyl)-2,3-difluorobenzamide (F1580)

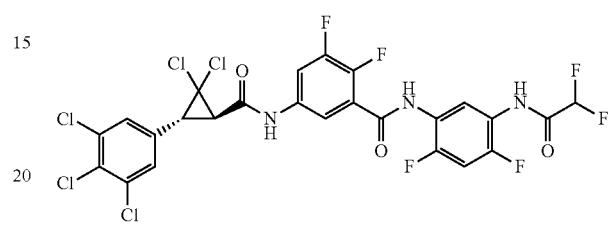

The title compound was synthesized with a reaction time of 24-48 hours and isolated as a glassy solid (0.061 g, 82%).

N-(5-Acetamido-2,4-difluorophenyl)-5-((1R,3R)-2,2-dichloro-3-(3,4,5-trichlorophenyl)cyclopropane-1-carboxamido)-2,3-difluorobenzamide (F1581)

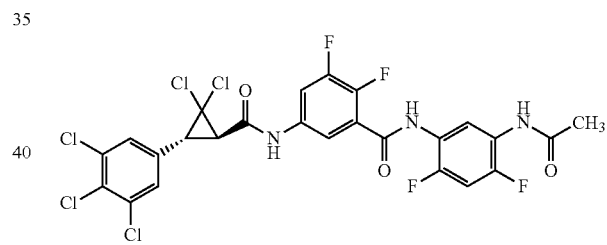

The title compound was synthesized with a reaction time of 24-48 hours and isolated as a glassy solid (0.055 g, 70%).

5-((1R,3R)-2,2-Dichloro-3-(3,4-dichlorophenyl)cyclopropane-1-carboxamido)-N-(2,4-difluoro-5-(2,2,2-trifluoroacetamido)phenyl)-2,3-difluorobenzamide (F1582)

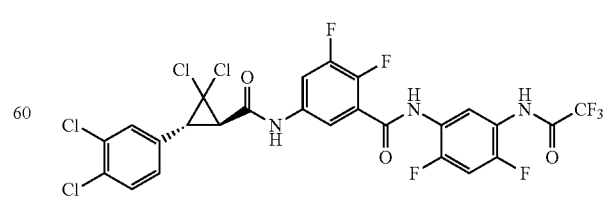

The title compound was synthesized with a reaction time of 24-48 hours and isolated as a glassy solid (0.053 g, 68%).

5-((1R,3R)-2,2-Dichloro-3-(3,4-dichlorophenyl)cyclopropane-1-carboxamido)-N-(5-(2,2-difluoroacetamido)(2,4-difluorophenyl)-2,3-difluorobenzamide (F1583)

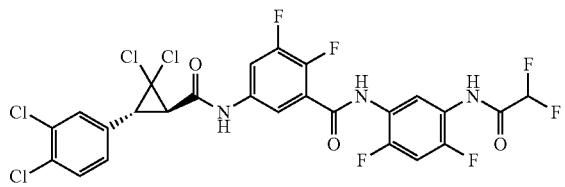 [SMILES: O=C(Nc1cc(NC(=O)C(F)F)c(F)cc1F)c1cc(NC(=O)[C@H]2[C@H](c3ccc(Cl)c(Cl)c3)C2(Cl)Cl)cc(F)c1F]

The title compound was synthesized with a reaction time of 24-48 hours and isolated as a glassy solid (0.052 g, 61%).

5-((1R,3R)-2,2-Dichloro-3-(4-fluoro-3-(trifluoromethyl)phenyl)cyclopropane-1-carboxamido)-N-(2,4-difluoro-5-(2,2,2-trifluoroacetamido)phenyl)-2,3-difluorobenzamide (F1584)

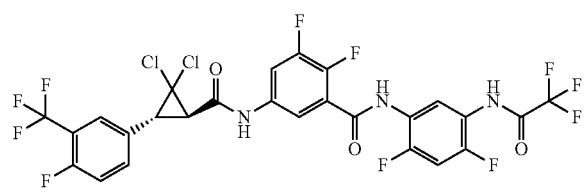 [SMILES: O=C(Nc1cc(NC(=O)C(F)(F)F)c(F)cc1F)c1cc(NC(=O)[C@H]2[C@H](c3ccc(F)c(C(F)(F)F)c3)C2(Cl)Cl)cc(F)c1F]

The title compound was synthesized with a reaction time of 24-48 hours and isolated as a Glassy solid (0.057 g, 74%).

N-(5-Acetamido-2,4-difluorophenyl)-5-((1R,3R)-2,2-dichloro-3-(3,4-dichlorophenyl)cyclopropane-1-carboxamido)-2,3-difluorobenzamide (F1585)

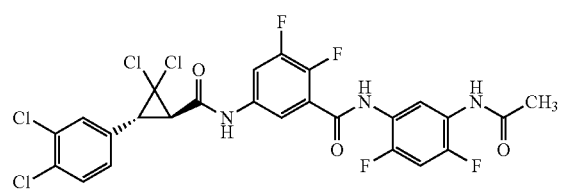 [SMILES: CC(=O)Nc1cc(NC(=O)c2cc(NC(=O)[C@H]3[C@H](c4ccc(Cl)c(Cl)c4)C3(Cl)Cl)cc(F)c2F)c(F)cc1F]

The title compound was synthesized with a reaction time of 24-48 hours and isolated as a brown glassy solid (0.060 g, 79%).

5-((1R,3R)-2,2-Dichloro-3-(4-fluoro-3-(trifluoromethyl)phenyl)cyclopropane-1-carboxamido)-N-(5-(2,2-difluoroacetamido)-2,4-difluorophenyl)-2,3-difluorobenzamide (F1586)

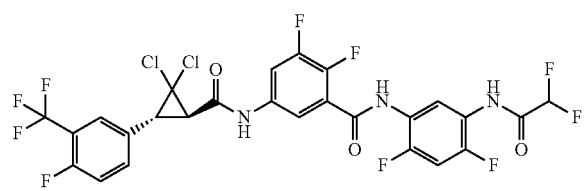 [SMILES: O=C(Nc1cc(NC(=O)C(F)F)c(F)cc1F)c1cc(NC(=O)[C@H]2[C@H](c3ccc(F)c(C(F)(F)F)c3)C2(Cl)Cl)cc(F)c1F]

The title compound was synthesized with a reaction time of 24-48 hours and isolated as a glassy solid (0.054 g, 72%).

N-(5-Acetamido-2,4-difluorophenyl)-5-((1R,3R)-2,2-dichloro-3-(4-fluoro-3-(trifluoromethyl)phenyl)cyclopropane-1-carboxamido)-2,3-difluorobenzamide (F1587)

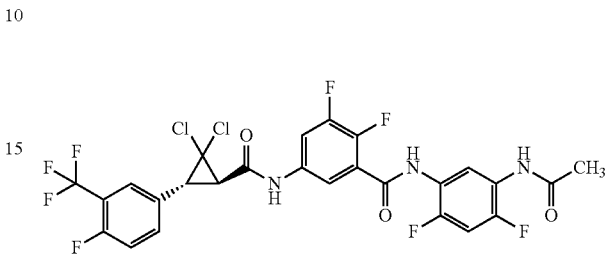

The title compound was synthesized with a reaction time of 24-48 hours and isolated as a glassy solid (0.055 g, 69%).

5-((1R,3R)-2,2-Dichloro-3-(3,4,5-trichlorophenyl)cyclopropane-1-carboxamido)-N-(2,6-difluoro-3-(2,2,2-trifluoroacetamido)phenyl)-2,3-difluorobenzamide (F1588)

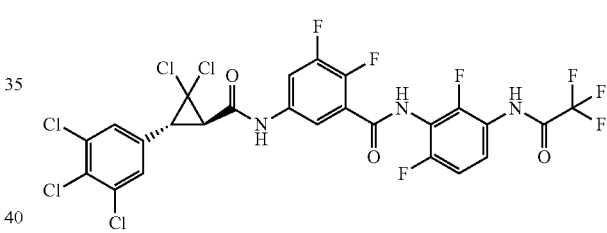

The title compound was synthesized with a reaction time of 24-48 hours and isolated s a glassy solid (0.060 g, 83%).

5-((1R,3R)-2,2-Dichloro-3-(3,4,5-trichlorophenyl)cyclopropane-1-carboxamido)-N-(3-(2,2-difluoroacetamido)-2,6-difluorophenyl)-2,3-difluorobenzamide (F1589)

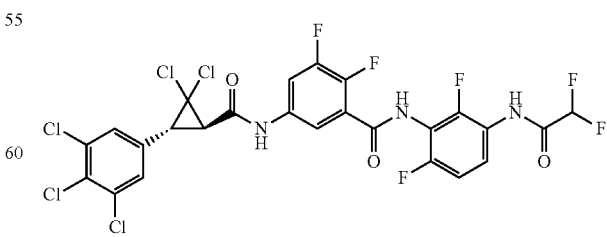

The title compound was synthesized with a reaction time of 24-48 hours and isolated as a glassy solid (0.046 g, 58%).

N-(3-Acetamido-2,6-difluorophenyl)-5-((1R,3R)-2,
2-dichloro-3-(3,4,5-trichlorophenyl)cyclopropane-1-
carboxamido)-2,3-difluorobenzamide (F1590)

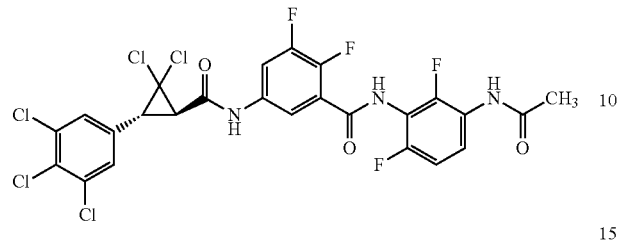

The title compound was synthesized with a reaction time of 24-48 hours and isolated as a glassy solid (0.066 g, 98%).

N-(3-Acetamido-2,4,6-trifluorophenyl)-2-chloro-5-
((1R,3R)-2,2-dichloro-3-(4-fluoro-3-(trifluorom-
ethyl)phenyl)cyclopropane-1-carboxamido)benz-
amide (F1613)

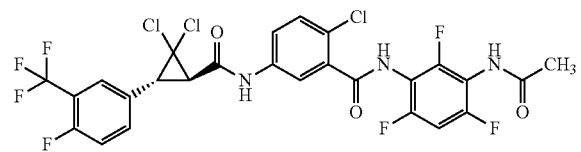 [SMILES: CC(=O)Nc1c(F)cc(F)c(NC(=O)c2cc(NC(=O)[C@H]3[C@H](c4ccc(F)c(C(F)(F)F)c4)C3(Cl)Cl)ccc2Cl)c1F]

Isolated as a white solid (0.076 g, 52%).

N-(3-Acetamido-2,4,6-trifluorophenyl)-2-chloro-5-
((1R,3R)-2,2-dichloro-3-(3-chloro-4-fluorophenyl)
cyclopropane-1-carboxamido)benzamide (F1627)

Isolated as a white solid (0.083 g, 55%).

N-(3-Acetamido-2,4,6-trifluorophenyl)-2-chloro-5-
((1R,3R)-2,2-dichloro-3-(3,5-dichlorophenyl)cyclo-
propane-1-carboxamido)benzamide (F1628)

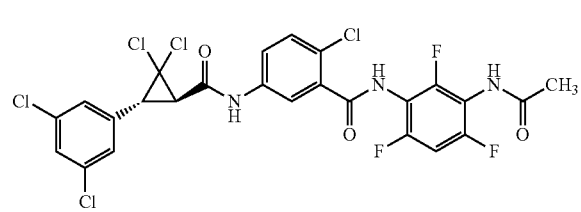 [SMILES: CC(=O)Nc1c(F)cc(F)c(NC(=O)c2cc(NC(=O)[C@H]3[C@H](c4cc(Cl)cc(Cl)c4)C3(Cl)Cl)ccc2Cl)c1F]

Isolated as a white solid (0.081 g, 55%).

N-(3-Acetamido-2,4,6-trifluorophenyl)-2-chloro-5-
((1R,3R)-2,2-dichloro-3-(3,4-dichlorophenyl)cyclo-
propane-1-carboxamido)benzamide (F1629)

Isolated as a white solid (0.095 g, 64%).

trans-N-(2-Acetamido-3,5-difluorophenyl)-2-chloro-
5-(2,2-dichloro-3-(3,5-dichlorophenyl)cyclopropane-
1-carboxamido)benzamide (F1632)

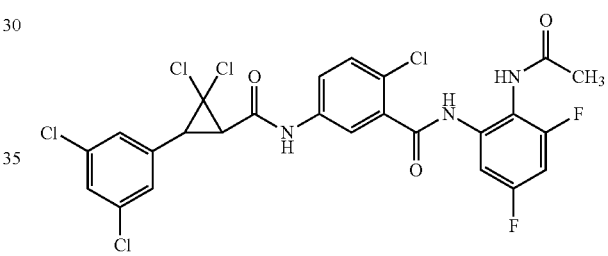

The title compound was synthesized with a reaction time of 24-48 hours and isolated as a waxy solid (0.038 g, 50%).

trans-N-(2-Acetamido-4,6-difluorophenyl)-2-chloro-
5-(2,2-dichloro-3-(3,5-dichlorophenyl)cyclopropane-
1-carboxamido)benzamide (F1633)

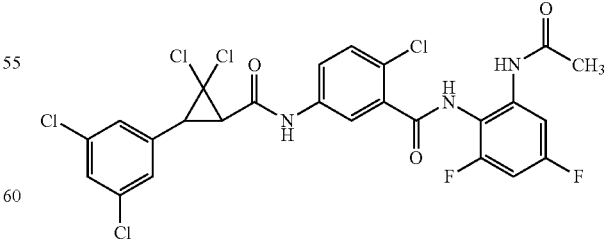

The title compound was synthesized with a reaction time of 24-48 hours and isolated as a pale waxy solid (0.035 g, 46%).

397 trans-N-(2-Acetamido-4,5-difluorophenyl)-2-chloro-5-(2,2-dichloro-3-(3,5-dichlorophenyl)cyclopropane-1-carboxamido)benzamide (F1634)

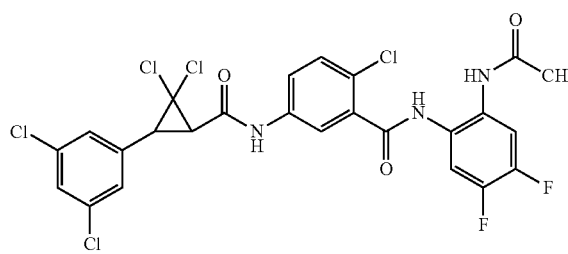

The title compound was synthesized with a reaction time of 24-48 hours and isolated as a pale solid (0.061 g, 80%).

trans-N-(5-Acetamido-2-fluorophenyl)-2-chloro-5-(2,2-dichloro-3-(3,5-dichlorophenyl)cyclopropane-1-carboxamido)benzamide (F1635)

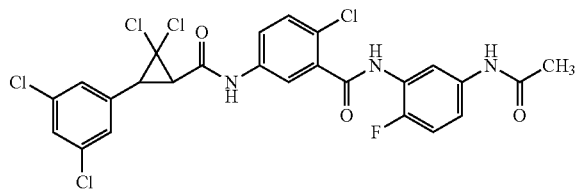 [SMILES: CC(=O)Nc1ccc(F)c(NC(=O)c2cc(NC(=O)C3C(c4cc(Cl)cc(Cl)c4)C3(Cl)Cl)ccc2Cl)c1]

The title compound was synthesized with a reaction time of 24-48 hours and isolated as a pale waxy solid (0.042 g, 54%).

trans-N-(2-Acetamido-6-fluorophenyl)-2-chloro-5-(2,2-dichloro-3-dichlorophenyl)cyclopropane-1-carboxamido)benzamide (F1636)

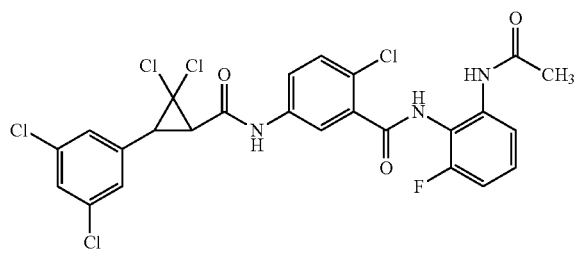 [SMILES: CC(=O)Nc1cccc(F)c1NC(=O)c1cc(NC(=O)C2C(c3cc(Cl)cc(Cl)c3)C2(Cl)Cl)ccc1Cl]

The title compound was synthesized with a reaction time of 24-48 hours and isolated as a waxy pale solid (0.041 g, 55%).

398 trans-N-(2-Acetamido-4-fluorophenyl)-2-chloro-5-(2,2-dichloro-3-(3,5-dichlorophenyl)cyclopropane-1-carboxamido)benzamide (F1637)

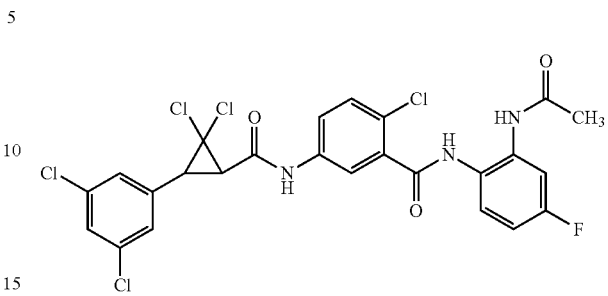

The title compound was synthesized with a reaction time of 24-48 hours and isolated as a pale semi solid (0.020 g, 24%).

trans-N-(3-Acetamido-4-fluorophenyl)-2-chloro-5-(2,2-dichloro-3-(3,5-dichlorophenyl)cyclopropane-1-carboxamido)benzamide (F1638)

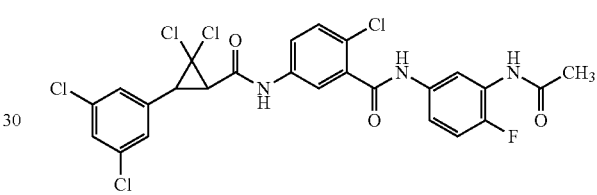

The title compound was synthesized with a reaction time of 24-48 hours and isolated as a pale solid (0.007 g, 10%).

trans-2-Chloro-5-(2,2-dichloro-3-(3,5-dichlorophenyl)cyclopropane-1-carboxamido)-N-(3-fluoro-5-(2,2,2-trifluoroacetamido)phenyl)benzamide (F1639)

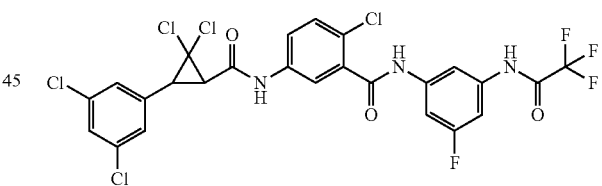

The title compound was synthesized with a reaction time of 24-48 hours and isolated as a pale solid (0.011 g, 13%).

trans-2-Chloro-5-(2,2-dichloro-3-(3,5-dichlorophenyl)cyclopropane-1-carboxamido)-N-(2-fluoro-5-(2,2,2-trifluoroacetamido)phenyl)benzamide (F1640)

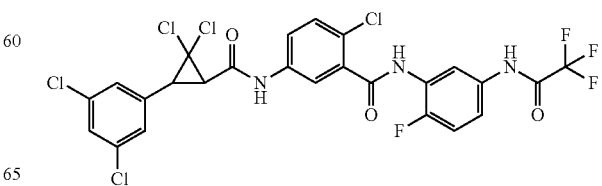

The title compound was synthesized with a reaction time of 24-48 hours and isolated as a pale solid (0.020 g, 23%).

trans-2-Chloro-5-(2,2-dichloro-3-(3,5-dichlorophenyl)cyclopropane-1-carboxamido)-N-(4-fluoro-3-(2,2,2-trifluoroacetamido)phenyl)benzamide (F1641)

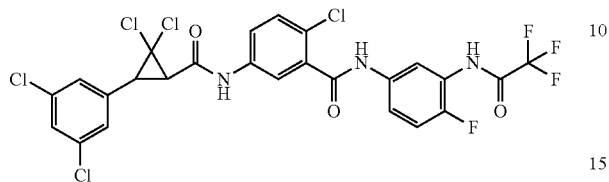

The title compound was synthesized with a reaction time of 24-48 hours and isolated as a pale solid (0.015 g, 21%).

tert-Butyl N-tert-butoxycarbonyl-N-[5-[[2-chloro-5-[[(1R,3R)-2,2-dichloro-3-[4-fluoro-3-(trifluoromethyl)phenyl]cyclopropanecarbonyl]amino]benzoyl]amino]-2,4-difluoro-3-methyl-phenyl]carbamate (F1670)

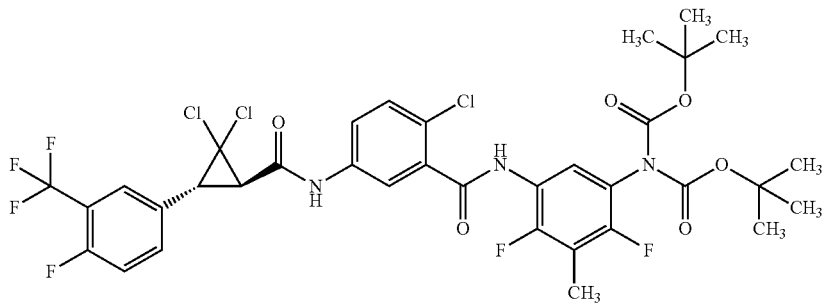 [SMILES: Cc1c(F)c(NC(=O)c2cc(NC(=O)[C@H]3[C@H](c4ccc(F)c(C(F)(F)F)c4)C3(Cl)Cl)ccc2Cl)cc(N(C(=O)OC(C)(C)C)C(=O)OC(C)(C)C)c1F]

Isolated as a white solid (0.240 g, 88%).

tert-Butyl N-tert-butoxycarbonyl-N-[3-[[2-chloro-5-[[(1R,3R)-2,2-dichloro-3-[3-fluoro-5-(trifluoromethyl)phenyl]cyclopropanecarbonyl]amino]benzoyl]amino]-2,6-difluoro-phenyl]carbamate (F1681)

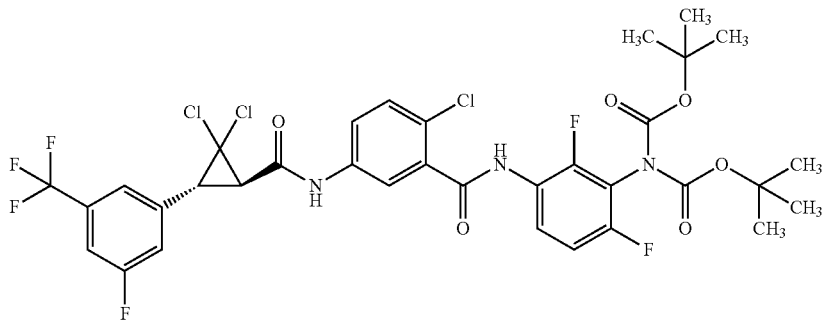 [SMILES: CC(C)(C)OC(=O)N(C(=O)OC(C)(C)C)c1c(F)ccc(NC(=O)c2cc(NC(=O)[C@H]3[C@H](c4cc(F)cc(C(F)(F)F)c4)C3(Cl)Cl)ccc2Cl)c1F]

Isolated as a white foam (1.14 g, 86%).

N-(4-Bromo-2-methyl-3-nitrophenyl)-2-chloro-5-((1R,3R)-2,2-dichloro-3-(4-fluoro-3-(trifluoromethyl)phenyl)cyclopropane-1-carboxamido)benzamide (F1688)

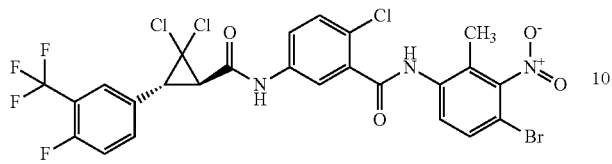

Isolated as a yellow foam (0.140 g, 92%).

tert-Butyl (5-(2-chloro-5-((1R,3R)-2,2-dichloro-3-(4-fluoro-3-(trifluoromethyl)phenyl)cyclopropane-1-carboxamido)benzamido)-2,3,4-trifluorophenyl)carbamate (F1736)

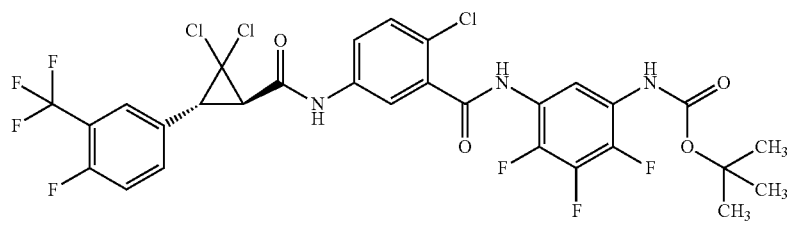 [SMILES: CC(C)(C)OC(=O)Nc1cc(NC(=O)c2cc(NC(=O)[C@H]3[C@H](c4ccc(F)c(C(F)(F)F)c4)C3(Cl)Cl)ccc2Cl)c(F)c(F)c1F]

Isolated as a white foam (0.288 g, 90%).

2-Chloro-5-((1R,3R)-2,2-dichloro-3-(4-fluoro-3-(trifluoromethyl)phenyl)cyclopropane-1-carboxamido)-N-(2,4-difluoro-3-iodophenyl)benzamide (F1758)

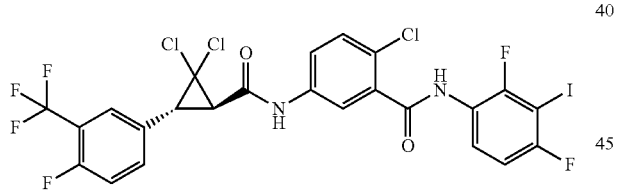

Isolated as a white foam (0.338 g, 71%).

tert-Butyl (3-(2-chloro-5-((1R,3R)-2,2-dichloro-3-(4-fluoro-3-(trifluoromethyl)phenyl)cyclopropane-1-carboxamido)benzamido)-2,6-difluorophenyl)(ethyl)carbamate (F1761)

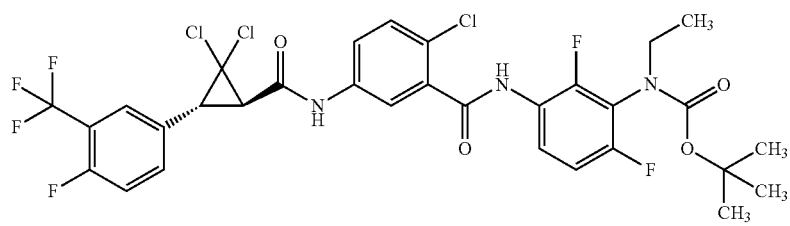 [SMILES: CCN(C(=O)OC(C)(C)C)c1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white foam (0.540 g, 54%).

403

2-Chloro-5-((1R,3R)-2,2-dichloro-3-(3,4-dichlorophenyl)cyclopropane-1-carboxamido)-N-(4-fluoro-3-(2,2,2-trifluoroacetamido)phenyl)benzamide (F1812)

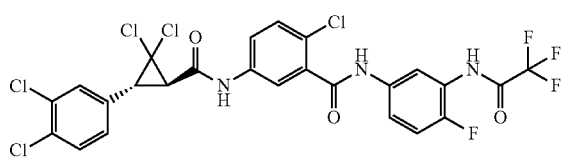

The title compound was synthesized with a reaction time of 24-48 hours and isolated as a foamy solid (0.140 g, 92%).

2-Chloro-5-((1R,3R)-2,2-dichloro-3-(3,5-dichlorophenyl)cyclopropane-1-carboxamido)-N-(4-fluoro-3-(2,2,2-trifluoroacetamido)phenyl)benzamide (F1813)

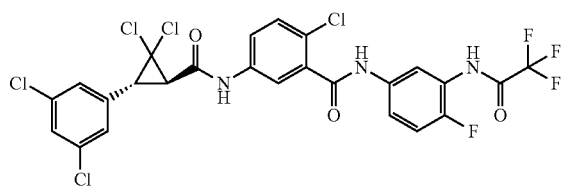 [SMILES: O=C(Nc1ccc(F)c(NC(=O)C(F)(F)F)c1)c1cc(NC(=O)[C@H]2[C@H](c3cc(Cl)cc(Cl)c3)C2(Cl)Cl)ccc1Cl]

The title compound was synthesized with a reaction time of 24-48 hours and isolated as a pale solid (0.142 g, 93%).

404

2-Chloro-5-((1R,3R)-2,2-dichloro-3-(3-chloro-4-fluorophenyl)cyclopropane-1-carboxamido)-N-(4-fluoro-3-(2,2,2-trifluoroacetamido)phenyl)benzamide (F1814)

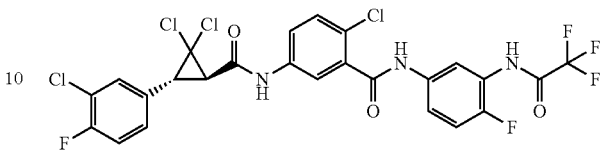

The title compound was synthesized with a reaction time of 24-48 hours and isolated as a pale solid (0.133 g, 90%).

2-Chloro-5-((1R,3R)-2,2-dichloro-3-(4-fluoro-3-(trifluoromethyl)phenyl)cyclopropane-1-carboxamido)-N-(4-fluoro-3-(2,2,2-trifluoroacetamido)phenyl)benzamide (F1815)

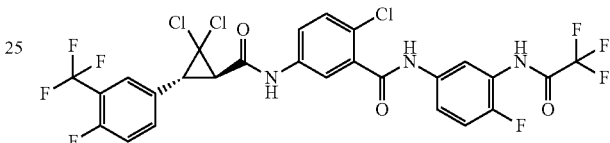

The title compound was synthesized with a reaction time of 24-48 hours and isolated as a pale solid (0.136 g, 87%).
The following compounds were prepared in like manner to the procedure outlined in Example 6:

2-Chloro-5-((1R,3R)-2,2-dichloro-3-(4-fluoro-3-(trifluoromethyl)phenyl)cyclopropane-1-carboxamido)-N-(3-(2,2-dichloropropanamido)-2,4-difluorophenyl)benzamide (F1351)

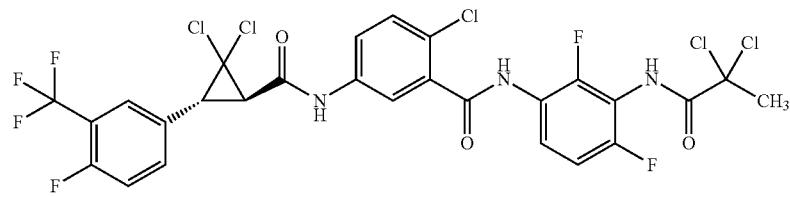 [SMILES: CC(F)(F)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white solid (0.062 g, 49%).

2-Chloro-5-((1R,3R)-2,2-dichloro-3-(4-fluoro-3-(trifluoromethyl)phenyl)cyclopropane-1-carboxamido)-N-(3-(2,2-difluoropropanamido)-2,4-difluorophenyl)benzamide (F1352)

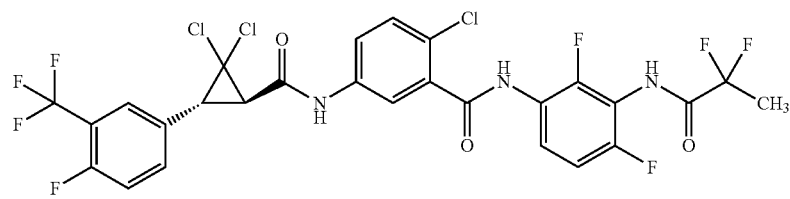

Isolated as a white solid (0.134 g, 74%).

N-(3-(2-Bromo-2-methylpropanamido)-2,4-difluorophenyl)-2-chloro-5-(((1R,3R)-2,2-dichloro-3-(4-fluoro-3-(trifluoromethyl)phenyl)cyclopropane-1-carboxamido)benzamide (F1354)

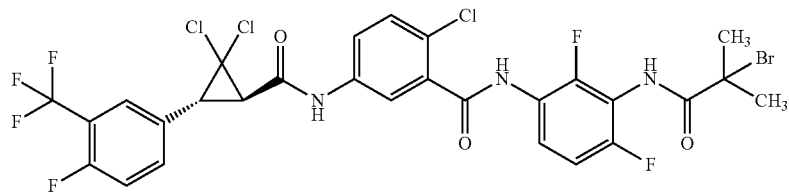 [SMILES: CC(C)(Br)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white solid (0.038 g, 29%).

2-Chloro-N-(3-(2,2-dibromoacetamido)-2,4-difluorophenyl)-5-(((1R,3R)-2,2-dichloro-3-(4-fluoro-3-(trifluoromethyl)phenyl)cyclopropane-1-carboxamido)benzamide (F1355)

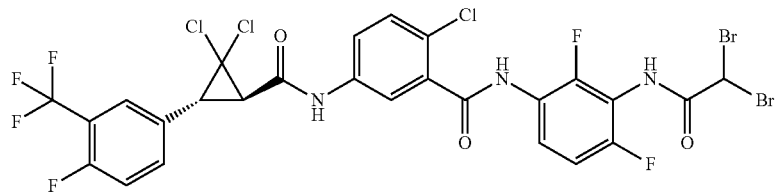 [SMILES: O=C(Nc1ccc(F)c(NC(=O)C(Br)Br)c1F)c1cc(NC(=O)[C@H]2[C@H](c3ccc(F)c(C(F)(F)F)c3)C2(Cl)Cl)ccc1Cl]

Isolated as a white solid (0.111 g, 79%).

2-Chloro-5-(((1R,3R)-2,2-dichloro-3-(4-fluoro-3-(trifluoromethyl)phenyl)cyclopropane-1-carboxamido)-N-(3-(2,2-difluorobutanamido)-2,4-difluorophenyl)benzamide (F1357)

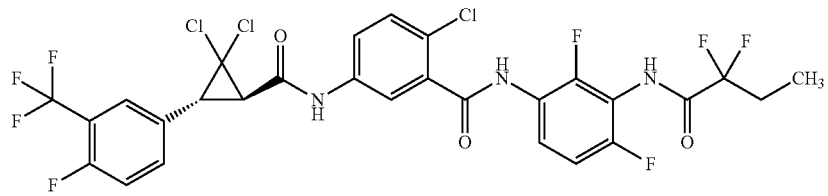

Isolated as a white solid (0.165 g, 89%).

2-Chloro-5-(((1R,3R)-2,2-dichloro-3-(4-fluoro-3-(trifluoromethyl)phenyl)cyclopropane-1-carboxamido)-N-(2,4-difluoro-3-(1-methylcyclopropane-1-carboxamido)phenyl)benzamide (F1362)

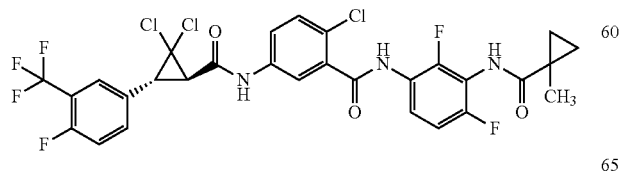

Isolated as a white solid (0.107 g, 89%).

2-Chloro-5-((1R,3R)-2,2-dichloro-3-(4-fluoro-3-(trifluoromethyl)phenyl)cyclopropane-1-carboxamido)-N-(3-(2-ethoxyacetamido)-2,4-difluorophenyl)benzamide (F1363)

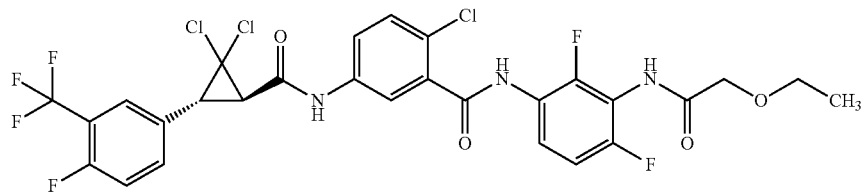

Isolated as a white foam (0.106 g, 88%).

2-Chloro-5-((1R,3R)-2,2-dichloro-3-(4-fluoro-3-(trifluoromethyl)phenyl)cyclopropane-1-carboxamido)-N-(3-(2-ethoxypropanamido)-2,4-difluorophenyl)benzamide (F1364)

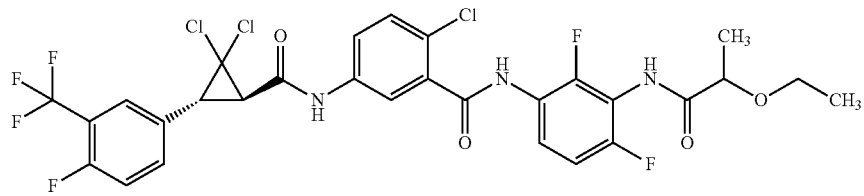 [SMILES: CCOC(C)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white solid (0.101 g, 82%).

2-Chloro-N-(3-(2-cyanoacetamido)-2,4-difluorophenyl)-5-((1R,3R)-2,2-dichloro-3-(4-fluoro-3-(trifluoromethyl)phenyl)cyclopropane-1-carboxamido)benzamide (F1369)

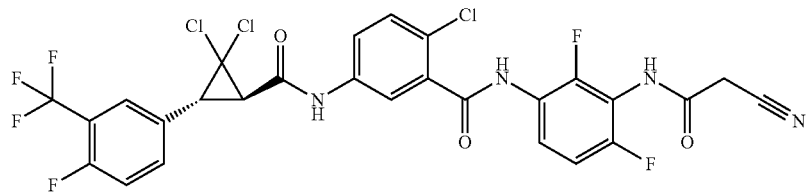 [SMILES: N#CCC(=O)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a yellow foam (0.112 g, 96%).

2-Chloro-5-((1R,3R)-2,2-dichloro-3-(4-fluoro-3-(trifluoromethyl)phenyl)cyclopropane-1-carboxamido)-N-(2,4-difluoro-3-propionamidophenyl)benzamide (F1371)

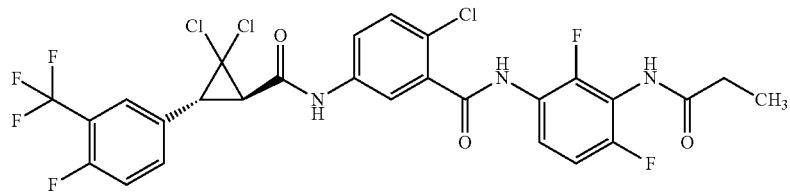 [SMILES: CCC(=O)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white solid (0.130 g, 78%).

2-Chloro-5-(((1R,3R)-2,2-dichloro-3-(4-fluoro-3-(trifluoromethyl)phenyl)cyclopropane-1-carboxamido)-N-(2,4-difluoro-3-pentanamidophenyl)benzamide (F1372)

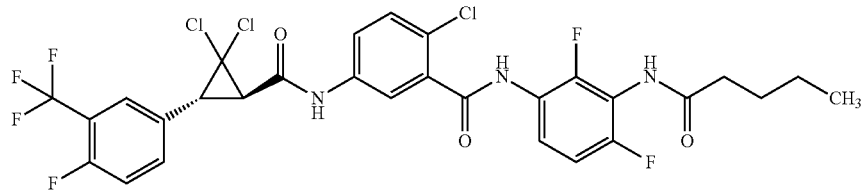 [SMILES: CCCCC(=O)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white foam (0.191 g, 80%).

N-(3-Butyramido-2,4-difluorophenyl)-2-chloro-5-((1R,3R)-2,2-dichloro-3-(4-fluoro-3-(trifluoromethyl)phenyl)cyclopropane-1-carboxamido)benzamide (F1385)

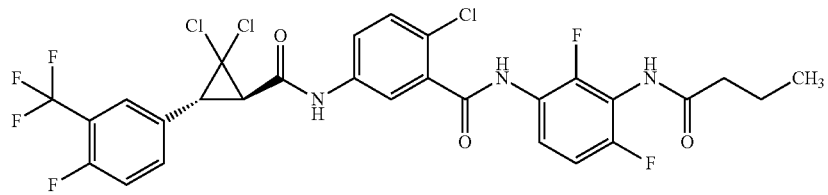

Isolated as a white solid (0.103 g, 88%).

2-Chloro-5-(((1R,3R)-2,2-dichloro-3-(4-fluoro-3-(trifluoromethyl)phenyl)cyclopropane-1-carboxamido)-N-(2,4-difluoro-3-(2,2,3,3,4,4,4-heptafluorobutanamido)phenyl)benzamide (F1450)

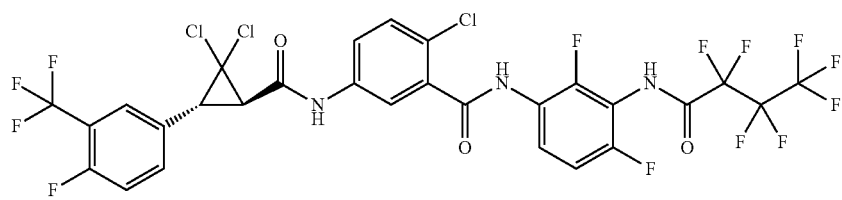 [SMILES: O=C(Nc1ccc(F)c(NC(=O)C(F)(F)C(F)(F)C(F)(F)F)c1F)c1cc(NC(=O)[C@H]2[C@H](c3ccc(F)c(C(F)(F)F)c3)C2(Cl)Cl)ccc1Cl]

Isolated as a white foam (0.119 g, 85%).

N-(3-Acetamido-2,6-difluorophenyl)-2-chloro-5-((1R,3R)-2,2-dichloro-3-(4-fluoro-3-(trifluoromethyl)phenyl)cyclopropane-1-carboxamido)benzamide (F1454)

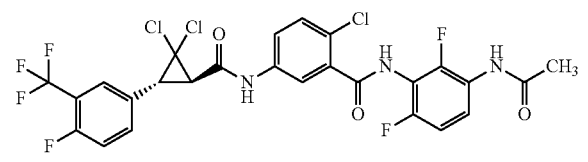 [SMILES: CC(=O)Nc1ccc(F)c(NC(=O)c2cc(NC(=O)[C@H]3[C@H](c4ccc(F)c(C(F)(F)F)c4)C3(Cl)Cl)ccc2Cl)c1F]

Isolated as a white foam (0.168 g, 65%).

N-(3-(2-Bromopropanamido)-2,4-difluorophenyl)-2-chloro-5-(((1R,3R)-2,2-dichloro-3-(4-fluoro-3-(trifluoromethyl)phenyl)cyclopropane-1-carboxamido)benzamide (F1479)

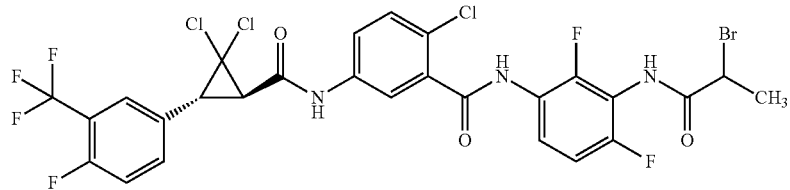 [SMILES: CC(Br)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white solid (0.120 g, 93%).

N-(3-(2-Chloro-5-(((1R,3R)-2,2-dichloro-3-(4-fluoro-3-(trifluoromethyl)phenyl)cyclopropane-1-carboxamido)benzamido)-2,6-difluorophenyl)tetrahydrofuran-3-carboxamide (F1480)

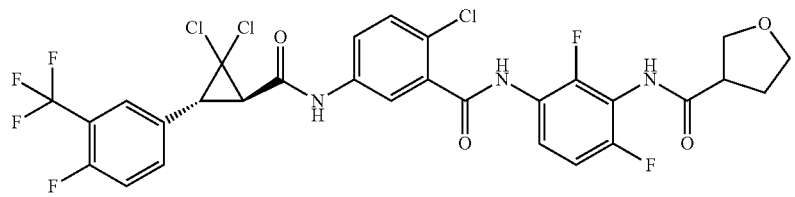

Isolated as a white foam (0.104 g, 85%).

2-Chloro-5-(((1R,3R)-2,2-dichloro-3-(4-fluoro-3-(trifluoromethyl)phenyl)cyclopropane-1-carboxamido)-N-(2,4-difluoro-3-(2,2,3,3-tetrafluorocyclobutane-1-carboxamido)phenyl)benzamide (F1481)

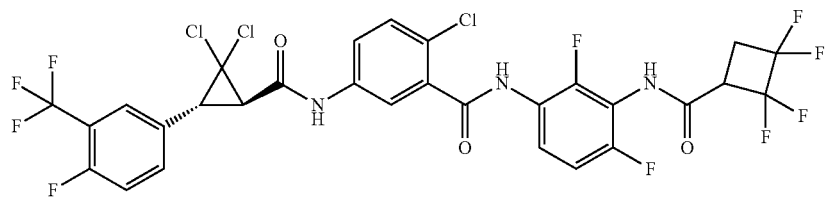 [SMILES: O=C(Nc1ccc(F)c(NC(=O)C2CC(F)(F)C2(F)F)c1F)c1cc(NC(=O)[C@H]2[C@H](c3ccc(F)c(C(F)(F)F)c3)C2(Cl)Cl)ccc1Cl]

Isolated as a white foam (0.114 g, 86%).

2-Chloro-5-(((1R,3R)-2,2-dichloro-3-(4-fluoro-3-(trifluoromethyl)phenyl)cyclopropane-1-carboxamido)-N-(2,4-difluoro-3-isobutyramidophenyl)benzamide (F1483)

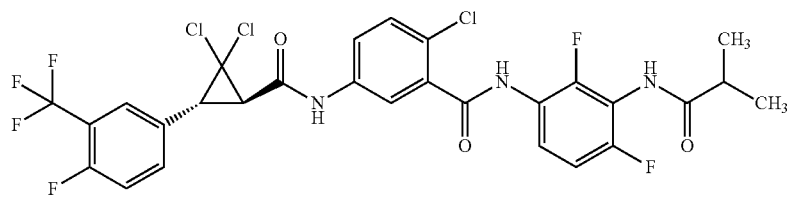 [SMILES: CC(C)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white solid (0.108 g, 92%).

2-Chloro-5-((1R,3R)-2,2-dichloro-3-(4-fluoro-3-(trifluoromethyl)phenyl)cyclopropane-1-carboxamido)-N-(2,4-difluoro-3-(3-oxocyclopentane-1-carboxamido)phenyl)benzamide (F1488)

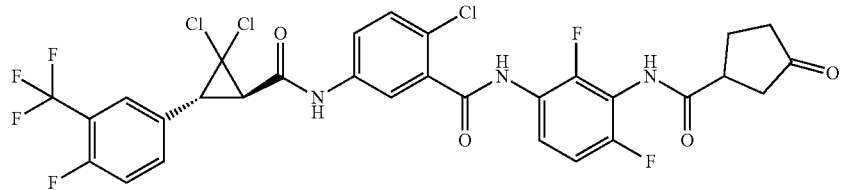 [SMILES: O=C1CCC(C(=O)Nc2c(F)ccc(NC(=O)c3cc(NC(=O)[C@H]4[C@H](c5ccc(F)c(C(F)(F)F)c5)C4(Cl)Cl)ccc3Cl)c2F)C1]

Isolated as a gold foam (0.113 g, 91%).

2-Chloro-5-((1R,3R)-2,2-dichloro-3-(4-fluoro-3-(trifluoromethyl)phenyl)cyclopropane-1-carboxamido)-N-(2,4-difluoro-3-(3-methoxypropanamido)phenyl)benzamide (F1489)

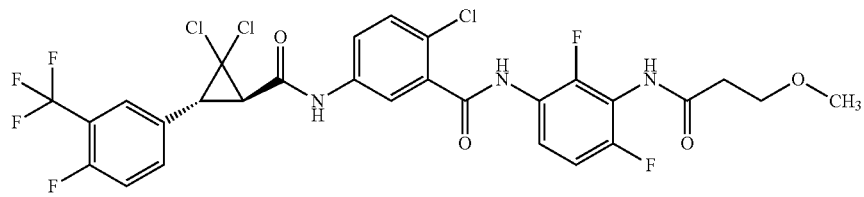

Isolated as a white foam (0.094 g, 78%).

N-(3-(2-Chloro-5-((1R,3R)-2,2-dichloro-3-(4-fluoro-3-(trifluoromethyl)phenyl)cyclopropane-1-carboxamido)benzamido)-2,6-difluorophenyl)oxetane-2-carboxamide (F1503)

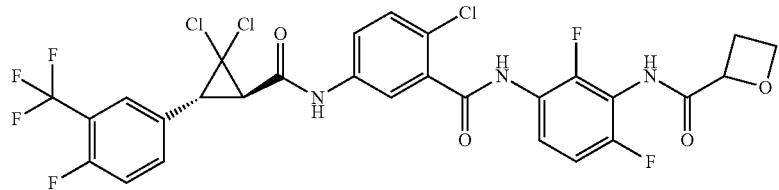 [SMILES: O=C(Nc1ccc(F)c(NC(=O)C2CCO2)c1F)c1cc(NC(=O)[C@H]2[C@H](c3ccc(F)c(C(F)(F)F)c3)C2(Cl)Cl)ccc1Cl]

Isolated as a white solid (0.036 g, 30%).

2-Chloro-5-((1R,3R)-2,2-dichloro-3-(4-fluoro-3-(trifluoromethyl)phenyl)cyclopropane-1-carboxamido)-N-(3-(2,2-dimethyl-3-oxocyclobutane-1-carboxamido)-2,4-difluorophenyl)benzamide (F1507)

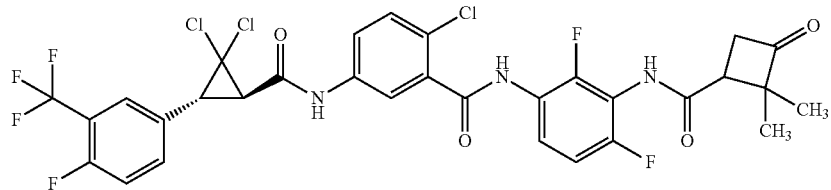 [SMILES: CC1(C)C(=O)CC1C(=O)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white solid (0.090 g, 71%).

N-(3-(2-Chloro-5-(((1R,3R)-2,2-dichloro-3-(4-fluoro-3-(trifluoromethyl)phenyl)cyclopropane-1-carboxamido)benzamido)-2,6-difluorophenyl)tetrahydrofuran-2-carboxamide (F1521)

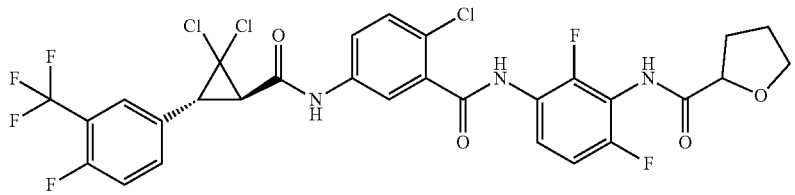 [SMILES: O=C(Nc1ccc(F)c(NC(=O)C2CCCO2)c1F)c1cc(NC(=O)[C@H]2[C@H](c3ccc(F)c(C(F)(F)F)c3)C2(Cl)Cl)ccc1Cl]

Isolated as a white foam (0.054 g, 44%).

2-Chloro-5-(((1R,3R)-2,2-dichloro-3-(4-fluoro-3-(trifluoromethyl)phenyl)cyclopropane-1-carboxamido)-N-(3-(2-ethoxy-2-methylpropanamido)-2,4-difluorophenyl)benzamide (F1603)

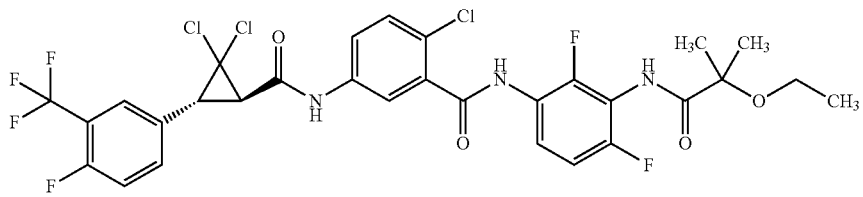 [SMILES: CCOC(C)(C)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a clear, colorless oil (0.047 g, 38%).

(2S,5S)—N-(3-(2-Chloro-5-(((1R,3R)-2,2-dichloro-3-(4-fluoro-3-(trifluoromethyl)phenyl)cyclopropane-1-carboxamido)benzamido)-2,6-difluorophenyl)-5-methyltetrahydrofuran-2-carboxamide (F1612)

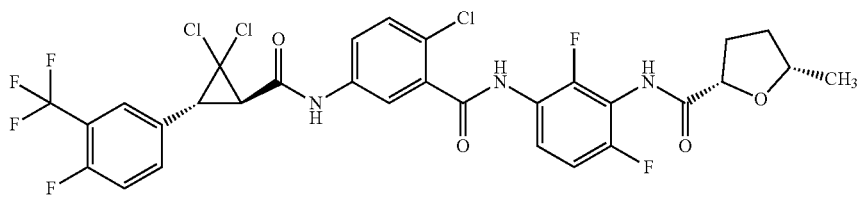 [SMILES: C[C@H]1CC[C@@H](C(=O)Nc2c(F)ccc(NC(=O)c3cc(NC(=O)[C@H]4[C@H](c5ccc(F)c(C(F)(F)F)c5)C4(Cl)Cl)ccc3Cl)c2F)O1]

Isolated as a white foam (0.100 g, 80%).

N-(3-(2-Chloro-5-(((1R,3R)-2,2-dichloro-3-(4-fluoro-3-(trifluoromethyl)phenyl)cyclopropane-1-carboxamido)benzamido)-2,6-difluorophenyl)-5-oxotetrahydrofuran-2-carboxamide (F1625)

Isolated as a white solid (0.110 g, 88%).

N-(3-(2-Chloro-5-(((1R,3R)-2,2-dichloro-3-(4-fluoro-3-(trifluoromethyl)phenyl)cyclopropane-1-carboxamido)benzamido)-2,6-difluorophenyl)-5-ethyltetrahydrofuran-2-carboxamide (F1626)

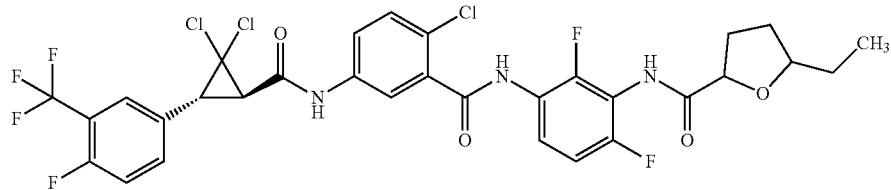 [SMILES: CCC1CCC(C(=O)Nc2c(F)ccc(NC(=O)c3cc(NC(=O)[C@H]4[C@H](c5ccc(F)c(C(F)(F)F)c5)C4(Cl)Cl)ccc3Cl)c2F)O1]

Isolated as a clear colorless oil (0.105 g, 82%).

2-Chloro-5-(((1R,3R)-2,2-dichloro-3-(4-fluoro-3-(trifluoromethyl)phenyl)cyclopropane-1-carboxamido)-N-(2,4-difluoro-3-(2-methylbutanamido)phenyl)benzamide (F1642)

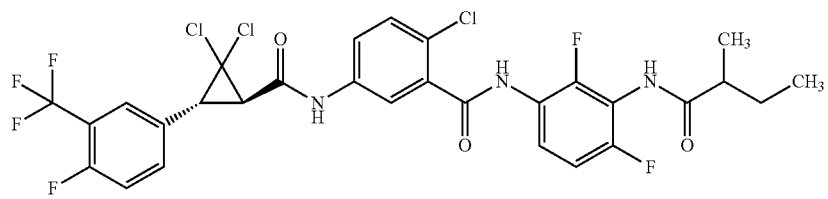 [SMILES: CCC(C)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white solid (0.092 g, 77%).

2-Chloro-N-(3-(cyclopentanecarboxamido)-2,4-difluorophenyl)-5-(((1R,3R)-2,2-dichloro-3-(4-fluoro-3-(trifluoromethyl)phenyl)cyclopropane-1-carboxamido)benzamide (F1643)

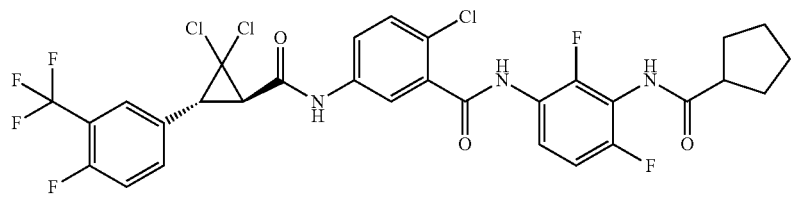

Isolated as a white solid (0.086 g, 70%).

2-Chloro-5-(((1R,3R)-2,2-dichloro-3-(4-fluoro-3-(trifluoromethyl)phenyl)cyclopropane-1-carboxamido)-N-(3-(3,3-difluorocyclobutane-1-carboxamido)-2,4-difluorophenyl)benzamide (F1644)

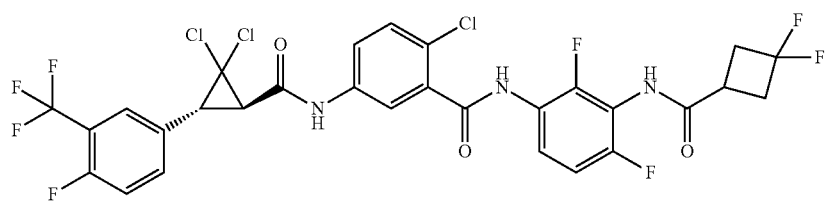 [SMILES: O=C(Nc1ccc(F)c(NC(=O)C2CC(F)(F)C2)c1F)c1cc(NC(=O)[C@H]2[C@H](c3ccc(F)c(C(F)(F)F)c3)C2(Cl)Cl)ccc1Cl]

Isolated as a white solid (0.100 g, 79%).

2-Chloro-N-(3-(2-chloropropanamido)-2,4-difluorophenyl)-5-(((1R,3R)-2,2-dichloro-3-(4-fluoro-3-(trifluoromethyl)phenyl)cyclopropane-1-carboxamido)benzamide (F1667)

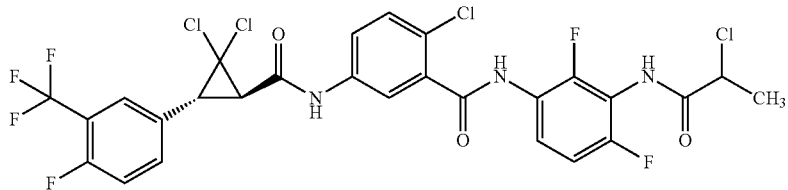

Isolated as a white solid (0.112 g, 92%).

2-Chloro-N-(3-(2-chlorobutanamido)-2,4-difluorophenyl)-5-(((1R,3R)-2,2-dichloro-3-(4-fluoro-3-(trifluoromethyl)phenyl)cyclopropane-1-carboxamido)benzamide (F1668)

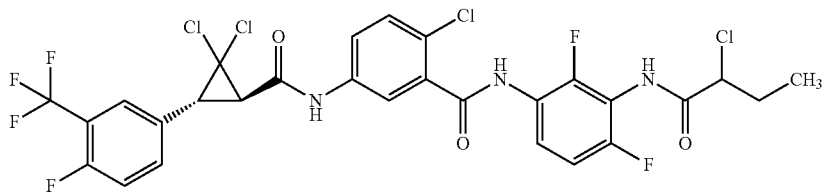

Isolated as a white solid (0.097 g, 78%).

2-Chloro-N-(3-(3-chlorobutanamido)-2,4-difluorophenyl)-5-(((1R,3R)-2,2-dichloro-3-(4-fluoro-3-(trifluoromethyl)phenyl)cyclopropane-1-carboxamido)benzamide (F1669)

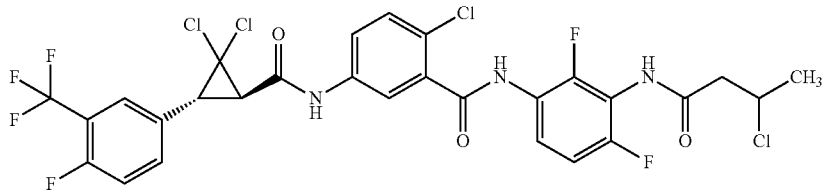

Isolated as a white solid (0.097 g, 78%).

N-(3-(2-Chloro-5-(((1R,3R)-2,2-dichloro-3-(3-(trifluoromethyl)phenyl)cyclopropane-1-carboxamido)benzamido)-2,6-difluorophenyl)tetrahydrofuran-2-carboxamide (F1676)

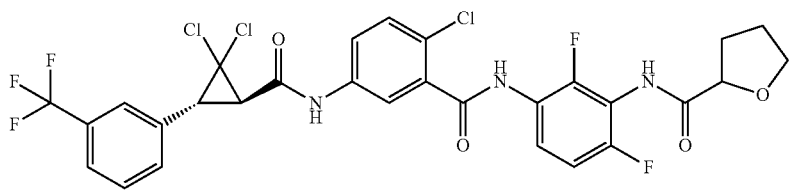 [SMILES: O=C(Nc1ccc(F)c(NC(=O)C2CCCO2)c1F)c1cc(NC(=O)[C@H]2[C@H](c3cccc(C(F)(F)F)c3)C2(Cl)Cl)ccc1Cl]

Isolated as a white solid (0.076 g, 82%).

2-Chloro-5-(((1R,3R)-2,2-dichloro-3-(3-(trifluoromethyl)phenyl)cyclopropane-1-carboxamido)-N-(2,4-difluoro-3-(2,2,3,3-tetrafluoropropanamido)phenyl)benzamide (F1677)

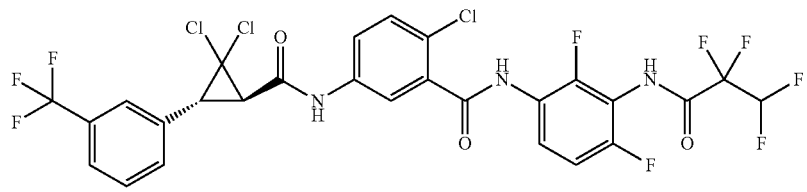 [SMILES: O=C(Nc1ccc(F)c(NC(=O)C(F)(F)C(F)F)c1F)c1cc(NC(=O)[C@H]2[C@H](c3cccc(C(F)(F)F)c3)C2(Cl)Cl)ccc1Cl]

Isolated as a clear colorless oil (0.061 g, 63%).

N-(3-Acetamido-2,4-difluorophenyl)-2-chloro-5-((1R,3R)-2,2-dichloro-3-(3-(trifluoromethyl)phenyl)cyclopropane-1-carboxamido)benzamide (F1678)

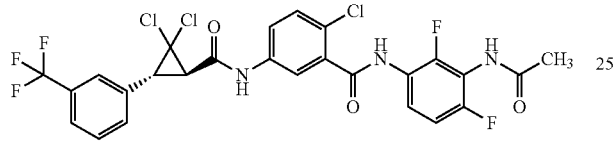

Isolated as a white solid (0.069 g, 81%).

2-Chloro-5-(((1R,3R)-2,2-dichloro-3-(3-(trifluoromethyl)phenyl)cyclopropane-1-carboxamido)-N-(2,4-difluoro-3-propionamidophenyl)benzamide (F1679)

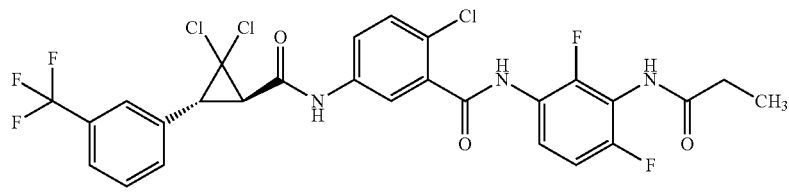 [SMILES: CCC(=O)Nc1c(F)ccc(NC(=O)c2cc(NC(=O)[C@H]3[C@H](c4cccc(C(F)(F)F)c4)C3(Cl)Cl)ccc2Cl)c1F]

Isolated as a white solid (0.070 g, 81%).

2-Chloro-N-(3-(2-cyclopropylacetamido)-2,4-difluorophenyl)-5-(((1R,3R)-2,2-dichloro-3-(4-fluoro-3-(trifluoromethyl)phenyl)cyclopropane-1-carboxamido)benzamide (F1682)

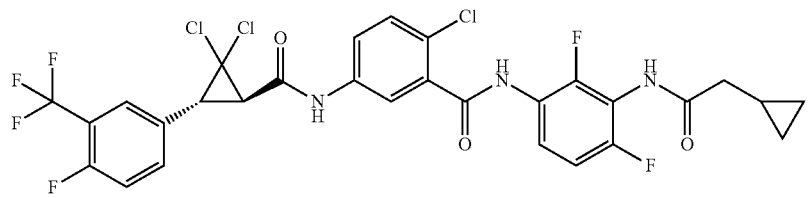 [SMILES: O=C(CC1CC1)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white foam (0.113 g, 94%).

2-Chloro-5-((1R,3R)-2,2-dichloro-3-(4-fluoro-3-(trifluoromethyl)phenyl)cyclopropane-1-carboxamido)-N-(2,4-difluoro-3-(3,3,3-trifluoropropanamido)phenyl)benzamide (F1683)

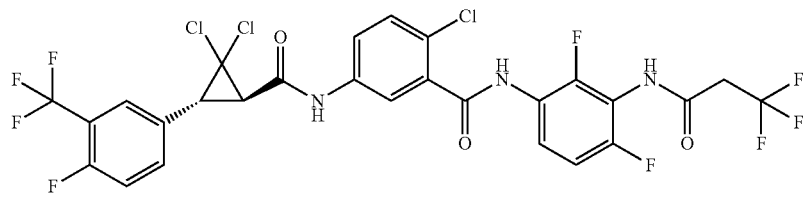 [SMILES: O=C(CC(F)(F)F)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white foam (0.114 g, 91%).

2-Chloro-5-((1R,3R)-2,2-dichloro-3-(4-fluoro-3-(trifluoromethyl)phenyl)cyclopropane-1-carboxamido)-N-(2,4-difluoro-3-((R)-2-methoxypropanamido)phenyl)benzamide (F1689)

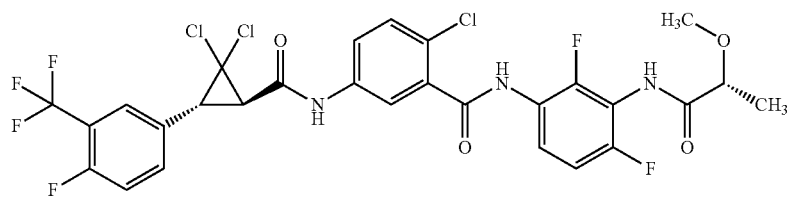 [SMILES: CO[C@H](C)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white foam (0.082 g, 68%).

(R)—N-(3-(2-Chloro-5-((1R,3R)-2,2-dichloro-3-(4-fluoro-3-(trifluoromethyl)phenyl)cyclopropane-1-carboxamido)benzamido)-2,6-difluorophenyl)tetrahydrofuran-2-carboxamide (F1691)

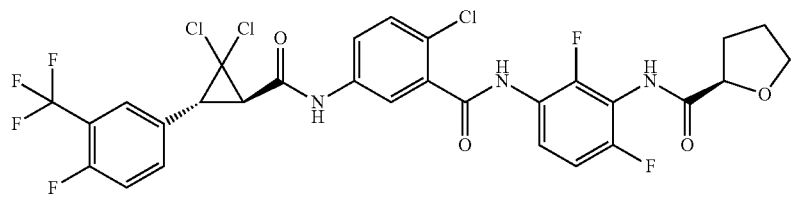 [SMILES: O=C(Nc1ccc(F)c(NC(=O)[C@H]2CCCO2)c1F)c1cc(NC(=O)[C@H]2[C@H](c3ccc(F)c(C(F)(F)F)c3)C2(Cl)Cl)ccc1Cl]

Isolated as a white foam (0.103 g, 84%).

(S)—N-(3-(2-Chloro-5-((1R,3R)-2,2-dichloro-3-(4-fluoro-3-(trifluoromethyl)phenyl)cyclopropane-1-carboxamido)benzamido)-2,6-difluorophenyl)tetrahydrofuran-2-carboxamide (F1692)

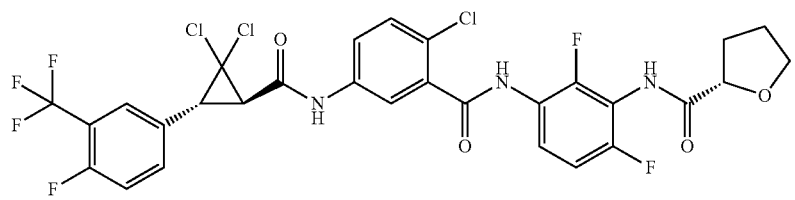

Isolated as a white foam (0.088 g, 72%).

N-(3-(2-Chloro-5-(((1R,3R)-2,2-dichloro-3-(3-fluoro-5-(trifluoromethyl)phenyl)cyclopropane-1-carboxamido)benzamido)-2,6-difluorophenyl)tetrahydrofuran-2-carboxamide (F1706)

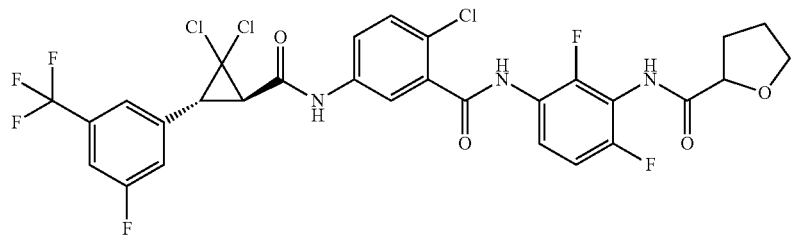 [SMILES: O=C(Nc1ccc(F)c(NC(=O)C2CCCO2)c1F)c1cc(NC(=O)[C@H]2[C@H](c3cc(F)cc(C(F)(F)F)c3)C2(Cl)Cl)ccc1Cl]

Isolated as a white solid (0.060 g, 65%).

2-Chloro-5-((1R,3R)-2,2-dichloro-3-(3-fluoro-5-(trifluoromethyl)phenyl)cyclopropane-1-carboxamido)-N-(2,4-difluoro-3-(2,2,3,3-tetrafluoropropanamido)phenyl)benzamide (F1707)

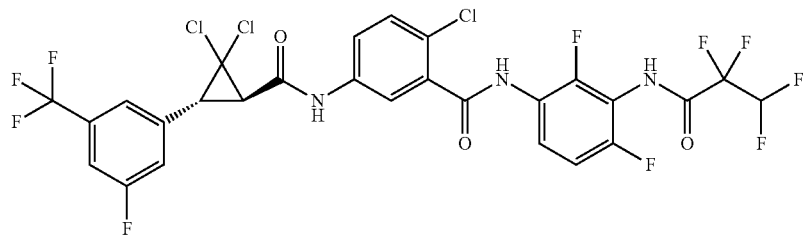 [SMILES: O=C(Nc1ccc(F)c(NC(=O)C(F)(F)C(F)F)c1F)c1cc(NC(=O)[C@H]2[C@H](c3cc(F)cc(C(F)(F)F)c3)C2(Cl)Cl)ccc1Cl]

Isolated as a clear, colorless oil (0.066 g, 69%).

N-(3-Acetamido-2,4-difluorophenyl)-2-chloro-5-((1R,3R)-2,2-dichloro-3-(3-fluoro-5-(trifluoromethyl)phenyl)cyclopropane-1-carboxamido)benzamide (F1708)

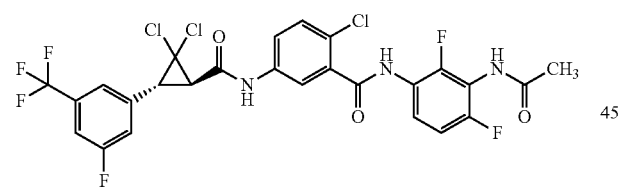

Isolated as a white solid (0.057 g, 67%).

2-Chloro-5-((1R,3R)-2,2-dichloro-3-(3-fluoro-5-(trifluoromethyl)phenyl)cyclopropane-1-carboxamido)-N-(2,4-difluoro-3-propionamidophenyl)benzamide (F1709)

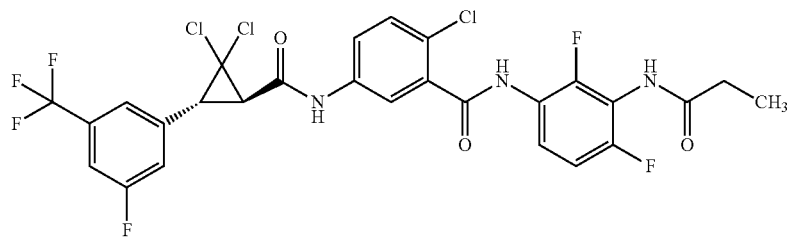 [SMILES: CCC(=O)Nc1c(F)ccc(NC(=O)c2cc(NC(=O)[C@H]3[C@H](c4cc(F)cc(C(F)(F)F)c4)C3(Cl)Cl)ccc2Cl)c1F]

Isolated as a white solid (0.063 g, 73%).

2-Chloro-5-((1R,3R)-2,2-dichloro-3-(3-fluoro-5-(trifluoromethyl)phenyl)cyclopropane-1-carboxamido)-N-(2,4-difluoro-3-(3,3,3-trifluoropropanamido)phenyl)benzamide (F1710)

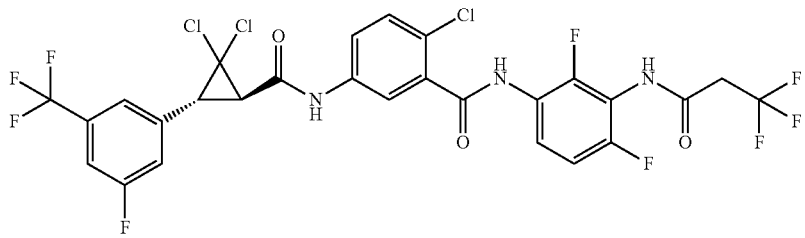 [SMILES: O=C(CC(F)(F)F)Nc1c(F)ccc(NC(=O)c2cc(NC(=O)[C@H]3[C@H](c4cc(F)cc(C(F)(F)F)c4)C3(Cl)Cl)ccc2Cl)c1F]

Isolated as a white solid (0.068 g, 73%).

2-Chloro-5-((1R,3R)-2,2-dichloro-3-(4-fluoro-3-(trifluoromethyl)phenyl)cyclopropane-1-carboxamido)-N-(2,4-difluoro-3-(2-methoxypropanamido)phenyl)benzamide (F1712)

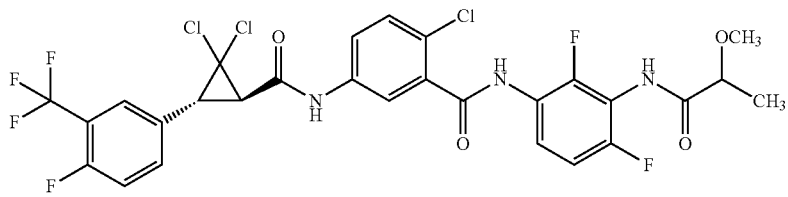

Isolated as a white solid (0.110 g, 91%).

N-(3-(5-((1R,3R)-3-(3-Bromo-4-fluorophenyl)-2,2-dichlorocyclopropane-1-carboxamido)-2-chlorobenzamido)-2,6-difluorophenyl)tetrahydrofuran-2-carboxamide (F1714)

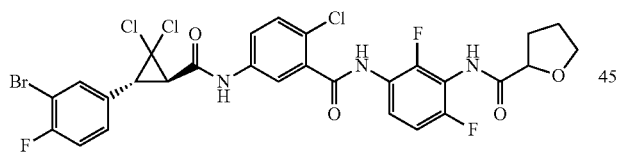

Isolated as a white solid (0.036 g, 59%).

5-((1R,3R)-3-(3-Bromo-4-fluorophenyl)-2,2-dichlorocyclopropane-1-carboxamido)-2-chloro-N-(2,4-difluoro-3-(2,2,3,3-tetrafluoropropanamido)phenyl)benzamide (F1715)

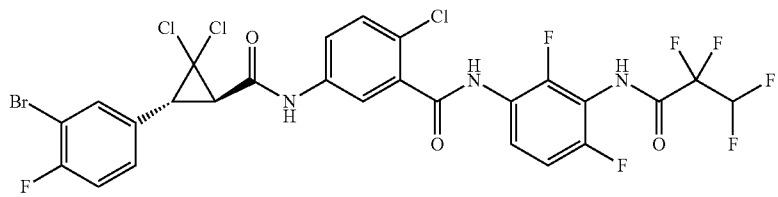

Isolated as a white solid (0.030 g, 47%).

429

N-(3-Acetamido-2,4-difluorophenyl)-5-((1R,3R)-3-(3-bromo-4-fluorophenyl)-2,2-dichlorocyclopropane-1-carboxamido)-2-chlorobenzamide (F1716)

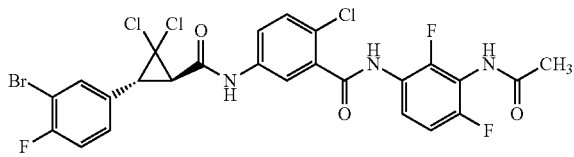

Isolated as a white solid (0.037 g, 66%).

430

5-((1R,3R)-3-(3-Bromo-4-fluorophenyl)-2,2-dichlorocyclopropane-1-carboxamido)-2-chloro-N-(2,4-difluoro-3-propionamidophenyl)benzamide (F1717)

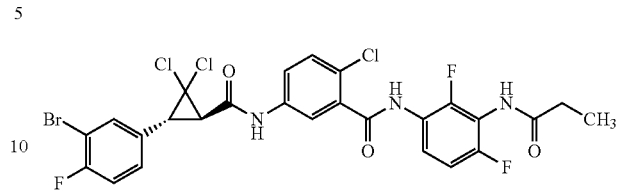

Isolated as a white solid (0.042 g, 73%).

5-((1R,3R)-3-(3-Bromo-4-fluorophenyl)-2,2-dichlorocyclopropane-1-carboxamido)-2-chloro-N-(2,4-difluoro-3-(3,3,3-trifluoropropanamido)phenyl)benzamide (F1718)

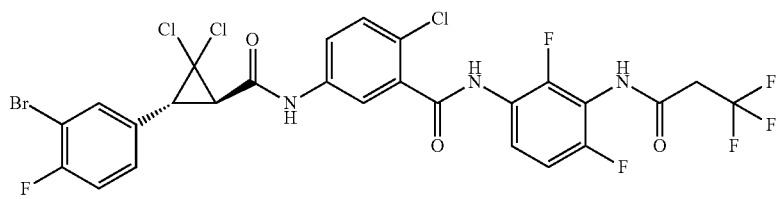

Isolated as a white solid (0.031 g, 50%).

2-Chloro-5-((1R,3R)-2,2-dichloro-3-(4-fluoro-3-(trifluoromethyl)phenyl)cyclopropane-1-carboxamido)-N-(2,4-difluoro-3-((S)-2-methoxypropanamido)phenyl)benzamide (F1720)

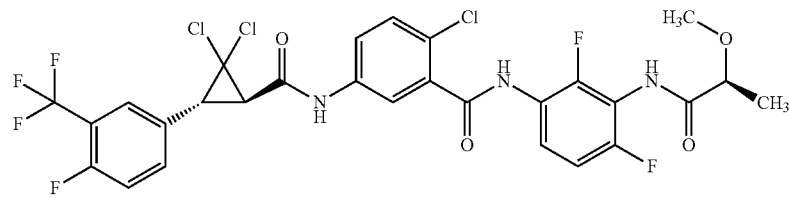 [SMILES: CO[C@@H](C)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white solid (0.101 g, 84%).

N-(3-(2-Chloro-5-((1R,3R)-2,2-dichloro-3-(4-fluoro-3-(trifluoromethyl)phenyl)cyclopropane-1-carboxamido)benzamido)-2,6-difluorophenyl)tetrahydrothiophene-2-carboxamide (F1721)

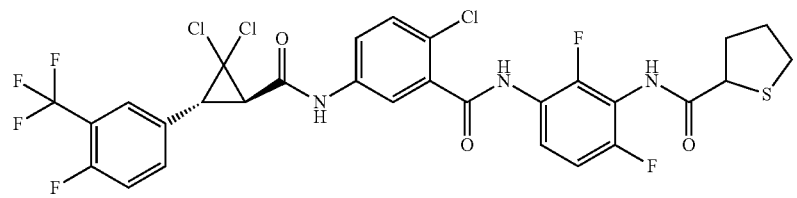

Isolated as a white solid (0.110 g, 88%).

N-(3-(2-Chloro-5-(((1R,3R)-2,2-dichloro-3-(4-fluoro-3-(trifluoromethyl)phenyl)cyclopropane-1-carboxamido)benzamido)-2,6-difluorophenyl)tetrahydro-2H-pyran-3-carboxamide (F1722)

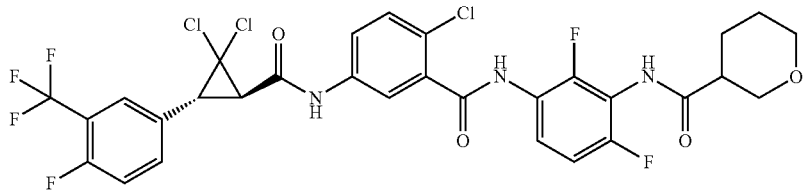 [SMILES: O=C(Nc1ccc(F)c(NC(=O)C2CCCOC2)c1F)c1cc(NC(=O)[C@H]2[C@H](c3ccc(F)c(C(F)(F)F)c3)C2(Cl)Cl)ccc1Cl]

Isolated as a white solid (0.102 g, 82%).

2-Chloro-5-((1R,3R)-2,2-dichloro-3-(4-fluoro-3-(trifluoromethyl)phenyl)cyclopropane-1-carboxamido)-N-(2,4-difluoro-3-(2-methoxyacetamido)phenyl)benzamide (F1724)

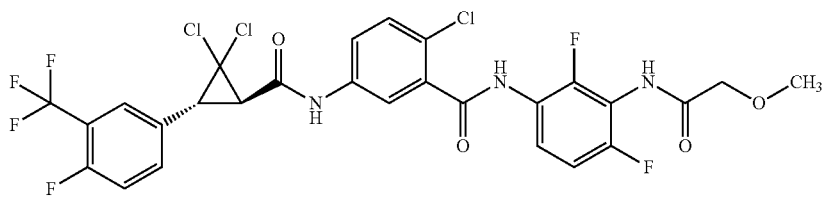

Isolated as a white solid (0.098 g, 83%).

2-Chloro-N-(3-(2-chloroacetamido)-2,4-difluorophenyl)-5-((1R,3R)-2,2-dichloro-3-(4-fluoro-3-(trifluoromethyl)phenyl)cyclopropane-1-carboxamido)benzamide (F1726)

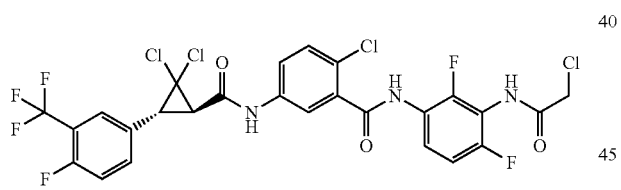

Isolated as a white foam (0.090 g, 76%).

2-Chloro-5-((1R,3R)-2,2-dichloro-3-(4-fluoro-3-(trifluoromethyl)phenyl)cyclopropane-1-carboxamido)-N-(3-(2,3-dichloropropanamido)-2,4-difluorophenyl)benzamide (F1728)

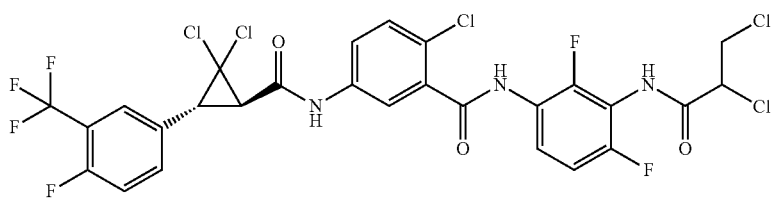 [SMILES: O=C(Nc1ccc(F)c(NC(=O)C(Cl)CCl)c1F)c1cc(NC(=O)[C@H]2[C@H](c3ccc(F)c(C(F)(F)F)c3)C2(Cl)Cl)ccc1Cl]

Isolated as a white foam (0.060 g, 47%).

2-Chloro-5-((1R,3R)-2,2-dichloro-3-(4-fluoro-3-(trifluoromethyl)phenyl)cyclopropane-1-carboxamido)-N-(2,4-difluoro-3-(3-fluoropropanamido)phenyl)benzamide (F1735)

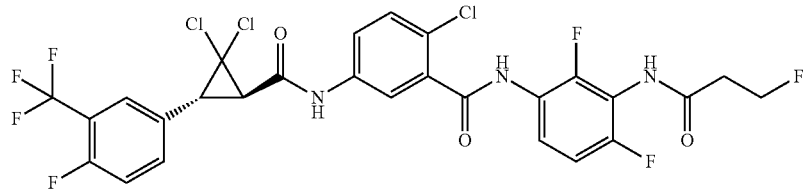 [SMILES: O=C(CCF)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white solid (0.100 g, 85%).

2-Chloro-5-((1R,3R)-2,2-dichloro-3-(3-(trifluoromethyl)phenyl)cyclopropane-1-carboxamido)-N-(3-(2-ethoxypropanamido)-2,4-difluorophenyl)benzamide (F1737)

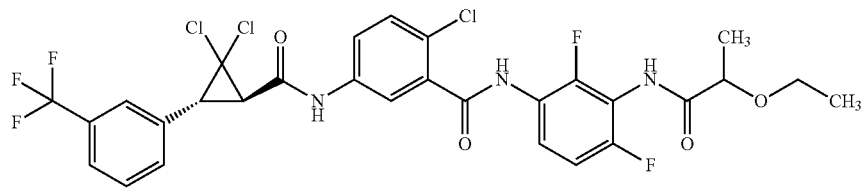 [SMILES: CCOC(C)C(=O)Nc1c(F)ccc(NC(=O)c2cc(NC(=O)[C@H]3[C@H](c4cccc(C(F)(F)F)c4)C3(Cl)Cl)ccc2Cl)c1F]

Isolated as a white solid (0.077 g, 83%).

2-Chloro-5-((1R,3R)-2,2-dichloro-3-(3-(trifluoromethyl)phenyl)cyclopropane-1-carboxamido)-N-(2,4-difluoro-3-(3,3,3-trifluoropropanamido)phenyl)benzamide (F1738)

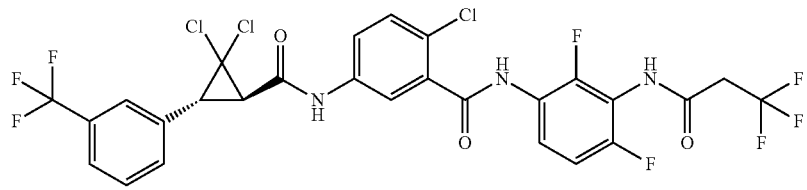 [SMILES: O=C(CC(F)(F)F)Nc1c(F)ccc(NC(=O)c2cc(NC(=O)[C@H]3[C@H](c4cccc(C(F)(F)F)c4)C3(Cl)Cl)ccc2Cl)c1F]

Isolated as a white solid (0.078 g, 83%).

2-Chloro-5-((1R,3R)-2,2-dichloro-3-(4-fluoro-3-(trifluoromethyl)phenyl)cyclopropane-1-carboxamido)-N-(2,4-difluoro-3-(2-propoxypropanamido)phenyl)benzamide (F1739)

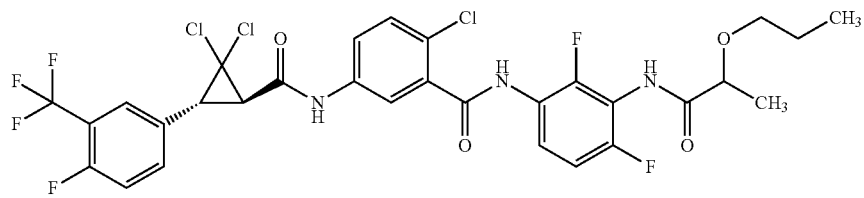 [SMILES: CCCOC(C)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white solid (0.101 g, 81%).

N-(5-Acetamido-2,3,4-trifluorophenyl)-2-chloro-5-((1R,3R)-2,2-dichloro-3-(4-fluoro-3-(trifluoromethyl)phenyl)cyclopropane-1-carboxamido)benzamide (F1743)

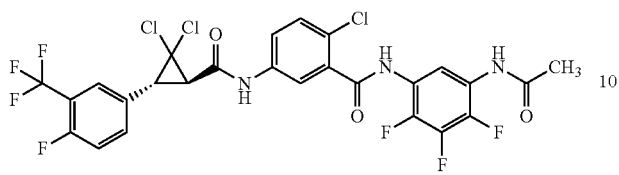

Isolated as a white foam (0.078 g, 92%).

2-Chloro-N-(3-(2-(cyclopropylmethoxy)propanamido)-2,4-difluorophenyl)-5-((1R,3R)-2,2-dichloro-3-(4-fluoro-3-(trifluoromethyl)phenyl)cyclopropane-1-carboxamido)benzamide (F1745)

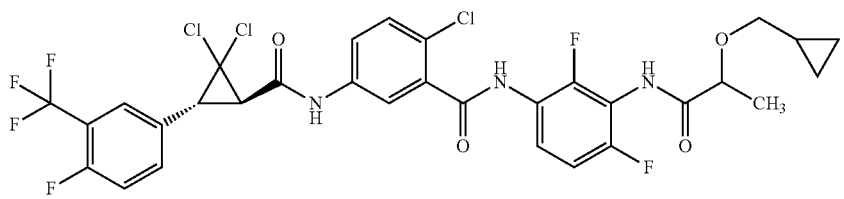 [SMILES: CC(OCC1CC1)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white solid (0.081 g, 85%).

2-Chloro-5-((1R,3R)-2,2-dichloro-3-(4-fluoro-3-(trifluoromethyl)phenyl)cyclopropane-1-carboxamido)-N-(2,4-difluoro-3-(2-isobutoxypropanamido)phenyl)benzamide (F1746)

Isolated as a white foam (0.067 g, 70%).

2-Chloro-5-((1R,3R)-2,2-dichloro-3-(4-fluoro-3-(trifluoromethyl)phenyl)cyclopropane-1-carboxamido)-N-(2,4-difluoro-3-(2-(2,2,2-trifluoroethoxy)propanamido)phenyl)benzamide (F1747)

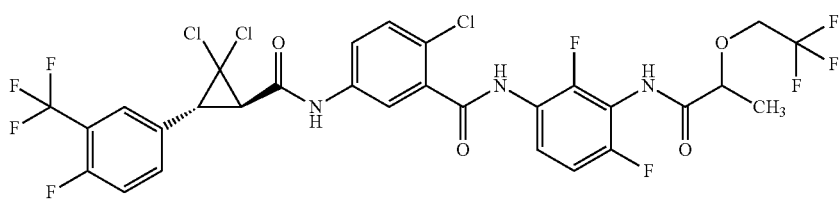 [SMILES: CC(OCC(F)(F)F)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white foam (0.081 g, 82%).

N-(3-(2-Chloro-5-(((1R,3R)-2,2-dichloro-3-(4-fluoro-3-(trifluoromethyl)phenyl)cyclopropane-1-carboxamido)benzamido)-2,6-difluorophenyl)-3-methyloxirane-2-carboxamide (F1748)

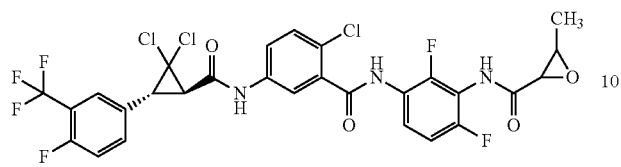

Isolated as a white solid (0.028 g, 31%).

2-Chloro-N-(3-(2-cyano-N-methylacetamido)-2,4-difluorophenyl)-5-((1R,3R)-2,2-dichloro-3-(4-fluoro-3-(trifluoromethyl)phenyl)cyclopropane-1-carboxamido)benzamide (F1752)

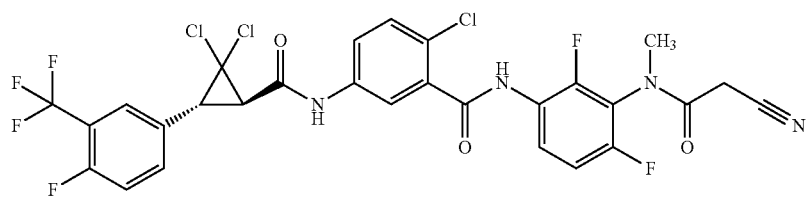 [SMILES: CN(C(=O)CC#N)c1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white foam (0.062 g, 72%).

2-Chloro-N-(3-(2-cyanopropanamido)-2,4-difluorophenyl)-5-((1R,3R)-2,2-dichloro-3-(4-fluoro-3-(trifluoromethyl)phenyl)cyclopropane-1-carboxamido)benzamide (F1755)

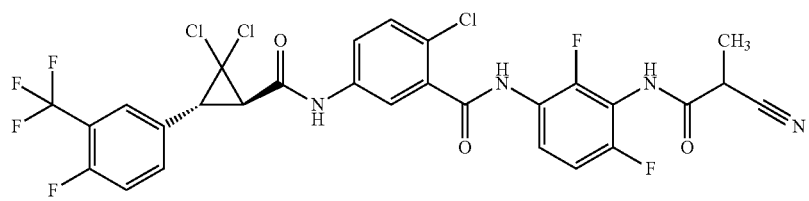

Isolated as a white solid (0.067 g, 75%).

2-Chloro-N-(3-(2-cyanobutanamido)-2,4-difluorophenyl)-5-((1R,3R)-2,2-dichloro-3-(4-fluoro-3-(trifluoromethyl)phenyl)cyclopropane-1-carboxamido)benzamide (F1756)

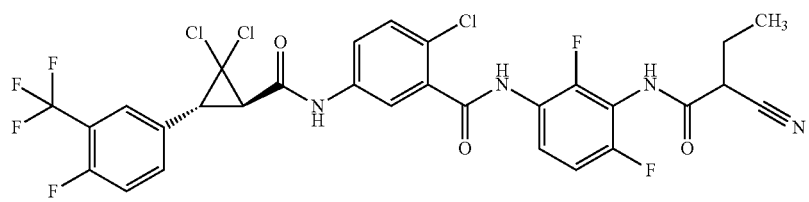 [SMILES: CCC(C#N)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white solid (0.033 g, 36%).

2-Chloro-5-(((1R,3R)-2,2-dichloro-3-(4-fluoro-3-(trifluoromethyl)phenyl)cyclopropane-1-carboxamido)-N-(3-(2-ethoxybutanamido)-2,4-difluorophenyl)benzamide (F1757)

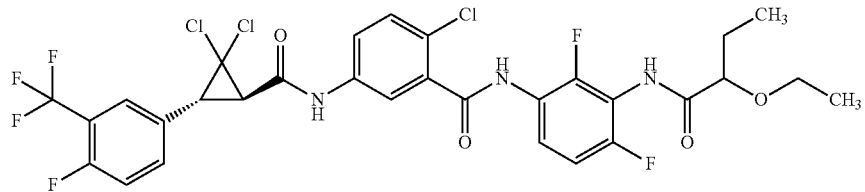 [SMILES: CCOC(CC)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white solid (0.026 g, 28%).

2-Chloro-5-(((1R,3R)-2,2-dichloro-3-(4-fluoro-3-(trifluoromethyl)phenyl)cyclopropane-1-carboxamido)-N-(3-(2-ethoxypentanamido)-2,4-difluorophenyl)benzamide (F1759)

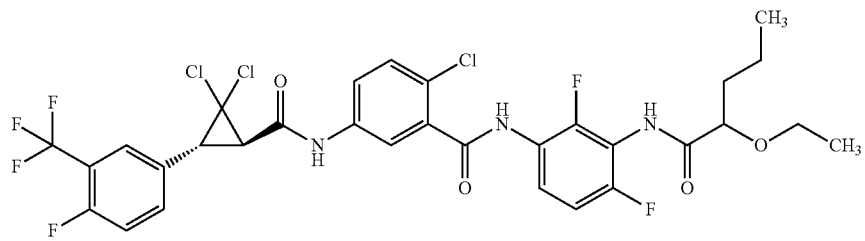 [SMILES: CCCC(OCC)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white solid (0.096 g, 75%).

2-Chloro-N-(3-(2-cyano-N-ethylacetamido)-2,4-difluorophenyl)-5-(((1R,3R)-2,2-dichloro-3-(4-fluoro-3-(trifluoromethyl)phenyl)cyclopropane-1-carboxamido)benzamide (F1763)

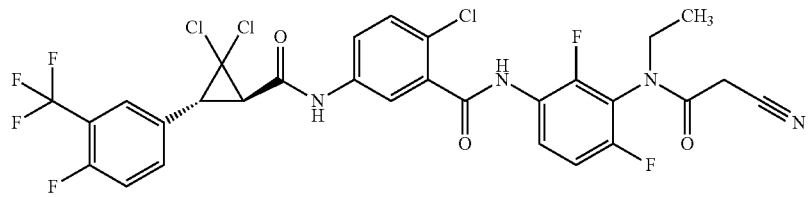 [SMILES: CCN(C(=O)CC#N)c1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white foam (0.071 g, 81%).

2-Chloro-N-(3-(2-cyano-N-ethylpropanamido)-2,4-difluorophenyl)-5-(((1R,3R)-2,2-dichloro-3-(4-fluoro-3-(trifluoromethyl)phenyl)cyclopropane-1-carboxamido)benzamide (F1764)

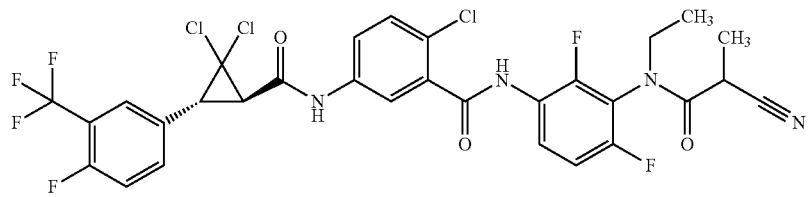 [SMILES: CCN(C(=O)C(C)C#N)c1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white foam (0.061 g, 68%).

2-Chloro-5-((1R,3R)-2,2-dichloro-3-(4-fluoro-3-(trifluoromethyl)phenyl)cyclopropane-1-carboxamido)-N-(2,4-difluoro-3-(2-(trifluoromethoxy)propanamido)phenyl)benzamide (F1771)

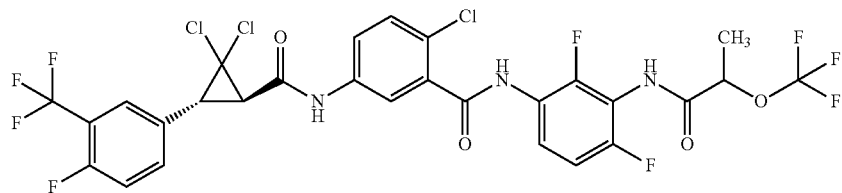 [SMILES: CC(OC(F)(F)F)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a tan foam (0.080 g, 82%).

2-Chloro-5-((1R,3R)-2,2-dichloro-3-(3-fluoro-5-(trifluoromethyl)phenyl)cyclopropane-1-carboxamido)-N-(2,4-difluoro-3-(2-(trifluoromethoxy)acetamido)phenyl)benzamide (F1772)

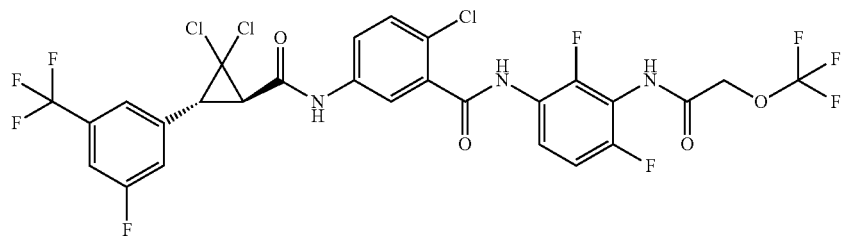 [SMILES: O=C(COC(F)(F)F)Nc1c(F)ccc(NC(=O)c2cc(NC(=O)[C@H]3[C@H](c4cc(F)cc(C(F)(F)F)c4)C3(Cl)Cl)ccc2Cl)c1F]

Isolated as a white foam (0.032 g, 36%).

2-Chloro-5-((1R,3R)-2,2-dichloro-3-(3-fluoro-5-(trifluoromethyl)phenyl)cyclopropane-1-carboxamido)-N-(2,4-difluoro-3-(2-(trifluoromethoxy)propanamido)phenyl)benzamide (F1773)

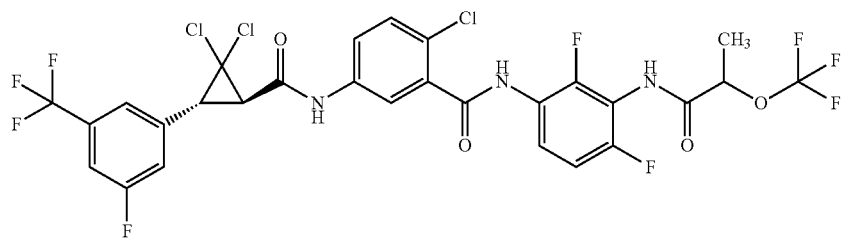 [SMILES: CC(OC(F)(F)F)C(=O)Nc1c(F)ccc(NC(=O)c2cc(NC(=O)[C@H]3[C@H](c4cc(F)cc(C(F)(F)F)c4)C3(Cl)Cl)ccc2Cl)c1F]

Isolated as a white foam (0.043 g, 47%).

2-Chloro-5-((1R,3R)-2,2-dichloro-3-(3-(trifluoromethyl)phenyl)cyclopropane-1-carboxamido)-N-(2,4-difluoro-3-(2-(trifluoromethoxy)acetamido)phenyl)benzamide (F1774)

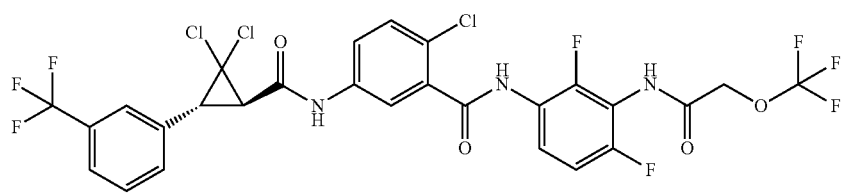 [SMILES: O=C(COC(F)(F)F)Nc1c(F)ccc(NC(=O)c2cc(NC(=O)[C@H]3[C@H](c4cccc(C(F)(F)F)c4)C3(Cl)Cl)ccc2Cl)c1F]

Isolated as a tan foam (0.071 g, 79%).

2-Chloro-5-(((1R,3R)-2,2-dichloro-3-(3-(trifluoromethyl)phenyl)cyclopropane-1-carboxamido)-N-(2,4-difluoro-3-(2-(trifluoromethoxy)propanamido)phenyl)benzamide (F1775)

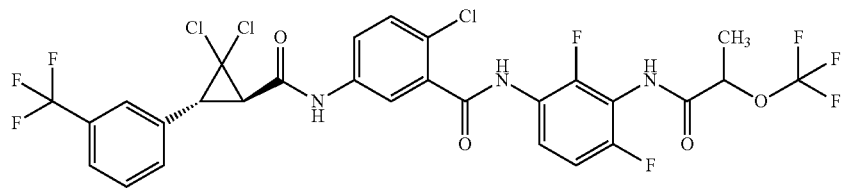 [SMILES: CC(OC(F)(F)F)C(=O)Nc1c(F)ccc(NC(=O)c2cc(NC(=O)[C@H]3[C@H](c4cccc(C(F)(F)F)c4)C3(Cl)Cl)ccc2Cl)c1F]

Isolated as a white solid (0.073 g, 80%).

5-((1R,3R)-3-(3-Bromo-4-fluorophenyl)-2,2-dichlorocyclopropane-1-carboxamido)-2-chloro-N-(2,4-difluoro-3-(2-(trifluoromethoxy)acetamido)phenyl)benzamide (F1780)

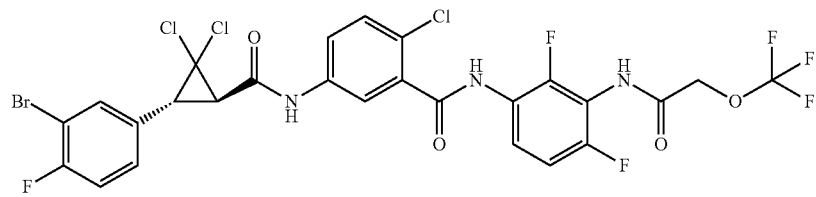

Isolated as a white solid (0.070 g, 79%).

5-((1R,3R)-3-(3-Bromo-4-fluorophenyl)-2,2-dichlorocyclopropane-1-carboxamido)-2-chloro-N-(2,4-difluoro-3-(2-(trifluoromethoxy)propanamido)phenyl)benzamide (F1781)

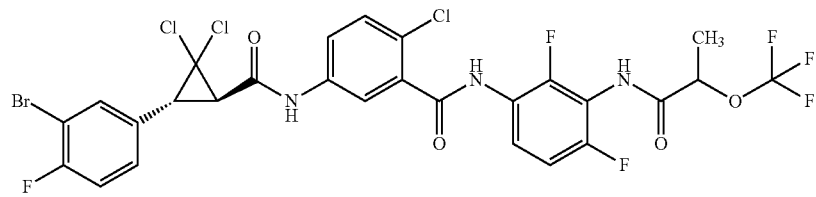

Isolated as a white solid (0.074 g, 82%).

N-(3-(2-Chloro-5-((1R,3R)-2,2-dichloro-3-(4-fluoro-3-(trifluoromethyl)phenyl)cyclopropane-1-carboxamido)benzamido)-2,6-difluorophenyl)-2,3,3,4,4,5,5-heptafluorotetrahydrofuran-2-carboxamide (F1782)

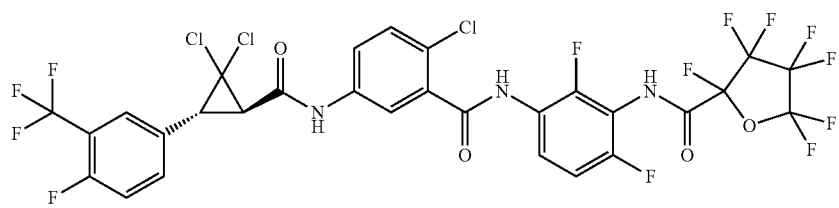 [SMILES: O=C(Nc1ccc(F)c(NC(=O)C2(F)OC(F)(F)C(F)(F)C2(F)F)c1F)c1cc(NC(=O)[C@H]2[C@H](c3ccc(F)c(C(F)(F)F)c3)C2(Cl)Cl)ccc1Cl]

Isolated as a white solid (0.079 g, 73%).

N-(3-(2-Chloro-5-(((1R,3R)-2,2-dichloro-3-(4-fluoro-
3-(trifluoromethyl)phenyl)cyclopropane-1-carbox-
amido)benzamido)-2,6-difluorophenyl)-2,3,3,4,4,5,5,
6,6-nonafluorotetrahydro-2H-pyran-2-carboxamide
(F1783)

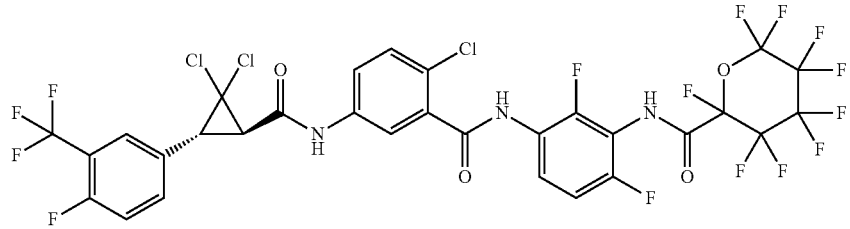 [SMILES: O=C(Nc1ccc(F)c(NC(=O)C2(F)OC(F)(F)C(F)(F)C(F)(F)C2(F)F)c1F)c1cc(NC(=O)[C@H]2[C@H](c3ccc(F)c(C(F)(F)F)c3)C2(Cl)Cl)ccc1Cl]

Isolated as a white solid (0.033 g, 29%).

2-Chloro-5-((1R,3R)-2,2-dichloro-3-(4-fluoro-3-
(trifluoromethyl)phenyl)cyclopropane-1-carbox-
amido)-N-(3-(N-ethyl-2-(trifluoromethoxy)acet-
amido)-2,4-difluorophenyl)benzamide (F1789)

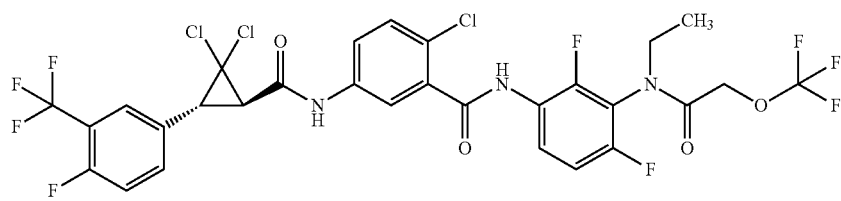 [SMILES: CCN(C(=O)COC(F)(F)F)c1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white solid (0.058 g, 61%).

2-Chloro-5-((1R,3R)-2,2-dichloro-3-(4-fluoro-3-
(trifluoromethyl)phenyl)cyclopropane-1-carbox-
amido)-N-(3-(2-(difluoromethoxy)acetamido)-2,4-
difluorophenyl)benzamide (F1790)

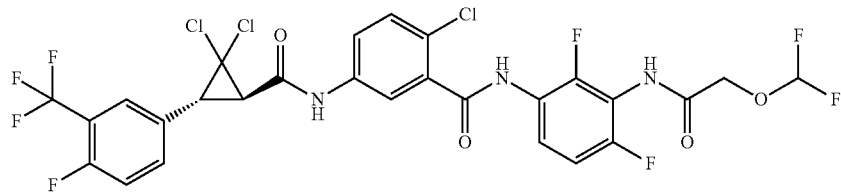 [SMILES: O=C(COC(F)F)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white foam (0.078 g, 84%).

2-Chloro-5-((1R,3R)-2,2-dichloro-3-(4-fluoro-3-
(trifluoromethyl)phenyl)cyclopropane-1-carbox-
amido)-N-(2,4-difluoro-3-(2-(perfluoroethoxy)acet-
amido)phenyl)benzamide (F1808)

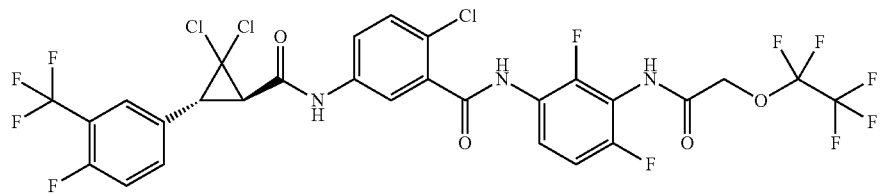 [SMILES: O=C(COC(F)(F)C(F)(F)F)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white solid (0.078 g, 76%).

N-(3-(2-Chloro-5-(((1R,3R)-2,2-dichloro-3-(4-fluoro-3-(trifluoromethyl)phenyl)cyclopropane-1-carboxamido)benzamido)-2,6-difluorophenyl)-2-methyltetrahydrofuran-2-carboxamide (F1809)

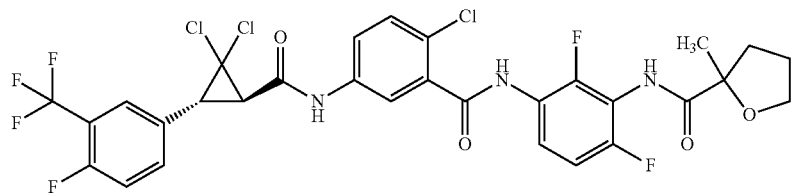 [SMILES: CC1(C(=O)Nc2c(F)ccc(NC(=O)c3cc(NC(=O)[C@H]4[C@H](c5ccc(F)c(C(F)(F)F)c5)C4(Cl)Cl)ccc3Cl)c2F)CCCO1]

Isolated as a white solid (0.061 g, 65%).

2-Chloro-N-(3-(2-cyano-N-(prop-2-yn-1-yl)acetamido)-2,4-difluorophenyl)-5-((1R,3R)-2,2-dichloro-3-(4-fluoro-3-(trifluoromethyl)phenyl)cyclopropane-1-carboxamido)benzamide (F1810)

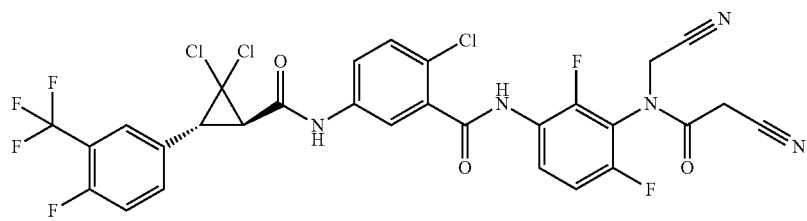 [SMILES: N#CCC(=O)N(CC#N)c1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white foam (0.144 g, 99%).

2-Chloro-5-((1R,3R)-2,2-dichloro-3-(4-fluoro-3-(trifluoromethyl)phenyl)cyclopropane-1-carboxamido)-N-(2,4-difluoro-3-(N-(prop-2-yn-1-yl)-2-(trifluoromethoxy)acetamido)phenyl)benzamide (F1811)

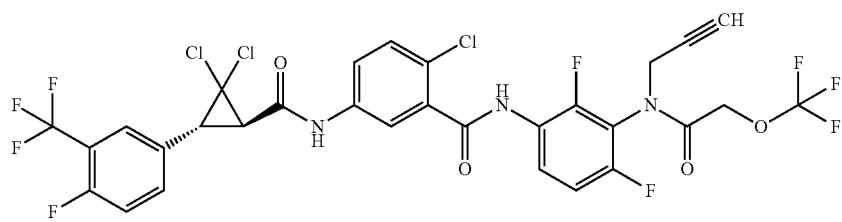 [SMILES: C#CCN(C(=O)COC(F)(F)F)c1c(F)ccc(NC(=O)c2cc(NC(=O)[C@H]3[C@H](c4ccc(F)c(C(F)(F)F)c4)C3(Cl)Cl)ccc2Cl)c1F]

Isolated as a clear, colorless oil (0.027 g, 20%).

2-Chloro-5-((1R,3R)-2,2-dichloro-3-(4-fluoro-3-(trifluoromethyl)phenyl)cyclopropane-1-carboxamido)-N-(2,4-difluoro-3-(1-((trifluoromethoxy)methyl)cyclopropane-1-carboxamido)phenyl)benzamide (F1821)

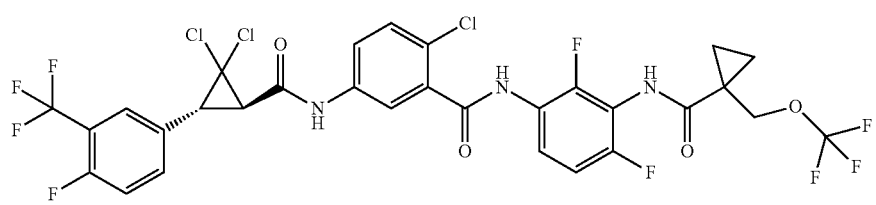 [SMILES: O=C(Nc1ccc(F)c(NC(=O)C2(COC(F)(F)F)CC2)c1F)c1cc(NC(=O)[C@H]2[C@H](c3ccc(F)c(C(F)(F)F)c3)C2(Cl)Cl)ccc1Cl]

Isolated as a white solid (0.024 g, 24%).

Ethyl 3-((3-(2-chloro-5-((1R,3R)-2,2-dichloro-3-(4-fluoro-3-(trifluoromethyl)phenyl)cyclopropane-1-carboxamido)benzamido)-2,6-difluorophenyl)amino)-2-fluoro-3-oxopropanoate (F1822)

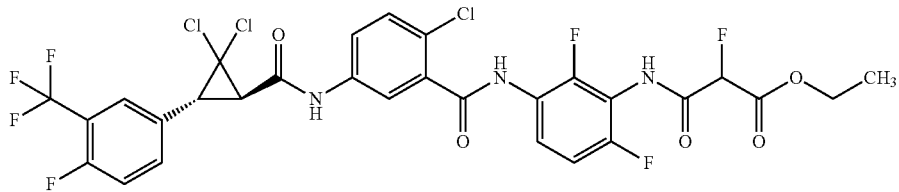 [SMILES: CCOC(=O)C(F)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white foam (0.097 g, 100%).

2-Chloro-N-(3-(2-cyano-N-(2-fluoroethyl)acetamido)-2,4-difluorophenyl)-5-((1R,3R)-2,2-dichloro-3-(4-fluoro-3-(trifluoromethyl)phenyl)cyclopropane-1-carboxamido)benzamide (F1823)

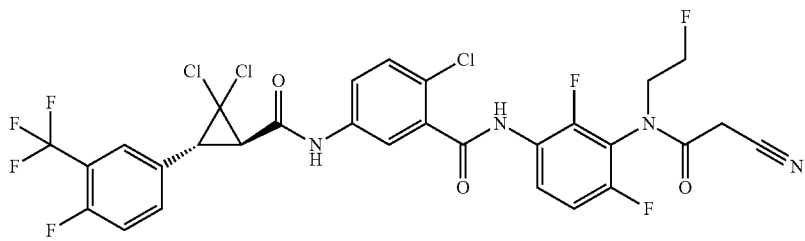 [SMILES: N#CCC(=O)N(CCF)c1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white foam (0.053 g, 68%).

2-Chloro-5-((1R,3R)-2,2-dichloro-3-(4-fluoro-3-(trifluoromethyl)phenyl)cyclopropane-1-carboxamido)-N-(3-(2-ethoxy-N-ethylpropanamido)-2,4-difluorophenyl)benzamide (F1827)

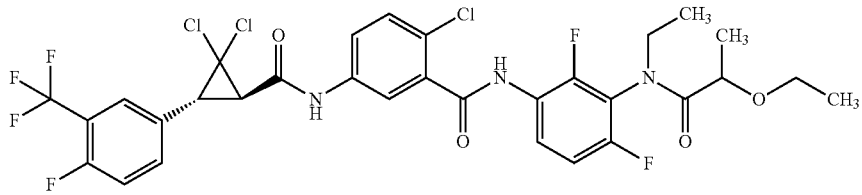 [SMILES: CCOC(C)C(=O)N(CC)c1c(F)ccc(NC(=O)c2cc(NC(=O)[C@H]3[C@H](c4ccc(F)c(C(F)(F)F)c4)C3(Cl)Cl)ccc2Cl)c1F]

Isolated as a gold oil (0.065 g, 71%).

2-Chloro-5-((1R,3R)-2,2-dichloro-3-(4-fluoro-3-(trifluoromethyl)phenyl)cyclopropane-1-carboxamido)-N-(3-(2-(difluoromethoxy)propanamido)-2,4-difluorophenyl)benzamide (F1828)

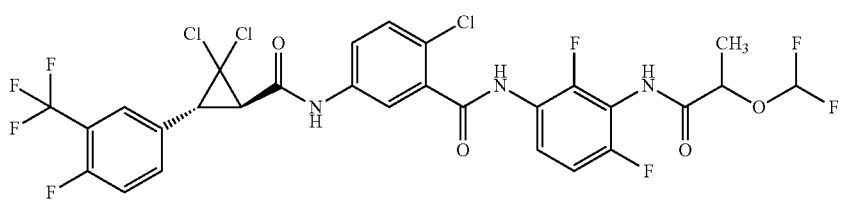 [SMILES: CC(OC(F)F)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white foam (0.037 g, 39%).

2-Chloro-5-((1R,3R)-2,2-dichloro-3-(4-fluoro-3-(trifluoromethyl)phenyl)cyclopropane-1-carboxamido)-N-(2,4-difluoro-3-(4,5,5,5-tetrafluoro-4-(trifluoromethyl)pentanamido)phenyl)benzamide (F1829)

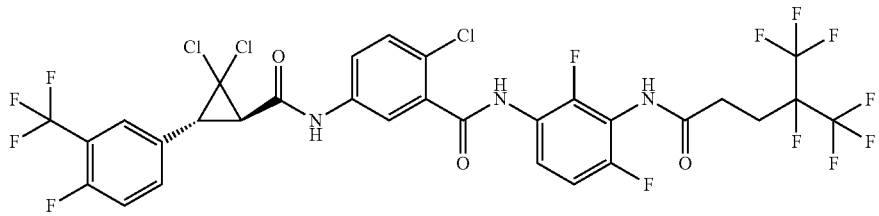 [SMILES: O=C(CCC(F)(C(F)(F)F)C(F)(F)F)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white foam (0.081 g, 75%).

2-Chloro-5-((1R,3R)-2,2-dichloro-3-(4-fluoro-3-(trifluoromethyl)phenyl)cyclopropane-1-carboxamido)-N-(2,4-difluoro-3-(5,5,5-trifluoropentanamido)phenyl)benzamide (F1830)

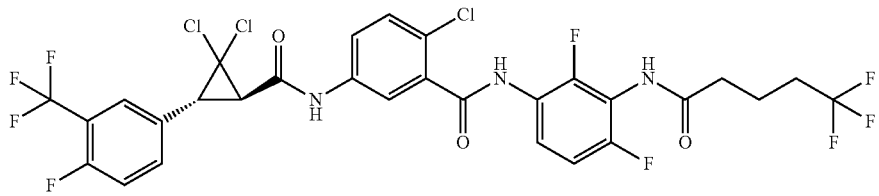

Isolated as a white solid (0.070 g, 72%).

N-(3-(2-Bromo-4,4,4-trifluorobutanamido)-2,4-difluorophenyl)-2-chloro-5-((1R,3R)-2,2-dichloro-3-(4-fluoro-3-(trifluoromethyl)phenyl)cyclopropane-1-carboxamido)benzamide (F1831)

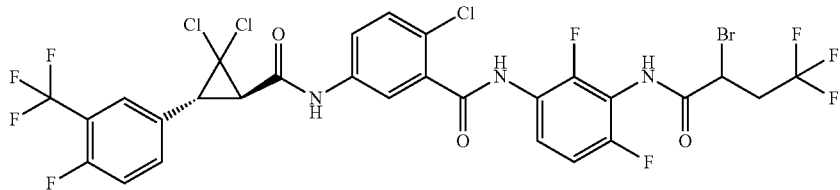 [SMILES: O=C(Nc1ccc(F)c(NC(=O)C(Br)CC(F)(F)F)c1F)c1cc(NC(=O)[C@H]2[C@H](c3ccc(F)c(C(F)(F)F)c3)C2(Cl)Cl)ccc1Cl]

Isolated as a white foam (0.073 g, 69%).

2-Chloro-5-((1R,3R)-2,2-dichloro-3-(4-fluoro-3-(trifluoromethyl)phenyl)cyclopropane-1-carboxamido)-N-(2,4-difluoro-3-(3,3,3-trifluoro-2-methylpropanamido)phenyl)benzamide (F1832)

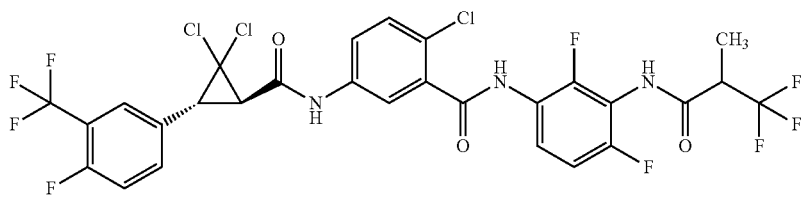 [SMILES: CC(C(=O)Nc1c(F)ccc(NC(=O)c2cc(NC(=O)[C@H]3[C@H](c4ccc(F)c(C(F)(F)F)c4)C3(Cl)Cl)ccc2Cl)c1F)C(F)(F)F]

Isolated as a white foam (0.032 g, 34%).

2-Chloro-5-((1R,3R)-2,2-dichloro-3-(4-fluoro-3-(trifluoromethyl)phenyl)cyclopropane-1-carboxamido)-N-(2,4-difluoro-3-(2,2,3,3-tetrafluoro-3-(trifluoromethoxy)propanamido)phenyl)benzamide (F1834)

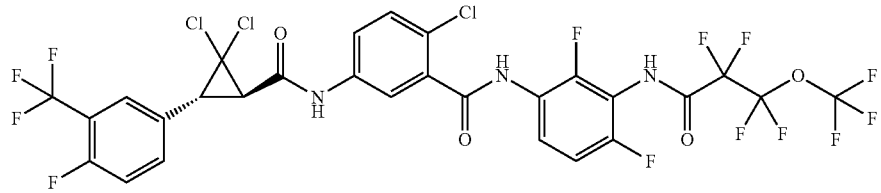

Isolated as a clear colorless oil (0.014 g, 13%).

2-Chloro-5-((1R,3R)-2,2-dichloro-3-(4-fluoro-3-(trifluoromethyl)phenyl)cyclopropane-1-carboxamido)-N-(2,4-difluoro-3-(4,4,4-trifluoro-2-methylbutanamido)phenyl)benzamide (F1835)

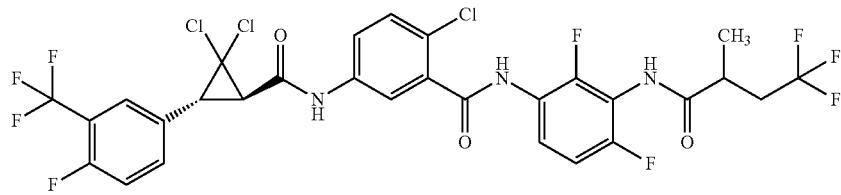

Isolated as a white solid (0.044 g, 45%).

2-Chloro-5-((1R,3R)-2,2-dichloro-3-(4-fluoro-3-(trifluoromethyl)phenyl)cyclopropane-1-carboxamido)-N-(2,4-difluoro-3-(2-(1-(trifluoromethyl)cyclopropyl)acetamido)phenyl)benzamide (F1836)

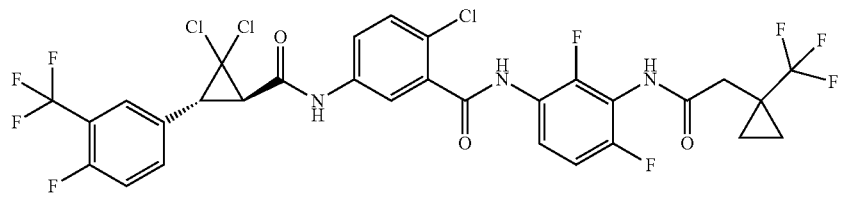 [SMILES: O=C(CC1(C(F)(F)F)CC1)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white solid (0.060 g, 61%).

N-(3-(2-Chloro-5-((1R,3R)-2,2-dichloro-3-(4-fluoro-3-(trifluoromethyl)phenyl)cyclopropane-1-carboxamido)benzamido)-2,6-difluorophenyl)-2-(trifluoromethyl)tetrahydrofuran-3-carboxamide (F1837)

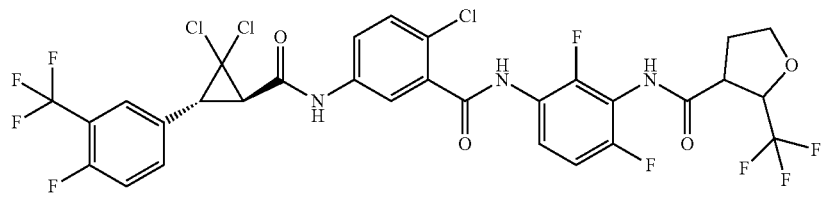 [SMILES: O=C(Nc1ccc(F)c(NC(=O)C2CCOC2C(F)(F)F)c1F)c1cc(NC(=O)[C@H]2[C@H](c3ccc(F)c(C(F)(F)F)c3)C2(Cl)Cl)ccc1Cl]

Isolated as a white solid (0.042 g, 42%).

2-Chloro-5-((1R,3R)-2,2-dichloro-3-(4-fluoro-3-(trifluoromethyl)phenyl)cyclopropane-1-carboxamido)-N-(2,4-difluoro-3-(2,2,3,4,4,4-hexafluorobutanamido)phenyl)benzamide (F1839)

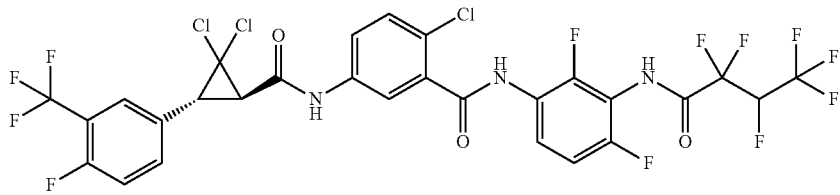

Isolated as a white solid (0.043 g, 42%).

2-Chloro-5-((1R,3R)-2,2-dichloro-3-(4-fluoro-3-(trifluoromethyl)phenyl)cyclopropane-1-carboxamido)-N-(2,4-difluoro-3-(4,4,4-trifluoro-3-oxobutanamido)phenyl)benzamide (F1840)

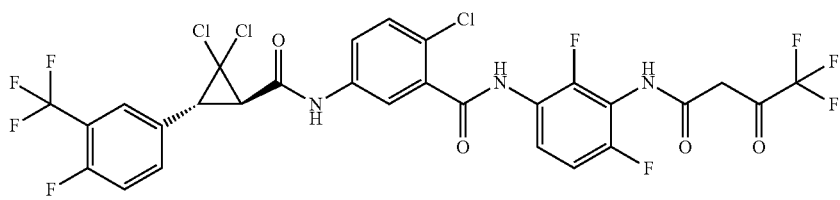 [SMILES: O=C(CC(=O)C(F)(F)F)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a gold solid (0.029 g, 30%).

2-Chloro-N-(3-(2-cyano-N-propylacetamido)-2,4-difluorophenyl)-5-((1R,3R)-2,2-dichloro-3-(4-fluoro-3-(trifluoromethyl)phenyl)cyclopropane-1-carboxamido)benzamide (F1841)

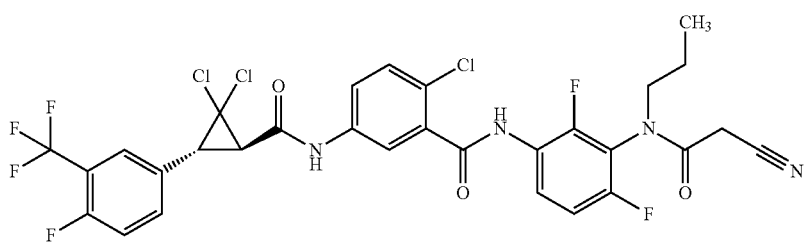 [SMILES: CCCN(C(=O)CC#N)c1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white solid (0.096 g, 64%).

2-Chloro-5-((1R,3R)-2,2-dichloro-3-(4-fluoro-3-(trifluoromethyl)phenyl)cyclopropane-1-carboxamido)-N-(3-(2-ethoxy-N-propylpropanamido)-2,4-difluorophenyl)benzamide (F1842)

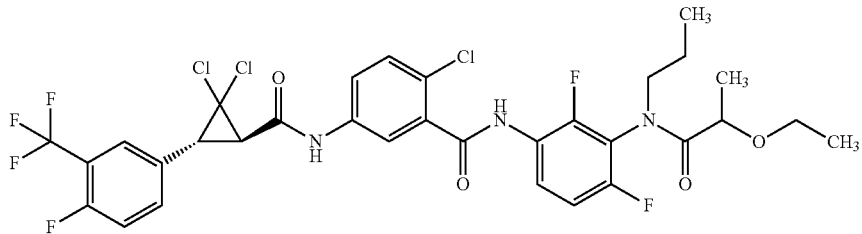 [SMILES: CCCN(C(=O)C(C)OCC)c1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white solid (0.056 g, 29%).

2-Chloro-5-((1R,3R)-2,2-dichloro-3-(4-fluoro-3-(trifluoromethyl)phenyl)cyclopropane-1-carboxamido)-N-(2,4-difluoro-3-(1-(trifluoromethyl)cyclobutane-1-carboxamido)phenyl)benzamide (F1849)

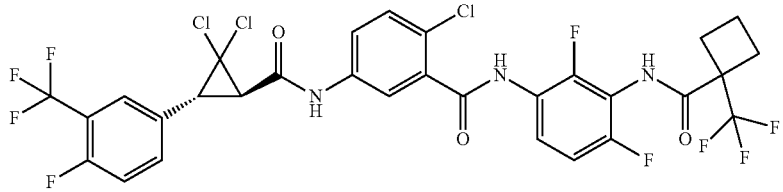 [SMILES: O=C(Nc1ccc(F)c(NC(=O)C2(C(F)(F)F)CCC2)c1F)c1cc(NC(=O)[C@H]2[C@H](c3ccc(F)c(C(F)(F)F)c3)C2(Cl)Cl)ccc1Cl]

Isolated as a white solid (0.006 g, 6%).

N-(3-(3-Bromopropanamido)-2,4-difluorophenyl)-2-chloro-5-((1R,3R)-2,2-dichloro-3-(4-fluoro-3-(trifluoromethyl)phenyl)cyclopropane-1-carboxamido)benzamide (F1851)

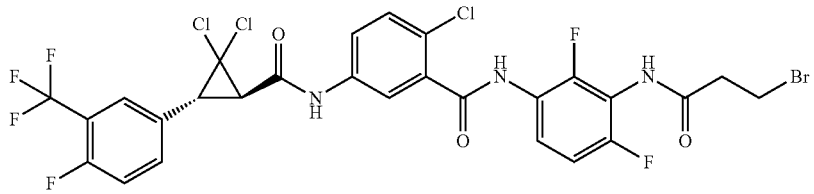 [SMILES: O=C(CCBr)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white solid (0.043 g, 44%).

N-(3-(3-Bromobutanamido)-2,4-difluorophenyl)-2-chloro-5-((1R,3R)-2,2-dichloro-3-(4-fluoro-3-(trifluoromethyl)phenyl)cyclopropane-1-carboxamido)benzamide (F1853)

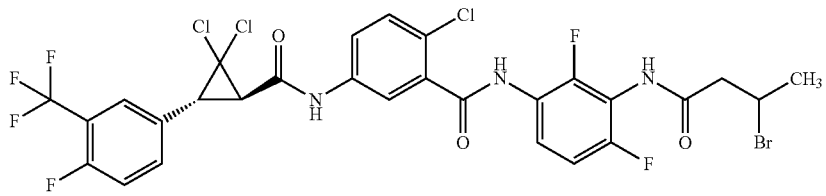

Isolated as a white solid (0.054 g, 55%).

2-Chloro-N-(3-(3-cyclopropylpropanamido)-2,4-difluorophenyl)-5-((1R,3R)-2,2-dichloro-3-(4-fluoro-3-(trifluoromethyl)phenyl)cyclopropane-1-carboxamido)benzamide (F1854)

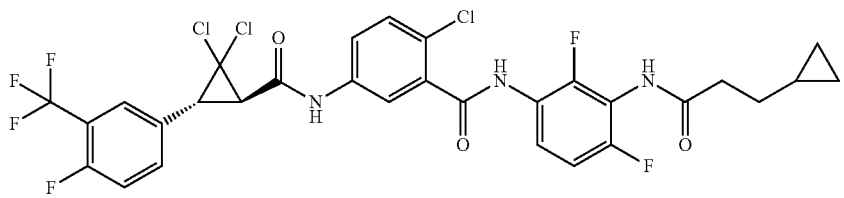 [SMILES: O=C(CCC1CC1)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white solid (0.061 g, 67%).

2-Chloro-N-(3-(3-cyanopropanamido)-2,4-difluoro-phenyl)-5-((1R,3R)-2,2-dichloro-3-(4-fluoro-3-(trifluoromethyl)phenyl)cyclopropane-1-carboxamido)benzamide (F1855)

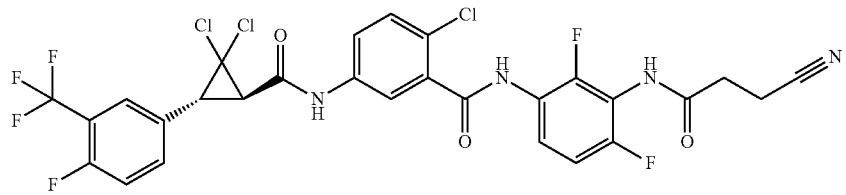 [SMILES: N#CCCC(=O)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white solid (0.007 g, 8%).

2-Chloro-5-((1R,3R)-2,2-dichloro-3-(4-fluoro-3-(trifluoromethyl)phenyl)cyclopropane-1-carboxamido)-N-(3-(5,5-dimethylhexanamido)-2,4-difluorophenyl)benzamide (F1856)

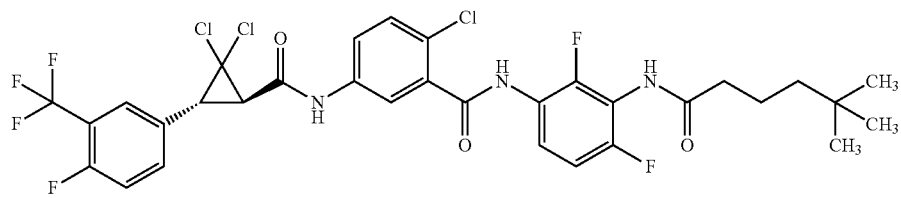 [SMILES: CC(C)(C)CCCC(=O)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white solid (0.074 g, 77%).

2-Chloro-N-(3-(4-cyanobutanamido)-2,4-difluoro-phenyl)-5-((1R,3R)-2,2-dichloro-3-(4-fluoro-3-(trifluoromethyl)phenyl)cyclopropane-1-carboxamido)benzamide (F1857)

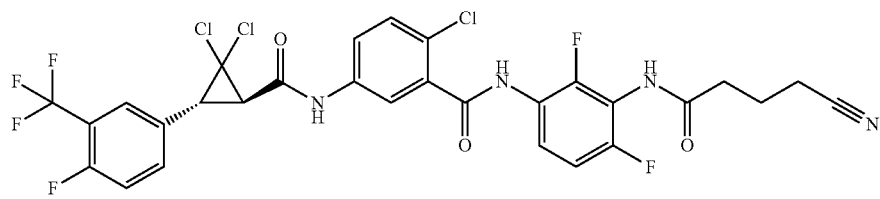 [SMILES: N#CCCCC(=O)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white solid (0.060 g, 66%).

2-Chloro-5-((1R,3R)-2,2-dichloro-3-(4-fluoro-3-(trifluoromethyl)phenyl)cyclopropane-1-carboxamido)-N-(2,4-difluoro-3-(4,5,5,5-tetrafluoro-4-(trifluoromethoxy)pentanamido)phenyl)benzamide (F1858)

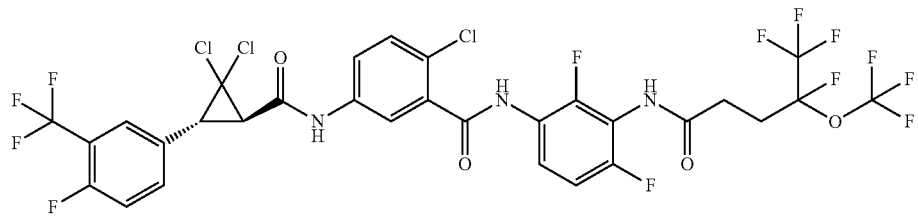 [SMILES: O=C(CCC(F)(OC(F)(F)F)C(F)(F)F)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white solid (0.082 g, 74%).

N-(3-((E)-But-2-enamido)-2,4-difluorophenyl)-2-chloro-5-((1R,3R)-2,2-dichloro-3-(4-fluoro-3-(trifluoromethyl)phenyl)cyclopropane-1-carboxamido)benzamide (F1868)

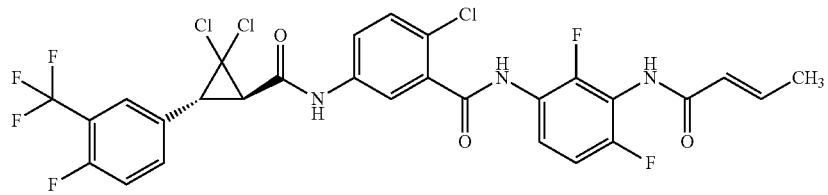

Isolated as a white solid (0.055 g, 47%).

2-Chloro-5-((1R,3R)-2,2-dichloro-3-(4-fluoro-3-(trifluoromethyl)phenyl)cyclopropane-1-carboxamido)-N-(2,4-difluoro-3-((E)-4,4,4-trifluorobut-2-enamido)phenyl)benzamide (F1869)

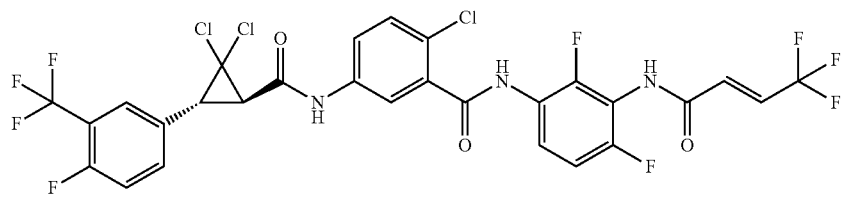 [SMILES: O=C(/C=C/C(F)(F)F)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white solid (0.0% g, 76%).

2-Chloro-5-((1R,3R)-2,2-dichloro-3-(4-fluoro-3-(trifluoromethyl)phenyl)cyclopropane-1-carboxamido)-N-(2,4-difluoro-3-(2-fluoroacrylamido)phenyl)benzamide (F1870)

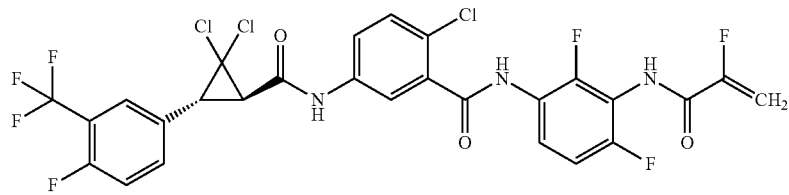 [SMILES: C=C(F)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white solid (0.064 g, 54%).

N-(3-(But-3-enamido)-2,4-difluorophenyl)-2-chloro-5-((1R,3R)-2,2-dichloro-3-(3-(trifluoromethyl)phenyl)cyclopropane-1-carboxamido)benzamide (F1878)

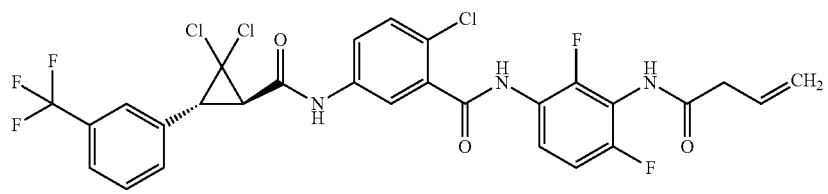 [SMILES: C=CCC(=O)Nc1c(F)ccc(NC(=O)c2cc(NC(=O)[C@H]3[C@H](c4cccc(C(F)(F)F)c4)C3(Cl)Cl)ccc2Cl)c1F]

Isolated as a white solid (0.076 g, 86%).

N-(3-(But-3-enamido)-2,4-difluorophenyl)-2-chloro-5-((1R,3R)-2,2-dichloro-3-(3-fluoro-5-(trifluoromethyl)phenyl)cyclopropane-1-carboxamido)benzamide (F1879)

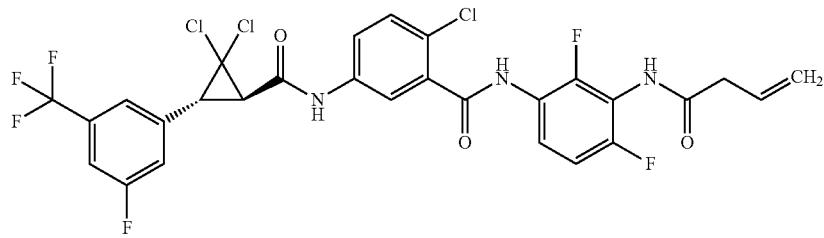 [SMILES: C=CCC(=O)Nc1c(F)ccc(NC(=O)c2cc(NC(=O)[C@H]3[C@H](c4cc(F)cc(C(F)(F)F)c4)C3(Cl)Cl)ccc2Cl)c1F]

Isolated as a white solid (0.076 g, 86%).

5-((1R,3R)-3-(3-Bromo-4-fluorophenyl)-2,2-dichlorocyclopropane-1-carboxamido)-N-(3-(but-3-enamido)-2,4-difluorophenyl)-2-chlorobenzamide (F1880)

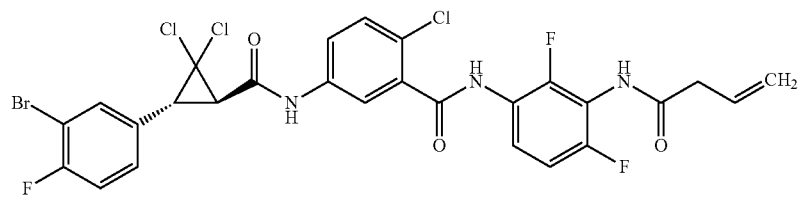

Isolated as a white solid (0.089 g, 100%).

The following compounds were prepared in like manner to the procedure outlined in Example 7:

Methyl 2-((3-(2-chloro-5-((1R,3R)-2,2-dichloro-3-(4-fluoro-3-(trifluoromethyl)phenyl)cyclopropane-1-carboxamido)benzamido)-2,6-difluorophenyl)amino)-2-oxoacetate (F1753)

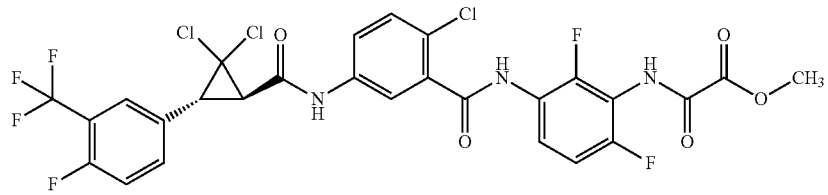 [SMILES: COC(=O)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white solid (0.064 g, 72%).

The following compounds were prepared in like manner to the procedure outlined in Example 9:

2-Chloro-5-((1R,3R)-2,2-dichloro-3-(4-fluoro-3-(trifluoromethyl)phenyl)cyclopropane-1-carboxamido)-N-(2,4-difluoro-3-((3,3,3-trifluoropropyl)sulfonamido)phenyl)benzamide (F1350)

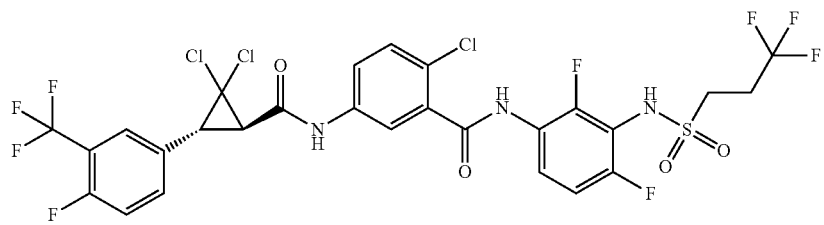 [SMILES: O=C(Nc1ccc(F)c(NS(=O)(=O)CCC(F)(F)F)c1F)c1cc(NC(=O)[C@H]2[C@H](c3ccc(F)c(C(F)(F)F)c3)C2(Cl)Cl)ccc1Cl]

Isolated as a clear colorless oil (0.019 g, 14%).

2-Chloro-5-(((1R,3R)-2,2-dichloro-3-(4-fluoro-3-(trifluoromethyl)phenyl)cyclopropane-1-carboxamido)-N-(3-(((2,2-dichlorocyclopropyl)methyl)sulfonamido)-2,4-difluorophenyl)benzamide (F1361)

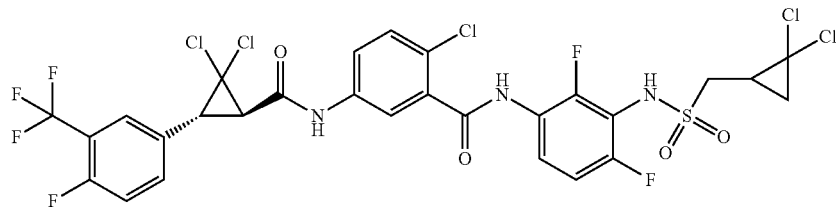 [SMILES: O=C(Nc1ccc(F)c(NS(=O)(=O)CC2CC2(Cl)Cl)c1F)c1cc(NC(=O)[C@H]2[C@H](c3ccc(F)c(C(F)(F)F)c3)C2(Cl)Cl)ccc1Cl]

Isolated as a white foam (0.028 g, 20%).
The following compounds were prepared in like manner to the procedure outlined in Example 10:

trans-tert-Butyl (4-(((4-(2-chloro-5-(2,2-dichloro-3-(3,5-dichlorophenyl)cyclopropane-1-carboxamido)benzamido)-3-methylphenyl)amino)methyl)phenyl)carbamate (F1348)

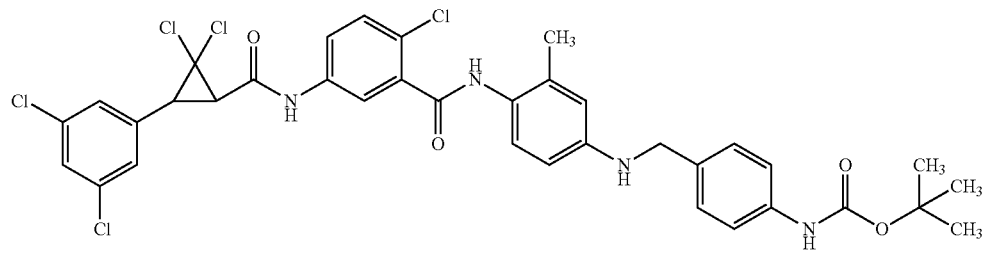 [SMILES: Cc1cc(NCc2ccc(NC(=O)OC(C)(C)C)cc2)ccc1NC(=O)c1cc(NC(=O)C2C(c3cc(Cl)cc(Cl)c3)C2(Cl)Cl)ccc1Cl]

Isolated as a yellow oil (0.109 g, 76%).
The following compounds were prepared in like manner to the procedure outlined in Example 12:

trans-2-Chloro-5-(2,2-dichloro-3-(3,5-dichlorophenyl)cyclopropane-1-carboxamido)-N-(4-((4-hydroxybenzyl)amino)-2-methylphenyl)benzamide (F1353)

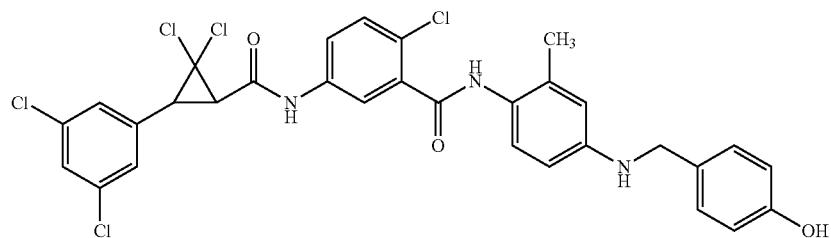 [SMILES: Cc1cc(NCc2ccc(O)cc2)ccc1NC(=O)c1cc(NC(=O)C2C(c3cc(Cl)cc(Cl)c3)C2(Cl)Cl)ccc1Cl]

Isolated as a pale yellow foam (0.057 g, 69%).

467

The following compounds were prepared in like manner to the procedure outlined in Example 13:

N-(3-Amino-2,6-difluorophenyl)-2-chloro-5-((1R,3R)-2,2-dichloro-3-(3,4,5-trichlorophenyl)cyclopropane-1-carboxamido)-3-fluorobenzamide (F1337)

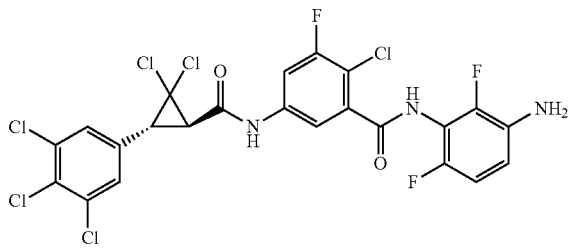 [SMILES: Nc1ccc(F)c(NC(=O)c2cc(NC(=O)[C@H]3[C@H](c4cc(Cl)c(Cl)c(Cl)c4)C3(Cl)Cl)cc(F)c2Cl)c1F]

Isolated as a white solid (0.166 g, 80%).

N-(3-Amino-2,6-difluorophenyl)-2-chloro-5-((1R,3R)-2,2-dichloro-3-(3,4-dichlorophenyl)cyclopropane-1-carboxamido)-3-fluorobenzamide (F1338)

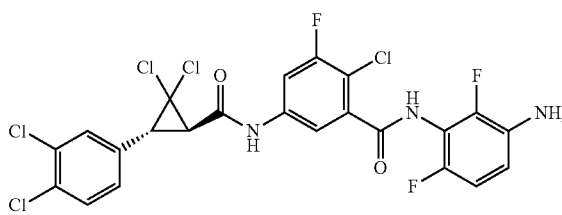

Isolated as an off-white powder (0.154 g, 73%).

468

N-(3-Amino-2,6-difluorophenyl)-2-chloro-5-((1R,3R)-2,2-dichloro-3-(4-fluoro-3-(trifluoromethyl)phenyl)cyclopropane-1-carboxamido)-3-fluorobenzamide (F1339)

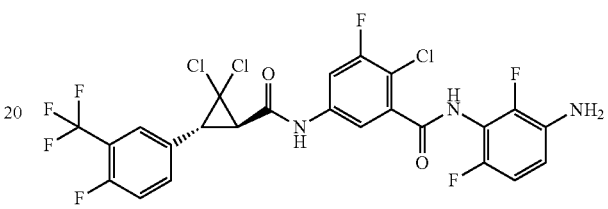

Isolated as a light yellow solid (0.153 g, 74%).

trans-N-(4-((4-Aminobenzyl)amino)-2-methylphenyl)-2-chloro-5-(2,2-dichloro-3-(3,5-dichlorophenyl)cyclopropane-1-carboxamido)benzamide (F1349)

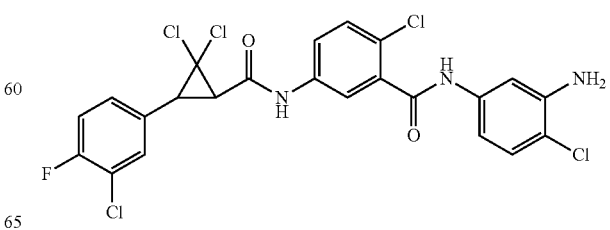

Isolated as a yellow solid (0.018 g, 26%).

trans-N-(3-Amino-4-chlorophenyl)-2-chloro-5-(2,2-dichloro-3-(3-chloro-4-fluorophenyl)cyclopropane-1-carboxamido)benzamide (F1365)

Isolated as a white solid (0.143 g, 84%).

469 trans-N-(4-Amino-3,5-dichlorophenyl)-2-chloro-5-(2,2-dichloro-3-(3-chloro-4-fluorophenyl)cyclopropane-1-carboxamido)benzamide (F1367)

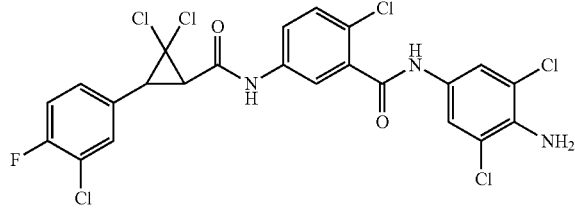 [SMILES: Nc1c(Cl)cc(NC(=O)c2cc(NC(=O)C3C(c4ccc(F)c(Cl)c4)C3(Cl)Cl)ccc2Cl)cc1Cl]

Isolated as a tan solid (0.154 g, 61%).

trans-N-(4-Amino-3-chlorophenyl)-2-chloro-5-(2,2-dichloro-3-(3-chloro-4-fluorophenyl)cyclopropane-1-carboxamido)benzamide (F1370)

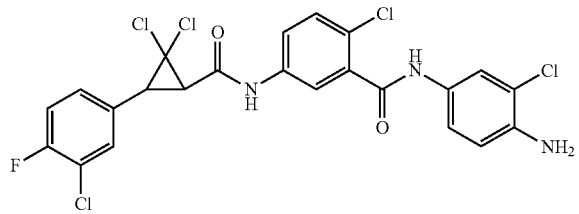 [SMILES: Nc1ccc(NC(=O)c2cc(NC(=O)C3C(c4ccc(F)c(Cl)c4)C3(Cl)Cl)ccc2Cl)cc1Cl]

Isolated as a white foam (0.170 g, 70%).

trans-N-(4-Amino-3-cyanophenyl)-2-chloro-5-(2,2-dichloro-3-(3-chloro-4-fluorophenyl)cyclopropane-1-carboxamido)benzamide (F1387)

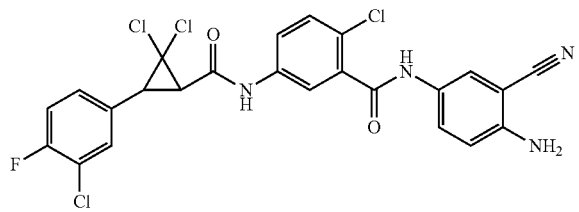 [SMILES: N#Cc1cc(NC(=O)c2cc(NC(=O)C3C(c4ccc(F)c(Cl)c4)C3(Cl)Cl)ccc2Cl)ccc1N]

Isolated as a white foam (0.106 g, 34%).

N-(4-Amino-2,3-dimethylphenyl)-2-chloro-5-((1R,3R)-2,2-dichloro-3-(4-fluoro-3-(trifluoromethyl)phenyl)cyclopropane-1-carboxamido)benzamide (F1389)

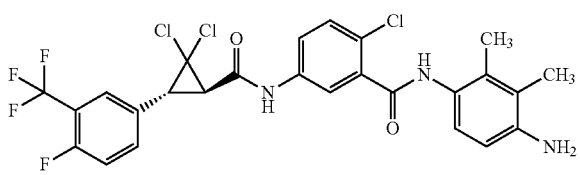 [SMILES: Cc1c(N)ccc(NC(=O)c2cc(NC(=O)[C@H]3[C@H](c4ccc(F)c(C(F)(F)F)c4)C3(Cl)Cl)ccc2Cl)c1C]

Isolated as a white solid (0.111 g, 64%).

470 trans-N-(4-Amino-3-(trifluoromethyl)phenyl)-2-chloro-5-(2,2-dichloro-3-(3-chloro-4-fluorophenyl)cyclopropane-1-carboxamido)benzamide (F1390)

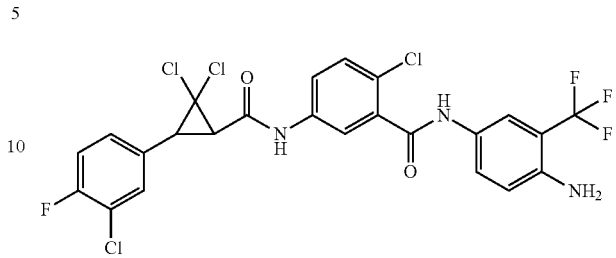

Isolated as a white foam (0.191 g, 67%).

N-(3-Amino-2,6-difluorophenyl)-2-chloro-5-((1R,3R)-2,2-dichloro-3-(4-fluoro-3-(trifluoromethyl)phenyl)cyclopropane-1-carboxamido)benzamide (F1391)

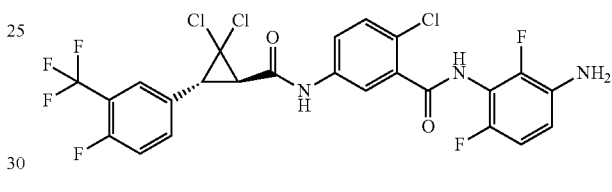

Isolated as a tan solid (0.600 g, 98%).

N-(5-Amino-2,4-difluorophenyl)-2-chloro-5-((1R,3R)-2,2-dichloro-3-(3-chloro-4-fluorophenyl)cyclopropane-1-carboxamido)-3-fluorobenzamide (F1395)

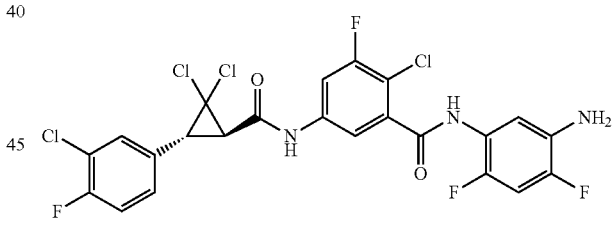

Isolated as a light-tan solid (0.276 g, 83%).

N-(5-Amino-2,4-difluorophenyl)-2-chloro-5-((1R,3R)-2,2-dichloro-3-(3,4-dichlorophenyl)cyclopropane-1-carboxamido)-3-fluorobenzamide (F1396)

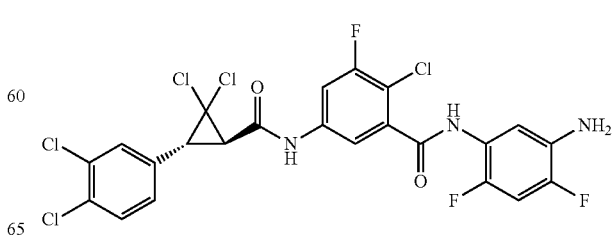

Isolated as a tan solid (0.319 g, 95%).

471

N-(5-Amino-2,4-difluorophenyl)-2-chloro-5-((1R,3R)-2,2-dichloro-3-(3,4,5-trichlorophenyl)cyclopropane-1-carboxamido)-3-fluorobenzamide (F1397)

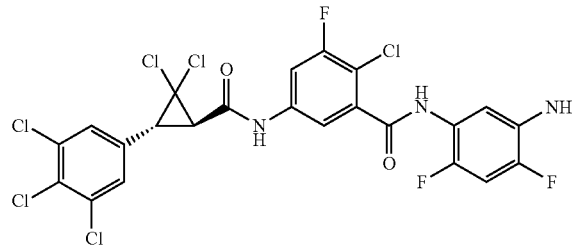

Isolated as a light-tan solid (0.302 g, 92%).

N-(5-Amino-2,4-difluorophenyl)-2-chloro-5-((1R,3R)-2,2-dichloro-3-(4-fluoro-3-(trifluoromethyl)phenyl)cyclopropane-1-carboxamido)-3-fluorobenzamide (F1398)

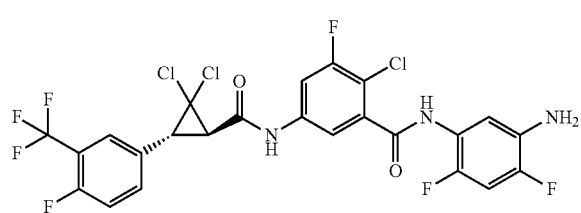 [SMILES: Nc1cc(NC(=O)c2cc(NC(=O)[C@H]3[C@H](c4ccc(F)c(C(F)(F)F)c4)C3(Cl)Cl)cc(F)c2Cl)c(F)cc1F]

Isolated as a tan solid (0.311 g, 92%).

N-(5-Amino-2,4-difluorophenyl)-2-chloro-5-((1R,3R)-2,2-dichloro-3-(3,5-dichlorophenyl)cyclopropane-1-carboxamido)-3-fluorobenzamide (F1399)

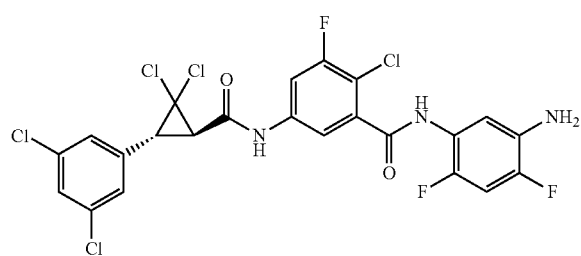 [SMILES: Nc1cc(NC(=O)c2cc(NC(=O)[C@H]3[C@H](c4cc(Cl)cc(Cl)c4)C3(Cl)Cl)cc(F)c2Cl)c(F)cc1F]

Isolated as a light-tan solid (0.301 g, 95%).

N-(3-Amino-4-methylphenyl)-2-chloro-5-((1R,3R)-2,2-dichloro-3-(4-fluoro-3-(trifluoromethyl)phenyl)cyclopropane-1-carboxamido)benzamide (F1413)

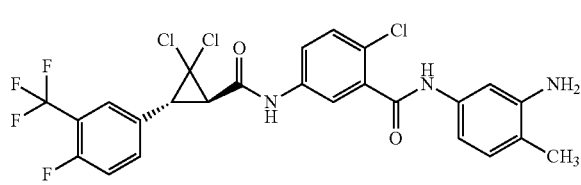 [SMILES: Cc1ccc(NC(=O)c2cc(NC(=O)[C@H]3[C@H](c4ccc(F)c(C(F)(F)F)c4)C3(Cl)Cl)ccc2Cl)cc1N]

Isolated as a white solid (0.143 g, 65%).

472

N-(3-Amino-2,6-difluorophenyl)-2-chloro-5-((1R,3R)-2,2-dichloro-3-(3,4-dichlorophenyl)cyclopropane-1-carboxamido)-3-methylbenzamide (F1426)

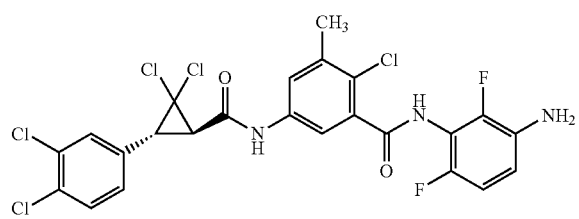

Isolated as a white powder (0.176 g, 76%).

N-(3-Amino-2,6-difluorophenyl)-2-chloro-5-((1R,3R)-2,2-dichloro-3-(3,4,5-trichlorophenyl)cyclopropane-1-carboxamido)-3-methylbenzamide (F1427)

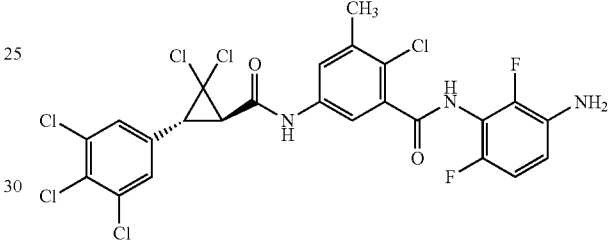

Isolated as an off-white solid (0.194 g, 82%).

N-(3-Amino-2,6-difluorophenyl)-2-chloro-5-((1R,3R)-2,2-dichloro-3-(4-fluoro-3-(trifluoromethyl)phenyl)cyclopropane-1-carboxamido)-3-methylbenzamide (F1428)

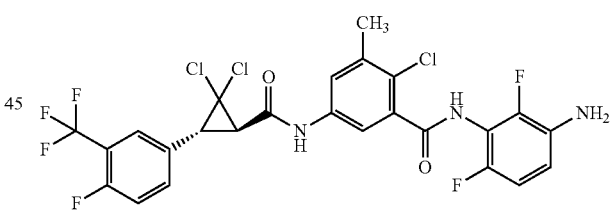

Isolated as a tan powder (0.163 g, 70%).

N-(3-Amino-2,4-difluorophenyl)-2-chloro-5-((1R,3R)-2,2-dichloro-3-(3,4-dichlorophenyl)cyclopropane-1-carboxamido)-3-methylbenzamide (F1446)

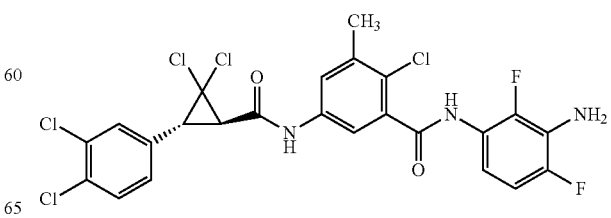

Isolated as an off-white solid (0.167 g, 66%).

N-(3-Amino-2-methylphenyl)-2-chloro-5-((1R,3R)-
2,2-dichloro-3-(4-fluoro-3-(trifluoromethyl)phenyl)
cyclopropane-1-carboxamido)benzamide (F1448)

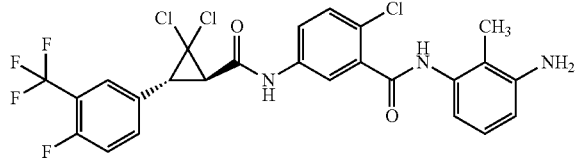 [SMILES: Cc1c(N)cccc1NC(=O)c1cc(NC(=O)[C@H]2[C@H](c3ccc(F)c(C(F)(F)F)c3)C2(Cl)Cl)ccc1Cl]

Isolated as a white solid (0.146 g, 80%).

N-(3-Amino-2,4-difluorophenyl)-2-chloro-5-((1R,
3R)-2,2-dichloro-3-(3,4,5-trichlorophenyl)cyclopro-
pane-1-carboxamido)-3-methylbenzamide (F1449)

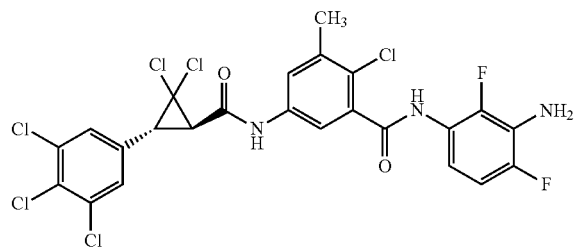 [SMILES: Cc1cc(NC(=O)[C@H]2[C@H](c3cc(Cl)c(Cl)c(Cl)c3)C2(Cl)Cl)cc(C(=O)Nc2ccc(F)c(N)c2F)c1Cl]

Isolated as an off-white solid (0.193 g, 78%).

N-(3-Amino-2,4-difluorophenyl)-2-chloro-5-((1R,
3R)-2,2-dichloro-3-(4-fluoro-3-(trifluoromethyl)
phenyl)cyclopropane-1-carboxamido)-3-methylbenz-
amide (F1458)

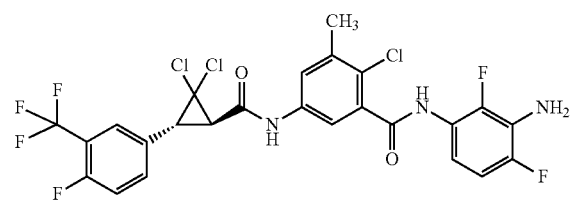 [SMILES: Cc1cc(NC(=O)[C@H]2[C@H](c3ccc(F)c(C(F)(F)F)c3)C2(Cl)Cl)cc(C(=O)Nc2ccc(F)c(N)c2F)c1Cl]

Isolated as an off-white powder (0.154 g, 64%).

N-(3-Amino-2,4-difluorophenyl)-5-((1R,3R)-2,2-
dichloro-3-(3,4-dichlorophenyl)cyclopropane-1-
carboxamido)-2-fluorobenzamide (F1459)

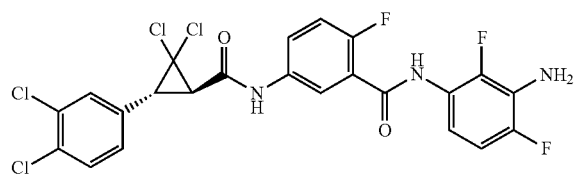 [SMILES: Nc1c(F)ccc(NC(=O)c2cc(NC(=O)[C@H]3[C@H](c4ccc(Cl)c(Cl)c4)C3(Cl)Cl)ccc2F)c1F]

Isolated as a light yellow foam (0.382 g, 80%).

N-(5-Amino-2,4-difluorophenyl)-2-chloro-5-((1R,
3R)-2,2-dichloro-3-(3,4-dichlorophenyl)cyclopro-
pane-1-carboxamido)-3-methylbenzamide (F1470)

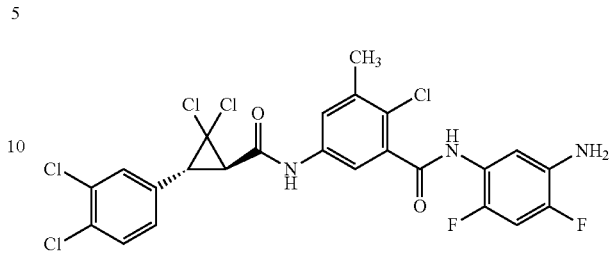

Isolated as an off-white powder (0.194 g, 85%).

N-(5-Amino-2,4-difluorophenyl)-2-chloro-5-((1R,
3R)-2,2-dichloro-3-(3,4,5-trichlorophenyl)cyclopro-
pane-1-carboxamido)-3-methylbenzamide (F1477)

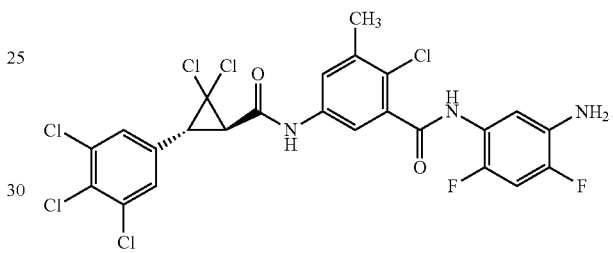

Isolated as an off-white powder (0.155 g, 61%).

N-(5-Amino-2,4-difluorophenyl)-2-chloro-5-((1R,
3R)-2,2-dichloro-3-(4-fluoro-3-(trifluoromethyl)
phenyl)cyclopropane-1-carboxamido)-3-methylbenz-
amide (F1478)

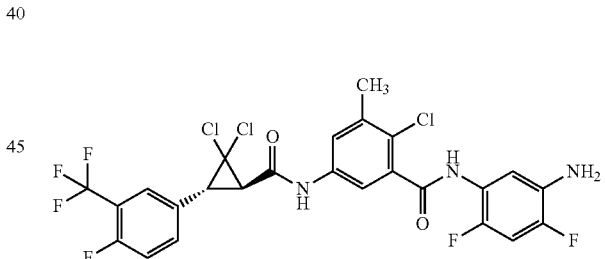

Isolated as an off-white powder (0.185 g, 70%).

N-(5-Amino-2,4-difluorophenyl)-5-((1R,3R)-2,2-
dichloro-3-(3,4-dichlorophenyl)cyclopropane-1-
carboxamido)-2-fluorobenzamide (F1490)

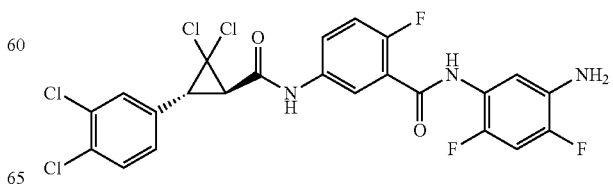

Isolated as a light brown foam (0.387 g, 89%).

2-Chloro-5-((1R,3R)-2,2-dichloro-3-(3,4-dichlorophenyl)cyclopropane-1-carboxamido)-N-(2,4-difluoro-3-(methylamino)phenyl)benzamide (F1550)

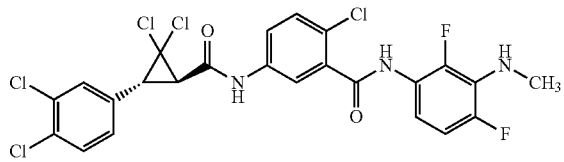 [SMILES: CNc1c(F)ccc(NC(=O)c2cc(NC(=O)[C@H]3[C@H](c4ccc(Cl)c(Cl)c4)C3(Cl)Cl)ccc2Cl)c1F]

Isolated as a yellow foam (0.870 g, 97%).

N-(5-Amino-2,4-difluorophenyl)-2-chloro-5-((1R,3R)-2,2-dichloro-3-(4-fluoro-3-(trifluoromethyl)phenyl)cyclopropane-1-carboxamido)benzamide (F1566)

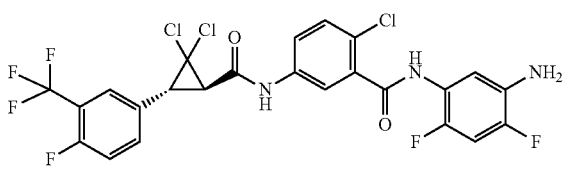 [SMILES: Nc1cc(NC(=O)c2cc(NC(=O)[C@H]3[C@H](c4ccc(F)c(C(F)(F)F)c4)C3(Cl)Cl)ccc2Cl)c(F)cc1F]

Isolated as a tan solid (0.210 g, 89%).

trans-N-(3-Amino-2,4-difluorophenyl)-2-chloro-5-(2,2-dichloro-3-(4-fluoro-3-iodophenyl)cyclopropane-1-carboxamido)benzamide (F1622)

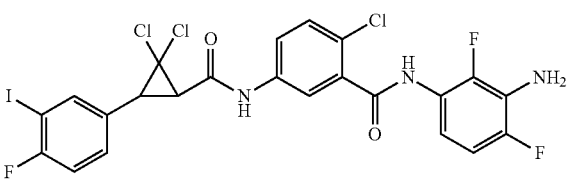 [SMILES: Nc1c(F)ccc(NC(=O)c2cc(NC(=O)C3C(c4ccc(F)c(I)c4)C3(Cl)Cl)ccc2Cl)c1F]

Isolated as a tan foam (0.108 g, 94%).

N-(3-Amino-2,4-difluorophenyl)-2-chloro-5-((1R,3R)-2,2-dichloro-3-(4-chloro-3-(trifluoromethyl)phenyl)cyclopropane-1-carboxamido)benzamide (F1631)

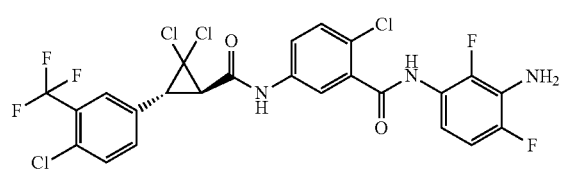 [SMILES: Nc1c(F)ccc(NC(=O)c2cc(NC(=O)[C@H]3[C@H](c4ccc(Cl)c(C(F)(F)F)c4)C3(Cl)Cl)ccc2Cl)c1F]

Isolated as a tan solid (0.64 g, 98%).

N-(3-Amino-2,4-difluorophenyl)-2-chloro-5-((1R,3R)-2,2-dichloro-3-(3-(trifluoromethyl)phenyl)cyclopropane-1-carboxamido)benzamide (F1666)

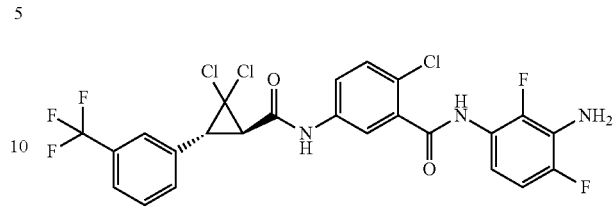

Isolated as a white solid (0.860 g, 85%).

N-(5-Amino-2,4-difluoro-3-methylphenyl)-2-chloro-5-((1R,3R)-2,2-dichloro-3-(4-fluoro-3-(trifluoromethyl)phenyl)cyclopropane-1-carboxamido)benzamide (F1674)

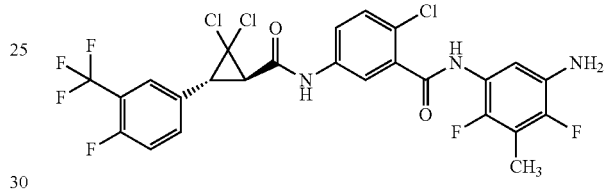

Isolated as a white solid (0.151 g, 79%).

N-(3-Amino-6-bromo-2-methylphenyl)-2-chloro-5-((1R,3R)-2,2-dichloro-3-(4-fluoro-3-(trifluoromethyl)phenyl)cyclopropane-1-carboxamido)benzamide (F1684)

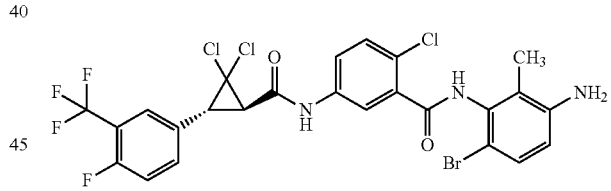

Isolated as a white solid (0.039 g, 75%).

N-(3-Amino-2,4-difluorophenyl)-2-chloro-5-((1R,3R)-2,2-dichloro-3-(3-fluoro-5-(trifluoromethyl)phenyl)cyclopropane-1-carboxamido)benzamide (F1687)

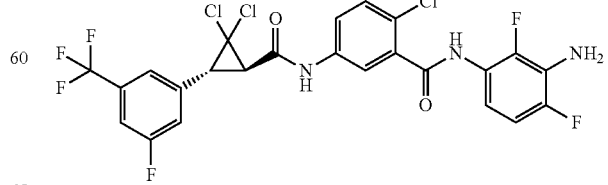

Isolated as a white solid (0.784 g, 87%).

477

N-(3-Amino-2,4-difluorophenyl)-5-((1R,3R)-3-(3-bromo-4-fluorophenyl)-2,2-dichlorocyclopropane-1-carboxamido)-2-chlorobenzamide (F1713)

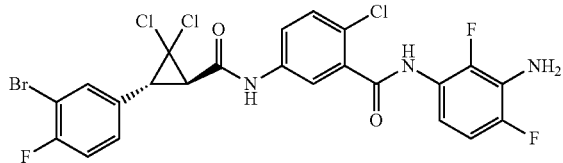

Isolated as a white solid (0.308 g, 85%).

N-(5-Amino-2,3,4-trifluorophenyl)-2-chloro-5-((1R,3R)-2,2-dichloro-3-(4-fluoro-3-(trifluoromethyl)phenyl)cyclopropane-1-carboxamido)benzamide (F1740)

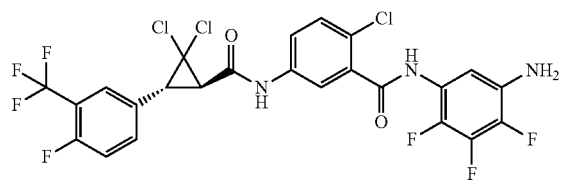 [SMILES: Nc1cc(NC(=O)c2cc(NC(=O)[C@H]3[C@H](c4ccc(F)c(C(F)(F)F)c4)C3(Cl)Cl)ccc2Cl)c(F)c(F)c1F]

Isolated as a white foam (0.188 g, 91%).

2-Chloro-5-((1R,3R)-2,2-dichloro-3-(4-fluoro-3-(trifluoromethyl)phenyl)cyclopropane-1-carboxamido)-N-(3-(ethylamino)-2,4-difluorophenyl)benzamide (F1762)

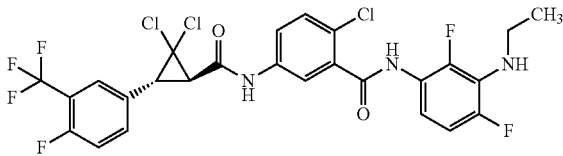 [SMILES: CCNc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white foam (0.424 g, 87%).

478

N-(3-Amino-2,4-difluorophenyl)-2-chloro-5-((1R,3R)-2,2-dichloro-3-(4-fluoro-3-(trifluoromethyl)phenyl)cyclopropane-1-carboxamido)-N-methylbenzamide (F1785)

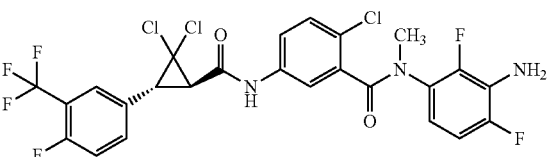

Isolated as a brown foam (0.565 g, 98%).

trans-N-(3-Amino-2,4-difluorophenyl)-5-(3-(3,5-bis(trifluoromethyl)phenyl)-2,2-dichlorocyclopropane-1-carboxamido)-2-chlorobenzamide (F1791)

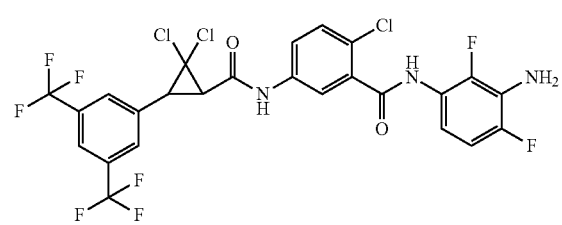 [SMILES: Nc1c(F)ccc(NC(=O)c2cc(NC(=O)C3C(c4cc(C(F)(F)F)cc(C(F)(F)F)c4)C3(Cl)Cl)ccc2Cl)c1F]

Isolated as a white foam (1.27 g, 98%).

2-Chloro-5-((1R,3R)-2,2-dichloro-3-(4-fluoro-3-(trifluoromethyl)phenyl)cyclopropane-1-carboxamido)-N-(2,4-difluoro-3-(prop-2-yn-1-ylamino)phenyl)benzamide (F1807)

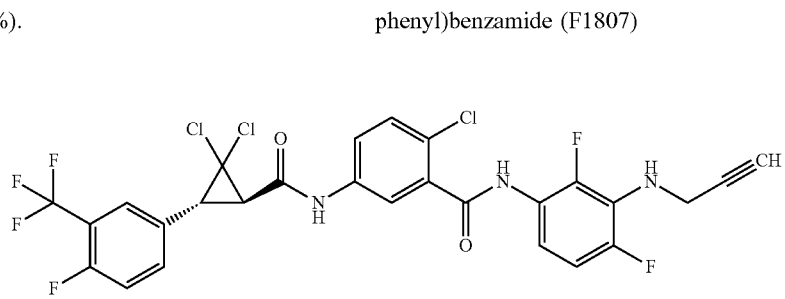

Isolated as an amber oil (0.215 g, 72%).

2-Chloro-5-((1R,3R)-2,2-dichloro-3-(4-fluoro-3-(trifluoromethyl)phenyl)cyclopropane-1-carboxamido)-N-(2,4-difluoro-3-((2-fluoroethyl)amino)phenyl)benzamide (F1826)

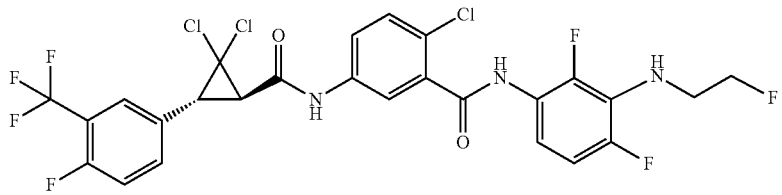 [SMILES: O=C(Nc1ccc(F)c(NCCF)c1F)c1cc(NC(=O)[C@H]2[C@H](c3ccc(F)c(C(F)(F)F)c3)C2(Cl)Cl)ccc1Cl]

Isolated as a gold oil (0.147 g, 68%).

2-Chloro-5-((1R,3R)-2,2-dichloro-3-(4-fluoro-3-(trifluoromethyl)phenyl)cyclopropane-1-carboxamido)-N-(2,4-difluoro-3-(propylamino)phenyl)benzamide (F1838)

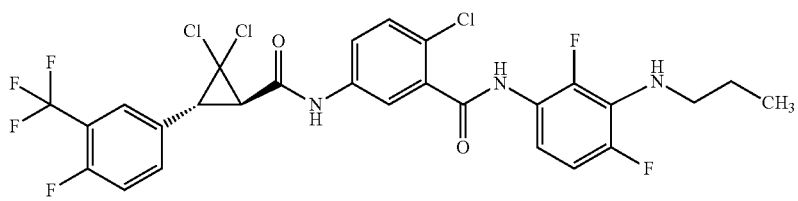 [SMILES: CCCNc1c(F)ccc(NC(=O)c2cc(NC(=O)[C@H]3[C@H](c4ccc(F)c(C(F)(F)F)c4)C3(Cl)Cl)ccc2Cl)c1F]

Isolated as a clear, colorless oil (0.331 g, 66%).

The following compounds were prepared in like manner to the procedure outlined in Example 14:

N-(3-Amino-2,6-difluorophenyl)-5-((1R,3R)-2,2-dichloro-3-(3,4,5-trichlorophenyl)cyclopropane-1-carboxamido)-2,3-difluorobenzamide (F1770)

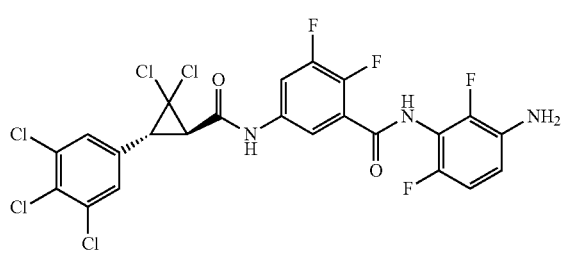 [SMILES: Nc1ccc(F)c(NC(=O)c2cc(NC(=O)[C@H]3[C@H](c4cc(Cl)c(Cl)c(Cl)c4)C3(Cl)Cl)cc(F)c2F)c1F]

Isolated as a white foam (0.274 g, 81%).

The following compounds were prepared in like manner to the procedure outlined in Example 15:

N-(3-Amino-4-bromo-2-methylphenyl)-2-chloro-5-((1R,3R)-2,2-dichloro-3-(4-fluoro-3-(trifluoromethyl)phenyl)cyclopropane-1-carboxamido)benzamide (F1690)

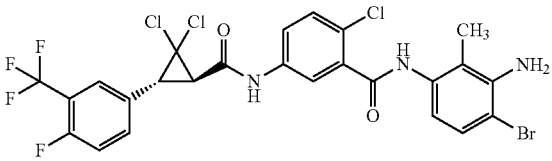 [SMILES: Cc1c(NC(=O)c2cc(NC(=O)[C@H]3[C@H](c4ccc(F)c(C(F)(F)F)c4)C3(Cl)Cl)ccc2Cl)ccc(Br)c1N]

Isolated as a white foam (0.090 g, 69%).

The following compounds were prepared in like manner to the procedure outlined in Example 18:

5-((1R,3R)-3-(3-Bromo-4-fluorophenyl)-2,2-dichlorocyclopropane-1-carboxamido)-2-chloro-N-(3-(2,2-difluoroacetamido)-2,4-difluorophenyl)benzamide (F1410)

Isolated as a white solid (0.059 g, 35%).

5-((1R,3R)-3-(3-Bromo-4-chlorophenyl)-2,2-dichlorocyclopropane-1-carboxamido)-2-chloro-N-(3-(2,2-difluoroacetamido)-2,4-difluorophenyl)benzamide (F1411)

Isolated as a white solid (0.053 g, 32%).

The following compounds were prepared in like manner to the procedure outlined in Example 20:

tert-Butyl N-tert-butoxycarbonyl-N-[5-[[2-chloro-5-[[(1R,3R)-2,2-dichloro-3-(3-chloro-4-fluoro-phenyl)cyclopropanecarbonyl]amino]-3-fluoro-benzoyl]amino]-2,4-difluoro-phenyl]carbamate (F1379)

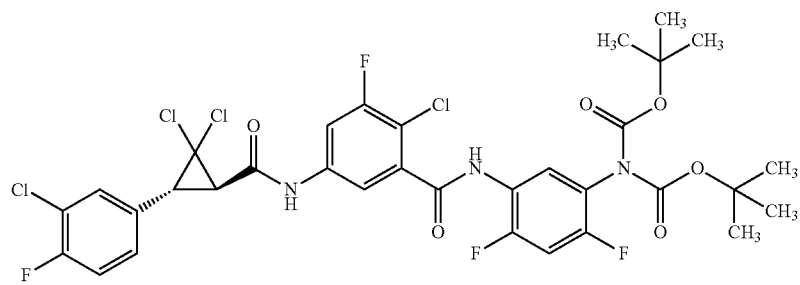 [SMILES: CC(C)(C)OC(=O)N(C(=O)OC(C)(C)C)c1cc(NC(=O)c2cc(NC(=O)[C@H]3[C@H](c4ccc(F)c(Cl)c4)C3(Cl)Cl)cc(F)c2Cl)c(F)cc1F]

Isolated as a white solid (0.429 g, 79%).

tert-Butyl N-tert-butoxycarbonyl-N-[5-[[2-chloro-5-[[(1R,3R)-2,2-dichloro-3-(3,4-dichlorophenyl)cyclopropanecarbonyl]amino]-3-fluoro-benzoyl]amino]-2,4-difluoro-phenyl]carbamate (F1380)

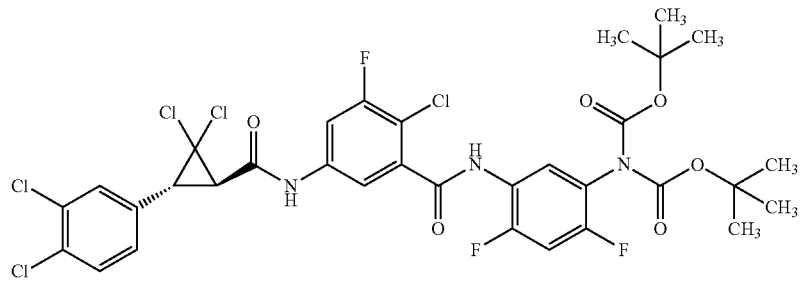

Isolated as a white solid (0.402 g, 69%).

tert-Butyl N-tert-butoxycarbonyl-N-[5-[[2-chloro-5-[[(1R,3R)-2,2-dichloro-3-(3,4,5-trichlorophenyl)cyclopropanecarbonyl]amino]-3-fluoro-benzoyl]amino]-2,4-difluoro-phenyl]carbamate (F1381)

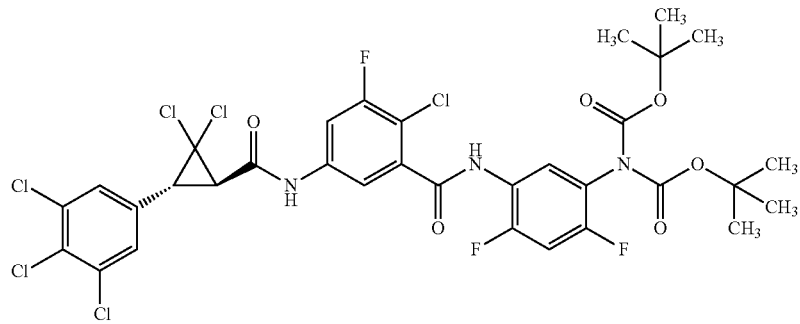 [SMILES: CC(C)(C)OC(=O)N(C(=O)OC(C)(C)C)c1cc(NC(=O)c2cc(NC(=O)[C@H]3[C@H](c4cc(Cl)c(Cl)c(Cl)c4)C3(Cl)Cl)cc(F)c2Cl)c(F)cc1F]

Isolated as a white solid (0.425 g, 70%).

tert-Butyl N-tert-butoxycarbonyl-N-[5-[[2-chloro-5-[[(1R,3R)-2,2-dichloro-3-[4-fluoro-3-(trifluoromethyl)phenyl]cyclopropanecarbonyl]amino]-3-fluoro-benzoyl]amino]-2,4-difluoro-phenyl]carbamate (F1382)

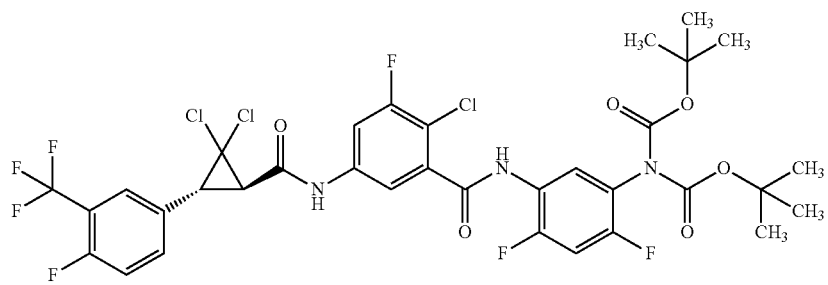 [SMILES: CC(C)(C)OC(=O)N(C(=O)OC(C)(C)C)c1cc(NC(=O)c2cc(NC(=O)[C@H]3[C@H](c4ccc(F)c(C(F)(F)F)c4)C3(Cl)Cl)cc(F)c2Cl)c(F)cc1F]

Isolated as a white solid (0.355 g, 62%).

tert-Butyl N-tert-butoxycarbonyl-N-[5-[[2-chloro-5-[[(1R,3R)-2,2-dichloro-3-(3,5-dichlorophenyl)cyclopropanecarbonyl]amino]-3-fluoro-benzoyl]amino]-2,4-difluoro-phenyl]carbamate (F1383)

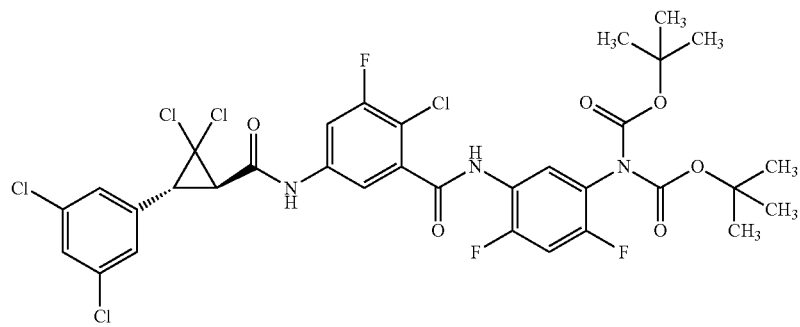 [SMILES: CC(C)(C)OC(=O)N(C(=O)OC(C)(C)C)c1cc(NC(=O)c2cc(NC(=O)[C@H]3[C@H](c4cc(Cl)cc(Cl)c4)C3(Cl)Cl)cc(F)c2Cl)c(F)cc1F]

Isolated as a white solid (0.266 g, 47%).

485

3-((1R,3R)-2,2-Dichloro-3-(3,4-dichlorophenyl) cyclopropane-1-carboxamido)-N-(3-(2,2-difluoroacetamido)-2,4-difluorophenyl)benzamide (F1447)

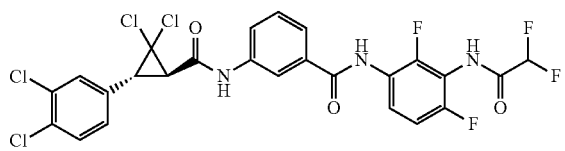 [SMILES: O=C(Nc1ccc(F)c(NC(=O)C(F)F)c1F)c1cccc(NC(=O)[C@H]2[C@H](c3ccc(Cl)c(Cl)c3)C2(Cl)Cl)c1]

Isolated as a white foam (0.123 g, 56%).

trans-5-(3-(3-Bromo-5-chlorophenyl)-2,2-dichlorocyclopropane-1-carboxamido)-2-chloro-N-(3-(2,2-difluoroacetamido)-2,4-difluorophenyl)benzamide (F1618)

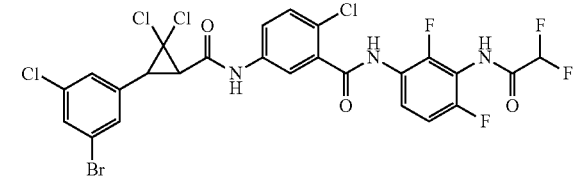 [SMILES: O=C(Nc1ccc(F)c(NC(=O)C(F)F)c1F)c1cc(NC(=O)C2C(c3cc(Cl)cc(Br)c3)C2(Cl)Cl)ccc1Cl]

Isolated as a white foam (0.077 g, 76%). The title compound was prepared from trans-3-(3-bromo-5-chorophenyl)-2,2-dichlorocyclopropane-1-carboxylic acid which was prepared via methods described in U.S. Patent Application Publication US20160304522A1 (C215).

486 trans-tert-Butyl N-[3-[[5-[[3-(3-bromo-4,5-dichlorophenyl)-2,2-dichlorocyclopropanecarbonyl]amino]-2-chlorobenzoyl]amino]-2,6-difluorophenyl]-N-tert-butoxycarbonyl-carbamate (F1619)

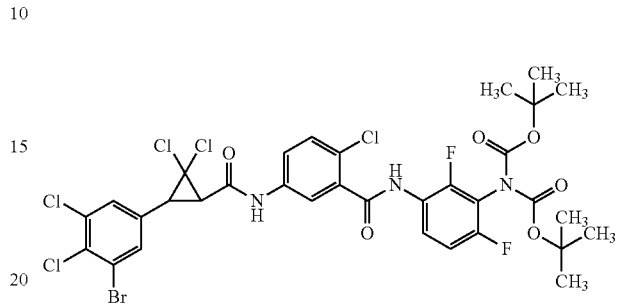

Isolated as a white solid (0.139 g, 88%).

trans-tert-Butyl N-tert-butoxycarbonyl-N-[3-[[2-chloro-5-[[2,2-dichloro-3-(4-fluoro-3-iodophenyl) cyclopropanecarbonyl]amino]benzoyl]amino]-2,6-difluorophenyl]carbamate (F1620)

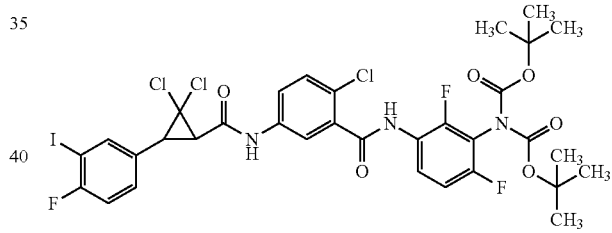

Isolated as a white solid (0.155 g, 97%).

tert-Butyl N-tert-butoxycarbonyl-N-[3-[[2-chloro-5-[[(1R,3R)-2,2-dichloro-3-[4-chloro-3-(trifluoromethyl)phenyl]cyclopropanecarbonyl]amino]benzoyl]amino]-2,6-difluoro-phenyl]carbamate (F1621)

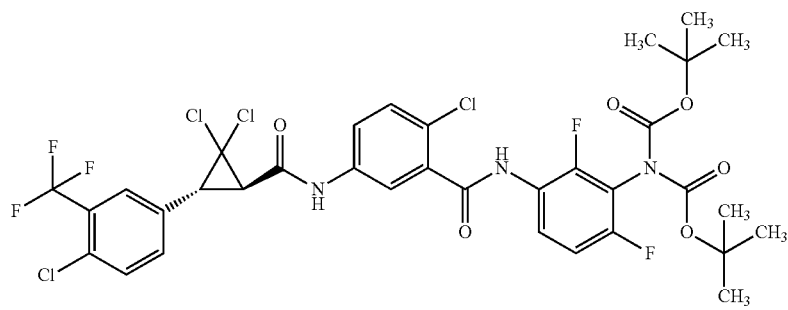 [SMILES: CC(C)(C)OC(=O)N(C(=O)OC(C)(C)C)c1c(F)ccc(NC(=O)c2cc(NC(=O)[C@H]3[C@H](c4ccc(Cl)c(C(F)(F)F)c4)C3(Cl)Cl)ccc2Cl)c1F]

Isolated as a colorless glass (0.87 g, 99%).

tert-Butyl N-tert-butoxycarbonyl-N-[3-[[2-chloro-5-[[(1R,3R)-2,2-dichloro-3-[3-(trifluoromethyl)phenyl]cyclopropanecarbonyl]amino]benzoyl]amino]-2,6-difluoro-phenyl]carbamate (F1665)

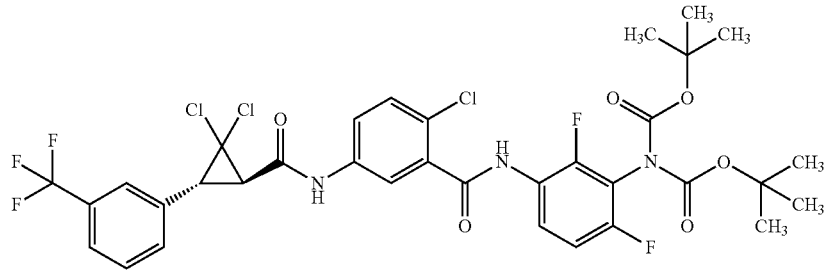 [SMILES: CC(C)(C)OC(=O)N(C(=O)OC(C)(C)C)c1c(F)ccc(NC(=O)c2cc(NC(=O)[C@H]3[C@H](c4cccc(C(F)(F)F)c4)C3(Cl)Cl)ccc2Cl)c1F]

Isolated as a white foam (1.35 g, 91%).

2-Chloro-5-((1R,3R)-2,2-dichloro-3-(3,4,5-trifluorophenyl)cyclopropane-1-carboxamido)-N-(2,4-difluorophenyl)benzamide (F1693)

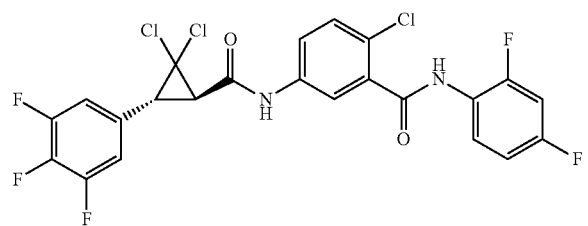 [SMILES: O=C(Nc1ccc(F)cc1F)c1cc(NC(=O)[C@H]2[C@H](c3cc(F)c(F)c(F)c3)C2(Cl)Cl)ccc1Cl]

Isolated as an off-white solid (0.500 g, 35%).

2-Chloro-5-((1S,3S)-2,2-dichloro-3-(3,4,5-trifluorophenyl)cyclopropane-1-carboxamido)-N-(2,4-difluorophenyl)benzamide (F1749)

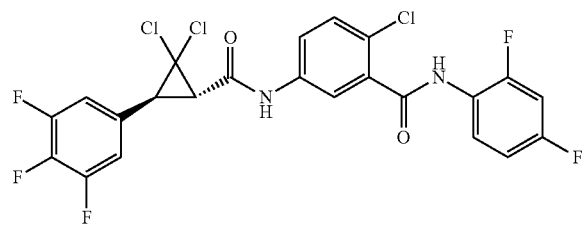 [SMILES: O=C(Nc1ccc(F)cc1F)c1cc(NC(=O)[C@@H]2[C@@H](c3cc(F)c(F)c(F)c3)C2(Cl)Cl)ccc1Cl]

Isolated as an off-white solid (0.360 g, 46%).

2-Chloro-5-((1R,3R)-2,2-dichloro-3-(3,4-difluorophenyl)cyclopropane-1-carboxamido)-N-(2,4-difluorophenyl)benzamide (F1750)

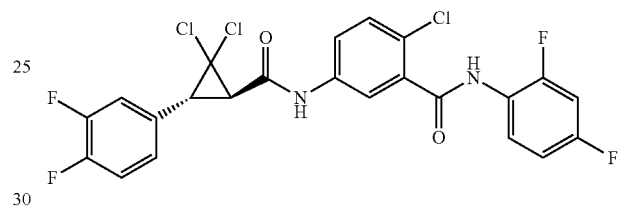

Isolated as an off-white solid (0.500 g, 50%).

2-Chloro-5-((1S,3S)-2,2-dichloro-3-(3,4-difluorophenyl)cyclopropane-1-carboxamido)-N-(2,4-difluorophenyl)benzamide (F1751)

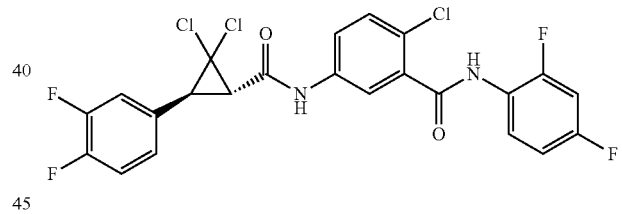

Isolated as a pale yellow solid (0.500 g, 50%).

tert-Butyl N-[3-[[5-[[(1R,3R)-3-(3-bromo-4-fluorophenyl)-2,2-dichlorocyclopropanecarbonyl]amino]-2-chloro-benzoyl]amino]-2,6-difluoro-phenyl]-N-tert-butoxycarbonyl-carbamate (F1776)

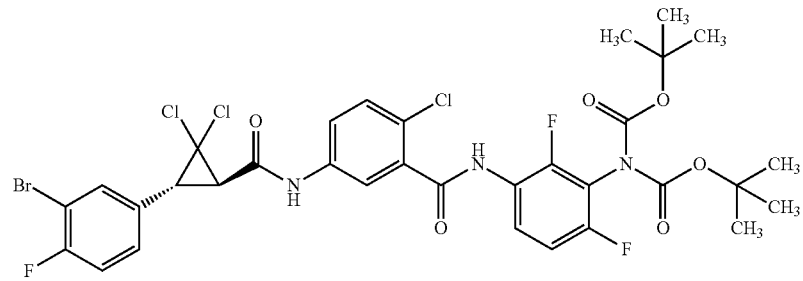

Isolated as a white solid (1.2 g, 93%).

tert-Butyl N-tert-butoxycarbonyl-N-[3-[[2-chloro-5-
[[(1R,3R)-2,2-dichloro-3-[4-fluoro-3-(trifluorom-
ethyl)phenyl]cyclopropanecarbonyl]amino]benzoyl]-
methyl-amino]-2,6-difluoro-phenyl)carbamate
(F1784)

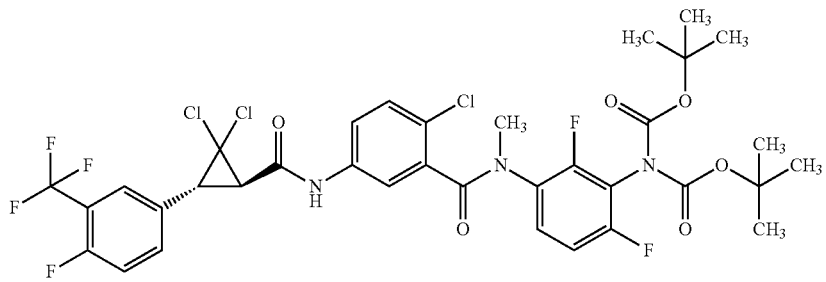 [SMILES: CN(C(=O)c1cc(NC(=O)[C@H]2[C@H](c3ccc(F)c(C(F)(F)F)c3)C2(Cl)Cl)ccc1Cl)c1ccc(F)c(N(C(=O)OC(C)(C)C)C(=O)OC(C)(C)C)c1F]

Isolated as a white foam (0.730 g, 82%).

trans-tert-Butyl N-[3-[[5-[[3-[3,5-bis(trifluorom-
ethyl)phenyl]-2,2-dichlorocyclopropanecarbonyl]
amino]-2-chloro-benzoyl]amino]-2,6-difluoro-phe-
nyl]-N-tert-butoxycarbonyl-carbamate (F1786)

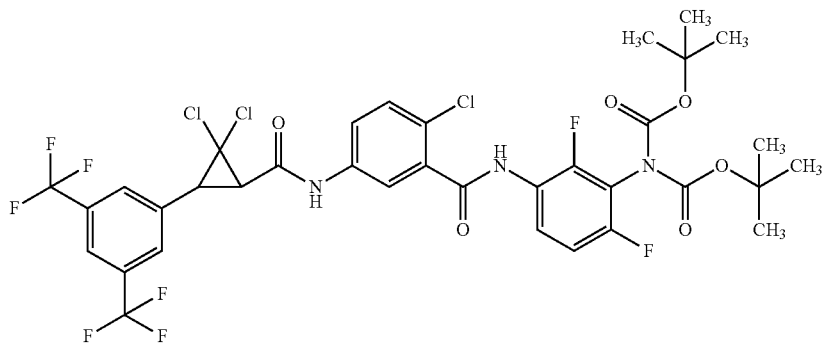 [SMILES: CC(C)(C)OC(=O)N(C(=O)OC(C)(C)C)c1c(F)ccc(NC(=O)c2cc(NC(=O)C3C(c4cc(C(F)(F)F)cc(C(F)(F)F)c4)C3(Cl)Cl)ccc2Cl)c1F]

Isolated as a white foam (1.7 g, 92%). The title compound was prepared from trans-3-(3,5-bis(trifluoromethyl)phenyl)-2,2-dichlorocyclopropanecarboxylic acid which was prepared via methods described in U.S. Patent Application Publication US20160304522A1 (C8).

trans-test-Butyl N-[3-[[5-[[3-[3-bromo-5-(trifluo-
romethyl)phenyl]-2,2-dichlorocyclopropanecarbo-
nyl]amino]-2-chloro-benzoyl]amino]-2,6-difluoro-
phenyl]-N-tert-butoxycarbonyl-carbamate (F1787)

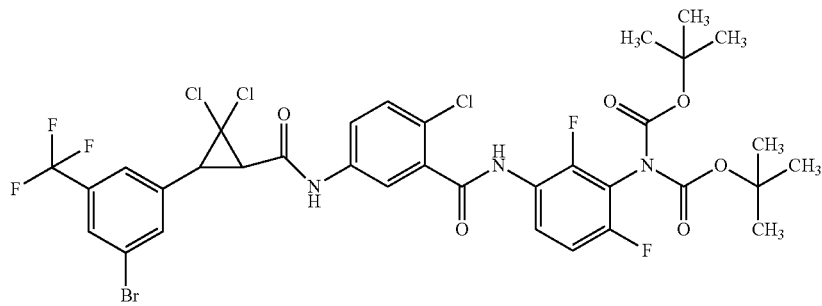 [SMILES: CC(C)(C)OC(=O)N(C(=O)OC(C)(C)C)c1c(F)ccc(NC(=O)c2cc(NC(=O)C3C(c4cc(Br)cc(C(F)(F)F)c4)C3(Cl)Cl)ccc2Cl)c1F]

Isolated as a white foam (1.7 g, 94%).

tert-Butyl N-tert-butoxycarbonyl-N-[3-[[2-chloro-5-[[(1R,3R)-2,2-dichloro-3-[4-fluoro-3-(trifluoromethyl)phenyl]cyclopropanecarbonyl]amino]benzoyl]amino]-2,6-difluoro-phenyl]carbamate (F1788)

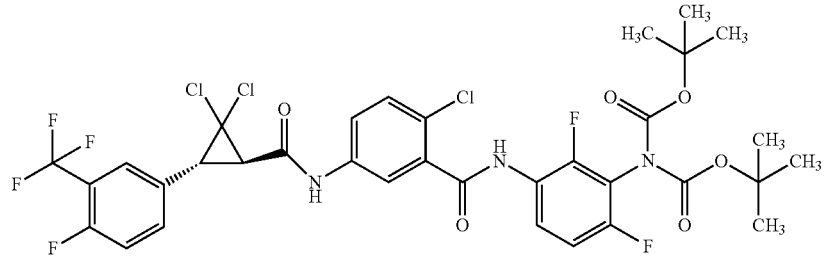 [SMILES: CC(C)(C)OC(=O)N(C(=O)OC(C)(C)C)c1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white foam (1.9 g, 94%).

trans-2-Chloro-5-(2,2-dichloro-3-(3,5-dichlorophenyl)cyclopropane-1-carboxamido)-N-(2-(2,2,2-trifluoroacetamido)ethyl)benzamide (F2066)

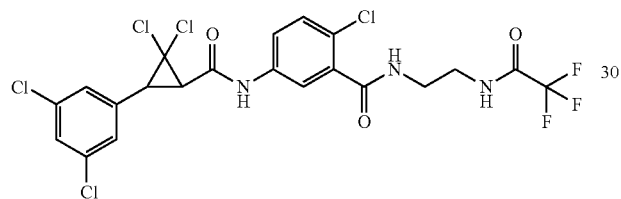

Isolated as a white solid (0.075 g, 24%).

trans-N-(3-Acetamidopropyl)-2-chloro-5-(2,2-dichloro-3-(3,5-dichlorophenyl)cyclopropane-1-carboxamido)benzamide (F2067)

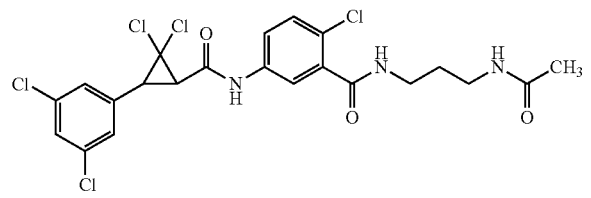 [SMILES: CC(=O)NCCCNC(=O)c1cc(NC(=O)C2C(c3cc(Cl)cc(Cl)c3)C2(Cl)Cl)ccc1Cl]

Isolated as a white solid (0.100 g, 34%).

trans-N-(4-Acetamidobutyl)-2-chloro-5-(2,2-dichloro-3-(3,5-dichlorophenyl)cyclopropane-1-carboxamido)benzamide (F2068)

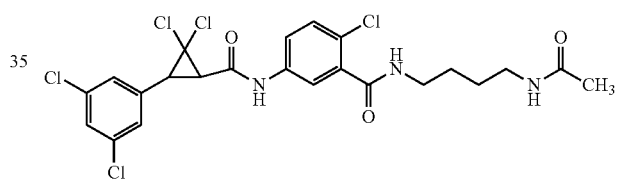

Isolated as a white solid (0.140 g, 47%).

trans-N-(5-Acetamidopentyl)-2-chloro-5-(2,2-dichloro-3-(3,5-dichlorophenyl)cyclopropane-1-carboxamido)benzamide (F2069)

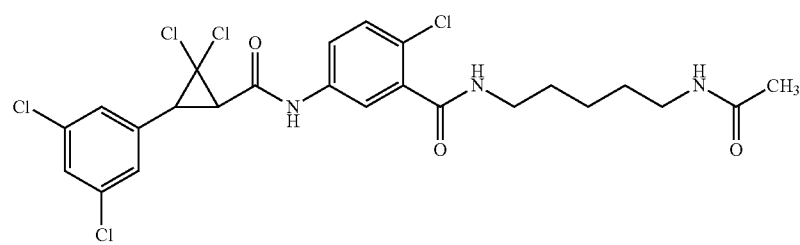 [SMILES: CC(=O)NCCCCCNC(=O)c1cc(NC(=O)C2C(c3cc(Cl)cc(Cl)c3)C2(Cl)Cl)ccc1Cl]

Isolated as a white solid (0.100 g, 33%).

493 trans-2-Chloro-5-(2,2-dichloro-3-(3,5-dichlorophenyl)cyclopropane-1-carboxamido)-N-(3-(methylamino)-3-oxopropyl)benzamide (F2070)

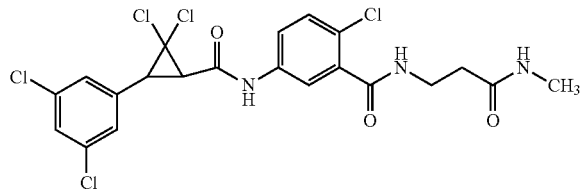 [SMILES: CNC(=O)CCNC(=O)c1cc(NC(=O)C2C(c3cc(Cl)cc(Cl)c3)C2(Cl)Cl)ccc1Cl]

Isolated as a white solid (0.090 g, 32%).

trans-2-Chloro-5-(2,2-dichloro-3-(3,5-dichlorophenyl)cyclopropane-1-carboxamido)-N-(2,2-difluoropropyl)benzamide (F2075)

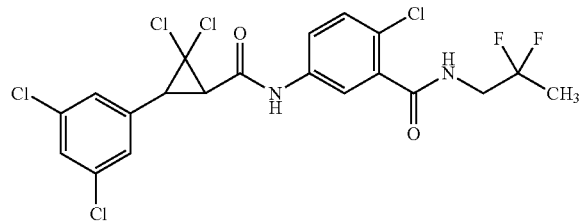 [SMILES: CC(F)(F)CNC(=O)c1cc(NC(=O)C2C(c3cc(Cl)cc(Cl)c3)C2(Cl)Cl)ccc1Cl]

Isolated as an off-white solid (0.150 g, 60%).

trans-Ethyl 3-(2-chloro-5-(2,2-dichloro-3-(3,5-dichlorophenyl)cyclopropane-1-carboxamido)benzamido)-2,2-difluoropropanoate (F2076)

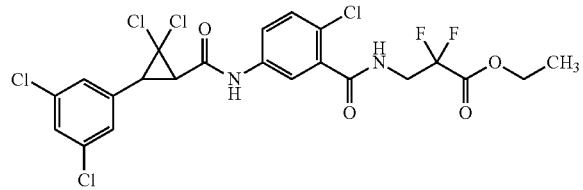 [SMILES: CCOC(=O)C(F)(F)CNC(=O)c1cc(NC(=O)C2C(c3cc(Cl)cc(Cl)c3)C2(Cl)Cl)ccc1Cl]

Isolated as a pale yellow solid (0.120 g, 46%).

trans-2-Chloro-5-(2,2-dichloro-3-(3,5-dichlorophenyl)cyclopropane-1-carboxamido)-N-(2,2-difluoro-2-phenylethyl)benzamide (F2077)

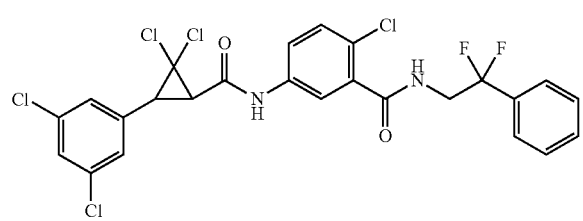 [SMILES: O=C(NCC(F)(F)c1ccccc1)c1cc(NC(=O)C2C(c3cc(Cl)cc(Cl)c3)C2(Cl)Cl)ccc1Cl]

Isolated as an off-white solid (0.150 g, 57%).

494 trans-2-Chloro-5-(2,2-dichloro-3-(3,5-dichlorophenyl)cyclopropane-1-carboxamido)-N-(2-oxo-2-(2,2,2-trifluoroethylamino)ethyl)benzamide (F2078)

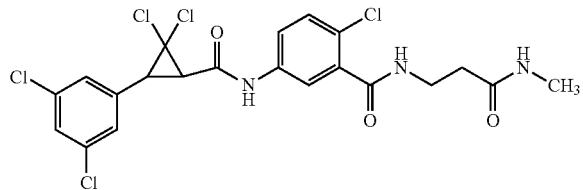

Isolated as an off-white said (0.063 g, 19%).

trans-2-Chloro-5-((1R,3R)-2,2-dichloro-3-(3,5-dichlorophenyl)cyclopropane-1-carboxamido)-N-(3-oxo-3-(2,2,2-trifluoroethylamino)propyl)benzamide (F2079)

Isolated as an off-white solid (0.140 g, 39%).

trans-2-Chloro-5-(2,2-dichloro-3-(3,5-dichlorophenyl)cyclopropane-1-carboxamido)-N-(4-oxo-4-(2,2,2-trifluoroethylamino)butyl)benzamide (F2080)

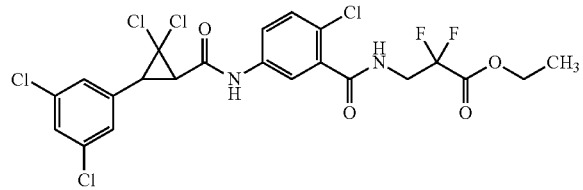

Isolated as an off-white solid (0.089 g, 26%).

trans-2-Chloro-5-(2,2-dichloro-3-(3,5-dichlorophenyl)cyclopropane-1-carboxamido)-N-(2-oxo-2-(3,3,3-trifluoropropylamino)ethyl)benzamide (F2081)

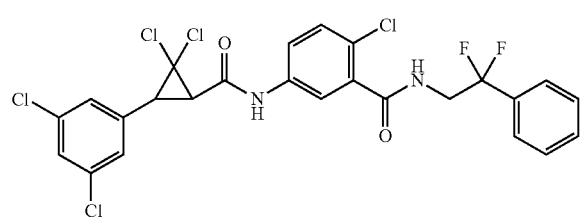

Isolated as an off-white solid (0.075 g, 19%).

495 trans-2-Chloro-5-(2,2-dichloro-3-(3,5-dichlorophenyl)cyclopropane-1-carboxamido)-N-(2-(2,2,2-trifluoroacetamido)ethyl)benzamide (F2082)

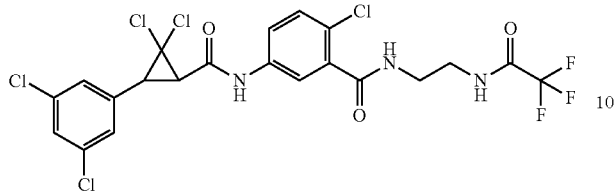

Isolated as an off-white solid (0.060 g, 32%).

trans-2-Chloro-5-(2,2-dichloro-3-(3,5-dichlorophenyl)cyclopropane-1-carboxamido)-N-(2,2-difluorobutyl)benzamide (F2086)

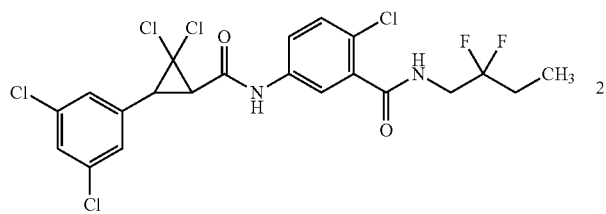

Isolated as an off-white solid (0.050 g, 28%).

trans-2-Chloro-5-(2,2-dichloro-3-(3,5-dichlorophenyl)cyclopropane-1-carboxamido)-N-(2,2-difluoropropyl)benzamide (F2087)

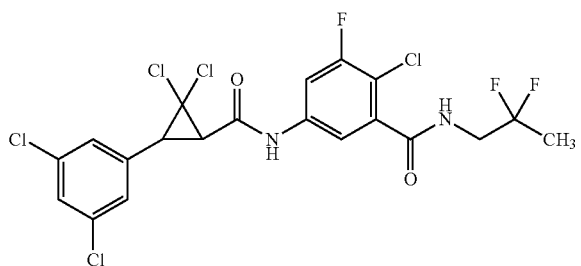 [SMILES: CC(F)(F)CNC(=O)c1cc(NC(=O)C2C(c3cc(Cl)cc(Cl)c3)C2(Cl)Cl)cc(F)c1Cl]

Isolated as an off-white solid (0.100 g, 60%).

trans-2-Chloro-5-(2,2-dichloro-3-(3,5-dichlorophenyl)cyclopropane-1-carboxamido)-N-(2,2-difluorobutyl)-3-fluorobenzamide (F2088)

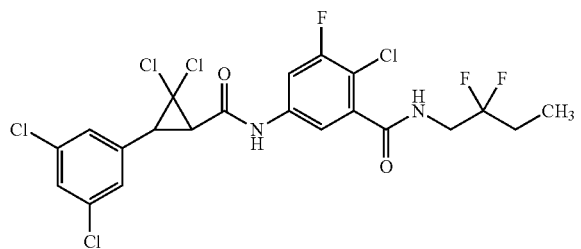 [SMILES: CCC(F)(F)CNC(=O)c1cc(NC(=O)C2C(c3cc(Cl)cc(Cl)c3)C2(Cl)Cl)cc(F)c1Cl]

Isolated as an off-white solid (0.150 g, 30%).

496 trans-Ethyl 3-(2-chloro-5-(2,2-dichloro-3-(3,5-dichlorophenyl)cyclopropane-1-carboxamido)-3-fluorobenzamido)-2,2-difluoropropanoate (F2089)

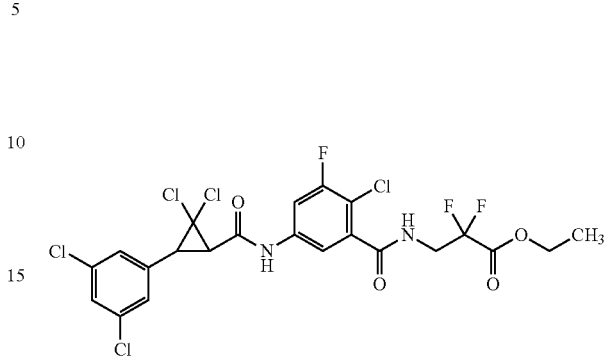

Isolated as an off-white solid (0.100 g, 21%).

trans-2-Chloro-5-(2,2-dichloro-3-(3,5-dichlorophenyl)cyclopropane-1-carboxamido)-3-fluoro-N-(2-oxopropyl)benzamide (F2090)

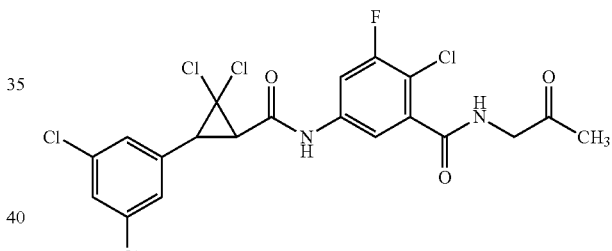

Isolated as an off-white solid (0.100 g, 18%).

trans-2-Chloro-5-(2,2-dichloro-3-(3,5-dichlorophenyl)cyclopropane-1-carboxamido)-N-(2,2-difluoro-2-phenylethyl)-3-fluorobenzamide (F2091)

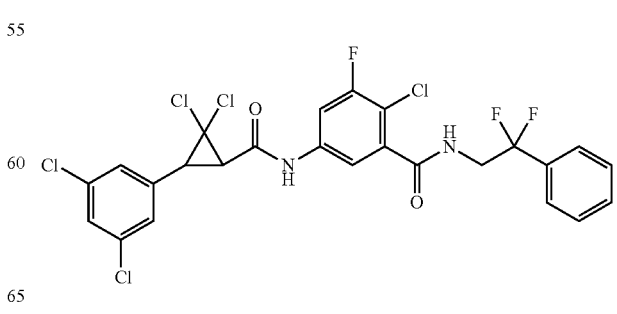

Isolated as an off-white solid (0.090 g, 13%).

trans-2-Chloro-5-(2,2-dichloro-3-(3,5-dichlorophenyl)cyclopropane-1-carboxamido)-N-(3-oxo-3-(3,3,3-trifluoropropylamino)propyl)benzamide (F2092)

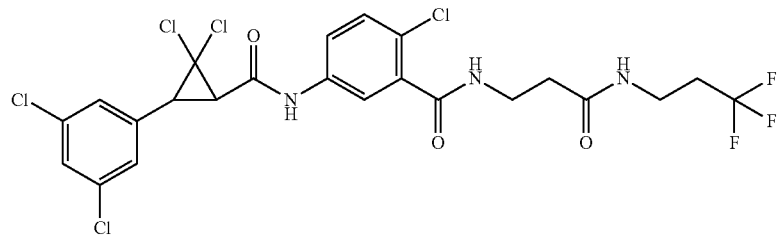 [SMILES: O=C(CCNC(=O)c1cc(NC(=O)C2C(c3cc(Cl)cc(Cl)c3)C2(Cl)Cl)ccc1Cl)NCCC(F)(F)F]

Isolated as an off-white solid (0.125 g, 31%).

trans-2-Chloro-5-(2,2-dichloro-3-(3,5-dichlorophenyl)cyclopropanecarboxamido)-N-(4-oxo-4-(3,3,3-trifluoropropylamino)butyl)benzamide (F2093)

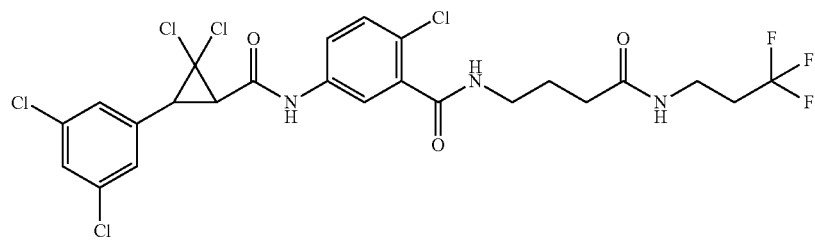 [SMILES: O=C(CCCNC(=O)c1cc(NC(=O)C2C(c3cc(Cl)cc(Cl)c3)C2(Cl)Cl)ccc1Cl)NCCC(F)(F)F]

Isolated as a pale pink solid (0.130 g, 31%).

trans-2-Chloro-5-(2,2-dichloro-3-(3,5-dichlorophenyl)cyclopropane-1-carboxamido)-N-(3-(2,2,2-trifluoroacetamido)propyl)benzamide (F2094)

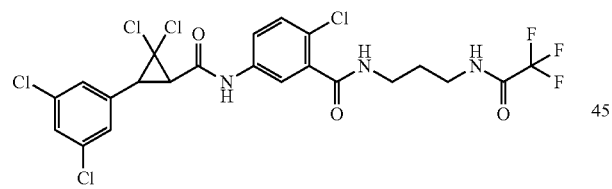

Isolated as an off-white solid (0.075 g, 19%).

trans-2-Chloro-5-(2,2-dichloro-3-(3,5-dichlorophenyl)cyclopropane-1-carboxamido)-N-(4-(2,2,2-trifluoroacetamido)butyl)benzamide (F2095)

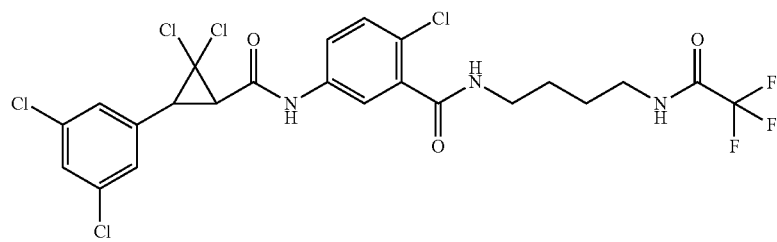 [SMILES: O=C(NCCCCNC(=O)C(F)(F)F)c1cc(NC(=O)C2C(c3cc(Cl)cc(Cl)c3)C2(Cl)Cl)ccc1Cl]

Isolated as an off-white solid (0.171 g, 42%).

trans-2-Chloro-5-(2,2-dichloro-3-(3,5-dichlorophenyl)cyclopropane-1-carboxamido)-N-(2-(2,2,3,3,3-pentafluoropropanamido)ethyl)benzamide (F2096)

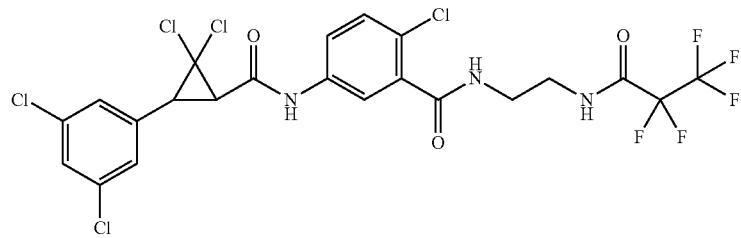 [SMILES: O=C(NCCNC(=O)C(F)(F)C(F)(F)F)c1cc(NC(=O)C2C(c3cc(Cl)cc(Cl)c3)C2(Cl)Cl)ccc1Cl]

Isolated as an off-white solid (0.170 g, 40%).

trans-2-Chloro-5-(2,2-dichloro-3-(3,5-dichlorophenyl)cyclopropane-1-carboxamido)-N-(3-(2,2,3,3,3-pentafluoropropanamido)propyl)benzamide (F2097)

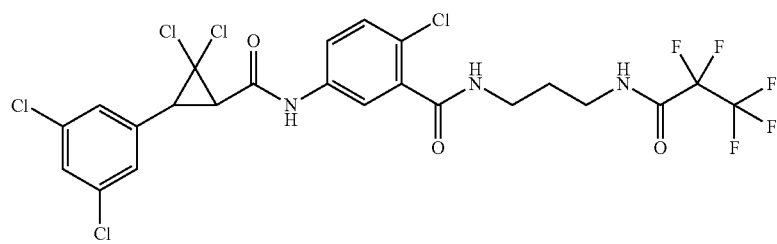 [SMILES: O=C(NCCCNC(=O)C(F)(F)C(F)(F)F)c1cc(NC(=O)C2C(c3cc(Cl)cc(Cl)c3)C2(Cl)Cl)ccc1Cl]

Isolated as a pale blue solid (0.131 g, 30%).

trans-2-Chloro-5-(2,2-dichloro-3-(3,5-dichlorophenyl)cyclopropane-1-carboxamido)-N-(4-(2,2,3,3,3-pentafluoropropanamido)butyl)benzamide (F2098)

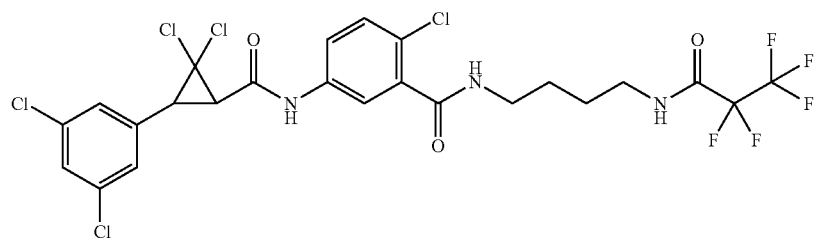 [SMILES: O=C(NCCCCNC(=O)C(F)(F)C(F)(F)F)c1cc(NC(=O)C2C(c3cc(Cl)cc(Cl)c3)C2(Cl)Cl)ccc1Cl]

Isolated as an off-white solid (0.151 g, 34%).

2-Chloro-5-((1R,3R)-2,2-dichloro-3-(3,4-difluorophenyl)cyclopropane-1-carboxamido)-N-(2,2,2-trifluoroethyl)benzamide (F2099)

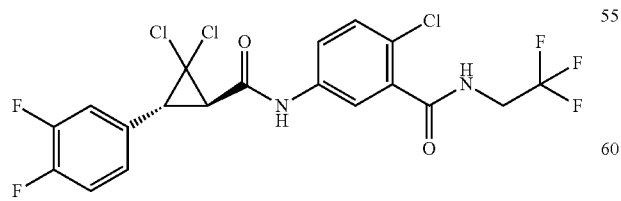

Isolated as an off-white solid (0.450 g, 48%). The title compound was prepared from 5-amino-2-chloro-N-(2,2,2-trifluoroethyl)benzamide, which was prepared using methods described in U.S. Patent Application Publication 20160302418A1 (C70).

501

2-Chloro-5-((1S,3S)-2,2-dichloro-3-(3,4-difluorophenyl)cyclopropane-1-carboxamido)-N-(2,2,2-trifluoroethyl)benzamide (F2100)

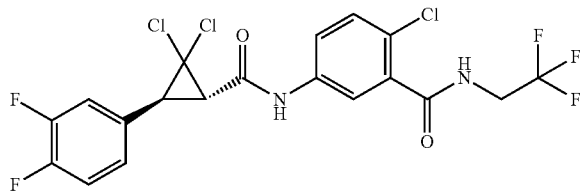 [SMILES: O=C(NCC(F)(F)F)c1cc(NC(=O)[C@@H]2[C@@H](c3ccc(F)c(F)c3)C2(Cl)Cl)ccc1Cl]

Isolated as an off-white solid (0.450 g, 48%). The title compound was prepared from 5-amino-2-chloro-N-(2,2,2-trifluoroethyl)benzamide, which was prepared using methods described in U.S. Patent Application Publication 20160302418A1 (C70).

The following compounds were prepared in like manner to the procedure outlined in Example 21:

trans-N-(3-Amino-2,4-difluorophenyl)-5-(3-(4-bromophenyl)-2,2-dichlorocyclopropane-1-carboxamido)-2-chlorobenzamide (F1591)

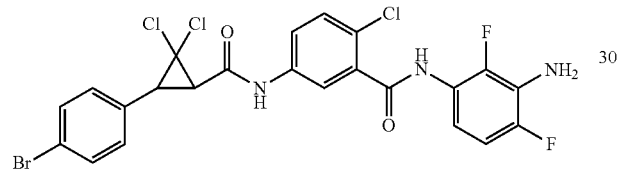

Isolated as a white foam (0.108 g, 36%).

trans-N-(3-Amino-2,4-difluorophenyl)-2-chloro-5-(2,2-dichloro-3-(4-fluorophenyl)cyclopropane-1-carboxamido)benzamide (F1592)

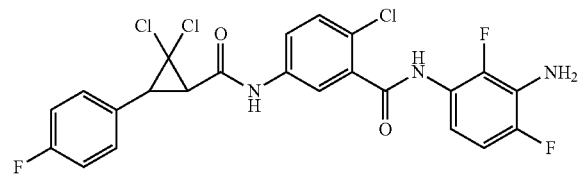 [SMILES: Nc1c(F)ccc(NC(=O)c2cc(NC(=O)C3C(c4ccc(F)cc4)C3(Cl)Cl)ccc2Cl)c1F]

Isolated as a white foam (0.092 g, 27%).

trans-N-(3-Amino-2,4-difluorophenyl)-2-chloro-5-(2,2-dichloro-3-(4-chlorophenyl)cyclopropane-1-carboxamido)benzamide (F1593)

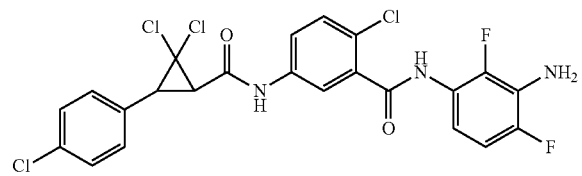 [SMILES: Nc1c(F)ccc(NC(=O)c2cc(NC(=O)C3C(c4ccc(Cl)cc4)C3(Cl)Cl)ccc2Cl)c1F]

Isolated as a white foam (0.162 g, 50%).

502 trans-N-(3-Amino-2,4-difluorophenyl)-5-(3-(3-bromophenyl)-2,2-dichlorocyclopropane-1-carboxamido)-2-chlorobenzamide (F1594)

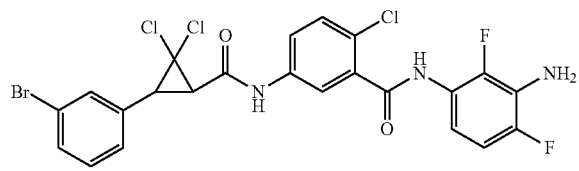 [SMILES: Nc1c(F)ccc(NC(=O)c2cc(NC(=O)C3C(c4cccc(Cl)c4)C3(Cl)Cl)ccc2Cl)c1F]

Isolated as a white foam (0.103 g, 34%).

trans-N-(3-Amino-2,4-difluorophenyl)-2-chloro-5-(2,2-dichloro-3-(3-chlorophenyl)cyclopropane-1-carboxamido)benzamide (F1595)

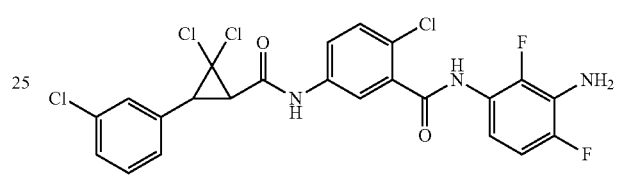

Isolated as a white foam (0.152 g, 47%).

trans-N-(3-Amino-2,4-difluorophenyl)-2-chloro-5-(2,2-dichloro-3-(3-fluorophenyl)cyclopropane-1-carboxamido)benzamide (F1596)

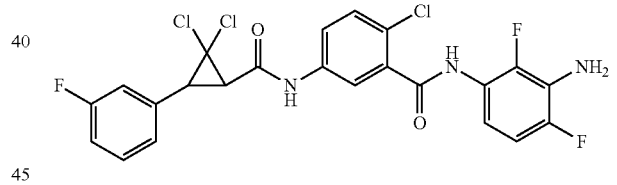

Isolated as a white foam (0.199 g, 59%).

The following compounds were prepared in like manner to the procedure outlined in Example 22:

trans-2-Chloro-5-(2,2-dichloro-3-(3,5-dichlorophenyl)cyclopropane-1-carboxamido)-N-(3,5-dichloro-4-hydroxyphenyl)benzamide (F1360)

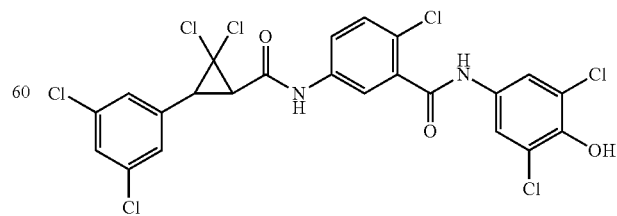

Isolated as a tan foam (0.096 g, 93%)

tert-Butyl (3-(2-chloro-5-((1R,3R)-2,2-dichloro-3-(3,4-dichlorophenyl)cyclopropane-1-carboxamido)-3-methylbenzamido)-2,4-difluorophenyl)carbamate (F1420)

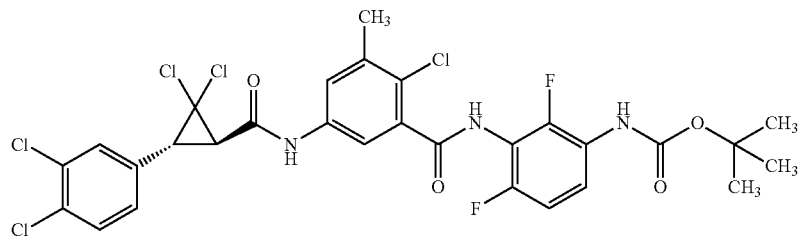 [SMILES: Cc1cc(NC(=O)[C@H]2[C@H](c3ccc(Cl)c(Cl)c3)C2(Cl)Cl)cc(C(=O)Nc2c(F)ccc(NC(=O)OC(C)(C)C)c2F)c1Cl]

Isolated as a tan foam (0.270 g, 91%).

tert-Butyl (3-(2-chloro-5-((1R,3R)-2,2-dichloro-3-(3,4,5-trichlorophenyl)cyclopropane-1-carboxamido)-3-methylbenzamido)-2,4-difluorophenyl)carbamate (F1421)

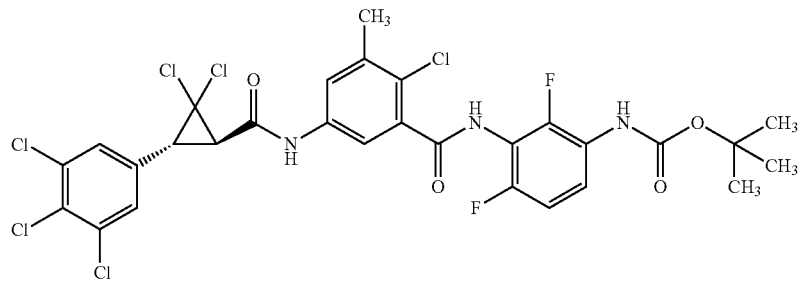 [SMILES: Cc1cc(NC(=O)[C@H]2[C@H](c3cc(Cl)c(Cl)c(Cl)c3)C2(Cl)Cl)cc(C(=O)Nc2c(F)ccc(NC(=O)OC(C)(C)C)c2F)c1Cl]

Isolated as an off-white solid (0.274 g, 94%).

tert-Butyl (3-(2-chloro-5-((1R,3R)-2,2-dichloro-3-(4-fluoro-3-(trifluoromethyl)phenyl)cyclopropane-1-carboxamido)-3-methylbenzamido)-2,4-difluorophenyl)carbamate (F1422)

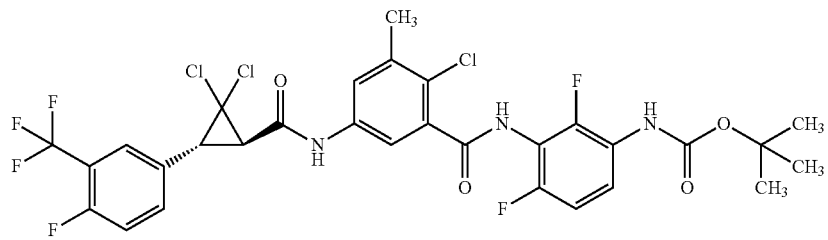 [SMILES: Cc1cc(NC(=O)[C@H]2[C@H](c3ccc(F)c(C(F)(F)F)c3)C2(Cl)Cl)cc(C(=O)Nc2c(F)ccc(NC(=O)OC(C)(C)C)c2F)c1Cl]

Isolated as an off-white solid (0.271 g, 100%).

tert-Butyl N-tert-butoxycarbonyl-N-[3-[[2-chloro-5-[[(1R,3R)-2,2-dichloro-3-(3,4-dichlorophenyl)cyclopropanecarbonyl]amino]-3-methyl-benzoyl]amino]-2,6-difluoro-phenyl]carbamate (F1423)

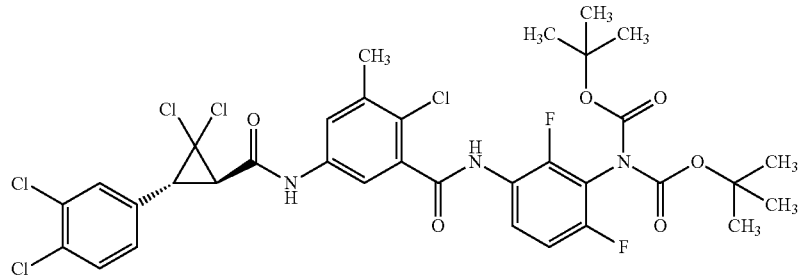 [SMILES: Cc1cc(NC(=O)[C@H]2[C@H](c3ccc(Cl)c(Cl)c3)C2(Cl)Cl)cc(C(=O)Nc2ccc(F)c(N(C(=O)OC(C)(C)C)C(=O)OC(C)(C)C)c2F)c1Cl]

Isolated as an off-white solid (0.320 g, 100%).

tert-Butyl N-tert-butoxycarbonyl-N-[3-[[2-chloro-5-[[(1R,3R)-2,2-dichloro-3-(3,4,5-trichlorophenyl)cyclopropanecarbonyl]amino]-3-methyl-benzoyl]amino]-2,6-difluoro-phenyl]carbamate (F1424)

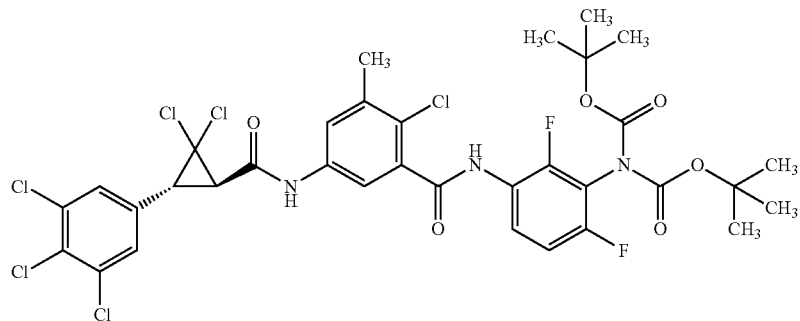 [SMILES: Cc1cc(NC(=O)[C@H]2[C@H](c3cc(Cl)c(Cl)c(Cl)c3)C2(Cl)Cl)cc(C(=O)Nc2ccc(F)c(N(C(=O)OC(C)(C)C)C(=O)OC(C)(C)C)c2F)c1Cl]

Isolated as an off-white solid (0.325 g, 98%).

tert-Butyl N-tert-butoxycarbonyl-N-[3-[[2-chloro-5-[[(1R,3R)-2,2-dichloro-3-[4-fluoro-3-(trifluoromethyl)phenyl]cyclopropanecarbonyl]amino]-3-methyl-benzoyl]amino]-2,6-difluoro-phenyl]carbamate (F1425)

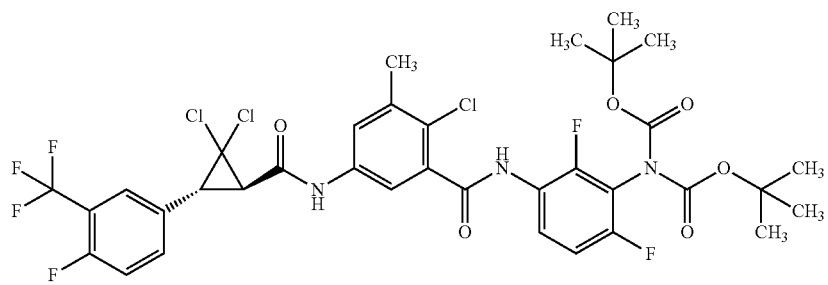 [SMILES: Cc1cc(NC(=O)[C@H]2[C@H](c3ccc(F)c(C(F)(F)F)c3)C2(Cl)Cl)cc(C(=O)Nc2ccc(F)c(N(C(=O)OC(C)(C)C)C(=O)OC(C)(C)C)c2F)c1Cl]

Isolated as an off-white solid (0.315 g, 100%).

tert-Butyl N-tert-butoxycarbonyl-N-[5-[[2-chloro-5-[[(1R,3R)-2,2-dichloro-3-(3,4-dichlorophenyl)cyclopropanecarbonyl]amino]-3-methyl-benzoyl]amino]-2,4-difluoro-phenyl]carbamate (F1455)

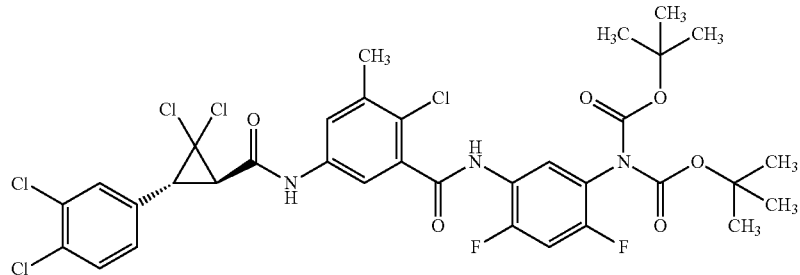 [SMILES: Cc1cc(NC(=O)[C@H]2[C@H](c3ccc(Cl)c(Cl)c3)C2(Cl)Cl)cc(C(=O)Nc2cc(N(C(=O)OC(C)(C)C)C(=O)OC(C)(C)C)c(F)cc2F)c1Cl]

Isolated as an off-white solid (0.305 g, 100%)

tert-Butyl N-tert-butoxycarbonyl-N-[5-[[2-chloro-5-[[(1R,3R)-2,2-dichloro-3-(3,4,5-trichlorophenyl)cyclopropanecarbonyl]amino]-3-methyl-benzoyl]amino]-2,4-difluoro-phenyl]carbamate (F1456)

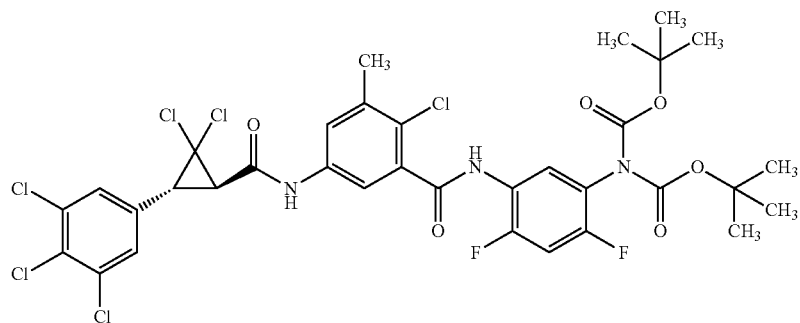 [SMILES: Cc1cc(NC(=O)[C@H]2[C@H](c3cc(Cl)c(Cl)c(Cl)c3)C2(Cl)Cl)cc(C(=O)Nc2cc(N(C(=O)OC(C)(C)C)C(=O)OC(C)(C)C)c(F)cc2F)c1Cl]

Isolated as an off-white solid (0.335 g, 100%)

tert-Butyl N-tert-butoxycarbonyl-N-[5-[[2-chloro-5-[[(1R,3R)-2,2-dichloro-3-[4-fluoro-3-(trifluoromethyl)phenyl]cyclopropanecarbonyl]amino]-3-methyl-benzoyl]amino]-2,4-difluoro-phenyl]carbamate (F1457)

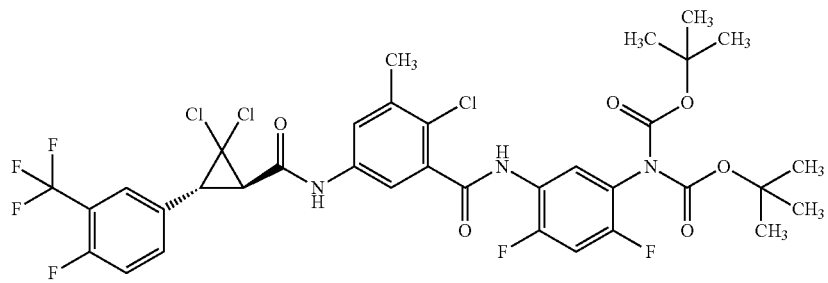 [SMILES: Cc1cc(NC(=O)[C@H]2[C@H](c3ccc(F)c(C(F)(F)F)c3)C2(Cl)Cl)cc(C(=O)Nc2cc(N(C(=O)OC(C)(C)C)C(=O)OC(C)(C)C)c(F)cc2F)c1Cl]

Isolated as an off-white solid (0.352 g, 100%).

The following compounds were prepared in like manner to the procedure outlined in Example 25:

2-Chloro-5-((1R,3R)-2,2-dichloro-3-(4-fluoro-3-(trifluoromethyl)phenyl)cyclopropane-1-carboxamido)-N-(3-(2,2-difluoro-N-methylacetamido)-2,4-difluorophenyl)benzamide (F1386)

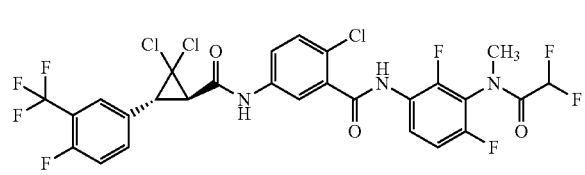 [SMILES: CN(C(=O)C(F)F)c1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white foam (0.122 g, 79%).

tert-Butyl-N-((tert-butoxy)carbonyl)-N-[5-[[5-[[(1R,3R)-2,2-dichloro-3-(3,4-dichlorophenyl)cyclopropanecarbonyl]amino]-2-fluoro-benzoyl]amino]-2,4-difluoro-phenyl]carbamate (F1467)

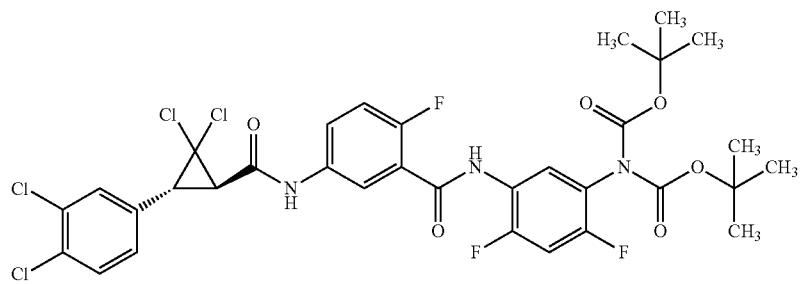 [SMILES: CC(C)(C)OC(=O)N(C(=O)OC(C)(C)C)c1cc(NC(=O)c2cc(NC(=O)[C@H]3[C@H](c4ccc(Cl)c(Cl)c4)C3(Cl)Cl)ccc2F)c(F)cc1F]

Isolated as a white solid (0.590 g, 68%).

N-(3-Acetamido-2,6-difluorophenyl)-2-chloro-5-((1R,3R)-2,2-dichloro-3-(3,4,5-trichlorophenyl)cyclopropane-1-carboxamido)benzamide (F1515)

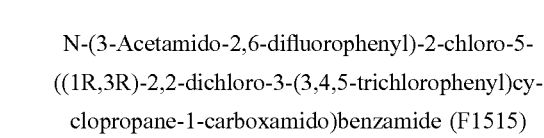

Isolated as a white solid (0.100 g, 73%).

2-Chloro-5-((1R,3R)-2,2-dichloro-3-(3,4,5-trichlorophenyl)cyclopropane-1-carboxamido)-N-(2,6-difluoro-3-(2,2,2-trifluoroacetamido)phenyl)benzamide (F1516)

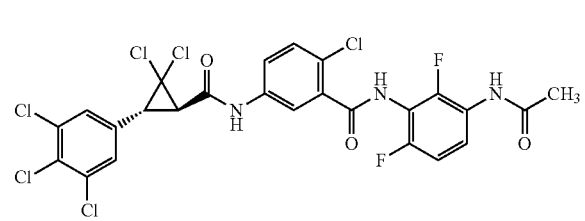 [SMILES: CC(=O)Nc1ccc(F)c(NC(=O)c2cc(NC(=O)[C@H]3[C@H](c4cc(Cl)c(Cl)c(Cl)c4)C3(Cl)Cl)ccc2Cl)c1F]

Isolated as a white solid (0.118 g, 79%).

N-(5-Acetamido-2,4-difluorophenyl)-2-chloro-5-((1R,3R)-2,2-dichloro-3-(3,4,5-trichlorophenyl)cyclopropane-1-carboxamido)benzamide (F1517)

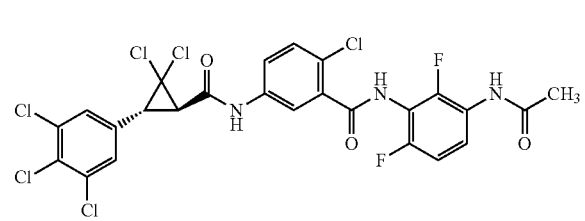 [SMILES: CC(=O)Nc1ccc(F)c(NC(=O)c2cc(NC(=O)[C@H]3[C@H](c4cc(Cl)c(Cl)c(Cl)c4)C3(Cl)Cl)ccc2Cl)c1F]

Isolated as a white solid (0.116 g, 85%).

511

2-Chloro-5-((1R,3R)-2,2-dichloro-3-(3,4,5-trichlorophenyl)cyclopropane-1-carboxamido)-N-(5-(2,2-difluoroacetamido)-2,4-difluorophenyl)benzamide (F1518)

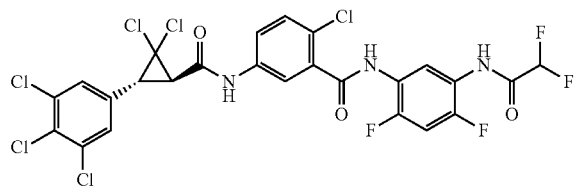 [SMILES: O=C(Nc1cc(NC(=O)C(F)F)c(F)cc1F)c1cc(NC(=O)[C@H]2[C@H](c3cc(Cl)c(Cl)c(Cl)c3)C2(Cl)Cl)ccc1Cl]

Isolated as a tan solid (0.114 g, 79%).

2-Chloro-5-((1R,3R)-2,2-dichloro-3-(3,4,5-trichlorophenyl)cyclopropane-1-carboxamido)-N-(2,4-difluoro-5-(2,2,2-trifluoroacetamido)phenyl)benzamide (F1519)

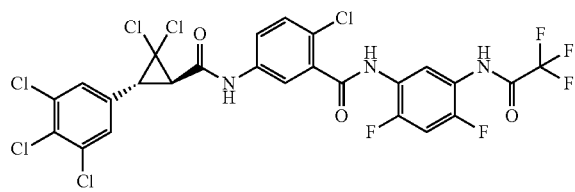 [SMILES: O=C(Nc1cc(NC(=O)C(F)(F)F)c(F)cc1F)c1cc(NC(=O)[C@H]2[C@H](c3cc(Cl)c(Cl)c(Cl)c3)C2(Cl)Cl)ccc1Cl]

Isolated as a white solid (0.118 g, 79%).

N-(3-Acetamido-2,4-difluorophenyl)-2-chloro-5-((1R,3R)-2,2-dichloro-3-(3,4,5-trichlorophenyl)cyclopropane-1-carboxamido)benzamide (F1532)

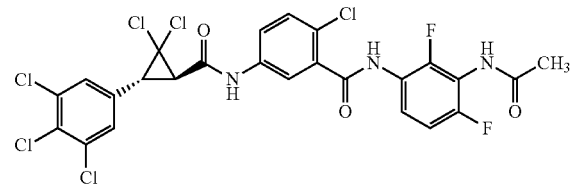 [SMILES: CC(=O)Nc1c(F)ccc(NC(=O)c2cc(NC(=O)[C@H]3[C@H](c4cc(Cl)c(Cl)c(Cl)c4)C3(Cl)Cl)ccc2Cl)c1F]

Isolated as a white solid (0.119 g, 87%).

2-Chloro-5-((1R,3R)-2,2-dichloro-3-(3,4,5-trichlorophenyl)cyclopropane-1-carboxamido)-N-(2,4-difluoro-3-(2,2,2-trifluoroacetamido)phenyl)benzamide (F1533)

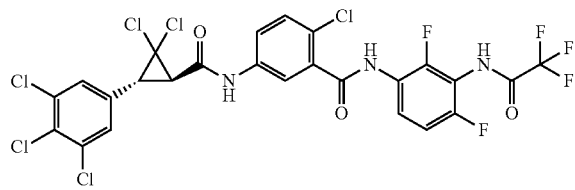 [SMILES: O=C(Nc1ccc(F)c(NC(=O)C(F)(F)F)c1F)c1cc(NC(=O)[C@H]2[C@H](c3cc(Cl)c(Cl)c(Cl)c3)C2(Cl)Cl)ccc1Cl]

Isolated as a white solid (0.121 g, 79%).

512

N-(3-Acetamido-2,6-difluorophenyl)-2-chloro-5-((1R,3R)-2,2-dichloro-3-(3,4-dichlorophenyl)cyclopropane-1-carboxamido)benzamide (F1536)

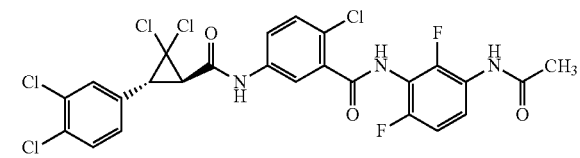 [SMILES: CC(=O)Nc1ccc(F)c(NC(=O)c2cc(NC(=O)[C@H]3[C@H](c4ccc(Cl)c(Cl)c4)C3(Cl)Cl)ccc2Cl)c1F]

Isolated as a white solid (0.131 g, 90%).

2-Chloro-5-((1R,3R)-2,2-dichloro-3-(3,4-dichlorophenyl)cyclopropane-1-carboxamido)-N-(2,6-difluoro-3-(2,2,2-trifluoroacetamido)phenyl)benzamide (F1537)

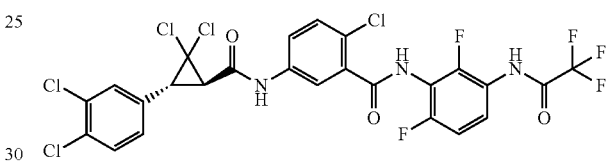

Isolated as a white solid (0.141 g, 91%).

2-Chloro-5-((1R,3R)-2,2-dichloro-3-(4-fluoro-3-(trifluoromethyl)phenyl)cyclopropane-1-carboxamido)-N-(2,6-difluoro-3-(2,2,2-trifluoroacetamido)phenyl)benzamide (F1538)

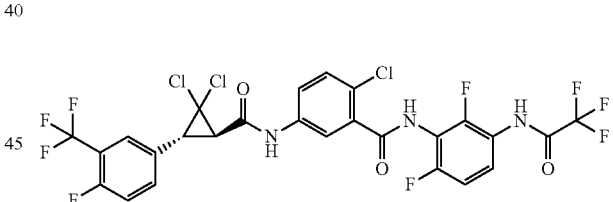

Isolated as a white solid (0.138 g, 90%).

N-(5-Acetamido-2,4-difluorophenyl)-2-chloro-5-((1R,3R)-2,2-dichloro-3-(4-fluoro-3-(trifluoromethyl)phenyl)cyclopropane-1-carboxamido)benzamide (F1539)

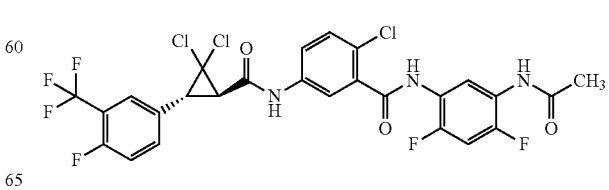

Isolated as a white solid (0.127 g, 90%).

2-Chloro-5-((1R,3R)-2,2-dichloro-3-(4-fluoro-3-(trifluoromethyl)phenyl)cyclopropane-1-carboxamido)-N-(5-(2,2-difluoroacetamido)-2,4-difluorophenyl)benzamide (F1540)

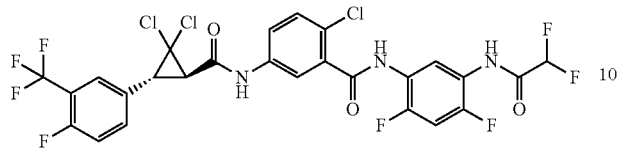

Isolated as a tan solid (0.137 g, 94%).

2-Chloro-5-((1R,3R)-2,2-dichloro-3-(4-fluoro-3-(trifluoromethyl)phenyl)cyclopropane-1-carboxamido)-N-(2,4-difluoro-5-(2,2,2-trifluoroacetamido)phenyl)benzamide (F1541)

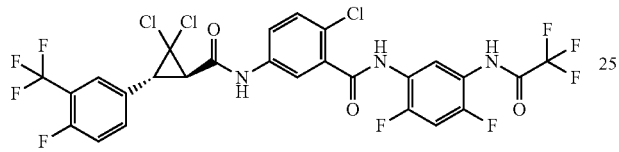

Isolated as a white solid (0.133 g, 89%).

tert-Butyl (3-(2-chloro-5-((1R,3R)-2,2-dichloro-3-(4-fluoro-3-(trifluoromethyl)phenyl)cyclopropane-1-carboxamido)benzamido)-2,4-difluorophenyl)carbamate (F1542)

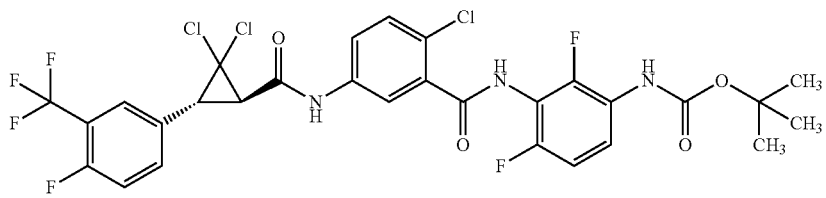 [SMILES: CC(C)(C)OC(=O)Nc1ccc(F)c(NC(=O)c2cc(NC(=O)[C@H]3[C@H](c4ccc(F)c(C(F)(F)F)c4)C3(Cl)Cl)ccc2Cl)c1F]

Isolated as a white solid (0.712 g, 93%).

tert-Butyl N-tert-butoxycarbonyl-N-[5-[[2-chloro-5-[[(1R,3R)-2,2-dichloro-3-[4-fluoro-3-(trifluoromethyl)phenyl]cyclopropanecarbonyl]amino]benzoyl]amino]-2,4-difluoro-phenyl]carbamate (F1563)

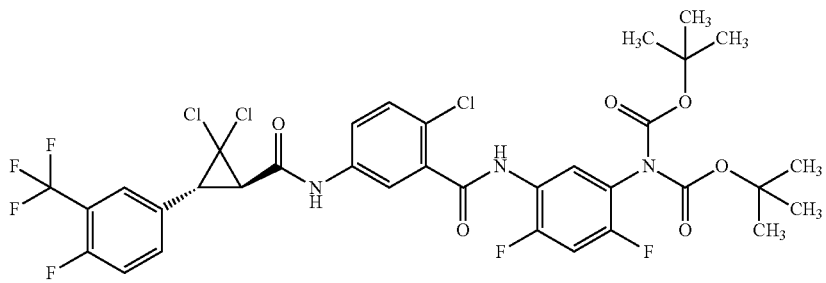 [SMILES: CC(C)(C)OC(=O)N(C(=O)OC(C)(C)C)c1cc(NC(=O)c2cc(NC(=O)[C@H]3[C@H](c4ccc(F)c(C(F)(F)F)c4)C3(Cl)Cl)ccc2Cl)c(F)cc1F]

Isolated as a white solid (0.310 g, 90%).

515

2-Chloro-5-((1R,3R)-2,2-dichloro-3-(4-fluoro-3-(trifluoromethyl)phenyl)cyclopropane-1-carboxamido)-4-fluoro-N-phenylbenzamide (F1723)

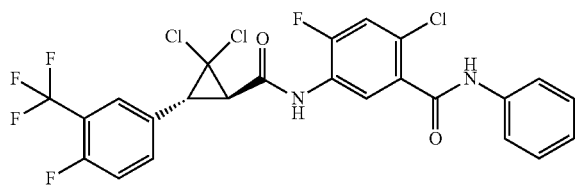 [SMILES: O=C(Nc1ccccc1)c1cc(NC(=O)[C@H]2[C@H](c3ccc(F)c(C(F)(F)F)c3)C2(Cl)Cl)c(F)cc1Cl]

Isolated as a light-tan solid (0.070 g, 79%).

2-Chloro-5-((1R,3R)-2,2-dichloro-3-(4-fluoro-3-(trifluoromethyl)phenyl)cyclopropane-1-carboxamido)-4-fluoro-N-(4-fluorophenyl)benzamide (F1725)

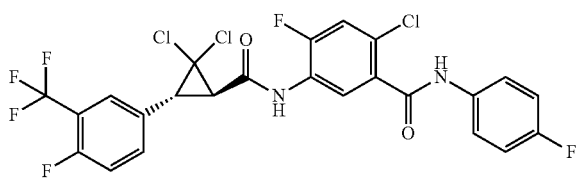 [SMILES: O=C(Nc1ccc(F)cc1)c1cc(NC(=O)[C@H]2[C@H](c3ccc(F)c(C(F)(F)F)c3)C2(Cl)Cl)c(F)cc1Cl]

Isolated as a light-tan solid (0.091 g, 97%).

2-Chloro-5-((1R,3R)-2,2-dichloro-3-(4-fluoro-3-(trifluoromethyl)phenyl)cyclopropane-1-carboxamido)-N-(2,4-difluorophenyl)-4-fluorobenzamide (F1727)

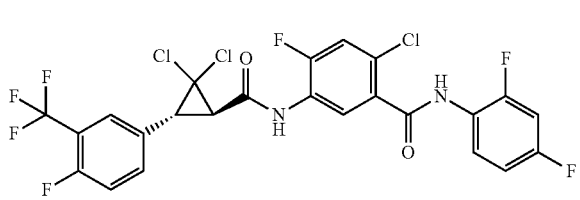 [SMILES: O=C(Nc1ccc(F)cc1F)c1cc(NC(=O)[C@H]2[C@H](c3ccc(F)c(C(F)(F)F)c3)C2(Cl)Cl)c(F)cc1Cl]

Isolated as a white solid (0.085 g, 88%).

516

2-Chloro-5-((1R,3R)-2,2-dichloro-3-(4-fluoro-3-(trifluoromethyl)phenyl)cyclopropane-1-carboxamido)-N-(3-(2,2-difluoroacetamido)-2,4-difluorophenyl)-4-fluorobenzamide (F1729)

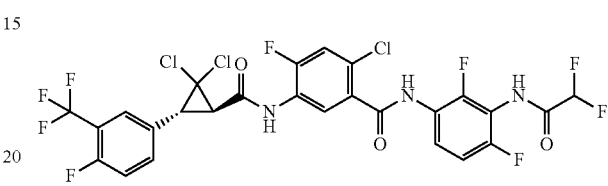

Isolated as a white solid (0.093 g, 83%).

tert-Butyl N-tert-butoxycarbonyl-N-[3-[[2-chloro-5-[[(1R,3R)-2,2-dichloro-3-[4-fluoro-3-(trifluoromethyl)phenyl]cyclopropanecarbonyl]amino]-4-fluoro-benzoyl]amino]-2,6-difluoro-phenyl]carbamate (F1730)

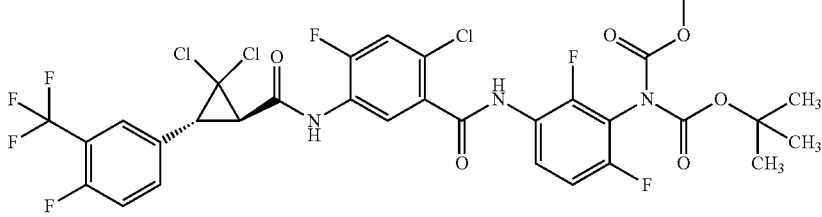

Isolated as a white solid (0.102 g, 79%).

5-((1R,3R)-2,2-Dichloro-3-(3,4,5-trichlorophenyl)cyclopropane-1-carboxamido)-N-(2,6-difluoro-3-nitrophenyl)-2,3-difluorobenzamide (F1765)

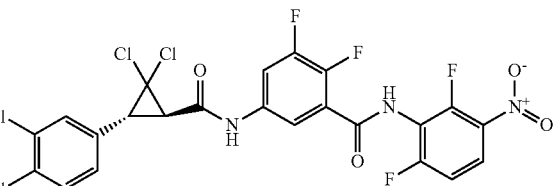

Isolated as a white foam (0.425 g, 44%).

tert-Butyl (3-(2-chloro-5-((1R,3R)-2,2-dichloro-3-(4-fluoro-3-(trifluoromethyl)phenyl)cyclopropane-1-carboxamido)benzamido)-2,6-difluorophenyl)(prop-2-yn-1-yl)carbamate (F1881)

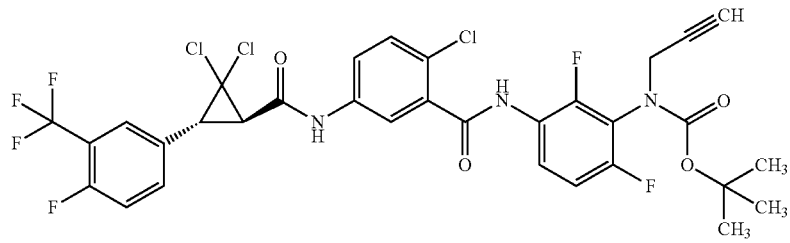 [SMILES: C#CCN(C(=O)OC(C)(C)C)c1c(F)ccc(NC(=O)c2cc(NC(=O)[C@H]3[C@H](c4ccc(F)c(C(F)(F)F)c4)C3(Cl)Cl)ccc2Cl)c1F]

Isolated as a yellow oil (0.33 g, 80%).

tert-Butyl (3-(2-chloro-5-((1R,3R)-2,2-dichloro-3-(4-fluoro-3-(trifluoromethyl)phenyl)cyclopropane-1-carboxamido)benzamido)-2,6-difluorophenyl)(2-fluoroethyl)carbamate (F1882)

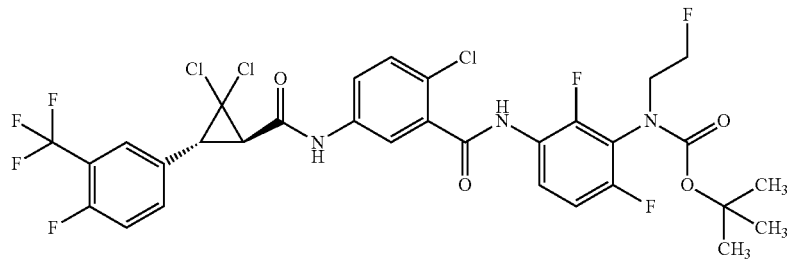 [SMILES: CC(C)(C)OC(=O)N(CCF)c1c(F)ccc(NC(=O)c2cc(NC(=O)[C@H]3[C@H](c4ccc(F)c(C(F)(F)F)c4)C3(Cl)Cl)ccc2Cl)c1F]

Isolated as an amber oil (0.24 g, 63%).

tert-Butyl (3-(2-chloro-5-((1R,3R)-2,2-dichloro-3-(4-fluoro-3-(trifluoromethyl)phenyl)cyclopropane-1-carboxamido)benzamido)-2,6-difluorophenyl)(propyl)carbamate (F1883)

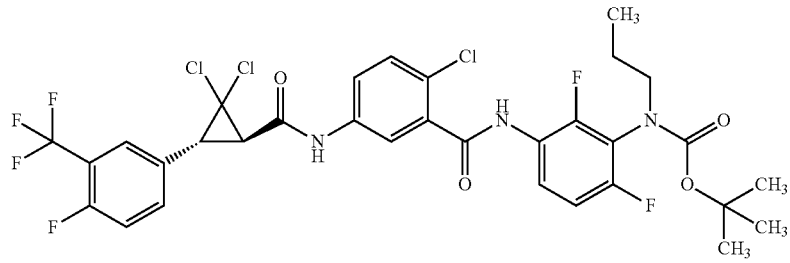 [SMILES: CCCN(C(=O)OC(C)(C)C)c1c(F)ccc(NC(=O)c2cc(NC(=O)[C@H]3[C@H](c4ccc(F)c(C(F)(F)F)c4)C3(Cl)Cl)ccc2Cl)c1F]

Isolated as a white foam (0.55 g, 65%).

2-Chloro-5-((1R,3R)-2,2-dichloro-3-(4-fluoro-3-(trifluoromethyl)phenyl)cyclopropane-1-carboxamido)-N-ethyl-4-fluorobenzamide (F2083)

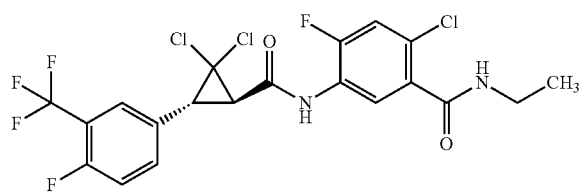 [SMILES: CCNC(=O)c1cc(NC(=O)[C@H]2[C@H](c3ccc(F)c(C(F)(F)F)c3)C2(Cl)Cl)c(F)cc1Cl]

Isolated as a white solid (0.051 g, 63%).

2-Chloro-5-((1R,3R)-2,2-dichloro-3-(4-fluoro-3-(trifluoromethyl)phenyl)cyclopropane-1-carboxamido)-4-fluoro-N-(2,2,2-trifluoroethyl)benzamide (F2084)

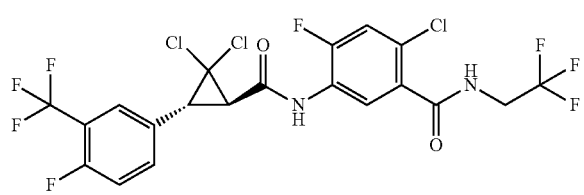 [SMILES: O=C(NCC(F)(F)F)c1cc(NC(=O)[C@H]2[C@H](c3ccc(F)c(C(F)(F)F)c3)C2(Cl)Cl)c(F)cc1Cl]

Isolated as a white solid (0.070 g, 78%).

2-Chloro-5-((1R,3R)-2,2-dichloro-3-(4-fluoro-3-(trifluoromethyl)phenyl)cyclopropane-1-carboxamido)-4-fluoro-N-(2,2,3,3,3-pentafluoropropyl)benzamide (F2085)

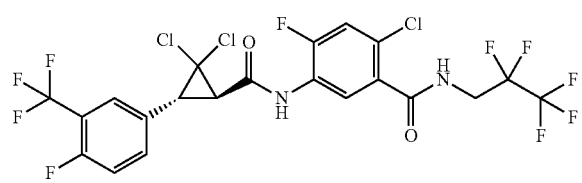 [SMILES: O=C(NCC(F)(F)C(F)(F)F)c1cc(NC(=O)[C@H]2[C@H](c3ccc(F)c(C(F)(F)F)c3)C2(Cl)Cl)c(F)cc1Cl]

Isolated as a white solid (0.078 g, 80%).

The following compounds were prepared in like manner to the procedure outlined in Example 32:

Ethyl (3-(2-chloro-5-((1R,3R)-2,2-dichloro-3-(3,4-dichlorophenyl)cyclopropane-1-carboxamido)benzamido)-2,6-difluorophenyl)carbamate (F1476)

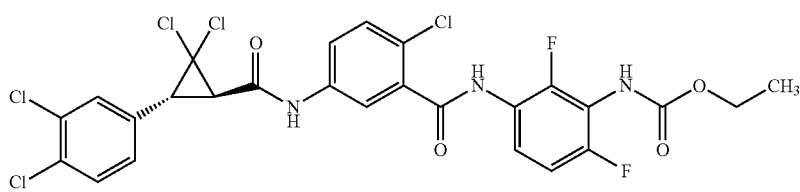 [SMILES: CCOC(=O)Nc1c(F)ccc(NC(=O)c2cc(NC(=O)[C@H]3[C@H](c4ccc(Cl)c(Cl)c4)C3(Cl)Cl)ccc2Cl)c1F]

Isolated as a tan foam (0.034 g, 30%).

The following compounds were prepared in like manner to the procedure outlined in Example 39:

2-Chloro-5-((1R,3R)-2,2-dichloro-3-(3,4-dichlorophenyl)cyclopropane-1-carboxamido)-3-methylbenzoic acid (C224)

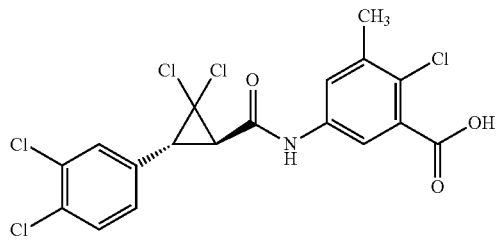 [SMILES: Cc1cc(NC(=O)[C@H]2[C@H](c3ccc(Cl)c(Cl)c3)C2(Cl)Cl)cc(C(=O)O)c1Cl]

Isolated as a white solid (0.60 g, 77%): mp 212-215° C.; $^1$H NMR (400 MHz, Acetone-$d_6$) δ 11.30 (br s, 1H), 10.09 (s, 1H), 8.07 (d, J=2.7 Hz, 1H), 7.83 (d, J=2.7 Hz, 1H), 7.68 (d, J=1.9 Hz, 1H), 7.63 (d, J=8.3 Hz, 1H), 7.45 (dd, J=8.3, 1.7 Hz, 1H), 3.63 (d, J=8.3 Hz, 1H), 3.38 (d, J=8.3 Hz, 1H), 2.42 (s, 3H); $^{13}$C NMR (101 MHz, Acetone-$d_6$) δ 166.20, 162.50, 138.25, 137.21, 134.35, 132.38, 131.88, 131.48, 130.99, 130.54, 129.20, 126.66, 123.79, 119.06, 62.01, 39.28, 37.38, 19.94; ESIMS m/z 468 ([M+H]$^+$).

2-Chloro-5-((1R,3R)-2,2-dichloro-3-(3,4,5-trichlorophenyl)cyclopropane-1-carboxamido)-3-methylbenzoic acid (C225)

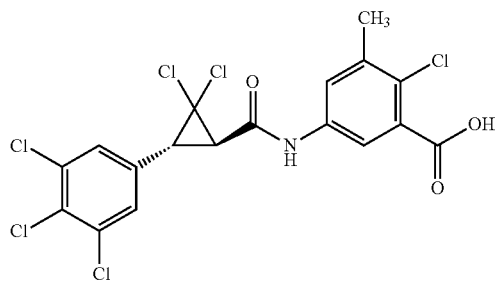 [SMILES: Cc1cc(NC(=O)[C@H]2[C@H](c3cc(Cl)c(Cl)c(Cl)c3)C2(Cl)Cl)cc(C(=O)O)c1Cl]

Isolated as a white solid (0.635 g, 85%): mp 195-200° C.; $^1$H NMR (400 MHz, Acetone-$d_6$) δ 10.09 (s, 1H), 8.06 (d, J=2.6 Hz, 1H), 7.83 (d, J=2.5 Hz, 1H), 7.71 (d, J=0.8 Hz, 2H), 3.66 (d, J=8.3 Hz, 1H), 3.45 (d, J=8.3 Hz, 1H), 2.42 (s, 3H); $^{13}$C NMR (101 MHz, Acetone-$d_6$) δ 166.18, 162.30, 138.26, 137.18, 134.90, 133.64, 132.39, 130.22, 129.76, 126.70, 123.79, 119.07, 61.79, 39.34, 37.08, 19.94; ESIMS m/z 501 ([M+H]$^+$).

2-Chloro-5-((1R,3R)-2,2-dichloro-3-(4-fluoro-3-(trifluoromethyl)phenyl)cyclopropane-1-carboxamido)-3-methylbenzoic acid (C226)

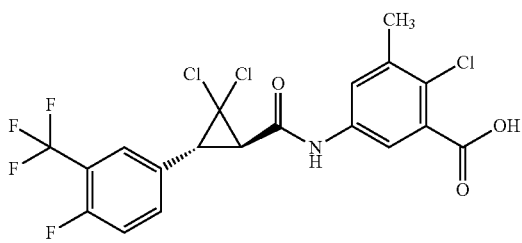

Isolated as a white solid (0.570 g, 75%): mp 190-193° C.; $^1$H NMR (400 MHz, Acetone-$d_6$) δ 11.39 (br s, 1H), 10.08 (s, 1H), 8.07 (d, J=2.6 Hz, 1H), 7.87-7.81 (m, 3H), 7.48 (t, J=9.9 Hz, 1H), 3.71 (d, J=8.3 Hz, 1H), 3.43 (d, J=8.3 Hz, 1H), 2.42 (s, 3H); $^{19}$F NMR (376 MHz, Acetone-$d_6$) δ −61.87 (d, J=12.8 Hz), −117.65 (q, J=12.8 Hz); ESIMS m/z 484 ([M+H]$^+$).

5-((1R,3R)-2,2-Dichloro-3-(3,4-dichlorophenyl)cyclopropane-1-carboxamido)-2-fluorobenzoic acid (C227)

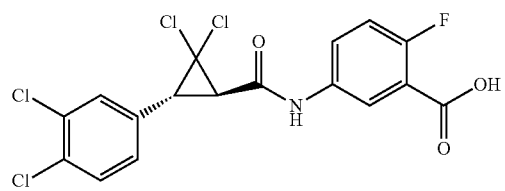 [SMILES: O=C(O)c1cc(NC(=O)[C@H]2[C@H](c3ccc(Cl)c(Cl)c3)C2(Cl)Cl)ccc1F]

Isolated as a grey foam (1.6 g, 93%): $^1$H NMR (400 MHz, DMSO-$d_6$) δ 13.32 (s, 1H), 10.86 (s, 1H), 8.21 (dd, J=6.6, 2.8 Hz, 1H), 7.85 (ddd, J=9.0, 4.1, 2.8 Hz, 1H), 7.75 (d, J=2.1 Hz, 1H), 7.69 (d, J=8.3 Hz, 1H), 7.42 (dd, J=8.4, 2.2 Hz, 1H), 7.31 (dd, J=10.5, 8.9 Hz, 1H), 3.59 (d, J=8.5 Hz, 1H), 3.43 (d, J=8.5 Hz, 1H); $^{19}$F NMR (376 MHz, DMSO-$d_6$) δ −116.06; ESIMS m/z 438 ([M+H]$^+$).

5-((1R,3R)-2,2-Dichloro-3-(3,4,5-trichlorophenyl)cyclopropane-1-carboxamido)-2-fluorobenzoic acid (C228)

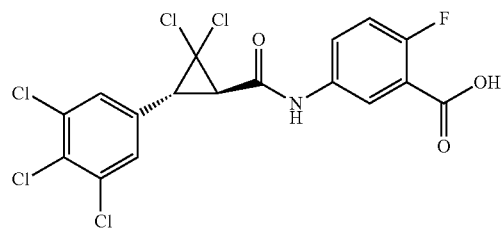 [SMILES: O=C(O)c1cc(NC(=O)[C@H]2[C@H](c3cc(Cl)c(Cl)c(Cl)c3)C2(Cl)Cl)ccc1F]

Isolated as a brown foam (1.15 g, 80%): $^1$H NMR (400 MHz, DMSO-$d_6$) δ 13.34 (s, 1H), 10.83 (s, 1H), 8.21 (dd, J=6.6, 2.8 Hz, 1H), 7.85 (ddd, J=9.0, 4.2, 2.9 Hz, 1H), 7.80 (s, 2H), 7.32 (dd, J=10.5, 8.9 Hz, 1H), 3.62 (d, J=8.5 Hz, 1H), 3.51 (d, J=8.5 Hz, 1H); $^{19}$F NMR (376 MHz, DMSO-$d_6$) δ −116.06; ESIMS m/z 472 ([M+H]$^+$).

5-((1R,3R)-2,2-Dichloro-3-(4-fluoro-3-(trifluoromethyl)phenyl)cyclopropane-1-carboxamido)-2-fluorobenzoic acid (C229)

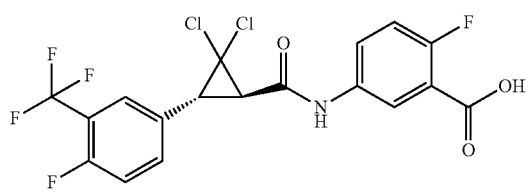 [SMILES: O=C(O)c1cc(NC(=O)[C@H]2[C@H](c3ccc(F)c(C(F)(F)F)c3)C2(Cl)Cl)ccc1F]

Isolated as a cream solid (1.01 g, 88%): $^1$H NMR (400 MHz, DMSO-$d_6$) δ 13.34 (s, 1H), 10.86 (s, 1H), 8.22 (dd, J=6.6, 2.9 Hz, 1H), 7.90-7.78 (m, 3H), 7.59 (dd, J=10.7, 8.6 Hz, 1H), 7.32 (dd, J=10.5, 8.9 Hz, 1H), 3.68 (d, J=8.4 Hz, 1H), 3.47 (d, J=8.5 Hz, 1H); $^{19}$F NMR (376 MHz, DMSO-$d_6$) δ −59.92 (d, J=12.9 Hz), −116.06, 116.98 (q, J=13.0 Hz); ESIMS m/z 454 ([M+H]$^+$).

5-((1R,3R)-2,2-Dichloro-3-(3,4,5-trichlorophenyl)cyclopropane-1-carboxamido)-2,3-difluorobenzoic acid (C230)

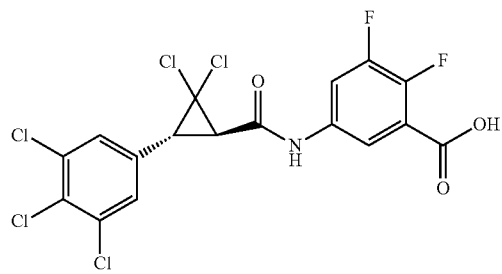 [SMILES: O=C(O)c1cc(NC(=O)[C@H]2[C@H](c3cc(Cl)c(Cl)c(Cl)c3)C2(Cl)Cl)cc(F)c1F]

Isolated as a brown foam (0.73 g, 88%): $^1$H NMR (400 MHz, DMSO-$d_6$) δ 13.69 (s, 1H), 11.02 (s, 1H), 8.00 (ddd, J=12.2, 6.6, 2.7 Hz, 1H), 7.93 (dt, J=4.7, 2.0 Hz, 1H), 7.81 (d, J=0.7 Hz, 2H), 3.66-3.61 (m, 1H), 3.53 (d, J=8.5 Hz, 1H); $^{19}$F NMR (376 MHz, DMSO-$d_6$) δ −135.50 (d, J=22.7 Hz), −142.58 (d, J=22.6 Hz); ESIMS m/z 488 ([M+H]$^+$).

2-Chloro-5-((1R,3R)-2,2-dichloro-3-(4-fluoro-3-(trifluoromethyl)phenyl)-cyclopropane-1-carboxamido)-4-fluorobenzoic acid (C231)

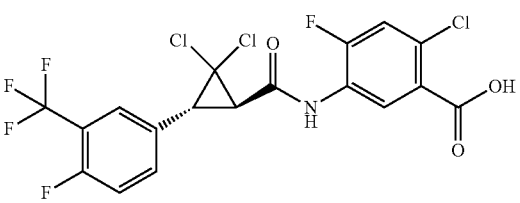 [SMILES: O=C(O)c1cc(NC(=O)[C@H]2[C@H](c3ccc(F)c(C(F)(F)F)c3)C2(Cl)Cl)c(F)cc1Cl]

Isolated as a cream-colored solid (1.23 g, 68%): mp 188-191° C.; $^1$H NMR (400 MHz, DMSO-$d_6$) δ 13.54 (s, 1H), 10.73 (s, 1H), 8.60 (d, J=8.4 Hz, 1H), 7.82 (ddd, J=11.1, 6.0, 2.4 Hz, 2H), 7.68 (d, J=10.7 Hz, 1H), 7.60 (dd, J=10.7, 8.5 Hz, 1H), 3.73 (d, J=8.5 Hz, 1H), 3.68 (d, J=8.6 Hz, 1H); $^{19}$F NMR (376 MHz, DMSO-$d_6$) δ −59.94 (d, J=12.4 Hz), −116.92 (q, J=12.4 Hz), −118.01; HRMS-ESI (m/z) [M+H]$^+$ calcd for $C_{18}H_9Cl_3F_6NO_3$, 486.9568; found, 486.9579.

2-Chloro-5-(((1R,3R)-2,2-dichloro-3-(4-fluoro-3-(trifluoromethyl)phenyl)-cyclopropane-1-carboxamido)benzoic acid (C232)

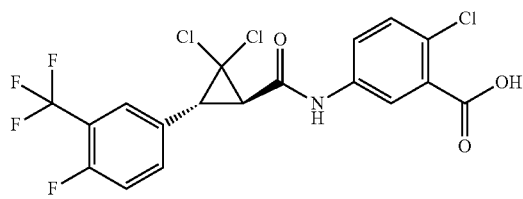 [SMILES: O=C(O)c1cc(NC(=O)[C@H]2[C@H](c3ccc(F)c(C(F)(F)F)c3)C2(Cl)Cl)ccc1Cl]

Isolated as a tan solid (5.8 g, 93%): $^1$H NMR (400 MHz, DMSO-$d_6$) δ 13.48 (s, 1H), 10.94 (s, 1H), 8.17 (d, J=2.7 Hz, 1H), 7.94-7.72 (m, 3H), 7.68-7.44 (m, 2H), 3.68 (d, J=8.4 Hz, 1H), 3.49 (d, J=8.5 Hz, 1H); $^{19}$F NMR (376 MHz, DMSO-$d_6$) δ −59.93 (d, J=12.6 Hz), −116.95 (q, J=12.5 Hz); ESIMS m/z 472 ([M+H]$^+$).

The following compounds were prepared in like manner to the procedure outlined in Example 40:

trans-2,2-Dichloro-3-(fluorophenyl)cyclopropane-1-carboxylic acid (C233)

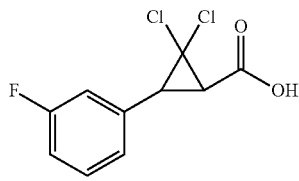

Isolated as a pale yellow solid (2.8 g, 52%): $^1$H NMR (400 MHz, DMSO-$d_6$) δ 13.39 (s, 1H), δ 7.46-7.39 (m, 1H), 7.29 (t, J=8.0 Hz, 2H), 7.21-7.15 (m, 1H), 3.45 (d, J=8.0 Hz, 1H), 3.41 (d, J=8.8 Hz, 1H); ESIMS m/z 247.11 ([M−H]$^-$).

trans-2,2-Dichloro-3-(3-chlorophenyl)cyclopropane-1-carboxylic acid (C234)

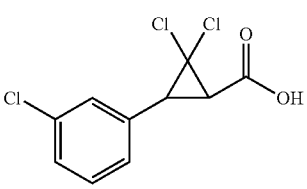

Isolated as a white solid (1.1 g, 23%): $^1$H NMR (400 MHz, DMSO-$d_6$) δ 13.39 (s, 1H), 7.52 (s, 1H), 7.42-7.38 (m, 3H), 3.45 (d, J=8.4 Hz, 1H), 3.41 (d, J=8.4 Hz, 1H); ESIMS m/z 262.73 ([M−H]$^-$).

trans-3-(3-Bromophenyl)-2,2-dichlorocyclopropane-1-carboxylic acid (C235)

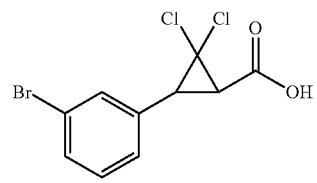 [SMILES: O=C(O)C1C(c2cccc(Cl)c2)C1(Cl)Cl]

Isolated as a white solid (1.25 g, 26%): $^1$H NMR (400 MHz, DMSO-$d_6$) δ 13.41 (s, 1H), 7.66 (s, 1H), 7.54 (d, J=7.6 Hz, 1H), 7.43 (d, J=7.6 Hz, 1H), 7.34 (t, J=8.0 Hz, 1H), 3.45 (d, J=8.8 Hz, 1H), 3.42 (d, J=8.4 Hz, 1H); ESIMS m/z 307.05 ([M−H]$^-$)

trans-2,2-Dichloro-3-(3-(trifluoromethoxy)phenyl)cyclopropane-1-carboxylic acid (C236)

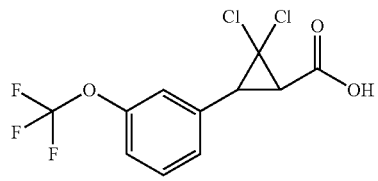 [SMILES: O=C(O)C1C(c2cccc(OC(F)(F)F)c2)C1(Cl)Cl]

Isolated as a pale yellow solid (1.8 g, 38%): $^1$H NMR (400 MHz, DMSO-$d_6$) δ 1339 (s, 1H), 7.54-7.43 (m, 3H), 7.34 (d, J=8.0 Hz, 1H), 3.51 (d, J=8.8 Hz, 1H), 3.44 (d, J=8.8 Hz, 1H); $^{19}$F NMR (376 MHz, DMSO-$d_6$) δ −56.76; ESIMS m/z 312.77 ([M−H]$^-$).

trans-2,2-Dichloro-3-(4-fluorophenyl)cyclopropane-1-carboxylic acid (C237)

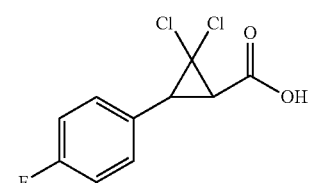

Isolated as a white solid (2.5 g, 43%): $^1$H NMR (400 MHz, DMSO-$d_6$) δ 13.39 (s, 1H), 7.46-7.42 (m, 2H), 7.23-7.17 (m, 2H), 3.41 (d, J=8.4 Hz, 1H), 3.30 (d, J=8.4 Hz, 1H); $^{19}$F NMR (376 MHz, DMSO-$d_6$) δ −114.31; ESIMS m/z 246.78 ([M−H]$^-$).

trans-2,2-Dichloro-3-(4-chlorophenyl)cyclopropane-1-carboxylic acid (C238)

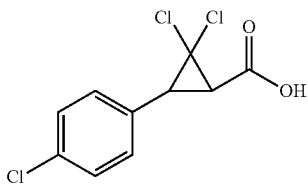

Isolated as a pale yellow solid (2.4 g, 44%): $^1$H NMR (400 MHz, DMSO-$d_6$) δ 13.29 (s, 1H), 7.48-7.42 (m, 4H), 3.43 (d, J=8.8 Hz, 1H), 3.33 (d, J=8.8 Hz, 1H); ESIMS m/z 262.73 ([M–H]$^-$).

trans-3-(4-Bromophenyl)-2,2-dichlorocyclopropane-1-carboxylic acid (C239)

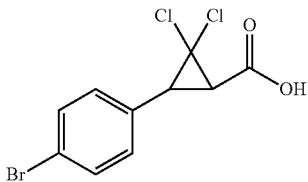 [SMILES: O=C(O)C1C(c2ccc(Cl)cc2)C1(Cl)Cl]

Isolated as a white solid (0.45 g, 9%): $^1$H NMR (400 MHz, DMSO-$d_6$) δ 7.56 (d, J=8.8 Hz, 2H), 7.36 (d, J=8.0 Hz, 2H), 3.38 (d, J=8.4 Hz, 1H), 3.28 (d, J=8.4 Hz, 1H); ESIMS m/z 306.72 ([M–H]$^-$).

The following compounds were prepared in like manner to the procedure outlined in Example 51:

trans-2,2-Dichloro-3-(4-fluoro-3-iodophenyl)cyclopropane-1-carboxylic acid (C240)

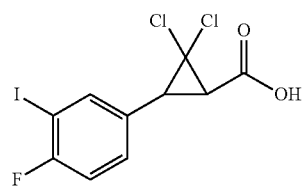

Isolated as a white solid (1.35 g, 80%): mp 147-149° C.; $^1$H NMR (400 MHz, CDCl$_3$) δ 7.67-7.62 (m, 1H), 7.62 (dd, J=6.4, 2.4 Hz, 1H), 6.93-6.88 (m, 1H), 3.45 (d, J=4.4 Hz, 1H), 2.88 (d, J=4.4 Hz, 1H); ESIMS m/z 374.98 ([M+H]$^+$).

trans-2,2-Dichloro-3-(3-(trifluoromethyl)phenyl)cyclopropane-1-carboxylic acid (C241)

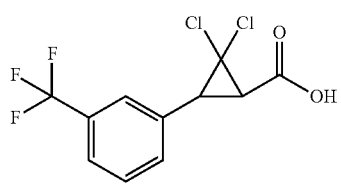

Isolated as a white solid (24 g, 43%): $^1$H NMR (400 MHz, CDCl$_3$) δ 9.55 (s, 1H), 7.66-7.59 (m, 1H), 7.57-7.44 (m, 3H), 3.55 (d, J=8.3 Hz, 1H), 2.94 (d, J=8.3 Hz, 1H); $^{19}$F NMR (376 MHz, CDCl$_3$) δ –62.70; ESIMS m/z 298 ([M–H]$^-$).

The following compounds were prepared in like manner to the procedure outlined in Example 55:

(1R,3R)-3-(3-Bromo-4-chlorophenyl)-2,2-dichlorocyclopropane-1-carboxylic acid (C242)

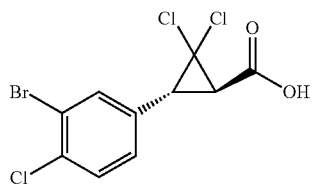

Isolated as a white solid (1.05 g, 42%, 93% ee): $^1$H NMR (400 MHz, CDCl$_3$) δ 7.53 (d, J=2.1 Hz, 1H), 7.47 (d, J=8.3 Hz, 1H), 7.17 (dd, J=8.4, 2.1 Hz, 1H), 3.43 (d, J=8.2 Hz, 1H), 2.86 (d, J=8.3 Hz, 1H); ESIMS m/z 343 ([M–H]$^-$). Racemic trans-3-(3-bromo-4-chlorophenyl)-2,2-dichlorocyclopropane-1-carboxylic acid can be prepared via methods described in U.S. Patent Application Publication US20160304522A1 (C422). The title compound was obtained from the racemate using (S)-1-phenylethan-1-amine and example 55 conditions.

The following compounds were prepared in like manner to the procedure outlined in Example 57:

tert-Butyl N-[5-[(5-amino-2-chloro-3-fluoro-benzoyl)amino]-2,4-difluoro-phenyl]-N-tert-butoxycarbonyl-carbamate (C245)

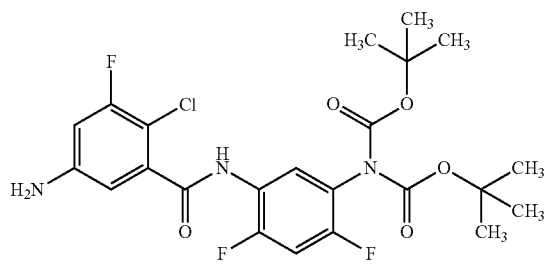 [SMILES: CC(C)(C)OC(=O)N(C(=O)OC(C)(C)C)c1cc(NC(=O)c2cc(N)cc(F)c2Cl)c(F)cc1F]

Isolated as a light-orange solid (3.125 g, 79%): 143-152° C.; $^1$H NMR (400 MHz, DMSO-$d_6$) δ 10.38 (s, 1H), 7.69 (t, J=8.1 Hz, 1H), 7.52 (t, J=10.1 Hz, 1H), 6.59 (ddd, J=7.7, 5.5, 2.5 Hz, 2H), 5.81 (s, 2H), 1.40 (s, 18H); $^{19}$F NMR (376 MHz, DMSO-$d_6$) δ –115.57, –117.36, –117.38, –121.88, –121.90; HRMS-ESI (m/z) [M+]$^+$ calcd for C$_{23}$H$_{25}$ClF$_3$N$_3$O$_5$, 515.1435; found, 515.1438.

The following compounds were prepared in like manner to the procedure outlined in Example 61:

N-(2,6-Difluoro-3-nitrophenyl)-N-ethyl-2,2-difluoroacetamide (C246)

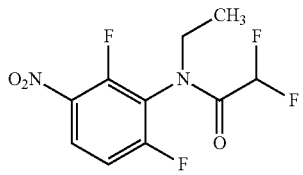

Isolated as a gold oil (0.45 g, 25%): ¹H NMR (400 MHz, CDCl₃) δ 8.39-8.15 (m, 1H), 7.21 (dddd, J=11.9, 9.7, 7.9, 2.0 Hz, 1H), 6.08 (dt, J=154.5, 53.3 Hz, 1H), 4.01-3.69 (m, 2H), 1.21 (tt, J=7.3, 1.2 Hz, 3H); ESIMS m/z 280 ([M+H]⁺).

N-Allyl-N-(2,6-difluoro-3-nitrophenyl)-2,2-difluoroacetamide (C247)

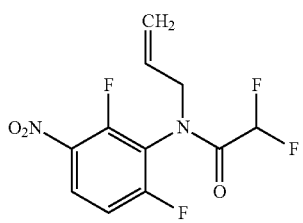 [SMILES: C=CCN(C(=O)C(F)F)c1c(F)ccc([N+](=O)[O-])c1F]

Isolated as a gold oil (0.21 g, 12%): ¹H NMR (300 MHz, CDCl₃) δ 8.23 (dddd, J=15.3, 9.5, 8.1, 5.5 Hz, 1H), 7.35-7.09 (m, 1H), 6.54-5.71 (m, 2H), 5.30-5.09 (m, 2H), 4.52-4.25 (m, 2H); ESIMS m/z 293 ([M+H]⁺).

N-(2,6-Difluoro-3-nitrophenyl)-N-methylacetamide (C248)

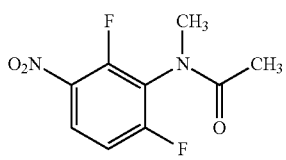 [SMILES: CC(=O)N(C)c1c(F)ccc([N+](=O)[O-])c1F]

Isolated as a tan solid (1.02 g, 61%): ¹H NMR (400 MHz, CDCl₃) δ 8.15 (dddd, J=31.6, 9.4, 8.1, 5.5 Hz, 1H), 7.32-7.05 (m, 1H), 3.31 (d, J=53.3 Hz, 3H), 2.13 (d, J=164.4 Hz, 3H); ESIMS m/z 231 ([M+H]⁺).

tert-Butyl (2,6-difluoro-3-nitrophenyl)(ethyl)carbamate (C249)

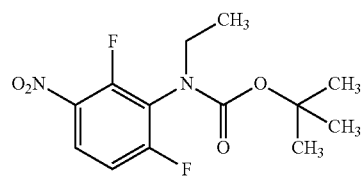 [SMILES: CCN(C(=O)OC(C)(C)C)c1c(F)ccc([N+](=O)[O-])c1F]

Isolated as a yellow oil (0.4 g, 69%): ¹H NMR (400 MHz, CDCl₃) δ 8.21-8.00 (m, 1H), 7.10 (ddd, J=9.8, 8.2, 2.0 Hz, 1H), 3.62 (dq, J=25.2, 7.3 Hz, 2H), 1.37 (s, 9H), 1.15 (dt, J=17.2, 7.2 Hz, 3H); ESIMS m/z 303 ([M+H]⁺).

tert-Butyl (2,6-difluoro-3-nitrophenyl)(prop-2-yn-1-yl)carbamate (C250)

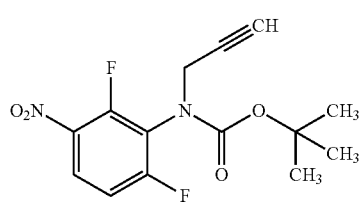 [SMILES: C#CCN(C(=O)OC(C)(C)C)c1c(F)ccc([N+](=O)[O-])c1F]

Isolated as a yellow oil (0.40 g, 67%): ¹H NMR (400 MHz, CDCl₃) δ 8.20-8.03 (m, 1H), 7.12 (ddd, J=9.7, 8.2, 2.0 Hz, 1H), 4.53-4.28 (m, 2H), 2.21 (dt, J=20.9, 2.6 Hz, 1H), 1.56 (d, J=3.4 Hz, 9H); ESIMS m/z 313 ([M+H]⁺).

tert-Butyl (2,6-difluoro-3-nitrophenyl)(2-fluoroethyl)carbamate (C251)

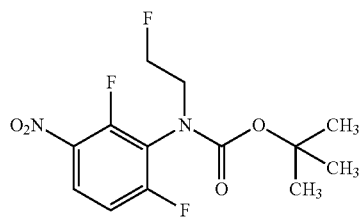

Isolated as a yellow oil (0.198 g, 32%): ¹H NMR (400 MHz, CDCl₃) δ 8.19-7.99 (m, 1H), 7.21-7.01 (m, 1H), 4.76-4.45 (m, 2H), 4.07-3.77 (m, 2H), 1.39 (s, 9H); ESIMS m/z 321 ([M+H]⁺).

tert-Butyl (2,6-difluoro-3-nitrophenyl)(propyl)carbamate (C252)

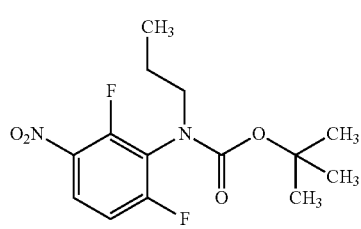 [SMILES: CCCN(C(=O)OC(C)(C)C)c1c(F)ccc([N+](=O)[O-])c1F]

Isolated as a yellow oil (0.350 g, 58%): ¹H NMR (400 MHz, CDCl₃) δ 8.09 (m, 1H), 7.10 (tt, J=9.5, 4.8 Hz, 1H), 3.64-3.48 (m, 2H), 1.56 (d, J=6.1 Hz, 4H), 1.38 (d, J=7.2 Hz, 7H), 0.92 (p, J=7.6 Hz, 3H); ESIMS m/z 317 ([M+H]⁺).

The following compounds were prepared in like manner to the procedure outlined in Example 62:

tert-Butyl (2,6-difluoro-3-nitrophenyl)(methyl)carbamate (C253)

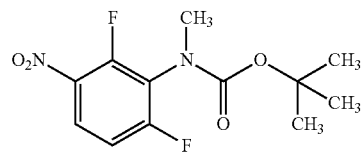

Isolated as a yellow oil (0.56 g, 76%): $^1$H NMR (400 MHz, DMSO-d$_6$) rotamers δ 8.32-8.19 (m, 1H), 7.49 (td, J=9.2, 1.9 Hz, 1H), 3.15 (s, 1H), 3.11 (s, 2H), 1.48 (s, 3H), 1.31 (s, 6H); $^{19}$F NMR (376 MHz, DMSO-d$_6$) rotamers δ −106.79 (d, J=11.4 Hz), −107.54 (d, J=11.3 Hz), −121.48 (d, J=11.4 Hz), −122.14 (d, J=11.4 Hz).

The following compounds were prepared in like manner to the procedure outlined in Example 65:

tert-Butyl N-tert-butoxycarbonyl-N-[5-[(2-chloro-3-fluoro-5-nitro-benzoyl)amino]-2,4-difluoro-phenyl]carbamate (C254)

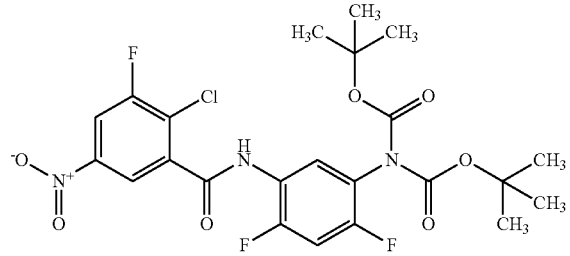

Isolated as a yellow solid (3.943 g, 85%): mp 172-175° C.; $^1$H NMR (400 MHz, DMSO-d$_6$) δ 10.74 (s, 1H), 8.52 (dd, J=8.8, 2.6 Hz, 1H), 8.44 (dd, J=2.6, 1.4 Hz, 1H), 7.90 (t, J=8.1 Hz, 1H), 7.57 (t, J=10.2 Hz, 1H), 1.42 (s, 18H); $^{19}$F NMR (376 MHz, DMSO-d$_6$) δ −109.73, −118.21, −118.22, −121.44, −121.46; HRMS-ESI (m/z) [M+]$^+$ calcd for C$_{23}$H$_{23}$ClF$_3$N$_3$O$_7$, 545.1177; found, 545.1179.

The following compounds were prepared in like manner to the procedure outlined in Example 67:

tert-Butyl (3-amino-2,6-difluorophenyl)(methyl)carbamate (C255)

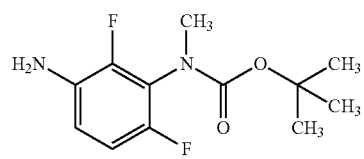 [SMILES: CN(C(=O)OC(C)(C)C)c1c(F)ccc([N+](=O)[O-])c1F]

Isolated as a white solid (0.45 g, 89%): $^1$H NMR (400 MHz, CDCl$_3$) rotamers δ 6.72 (td, J=9.1, 1.9 Hz, 1H), 6.68-6.58 (m, 1H), 3.59 (s, 2H), 3.16 (s, 3H), 1.53 (s, 2H), 1.37 (s, 7H); $^{19}$F NMR (376 MHz, CDCl$_3$) rotamers δ −132.31, −132.53, −138.84, −139.43; EIMS m/z 258.

tert-Butyl N-(5-amino-2-chloro-phenyl)-N-tert-butoxycarbonyl-carbamate (C256)

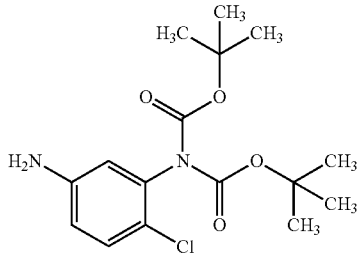

Isolated as a grey solid (1.7 g, 78%): $^1$H NMR (400 MHz, CDCl$_3$) δ 7.15 (d, J=8.5 Hz, 1H), 6.62-6.51 (m, 2H), 3.74 (s, 2H), 1.42 (s, 18H); $^{13}$C NMR (101 MHz, CDCl$_3$) δ 150.87, 145.76, 137.39, 129.65, 121.50, 116.14, 115.67, 82.71, 27.85; ESIMS m/z 341 ([M−H]$^-$).

tert-Butyl N-(4-amino-2,6-dichloro-phenyl)-N-tert-butoxycarbonyl-carbamate (C257)

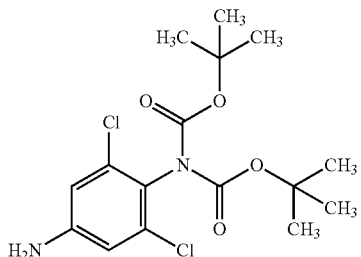

Isolated as a tan solid (1.88 g, 85%): $^1$H NMR (400 MHz, CDCl$_3$) δ 6.64 (s, 2H), 3.95 (s, 2H), 1.41 (s, 18H); $^{13}$C NMR (101 MHz, CDCl$_3$) δ 150.32, 147.10, 134.34, 125.31, 113.81, 82.64, 27.77; ESIMS m/z 376 ([M−H]$^-$).

tert-Butyl N-(4-amino-2-chloro-phenyl)-N-tert-butoxycarbonyl-carbamate (C258)

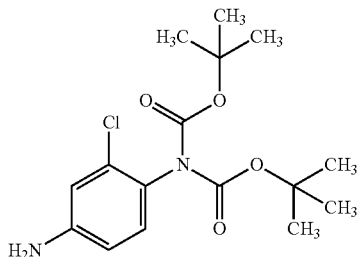

Isolated as a tan solid (1.96 g, 93%): $^1$H NMR (400 MHz, CDCl$_3$) δ 6.93 (d, J=8.5 Hz, 1H), 6.71 (d, J=2.6 Hz, 1H), 6.52 (dd, J=8.5, 2.6 Hz, 1H), 3.80 (s, 2H), 1.41 (s, 18H); $^{13}$C NMR (101 MHz, CDCl$_3$) δ 151.33, 146.96, 132.95, 130.03, 127.62, 115.23, 113.59, 82.43, 27.86; ESIMS m/z 341 ([M−H]$^-$).

531 tert-Butyl N-(4-amino-2-cyano-phenyl)-N-tert-butoxycarbonyl-carbamate (C259)

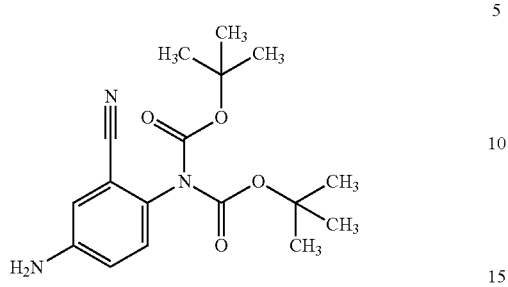

Isolated as a white solid (2.45 g, 85%): $^1$H NMR (300 MHz, CDCl$_3$) δ 7.01 (dd, J=8.6, 0.4 Hz, 1H), 6.94-6.76 (m, 2H), 4.10 (d, J=7.1 Hz, 2H), 1.43 (s, 18H); $^{13}$C NMR (75 MHz, CDCl$_3$) δ 150.99, 146.11, 132.35, 130.02, 119.18, 117.76, 116.21, 113.30, 83.42, 27.85; ESIMS m/z 332 ([M−H]$^−$).

tert-Butyl N-(4-amino-2,3-dimethyl-phenyl)-N-tert-butoxycarbonyl-carbamate (C260)

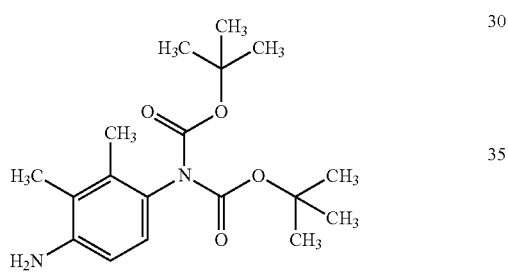

Isolated as a white solid (0.19 g, 38%): $^1$H NMR (400 MHz, CDCl$_3$) δ 6.76 (d, J=8.3 Hz, 1H), 6.53 (d, J=8.4 Hz, 1H), 3.18 (s, 2H), 2.08 (d, J=1.9 Hz, 6H), 1.42 (s, 18H); ESIMS m/z 335 ([M−H]$^−$).

tert-Butyl N-[4-amino-2-(trifluoromethyl)phenyl]-N-tert-butoxycarbonyl-carbamate (C261)

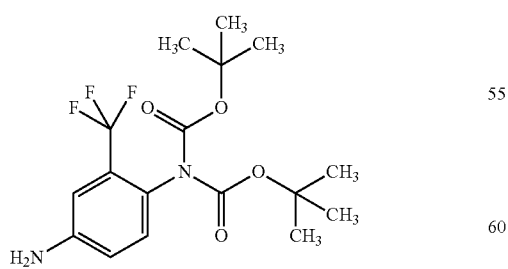

Isolated as a white solid (0.19 g, 38%): $^1$H NMR (400 MHz, CDCl$_3$) δ 6.99-6.88 (m, 2H), 6.78 (dd, J=8.5, 2.7 Hz, 1H), 3.99 (s, 2H), 1.38 (s, 18H); $^{19}$F NMR (376 MHz, CDCl$_3$) δ −61.98; ESIMS m/z 375 ([M−H]$^−$).

532 tert-Butyl (5-amino-2-methylphenyl)carbamate (C262)

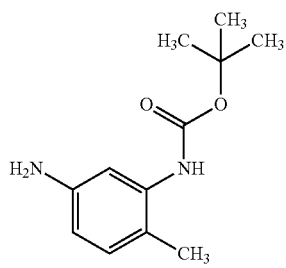

Isolated as a brown foam (1.33 g, 91%): $^1$H NMR (400 MHz, CDCl$_3$) δ 6.96 (d, J=8.1 Hz, 1H), 6.70 (s, 1H), 6.56 (dd, J=8.1, 2.5 Hz, 1H), 6.44 (s, 1H), 3.48 (s, 2H), 2.06 (s, 3H), 1.43 (s, 9H); ESIMS m/z 221 ([M−H]$^−$).

tert-Butyl N-(3-amino-2-methyl-phenyl)-N-tert-butoxycarbonyl-carbamate (C263)

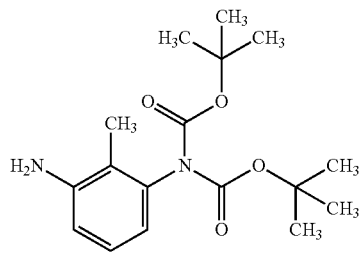

Isolated as a white solid (0.98 g, 89%): $^1$H NMR (400 MHz, CDCl$_3$) δ 6.98 (t, J=7.9 Hz, 1H), 6.63 (dd, J=8.0, 1.1 Hz, 1H), 6.55 (dd, J=7.8, 1.1 Hz, 1H), 3.61 (s, 2H), 1.99 (s, 3H), 1.41 (s, 18H); $^{13}$C NMR (101 MHz, CDCl$_3$) δ 151.83, 145.13, 138.90, 126.28, 120.32, 118.63, 114.63, 82.19, 27.92, 11.37; ESIMS m/z 323 ([M+H]$^+$).

tert-Butyl N-(5-amino-2,4-difluoro-3-methyl-phenyl)-N-tert-butoxycarbonyl-carbamate (C264)

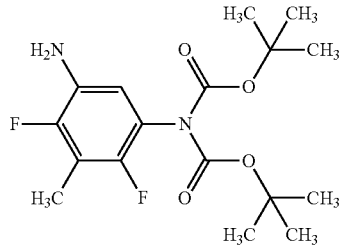 [SMILES: Cc1c(F)c(N)cc(N(C(=O)OC(C)(C)C)C(=O)OC(C)(C)C)c1F]

Isolated as a tan solid (0.71 g, 83%): $^1$H NMR (400 MHz, CDCl$_3$) δ 6.49-6.40 (m, 1H), 3.56 (s, 2H), 2.19 (t, J=2.1 Hz, 3H), 1.44 (s, 18H); $^{19}$F NMR (376 MHz, CDCl$_3$) δ −135.31, −135.93; ESIMS m/z 359 ([M+H]$^+$).

N-(3-Amino-2,6-difluorophenyl)-N-ethyl-2,2-difluoroacetamide (C265)

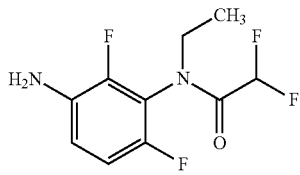

Isolated as a gold oil (0.36 g, 86%): $^1$H NMR (400 MHz, CDCl$_3$) δ 6.94-6.75 (m, 2H), 5.80 (t, J=53.5 Hz, 1H), 3.92-3.66 (m, 2H), 1.17 (tt, J=7.2, 1.1 Hz, 3H); ESIMS m/z 251 ([M+H]$^+$).

N-(3-Amino-2,6-difluorophenyl)-N-methylacetamide (C266)

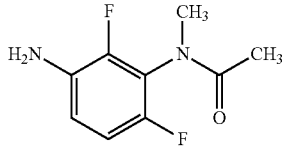

Isolated as a brown oil (0.74 g, 76%): $^1$H NMR (400 MHz, CDCl$_3$) δ 6.96-6.67 (m, 2H), 3.94 (d, J=47.1 Hz, 2H), 3.20 (s, 3H), 1.91 (s, 3H); ESIMS m/z 231 ([M+H]$^+$).

tert-Butyl (3-amino-2,6-difluorophenyl)(ethyl)carbamate (C267)

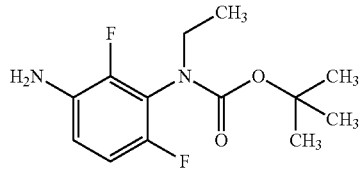

Isolated as a pink solid (0.36 g, 92%): $^1$H NMR (400 MHz, CDCl$_3$) δ 6.87-6.58 (m, 2H), 3.60 (dtt, J=18.7, 11.8, 5.8 Hz, 4H), 1.36 (s, 9H), 1.11 (dt, J=14.6, 7.1 Hz, 3H); ESIMS m/z 273 ([M+H]$^+$).

tert-Butyl (3-amino-2,6-difluorophenyl)(2-fluoroethyl)carbamate (C268)

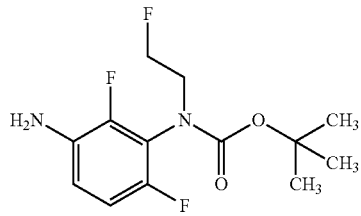

Isolated as a gold oil (0.153 g, 81%): $^1$H NMR (400 MHz, CDCl$_3$) δ 6.86-6.55 (m, 2H), 4.68-4.43 (m, 2H), 3.85 (ddt, J=26.3, 11.8, 5.8 Hz, 2H), 3.67 (s, 2H), 1.37 (s, 9H); ESIMS m/z 291 ([M+H]$^+$).

tert-Butyl (3-amino-2,6-difluorophenyl)(propyl)carbamate (C269)

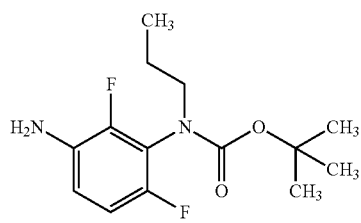

Isolated as a tan solid (0.310 g, 93%): $^1$H NMR (400 MHz, CDCl$_3$) δ 6.85-6.55 (m, 2H), 3.94-2.96 (m, 4H), 1.36 (s, 11H), 0.89 (q, J=7.8 Hz, 3H); ESIMS m/z 287 ([M+H]$^+$).

The following compounds were prepared in like manner to the procedure outlined in Example 68:

tert-Butyl N-tert-butoxycarbonyl-N-(2-chloro-5-nitro-phenyl)carbamate (C270)

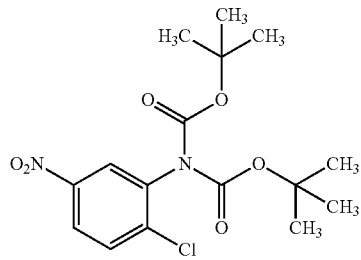 [SMILES: CC(C)(C)OC(=O)N(C(=O)OC(C)(C)C)c1cc([N+](=O)[O-])ccc1Cl]

Isolated as a white solid (2.26 g, 66%): $^1$H NMR (400 MHz, CDCl$_3$) δ 8.20-8.10 (m, 2H), 7.63 (d, J=8.8 Hz, 1H), 1.42 (s, 18H); $^{13}$C NMR (101 MHz, CDCl$_3$) δ 149.83, 146.69, 140.24, 138.31, 130.25, 125.29, 123.68, 84.04, 27.80; ESIMS m/z 373 ([M−H]$^−$).

tert-Butyl N-tert-butoxycarbonyl-N-(2,6-dichloro-4-nitro-phenyl)carbamate (C271)

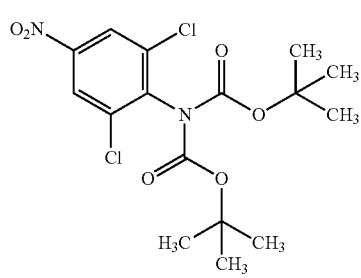 [SMILES: CC(C)(C)OC(=O)N(C(=O)OC(C)(C)C)c1c(Cl)cc([N+](=O)[O-])cc1Cl]

Isolated as a gold oil (2.26 g, 73%): $^1$H NMR (400 MHz, CDCl$_3$) δ 8.25 (s, 2H), 1.41 (s, 18H); $^{13}$C NMR (101 MHz, CDCl$_3$) δ 152.16, 148.46, 146.81, 141.22, 135.61, 123.13, 84.25, 27.69; ESIMS m/z 408 ([M−H]$^-$).

tert-Butyl N-tert-butoxycarbonyl-N-(2-chloro-4-nitro-phenyl)carbamate (C272)

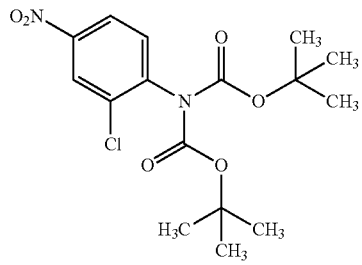

Isolated as a white solid (3.3 g, 97%): $^1$H NMR (400 MHz, CDCl$_3$) δ 8.34 (d, J=2.6 Hz, 1H), 8.17 (dd, J=8.7, 2.5 Hz, 1H), 7.43 (d, J=8.7 Hz, 1H), 1.41 (s, 18H); $^{13}$C NMR (101 MHz, CDCl$_3$) δ 149.57, 147.24, 143.02, 134.09, 130.62, 124.92, 122.33, 83.99, 27.76; ESIMS m/z 371 ([M−H]$^-$).

tert-Butyl N-tert-butoxycarbonyl-N-(2-cyano-4-nitro-phenyl)carbamate (C273)

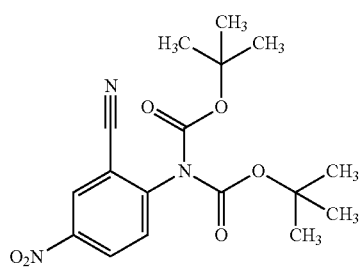

Isolated as a yellow solid (3.0 g, 86%): $^1$H NMR (300 MHz, CDCl$_3$) δ 8.56 (d, J=2.6 Hz, 1H), 8.47 (dd, J=8.8, 2.6 Hz, 1H), 7.52 (d, J=8.8 Hz, 1H), 1.47 (s, 18H); $^{13}$C NMR (75 MHz, CDCl$_3$) δ 149.52, 147.35, 146.52, 130.85, 128.04, 128.01, 114.68, 114.00, 85.19, 27.81; ESIMS m/z 362 ([M−H]$^-$).

tert-Butyl N-tert-butoxycarbonyl-N-(2,3-dimethyl-4-nitro-phenyl)carbamate (C274)

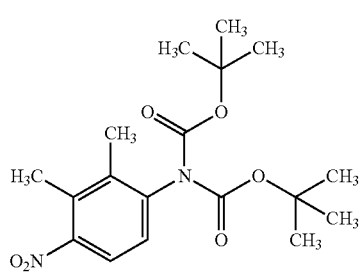 [SMILES: Cc1c(N(C(=O)OC(C)(C)C)C(=O)OC(C)(C)C)ccc([N+](=O)[O-])c1C]

Isolated as a white solid (0.52 g, 25%): $^1$H NMR (400 MHz, CDCl$_3$) δ 7.63 (d, J=8.6 Hz, 1H), 7.09 (d, J=8.6 Hz, 1H), 2.42 (s, 3H), 2.20 (s, 3H), 1.42 (s, 18H); $^{13}$C NMR (101 MHz, CDCl$_3$) δ 150.90, 150.17, 141.64, 137.39, 131.88, 126.47, 121.86, 83.36, 27.89, 15.94, 14.65; ESIMS m/z 365 ([M−H]$^-$).

tert-Butyl N-tert-butoxycarbonyl-N-[4-nitro-2-(trifluoromethyl)phenyl]carbamate (C275)

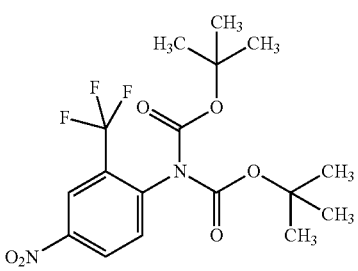 [SMILES: CC(C)(C)OC(=O)N(C(=O)OC(C)(C)C)c1ccc([N+](=O)[O-])cc1C(F)(F)F]

Isolated as a yellow solid (2.93 g, 94%): $^1$H NMR (400 MHz, CDCl$_3$) δ 8.58 (d, J=2.6 Hz, 1H), 8.45 (dd, J=8.7, 2.6 Hz, 1H), 7.50 (d, J=8.7 Hz, 1H), 1.39 (s, 18H); $^{19}$F NMR (376 MHz, CDCl$_3$) δ −62.25; ESIMS m/z 405 ([M−H]$^-$).

tert-Butyl (2-methyl-5-nitrophenyl)carbamate (C276)

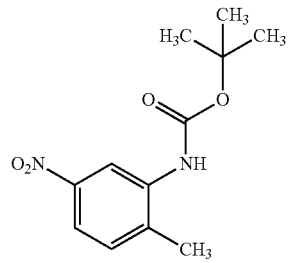 [SMILES: Cc1ccc([N+](=O)[O-])cc1NC(=O)OC(C)(C)C]

Isolated as a white solid (1.58 g, 63%): $^1$H NMR (400 MHz, CDCl$_3$) δ 8.21 (s, 1H), 8.14 (dd, J=8.5, 2.3 Hz, 2H), 7.43 (d, J=8.4 Hz, 1H), 2.40 (s, 3H), 1.45 (s, 9H); $^{13}$C NMR (101 MHz, CDCl$_3$) δ 151.02, 146.64, 138.69, 131.30, 123.88, 123.38, 84.52, 27.86, 18.10; ESIMS m/z 253 ([M+H]$^+$).

tert-Butyl N-tert-butoxycarbonyl-N-(2-methyl-3-nitro-phenyl)carbamate (C277)

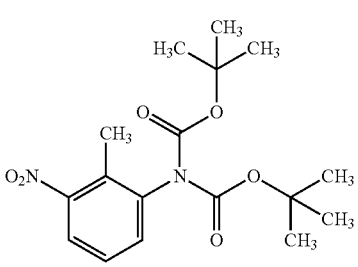 [SMILES: Cc1c(N(C(=O)OC(C)(C)C)C(=O)OC(C)(C)C)cccc1[N+](=O)[O-]]

Isolated as a white solid (1.15 g, 31%): ¹H NMR (400 MHz, CDCl₃) δ 7.91-7.81 (m, 1H), 7.41-7.25 (m, 2H), 2.37 (s, 3H), 1.41 (s, 18H); ESIMS m/z 353 ([M+H]+).

tert-Butyl N-tert-butoxycarbonyl-N-(2,4-difluoro-3-methyl-5-nitro-phenyl)carbamate (C278)

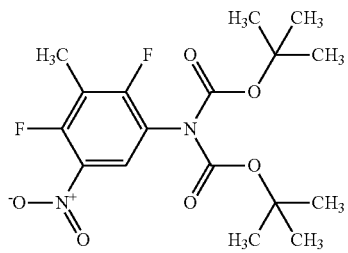

Isolated as a gold solid (0.87 g, 40%): ¹H NMR (400 MHz, CDCl₃) δ 7.88 (t, J=7.7 Hz, 1H), 2.32 (t, J=2.2 Hz, 3H), 1.46 (s, 18H); ¹⁹F NMR (376 MHz, CDCl₃) δ −108.86, −108.91, −115.35, −115.39; ESIMS m/z 389 ([M+H]⁺).

The following compounds were prepared in like manner to the procedure outlined in Example 70:

N-(3-Amino-2,4,6-trifluorophenyl)acetamide (C279)

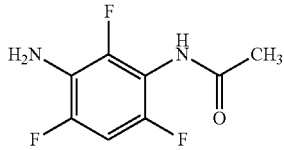

Isolated as a tan solid (2.8 g, 37%-three steps from 2,4,6-thfluoroaniline): ¹H NMR (400 MHz, DMSO-d₆) δ 9.50 (s, 1H), 7.11-7.00 (m, 1H), 5.07 (s, 2H), 2.04 (s, 3H); ¹⁹F NMR (376 MHz, DMSO-d₆) δ −131.69, −131.69, −131.72, −131.73, −134.98, −135.69, −135.70, −135.72, −135.73; ESIMS m/z 205 ([M+H]⁺).

The following compounds were prepared in like manner to the procedure outlined in Example R4:

(1R,3R)-3-(3-Bromo-4-fluorophenyl)-2,2-dichloro-cyclopropane-1.-carboxylic acid (C243)

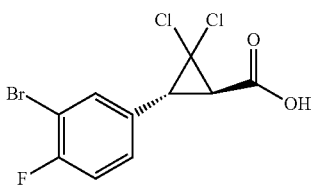 [SMILES: O=C(O)[C@H]1[C@H](c2ccc(F)c(Br)c2)C1(Cl)Cl]

Isolated as a white solid (4.0 g, 40%): ¹H NMR (400 MHz, CDCl₃) δ 7.53 (d, J=2.1 Hz, 1H), 7.47 (d, J=8.3 Hz, 1H), 7.17 (dd, J=8.4, 2.1 Hz, 1H), 3.43 (d, J=8.2 Hz, 1H), 2.86 (d, J=8.3 Hz, 1H); ESIMS m/z 343 ([M-H]⁻). Racemic trans-3-(3-Bromo-4-fluorophenyl)-2,2-dichlorocyclopropane-1-carboxylic acid can be prepared via methods described in U.S. Patent Application Publication US20160304522A1 (C430).

(1R,3R)-2,2-Dichloro-3-(4-chloro-3-(trifluoromethyl)phenyl)cyclopropane-1-carboxylic acid (C244)

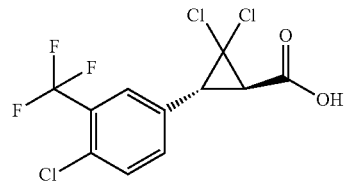 [SMILES: O=C(O)[C@H]1[C@H](c2ccc(Cl)c(C(F)(F)F)c2)C1(Cl)Cl]

Isolated as a white solid (0.37 g, 25%, 97% ee): ¹H NMR (400 MHz, DMSO-d₆) δ 13.41 (s, 1H), 7.96 (d, J=1.6 Hz, 1H), 7.79-7.71 (m, 2H), 3.69-3.50 (m, 2H).

(1R,3R)-2,2-Dichloro-3-(3-(trifluoromethyl)phenyl)cyclopropane-1-carboxylic acid (C280)

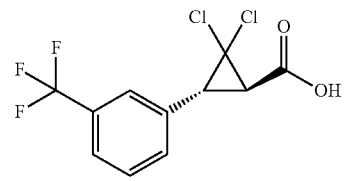 [SMILES: O=C(O)[C@H]1[C@H](c2cccc(C(F)(F)F)c2)C1(Cl)Cl]

Isolated as a white solid (3.4 g, 95% ee, 26% yield): ¹H NMR (400 MHz, CDCl₃) δ 10.38 (s, 1H), 7.66-7.59 (m, 1H), 7.57-7.44 (m, 3H), 3.55 (d, J=8.3 Hz, 1H), 2.94 (d, J=8.3 Hz, 1H); ¹⁹F NMR (376 MHz, CDCl₃) δ −62.70; ESIMS m/z 298 ([M−H]⁻).

(1R,3R)-2,2-Dichloro-3-(3-fluoro-5-(trifluoromethyl)phenyl)cyclopropane-1-carboxylic acid (C281)

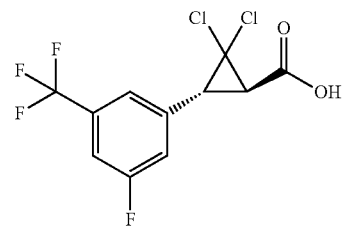 [SMILES: O=C(O)[C@H]1[C@H](c2cc(F)cc(C(F)(F)F)c2)C1(Cl)Cl]

Isolated as a white solid (2.5 g, 95% ee, 24% yield): ¹H NMR (400 MHz, CDCl₃) δ 10.93 (s, 1H), 7.34 (dd, J=7.1, 1.9 Hz, 2H), 7.20 (dt, J=8.8, 2.0 Hz, 1H), 3.54 (d, J=8.3 Hz, 1H), 2.93 (d, J=8.3 Hz, 1H); ¹⁹F NMR (376 MHz, CDCl₃) δ −62.86, −109.50; ESIMS m/z 316 ([M−H]⁻).

Example 82: Preparation of N-(3-acetamido-2,6-difluorophenyl)-2-chloro-5-((1R,3R)-2,2-dichloro-3-(3,5-dichlorophenyl)cyclopropane-1-carboxamido)-3-fluorobenzamide (F1505)

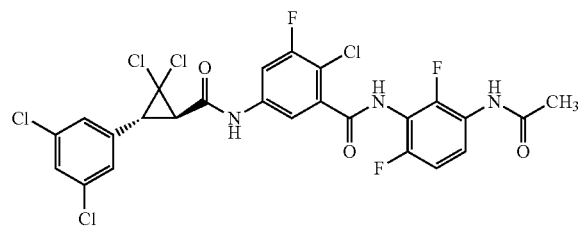 [SMILES: CC(=O)Nc1ccc(F)c(NC(=O)c2cc(NC(=O)[C@H]3[C@H](c4cc(Cl)cc(Cl)c4)C3(Cl)Cl)cc(F)c2Cl)c1F]

N-(3-Amino-2,6-difluorophenyl)-2-chloro-5-((1R,3R)-2,2-dichloro-3-(3,5-dichlorophenyl)cyclopropane-1-carboxamido)-3-fluorobenzamide (F1336) (0.041 g, 0.069 mmol) and sodium bicarbonate (0.029 g, 0.343 mmol) were weighed into a 1-dram vial containing a stir bar. Ethyl acetate (0.7 mL) was added, and acetyl chloride (6 µL, 0.084 mmol) was added via syringe. The heterogeneous mixture was allowed to stir for 3 hours at room temperature. The reaction mixture was diluted with ethyl acetate and saturated aqueous sodium bicarbonate; the layers were separated; and the organic layer was dried over sodium sulfate. Filtration and concentration gave the title compound as a white powder (0.044 g, 100%).

The following compounds were prepared in like manner to the procedure outlined in Example 82:

N-(3-Acetamido-2,6-difluorophenyl)-2-chloro-5-((1R,3R)-2,2-dichloro-3-(3,4,5-trichlorophenyl)cyclopropane-1-carboxamido)-3-fluorobenzamide (F1520)

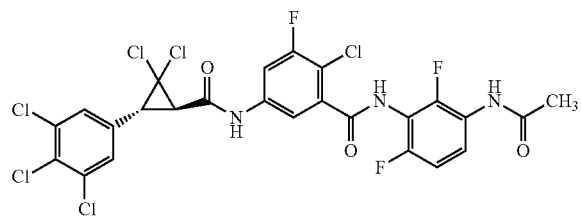 [SMILES: CC(=O)Nc1ccc(F)c(NC(=O)c2cc(NC(=O)[C@H]3[C@H](c4cc(Cl)c(Cl)c(Cl)c4)C3(Cl)Cl)cc(F)c2Cl)c1F]

Isolated as a white powder (0.047 g, 98%).

N-(3-Acetamido-2,6-difluorophenyl)-2-chloro-5-((1R,3R)-2,2-dichloro-3-(3,4-dichlorophenyl)cyclopropane-1-carboxamido)-3-fluorobenzamide (F1522)

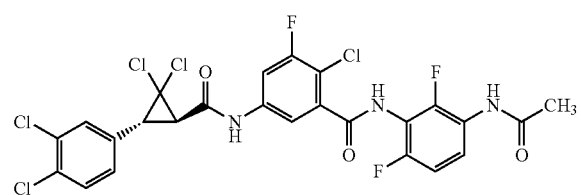 [SMILES: CC(=O)Nc1ccc(F)c(NC(=O)c2cc(NC(=O)[C@H]3[C@H](c4ccc(Cl)c(Cl)c4)C3(Cl)Cl)cc(F)c2Cl)c1F]

Isolated as a tan powder (0.044 g, 98%).

N-(3-Acetamido-2,6-difluorophenyl)-2-chloro-5-((1R,3R)-2,2-dichloro-3-(3,4-dichlorophenyl)cyclopropane-1-carboxamido)-3-methylbenzamide (F1523)

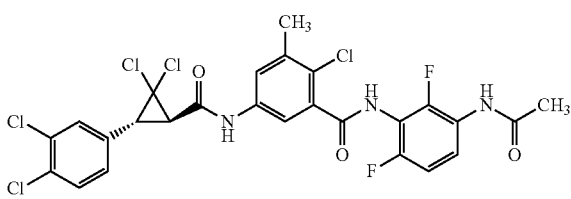 [SMILES: CC(=O)Nc1ccc(F)c(NC(=O)c2cc(NC(=O)[C@H]3[C@H](c4ccc(Cl)c(Cl)c4)C3(Cl)Cl)cc(C)c2Cl)c1F]

Isolated as a tan powder (0.052 g, 100%).

N-(3-Acetamido-2,6-difluorophenyl)-2-chloro-5-((1R,3R)-2,2-dichloro-3-(3,4,5-trichlorophenyl)cyclopropane-1-carboxamido)-3-methylbenzamide (F1524)

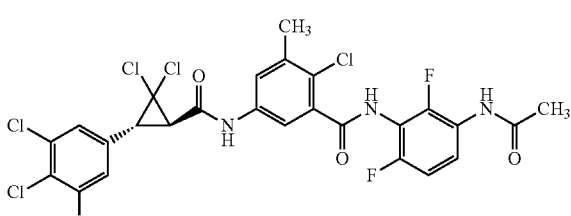

Isolated as a tan solid (0.053 g, 92%).

N-(3-Acetamido-2,6-difluorophenyl)-2-chloro-5-((1R,3R)-2,2-dichloro-3-(4-fluoro-3-(trifluoromethyl)phenyl)cyclopropane-1-carboxamido)-3-methylbenzamide (F1525)

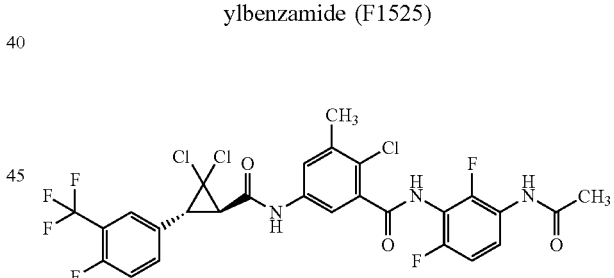

Isolated as a tan powder (0.036 g, 91%).

N-(3-Acetamido-2,4-difluorophenyl)-2-chloro-5-((1R,3R)-2,2-dichloro-3-(3,4-dichlorophenyl)cyclopropane-1-carboxamido)-3-methylbenzamide (F1543)

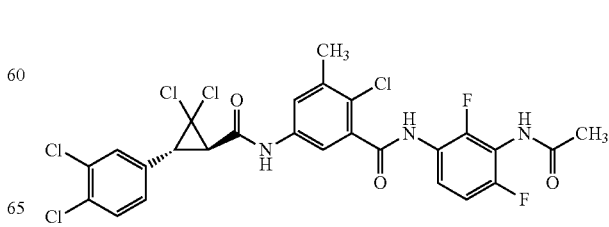

Isolated as a tan powder (0.029 g, 97%).

541

N-(3-Acetamido-2,4-difluorophenyl)-2-chloro-5-((1R,3R)-2,2-dichloro-3-(3,4,5-trichlorophenyl)cyclopropane-1-carboxamido)-3-methylbenzamide (F1544)

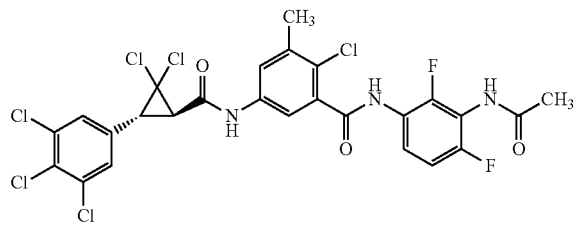 [SMILES: CC(=O)Nc1c(F)ccc(NC(=O)c2cc(NC(=O)[C@H]3[C@H](c4cc(Cl)c(Cl)c(Cl)c4)C3(Cl)Cl)cc(C)c2Cl)c1F]

Isolated as a tan powder (0.052 g, 94%).

N-(3-acetamido-2,4-difluorophenyl)-2-chloro-5-((1R,3R)-2,2-dichloro-3-(4-fluoro-3-(trifluoromethyl)phenyl)cyclopropane-1-carboxamido)-3-methylbenzamide (F1545)

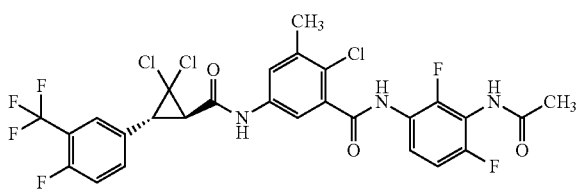 [SMILES: CC(=O)Nc1c(F)ccc(NC(=O)c2cc(NC(=O)[C@H]3[C@H](c4ccc(F)c(C(F)(F)F)c4)C3(Cl)Cl)cc(C)c2Cl)c1F]

Isolated as a tan powder (0.039 g, 99%).

N-(5-Acetamido-2,4-difluorophenyl)-2-chloro-5-((1R,3R)-2,2-dichloro-3-(3,4-dichlorophenyl)cyclopropane-1-carboxamido)-3-methylbenzamide (F1546)

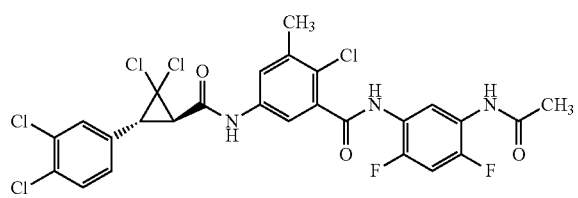 [SMILES: CC(=O)Nc1cc(NC(=O)c2cc(NC(=O)[C@H]3[C@H](c4ccc(Cl)c(Cl)c4)C3(Cl)Cl)cc(C)c2Cl)c(F)cc1F]

Isolated as a peach-colored powder (0.044 g, 98%).

N-(5-Acetamido-2,4-difluorophenyl)-3-((1R,3R)-2,2-dichloro-3-(3,4,5-trichlorophenyl)cyclopropane-1-carboxamido)-5-methylbenzamide (F1547)

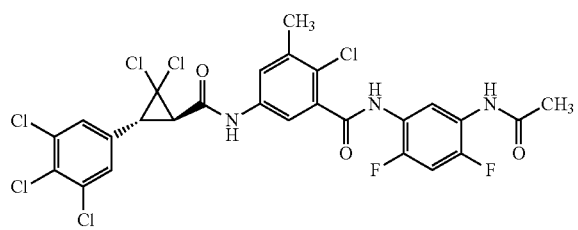 [SMILES: CC(=O)Nc1cc(NC(=O)c2cc(NC(=O)[C@H]3[C@H](c4cc(Cl)c(Cl)c(Cl)c4)C3(Cl)Cl)cc(C)c2Cl)c(F)cc1F]

Isolated as an off-white solid (0.048 g, 78%).

542

N-(5-Acetamido-2,4-difluorophenyl)-2-chloro-5-((1R,3R)-2,2-dichloro-3-(4-fluoro-3-(trifluoromethyl)phenyl)cyclopropane-1-carboxamido)-3-methylbenzamide (F1548)

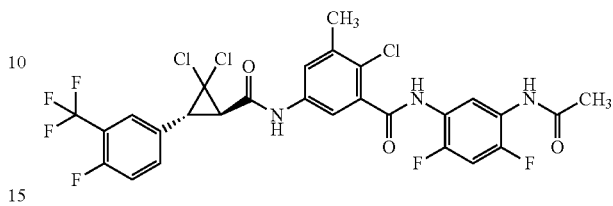

Isolated as an off-white solid (0.037 g, 94%).

Example 83: Preparation of 6-chloro-3-((1R,3R)-2,2-dichloro-3-(3-chloro-4-fluorophenyl)cyclopropane-1-carboxamido)-2-fluoro-N-(4-fluorophenyl)benzamide (F1465)

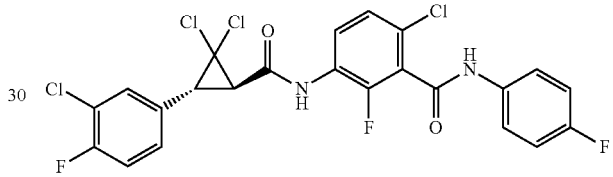

Step 1: To a solution of tert-butyl (4-chloro-2-fluoro-3-((4-fluorophenyl)carbamoyl)phenyl)carbamate (C310; 0.066 g, 0.172 mmol) in dichloromethane (1 mL) was added hydrogen chloride (0.431 mL, 1.724 mmol) as a 4 M solution in dioxane, and the resulting turbid mixture was stirred at room temperature for 16 hours. The solvent was evaporated under reduced pressure and the residue was suspended in dichloromethane and concentrated under a stream of nitrogen to give the intermediate hydrochloride salt which was used immediately in the next step.

Step 2: To a mixture of (1R,3R)-2,2-dichloro-3-(4-chloro-3-fluorophenyl)cyclopropane-1-carboxylic acid (C93; 0.049 g, 0.172 mmol) and the freshly prepared intermediate aniline hydrochloride in ethyl acetate (1 mL) were added pyridine (0.074 mL, 0.69 mmol) followed by a 50% solution of 2,4,6-tripropyl-1,3,5,2,4,6-trioxatriphosphinane 2,4,6-trioxide (0.103 mL, 0.345 mmol) in ethyl acetate, and the resulting light-orange solution was warmed to 50° C. and stirred for 16 hours. The reaction mixture was concentrated under a stream of nitrogen, and the resulting red, viscous oil was purified by automated flash chromatography (silica gel; 0→50% ethyl acetate in hexanes). The resulting glassy oil was dissolved/suspended in diethyl ether (1 mL) and treated with hexanes until turbid (few drops). The solvents were evaporated under a stream of nitrogen to give the title compound as a light tan solid (0.081 mg, 85%).

The following compounds were prepared in like manner to the procedure outlined in Example 83:

6-Chloro-3-((1R,3R)-2,2-dichloro-3-(3-chloro-4-fluorophenyl)cyclopropane-1-carboxamido)-N-(2,4-difluorophenyl)-2-fluorobenzamide (F1464)

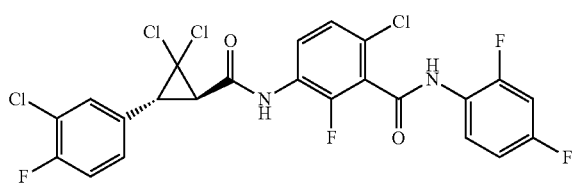 [SMILES: O=C(Nc1ccc(F)cc1F)c1c(Cl)ccc(NC(=O)[C@H]2[C@H](c3ccc(F)c(Cl)c3)C2(Cl)Cl)c1F]

Isolated as a white solid (0.036 g, 61%).

6-Chloro-3-((1R,3R)-2,2-dichloro-3-(3-chloro-4-fluorophenyl)cyclopropane-1-carboxamido)-2-fluoro-N-phenylbenzamide (F1466)

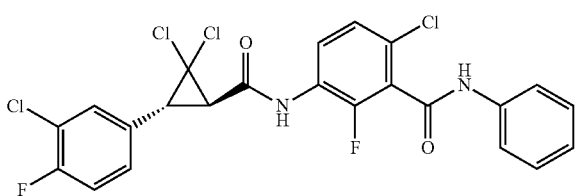 [SMILES: O=C(Nc1ccccc1)c1c(Cl)ccc(NC(=O)[C@H]2[C@H](c3ccc(F)c(Cl)c3)C2(Cl)Cl)c1F]

Isolated as a white solid (0.076 g, 77%).

N-(3-Amino-2,4-difluorophenyl)-6-chloro-3-((1R,3R)-2,2-dichloro-3-(3-chloro-4-fluorophenyl)cyclopropane-1-carboxamido)-2-fluorobenzamide (F1508)

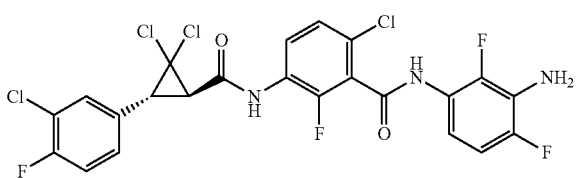 [SMILES: Nc1c(F)ccc(NC(=O)c2c(Cl)ccc(NC(=O)[C@H]3[C@H](c4ccc(F)c(Cl)c4)C3(Cl)Cl)c2F)c1F]

Isolated as a white solid (0.028 g, 41%).

6-Chloro-3-((1R,3R)-2,2-dichloro-3-(3-chloro-4-fluorophenyl)cyclopropane-1-carboxamido)-N-ethyl-2-fluorobenzamide (F2071)

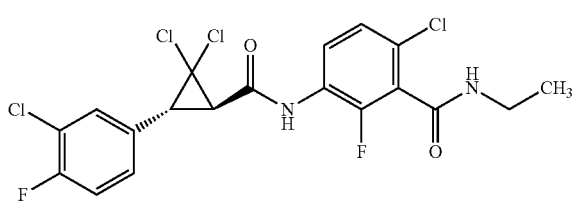 [SMILES: CCNC(=O)c1c(Cl)ccc(NC(=O)[C@H]2[C@H](c3ccc(F)c(Cl)c3)C2(Cl)Cl)c1F]

Isolated as a white solid (0.024 g, 55%).

6-Chloro-3-((1R,3R)-2,2-dichloro-3-(3-chloro-4-fluorophenyl)cyclopropane-1-carboxamido)-2-fluoro-N-(2,2,2-trifluoroethyl)benzamide (F2072)

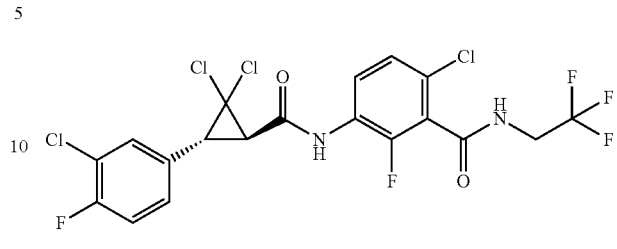

Isolated as a white solid (0.030 g, 70%).

6-Chloro-3-((1R,3R)-2,2-dichloro-3-(3-chloro-4-fluorophenyl)cyclopropane-1-carboxamido)-2-fluoro-N-(2,2,3,3,3-pentafluoropropyl)benzamide (F2073)

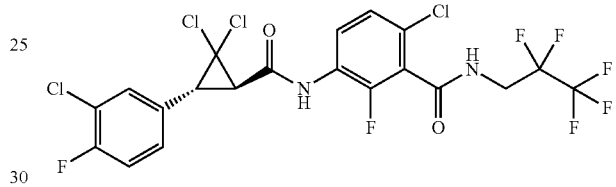

Isolated as a white solid (0.038 g, 77%).

6-Chloro-N-(3-chloropropyl)-3-((1R,3R)-2,2-dichloro-3-(3-chloro-4-fluorophenyl)cyclopropane-1-carboxamido)-2-fluorobenzamide (F2074)

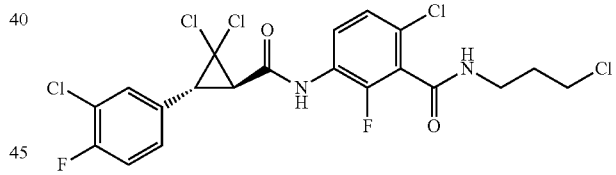

Isolated as a white solid (0.028 g, 76%).

Example 84: Preparation of trans-2-chloro-5-(2,2-dichloro-3-(3,5-dichlorophenyl)cyclopropane-1-carboxamido)-3-fluorobenzoic acid (C282)

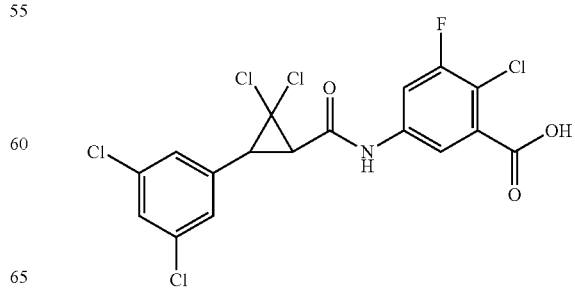

To a stirred solution of trans-2,2-dichloro-3-(3,5-dichlorophenyl)cyclopropane-1-carboxylic acid (C1 in U.S. Patent Application Publication US20160304522A1; 0.25 g, 0.83 mmol) in ethyl acetate (15 mL) were added 5-amino-2-chloro-3-fluorobenzoic acid (C196; 0.15 g, 0.83 mmol), 2,4,6-tripropyl-1,3,5,2,4,6-trioxatriphosphinane 2,4,6-trioxide (50% solution in ethyl acetate; 1 mL, 3.34 mmol), and pyridine (0.8 mL, 4.18 mmol). The reaction mixture was stirred at room temperature for 16 hours. The reaction mixture was filtered through a pad of Celite®, and the pad was washed with ethyl acetate. The filtrate was concentrated under reduced pressure. The title compound was isolated as a pale yellow liquid (0.4 g) which was used in the next step without further purification: ESIMS m/z 468.90 ([M−H]−).

Example 85: Supercritical Fluid Chromatography (SFC) Purification of (1R,3R)-2,2-dichloro-3-(3,4,5-trifluorophenyl)cyclopropane-1-carboxylic acid (C283) and (1S,3S)-2,2-dichloro-3-(3,4,5-trifluorophenyl)cyclopropane-1-carboxylic acid (C284)

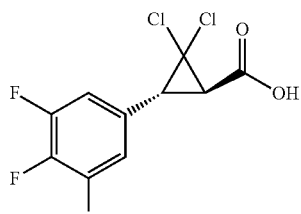
C283

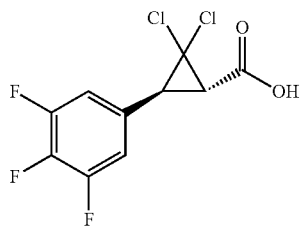
C284

Racemic (trans)-2,2-dichloro-3-(3,4,5-trifluorophenyl)cyclopropane-1-carboxylic acid (U.S. Patent Application Publication US20160304522A1 (C228); 2.29 g) was separated by Preparative SFC on a Chiralpak IE column (30×250 mm, 5 μm) using 90:10 CO$_2$/0.5% isopropylamine in isopropanol and 100.0 bar back pressure to give the title compounds: (C283) (0.9 g, peak 2); (C284) (0.9 g, peak 1).

The following compounds were prepared in like manner to the procedure outlined in Example 85:

(1R,3R)-2,2-Dichloro-3-(3,4-difluorophenyl)cyclopropane-1-carboxylic acid (C285)

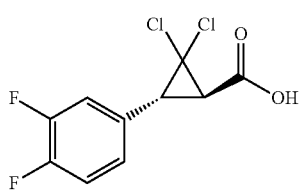 [SMILES: O=C(O)[C@H]1[C@H](c2ccc(F)c(F)c2)C1(Cl)Cl]

(1.5 g, peak 2): $^1$H NMR (300 MHz, DMSO-d$_6$) δ 13.36 (br s, 1H), 7.58 (ddd, J=2.0, 7.7, 11.9 Hz, 1H), 7.45 (td, J=8.6, 10.6 Hz, 1H), 7.32 (br d, J=1.8 Hz, 1H), 3.50-3.40 (m, 2H); ESIMS m/z 264.81 ([M−H]−). The title compound was obtained via resolution of racemic trans-2,2-dichloro-3-(3,4-difluorophenyl)cyclopropane-1-carboxylic acid (U.S. Patent Application Publication US20160304522A1 (C421)).

(1S,3S)-2,2-Dichloro-3-(3,4-difluorophenyl)cyclopropane-1-carboxylic acid (C286)

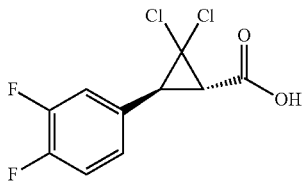 [SMILES: O=C(O)[C@@H]1[C@@H](c2ccc(F)c(F)c2)C1(Cl)Cl]

(1.5 g, peak 1): $^1$H NMR (300 MHz, DMSO-d$_6$) δ 13.36 (br s, 1H), 7.58 (ddd, J=2.0, 7.8, 11.8 Hz, 1H), 7.45 (td, J=8.4, 10.6 Hz, 1H), 7.36-7.26 (m, 1H), 3.52-3.42 (m, 2H); ESIMS m/z 264.81 ([M−H]−). The title compound was obtained via resolution of racemic trans-2,2-dichloro-3-(3,4-difluorophenyl)cyclopropane-1-carboxylic acid (U.S. Patent Application Publication US20160304522A1 (C421)).

Example 86: Preparation of N-(5-amino-2,4-difluorophenyl)-2,2-difluoroacetamide (C287)

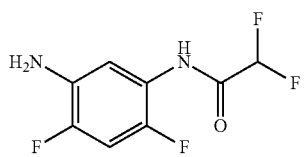

2,2-Difluoroacetic anhydride (2 mL, 2.87 mmol) was added to 2,4-difluoro-5-nitroaniline (0.5 g, 2.87 mmol) in a 40 mL glass vial with stir bar. The reaction mixture was stirred overnight. The mixture was dried and the crude product was dissolved in ethyl acetate (10 mL). Palladium (5% on carbon, 500 mg) was added to the vial, and the mixture was stirred overnight under a balloon of hydrogen. The mixture was filtered through a pad of Celite®, rinsed with ethyl acetate and the solvent removed under reduced pressure. The title compound was isolated as a brown solid (0.354 g, 50%): $^1$H NMR (400 MHz, CDCl$_3$) δ 7.98 (s, 1H), 7.79 (dd, J=9.2, 7.7 Hz, 1H), 6.87 (t, J=10.3 Hz, 1H), 6.02 (t, J=54.2 Hz, 1H), 3.71 (s, 2H); $^{19}$F NMR (376 MHz, CDCl$_3$) δ −125.72, −134.01, −140.54, −140.54; ESIMS m/z 223 ([M+H]+).

The following compounds were prepared in like manner to the procedure outlined in Example 86:

N-(5-Amino-2,4-difluorophenyl)-2,2,2-trifluoroacetamide (C288)

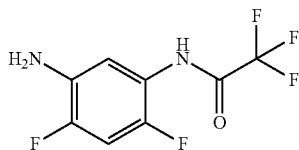 [SMILES: Nc1cc(NC(=O)C(F)(F)F)c(F)cc1F]

Isolated as a grey solid (0.383 g, 50%): $^1$H NMR (400 MHz, CDCl$_3$) δ 7.93 (s, 1H), 7.74 (dd, J=9.0, 7.7 Hz, 1H), 6.89 (t, J=10.3 Hz, 1H), 3.35 (s, 2H); $^{19}$F NMR (376 MHz, CDCl$_3$) δ −75.74, −133.08, −140.33; ESIMS m/z 241 ([M+H]$^+$).

N-(5-Amino-2,4-difluorophenyl)acetamide (C289)

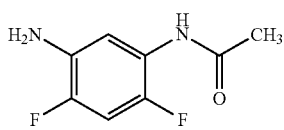

Isolated as a brown solid (1.06 g, 90%): $^1$H NMR (400 MHz, CDCl$_3$) δ 7.82 (dd, J=9.4, 7.9 Hz, 1H), 7.20 (s, 1H), 6.80 (t, J=10.5 Hz, 1H), 3.63 (s, 2H), 2.19 (s, 3H); $^{19}$F NMR (376 MHz, CDCl$_3$) δ −136.64, −141.55; ESIMS m/z 187 ([M+H]$^+$).

N-(2-Amino-3-fluorophenyl)acetamide (C290)

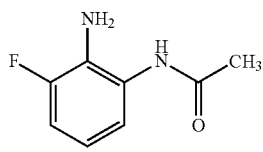

Isolated as a pale solid (1.07 g, 90%): $^1$H NMR (400 MHz, DMSO-d$_6$) δ 9.26 (s, 1H), 7.07 (dt, J=8.0, 1.3 Hz, 1H), 6.87 (ddd, J=11.0, 8.2, 1.4 Hz, 1H), 6.52 (td, J=8.1, 5.9 Hz, 1H), 4.84 (s, 2H), 2.05 (s, 3H); $^{19}$F NMR (376 MHz, DMSO-d$_6$) δ −133.10.

N-(2-amino-5-fluorophenyl)acetamide (C291)

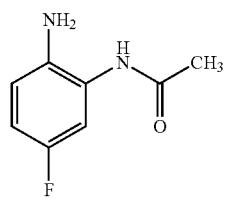

Isolated as a brown solid (1.06 g, 90%): $^1$H NMR (400 MHz, DMSO-d$_6$) δ 9.13 (s, 1H), 7.22 (dd, J=10.7, 2.8 Hz, 1H), 6.82-6.60 (m, 2H), 4.79 (s, 2H), 2.05 (s, 3H); $^{19}$F NMR (376 MHz, DMSO-d$_6$) δ −127.99.

N-(5-Amino-2-fluorophenyl)acetamide (C292)

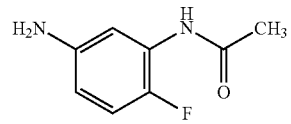

Isolated as a pale solid (1.07 g, 90%): $^1$H NMR (400 MHz, DMSO-d$_6$) δ 9.40 (s, 1H), 7.13 (dd, J=6.9, 2.8 Hz, 1H), 6.84 (dd, J=10.9, 8.7 Hz, 1H), 6.33-6.17 (m, 1H), 4.93 (s, 2H), 2.04 (s, 3H); $^{19}$F NMR (376 MHz, DMSO-d$_6$) δ −141.63.

N-(3-Amino-4-fluorophenyl)acetamide (C293)

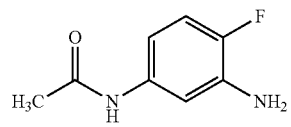

Isolated as a pale solid (1.08 g, 90%): $^1$H NMR (400 MHz, DMSO-d$_6$) δ 9.66 (s, 1H), 7.11 (dd, J=8.5, 2.6 Hz, 1H), 6.85 (dd, J=11.3, 8.7 Hz, 1H), 6.63 (ddd, J=8.7, 4.0, 2.6 Hz, 1H), 5.11 (s, 2H), 1.98 (s, 3H); $^{19}$F NMR (376 MHz, DMSO-d$_6$) δ −141.04.

N-(2-Amino-4,6-difluorophenyl)acetamide (C294)

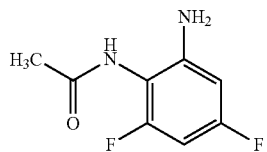

Isolated as a brown solid (1.06 g, 90%); $^1$H NMR (400 MHz, DMSO-d$_6$) δ 8.89 (s, 1H), 6.35-6.20 (m, 2H), 5.51 (s, 2H), 2.00 (s, 3H); $^{19}$F NMR (376 MHz, DMSO-d$_6$) δ −113.54, −113.56, −117.69, −117.71.

N-(2-Amino-3,5-difluorophenyl)acetamide (C295)

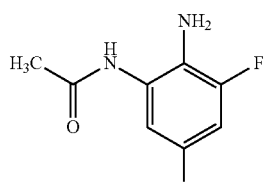

Isolated as a black solid (1.1 g, 90%): $^1$H NMR (400 MHz, DMSO-d$_6$) δ 9.31 (s, 1H), 7.19 (dt, J=10.8, 2.3 Hz, 1H), 6.90 (ddd, J=11.5, 8.8, 2.9 Hz, 1H), 4.78 (s, 2H), 2.07 (s, 3H); $^{19}$F NMR (376 MHz, DMSO-d$_6$) δ −126.81, −129.59.71.

N-(2-Amino-4,5-difluorophenyl)acetamide (C296)

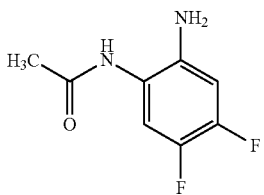

Isolated as a gray solid (1.06 g, 90%): $^1$H NMR (400 MHz, DMSO-d$_6$) δ 9.11 (s, 1H), 7.31 (dd, J=12.5, 8.8 Hz, 1H), 6.65 (dd, J=13.0, 8.1 Hz, 1H), 5.07 (s, 2H), 2.03 (s, 3H); $^{19}$F NMR (376 MHz, DMSO-d$_6$) δ −142.62 (d, J=24.2 Hz), −153.98 (d, J=23.7 Hz).

N-(2-Amino-4,6-difluorophenyl)-2,2,2-trifluoroacetamide (C297)

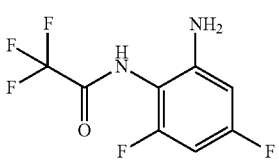 [SMILES: Nc1cc(F)cc(F)c1NC(=O)C(F)(F)F]

Isolated as a brown solid (1.06 g, 90%): $^1$H NMR (400 MHz, DMSO-d$_6$) δ 14.52 (s, 1H), 7.67-7.18 (m, 2H); $^{19}$F NMR (376 MHz, DMSO-d$_6$) δ −63.00, −113.06, −123.55.

N-(6-Amino-2,3-difluorophenyl)-2,2,2-trifluoroacetamide (C298)

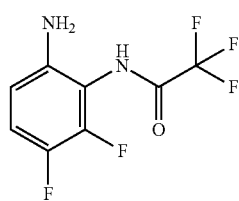 [SMILES: Nc1ccc(F)c(F)c1NC(=O)C(F)(F)F]

Isolated as a brown solid (0.34 g, 50%): $^1$H NMR (400 MHz, DMSO-d$_6$) δ 14.51 (s, 1H), 7.51 (ddt, J=19.3, 13.2, 7.1 Hz, 2H); $^{19}$F NMR (376 MHz, DMSO-d$_6$) δ −63.06, −147.20, −153.46 (d, J=21.0 Hz).

N-(2-Amino-4,5-difluorophenyl)-2,2,2-trifluoroacetamide (C299)

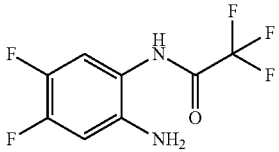

Isolated as a brown solid (0.38 g, 50%): $^1$H NMR (400 MHz, DMSO-d$_6$) δ 14.30 (s, 1H), 7.84 (s, 2H); $^{19}$F NMR (376 MHz, DMSO-d$_6$) δ −62.94, −62.95, −139.23, −142.16.

N-(2-Amino-3,5-difluorophenyl)-2,2,2-trifluoroacetamide (C300)

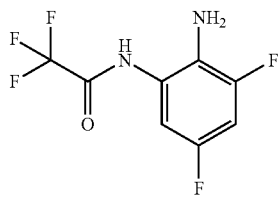

Isolated as a gray solid (0.38 g, 50%): $^1$H NMR (400 MHz, DMSO-d$_6$) δ 14.54 (s, 1H), 7.40 (d, J=8.2 Hz, 1H), 731 (t, J=10.6 Hz, 1H); $^{19}$F NMR (376 MHz, DMSO-d$_6$) δ −63.00, −113.06, −123.56.

N-(2-Amino-5-fluorophenyl)-2,2,2-trifluoroacetamide (C301)

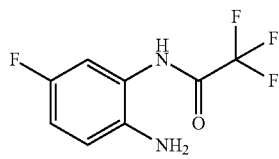

Isolated as a pale solid (0.39 g, 50%): $^1$H NMR (400 MHz, DMSO-d$_6$) δ 12.89 (s, 1H), 7.68 (ddd, J=12.2, 9.2, 3.5 Hz, 2H), 7.40 (td, J=9.3, 2.4 Hz, 1H); $^{19}$F NMR (376 MHz, DMSO-d$_6$) δ −62.70, −118.54.

N-(5-Amino-2-fluorophenyl)-2,2,2-trifluoroacetamide (C302)

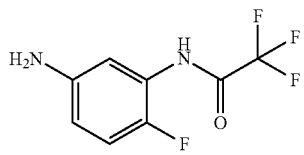

Isolated as a black solid (0.4 g, 50%): $^1$H NMR (400 MHz, CDCl$_3$) δ 8.01 (s, 1H), 7.66 (dd, J=6.5, 2.8 Hz, 1H), 6.94 (dd, J=10.5, 8.8 Hz, 1H), 6.45 (ddd, J=8.8, 4.2, 2.8 Hz, 1H); $^{19}$F NMR (376 MHz, CDCl$_3$) δ −75.79, −144.06.

N-(3-Amino-4-fluorophenyl)-2,2,2-trifluoroacetamide (C303)

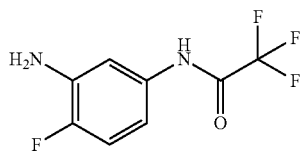

Isolated as a gray solid (0.42 g, 50%): ¹H NMR (400 MHz, CDCl₃) δ 7.72 (s, 1H), 7.22 (dd, J=7.8, 2.6 Hz, 1H), 6.97 (dd, J=10.5, 8.7 Hz, 1H), 6.69 (ddd, J=8.7, 3.9, 2.7 Hz, 1H), 3.86 (s, 2H); ¹⁹F NMR (376 MHz, CDCl₃) δ −75.74, −136.95.

N-(3-Amino-5-fluorophenyl)-2,2,2-trifluoroacetamide (C304)

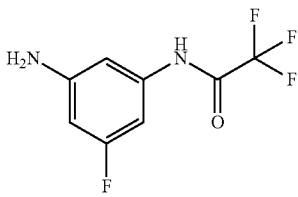

Isolated as a gray solid (0.40 g, 50%): ¹H NMR (400 MHz, CDCl₃) δ 7.71 (s, 1H), 6.80 (td, J=2.0, 0.7 Hz, 1H), 6.63 (dt, J=9.9, 2.1 Hz, 1H), 6.25 (dt, J=10.3, 2.1 Hz, 1H), 3.90 (s, 2H); ¹⁹F NMR (376 MHz, CDCl₃) δ −75.79, −110.83.

N-(2-Amino-3-fluorophenyl)-2,2,2-trifluoroacetamide (C305)

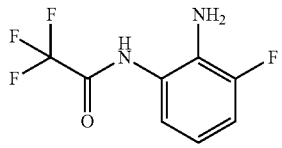 [SMILES: Nc1c(F)cccc1NC(=O)C(F)(F)F]

Isolated as a brown solid (0.39 g, 50%): ¹H NMR (400 MHz, DMSO-d₆) δ 14.36 (s, 1H), 7.51 (s, 1H), 7.40 (td, J=8.1, 4.8 Hz, 1H), 7.20 (t, J=9.5 Hz, 1H); ¹⁹F NMR (376 MHz, DMSO-d₆) δ −62.86, −127.62.

N-(2-Amino-6-fluorophenyl)-2,2,2-trifluoroacetamide (C306)

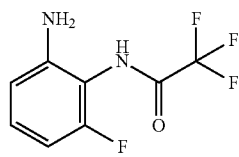 [SMILES: Nc1cccc(F)c1NC(=O)C(F)(F)F]

Isolated as a gray solid (0.4 g, 50%): ¹H NMR (400 MHz, DMSO-d₆) δ 14.33 (s, 1H), 7.60-7.43 (m, 1H), 7.44-7.32 (m, 1H), 7.20 (d, J=9.0 Hz, 1H); ¹⁹F NMR (376 MHz, DMSO-d₆) δ −62.74, −62.75, −62.87, −127.60.

Example 87: Preparation of N-(3-amino-2,4-difluorophenyl)-2,2-difluoroacetamide hydrochloride (C307)

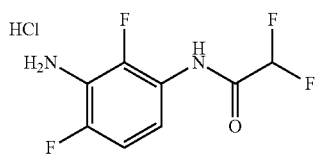 [SMILES: Cl ; Nc1c(F)ccc(NC(=O)C(F)F)c1F]

To a solution of tert-butyl-N-(3-amino-2,6-difluoro-phenyl)-N-tert-butoxycarbonyl-carbamate (C182) (1.0 g, 2.90 mmol) in dichloromethane (30 mL) was added 2,2-difluoroacetic anhydride (2.5 mL, 3.59 mmol). The reaction mixture was stirred overnight at room temperature and then concentrated under reduced pressure. The crude product was dissolved in dichloromethane (30 mL). Hydrochloric acid (4 M in dioxane, 7.25 mL) was added to the solution, and the reaction mixture was stirred at room temperature for 6 hours. The precipitate that formed was filtered and washed with cold dichloromethane. The title compound was isolated as a white solid (0.74 g, 98%): ¹H NMR (400 MHz, DMSO-d₆) δ 10.47 (s, 1H), 6.91 (ddd, J=10.7, 8.9, 1.9 Hz, 1H), 6.76 (td, J=8.5, 5.5 Hz, 1H), 6.44 (t, J=53.5 Hz, 1H), 5.09 (s, 3H); ¹⁹F NMR (376 MHz, DMSO-d₆) δ −125.40, −133.15 (d, J=14.3 Hz), −138.66 (d, J=14.4 Hz).

The following compounds were prepared in like manner to the procedure outlined in Example 87:

N-(3-Amino-2,4-difluorophenyl)-2,2,2-trifluoroacetamide hydrochloride (C308)

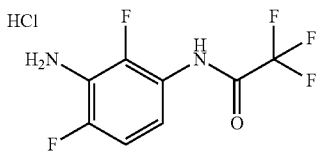 [SMILES: Cl ; Nc1c(F)ccc(NC(=O)C(F)(F)F)c1F]

Isolated as a brown solid (0.80 g, 99%): ¹H NMR (400 MHz, DMSO-d₆) δ 11.09 (s, 1H), 6.95 (ddd, J=10.7, 8.8, 1.9 Hz, 1H), 6.57 (td, J=8.4, 5.4 Hz, 1H), 5.56 (s, 3H); ¹⁹F NMR (376 MHz, DMSO-d₆) δ −73.91, −131.57 (d, J=15.6 Hz), −137.08 (d, J=15.6 Hz).

N-(3-Amino-2,4-difluorophenyl)acetamide hydrochloride (C309)

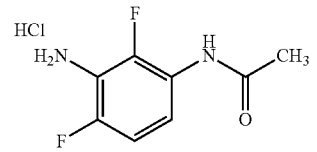

Isolated as a brown solid (0.60 g, 93%): ¹H NMR (400 MHz, DMSO-d₆) δ 9.55 (s, 1H), 6.91 (td, J=8.5, 5.7 Hz, 1H), 6.83 (ddd, J=10.7, 8.9, 1.8 Hz, 1H), 5.94 (s, 3H), 2.04 (s, 3H); ¹⁹F NMR (376 MHz, DMSO-d₆) δ −135.33 (d, J=12.4 Hz), −140.18 (d, J=12.3 Hz).

Example 88: Preparation of tert-butyl (4-chloro-2-fluoro-3-((4-fluorophenyl)carbamoyl)phenyl)carbamate (C310)

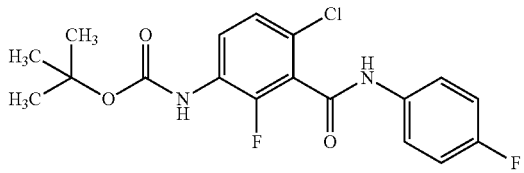 [SMILES: CC(C)(C)OC(=O)Nc1ccc(Cl)c(C(=O)Nc2ccc(F)cc2)c1F]

To a solution of 3-((tert-butoxycarbonyl)amino)-6-chloro-2-fluorobenzoic acid (C318; 85.0 mg, 0.293 mmol) and 4-fluoroaniline (34.2 mg, 0.308 mmol) in ethyl acetate (2.5 mL) were added pyridine (0.094 mL, 0.880 mmol) followed by 2,4,6-tripropyl-1,3,5,2,4,6-trioxatriphosphinane 2,4,6-trioxide (0.35 mL, 0.587 mmol), and the resulting light-yellow solution was warmed to 50° C. and stirred for 8 hours. The reaction mixture was concentrated under a stream of nitrogen, and the resulting red-orange oil was purified by automated flash chromatography (silica gel; 0→65% ethyl acetate in hexanes). The title compound was isolated as a white solid (0.075 g, 66%): mp 145-148° C.; $^1$H NMR (400 MHz, DMSO-d$_6$) δ 10.83 (s, 1H), 9.32 (s, 1H), 7.80-7.64 (m, 3H), 7.36 (dd, J=8.8, 1.4 Hz, 1H), 7.27-7.16 (m, 2H), 1.47 (s, 9H); $^{19}$F NMR (376 MHz, DMSO-d$_6$) δ −118.08, −124.58; ESIMS m/z 381 ([M−H]$^−$).

The following compounds were prepared in like manner to the procedure outlined in Example 88:

tert-Butyl (4-chloro-2-fluoro-3-(phenylcarbamoyl)phenyl)carbamate (C311)

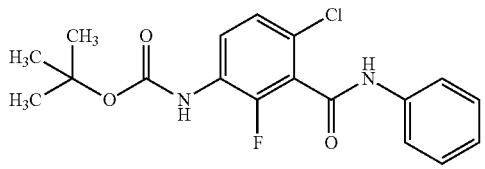 [SMILES: CC(C)(C)OC(=O)Nc1ccc(Cl)c(C(=O)Nc2ccccc2)c1F]

Isolated as a white solid (0.085 g, 79%): mp 91-94° C.; $^1$H NMR (400 MHz, DMSO-d$_6$) δ 10.76 (s, 1H), 9.31 (s, 1H), 7.74 (t, J=8.7 Hz, 1H), 7.71 7.66 (m, 2H), 7.42-7.29 (m, 3H), 7.21-7.06 (m, 1H), 1.47 (s, 9H); $^{19}$F NMR (376 MHz, DMSO-d$_6$) δ −124.64; ESIMS m/z 363 ([M−H]$^−$).

tert-Butyl (4-chloro-3-((2,4-difluorophenyl)carbamoyl)-2-fluorophenyl)carbamate (C312)

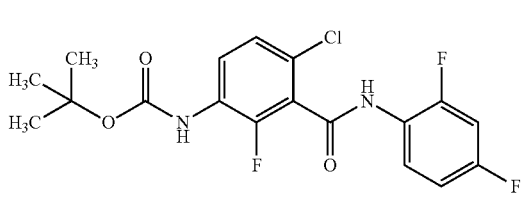 [SMILES: CC(C)(C)OC(=O)Nc1ccc(Cl)c(C(=O)Nc2ccc(F)cc2F)c1F]

Isolated as a white solid (0.048 g, 40%): mp 136-139° C.; $^1$H NMR (400 MHz, DMSO-d$_6$) δ 10.66 (s, 1H), 9.31 (s, 1H), 7.81 (td, J=8.9, 6.1 Hz, 1H), 7.74 (t, J=8.6 Hz, 1H), 7.43-7.32 (m, 2H), 7.18-7.10 (m, 1H), 1.47 (s, 9H); $^{19}$F NMR (376 MHz, DMSO-d$_6$) δ −113.14, −113.16, −117.72, −117.74, −124.47; ESIMS m/z 399 ([M−H]$^−$).

tert-Butyl (tert-butoxycarbonyl)(3-(3-((tert-butoxycarbonyl)amino)-6-chloro-2-fluorobenzamido)-2,6-difluorophenyl)carbamate (C313)

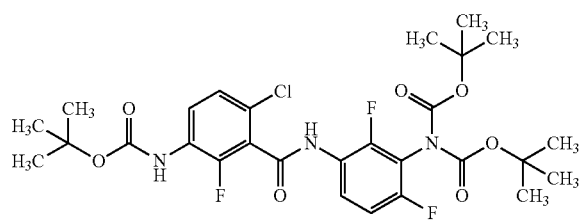 [SMILES: CC(C)(C)OC(=O)Nc1ccc(Cl)c(C(=O)Nc2ccc(F)c(N(C(=O)OC(C)(C)C)C(=O)OC(C)(C)C)c2F)c1F]

Isolated as a white solid (0.076 g, 34%): mp 83-88° C.; $^1$H NMR (400 MHz, DMSO-d$_6$) δ 10.75 (s, 1H), 9.30 (s, 1H), 7.88-7.68 (m, 2H), 7.35 (dd, J=8.8, 1.4 Hz, 1H), 7.32-7.23 (m, 1H), 1.47 (s, 9H), 1.40 (s, 18H); $^{19}$F NMR (376 MHz, DMSO-d$_6$) δ −123.39, −124.42, −126.90; ESIMS m/z 614 ([M−2H]$^−$).

tert-Butyl (4-chloro-3-(ethylcarbamoyl)-2-fluorophenyl)carbamate (C314)

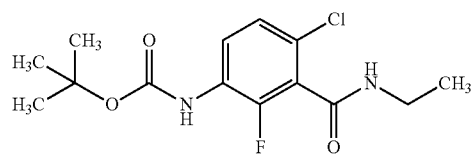 [SMILES: CCNC(=O)c1c(Cl)ccc(NC(=O)OC(C)(C)C)c1F]

Isolated as a white solid (0.032 g, 34%): mp 145-147° C.; $^1$H NMR (400 MHz, DMSO-d$_6$) δ 9.21 (s, 1H), 8.66 (t, J=5.6 Hz, 1H), 7.65 (t, J=8.6 Hz, 1H), 7.26 (dd, J=8.8, 1.5 Hz, 1H), 3.25 (qd, J=7.2, 5.5 Hz, 2H), 1.46 (s, 9H), 1.10 (t, J=7.2 Hz, 3H); $^{19}$F NMR (376 MHz, DMSO-d$_6$) δ −124.90; ESIMS m/z 315 ([M−H]$^−$).

tert-Butyl (4-chloro-2-fluoro-3-((2,2,2-trifluoroethyl)carbamoyl)phenyl)-carbamate (C315)

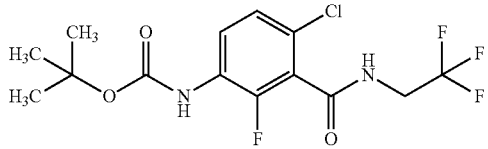 [SMILES: CC(C)(C)OC(=O)Nc1ccc(Cl)c(C(=O)NCC(F)(F)F)c1F]

Isolated as a white solid (0.035 g, 32%): mp 177-180° C.; $^1$H NMR (400 MHz, DMSO-d$_6$) δ 9.42 (t, J=6.2 Hz, 1H), 9.27 (s, 1H), 7.70 (t, J=8.6 Hz, 1H), 7.31 (dd, J=8.8, 1.4 Hz, 1H), 4.19-4.00 (m, 2H), 1.46 (s, 9H); $^{19}$F NMR (376 MHz, DMSO-d$_6$) δ −70.42, −124.62; ESIMS m/z 369 ([M−F]$^−$).

tert-Butyl (4-chloro-2-fluoro-3-((2,2,3,3,3-pentafluoropropyl)carbamoyl)phenyl)-carbamate (C316)

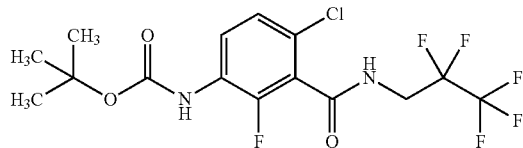 [SMILES: CC(C)(C)OC(=O)Nc1ccc(Cl)c(C(=O)NCC(F)(F)C(F)(F)F)c1F]

Isolated as a white solid (0.047 g, 38%): mp 152-155° C.; $^1$H NMR (400 MHz, DMSO-d$_6$) δ 9.44 (t, J=6.3 Hz, 1H), 9.26 (s, 1H), 7.70 (t, J=8.6 Hz, 1H), 7.31 (dd, J=8.9, 1.4 Hz, 1H), 4.15 (td, J=15.7, 5.7 Hz, 2H), 1.46 (s, 9H); $^{19}$F NMR (376 MHz, DMSO-d$_6$) δ −83.41, −120.04, −124.47; ESIMS m/z 419 ([M−H]$^-$).

tert-Butyl (4-chloro-3-((3-chloropropyl)carbamoyl)-2-fluorophenyl)carbamate (C317)

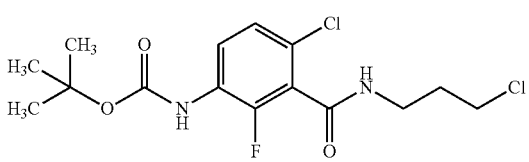 [SMILES: CC(C)(C)OC(=O)Nc1ccc(Cl)c(C(=O)NCCCCl)c1F]

Isolated as a white solid (0.032 g, 30%): mp 126-128° C.; $^1$H NMR (400 MHz, DMSO-d$_6$) δ 9.23 (s, 1H), 8.77 (t, J=5.6 Hz, 1H), 7.66 (t, J=8.6 Hz, 1H), 7.28 (dd, J=8.8, 1.4 Hz, 1H), 3.70 (t, J=6.6 Hz, 2H), 3.40-3.36 (m, 2H), 1.95 (p, J=6.6 Hz, 2H), 1.46 (s, 9H); $^{19}$F NMR (376 MHz, DMSO-d$_6$) δ −124.88; ESIMS m/z 363 ([M−2H]$^-$).

Example 89: Preparation of 3-((tert-butoxycarbonyl)amino)-6-chloro-2-fluorobenzoic acid (C318)

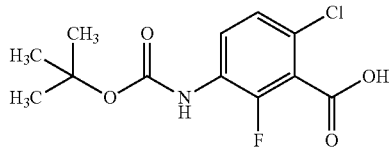 [SMILES: CC(C)(C)OC(=O)Nc1ccc(Cl)c(C(=O)O)c1F]

To a suspension of ethyl 3-[bis(tert-butoxycarbonyl)amino]-6-chloro-2-fluorobenzoate (C319; 7.57 g, 18.1 mmol) in a 2:1 mixture of tetrahydrofuran (48 mL) and water (24 mL) was added lithium hydroxide monohydrate (2.28 g, 54.3 mmol), and the resulting turbid mixture was vigorously stirred for 16 hours at room temperature, at which point LC-MS analysis indicated only starting material and the starting material with one of the Boc groups cleaved. The reaction mixture was diluted with methanol (25 mL) and the mixture was stirred at room temperature for 16 hours, at which point LC-MS indicated full consumption of the ester starting material. The organics were evaporated under reduced pressure, and the residual aqueous mixture (cream colored precipitate) was diluted with ethyl acetate (~200 mL) and vigorously stirred while the pH was adjusted (6-7) by the dropwise addition of 1 N aqueous hydrogen chloride (~35 mL). The phases were separated and the aqueous phase was extracted with additional ethyl acetate (2×50 mL). The combined organic extracts were washed successively with water (100 mL) and brine (2×75 mL), dried over sodium sulfate, filtered, and concentrated. The title compound was isolated as a colorless, glassy solid (1.465 g, 27%): mp 79-84° C.; $^1$H NMR (400 MHz, DMSO-d$_6$) δ 9.12 (s, 1H), 7.58 (t, J=8.6 Hz, 1H), 7.21 (dd, J=8.8, 1.4 Hz, 1H), 1.46 (s, 9H); $^{13}$C NMR (101 MHz, DMSO-d$_6$) δ 170.20, 163.68, 152.78, 151.13, 148.66, 125.75, 125.63, 124.53, 124.50, 123.63, 79.62, 59.64, 27.90, 20.65, 13.99; $^{19}$F NMR (376 MHz, DMSO-d$_6$) δ −124.86; ESIMS m/z 288 ([M−H]$^-$).

Example 90: Preparation of ethyl 3-[bis(tert-butoxycarbonyl)amino]-6-chloro-2-fluorobenzoate (C319)

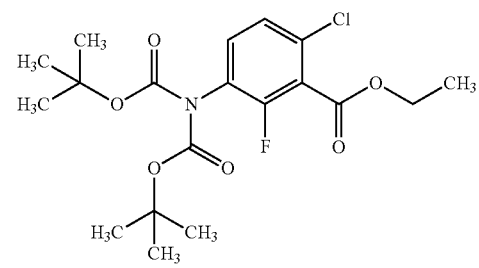

To a solution of ethyl 3-amino-6-chloro-2-fluorobenzoate (C320; 8.5 g, 39.1 mmol) in N,N-dimethylformamide (32.5 mL) were sequentially added added N,N-dimethylpyridin-4-amine (0.239 g, 1.95 mmol), N-ethyl-N-isopropylpropan-2-amine (20.4 mL, 117 mmol), and di-tert-butyl dicarbonate (25.6 g, 117 mmol; added in portions), and the resulting light yellow solution was stirred at room temperature for approximately 16 hours. The reaction mixture was treated with additional di-tert-butyl dicarbonate (3.00 g, 13.7 mmol), stirred for 3 hours at room temperature, and partitioned between ethyl acetate (200 mL) and 5% aqueous solution of sodium bicarbonate (600 mL). The phases were separated, and the aqueous phase was extracted with diethyl ether (150 mL). Each of the organic extracts was washed with water (ethyl acetate: 3×200 mL; diethyl ether: 2×100 mL). The extracts were combined, dried over sodium sulfate, filtered, and concentrated to a viscous, red oil. The crude oil was purified by automated flash chromatography (Silica gel; 0→30% ethyl acetate in hexanes) to give the title compound as viscous, gold oil which slowly solidifies upon standing (12.55 g, 77%): mp 91-95° C.; $^1$H NMR (400 MHz, CDCl$_3$) δ 7.25-7.13 (m, 2H), 4.45 (q, J=7.2 Hz, 2H), 1.45-1.36 (m, 21H); $^{13}$C NMR (101 MHz, CDCl$_3$) δ 162.51, 156.15, 153.60, 150.19, 131.43, 131.38, 131.19, 131.17, 126.73, 126.60, 125.14, 125.10, 123.16, 122.97, 83.74, 62.41, 27.81, 14.11; $^{19}$F NMR (376 MHz, CDCl$_3$) δ −119.43.

Example 91: Preparation of ethyl 3-amino-6-chloro-2-fluorobenzoate (C320)

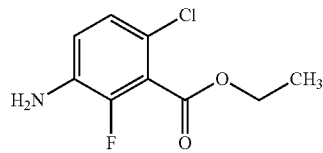

To a solution of 4-chloro-2-fluoroaniline (11 g, 76 mmol) in anhydrous tetrahydrofuran (151 mL) cooled to −76° C. was added butyllithium (31.7 mL, 79 mmol) as a 2.5 M solution in hexanes at a rate which maintained the temperature between below −68° C., and the resulting greenish-brown solution was stirred at −75° C. for 45 minutes. The heterogeneous brown reaction mixture was treated with a tetrahydrofuran solution (50 mL) of 1,2-bis(chlorodimethylsilyl)ethane (17.24 g, 80 mmol) at a rate which maintained the temperature between −68 and −75° C. Following the addition, the resulting brown solution was stirred at −75° C. for 75 minutes.

The resulting brown solution was treated with butyllithium (31.7 mL, 79 mmol) at a rate which maintained the temperature below −70° C., and the resulting solution was stirred at −74° C. for 30 minutes. The cooling bath was removed and the reaction solution was allowed to slowly warm to 15° C. over approximately a 2-hour period.

The solution was cooled to −72° C. and treated dropwise with butyllithium (31.7 mL, 79 mmol) at a rate which maintained the temperature below −70° C. After stirring for 60 minutes at −74° C., the resulting amber-brown solution was treated with ethyl carbonochloridate (10.66 g, 98 mmol) dropwise at a rate which maintained the temperature below −70° C., and the resulting dark solution was allowed to slowly warm to room temperature as the dry ice was consumed.

The resulting heterogeneous mixture (tan ppt) was cooled to 0° C. and quenched by the cautious addition of 3 N aqueous hydrogen chloride (140 mL, 0.42 mmol). The ice bath was removed and the resulting dark solution was stirred at room temperature for 60 minutes. The pH was adjusted to ~8 by the careful addition of solid sodium carbonate (~28 g) and the mixture was extracted with ethyl acetate (3×150 mL). The combined extracts were washed with brine (3×100 mL), dried over sodium sulfate, filtered, and concentrated to a dark oil. The crude oil was purified by automated flash chromatography (silica gel; 0→30% ethyl acetate in hexanes) to give the title compound as a light-orange oil (8.96 g, 54%): $^1$H NMR (400 MHz, CDCl$_3$) δ 6.97 (dd, J=8.6, 1.5 Hz, 1H), 6.73 (t, J=8.9 Hz, 1H), 4.43 (q, J=7.1 Hz, 2H), 3.84 (s, 2H), 1.40 (t, J=7.2 Hz, 3H); $^{13}$C NMR (101 MHz, CDCl$_3$) δ 163.49, 149.38, 146.94, 133.85, 133.73, 125.36, 125.32, 122.35, 122.18, 119.48, 119.44, 117.95, 117.90, 62.19, 14.14; $^{19}$F NMR (376 MHz, CDCl$_3$) δ −134.47; EIMS m/z 217.

Example 92: Preparation of N-(3-amino-2,6-dichlorophenyl)acetamide (C321)

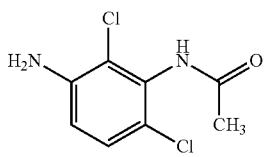

Step 1: Preparation of tert-butyl (3-acetamido-2,4-dichlorophenyl)carbamate

3-Acetamido-2,4-dichlorobenzoic acid (1 g, 4.03 mmol) was added portionwise to a stirred solution of diphenylphosphoryl azide (1.47 g, 5.34 mmol), and triethylamine (0.54 g, 5.34 mmol) in anhydrous tert-butanol (25 mL). The resulting gold solution was heated at 80° C. for 1 hour, then cooled and quenched with water (20 mL). The resulting aqueous mixture was extracted with ethyl acetate (2×50 mL) and washed with saturated aqueous sodium bicarbonate solution (50 mL) and saturated aqueous sodium chloride solution (50 mL). The organic extracts were dried over anhydrous magnesium sulfate, filtered and concentrated under vacuum on a rotary evaporator. Purification by flash silica gel column chromatography using 0-30% ethyl acetate in hexanes as eluent gave the title compound as a white solid (0.72 g, 44%): $^1$H NMR (400 MHz, CDCl$_3$) δ 8.02 (d, J=9.1 Hz, 1H), 7.32-7.25 (m, 2H), 6.96 (s, 1H), 2.23 (s, 3H), 1.54 (s, 9H); ESIMS m/z 320 ([M+H]$^+$).

Step 2: Preparation of N-(3-amino-2,6-dichlorophenyl)acetamide

4 M Hydrogen chloride in 1,4-dioxane (2.8 mL, 11.3 mmol) was added dropwise to a stirred solution of tort-butyl (3-acetamido-2,4-dichlorophenyl)carbamate (0.72 g, 2.25 mmol) in dichloromethane (5 mL). The resulting suspension of solid was stirred for 11 hours at 23° C. and then concentrated under vacuum on a rotary evaporator. The resulting crude product was slurried in dichloromethane (2 mL) and treated with triethylamine until a solution formed (~0.3 mL). Purification by silica gel flash chromatography using 0-100% ethyl acetate in hexanes as eluent provided the title compound as a white solid. (0.45 g, 87%): $^1$H NMR (400 MHz, DMSO-d$_6$) δ 9.60 (s, 1H), 7.13 (d, J=8.8 Hz, 1H), 6.73 (d, J=8.8 Hz, 1H), 5.54 (s, 2H), 2.02 (s, 3H); $^{13}$C NMR (101 MHz, DMSO-d$_6$) δ 168.34, 145.19, 133.52, 127.82, 119.20, 117.75, 114.48, 22.92; ESIMS m/z 220 ([M+H]$^+$).

Example 93: Preparation of 5-amino-2-chloro-N-(2,2-difluoropropyl)benzamide (C322)

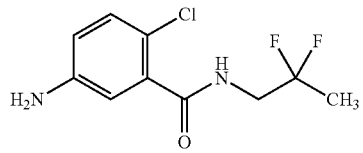

To a solution of 2-chloro-N-(2,2-difluoropropyl)-5-nitrobenzamide (C386; 0.45 g, 1.61 mmol) in a mixture of tetrahydrofuran-ethanol-water (3:2:1, 12 mL) were added iron powder (0.54 g, 9.71 mmol) and ammonium chloride (0.86 g, 16.18 mmol), and the reaction mixture was stirred at 80° C. for 8 hours. The reaction mixture was filtered through a pad of Celite® and washed with ethyl acetate (50 mL) and methanol (30 mL). The filtrate was concentrated under reduced pressure, and the residue was taken up in water and made basic with sodium bicarbonate solution. The aqueous layer was extracted with ethyl acetate (3×20 mL), and the organic layer was dried over anhydrous Na$_2$SO$_4$, filtered and concentrated under reduced pressure. Purification by preparative high-performance liquid chromatography (HPLC) afforded the title compound as an off-white solid (0.24 g, 63%): mp 99-101° C.; $^1$H NMR (400 MHz, DMSO-d$_6$) δ 8.68 (t, J=6.4 Hz, 1H), 7.06 (d, J=1.6, 7.2 Hz, 1H), 6.62-6.55 (m, 2H), 5.39 (s, 2H), 3.68-3.58 (m, 2H), 1.63 (t, J=19.1 Hz, 3H); ESIMS m/z 249.10 ([M+H]$^+$).

The following compounds were prepared in like manner to the procedure outlined in Example 93:

5-Amino-2-chloro-N-(2,2-difluorobutyl)benzamide (C323)

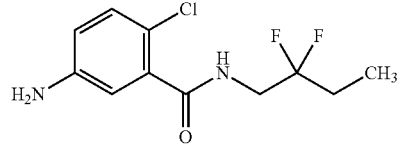

Isolated as an off-white solid (0.21 g, 52%): mp 82-84° C.; $^1$H NMR (400 MHz, DMSO-d$_6$) δ 8.64 (t, J=6.4 Hz, 1H), 7.06 (d, J=8.4 Hz, 1H), 6.62-6.54 (m, 2H), 5.39 (s, 2H), 3.66-3.61 (m, 2H), 2.04-1.83 (m, 2H), 0.98 (t, J=7.6 Hz, 3H); $^{19}$F NMR (376 MHz, DMSO-d$_6$) δ −102.95; ESIMS m/z 263.12 ([M+H]$^+$).

Ethyl 3-(5-amino-2-chlorobenzamido)-2,2-difluoropropanoate (C324)

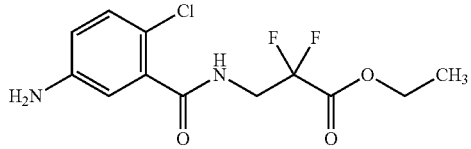

Isolated as a yellow solid (0.095 g, 18%): mp 100-102° C.; $^1$H NMR (400 MHz, DMSO-d$_6$) δ 8.78 (t, J=6.4 Hz, 1H), 7.06 (d, J=8.0 Hz, 1H), 6.59 (dd, J=2.4, 8.8 Hz, 1H), 6.55 (d, J=2.8 Hz, 1H), 5.42 (s, 2H), 4.28 (q, J=6.8 Hz, 2H), 3.93-3.84 (m, 2H), 1.28 (t, J=7.2 Hz, 3H); $^{19}$F NMR (376 MHz, DMSO-d$_6$) δ −109.55; ESIMS m/z 307.12 ([M+H]$^+$).

5-Amino-2-chloro-N-(2,2-difluoro-2-phenylethyl)benzamide (C325)

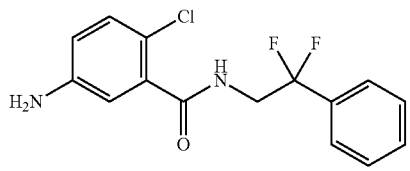

Isolated as a brown solid (0.22 g, 37%): mp 109-111° C.; $^1$H NMR (400 MHz, DMSO-d$_6$) δ 8.71 (t, J=6.4 Hz, 1H), 7.61-7.46 (m, 5H), 7.03 (d, J=8.8 Hz, 1H), 6.57 (dd, J=2.8, 8.4 Hz, 1H), 6.50 (d, J=2.8 Hz, 1H), 5.38 (s, 2H), 4.00-3.90 (m, 2H); ESIMS m/z 311.16 ([M+H]$^+$).

5-Amino-2-chloro-N-(2-oxopropyl)benzamide (C326)

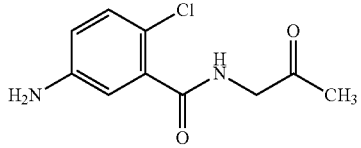

Isolated as an off-white solid (0.2 g, 57%): mp 118-120° C.; $^1$H NMR (400 MHz, DMSO-d$_6$) δ 8.54 (t, J=5.6 Hz, 1H), 7.06 (d, J=8.8 Hz, 1H), 6.66 (d, J=2.4 Hz, 1H), 6.59 (dd, J=2.4, 8.4 Hz, 1H), 5.42 (s, 2H), 3.98 (d, J=5.6 Hz, 2H), 2.12 (s, 3H); ESIMS m/z 227.30 ([M+H]$^+$).

5-Amino-2-chloro-N-(2-oxobutyl)benzamide (C327)

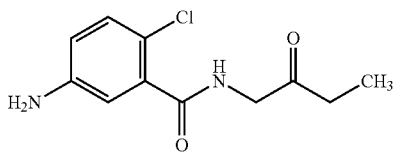

Isolated as an off-white solid (0.25 g, 26%): mp 91-93° C.; $^1$H NMR (400 MHz, DMSO-d$_6$) δ 8.52 (t, J=5.6 Hz, 1H), 7.06 (d, J=8.4 Hz, 1H), 6.66 (d, J=2.8 Hz, 1H), 6.59 (dd, J=2.4, 8.8 Hz, 1H), 5.42 (s, 2H), 3.99 (d, J=5.8 Hz, 2H), 2.49-2.41 (m, 2H), 0.96 (t, J=7.2 Hz, 3H); ESIMS m/z 241.06 ([M+H]$^+$).

5-Amino-2-chloro-N-(4-methyl-2-oxopentyl)benzamide (C328)

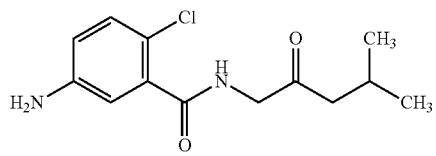

Isolated as an off-white solid (0.2 g, 23%): mp 115-117° C.; $^1$H NMR (400 MHz, DMSO-d$_6$) δ 8.50 (t, J=5.6 Hz, 1H), 7.06 (d, J=8.4 Hz, 1H), 6.66 (d, J=2.8 Hz, 1H), 6.59 (dd, J=2.4, 8.8 Hz, 1H), 5.43 (s, 2H), 3.97 (d, J=6.0 Hz, 2H), 2.36 (d, J=6.8 Hz, 2H), 2.13-1.99 (m, 1H), 0.88 (d, J=6.4 Hz, 6H); ESIMS m/z 269.06 ([M+H]$^+$).

5-Amino-2-chloro-N-(2-oxo-2-phenylethyl)benzamide (C329)

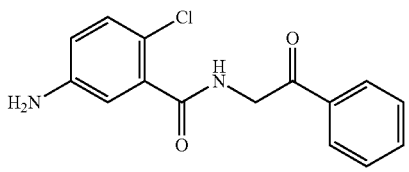

Isolated as an off-white solid (0.06 g, 17%): mp 132-134° C.; $^1$H NMR (400 MHz, DMSO-d$_6$) δ 8.54 (t, J=5.6 Hz, 1H), 8.03 (d, J=7.2 Hz, 2H), 7.70-7.66 (m, 1H), 7.59-7.54 (m, 2H), 7.07 (d, J=8.4 Hz, 1H), 6.73 (d, J=2.8 Hz, 1H), 6.60 (dd, J=2.8, 8.4 Hz, 1H), 5.42 (s, 2H), 4.71 (d, J=6.0 Hz, 2H); ESIMS m/z 289.14 ([M+H]$^+$).

5-Amino-2-chloro-N-(2,2-difluoropropyl)-3-fluorobenzamide (C330)

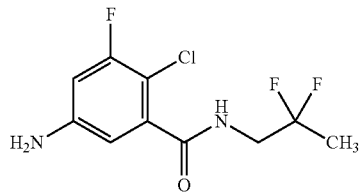

Isolated as an off-white solid (0.2 g, 63%): mp 107-109° C.; $^1$H NMR (400 MHz, DMSO-d$_6$) δ 8.80 (t, J=6.4 Hz, 1H), 6.53 (dd, J=2.8, 12.0 Hz, 1H), 6.43 (d, J=1.6 Hz, 1H), 5.73 (br s, 2H), 3.69-3.60 (m, 2H), 1.63 (t, J=18.8 Hz, 3H); $^{19}$F NMR (376 MHz, DMSO-d$_6$) δ −93.66, −115.77; ESIMS m/z 267.08 ([M+H]$^+$).

5-Amino-2-chloro-N-(2,2-difluorobutyl)-3-fluorobenzamide (C331)

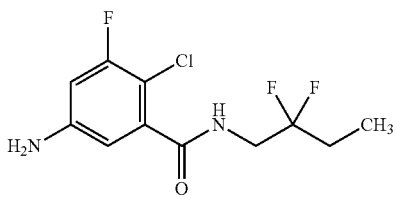

Isolated as an off-white solid (0.19 g, 53%): mp 79-81° C.; $^1$H NMR (400 MHz, DMSO-d$_6$) δ 8.81 (t, J=6.0 Hz, 1H), 6.56 (dd, J=2.8, 12.4 Hz, 1H), 6.45-6.42 (m, 1H), 5.72 (br s, 2H), 3.70-3.60 (m, 2H), 1.97-1.86 (m, 2H), 0.98 (t, J=8.0 Hz, 3H); $^{19}$F NMR (376 MHz, DMSO-d$_6$) δ −103.09, −115.77; ESIMS m/z 281.14 ([M+H]$^+$).

Ethyl 3-(5-amino-2-chloro-3-fluorobenzamido)-2,2-difluoropropanoate (C332)

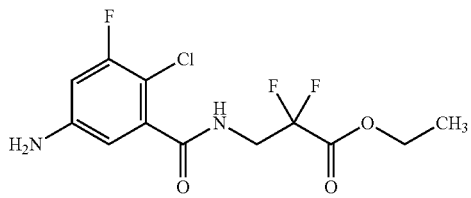

Isolated as an off-white solid (0.12 g, 19%): mp 83-85° C.; $^1$H NMR (400 MHz, DMSO-d$_6$) δ 8.92 (t, J=6.4 Hz, 1H), 6.54 (dd, J=2.4, 11.6 Hz, 1H), 6.42-6.40 (m, 1H), 5.76 (br s, 2H), 4.28 (q, J=7.2 Hz, 2H), 3.95-3.85 (m, 2H), 1.28 (t, J=6.8 Hz, 3H); $^{19}$F NMR (376 MHz, DMSO-d$_6$) δ −109.59, −115.63; ESIMS m/z 325.17 ([M+H]$^+$).

5-Amino-2-chloro-3-fluoro-N-(2-oxobutyl)benzamide (C333)

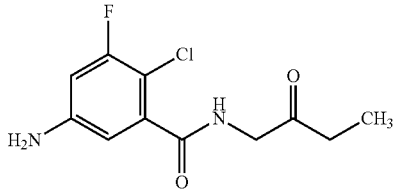

Isolated as an off-white solid (0.14 g, 40%): mp 96-98° C.; $^1$H NMR (400 MHz, DMSO-d$_6$) δ 8.65 (t, J=6.0 Hz, 1H), 6.55-6.50 (m, 2H), 5.76 (br s, 2H), 4.01 (d, J=5.6, Hz, 2H), 2.49-2.46 (m, 2H), 0.95 (t, J=7.2 Hz, 3H); $^{19}$F NMR (376 MHz, DMSO-d$_6$) δ −115.66; ESIMS m/z 259.12 ([M+H]$^+$).

5-Amino-2-chloro-3-fluoro-N-(4-methyl-2-oxopentyl)benzamide (C334)

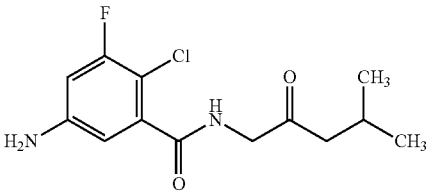

Isolated as an off-white solid (0.32 g, 58%): mp 99-101° C.; $^1$H NMR (400 MHz, DMSO-d$_6$) δ 8.58 (t, J=6.0 Hz, 1H), 6.54-6.51 (m, 2H), 5.74 (br s, 2H), 3.98 (d, J=6.0 Hz, 2H), 2.35 (d, J=6.8 Hz, 2H) 2.08-2.01 (m, 1H), 0.88 (d, J=6.8 Hz, 6H); $^{19}$F NMR (376 MHz, DMSO-d$_6$) δ −115.68; ESIMS m/z 287.15 ([M+H]$^+$).

5-Amino-2-chloro-3-fluoro-N-(2-oxo-2-phenylethyl)benzamide (C335)

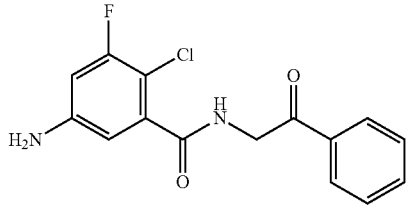 [SMILES: Nc1cc(F)c(Cl)c(C(=O)NCC(=O)c2ccccc2)c1]

Isolated as an off-white solid (0.21 g, 57%): mp 147-149° C.; $^1$H NMR (400 MHz, DMSO-d$_6$) δ 8.67 (t, J=5.6 Hz, 1H), 8.04-8.01 (m, 2H), 7.70-7.66 (m, 1H), 7.56 (t, J=8.0 Hz, 2H), 6.58-6.52 (m, 2H), 5.76 (br s, 2H), 4.72 (d, J=5.6 Hz, 2H); $^{19}$F NMR (376 MHz, DMSO-d$_6$) δ −115.29; ESIMS m/z 307.19 ([M+H]$^+$).

5-Amino-2-chloro-3-fluoro-N-(2-oxopropyl)benzamide (C336)

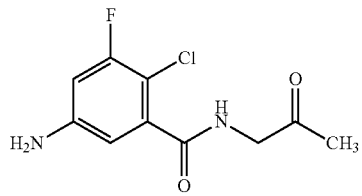

Isolated as an off-white solid (0.075 g, 30%): mp 126-128° C.; $^1$H NMR (400 MHz, DMSO-d$_6$) δ 8.65 (t, J=5.6 Hz, 1H), 6.55-6.50 (m, 2H), 5.76 (br s, 2H), 4.01 (d, J=6.0 Hz, 2H), 2.13 (s, 3H); $^{19}$F NMR (376 MHz, DMSO-d$_6$) δ −115.66; ESIMS m/z 245.03 ([M+H]$^+$).

5-Amino 2-chloro-N-(2,2-difluoro-2-phenylethyl)-3-fluorobenzamide (C337)

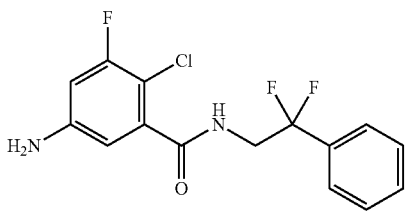

Isolated as an off-white solid (0.25 g, 60%): mp 136-138° C.; $^1$H NMR (400 MHz, DMSO-d$_6$) δ 8.83 (t, J=6.4 Hz, 1H), 7.58-7.49 (m, 5H), 6.51 (dd, J=2.4, 11.6 Hz, 1H), 6.36-6.31 (m, 1H), 5.72 (br s, 2H), 4.01-3.91 (m, 2H); $^{19}$F NMR (376 MHz, DMSO-d$_6$) δ −98.49, −115.60; ESIMS m/z 329.17 ([M+H]$^+$).

Example 94: Preparation of 5-amino-2-chloro-N-(2-oxo-2-(2,2,2-trifluoroethylamino)ethyl)benzamide (C338)

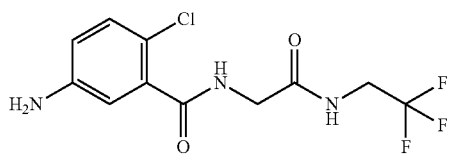 [SMILES: Nc1ccc(Cl)c(C(=O)NCC(=O)NCC(F)(F)F)c1]

To a solution of 5-amino-2-chlorobenzoic acid (0.6 g, 3.49 mmol) in dichloromethane (10 mL) were added sequentially 2-amino-N-(2,2,2-trifluoroethyl)acetamide (C350; 0.8 g, 4.20 mmol), N-(3-dimethylaminopropyl)-N′-ethylcarbodiimide hydrochloride (2 g, 10.5 mmol), diisopropylethylamine (1.73 mL, 10.5 mmol), and 4-(dimethylamino)pyridine (cat.), and the reaction mixture was stirred at room temperature for 16 hours. The reaction mixture was concentrated under reduced pressure. Purification by column chromatography (silica gel 100-200 mesh) eluting with 5-10% ethyl acetate in methanol afforded the title compound as an off-white solid (0.28 g, 26%): mp 109-111° C.; $^1$H NMR (400 MHz, DMSO-d$_6$) δ 8.47 (t, J=5.6 Hz, 1H), 8.42 (t, J=6.0 Hz, 1H), 7.05 (d, J=8.4 Hz, 1H), 6.68 (d, J=2.8 Hz, 1H), 6.58 (dd, J=2.4, 8.8 Hz, 1H), 5.38 (m, 2H), 3.98-3.89 (m, 2H), 3.87 (d, J=6.0 Hz, 2H); ESIMS m/z 310.15 ([M+H]$^+$).

The following compounds were prepared in like manner to the procedure outlined in Example 94:

5-Amino-2-chloro-N-(3-oxo-3-((2,2,2-trifluoroethyl)amino)propyl)benzamide (C339)

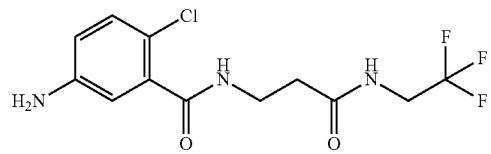 [SMILES: Nc1ccc(Cl)c(C(=O)NCCC(=O)NCC(F)(F)F)c1]

Isolated as an off-white solid (0.17 g, 15%): mp 148-150° C.; $^1$H NMR (400 MHz, DMSO-d$_6$) δ 8.56 (t, J=6.4 Hz, 1H), 8.22 (t, J=5.2 Hz, 1H), 7.04 (d, J=8.4 Hz, 1H), 6.58-6.54 (m, 2H), 5.33 (s, 2H), 3.92-3.84 (m, 2H), 3.41-3.35 (m, 2H), 2.44 (t, J=7.2 Hz, 2H); $^{19}$F NMR (376 MHz, DMSO-d$_6$) δ −70.71; ESIMS m/z 324.20 ([M+H]$^+$).

5-Amino-2-chloro-N-(4-oxo-4-((2,2,2-trifluoroethyl)amino)butyl)benzamide (C340)

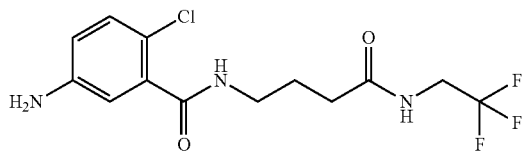 [SMILES: Nc1ccc(Cl)c(C(=O)NCCCC(=O)NCC(F)(F)F)c1]

Isolated as an off-white solid (0.59 g, 25%): mp 136-138° C.; $^1$H NMR (400 MHz, DMSO-d$_6$) δ 8.46 (t, J=6.4 Hz, 1H), 8.22 (t, J=5.2 Hz, 1H), 7.05-7.02 (m, 1H), 6.58-6.55 (m, 2H), 5.34 (s, 2H), 3.93-3.84 (m, 2H), 3.28-3.14 (m, 2H), 2.23 (t, J=7.2 Hz, 2H), 1.75-1.68 (m, 2H); $^{19}$F NMR (376 MHz, DMSO-d$_6$) δ −70.85; ESIMS m/z 338.18 ([M+H]$^+$).

5-Amino-2-chloro-N-(2-oxo-2-((3,3,3-trifluoropropyl)amino)ethyl)benzamide (C341)

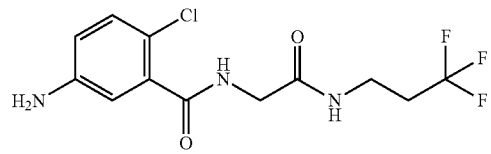 [SMILES: Nc1ccc(Cl)c(C(=O)NCC(=O)NCCC(F)(F)F)c1]

Isolated as an off-white solid (0.98 g, 33%): mp 110-112° C.; $^1$H NMR (400 MHz, DMSO-d$_6$) δ 8.39 (t, J=6.0 Hz, 1H), 8.04 (t, J=5.6, 1H), 7.06 (d, J=8.4 Hz, 1H), 6.68 (d, J=3.2 Hz, 1H), 6.58 (dd, J=2.4, 8.4 Hz, 1H), 5.39 (s, 2H), 3.78 (d, J=6.0 Hz, 2H), 3.35-3.30 (m, 2H), 2.49-2.39 (m, 2H); $^{19}$F NMR (376 MHz, DMSO-d$_6$) δ −63.98; ESIMS m/z 324.13 ([M+H]$^+$).

5-Amino-2-chloro-N-(3-oxo-3-((3,3,3-trifluoropropyl)amino)propyl)benzamide (C342)

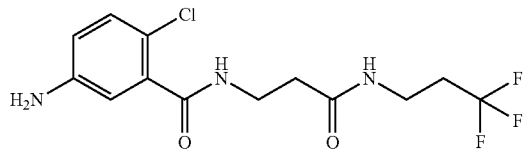 [SMILES: Nc1ccc(Cl)c(C(=O)NCCC(=O)NCCC(F)(F)F)c1]

Isolated as an off-white solid (0.83 g, 28%): mp 109-111° C.; $^1$H NMR (400 MHz, DMSO-d$_6$) δ 8.23 (t, J=5.6 Hz, 1H), 8.13 (t, J=5.6 Hz, 1H), 7.04 (d, J=8.4 Hz, 1H), 6.57 (d, J=3.2 Hz, 1H), 6.56-6.54 (m, 1H), 5.36 (s, 2H), 3.39-3.34 (m, 2H), 3.30-3.25 (m, 2H), 2.50-2.31 (m, 4H); $^{19}$F NMR (376 MHz, DMSO-d$_6$) δ −63.98; ESIMS m/z 338.15 ([M+H]$^+$).

5-Amino-2-chloro-N-(4-oxo-4-((3,3,3-trifluoropropyl)amino)butyl)benzamide (C343)

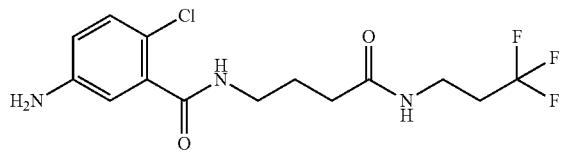 [SMILES: Nc1ccc(Cl)c(C(=O)NCCCC(=O)NCCC(F)(F)F)c1]

Isolated as an off-white solid (0.51 g, 17%): mp 121-123° C.; $^1$H NMR (400 MHz, DMSO-d$_6$) δ 8.24 (t, J=6.0 Hz, 1H), 8.02 (t, J=5.2 Hz, 1H), 7.04 (d, J=8.8 Hz, 1H), 6.57-6.55 (m, 2H), 5.36 (s, 2H), 3.30-3.24 (m, 2H), 3.18-3.13 (m, 2H), 2.50-2.35 (m, 2H), 2.13 (t, J=7.2 Hz, 2H), 1.73-1.65 (m, 2H); $^{19}$F NMR (376 MHz, DMSO-d$_6$) δ −63.91; ESIMS m/z 352.41 ([M+H]$^+$).

5-Amino-2-chloro-N-(2-(2,2,2-trifluoroacetamido)ethyl)benzamide (C344)

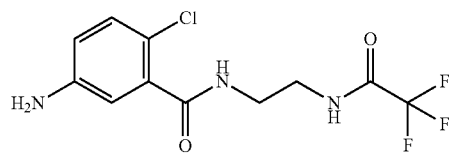 [SMILES: Nc1ccc(Cl)c(C(=O)NCCNC(=O)C(F)(F)F)c1]

Isolated as an off-white solid (0.32 g, 18%): mp 157-159° C.; $^1$H NMR (400 MHz, DMSO-d$_6$) δ 9.38-9.35 (m, 1H), 8.38-8.36 (m, 1H), 7.06-7.03 (m, 1H), 6.60-6.56 (m, 2H), 5.34 (s, 2H), 3.37-3.28 (m, 4H); $^{19}$F NMR (376 MHz, DMSO-d$_6$) δ −74.47; ESIMS m/z 310.15 ([M+H]$^+$).

5-Amino-2-chloro-N-(3-(2,2,2-trifluoroacetamido)propyl)benzamide (C345)

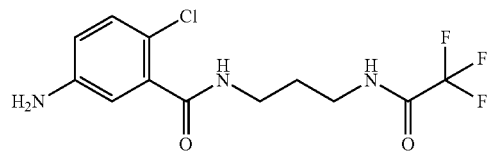 [SMILES: Nc1ccc(Cl)c(C(=O)NCCCNC(=O)C(F)(F)F)c1]

Isolated as an off-white solid (0.80 g, 28%): mp 105-107° C.; $^1$H NMR (400 MHz, DMSO-d$_6$) δ 9.38-9.36 (m, 1H), 8.25 (t, J=5.6 Hz, 1H), 7.04 (dd, J=2.0, 7.2 Hz, 1H), 6.59-6.56 (m, 2H), 5.35 (s, 2H), 3.29-3.17 (m, 4H), 1.74-1.67 (m, 2H); $^{19}$F NMR (376 MHz, DMSO-d$_6$) δ −74.42; ESIMS m/z 324.24 ([M+H]$^+$).

5-Amino-2-chloro-N-(4-(2,2,2-trifluoroacetamido)butyl)benzamide (C346)

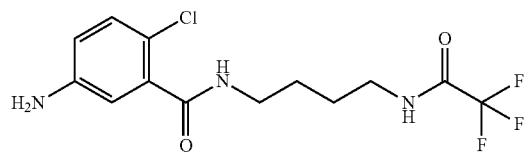

Isolated as a pale yellow gummy solid (0.98 g, 34%): $^1$H NMR (400 MHz, DMSO-d$_6$) δ 9.44 (t, J=5.6 Hz, 1H), 8.25 (t, J=5.6 Hz, 1H), 7.04 (d, J=8.4 Hz, 1H), 6.57 (d, J=2.8 Hz, 1H), 6.55-6.54 (m, 1H), 5.37 (s, 2H), 3.22-3.15 (m, 4H), 1.57-1.45 (m, 4H); $^{19}$F NMR (376 MHz, DMSO-d$_6$) δ −74.36; IR 749.91 cm$^{-1}$ (C—Cl stretching); ESIMS m/z 338.37 ([M+H]$^+$).

5-Amino-2-chloro-N-(2-(2,2,3,3,3-pentafluoropropanamido)ethyl)benzamide (C347)

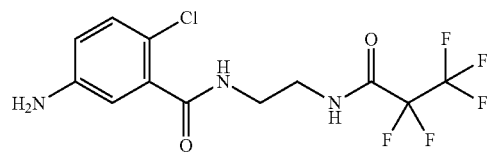 [SMILES: Nc1ccc(Cl)c(C(=O)NCCNC(=O)C(F)(F)C(F)(F)F)c1]

Isolated as an off-white solid (0.97 g, 46%): mp 150-152° C.; $^1$H NMR (400 MHz, DMSO-d$_6$) δ 9.48 (t, J=5.6 Hz, 1H), 8.32 (t, J=5.2 Hz, 1H), 7.05 (d, J=9.2 Hz, 1H), 6.59-6.57 (m, 2H), 5.34 (s, 2H), 3.38-3.29 (m, 4H); $^{19}$F NMR (376 MHz, DMSO-d$_6$) δ −82.30, −121.85; ESIMS m/z 360.36 ([M+H]$^+$).

5-Amino-2-chloro-N-(3-(2,2,3,3,3-pentafluoropropanamido)propyl)benzamide (C348)

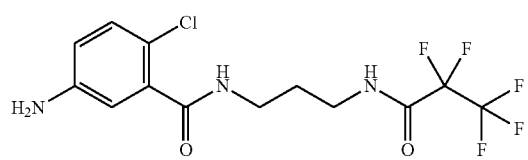 [SMILES: Nc1ccc(Cl)c(C(=O)NCCCNC(=O)C(F)(F)C(F)(F)F)c1]

Isolated as an off-white solid (0.70 g, 21%): mp 118-120° C.; $^1$H NMR (400 MHz, DMSO-d$_6$) δ 9.50 (t, J=5.6 Hz, 1H), 8.27 (t, J=6.0 Hz, 1H), 7.05 (dd, J=2.0, 7.6 Hz, 1H), 6.59-6.56 (m, 2H), 5.37 (s, 2H), 3.32-3.25 (m, 2H), 3.22-3.16 (m, 2H), 1.74-1.67 (m, 2H); $^{19}$F NMR (376 MHz, DMSO-d$_6$) δ −82.37, −121.89; ESIMS m/z 374.33 ([M+H]$^+$).

567

5-Amino-2-chloro-N-(4-(2,2,3,3,3-pentafluoropropanamido)butyl)benzamide (C349)

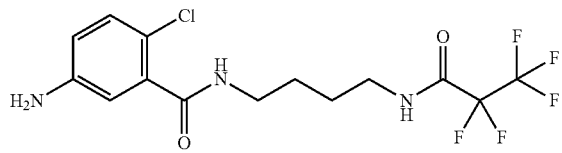 [SMILES: Nc1ccc(Cl)c(C(=O)NCCCCNC(=O)C(F)(F)C(F)(F)F)c1]

Isolated as a brown gummy solid (0.36 g, 11%): IR 749.81 (C—Cl stretching) cm$^{-1}$; $^1$H NMR (400 MHz, DMSO-d$_6$) δ 9.47-9.46 (m, 1H), 8.21 (t, J=5.2 Hz, 1H), 7.04 (d, J=8.0 Hz, 1H), 6.58-6.55 (m, 2H), 5.33 (s, 2H), 3.29-3.15 (m, 4H), 1.57-1.44 (m, 4H); $^{19}$F NMR (376 MHz, DMSO-d$_6$) δ −82.35, −121.76; ESIMS m/z 388 ([M+H]$^+$).

Example 95: Preparation of 2-amino-N-(2,2,2-trifluoroethyl)acetamide hydrochloride (C350)

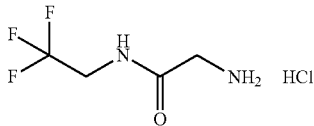

To a stirred solution of tert-butyl (2-oxo-2-((2,2,2-trifluoroethyl)amino)ethyl)carbamate (C362; 3 g, 15.6 mmol) in dioxane (20 mL) was added 4 M HCl in dioxane (23 mL, 93.8 mmol) dropwise at 0° C., and the reaction mixture was stirred at room temperature for 10 hours. The reaction mixture was concentrated under reduced pressure. The title compound was isolated as an off-white solid (2.4 g), which was used without purification: $^1$H NMR (300 MHz, DMSO-d$_6$) δ 9.17-9.13 (m, 1H), 8.21 (br s, 3H), 4.07-3.95 (m, 2H), 3.67-3.64 (m, 2H).

The following compounds were prepared in like manner to the procedure outlined in Example 95:

3-Amino-N-(2,2,2-trifluoroethyl)propanamide hydrochloride (C351)

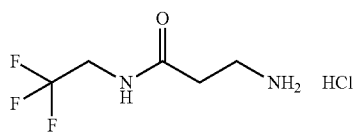 [SMILES: NCCC(=O)NCC(F)(F)F ; Cl]

Isolated as an off-white solid (2.3 g), which was used without purification: $^1$H NMR (300 MHz, DMSO-d$_6$) δ 8.93 (br s, 1H), 8.21 (br s, 3H), 3.97-3.85 (m, 2H), 2.98-2.94 (m, 2H), 2.65-2.60 (m, 2H).

568

4-Amino-N-(2,2,2-trifluoroethyl)butanamide hydrochloride (C352)

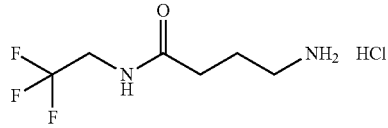 [SMILES: NCCCC(=O)NCC(F)(F)F ; Cl]

Isolated as an off-white solid (2 g). The product was used in the next step without purification and analysis.

2-Amino-N-(3,3,3-trifluoropropyl)acetamide hydrochloride (C353)

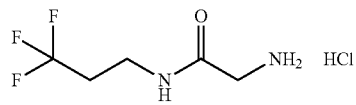 [SMILES: NCC(=O)NCCC(F)(F)F ; Cl]

Isolated as an off-white solid (2.4 g). The product was used in the next step without purification and analysis.

3-Amino-N-(3,3,3-trifluoropropyl)propanamide hydrochloride (C354)

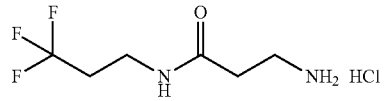 [SMILES: NCCC(=O)NCCC(F)(F)F ; Cl]

Isolated as an off-white solid (2.7 g). The product was used in the next step without purification and analysis.

4-Amino-N-(3,3,3-trifluoropropyl)butanamide hydrochloride (C355)

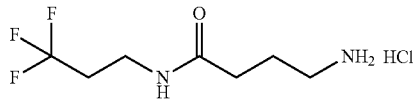 [SMILES: NCCCC(=O)NCCC(F)(F)F ; Cl]

Isolated as an off-white solid (2.7 g), which was used without purification: $^1$H NMR (300 MHz, DMSO-d$_6$) δ 8.26 (br s, 1H), 8.01 (br s, 3H), 3.31-3.24 (m, 2H), 2.78-2.72 (m, 2H), 2.51-2.36 (m, 2H), 2.18 (t, J=7.5 Hz, 2H), 1.82-1.72 (m, 2H).

N-(2-Aminoethyl)-2,2,2-trifluoroacetamide hydrochloride (C356)

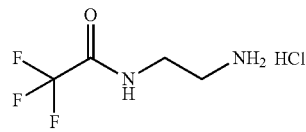

Isolated as an off-white solid (2.1 g), which was used without purification: ¹H NMR (300 MHz, DMSO-d$_6$) δ 9.67 (br s, 1H), 8.24 (br s, 3H), 3.50-3.44 (m, 2H), 2.98-2.93 (m, 2H).

N-(3-Aminopropyl)-2,2,2-trifluoroacetamide hydrochloride (C357)

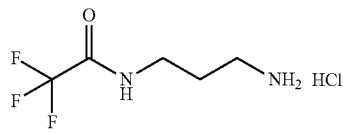 [SMILES: NCCCNC(=O)C(F)(F)F ; Cl]

Isolated as an off-white solid (1.7 g). The product was used in the next step without purification and analysis.

N-(4-Aminobutyl)-2,2,2-trifluoroacetamide hydrochloride (C358)

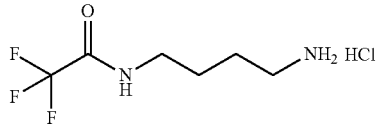 [SMILES: NCCCCNC(=O)C(F)(F)F ; Cl]

Isolated as an off-white solid (3.2 g). The product was used in the next step without purification and analysis.

N-(2-Aminoethyl)-2,2,3,3,3-pentafluoropropanamide hydrochloride (C359)

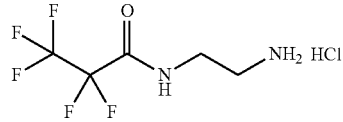 [SMILES: NCCNC(=O)C(F)(F)C(F)(F)F ; Cl]

Isolated as an off-white solid (2.9 g), which was used without purification: ¹H NMR (300 MHz, DMSO-d$_6$) δ 9.78 (br s, 1H), 8.23 (br s, 3H), 3.56-3.38 (m, 2H), 2.96-2.94 (m, 2H), N-(3-Aminopropyl)-2,2,3,3,3-pentafluoropropanamide hydrochloride (C360)

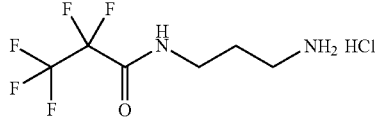 [SMILES: NCCCNC(=O)C(F)(F)C(F)(F)F ; Cl]

Isolated as an off-white solid (2.9 g): The product was used in the next step without purification and analysis.

N-(4-Aminobutyl)-2,2,3,3,3-pentafluoropropanamide hydrochloride (C361)

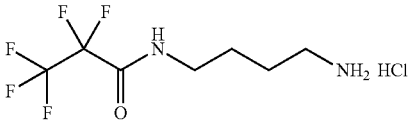 [SMILES: NCCCCNC(=O)C(F)(F)C(F)(F)F ; Cl]

Isolated as an off-white solid (3.1 g), which was used without purification: ¹H NMR (300 MHz, DMSO-d$_6$) δ 9.65 (br s, 1H), 8.10 (br s, 3H), 3.23-3.21 (m, 2H), 2.78-2.76 (m, 2H), 1.55-1.54 (m, 4H).

Example 96: Preparation of tert-butyl (2-oxo-2-((2,2,2-trifluoroethyl)amino)ethyl)carbamate (C362)

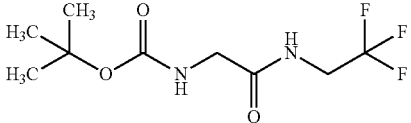 [SMILES: CC(C)(C)OC(=O)NCC(=O)NCC(F)(F)F]

To a solution of (tert-butoxycarbonyl)glycine (3 g, 17.1 mmol) in ethyl acetate (25 mL) were added sequentially 2,2,2-trifluoroethan-1-amine (2.55 g, 18.8 mmol), 2,4,6-tripropyl-1,3,5,2,4,6-trioxatriphosphinane 2,4,6-trioxide (50% solution in ethyl acetate; 22 mL, 68.5 mmol), and pyridine (4.4 mL, 54.8 mmol). The reaction mixture was stirred at room temperature for 16 hours, then poured into water and extracted with ethyl acetate (2×50 mL). The organic layer was dried over anhydrous Na$_2$SO$_4$, filtered and concentrated under reduced pressure to afford the title compound as an off-white solid (3 g), which was used in the next step without purification and analysis.

The following compounds were prepared in like manner to the procedure outlined in Example 96:

tert-Butyl (3-oxo-3-((2,2,2-trifluoroethyl)amino)propyl)carbamate (C363)

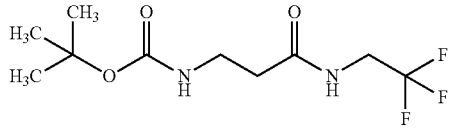 [SMILES: CC(C)(C)OC(=O)NCCC(=O)NCC(F)(F)F]

Isolated as an off-white solid (2.9 g). The product was used in the next step without purification and analysis.

tert-Butyl (4-oxo-4-((2,2,2-trifluoroethyl)amino)butyl)carbamate (C364)

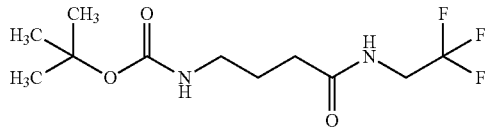 [SMILES: CC(C)(C)OC(=O)NCCCC(=O)NCC(F)(F)F]

Isolated as an off-white solid (2.9 g). The product was used in the next step without purification: ¹H NMR (300 MHz, DMSO-d₆) δ 8.49-8.45 (m, 1H), 6.83-6.79 (m, 1H), 3.93-3.81 (m, 2H), 2.89 (dd, J=6.0, 13.2 Hz, 2H), 2.16-2.11 (m, 2H), 1.64-1.54 (m, 2H), 1.37 (s, 9H).

tert-Butyl (2-oxo-2-((3,3,3-trifluoropropyl)amino)ethyl)carbamate (C365)

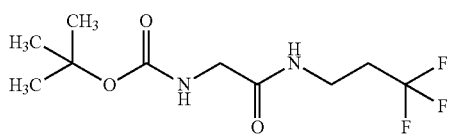 [SMILES: CC(C)(C)OC(=O)NCC(=O)NCCC(F)(F)F]

Isolated as an off-white solid (2.8 g). The product was used in the next step without purification: ¹H NMR (300 MHz, DMSO-d₆) δ 8.00-7.98 (m, 1H), 7.00-6.96 (m, 1H), 3.50-3.25 (m, 4H), 2.50-2.34 (m, 2H), 1.38 (s, 9H).

tert-Butyl (3-oxo-3-((3,3,3-trifluoropropyl)amino)propyl)carbamate (C366)

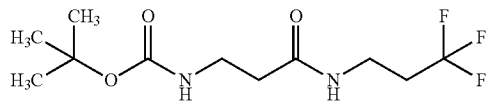 [SMILES: CC(C)(C)OC(=O)NCCC(=O)NCCC(F)(F)F]

Isolated as an off-white solid (3.2 g). The product was used in the next step without purification: ¹H NMR (300 MHz, DMSO-d₆) δ 8.11-8.07 (m, 1H), 6.78-6.74 (m, 1H), 3.29-3.22 (m, 2H), 3.14-3.08 (m, 2H), 2.51-2.19 (m, 4H), 1.37 (s, 9H).

tert-Butyl (4-oxo-4-((3,3,3-trifluoropropyl)amino)butyl)carbamate (C367)

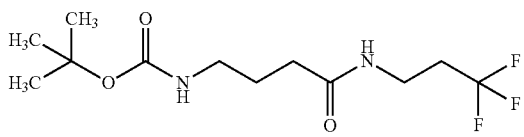 [SMILES: CC(C)(C)OC(=O)NCCCC(=O)NCCC(F)(F)F]

Isolated as an off-white solid (3.8 g, crude). The product was used in the next step without purification: ¹H NMR (300 MHz, DMSO-d₆) δ 8.05-8.01 (m, 1H), 6.83-6.79 (m, 1H), 3.29-3.22 (m, 2H), 2.91-2.85 (m, 2H), 2.45-2.33 (m, 2H), 2.06-1.99 (m, 2H), 1.62-1.52 (m, 2H), 1.37 (s, 9H).

Example 97: Preparation of tert-butyl (2-(2,2,2-trifluoroacetamido)ethyl)carbamate (C368)

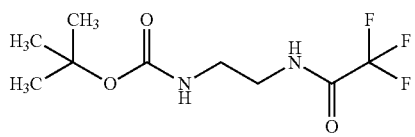 [SMILES: CC(C)(C)OC(=O)NCCNC(=O)C(F)(F)F]

To a solution of tert-butyl (2-aminoethyl)carbamate (3 g, 18.8 mmol) in tetrahydrofuran (25 mL) was added ethyl trifluoroacetate (2.7 g, 18.8 mmol), and the reaction mixture was stirred at room temperature for 16 hours. The reaction mixture was concentrated under reduced pressure. The title compound was isolated as an off-white solid (2.8 g), which was used in the next step without any purification: ESIMS m/z 257.40 ([M+H]⁺).

The following compounds were prepared in like manner to the procedure outlined in Example 97:

tert-Butyl (3-(2,2,2-trifluoroacetamido)propyl)carbamate (C369)

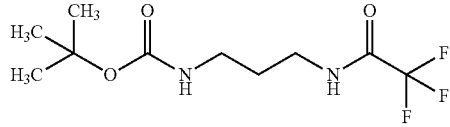 [SMILES: CC(C)(C)OC(=O)NCCCNC(=O)C(F)(F)F]

Isolated as an off-white solid (3.0 g). The product was used in the next step without purification: ESIMS m/z 271.40 ([M+H]⁺).

tert-Butyl (4-(2,2,2-trifluoroacetamido)butyl)carbamate (C370)

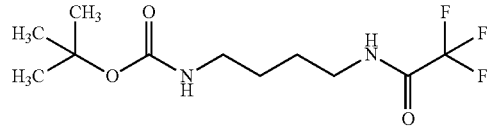 [SMILES: CC(C)(C)OC(=O)NCCCCNC(=O)C(F)(F)F]

Isolated as an off-white solid (2.8 g). The product was used in the next step without purification: ESIMS m/z 285.41 ([M+H]⁺).

tert-Butyl (2-(2,2,3,3,3-pentafluoropropanamido)ethyl)carbamate (C371)

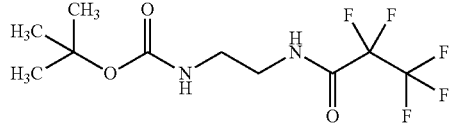 [SMILES: CC(C)(C)OC(=O)NCCNC(=O)C(F)(F)C(F)(F)F]

Isolated as an off-white solid (3.8 g). The product was used in the next step without purification: ESIMS m/z 307.37 ([M+H]⁺).

tert-Butyl (3-(2,2,3,3,3-pentafluoropropanamido)propyl)carbamate (C372)

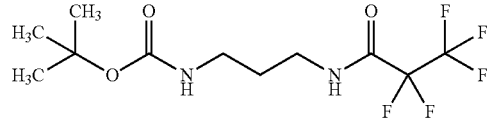 [SMILES: CC(C)(C)OC(=O)NCCCNC(=O)C(F)(F)C(F)(F)F]

Isolated as an off-white solid (4.3 g). The product was used in the next step without purification and analysis.

tert-Butyl (4-(2,2,3,3,3-pentafluoropropanamido)butyl)carbamate (C373)

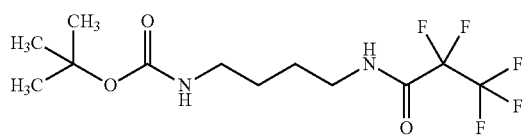 [SMILES: CC(C)(C)OC(=O)NCCCCNC(=O)C(F)(F)C(F)(F)F]

Isolated as an off-white solid (2.7 g). The product was used in the next step without purification and analysis.

Example 98: Preparation of 5-amino-2-chloro-3-fluorobenzoic acid (C196)

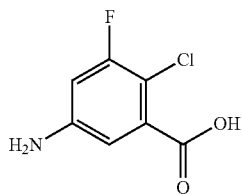 [SMILES: Nc1cc(F)c(Cl)c(C(=O)O)c1]

To a solution of 2-chloro-3-fluoro-5-nitrobenzoic acid (C206; 0.25 g, 1.14 mmol) in ethyl acetate (20 mL) was added 10% palladium on carbon (0.07 g), and the reaction mixture was stirred under a hydrogen atmosphere (20 pounds per square inch (psi)) for 16 hours. The reaction mixture was filtered through a pad of Celite® and washed with ethyl acetate, and the filtrate was concentrated under reduced pressure. The unpurified product was triturated with n-pentane. The title compound was isolated as an off-white solid (0.18 g, 82%): $^1$H NMR (300 MHz, DMSO-d$_6$) δ 13.24 (br s, 1H), 6.82-6.81 (m, 1H), 6.61 (dd, J=2.7, 12.0 Hz, 1H), 5.80 (br s, 2H); ESIMS m/z 189.95 ([M+H]$^+$).

Example 99: Preparation of N-allyl-N-(3-amino-2,6-difluorophenyl)-2,2-difluoroacetamide (C375)

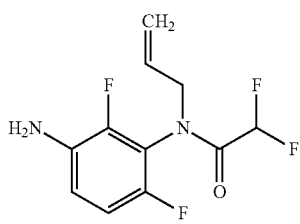

Anhydrous tin chloride (0.62 g, 3.25 mmol) was added portionwise to a stirred solution of N-allyl-N-(2,6-difluoro-3-nitrophenyl)-2,2-difluoroacetamide (C247; 0.19 g, 0.65 mmol), in 1:1 methanol-dichloromethane (10 mL) at 5° C. The resulting yellow solution was stirred at 0-5° C. for 2 hours and for 13 hours at 24° C. The reaction mixture was concentrated under vacuum on a rotary evaporator. Purification by silica gel flash chromatography using 0-60% ethyl acetate in hexanes as eluent afforded the title compound as a gold oil (0.15 g, 83%): $^1$H NMR (300 MHz, CDCl$_3$) δ 6.96-6.82 (m, 2H), 6.06-5.62 (m, 2H), 5.23-5.07 (m, 2H), 4.33 (h, J=7.6, 7.0 Hz, 2H), 3.61 (s, 2H); ESIMS m/z 263 ([M+H]$^+$).

The following compounds were prepared in like manner to the procedure outlined in Example 99:

tert-Butyl (3-amino-2,6-difluorophenyl)(prop-2-yn-1-yl)carbamate (C376)

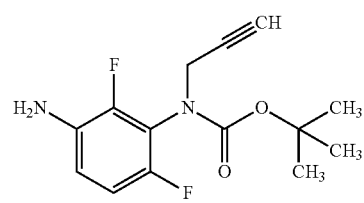

Isolated as a tan solid (0.151 g, 42%): $^1$H NMR (400 MHz, CDCl$_3$) δ 6.86-6.59 (m, 2H), 4.47-4.26 (m, 2H), 3.62 (s, 2H), 2.17 (dt, J=18.7, 2.5 Hz, 1H), 1.55 (s, 9H); ESIMS m/z 283 ([M+H]$^+$).

Example 100: Preparation of tert-butyl (2,6-difluoro-3-nitrophenyl)carbamate (C377)

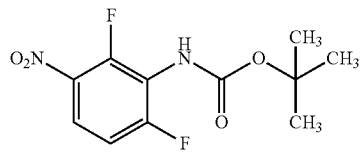 [SMILES: CC(C)(C)OC(=O)Nc1c(F)ccc([N+](=O)[O-])c1F]

To a solution of tert-butyl-N-((tert-butoxy)carbonyl)-N-(2,6-difluoro-3-nitrophenyl)carbamate (C190) (2.60 g, 6.60 mmol) in ethyl acetate (66 mL) was added trifluoroacetic acid (7.60 g, 66.0 mmol). The reaction mixture was stirred at room temperature for 5 days. Additional trifluoroacetic acid (6.02 g, 52.3 mmol) was added, and the reaction mixture was stirred for an additional 5 days. The reaction mixture was transferred to a separatory funnel and washed successively with saturated aqueous sodium bicarbonate solution until the pH of the organic layer was >3. The organic layer was then washed with brine, passed through a phase separator to dry and concentrated. Purification by column chromatography using 0 to 20% ethyl acetate/hexanes as eluent afforded the title compound as a light yellow solid (1.32 g, 73%): $^1$H NMR (400 MHz, DMSO-d$_6$) δ 9.28 (s, 1H), 8.15 (ddd, J=9.5, 8.3, 5.5 Hz, 1H), 7.43 (td, J=9.2, 1.9 Hz, 1H), 1.45 (s, 9H); $^{19}$F NMR (376 MHz, DMSO-d$_6$) δ −106.41, −121.41; ESIMS m/z 273 ([M−H]$^-$).

Example 101: Preparation of 2-chloro-N-(2,2-difluoropropyl)-3-fluoro-5-nitrobenzamide (C378)

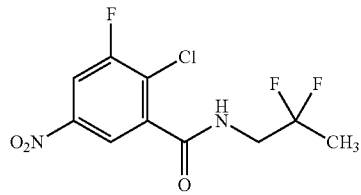 [SMILES: CC(F)(F)CNC(=O)c1cc([N+](=O)[O-])cc(F)c1Cl]

To a solution of 2-chloro-3-fluoro-5-nitrobenzoic acid (C206; 0.5 g, 2.28 mmol) in ethyl acetate (15 mL) were added 2,2-difluoropropan-1-amine (0.3 g, 2.28 mmol), 2,4,6-tripropyl-1,3,5,2,4,6-trioxatriphosphinane 2,4,6-trioxide [50% solution in ethyl acetate] (2.7 mL, 9.13 mmol), pyridine (0.92 mL, 11.41 mmol). The reaction mixture was stirred at room temperature for 16 hours. The reaction mixture was diluted with water and extracted with ethyl acetate (2×20 mL). The organic layer was dried over anhydrous $Na_2SO_4$, filtered and concentrated under reduced pressure. Purification by column chromatography (silica gel 100-200 mesh) eluting with 15-20% ethyl acetate in petroleum ether afforded the title compound as an off-white solid (0.35 g, 60%): $^1$H NMR (300 MHz, $CDCl_3$) δ 8.35-8.33 (m, 1H), 8.13 (dd, J=2.7, 7.8 Hz, 1H), 6.44-6.41 (m, 1H), 3.97-3.85 (m, 2H), 1.74 (t, J=18.6 Hz, 3H); ESIMS m/z 294.91 ([M+H]$^+$).

The following compounds were prepared in like manner to the procedure outlined in Example 101:

2-Chloro-N-(2,2-difluorobutyl)-3-fluoro-5-nitrobenzamide (C379)

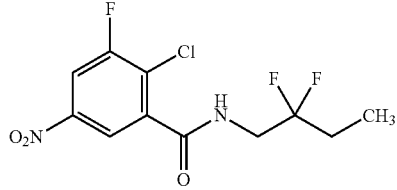 [SMILES: CCC(F)(F)CNC(=O)c1cc([N+](=O)[O-])cc(F)c1Cl]

Isolated as an off-white solid (0.4 g, 56%): $^1$H NMR (300 MHz, $CDCl_3$) δ 8.35-8.33 (m, 1H), 8.12 (dd, J=2.4, 8.1 Hz, 1H), 6.48-6.42 (m, 1H), 3.97-3.85 (m, 2H), 2.07-1.91 (m, 2H), 1.12 (t, J=7.8 Hz, 3H); ESIMS m/z 310.94 ([M+H]$^+$).

Ethyl 3-(2-chloro-3-fluoro-5-nitrobenzamido)-2,2-difluoropropanoate (C380)

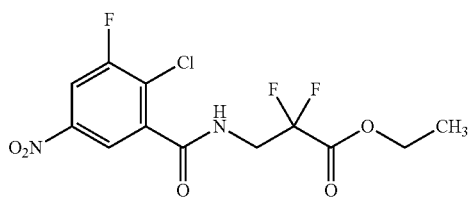 [SMILES: CCOC(=O)C(F)(F)CNC(=O)c1cc([N+](=O)[O-])cc(F)c1Cl]

Isolated as a brown liquid (0.7 g). The product was used in the next step without purification: ESIMS m/z 355.15 ([M+H]$^+$).

2-Chloro-N-(2,2-difluoro-2-phenylethyl)-3-fluoro-5-nitrobenzamide (C381)

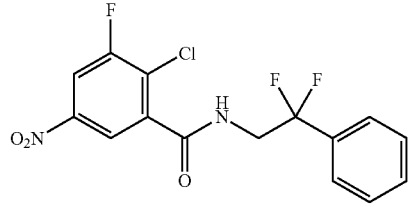 [SMILES: O=C(NCC(F)(F)c1ccccc1)c1cc([N+](=O)[O-])cc(F)c1Cl]

Isolated as an off-white solid (0.4 g, 56%): $^1$H NMR (300 MHz, $CDCl_3$) δ 8.26-8.23 (m, 1H), 8.10 (dd, J=2.4, 7.8 Hz, 1H), 7.62-7.48 (m, 5H), 6.48-6.41 (m, 1H), 4.23-4.11 (m, 2H); ESIMS m/z 359.15 ([M+H]$^+$).

2-Chloro-3-fluoro-5-nitro-N-(2-oxopropyl)benzamide (C382)

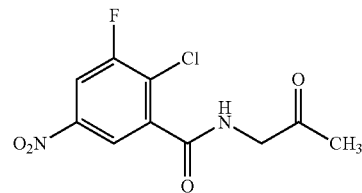 [SMILES: CC(=O)CNC(=O)c1cc([N+](=O)[O-])cc(F)c1Cl]

Isolated as an off-white solid (0.21 g, 32%): $^1$H NMR (400 MHz, $CDCl_3$) δ 8.37-8.34 (m, 1H), 8.11 (dd, J=2.4, 8.4 Hz, 1H), 7.05-7.01 (m, 1H), 4.40 (d, J=4.4 Hz, 2H), 2.31 (s, 3H); ESIMS m/z 274.94 ([M+H]$^+$).

2-Chloro-3-fluoro-5-nitro-N-(2-oxobutyl)benzamide (C383)

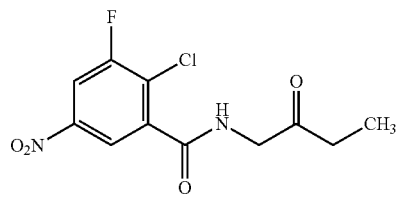 [SMILES: CCC(=O)CNC(=O)c1cc([N+](=O)[O-])cc(F)c1Cl]

Isolated as a brown liquid (0.35 g). The product was used in the next step without purification: ESIMS m/z 289.15 ([M+H]$^+$).

2-Chloro-3-fluoro-N-(4-methyl-2-oxopentyl)-5-nitrobenzamide (C384)

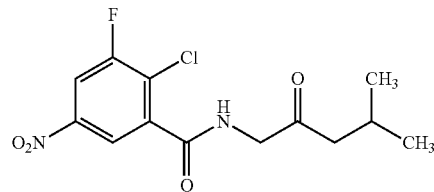 [SMILES: CC(C)CC(=O)CNC(=O)c1cc([N+](=O)[O-])cc(F)c1Cl]

Isolated as an off-white solid (0.4 g, 58%): $^1$H NMR (300 MHz, CDCl$_3$) δ 8.39-8.36 (m, 1H), 8.12 (dd, J=2.4, 7.8 Hz, 1H), 7.09-7.06 (m, 1H), 4.35 (d, J=4.2 Hz, 2H), 2.42 (d, J=6.9 Hz, 2H), 2.27-2.18 (m, 1H), 0.98 (d, J=6.6 Hz, 6H); ESIMS m/z 317.05 ([M+H]$^+$).

2-Chloro-3-fluoro-5-nitro-N-(2-oxo-2-phenylethyl)benzamide (C385)

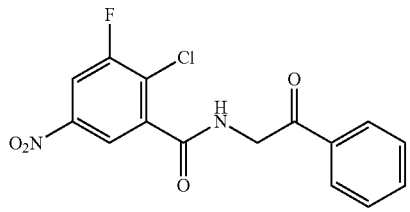 [SMILES: O=C(CNC(=O)c1cc([N+](=O)[O-])cc(F)c1Cl)c1ccccc1]

Isolated as an off-white solid (0.4 g, 56%): $^1$H NMR (300 MHz, CDCl$_3$) δ 8.43-8.43 (m, 1H), 8.13 (dd, J=2.4, 7.8 Hz, 1H), 8.03 (d, J=7.2 Hz, 2H), 7.71-7.65 (m, 1H), 7.58-7.53 (m, 2H), 7.44-7.41 (m, 1H), 5.01 (d, J=4.2 Hz, 2H); ESIMS m/z 337.17 ([M+H]$^+$).

Example 102: Preparation of 2-chloro-N-(2,2-difluoropropyl)-5-nitrobenzamide (C386)

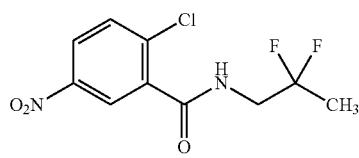 [SMILES: CC(F)(F)CNC(=O)c1cc([N+](=O)[O-])ccc1Cl]

To a solution of 2-chloro-5-nitrobenzoic acid (0.7 g, 3.5 mmol) in dichloromethane (10 mL) were added sequentially 1-[bis(dimethylamino)methylene]-1H-1,2,3-triazolo[4,5-b]pyridinium 3-oxid hexafluorophosphate (HATU; 4.0 g, 10.4 mmol), diisopropylethylamine (3 mL, 17.36 mmol) and 2,2-difluoropropan-1-amine (0.5 g, 3.8 mmol). The reaction mixture was stirred at room temperature for 16 hours. The reaction mixture was poured into water and was extracted with dichloromethane (2×20 mL). The organic layer was washed with brine, dried over Na$_2$SO$_4$ and concentrated under reduced pressure. Purification by column chromatography (silica gel 100-200 mesh) eluting with 40-50% ethyl acetate in petroleum ether afforded the title compound as an off-white solid (0.9 g, 93%): $^1$H NMR (400 MHz, CDCl$_3$) δ 8.53 (d, J=2.4 Hz, 1H), 8.24 (dd, J=2.4, 8.8 Hz, 1H), 7.63 (d, J=8.8 Hz, 1H), 6.46-6.41 (m, 1H), 3.94-3.86 (m, 2H), 1.73 (t, J=18.8 Hz, 3H); ESIMS m/z 279.12 ([M+H]$^+$).

The following compounds were prepared in like manner to the procedure outlined in Example 102:

2-Chloro-N-(2,2-difluorobutyl)-5-nitrobenzamide (C387)

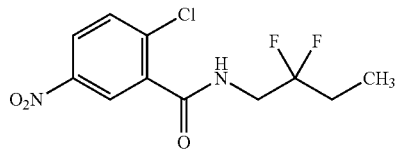 [SMILES: CCC(F)(F)CNC(=O)c1cc([N+](=O)[O-])ccc1Cl]

Isolated as an off-white solid (0.4 g, 54%): $^1$H NMR (300 MHz, CDCl$_3$) δ 8.53 (d, J=3.0 Hz, 1H), 8.24 (dd, J=3.3, 8.7 Hz, 1H), 7.62 (d, J=8.7 Hz, 1H), 6.47-6.44 (m, 1H), 3.97-3.72 (m, 2H), 2.05-1.91 (m, 2H), 1.11 (t, J=7.5 Hz, 3H).

Ethyl 3-(2-chloro-5-nitrobenzamido)-2,2-difluoropropanoate (C388)

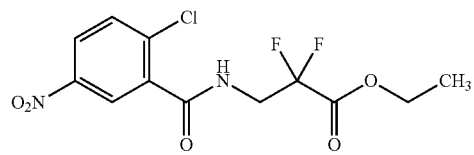 [SMILES: CCOC(=O)C(F)(F)CNC(=O)c1cc([N+](=O)[O-])ccc1Cl]

Isolated as an off-white solid (0.7 g, 85%); $^1$H NMR (300 MHz, CDCl$_3$) δ 8.52 (d, J=2.4 Hz, 1H), 8.25 (dd, J=2.7, 8.7 Hz, 1H), 7.63 (d, J=9.2 Hz, 1H), 6.54-6.52 (m, 1H), 4.38 (q, J=6.9 Hz, 2H), 4.22-4.11 (m, 2H), 1.39 (t, J=7.2 Hz, 3H); ESIMS m/z 336.98 ([M+H]$^+$).

2-Chloro-N-(2,2-difluoro-2-phenylethyl)-5-nitrobenzamide (C389)

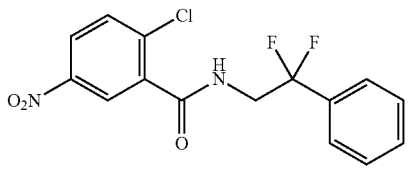 [SMILES: O=C(NCC(F)(F)c1ccccc1)c1cc([N+](=O)[O-])ccc1Cl]

Isolated as an off-white solid (0.68 g, 80%); $^1$H NMR (300 MHz, CDCl$_3$) δ 8.42 (d, J=1.2 Hz, 1H), 8.22 (dd, J=1.5, 9.3 Hz, 1H), 7.61-7.47 (m, 6H), 6.54-6.51 (m, 1H), 4.32-4.10 (m, 2H); ESIMS m/z 341.14 ([M+H]$^+$).

2-Chloro-5-nitro-N-(2-oxopropyl)benzamide (C390)

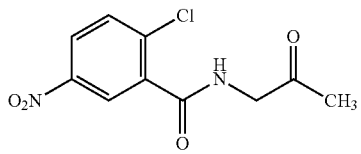

Isolated as a yellow solid (0.6 g, 50%): $^1$H NMR (300 MHz, CDCl$_3$) δ 8.53 (d, J=2.4 Hz, 1H), 8.22 (dd, J=2.1, 8.4 Hz, 1H), 7.61 (d, J=9.2 Hz, 1H), 7.09-7.06 (m, 1H), 4.39 (d, J=4.5 Hz, 2H), 2.28 (s, 3H); ESIMS m/z 257.01 ([M+H]$^+$).

2-Chloro-5-nitro-N-(2-oxobutyl)benzamide (C391)

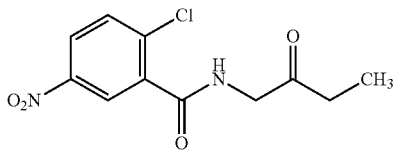 [SMILES: CCC(=O)CNC(=O)c1cc([N+](=O)[O-])ccc1Cl]

Isolated as an off-white solid (0.6 g, 38%): ESIMS m/z 271.01 ([M+H]$^+$).

2-Chloro-N-(4-methyl-2-oxopentyl)-5-nitrobenzamide (C392)

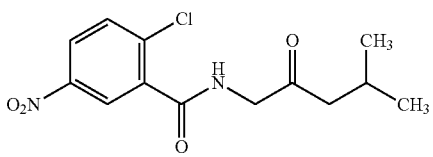

Isolated as a yellow solid (1.2 g, 81%): $^1$H NMR (400 MHz, DMSO-d$_6$) δ 7.06 (d, J=8.4 Hz, 1H), 6.66 (d, J=2.4 Hz, 1H), 6.50 (dd, J=2.8, 8.4 Hz, 1H), 3.97 (d, J=6.0 Hz, 2H), 2.36 (d, J=6.8 Hz, 2H) 2.09-2.00 (m, 1H), 0.88 (d, J=6.9 Hz, 6H).

2-Chloro-5-nitro-N-(2-oxo-2-phenylethyl)benzamide (C393)

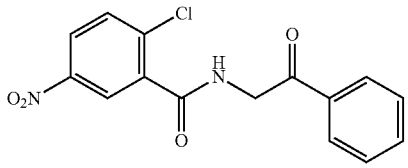 [SMILES: O=C(CNC(=O)c1cc([N+](=O)[O-])ccc1Cl)c1ccccc1]

Isolated as an off-white solid (0.6 g, 50%): ESIMS m/z 319.21 ([M+H]$^+$).

Example 103: Preparative-SFC Separation of 5-((1S,3S)-2,2-dichloro-3-(3,5-dichlorophenyl)cyclopropane-1-carboxamido)-2-fluoro-N-(4-fluorophenyl)benzamide (F1373) and 5-((1R,3R)-2,2-dichloro-3-(3,5-dichlorophenyl)cyclopropane-1-carboxamido)-2-fluoro-N-(4-fluorophenyl)benzamide (F1374)

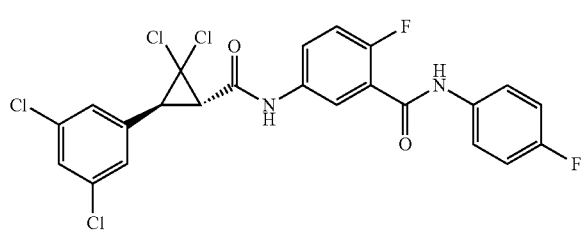

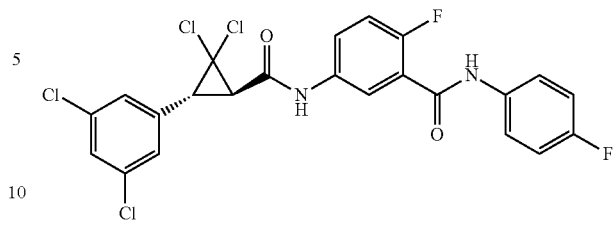

Racemic 5-((trans)-2,2-dichloro-3-(3,5-dichlorophenyl)cyclopropane-1-carboxamido)-2-fluoro-N-(4-fluorophenyl)benzamide (U.S. Patent Application Publication US20160304522A1 (F129)) was separated by preparative-SFC utilizing the following conditions: IC column (20 mm×250 mm), 5 μm; 35/65 MeOH (0.2% diethylamine)/CO$_2$, 40 g/min to give 5-((1S,3S)-2,2-dichloro-3-(3,5-dichlorophenyl)cyclopropane-1-carboxamido)-2-fluoro-N-(4-fluorophenyl)benzamide (F1373) (2$^{nd}$ eluting enantiomer, 100% ee) and 5-((1R,3R)-2,2-dichloro-3-(3,5-dichlorophenyl)cyclopropane-1-carboxamido)-2-fluoro-N-(4-fluorophenyl)benzamide (F1374) (1$^{st}$ eluting enantiomer, 98.5% ee).

Example 104: Preparative-HPLC Separation of 5-((1R,3R)-2,2-dichloro-3-(3,5-dichlorophenyl)cyclopropane-1-carboxamido)-N-(2,4-difluorophenyl)-2-fluorobenzamide (F1375) and 5-((1S,3S)-2,2-dichloro-3-(3,5-dichlorophenyl)cyclopropane-1-carboxamido)-N-(2,4-difluorophenyl)-2-fluorobenzamide (F1376)

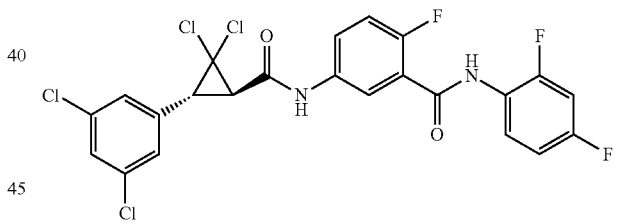

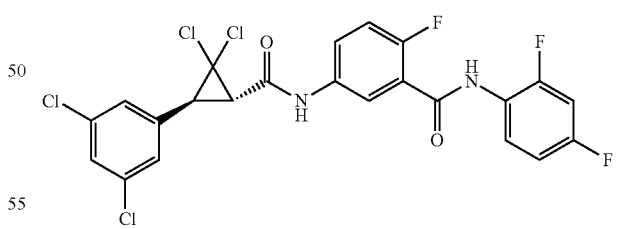

Racemic 5-((trans)-2,2-dichloro-3-(3,5-dichlorophenyl)cyclopropane-1-carboxamido)-N-(2,4-difluorophenyl)-2-fluorobenzamide (U.S. Patent Application Publication US20160304522A1 (F61)) was separated by preparative HPLC utilizing the following conditions: OJ-H column (20 mm×250 mm), 5 μm; 50/50 isopropanol (0.2% diethylamine)/hexane, 4.0 mL/min to give 5-((1R,3R)-2,2-dichloro-3-(3,5-dichlorophenyl)cyclopropane-1-carboxamido)-N-(2,4-difluorophenyl)-2-fluorobenzamide (F1375) (1$^{st}$ eluting enantiomer, 96.2% ee) and 5-((1S,3S)-2,2-dichloro-3-(3,5- dichlorophenyl)cyclopropane-1-carboxamido)-N-(2,4-difluorophenyl)-2-fluorobenzamide (F1376) ($2^{nd}$ eluting enantiomer, 96.0% ee).

Example 105: Preparative-SFC Separation of 2-chloro-5-((1R,3R)-2,2-dichloro-3-(3,5-dichlorophenyl)cyclopropane-1-carboxamido)-N-(2,4,6-trifluorophenyl)benzamide (F1377) and 2-chloro-5-((1S,3S)-2,2-dichloro-3-(3,5-dichlorophenyl) cyclopropane-1-carboxamido)-N-(2,4,6-trifluorophenyl)benzamide (F1378)

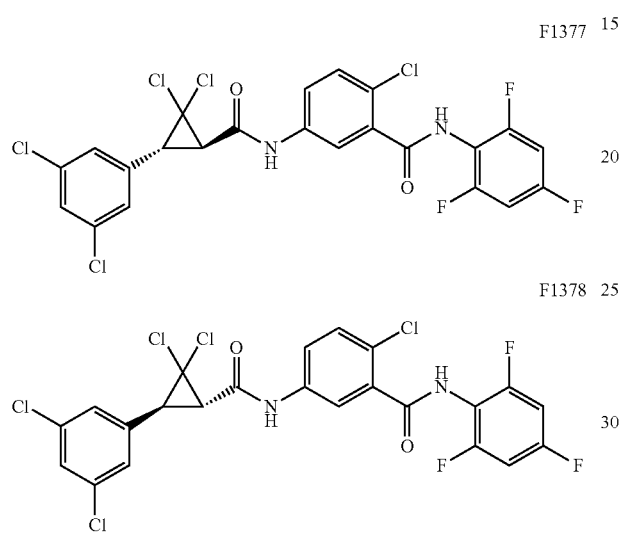

Racemic 2-Chloro-5-((trans)-2,2-dichloro-3-(3,5-dichlorophenyl)cyclopropane-1-carboxamido)-N-(2,4,6-trifluorophenyl)benzamide (U.S. Patent Application Publication US20160304522A1 (F24)) was separated by preparative-SFC utilizing the following conditions: IC column (20 mm×250 mm), 5 μm; 35/65 MeOH (0.2% diethylamine)/ $CO_2$, 40 g/min to give 2-chloro-5-((1R,3R)-2,2-dichloro-3-(3,5-dichlorophenyl)cyclopropane-1-carboxamido)-N-(2,4,6-trifluorophenyl)benzamide (F1377) ($1^{st}$ eluting enantiomer, 100% ee) and 2-chloro-5-((1S,3S)-2,2-dichloro-3-(3,5-dichlorophenyl)cyclopropane-1-carboxamido)-N-(2,4,6-trifluorophenyl)benzamide (F1378) ($2^{nd}$ eluting enantiomer, 100% ee).

It is recognized that some reagents and reaction conditions may not be compatible with certain functionalities that may be present in certain molecules of Formula One or certain molecules used in the preparation of certain molecules of Formula One. In such cases, it may be necessary to employ standard protection and deprotection protocols comprehensively reported in the literature and well known to a person skilled in the art. In addition, in some cases it may be necessary to perform further routine synthetic steps not described herein to complete the synthesis of desired molecules. A person skilled in the art will also recognize that it may be possible to achieve the synthesis of desired molecules by performing some of the steps of the synthetic routes in a different order to that described. A person skilled in the art will also recognize that it may be possible to perform standard functional group interconversions or substitution reactions on desired molecules to introduce or modify substituents.

Biological Assays

The following bioassays against Beet Armyworm (*Spodoptera exigua*), Cabbage Looper (*Trichoplusia ni*), and Yellow Fever Mosquito (*Aedes aegypti*), are included herein due to the damage they inflict. Furthermore, the Beet Armyworm and Cabbage Looper are two good indicator species for a broad range of chewing pests. Additionally, the Green Peach Aphid is a good indicator species for a broad range of sap-feeding pests. The results with these four indicator species along with the Yellow Fever Mosquito show the broad usefulness of the molecules of Formula One in controlling pests in Phyla Arthropoda, Mollusca, and Nematoda (Drewes et al.)

Example A: Bioassays on Beet Armyworm (*Spodoptera exigua*, LAPHEG) ("BAW") and Cabbage Looper (*Trichoplusia ni*, TRIPNI) ("CL")

Beet armyworm is a serious pest of economic concern for alfalfa, asparagus, beets, citrus, corn, cotton, onions, peas, peppers, potatoes, soybeans, sugar beets, sunflowers, tobacco, and tomatoes, among other crops. It is native to Southeast Asia but is now found in Africa, Australia, Japan, North America, and Southern Europe. The larvae may feed in large swarms causing devastating crop losses. It is known to be resistant to several pesticides.

Cabbage looper is a serious pest found throughout the world. It attacks alfalfa, beans, beets, broccoli, Brussel sprouts, cabbage, cantaloupe, cauliflower, celery, collards, cotton, cucumbers, eggplant, kale, lettuce, melons, mustard, parsley, peas, peppers, potatoes, soybeans, spinach, squash, tomatoes, turnips, and watermelons, among other crops. This species is very destructive to plants due to its voracious appetite. The larvae consume three times their weight in food daily. The feeding sites are marked by large accumulations of sticky, wet, fecal material, which may contribute to higher disease pressure thereby causing secondary problems on the plants in the site. It is known to be resistant to several pesticides.

Consequently, because of the above factors control of these pests is important. Furthermore, molecules that control these pests (BAW and CL), which are known as chewing pests, will be useful in controlling other pests that chew on plants.

Certain molecules disclosed in this document were tested against BAW and CL using procedures described in the following examples. In the reporting of the results, the "BAW & CL Rating Table" was used (See Table Section).

Bioassays on BAW

Bioassays on BAW were conducted using a 128-well diet tray assay. One to five second instar BAW larvae were placed in each well (3 mL) of the diet tray that had been previously filled with 1 mL of artificial diet to which 50 μg/$cm^2$ of the test molecule (dissolved in 50 μL of 90:10 acetone-water mixture) had been applied (to each of eight wells) and then allowed to dry. Trays were covered with a clear self-adhesive cover, vented to allow gas exchange, and held at 25° C., 14:10 light-dark for five to seven days. Percent mortality was recorded for the larvae in each well; activity in the eight wells was then averaged. The results are indicated in the table entitled "Table ABC: Biological Results" (See Table Section).

Bioassays on CL

Bioassays on CL were conducted using a 128-well diet tray assay. One to five second instar CL larvae were placed in each well (3 mL) of the diet tray that had been previously filled with 1 mL of artificial diet to which 50 μg/$cm^2$ of the test molecule (dissolved in 50 μL of 90:10 acetone-water mixture) had been applied (to each of eight wells) and then allowed to dry. Trays were covered with a clear self-adhesive cover, vented to allow gas exchange, and held at 25° C., 14:10 light-dark for five to seven days. Percent mortality was recorded for the larvae in each well; activity in the eight wells was then averaged. The results are indicated in the table entitled "Table ABC: Biological Results" (See Table Section).

Example B: Bioassays on Green Peach Aphid (*Myzus persicae*, MYZUPE) ("GPA")

GPA is the most significant aphid pest of peach trees, causing decreased growth, shriveling of the leaves, and the death of various tissues. It is also hazardous because it acts as a vector for the transport of plant viruses, such as potato virus Y and potato leafroll virus to members of the nightshade/potato family Solanaceae, and various mosaic viruses to many other food crops. GPA attacks such plants as broccoli, burdock, cabbage, carrot, cauliflower, daikon, eggplant, green beans, lettuce, macadamia, papaya, peppers, sweet potatoes, tomatoes, watercress, and zucchini, among other crops. GPA also attacks many ornamental crops such as carnation, chrysanthemum, flowering white cabbage, poinsettia, and roses. GPA has developed resistance to many pesticides. Currently, it is a pest that has the third largest number of reported cases of insect resistance (Sparks et al.). Consequently, because of the above factors control of this pest is important. Furthermore, molecules that control this pest (GPA), which is known as a sap-feeding pest, are useful in controlling other pests that feed on the sap from plants.

Certain molecules disclosed in this document were tested against GPA using procedures described in the following example. In the reporting of the results, the "GPA & YFM Rating Table" was used (See Table Section).

Cabbage seedlings grown in 3-inch pots, with 2-3 small (3-5 cm) true leaves, were used as test substrate. The seedlings were infested with 20-50 GPA (wingless adult and nymph stages) one day prior to chemical application. Four pots with individual seedlings were used for each treatment. Test molecules (2 mg) were dissolved in 2 mL of acetone/methanol (1:1) solvent, forming stock solutions of 1000 ppm test molecule. The stock solutions were diluted 5× with 0.025% Tween 20 in water to obtain the solution at 200 ppm test molecule. A hand-held aspirator-type sprayer was used for spraying a solution to both sides of cabbage leaves until runoff. Reference plants (solvent check) were sprayed with the diluent only containing 20% by volume of acetone/methanol (1:1) solvent. Treated plants were held in a holding room for three days at approximately 25° C. and ambient relative humidity (RH) prior to grading. Evaluation was conducted by counting the number of live aphids per plant under a microscope. Percent control was measured using Abbott's correction formula (W. S. Abbott, "A Method of Computing the Effectiveness of an Insecticide" J. Econ. Entomol. 18 (1925), pp. 265-267) as follows. Corrected % Control=100*(X−Y)/X where X=No. of live aphids on solvent check plants and Y=No. of live aphids on treated plants. The results are indicated in the table entitled "Table ABC: Biological Results" (See Table Section).

Example C: Bioassays on Yellow Fever Mosquito (*Aedes aegypti*, AEDSAE) ("YFM")

YFM prefers to feed on humans during the daytime and is most frequently found in or near human habitations. YFM is a vector for transmitting several diseases. It is a mosquito that can spread the dengue fever and yellow fever viruses. Yellow fever is the second most dangerous mosquito-borne disease after malaria. Yellow fever is an acute viral hemorrhagic disease and up to 50% of severely affected persons without treatment will die from yellow fever. There are an estimated 200,000 cases of yellow fever, causing 30,000 deaths worldwide each year. Dengue fever is a nasty, viral disease; it is sometimes called "breakbone fever" or "breakheart fever" because of the intense pain it can produce. Dengue fever kills about 20,000 people annually. Consequently, because of the above factors control of this pest is important. Furthermore, molecules that control this pest (YFM), which is known as a sucking pest, are useful in controlling other pests that cause human and animal suffering.

Certain molecules disclosed in this document were tested against YFM using procedures described in the following paragraph. In the reporting of the results, the "GPA & YFM Rating Table" was used (See Table Section).

Master plates containing 400 µg of a molecule dissolved in 100 µL of dimethyl sulfoxide (DMSO) (equivalent to a 4000 ppm solution) are used. A master plate of assembled molecules contains 15 µL per well. To this plate, 135 µL of a 90:10 water/acetone mixture is added to each well. A robot (Biomek® NXP Laboratory Automation Workstation) is programmed to dispense 15 µL aspirations from the master plate into an empty 96-well shallow plate ("daughter" plate). There are 6 reps ("daughter" plates) created per master. The created "daughter" plates are then immediately infested with YFM larvae.

The day before plates are to be treated, mosquito eggs are placed in Millipore water containing liver powder to begin hatching (4 g into 400 mL). After the "daughter" plates are created using the robot, they are infested with 220 µL of the liver powder/larval mosquito mixture (about 1 day-old larvae). After plates are infested with mosquito larvae, a non-evaporative lid is used to cover the plate to reduce drying. Plates are held at room temperature for 3 days prior to grading. After 3 days, each well is observed and scored based on mortality. The results are indicated in the table entitled "Table ABC: Biological Results" (See Table Section).

Agriculturally Acceptable Acid Addition Salts, Salt Derivatives, Solvates, Ester Derivatives, Polymorphs, Isotopes, and Radionuclides Molecules of Formula One may be formulated into agriculturally acceptable acid addition salts. By way of a non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxyl-methanesulfonic, and hydroxyethanesulfonic acids. Additionally, by way of a non-limiting example, an acid function can form salts including those derived from alkali or alkaline earth metals and those derived from ammonia and amines. Examples of preferred cations include sodium, potassium, and magnesium.

Molecules of Formula One may be formulated into salt derivatives. By way of a non-limiting example, a salt derivative may be prepared by contacting a free base with a sufficient amount of the desired acid to produce a salt. A free base may be regenerated by treating the salt with a suitable dilute aqueous base solution such as dilute aqueous sodium hydroxide, potassium carbonate, ammonia, and sodium bicarbonate. As an example, in many cases, a pesticide, such as 2,4-D, is made more water-soluble by converting it to its dimethylamine salt.

Molecules of Formula One may be formulated into stable complexes with a solvent, such that the complex remains intact after the non-complexed solvent is removed. These complexes are often referred to as "solvates." However, it is particularly desirable to form stable hydrates with water as the solvent.

Molecules of Formula One containing an acid functionality may be made into ester derivatives. These ester derivatives can then be applied in the same manner as the molecules disclosed in this document are applied.

Molecules of Formula One may be made as various crystal polymorphs. Polymorphism is important in the development of agrochemicals since different crystal polymorphs or structures of the same molecule can have vastly different physical properties and biological performances.

Molecules of Formula One may be made with different isotopes. Of particular importance are molecules having $^2H$ (also known as deuterium) or $^3H$ (also known as tritium) in place of $^1H$. Molecules of Formula One may be made with different radionuclides. Of particular importance are molecules having $^{14}C$ (also known as radiocarbon). Molecules of Formula One having deuterium, tritium, or $^{14}C$ may be used in biological studies allowing tracing in chemical and physiological processes and half-life studies, as well as, MoA studies.

Combinations

In another embodiment of this invention, molecules of Formula One may be used in combination (such as, in a compositional mixture, or a simultaneous or sequential application) with one or more active ingredients.

In another embodiment of this invention, molecules of Formula One may be used in combination (such as, in a compositional mixture, or a simultaneous or sequential application) with one or more active ingredients each having a MoA that is the same as, similar to, but more likely—different from, the MoA of the molecules of Formula One.

In another embodiment, molecules of Formula One may be used in combination (such as, in a compositional mixture, or a simultaneous or sequential application) with one or more molecules having acaricidal, algicidal, avicidal, bactericidal, fungicidal, herbicidal, insecticidal, molluscicidal, nematicidal, rodenticidal, and/or virucidal properties.

In another embodiment, the molecules of Formula One may be used in combination (such as, in a compositional mixture, or a simultaneous or sequential application) with one or more molecules that are antifeedants, bird repellents, chemosterilants, herbicide safeness, insect attractants, insect repellents, mammal repellents, mating disrupters, plant activators, plant growth regulators, and/or synergists.

In another embodiment, molecules of Formula One may also be used in combination (such as in a compositional mixture, or a simultaneous or sequential application) with one or more biopesticides.

In another embodiment, in a pesticidal composition combinations of a molecule of Formula One and an active ingredient may be used in a wide variety of weight ratios. For example, in a two-component mixture, the weight ratio of a molecule of Formula One to an active ingredient, the weight ratios in Table B may be used. However, in general, weight ratios less than about 10:1 to about 1:10 are preferred. It is also preferred sometimes to use a three, four, five, six, seven, or more, component mixture comprising a molecule of Formula One and an additional two or more active ingredients.

Weight ratios of a molecule of Formula One to an active ingredient may also be depicted as X:Y; wherein X is the parts by weight of a molecule of Formula One and Y is the parts by weight of active ingredient. The numerical range of the parts by weight for X is $0<X\leq100$ and the parts by weight for Y is $0<Y\leq100$ and is shown graphically in TABLE C. By way of non-limiting example, the weight ratio of a molecule of Formula One to an active ingredient may be 20:1.

Ranges of weight ratios of a molecule of Formula One to an active ingredient may be depicted as $X_1:Y_1$ to $X_2:Y_2$, wherein X and Y are defined as above.

In one embodiment, the range of weight ratios may be $X_1:Y_1$ to $X_2:Y_2$, wherein $X_1>Y_1$ and $X_2<Y_2$. By way of non-limiting example, the range of a weight ratio of a molecule of Formula One to an active ingredient may be between 3:1 and 1:3, inclusive of the endpoints.

In another embodiment, the range of weight ratios may be $X_1:Y_1$ to $X_2:Y_2$, wherein $X_1>Y_1$ and $X_2>Y_2$. By way of non-limiting example, the range of weight ratio of a molecule of Formula One to an active ingredient may be between 15:1 and 3:1, inclusive of the endpoints.

In another embodiment, the range of weight ratios may be $X_1:Y_1$ to $X_2:Y_2$, wherein $X_1<Y_1$ and $X_2<Y_2$. By way of non-limiting example, the range of weight ratios of a molecule of Formula One to an active ingredient may be between about 1:3 and about 1:20, inclusive of the endpoints.

Formulations

A pesticide is many times not suitable for application in its pure form. It is usually necessary to acid other substances so that the pesticide may be used at the required concentration and in an appropriate form, permitting ease of application, handling, transportation, storage, and maximum pesticide activity. Thus, pesticides are formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra-low volume solutions.

Pesticides are applied most often as aqueous suspensions or emulsions prepared from concentrated formulations of such pesticides. Such water-soluble, water-suspendable, or emulsifiable formulations are either solids, usually known as wettable powders, water dispersible granules, liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually selected from among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and non-ionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are selected from conventional anionic and non-ionic surfactants.

Aqueous suspensions comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums may, also be added to increase the density and viscosity of the aqueous carrier. It is often most effective to grind and mix the pesticide at the same time by preparing the aqueous mixture and homogenizing it in an implement such as a sand mill, ball mill, or piston-type homogenizer. The pesticide in suspension might be microencapsulated in plastic polymer.

Oil dispersions (OD) comprise suspensions of organic solvent-insoluble pesticides finely dispersed in a mixture of organic solvent and emulsifiers at a concentration in the range from about 2% to about 50% by weight. One or more pesticide might be dissolved in the organic solvent. Useful organic solvents include aromatics, especially xylenes and petroleum fractions, especially the high-boiling naphthalenic and olefinic portions of petroleum such as heavy aromatic naphtha. Other solvents may include vegetable oils, seed oils, and esters of vegetable and seed oils. Suitable emulsifiers for oil dispersions are selected from conventional anionic and non-ionic surfactants. Thickeners or gelling agents are added in the formulation of oil dispersions to modify the rheology or flow properties of the liquid and to prevent separation and settling of the dispersed particles or droplets.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier, which has been pre-formed to the appropriate particle size, in the range of from about 0.5 mm to about 3 mm. Such compositions may also be formulated by making a dough or paste of the carrier and molecule, and then crushing and drying to obtain the desired granular particle size. Another form of granules is a water emulsifiable granule (EG). It is a formulation consisting of granules to be applied as a conventional oil-in-water emulsion of the active ingredient(s), either solubilized or diluted in an organic solvent, after disintegration and dissolution in water. Water emulsifiable granules comprise one or several active ingredient(s), either solubilized or diluted in a suitable organic solvent that is (are) absorbed in a water soluble polymeric shell or some other type of soluble or insoluble matrix.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. Dusts may be applied as a seed dressing or as a foliage application with a dust blower machine.

It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions, the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait, they also consume the pesticide. Baits may take the form of granules, gels, flowable powders, liquids, or solids. Baits may be used in pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Fumigants are applied to control stored product pests under gas proof sheets, in gas sealed rooms or buildings, or in special chambers.

Pesticides may be microencapsulated by suspending the pesticide particles or droplets in plastic polymers of various types. By altering, the chemistry of the polymer or by changing factors in the processing, microcapsules may be formed of various sizes, solubility, wall thicknesses, and degrees of penetrability. These factors govern the speed with which the active ingredient within is released, which in turn, affects the residual performance, speed of action, and odor of the product. The microcapsules might be formulated as suspension concentrates or water dispersible granules.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one molecule which is agriculturally active, and is individually coated with a monolamellar or oligolamellar layer comprising: (1) at least one non-ionic lipophilic surface-active agent, (2) at least one non-ionic hydrophilic surface-active agent, and (3) at least one ionic surface-active agent, wherein the globules having a mean particle diameter of less than 800 nanometers.

Other Formulation Components

Generally, when the molecules disclosed in Formula One are used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, anti-foam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulfate, sodium dioctyl sulfosuccinate, alkyl phenol ethoxylates, and aliphatic alcohol ethoxylates.

A dispersing agent is a substance that adsorbs onto the surface of particles, helps to preserve the state of dispersion of the particles, and prevents them from reaggregating. Dispersing agents are added to agrochemical formulations to facilitate dispersion and suspension during manufacture, and to ensure the particles redisperse into water in a spray tank. They are widely used in wettable powders, suspension concentrates, and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulfonates. For suspension concentrates, very good adsorption and stabilization are obtained using polyelectrolytes, such as sodium-naphthalene-sulfonate-formaldehyde-condensates.
Tristyrylphenol ethoxylate phosphate esters are also used. Non-ionics such as alkylarylethylene oxide condensates and EO-PO block copolymers are sometimes combined with avionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulfonates, sodium naphthalene sulfonate formaldehyde condensates, tristyrylphenol-ethoxylate-phosphate-esters, aliphatic alcohol ethoxylates, alkyl ethoxylates, EO-PO block copolymers, and graft copolymers.

An emulsifying agent is a substance that stabilizes a suspension of droplets of one liquid phase in another liquid phase. Without the emulsifying agent, the two liquids would separate into two immiscible liquid phases. The most commonly used emulsifier blends contain an alkylphenol or an aliphatic alcohol with twelve or more ethylene oxide units and the oil-soluble calcium salt of dodecylbenzenesulfonic acid. A range of hydrophile-lipophile balance ("HLB") values from about 8 to about 18 will normally provide good stable emulsions. Emulsion stability can sometimes be improved by the addition of a small amount of an EO-PO block copolymer surfactant.

A solubilizing agent is a surfactant that will form micelles in water at concentrations above the critical micelle concentration. The micelles are then able to dissolve or solubilize water-insoluble materials inside the hydrophobic part of the micelle. The types of surfactants usually used for solubilization are non-ionics, sorbitan monooleates, sorbitan monooleate ethoxylates, and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often non-ionics such as: alkyl ethoxylates, linear aliphatic alcohol ethoxylates, and aliphatic amine ethoxylates.

A carrier or diluent in an agricultural formulation is a material added to the pesticide to give a product of the required strength. Carriers are usually materials with high absorptive capacities, while diluents are usually materials with low absorptive capacities. Carriers and diluents are used in the formulation of dusts, wettable powders, granules, and water-dispersible granules.

Organic solvents are used mainly in the formulation of emulsifiable concentrates, oil-in-water emulsions, suspoemulsions, oil dispersions, and ultra-low volume formulations, and to a lesser extent, granular formulations. Sometimes mixtures of solvents are used. The first main groups of solvents are aliphatic paraffinic oils such as kerosene or refined paraffins. The second main group and the most common) comprises the aromatic solvents such as xylene and higher molecular weight fractions of C9 and C10 aromatic solvents. Chlorinated hydrocarbons are useful as cosolvents to prevent crystallization of pesticides when the formulation is emulsified into water. Alcohols are sometimes used as cosolvents to increase solvent power. Other solvents may include vegetable oils, seed oils, and esters of vegetable and seed oils.

Thickeners or gelling agents are used mainly in the formulation of suspension concentrates, oil dispersions, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate and oil dispersion formulations using clays and silicas. Examples of these types of materials, include, but are not limited to, montmorillonite, bentonite, magnesium aluminum silicate, and attapulgite. Water-soluble polysaccharides in water based suspension concentrates have been used as thickening-gelling agents for many years. The types of polysaccharides most commonly used are natural extracts of seeds and seaweeds or are synthetic derivatives of cellulose. Examples of these types of materials include, but are not limited to, guar gum, locust bean gum, carrageenam, alginates, methyl cellulose, sodium carboxymethyl cellulose (SCMC), and hydroxyethyl cellulose (HEC). Other types of anti-settling agents are based on modified starches, polyacrylates, polyvinyl alcohol, and polyethylene oxide. Another good anti-settling agent is xanthan gum.

Microorganisms can cause spoilage of formulated products. Therefore, preservation agents are used to eliminate or reduce their effect. Examples of such agents include, but are not limited to: propionic acid and its sodium salt, sorbic acid and its sodium or potassium salts, benzoic acid and its sodium salt, p-hydroxybenzoic acid sodium salt, methyl p-hydroxybenzoate, and 1,2-benzisothiazolin-3-one (BIT).

The presence of surfactants often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane, while the non-silicone anti-foam agents are water-insoluble oils, such as octanol and nonanol, or silica. In both cases, the function of the anti-foam agent is to displace the surfactant from the air-water interface.

"Green" agents (e.g., adjuvants, surfactants, solvents) can reduce the overall environmental footprint of crop protection formulations. Green agents are biodegradable and generally derived from natural and/or sustainable sources, e.g. plant and animal sources. Specific examples are: vegetable oils, seed oils, and esters thereof, also alkoxylated alkyl polyglucosides.

Applications

Molecules of Formula One may be applied to any locus. Particular loci to apply such molecules include loci where alfalfa, almonds, apples, barley, beans, canola, corn, cotton, crucifers, flowers, fodder species (Rye Grass, Sudan Grass, Tail Fescue, Kentucky Blue Grass, and Clover), fruits, lettuce, oats, oil seed crops, oranges, peanuts, pears, peppers, potatoes, rice, sorghum, soybeans, strawberries, sugarcane, sugarbeets, sunflowers, tobacco, tomatoes, wheat (for example, Hard Red Winter Wheat, Soft Red Winter Wheat, White Winter Wheat, Hard Red Spring Wheat, and Durum Spring Wheat), and other valuable crops are growing or the seeds thereof are going to be planted.

Molecules of Formula One may also be applied where plants, such as crops, are growing and where there are low levels (even no actual presence) of pests that can commercially damage such plants. Applying such molecules in such locus is to benefit the plants being grown in such locus. Such benefits, may include, but are not limited to: helping the plant grow a better root system; helping the plant better withstand stressful growing conditions; improving the health of a plant; improving the yield of a plant (e.g. increased biomass and/or increased content of valuable ingredients); improving the vigor of a plant (e.g. improved plant growth and/or greener leaves); improving the quality of a plant (e.g. improved content or composition of certain ingredients); and improving the tolerance to abiotic and/or biotic stress of the plant.

Molecules of Formula One may be applied with ammonium sulfate when growing various plants as this may provide additional benefits.

Molecules of Formula One may be applied on, in, or around plants genetically modified to express specialized traits, such as *Bacillus thuringiensis* (for example, Cry1Ab, Cry1Ac, Cry1Fa, Cry1A.105, Cry2Ab, Vip3A, mCry3A, Cry3Ab, Cry3Bb, Cry34Ab1/Cry35Ab1), other insecticidal toxins, or those expressing herbicide tolerance, or those with "stacked" foreign genes expressing insecticidal toxins, herbicide tolerance, nutrition-enhancement, or any other beneficial traits.

Molecules of Formula One may be applied to the foliar and/or fruiting portions of plants to control pests. Either such molecules will come in direct contact with the pest, or the pest will consume such molecules when eating the plant or while extracting sap or other nutrients from the plant.

Molecules of Formula One may also be applied to the soil, and when applied in this manner, root and stem feeding pests may be controlled. The roots may absorb such molecules thereby taking it up into the foliar portions of the plant to control above ground chewing and sap feeding pests.

Systemic movement of pesticides in plants may be utilized to control pests on one portion of the plant by applying (for example by spraying a locus) a molecule of Formula One to a different portion of the plant. For example, control of foliar-feeding insects may be achieved by drip irrigation or furrow application, by treating the soil with for example pre- or post-planting soil drench, or by treating the seeds of a plant before planting.

Molecules of Formula One may be used with baits. Generally, with baits, the baits are placed in the ground where, for example, termites can come into contact with, and/or be attracted to, the bait. Baits can also be applied to a surface of a building, (horizontal, vertical, or slant surface) where, for example, ants, termites, cockroaches, and flies, can come into contact with, and/or be attracted to, the bait.

Molecules of Formula One may be encapsulated inside, or placed on the surface of a capsule. The size of the capsules can range from nanometer size (about 100-900 nanometers in diameter) to micrometer size (about 10-900 microns in diameter).

Molecules of Formula One may be applied to eggs of pests. Because of the unique ability of the eggs of some pests to resist certain pesticides, repeated applications of such molecules may be desirable to control newly emerged larvae.

Molecules of Formula One may be applied as seed treatments. Seed treatments may be applied to all types of seeds, including those from which plants genetically modified to express specialized traits will germinate. Representative examples include those expressing proteins toxic to invertebrate pests, such as *Bacillus thuringiensis* or other insecticidal toxins, those expressing herbicide tolerance, such as "Roundup Ready" seed, or those with "stacked" foreign genes expressing insecticidal toxins, herbicide tolerance, nutrition-enhancement, drought tolerance, or any other beneficial traits. Furthermore, such seed treatments with molecules of Formula One may further enhance the ability of a plant to withstand stressful growing conditions better. This results in a healthier, more vigorous plant, which can lead to higher yields at harvest time. Generally, about 1 gram of such molecules to about 500 grams per 100,000 seeds is expected to provide good benefits, amounts from about 10 grams to about 100 grams per 100,000 seeds is expected to provide better benefits, and amounts from about 25 grams to about 75 grams per 100,000 seeds is expected to provide even better benefits. Molecules of Formula One may be applied with one or more active ingredients in a soil amendment.

Molecules of Formula One may be used for controlling endoparasites and ectoparasites in the veterinary medicine sector or in the field of non-human-animal keeping. Such molecules may be applied by oral administration in the form of, for example, tablets, capsules, drinks, granules, by dermal application in the form of, for example, dipping, spraying, pouring on, spotting on, and dusting, and by parenteral administration in the form of, for example, an injection.

Molecules of Formula One may also be employed advantageously in livestock keeping, for example, cattle, chickens, geese, goats, pigs, sheep, and turkeys. They may also be employed advantageously in pets such as, horses, dogs, and cats. Particular pests to control would be flies, fleas, and ticks that are bothersome to such animals. Suitable formulations are administered orally to the animals with the drinking water or feed. The dosages and formulations that are suitable depend on the species.

Molecules of Formula One may also be used for controlling parasitic worms, especially of the intestine, in the animals listed above.

Molecules of Formula One may also be employed in therapeutic methods for human health care. Such methods include, but are limited to, oral administration in the form of, for example, tablets, capsules, drinks, granules, and by dermal application.

Molecules of Formula One may also be applied to invasive pests. Pests around the world have been migrating to new environments (for such pest) and thereafter becoming a new invasive species in such new environment. Such molecules may also be used on such new invasive species to control them in such new environments.

The headings in this document are for convenience only and must not be used to interpret any portion hereof.

TABLES

TABLE B

| Weight Ratios |
| --- |
| Molecule of the Formula One:active ingredient |
| 100:1 to 1:100 |
| 50:1 to 1:50 |
| 20:1 to 1:20 |
| 10:1 to 1:10 |
| 5:1 to 1:5 |
| 3:1 to 1:3 |
| 2:1 to 1:2 |
| 1:1 |

TABLE C

| active ingredients (Y) Parts by weight | 100 | X,Y | | X,Y | | | X,Y | | | |
|---|---|---|---|---|---|---|---|---|---|---|
| | 50 | X,Y | X,Y | X,Y | | | X,Y | X,Y | | |
| | 20 | X,Y | | X,Y | X,Y | | X,Y | | X,Y | |
| | 15 | X,Y | X,Y | | | | | X,Y | X,Y | X,Y |
| | 10 | X,Y | | X,Y | | | | | | |
| | 5 | X,Y | X,Y | X,Y | | | X,Y | | | |
| | 3 | X,Y | X,Y | | X,Y | X,Y | | X,Y | X,Y | X,Y |
| | 2 | X,Y | | X,Y | X,Y | | X,Y | | X,Y | |
| | 1 | X,Y | X,Y | X,Y | X,Y | X,Y | X,Y | X,Y | X,Y | X,Y |
| | | 1 | 2 | 3 | 5 | 10 | 15 | 20 | 50 | 100 |
| | | molecule of Formula One (X) Parts by weight | | | | | | | | |

TABLE 2

Structure and preparation method for F Series molecules

| No. | Structure | Prep.* |
|---|---|---|
| F1004 | 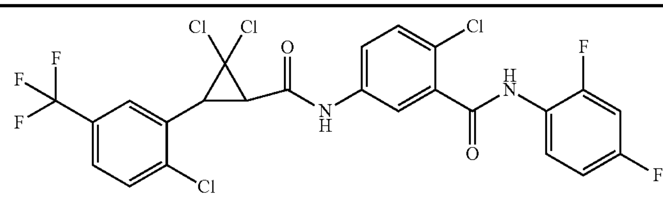 | 20 |
| F1005 | 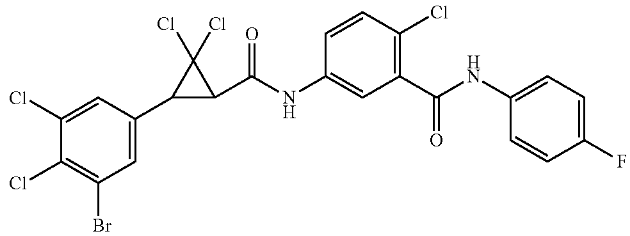 [SMILES: O=C(Nc1ccc(F)cc1)c1cc(NC(=O)C2C(c3cc(Cl)c(Cl)c(Br)c3)C2(Cl)Cl)ccc1Cl] | 18 |
| F1006 | 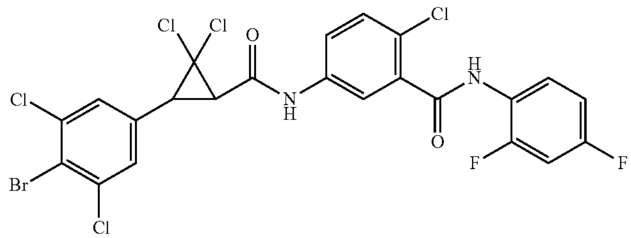 [SMILES: O=C(Nc1ccc(F)cc1F)c1cc(NC(=O)C2C(c3cc(Cl)c(Br)c(Cl)c3)C2(Cl)Cl)ccc1Cl] | 18 |
| F1007 | 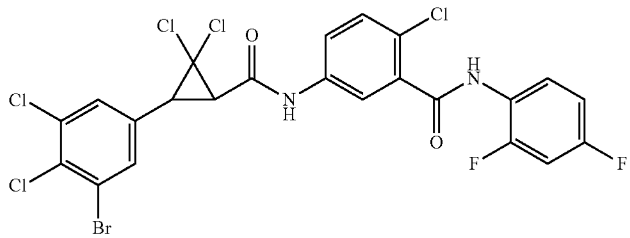 [SMILES: O=C(Nc1ccc(F)cc1F)c1cc(NC(=O)C2C(c3cc(Cl)c(Cl)c(Br)c3)C2(Cl)Cl)ccc1Cl] | 18 |
| F1009 | 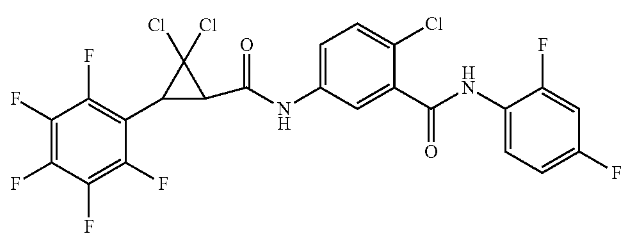 [SMILES: O=C(Nc1ccc(F)cc1F)c1cc(NC(=O)C2C(c3c(F)c(F)c(F)c(F)c3F)C2(Cl)Cl)ccc1Cl] | 20 |

TABLE 2-continued

Structure and preparation method for F Series molecules

| No. | Structure | Prep.* |
|---|---|---|
| F1010 | 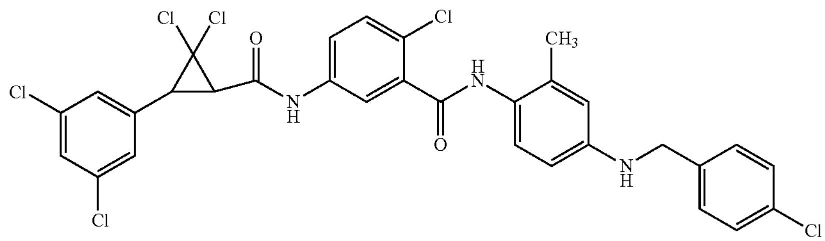 [SMILES: Cc1cc(NCc2ccc(Cl)cc2)ccc1NC(=O)c1cc(NC(=O)C2C(c3cc(Cl)cc(Cl)c3)C2(Cl)Cl)ccc1Cl] | 20 |
| F1011 | 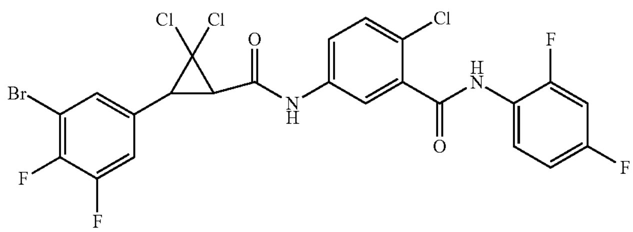 | 20 |
| F1012 | 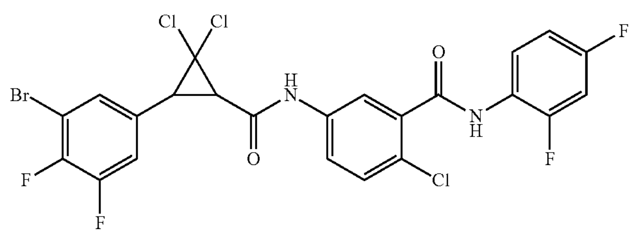 [SMILES: O=C(Nc1ccc(F)cc1F)c1cc(NC(=O)C2C(c3cc(F)c(F)c(Br)c3)C2(Cl)Cl)ccc1Cl] | 20 |
| F1022 | 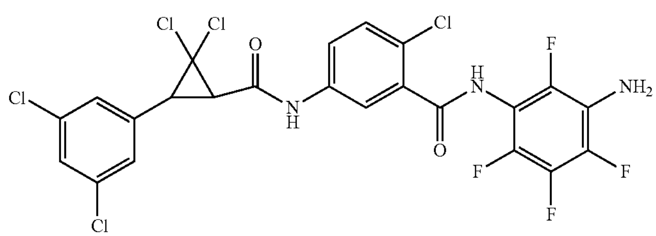 [SMILES: Nc1c(F)c(F)c(F)c(NC(=O)c2cc(NC(=O)C3C(c4cc(Cl)cc(Cl)c4)C3(Cl)Cl)ccc2Cl)c1F] | 25 |
| F1023 | 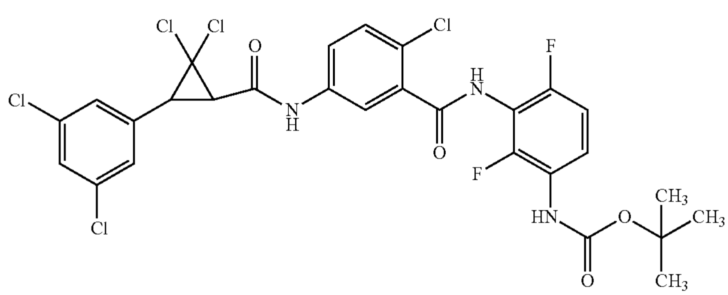 [SMILES: CC(C)(C)OC(=O)Nc1ccc(F)c(NC(=O)c2cc(NC(=O)C3C(c4cc(Cl)cc(Cl)c4)C3(Cl)Cl)ccc2Cl)c1F] | 25 |
| F1024 | 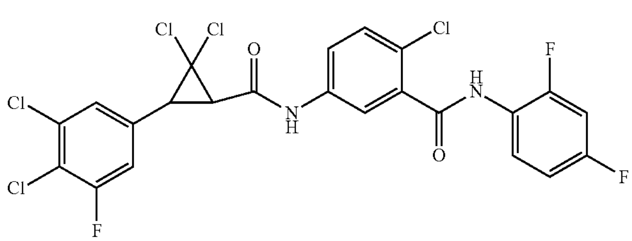 [SMILES: O=C(Nc1ccc(F)cc1F)c1cc(NC(=O)C2C(c3cc(F)c(Cl)c(Cl)c3)C2(Cl)Cl)ccc1Cl] | 20 |

TABLE 2-continued

Structure and preparation method for F Series molecules

| No. | Structure | Prep.* |
|---|---|---|
| F1025 | 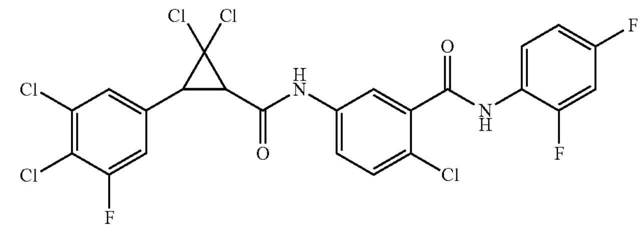 [SMILES: O=C(Nc1ccc(F)cc1F)c1cc(NC(=O)C2C(c3cc(F)c(Cl)c(Cl)c3)C2(Cl)Cl)ccc1Cl] | 20 |
| F1026 | 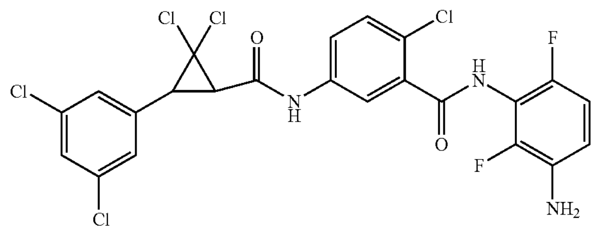 [SMILES: Nc1ccc(F)c(NC(=O)c2cc(NC(=O)C3C(c4cc(Cl)cc(Cl)c4)C3(Cl)Cl)ccc2Cl)c1F] | 12 |
| F1027 | 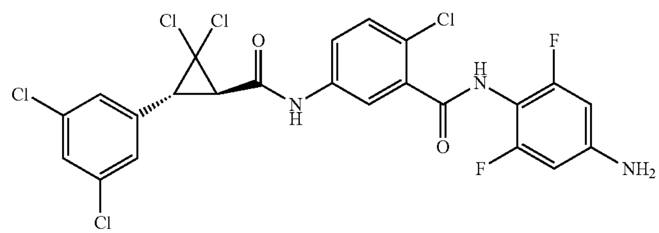 [SMILES: Nc1cc(F)c(NC(=O)c2cc(NC(=O)[C@H]3[C@H](c4cc(Cl)cc(Cl)c4)C3(Cl)Cl)ccc2Cl)c(F)c1] | 27 |
| F1028 | 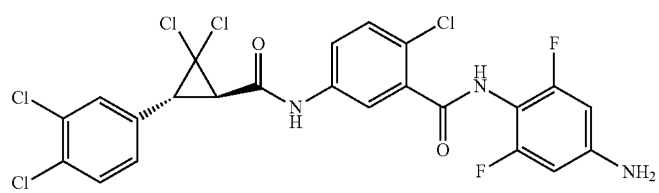 [SMILES: Nc1cc(F)c(NC(=O)c2cc(NC(=O)[C@H]3[C@H](c4ccc(Cl)c(Cl)c4)C3(Cl)Cl)ccc2Cl)c(F)c1] | 27 |
| F1029 | 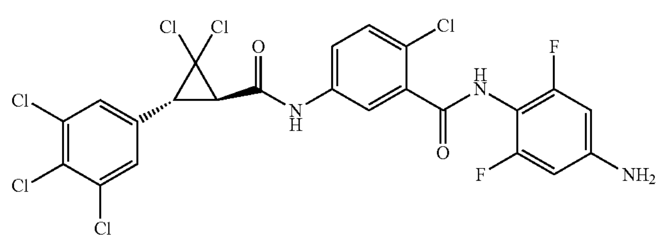 [SMILES: Nc1cc(F)c(NC(=O)c2cc(NC(=O)[C@H]3[C@H](c4cc(Cl)c(Cl)c(Cl)c4)C3(Cl)Cl)ccc2Cl)c(F)c1] | 27 |
| F1030 | 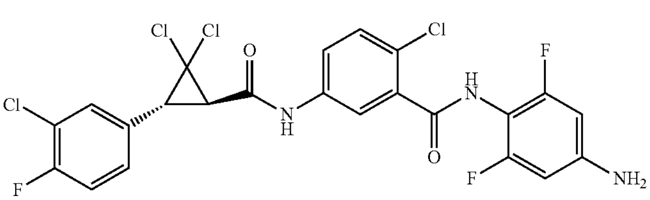 | 27 |

TABLE 2-continued

Structure and preparation method for F Series molecules

| No. | Structure | Prep.* |
|---|---|---|
| F1031 | 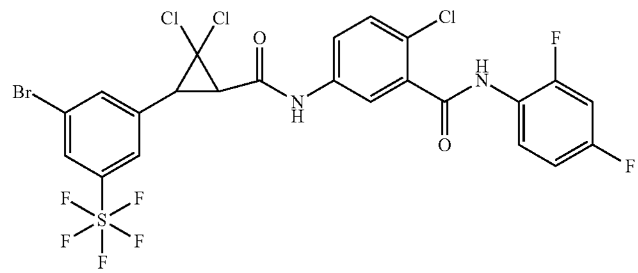 | 20 |
| F1032 | 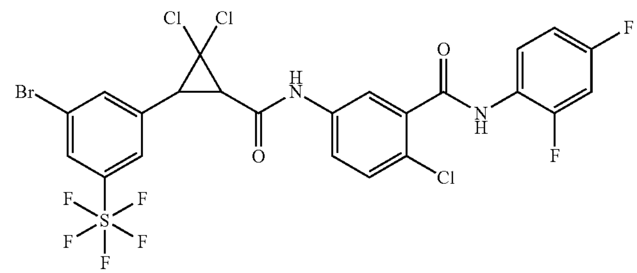 [SMILES: O=C(Nc1ccc(F)cc1F)c1cc(NC(=O)C2C(c3cc(Br)cc(S(F)(F)(F)(F)F)c3)C2(Cl)Cl)ccc1Cl] | 20 |
| F1033 | 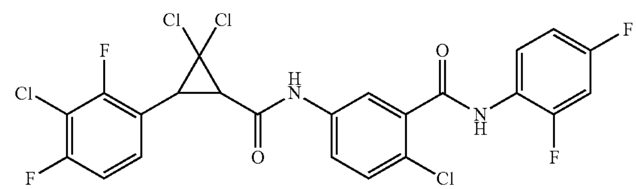 [SMILES: O=C(Nc1ccc(F)cc1F)c1cc(NC(=O)C2C(c3ccc(F)c(Cl)c3F)C2(Cl)Cl)ccc1Cl] | 20 |
| F1034 | 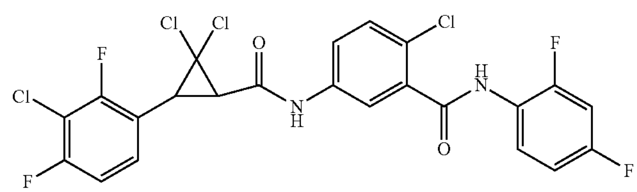 [SMILES: O=C(Nc1ccc(F)cc1F)c1cc(NC(=O)C2C(c3ccc(F)c(Cl)c3F)C2(Cl)Cl)ccc1Cl] | 20 |
| F1035 | 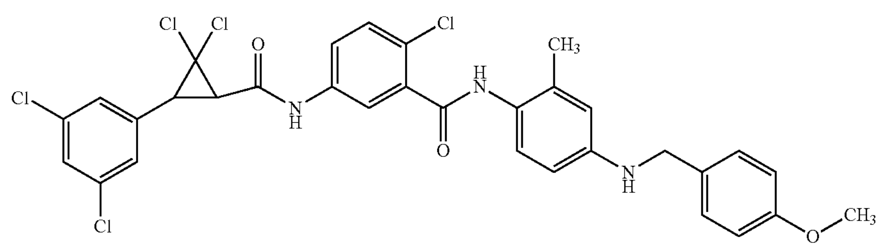 [SMILES: COc1ccc(CNc2ccc(NC(=O)c3cc(NC(=O)C4C(c5cc(Cl)cc(Cl)c5)C4(Cl)Cl)ccc3Cl)c(C)c2)cc1] | 10 |
| F1036 | 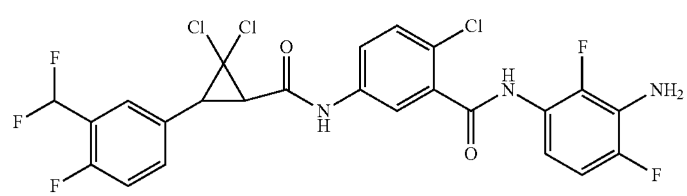 [SMILES: Nc1c(F)ccc(NC(=O)c2cc(NC(=O)C3C(c4ccc(Cl)c(C(F)F)c4)C3(Cl)Cl)ccc2Cl)c1F] | 27 |
| F1037 | 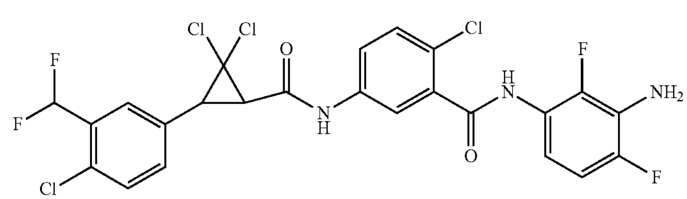 | 27 |

TABLE 2-continued

Structure and preparation method for F Series molecules

| No. | Structure | Prep.* |
|---|---|---|
| F1038 | 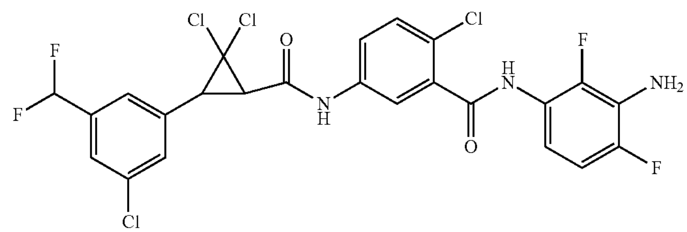 [SMILES: Nc1c(F)ccc(NC(=O)c2cc(NC(=O)C3C(c4cc(Cl)cc(C(F)F)c4)C3(Cl)Cl)ccc2Cl)c1F] | 27 |
| F1039 | 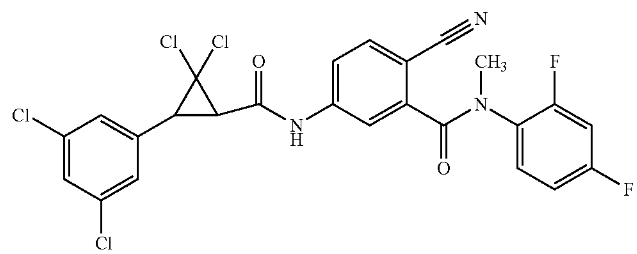 [SMILES: CN(C(=O)c1cc(NC(=O)C2C(c3cc(Cl)cc(Cl)c3)C2(Cl)Cl)ccc1C#N)c1ccc(F)cc1F] | 18 |
| F1040 | 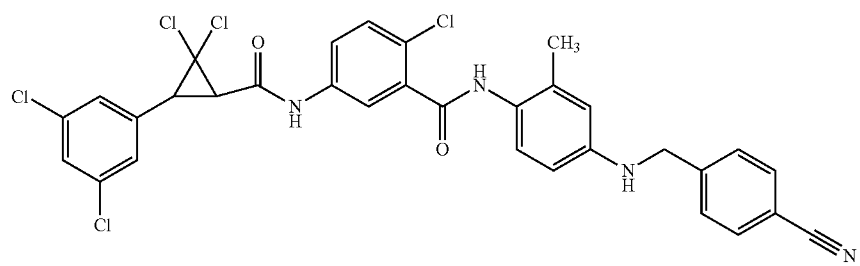 [SMILES: Cc1cc(NCc2ccc(C#N)cc2)ccc1NC(=O)c1cc(NC(=O)C2C(c3cc(Cl)cc(Cl)c3)C2(Cl)Cl)ccc1Cl] | 10 |
| F1041 | 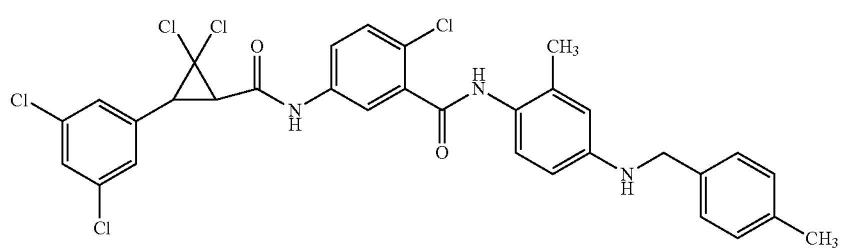 [SMILES: Cc1ccc(CNc2ccc(NC(=O)c3cc(NC(=O)C4C(c5cc(Cl)cc(Cl)c5)C4(Cl)Cl)ccc3Cl)c(C)c2)cc1] | 10 |
| F1042 | 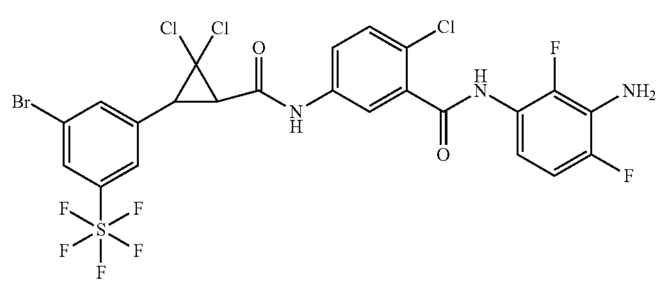 | 12 |
| F1043 | 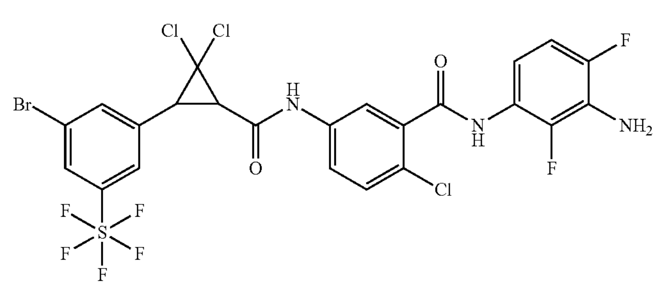 | 12 |

TABLE 2-continued

Structure and preparation method for F Series molecules

| No. | Structure | Prep.* |
|---|---|---|
| F1044 | 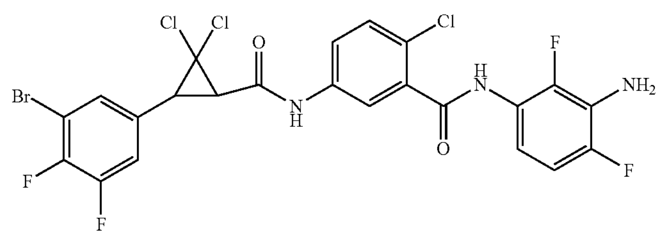 | 12 |
| F1045 | 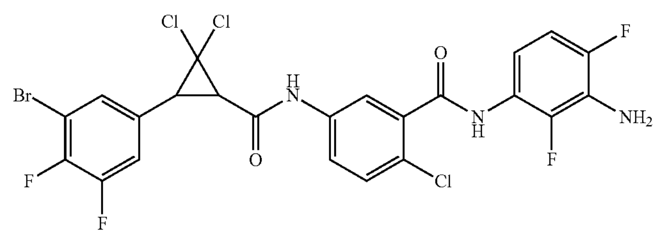 [SMILES: Nc1c(F)ccc(NC(=O)c2cc(NC(=O)C3C(c4cc(F)c(F)c(Br)c4)C3(Cl)Cl)ccc2Cl)c1F] | 12 |
| F1046 | 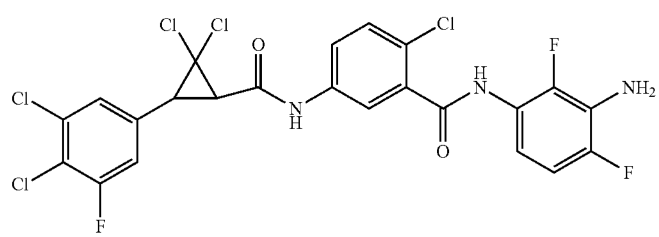 [SMILES: Nc1c(F)ccc(NC(=O)c2cc(NC(=O)C3C(c4cc(F)c(Cl)c(Cl)c4)C3(Cl)Cl)ccc2Cl)c1F] | 12 |
| F1047 | 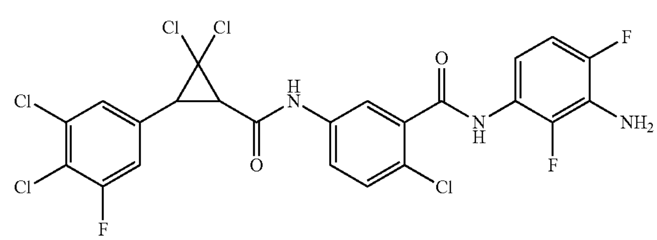 [SMILES: Nc1c(F)ccc(NC(=O)c2cc(NC(=O)C3C(c4cc(F)c(Cl)c(Cl)c4)C3(Cl)Cl)ccc2Cl)c1F] | 12 |
| F1048 | 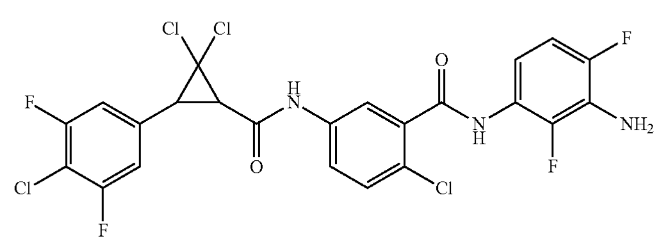 [SMILES: Nc1c(F)ccc(NC(=O)c2cc(NC(=O)C3C(c4cc(F)c(Cl)c(F)c4)C3(Cl)Cl)ccc2Cl)c1F] | 12 |
| F1049 | 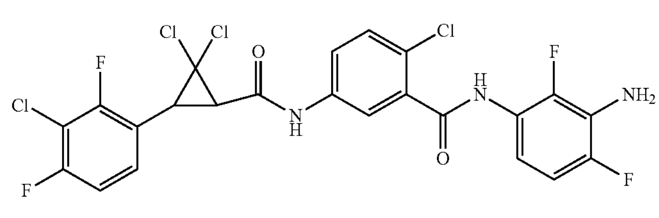 [SMILES: Nc1c(F)ccc(NC(=O)c2cc(NC(=O)C3C(c4ccc(F)c(Cl)c4F)C3(Cl)Cl)ccc2Cl)c1F] | 12 |

TABLE 2-continued

Structure and preparation method for F Series molecules

| No. | Structure | Prep.* |
|---|---|---|
| F1050 | 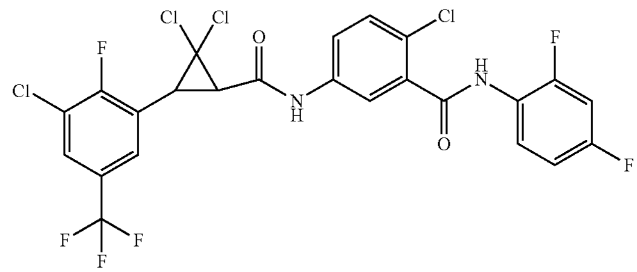 [SMILES: O=C(Nc1ccc(F)cc1F)c1cc(NC(=O)C2C(c3cc(C(F)(F)F)cc(Cl)c3F)C2(Cl)Cl)ccc1Cl] | 20 |
| F1051 | 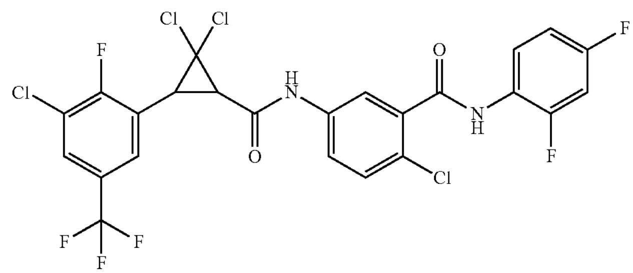 [SMILES: O=C(Nc1ccc(F)cc1F)c1cc(NC(=O)C2C(c3cc(C(F)(F)F)cc(Cl)c3F)C2(Cl)Cl)ccc1Cl] | 20 |
| F1053 | 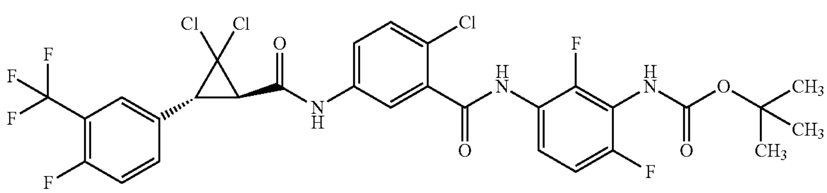 [SMILES: CC(C)(C)OC(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 20 |
| F1054 | 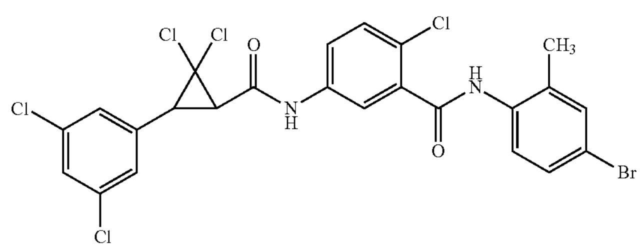 [SMILES: Cc1cc(Br)ccc1NC(=O)c1cc(NC(=O)C2C(c3cc(Cl)cc(Cl)c3)C2(Cl)Cl)ccc1Cl] | 25 |
| F1055 | 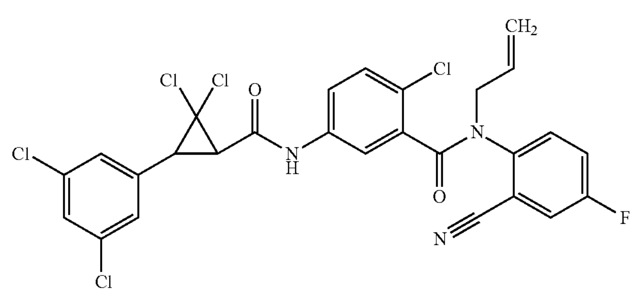 [SMILES: C=CCN(C(=O)c1cc(NC(=O)C2C(c3cc(Cl)cc(Cl)c3)C2(Cl)Cl)ccc1Cl)c1ccc(F)cc1C#N] | 18 |
| F1056 | 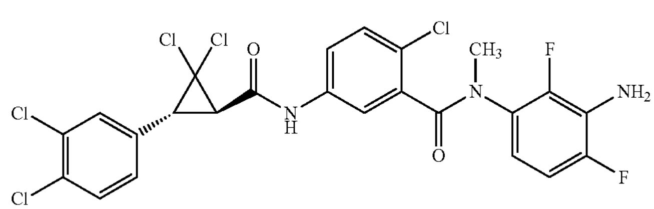 [SMILES: CN(C(=O)c1cc(NC(=O)[C@H]2[C@H](c3ccc(Cl)c(Cl)c3)C2(Cl)Cl)ccc1Cl)c1ccc(F)c(N)c1F] | 12 |

TABLE 2-continued

Structure and preparation method for F Series molecules

| No. | Structure | Prep.* |
|---|---|---|
| F1057 | 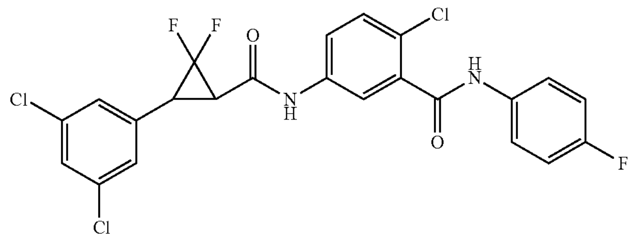 [SMILES: O=C(Nc1ccc(F)cc1)c1cc(NC(=O)C2C(c3cc(Cl)cc(Cl)c3)C2(F)F)ccc1Cl] | 18 |
| F1058 | 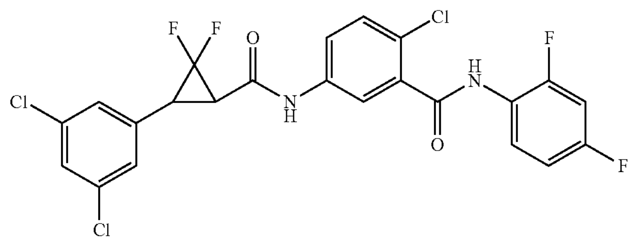 [SMILES: O=C(Nc1ccc(F)cc1F)c1cc(NC(=O)C2C(c3cc(Cl)cc(Cl)c3)C2(F)F)ccc1Cl] | 18 |
| F1059 | 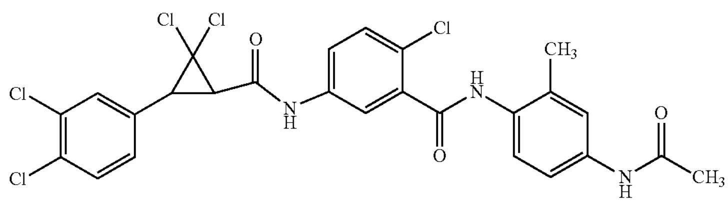 [SMILES: CC(=O)Nc1ccc(NC(=O)c2cc(NC(=O)C3C(c4ccc(Cl)c(Cl)c4)C3(Cl)Cl)ccc2Cl)c(C)c1] | 7 |
| F1060 | 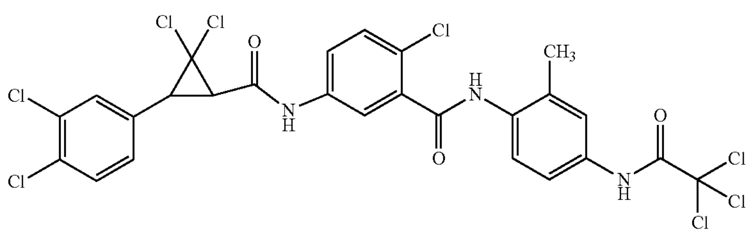 [SMILES: Cc1cc(NC(=O)C(Cl)(Cl)Cl)ccc1NC(=O)c1cc(NC(=O)C2C(c3ccc(Cl)c(Cl)c3)C2(Cl)Cl)ccc1Cl] | 7 |
| F1061 | 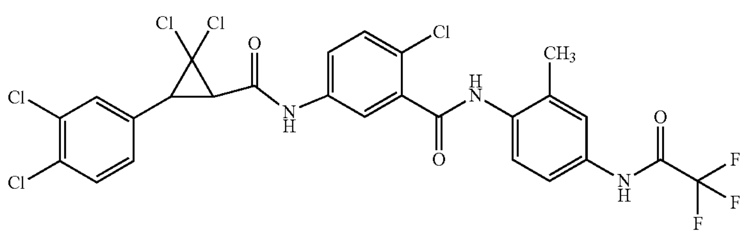 [SMILES: Cc1cc(NC(=O)C(F)(F)F)ccc1NC(=O)c1cc(NC(=O)C2C(c3ccc(Cl)c(Cl)c3)C2(Cl)Cl)ccc1Cl] | 1 |
| F1062 | 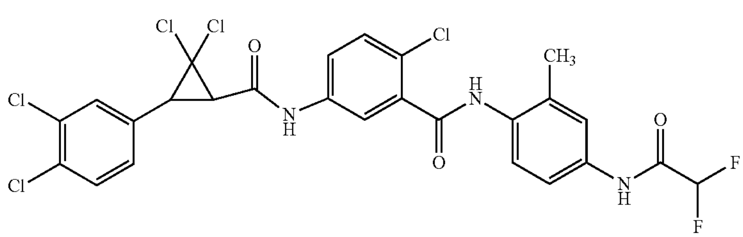 [SMILES: Cc1cc(NC(=O)C(F)F)ccc1NC(=O)c1cc(NC(=O)C2C(c3ccc(Cl)c(Cl)c3)C2(Cl)Cl)ccc1Cl] | 1 |

TABLE 2-continued

Structure and preparation method for F Series molecules

| No. | Structure | Prep.* |
|---|---|---|
| F1063 | 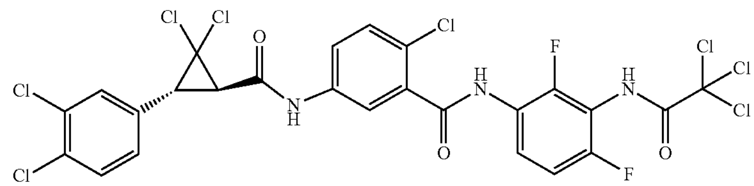 [SMILES: O=C(Nc1ccc(F)c(NC(=O)C(Cl)(Cl)Cl)c1F)c1cc(NC(=O)[C@H]2[C@H](c3ccc(Cl)c(Cl)c3)C2(Cl)Cl)ccc1Cl] | 7 |
| F1064 | 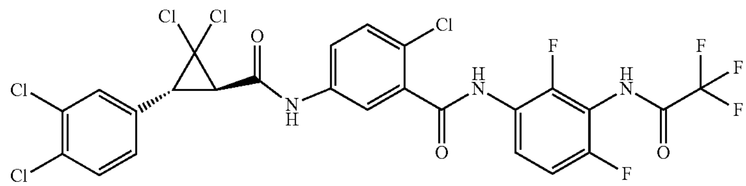 [SMILES: O=C(Nc1ccc(F)c(NC(=O)C(F)(F)F)c1F)c1cc(NC(=O)[C@H]2[C@H](c3ccc(Cl)c(Cl)c3)C2(Cl)Cl)ccc1Cl] | 1 |
| F1065 | 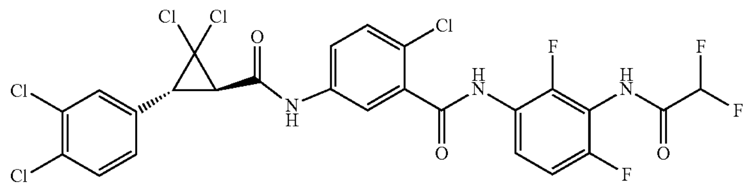 [SMILES: O=C(Nc1ccc(F)c(NC(=O)C(F)F)c1F)c1cc(NC(=O)[C@H]2[C@H](c3ccc(Cl)c(Cl)c3)C2(Cl)Cl)ccc1Cl] | 1 |
| F1070 | 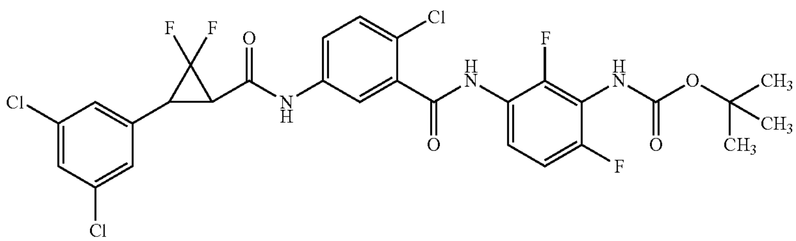 [SMILES: CC(C)(C)OC(=O)Nc1c(F)ccc(NC(=O)c2cc(NC(=O)C3C(c4cc(Cl)cc(Cl)c4)C3(F)F)ccc2Cl)c1F] | 18 |
| F1071 | 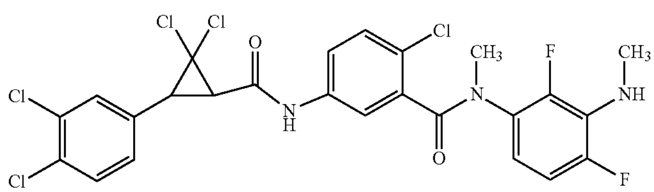 [SMILES: CNc1c(F)ccc(N(C)C(=O)c2cc(NC(=O)C3C(c4ccc(Cl)c(Cl)c4)C3(Cl)Cl)ccc2Cl)c1F] | 18 |
| F1072 | 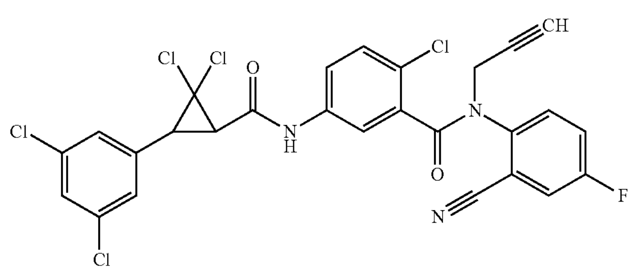 [SMILES: C#CCN(C(=O)c1cc(NC(=O)C2C(c3cc(Cl)cc(Cl)c3)C2(Cl)Cl)ccc1Cl)c1ccc(F)cc1C#N] | 18 |
| F1073 | 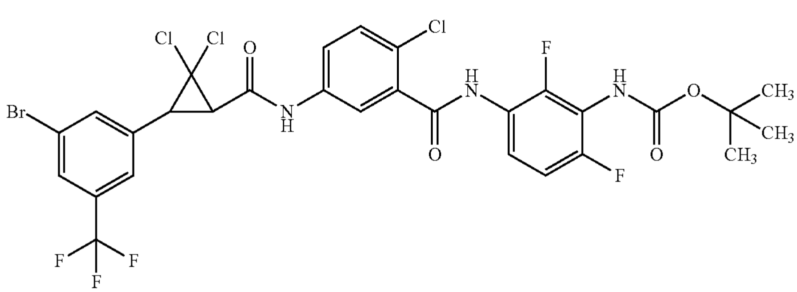 [SMILES: CC(C)(C)OC(=O)Nc1c(F)ccc(NC(=O)c2cc(NC(=O)C3C(c4cc(Br)cc(C(F)(F)F)c4)C3(Cl)Cl)ccc2Cl)c1F] | 20 |

TABLE 2-continued

Structure and preparation method for F Series molecules

| No. | Structure | Prep.* |
|---|---|---|
| F1074 | 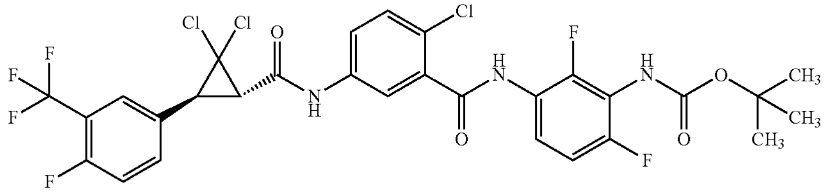 [SMILES: CC(C)(C)OC(=O)Nc1c(F)ccc(NC(=O)c2cc(NC(=O)[C@@H]3[C@@H](c4ccc(F)c(C(F)(F)F)c4)C3(Cl)Cl)ccc2Cl)c1F] | 20 |
| F1075 | 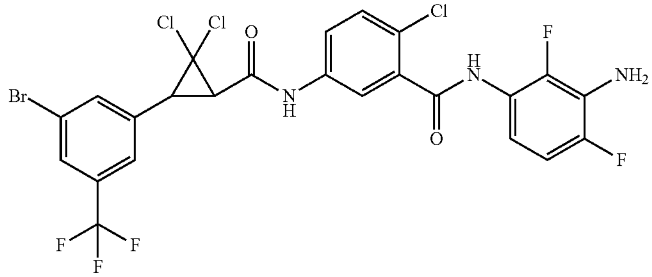 [SMILES: Nc1c(F)ccc(NC(=O)c2cc(NC(=O)C3C(c4cc(Br)cc(C(F)(F)F)c4)C3(Cl)Cl)ccc2Cl)c1F] | 12 |
| F1077 | 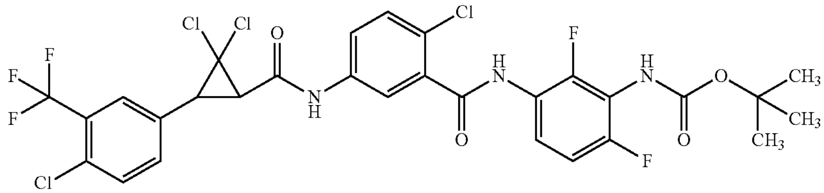 [SMILES: CC(C)(C)OC(=O)Nc1c(F)ccc(NC(=O)c2cc(NC(=O)C3C(c4ccc(Cl)c(C(F)(F)F)c4)C3(Cl)Cl)ccc2Cl)c1F] | 20 |
| F1078 | 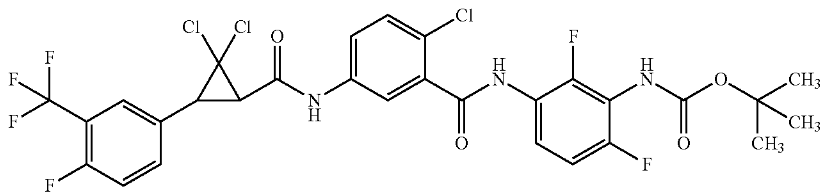 [SMILES: CC(C)(C)OC(=O)Nc1c(F)ccc(NC(=O)c2cc(NC(=O)C3C(c4ccc(F)c(C(F)(F)F)c4)C3(Cl)Cl)ccc2Cl)c1F] | 20 |
| F1079 | 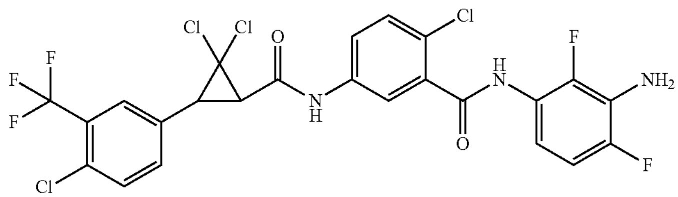 [SMILES: Nc1c(F)ccc(NC(=O)c2cc(NC(=O)C3C(c4ccc(Cl)c(C(F)(F)F)c4)C3(Cl)Cl)ccc2Cl)c1F] | 12 |
| F1080 | 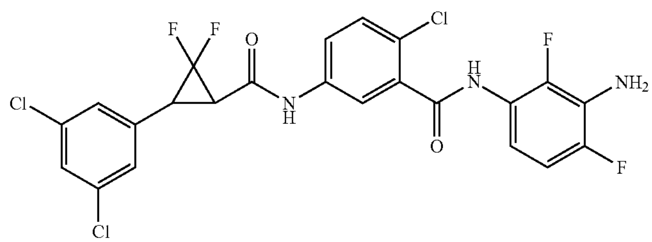 [SMILES: Nc1c(F)ccc(NC(=O)c2cc(NC(=O)C3C(c4cc(Cl)cc(Cl)c4)C3(F)F)ccc2Cl)c1F] | 13 |
| F1081 | 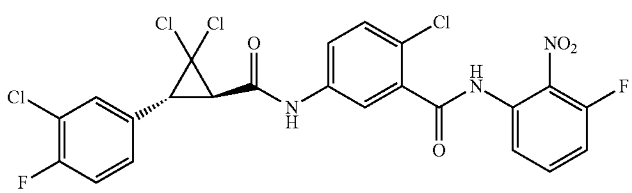 | 25 |

TABLE 2-continued
Structure and preparation method for F Series molecules
| No. | Structure | Prep.* |
|---|---|---|
| F1082 | 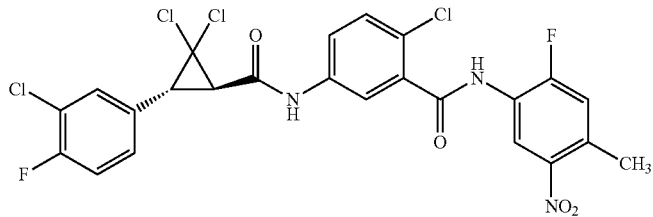 [SMILES: Cc1cc(F)c(NC(=O)c2cc(NC(=O)[C@H]3[C@H](c4ccc(F)c(Cl)c4)C3(Cl)Cl)ccc2Cl)cc1[N+](=O)[O-]] | 25 |
| F1083 | 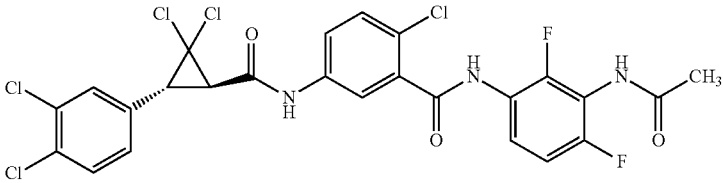 [SMILES: CC(=O)Nc1c(F)ccc(NC(=O)c2cc(NC(=O)[C@H]3[C@H](c4ccc(Cl)c(Cl)c4)C3(Cl)Cl)ccc2Cl)c1F] | 2 |
| F1084 | 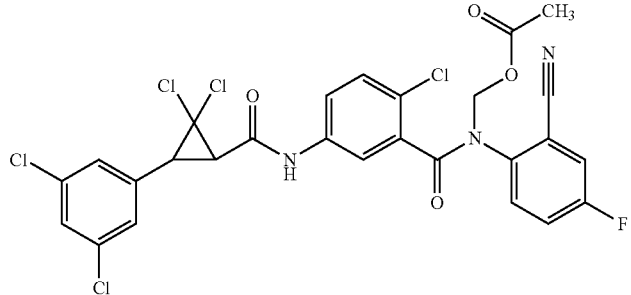 [SMILES: CC(=O)OCN(C(=O)c1cc(NC(=O)C2C(c3cc(Cl)cc(Cl)c3)C2(Cl)Cl)ccc1Cl)c1ccc(F)cc1C#N] | 18 |
| F1085 | 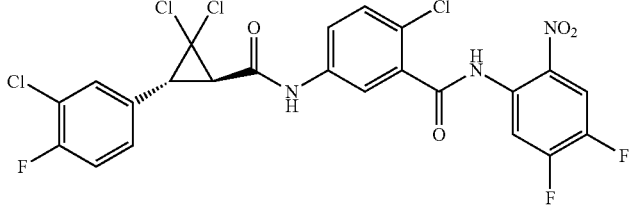 | 25 |
| F1086 | 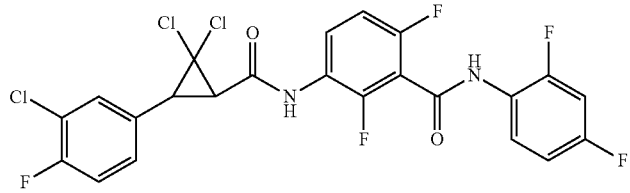 [SMILES: O=C(Nc1ccc(F)cc1F)c1c(F)ccc(NC(=O)C2C(c3ccc(F)c(Cl)c3)C2(Cl)Cl)c1F] | 20 |
| F1087 | 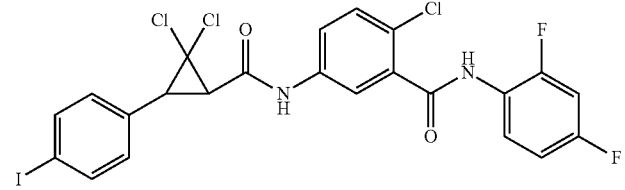 [SMILES: O=C(Nc1ccc(F)cc1F)c1cc(NC(=O)C2C(c3ccc(I)cc3)C2(Cl)Cl)ccc1Cl] | 18 |

TABLE 2-continued

Structure and preparation method for F Series molecules

| No. | Structure | Prep.* |
|---|---|---|
| F1088 | 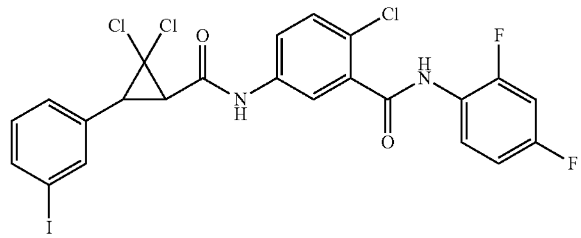 [SMILES: O=C(Nc1ccc(F)cc1F)c1cc(NC(=O)C2C(c3cccc(I)c3)C2(Cl)Cl)ccc1Cl] | 18 |
| F1089 | 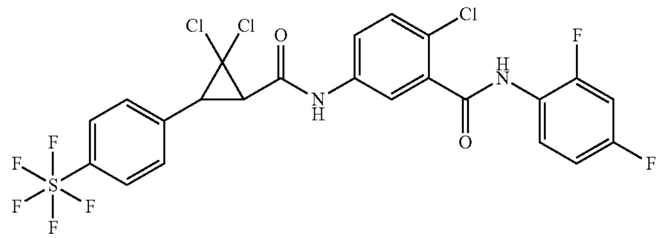 [SMILES: O=C(Nc1ccc(F)cc1F)c1cc(NC(=O)C2C(c3ccc(S(F)(F)(F)(F)F)cc3)C2(Cl)Cl)ccc1Cl] | 18 |
| F1090 | 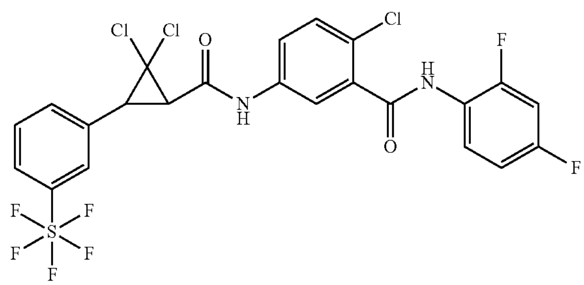 [SMILES: O=C(Nc1ccc(F)cc1F)c1cc(NC(=O)C2C(c3cccc(S(F)(F)(F)(F)F)c3)C2(Cl)Cl)ccc1Cl] | 18 |
| F1091 | 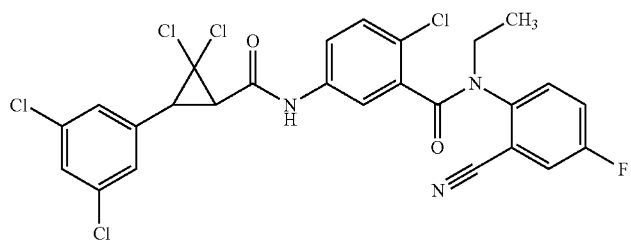 [SMILES: CCN(C(=O)c1cc(NC(=O)C2C(c3cc(Cl)cc(Cl)c3)C2(Cl)Cl)ccc1Cl)c1ccc(F)cc1C#N] | 18 |
| F1092 | 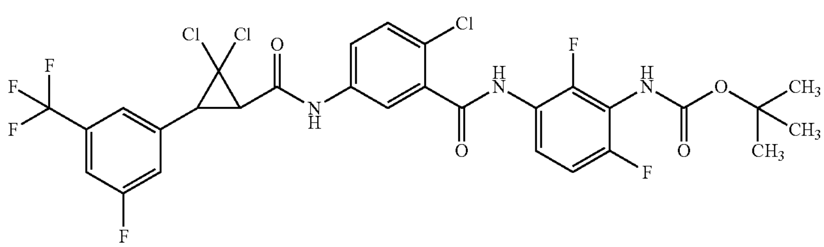 | 20 |
| F1093 | 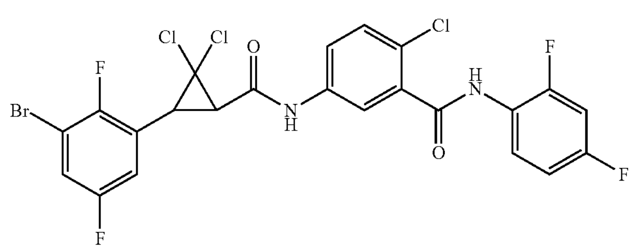 | 20 |

TABLE 2-continued

Structure and preparation method for F Series molecules

| No. | Structure | Prep.* |
|---|---|---|
| F1094 | 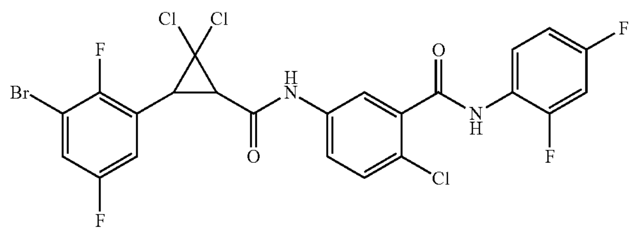 [SMILES: O=C(Nc1ccc(F)cc1F)c1cc(NC(=O)C2C(c3cc(F)cc(Br)c3F)C2(Cl)Cl)ccc1Cl] | 20 |
| F1095 | 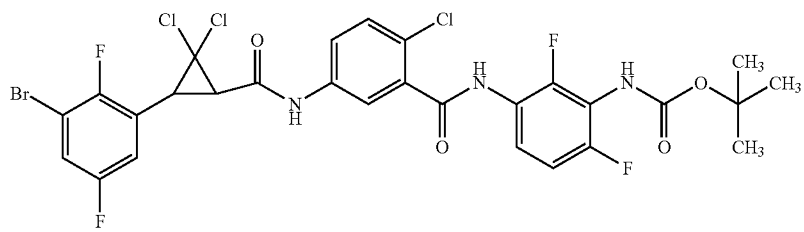 [SMILES: CC(C)(C)OC(=O)Nc1c(F)ccc(NC(=O)c2cc(NC(=O)C3C(c4cc(F)cc(Br)c4F)C3(Cl)Cl)ccc2Cl)c1F] | 20 |
| F1096 | 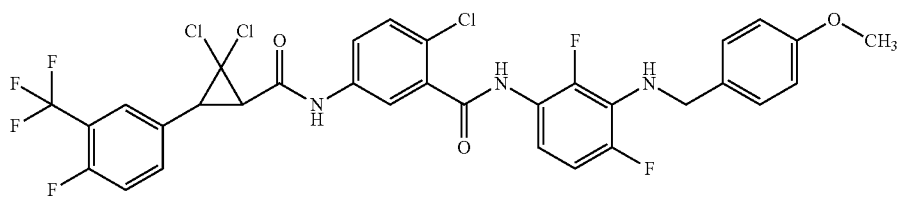 [SMILES: COc1ccc(CNc2c(F)ccc(NC(=O)c3cc(NC(=O)C4C(c5ccc(F)c(C(F)(F)F)c5)C4(Cl)Cl)ccc3Cl)c2F)cc1] | 20 |
| F1097 | 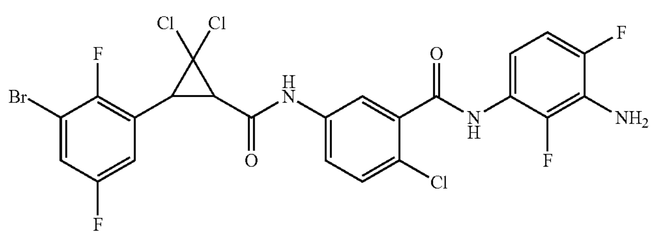 | 12 |
| F1098 | 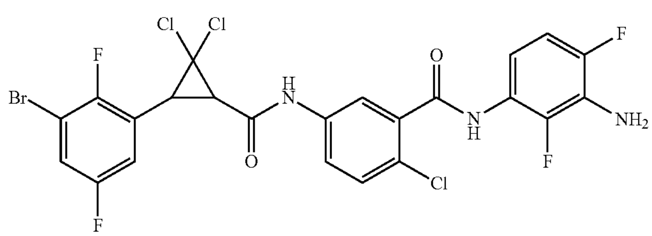 [SMILES: Nc1c(F)ccc(NC(=O)c2cc(NC(=O)C3C(c4cc(F)cc(Br)c4F)C3(Cl)Cl)ccc2Cl)c1F] | 12 |
| F1099 | 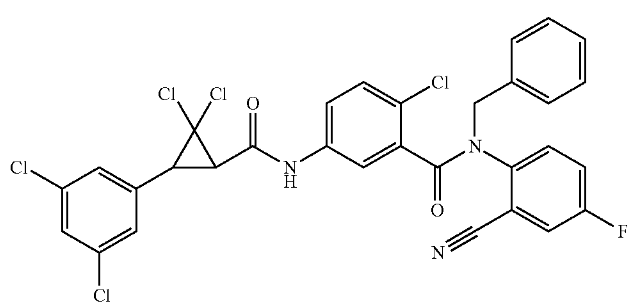 [SMILES: N#Cc1cc(F)ccc1N(Cc1ccccc1)C(=O)c1cc(NC(=O)C2C(c3cc(Cl)cc(Cl)c3)C2(Cl)Cl)ccc1Cl] | 18 |

TABLE 2-continued

Structure and preparation method for F Series molecules

| No. | Structure | Prep.* |
|---|---|---|
| F1100 | 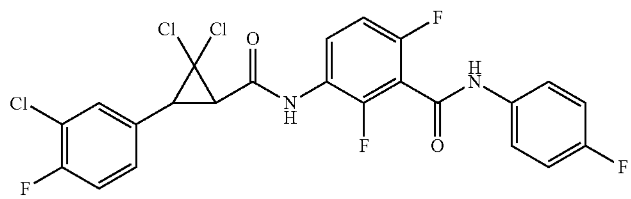 [SMILES: O=C(Nc1ccc(F)cc1)c1c(F)ccc(NC(=O)C2C(c3ccc(F)c(Cl)c3)C2(Cl)Cl)c1F] | 20 |
| F1101 | 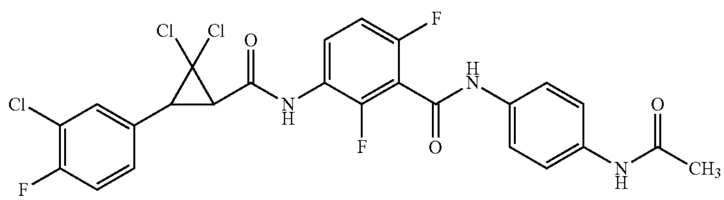 [SMILES: CC(=O)Nc1ccc(NC(=O)c2c(F)ccc(NC(=O)C3C(c4ccc(F)c(Cl)c4)C3(Cl)Cl)c2F)cc1] | 20 |
| F1102 | 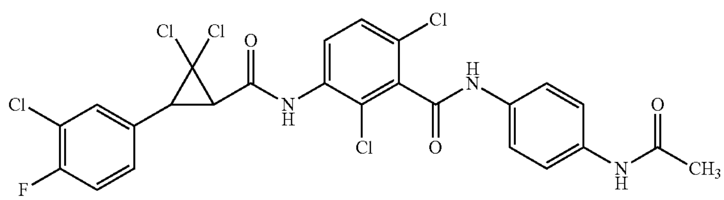 [SMILES: CC(=O)Nc1ccc(NC(=O)c2c(Cl)ccc(NC(=O)C3C(c4ccc(F)c(Cl)c4)C3(Cl)Cl)c2Cl)cc1] | 20 |
| F1103 | 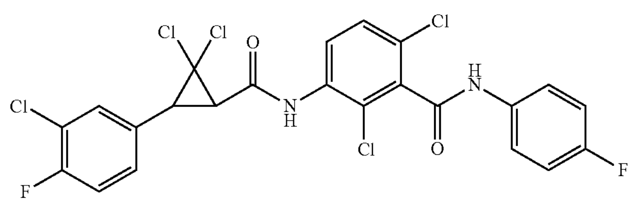 [SMILES: O=C(Nc1ccc(F)cc1)c1c(Cl)ccc(NC(=O)C2C(c3ccc(F)c(Cl)c3)C2(Cl)Cl)c1Cl] | 20 |
| F1104 | 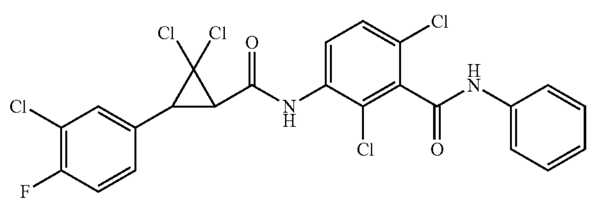 | 20 |
| F1105 | 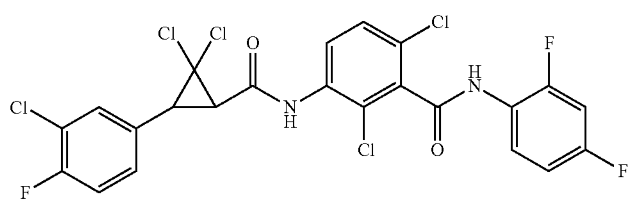 | 20 |
| F1106 | 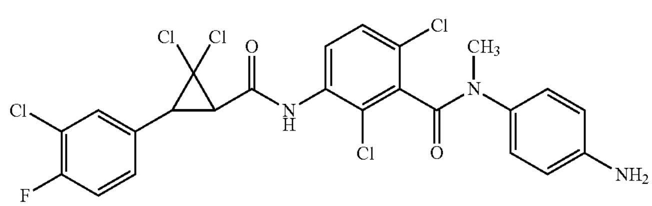 [SMILES: CN(C(=O)c1c(Cl)ccc(NC(=O)C2C(c3ccc(F)c(Cl)c3)C2(Cl)Cl)c1Cl)c1ccc(N)cc1] | 20 |

TABLE 2-continued

Structure and preparation method for F Series molecules

| No. | Structure | Prep.* |
|---|---|---|
| F1107 | 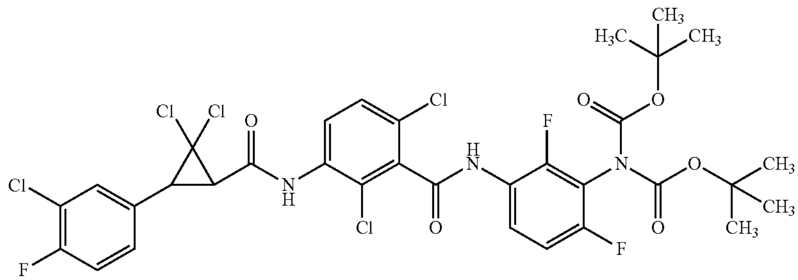 | 20 |
| F1108 | 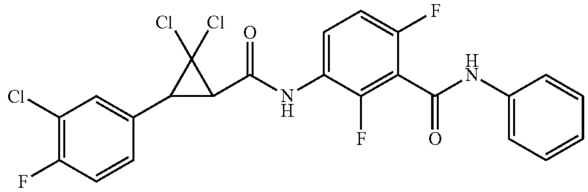 [SMILES: O=C(Nc1ccccc1)c1c(F)ccc(NC(=O)C2C(c3ccc(F)c(Cl)c3)C2(Cl)Cl)c1F] | 20 |
| F1109 | 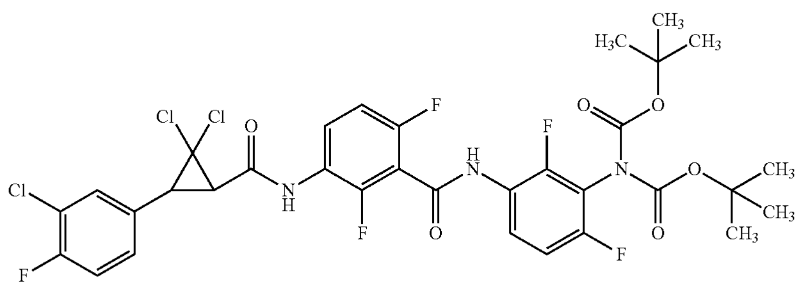 | 20 |
| F1110 | 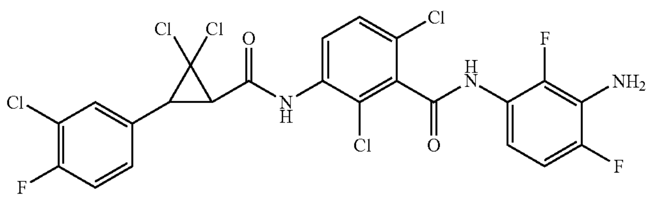 | 13 |
| F1111 | 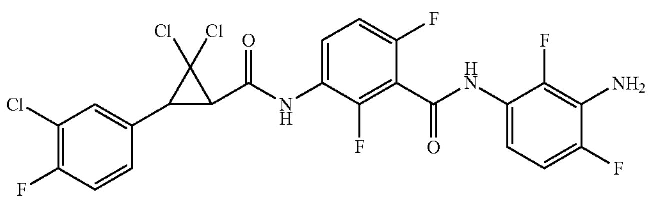 [SMILES: Nc1c(F)ccc(NC(=O)c2c(F)ccc(NC(=O)C3C(c4ccc(F)c(Cl)c4)C3(Cl)Cl)c2F)c1F] | 13 |
| F1112 | 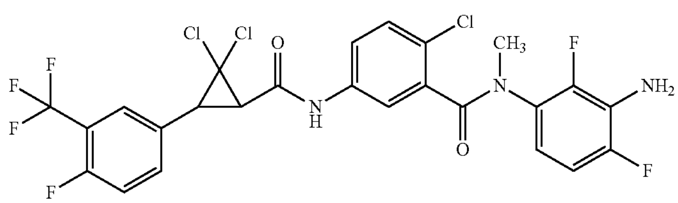 [SMILES: CN(C(=O)c1cc(NC(=O)C2C(c3ccc(F)c(C(F)(F)F)c3)C2(Cl)Cl)ccc1Cl)c1ccc(F)c(N)c1F] | 19 |

TABLE 2-continued
Structure and preparation method for F Series molecules
| No. | Structure | Prep.* |
|---|---|---|
| F1113 | 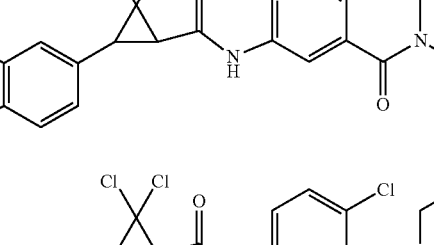 | 19 |
| F1114 | 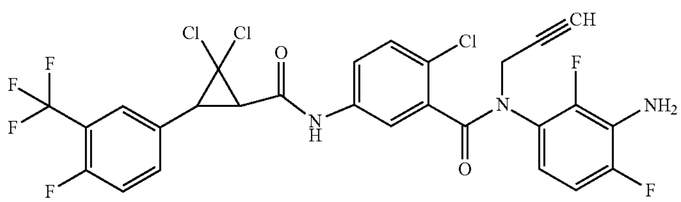 [SMILES: C#CCN(C(=O)c1cc(NC(=O)C2C(c3ccc(F)c(C(F)(F)F)c3)C2(Cl)Cl)ccc1Cl)c1ccc(F)c(N)c1F] | 19 |
| F1115 | 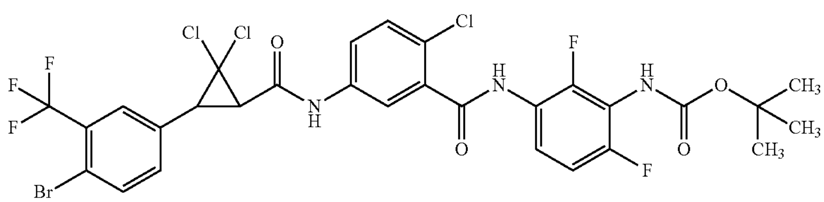 | 20 |
| F1116 | 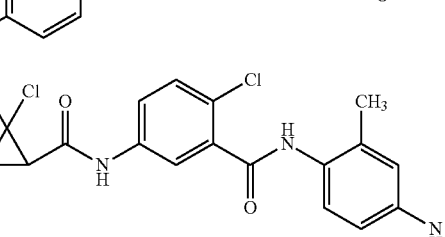 | 12 |
| F1117 | 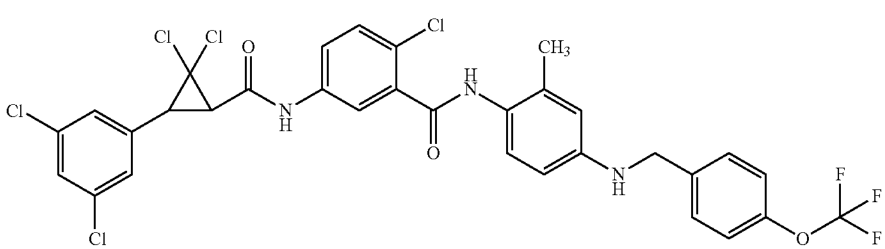 [SMILES: Cc1cc(NCc2ccc(OC(F)(F)F)cc2)ccc1NC(=O)c1cc(NC(=O)C2C(c3cc(Cl)cc(Cl)c3)C2(Cl)Cl)ccc1Cl] | 10 |
| F1118 | 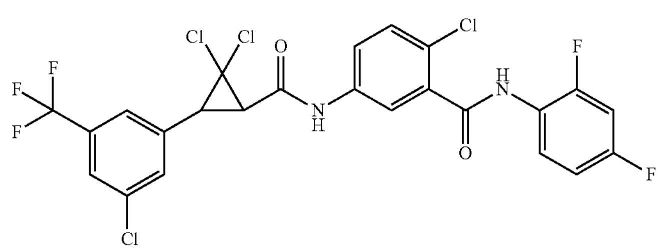 [SMILES: O=C(Nc1ccc(F)cc1F)c1cc(NC(=O)C2C(c3cc(Cl)cc(C(F)(F)F)c3)C2(Cl)Cl)ccc1Cl] | 20 |
| F1119 | 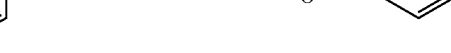 | 20 |

TABLE 2-continued

Structure and preparation method for F Series molecules

| No. | Structure | Prep.* |
|---|---|---|
| F1120 | 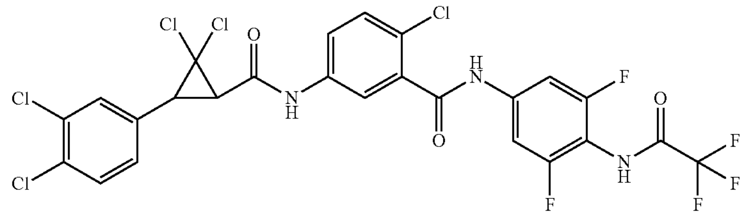 [SMILES: O=C(Nc1cc(F)c(NC(=O)C(F)(F)F)c(F)c1)c1cc(NC(=O)C2C(c3ccc(Cl)c(Cl)c3)C2(Cl)Cl)ccc1Cl] | 1 |
| F1121 | 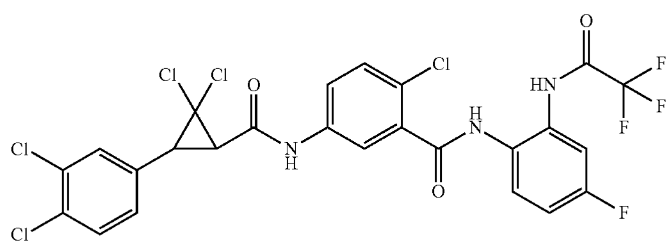 [SMILES: O=C(Nc1ccc(F)cc1NC(=O)C(F)(F)F)c1cc(NC(=O)C2C(c3ccc(Cl)c(Cl)c3)C2(Cl)Cl)ccc1Cl] | 1 |
| F1122 | 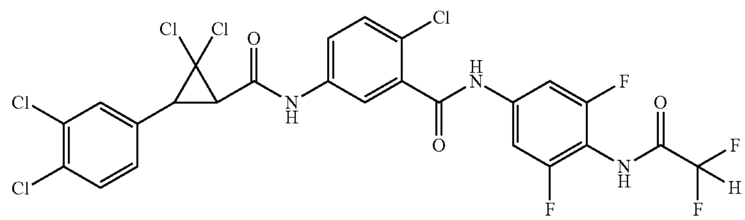 [SMILES: O=C(Nc1cc(F)c(NC(=O)C(F)F)c(F)c1)c1cc(NC(=O)C2C(c3ccc(Cl)c(Cl)c3)C2(Cl)Cl)ccc1Cl] | 1 |
| F1123 | 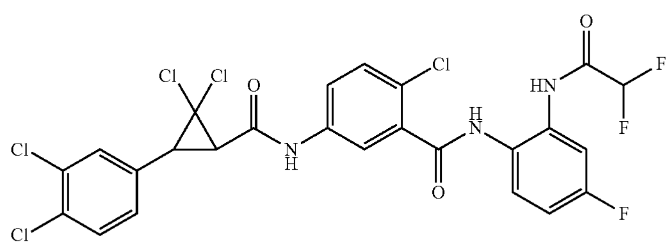 [SMILES: O=C(Nc1ccc(F)cc1NC(=O)C(F)F)c1cc(NC(=O)C2C(c3ccc(Cl)c(Cl)c3)C2(Cl)Cl)ccc1Cl] | 1 |
| F1124 | 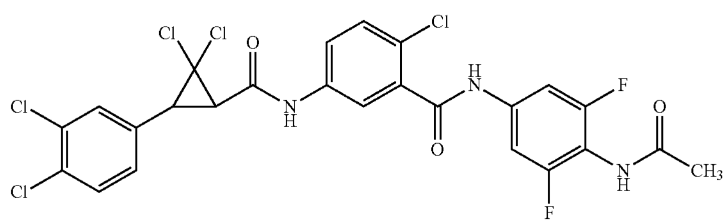 [SMILES: CC(=O)Nc1c(F)cc(NC(=O)c2cc(NC(=O)C3C(c4ccc(Cl)c(Cl)c4)C3(Cl)Cl)ccc2Cl)cc1F] | 2 |
| F1125 | 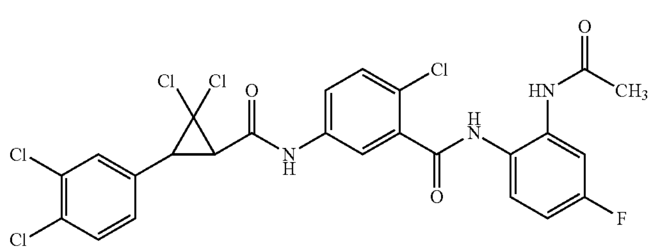 [SMILES: CC(=O)Nc1cc(F)ccc1NC(=O)c1cc(NC(=O)C2C(c3ccc(Cl)c(Cl)c3)C2(Cl)Cl)ccc1Cl] | 2 |

TABLE 2-continued

Structure and preparation method for F Series molecules

| No. | Structure | Prep.* |
|---|---|---|
| F1126 | 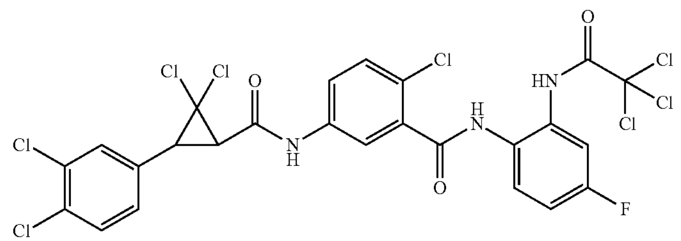 [SMILES: O=C(Nc1ccc(F)cc1NC(=O)C(Cl)(Cl)Cl)c1cc(NC(=O)C2C(c3ccc(Cl)c(Cl)c3)C2(Cl)Cl)ccc1Cl] | 2 |
| F1127 | 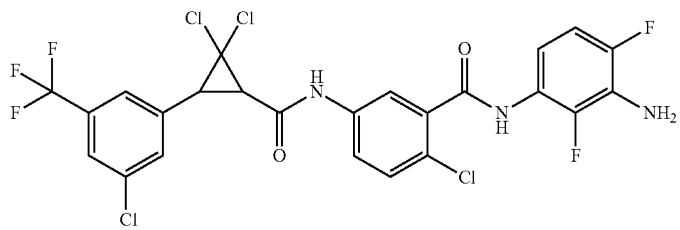 [SMILES: Nc1c(F)ccc(NC(=O)c2cc(NC(=O)C3C(c4cc(Cl)cc(C(F)(F)F)c4)C3(Cl)Cl)ccc2Cl)c1F] | 12 |
| F1128 | 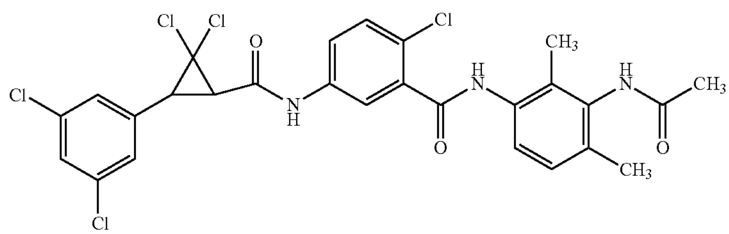 [SMILES: CC(=O)Nc1c(C)ccc(NC(=O)c2cc(NC(=O)C3C(c4cc(Cl)cc(Cl)c4)C3(Cl)Cl)ccc2Cl)c1C] | 25 |
| F1129 | 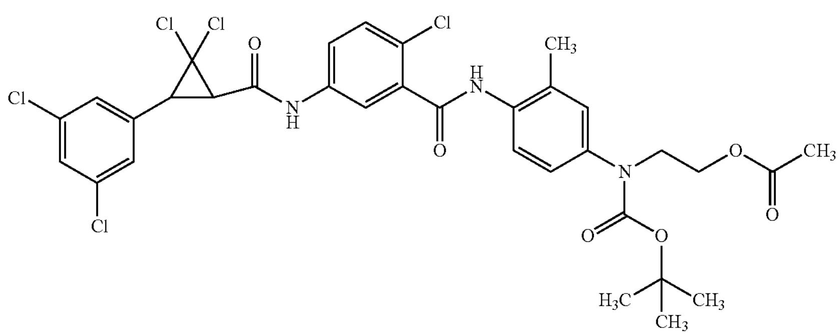 [SMILES: CC(=O)OCCN(C(=O)OC(C)(C)C)c1ccc(NC(=O)c2cc(NC(=O)C3C(c4cc(Cl)cc(Cl)c4)C3(Cl)Cl)ccc2Cl)c(C)c1] | 25 |
| F1130 | 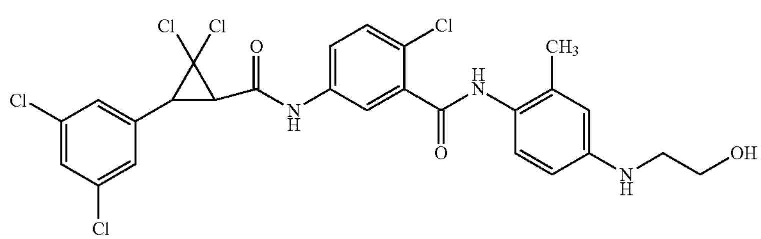 [SMILES: Cc1cc(NCCO)ccc1NC(=O)c1cc(NC(=O)C2C(c3cc(Cl)cc(Cl)c3)C2(Cl)Cl)ccc1Cl] | 12 |
| F1133 | 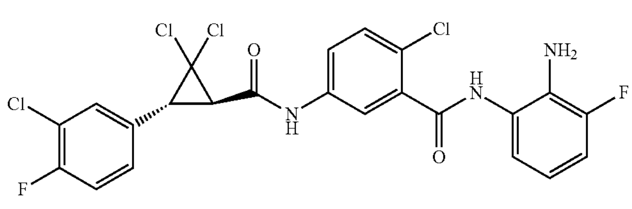 [SMILES: Nc1c(F)cccc1NC(=O)c1cc(NC(=O)[C@H]2[C@H](c3ccc(F)c(Cl)c3)C2(Cl)Cl)ccc1Cl] | 14 |

TABLE 2-continued

Structure and preparation method for F Series molecules

| No. | Structure | Prep.* |
|---|---|---|
| F1134 | 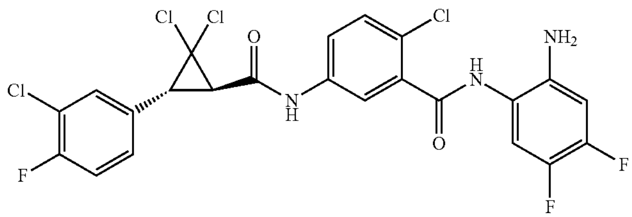 [SMILES: Nc1cc(F)c(F)cc1NC(=O)c1cc(NC(=O)[C@H]2[C@H](c3ccc(F)c(Cl)c3)C2(Cl)Cl)ccc1Cl] | 14 |
| F1135 | 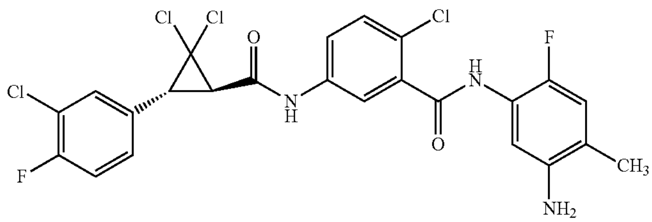 | 14 |
| F1136 | 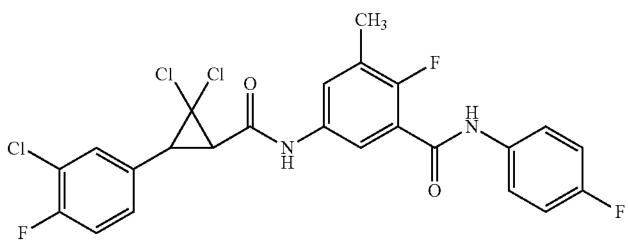 [SMILES: Cc1cc(NC(=O)C2C(c3ccc(F)c(Cl)c3)C2(Cl)Cl)cc(C(=O)Nc2ccc(F)cc2)c1F] | 25 |
| F1137 | 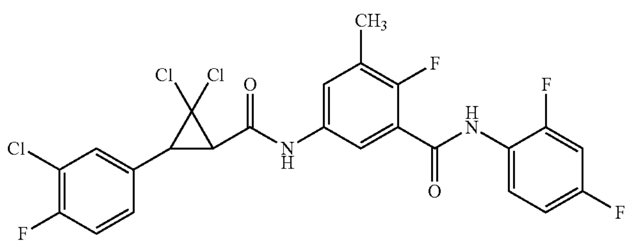 [SMILES: Cc1cc(NC(=O)C2C(c3ccc(F)c(Cl)c3)C2(Cl)Cl)cc(C(=O)Nc2ccc(F)cc2F)c1F] | 25 |
| F1138 | 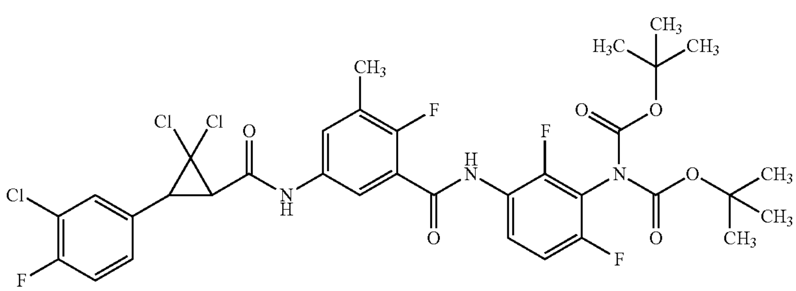 | 25 |
| F1139 | 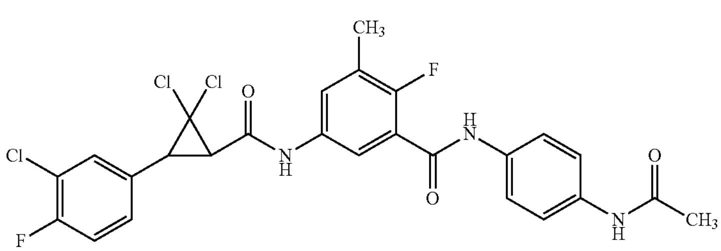 [SMILES: CC(=O)Nc1ccc(NC(=O)c2cc(NC(=O)C3C(c4ccc(F)c(Cl)c4)C3(Cl)Cl)cc(C)c2F)cc1] | 25 |

TABLE 2-continued

Structure and preparation method for F Series molecules

| No. | Structure | Prep.* |
|---|---|---|
| F1140 | 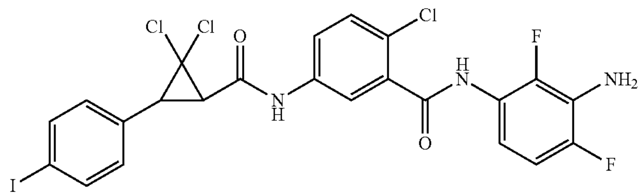 [SMILES: Nc1c(F)ccc(NC(=O)c2cc(NC(=O)C3C(c4ccc(I)cc4)C3(Cl)Cl)ccc2Cl)c1F] | 18 |
| F1141 | 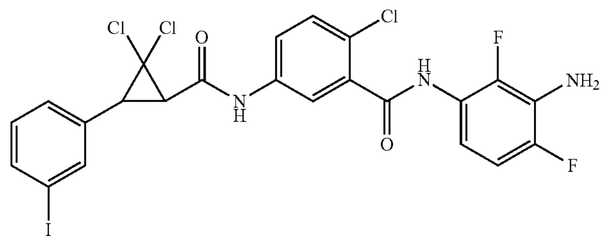 [SMILES: Nc1c(F)ccc(NC(=O)c2cc(NC(=O)C3C(c4cccc(I)c4)C3(Cl)Cl)ccc2Cl)c1F] | 18 |
| F1142 | 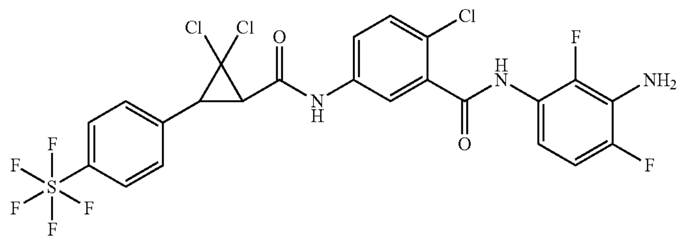 [SMILES: Nc1c(F)ccc(NC(=O)c2cc(NC(=O)C3C(c4ccc(S(F)(F)(F)(F)F)cc4)C3(Cl)Cl)ccc2Cl)c1F] | 18 |
| F1143 | 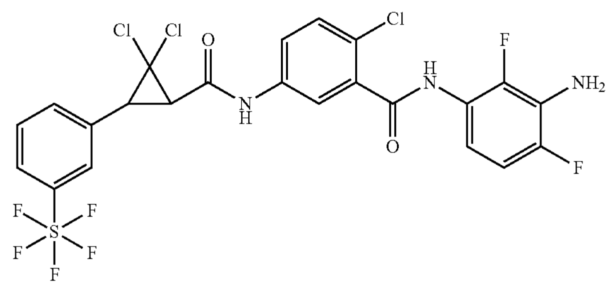 [SMILES: Nc1c(F)ccc(NC(=O)c2cc(NC(=O)C3C(c4cccc(S(F)(F)(F)(F)F)c4)C3(Cl)Cl)ccc2Cl)c1F] | 18 |
| F1144 | 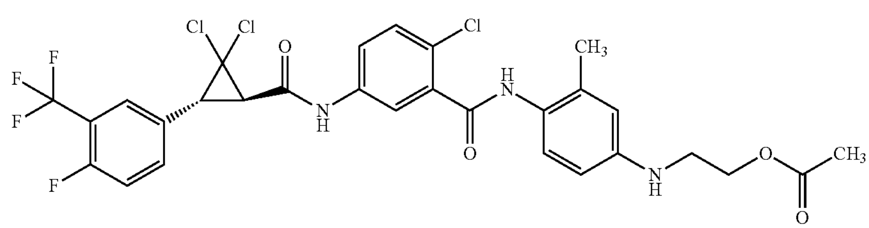 [SMILES: CC(=O)OCCNc1ccc(NC(=O)c2cc(NC(=O)[C@H]3[C@H](c4ccc(F)c(C(F)(F)F)c4)C3(Cl)Cl)ccc2Cl)c(C)c1] | 12 |
| F1145 | 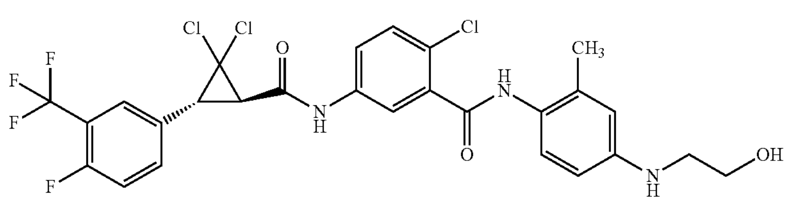 [SMILES: Cc1cc(NCCO)ccc1NC(=O)c1cc(NC(=O)[C@H]2[C@H](c3ccc(F)c(C(F)(F)F)c3)C2(Cl)Cl)ccc1Cl] | 12 |

TABLE 2-continued

Structure and preparation method for F Series molecules

| No. | Structure | Prep.* |
|---|---|---|
| F1146 | 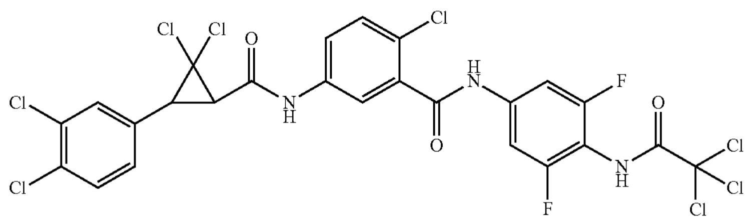 [SMILES: O=C(Nc1cc(F)c(NC(=O)C(Cl)(Cl)Cl)c(F)c1)c1cc(NC(=O)C2C(c3ccc(Cl)c(Cl)c3)C2(Cl)Cl)ccc1Cl] | 1 |
| F1147 | 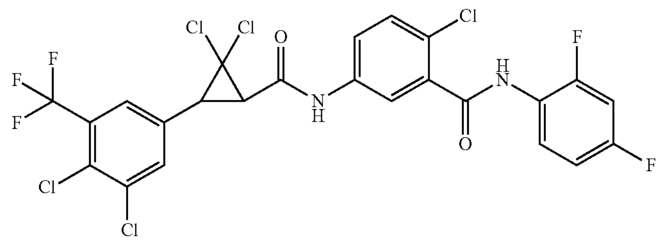 | 20 |
| F1148 | 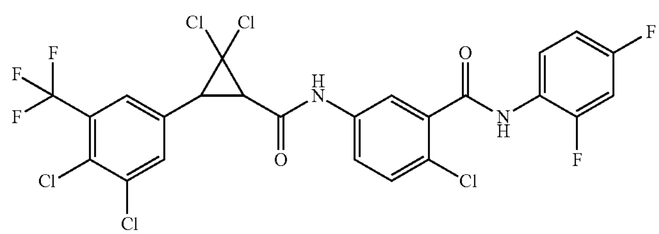 | 20 |
| F1149 | 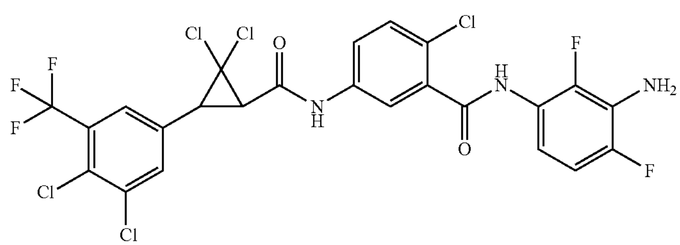 [SMILES: Nc1c(F)ccc(NC(=O)c2cc(NC(=O)C3C(c4cc(Cl)c(Cl)c(C(F)(F)F)c4)C3(Cl)Cl)ccc2Cl)c1F] | 12 |
| F1150 | 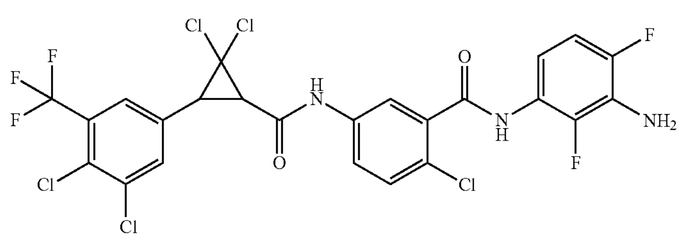 [SMILES: Nc1c(F)ccc(NC(=O)c2cc(NC(=O)C3C(c4cc(Cl)c(Cl)c(C(F)(F)F)c4)C3(Cl)Cl)ccc2Cl)c1F] | 12 |
| F1151 | 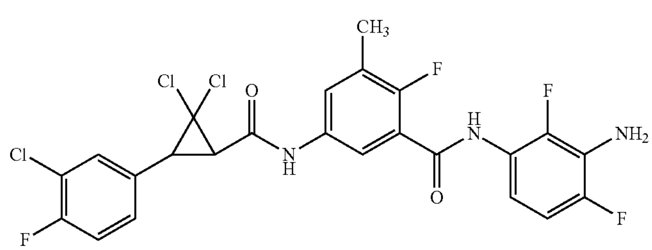 [SMILES: Cc1cc(NC(=O)C2C(c3ccc(F)c(Cl)c3)C2(Cl)Cl)cc(C(=O)Nc2ccc(F)c(N)c2F)c1F] | 13 |

TABLE 2-continued

Structure and preparation method for F Series molecules

| No. | Structure | Prep.* |
|---|---|---|
| F1152 | 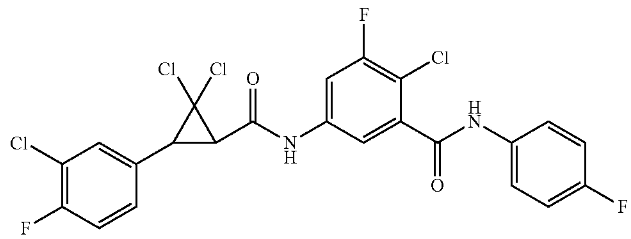 [SMILES: O=C(Nc1ccc(F)cc1)c1cc(NC(=O)C2C(c3ccc(F)c(Cl)c3)C2(Cl)Cl)cc(F)c1Cl] | 25 |
| F1153 | 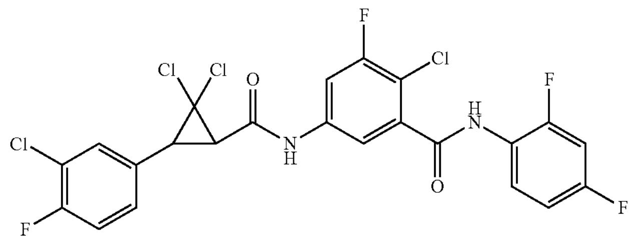 [SMILES: O=C(Nc1ccc(F)cc1F)c1cc(NC(=O)C2C(c3ccc(F)c(Cl)c3)C2(Cl)Cl)cc(F)c1Cl] | 25 |
| F1154 | 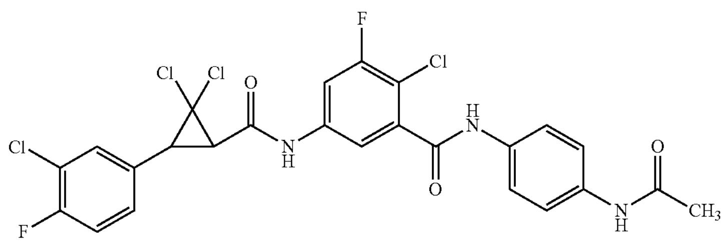 [SMILES: CC(=O)Nc1ccc(NC(=O)c2cc(NC(=O)C3C(c4ccc(F)c(Cl)c4)C3(Cl)Cl)cc(F)c2Cl)cc1] | 25 |
| F1155 | 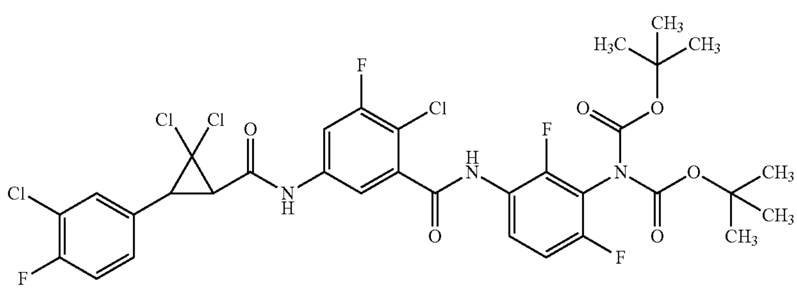 [SMILES: CC(C)(C)OC(=O)N(C(=O)OC(C)(C)C)c1c(F)ccc(NC(=O)c2cc(NC(=O)C3C(c4ccc(F)c(Cl)c4)C3(Cl)Cl)cc(F)c2Cl)c1F] | 25 |
| F1156 | 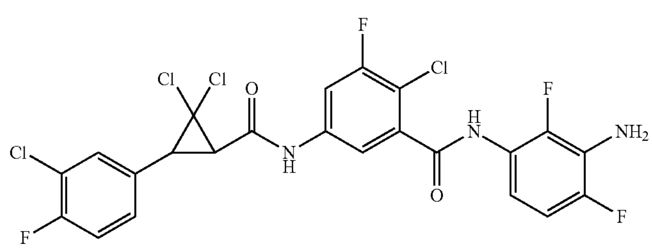 [SMILES: Nc1c(F)ccc(NC(=O)c2cc(NC(=O)C3C(c4ccc(F)c(Cl)c4)C3(Cl)Cl)cc(F)c2Cl)c1F] | 13 |

TABLE 2-continued

Structure and preparation method for F Series molecules

| No. | Structure | Prep.* |
|---|---|---|
| F1157 | 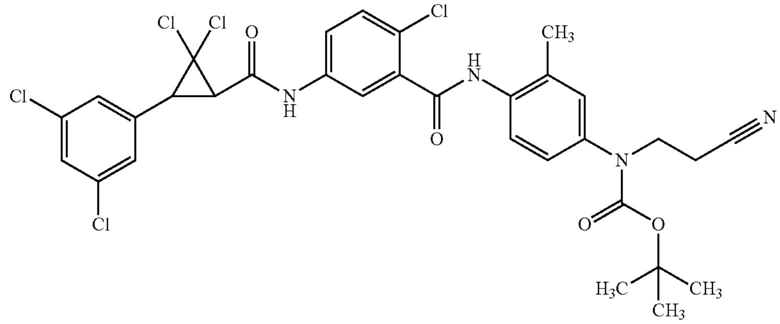 [SMILES: Cc1cc(N(CCC#N)C(=O)OC(C)(C)C)ccc1NC(=O)c1cc(NC(=O)C2C(c3cc(Cl)cc(Cl)c3)C2(Cl)Cl)ccc1Cl] | 25 |
| F1158 | 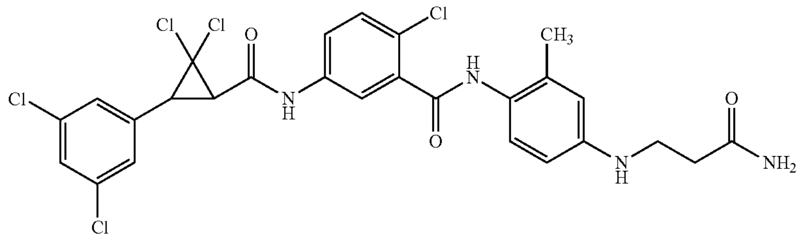 [SMILES: Cc1cc(NCCC(N)=O)ccc1NC(=O)c1cc(NC(=O)C2C(c3cc(Cl)cc(Cl)c3)C2(Cl)Cl)ccc1Cl] | 12 |
| F1159 | 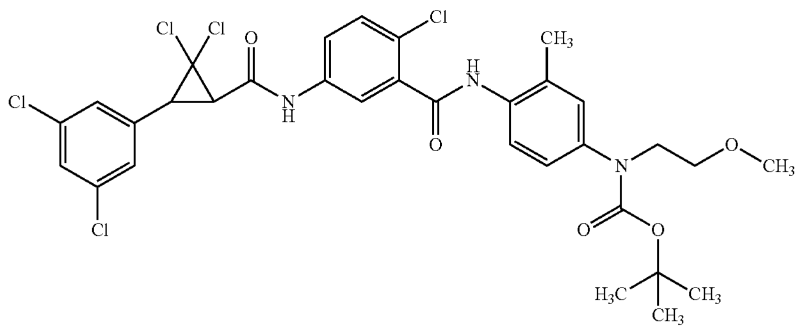 [SMILES: COCCN(C(=O)OC(C)(C)C)c1ccc(NC(=O)c2cc(NC(=O)C3C(c4cc(Cl)cc(Cl)c4)C3(Cl)Cl)ccc2Cl)c(C)c1] | 25 |
| F1160 | 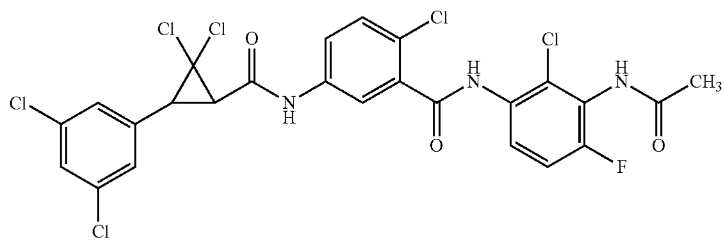 [SMILES: CC(=O)Nc1c(F)ccc(NC(=O)c2cc(NC(=O)C3C(c4cc(Cl)cc(Cl)c4)C3(Cl)Cl)ccc2Cl)c1Cl] | 25 |
| F1161 | 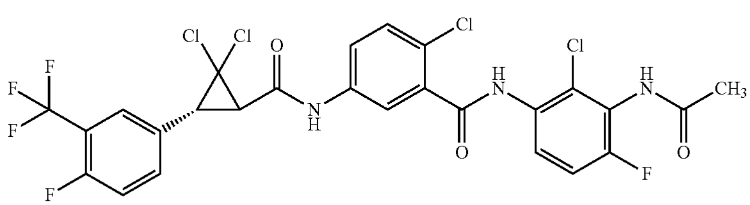 [SMILES: CC(=O)Nc1c(F)ccc(NC(=O)c2cc(NC(=O)C3[C@H](c4ccc(F)c(C(F)(F)F)c4)C3(Cl)Cl)ccc2Cl)c1Cl] | 25 |

TABLE 2-continued

Structure and preparation method for F Series molecules

| No. | Structure | Prep.* |
|---|---|---|
| F1162 | 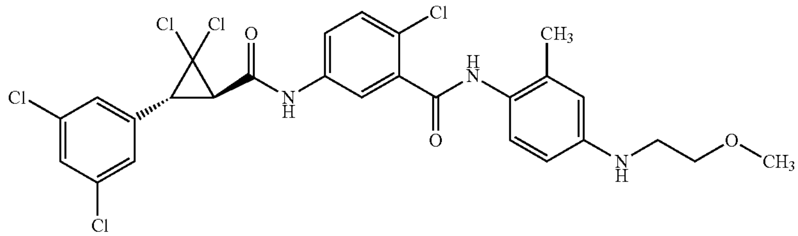 [SMILES: COCCNc1ccc(NC(=O)c2cc(NC(=O)[C@H]3[C@H](c4cc(Cl)cc(Cl)c4)C3(Cl)Cl)ccc2Cl)c(C)c1] | 12 |
| F1163 | 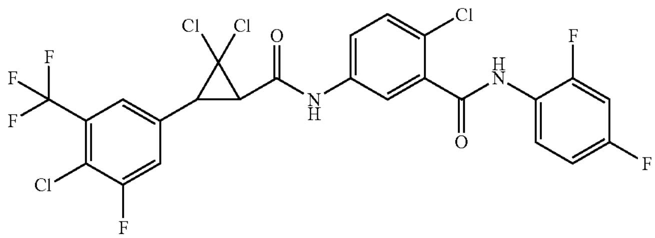 [SMILES: O=C(Nc1ccc(F)cc1F)c1cc(NC(=O)C2C(c3cc(F)c(Cl)c(C(F)(F)F)c3)C2(Cl)Cl)ccc1Cl] | 20 |
| F1164 | 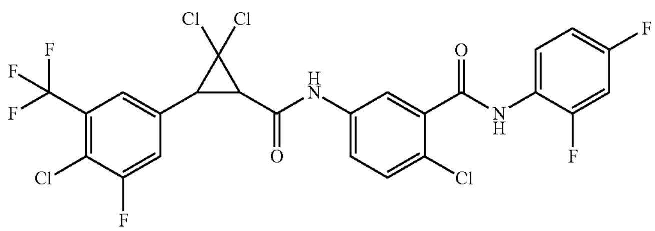 [SMILES: O=C(Nc1ccc(F)cc1F)c1cc(NC(=O)C2C(c3cc(F)c(Cl)c(C(F)(F)F)c3)C2(Cl)Cl)ccc1Cl] | 20 |
| F1165 | 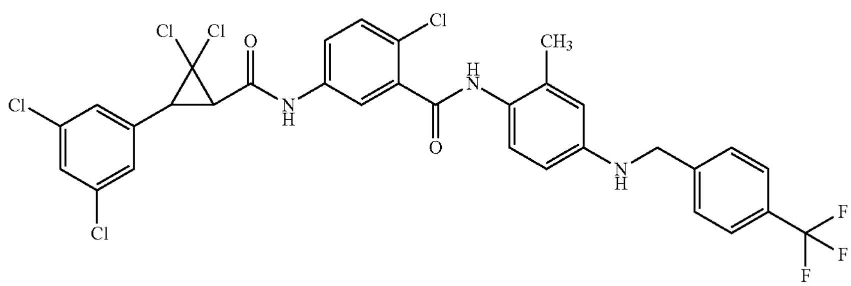 [SMILES: Cc1cc(NCc2ccc(C(F)(F)F)cc2)ccc1NC(=O)c1cc(NC(=O)C2C(c3cc(Cl)cc(Cl)c3)C2(Cl)Cl)ccc1Cl] | 10 |
| F1166 | 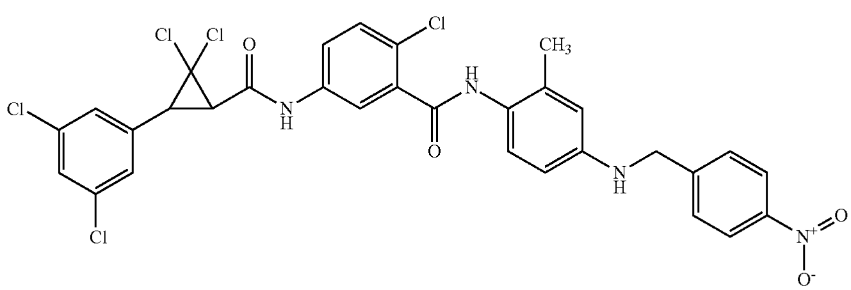 [SMILES: Cc1cc(NCc2ccc([N+](=O)[O-])cc2)ccc1NC(=O)c1cc(NC(=O)C2C(c3cc(Cl)cc(Cl)c3)C2(Cl)Cl)ccc1Cl] | 10 |
| F1167 | 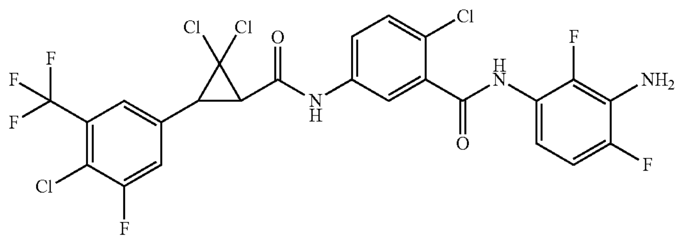 | 12 |

TABLE 2-continued

Structure and preparation method for F Series molecules

| No. | Structure | Prep.* |
|---|---|---|
| F1168 | 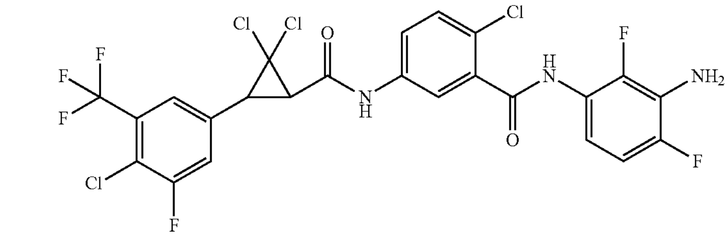 [SMILES: Nc1c(F)ccc(NC(=O)c2cc(NC(=O)C3C(c4cc(F)c(Cl)c(C(F)(F)F)c4)C3(Cl)Cl)ccc2Cl)c1F] | 12 |
| F1169 | 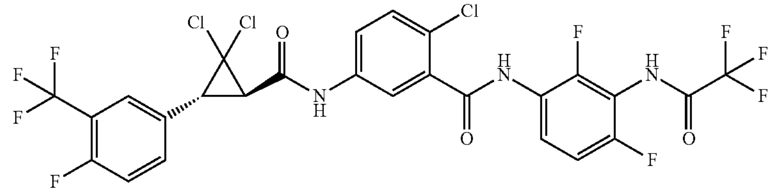 [SMILES: O=C(Nc1ccc(F)c(NC(=O)C(F)(F)F)c1F)c1cc(NC(=O)[C@H]2[C@H](c3ccc(F)c(C(F)(F)F)c3)C2(Cl)Cl)ccc1Cl] | 1 |
| F1170 | 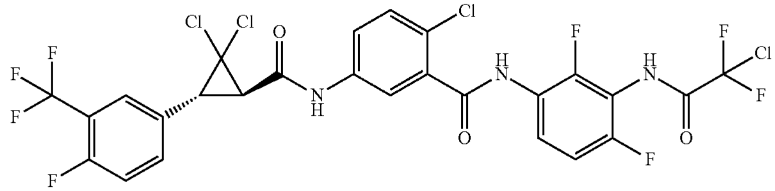 [SMILES: O=C(Nc1ccc(F)c(NC(=O)C(F)(F)Cl)c1F)c1cc(NC(=O)[C@H]2[C@H](c3ccc(F)c(C(F)(F)F)c3)C2(Cl)Cl)ccc1Cl] | 1 |
| F1171 | 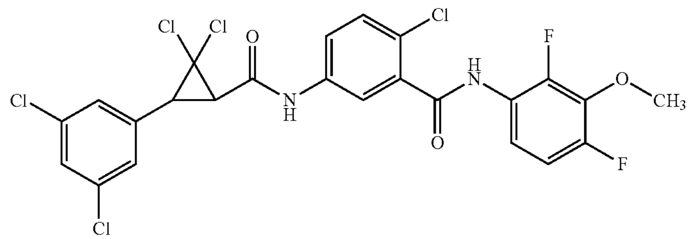 [SMILES: COc1c(F)ccc(NC(=O)c2cc(NC(=O)C3C(c4cc(Cl)cc(Cl)c4)C3(Cl)Cl)ccc2Cl)c1F] | 22 |
| F1172 | 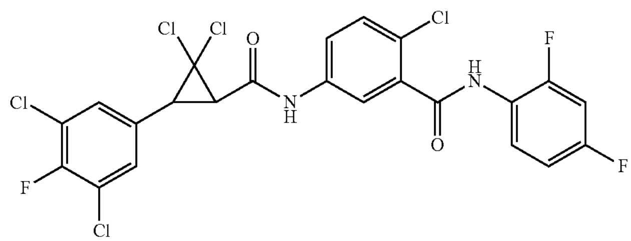 | 20 |
| F1173 | 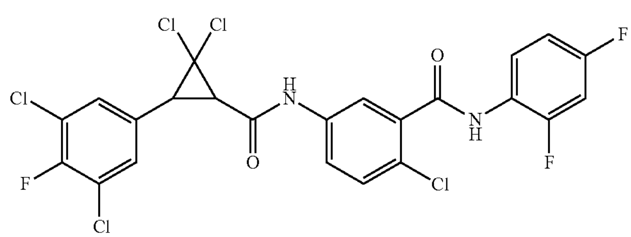 [SMILES: O=C(Nc1ccc(F)cc1F)c1cc(NC(=O)C2C(c3cc(Cl)c(F)c(Cl)c3)C2(Cl)Cl)ccc1Cl] | 20 |
| F1174 | 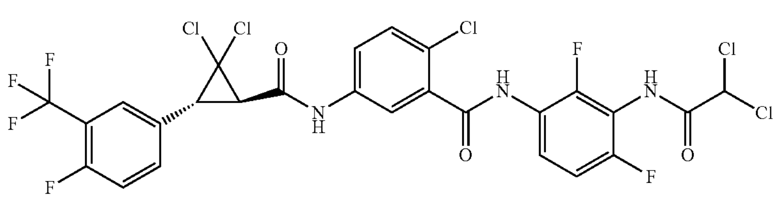 [SMILES: O=C(Nc1ccc(F)c(NC(=O)C(Cl)Cl)c1F)c1cc(NC(=O)[C@H]2[C@H](c3ccc(F)c(C(F)(F)F)c3)C2(Cl)Cl)ccc1Cl] | 1 |

TABLE 2-continued

Structure and preparation method for F Series molecules

| No. | Structure | Prep.* |
|---|---|---|
| F1176 | 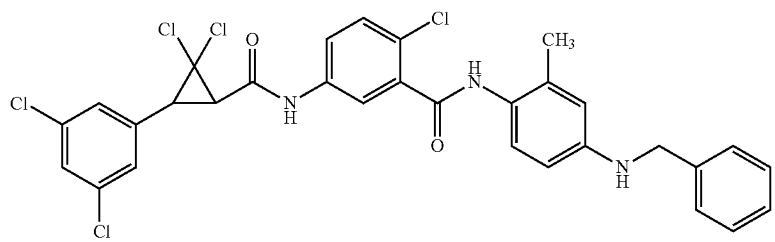 [SMILES: Cc1cc(NCc2ccccc2)ccc1NC(=O)c1cc(NC(=O)C2C(c3cc(Cl)cc(Cl)c3)C2(Cl)Cl)ccc1Cl] | 10 |
| F1177 | 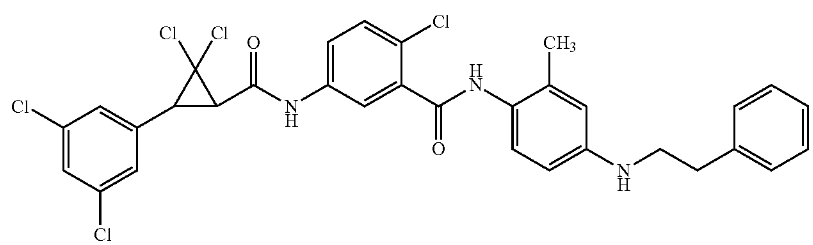 [SMILES: Cc1cc(NCCc2ccccc2)ccc1NC(=O)c1cc(NC(=O)C2C(c3cc(Cl)cc(Cl)c3)C2(Cl)Cl)ccc1Cl] | 10 |
| F1178 | 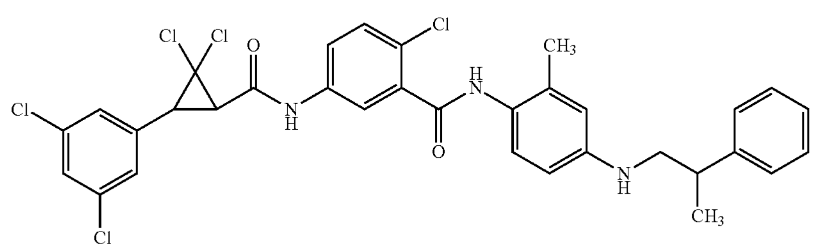 [SMILES: Cc1cc(NCC(C)c2ccccc2)ccc1NC(=O)c1cc(NC(=O)C2C(c3cc(Cl)cc(Cl)c3)C2(Cl)Cl)ccc1Cl] | 10 |
| F1179 | 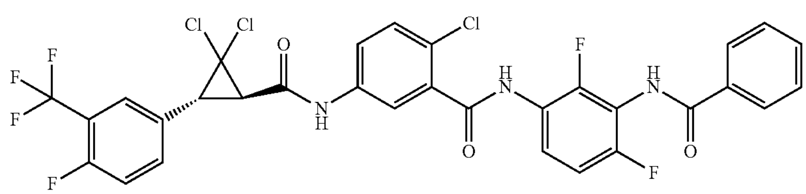 [SMILES: O=C(Nc1c(F)ccc(NC(=O)c2cc(NC(=O)[C@H]3[C@H](c4ccc(F)c(C(F)(F)F)c4)C3(Cl)Cl)ccc2Cl)c1F)c1ccccc1] | 1 |
| F1180 | 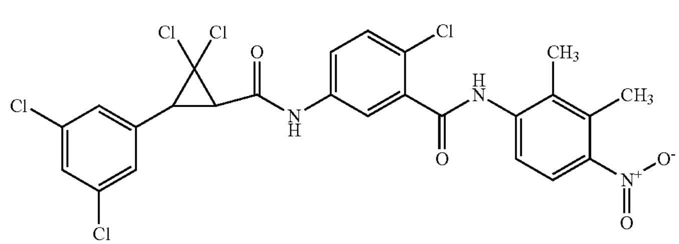 [SMILES: Cc1c(NC(=O)c2cc(NC(=O)C3C(c4cc(Cl)cc(Cl)c4)C3(Cl)Cl)ccc2Cl)ccc([N+](=O)[O-])c1C] | 25 |
| F1181 | 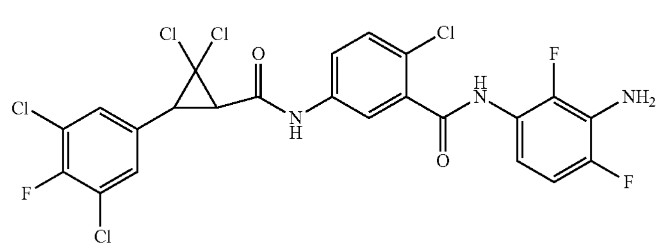 [SMILES: Nc1c(F)ccc(NC(=O)c2cc(NC(=O)C3C(c4cc(Cl)c(F)c(Cl)c4)C3(Cl)Cl)ccc2Cl)c1F] | 12 |

TABLE 2-continued

Structure and preparation method for F Series molecules

| No. | Structure | Prep.* |
|---|---|---|
| F1182 | 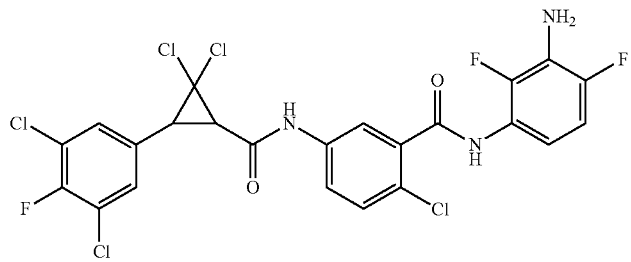 [SMILES: Nc1c(F)ccc(NC(=O)c2cc(NC(=O)C3C(c4cc(Cl)c(F)c(Cl)c4)C3(Cl)Cl)ccc2Cl)c1F] | 12 |
| F1183 | 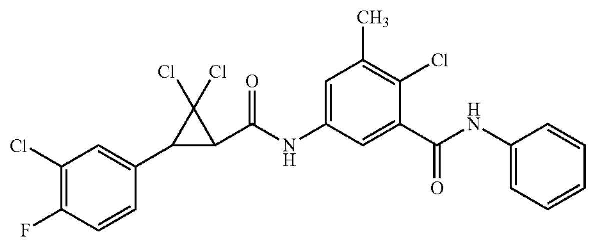 [SMILES: Cc1cc(NC(=O)C2C(c3ccc(F)c(Cl)c3)C2(Cl)Cl)cc(C(=O)Nc2ccccc2)c1Cl] | 25 |
| F1184 | 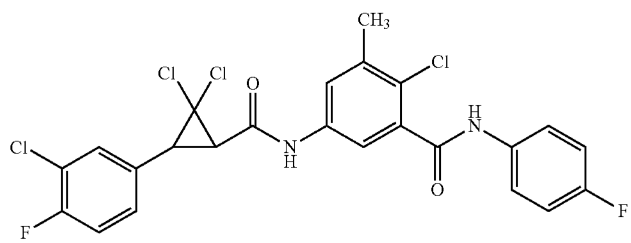 | 25 |
| F1185 | 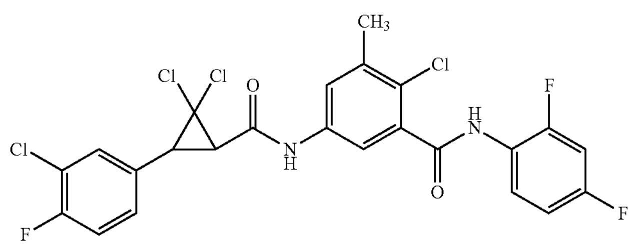 [SMILES: Cc1cc(NC(=O)C2C(c3ccc(F)c(Cl)c3)C2(Cl)Cl)cc(C(=O)Nc2ccc(F)cc2F)c1Cl] | 25 |
| F1186 | 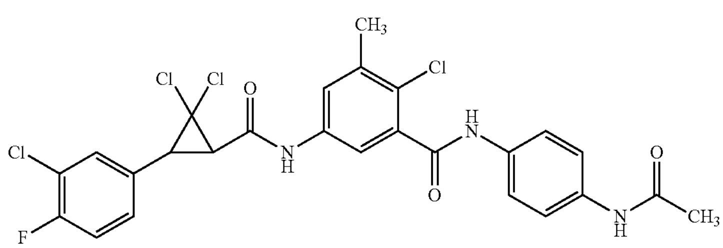 [SMILES: CC(=O)Nc1ccc(NC(=O)c2cc(NC(=O)C3C(c4ccc(F)c(Cl)c4)C3(Cl)Cl)cc(C)c2Cl)cc1] | 25 |
| F1187 | 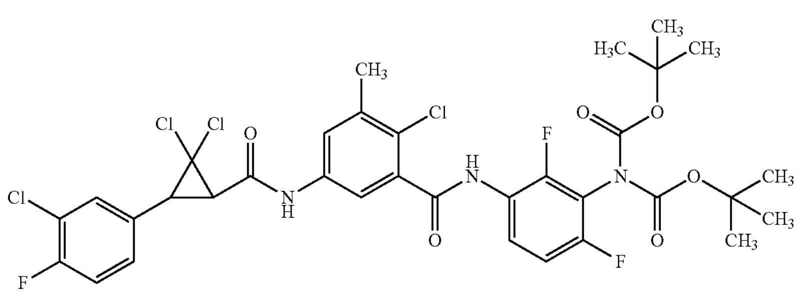 | 25 |

TABLE 2-continued

Structure and preparation method for F Series molecules

| No. | Structure | Prep.* |
|---|---|---|
| F1188 | 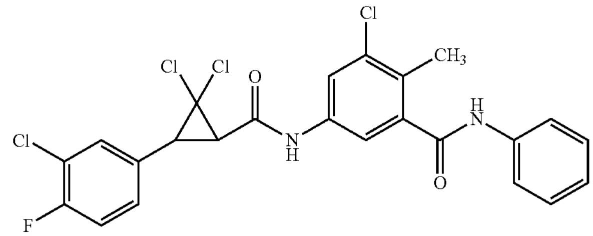 [SMILES: Cc1c(Cl)cc(NC(=O)C2C(c3ccc(F)c(Cl)c3)C2(Cl)Cl)cc1C(=O)Nc1ccccc1] | 25 |
| F1189 | 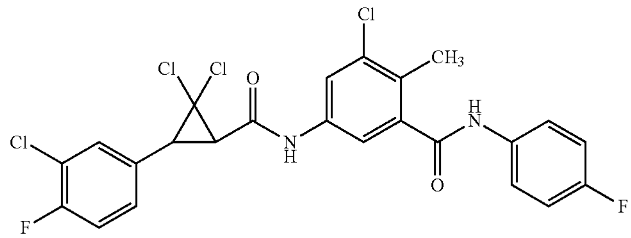 [SMILES: Cc1c(Cl)cc(NC(=O)C2C(c3ccc(F)c(Cl)c3)C2(Cl)Cl)cc1C(=O)Nc1ccc(F)cc1] | 25 |
| F1190 | 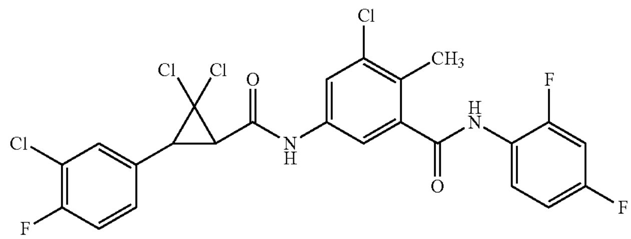 | 25 |
| F1191 | 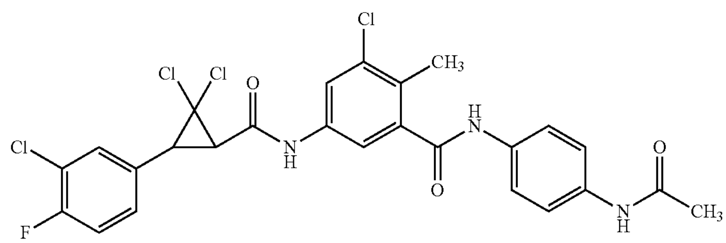 [SMILES: CC(=O)Nc1ccc(NC(=O)c2cc(NC(=O)C3C(c4ccc(F)c(Cl)c4)C3(Cl)Cl)cc(Cl)c2C)cc1] | 25 |
| F1192 | 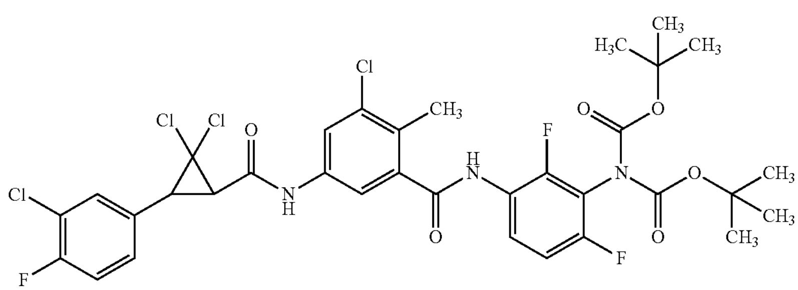 [SMILES: Cc1c(Cl)cc(NC(=O)C2C(c3ccc(F)c(Cl)c3)C2(Cl)Cl)cc1C(=O)Nc1ccc(F)c(N(C(=O)OC(C)(C)C)C(=O)OC(C)(C)C)c1F] | 25 |
| F1193 | 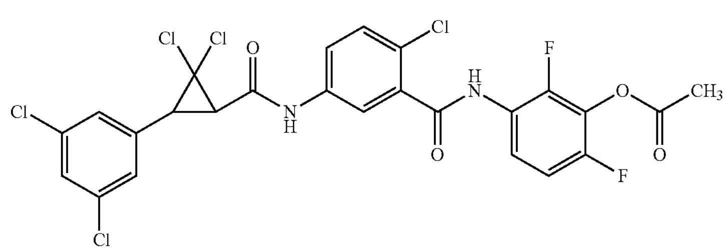 [SMILES: CC(=O)Oc1c(F)ccc(NC(=O)c2cc(NC(=O)C3C(c4cc(Cl)cc(Cl)c4)C3(Cl)Cl)ccc2Cl)c1F] | 22 |

TABLE 2-continued

Structure and preparation method for F Series molecules

| No. | Structure | Prep.* |
|---|---|---|
| F1194 | 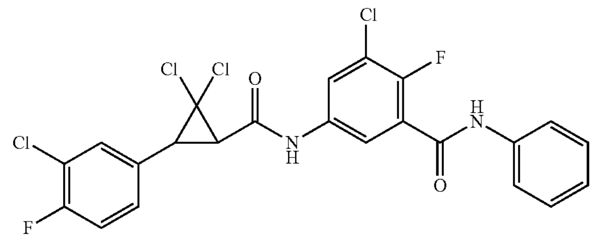 | 25 |
| F1195 | 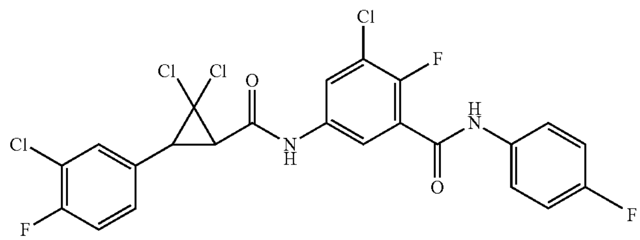 | 25 |
| F1196 | 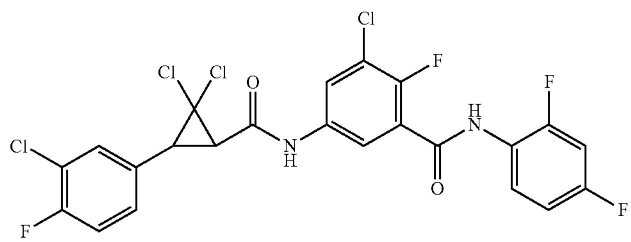 | 25 |
| F1197 | 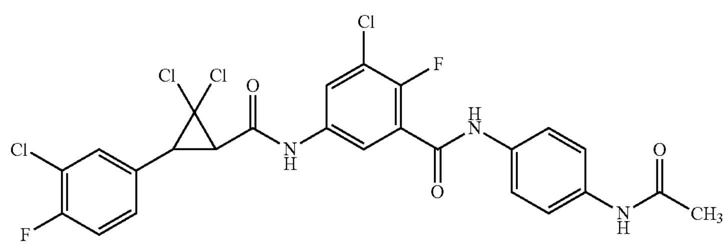 | 25 |
| F1198 | 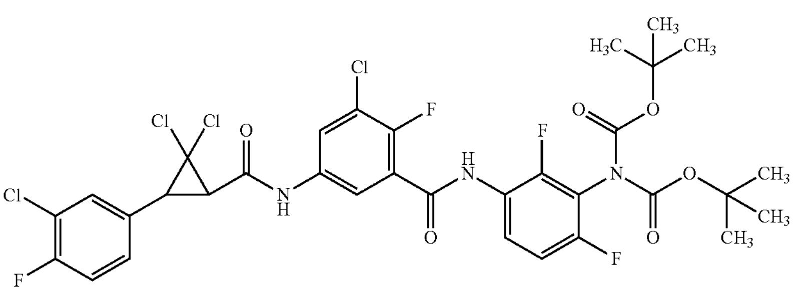 | 25 |
| F1199 | 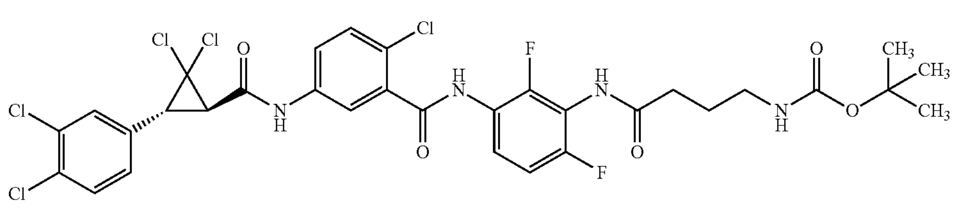 [SMILES: CC(C)(C)OC(=O)NCCCC(=O)Nc1c(F)ccc(NC(=O)c2cc(NC(=O)[C@H]3[C@H](c4ccc(Cl)c(Cl)c4)C3(Cl)Cl)ccc2Cl)c1F] | 4 |

TABLE 2-continued

Structure and preparation method for F Series molecules

| No. | Structure | Prep.* |
|---|---|---|
| F1200 | 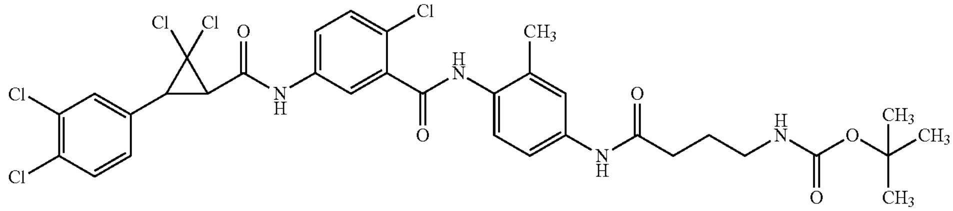 [SMILES: Cc1cc(NC(=O)CCCNC(=O)OC(C)(C)C)ccc1NC(=O)c1cc(NC(=O)C2C(c3ccc(Cl)c(Cl)c3)C2(Cl)Cl)ccc1Cl] | 4 |
| F1201 | 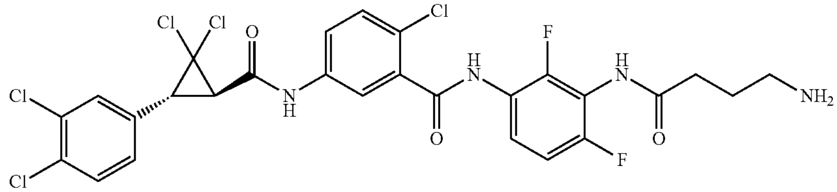 [SMILES: NCCCC(=O)Nc1c(F)ccc(NC(=O)c2cc(NC(=O)[C@H]3[C@H](c4ccc(Cl)c(Cl)c4)C3(Cl)Cl)ccc2Cl)c1F] | 13 |
| F1202 | 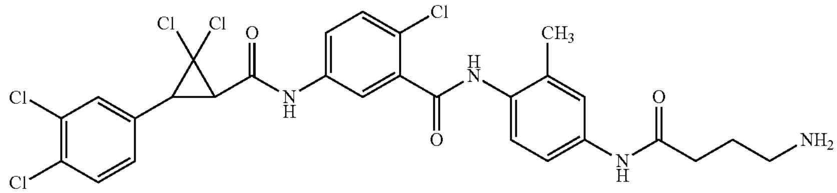 [SMILES: Cc1cc(NC(=O)CCCN)ccc1NC(=O)c1cc(NC(=O)C2C(c3ccc(Cl)c(Cl)c3)C2(Cl)Cl)ccc1Cl] | 13 |
| F1203 | 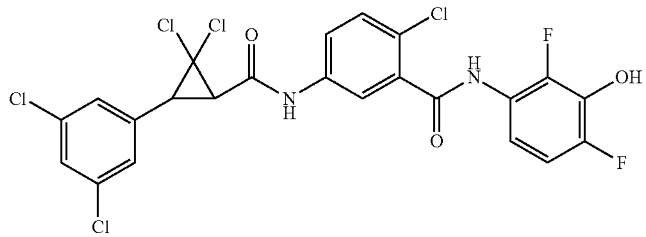 [SMILES: O=C(Nc1ccc(F)c(O)c1F)c1cc(NC(=O)C2C(c3cc(Cl)cc(Cl)c3)C2(Cl)Cl)ccc1Cl] | 16 |
| F1204 | 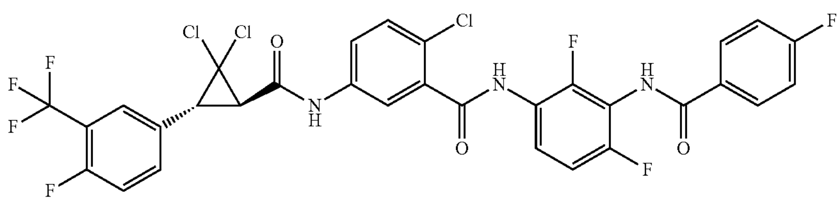 [SMILES: O=C(Nc1c(F)ccc(NC(=O)c2cc(NC(=O)[C@H]3[C@H](c4ccc(F)c(C(F)(F)F)c4)C3(Cl)Cl)ccc2Cl)c1F)c1ccc(F)cc1] | 4 |
| F1205 | 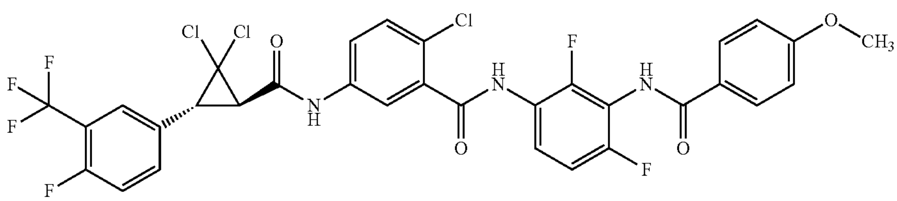 [SMILES: COc1ccc(C(=O)Nc2c(F)ccc(NC(=O)c3cc(NC(=O)[C@H]4[C@H](c5ccc(F)c(C(F)(F)F)c5)C4(Cl)Cl)ccc3Cl)c2F)cc1] | 4 |
| F1206 | 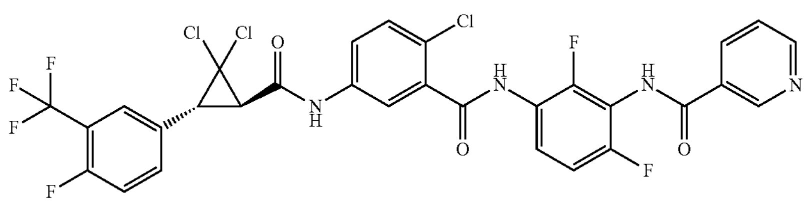 [SMILES: O=C(Nc1c(F)ccc(NC(=O)c2cc(NC(=O)[C@H]3[C@H](c4ccc(F)c(C(F)(F)F)c4)C3(Cl)Cl)ccc2Cl)c1F)c1cccnc1] | 4 |

TABLE 2-continued

Structure and preparation method for F Series molecules

| No. | Structure | Prep.* |
|---|---|---|
| F1207 | 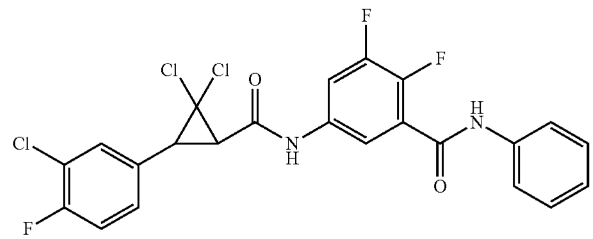 [SMILES: O=C(Nc1ccccc1)c1cc(NC(=O)C2C(c3ccc(F)c(Cl)c3)C2(Cl)Cl)cc(F)c1F] | 25 |
| F1208 | 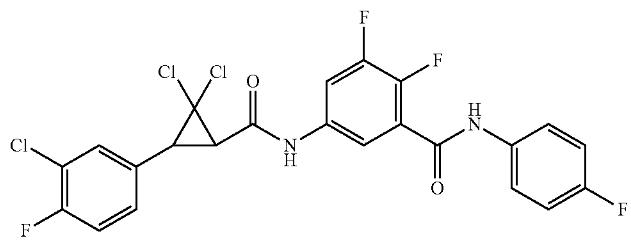 [SMILES: O=C(Nc1ccc(F)cc1)c1cc(NC(=O)C2C(c3ccc(F)c(Cl)c3)C2(Cl)Cl)cc(F)c1F] | 25 |
| F1209 | 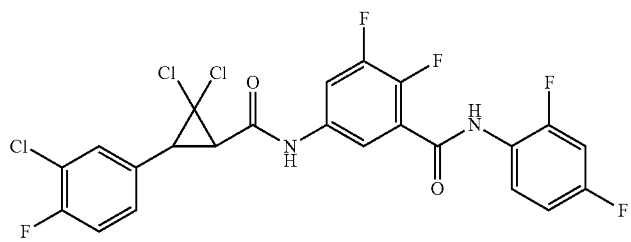 [SMILES: O=C(Nc1ccc(F)cc1F)c1cc(NC(=O)C2C(c3ccc(F)c(Cl)c3)C2(Cl)Cl)cc(F)c1F] | 25 |
| F1210 | 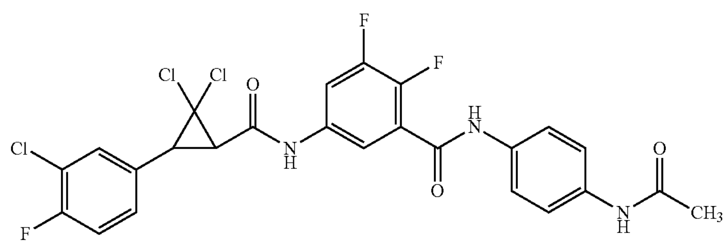 [SMILES: CC(=O)Nc1ccc(NC(=O)c2cc(NC(=O)C3C(c4ccc(F)c(Cl)c4)C3(Cl)Cl)cc(F)c2F)cc1] | 25 |
| F1211 | 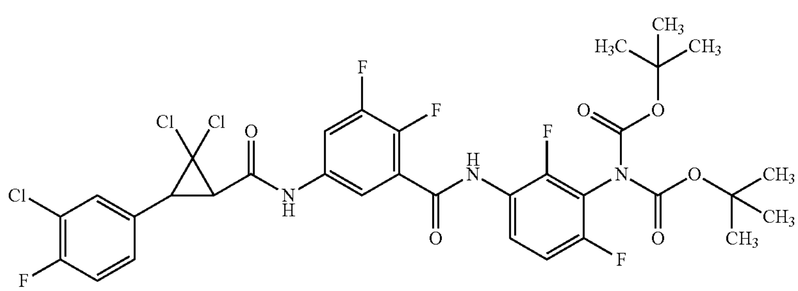 [SMILES: CC(C)(C)OC(=O)N(C(=O)OC(C)(C)C)c1c(F)ccc(NC(=O)c2cc(NC(=O)C3C(c4ccc(F)c(Cl)c4)C3(Cl)Cl)cc(F)c2F)c1F] | 25 |
| F1212 | 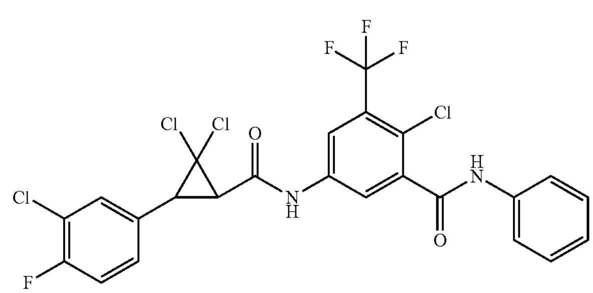 [SMILES: O=C(Nc1ccccc1)c1cc(NC(=O)C2C(c3ccc(F)c(Cl)c3)C2(Cl)Cl)cc(C(F)(F)F)c1Cl] | 25 |

TABLE 2-continued

Structure and preparation method for F Series molecules

| No. | Structure | Prep.* |
|---|---|---|
| F1213 | 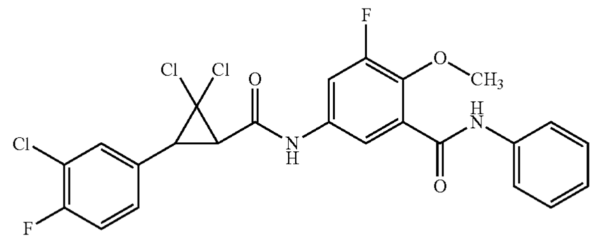 [SMILES: COc1c(F)cc(NC(=O)C2C(c3ccc(F)c(Cl)c3)C2(Cl)Cl)cc1C(=O)Nc1ccccc1] | 25 |
| F1214 | 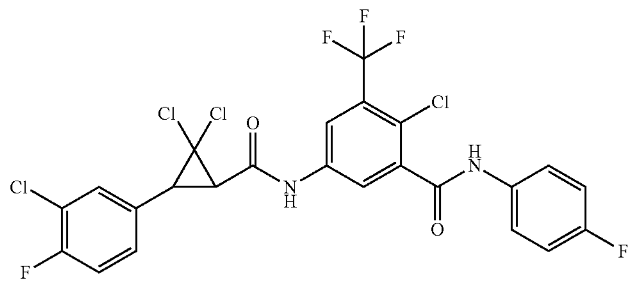 [SMILES: O=C(Nc1ccc(F)cc1)c1cc(NC(=O)C2C(c3ccc(F)c(Cl)c3)C2(Cl)Cl)cc(C(F)(F)F)c1Cl] | 25 |
| F1215 | 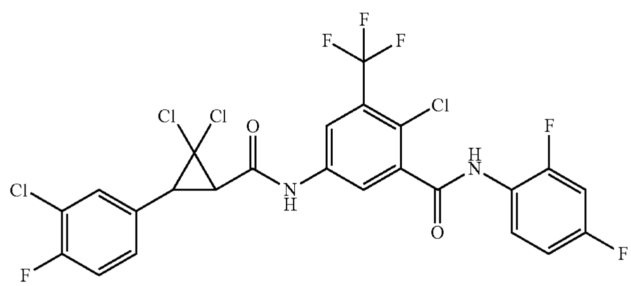 [SMILES: O=C(Nc1ccc(F)cc1F)c1cc(NC(=O)C2C(c3ccc(F)c(Cl)c3)C2(Cl)Cl)cc(C(F)(F)F)c1Cl] | 25 |
| F1216 | 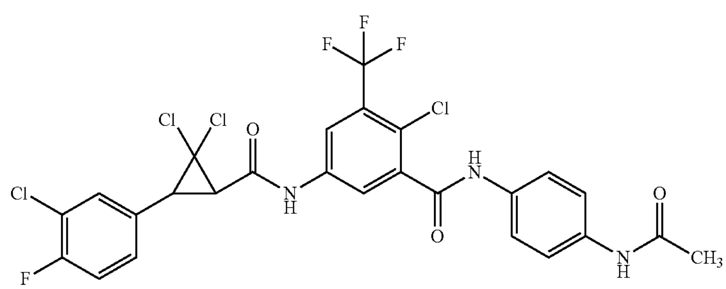 [SMILES: CC(=O)Nc1ccc(NC(=O)c2cc(NC(=O)C3C(c4ccc(F)c(Cl)c4)C3(Cl)Cl)cc(C(F)(F)F)c2Cl)cc1] | 25 |
| F1217 | 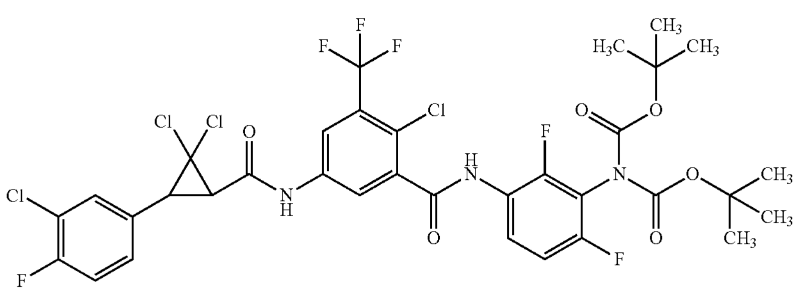 [SMILES: CC(C)(C)OC(=O)N(C(=O)OC(C)(C)C)c1c(F)ccc(NC(=O)c2cc(NC(=O)C3C(c4ccc(F)c(Cl)c4)C3(Cl)Cl)cc(C(F)(F)F)c2Cl)c1F] | 25 |

TABLE 2-continued

Structure and preparation method for F Series molecules

| No. | Structure | Prep.* |
|---|---|---|
| F1218 | 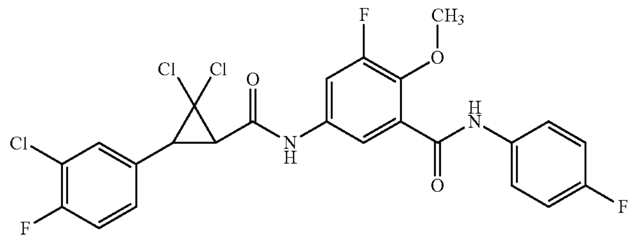 [SMILES: COc1c(F)cc(NC(=O)C2C(c3ccc(F)c(Cl)c3)C2(Cl)Cl)cc1C(=O)Nc1ccc(F)cc1] | 25 |
| F1219 | 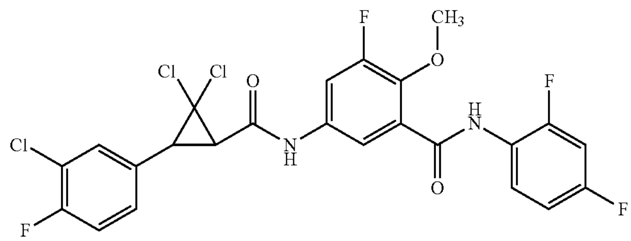 [SMILES: COc1c(F)cc(NC(=O)C2C(c3ccc(F)c(Cl)c3)C2(Cl)Cl)cc1C(=O)Nc1ccc(F)cc1F] | 25 |
| F1220 | 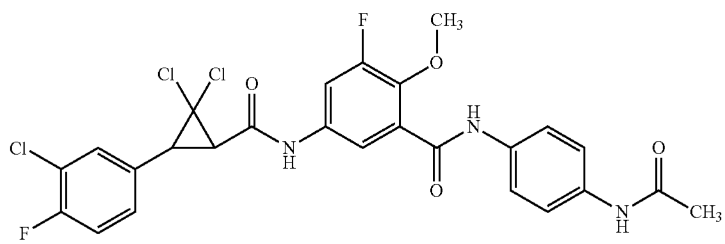 [SMILES: COc1c(F)cc(NC(=O)C2C(c3ccc(F)c(Cl)c3)C2(Cl)Cl)cc1C(=O)Nc1ccc(NC(C)=O)cc1] | 25 |
| F1221 | 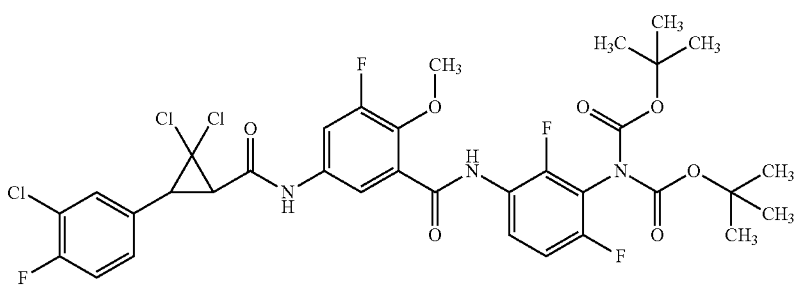 | 25 |
| F1222 | 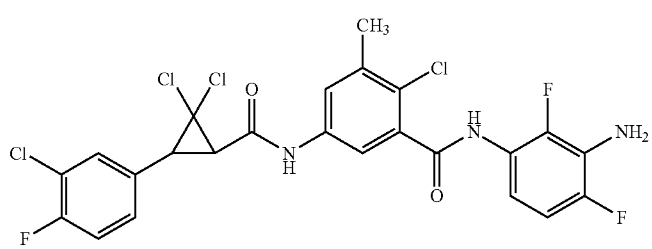 [SMILES: Cc1cc(NC(=O)C2C(c3ccc(F)c(Cl)c3)C2(Cl)Cl)cc(C(=O)Nc2ccc(F)c(N)c2F)c1Cl] | 13 |
| F1223 | 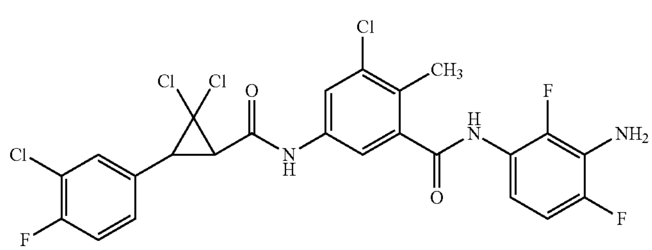 | 13 |

TABLE 2-continued

Structure and preparation method for F Series molecules

| No. | Structure | Prep.* |
|---|---|---|
| F1224 | 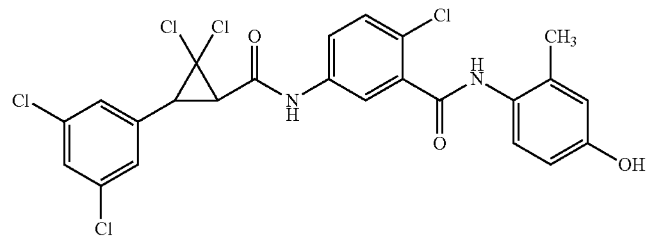 [SMILES: Cc1cc(O)ccc1NC(=O)c1cc(NC(=O)C2C(c3cc(Cl)cc(Cl)c3)C2(Cl)Cl)ccc1Cl] | 23 |
| F1225 | 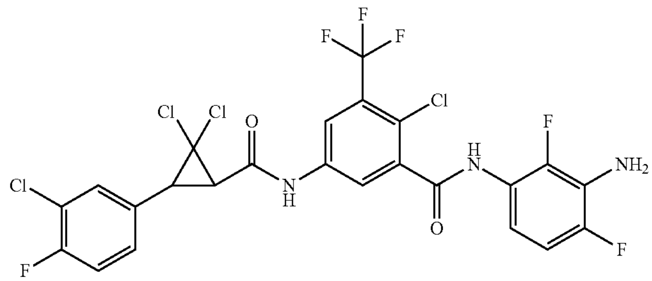 [SMILES: Nc1c(F)ccc(NC(=O)c2cc(NC(=O)C3C(c4ccc(F)c(Cl)c4)C3(Cl)Cl)cc(C(F)(F)F)c2Cl)c1F] | 13 |
| F1226 | 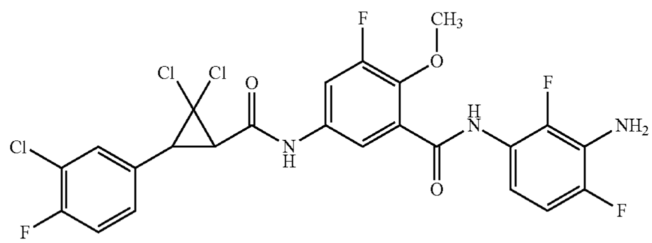 [SMILES: COc1c(F)cc(NC(=O)C2C(c3ccc(F)c(Cl)c3)C2(Cl)Cl)cc1C(=O)Nc1ccc(F)c(N)c1F] | 13 |
| F1227 | 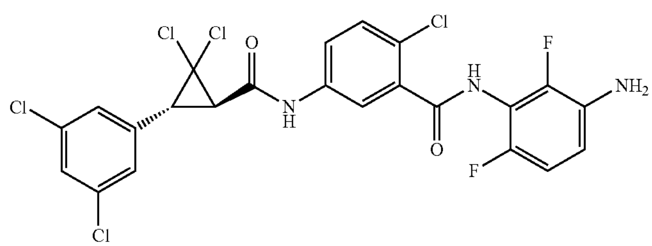 [SMILES: Nc1ccc(F)c(NC(=O)c2cc(NC(=O)[C@H]3[C@H](c4cc(Cl)cc(Cl)c4)C3(Cl)Cl)ccc2Cl)c1F] | 13 |
| F1228 | 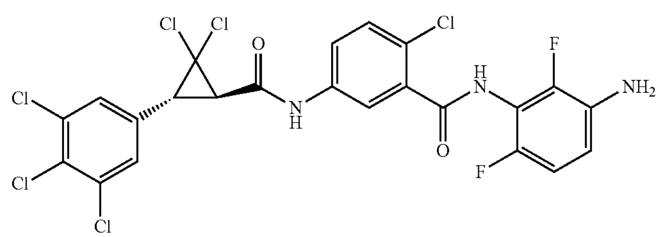 [SMILES: Nc1ccc(F)c(NC(=O)c2cc(NC(=O)[C@H]3[C@H](c4cc(Cl)c(Cl)c(Cl)c4)C3(Cl)Cl)ccc2Cl)c1F] | 13 |
| F1229 | 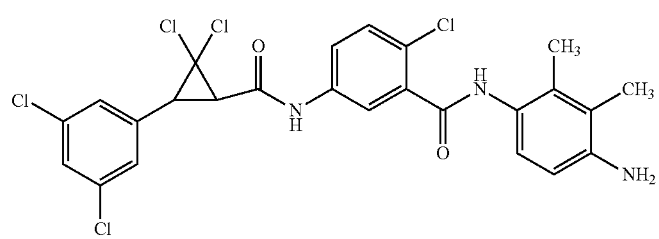 [SMILES: Cc1c(N)ccc(NC(=O)c2cc(NC(=O)C3C(c4cc(Cl)cc(Cl)c4)C3(Cl)Cl)ccc2Cl)c1C] | 15 |

TABLE 2-continued

Structure and preparation method for F Series molecules

| No. | Structure | Prep.* |
|---|---|---|
| F1231 | 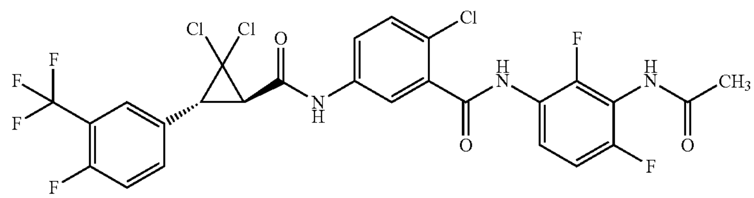 [SMILES: CC(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 4 |
| F1232 | 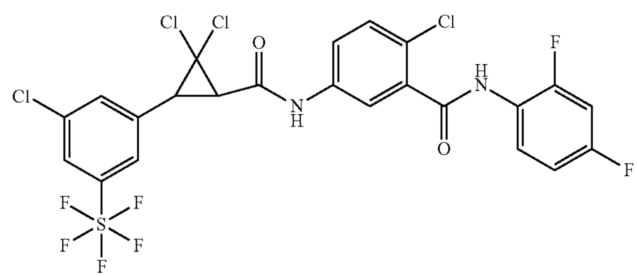 [SMILES: O=C(Nc1ccc(F)cc1F)c1cc(NC(=O)C2C(c3cc(Cl)cc(S(F)(F)(F)(F)F)c3)C2(Cl)Cl)ccc1Cl] | 20 |
| F1233 | 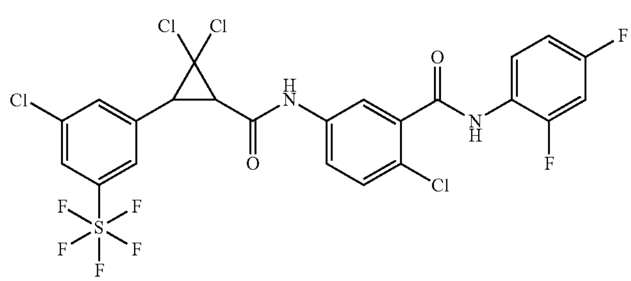 [SMILES: O=C(Nc1ccc(F)cc1F)c1cc(NC(=O)C2C(c3cc(Cl)cc(S(F)(F)(F)(F)F)c3)C2(Cl)Cl)ccc1Cl] | 20 |
| F1234 | 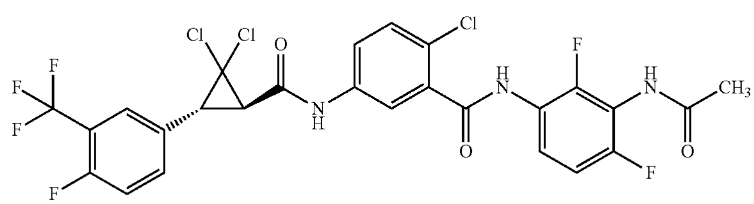 [SMILES: CC(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 2 |
| F1235 | 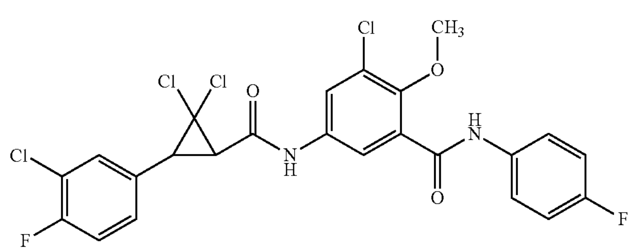 | 25 |
| F1236 | 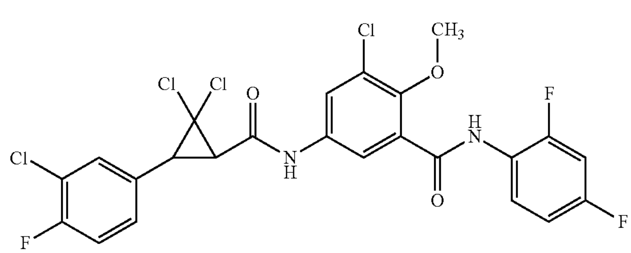 [SMILES: COc1c(Cl)cc(NC(=O)C2C(c3ccc(F)c(Cl)c3)C2(Cl)Cl)cc1C(=O)Nc1ccc(F)cc1F] | 25 |

TABLE 2-continued

Structure and preparation method for F Series molecules

| No. | Structure | Prep.* |
|---|---|---|
| F1237 | 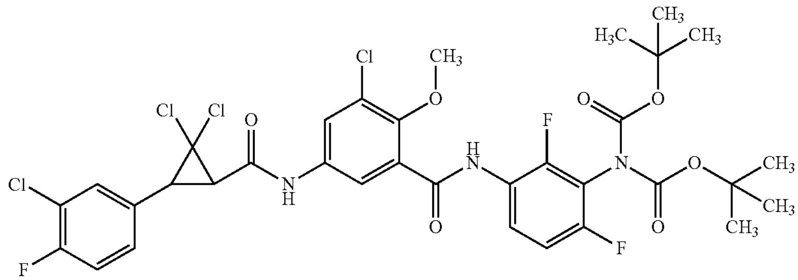 [SMILES: COc1c(Cl)cc(NC(=O)C2C(c3ccc(F)c(Cl)c3)C2(Cl)Cl)cc1C(=O)Nc1ccc(F)c(N(C(=O)OC(C)(C)C)C(=O)OC(C)(C)C)c1F] | 25 |
| F1238 | 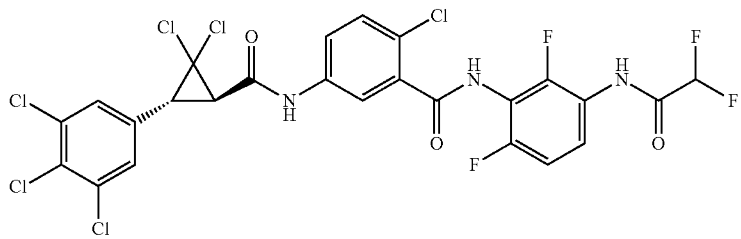 [SMILES: O=C(Nc1c(F)ccc(NC(=O)C(F)F)c1F)c1cc(NC(=O)[C@H]2[C@H](c3cc(Cl)c(Cl)c(Cl)c3)C2(Cl)Cl)ccc1Cl] | 2 |
| F1239 | 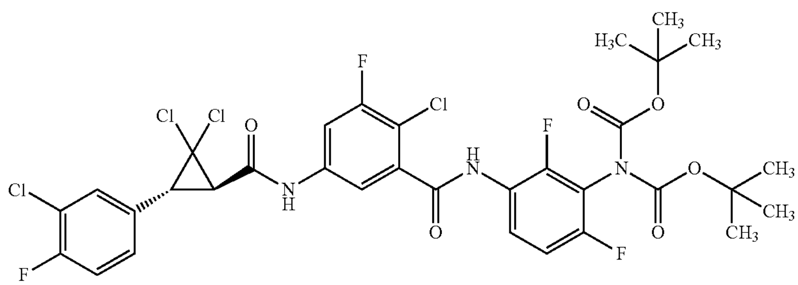 [SMILES: CC(C)(C)OC(=O)N(C(=O)OC(C)(C)C)c1c(F)ccc(NC(=O)c2cc(NC(=O)[C@H]3[C@H](c4ccc(F)c(Cl)c4)C3(Cl)Cl)cc(F)c2Cl)c1F] | 25 |
| F1240 | 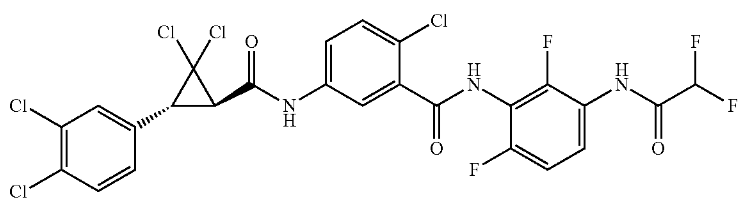 [SMILES: O=C(Nc1c(F)ccc(NC(=O)C(F)F)c1F)c1cc(NC(=O)[C@H]2[C@H](c3ccc(Cl)c(Cl)c3)C2(Cl)Cl)ccc1Cl] | 2 |
| F1241 | 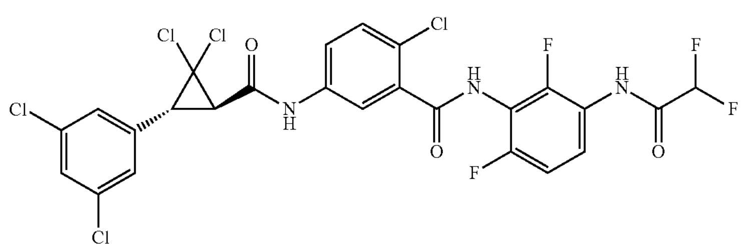 [SMILES: O=C(Nc1c(F)ccc(NC(=O)C(F)F)c1F)c1cc(NC(=O)[C@H]2[C@H](c3cc(Cl)cc(Cl)c3)C2(Cl)Cl)ccc1Cl] | 2 |
| F1242 | 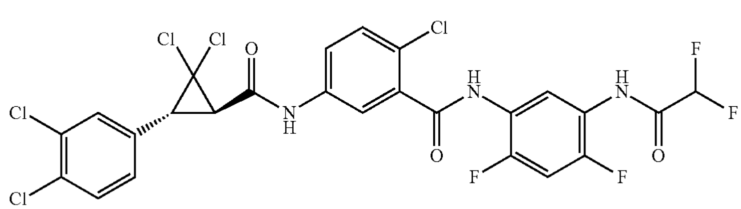 [SMILES: O=C(Nc1cc(NC(=O)C(F)F)c(F)cc1F)c1cc(NC(=O)[C@H]2[C@H](c3ccc(Cl)c(Cl)c3)C2(Cl)Cl)ccc1Cl] | 2 |

TABLE 2-continued

Structure and preparation method for F Series molecules

| No. | Structure | Prep.* |
|---|---|---|
| F1243 | 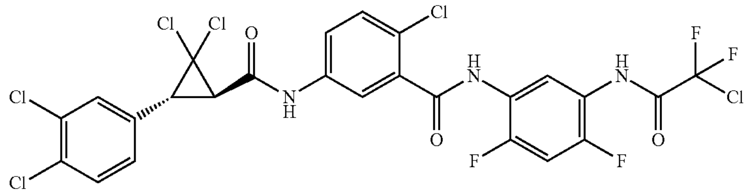 [SMILES: O=C(Nc1cc(NC(=O)C(F)(F)Cl)c(F)cc1F)c1cc(NC(=O)[C@H]2[C@H](c3ccc(Cl)c(Cl)c3)C2(Cl)Cl)ccc1Cl] | 2 |
| F1244 | 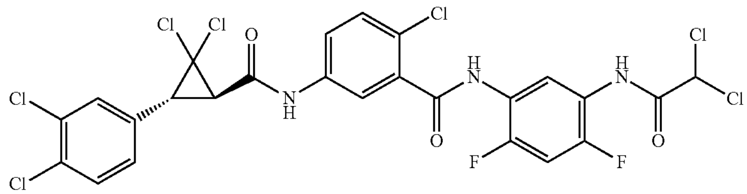 [SMILES: O=C(Nc1cc(NC(=O)C(Cl)Cl)c(F)cc1F)c1cc(NC(=O)[C@H]2[C@H](c3ccc(Cl)c(Cl)c3)C2(Cl)Cl)ccc1Cl] | 2 |
| F1245 | 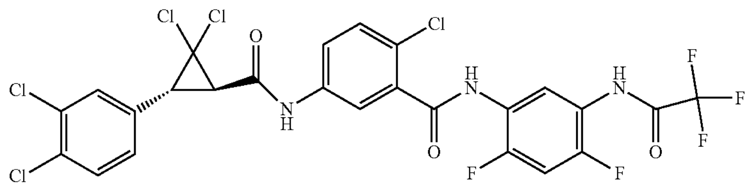 [SMILES: O=C(Nc1cc(NC(=O)C(F)(F)F)c(F)cc1F)c1cc(NC(=O)[C@H]2[C@H](c3ccc(Cl)c(Cl)c3)C2(Cl)Cl)ccc1Cl] | 2 |
| F1246 | 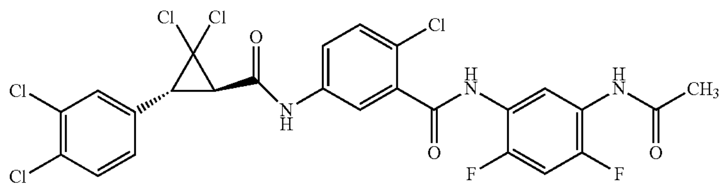 [SMILES: CC(=O)Nc1cc(NC(=O)c2cc(NC(=O)[C@H]3[C@H](c4ccc(Cl)c(Cl)c4)C3(Cl)Cl)ccc2Cl)c(F)cc1F] | 2 |
| F1247 | 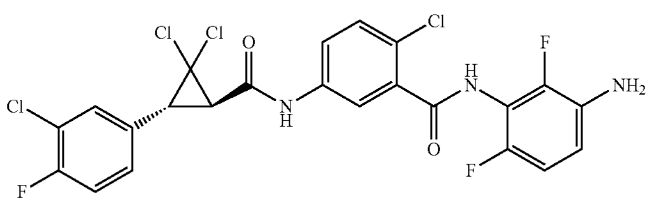 [SMILES: Nc1ccc(F)c(NC(=O)c2cc(NC(=O)[C@H]3[C@H](c4ccc(F)c(Cl)c4)C3(Cl)Cl)ccc2Cl)c1F] | 13 |
| F1248 | 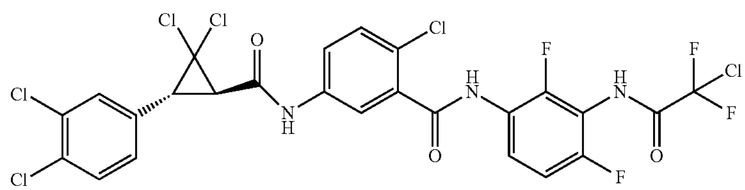 [SMILES: O=C(Nc1ccc(F)c(NC(=O)C(F)(F)Cl)c1F)c1cc(NC(=O)[C@H]2[C@H](c3ccc(Cl)c(Cl)c3)C2(Cl)Cl)ccc1Cl] | 2 |
| F1249 | 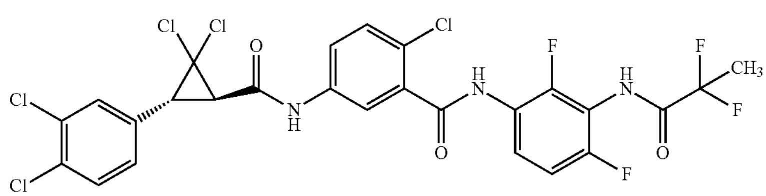 [SMILES: CC(F)(F)C(=O)Nc1c(F)ccc(NC(=O)c2cc(NC(=O)[C@H]3[C@H](c4ccc(Cl)c(Cl)c4)C3(Cl)Cl)ccc2Cl)c1F] | 4 |
| F1250 | 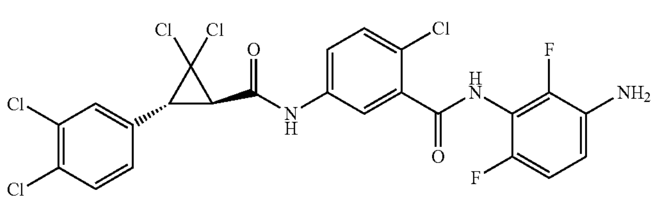 [SMILES: Nc1ccc(F)c(NC(=O)c2cc(NC(=O)[C@H]3[C@H](c4ccc(Cl)c(Cl)c4)C3(Cl)Cl)ccc2Cl)c1F] | 13 |

TABLE 2-continued

Structure and preparation method for F Series molecules

| No. | Structure | Prep.* |
|---|---|---|
| F1251 | 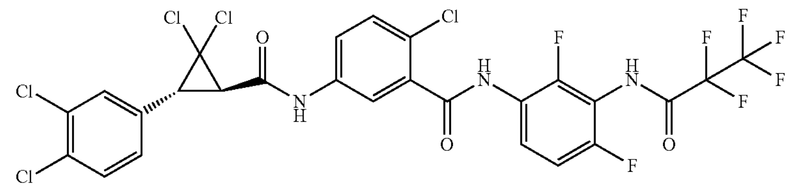 [SMILES: O=C(Nc1ccc(F)c(NC(=O)C(F)(F)C(F)(F)F)c1F)c1cc(NC(=O)[C@H]2[C@H](c3ccc(Cl)c(Cl)c3)C2(Cl)Cl)ccc1Cl] | 2 |
| F1252 | 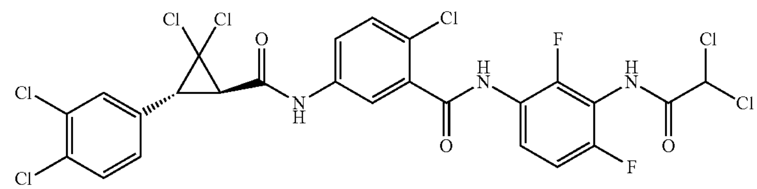 [SMILES: O=C(Nc1ccc(F)c(NC(=O)C(Cl)Cl)c1F)c1cc(NC(=O)[C@H]2[C@H](c3ccc(Cl)c(Cl)c3)C2(Cl)Cl)ccc1Cl] | 2 |
| F1253 | 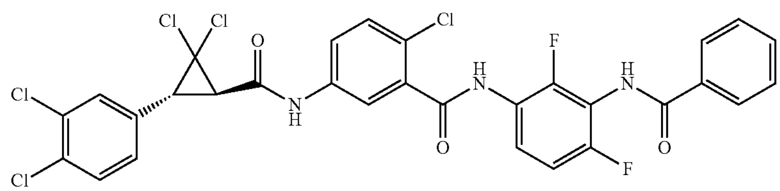 [SMILES: O=C(Nc1c(F)ccc(NC(=O)c2cc(NC(=O)[C@H]3[C@H](c4ccc(Cl)c(Cl)c4)C3(Cl)Cl)ccc2Cl)c1F)c1ccccc1] | 4 |
| F1254 | 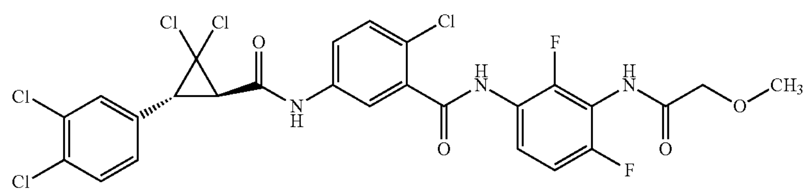 [SMILES: COCC(=O)Nc1c(F)ccc(NC(=O)c2cc(NC(=O)[C@H]3[C@H](c4ccc(Cl)c(Cl)c4)C3(Cl)Cl)ccc2Cl)c1F] | 7 |
| F1255 | 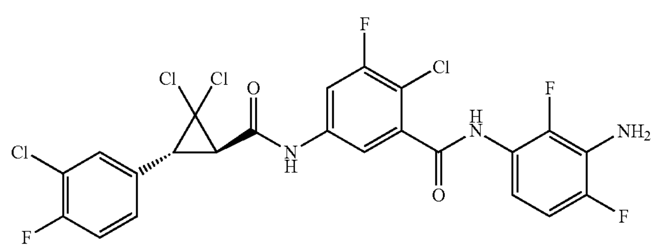 | 13 |
| F1256 | 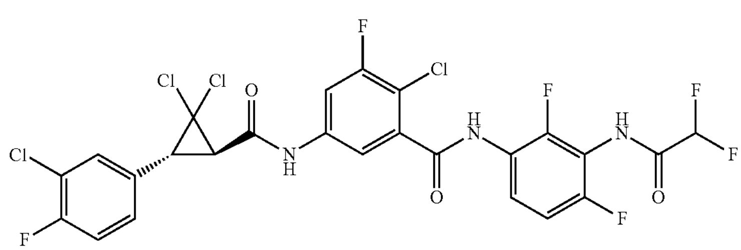 [SMILES: O=C(Nc1ccc(F)c(NC(=O)C(F)F)c1F)c1cc(NC(=O)[C@H]2[C@H](c3ccc(F)c(Cl)c3)C2(Cl)Cl)cc(F)c1Cl] | 1 |
| F1257 | 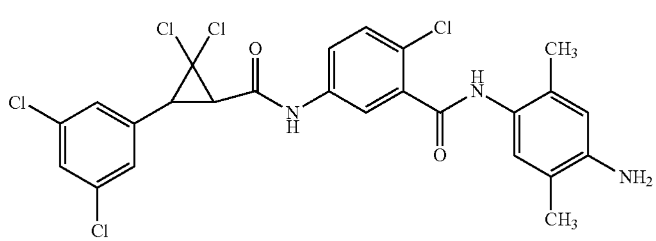 [SMILES: Cc1cc(NC(=O)c2cc(NC(=O)C3C(c4cc(Cl)cc(Cl)c4)C3(Cl)Cl)ccc2Cl)c(C)cc1N] | 15 |

TABLE 2-continued

Structure and preparation method for F Series molecules

| No. | Structure | Prep.* |
|---|---|---|
| F1258 | 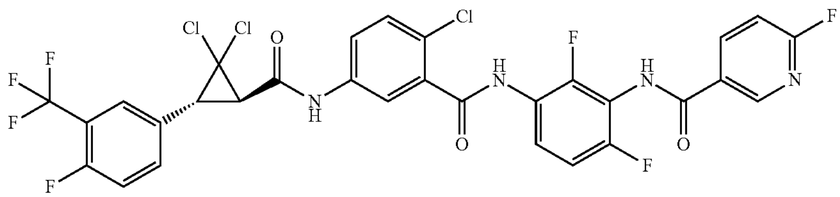 [SMILES: O=C(Nc1c(F)ccc(NC(=O)c2cc(NC(=O)[C@H]3[C@H](c4ccc(F)c(C(F)(F)F)c4)C3(Cl)Cl)ccc2Cl)c1F)c1ccc(F)nc1] | 4 |
| F1259 | 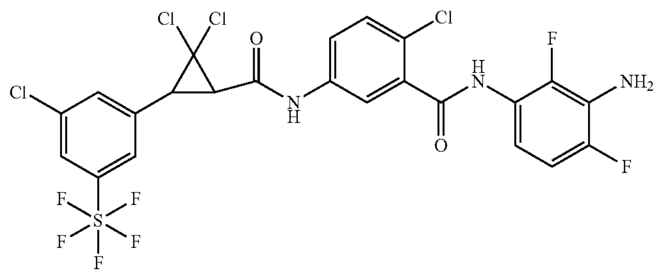 [SMILES: Nc1c(F)ccc(NC(=O)c2cc(NC(=O)C3C(c4cc(Cl)cc(S(F)(F)(F)(F)F)c4)C3(Cl)Cl)ccc2Cl)c1F] | 12 |
| F1260 | 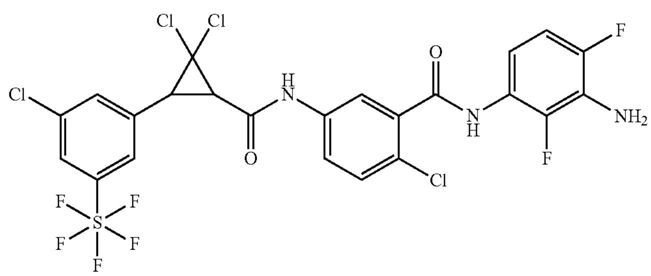 [SMILES: Nc1c(F)ccc(NC(=O)c2cc(NC(=O)C3C(c4cc(Cl)cc(S(F)(F)(F)(F)F)c4)C3(Cl)Cl)ccc2Cl)c1F] | 12 |
| F1261 | 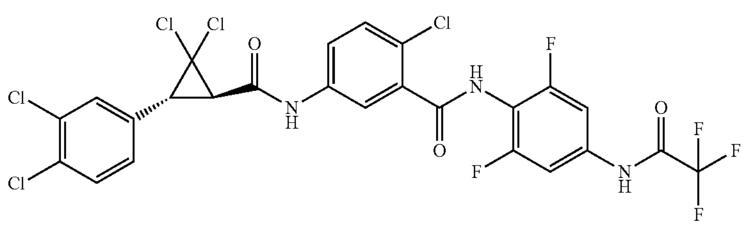 [SMILES: O=C(Nc1c(F)cc(NC(=O)C(F)(F)F)cc1F)c1cc(NC(=O)[C@H]2[C@H](c3ccc(Cl)c(Cl)c3)C2(Cl)Cl)ccc1Cl] | 1 |
| F1262 | 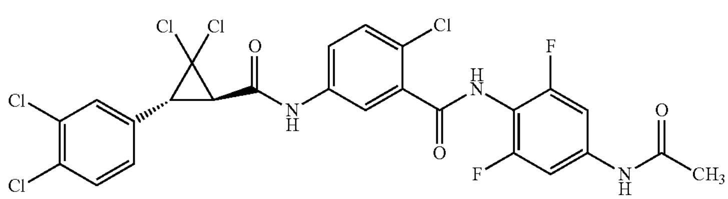 [SMILES: CC(=O)Nc1cc(F)c(NC(=O)c2cc(NC(=O)[C@H]3[C@H](c4ccc(Cl)c(Cl)c4)C3(Cl)Cl)ccc2Cl)c(F)c1] | 2 |
| F1263 | 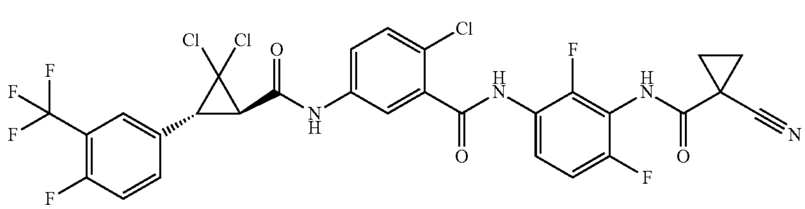 [SMILES: N#CC1(C(=O)Nc2c(F)ccc(NC(=O)c3cc(NC(=O)[C@H]4[C@H](c5ccc(F)c(C(F)(F)F)c5)C4(Cl)Cl)ccc3Cl)c2F)CC1] | 4 |

TABLE 2-continued

Structure and preparation method for F Series molecules

| No. | Structure | Prep.* |
|---|---|---|
| F1264 | 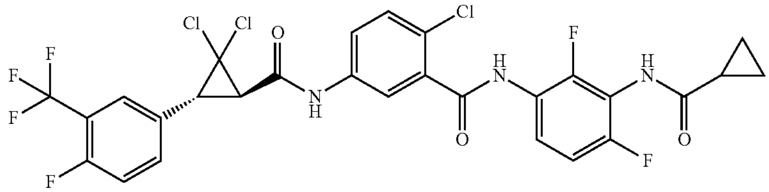 [SMILES: O=C(Nc1ccc(F)c(NC(=O)C2CC2)c1F)c1cc(NC(=O)[C@H]2[C@H](c3ccc(F)c(C(F)(F)F)c3)C2(Cl)Cl)ccc1Cl] | 4 |
| F1265 | 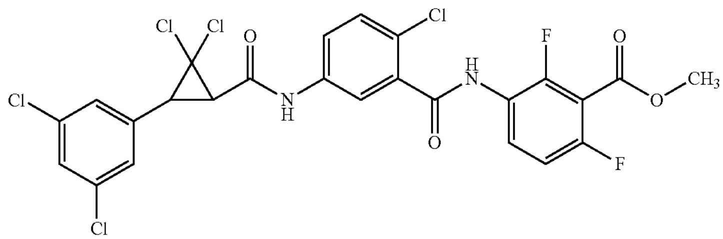 [SMILES: COC(=O)c1c(F)ccc(NC(=O)c2cc(NC(=O)C3C(c4cc(Cl)cc(Cl)c4)C3(Cl)Cl)ccc2Cl)c1F] | 22 |
| F1266 | 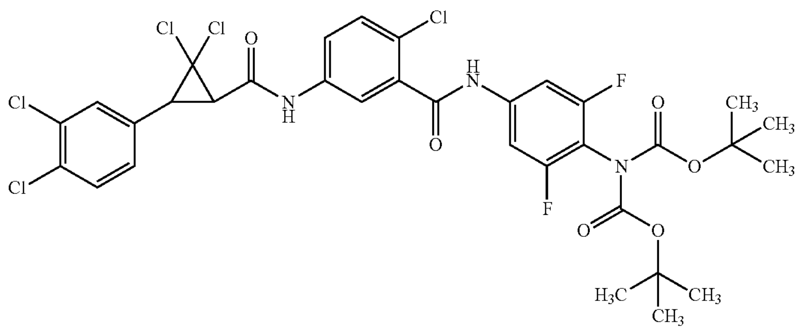 [SMILES: CC(C)(C)OC(=O)N(C(=O)OC(C)(C)C)c1c(F)cc(NC(=O)c2cc(NC(=O)C3C(c4ccc(Cl)c(Cl)c4)C3(Cl)Cl)ccc2Cl)cc1F] | 25 |
| F1268 | 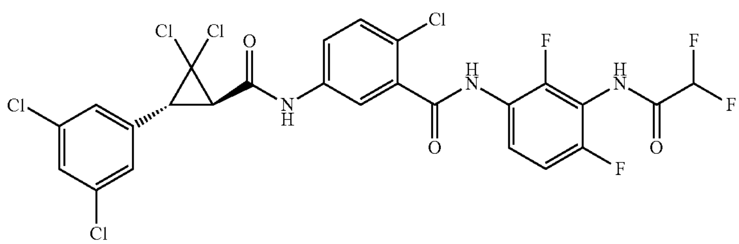 [SMILES: O=C(Nc1ccc(F)c(NC(=O)C(F)F)c1F)c1cc(NC(=O)[C@H]2[C@H](c3cc(Cl)cc(Cl)c3)C2(Cl)Cl)ccc1Cl] | 25 |
| F1269 | 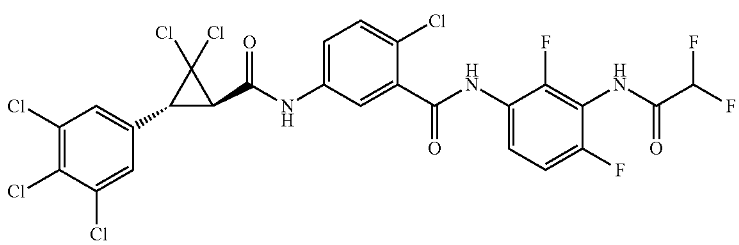 [SMILES: O=C(Nc1ccc(F)c(NC(=O)C(F)F)c1F)c1cc(NC(=O)[C@H]2[C@H](c3cc(Cl)c(Cl)c(Cl)c3)C2(Cl)Cl)ccc1Cl] | 25 |
| F1270 | 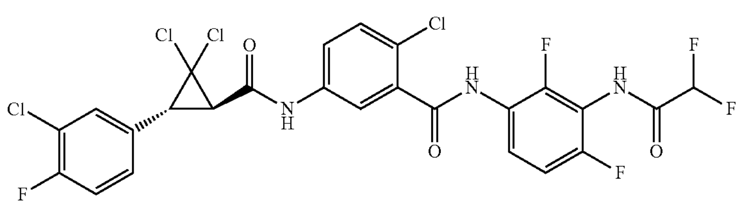 [SMILES: O=C(Nc1ccc(F)c(NC(=O)C(F)F)c1F)c1cc(NC(=O)[C@H]2[C@H](c3ccc(F)c(Cl)c3)C2(Cl)Cl)ccc1Cl] | 25 |

TABLE 2-continued

Structure and preparation method for F Series molecules

| No. | Structure | Prep.* |
|---|---|---|
| F1271 | 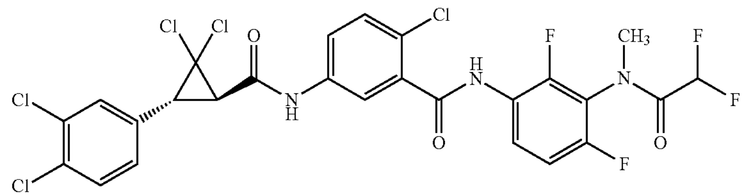 [SMILES: CN(C(=O)C(F)F)c1c(F)ccc(NC(=O)c2cc(NC(=O)[C@H]3[C@H](c4ccc(Cl)c(Cl)c4)C3(Cl)Cl)ccc2Cl)c1F] | 25 |
| F1272 | 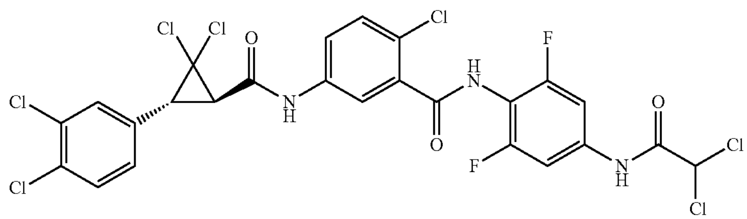 [SMILES: O=C(Nc1c(F)cc(NC(=O)C(Cl)Cl)cc1F)c1cc(NC(=O)[C@H]2[C@H](c3ccc(Cl)c(Cl)c3)C2(Cl)Cl)ccc1Cl] | 2 |
| F1273 | 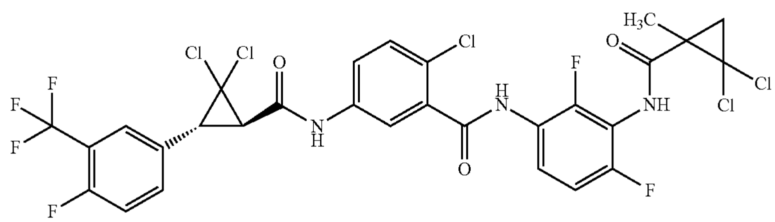 [SMILES: CC1(C(=O)Nc2c(F)ccc(NC(=O)c3cc(NC(=O)[C@H]4[C@H](c5ccc(F)c(C(F)(F)F)c5)C4(Cl)Cl)ccc3Cl)c2F)CC1(Cl)Cl] | 4 |
| F1274 | 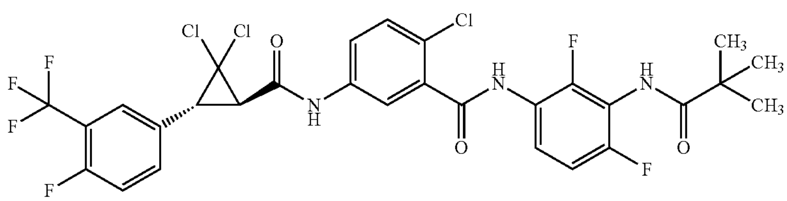 | 4 |
| F1275 | 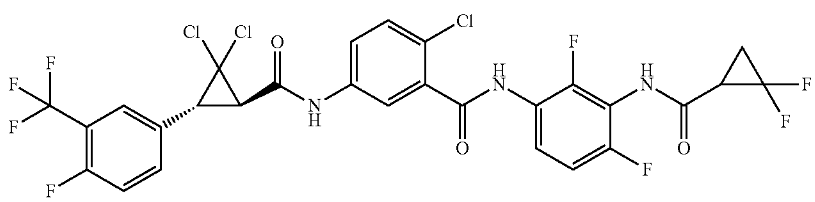 [SMILES: O=C(Nc1ccc(F)c(NC(=O)C2CC2(F)F)c1F)c1cc(NC(=O)[C@H]2[C@H](c3ccc(F)c(C(F)(F)F)c3)C2(Cl)Cl)ccc1Cl] | 4 |
| F1276 | 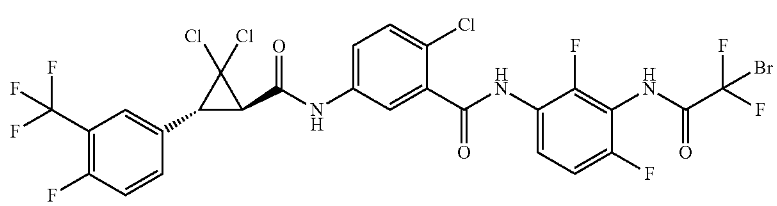 [SMILES: O=C(Nc1ccc(F)c(NC(=O)C(F)(F)Br)c1F)c1cc(NC(=O)[C@H]2[C@H](c3ccc(F)c(C(F)(F)F)c3)C2(Cl)Cl)ccc1Cl] | 4 |
| F1277 | 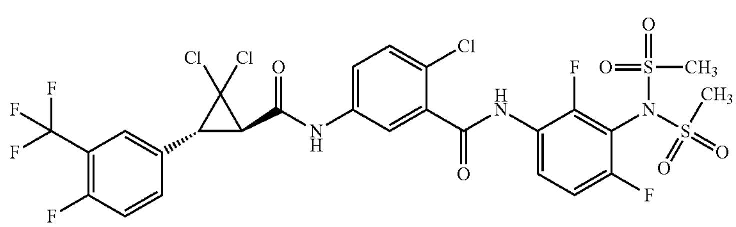 [SMILES: CS(=O)(=O)N(c1c(F)ccc(NC(=O)c2cc(NC(=O)[C@H]3[C@H](c4ccc(F)c(C(F)(F)F)c4)C3(Cl)Cl)ccc2Cl)c1F)S(C)(=O)=O] | 8 |

TABLE 2-continued
Structure and preparation method for F Series molecules
| No. | Structure | Prep.* |
|---|---|---|
| F1278 | 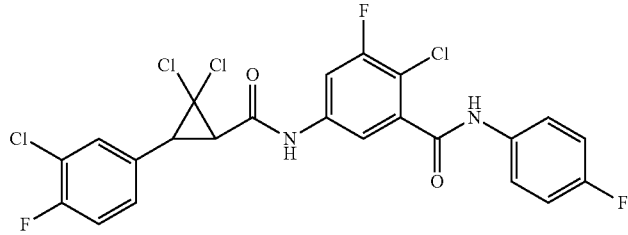 [SMILES: O=C(Nc1ccc(F)cc1)c1cc(NC(=O)C2C(c3ccc(F)c(Cl)c3)C2(Cl)Cl)cc(F)c1Cl] | 25 |
| F1279 | 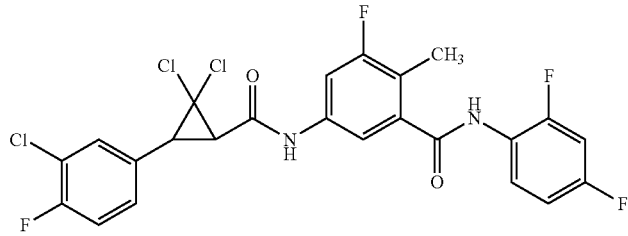 [SMILES: Cc1c(F)cc(NC(=O)C2C(c3ccc(F)c(Cl)c3)C2(Cl)Cl)cc1C(=O)Nc1ccc(F)cc1F] | 25 |
| F1280 | 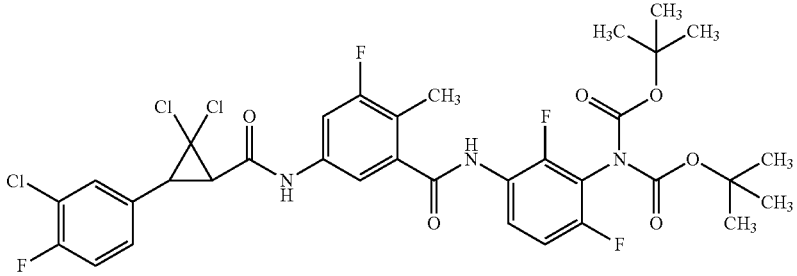 | 25 |
| F1281 | 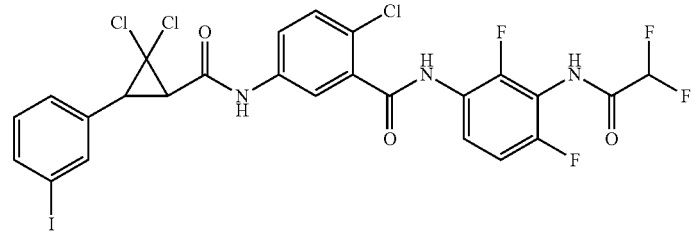 [SMILES: O=C(Nc1ccc(F)c(NC(=O)C(F)F)c1F)c1cc(NC(=O)C2C(c3cccc(I)c3)C2(Cl)Cl)ccc1Cl] | 18 |
| F1282 | 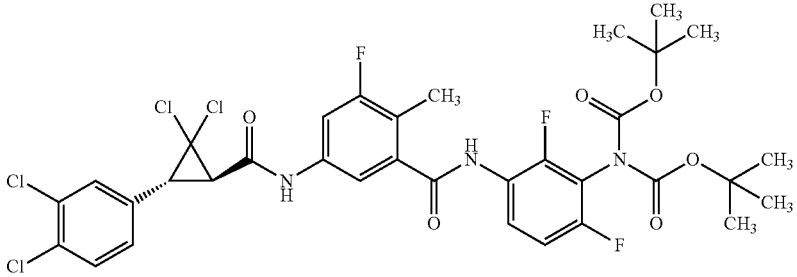 [SMILES: Cc1c(F)cc(NC(=O)[C@H]2[C@H](c3ccc(Cl)c(Cl)c3)C2(Cl)Cl)cc1C(=O)Nc1ccc(F)c(N(C(=O)OC(C)(C)C)C(=O)OC(C)(C)C)c1F] | 20 |

TABLE 2-continued
Structure and preparation method for F Series molecules
| No. | Structure | Prep.* |
|---|---|---|
| F1283 | 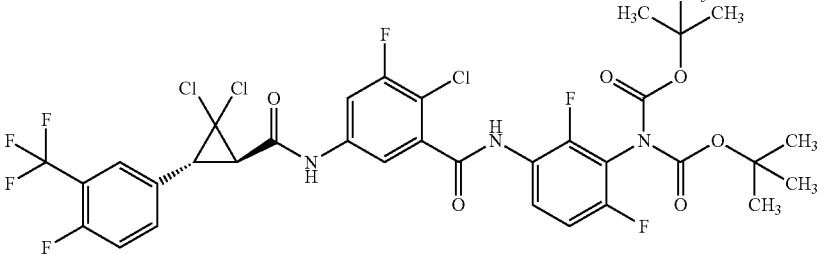 | 20 |
| F1284 | 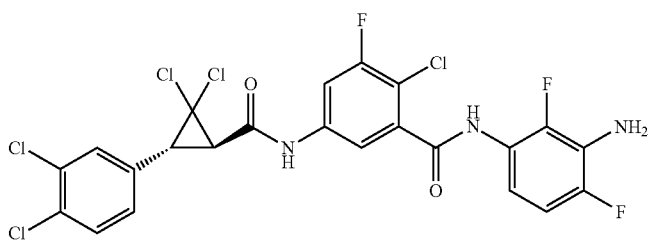 [SMILES: Nc1c(F)ccc(NC(=O)c2cc(NC(=O)[C@H]3[C@H](c4ccc(Cl)c(Cl)c4)C3(Cl)Cl)cc(F)c2Cl)c1F] | 13 |
| F1285 | 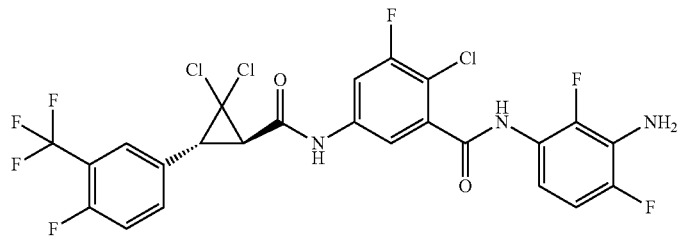 [SMILES: Nc1c(F)ccc(NC(=O)c2cc(NC(=O)[C@H]3[C@H](c4ccc(F)c(C(F)(F)F)c4)C3(Cl)Cl)cc(F)c2Cl)c1F] | 13 |
| F1286 | 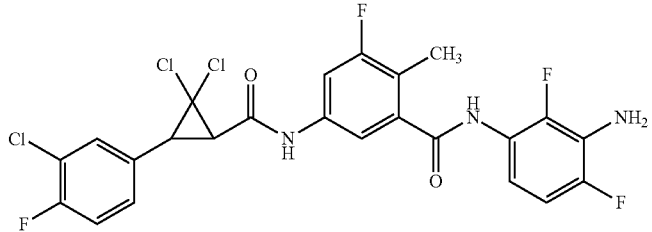 [SMILES: Cc1c(F)cc(NC(=O)C2C(c3ccc(F)c(Cl)c3)C2(Cl)Cl)cc1C(=O)Nc1ccc(F)c(N)c1F] | 13 |
| F1287 | 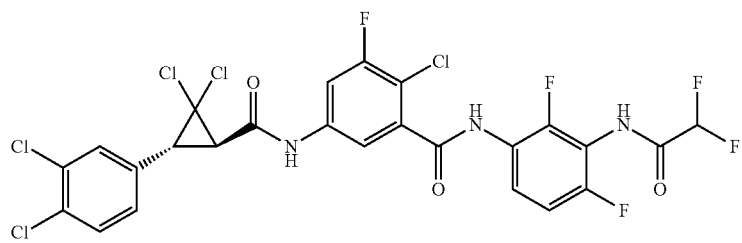 [SMILES: O=C(Nc1ccc(F)c(NC(=O)C(F)F)c1F)c1cc(NC(=O)[C@H]2[C@H](c3ccc(Cl)c(Cl)c3)C2(Cl)Cl)cc(F)c1Cl] | 1 |
| F1288 | 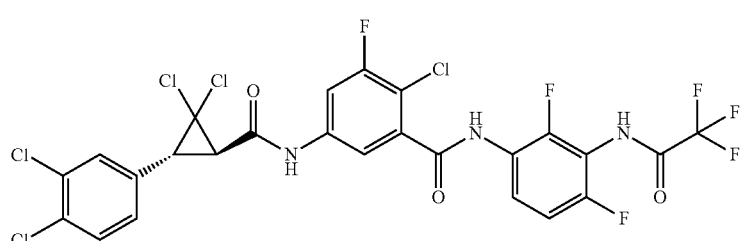 | 1 |

TABLE 2-continued

Structure and preparation method for F Series molecules

| No. | Structure | Prep.* |
|---|---|---|
| F1289 | 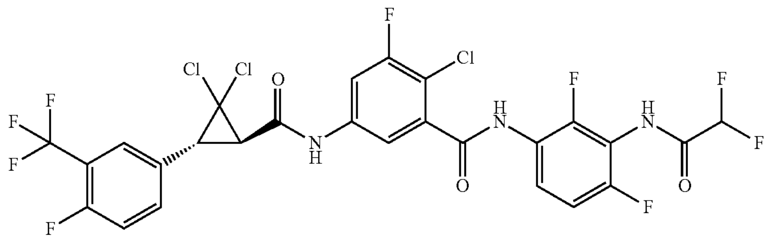 [SMILES: O=C(Nc1ccc(F)c(NC(=O)C(F)F)c1F)c1cc(NC(=O)[C@H]2[C@H](c3ccc(F)c(C(F)(F)F)c3)C2(Cl)Cl)cc(F)c1Cl] | 1 |
| F1290 | 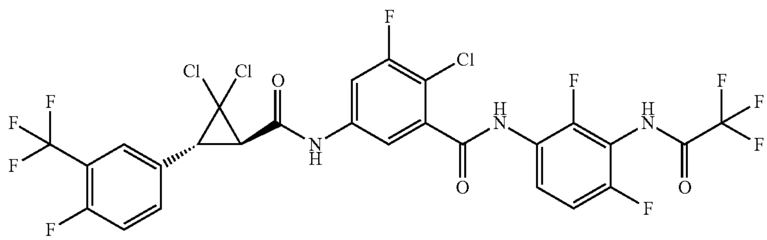 [SMILES: O=C(Nc1ccc(F)c(NC(=O)C(F)(F)F)c1F)c1cc(NC(=O)[C@H]2[C@H](c3ccc(F)c(C(F)(F)F)c3)C2(Cl)Cl)cc(F)c1Cl] | 1 |
| F1291 | 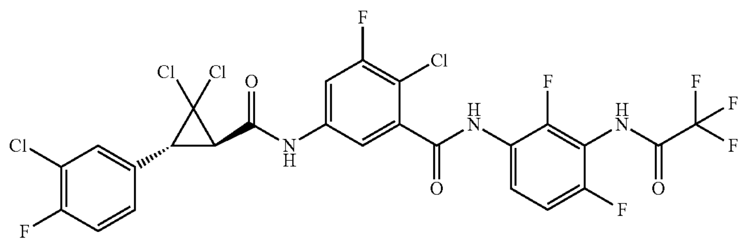 [SMILES: O=C(Nc1ccc(F)c(NC(=O)C(F)(F)F)c1F)c1cc(NC(=O)[C@H]2[C@H](c3ccc(F)c(Cl)c3)C2(Cl)Cl)cc(F)c1Cl] | 1 |
| F1292 | 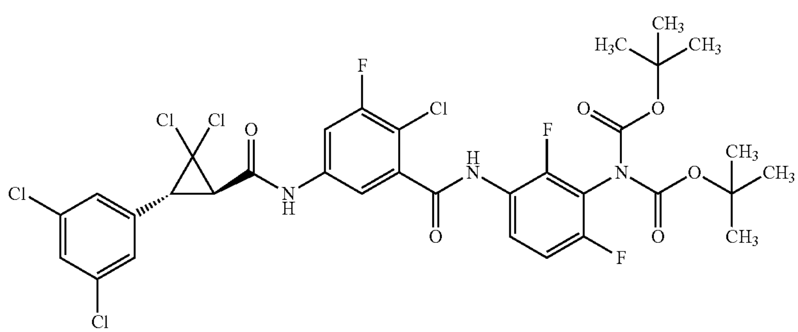 [SMILES: CC(C)(C)OC(=O)N(C(=O)OC(C)(C)C)c1c(F)ccc(NC(=O)c2cc(NC(=O)[C@H]3[C@H](c4cc(Cl)cc(Cl)c4)C3(Cl)Cl)cc(F)c2Cl)c1F] | 17 |
| F1293 | 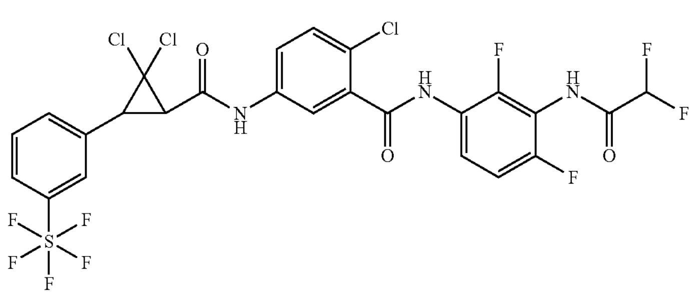 [SMILES: O=C(Nc1ccc(F)c(NC(=O)C(F)F)c1F)c1cc(NC(=O)C2C(c3cccc(S(F)(F)(F)(F)F)c3)C2(Cl)Cl)ccc1Cl] | 18 |

TABLE 2-continued

Structure and preparation method for F Series molecules

| No. | Structure | Prep.* |
|---|---|---|
| F1294 | 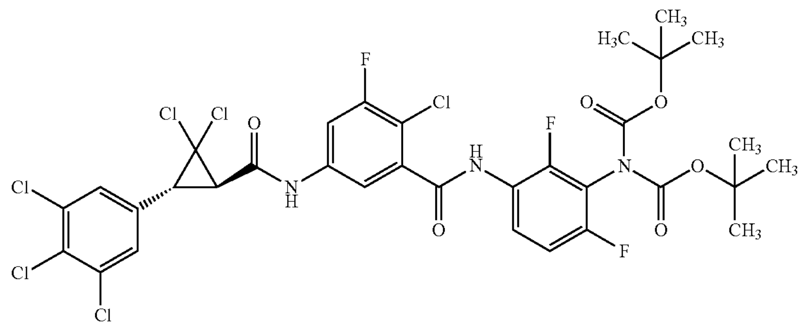 [SMILES: CC(C)(C)OC(=O)N(C(=O)OC(C)(C)C)c1c(F)ccc(NC(=O)c2cc(NC(=O)[C@H]3[C@H](c4cc(Cl)c(Cl)c(Cl)c4)C3(Cl)Cl)cc(F)c2Cl)c1F] | 17 |
| F1295 | 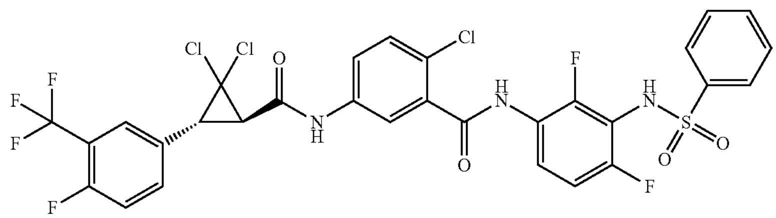 [SMILES: O=C(Nc1ccc(F)c(NS(=O)(=O)c2ccccc2)c1F)c1cc(NC(=O)[C@H]2[C@H](c3ccc(F)c(C(F)(F)F)c3)C2(Cl)Cl)ccc1Cl] | 9 |
| F1296 | 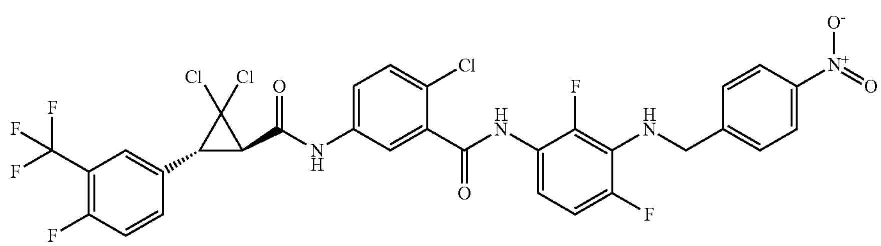 [SMILES: O=C(Nc1ccc(F)c(NCc2ccc([N+](=O)[O-])cc2)c1F)c1cc(NC(=O)[C@H]2[C@H](c3ccc(F)c(C(F)(F)F)c3)C2(Cl)Cl)ccc1Cl] | 10 |
| F1297 | 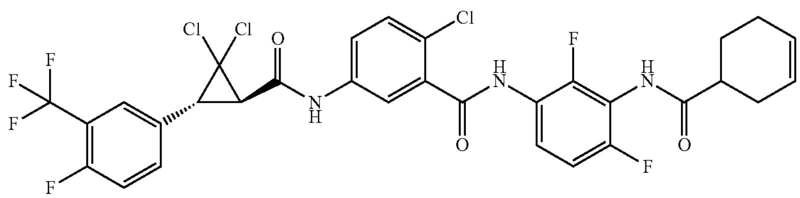 [SMILES: O=C(Nc1ccc(F)c(NC(=O)C2CC=CCC2)c1F)c1cc(NC(=O)[C@H]2[C@H](c3ccc(F)c(C(F)(F)F)c3)C2(Cl)Cl)ccc1Cl] | 4 |
| F1298 | 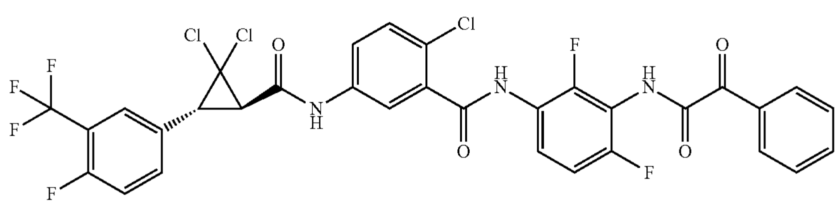 [SMILES: O=C(Nc1c(F)ccc(NC(=O)c2cc(NC(=O)[C@H]3[C@H](c4ccc(F)c(C(F)(F)F)c4)C3(Cl)Cl)ccc2Cl)c1F)C(=O)c1ccccc1] | 4 |
| F1299 | 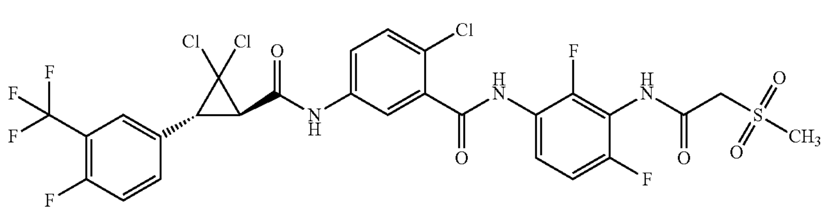 [SMILES: CS(=O)(=O)CC(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 4 |

TABLE 2-continued

Structure and preparation method for F Series molecules

| No. | Structure | Prep.* |
|---|---|---|
| F1300 | 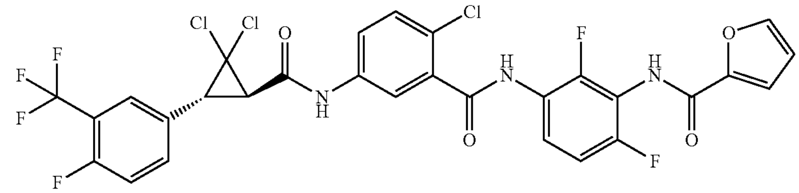 [SMILES: O=C(Nc1c(F)ccc(NC(=O)c2cc(NC(=O)[C@H]3[C@H](c4ccc(F)c(C(F)(F)F)c4)C3(Cl)Cl)ccc2Cl)c1F)c1ccco1] | 4 |
| F1301 | 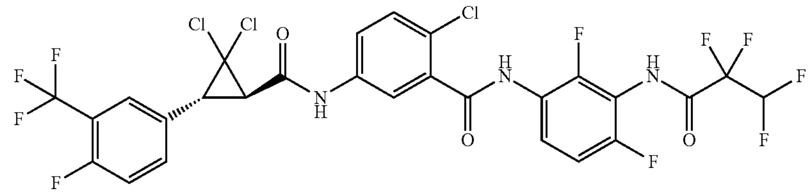 [SMILES: O=C(Nc1ccc(F)c(NC(=O)C(F)(F)C(F)F)c1F)c1cc(NC(=O)[C@H]2[C@H](c3ccc(F)c(C(F)(F)F)c3)C2(Cl)Cl)ccc1Cl] | 4 |
| F1302 | 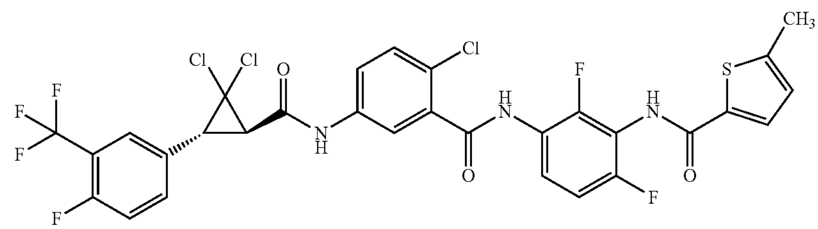 [SMILES: Cc1ccc(C(=O)Nc2c(F)ccc(NC(=O)c3cc(NC(=O)[C@H]4[C@H](c5ccc(F)c(C(F)(F)F)c5)C4(Cl)Cl)ccc3Cl)c2F)s1] | 4 |
| F1303 | 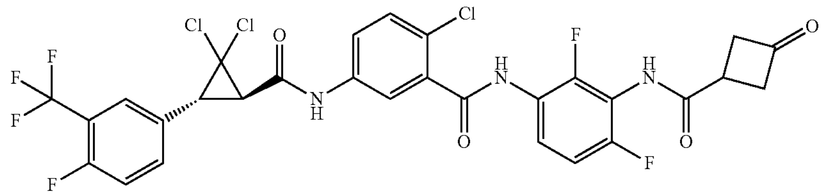 [SMILES: O=C1CC(C(=O)Nc2c(F)ccc(NC(=O)c3cc(NC(=O)[C@H]4[C@H](c5ccc(F)c(C(F)(F)F)c5)C4(Cl)Cl)ccc3Cl)c2F)C1] | 4 |
| F1304 | 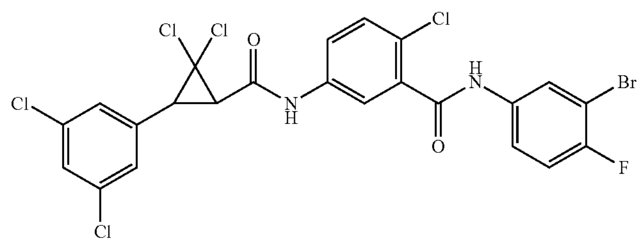 [SMILES: O=C(Nc1ccc(F)c(Br)c1)c1cc(NC(=O)C2C(c3cc(Cl)cc(Cl)c3)C2(Cl)Cl)ccc1Cl] | 25 |
| F1305 | 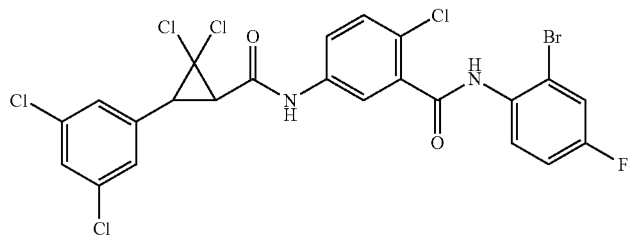 [SMILES: O=C(Nc1ccc(F)cc1Br)c1cc(NC(=O)C2C(c3cc(Cl)cc(Cl)c3)C2(Cl)Cl)ccc1Cl] | 25 |
| F1306 | 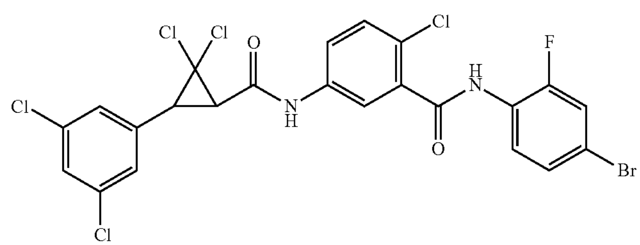 [SMILES: O=C(Nc1ccc(Br)cc1F)c1cc(NC(=O)C2C(c3cc(Cl)cc(Cl)c3)C2(Cl)Cl)ccc1Cl] | 25 |

TABLE 2-continued

Structure and preparation method for F Series molecules

| No. | Structure | Prep.* |
|---|---|---|
| F1307 | 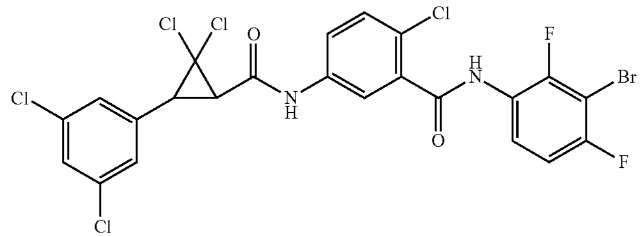 | 25 |
| F1308 | 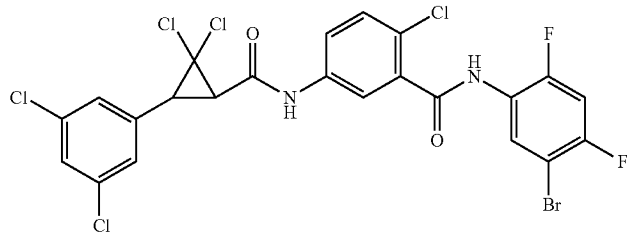 [SMILES: O=C(Nc1cc(Br)c(F)cc1F)c1cc(NC(=O)C2C(c3cc(Cl)cc(Cl)c3)C2(Cl)Cl)ccc1Cl] | 25 |
| F1309 | 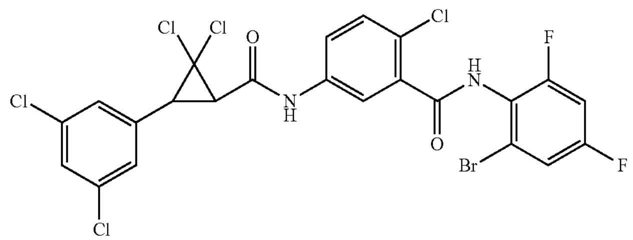 [SMILES: O=C(Nc1c(F)cc(F)cc1Br)c1cc(NC(=O)C2C(c3cc(Cl)cc(Cl)c3)C2(Cl)Cl)ccc1Cl] | 25 |
| F1311 | 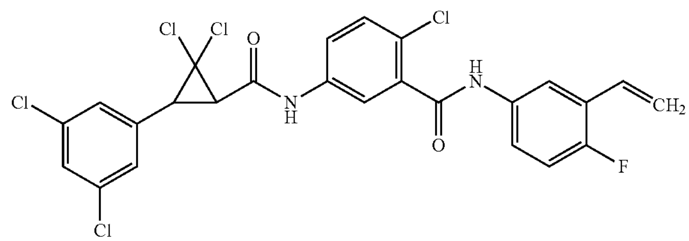 [SMILES: C=Cc1cc(NC(=O)c2cc(NC(=O)C3C(c4cc(Cl)cc(Cl)c4)C3(Cl)Cl)ccc2Cl)ccc1F] | 11 |
| F1312 | 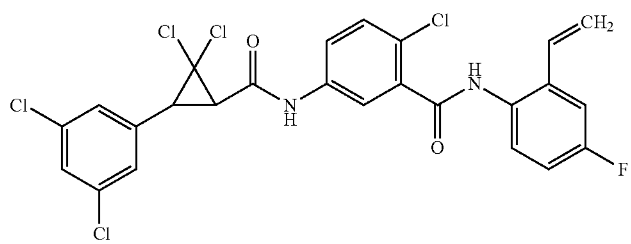 [SMILES: C=Cc1cc(F)ccc1NC(=O)c1cc(NC(=O)C2C(c3cc(Cl)cc(Cl)c3)C2(Cl)Cl)ccc1Cl] | 11 |
| F1313 | 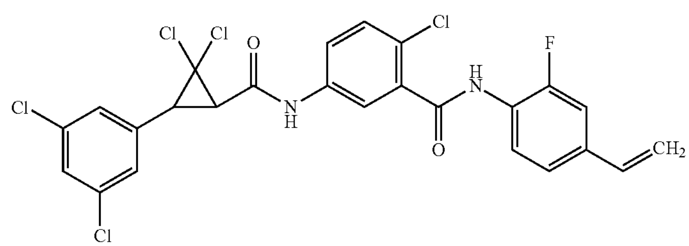 [SMILES: C=Cc1ccc(NC(=O)c2cc(NC(=O)C3C(c4cc(Cl)cc(Cl)c4)C3(Cl)Cl)ccc2Cl)c(F)c1] | 11 |

TABLE 2-continued

Structure and preparation method for F Series molecules

| No. | Structure | Prep.* |
|---|---|---|
| F1314 | 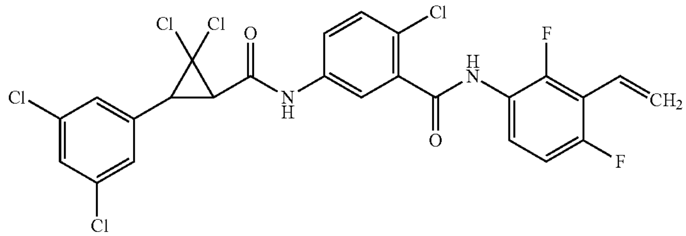 [SMILES: C=Cc1c(F)ccc(NC(=O)c2cc(NC(=O)C3C(c4cc(Cl)cc(Cl)c4)C3(Cl)Cl)ccc2Cl)c1F] | 11 |
| F1315 | 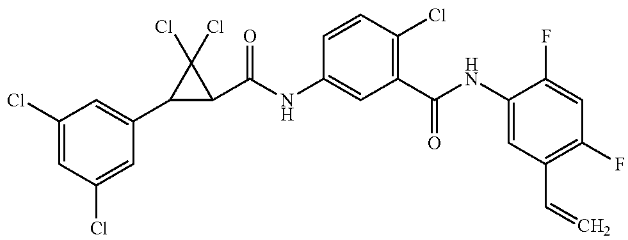 [SMILES: C=Cc1cc(NC(=O)c2cc(NC(=O)C3C(c4cc(Cl)cc(Cl)c4)C3(Cl)Cl)ccc2Cl)c(F)cc1F] | 11 |
| F1316 | 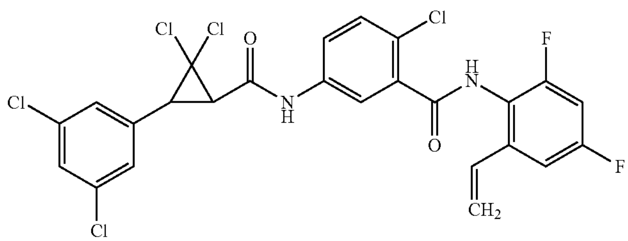 [SMILES: C=Cc1cc(F)cc(F)c1NC(=O)c1cc(NC(=O)C2C(c3cc(Cl)cc(Cl)c3)C2(Cl)Cl)ccc1Cl] | 11 |
| F1317 | 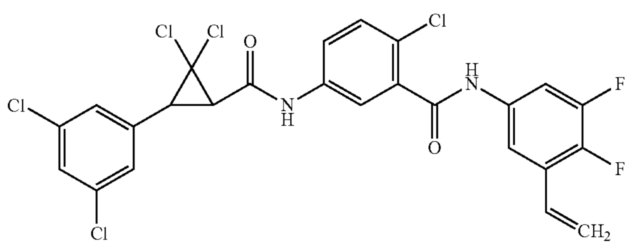 [SMILES: C=Cc1cc(NC(=O)c2cc(NC(=O)C3C(c4cc(Cl)cc(Cl)c4)C3(Cl)Cl)ccc2Cl)cc(F)c1F] | 11 |
| F1318 | 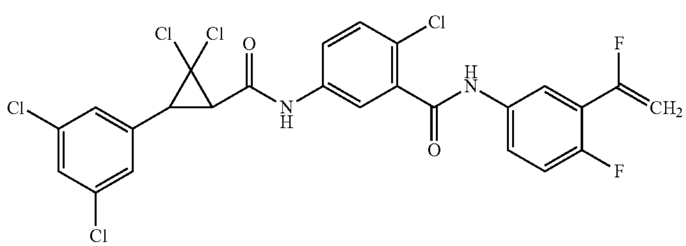 [SMILES: C=C(F)c1cc(NC(=O)c2cc(NC(=O)C3C(c4cc(Cl)cc(Cl)c4)C3(Cl)Cl)ccc2Cl)ccc1F] | 11 |
| F1319 | 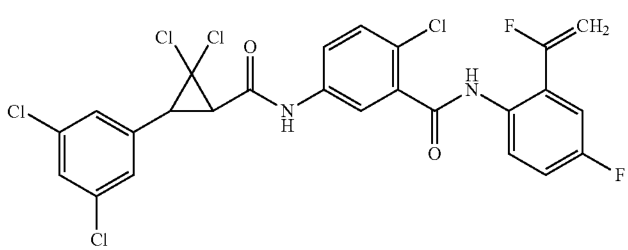 [SMILES: C=C(F)c1cc(F)ccc1NC(=O)c1cc(NC(=O)C2C(c3cc(Cl)cc(Cl)c3)C2(Cl)Cl)ccc1Cl] | 11 |

TABLE 2-continued

Structure and preparation method for F Series molecules

| No. | Structure | Prep.* |
|---|---|---|
| F1320 | 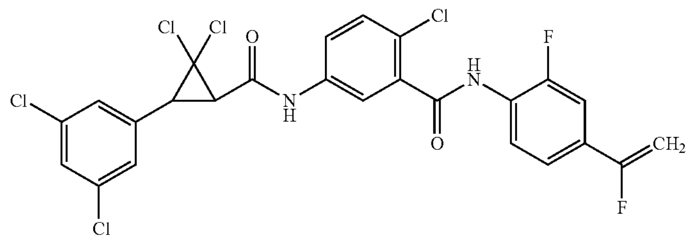 [SMILES: C=C(F)c1ccc(NC(=O)c2cc(NC(=O)C3C(c4cc(Cl)cc(Cl)c4)C3(Cl)Cl)ccc2Cl)c(F)c1] | 11 |
| F1321 | 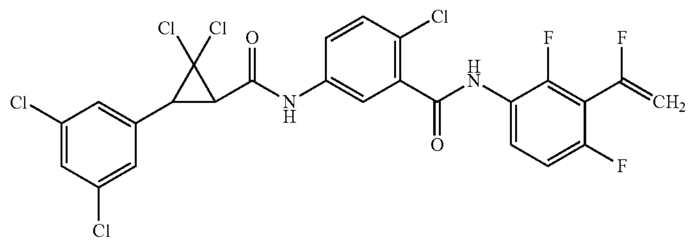 [SMILES: C=C(F)c1c(F)ccc(NC(=O)c2cc(NC(=O)C3C(c4cc(Cl)cc(Cl)c4)C3(Cl)Cl)ccc2Cl)c1F] | 11 |
| F1322 | 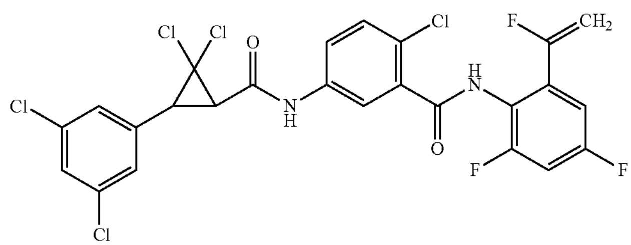 [SMILES: C=C(F)c1cc(F)cc(F)c1NC(=O)c1cc(NC(=O)C2C(c3cc(Cl)cc(Cl)c3)C2(Cl)Cl)ccc1Cl] | 11 |
| F1323 | 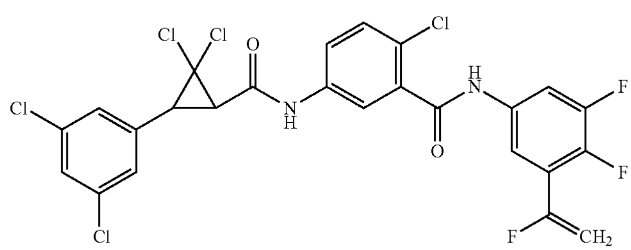 [SMILES: C=C(F)c1cc(NC(=O)c2cc(NC(=O)C3C(c4cc(Cl)cc(Cl)c4)C3(Cl)Cl)ccc2Cl)cc(F)c1F] | 11 |
| F1324 | 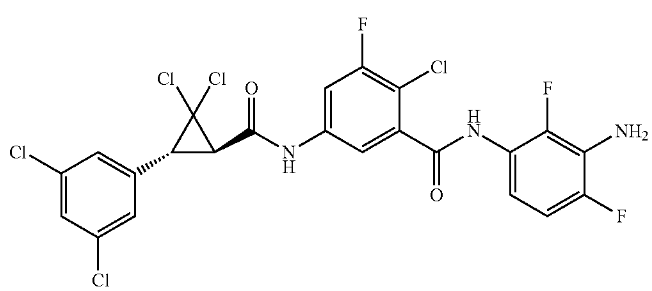 [SMILES: Nc1c(F)ccc(NC(=O)c2cc(NC(=O)[C@H]3[C@H](c4cc(Cl)cc(Cl)c4)C3(Cl)Cl)cc(F)c2Cl)c1F] | 13 |
| F1325 | 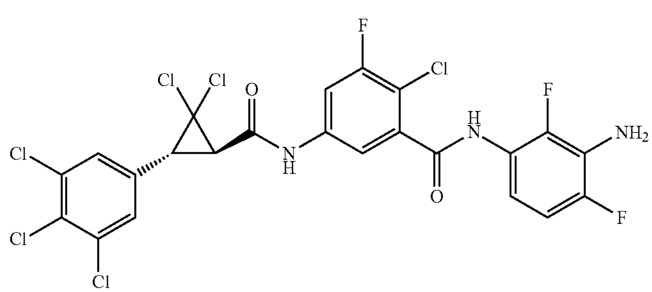 [SMILES: Nc1c(F)ccc(NC(=O)c2cc(NC(=O)[C@H]3[C@H](c4cc(Cl)c(Cl)c(Cl)c4)C3(Cl)Cl)cc(F)c2Cl)c1F] | 13 |

TABLE 2-continued

Structure and preparation method for F Series molecules

| No. | Structure | Prep.* |
|---|---|---|
| F1326 | 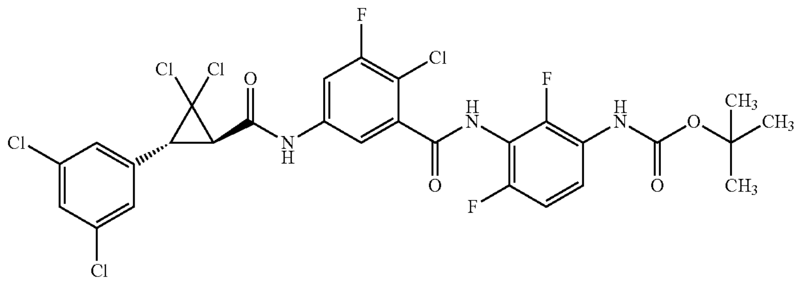 [SMILES: CC(C)(C)OC(=O)Nc1ccc(F)c(NC(=O)c2cc(NC(=O)[C@H]3[C@H](c4cc(Cl)cc(Cl)c4)C3(Cl)Cl)cc(F)c2Cl)c1F] | 17 |
| F1327 | 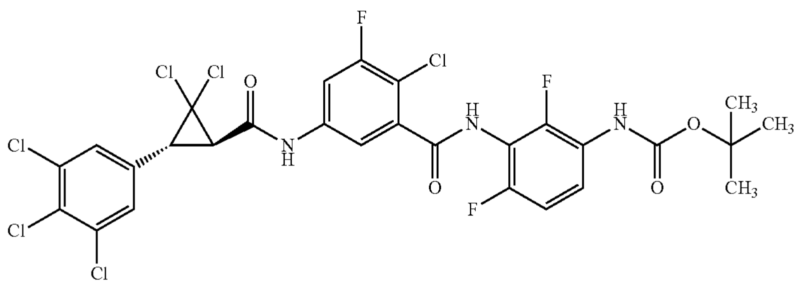 [SMILES: CC(C)(C)OC(=O)Nc1ccc(F)c(NC(=O)c2cc(NC(=O)[C@H]3[C@H](c4cc(Cl)c(Cl)c(Cl)c4)C3(Cl)Cl)cc(F)c2Cl)c1F] | 17 |
| F1328 | 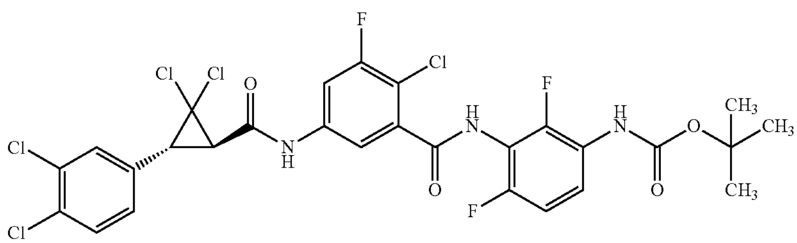 [SMILES: CC(C)(C)OC(=O)Nc1ccc(F)c(NC(=O)c2cc(NC(=O)[C@H]3[C@H](c4ccc(Cl)c(Cl)c4)C3(Cl)Cl)cc(F)c2Cl)c1F] | 17 |
| F1329 | 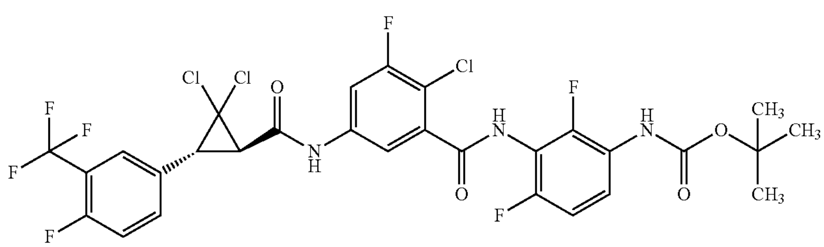 [SMILES: CC(C)(C)OC(=O)Nc1ccc(F)c(NC(=O)c2cc(NC(=O)[C@H]3[C@H](c4ccc(F)c(C(F)(F)F)c4)C3(Cl)Cl)cc(F)c2Cl)c1F] | 17 |
| F1330 | 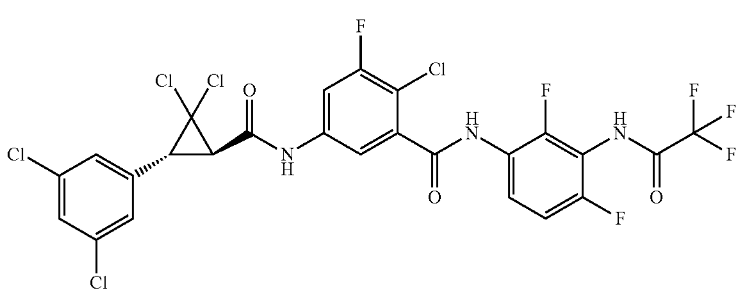 [SMILES: O=C(Nc1ccc(F)c(NC(=O)C(F)(F)F)c1F)c1cc(NC(=O)[C@H]2[C@H](c3cc(Cl)cc(Cl)c3)C2(Cl)Cl)cc(F)c1Cl] | 1 |

TABLE 2-continued

Structure and preparation method for F Series molecules

| No. | Structure | Prep.* |
|---|---|---|
| F1331 | 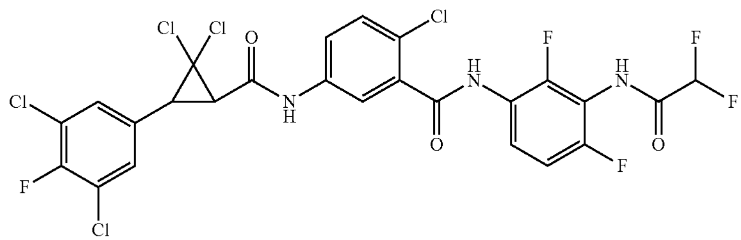 [SMILES: O=C(Nc1ccc(F)c(NC(=O)C(F)F)c1F)c1cc(NC(=O)C2C(c3cc(Cl)c(F)c(Cl)c3)C2(Cl)Cl)ccc1Cl] | 1 |
| F1332 | 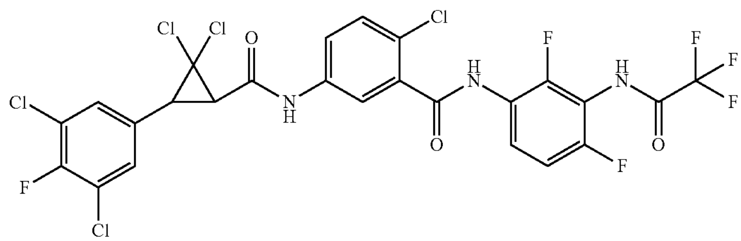 [SMILES: O=C(Nc1ccc(F)c(NC(=O)C(F)(F)F)c1F)c1cc(NC(=O)C2C(c3cc(Cl)c(F)c(Cl)c3)C2(Cl)Cl)ccc1Cl] | 1 |
| F1333 | 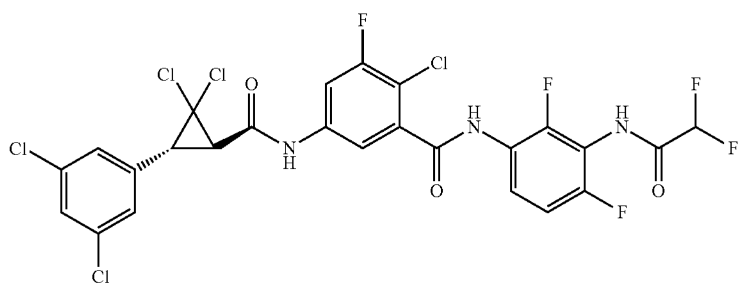 | 1 |
| F1334 | 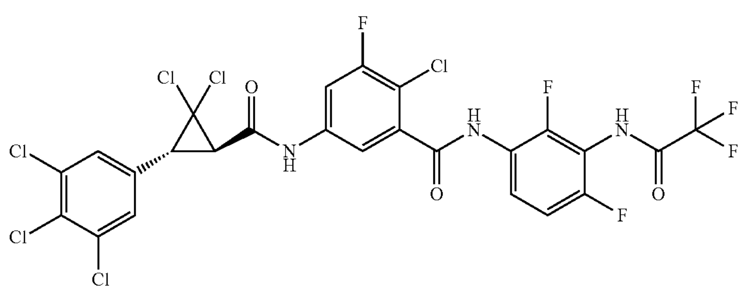 [SMILES: O=C(Nc1ccc(F)c(NC(=O)C(F)(F)F)c1F)c1cc(NC(=O)[C@H]2[C@H](c3cc(Cl)c(Cl)c(Cl)c3)C2(Cl)Cl)cc(F)c1Cl] | 1 |
| F1335 | 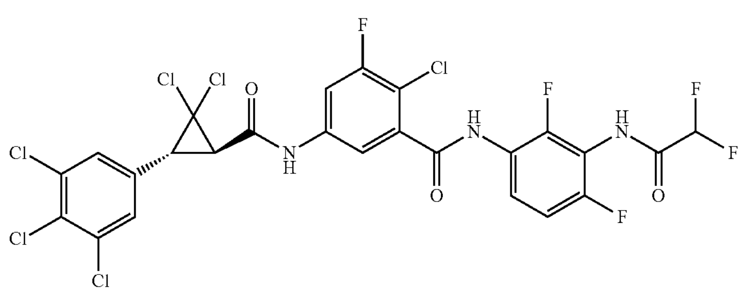 [SMILES: O=C(Nc1ccc(F)c(NC(=O)C(F)F)c1F)c1cc(NC(=O)[C@H]2[C@H](c3cc(Cl)c(Cl)c(Cl)c3)C2(Cl)Cl)cc(F)c1Cl] | 1 |

TABLE 2-continued

Structure and preparation method for F Series molecules

| No. | Structure | Prep.* |
|---|---|---|
| F1336 | 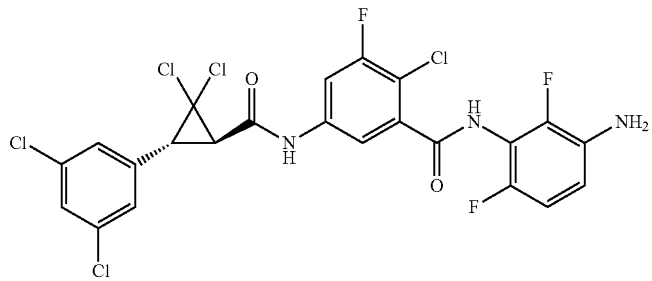 [SMILES: Nc1ccc(F)c(NC(=O)c2cc(NC(=O)[C@H]3[C@H](c4cc(Cl)cc(Cl)c4)C3(Cl)Cl)cc(F)c2Cl)c1F] | 13 |
| F1337 | 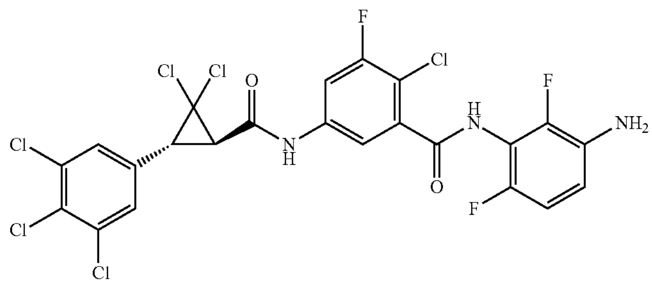 [SMILES: Nc1ccc(F)c(NC(=O)c2cc(NC(=O)[C@H]3[C@H](c4cc(Cl)c(Cl)c(Cl)c4)C3(Cl)Cl)cc(F)c2Cl)c1F] | 13 |
| F1338 | 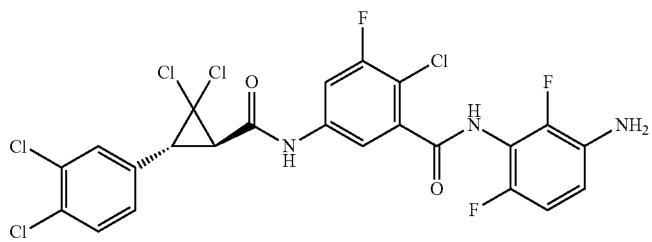 [SMILES: Nc1ccc(F)c(NC(=O)c2cc(NC(=O)[C@H]3[C@H](c4ccc(Cl)c(Cl)c4)C3(Cl)Cl)cc(F)c2Cl)c1F] | 13 |
| F1339 | 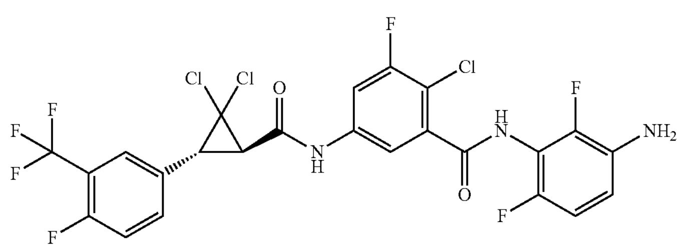 [SMILES: Nc1ccc(F)c(NC(=O)c2cc(NC(=O)[C@H]3[C@H](c4ccc(F)c(C(F)(F)F)c4)C3(Cl)Cl)cc(F)c2Cl)c1F] | 13 |
| F1340 | 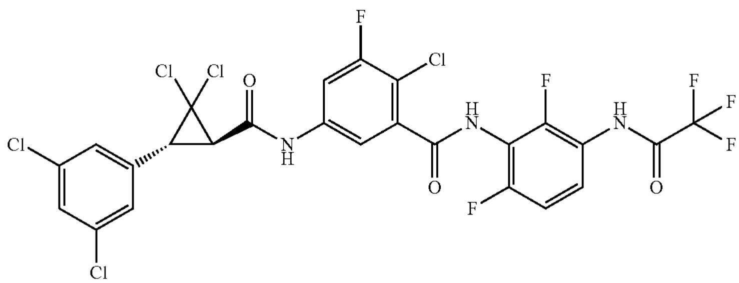 [SMILES: O=C(Nc1c(F)ccc(NC(=O)C(F)(F)F)c1F)c1cc(NC(=O)[C@H]2[C@H](c3cc(Cl)cc(Cl)c3)C2(Cl)Cl)cc(F)c1Cl] | 3 |

TABLE 2-continued

Structure and preparation method for F Series molecules

| No. | Structure | Prep.* |
|-----|-----------|--------|
| F1341 | 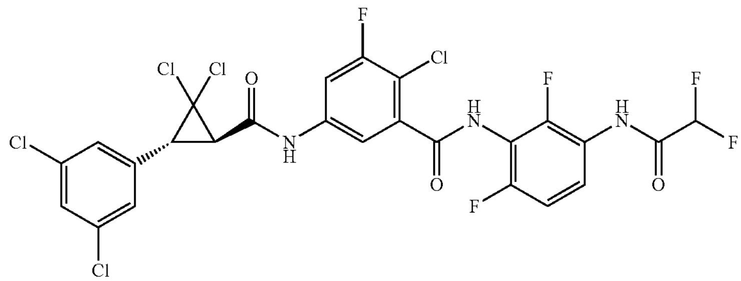 [SMILES: O=C(Nc1c(F)ccc(NC(=O)C(F)F)c1F)c1cc(NC(=O)[C@H]2[C@H](c3cc(Cl)cc(Cl)c3)C2(Cl)Cl)cc(F)c1Cl] | 3 |
| F1342 | 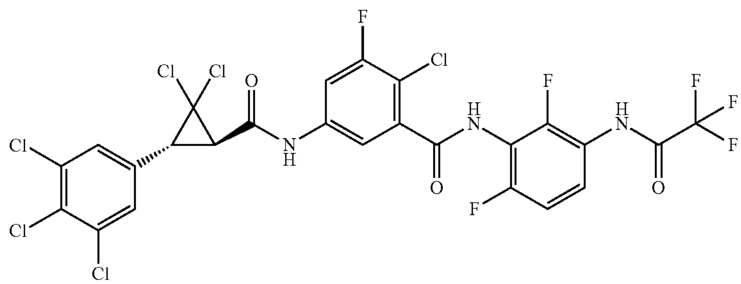 [SMILES: O=C(Nc1c(F)ccc(NC(=O)C(F)(F)F)c1F)c1cc(NC(=O)[C@H]2[C@H](c3cc(Cl)c(Cl)c(Cl)c3)C2(Cl)Cl)cc(F)c1Cl] | 3 |
| F1343 | 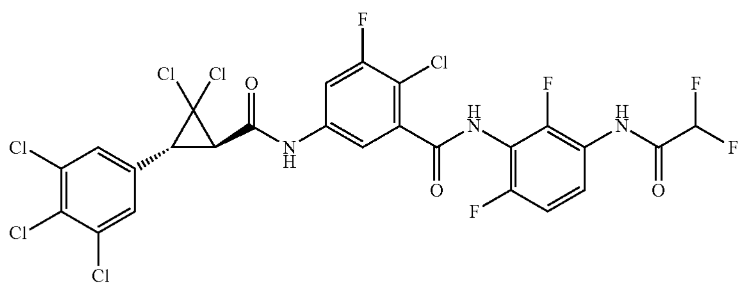 [SMILES: O=C(Nc1c(F)ccc(NC(=O)C(F)F)c1F)c1cc(NC(=O)[C@H]2[C@H](c3cc(Cl)c(Cl)c(Cl)c3)C2(Cl)Cl)cc(F)c1Cl] | 3 |
| F1344 | 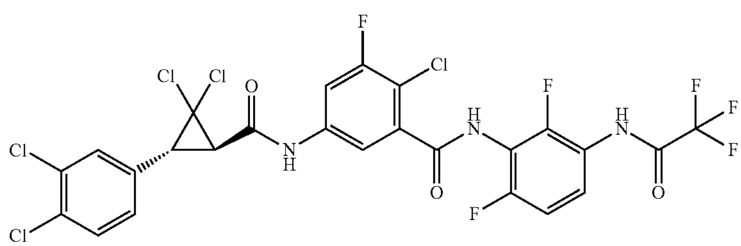 [SMILES: O=C(Nc1c(F)ccc(NC(=O)C(F)(F)F)c1F)c1cc(NC(=O)[C@H]2[C@H](c3ccc(Cl)c(Cl)c3)C2(Cl)Cl)cc(F)c1Cl] | 3 |
| F1345 | 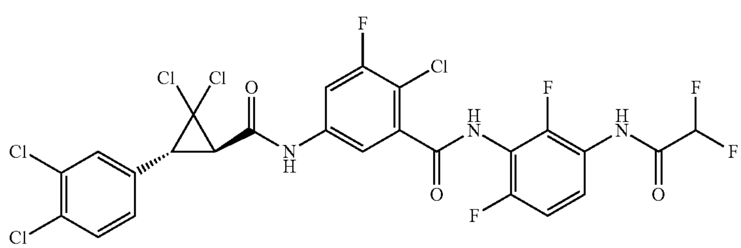 [SMILES: O=C(Nc1c(F)ccc(NC(=O)C(F)F)c1F)c1cc(NC(=O)[C@H]2[C@H](c3ccc(Cl)c(Cl)c3)C2(Cl)Cl)cc(F)c1Cl] | 3 |

TABLE 2-continued

Structure and preparation method for F Series molecules

| No. | Structure | Prep.* |
|---|---|---|
| F1346 | 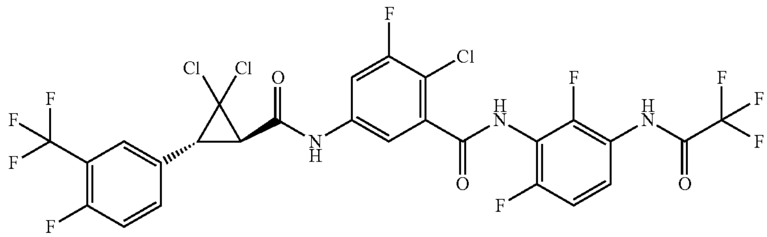 [SMILES: O=C(Nc1c(F)ccc(NC(=O)C(F)(F)F)c1F)c1cc(NC(=O)[C@H]2[C@H](c3ccc(F)c(C(F)(F)F)c3)C2(Cl)Cl)cc(F)c1Cl] | 3 |
| F1347 | 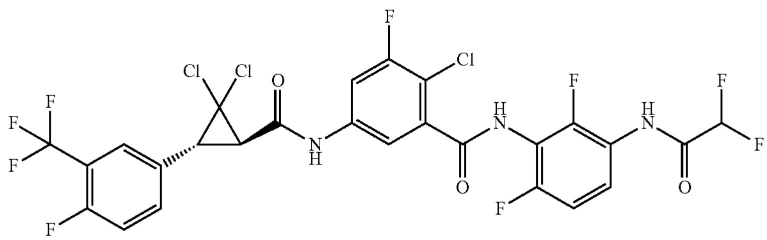 [SMILES: O=C(Nc1c(F)ccc(NC(=O)C(F)F)c1F)c1cc(NC(=O)[C@H]2[C@H](c3ccc(F)c(C(F)(F)F)c3)C2(Cl)Cl)cc(F)c1Cl] | 3 |
| F1348 | 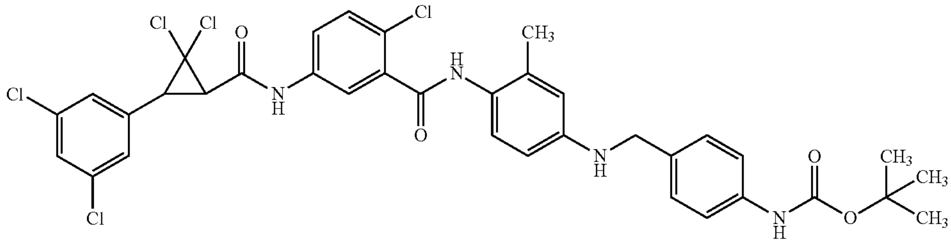 [SMILES: Cc1cc(NCc2ccc(NC(=O)OC(C)(C)C)cc2)ccc1NC(=O)c1cc(NC(=O)C2C(c3cc(Cl)cc(Cl)c3)C2(Cl)Cl)ccc1Cl] | 10 |
| F1349 | 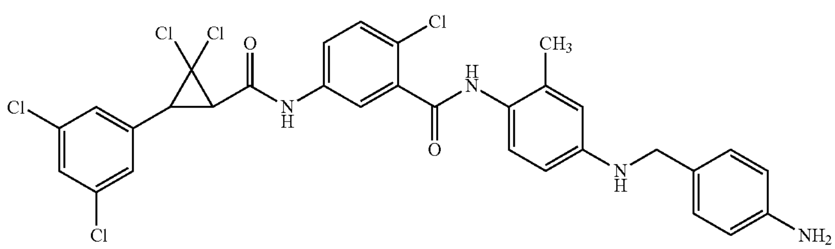 [SMILES: Cc1cc(NCc2ccc(N)cc2)ccc1NC(=O)c1cc(NC(=O)C2C(c3cc(Cl)cc(Cl)c3)C2(Cl)Cl)ccc1Cl] | 13 |
| F1350 | 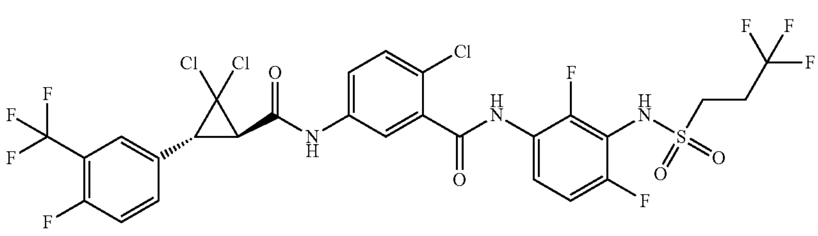 [SMILES: O=C(Nc1ccc(F)c(NS(=O)(=O)CCC(F)(F)F)c1F)c1cc(NC(=O)[C@H]2[C@H](c3ccc(F)c(C(F)(F)F)c3)C2(Cl)Cl)ccc1Cl] | 9 |
| F1351 | 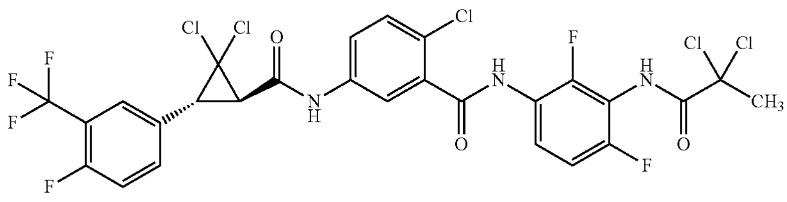 [SMILES: CC(Cl)(Cl)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |

TABLE 2-continued

Structure and preparation method for F Series molecules

| No. | Structure | Prep.* |
|---|---|---|
| F1352 | 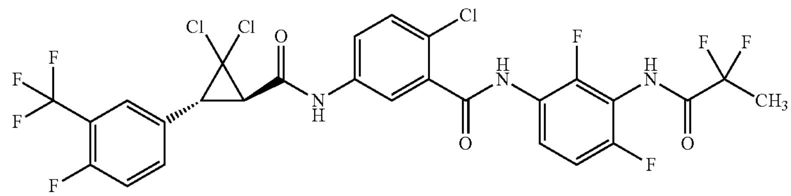 [SMILES: CC(F)(F)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1353 | 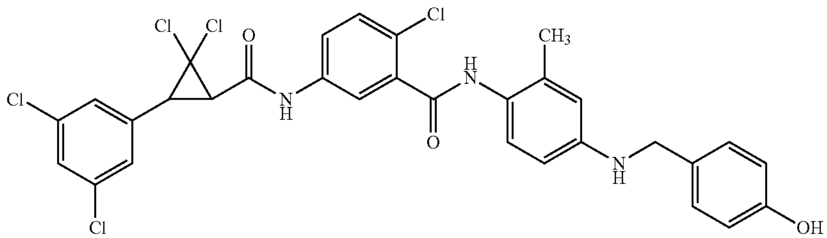 [SMILES: Cc1cc(NCc2ccc(O)cc2)ccc1NC(=O)c1cc(NC(=O)C2C(c3cc(Cl)cc(Cl)c3)C2(Cl)Cl)ccc1Cl] | 12 |
| F1354 | 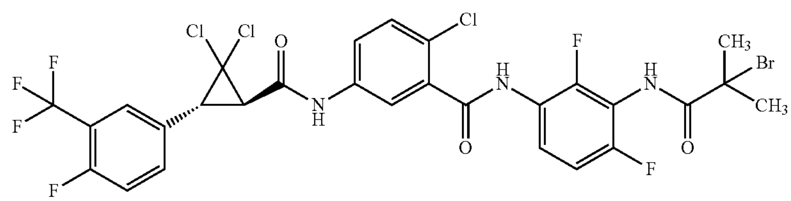 [SMILES: CC(C)(Br)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1355 | 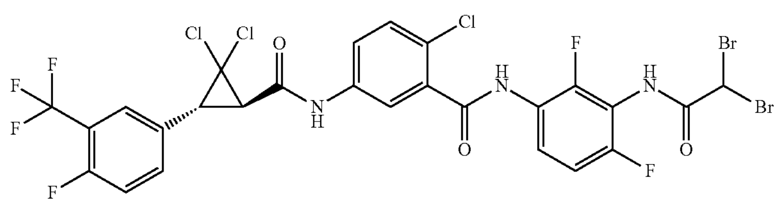 [SMILES: O=C(Nc1ccc(F)c(NC(=O)C(Br)Br)c1F)c1cc(NC(=O)[C@H]2[C@H](c3ccc(F)c(C(F)(F)F)c3)C2(Cl)Cl)ccc1Cl] | 6 |
| F1356 | 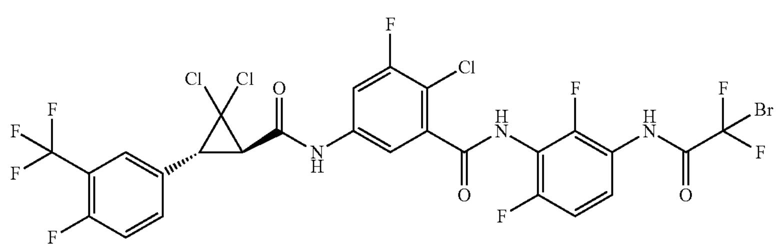 [SMILES: O=C(Nc1c(F)ccc(NC(=O)C(F)(F)Br)c1F)c1cc(NC(=O)[C@H]2[C@H](c3ccc(F)c(C(F)(F)F)c3)C2(Cl)Cl)cc(F)c1Cl] | 3 |
| F1357 | 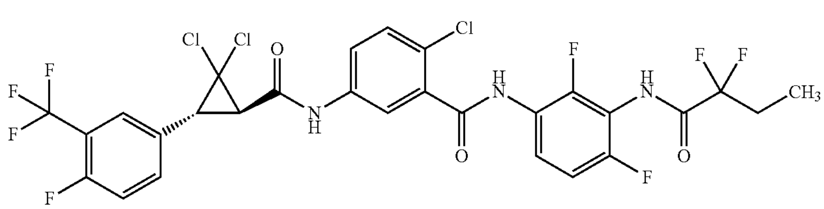 [SMILES: CCC(F)(F)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1358 | 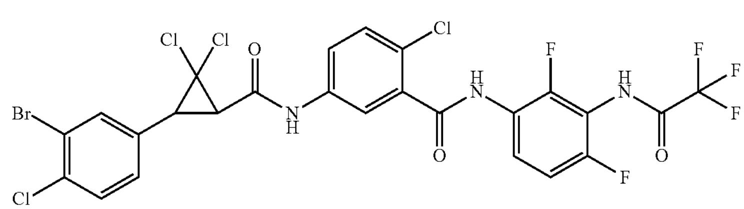 [SMILES: O=C(Nc1ccc(F)c(NC(=O)C(F)(F)F)c1F)c1cc(NC(=O)C2C(c3ccc(Cl)c(Br)c3)C2(Cl)Cl)ccc1Cl] | 1 |

| No. | Structure | Prep.* |
|---|---|---|
| F1359 | 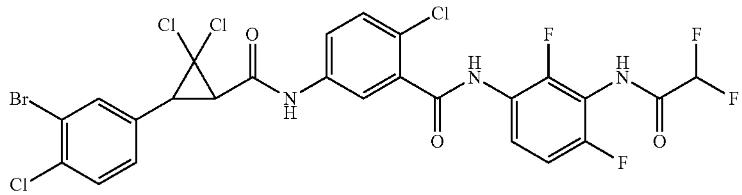 [SMILES: O=C(Nc1ccc(F)c(NC(=O)C(F)F)c1F)c1cc(NC(=O)C2C(c3ccc(Cl)c(Br)c3)C2(Cl)Cl)ccc1Cl] | 1 |
| F1360 | 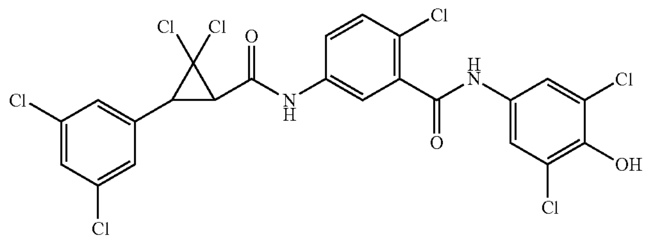 [SMILES: O=C(Nc1cc(Cl)c(O)c(Cl)c1)c1cc(NC(=O)C2C(c3cc(Cl)cc(Cl)c3)C2(Cl)Cl)ccc1Cl] | 22 |
| F1361 | 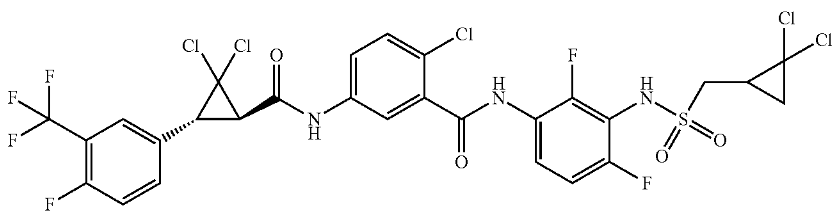 [SMILES: O=C(Nc1ccc(F)c(NS(=O)(=O)CC2CC2(Cl)Cl)c1F)c1cc(NC(=O)[C@H]2[C@H](c3ccc(F)c(C(F)(F)F)c3)C2(Cl)Cl)ccc1Cl] | 9 |
| F1362 | 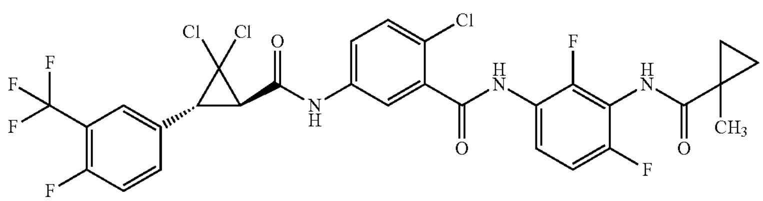 [SMILES: CC1(C(=O)Nc2c(F)ccc(NC(=O)c3cc(NC(=O)[C@H]4[C@H](c5ccc(F)c(C(F)(F)F)c5)C4(Cl)Cl)ccc3Cl)c2F)CC1] | 6 |
| F1363 | 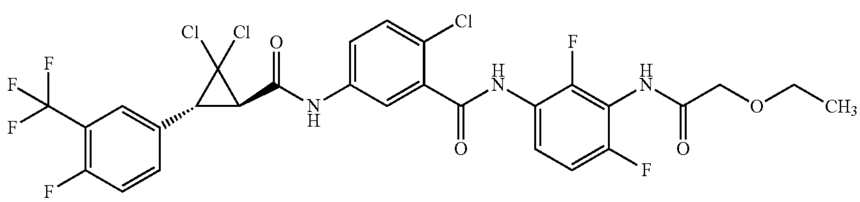 | 6 |
| F1364 | 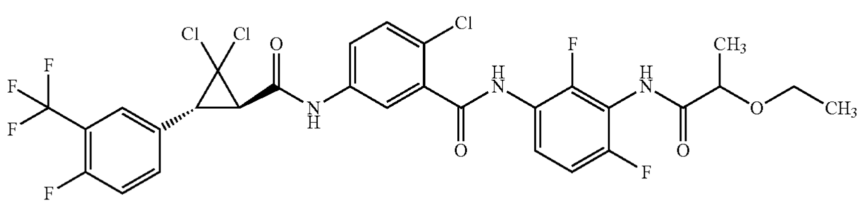 [SMILES: CCOC(C)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1365 | 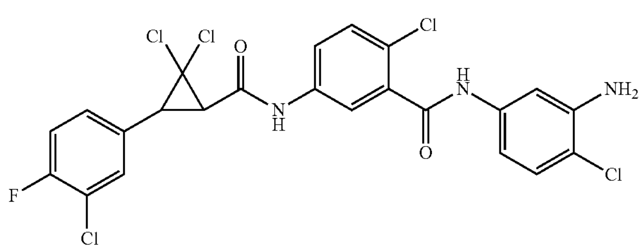 [SMILES: Nc1cc(NC(=O)c2cc(NC(=O)C3C(c4ccc(F)c(Cl)c4)C3(Cl)Cl)ccc2Cl)ccc1Cl] | 13 |

TABLE 2-continued

Structure and preparation method for F Series molecules

| No. | Structure | Prep.* |
|---|---|---|
| F1366 | 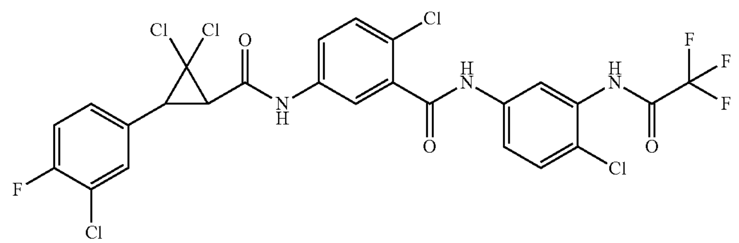 [SMILES: O=C(Nc1ccc(Cl)c(NC(=O)C(F)(F)F)c1)c1cc(NC(=O)C2C(c3ccc(F)c(Cl)c3)C2(Cl)Cl)ccc1Cl] | 1 |
| F1367 | 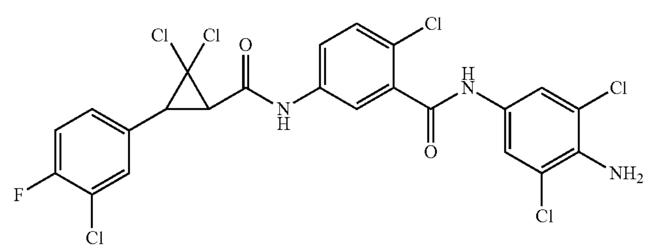 [SMILES: Nc1c(Cl)cc(NC(=O)c2cc(NC(=O)C3C(c4ccc(F)c(Cl)c4)C3(Cl)Cl)ccc2Cl)cc1Cl] | 13 |
| F1368 | 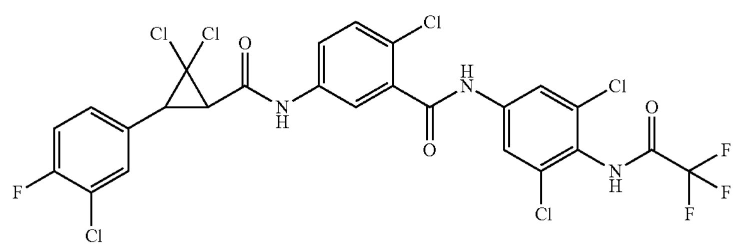 [SMILES: O=C(Nc1cc(Cl)c(NC(=O)C(F)(F)F)c(Cl)c1)c1cc(NC(=O)C2C(c3ccc(F)c(Cl)c3)C2(Cl)Cl)ccc1Cl] | 1 |
| F1369 | 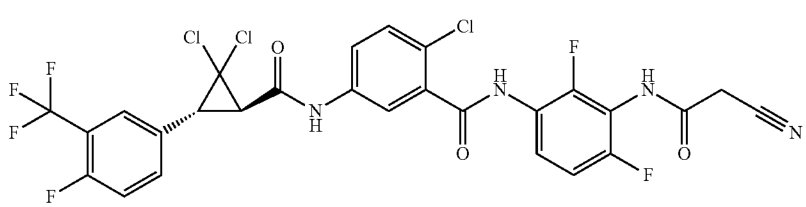 [SMILES: N#CCC(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1370 | 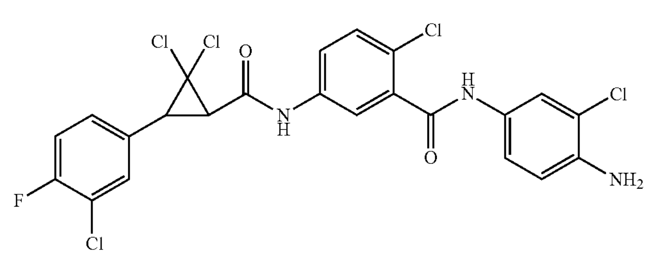 [SMILES: Nc1ccc(NC(=O)c2cc(NC(=O)C3C(c4ccc(F)c(Cl)c4)C3(Cl)Cl)ccc2Cl)cc1Cl] | 13 |
| F1371 | 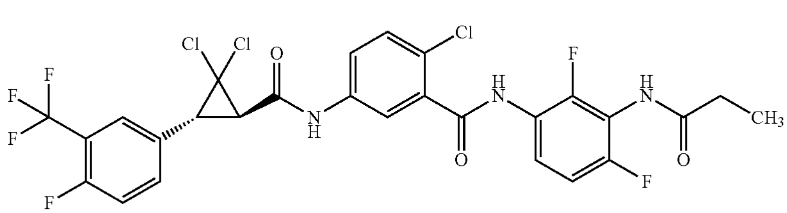 [SMILES: CCC(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |

TABLE 2-continued

Structure and preparation method for F Series molecules

| No. | Structure | Prep.* |
|---|---|---|
| F1372 | 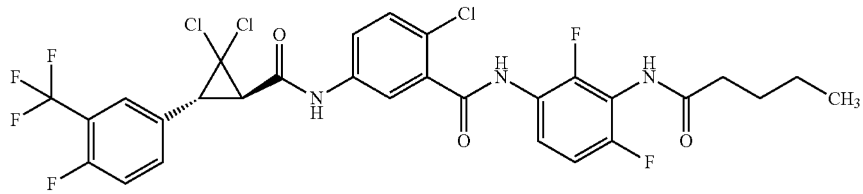 [SMILES: CCCCC(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1373 | 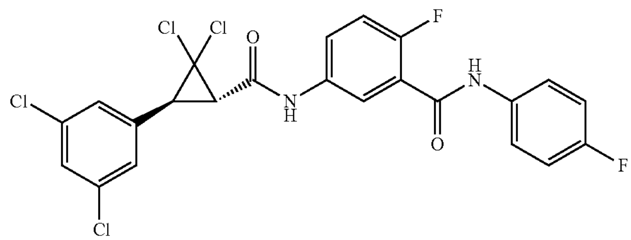 [SMILES: O=C(Nc1ccc(F)cc1)c1cc(NC(=O)[C@@H]2[C@@H](c3cc(Cl)cc(Cl)c3)C2(Cl)Cl)ccc1F] | 103 |
| F1374 | 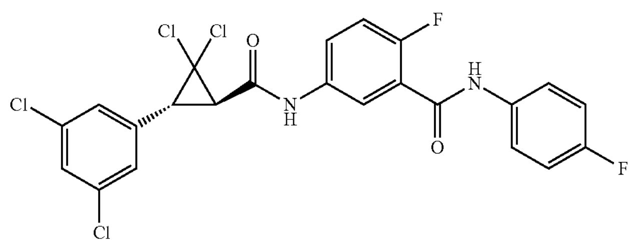 [SMILES: O=C(Nc1ccc(F)cc1)c1cc(NC(=O)[C@H]2[C@H](c3cc(Cl)cc(Cl)c3)C2(Cl)Cl)ccc1F] | 103 |
| F1375 | 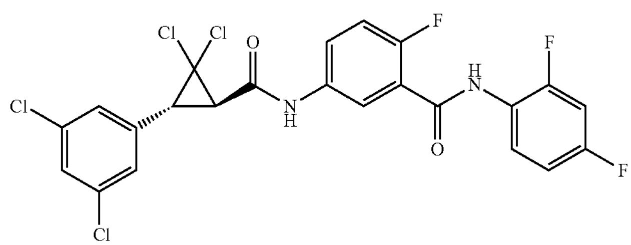 [SMILES: O=C(Nc1ccc(F)cc1F)c1cc(NC(=O)[C@H]2[C@H](c3cc(Cl)cc(Cl)c3)C2(Cl)Cl)ccc1F] | 104 |
| F1376 | 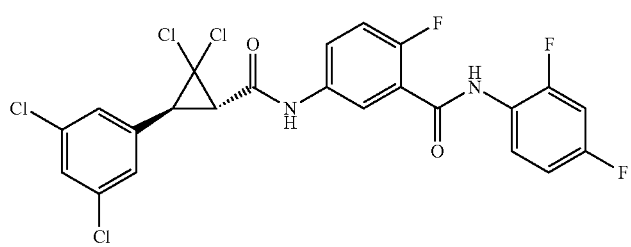 [SMILES: O=C(Nc1ccc(F)cc1F)c1cc(NC(=O)[C@@H]2[C@@H](c3cc(Cl)cc(Cl)c3)C2(Cl)Cl)ccc1F] | 104 |
| F1377 | 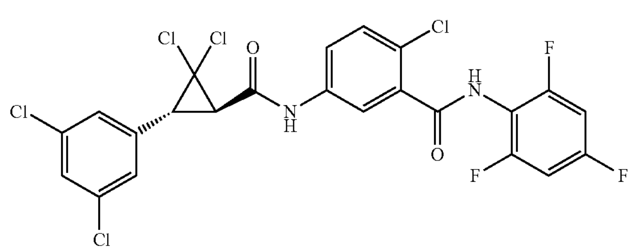 [SMILES: O=C(Nc1c(F)cc(F)cc1F)c1cc(NC(=O)[C@H]2[C@H](c3cc(Cl)cc(Cl)c3)C2(Cl)Cl)ccc1Cl] | 105 |

TABLE 2-continued
Structure and preparation method for F Series molecules
| No. | Structure | Prep.* |
|---|---|---|
| F1378 | 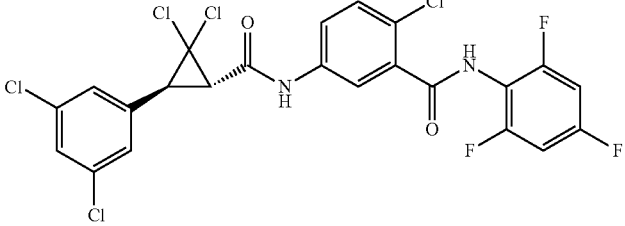 | 105 |
| F1379 | 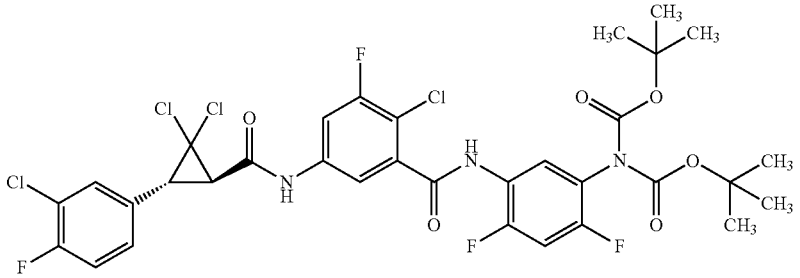 [SMILES: CC(C)(C)OC(=O)N(C(=O)OC(C)(C)C)c1cc(NC(=O)c2cc(NC(=O)[C@H]3[C@H](c4ccc(F)c(Cl)c4)C3(Cl)Cl)cc(F)c2Cl)c(F)cc1F] | 20 |
| F1380 | 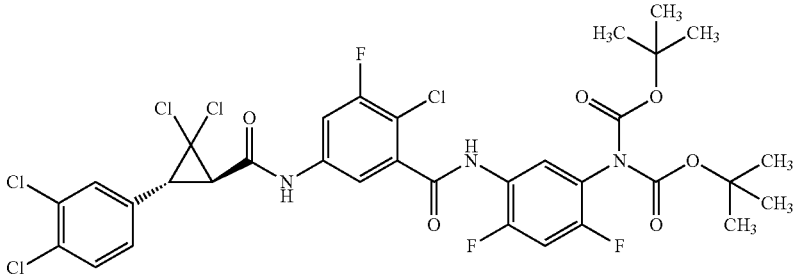 | 20 |
| F1381 | 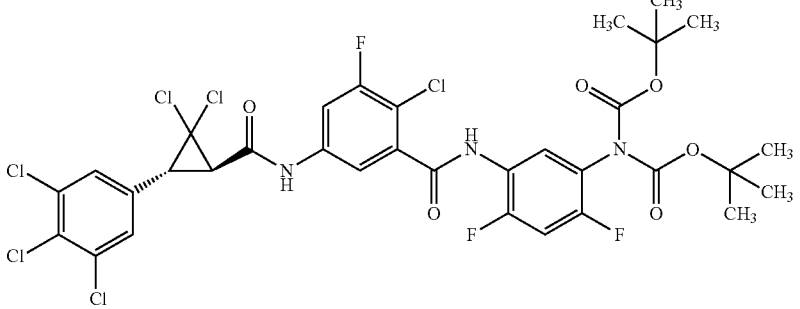 | 20 |
| F1382 | 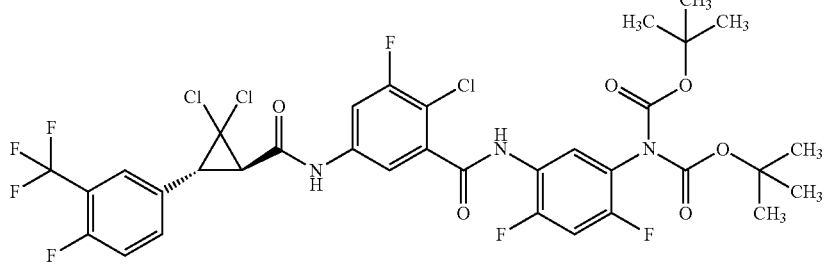 | 20 |

TABLE 2-continued

Structure and preparation method for F Series molecules

| No. | Structure | Prep.* |
|---|---|---|
| F1383 | 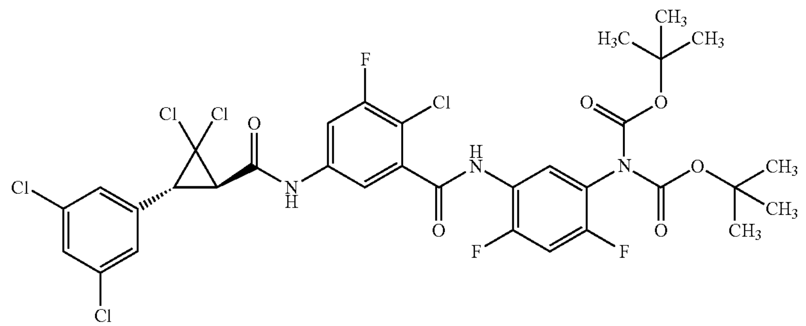 [SMILES: CC(C)(C)OC(=O)N(C(=O)OC(C)(C)C)c1cc(NC(=O)c2cc(NC(=O)[C@H]3[C@H](c4cc(Cl)cc(Cl)c4)C3(Cl)Cl)cc(F)c2Cl)c(F)cc1F] | 20 |
| F1384 | 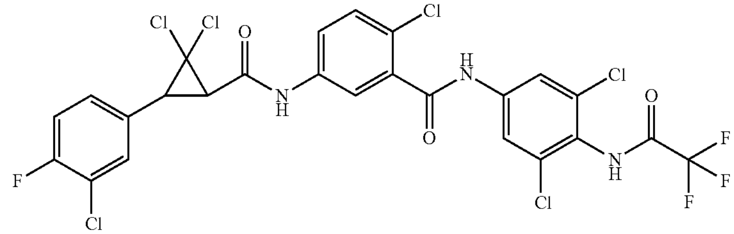 [SMILES: O=C(Nc1cc(Cl)c(NC(=O)C(F)(F)F)c(Cl)c1)c1cc(NC(=O)C2C(c3ccc(F)c(Cl)c3)C2(Cl)Cl)ccc1Cl] | 1 |
| F1385 | 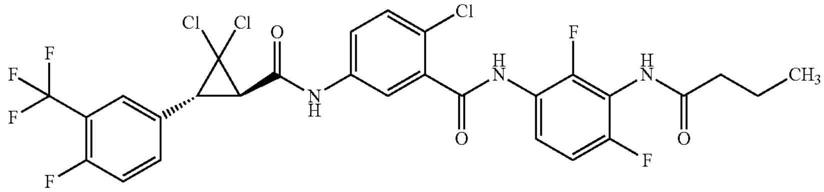 | 6 |
| F1386 | 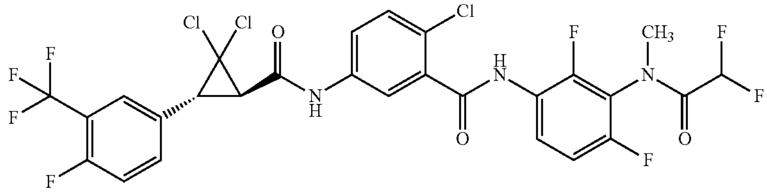 [SMILES: CN(C(=O)C(F)F)c1c(F)ccc(NC(=O)c2cc(NC(=O)[C@H]3[C@H](c4ccc(F)c(C(F)(F)F)c4)C3(Cl)Cl)ccc2Cl)c1F] | 25 |
| F1387 | 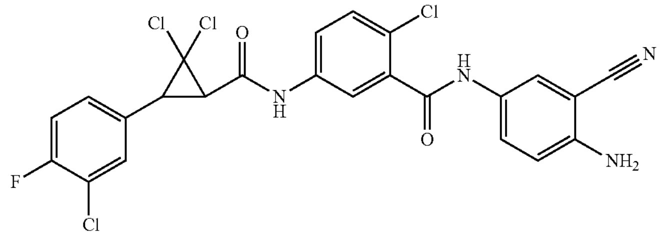 [SMILES: N#Cc1cc(NC(=O)c2cc(NC(=O)C3C(c4ccc(F)c(Cl)c4)C3(Cl)Cl)ccc2Cl)ccc1N] | 13 |
| F1388 | 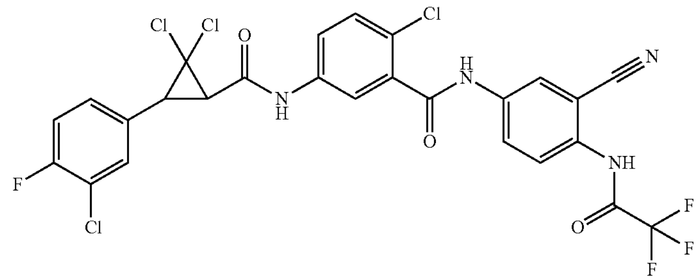 [SMILES: N#Cc1cc(NC(=O)c2cc(NC(=O)C3C(c4ccc(F)c(Cl)c4)C3(Cl)Cl)ccc2Cl)ccc1NC(=O)C(F)(F)F] | 1 |

TABLE 2-continued

Structure and preparation method for F Series molecules

| No. | Structure | Prep.* |
|---|---|---|
| F1389 | 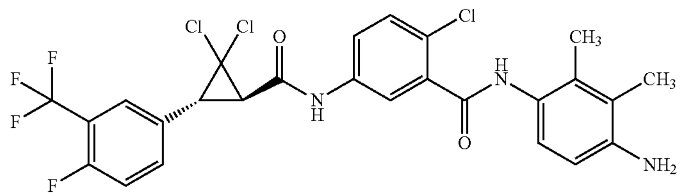 [SMILES: Cc1c(N)ccc(NC(=O)c2cc(NC(=O)[C@H]3[C@H](c4ccc(F)c(C(F)(F)F)c4)C3(Cl)Cl)ccc2Cl)c1C] | 13 |
| F1390 | 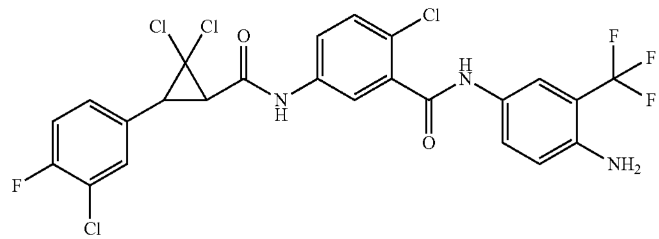 [SMILES: Nc1ccc(NC(=O)c2cc(NC(=O)C3C(c4ccc(F)c(Cl)c4)C3(Cl)Cl)ccc2Cl)cc1C(F)(F)F] | 13 |
| F1391 | 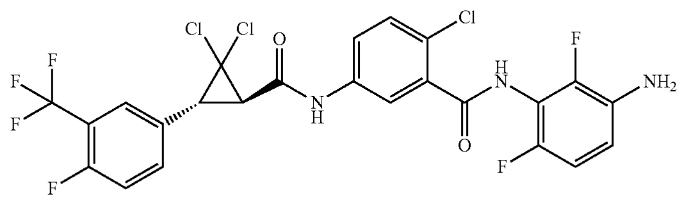 [SMILES: Nc1ccc(F)c(NC(=O)c2cc(NC(=O)[C@H]3[C@H](c4ccc(F)c(C(F)(F)F)c4)C3(Cl)Cl)ccc2Cl)c1F] | 13 |
| F1392 | 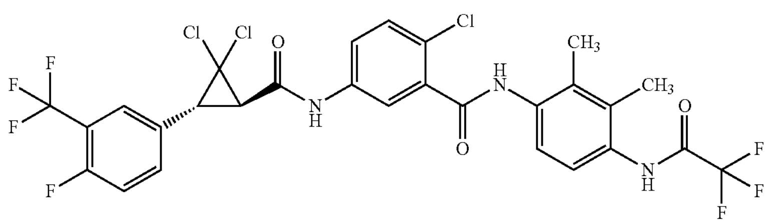 [SMILES: Cc1c(NC(=O)c2cc(NC(=O)[C@H]3[C@H](c4ccc(F)c(C(F)(F)F)c4)C3(Cl)Cl)ccc2Cl)ccc(NC(=O)C(F)(F)F)c1C] | 1 |
| F1393 | 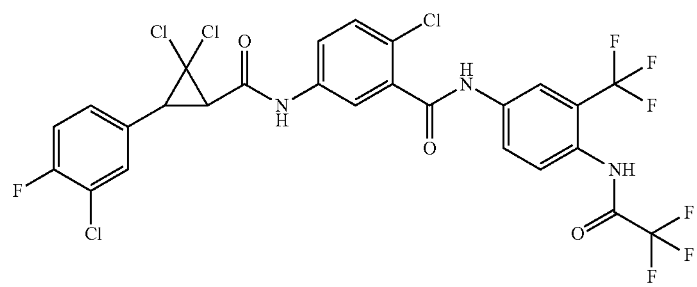 [SMILES: O=C(Nc1ccc(NC(=O)C(F)(F)F)c(C(F)(F)F)c1)c1cc(NC(=O)C2C(c3ccc(F)c(Cl)c3)C2(Cl)Cl)ccc1Cl] | 1 |
| F1394 | 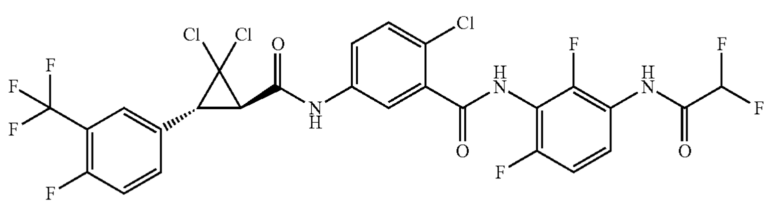 [SMILES: O=C(Nc1c(F)ccc(NC(=O)C(F)F)c1F)c1cc(NC(=O)[C@H]2[C@H](c3ccc(F)c(C(F)(F)F)c3)C2(Cl)Cl)ccc1Cl] | 1 |

TABLE 2-continued

Structure and preparation method for F Series molecules

| No. | Structure | Prep.* |
|---|---|---|
| F1395 | 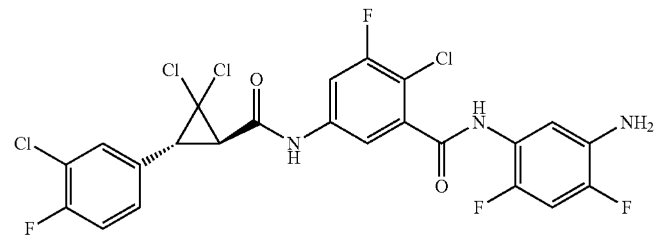 [SMILES: Nc1cc(NC(=O)c2cc(NC(=O)[C@H]3[C@H](c4ccc(F)c(Cl)c4)C3(Cl)Cl)cc(F)c2Cl)c(F)cc1F] | 13 |
| F1396 | 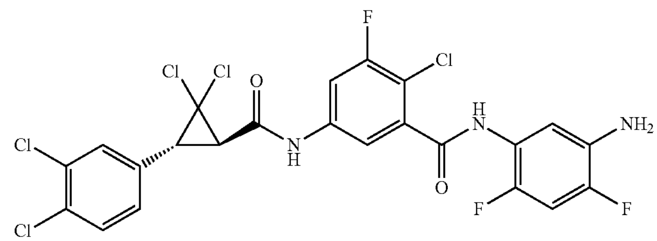 [SMILES: Nc1cc(NC(=O)c2cc(NC(=O)[C@H]3[C@H](c4ccc(Cl)c(Cl)c4)C3(Cl)Cl)cc(F)c2Cl)c(F)cc1F] | 13 |
| F1397 | 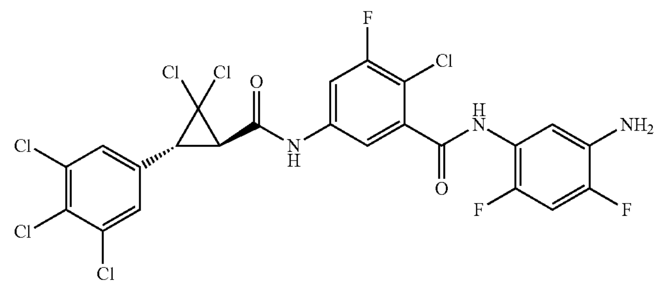 [SMILES: Nc1cc(NC(=O)c2cc(NC(=O)[C@H]3[C@H](c4cc(Cl)c(Cl)c(Cl)c4)C3(Cl)Cl)cc(F)c2Cl)c(F)cc1F] | 13 |
| F1398 | 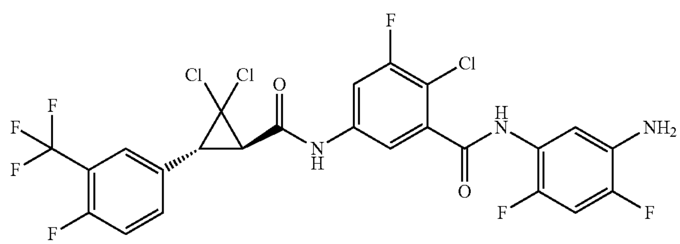 [SMILES: Nc1cc(NC(=O)c2cc(NC(=O)[C@H]3[C@H](c4ccc(F)c(C(F)(F)F)c4)C3(Cl)Cl)cc(F)c2Cl)c(F)cc1F] | 13 |
| F1399 | 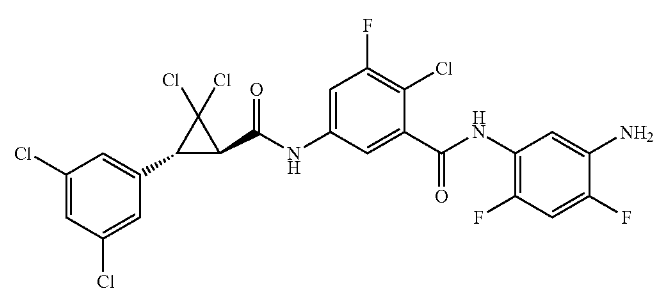 [SMILES: Nc1cc(NC(=O)c2cc(NC(=O)[C@H]3[C@H](c4cc(Cl)cc(Cl)c4)C3(Cl)Cl)cc(F)c2Cl)c(F)cc1F] | 13 |
| F1400 | 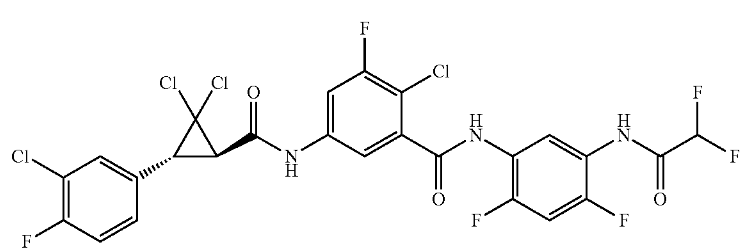 [SMILES: O=C(Nc1cc(NC(=O)C(F)F)c(F)cc1F)c1cc(NC(=O)[C@H]2[C@H](c3ccc(F)c(Cl)c3)C2(Cl)Cl)cc(F)c1Cl] | 3 |

TABLE 2-continued

Structure and preparation method for F Series molecules

| No. | Structure | Prep.* |
|---|---|---|
| F1401 | 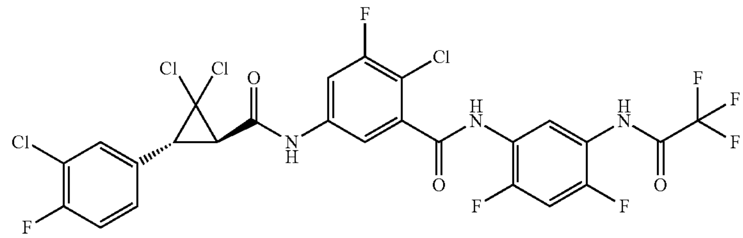 [SMILES: O=C(Nc1cc(NC(=O)C(F)(F)F)c(F)cc1F)c1cc(NC(=O)[C@H]2[C@H](c3ccc(F)c(Cl)c3)C2(Cl)Cl)cc(F)c1Cl] | 3 |
| F1402 | 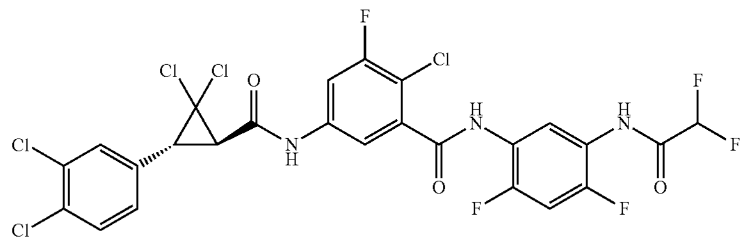 [SMILES: O=C(Nc1cc(NC(=O)C(F)F)c(F)cc1F)c1cc(NC(=O)[C@H]2[C@H](c3ccc(Cl)c(Cl)c3)C2(Cl)Cl)cc(F)c1Cl] | 3 |
| F1403 | 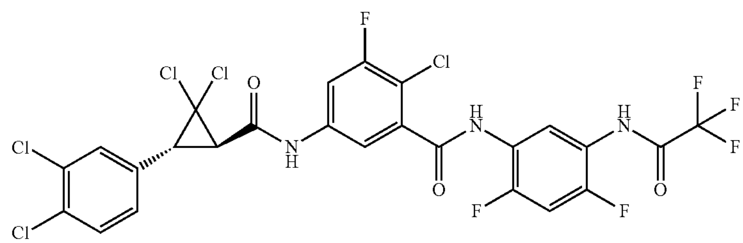 [SMILES: O=C(Nc1cc(NC(=O)C(F)(F)F)c(F)cc1F)c1cc(NC(=O)[C@H]2[C@H](c3ccc(Cl)c(Cl)c3)C2(Cl)Cl)cc(F)c1Cl] | 3 |
| F1404 | 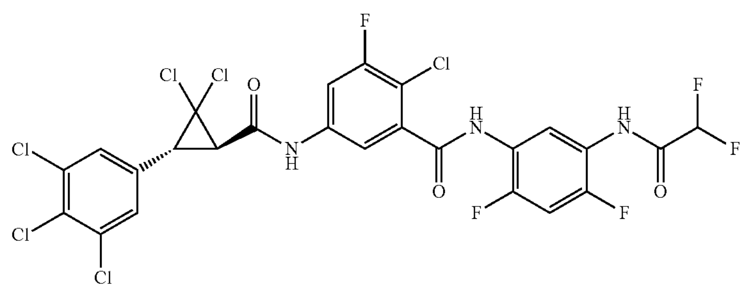 [SMILES: O=C(Nc1cc(NC(=O)C(F)F)c(F)cc1F)c1cc(NC(=O)[C@H]2[C@H](c3cc(Cl)c(Cl)c(Cl)c3)C2(Cl)Cl)cc(F)c1Cl] | 3 |
| F1405 | 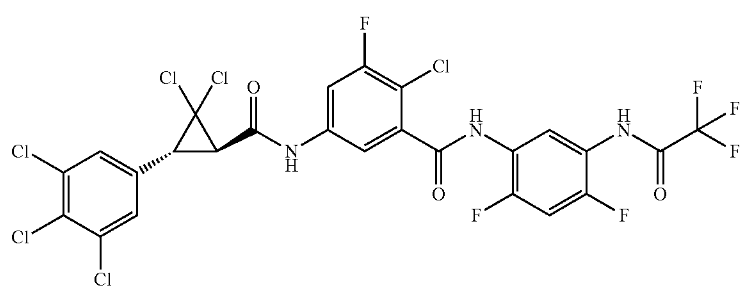 [SMILES: O=C(Nc1cc(NC(=O)C(F)(F)F)c(F)cc1F)c1cc(NC(=O)[C@H]2[C@H](c3cc(Cl)c(Cl)c(Cl)c3)C2(Cl)Cl)cc(F)c1Cl] | 3 |
| F1406 | 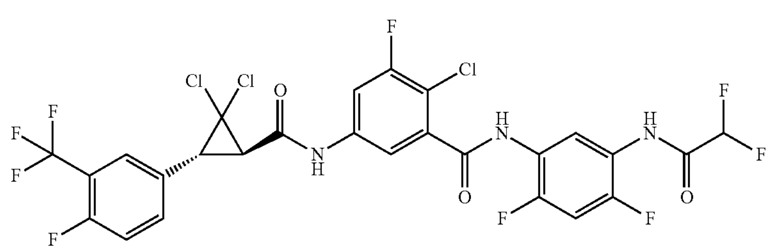 [SMILES: O=C(Nc1cc(NC(=O)C(F)F)c(F)cc1F)c1cc(NC(=O)[C@H]2[C@H](c3ccc(F)c(C(F)(F)F)c3)C2(Cl)Cl)cc(F)c1Cl] | 3 |

TABLE 2-continued

Structure and preparation method for F Series molecules

| No. | Structure | Prep.* |
|---|---|---|
| F1407 | 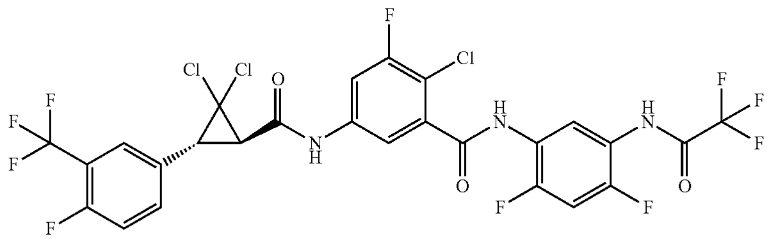 [SMILES: O=C(Nc1cc(NC(=O)C(F)(F)F)c(F)cc1F)c1cc(NC(=O)[C@H]2[C@H](c3ccc(F)c(C(F)(F)F)c3)C2(Cl)Cl)cc(F)c1Cl] | 3 |
| F1408 | 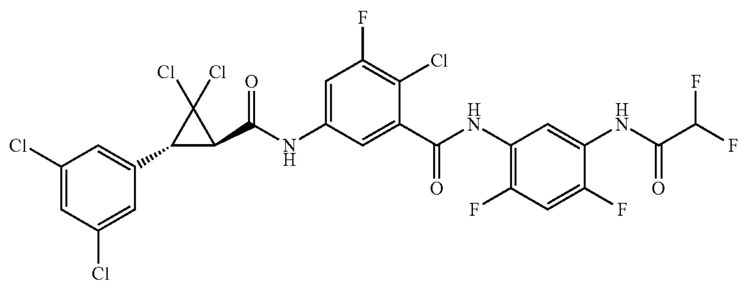 [SMILES: O=C(Nc1cc(NC(=O)C(F)F)c(F)cc1F)c1cc(NC(=O)[C@H]2[C@H](c3cc(Cl)cc(Cl)c3)C2(Cl)Cl)cc(F)c1Cl] | 3 |
| F1409 | 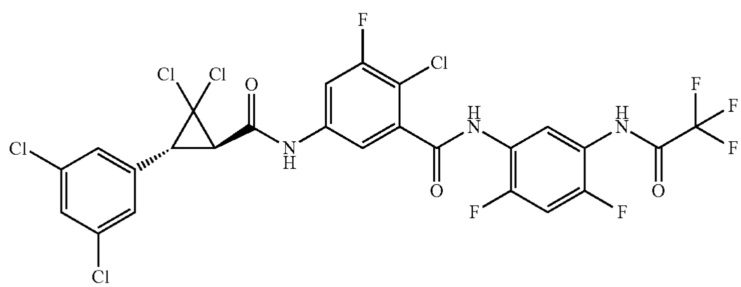 [SMILES: O=C(Nc1cc(NC(=O)C(F)(F)F)c(F)cc1F)c1cc(NC(=O)[C@H]2[C@H](c3cc(Cl)cc(Cl)c3)C2(Cl)Cl)cc(F)c1Cl] | 3 |
| F1410 | 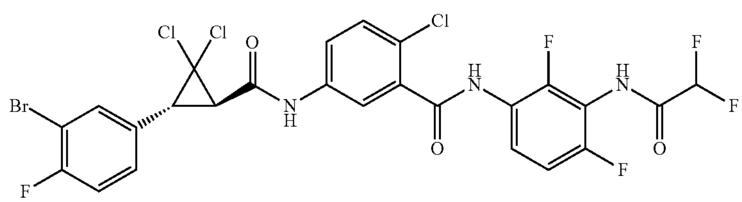 [SMILES: O=C(Nc1ccc(F)c(NC(=O)C(F)F)c1F)c1cc(NC(=O)[C@H]2[C@H](c3ccc(Cl)c(Br)c3)C2(Cl)Cl)ccc1Cl] | 18 |
| F1411 | 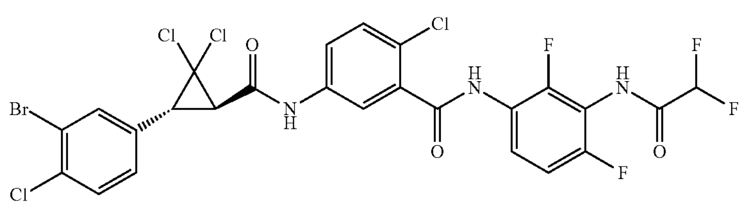 | 18 |
| F1412 | 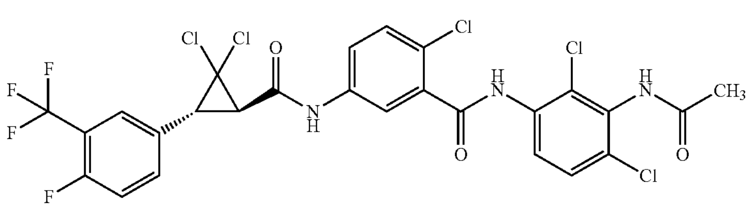 [SMILES: CC(=O)Nc1c(Cl)ccc(NC(=O)c2cc(NC(=O)[C@H]3[C@H](c4ccc(F)c(C(F)(F)F)c4)C3(Cl)Cl)ccc2Cl)c1Cl] | 5 |

TABLE 2-continued

Structure and preparation method for F Series molecules

| No. | Structure | Prep.* |
|---|---|---|
| F1414 | 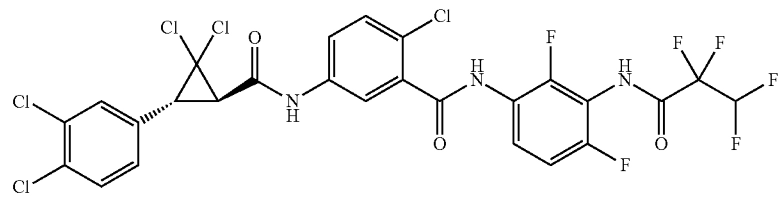 [SMILES: O=C(Nc1ccc(F)c(NC(=O)C(F)(F)C(F)F)c1F)c1cc(NC(=O)[C@H]2[C@H](c3ccc(Cl)c(Cl)c3)C2(Cl)Cl)ccc1Cl] | 4 |
| F1415 | 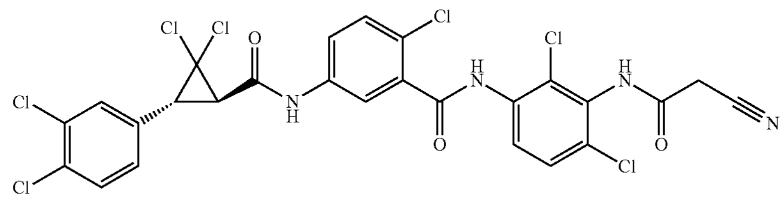 [SMILES: N#CCC(=O)Nc1c(Cl)ccc(NC(=O)c2cc(NC(=O)[C@H]3[C@H](c4ccc(Cl)c(Cl)c4)C3(Cl)Cl)ccc2Cl)c1Cl] | 4 |
| F1416 | 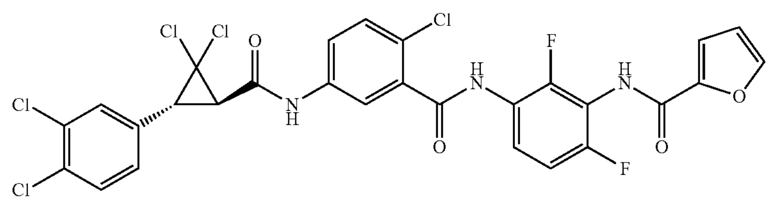 [SMILES: O=C(Nc1c(F)ccc(NC(=O)c2cc(NC(=O)[C@H]3[C@H](c4ccc(Cl)c(Cl)c4)C3(Cl)Cl)ccc2Cl)c1F)c1ccco1] | 4 |
| F1417 | 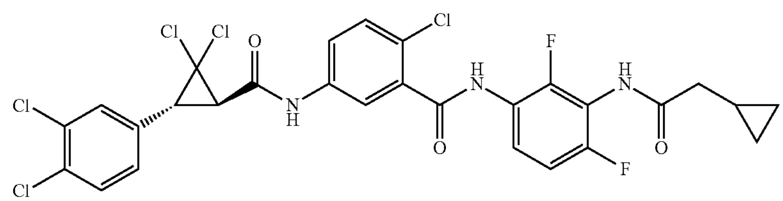 [SMILES: O=C(CC1CC1)Nc1c(F)ccc(NC(=O)c2cc(NC(=O)[C@H]3[C@H](c4ccc(Cl)c(Cl)c4)C3(Cl)Cl)ccc2Cl)c1F] | 4 |
| F1418 | 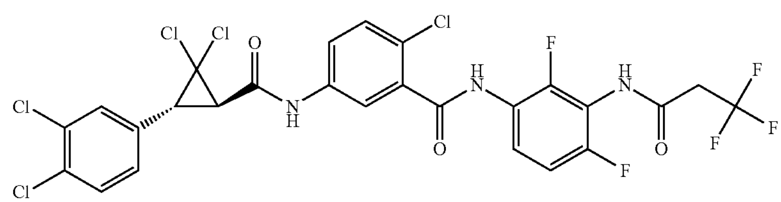 [SMILES: O=C(CC(F)(F)F)Nc1c(F)ccc(NC(=O)c2cc(NC(=O)[C@H]3[C@H](c4ccc(Cl)c(Cl)c4)C3(Cl)Cl)ccc2Cl)c1F] | 4 |
| F1419 | 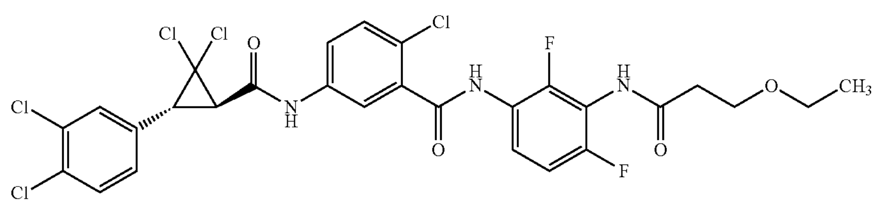 [SMILES: CCOCCC(=O)Nc1c(F)ccc(NC(=O)c2cc(NC(=O)[C@H]3[C@H](c4ccc(Cl)c(Cl)c4)C3(Cl)Cl)ccc2Cl)c1F] | 4 |
| F1420 | 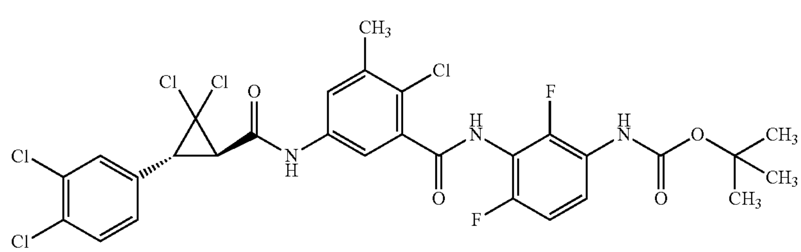 [SMILES: Cc1cc(NC(=O)[C@H]2[C@H](c3ccc(Cl)c(Cl)c3)C2(Cl)Cl)cc(C(=O)Nc2c(F)ccc(NC(=O)OC(C)(C)C)c2F)c1Cl] | 22 |

TABLE 2-continued

Structure and preparation method for F Series molecules

| No. | Structure | Prep.* |
|---|---|---|
| F1421 | 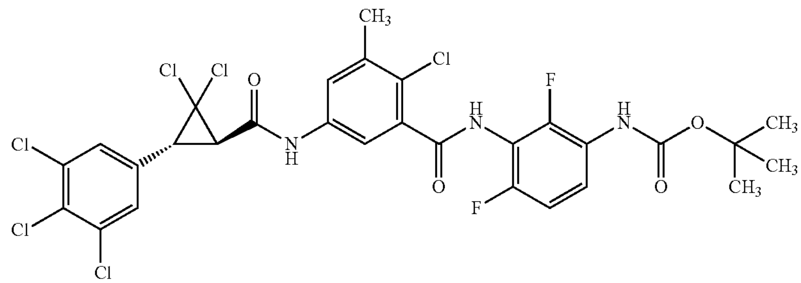 [SMILES: Cc1cc(NC(=O)[C@H]2[C@H](c3cc(Cl)c(Cl)c(Cl)c3)C2(Cl)Cl)cc(C(=O)Nc2c(F)ccc(NC(=O)OC(C)(C)C)c2F)c1Cl] | 22 |
| F1422 | 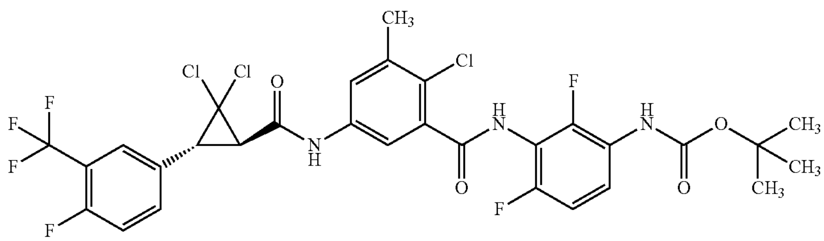 [SMILES: Cc1cc(NC(=O)[C@H]2[C@H](c3ccc(F)c(C(F)(F)F)c3)C2(Cl)Cl)cc(C(=O)Nc2c(F)ccc(NC(=O)OC(C)(C)C)c2F)c1Cl] | 22 |
| F1423 | 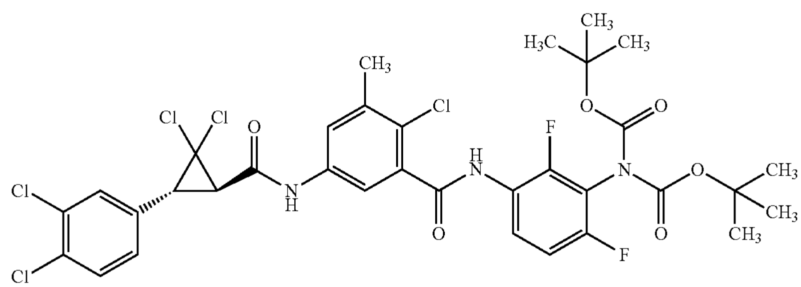 [SMILES: Cc1cc(NC(=O)[C@H]2[C@H](c3ccc(Cl)c(Cl)c3)C2(Cl)Cl)cc(C(=O)Nc2ccc(F)c(N(C(=O)OC(C)(C)C)C(=O)OC(C)(C)C)c2F)c1Cl] | 22 |
| F1424 | 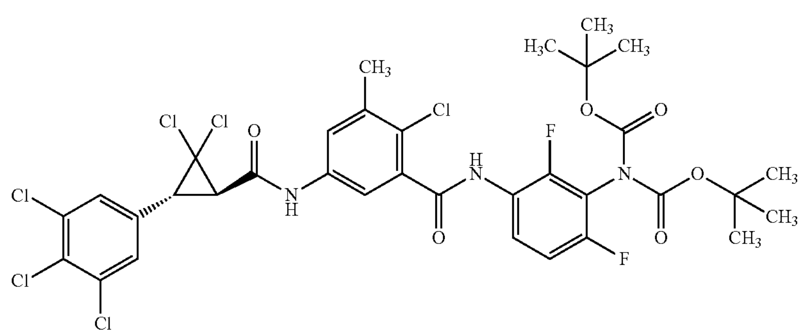 [SMILES: Cc1cc(NC(=O)[C@H]2[C@H](c3cc(Cl)c(Cl)c(Cl)c3)C2(Cl)Cl)cc(C(=O)Nc2ccc(F)c(N(C(=O)OC(C)(C)C)C(=O)OC(C)(C)C)c2F)c1Cl] | 22 |
| F1425 | 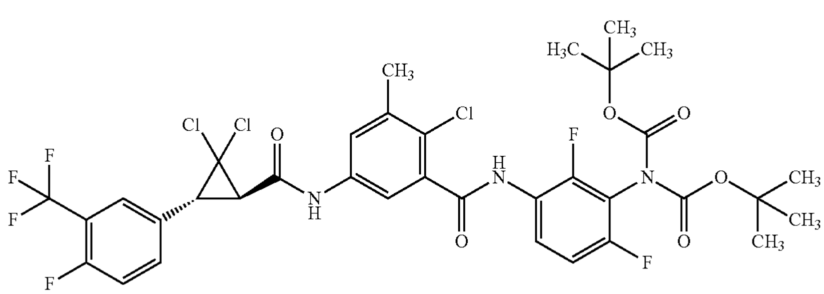 [SMILES: Cc1cc(NC(=O)[C@H]2[C@H](c3ccc(F)c(C(F)(F)F)c3)C2(Cl)Cl)cc(C(=O)Nc2ccc(F)c(N(C(=O)OC(C)(C)C)C(=O)OC(C)(C)C)c2F)c1Cl] | 22 |

| | TABLE 2-continued | |
|---|---|---|
| | Structure and preparation method for F Series molecules | |
| No. | Structure | Prep.* |
| F1426 | | 13 |
| F1427 | | 13 |
| F1428 | | 13 |
| F1429 | | 3 |
| F1430 | | 3 |
| F1431 | | 3 |

TABLE 2-continued

Structure and preparation method for F Series molecules

| No. | Structure | Prep.* |
|---|---|---|
| F1432 | 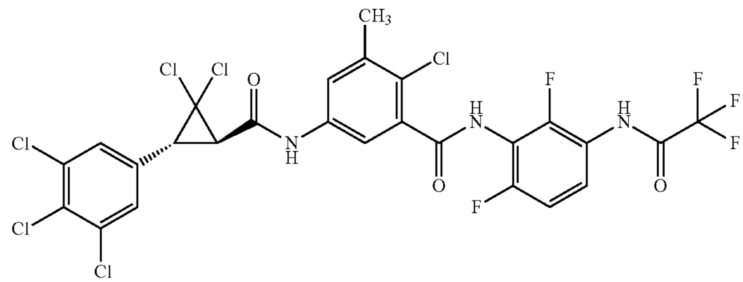 [SMILES: Cc1cc(NC(=O)[C@H]2[C@H](c3cc(Cl)c(Cl)c(Cl)c3)C2(Cl)Cl)cc(C(=O)Nc2c(F)ccc(NC(=O)C(F)(F)F)c2F)c1Cl] | 3 |
| F1433 | 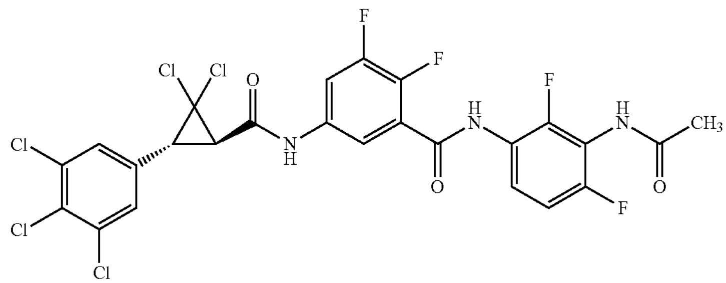 [SMILES: CC(=O)Nc1c(F)ccc(NC(=O)c2cc(NC(=O)[C@H]3[C@H](c4cc(Cl)c(Cl)c(Cl)c4)C3(Cl)Cl)cc(F)c2F)c1F] | 5 |
| F1434 | 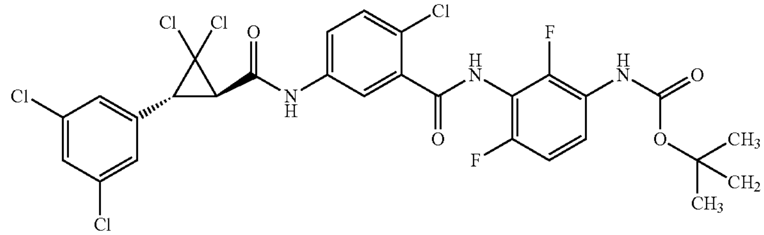 [SMILES: CC(C)(C)OC(=O)Nc1ccc(F)c(NC(=O)c2cc(NC(=O)[C@H]3[C@H](c4cc(Cl)cc(Cl)c4)C3(Cl)Cl)ccc2Cl)c1F] | 5 |
| F1435 | 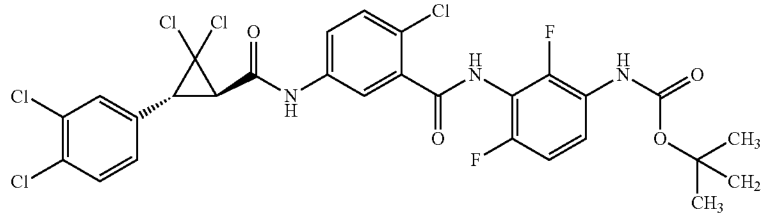 [SMILES: CC(C)(C)OC(=O)Nc1ccc(F)c(NC(=O)c2cc(NC(=O)[C@H]3[C@H](c4ccc(Cl)c(Cl)c4)C3(Cl)Cl)ccc2Cl)c1F] | 5 |
| F1436 | 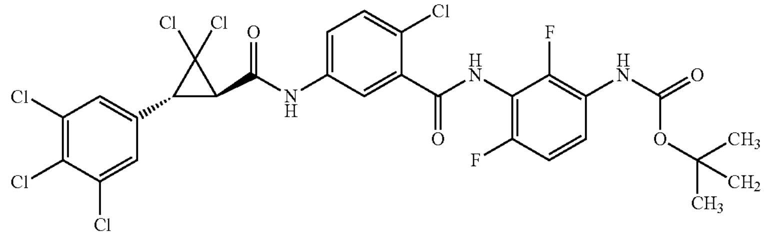 [SMILES: CC(C)(C)OC(=O)Nc1ccc(F)c(NC(=O)c2cc(NC(=O)[C@H]3[C@H](c4cc(Cl)c(Cl)c(Cl)c4)C3(Cl)Cl)ccc2Cl)c1F] | 5 |
| F1437 | 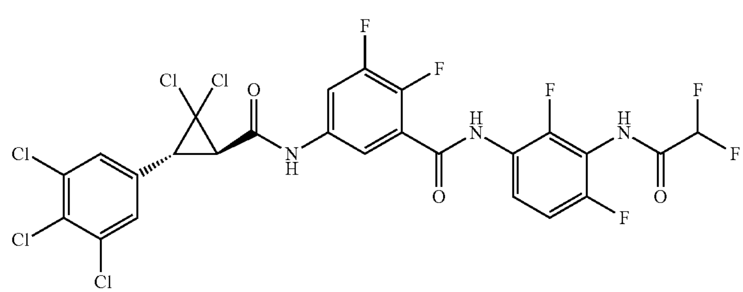 | 5 |

TABLE 2-continued

Structure and preparation method for F Series molecules

| No. | Structure | Prep.* |
|---|---|---|
| F1438 | 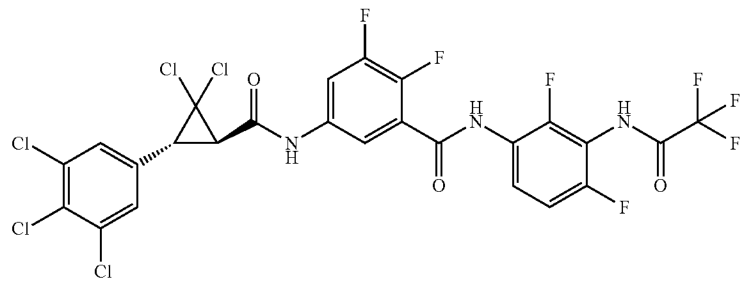 [SMILES: O=C(Nc1ccc(F)c(NC(=O)C(F)(F)F)c1F)c1cc(NC(=O)[C@H]2[C@H](c3cc(Cl)c(Cl)c(Cl)c3)C2(Cl)Cl)cc(F)c1F] | 5 |
| F1439 | 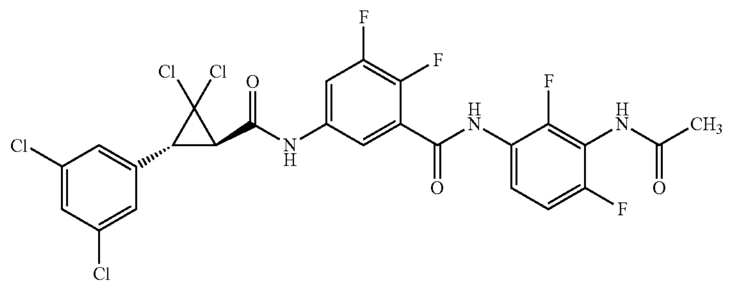 [SMILES: CC(=O)Nc1c(F)ccc(NC(=O)c2cc(NC(=O)[C@H]3[C@H](c4cc(Cl)cc(Cl)c4)C3(Cl)Cl)cc(F)c2F)c1F] | 5 |
| F1440 | 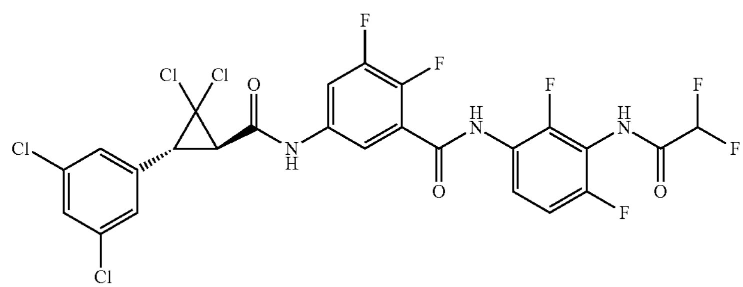 [SMILES: O=C(Nc1ccc(F)c(NC(=O)C(F)F)c1F)c1cc(NC(=O)[C@H]2[C@H](c3cc(Cl)cc(Cl)c3)C2(Cl)Cl)cc(F)c1F] | 5 |
| F1441 | 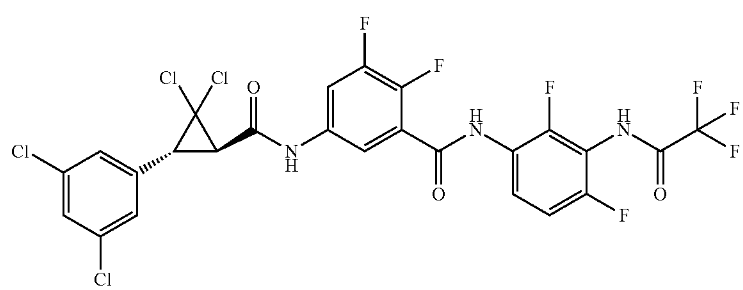 | 5 |
| F1442 | 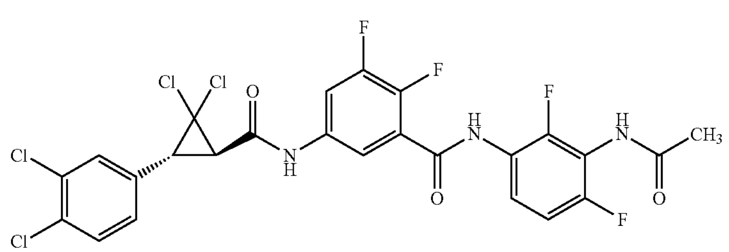 [SMILES: CC(=O)Nc1c(F)ccc(NC(=O)c2cc(NC(=O)[C@H]3[C@H](c4ccc(Cl)c(Cl)c4)C3(Cl)Cl)cc(F)c2F)c1F] | 5 |

TABLE 2-continued

Structure and preparation method for F Series molecules

| No. | Structure | Prep.* |
|---|---|---|
| F1443 | 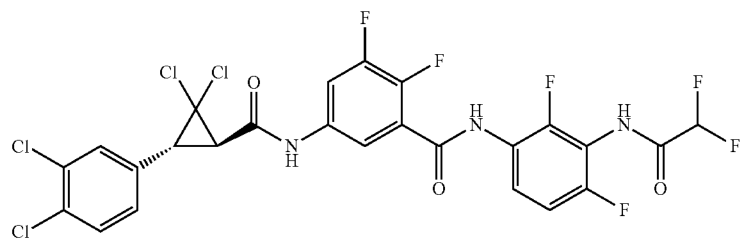 [SMILES: O=C(Nc1ccc(F)c(NC(=O)C(F)F)c1F)c1cc(NC(=O)[C@H]2[C@H](c3ccc(Cl)c(Cl)c3)C2(Cl)Cl)cc(F)c1F] | 5 |
| F1444 | 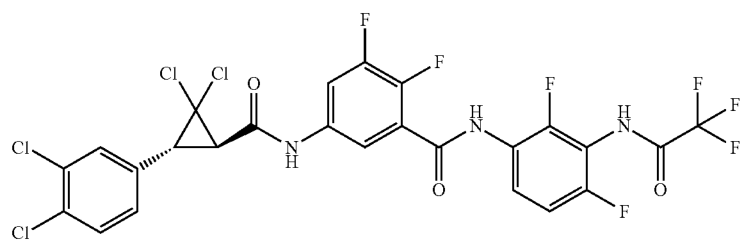 [SMILES: O=C(Nc1ccc(F)c(NC(=O)C(F)(F)F)c1F)c1cc(NC(=O)[C@H]2[C@H](c3ccc(Cl)c(Cl)c3)C2(Cl)Cl)cc(F)c1F] | 5 |
| F1445 | 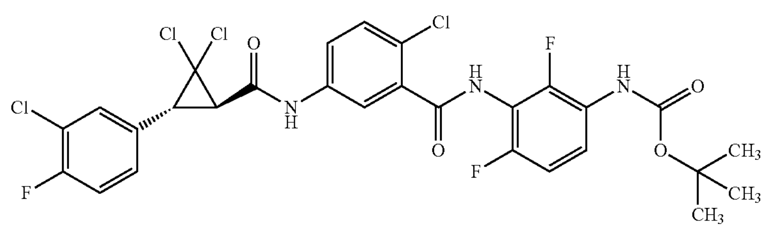 [SMILES: CC(C)(C)OC(=O)Nc1ccc(F)c(NC(=O)c2cc(NC(=O)[C@H]3[C@H](c4ccc(F)c(Cl)c4)C3(Cl)Cl)ccc2Cl)c1F] | 5 |
| F1446 | 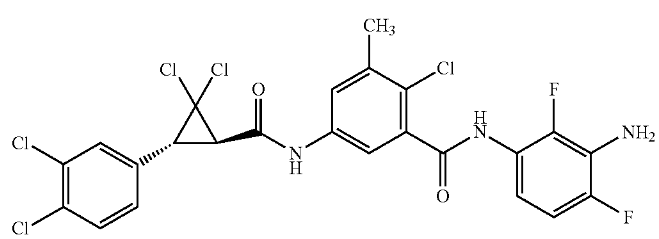 [SMILES: Cc1cc(NC(=O)[C@H]2[C@H](c3ccc(Cl)c(Cl)c3)C2(Cl)Cl)cc(C(=O)Nc2ccc(F)c(N)c2F)c1Cl] | 13 |
| F1447 | 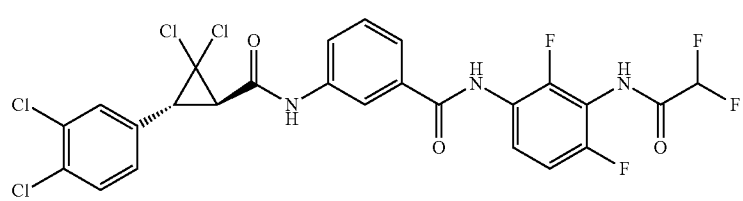 [SMILES: O=C(Nc1ccc(F)c(NC(=O)C(F)F)c1F)c1cccc(NC(=O)[C@H]2[C@H](c3ccc(Cl)c(Cl)c3)C2(Cl)Cl)c1] | 20 |
| F1448 | 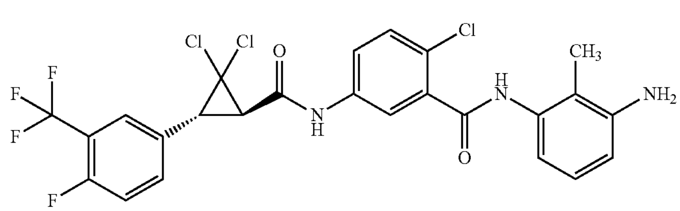 [SMILES: Cc1c(N)cccc1NC(=O)c1cc(NC(=O)[C@H]2[C@H](c3ccc(F)c(C(F)(F)F)c3)C2(Cl)Cl)ccc1Cl] | 13 |

TABLE 2-continued

Structure and preparation method for F Series molecules

| No. | Structure | Prep.* |
|---|---|---|
| F1449 | 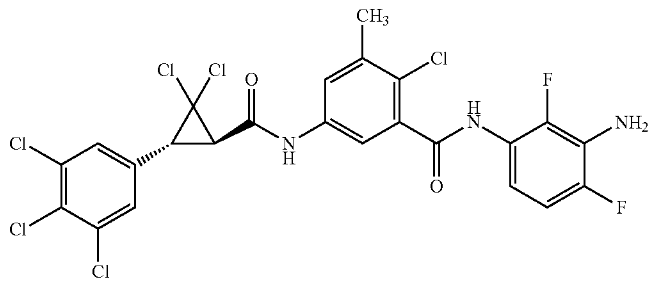 [SMILES: Cc1cc(NC(=O)[C@H]2[C@H](c3cc(Cl)c(Cl)c(Cl)c3)C2(Cl)Cl)cc(C(=O)Nc2ccc(F)c(N)c2F)c1Cl] | 13 |
| F1450 | 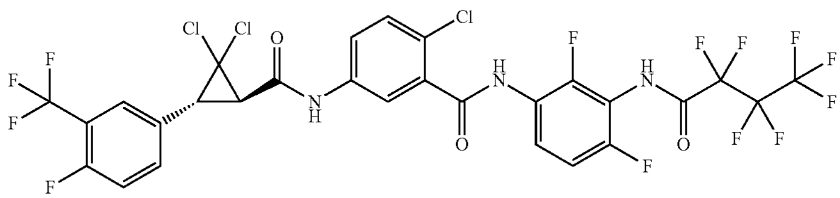 [SMILES: O=C(Nc1ccc(F)c(NC(=O)C(F)(F)C(F)(F)C(F)(F)F)c1F)c1cc(NC(=O)[C@H]2[C@H](c3ccc(F)c(C(F)(F)F)c3)C2(Cl)Cl)ccc1Cl] | 6 |
| F1451 | 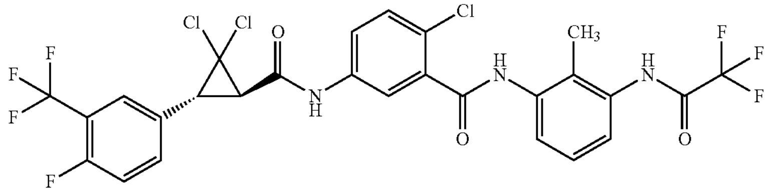 [SMILES: Cc1c(NC(=O)c2cc(NC(=O)[C@H]3[C@H](c4ccc(F)c(C(F)(F)F)c4)C3(Cl)Cl)ccc2Cl)cccc1NC(=O)C(F)(F)F] | 1 |
| F1452 | 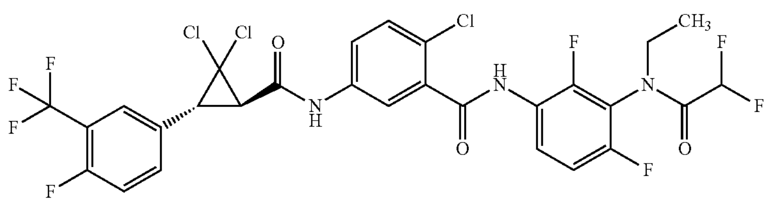 [SMILES: CCN(C(=O)C(F)F)c1c(F)ccc(NC(=O)c2cc(NC(=O)[C@H]3[C@H](c4ccc(F)c(C(F)(F)F)c4)C3(Cl)Cl)ccc2Cl)c1F] | 5 |
| F1453 | 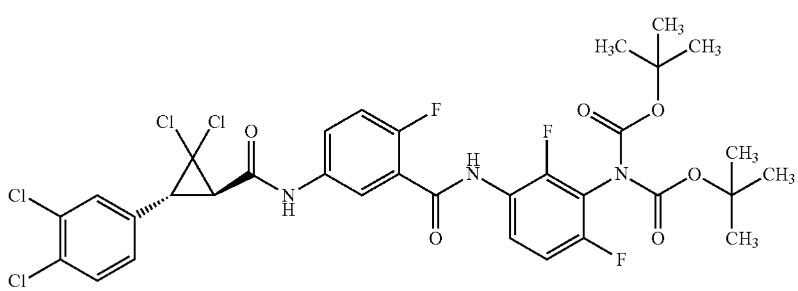 [SMILES: CC(C)(C)OC(=O)N(C(=O)OC(C)(C)C)c1c(F)ccc(NC(=O)c2cc(NC(=O)[C@H]3[C@H](c4ccc(Cl)c(Cl)c4)C3(Cl)Cl)ccc2F)c1F] | 5 |
| F1454 | 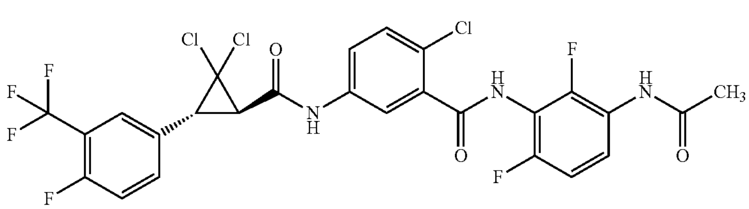 [SMILES: CC(=O)Nc1ccc(F)c(NC(=O)c2cc(NC(=O)[C@H]3[C@H](c4ccc(F)c(C(F)(F)F)c4)C3(Cl)Cl)ccc2Cl)c1F] | 6 |

TABLE 2-continued

Structure and preparation method for F Series molecules

| No. | Structure | Prep.* |
|---|---|---|
| F1455 | 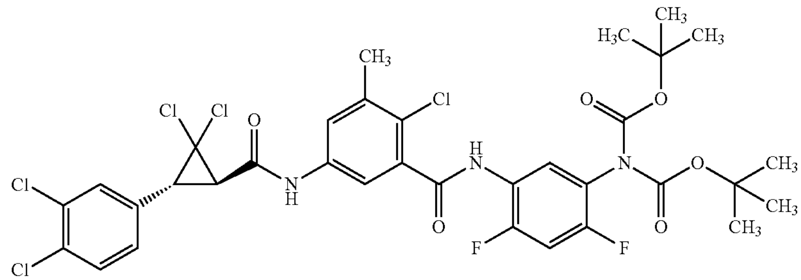 [SMILES: Cc1cc(NC(=O)[C@H]2[C@H](c3ccc(Cl)c(Cl)c3)C2(Cl)Cl)cc(C(=O)Nc2cc(N(C(=O)OC(C)(C)C)C(=O)OC(C)(C)C)c(F)cc2F)c1Cl] | 22 |
| F1456 | 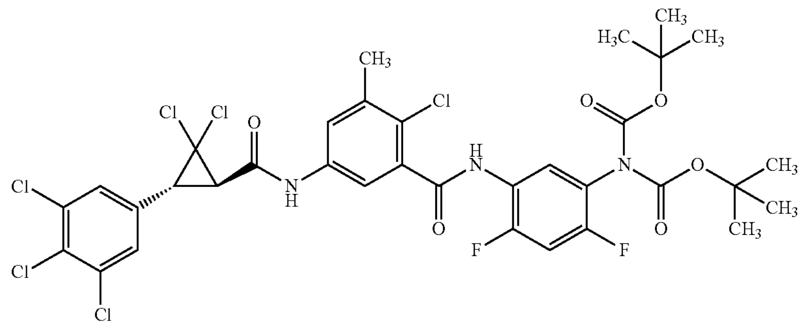 [SMILES: Cc1cc(NC(=O)[C@H]2[C@H](c3cc(Cl)c(Cl)c(Cl)c3)C2(Cl)Cl)cc(C(=O)Nc2cc(N(C(=O)OC(C)(C)C)C(=O)OC(C)(C)C)c(F)cc2F)c1Cl] | 22 |
| F1457 | 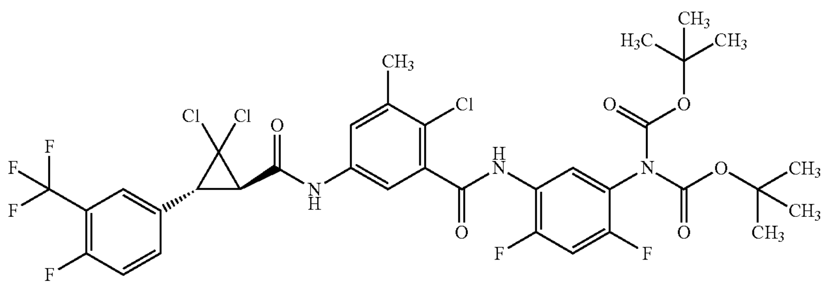 [SMILES: Cc1cc(NC(=O)[C@H]2[C@H](c3ccc(F)c(C(F)(F)F)c3)C2(Cl)Cl)cc(C(=O)Nc2cc(N(C(=O)OC(C)(C)C)C(=O)OC(C)(C)C)c(F)cc2F)c1Cl] | 22 |
| F1458 | 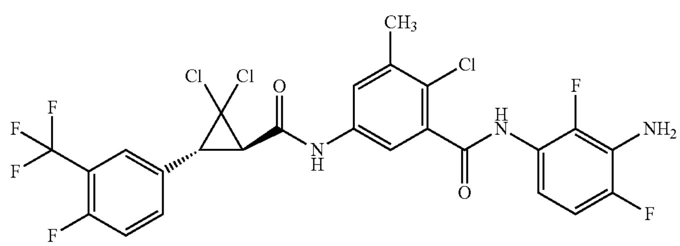 [SMILES: Cc1cc(NC(=O)[C@H]2[C@H](c3ccc(F)c(C(F)(F)F)c3)C2(Cl)Cl)cc(C(=O)Nc2ccc(F)c(N)c2F)c1Cl] | 13 |
| F1459 | 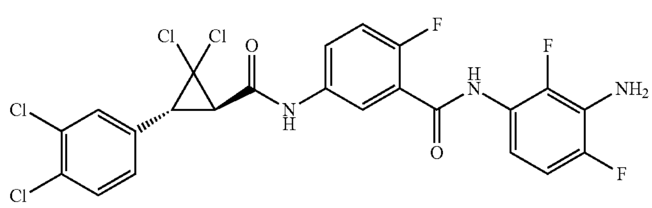 [SMILES: Nc1c(F)ccc(NC(=O)c2cc(NC(=O)[C@H]3[C@H](c4ccc(Cl)c(Cl)c4)C3(Cl)Cl)ccc2F)c1F] | 13 |
| F1460 | 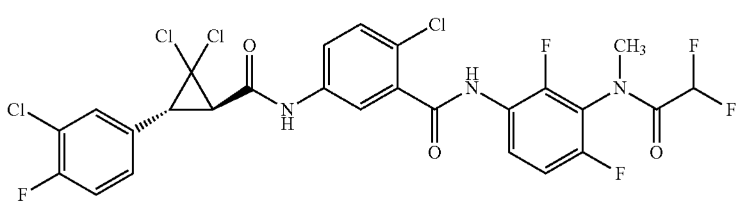 | 5 |

TABLE 2-continued

Structure and preparation method for F Series molecules

| No. | Structure | Prep.* |
|---|---|---|
| F1461 | 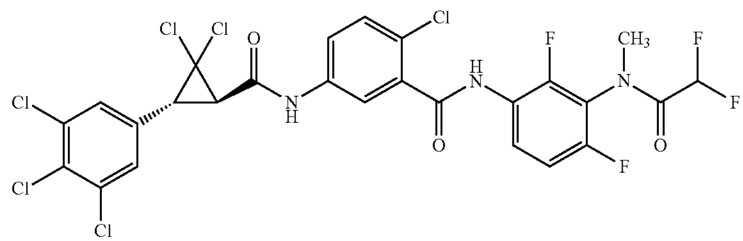 [SMILES: CN(C(=O)C(F)F)c1c(F)ccc(NC(=O)c2cc(NC(=O)[C@H]3[C@H](c4cc(Cl)c(Cl)c(Cl)c4)C3(Cl)Cl)ccc2Cl)c1F] | 5 |
| F1462 | 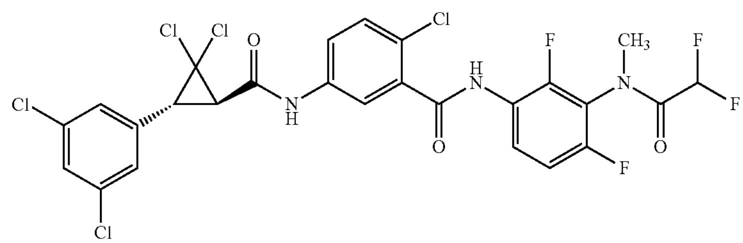 [SMILES: CN(C(=O)C(F)F)c1c(F)ccc(NC(=O)c2cc(NC(=O)[C@H]3[C@H](c4cc(Cl)cc(Cl)c4)C3(Cl)Cl)ccc2Cl)c1F] | 5 |
| F1463 | 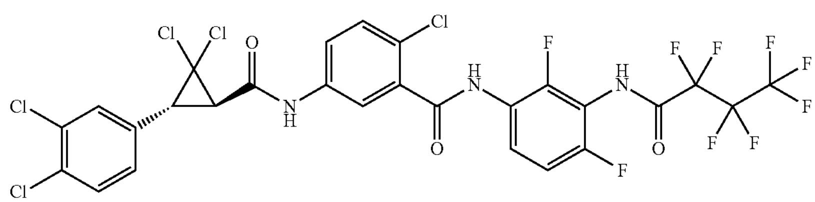 [SMILES: O=C(Nc1ccc(F)c(NC(=O)C(F)(F)C(F)(F)C(F)(F)F)c1F)c1cc(NC(=O)[C@H]2[C@H](c3ccc(Cl)c(Cl)c3)C2(Cl)Cl)ccc1Cl] | 4 |
| F1464 | 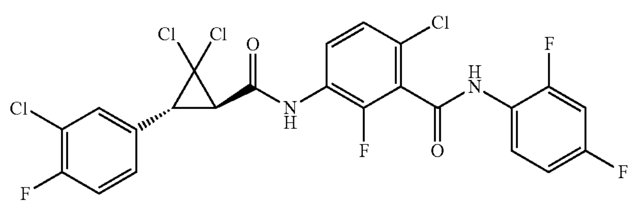 [SMILES: O=C(Nc1ccc(F)cc1F)c1c(Cl)ccc(NC(=O)[C@H]2[C@H](c3ccc(F)c(Cl)c3)C2(Cl)Cl)c1F] | 83 |
| F1465 | 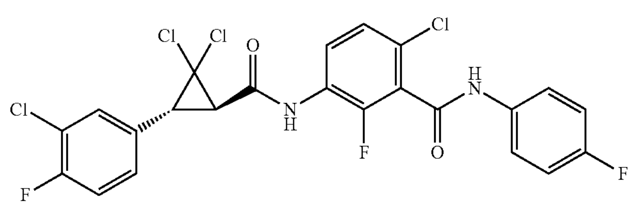 [SMILES: O=C(Nc1ccc(F)cc1)c1c(Cl)ccc(NC(=O)[C@H]2[C@H](c3ccc(F)c(Cl)c3)C2(Cl)Cl)c1F] | 83 |
| F1466 | 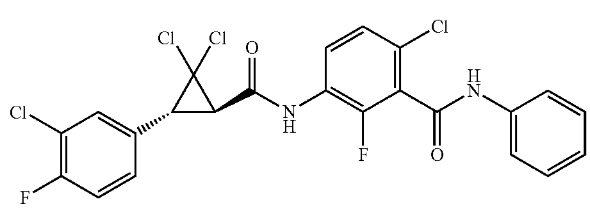 [SMILES: O=C(Nc1ccccc1)c1c(Cl)ccc(NC(=O)[C@H]2[C@H](c3ccc(F)c(Cl)c3)C2(Cl)Cl)c1F] | 83 |

US 10,258,045 B2
TABLE 2-continued
Structure and preparation method for F Series molecules
| No. | Structure | Prep.* |
|---|---|---|
| F1467 | 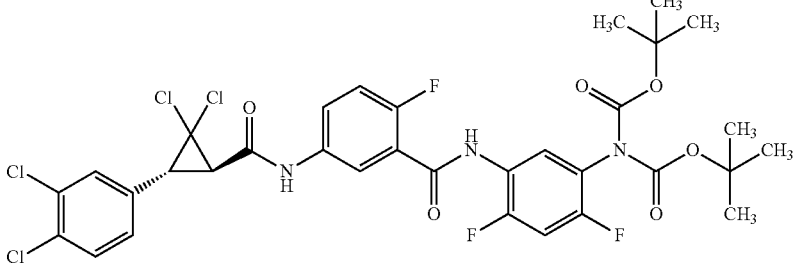 | 25 |
| F1468 | 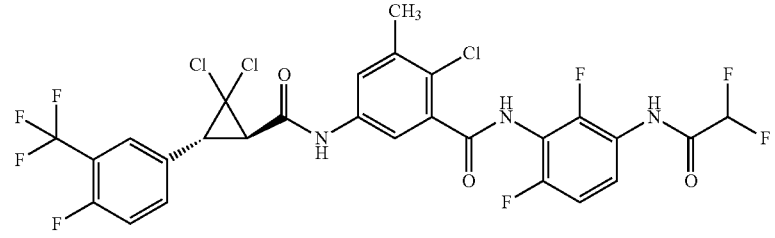 [SMILES: Cc1cc(NC(=O)[C@H]2[C@H](c3ccc(F)c(C(F)(F)F)c3)C2(Cl)Cl)cc(C(=O)Nc2c(F)ccc(NC(=O)C(F)F)c2F)c1Cl] | 3 |
| F1469 | 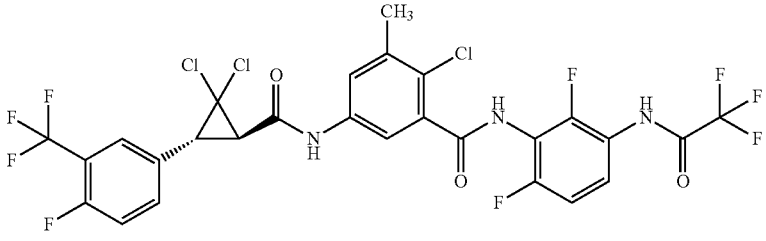 | 3 |
| F1470 | 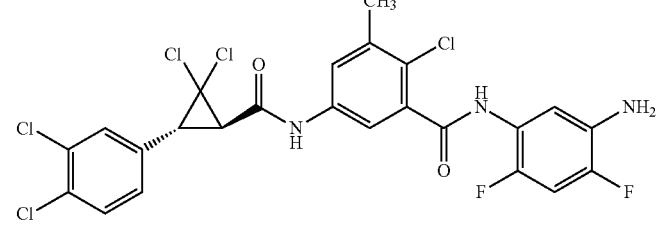 | 13 |
| F1471 | 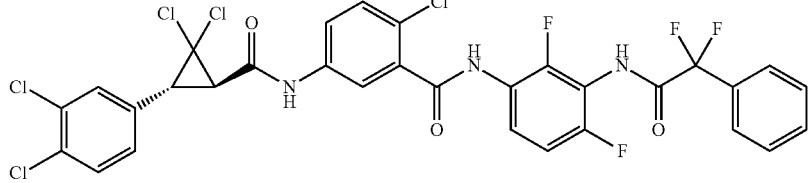 | 4 |
| F1472 | 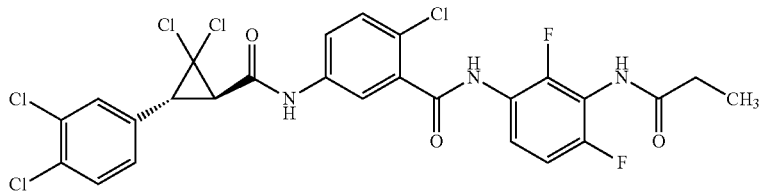 | 4 |

| No. | Structure | Prep.* |
|---|---|---|
| F1473 | 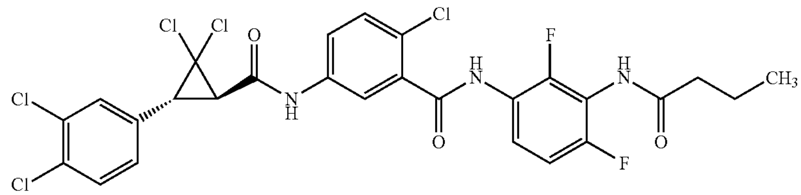 [SMILES: CCCC(=O)Nc1c(F)ccc(NC(=O)c2cc(NC(=O)[C@H]3[C@H](c4ccc(Cl)c(Cl)c4)C3(Cl)Cl)ccc2Cl)c1F] | 4 |
| F1474 | 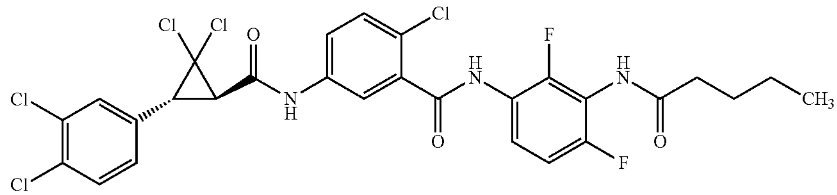 [SMILES: CCCCC(=O)Nc1c(F)ccc(NC(=O)c2cc(NC(=O)[C@H]3[C@H](c4ccc(Cl)c(Cl)c4)C3(Cl)Cl)ccc2Cl)c1F] | 4 |
| F1475 | 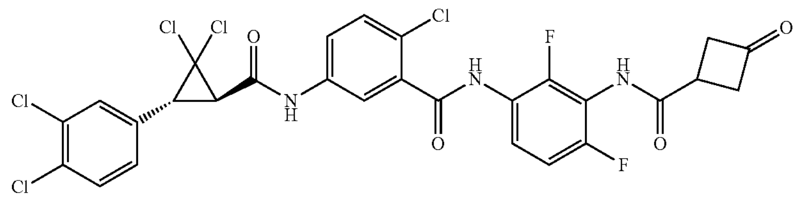 [SMILES: O=C1CC(C(=O)Nc2c(F)ccc(NC(=O)c3cc(NC(=O)[C@H]4[C@H](c5ccc(Cl)c(Cl)c5)C4(Cl)Cl)ccc3Cl)c2F)C1] | 4 |
| F1476 | 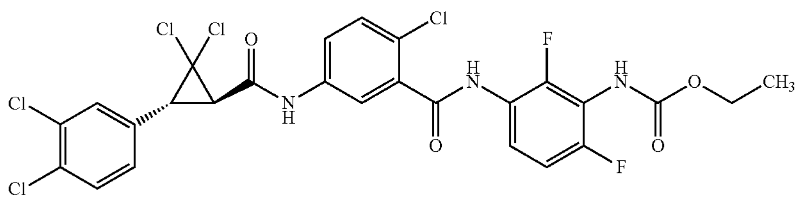 [SMILES: CCOC(=O)Nc1c(F)ccc(NC(=O)c2cc(NC(=O)[C@H]3[C@H](c4ccc(Cl)c(Cl)c4)C3(Cl)Cl)ccc2Cl)c1F] | 32 |
| F1477 | 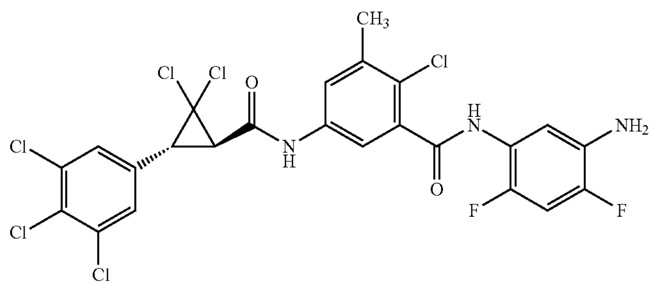 [SMILES: Cc1cc(NC(=O)[C@H]2[C@H](c3cc(Cl)c(Cl)c(Cl)c3)C2(Cl)Cl)cc(C(=O)Nc2cc(N)c(F)cc2F)c1Cl] | 13 |
| F1478 | 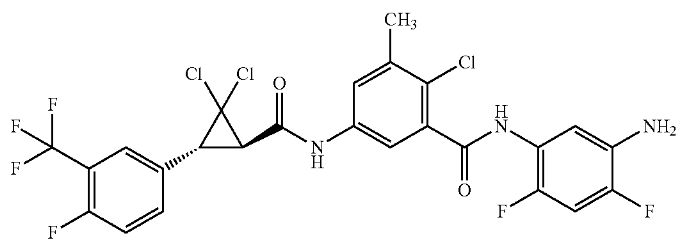 [SMILES: Cc1cc(NC(=O)[C@H]2[C@H](c3ccc(F)c(C(F)(F)F)c3)C2(Cl)Cl)cc(C(=O)Nc2cc(N)c(F)cc2F)c1Cl] | 13 |
| F1479 | 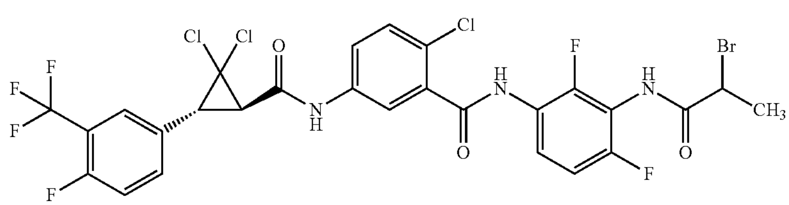 [SMILES: CC(Br)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |

TABLE 2-continued
Structure and preparation method for F Series molecules
| No. | Structure | Prep.* |
|---|---|---|
| F1480 | 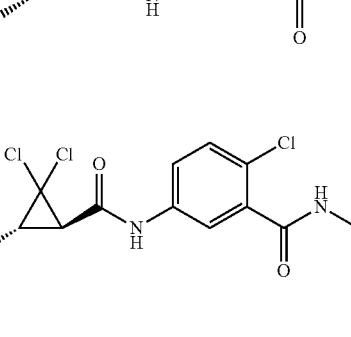 | 6 |
| F1481 | 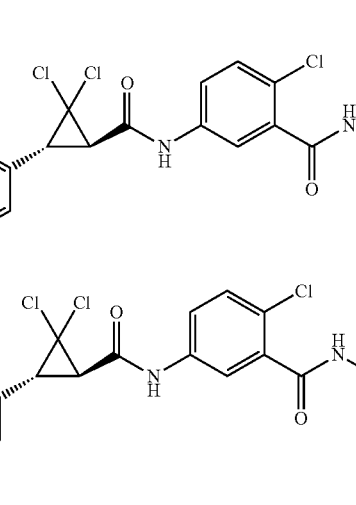 | 6 |
| F1482 | 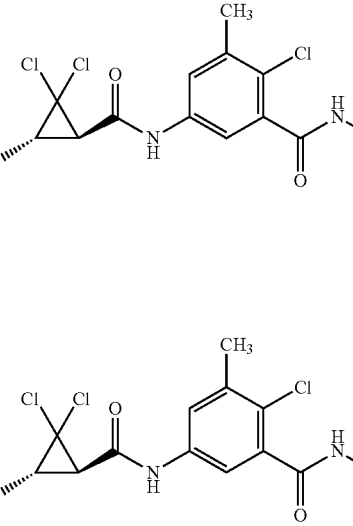 | 5 |
| F1483 | 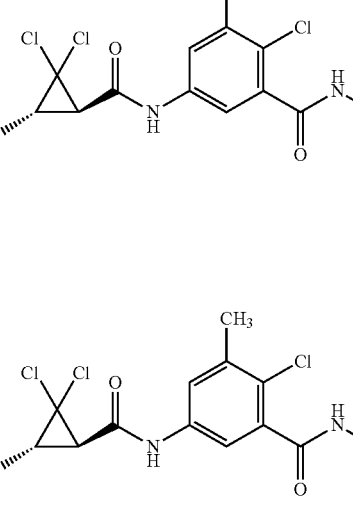 | 6 |
| F1484 | 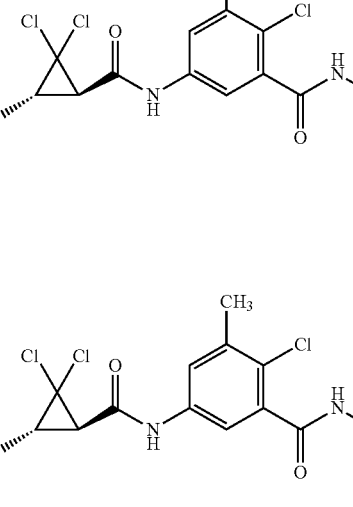 | 3 |
| F1485 | 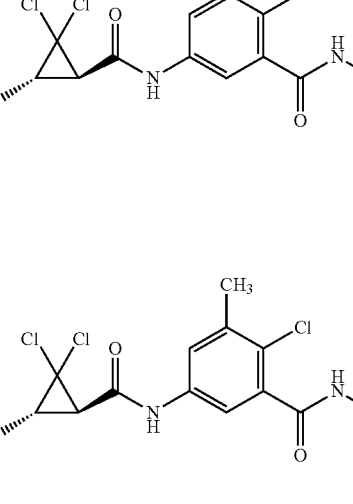 | 3 |

TABLE 2-continued

Structure and preparation method for F Series molecules

| No. | Structure | Prep.* |
|---|---|---|
| F1486 | 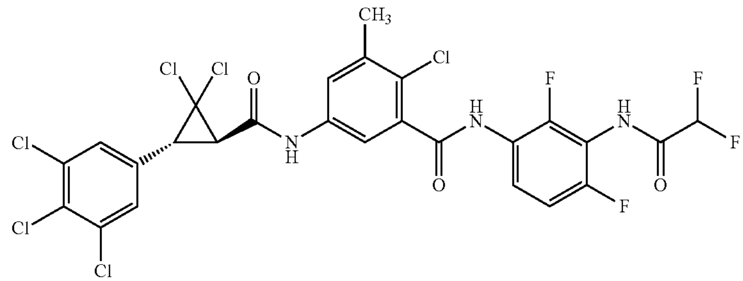 [SMILES: Cc1cc(NC(=O)[C@H]2[C@H](c3cc(Cl)c(Cl)c(Cl)c3)C2(Cl)Cl)cc(C(=O)Nc2ccc(F)c(NC(=O)C(F)F)c2F)c1Cl] | 3 |
| F1487 | 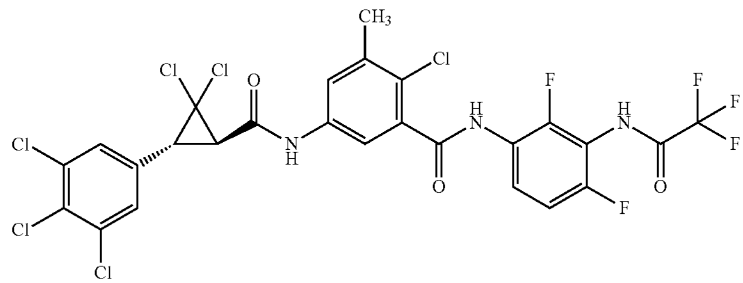 [SMILES: Cc1cc(NC(=O)[C@H]2[C@H](c3cc(Cl)c(Cl)c(Cl)c3)C2(Cl)Cl)cc(C(=O)Nc2ccc(F)c(NC(=O)C(F)(F)F)c2F)c1Cl] | 3 |
| F1488 | 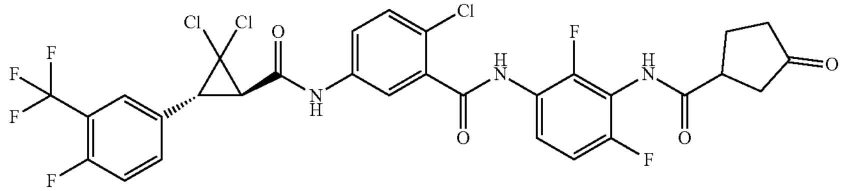 [SMILES: O=C1CCC(C(=O)Nc2c(F)ccc(NC(=O)c3cc(NC(=O)[C@H]4[C@H](c5ccc(F)c(C(F)(F)F)c5)C4(Cl)Cl)ccc3Cl)c2F)C1] | 6 |
| F1489 | 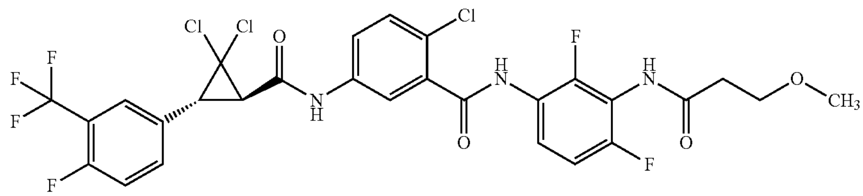 | 6 |
| F1490 | 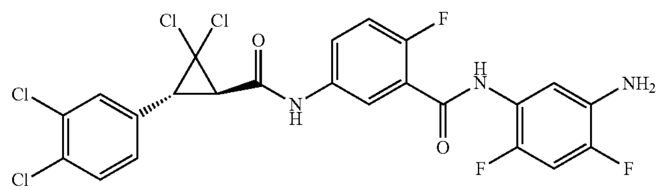 [SMILES: Nc1cc(NC(=O)c2cc(NC(=O)[C@H]3[C@H](c4ccc(Cl)c(Cl)c4)C3(Cl)Cl)ccc2F)c(F)cc1F] | 13 |
| F1491 | 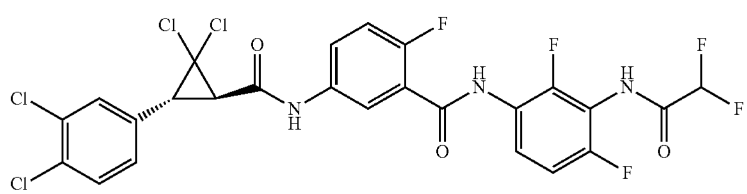 [SMILES: O=C(Nc1ccc(F)c(NC(=O)C(F)F)c1F)c1cc(NC(=O)[C@H]2[C@H](c3ccc(Cl)c(Cl)c3)C2(Cl)Cl)ccc1F] | 1 |
| F1492 | 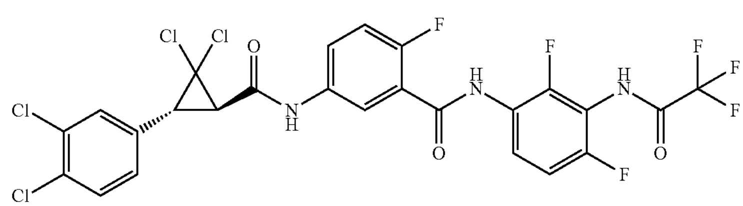 [SMILES: O=C(Nc1ccc(F)c(NC(=O)C(F)(F)F)c1F)c1cc(NC(=O)[C@H]2[C@H](c3ccc(Cl)c(Cl)c3)C2(Cl)Cl)ccc1F] | 1 |

TABLE 2-continued

Structure and preparation method for F Series molecules

| No. | Structure | Prep.* |
|---|---|---|
| F1493 | 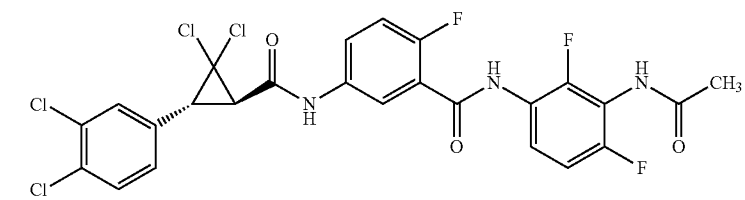 [SMILES: CC(=O)Nc1c(F)ccc(NC(=O)c2cc(NC(=O)[C@H]3[C@H](c4ccc(Cl)c(Cl)c4)C3(Cl)Cl)ccc2F)c1F] | 2 |
| F1494 | 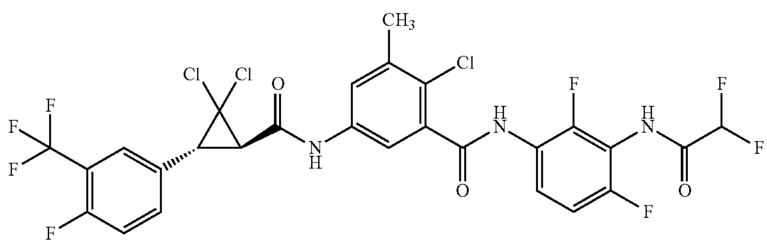 [SMILES: Cc1cc(NC(=O)[C@H]2[C@H](c3ccc(F)c(C(F)(F)F)c3)C2(Cl)Cl)cc(C(=O)Nc2ccc(F)c(NC(=O)C(F)F)c2F)c1Cl] | 3 |
| F1495 | 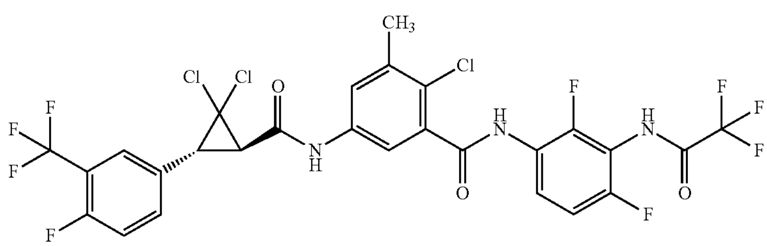 [SMILES: Cc1cc(NC(=O)[C@H]2[C@H](c3ccc(F)c(C(F)(F)F)c3)C2(Cl)Cl)cc(C(=O)Nc2ccc(F)c(NC(=O)C(F)(F)F)c2F)c1Cl] | 3 |
| F1496 | 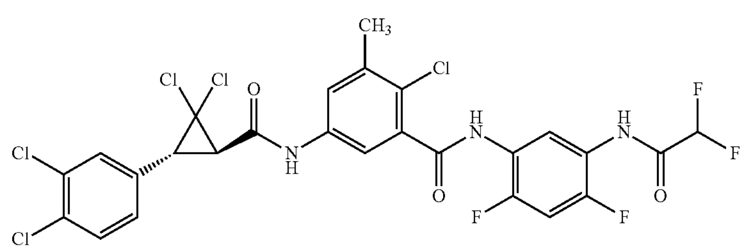 [SMILES: Cc1cc(NC(=O)[C@H]2[C@H](c3ccc(Cl)c(Cl)c3)C2(Cl)Cl)cc(C(=O)Nc2cc(NC(=O)C(F)F)c(F)cc2F)c1Cl] | 3 |
| F1497 | 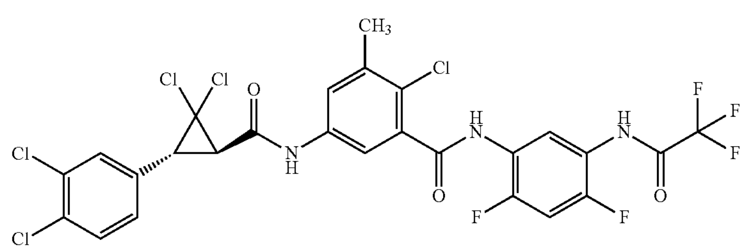 [SMILES: Cc1cc(NC(=O)[C@H]2[C@H](c3ccc(Cl)c(Cl)c3)C2(Cl)Cl)cc(C(=O)Nc2cc(NC(=O)C(F)(F)F)c(F)cc2F)c1Cl] | 3 |
| F1498 | 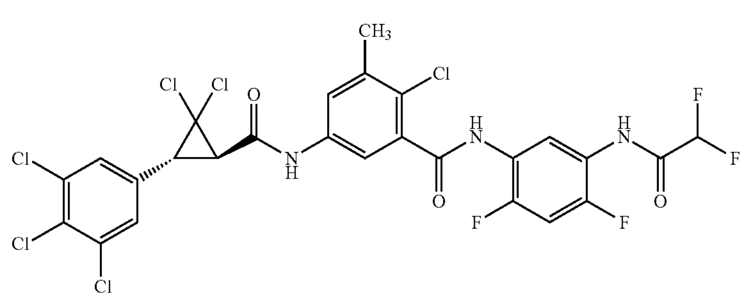 [SMILES: Cc1cc(NC(=O)[C@H]2[C@H](c3cc(Cl)c(Cl)c(Cl)c3)C2(Cl)Cl)cc(C(=O)Nc2cc(NC(=O)C(F)F)c(F)cc2F)c1Cl] | 3 |

TABLE 2-continued

Structure and preparation method for F Series molecules

| No. | Structure | Prep.* |
|---|---|---|
| F1499 | 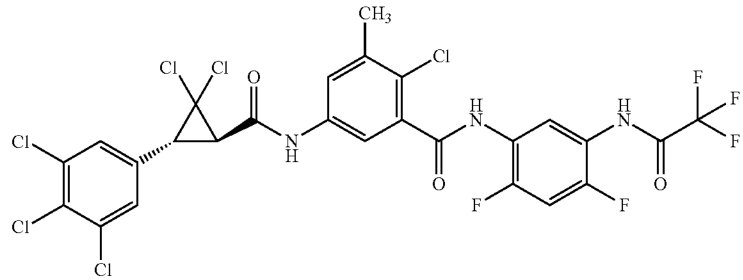 [SMILES: Cc1cc(NC(=O)[C@H]2[C@H](c3cc(Cl)c(Cl)c(Cl)c3)C2(Cl)Cl)cc(C(=O)Nc2cc(NC(=O)C(F)(F)F)c(F)cc2F)c1Cl] | 3 |
| F1500 | 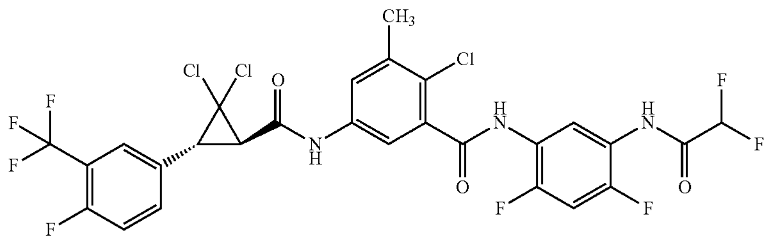 [SMILES: Cc1cc(NC(=O)[C@H]2[C@H](c3ccc(F)c(C(F)(F)F)c3)C2(Cl)Cl)cc(C(=O)Nc2cc(NC(=O)C(F)F)c(F)cc2F)c1Cl] | 3 |
| F1501 | 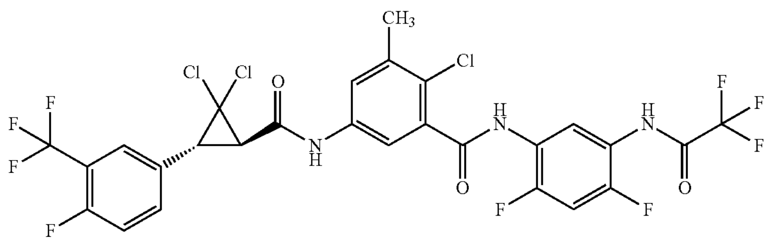 [SMILES: Cc1cc(NC(=O)[C@H]2[C@H](c3ccc(F)c(C(F)(F)F)c3)C2(Cl)Cl)cc(C(=O)Nc2cc(NC(=O)C(F)(F)F)c(F)cc2F)c1Cl] | 3 |
| F1502 | 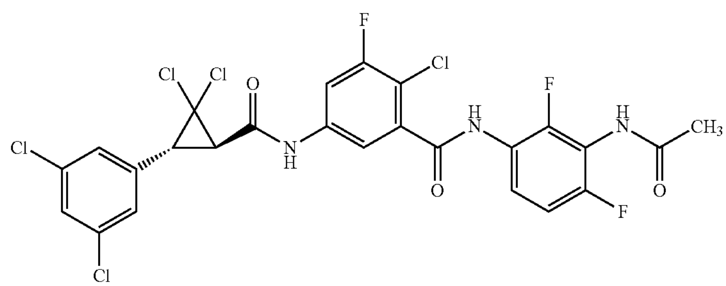 [SMILES: CC(=O)Nc1c(F)ccc(NC(=O)c2cc(NC(=O)[C@H]3[C@H](c4cc(Cl)cc(Cl)c4)C3(Cl)Cl)cc(F)c2Cl)c1F] | 3 |
| F1503 | 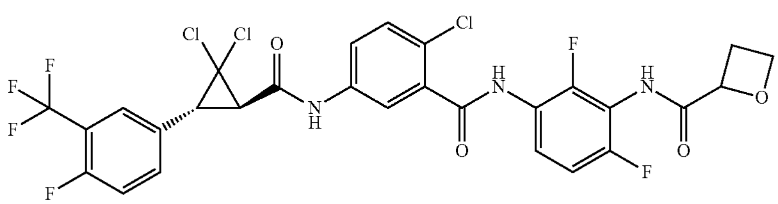 [SMILES: O=C(Nc1ccc(F)c(NC(=O)C2CCO2)c1F)c1cc(NC(=O)[C@H]2[C@H](c3ccc(F)c(C(F)(F)F)c3)C2(Cl)Cl)ccc1Cl] | 6 |
| F1504 | 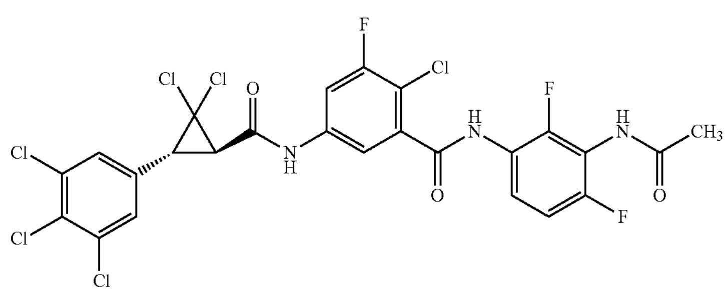 [SMILES: CC(=O)Nc1c(F)ccc(NC(=O)c2cc(NC(=O)[C@H]3[C@H](c4cc(Cl)c(Cl)c(Cl)c4)C3(Cl)Cl)cc(F)c2Cl)c1F] | 3 |

TABLE 2-continued

Structure and preparation method for F Series molecules

| No. | Structure | Prep.* |
|---|---|---|
| F1505 | 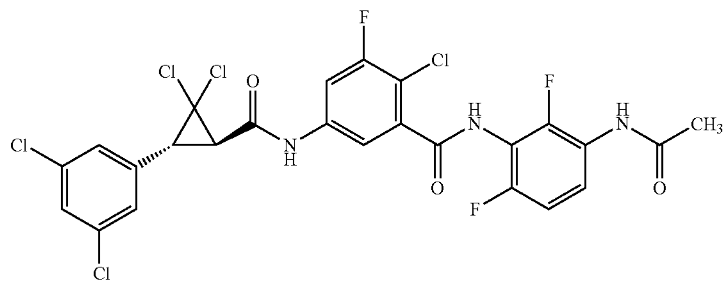 [SMILES: CC(=O)Nc1ccc(F)c(NC(=O)c2cc(NC(=O)[C@H]3[C@H](c4cc(Cl)cc(Cl)c4)C3(Cl)Cl)cc(F)c2Cl)c1F] | 82 |
| F1506 | 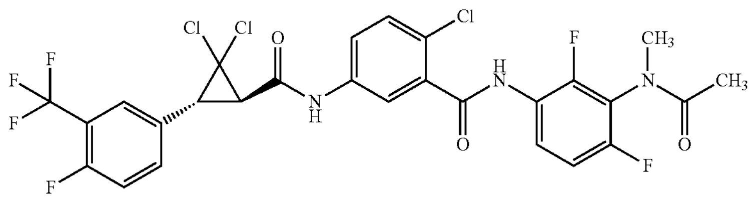 [SMILES: CC(=O)N(C)c1c(F)ccc(NC(=O)c2cc(NC(=O)[C@H]3[C@H](c4ccc(F)c(C(F)(F)F)c4)C3(Cl)Cl)ccc2Cl)c1F] | |
| F1507 | 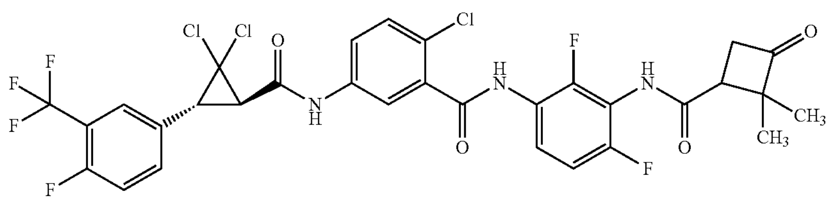 [SMILES: CC1(C)C(=O)CC1C(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1508 | 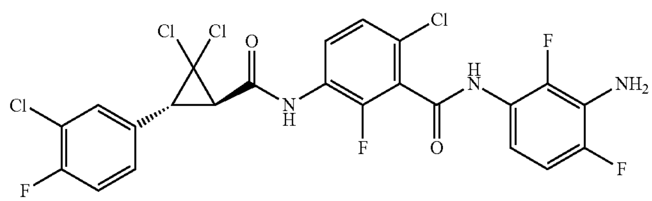 [SMILES: Nc1c(F)ccc(NC(=O)c2c(Cl)ccc(NC(=O)[C@H]3[C@H](c4ccc(F)c(Cl)c4)C3(Cl)Cl)c2F)c1F] | 83 |
| F1509 | 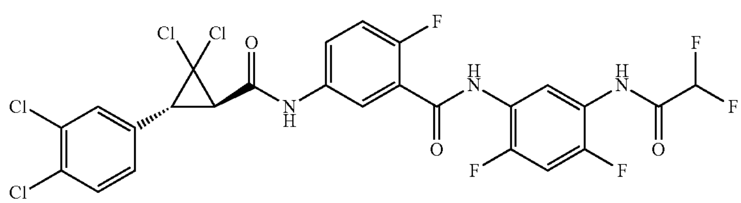 [SMILES: O=C(Nc1cc(NC(=O)C(F)F)c(F)cc1F)c1cc(NC(=O)[C@H]2[C@H](c3ccc(Cl)c(Cl)c3)C2(Cl)Cl)ccc1F] | 1 |
| F1510 | 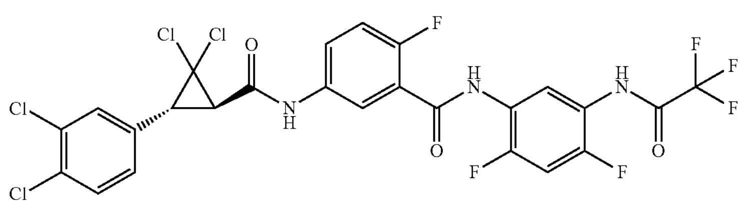 [SMILES: O=C(Nc1cc(NC(=O)C(F)(F)F)c(F)cc1F)c1cc(NC(=O)[C@H]2[C@H](c3ccc(Cl)c(Cl)c3)C2(Cl)Cl)ccc1F] | 1 |
| F1511 | 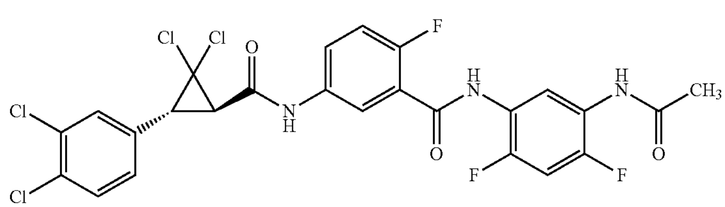 [SMILES: CC(=O)Nc1cc(NC(=O)c2cc(NC(=O)[C@H]3[C@H](c4ccc(Cl)c(Cl)c4)C3(Cl)Cl)ccc2F)c(F)cc1F] | 2 |

TABLE 2-continued

Structure and preparation method for F Series molecules

| No. | Structure | Prep.* |
|---|---|---|
| F1512 | 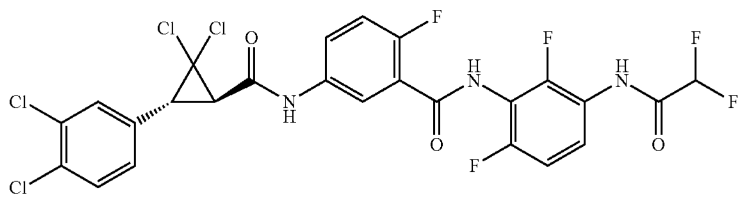 [SMILES: O=C(Nc1c(F)ccc(NC(=O)C(F)F)c1F)c1cc(NC(=O)[C@H]2[C@H](c3ccc(Cl)c(Cl)c3)C2(Cl)Cl)ccc1F] | 5 |
| F1513 | 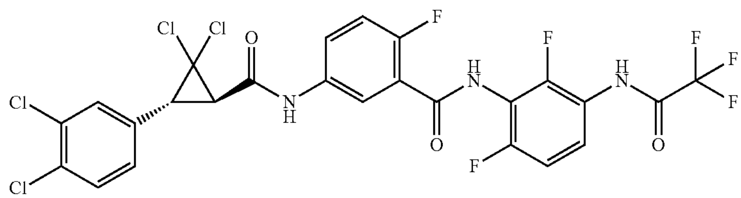 [SMILES: O=C(Nc1c(F)ccc(NC(=O)C(F)(F)F)c1F)c1cc(NC(=O)[C@H]2[C@H](c3ccc(Cl)c(Cl)c3)C2(Cl)Cl)ccc1F] | 5 |
| F1514 | 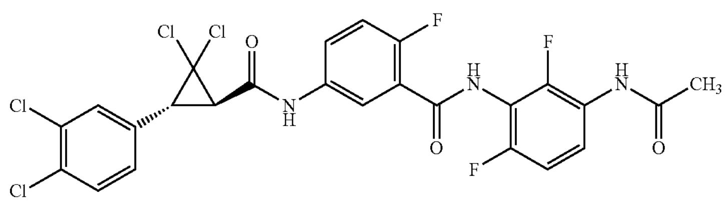 | 5 |
| F1515 | 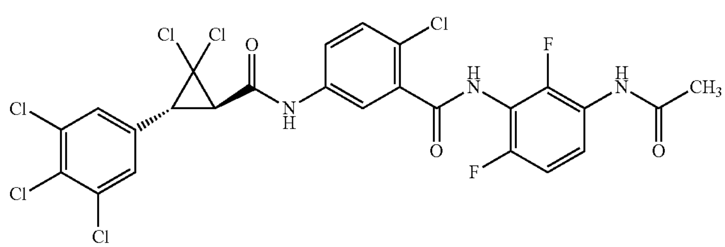 [SMILES: CC(=O)Nc1ccc(F)c(NC(=O)c2cc(NC(=O)[C@H]3[C@H](c4cc(Cl)c(Cl)c(Cl)c4)C3(Cl)Cl)ccc2Cl)c1F] | 25 |
| F1516 | 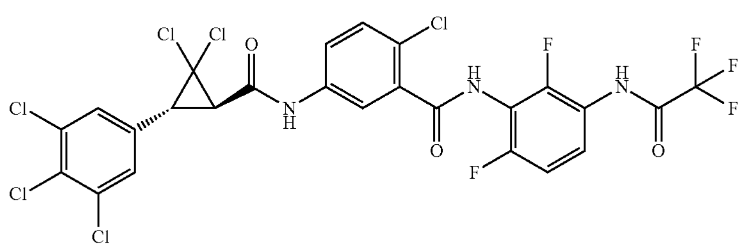 [SMILES: O=C(Nc1c(F)ccc(NC(=O)C(F)(F)F)c1F)c1cc(NC(=O)[C@H]2[C@H](c3cc(Cl)c(Cl)c(Cl)c3)C2(Cl)Cl)ccc1Cl] | 25 |
| F1517 | 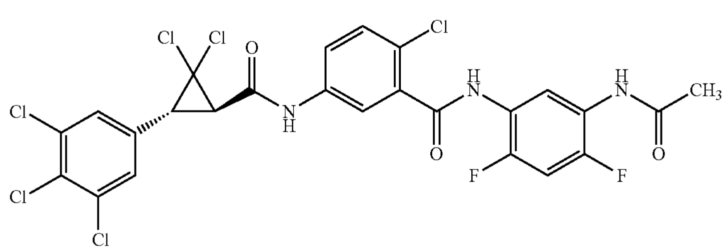 | 25 |

TABLE 2-continued

Structure and preparation method for F Series molecules

| No. | Structure | Prep.* |
|---|---|---|
| F1518 | 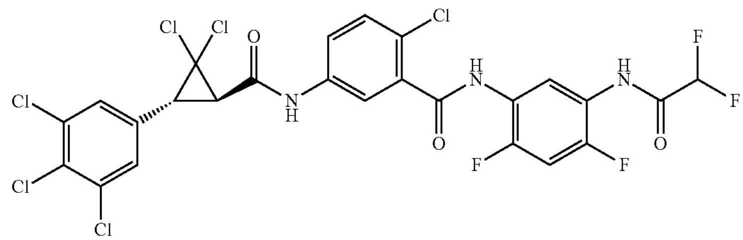 | 25 |
| F1519 | 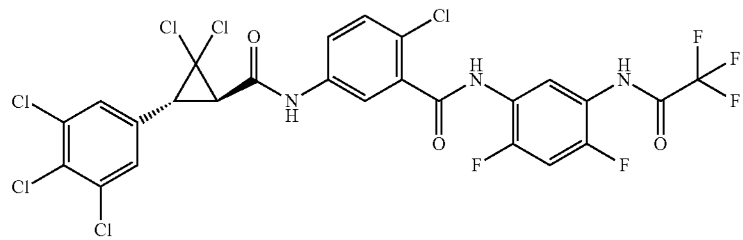 [SMILES: O=C(Nc1cc(NC(=O)C(F)(F)F)c(F)cc1F)c1cc(NC(=O)[C@H]2[C@H](c3cc(Cl)c(Cl)c(Cl)c3)C2(Cl)Cl)ccc1Cl] | 25 |
| F1520 | 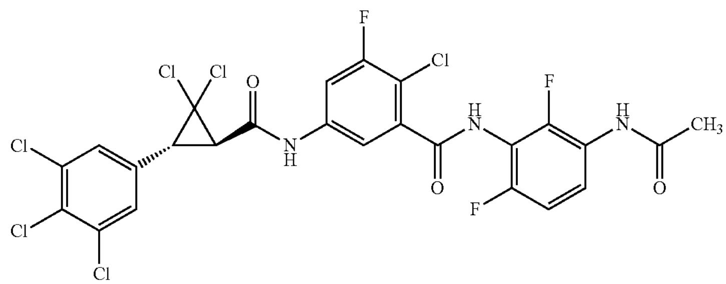 [SMILES: CC(=O)Nc1ccc(F)c(NC(=O)c2cc(NC(=O)[C@H]3[C@H](c4cc(Cl)c(Cl)c(Cl)c4)C3(Cl)Cl)cc(F)c2Cl)c1F] | 82 |
| F1521 | 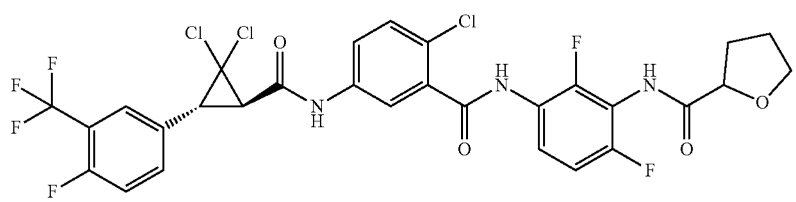 [SMILES: O=C(Nc1ccc(F)c(NC(=O)C2CCCO2)c1F)c1cc(NC(=O)[C@H]2[C@H](c3ccc(F)c(C(F)(F)F)c3)C2(Cl)Cl)ccc1Cl] | 6 |
| F1522 | 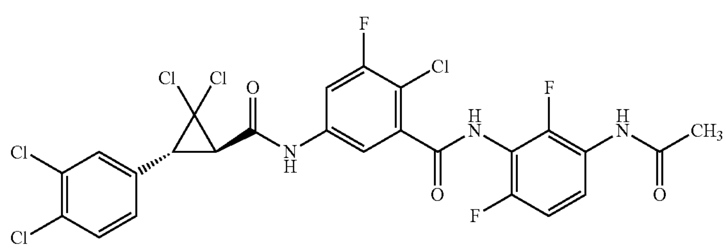 [SMILES: CC(=O)Nc1ccc(F)c(NC(=O)c2cc(NC(=O)[C@H]3[C@H](c4ccc(Cl)c(Cl)c4)C3(Cl)Cl)cc(F)c2Cl)c1F] | 82 |
| F1523 | 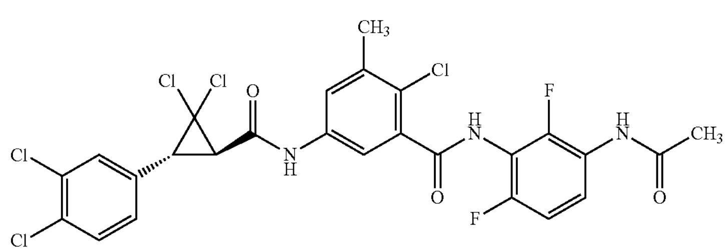 [SMILES: CC(=O)Nc1ccc(F)c(NC(=O)c2cc(NC(=O)[C@H]3[C@H](c4ccc(Cl)c(Cl)c4)C3(Cl)Cl)cc(C)c2Cl)c1F] | 82 |

TABLE 2-continued

Structure and preparation method for F Series molecules

| No. | Structure | Prep.* |
|---|---|---|
| F1524 | 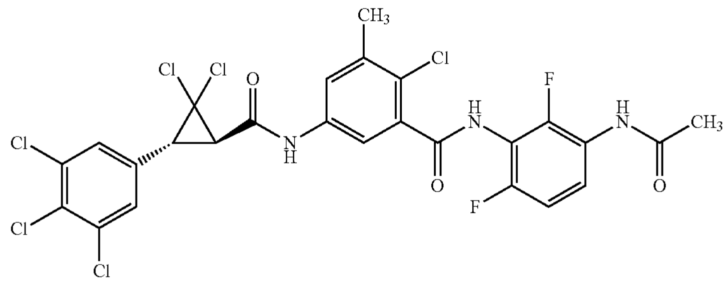 [SMILES: CC(=O)Nc1ccc(F)c(NC(=O)c2cc(NC(=O)[C@H]3[C@H](c4cc(Cl)c(Cl)c(Cl)c4)C3(Cl)Cl)cc(C)c2Cl)c1F] | 82 |
| F1525 | 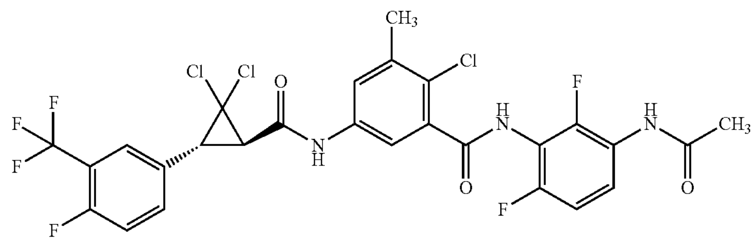 [SMILES: CC(=O)Nc1ccc(F)c(NC(=O)c2cc(NC(=O)[C@H]3[C@H](c4ccc(F)c(C(F)(F)F)c4)C3(Cl)Cl)cc(C)c2Cl)c1F] | 82 |
| F1526 | 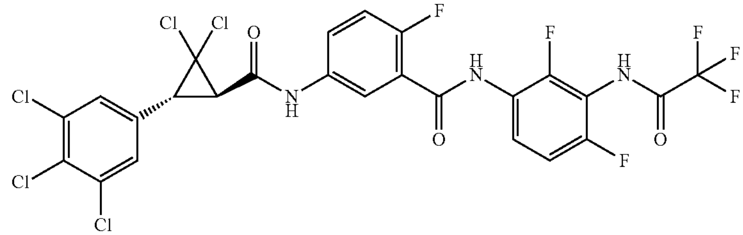 [SMILES: O=C(Nc1ccc(F)c(NC(=O)C(F)(F)F)c1F)c1cc(NC(=O)[C@H]2[C@H](c3cc(Cl)c(Cl)c(Cl)c3)C2(Cl)Cl)ccc1F] | 5 |
| F1527 | 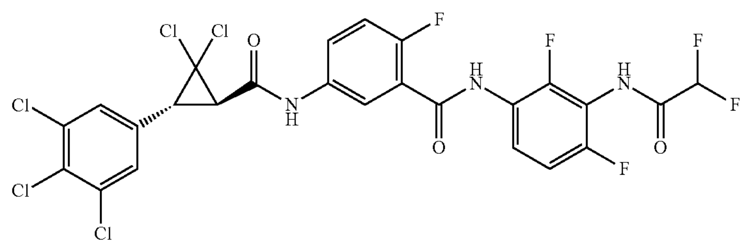 [SMILES: O=C(Nc1ccc(F)c(NC(=O)C(F)F)c1F)c1cc(NC(=O)[C@H]2[C@H](c3cc(Cl)c(Cl)c(Cl)c3)C2(Cl)Cl)ccc1F] | 5 |
| F1528 | 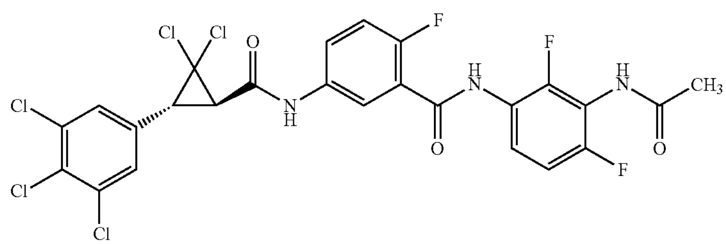 [SMILES: CC(=O)Nc1c(F)ccc(NC(=O)c2cc(NC(=O)[C@H]3[C@H](c4cc(Cl)c(Cl)c(Cl)c4)C3(Cl)Cl)ccc2F)c1F] | 5 |
| F1529 | 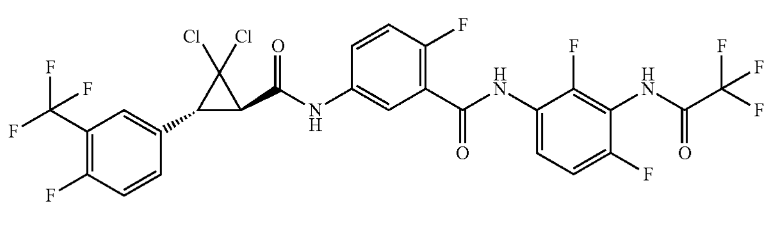 [SMILES: O=C(Nc1ccc(F)c(NC(=O)C(F)(F)F)c1F)c1cc(NC(=O)[C@H]2[C@H](c3ccc(F)c(C(F)(F)F)c3)C2(Cl)Cl)ccc1F] | 5 |

TABLE 2-continued

Structure and preparation method for F Series molecules

| No. | Structure | Prep.* |
|---|---|---|
| F1530 | 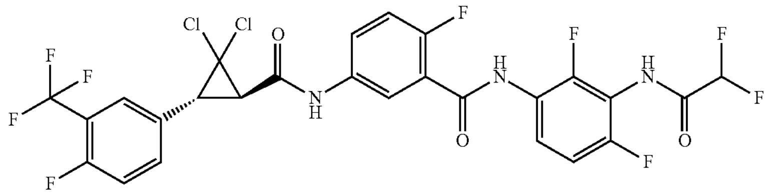 [SMILES: O=C(Nc1ccc(F)c(NC(=O)C(F)F)c1F)c1cc(NC(=O)[C@H]2[C@H](c3ccc(F)c(C(F)(F)F)c3)C2(Cl)Cl)ccc1F] | 5 |
| F1531 | 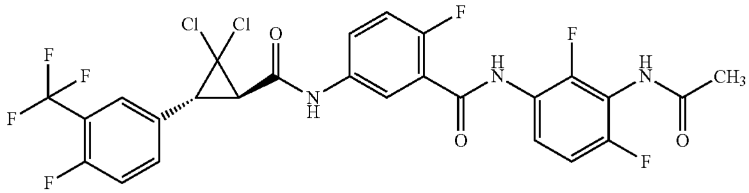 [SMILES: CC(=O)Nc1c(F)ccc(NC(=O)c2cc(NC(=O)[C@H]3[C@H](c4ccc(F)c(C(F)(F)F)c4)C3(Cl)Cl)ccc2F)c1F] | 5 |
| F1532 | 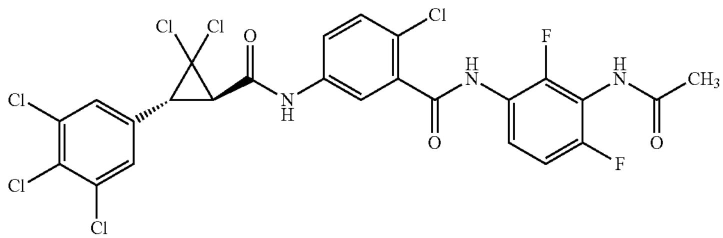 [SMILES: CC(=O)Nc1c(F)ccc(NC(=O)c2cc(NC(=O)[C@H]3[C@H](c4cc(Cl)c(Cl)c(Cl)c4)C3(Cl)Cl)ccc2Cl)c1F] | 25 |
| F1533 | 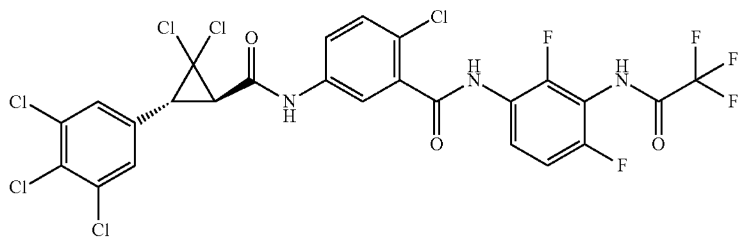 | 25 |
| F1534 | 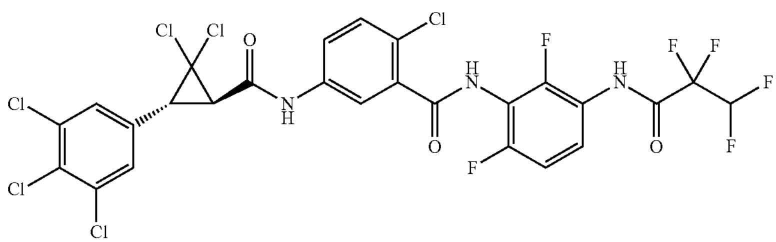 [SMILES: O=C(Nc1c(F)ccc(NC(=O)C(F)(F)C(F)F)c1F)c1cc(NC(=O)[C@H]2[C@H](c3cc(Cl)c(Cl)c(Cl)c3)C2(Cl)Cl)ccc1Cl] | 4 |
| F1535 | 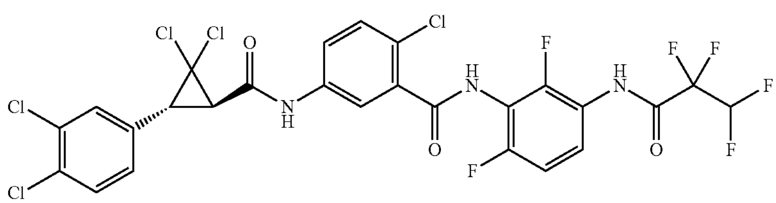 [SMILES: O=C(Nc1c(F)ccc(NC(=O)C(F)(F)C(F)F)c1F)c1cc(NC(=O)[C@H]2[C@H](c3ccc(Cl)c(Cl)c3)C2(Cl)Cl)ccc1Cl] | 4 |
| F1536 | 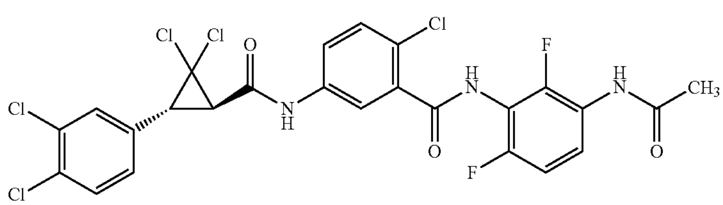 [SMILES: CC(=O)Nc1ccc(F)c(NC(=O)c2cc(NC(=O)[C@H]3[C@H](c4ccc(Cl)c(Cl)c4)C3(Cl)Cl)ccc2Cl)c1F] | 25 |

TABLE 2-continued

Structure and preparation method for F Series molecules

| No. | Structure | Prep.* |
|---|---|---|
| F1537 | 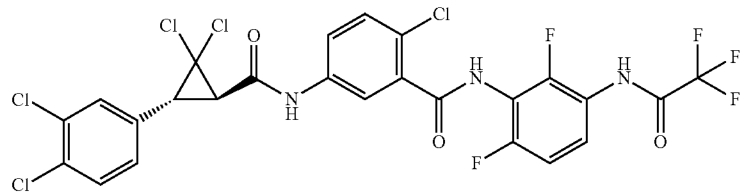 [SMILES: O=C(Nc1c(F)ccc(NC(=O)C(F)(F)F)c1F)c1cc(NC(=O)[C@H]2[C@H](c3ccc(Cl)c(Cl)c3)C2(Cl)Cl)ccc1Cl] | 25 |
| F1538 | 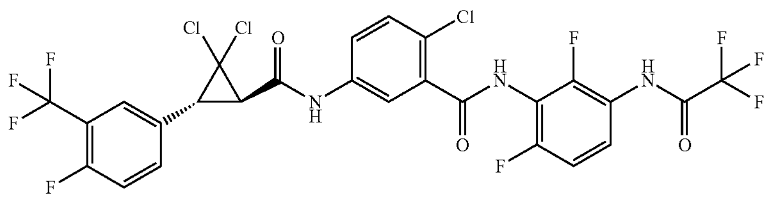 [SMILES: O=C(Nc1c(F)ccc(NC(=O)C(F)(F)F)c1F)c1cc(NC(=O)[C@H]2[C@H](c3ccc(F)c(C(F)(F)F)c3)C2(Cl)Cl)ccc1Cl] | 25 |
| F1539 | 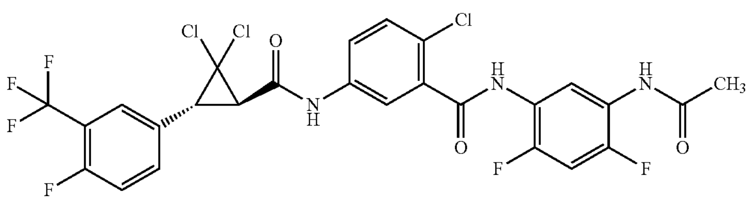 [SMILES: CC(=O)Nc1cc(NC(=O)c2cc(NC(=O)[C@H]3[C@H](c4ccc(F)c(C(F)(F)F)c4)C3(Cl)Cl)ccc2Cl)c(F)cc1F] | 25 |
| F1540 | 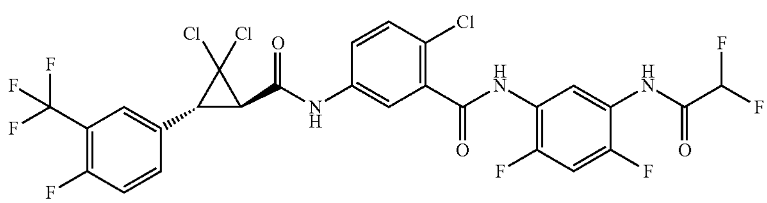 [SMILES: O=C(Nc1cc(NC(=O)C(F)F)c(F)cc1F)c1cc(NC(=O)[C@H]2[C@H](c3ccc(F)c(C(F)(F)F)c3)C2(Cl)Cl)ccc1Cl] | 25 |
| F1541 | 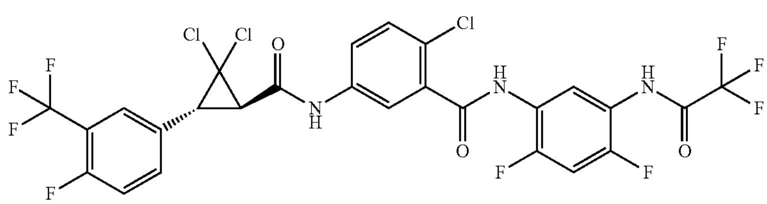 [SMILES: O=C(Nc1cc(NC(=O)C(F)(F)F)c(F)cc1F)c1cc(NC(=O)[C@H]2[C@H](c3ccc(F)c(C(F)(F)F)c3)C2(Cl)Cl)ccc1Cl] | 25 |
| F1542 | 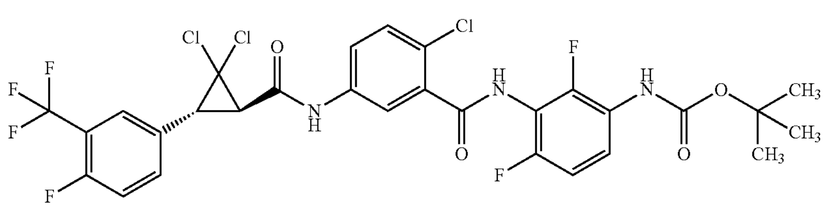 [SMILES: CC(C)(C)OC(=O)Nc1ccc(F)c(NC(=O)c2cc(NC(=O)[C@H]3[C@H](c4ccc(F)c(C(F)(F)F)c4)C3(Cl)Cl)ccc2Cl)c1F] | 25 |
| F1543 | 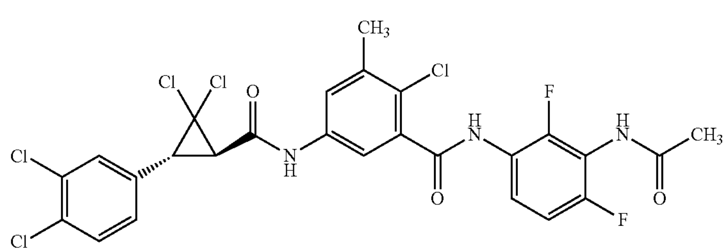 [SMILES: CC(=O)Nc1c(F)ccc(NC(=O)c2cc(NC(=O)[C@H]3[C@H](c4ccc(Cl)c(Cl)c4)C3(Cl)Cl)cc(C)c2Cl)c1F] | 82 |

TABLE 2-continued

Structure and preparation method for F Series molecules

| No. | Structure | Prep.* |
|---|---|---|
| F1544 | 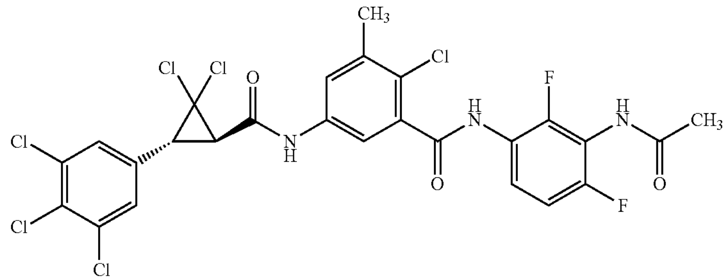 | 82 |
| F1545 | 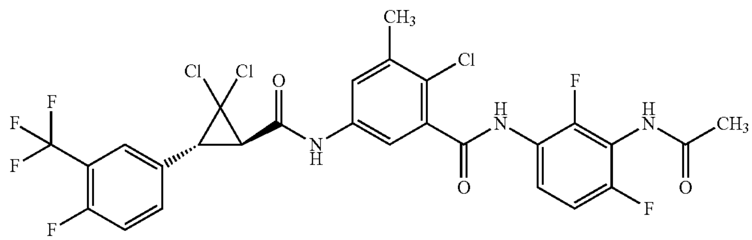 [SMILES: CC(=O)Nc1c(F)ccc(NC(=O)c2cc(NC(=O)[C@H]3[C@H](c4ccc(F)c(C(F)(F)F)c4)C3(Cl)Cl)cc(C)c2Cl)c1F] | 82 |
| F1546 | 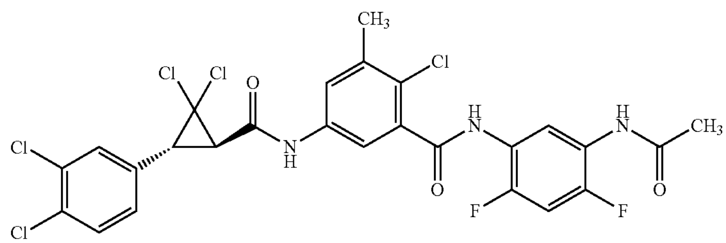 [SMILES: CC(=O)Nc1cc(NC(=O)c2cc(NC(=O)[C@H]3[C@H](c4ccc(Cl)c(Cl)c4)C3(Cl)Cl)cc(C)c2Cl)c(F)cc1F] | 82 |
| F1547 | 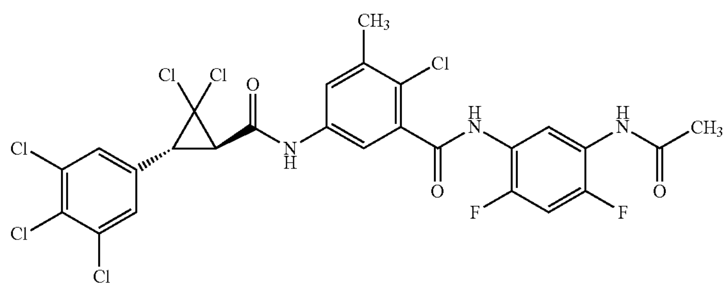 [SMILES: CC(=O)Nc1cc(NC(=O)c2cc(NC(=O)[C@H]3[C@H](c4cc(Cl)c(Cl)c(Cl)c4)C3(Cl)Cl)cc(C)c2Cl)c(F)cc1F] | 82 |
| F1548 | 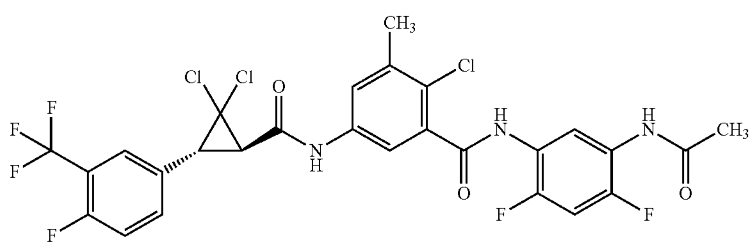 [SMILES: CC(=O)Nc1cc(NC(=O)c2cc(NC(=O)[C@H]3[C@H](c4ccc(F)c(C(F)(F)F)c4)C3(Cl)Cl)cc(C)c2Cl)c(F)cc1F] | 82 |
| F1549 | 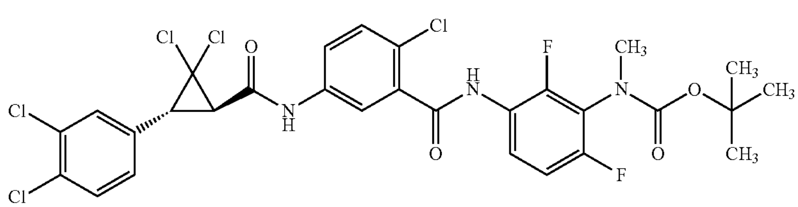 [SMILES: CN(C(=O)OC(C)(C)C)c1c(F)ccc(NC(=O)c2cc(NC(=O)[C@H]3[C@H](c4ccc(Cl)c(Cl)c4)C3(Cl)Cl)ccc2Cl)c1F] | 5 |

TABLE 2-continued

Structure and preparation method for F Series molecules

| No. | Structure | Prep.* |
|---|---|---|
| F1550 | 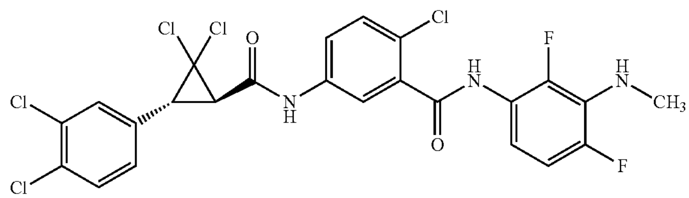 [SMILES: CNc1c(F)ccc(NC(=O)c2cc(NC(=O)[C@H]3[C@H](c4ccc(Cl)c(Cl)c4)C3(Cl)Cl)ccc2Cl)c1F] | 13 |
| F1551 | 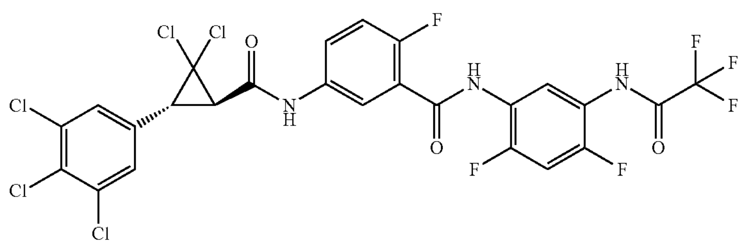 | 5 |
| F1552 | 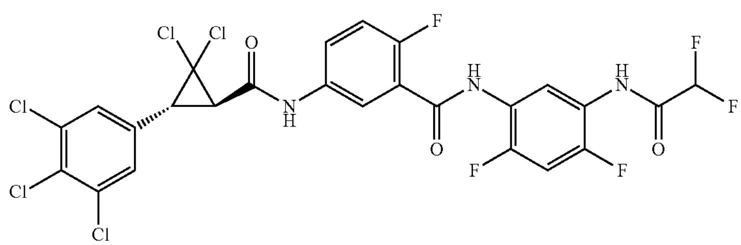 [SMILES: O=C(Nc1cc(NC(=O)C(F)F)c(F)cc1F)c1cc(NC(=O)[C@H]2[C@H](c3cc(Cl)c(Cl)c(Cl)c3)C2(Cl)Cl)ccc1F] | 5 |
| F1553 | 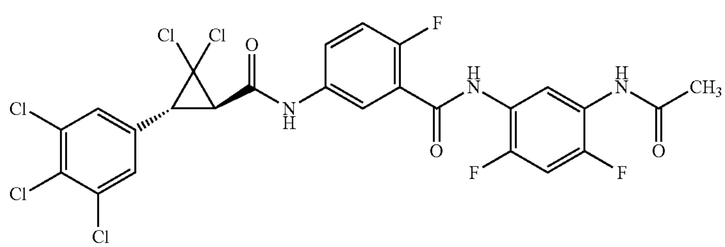 [SMILES: CC(=O)Nc1cc(NC(=O)c2cc(NC(=O)[C@H]3[C@H](c4cc(Cl)c(Cl)c(Cl)c4)C3(Cl)Cl)ccc2F)c(F)cc1F] | 5 |
| F1554 | 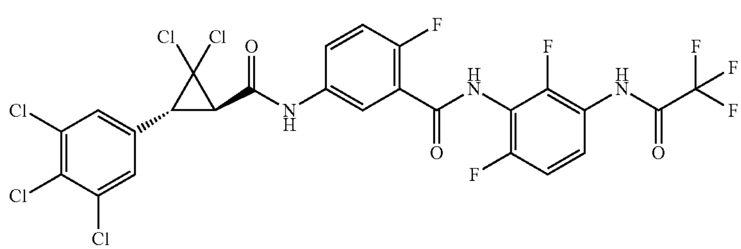 [SMILES: O=C(Nc1c(F)ccc(NC(=O)C(F)(F)F)c1F)c1cc(NC(=O)[C@H]2[C@H](c3cc(Cl)c(Cl)c(Cl)c3)C2(Cl)Cl)ccc1F] | 5 |
| F1555 | 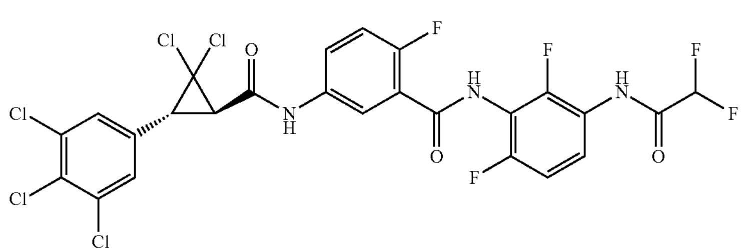 [SMILES: O=C(Nc1c(F)ccc(NC(=O)C(F)F)c1F)c1cc(NC(=O)[C@H]2[C@H](c3cc(Cl)c(Cl)c(Cl)c3)C2(Cl)Cl)ccc1F] | 5 |

TABLE 2-continued

Structure and preparation method for F Series molecules

| No. | Structure | Prep.* |
|---|---|---|
| F1556 | 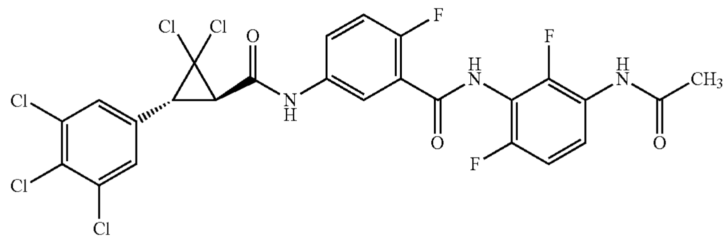 [SMILES: CC(=O)Nc1ccc(F)c(NC(=O)c2cc(NC(=O)[C@H]3[C@H](c4cc(Cl)c(Cl)c(Cl)c4)C3(Cl)Cl)ccc2F)c1F] | 5 |
| F1557 | 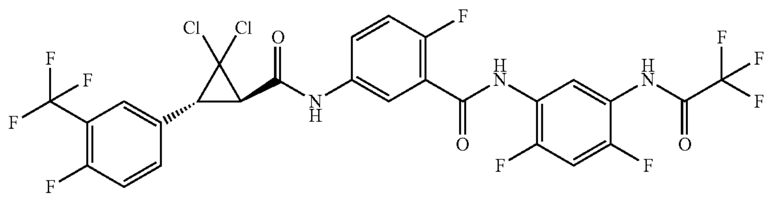 [SMILES: O=C(Nc1cc(NC(=O)C(F)(F)F)c(F)cc1F)c1cc(NC(=O)[C@H]2[C@H](c3ccc(F)c(C(F)(F)F)c3)C2(Cl)Cl)ccc1F] | 5 |
| F1558 | 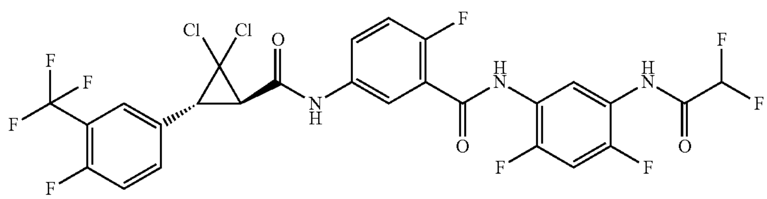 [SMILES: O=C(Nc1cc(NC(=O)C(F)F)c(F)cc1F)c1cc(NC(=O)[C@H]2[C@H](c3ccc(F)c(C(F)(F)F)c3)C2(Cl)Cl)ccc1F] | 5 |
| F1559 | 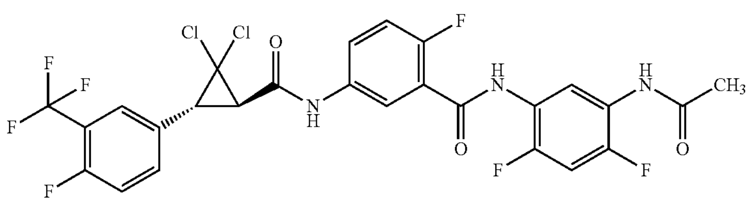 [SMILES: CC(=O)Nc1cc(NC(=O)c2cc(NC(=O)[C@H]3[C@H](c4ccc(F)c(C(F)(F)F)c4)C3(Cl)Cl)ccc2F)c(F)cc1F] | 5 |
| F1560 | 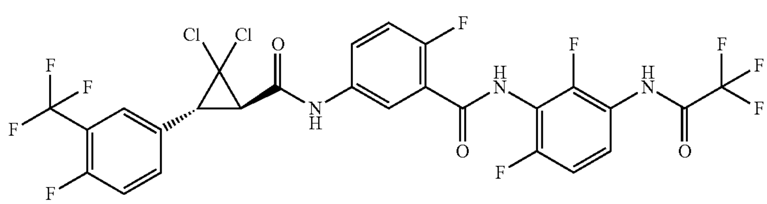 [SMILES: O=C(Nc1c(F)ccc(NC(=O)C(F)(F)F)c1F)c1cc(NC(=O)[C@H]2[C@H](c3ccc(F)c(C(F)(F)F)c3)C2(Cl)Cl)ccc1F] | 5 |
| F1561 | 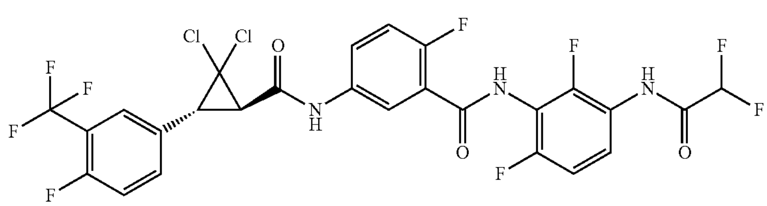 [SMILES: O=C(Nc1c(F)ccc(NC(=O)C(F)F)c1F)c1cc(NC(=O)[C@H]2[C@H](c3ccc(F)c(C(F)(F)F)c3)C2(Cl)Cl)ccc1F] | 5 |
| F1562 | 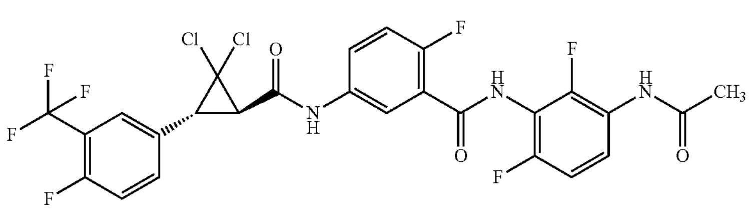 [SMILES: CC(=O)Nc1ccc(F)c(NC(=O)c2cc(NC(=O)[C@H]3[C@H](c4ccc(F)c(C(F)(F)F)c4)C3(Cl)Cl)ccc2F)c1F] | 5 |

TABLE 2-continued

Structure and preparation method for F Series molecules

| No. | Structure | Prep.* |
|---|---|---|
| F1563 | 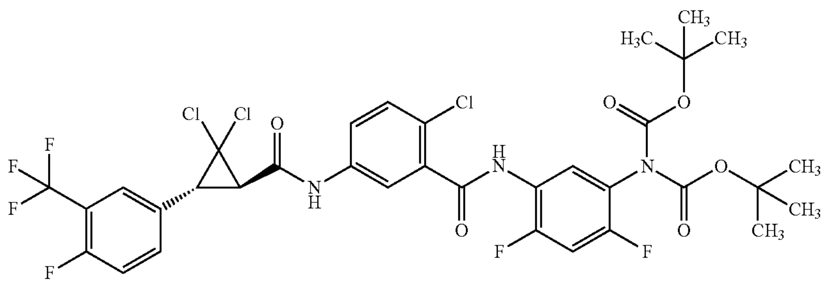 [SMILES: CC(C)(C)OC(=O)N(C(=O)OC(C)(C)C)c1cc(NC(=O)c2cc(NC(=O)[C@H]3[C@H](c4ccc(F)c(C(F)(F)F)c4)C3(Cl)Cl)ccc2Cl)c(F)cc1F] | 25 |
| F1564 | 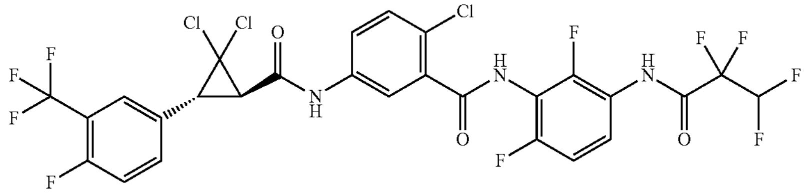 [SMILES: O=C(Nc1c(F)ccc(NC(=O)C(F)(F)C(F)F)c1F)c1cc(NC(=O)[C@H]2[C@H](c3ccc(F)c(C(F)(F)F)c3)C2(Cl)Cl)ccc1Cl] | 4 |
| F1565 | 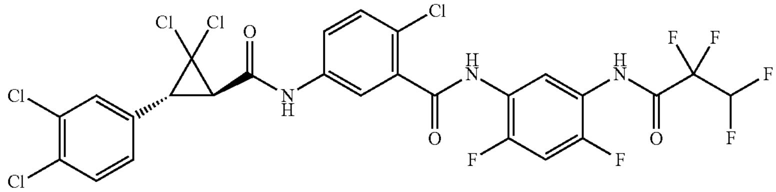 [SMILES: O=C(Nc1cc(NC(=O)C(F)(F)C(F)F)c(F)cc1F)c1cc(NC(=O)[C@H]2[C@H](c3ccc(Cl)c(Cl)c3)C2(Cl)Cl)ccc1Cl] | 4 |
| F1566 | 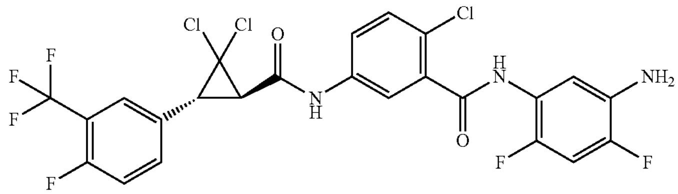 [SMILES: Nc1cc(NC(=O)c2cc(NC(=O)[C@H]3[C@H](c4ccc(F)c(C(F)(F)F)c4)C3(Cl)Cl)ccc2Cl)c(F)cc1F] | 13 |
| F1567 | 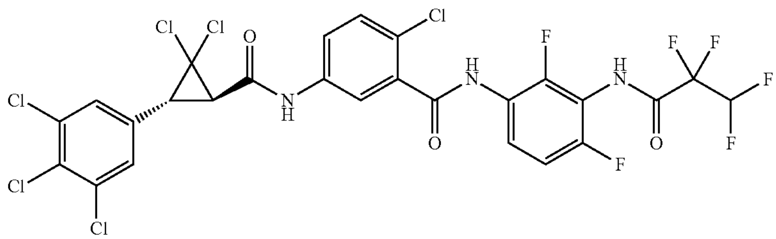 [SMILES: O=C(Nc1ccc(F)c(NC(=O)C(F)(F)C(F)F)c1F)c1cc(NC(=O)[C@H]2[C@H](c3cc(Cl)c(Cl)c(Cl)c3)C2(Cl)Cl)ccc1Cl] | 4 |
| F1568 | 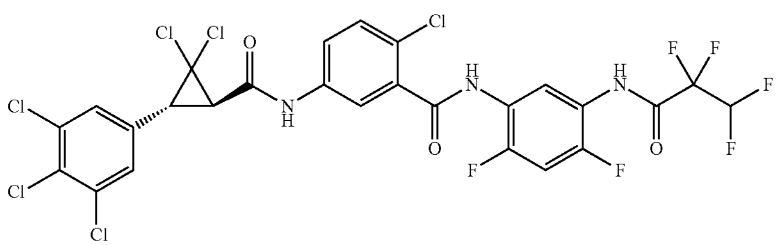 [SMILES: O=C(Nc1cc(NC(=O)C(F)(F)C(F)F)c(F)cc1F)c1cc(NC(=O)[C@H]2[C@H](c3cc(Cl)c(Cl)c(Cl)c3)C2(Cl)Cl)ccc1Cl] | 4 |

TABLE 2-continued

Structure and preparation method for F Series molecules

| No. | Structure | Prep.* |
|---|---|---|
| F1569 | 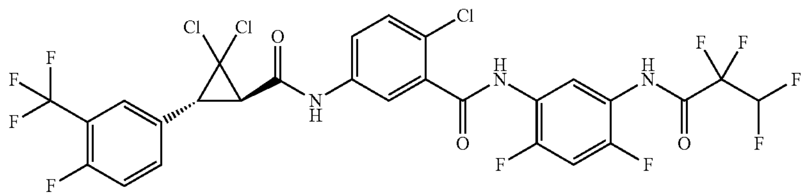 [SMILES: O=C(Nc1cc(NC(=O)C(F)(F)C(F)F)c(F)cc1F)c1cc(NC(=O)[C@H]2[C@H](c3ccc(F)c(C(F)(F)F)c3)C2(Cl)Cl)ccc1Cl] | 4 |
| F1570 | 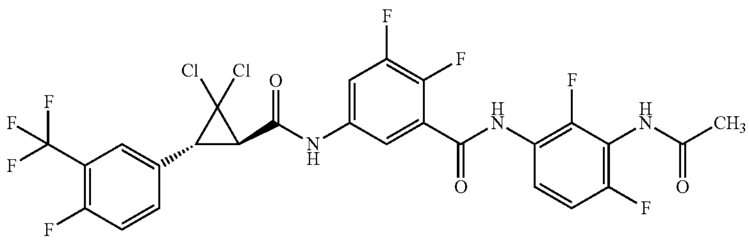 [SMILES: CC(=O)Nc1c(F)ccc(NC(=O)c2cc(NC(=O)[C@H]3[C@H](c4ccc(F)c(C(F)(F)F)c4)C3(Cl)Cl)cc(F)c2F)c1F] | 5 |
| F1571 | 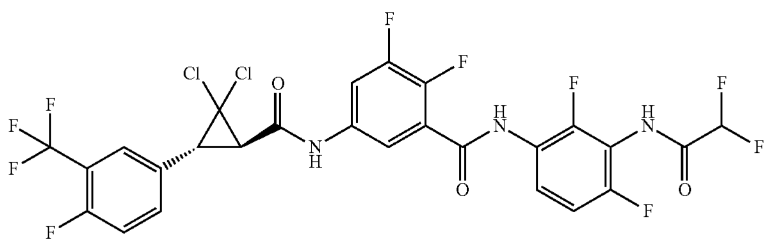 [SMILES: O=C(Nc1ccc(F)c(NC(=O)C(F)F)c1F)c1cc(NC(=O)[C@H]2[C@H](c3ccc(F)c(C(F)(F)F)c3)C2(Cl)Cl)cc(F)c1F] | 5 |
| F1572 | 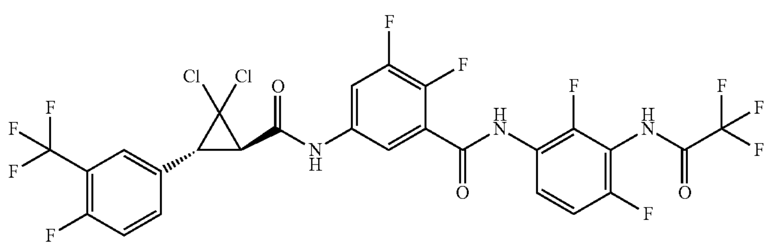 [SMILES: O=C(Nc1ccc(F)c(NC(=O)C(F)(F)F)c1F)c1cc(NC(=O)[C@H]2[C@H](c3ccc(F)c(C(F)(F)F)c3)C2(Cl)Cl)cc(F)c1F] | 5 |
| F1573 | 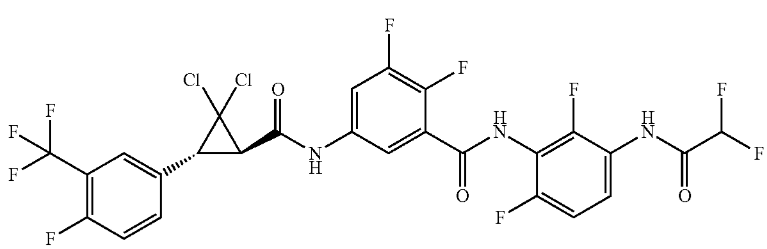 [SMILES: O=C(Nc1c(F)ccc(NC(=O)C(F)F)c1F)c1cc(NC(=O)[C@H]2[C@H](c3ccc(F)c(C(F)(F)F)c3)C2(Cl)Cl)cc(F)c1F] | 5 |
| F1574 | 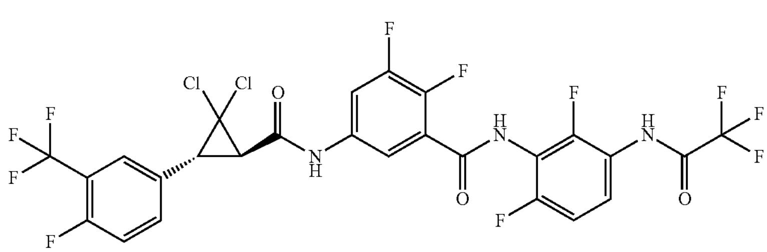 [SMILES: O=C(Nc1c(F)ccc(NC(=O)C(F)(F)F)c1F)c1cc(NC(=O)[C@H]2[C@H](c3ccc(F)c(C(F)(F)F)c3)C2(Cl)Cl)cc(F)c1F] | 5 |

TABLE 2-continued

Structure and preparation method for F Series molecules

| No. | Structure | Prep.* |
|---|---|---|
| F1575 | 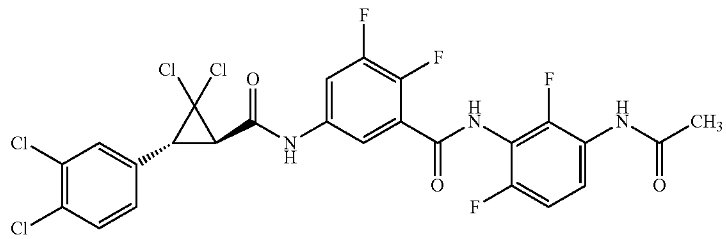 [SMILES: CC(=O)Nc1ccc(F)c(NC(=O)c2cc(NC(=O)[C@H]3[C@H](c4ccc(Cl)c(Cl)c4)C3(Cl)Cl)cc(F)c2F)c1F] | 5 |
| F1576 | 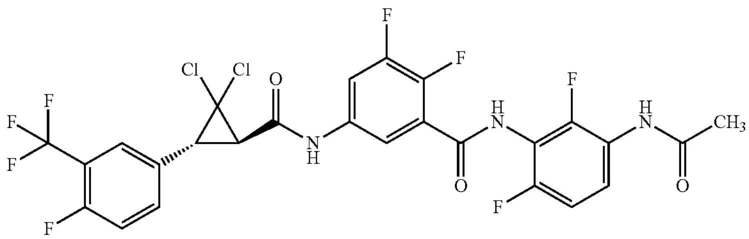 [SMILES: CC(=O)Nc1ccc(F)c(NC(=O)c2cc(NC(=O)[C@H]3[C@H](c4ccc(F)c(C(F)(F)F)c4)C3(Cl)Cl)cc(F)c2F)c1F] | 5 |
| F1577 | 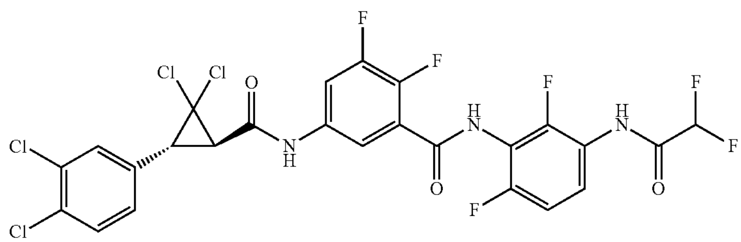 [SMILES: O=C(Nc1c(F)ccc(NC(=O)C(F)F)c1F)c1cc(NC(=O)[C@H]2[C@H](c3ccc(Cl)c(Cl)c3)C2(Cl)Cl)cc(F)c1F] | 5 |
| F1578 | 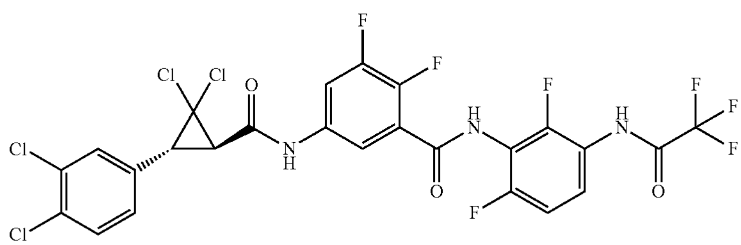 [SMILES: O=C(Nc1c(F)ccc(NC(=O)C(F)(F)F)c1F)c1cc(NC(=O)[C@H]2[C@H](c3ccc(Cl)c(Cl)c3)C2(Cl)Cl)cc(F)c1F] | 5 |
| F1579 | 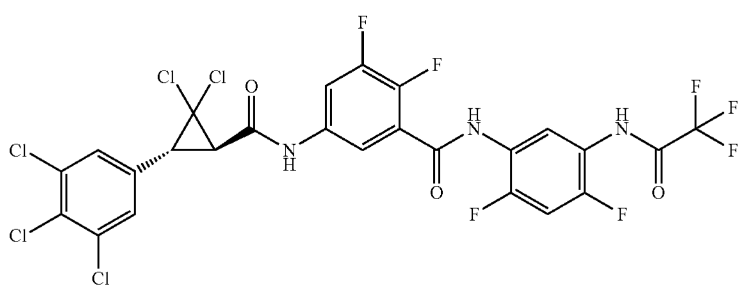 [SMILES: O=C(Nc1cc(NC(=O)C(F)(F)F)c(F)cc1F)c1cc(NC(=O)[C@H]2[C@H](c3cc(Cl)c(Cl)c(Cl)c3)C2(Cl)Cl)cc(F)c1F] | 5 |
| F1580 | 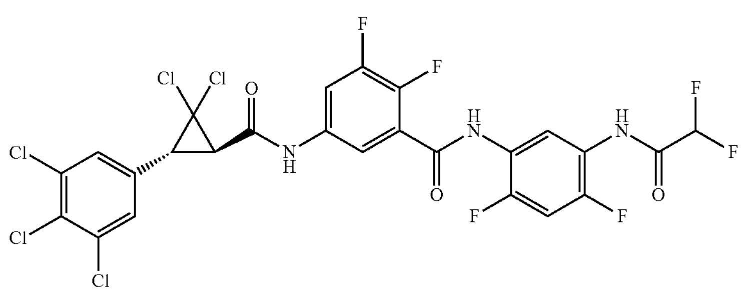 [SMILES: O=C(Nc1cc(NC(=O)C(F)F)c(F)cc1F)c1cc(NC(=O)[C@H]2[C@H](c3cc(Cl)c(Cl)c(Cl)c3)C2(Cl)Cl)cc(F)c1F] | 5 |

TABLE 2-continued

Structure and preparation method for F Series molecules

| No. | Structure | Prep.* |
|---|---|---|
| F1581 | 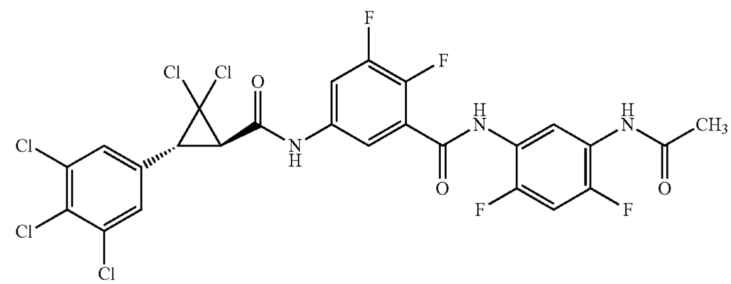 [SMILES: CC(=O)Nc1cc(NC(=O)c2cc(NC(=O)[C@H]3[C@H](c4cc(Cl)c(Cl)c(Cl)c4)C3(Cl)Cl)cc(F)c2F)c(F)cc1F] | 5 |
| F1582 | 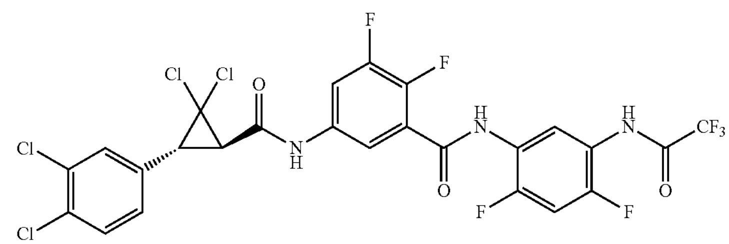 [SMILES: O=C(Nc1cc(NC(=O)C(F)(F)F)c(F)cc1F)c1cc(NC(=O)[C@H]2[C@H](c3ccc(Cl)c(Cl)c3)C2(Cl)Cl)cc(F)c1F] | 5 |
| F1583 | 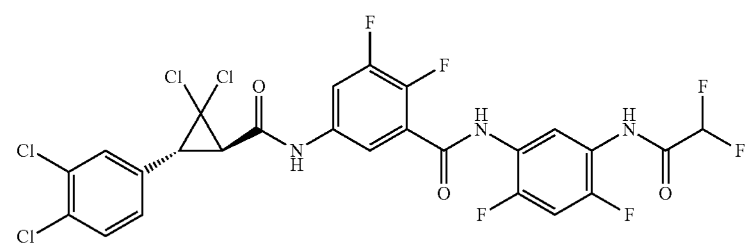 [SMILES: O=C(Nc1cc(NC(=O)C(F)F)c(F)cc1F)c1cc(NC(=O)[C@H]2[C@H](c3ccc(Cl)c(Cl)c3)C2(Cl)Cl)cc(F)c1F] | 5 |
| F1584 | 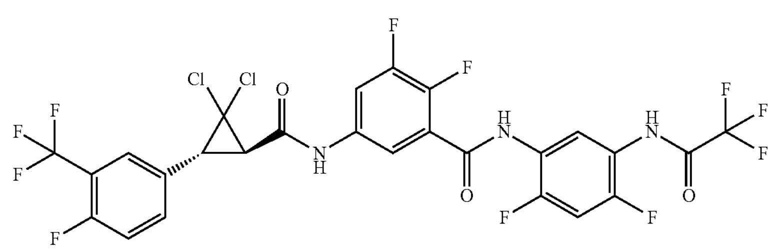 [SMILES: O=C(Nc1cc(NC(=O)C(F)(F)F)c(F)cc1F)c1cc(NC(=O)[C@H]2[C@H](c3ccc(F)c(C(F)(F)F)c3)C2(Cl)Cl)cc(F)c1F] | 5 |
| F1585 | 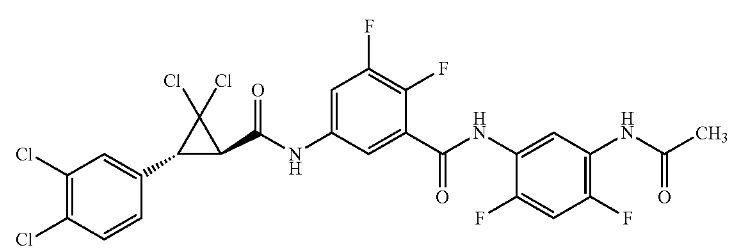 [SMILES: CC(=O)Nc1cc(NC(=O)c2cc(NC(=O)[C@H]3[C@H](c4ccc(Cl)c(Cl)c4)C3(Cl)Cl)cc(F)c2F)c(F)cc1F] | 5 |
| F1586 | 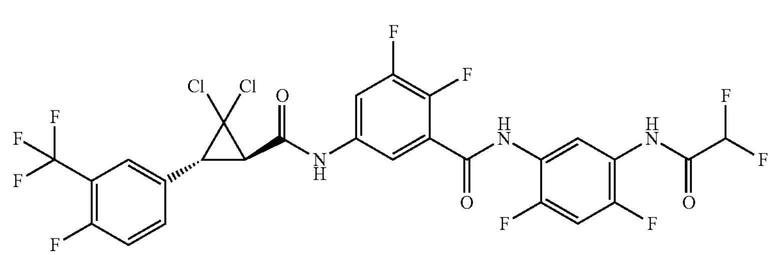 [SMILES: O=C(Nc1cc(NC(=O)C(F)F)c(F)cc1F)c1cc(NC(=O)[C@H]2[C@H](c3ccc(F)c(C(F)(F)F)c3)C2(Cl)Cl)cc(F)c1F] | 5 |

TABLE 2-continued

Structure and preparation method for F Series molecules

| No. | Structure | Prep.* |
|---|---|---|
| F1587 | 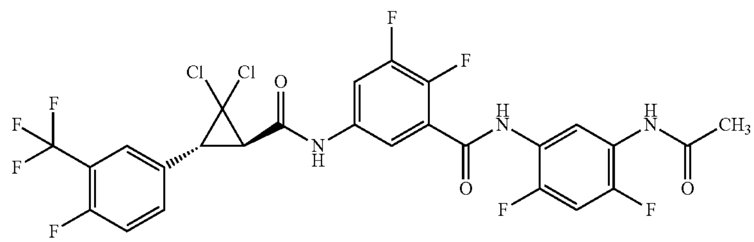 [SMILES: CC(=O)Nc1cc(NC(=O)c2cc(NC(=O)[C@H]3[C@H](c4ccc(F)c(C(F)(F)F)c4)C3(Cl)Cl)cc(F)c2F)c(F)cc1F] | 5 |
| F1588 | 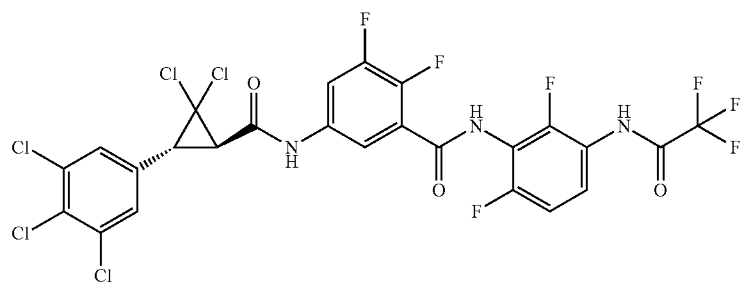 [SMILES: O=C(Nc1c(F)ccc(NC(=O)C(F)(F)F)c1F)c1cc(NC(=O)[C@H]2[C@H](c3cc(Cl)c(Cl)c(Cl)c3)C2(Cl)Cl)cc(F)c1F] | 5 |
| F1589 | 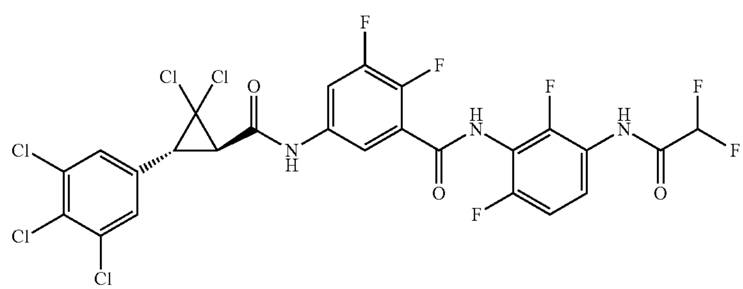 [SMILES: O=C(Nc1c(F)ccc(NC(=O)C(F)F)c1F)c1cc(NC(=O)[C@H]2[C@H](c3cc(Cl)c(Cl)c(Cl)c3)C2(Cl)Cl)cc(F)c1F] | 5 |
| F1590 | 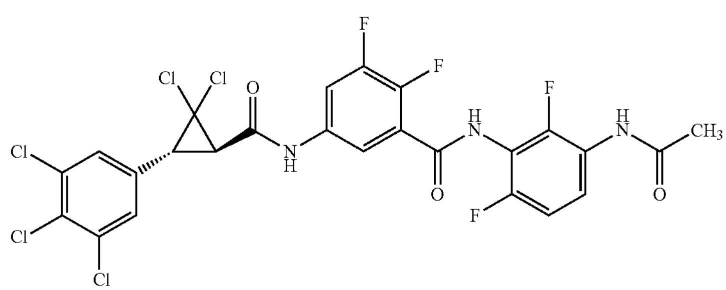 [SMILES: CC(=O)Nc1ccc(F)c(NC(=O)c2cc(NC(=O)[C@H]3[C@H](c4cc(Cl)c(Cl)c(Cl)c4)C3(Cl)Cl)cc(F)c2F)c1F] | 5 |
| F1591 | 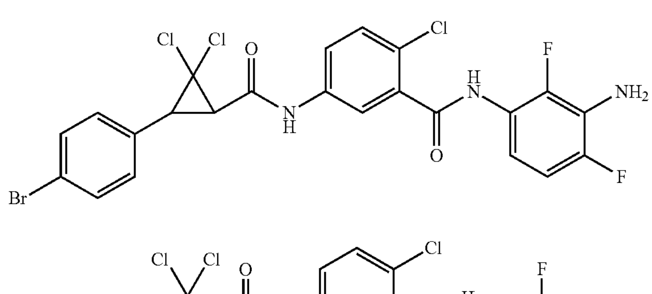 | 21 |
| F1592 | 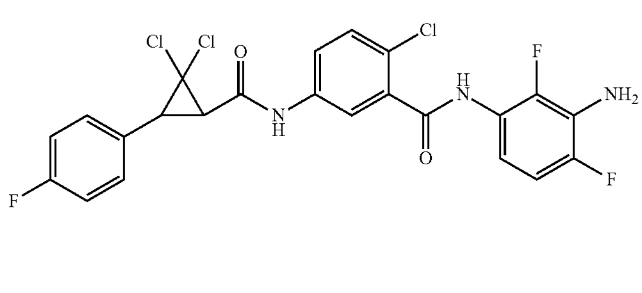 | 21 |

TABLE 2-continued

Structure and preparation method for F Series molecules

| No. | Structure | Prep.* |
|---|---|---|
| F1593 | 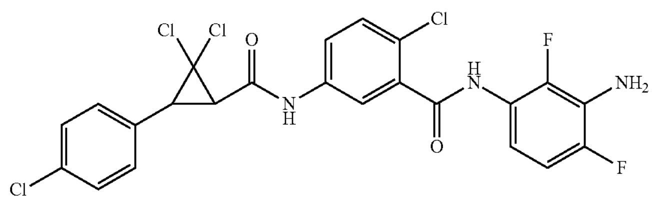 [SMILES: Nc1c(F)ccc(NC(=O)c2cc(NC(=O)C3C(c4ccc(Cl)cc4)C3(Cl)Cl)ccc2Cl)c1F] | 21 |
| F1594 | 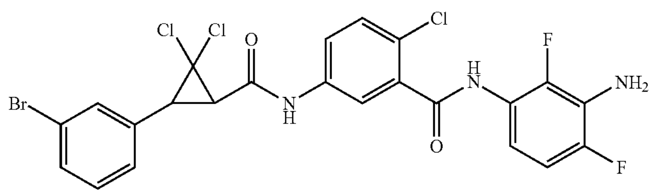 [SMILES: Nc1c(F)ccc(NC(=O)c2cc(NC(=O)C3C(c4cccc(Cl)c4)C3(Cl)Cl)ccc2Cl)c1F] | 21 |
| F1595 | 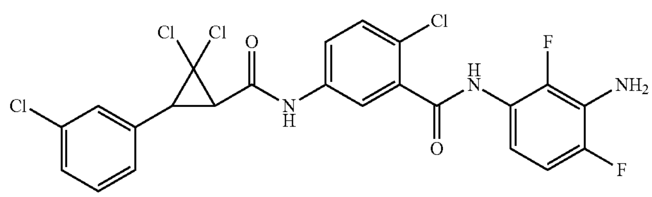 | 21 |
| F1596 | 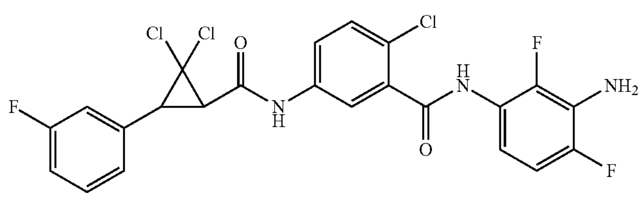 [SMILES: Nc1c(F)ccc(NC(=O)c2cc(NC(=O)C3C(c4cccc(F)c4)C3(Cl)Cl)ccc2Cl)c1F] | 21 |
| F1597 | 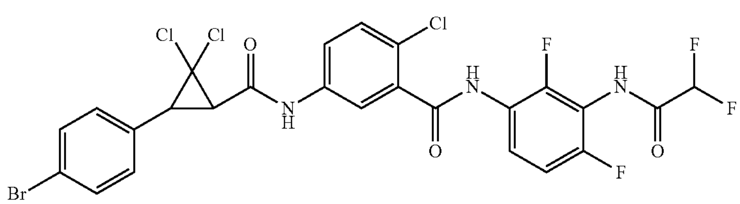 [SMILES: O=C(Nc1ccc(F)c(NC(=O)C(F)F)c1F)c1cc(NC(=O)C2C(c3ccc(Br)cc3)C2(Cl)Cl)ccc1Cl] | 1 |
| F1598 | 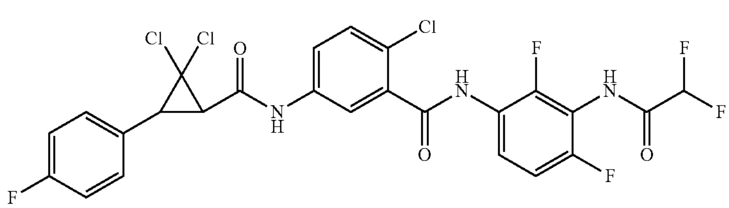 [SMILES: O=C(Nc1ccc(F)c(NC(=O)C(F)F)c1F)c1cc(NC(=O)C2C(c3ccc(F)cc3)C2(Cl)Cl)ccc1Cl] | 1 |
| F1599 | 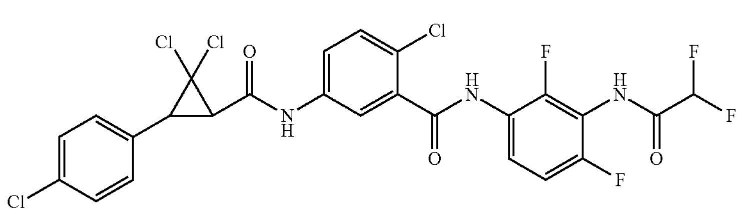 [SMILES: O=C(Nc1ccc(F)c(NC(=O)C(F)F)c1F)c1cc(NC(=O)C2C(c3ccc(Cl)cc3)C2(Cl)Cl)ccc1Cl] | 1 |

TABLE 2-continued

Structure and preparation method for F Series molecules

| No. | Structure | Prep.* |
|---|---|---|
| F1600 | 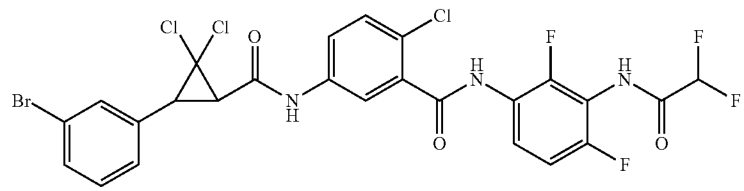 [SMILES: O=C(Nc1ccc(F)c(NC(=O)C(F)F)c1F)c1cc(NC(=O)C2C(c3cccc(Br)c3)C2(Cl)Cl)ccc1Cl] | 1 |
| F1601 | 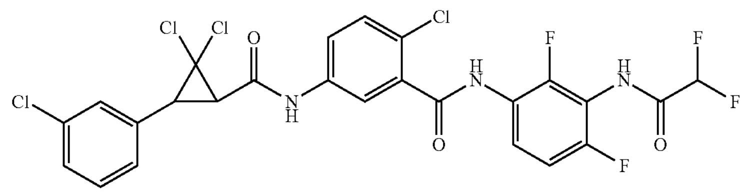 [SMILES: O=C(Nc1ccc(F)c(NC(=O)C(F)F)c1F)c1cc(NC(=O)C2C(c3cccc(Cl)c3)C2(Cl)Cl)ccc1Cl] | 1 |
| F1602 | 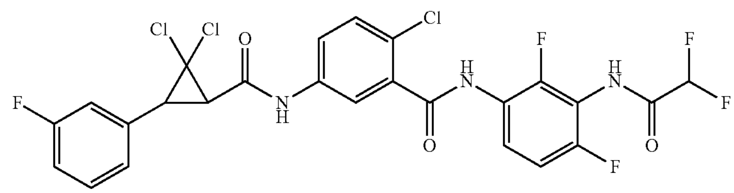 [SMILES: O=C(Nc1ccc(F)c(NC(=O)C(F)F)c1F)c1cc(NC(=O)C2C(c3cccc(F)c3)C2(Cl)Cl)ccc1Cl] | 1 |
| F1603 | 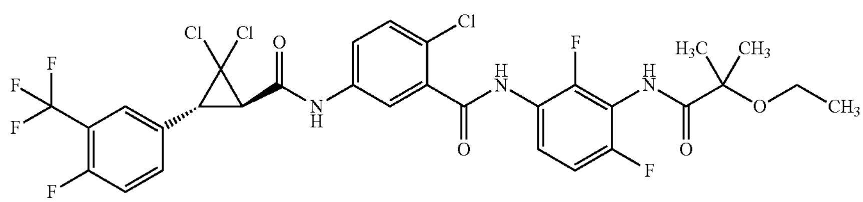 [SMILES: CCOC(C)(C)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1604 | 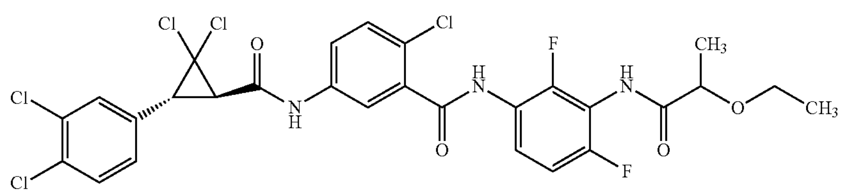 [SMILES: CCOC(C)C(=O)Nc1c(F)ccc(NC(=O)c2cc(NC(=O)[C@H]3[C@H](c4ccc(Cl)c(Cl)c4)C3(Cl)Cl)ccc2Cl)c1F] | 4 |
| F1605 | 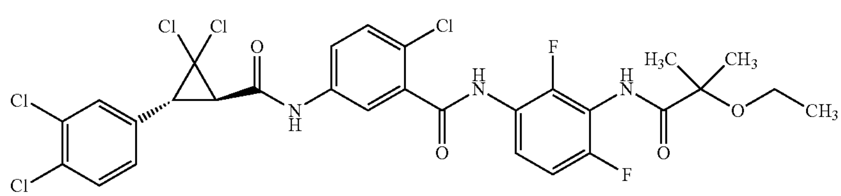 [SMILES: CCOC(C)(C)C(=O)Nc1c(F)ccc(NC(=O)c2cc(NC(=O)[C@H]3[C@H](c4ccc(Cl)c(Cl)c4)C3(Cl)Cl)ccc2Cl)c1F] | 4 |
| F1606 | 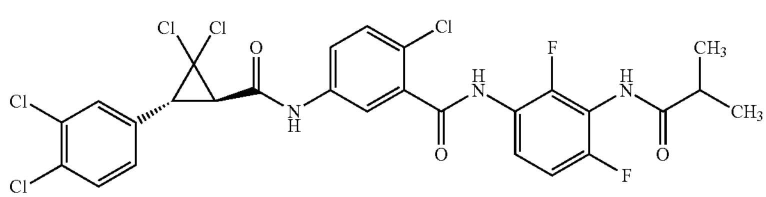 [SMILES: CC(C)C(=O)Nc1c(F)ccc(NC(=O)c2cc(NC(=O)[C@H]3[C@H](c4ccc(Cl)c(Cl)c4)C3(Cl)Cl)ccc2Cl)c1F] | 4 |

TABLE 2-continued

Structure and preparation method for F Series molecules

| No. | Structure | Prep.* |
|---|---|---|
| F1607 | 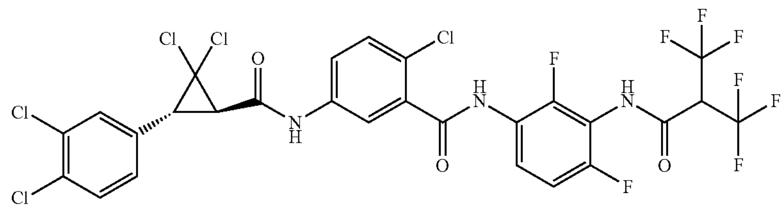 [SMILES: O=C(Nc1ccc(F)c(NC(=O)C(C(F)(F)F)C(F)(F)F)c1F)c1cc(NC(=O)[C@H]2[C@H](c3ccc(Cl)c(Cl)c3)C2(Cl)Cl)ccc1Cl] | 4 |
| F1608 | 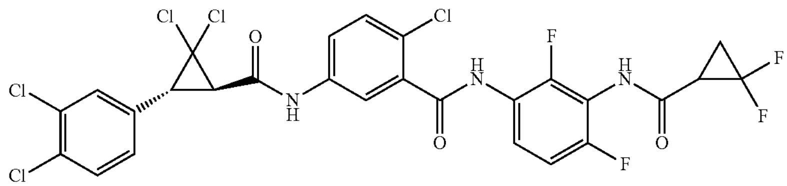 [SMILES: O=C(Nc1ccc(F)c(NC(=O)C2CC2(F)F)c1F)c1cc(NC(=O)[C@H]2[C@H](c3ccc(Cl)c(Cl)c3)C2(Cl)Cl)ccc1Cl] | 4 |
| F1609 | 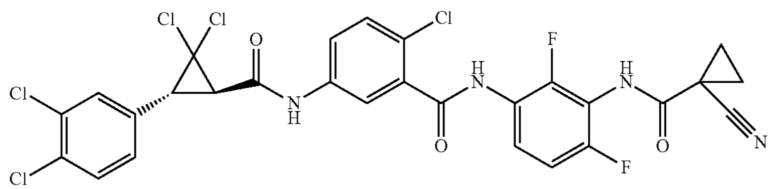 [SMILES: N#CC1(C(=O)Nc2c(F)ccc(NC(=O)c3cc(NC(=O)[C@H]4[C@H](c5ccc(Cl)c(Cl)c5)C4(Cl)Cl)ccc3Cl)c2F)CC1] | 4 |
| F1610 | 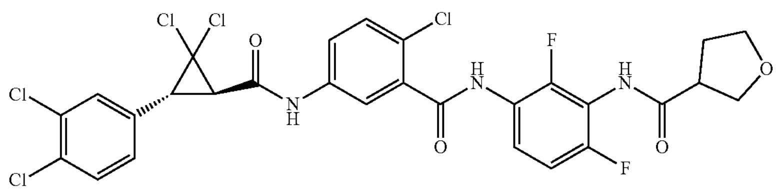 [SMILES: O=C(Nc1ccc(F)c(NC(=O)C2CCOC2)c1F)c1cc(NC(=O)[C@H]2[C@H](c3ccc(Cl)c(Cl)c3)C2(Cl)Cl)ccc1Cl] | 4 |
| F1611 | 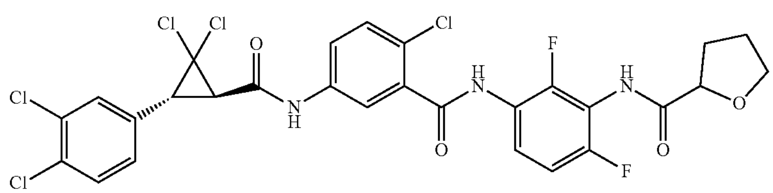 [SMILES: O=C(Nc1ccc(F)c(NC(=O)C2CCCO2)c1F)c1cc(NC(=O)[C@H]2[C@H](c3ccc(Cl)c(Cl)c3)C2(Cl)Cl)ccc1Cl] | 4 |
| F1612 | 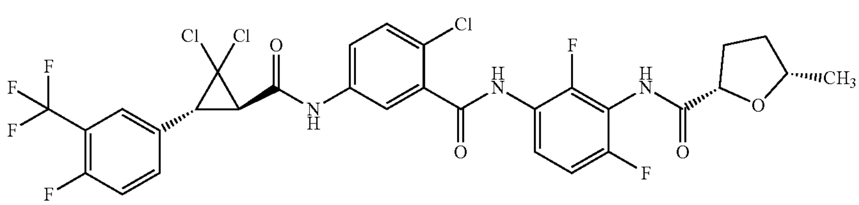 [SMILES: C[C@H]1CC[C@@H](C(=O)Nc2c(F)ccc(NC(=O)c3cc(NC(=O)[C@H]4[C@H](c5ccc(F)c(C(F)(F)F)c5)C4(Cl)Cl)ccc3Cl)c2F)O1] | 6 |
| F1613 | 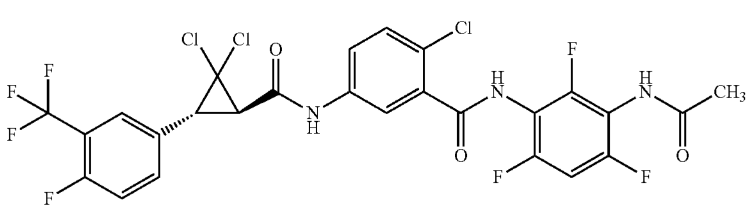 | 5 |

TABLE 2-continued

Structure and preparation method for F Series molecules

| No. | Structure | Prep.* |
|---|---|---|
| F1614 | 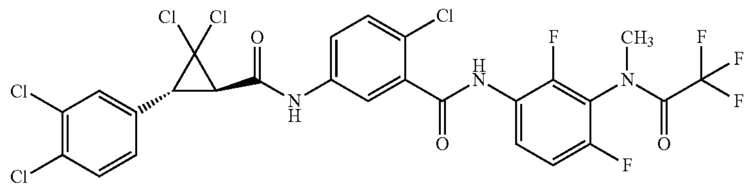 [SMILES: CN(C(=O)C(F)(F)F)c1c(F)ccc(NC(=O)c2cc(NC(=O)[C@H]3[C@H](c4ccc(Cl)c(Cl)c4)C3(Cl)Cl)ccc2Cl)c1F] | 1 |
| F1615 | 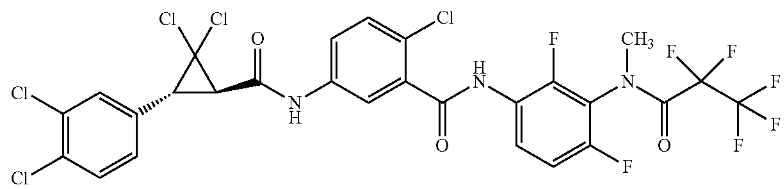 [SMILES: CN(C(=O)C(F)(F)C(F)(F)F)c1c(F)ccc(NC(=O)c2cc(NC(=O)[C@H]3[C@H](c4ccc(Cl)c(Cl)c4)C3(Cl)Cl)ccc2Cl)c1F] | 1 |
| F1616 | 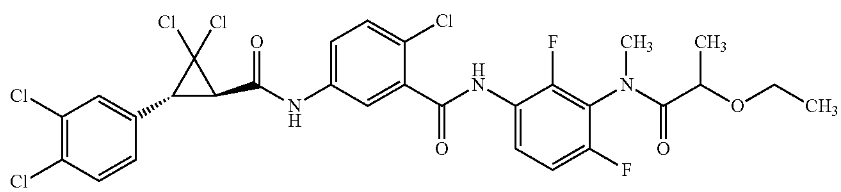 [SMILES: CCOC(C)C(=O)N(C)c1c(F)ccc(NC(=O)c2cc(NC(=O)[C@H]3[C@H](c4ccc(Cl)c(Cl)c4)C3(Cl)Cl)ccc2Cl)c1F] | 4 |
| F1617 | 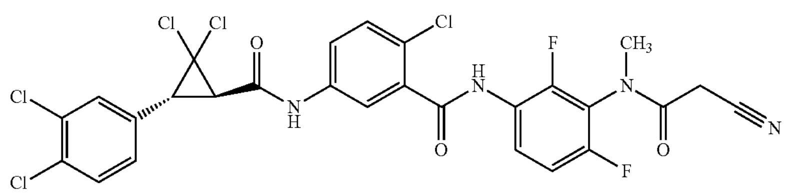 [SMILES: CN(C(=O)CC#N)c1c(F)ccc(NC(=O)c2cc(NC(=O)[C@H]3[C@H](c4ccc(Cl)c(Cl)c4)C3(Cl)Cl)ccc2Cl)c1F] | 4 |
| F1618 | 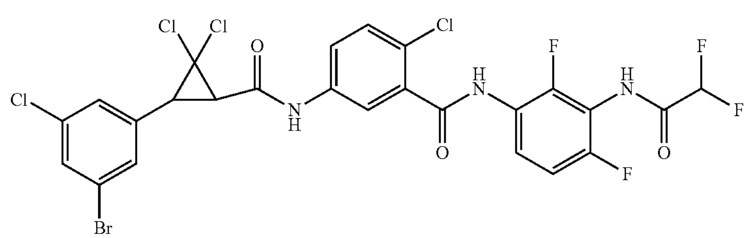 [SMILES: O=C(Nc1ccc(F)c(NC(=O)C(F)F)c1F)c1cc(NC(=O)C2C(c3cc(Cl)cc(Br)c3)C2(Cl)Cl)ccc1Cl] | 20 |
| F1619 | 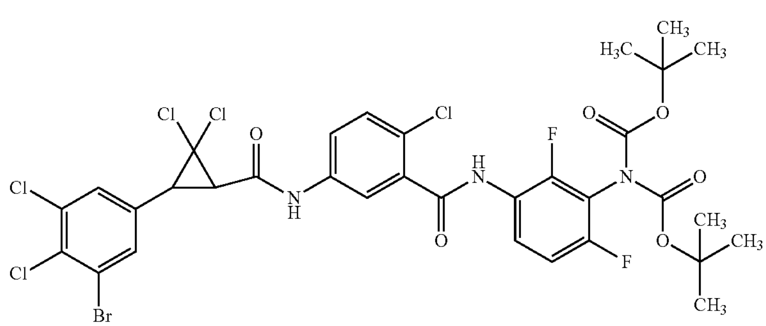 [SMILES: CC(C)(C)OC(=O)N(C(=O)OC(C)(C)C)c1c(F)ccc(NC(=O)c2cc(NC(=O)C3C(c4cc(Cl)c(Cl)c(Br)c4)C3(Cl)Cl)ccc2Cl)c1F] | 20 |

TABLE 2-continued

Structure and preparation method for F Series molecules

| No. | Structure | Prep.* |
|---|---|---|
| F1620 | 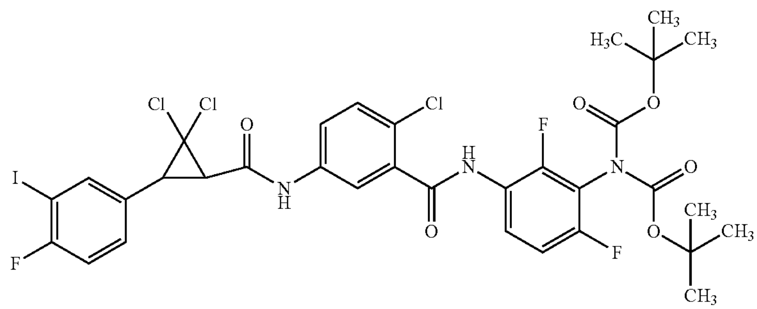 [SMILES: CC(C)(C)OC(=O)N(C(=O)OC(C)(C)C)c1c(F)ccc(NC(=O)c2cc(NC(=O)C3C(c4ccc(F)c(I)c4)C3(Cl)Cl)ccc2Cl)c1F] | 20 |
| F1621 | 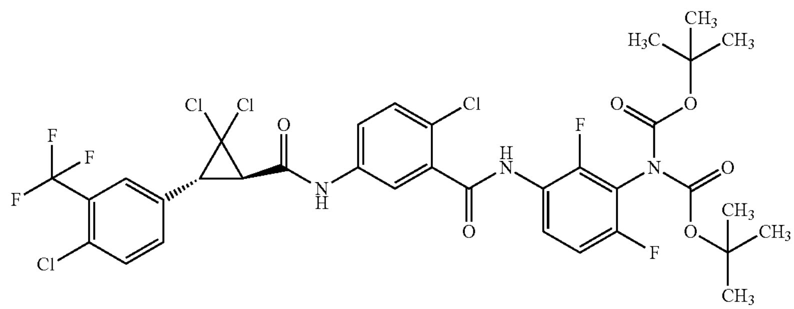 [SMILES: CC(C)(C)OC(=O)N(C(=O)OC(C)(C)C)c1c(F)ccc(NC(=O)c2cc(NC(=O)[C@H]3[C@H](c4ccc(Cl)c(C(F)(F)F)c4)C3(Cl)Cl)ccc2Cl)c1F] | 20 |
| F1622 | 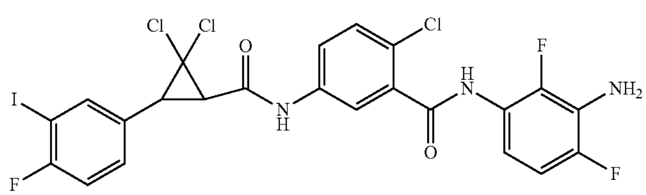 [SMILES: Nc1c(F)ccc(NC(=O)c2cc(NC(=O)C3C(c4ccc(F)c(I)c4)C3(Cl)Cl)ccc2Cl)c1F] | 13 |
| F1623 | 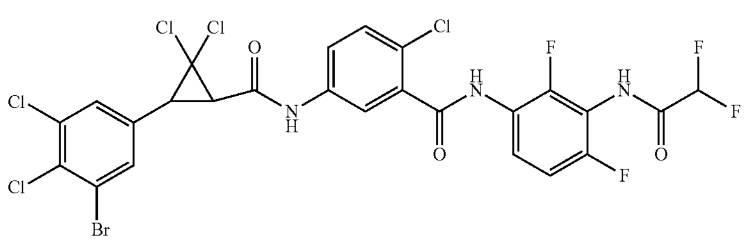 [SMILES: O=C(Nc1ccc(F)c(NC(=O)C(F)F)c1F)c1cc(NC(=O)C2C(c3cc(Cl)c(Cl)c(Br)c3)C2(Cl)Cl)ccc1Cl] | 1 |
| F1624 | 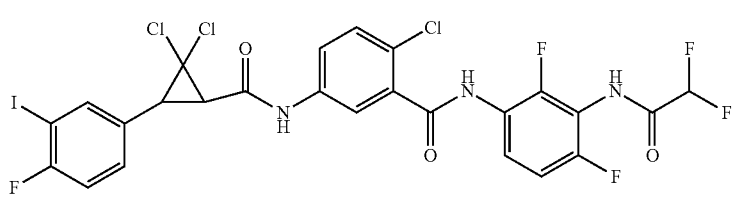 [SMILES: O=C(Nc1ccc(F)c(NC(=O)C(F)F)c1F)c1cc(NC(=O)C2C(c3ccc(F)c(I)c3)C2(Cl)Cl)ccc1Cl] | 1 |
| F1625 | 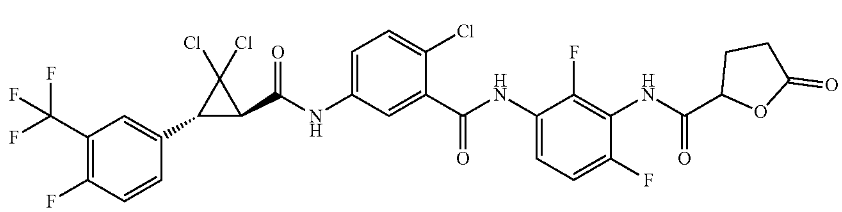 | 6 |

TABLE 2-continued

Structure and preparation method for F Series molecules

| No. | Structure | Prep.* |
|---|---|---|
| F1626 | 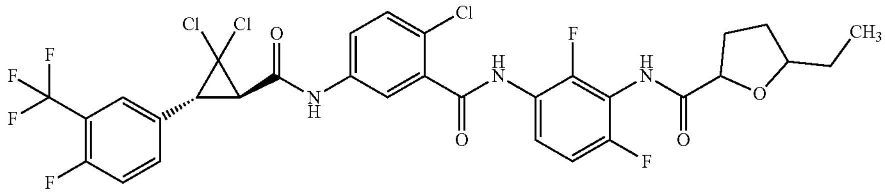 [SMILES: CCC1CCC(C(=O)Nc2c(F)ccc(NC(=O)c3cc(NC(=O)[C@H]4[C@H](c5ccc(F)c(C(F)(F)F)c5)C4(Cl)Cl)ccc3Cl)c2F)O1] | 6 |
| F1627 | 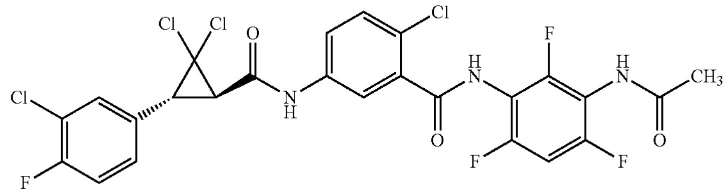 [SMILES: CC(=O)Nc1c(F)cc(F)c(NC(=O)c2cc(NC(=O)[C@H]3[C@H](c4ccc(F)c(Cl)c4)C3(Cl)Cl)ccc2Cl)c1F] | 5 |
| F1628 | 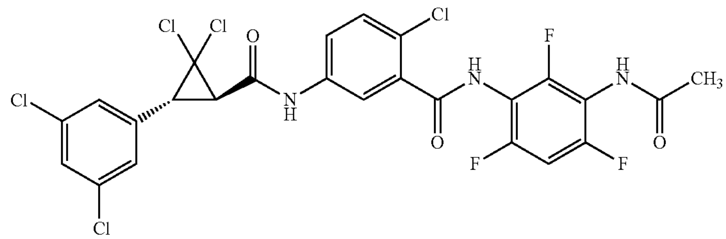 [SMILES: CC(=O)Nc1c(F)cc(F)c(NC(=O)c2cc(NC(=O)[C@H]3[C@H](c4cc(Cl)cc(Cl)c4)C3(Cl)Cl)ccc2Cl)c1F] | 5 |
| F1629 | 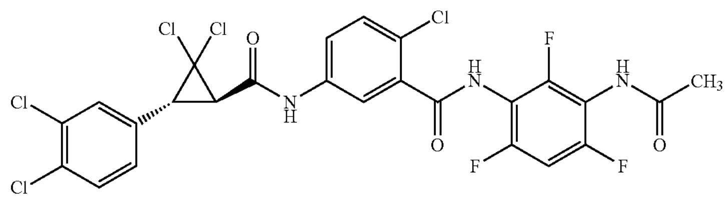 [SMILES: CC(=O)Nc1c(F)cc(F)c(NC(=O)c2cc(NC(=O)[C@H]3[C@H](c4ccc(Cl)c(Cl)c4)C3(Cl)Cl)ccc2Cl)c1F] | 5 |
| F1630 | 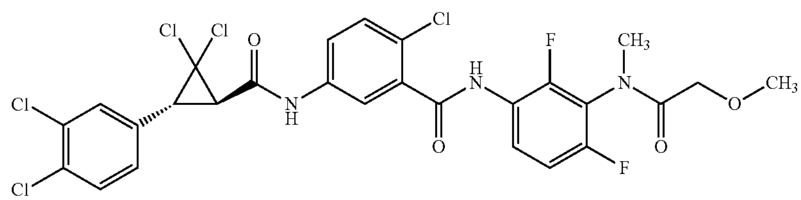 [SMILES: COCC(=O)N(C)c1c(F)ccc(NC(=O)c2cc(NC(=O)[C@H]3[C@H](c4ccc(Cl)c(Cl)c4)C3(Cl)Cl)ccc2Cl)c1F] | 4 |
| F1631 | 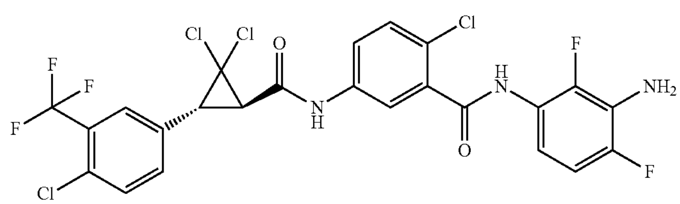 [SMILES: Nc1c(F)ccc(NC(=O)c2cc(NC(=O)[C@H]3[C@H](c4ccc(Cl)c(C(F)(F)F)c4)C3(Cl)Cl)ccc2Cl)c1F] | 13 |
| F1632 | 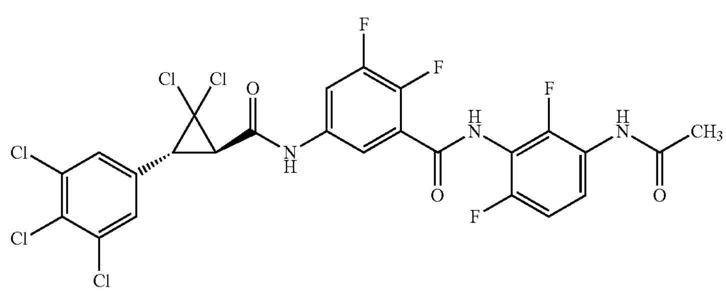 [SMILES: CC(=O)Nc1ccc(F)c(NC(=O)c2cc(NC(=O)[C@H]3[C@H](c4cc(Cl)c(Cl)c(Cl)c4)C3(Cl)Cl)cc(F)c2F)c1F] | 5 |

TABLE 2-continued
Structure and preparation method for F Series molecules
| No. | Structure | Prep.* |
|---|---|---|
| F1633 | 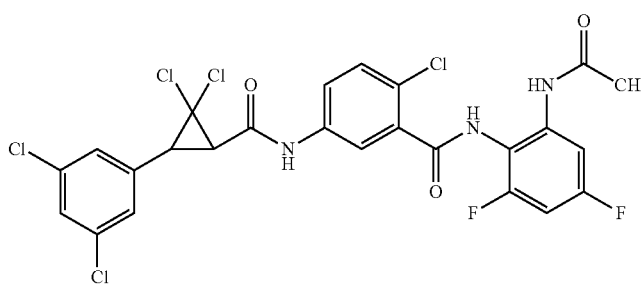 | 5 |
| F1634 | 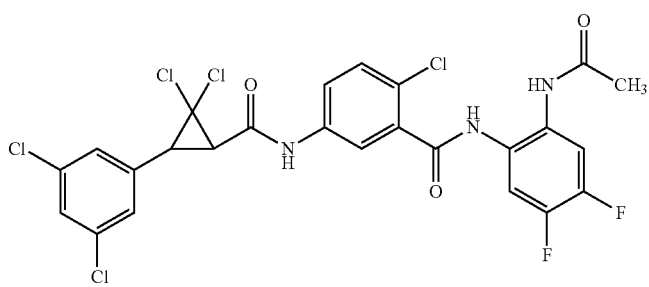 [SMILES: CC(=O)Nc1cc(F)c(F)cc1NC(=O)c1cc(NC(=O)C2C(c3cc(Cl)cc(Cl)c3)C2(Cl)Cl)ccc1Cl] | 5 |
| F1635 | 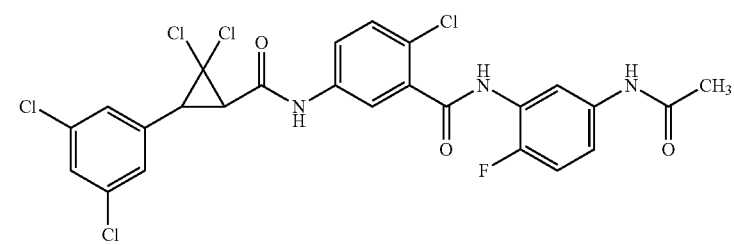 [SMILES: CC(=O)Nc1ccc(F)c(NC(=O)c2cc(NC(=O)C3C(c4cc(Cl)cc(Cl)c4)C3(Cl)Cl)ccc2Cl)c1] | 5 |
| F1636 | 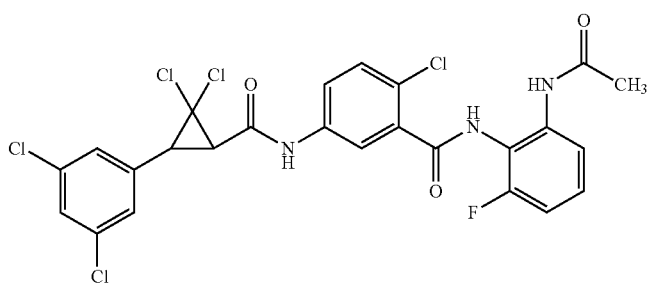 [SMILES: CC(=O)Nc1cccc(F)c1NC(=O)c1cc(NC(=O)C2C(c3cc(Cl)cc(Cl)c3)C2(Cl)Cl)ccc1Cl] | 5 |
| F1637 | 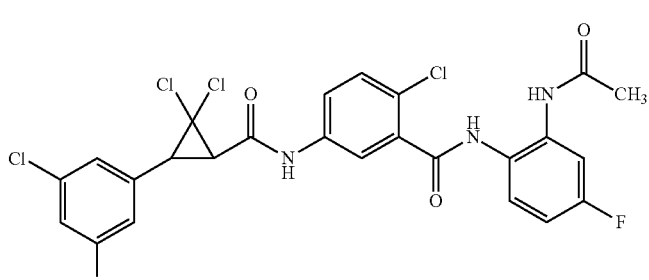 | 5 |

TABLE 2-continued

Structure and preparation method for F Series molecules

| No. | Structure | Prep.* |
|---|---|---|
| F1638 | 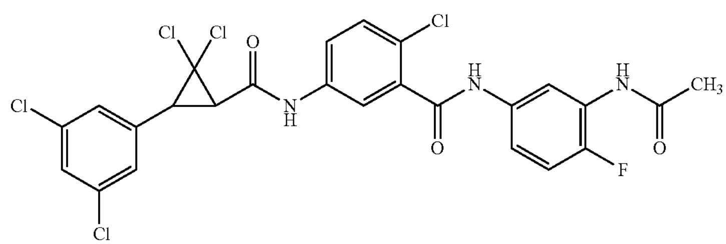 [SMILES: CC(=O)Nc1cc(NC(=O)c2cc(NC(=O)C3C(c4cc(Cl)cc(Cl)c4)C3(Cl)Cl)ccc2Cl)ccc1F] | 5 |
| F1639 | 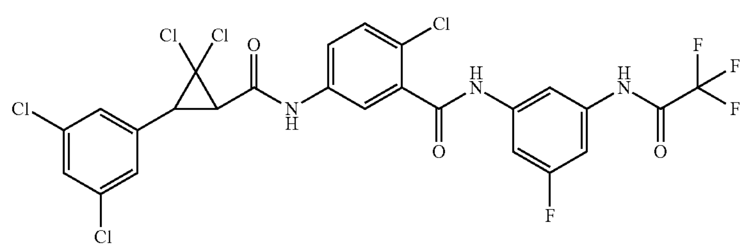 [SMILES: O=C(Nc1cc(F)cc(NC(=O)C(F)(F)F)c1)c1cc(NC(=O)C2C(c3cc(Cl)cc(Cl)c3)C2(Cl)Cl)ccc1Cl] | 5 |
| F1640 | 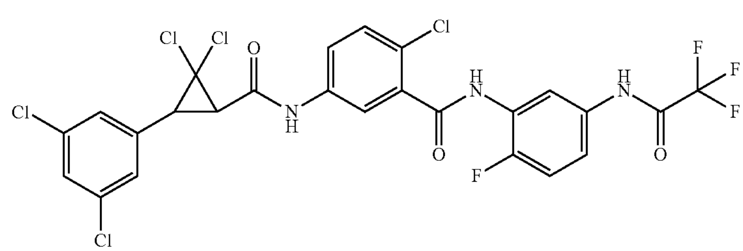 [SMILES: O=C(Nc1cc(NC(=O)C(F)(F)F)ccc1F)c1cc(NC(=O)C2C(c3cc(Cl)cc(Cl)c3)C2(Cl)Cl)ccc1Cl] | 5 |
| F1641 | 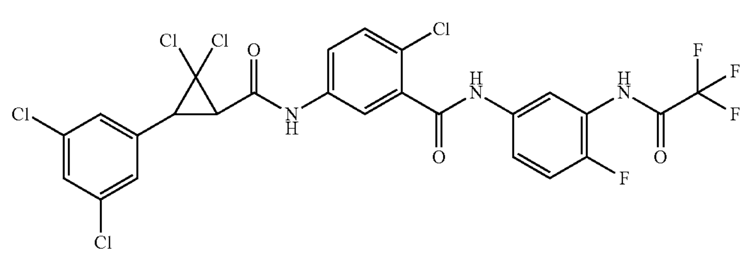 [SMILES: O=C(Nc1ccc(F)c(NC(=O)C(F)(F)F)c1)c1cc(NC(=O)C2C(c3cc(Cl)cc(Cl)c3)C2(Cl)Cl)ccc1Cl] | 5 |
| F1642 | 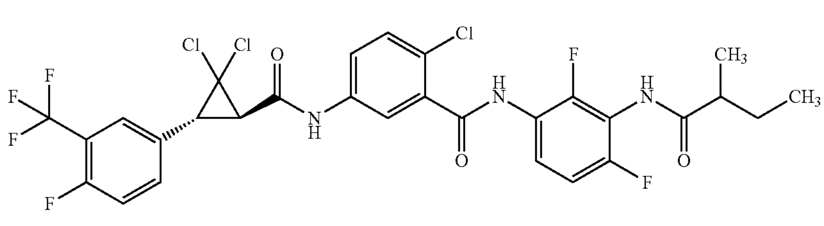 [SMILES: CCC(C)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1643 | 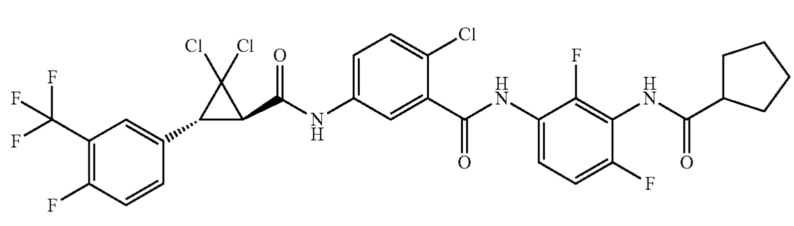 [SMILES: O=C(Nc1ccc(F)c(NC(=O)C2CCCC2)c1F)c1cc(NC(=O)[C@H]2[C@H](c3ccc(F)c(C(F)(F)F)c3)C2(Cl)Cl)ccc1Cl] | 6 |

TABLE 2-continued

Structure and preparation method for F Series molecules

| No. | Structure | Prep.* |
|---|---|---|
| F1644 | 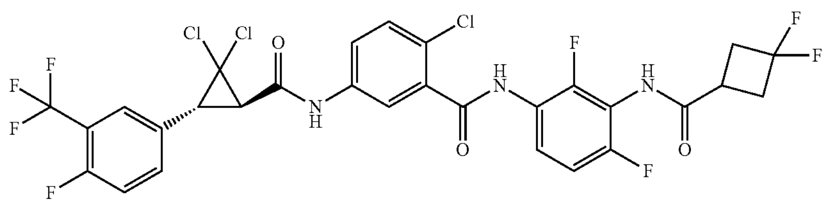 [SMILES: O=C(Nc1ccc(F)c(NC(=O)C2CC(F)(F)C2)c1F)c1cc(NC(=O)[C@H]2[C@H](c3ccc(F)c(C(F)(F)F)c3)C2(Cl)Cl)ccc1Cl] | 6 |
| F1645 | 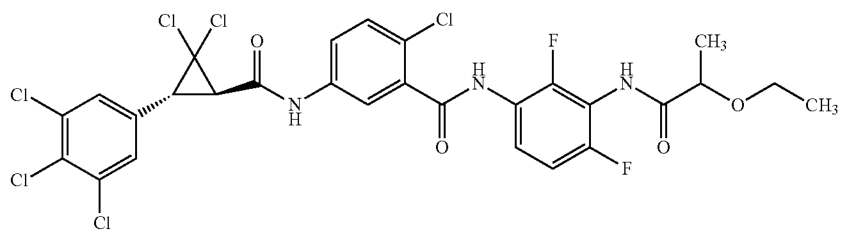 [SMILES: CCOC(C)C(=O)Nc1c(F)ccc(NC(=O)c2cc(NC(=O)[C@H]3[C@H](c4cc(Cl)c(Cl)c(Cl)c4)C3(Cl)Cl)ccc2Cl)c1F] | 4 |
| F1646 | 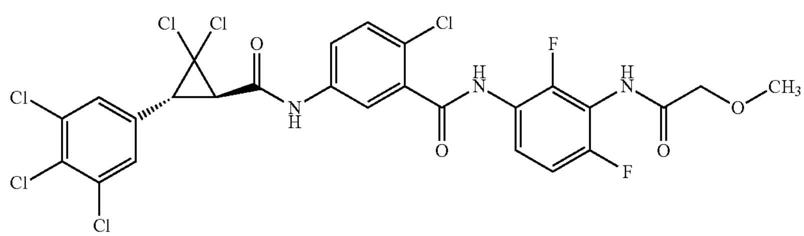 [SMILES: COCC(=O)Nc1c(F)ccc(NC(=O)c2cc(NC(=O)[C@H]3[C@H](c4cc(Cl)c(Cl)c(Cl)c4)C3(Cl)Cl)ccc2Cl)c1F] | 4 |
| F1647 | 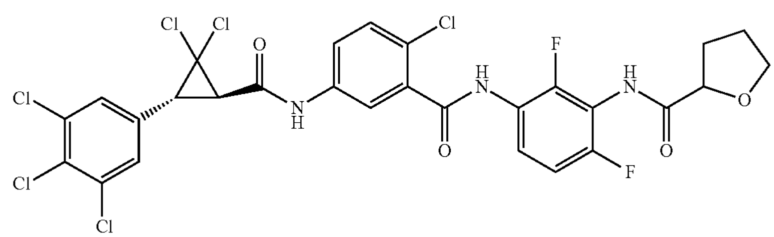 [SMILES: O=C(Nc1ccc(F)c(NC(=O)C2CCCO2)c1F)c1cc(NC(=O)[C@H]2[C@H](c3cc(Cl)c(Cl)c(Cl)c3)C2(Cl)Cl)ccc1Cl] | 4 |
| F1648 | 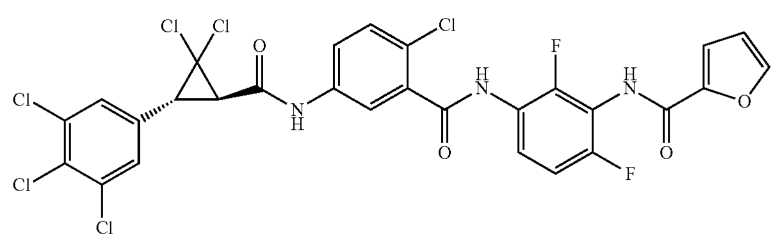 [SMILES: O=C(Nc1c(F)ccc(NC(=O)c2cc(NC(=O)[C@H]3[C@H](c4cc(Cl)c(Cl)c(Cl)c4)C3(Cl)Cl)ccc2Cl)c1F)c1ccco1] | 4 |
| F1649 | 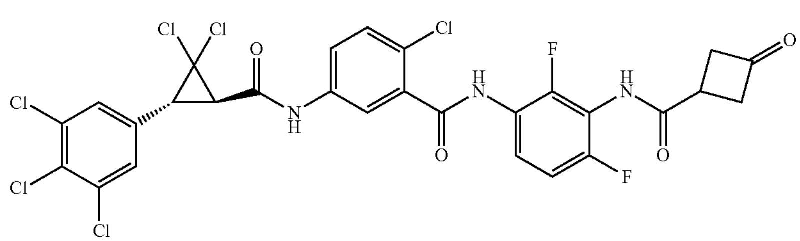 [SMILES: O=C1CC(C(=O)Nc2c(F)ccc(NC(=O)c3cc(NC(=O)[C@H]4[C@H](c5cc(Cl)c(Cl)c(Cl)c5)C4(Cl)Cl)ccc3Cl)c2F)C1] | 4 |

TABLE 2-continued

Structure and preparation method for F Series molecules

| No. | Structure | Prep.* |
|---|---|---|
| F1650 | 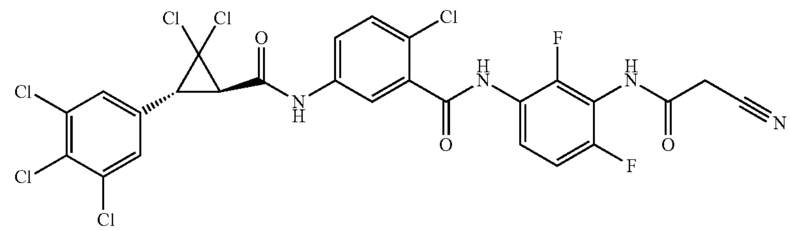 [SMILES: N#CCC(=O)Nc1c(F)ccc(NC(=O)c2cc(NC(=O)[C@H]3[C@H](c4cc(Cl)c(Cl)c(Cl)c4)C3(Cl)Cl)ccc2Cl)c1F] | 4 |
| F1651 | 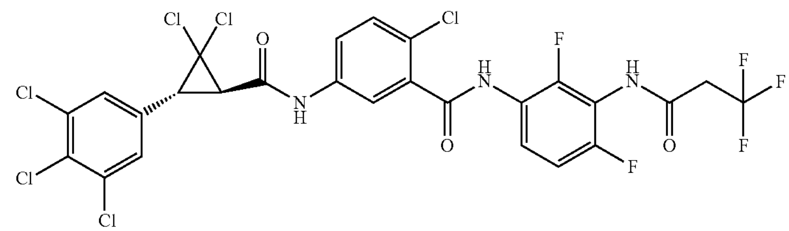 [SMILES: O=C(CC(F)(F)F)Nc1c(F)ccc(NC(=O)c2cc(NC(=O)[C@H]3[C@H](c4cc(Cl)c(Cl)c(Cl)c4)C3(Cl)Cl)ccc2Cl)c1F] | 4 |
| F1652 | 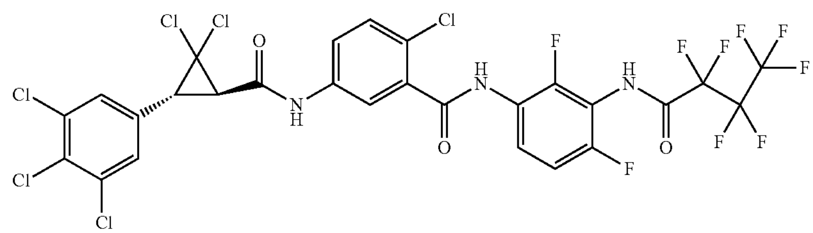 [SMILES: O=C(Nc1ccc(F)c(NC(=O)C(F)(F)C(F)(F)C(F)(F)F)c1F)c1cc(NC(=O)[C@H]2[C@H](c3cc(Cl)c(Cl)c(Cl)c3)C2(Cl)Cl)ccc1Cl] | 4 |
| F1653 | 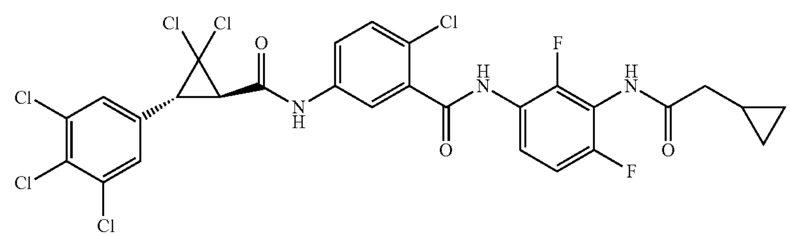 [SMILES: O=C(CC1CC1)Nc1c(F)ccc(NC(=O)c2cc(NC(=O)[C@H]3[C@H](c4cc(Cl)c(Cl)c(Cl)c4)C3(Cl)Cl)ccc2Cl)c1F] | 4 |
| F1654 | 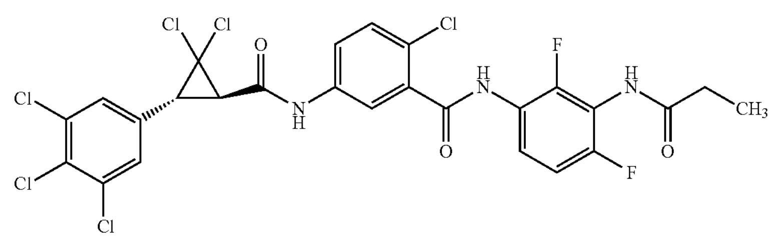 [SMILES: CCC(=O)Nc1c(F)ccc(NC(=O)c2cc(NC(=O)[C@H]3[C@H](c4cc(Cl)c(Cl)c(Cl)c4)C3(Cl)Cl)ccc2Cl)c1F] | 4 |
| F1655 | 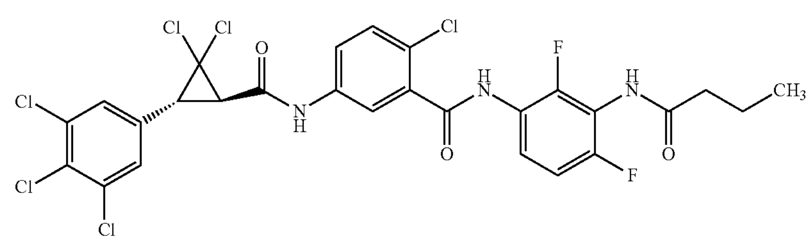 | 4 |

TABLE 2-continued

Structure and preparation method for F Series molecules

| No. | Structure | Prep.* |
|---|---|---|
| F1656 | 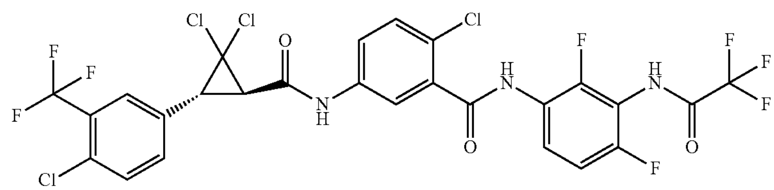 [SMILES: O=C(Nc1ccc(F)c(NC(=O)C(F)(F)F)c1F)c1cc(NC(=O)[C@H]2[C@H](c3ccc(Cl)c(C(F)(F)F)c3)C2(Cl)Cl)ccc1Cl] | 1 |
| F1657 | 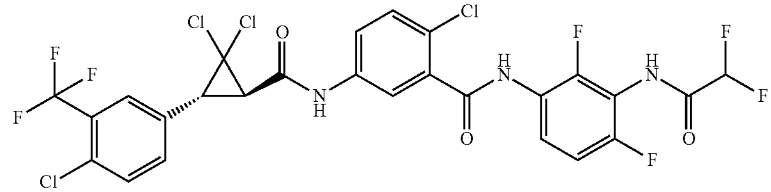 [SMILES: O=C(Nc1ccc(F)c(NC(=O)C(F)F)c1F)c1cc(NC(=O)[C@H]2[C@H](c3ccc(Cl)c(C(F)(F)F)c3)C2(Cl)Cl)ccc1Cl] | 1 |
| F1658 | 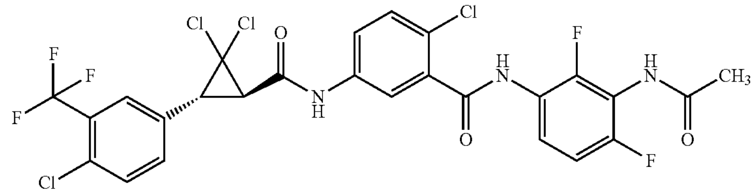 [SMILES: CC(=O)Nc1c(F)ccc(NC(=O)c2cc(NC(=O)[C@H]3[C@H](c4ccc(Cl)c(C(F)(F)F)c4)C3(Cl)Cl)ccc2Cl)c1F] | 2 |
| F1659 | 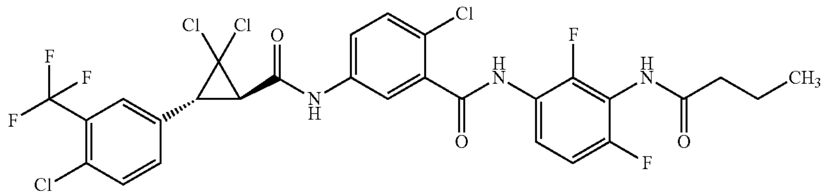 [SMILES: CCCC(=O)Nc1c(F)ccc(NC(=O)c2cc(NC(=O)[C@H]3[C@H](c4ccc(Cl)c(C(F)(F)F)c4)C3(Cl)Cl)ccc2Cl)c1F] | 4 |
| F1660 | 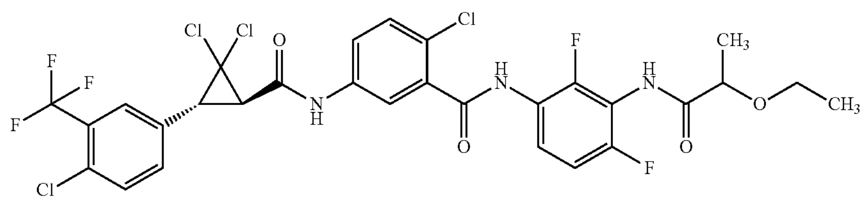 [SMILES: CCOC(C)C(=O)Nc1c(F)ccc(NC(=O)c2cc(NC(=O)[C@H]3[C@H](c4ccc(Cl)c(C(F)(F)F)c4)C3(Cl)Cl)ccc2Cl)c1F] | 4 |
| F1661 | 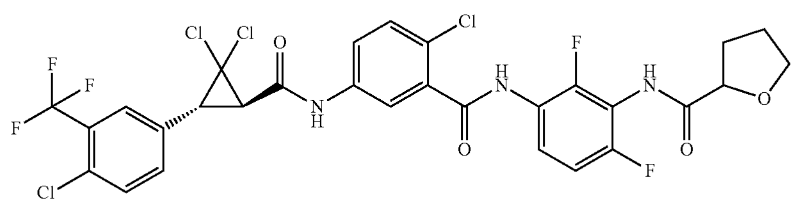 [SMILES: O=C(Nc1ccc(F)c(NC(=O)C2CCCO2)c1F)c1cc(NC(=O)[C@H]2[C@H](c3ccc(Cl)c(C(F)(F)F)c3)C2(Cl)Cl)ccc1Cl] | 4 |
| F1662 | 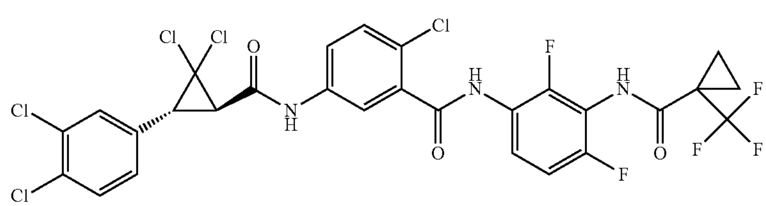 [SMILES: O=C(Nc1ccc(F)c(NC(=O)C2(C(F)(F)F)CC2)c1F)c1cc(NC(=O)[C@H]2[C@H](c3ccc(Cl)c(Cl)c3)C2(Cl)Cl)ccc1Cl] | 4 |

TABLE 2-continued

Structure and preparation method for F Series molecules

| No. | Structure | Prep.* |
|---|---|---|
| F1663 | 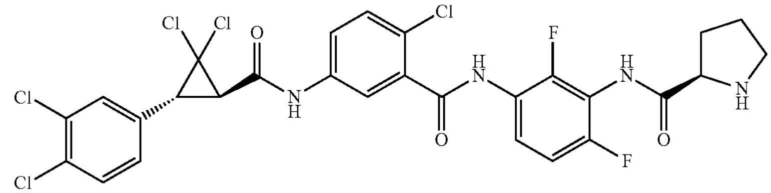 [SMILES: O=C(Nc1ccc(F)c(NC(=O)[C@H]2CCCN2)c1F)c1cc(NC(=O)[C@H]2[C@H](c3ccc(Cl)c(Cl)c3)C2(Cl)Cl)ccc1Cl] | 4 |
| F1664 | 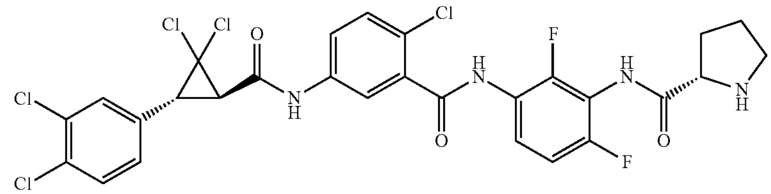 [SMILES: O=C(Nc1ccc(F)c(NC(=O)[C@@H]2CCCN2)c1F)c1cc(NC(=O)[C@H]2[C@H](c3ccc(Cl)c(Cl)c3)C2(Cl)Cl)ccc1Cl] | 4 |
| F1665 | 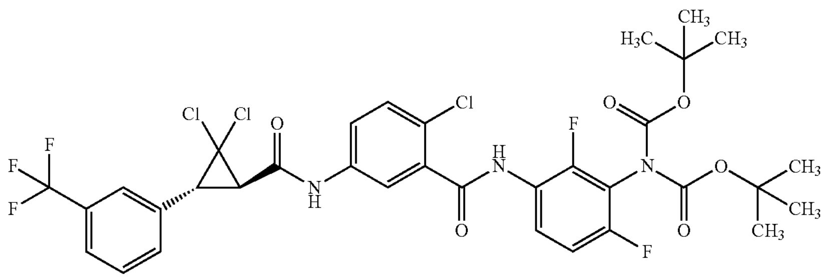 [SMILES: CC(C)(C)OC(=O)N(C(=O)OC(C)(C)C)c1c(F)ccc(NC(=O)c2cc(NC(=O)[C@H]3[C@H](c4cccc(C(F)(F)F)c4)C3(Cl)Cl)ccc2Cl)c1F] | 20 |
| F1666 | 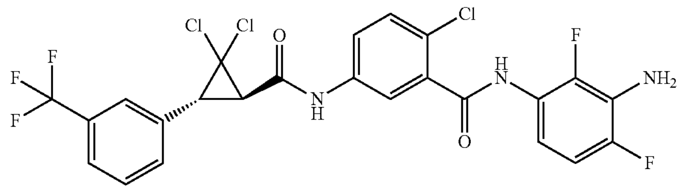 [SMILES: Nc1c(F)ccc(NC(=O)c2cc(NC(=O)[C@H]3[C@H](c4cccc(C(F)(F)F)c4)C3(Cl)Cl)ccc2Cl)c1F] | 13 |
| F1667 | 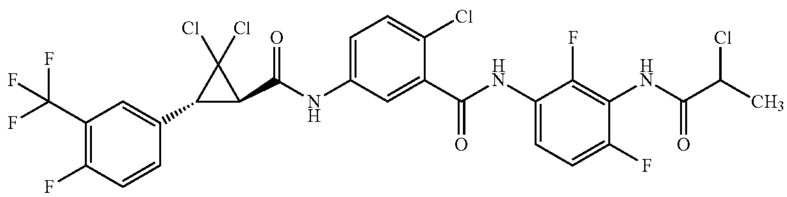 | 6 |
| F1668 | 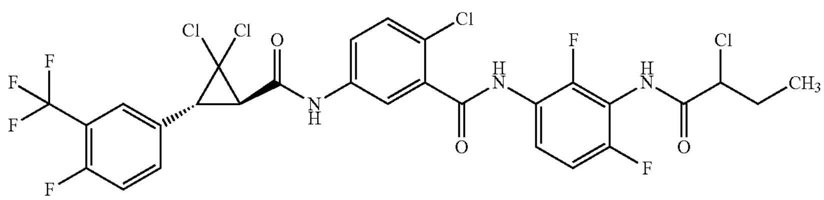 [SMILES: CCC(Cl)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1669 | 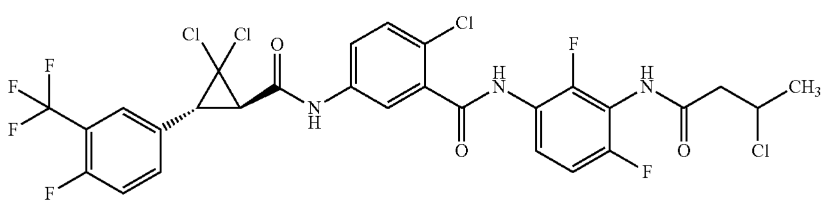 [SMILES: CC(Cl)CC(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |

TABLE 2-continued
Structure and preparation method for F Series molecules
| No. | Structure | Prep.* |
|---|---|---|
| F1670 | 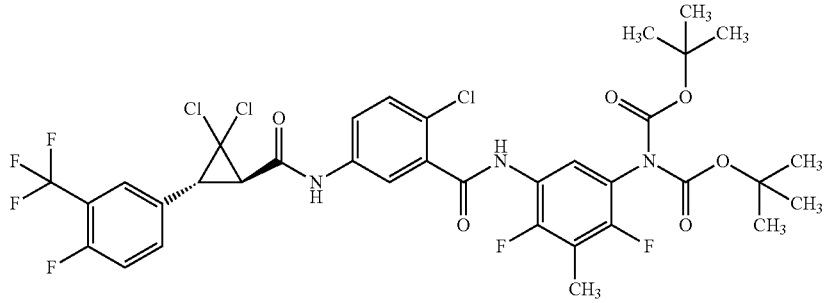 [SMILES: Cc1c(F)c(NC(=O)c2cc(NC(=O)[C@H]3[C@H](c4ccc(F)c(C(F)(F)F)c4)C3(Cl)Cl)ccc2Cl)cc(N(C(=O)OC(C)(C)C)C(=O)OC(C)(C)C)c1F] | 5 |
| F1671 | 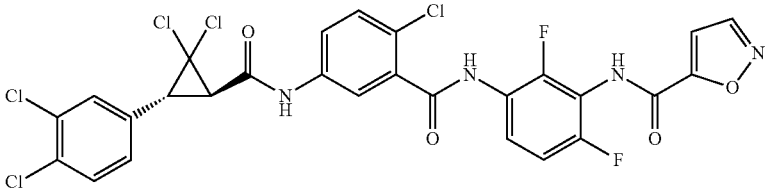 [SMILES: O=C(Nc1c(F)ccc(NC(=O)c2cc(NC(=O)[C@H]3[C@H](c4ccc(Cl)c(Cl)c4)C3(Cl)Cl)ccc2Cl)c1F)c1ccno1] | 4 |
| F1672 | 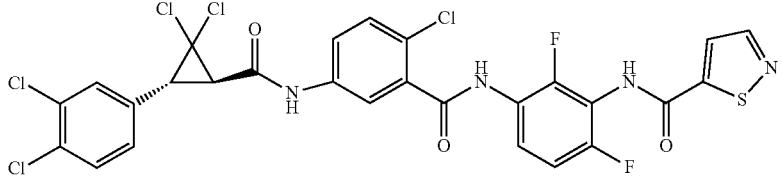 [SMILES: O=C(Nc1c(F)ccc(NC(=O)c2cc(NC(=O)[C@H]3[C@H](c4ccc(Cl)c(Cl)c4)C3(Cl)Cl)ccc2Cl)c1F)c1ccns1] | 4 |
| F1673 | 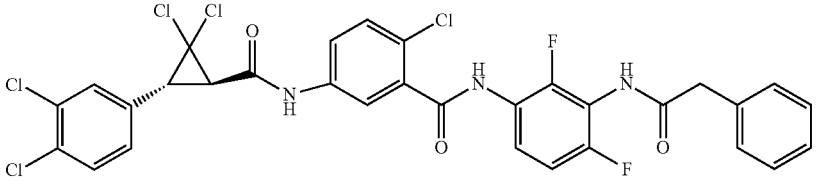 [SMILES: O=C(Cc1ccccc1)Nc1c(F)ccc(NC(=O)c2cc(NC(=O)[C@H]3[C@H](c4ccc(Cl)c(Cl)c4)C3(Cl)Cl)ccc2Cl)c1F] | 4 |
| F1674 | 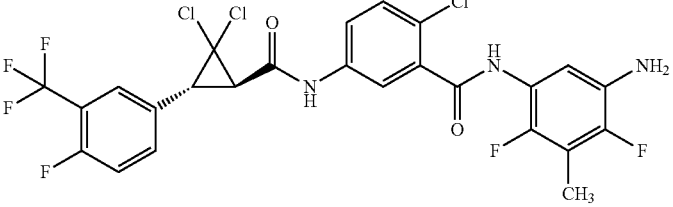 | 13 |
| F1675 | 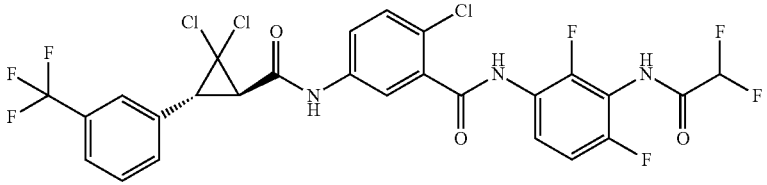 [SMILES: O=C(Nc1ccc(F)c(NC(=O)C(F)F)c1F)c1cc(NC(=O)[C@H]2[C@H](c3cccc(C(F)(F)F)c3)C2(Cl)Cl)ccc1Cl] | 1 |
| F1676 | 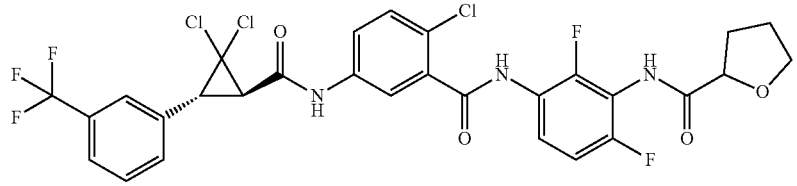 [SMILES: O=C(Nc1ccc(F)c(NC(=O)C2CCCO2)c1F)c1cc(NC(=O)[C@H]2[C@H](c3cccc(C(F)(F)F)c3)C2(Cl)Cl)ccc1Cl] | 6 |

TABLE 2-continued

Structure and preparation method for F Series molecules

| No. | Structure | Prep.* |
|---|---|---|
| F1677 | 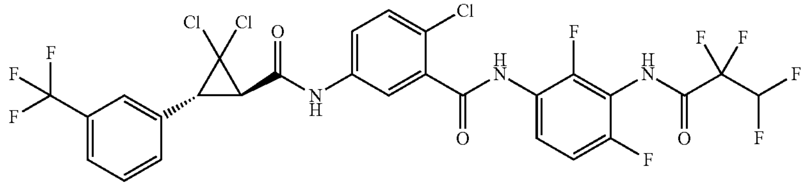 [SMILES: O=C(Nc1ccc(F)c(NC(=O)C(F)(F)C(F)F)c1F)c1cc(NC(=O)[C@H]2[C@H](c3cccc(C(F)(F)F)c3)C2(Cl)Cl)ccc1Cl] | 6 |
| F1678 | 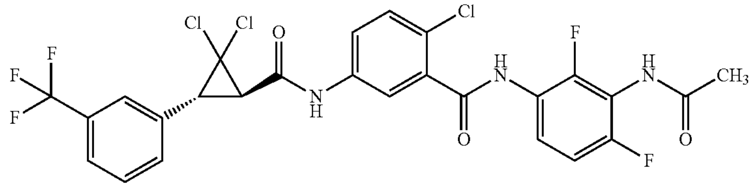 [SMILES: CC(=O)Nc1c(F)ccc(NC(=O)c2cc(NC(=O)[C@H]3[C@H](c4cccc(C(F)(F)F)c4)C3(Cl)Cl)ccc2Cl)c1F] | 6 |
| F1679 | 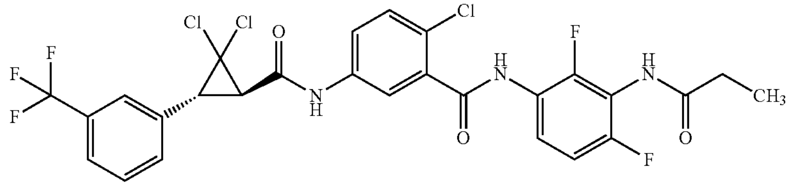 [SMILES: CCC(=O)Nc1c(F)ccc(NC(=O)c2cc(NC(=O)[C@H]3[C@H](c4cccc(C(F)(F)F)c4)C3(Cl)Cl)ccc2Cl)c1F] | 6 |
| F1680 | 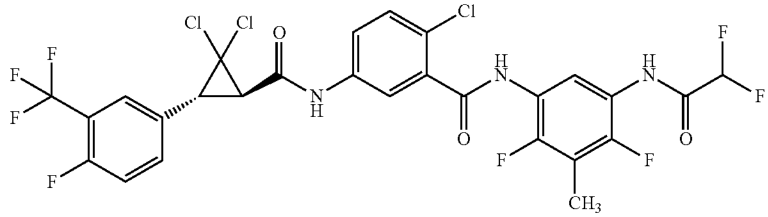 [SMILES: Cc1c(F)c(NC(=O)c2cc(NC(=O)[C@H]3[C@H](c4ccc(F)c(C(F)(F)F)c4)C3(Cl)Cl)ccc2Cl)cc(NC(=O)C(F)F)c1F] | 1 |
| F1681 | 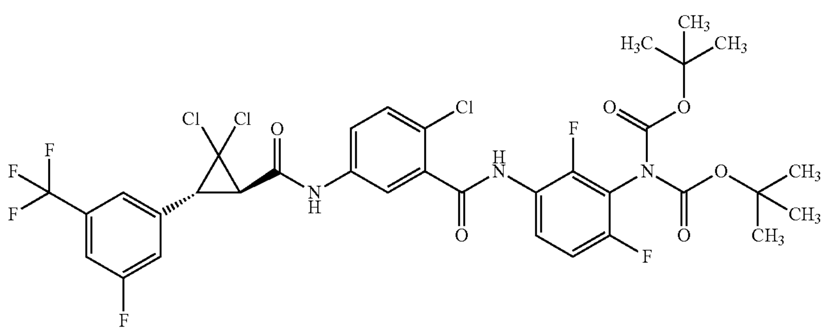 [SMILES: CC(C)(C)OC(=O)N(C(=O)OC(C)(C)C)c1c(F)ccc(NC(=O)c2cc(NC(=O)[C@H]3[C@H](c4cc(F)cc(C(F)(F)F)c4)C3(Cl)Cl)ccc2Cl)c1F] | 5 |
| F1682 | 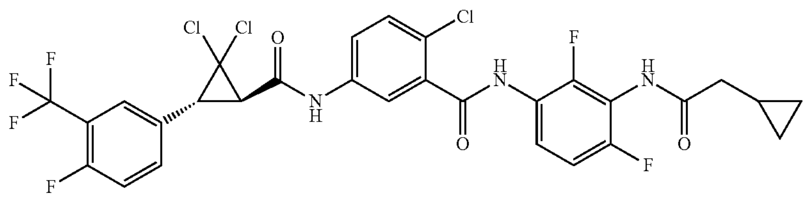 [SMILES: O=C(CC1CC1)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1683 | 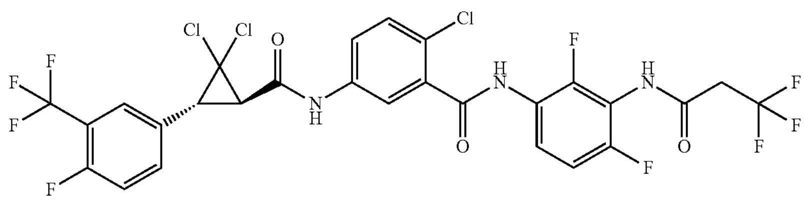 [SMILES: O=C(CC(F)(F)F)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |

TABLE 2-continued

Structure and preparation method for F Series molecules

| No. | Structure | Prep.* |
|---|---|---|
| F1684 | 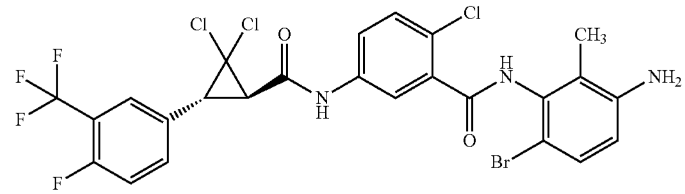 [SMILES: Cc1c(N)ccc(Br)c1NC(=O)c1cc(NC(=O)[C@H]2[C@H](c3ccc(F)c(C(F)(F)F)c3)C2(Cl)Cl)ccc1Cl] | 13 |
| F1685 | 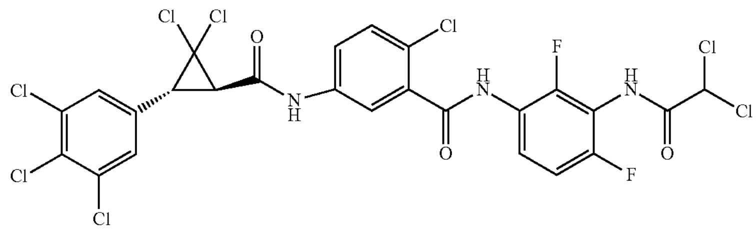 [SMILES: O=C(Nc1ccc(F)c(NC(=O)C(Cl)Cl)c1F)c1cc(NC(=O)[C@H]2[C@H](c3cc(Cl)c(Cl)c(Cl)c3)C2(Cl)Cl)ccc1Cl] | 4 |
| F1686 | 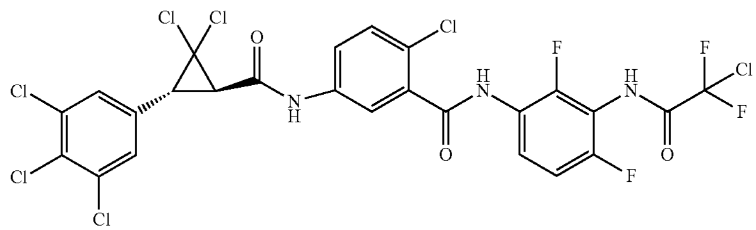 [SMILES: O=C(Nc1ccc(F)c(NC(=O)C(F)(F)Cl)c1F)c1cc(NC(=O)[C@H]2[C@H](c3cc(Cl)c(Cl)c(Cl)c3)C2(Cl)Cl)ccc1Cl] | 4 |
| F1687 | 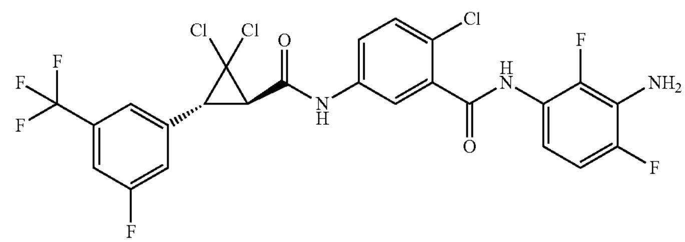 [SMILES: Nc1c(F)ccc(NC(=O)c2cc(NC(=O)[C@H]3[C@H](c4cc(F)cc(C(F)(F)F)c4)C3(Cl)Cl)ccc2Cl)c1F] | 13 |
| F1688 | 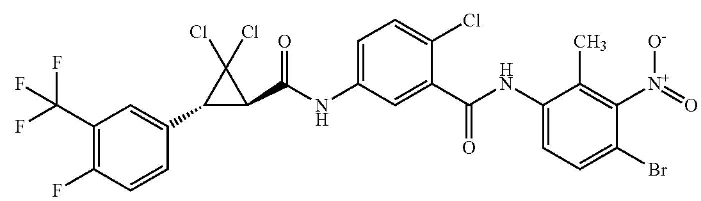 [SMILES: Cc1c(NC(=O)c2cc(NC(=O)[C@H]3[C@H](c4ccc(F)c(C(F)(F)F)c4)C3(Cl)Cl)ccc2Cl)ccc(Br)c1[N+](=O)[O-]] | 5 |
| F1689 | 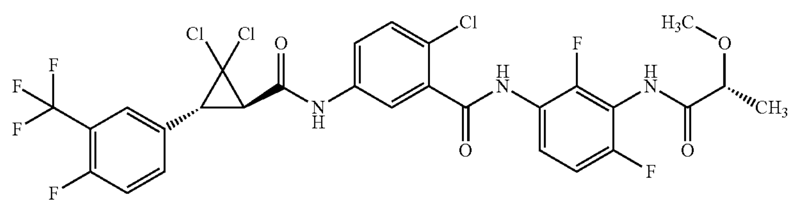 [SMILES: CO[C@H](C)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1690 | 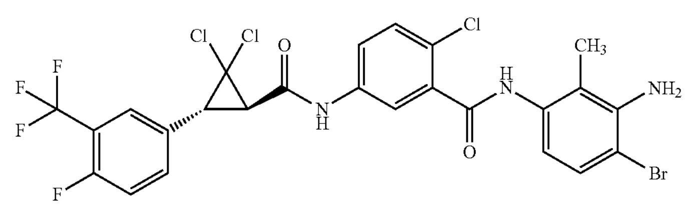 [SMILES: Cc1c(NC(=O)c2cc(NC(=O)[C@H]3[C@H](c4ccc(F)c(C(F)(F)F)c4)C3(Cl)Cl)ccc2Cl)ccc(Br)c1N] | 15 |

TABLE 2-continued
Structure and preparation method for F Series molecules
| No. | Structure | Prep.* |
|---|---|---|
| F1691 | 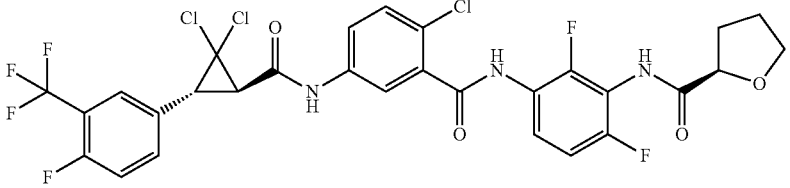 [SMILES: O=C(Nc1ccc(F)c(NC(=O)[C@H]2CCCO2)c1F)c1cc(NC(=O)[C@H]2[C@H](c3ccc(F)c(C(F)(F)F)c3)C2(Cl)Cl)ccc1Cl] | 6 |
| F1692 | 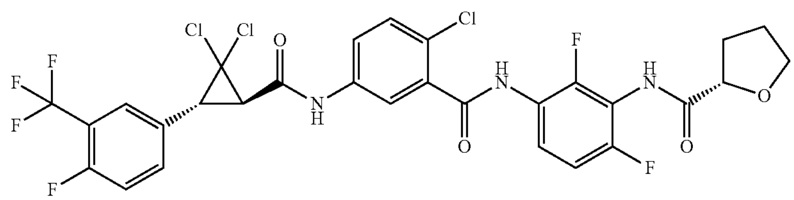 [SMILES: O=C(Nc1ccc(F)c(NC(=O)[C@@H]2CCCO2)c1F)c1cc(NC(=O)[C@H]2[C@H](c3ccc(F)c(C(F)(F)F)c3)C2(Cl)Cl)ccc1Cl] | 6 |
| F1693 | 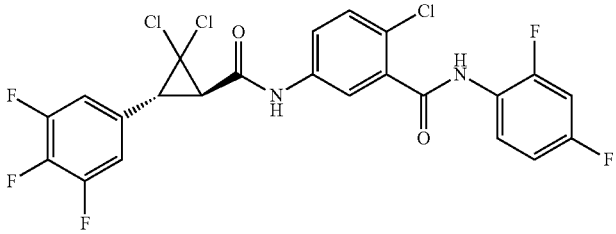 [SMILES: O=C(Nc1ccc(F)cc1F)c1cc(NC(=O)[C@H]2[C@H](c3cc(F)c(F)c(F)c3)C2(Cl)Cl)ccc1Cl] | 20 |
| F1694 | 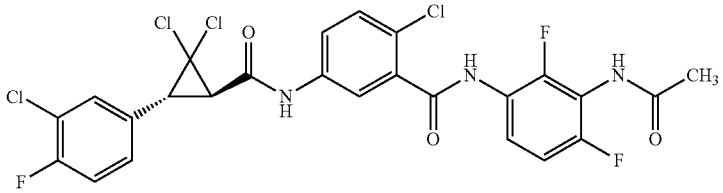 | 2 |
| F1695 | 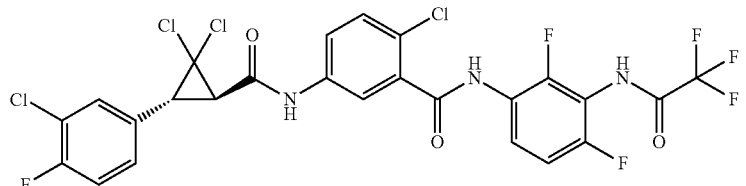 | 1 |
| F1696 | 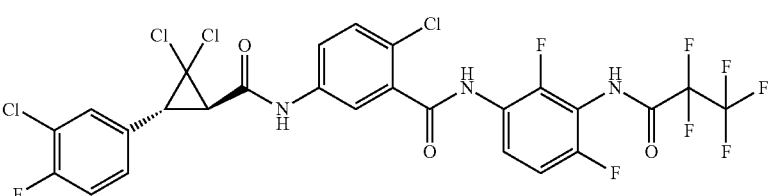 | 1 |
| F1697 | 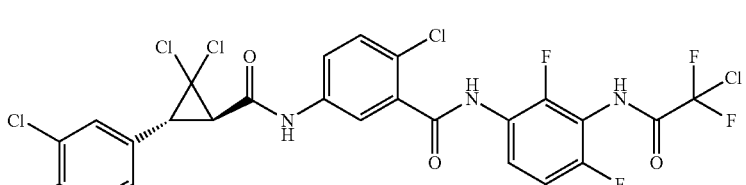 | 4 |

TABLE 2-continued

Structure and preparation method for F Series molecules

| No. | Structure | Prep.* |
|---|---|---|
| F1698 | 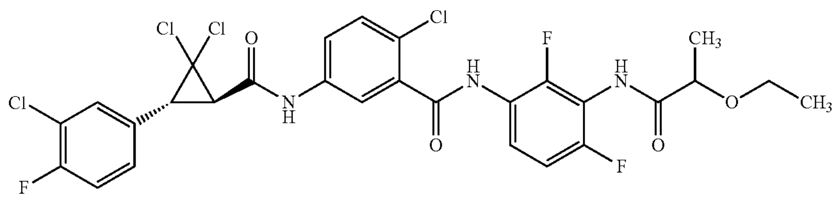 [SMILES: CCOC(C)C(=O)Nc1c(F)ccc(NC(=O)c2cc(NC(=O)[C@H]3[C@H](c4ccc(F)c(Cl)c4)C3(Cl)Cl)ccc2Cl)c1F] | 4 |
| F1699 | 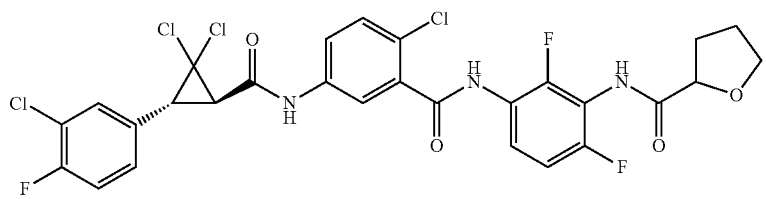 | 4 |
| F1700 | 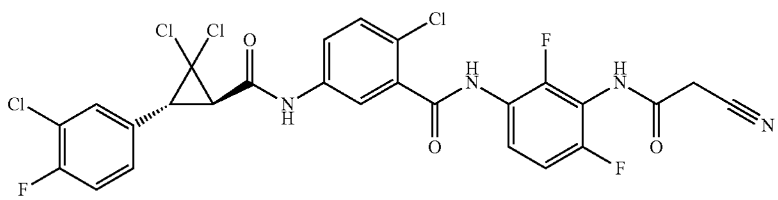 [SMILES: N#CCC(=O)Nc1c(F)ccc(NC(=O)c2cc(NC(=O)[C@H]3[C@H](c4ccc(F)c(Cl)c4)C3(Cl)Cl)ccc2Cl)c1F] | 4 |
| F1701 | 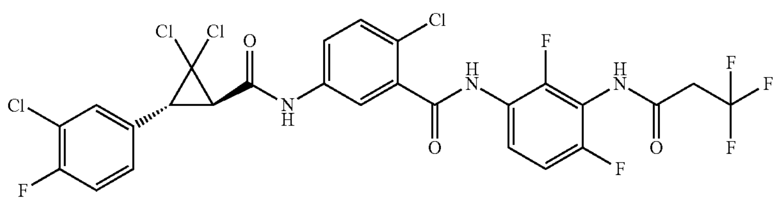 [SMILES: O=C(CC(F)(F)F)Nc1c(F)ccc(NC(=O)c2cc(NC(=O)[C@H]3[C@H](c4ccc(F)c(Cl)c4)C3(Cl)Cl)ccc2Cl)c1F] | 4 |
| F1702 | 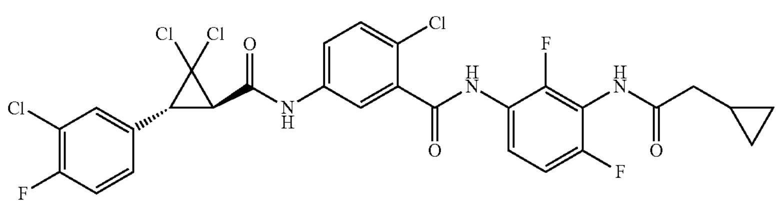 [SMILES: O=C(CC1CC1)Nc1c(F)ccc(NC(=O)c2cc(NC(=O)[C@H]3[C@H](c4ccc(F)c(Cl)c4)C3(Cl)Cl)ccc2Cl)c1F] | 4 |
| F1703 | 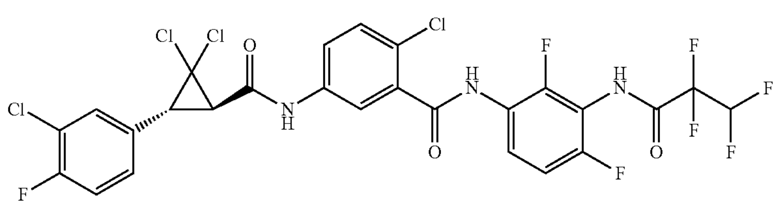 [SMILES: O=C(Nc1ccc(F)c(NC(=O)C(F)(F)C(F)F)c1F)c1cc(NC(=O)[C@H]2[C@H](c3ccc(F)c(Cl)c3)C2(Cl)Cl)ccc1Cl] | 4 |
| F1704 | 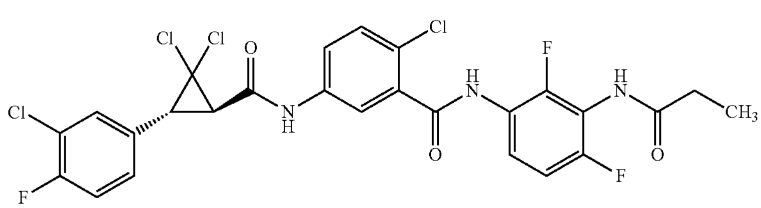 [SMILES: CCC(=O)Nc1c(F)ccc(NC(=O)c2cc(NC(=O)[C@H]3[C@H](c4ccc(F)c(Cl)c4)C3(Cl)Cl)ccc2Cl)c1F] | 4 |

TABLE 2-continued
Structure and preparation method for F Series molecules
| No. | Structure | Prep.* |
|---|---|---|
| F1705 | 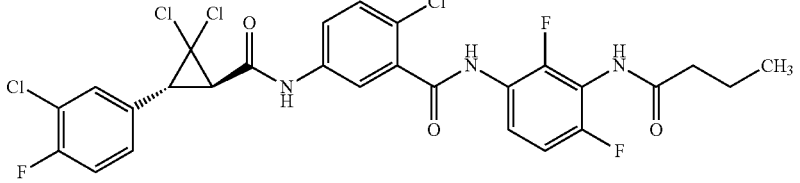 | 4 |
| F1706 | 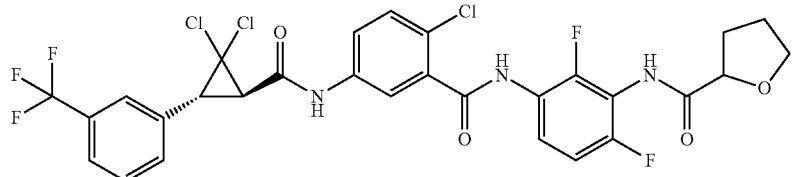 | 6 |
| F1707 | 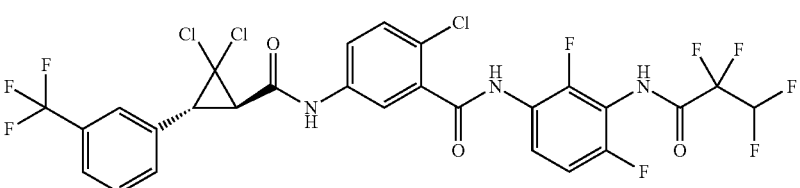 | 6 |
| F1708 | 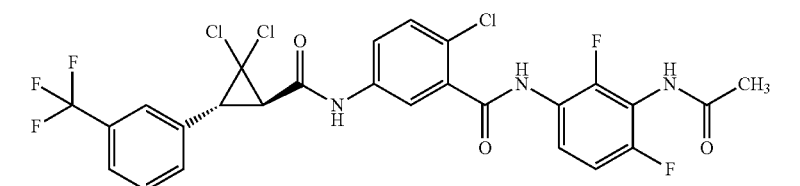 | 6 |
| F1709 | 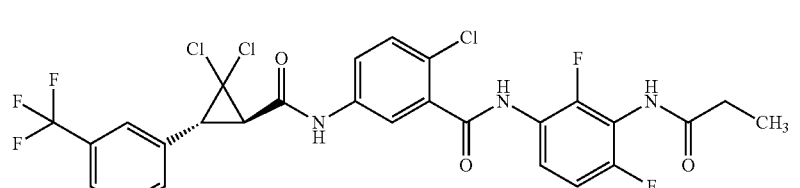 | 6 |
| F1710 | 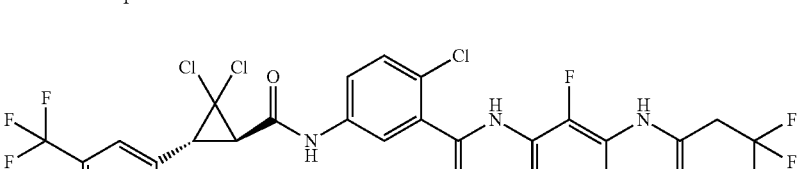 | 6 |

TABLE 2-continued
Structure and preparation method for F Series molecules
| No. | Structure | Prep.* |
|---|---|---|
| F1711 | 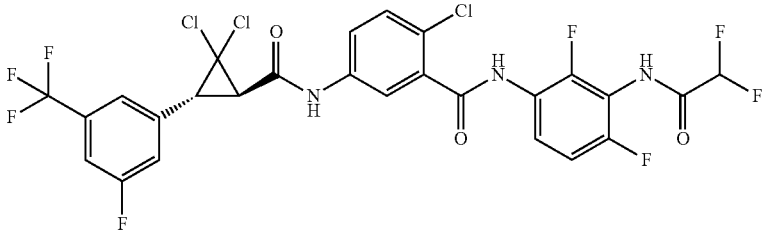 [SMILES: O=C(Nc1ccc(F)c(NC(=O)C(F)F)c1F)c1cc(NC(=O)[C@H]2[C@H](c3cc(F)cc(C(F)(F)F)c3)C2(Cl)Cl)ccc1Cl] | 1 |
| F1712 | 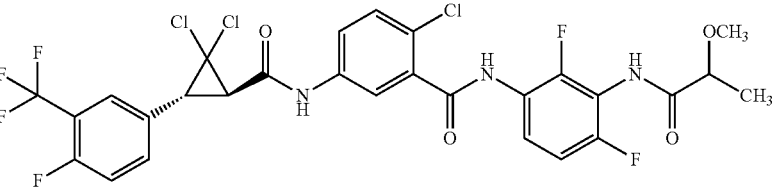 | 6 |
| F1713 | 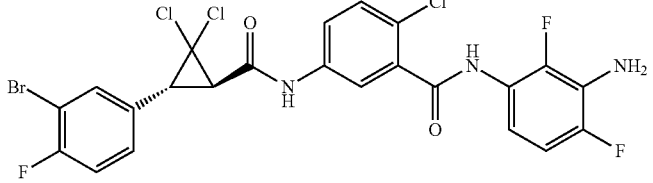 | 13 |
| F1714 | 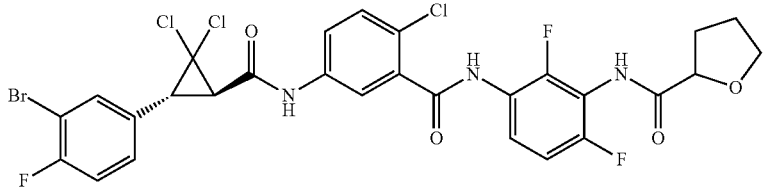 | 6 |
| F1715 | 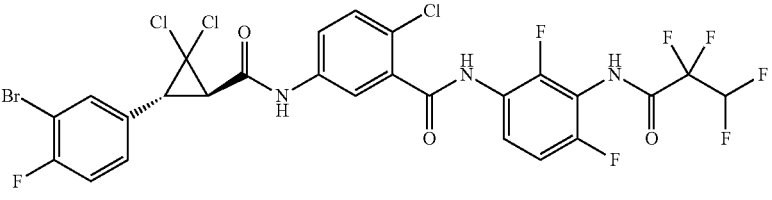 | 6 |
| F1716 | 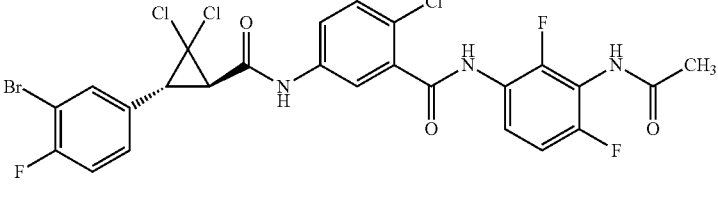 | 6 |
| F1717 | 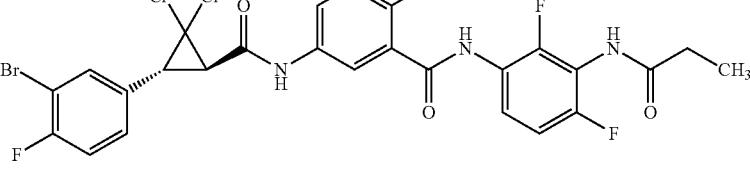 | 6 |

TABLE 2-continued

Structure and preparation method for F Series molecules

| No. | Structure | Prep.* |
|---|---|---|
| F1718 | 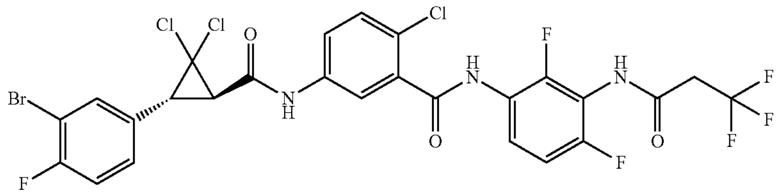 [SMILES: O=C(CC(F)(F)F)Nc1c(F)ccc(NC(=O)c2cc(NC(=O)[C@H]3[C@H](c4ccc(F)c(Br)c4)C3(Cl)Cl)ccc2Cl)c1F] | 6 |
| F1719 | 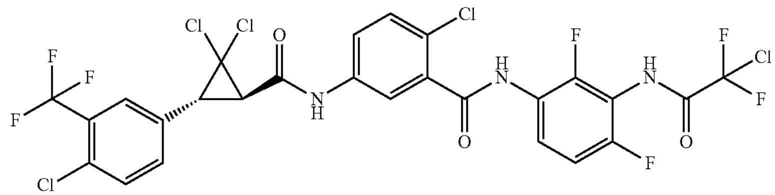 [SMILES: O=C(Nc1ccc(F)c(NC(=O)C(F)(F)Cl)c1F)c1cc(NC(=O)[C@H]2[C@H](c3ccc(Cl)c(C(F)(F)F)c3)C2(Cl)Cl)ccc1Cl] | 4 |
| F1720 | 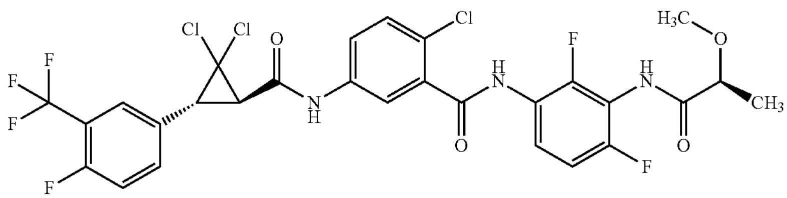 [SMILES: CO[C@@H](C)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1721 | 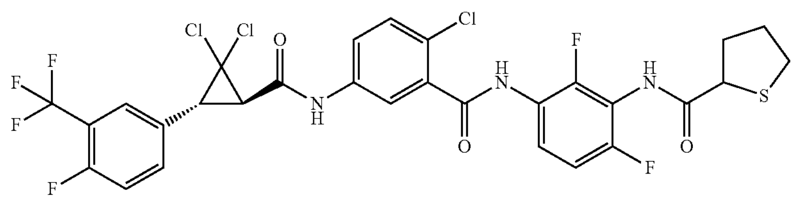 [SMILES: O=C(Nc1ccc(F)c(NC(=O)C2CCCS2)c1F)c1cc(NC(=O)[C@H]2[C@H](c3ccc(F)c(C(F)(F)F)c3)C2(Cl)Cl)ccc1Cl] | 6 |
| F1722 | 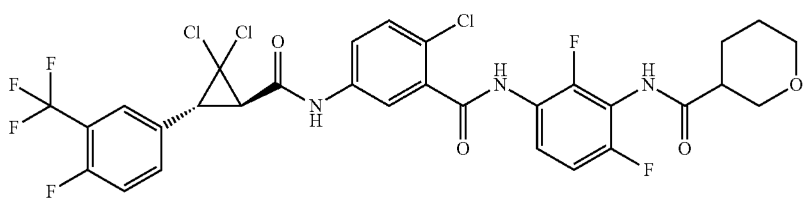 [SMILES: O=C(Nc1ccc(F)c(NC(=O)C2CCCOC2)c1F)c1cc(NC(=O)[C@H]2[C@H](c3ccc(F)c(C(F)(F)F)c3)C2(Cl)Cl)ccc1Cl] | 6 |
| F1723 | 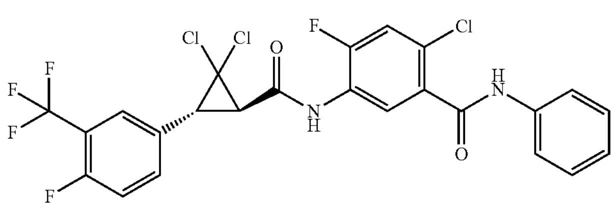 [SMILES: O=C(Nc1ccccc1)c1cc(NC(=O)[C@H]2[C@H](c3ccc(F)c(C(F)(F)F)c3)C2(Cl)Cl)c(F)cc1Cl] | 25 |
| F1724 | 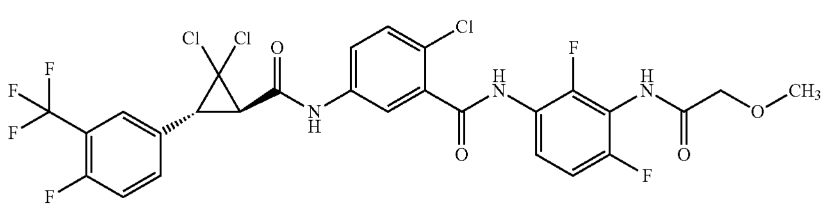 [SMILES: COCC(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |

TABLE 2-continued
Structure and preparation method for F Series molecules
| No. | Structure | Prep.* |
|---|---|---|
| F1725 | 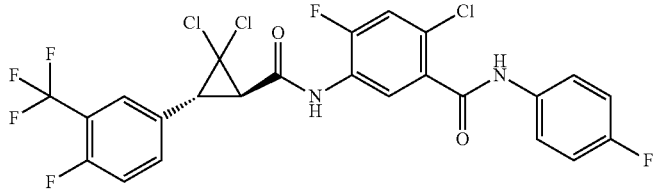 [SMILES: O=C(Nc1ccc(F)cc1)c1cc(NC(=O)[C@H]2[C@H](c3ccc(F)c(C(F)(F)F)c3)C2(Cl)Cl)c(F)cc1Cl] | 25 |
| F1726 | 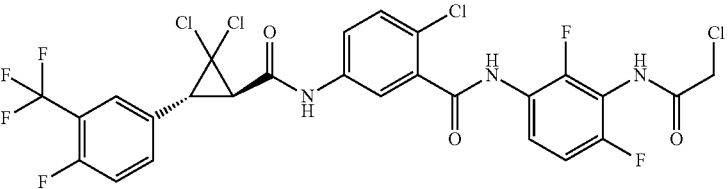 [SMILES: O=C(CCl)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1727 | 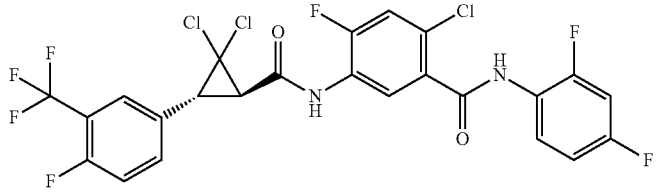 [SMILES: O=C(Nc1ccc(F)cc1F)c1cc(NC(=O)[C@H]2[C@H](c3ccc(F)c(C(F)(F)F)c3)C2(Cl)Cl)c(F)cc1Cl] | 25 |
| F1728 | 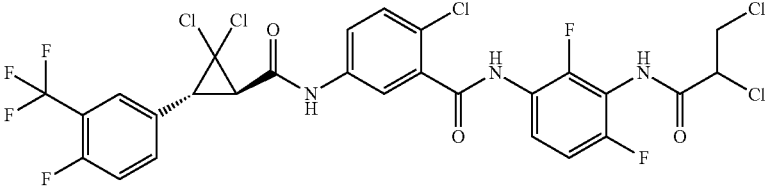 [SMILES: O=C(Nc1ccc(F)c(NC(=O)C(Cl)CCl)c1F)c1cc(NC(=O)[C@H]2[C@H](c3ccc(F)c(C(F)(F)F)c3)C2(Cl)Cl)ccc1Cl] | 6 |
| F1729 | 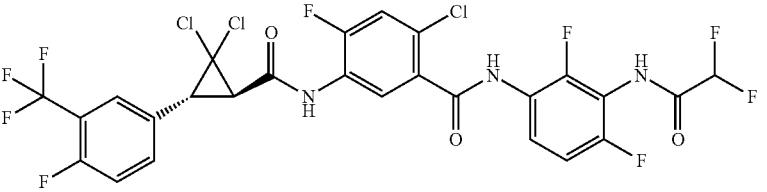 [SMILES: O=C(Nc1ccc(F)c(NC(=O)C(F)F)c1F)c1cc(NC(=O)[C@H]2[C@H](c3ccc(F)c(C(F)(F)F)c3)C2(Cl)Cl)c(F)cc1Cl] | 25 |
| F1731 | 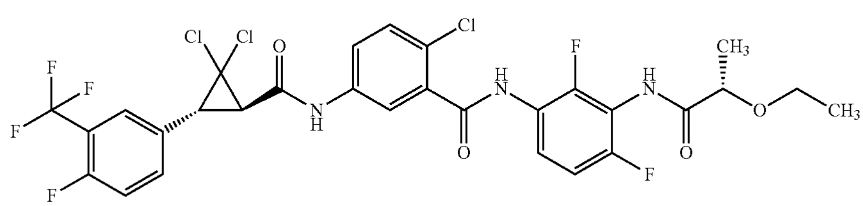 [SMILES: CCO[C@@H](C)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 4 |
| F1732 | 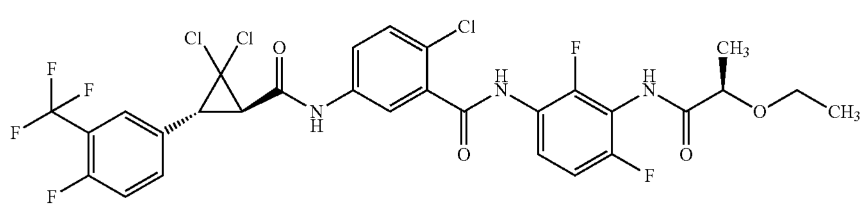 [SMILES: CCO[C@H](C)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 25 |

TABLE 2-continued

Structure and preparation method for F Series molecules

| No. | Structure | Prep.* |
|---|---|---|
| F1733 | 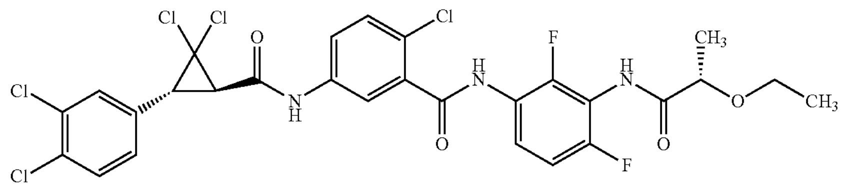 [SMILES: CCO[C@@H](C)C(=O)Nc1c(F)ccc(NC(=O)c2cc(NC(=O)[C@H]3[C@H](c4ccc(Cl)c(Cl)c4)C3(Cl)Cl)ccc2Cl)c1F] | 25 |
| F1734 | 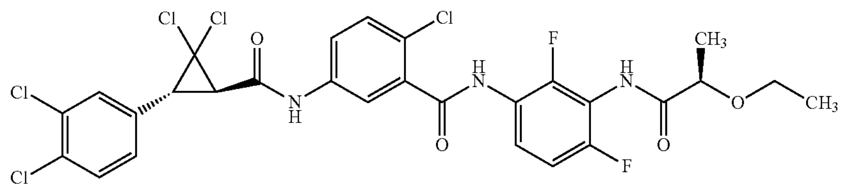 [SMILES: CCO[C@H](C)C(=O)Nc1c(F)ccc(NC(=O)c2cc(NC(=O)[C@H]3[C@H](c4ccc(Cl)c(Cl)c4)C3(Cl)Cl)ccc2Cl)c1F] | 25 |
| F1735 | 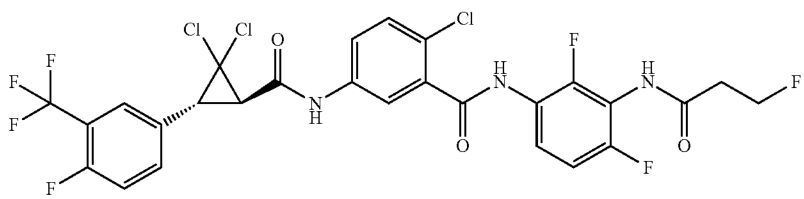 [SMILES: O=C(CCF)Nc1c(F)ccc(NC(=O)c2cc(NC(=O)[C@H]3[C@H](c4ccc(F)c(C(F)(F)F)c4)C3(Cl)Cl)ccc2Cl)c1F] | 25 |
| F1736 | 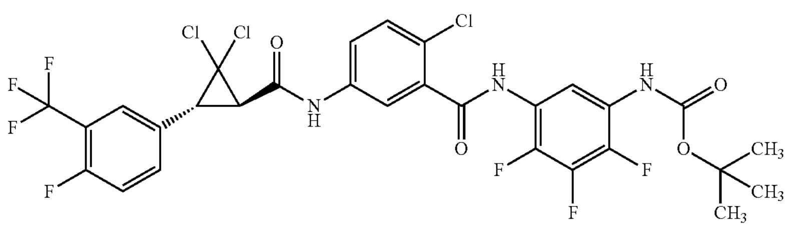 [SMILES: CC(C)(C)OC(=O)Nc1cc(NC(=O)c2cc(NC(=O)[C@H]3[C@H](c4ccc(F)c(C(F)(F)F)c4)C3(Cl)Cl)ccc2Cl)c(F)c(F)c1F] | 25 |
| F1737 | 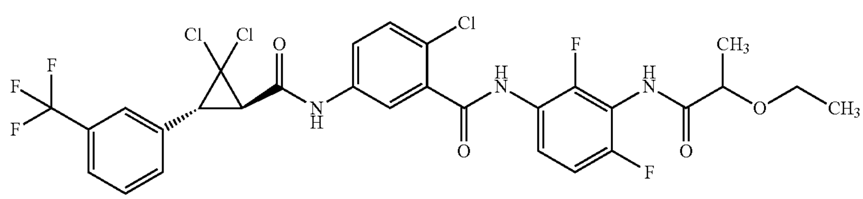 [SMILES: CCOC(C)C(=O)Nc1c(F)ccc(NC(=O)c2cc(NC(=O)[C@H]3[C@H](c4cccc(C(F)(F)F)c4)C3(Cl)Cl)ccc2Cl)c1F] | 25 |
| F1738 | 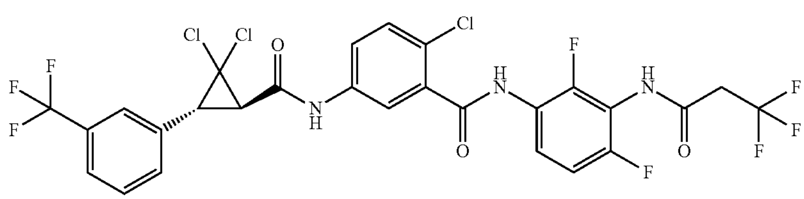 [SMILES: O=C(CC(F)(F)F)Nc1c(F)ccc(NC(=O)c2cc(NC(=O)[C@H]3[C@H](c4cccc(C(F)(F)F)c4)C3(Cl)Cl)ccc2Cl)c1F] | 25 |
| F1739 | 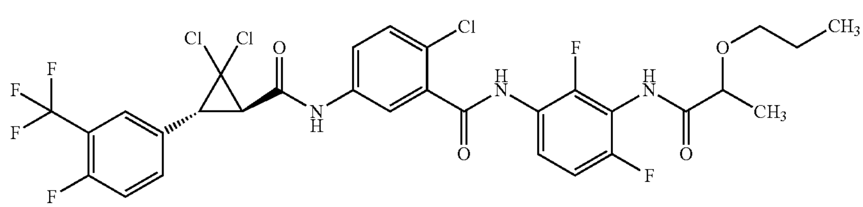 [SMILES: CCCOC(C)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 25 |

TABLE 2-continued
Structure and preparation method for F Series molecules
| No. | Structure | Prep.* |
|---|---|---|
| F1740 | 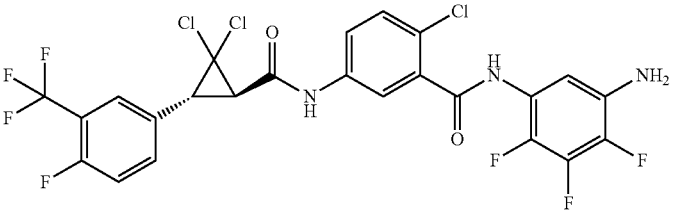 [SMILES: Nc1cc(NC(=O)c2cc(NC(=O)[C@H]3[C@H](c4ccc(F)c(C(F)(F)F)c4)C3(Cl)Cl)ccc2Cl)c(F)c(F)c1F] | 13 |
| F1741 | 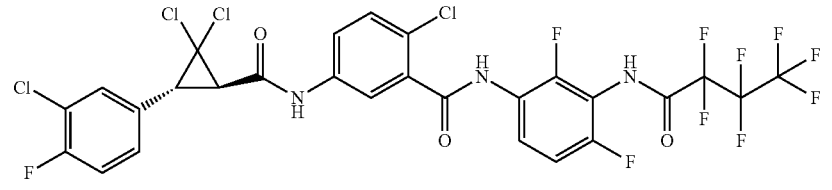 [SMILES: O=C(Nc1ccc(F)c(NC(=O)C(F)(F)C(F)(F)C(F)(F)F)c1F)c1cc(NC(=O)[C@H]2[C@H](c3ccc(F)c(Cl)c3)C2(Cl)Cl)ccc1Cl] | 4 |
| F1742 | 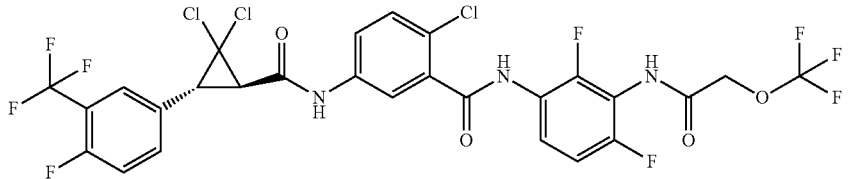 [SMILES: O=C(COC(F)(F)F)Nc1c(F)ccc(NC(=O)c2cc(NC(=O)[C@H]3[C@H](c4ccc(F)c(C(F)(F)F)c4)C3(Cl)Cl)ccc2Cl)c1F] | 4 |
| F1743 | 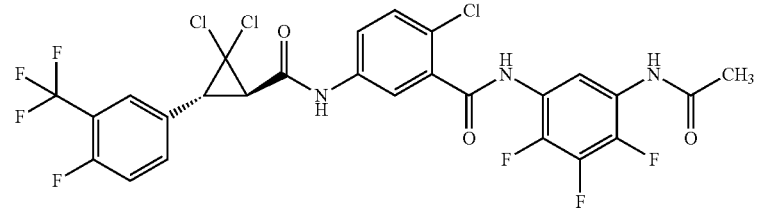 [SMILES: CC(=O)Nc1cc(NC(=O)c2cc(NC(=O)[C@H]3[C@H](c4ccc(F)c(C(F)(F)F)c4)C3(Cl)Cl)ccc2Cl)c(F)c(F)c1F] | 6 |
| F1744 | 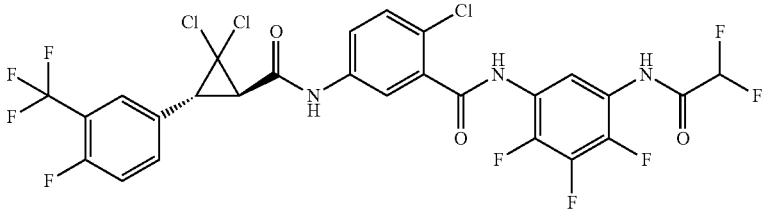 [SMILES: O=C(Nc1cc(NC(=O)C(F)F)c(F)c(F)c1F)c1cc(NC(=O)[C@H]2[C@H](c3ccc(F)c(C(F)(F)F)c3)C2(Cl)Cl)ccc1Cl] | 1 |
| F1745 | 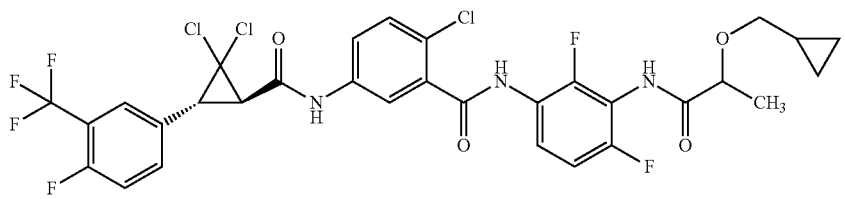 [SMILES: CC(OCC1CC1)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1746 | 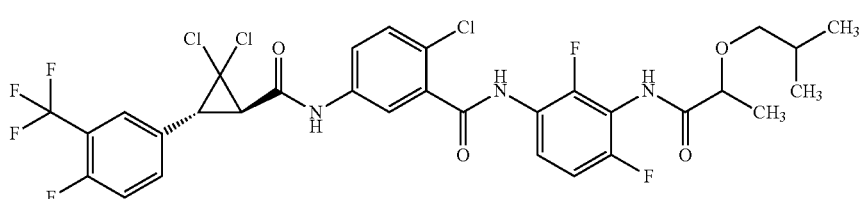 | 6 |

TABLE 2-continued

Structure and preparation method for F Series molecules

| No. | Structure | Prep.* |
|---|---|---|
| F1747 | 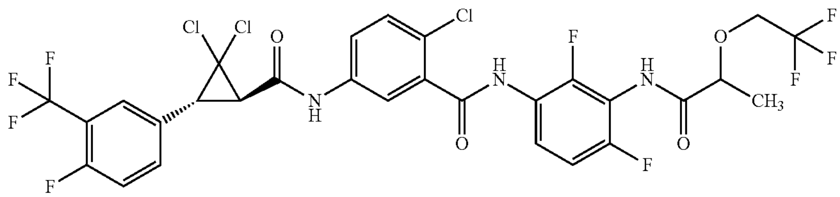 [SMILES: CC(OCC(F)(F)F)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1748 | 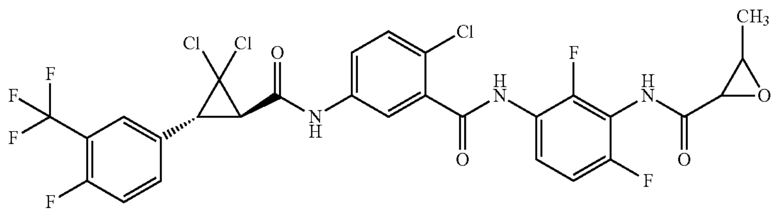 [SMILES: CC1OC1C(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1749 | 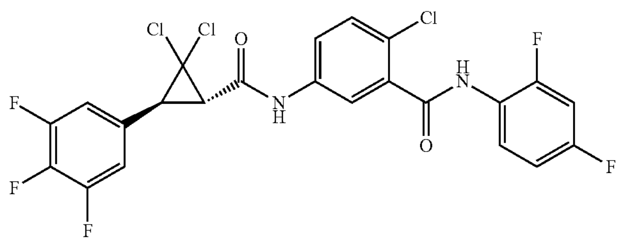 [SMILES: O=C(Nc1ccc(F)cc1F)c1cc(NC(=O)[C@@H]2[C@@H](c3cc(F)c(F)c(F)c3)C2(Cl)Cl)ccc1Cl] | 20 |
| F1750 | 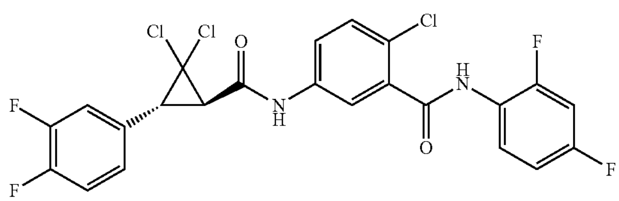 [SMILES: O=C(Nc1ccc(F)cc1F)c1cc(NC(=O)[C@H]2[C@H](c3ccc(F)c(F)c3)C2(Cl)Cl)ccc1Cl] | 20 |
| F1751 | 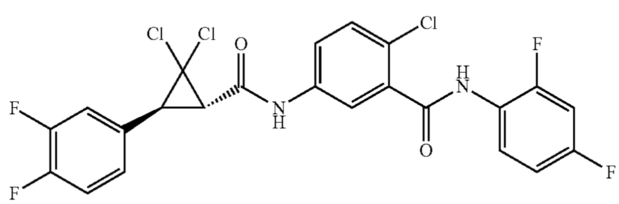 [SMILES: O=C(Nc1ccc(F)cc1F)c1cc(NC(=O)[C@@H]2[C@@H](c3ccc(F)c(F)c3)C2(Cl)Cl)ccc1Cl] | 20 |
| F1752 | 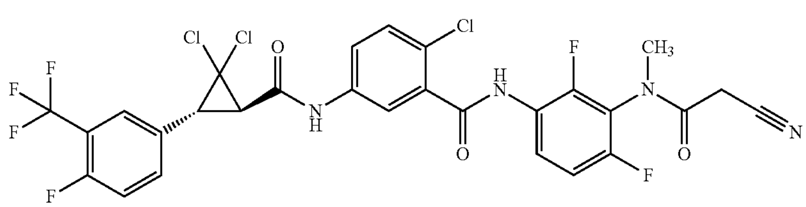 [SMILES: CN(C(=O)CC#N)c1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1753 | 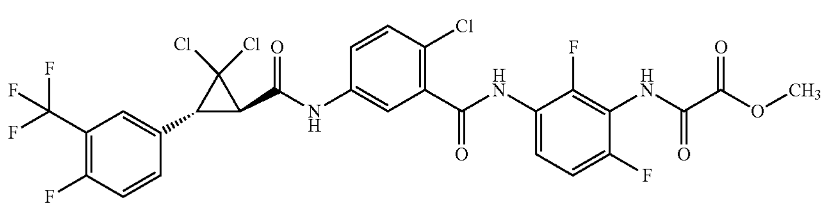 [SMILES: COC(=O)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 7 |

TABLE 2-continued

Structure and preparation method for F Series molecules

| No. | Structure | Prep.* |
|---|---|---|
| F1754 | 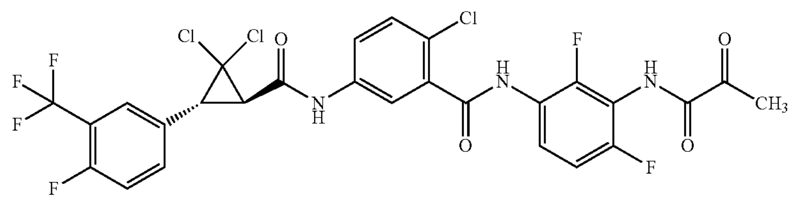 [SMILES: CC(=O)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 4 |
| F1755 | 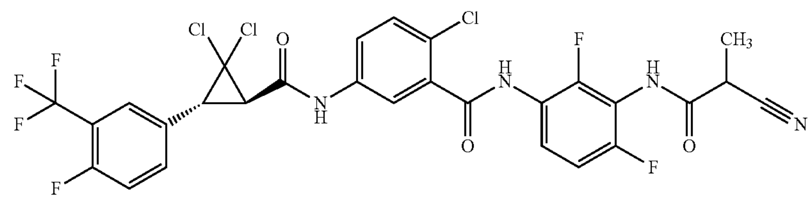 [SMILES: CC(C#N)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1756 | 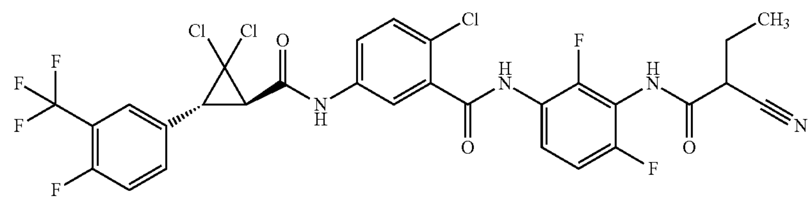 [SMILES: CCC(C#N)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1757 | 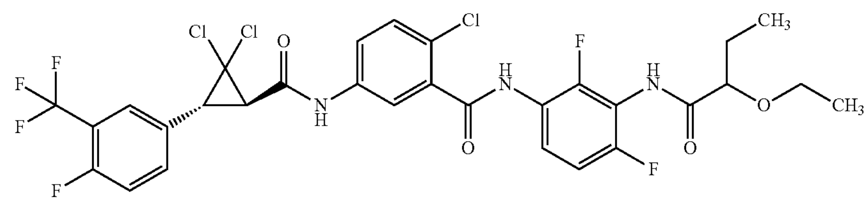 [SMILES: CCOC(CC)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1758 | 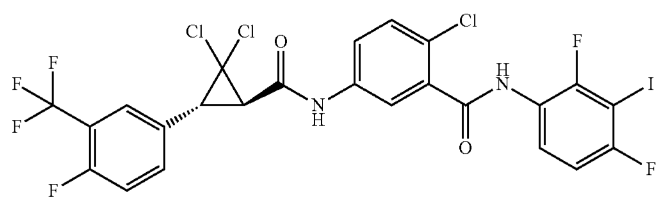 [SMILES: O=C(Nc1ccc(F)c(I)c1F)c1cc(NC(=O)[C@H]2[C@H](c3ccc(F)c(C(F)(F)F)c3)C2(Cl)Cl)ccc1Cl] | 5 |
| F1759 | 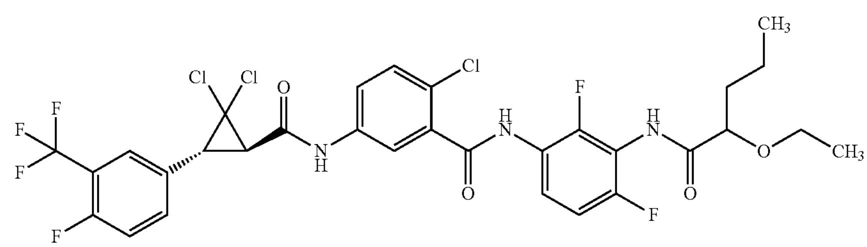 [SMILES: CCCC(OCC)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1760 | 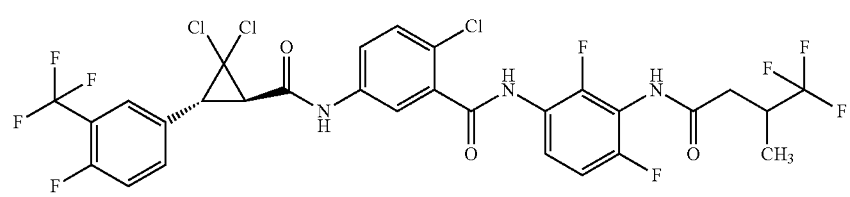 [SMILES: CC(CC(=O)Nc1c(F)ccc(NC(=O)c2cc(NC(=O)[C@H]3[C@H](c4ccc(F)c(C(F)(F)F)c4)C3(Cl)Cl)ccc2Cl)c1F)C(F)(F)F] | 4 |

TABLE 2-continued

Structure and preparation method for F Series molecules

| No. | Structure | Prep.* |
|---|---|---|
| F1761 | 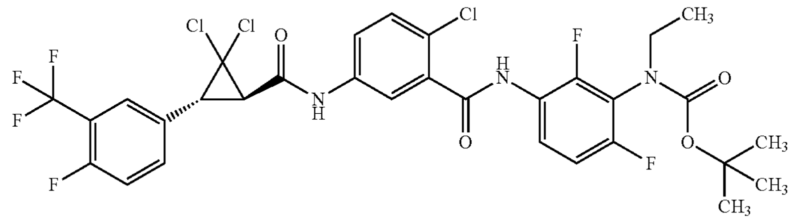 [SMILES: CCN(C(=O)OC(C)(C)C)c1c(F)ccc(NC(=O)c2cc(NC(=O)[C@H]3[C@H](c4ccc(F)c(C(F)(F)F)c4)C3(Cl)Cl)ccc2Cl)c1F] | 5 |
| F1762 | 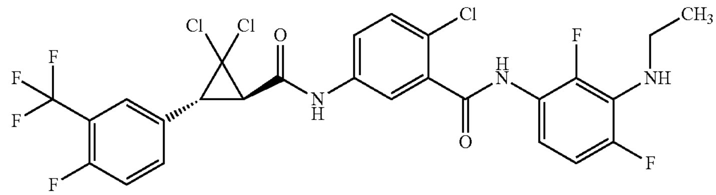 [SMILES: CCNc1c(F)ccc(NC(=O)c2cc(NC(=O)[C@H]3[C@H](c4ccc(F)c(C(F)(F)F)c4)C3(Cl)Cl)ccc2Cl)c1F] | 13 |
| F1763 | 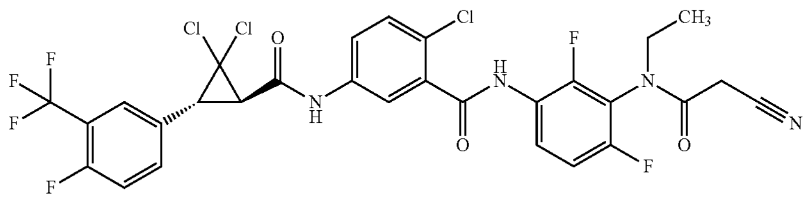 [SMILES: CCN(C(=O)CC#N)c1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1764 | 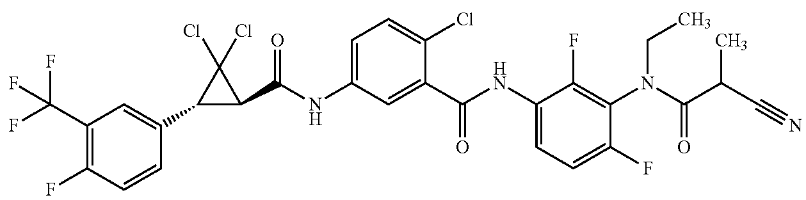 [SMILES: CCN(C(=O)C(C)C#N)c1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1765 | 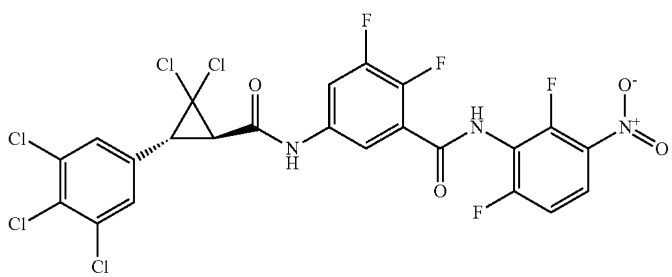 [SMILES: O=C(Nc1c(F)ccc([N+](=O)[O-])c1F)c1cc(NC(=O)[C@H]2[C@H](c3cc(Cl)c(Cl)c(Cl)c3)C2(Cl)Cl)cc(F)c1F] | 25 |
| F1766 | 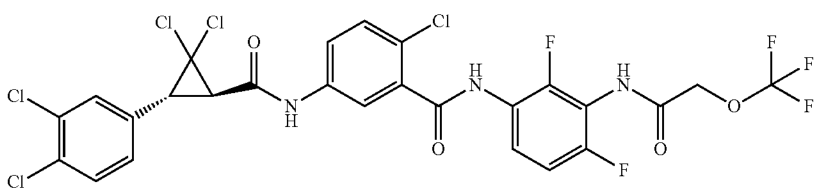 [SMILES: O=C(COC(F)(F)F)Nc1c(F)ccc(NC(=O)c2cc(NC(=O)[C@H]3[C@H](c4ccc(Cl)c(Cl)c4)C3(Cl)Cl)ccc2Cl)c1F] | 4 |
| F1767 | 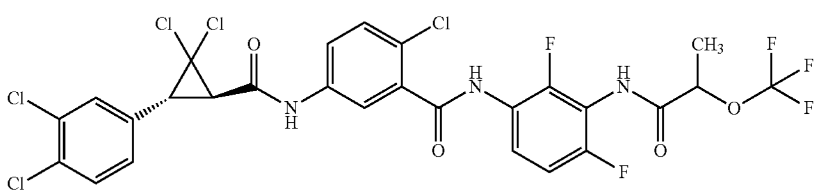 [SMILES: CC(OC(F)(F)F)C(=O)Nc1c(F)ccc(NC(=O)c2cc(NC(=O)[C@H]3[C@H](c4ccc(Cl)c(Cl)c4)C3(Cl)Cl)ccc2Cl)c1F] | 4 |

TABLE 2-continued
Structure and preparation method for F Series molecules
| No. | Structure | Prep.* |
|---|---|---|
| F1768 | 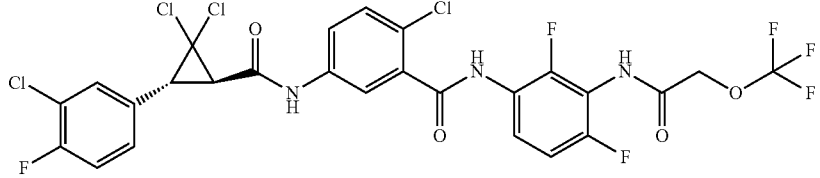 [SMILES: O=C(COC(F)(F)F)Nc1c(F)ccc(NC(=O)c2cc(NC(=O)[C@H]3[C@H](c4ccc(F)c(Cl)c4)C3(Cl)Cl)ccc2Cl)c1F] | 4 |
| F1769 | 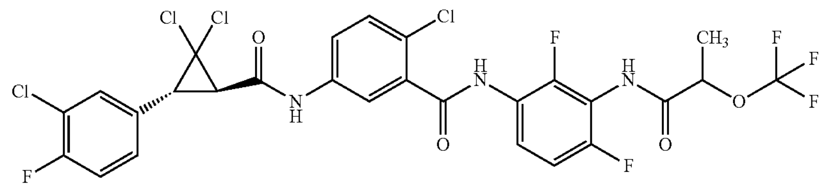 [SMILES: CC(OC(F)(F)F)C(=O)Nc1c(F)ccc(NC(=O)c2cc(NC(=O)[C@H]3[C@H](c4ccc(F)c(Cl)c4)C3(Cl)Cl)ccc2Cl)c1F] | 4 |
| F1770 | 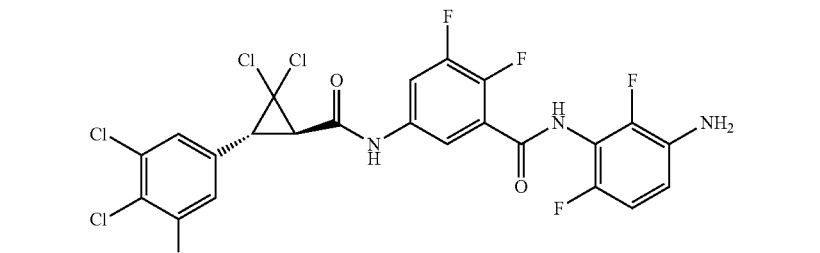 | 14 |
| F1771 | 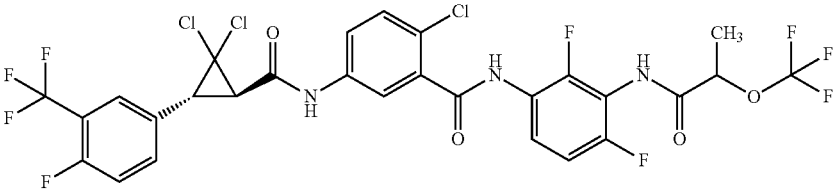 [SMILES: CC(OC(F)(F)F)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1772 | 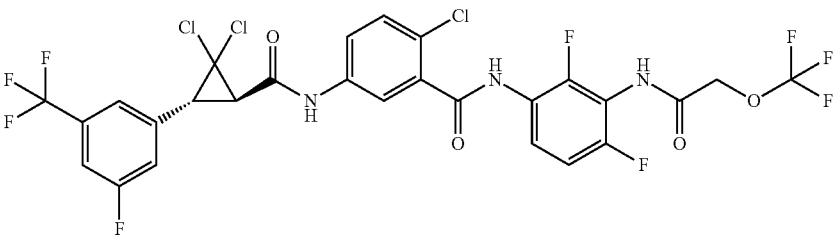 [SMILES: O=C(COC(F)(F)F)Nc1c(F)ccc(NC(=O)c2cc(NC(=O)[C@H]3[C@H](c4cc(F)cc(C(F)(F)F)c4)C3(Cl)Cl)ccc2Cl)c1F] | 6 |
| F1773 | 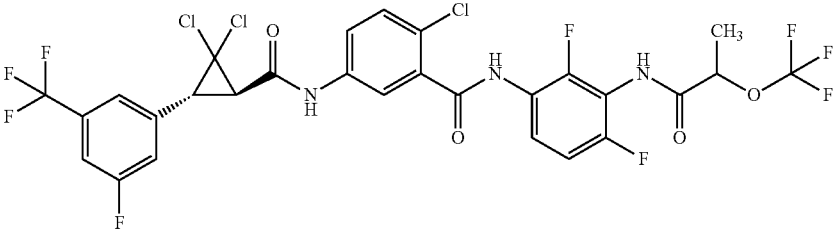 [SMILES: CC(OC(F)(F)F)C(=O)Nc1c(F)ccc(NC(=O)c2cc(NC(=O)[C@H]3[C@H](c4cc(F)cc(C(F)(F)F)c4)C3(Cl)Cl)ccc2Cl)c1F] | 6 |
| F1774 | 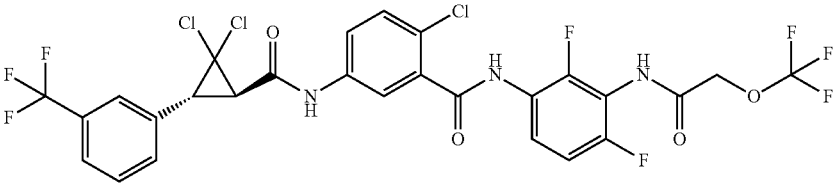 [SMILES: O=C(COC(F)(F)F)Nc1c(F)ccc(NC(=O)c2cc(NC(=O)[C@H]3[C@H](c4cccc(C(F)(F)F)c4)C3(Cl)Cl)ccc2Cl)c1F] | 6 |

TABLE 2-continued
Structure and preparation method for F Series molecules
| No. | Structure | Prep.* |
|---|---|---|
| F1775 | 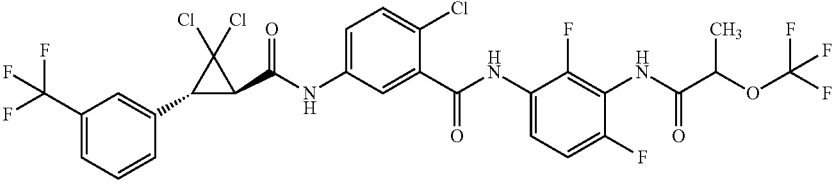 [SMILES: CC(OC(F)(F)F)C(=O)Nc1c(F)ccc(NC(=O)c2cc(NC(=O)[C@H]3[C@H](c4cccc(C(F)(F)F)c4)C3(Cl)Cl)ccc2Cl)c1F] | 6 |
| F1776 | 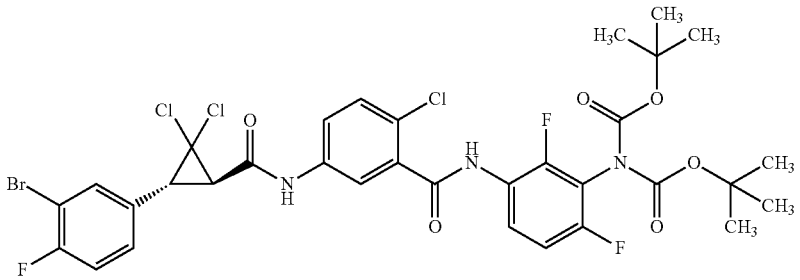 | 20 |
| F1777 | 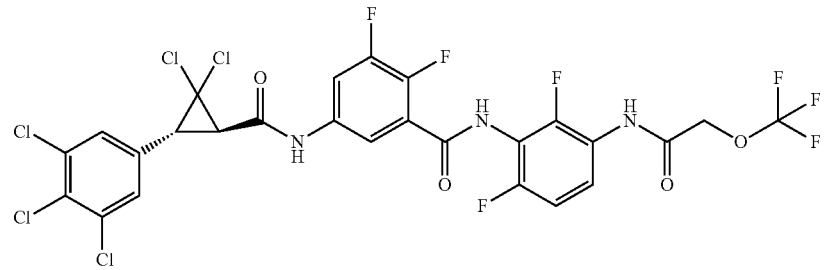 [SMILES: O=C(COC(F)(F)F)Nc1ccc(F)c(NC(=O)c2cc(NC(=O)[C@H]3[C@H](c4cc(Cl)c(Cl)c(Cl)c4)C3(Cl)Cl)cc(F)c2F)c1F] | 4 |
| F1778 | 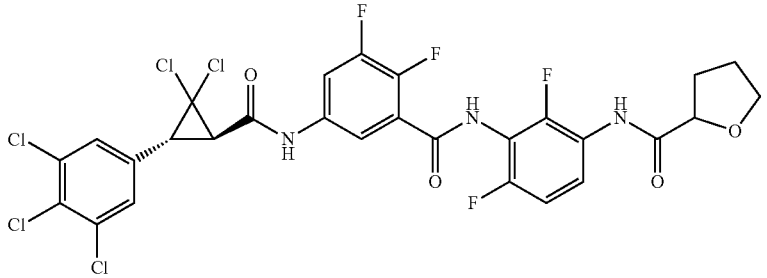 [SMILES: O=C(Nc1c(F)ccc(NC(=O)C2CCCO2)c1F)c1cc(NC(=O)[C@H]2[C@H](c3cc(Cl)c(Cl)c(Cl)c3)C2(Cl)Cl)cc(F)c1F] | 4 |
| F1779 | 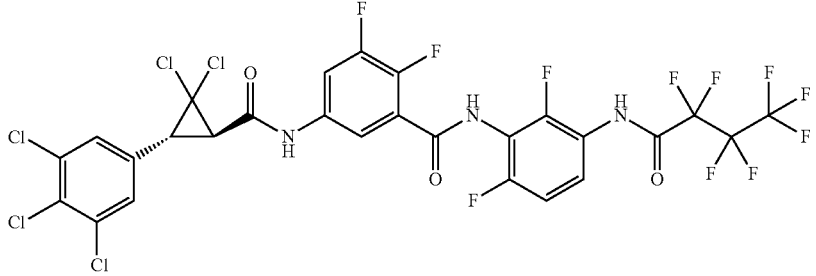 [SMILES: O=C(Nc1c(F)ccc(NC(=O)C(F)(F)C(F)(F)C(F)(F)F)c1F)c1cc(NC(=O)[C@H]2[C@H](c3cc(Cl)c(Cl)c(Cl)c3)C2(Cl)Cl)cc(F)c1F] | 4 |
| F1780 | 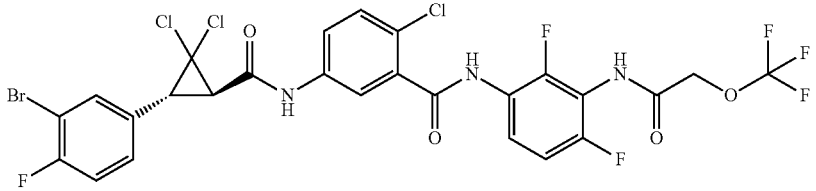 | 6 |

TABLE 2-continued

Structure and preparation method for F Series molecules

| No. | Structure | Prep.* |
|---|---|---|
| F1781 | 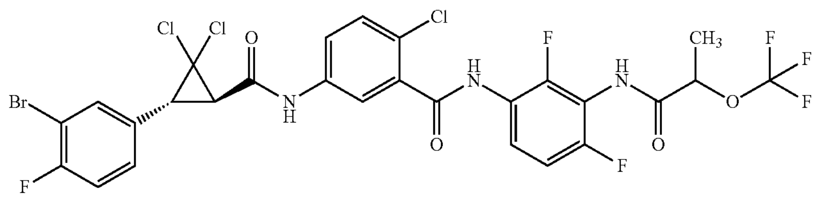 [SMILES: CC(OC(F)(F)F)C(=O)Nc1c(F)ccc(NC(=O)c2cc(NC(=O)[C@H]3[C@H](c4ccc(F)c(Br)c4)C3(Cl)Cl)ccc2Cl)c1F] | 6 |
| F1782 | 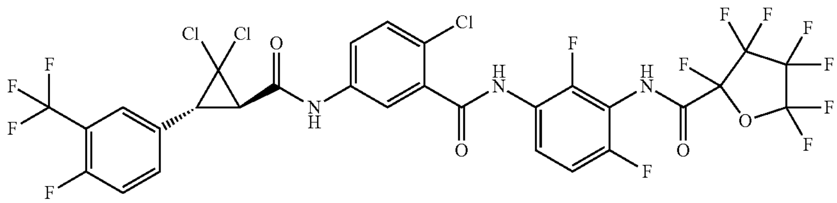 [SMILES: O=C(Nc1ccc(F)c(NC(=O)C2(F)OC(F)(F)C(F)(F)C2(F)F)c1F)c1cc(NC(=O)[C@H]2[C@H](c3ccc(F)c(C(F)(F)F)c3)C2(Cl)Cl)ccc1Cl] | 6 |
| F1783 | 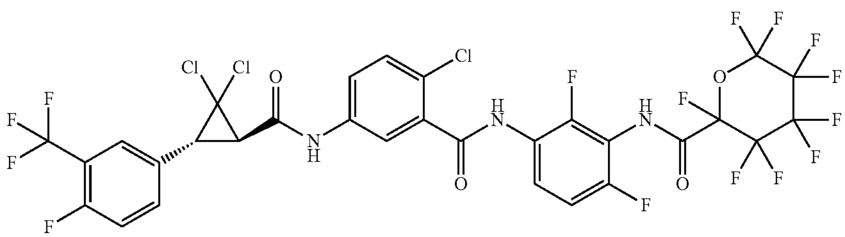 [SMILES: O=C(Nc1ccc(F)c(NC(=O)C2(F)OC(F)(F)C(F)(F)C(F)(F)C2(F)F)c1F)c1cc(NC(=O)[C@H]2[C@H](c3ccc(F)c(C(F)(F)F)c3)C2(Cl)Cl)ccc1Cl] | 6 |
| F1784 | 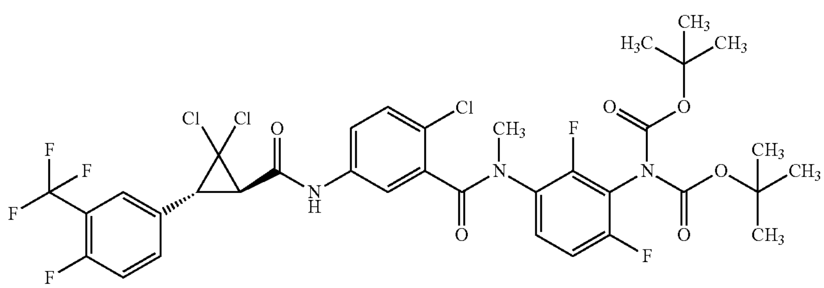 [SMILES: CN(C(=O)c1cc(NC(=O)[C@H]2[C@H](c3ccc(F)c(C(F)(F)F)c3)C2(Cl)Cl)ccc1Cl)c1ccc(F)c(N(C(=O)OC(C)(C)C)C(=O)OC(C)(C)C)c1F] | 20 |
| F1785 | 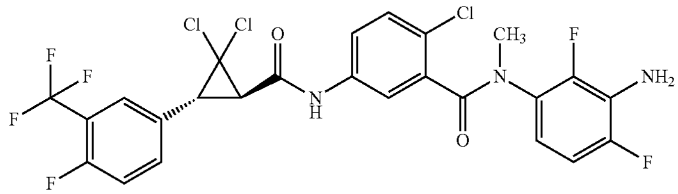 [SMILES: CN(C(=O)c1cc(NC(=O)[C@H]2[C@H](c3ccc(F)c(C(F)(F)F)c3)C2(Cl)Cl)ccc1Cl)c1ccc(F)c(N)c1F] | 13 |
| F1786 | 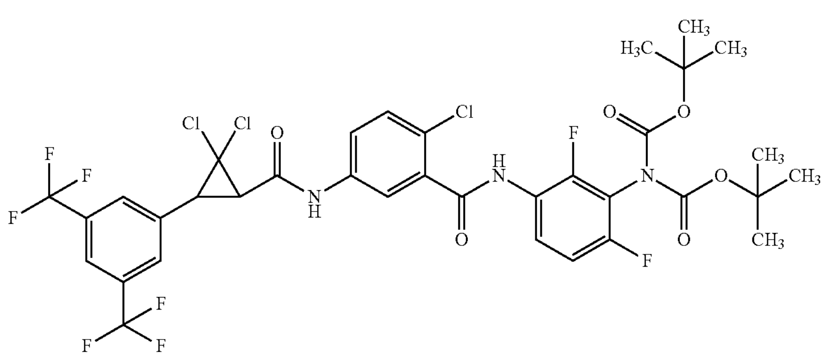 [SMILES: CC(C)(C)OC(=O)N(C(=O)OC(C)(C)C)c1c(F)ccc(NC(=O)c2cc(NC(=O)C3C(c4cc(C(F)(F)F)cc(C(F)(F)F)c4)C3(Cl)Cl)ccc2Cl)c1F] | 20 |

TABLE 2-continued
Structure and preparation method for F Series molecules
| No. | Structure | Prep.* |
|---|---|---|
| F1787 | 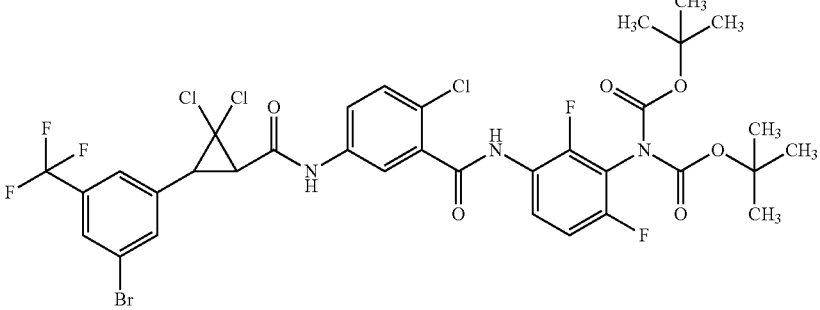 | 20 |
| F1788 | 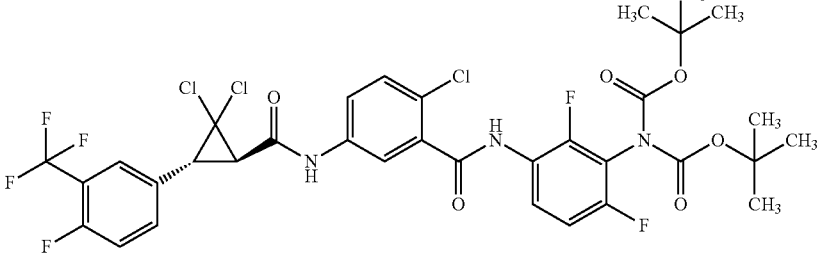 | 20 |
| F1789 | 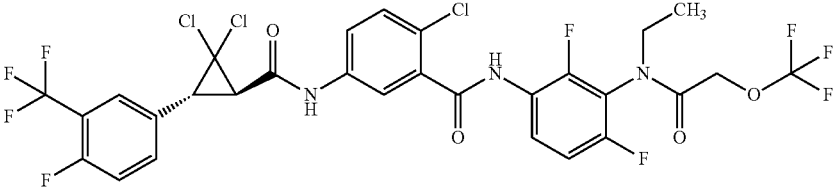 [SMILES: CCN(C(=O)COC(F)(F)F)c1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1790 | 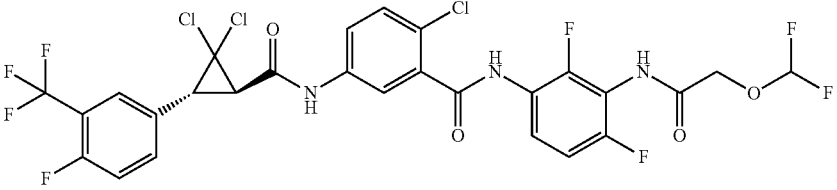 [SMILES: O=C(COC(F)F)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1791 | 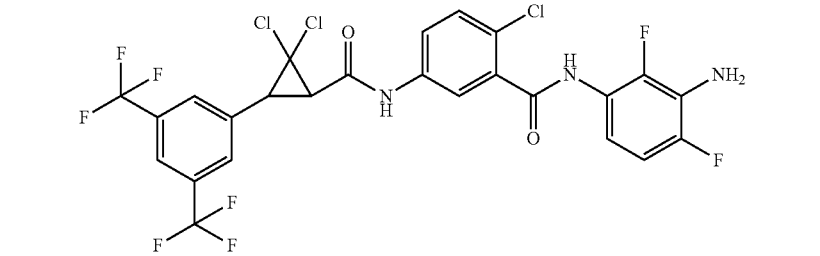 [SMILES: Nc1c(F)ccc(NC(=O)c2cc(NC(=O)C3C(c4cc(C(F)(F)F)cc(C(F)(F)F)c4)C3(Cl)Cl)ccc2Cl)c1F] | 13 |
| F1792 | 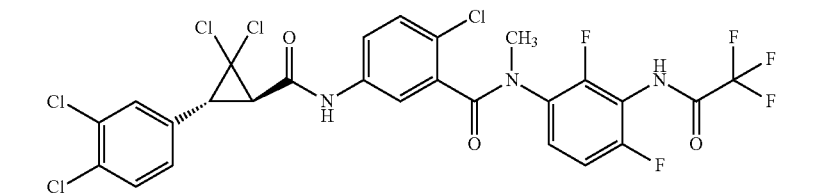 [SMILES: CN(C(=O)c1cc(NC(=O)[C@H]2[C@H](c3ccc(Cl)c(Cl)c3)C2(Cl)Cl)ccc1Cl)c1ccc(F)c(NC(=O)C(F)(F)F)c1F] | 1 |

TABLE 2-continued

Structure and preparation method for F Series molecules

| No. | Structure | Prep.* |
|---|---|---|
| F1793 | 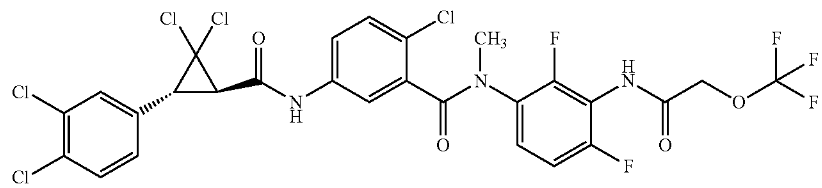 [SMILES: CN(C(=O)c1cc(NC(=O)[C@H]2[C@H](c3ccc(Cl)c(Cl)c3)C2(Cl)Cl)ccc1Cl)c1ccc(F)c(NC(=O)COC(F)(F)F)c1F] | 4 |
| F1794 | 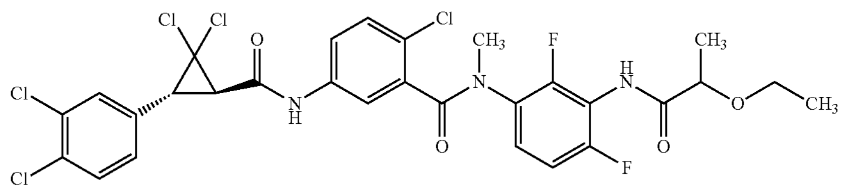 [SMILES: CCOC(C)C(=O)Nc1c(F)ccc(N(C)C(=O)c2cc(NC(=O)[C@H]3[C@H](c4ccc(Cl)c(Cl)c4)C3(Cl)Cl)ccc2Cl)c1F] | 4 |
| F1795 | 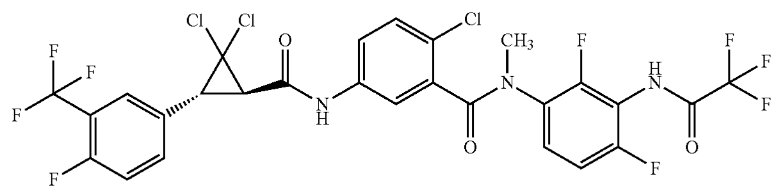 [SMILES: CN(C(=O)c1cc(NC(=O)[C@H]2[C@H](c3ccc(F)c(C(F)(F)F)c3)C2(Cl)Cl)ccc1Cl)c1ccc(F)c(NC(=O)C(F)(F)F)c1F] | 25 |
| F1796 | 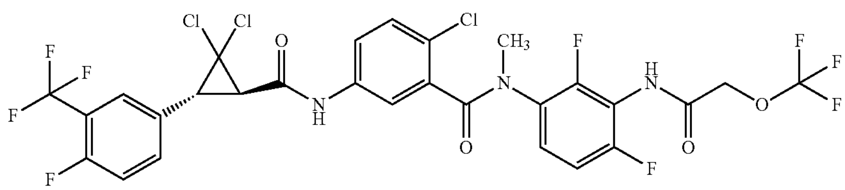 [SMILES: CN(C(=O)c1cc(NC(=O)[C@H]2[C@H](c3ccc(F)c(C(F)(F)F)c3)C2(Cl)Cl)ccc1Cl)c1ccc(F)c(NC(=O)COC(F)(F)F)c1F] | 25 |
| F1797 | 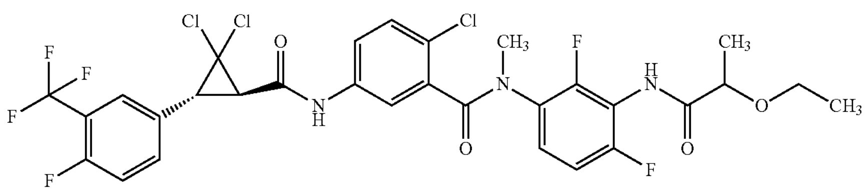 [SMILES: CCOC(C)C(=O)Nc1c(F)ccc(N(C)C(=O)c2cc(NC(=O)[C@H]3[C@H](c4ccc(F)c(C(F)(F)F)c4)C3(Cl)Cl)ccc2Cl)c1F] | 25 |
| F1798 | 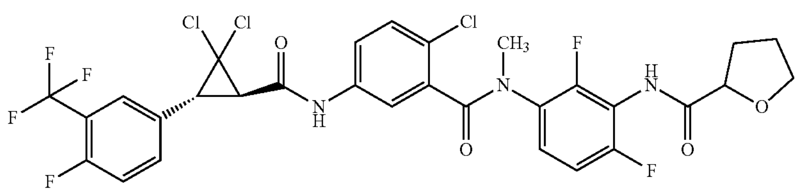 [SMILES: CN(C(=O)c1cc(NC(=O)[C@H]2[C@H](c3ccc(F)c(C(F)(F)F)c3)C2(Cl)Cl)ccc1Cl)c1ccc(F)c(NC(=O)C2CCCO2)c1F] | 25 |
| F1799 | 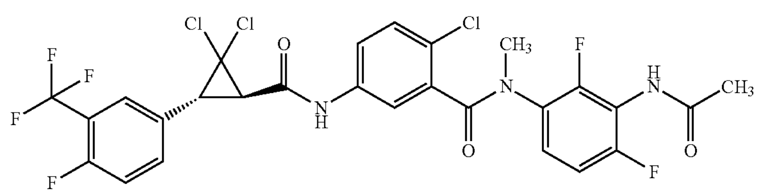 [SMILES: CC(=O)Nc1c(F)ccc(N(C)C(=O)c2cc(NC(=O)[C@H]3[C@H](c4ccc(F)c(C(F)(F)F)c4)C3(Cl)Cl)ccc2Cl)c1F] | 25 |
| F1800 | 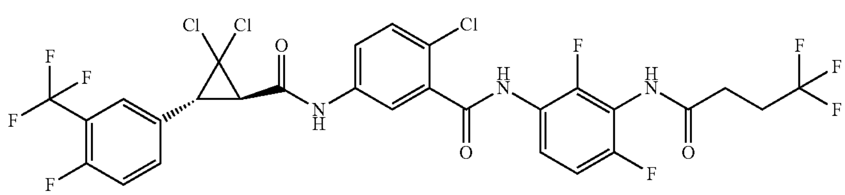 | 25 |

TABLE 2-continued

Structure and preparation method for F Series molecules

| No. | Structure | Prep.* |
|---|---|---|
| F1801 | 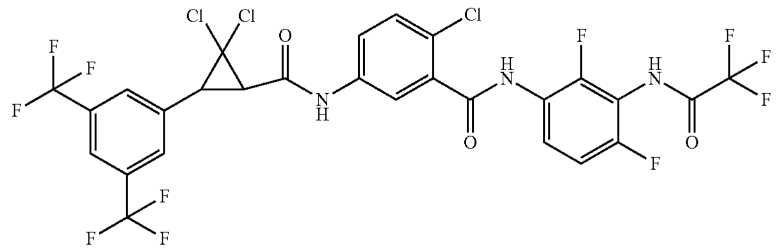 [SMILES: O=C(Nc1ccc(F)c(NC(=O)C(F)(F)F)c1F)c1cc(NC(=O)C2C(c3cc(C(F)(F)F)cc(C(F)(F)F)c3)C2(Cl)Cl)ccc1Cl] | 25 |
| F1802 | 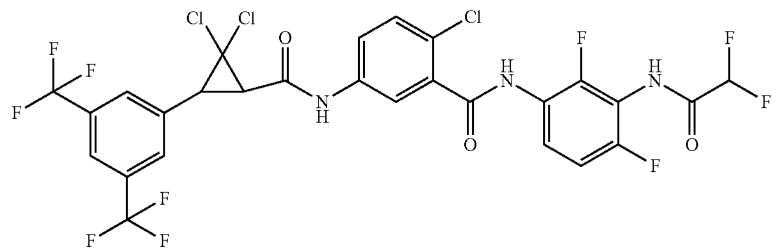 [SMILES: O=C(Nc1ccc(F)c(NC(=O)C(F)F)c1F)c1cc(NC(=O)C2C(c3cc(C(F)(F)F)cc(C(F)(F)F)c3)C2(Cl)Cl)ccc1Cl] | 1 |
| F1803 | 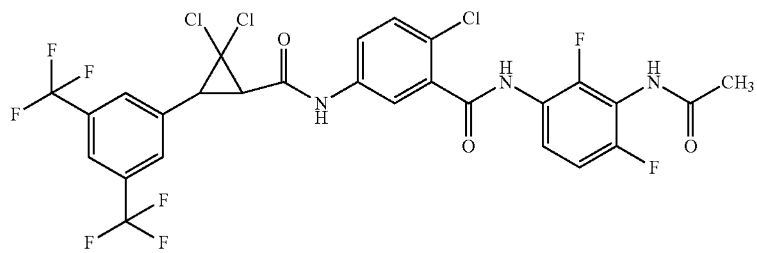 [SMILES: CC(=O)Nc1c(F)ccc(NC(=O)c2cc(NC(=O)C3C(c4cc(C(F)(F)F)cc(C(F)(F)F)c4)C3(Cl)Cl)ccc2Cl)c1F] | 2 |
| F1804 | 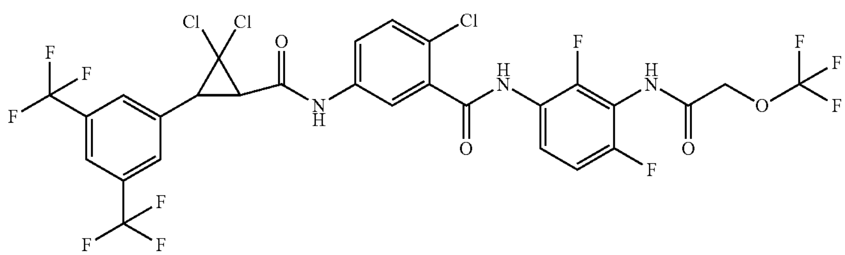 [SMILES: O=C(COC(F)(F)F)Nc1c(F)ccc(NC(=O)c2cc(NC(=O)C3C(c4cc(C(F)(F)F)cc(C(F)(F)F)c4)C3(Cl)Cl)ccc2Cl)c1F] | 4 |
| F1805 | 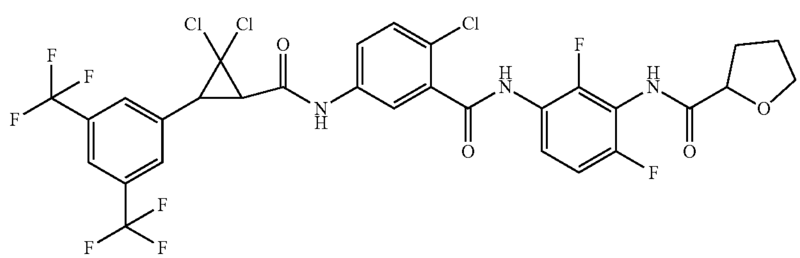 [SMILES: O=C(Nc1ccc(F)c(NC(=O)C2CCCO2)c1F)c1cc(NC(=O)C2C(c3cc(C(F)(F)F)cc(C(F)(F)F)c3)C2(Cl)Cl)ccc1Cl] | 4 |
| F1806 | 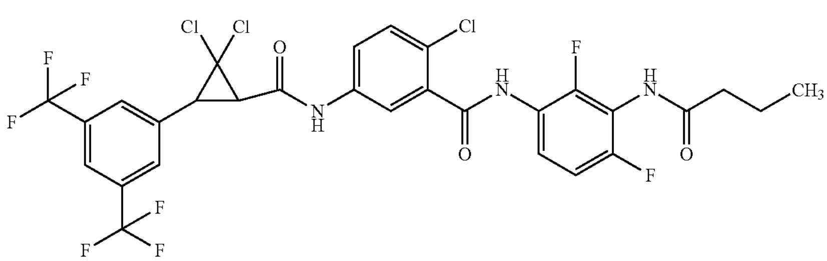 [SMILES: CCCC(=O)Nc1c(F)ccc(NC(=O)c2cc(NC(=O)C3C(c4cc(C(F)(F)F)cc(C(F)(F)F)c4)C3(Cl)Cl)ccc2Cl)c1F] | 4 |

TABLE 2-continued

Structure and preparation method for F Series molecules

| No. | Structure | Prep.* |
|---|---|---|
| F1807 | 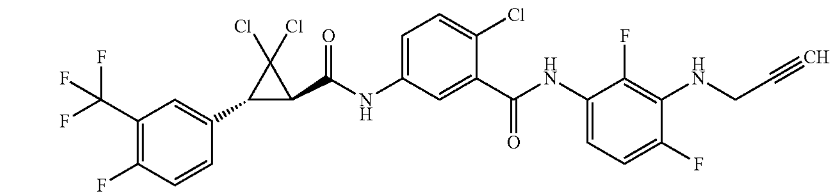 [SMILES: C#CCNc1c(F)ccc(NC(=O)c2cc(NC(=O)[C@H]3[C@H](c4ccc(F)c(C(F)(F)F)c4)C3(Cl)Cl)ccc2Cl)c1F] | 13 |
| F1808 | 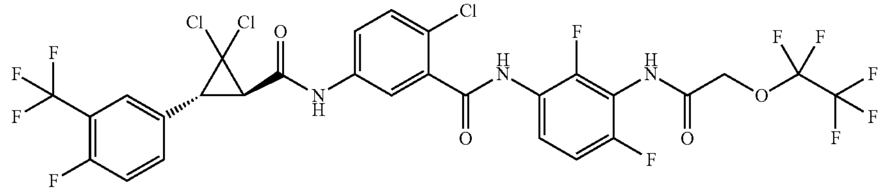 [SMILES: O=C(COC(F)(F)C(F)(F)F)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1809 | 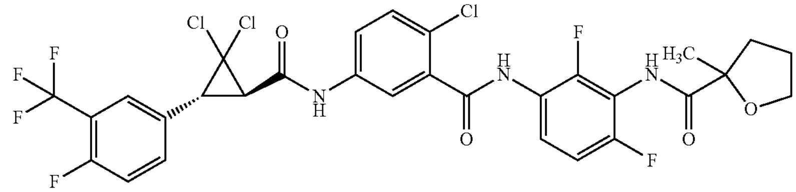 [SMILES: CC1(C(=O)Nc2c(F)ccc(NC(=O)c3cc(NC(=O)[C@H]4[C@H](c5ccc(F)c(C(F)(F)F)c5)C4(Cl)Cl)ccc3Cl)c2F)CCCO1] | 6 |
| F1810 | 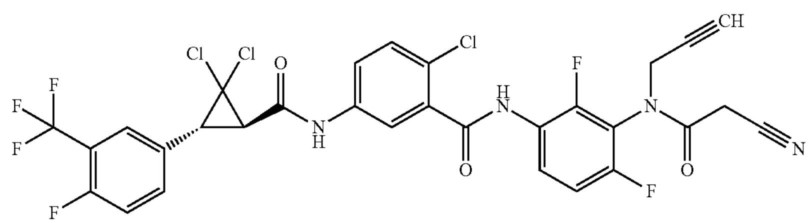 [SMILES: C#CCN(C(=O)CC#N)c1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1811 | 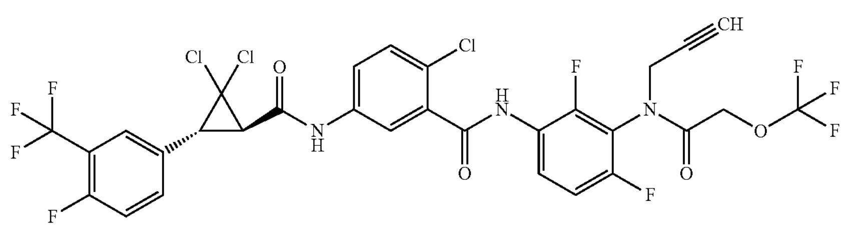 [SMILES: C#CCN(C(=O)COC(F)(F)F)c1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1812 | 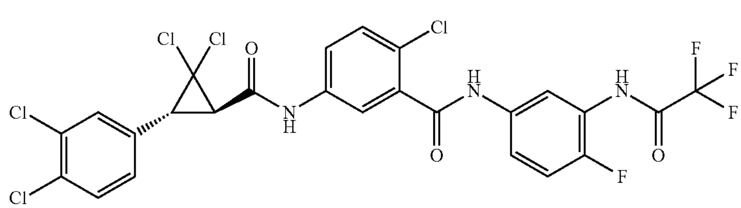 [SMILES: O=C(Nc1ccc(F)c(NC(=O)C(F)(F)F)c1)c1cc(NC(=O)[C@H]2[C@H](c3ccc(Cl)c(Cl)c3)C2(Cl)Cl)ccc1Cl] | 5 |
| F1813 | 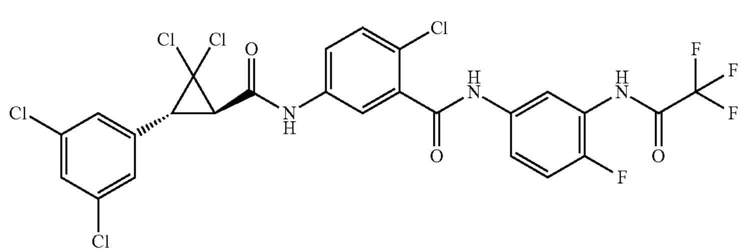 [SMILES: O=C(Nc1ccc(F)c(NC(=O)C(F)(F)F)c1)c1cc(NC(=O)[C@H]2[C@H](c3cc(Cl)cc(Cl)c3)C2(Cl)Cl)ccc1Cl] | 5 |

TABLE 2-continued

Structure and preparation method for F Series molecules

| No. | Structure | Prep.* |
|---|---|---|
| F1814 | 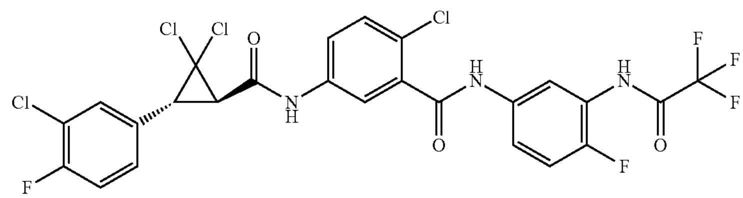 | 5 |
| F1815 | 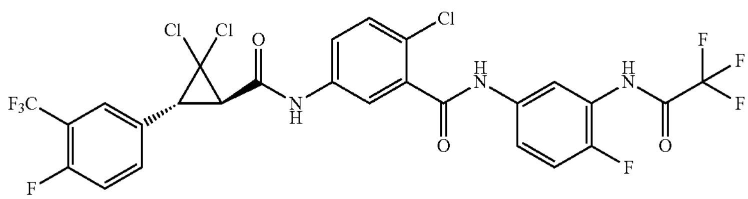 [SMILES: O=C(Nc1ccc(F)c(NC(=O)C(F)(F)F)c1)c1cc(NC(=O)[C@H]2[C@H](c3ccc(F)c(C(F)(F)F)c3)C2(Cl)Cl)ccc1Cl] | 5 |
| F1816 | 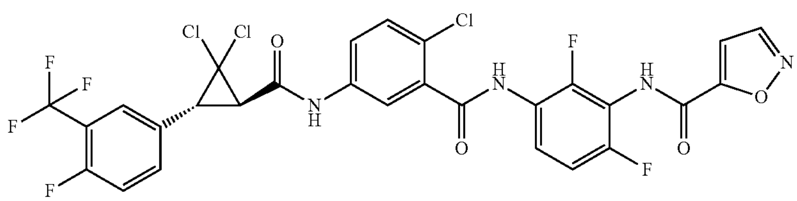 | 4 |
| F1817 | 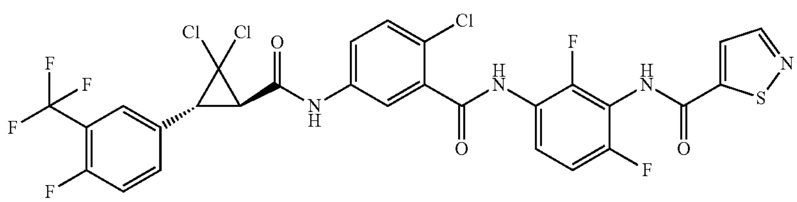 [SMILES: O=C(Nc1c(F)ccc(NC(=O)c2cc(NC(=O)[C@H]3[C@H](c4ccc(F)c(C(F)(F)F)c4)C3(Cl)Cl)ccc2Cl)c1F)c1ccns1] | 4 |
| F1818 | 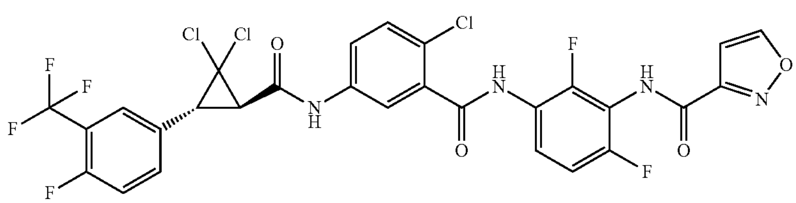 [SMILES: O=C(Nc1c(F)ccc(NC(=O)c2cc(NC(=O)[C@H]3[C@H](c4ccc(F)c(C(F)(F)F)c4)C3(Cl)Cl)ccc2Cl)c1F)c1ccon1] | 4 |
| F1819 | 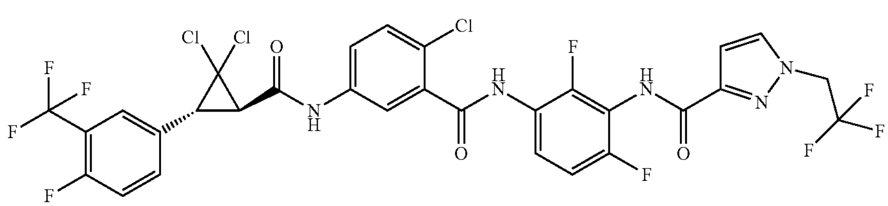 [SMILES: O=C(Nc1c(F)ccc(NC(=O)c2cc(NC(=O)[C@H]3[C@H](c4ccc(F)c(C(F)(F)F)c4)C3(Cl)Cl)ccc2Cl)c1F)c1ccn(CC(F)(F)F)n1] | 4 |
| F1820 | 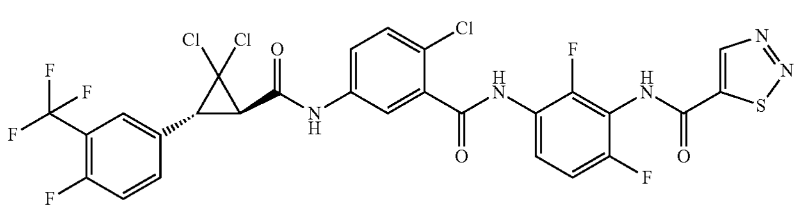 [SMILES: O=C(Nc1c(F)ccc(NC(=O)c2cc(NC(=O)[C@H]3[C@H](c4ccc(F)c(C(F)(F)F)c4)C3(Cl)Cl)ccc2Cl)c1F)c1cnns1] | 4 |

TABLE 2-continued

Structure and preparation method for F Series molecules

| No. | Structure | Prep.* |
|---|---|---|
| F1821 | 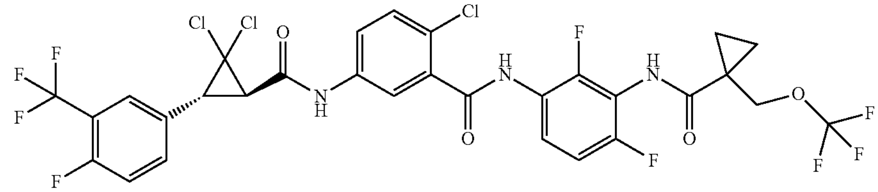 [SMILES: O=C(Nc1ccc(F)c(NC(=O)C2(COC(F)(F)F)CC2)c1F)c1cc(NC(=O)[C@H]2[C@H](c3ccc(F)c(C(F)(F)F)c3)C2(Cl)Cl)ccc1Cl] | 6 |
| F1822 | 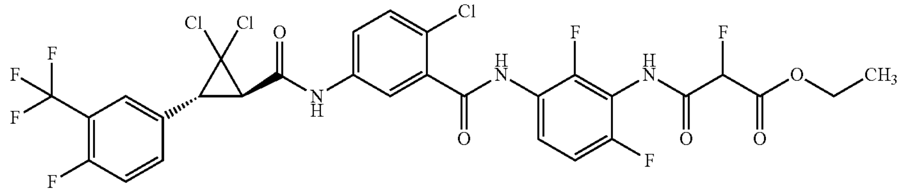 [SMILES: CCOC(=O)C(F)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1823 | 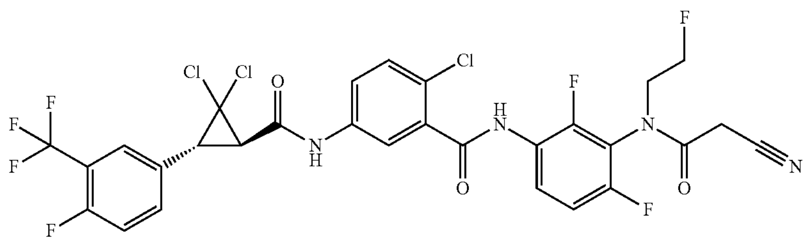 [SMILES: N#CCC(=O)N(CCF)c1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1824 | 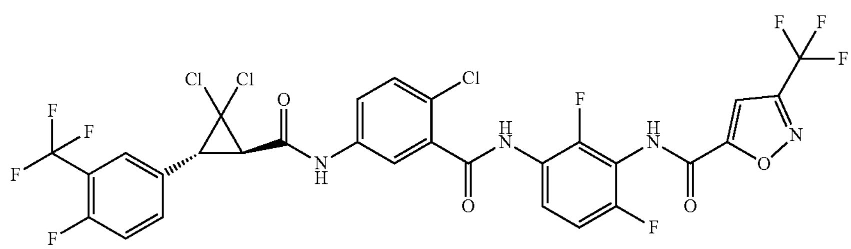 [SMILES: O=C(Nc1c(F)ccc(NC(=O)c2cc(NC(=O)[C@H]3[C@H](c4ccc(F)c(C(F)(F)F)c4)C3(Cl)Cl)ccc2Cl)c1F)c1cc(C(F)(F)F)no1] | 4 |
| F1825 | 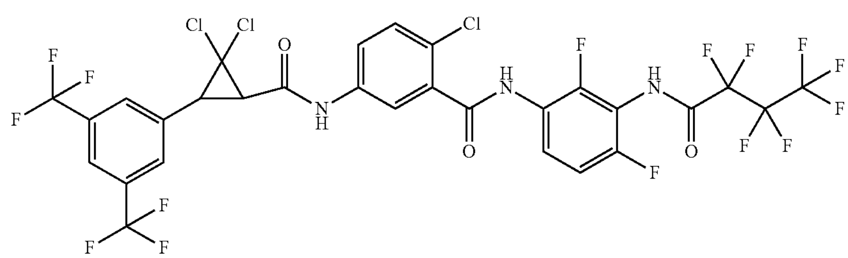 [SMILES: O=C(Nc1ccc(F)c(NC(=O)C(F)(F)C(F)(F)C(F)(F)F)c1F)c1cc(NC(=O)C2C(c3cc(C(F)(F)F)cc(C(F)(F)F)c3)C2(Cl)Cl)ccc1Cl] | 4 |
| F1826 | 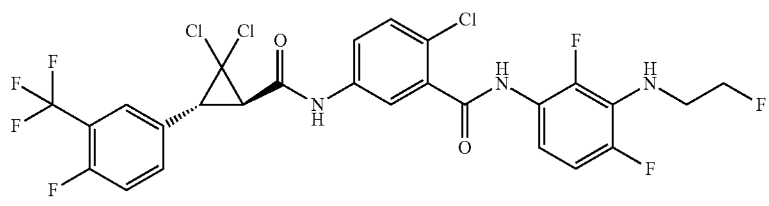 [SMILES: O=C(Nc1ccc(F)c(NCCF)c1F)c1cc(NC(=O)[C@H]2[C@H](c3ccc(F)c(C(F)(F)F)c3)C2(Cl)Cl)ccc1Cl] | 13 |
| F1827 | 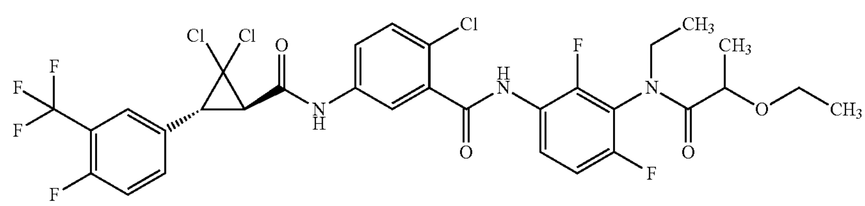 [SMILES: CCOC(C)C(=O)N(CC)c1c(F)ccc(NC(=O)c2cc(NC(=O)[C@H]3[C@H](c4ccc(F)c(C(F)(F)F)c4)C3(Cl)Cl)ccc2Cl)c1F] | 6 |

TABLE 2-continued

Structure and preparation method for F Series molecules

| No. | Structure | Prep.* |
|---|---|---|
| F1828 | 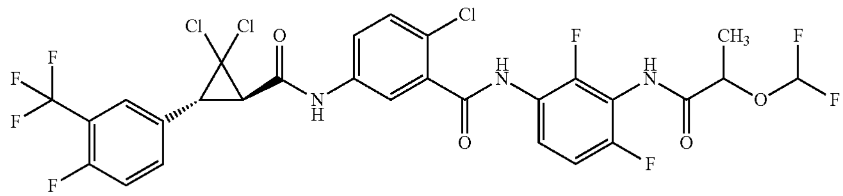 [SMILES: CC(OC(F)F)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1829 | 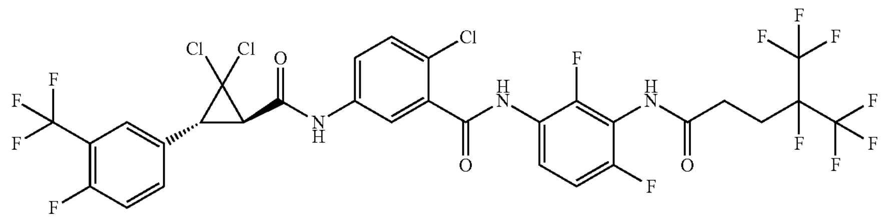 [SMILES: O=C(CCC(F)(C(F)(F)F)C(F)(F)F)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1830 | 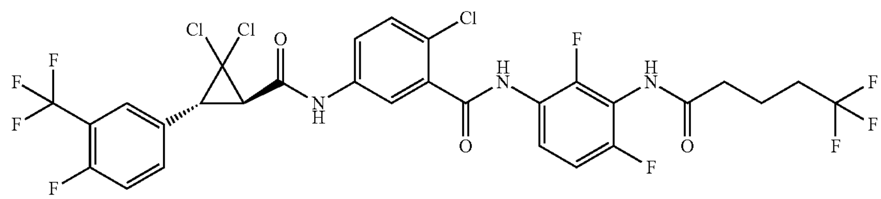 [SMILES: O=C(CCCC(F)(F)F)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1831 | 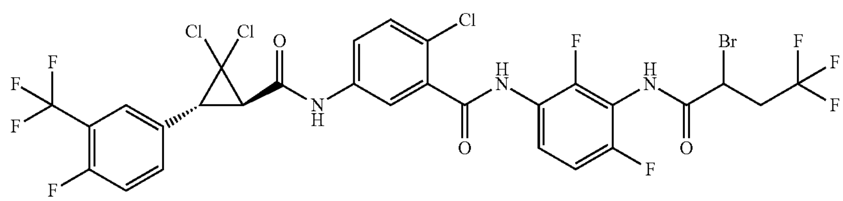 [SMILES: O=C(Nc1ccc(F)c(NC(=O)C(Br)CC(F)(F)F)c1F)c1cc(NC(=O)[C@H]2[C@H](c3ccc(F)c(C(F)(F)F)c3)C2(Cl)Cl)ccc1Cl] | 6 |
| F1832 | 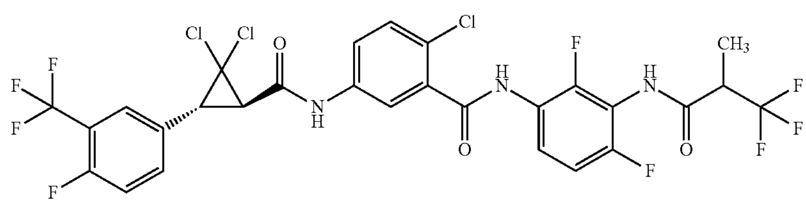 [SMILES: CC(C(=O)Nc1c(F)ccc(NC(=O)c2cc(NC(=O)[C@H]3[C@H](c4ccc(F)c(C(F)(F)F)c4)C3(Cl)Cl)ccc2Cl)c1F)C(F)(F)F] | 6 |
| F1833 | 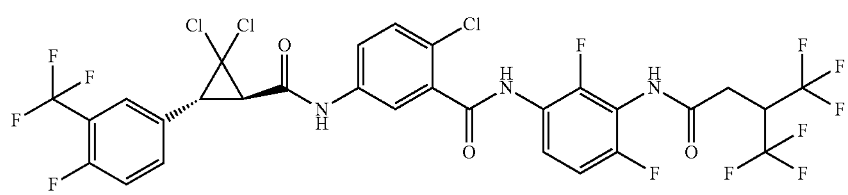 [SMILES: O=C(CC(C(F)(F)F)C(F)(F)F)Nc1c(F)ccc(NC(=O)c2cc(NC(=O)[C@H]3[C@H](c4ccc(F)c(C(F)(F)F)c4)C3(Cl)Cl)ccc2Cl)c1F] | 4 |
| F1834 | 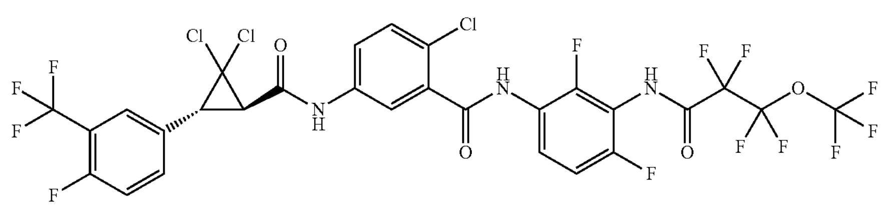 [SMILES: O=C(Nc1ccc(F)c(NC(=O)C(F)(F)C(F)(F)OC(F)(F)F)c1F)c1cc(NC(=O)[C@H]2[C@H](c3ccc(F)c(C(F)(F)F)c3)C2(Cl)Cl)ccc1Cl] | 6 |

TABLE 2-continued

Structure and preparation method for F Series molecules

| No. | Structure | Prep.* |
|---|---|---|
| F1835 | 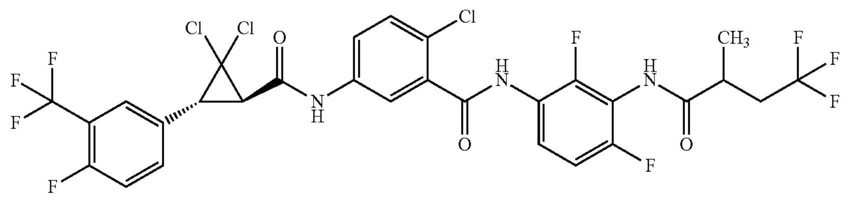 | 6 |
| F1836 | 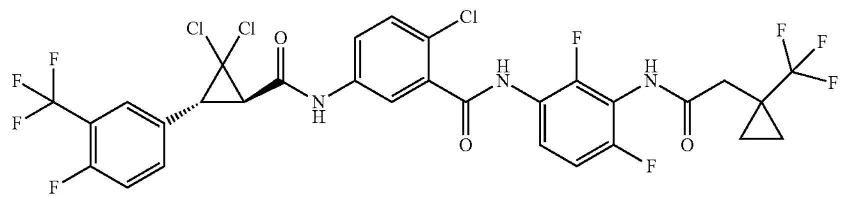 [SMILES: O=C(CC1(C(F)(F)F)CC1)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1837 | 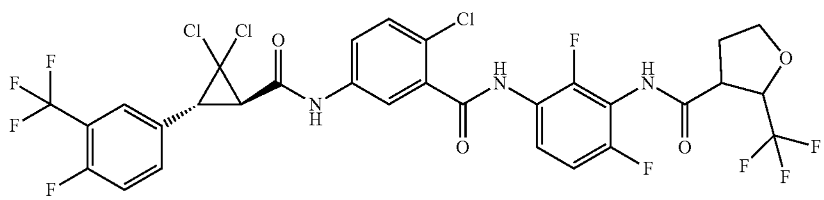 [SMILES: O=C(Nc1ccc(F)c(NC(=O)C2CCOC2C(F)(F)F)c1F)c1cc(NC(=O)[C@H]2[C@H](c3ccc(F)c(C(F)(F)F)c3)C2(Cl)Cl)ccc1Cl] | 6 |
| F1838 | 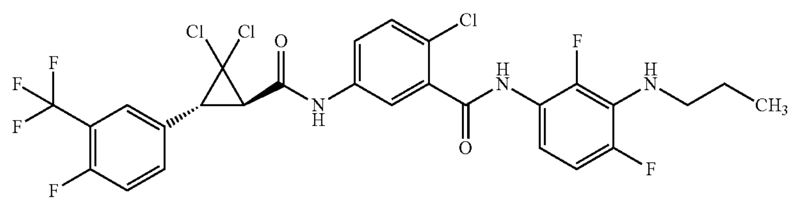 [SMILES: CCCNc1c(F)ccc(NC(=O)c2cc(NC(=O)[C@H]3[C@H](c4ccc(F)c(C(F)(F)F)c4)C3(Cl)Cl)ccc2Cl)c1F] | 13 |
| F1839 | 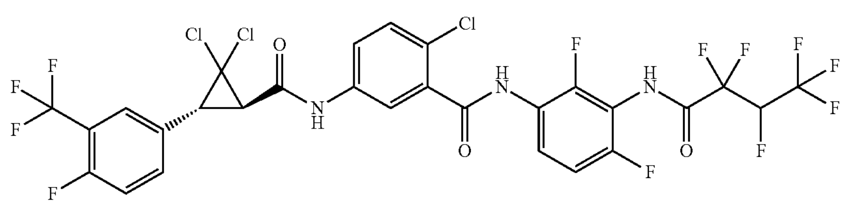 [SMILES: O=C(Nc1ccc(F)c(NC(=O)C(F)(F)C(F)C(F)(F)F)c1F)c1cc(NC(=O)[C@H]2[C@H](c3ccc(F)c(C(F)(F)F)c3)C2(Cl)Cl)ccc1Cl] | 6 |
| F1840 | 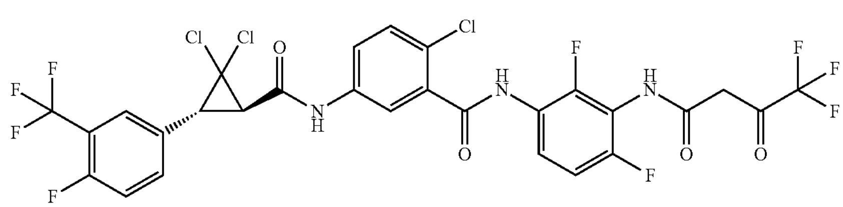 [SMILES: O=C(CC(=O)C(F)(F)F)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1841 | 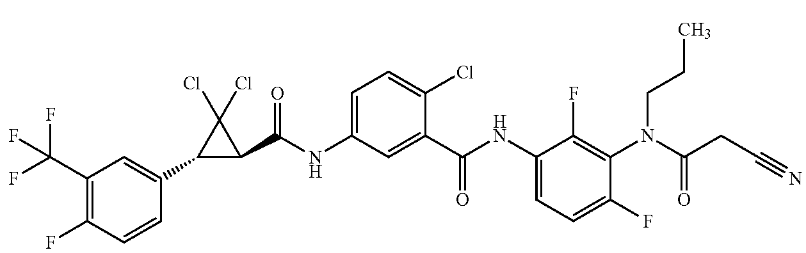 [SMILES: CCCN(C(=O)CC#N)c1c(F)ccc(NC(=O)c2cc(NC(=O)[C@H]3[C@H](c4ccc(F)c(C(F)(F)F)c4)C3(Cl)Cl)ccc2Cl)c1F] | 6 |

TABLE 2-continued

Structure and preparation method for F Series molecules

| No. | Structure | Prep.* |
|---|---|---|
| F1842 | 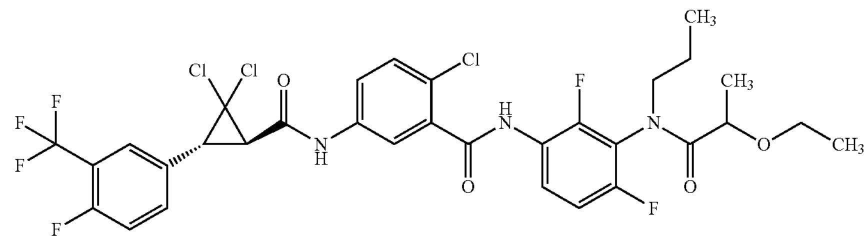 [SMILES: CCCN(C(=O)C(C)OCC)c1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1843 | 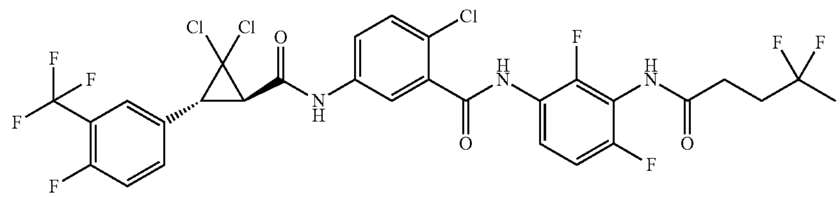 [SMILES: CC(F)(F)CCC(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 4 |
| F1844 | 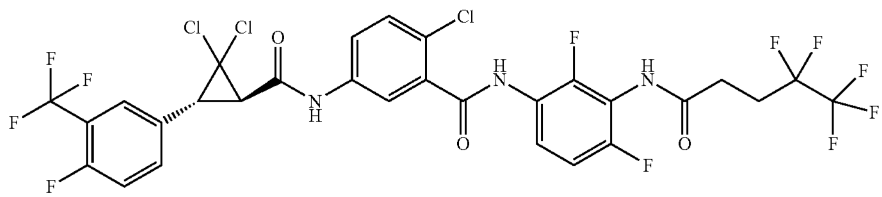 [SMILES: O=C(CCC(F)(F)C(F)(F)F)Nc1c(F)ccc(NC(=O)c2cc(NC(=O)[C@H]3[C@H](c4ccc(F)c(C(F)(F)F)c4)C3(Cl)Cl)ccc2Cl)c1F] | 4 |
| F1845 | 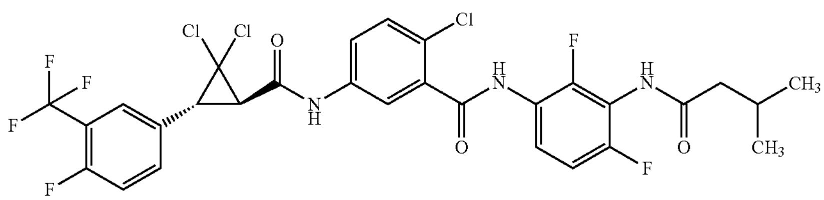 [SMILES: CC(C)CC(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 4 |
| F1846 | 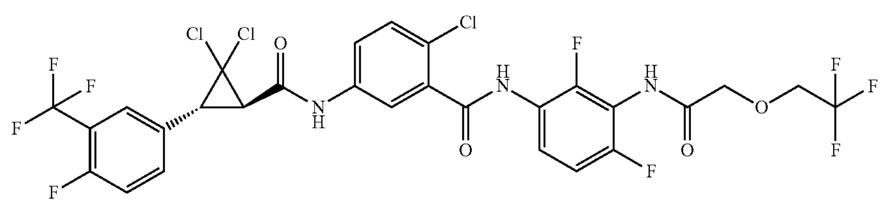 [SMILES: O=C(COCC(F)(F)F)Nc1c(F)ccc(NC(=O)c2cc(NC(=O)[C@H]3[C@H](c4ccc(F)c(C(F)(F)F)c4)C3(Cl)Cl)ccc2Cl)c1F] | 4 |
| F1847 | 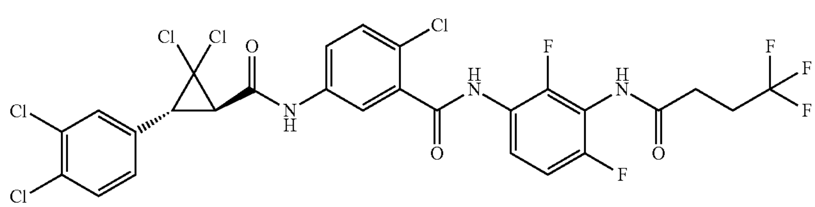 [SMILES: O=C(CCC(F)(F)F)Nc1c(F)ccc(NC(=O)c2cc(NC(=O)[C@H]3[C@H](c4ccc(Cl)c(Cl)c4)C3(Cl)Cl)ccc2Cl)c1F] | 4 |
| F1848 | 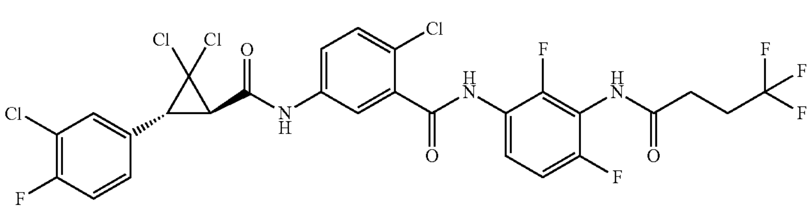 [SMILES: O=C(CCC(F)(F)F)Nc1c(F)ccc(NC(=O)c2cc(NC(=O)[C@H]3[C@H](c4ccc(F)c(Cl)c4)C3(Cl)Cl)ccc2Cl)c1F] | 4 |

TABLE 2-continued
Structure and preparation method for F Series molecules
| No. | Structure | Prep.* |
|---|---|---|
| F1849 | 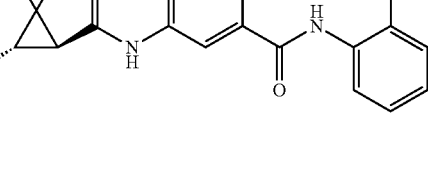 | 6 |
| F1850 | 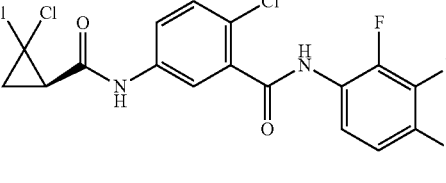 | 4 |
| F1851 | 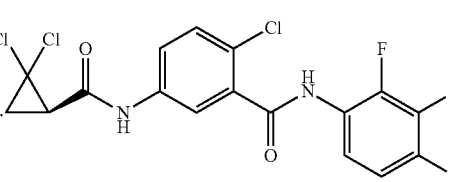 | 6 |
| F1853 | 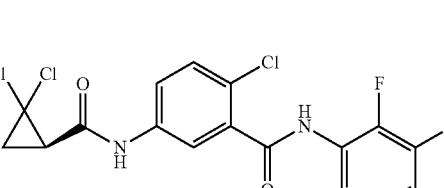 | 6 |
| F1854 | 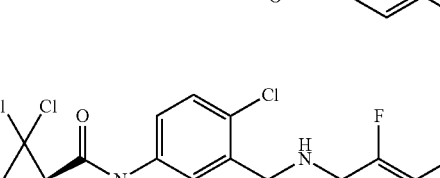 | 6 |
| F1855 | 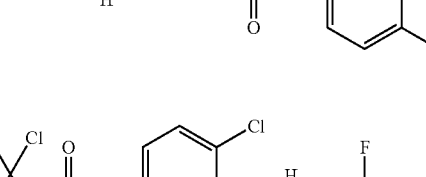 | 6 |
| F1856 | 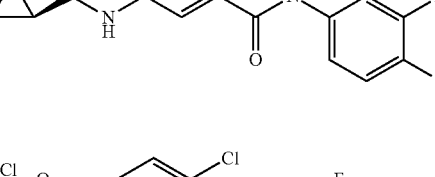 | 6 |

TABLE 2-continued

Structure and preparation method for F Series molecules

| No. | Structure | Prep.* |
|---|---|---|
| F1857 | 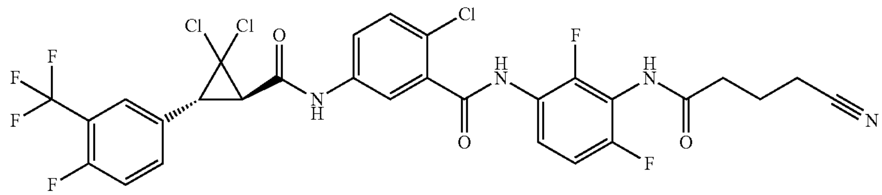 [SMILES: N#CCCCC(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1858 | 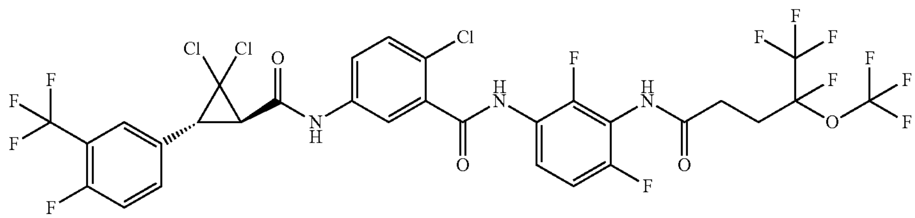 [SMILES: O=C(CCC(F)(OC(F)(F)F)C(F)(F)F)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1860 | 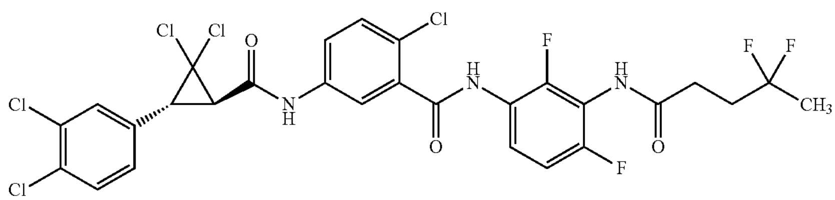 [SMILES: CC(F)(F)CCC(=O)Nc1c(F)ccc(NC(=O)c2cc(NC(=O)[C@H]3[C@H](c4ccc(Cl)c(Cl)c4)C3(Cl)Cl)ccc2Cl)c1F] | 4 |
| F1861 | 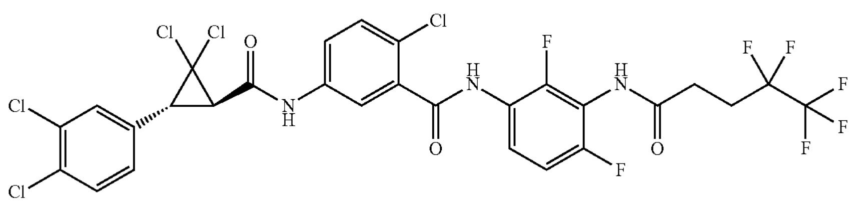 [SMILES: O=C(CCC(F)(F)C(F)(F)F)Nc1c(F)ccc(NC(=O)c2cc(NC(=O)[C@H]3[C@H](c4ccc(Cl)c(Cl)c4)C3(Cl)Cl)ccc2Cl)c1F] | 4 |
| F1862 | 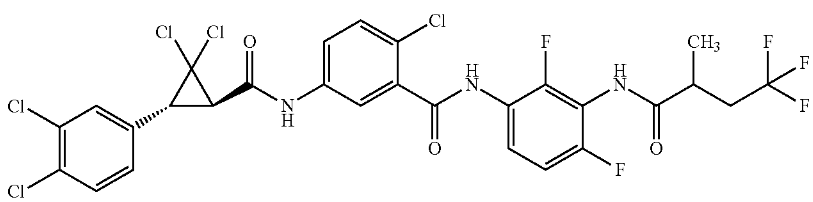 [SMILES: CC(CC(F)(F)F)C(=O)Nc1c(F)ccc(NC(=O)c2cc(NC(=O)[C@H]3[C@H](c4ccc(Cl)c(Cl)c4)C3(Cl)Cl)ccc2Cl)c1F] | 4 |
| F1863 | 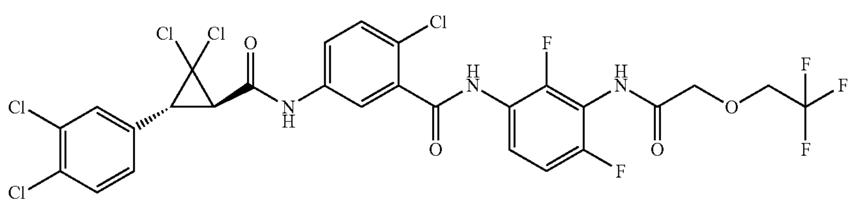 [SMILES: O=C(COCC(F)(F)F)Nc1c(F)ccc(NC(=O)c2cc(NC(=O)[C@H]3[C@H](c4ccc(Cl)c(Cl)c4)C3(Cl)Cl)ccc2Cl)c1F] | 4 |
| F1864 | 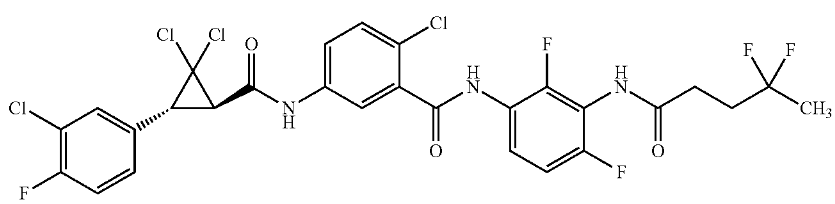 [SMILES: CC(F)(F)CCC(=O)Nc1c(F)ccc(NC(=O)c2cc(NC(=O)[C@H]3[C@H](c4ccc(F)c(Cl)c4)C3(Cl)Cl)ccc2Cl)c1F] | 4 |

TABLE 2-continued

Structure and preparation method for F Series molecules

| No. | Structure | Prep.* |
|---|---|---|
| F1865 | 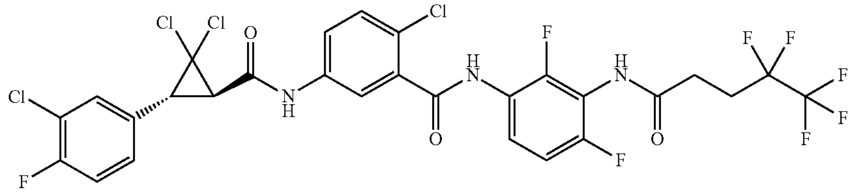 [SMILES: O=C(CCC(F)(F)C(F)(F)F)Nc1c(F)ccc(NC(=O)c2cc(NC(=O)[C@H]3[C@H](c4ccc(F)c(Cl)c4)C3(Cl)Cl)ccc2Cl)c1F] | 4 |
| F1866 | 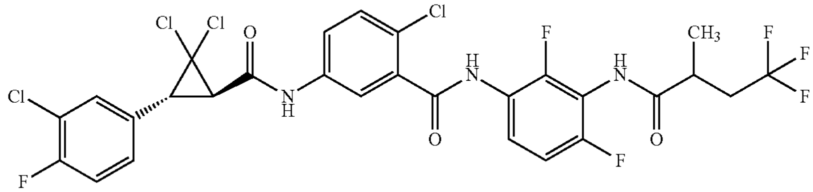 [SMILES: CC(CC(F)(F)F)C(=O)Nc1c(F)ccc(NC(=O)c2cc(NC(=O)[C@H]3[C@H](c4ccc(F)c(Cl)c4)C3(Cl)Cl)ccc2Cl)c1F] | 4 |
| F1867 | 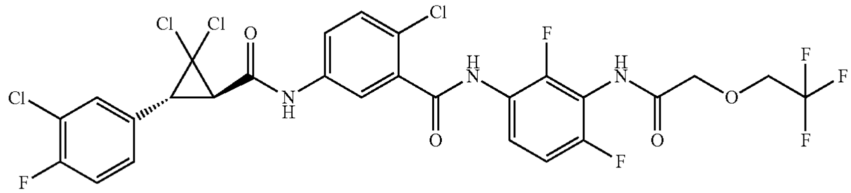 [SMILES: O=C(COCC(F)(F)F)Nc1c(F)ccc(NC(=O)c2cc(NC(=O)[C@H]3[C@H](c4ccc(F)c(Cl)c4)C3(Cl)Cl)ccc2Cl)c1F] | 4 |
| F1868 | 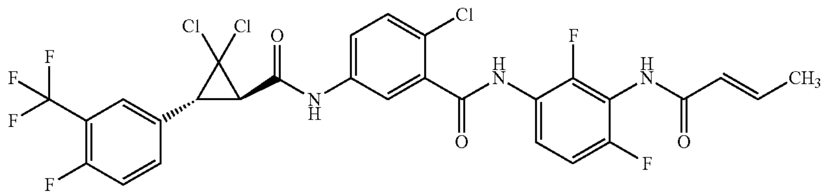 [SMILES: C/C=C/C(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1869 | 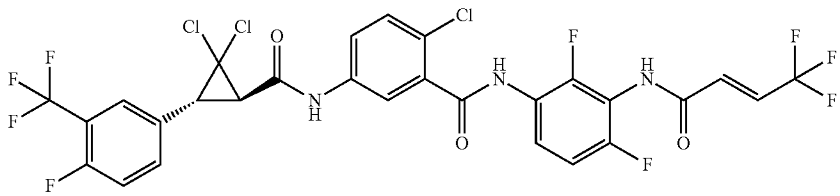 [SMILES: O=C(/C=C/C(F)(F)F)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1870 | 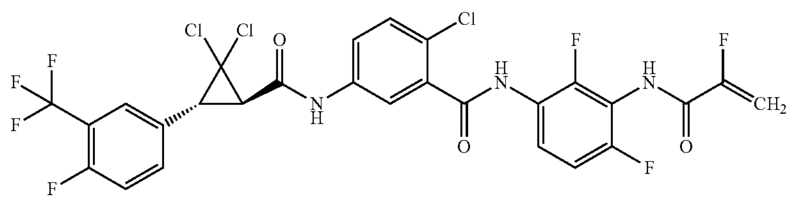 [SMILES: C=C(F)C(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 6 |
| F1871 | 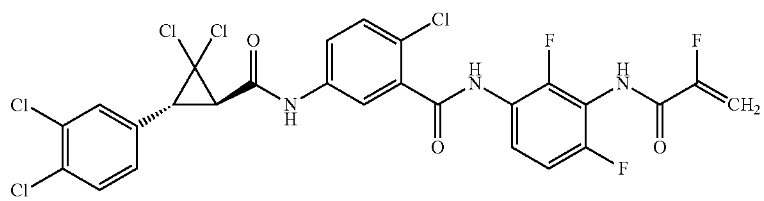 [SMILES: C=C(F)C(=O)Nc1c(F)ccc(NC(=O)c2cc(NC(=O)[C@H]3[C@H](c4ccc(Cl)c(Cl)c4)C3(Cl)Cl)ccc2Cl)c1F] | 4 |

TABLE 2-continued

Structure and preparation method for F Series molecules

| No. | Structure | Prep.* |
|---|---|---|
| F1872 | 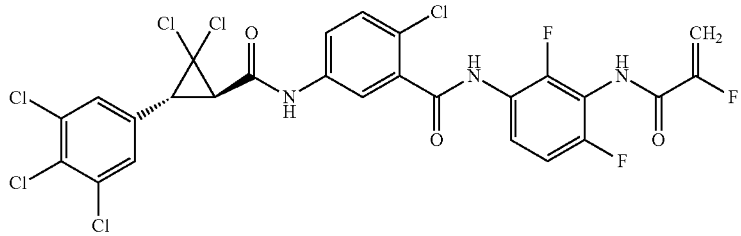 [SMILES: C=C(F)C(=O)Nc1c(F)ccc(NC(=O)c2cc(NC(=O)[C@H]3[C@H](c4cc(Cl)c(Cl)c(Cl)c4)C3(Cl)Cl)ccc2Cl)c1F] | 4 |
| F1873 | 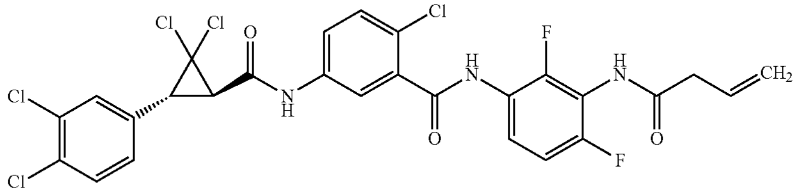 [SMILES: C=CCC(=O)Nc1c(F)ccc(NC(=O)c2cc(NC(=O)[C@H]3[C@H](c4ccc(Cl)c(Cl)c4)C3(Cl)Cl)ccc2Cl)c1F] | 4 |
| F1874 | 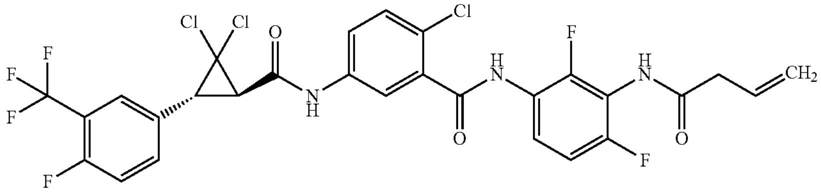 [SMILES: C=CCC(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 4 |
| F1875 | 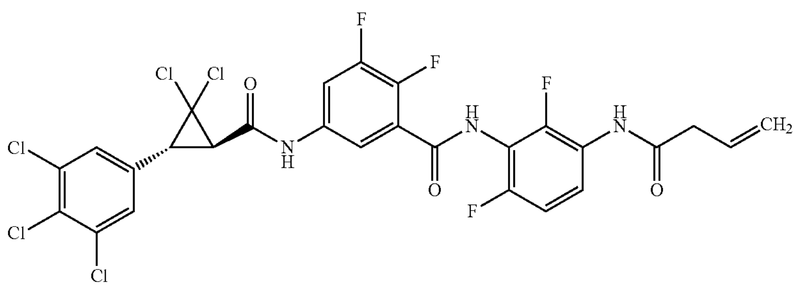 [SMILES: C=CCC(=O)Nc1ccc(F)c(NC(=O)c2cc(NC(=O)[C@H]3[C@H](c4cc(Cl)c(Cl)c(Cl)c4)C3(Cl)Cl)cc(F)c2F)c1F] | 4 |
| F1876 | 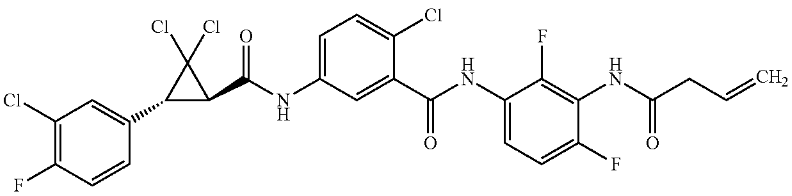 | 4 |
| F1877 | 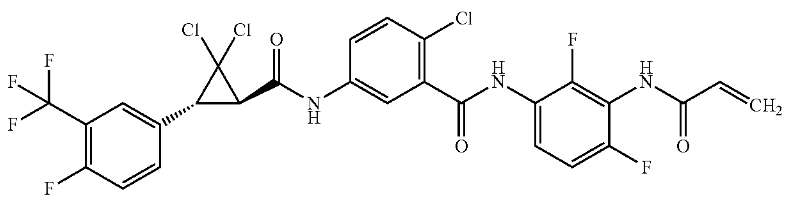 [SMILES: C=CC(=O)Nc1c(F)ccc(NC(=O)c2cc(NC(=O)[C@H]3[C@H](c4ccc(F)c(C(F)(F)F)c4)C3(Cl)Cl)ccc2Cl)c1F] | 4 |
| F1878 | 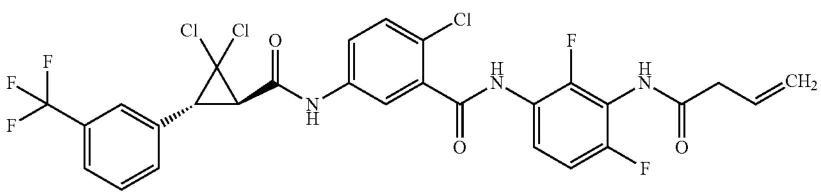 [SMILES: C=CCC(=O)Nc1c(F)ccc(NC(=O)c2cc(NC(=O)[C@H]3[C@H](c4cccc(C(F)(F)F)c4)C3(Cl)Cl)ccc2Cl)c1F] | 6 |

TABLE 2-continued

Structure and preparation method for F Series molecules

| No. | Structure | Prep.* |
|---|---|---|
| F1879 | 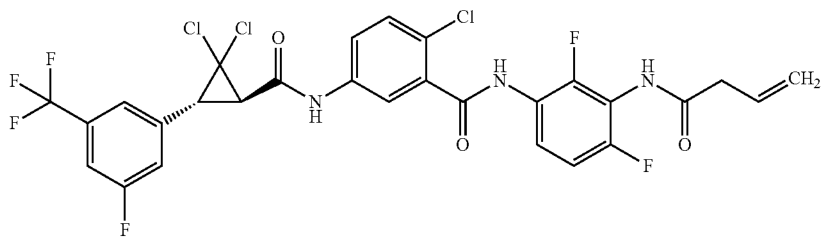 [SMILES: C=CCC(=O)Nc1c(F)ccc(NC(=O)c2cc(NC(=O)[C@H]3[C@H](c4cc(F)cc(C(F)(F)F)c4)C3(Cl)Cl)ccc2Cl)c1F] | 6 |
| F1880 | 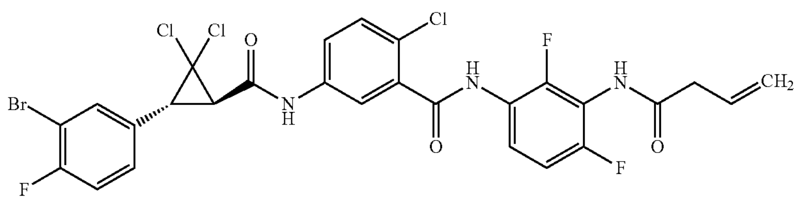 | 6 |
| F1881 | 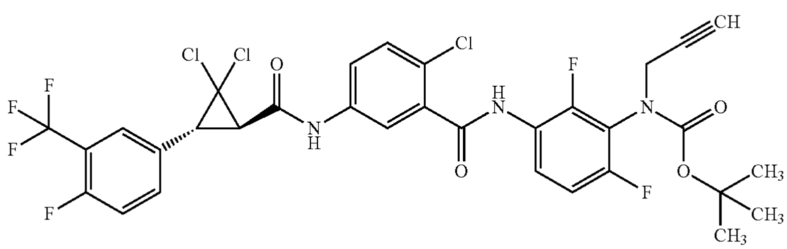 [SMILES: C#CCN(C(=O)OC(C)(C)C)c1c(F)ccc(NC(=O)c2cc(NC(=O)[C@H]3[C@H](c4ccc(F)c(C(F)(F)F)c4)C3(Cl)Cl)ccc2Cl)c1F] | 25 |
| F1882 | 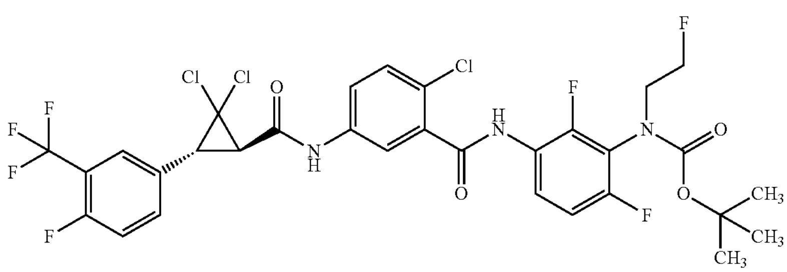 [SMILES: CC(C)(C)OC(=O)N(CCF)c1c(F)ccc(NC(=O)c2cc(NC(=O)[C@H]3[C@H](c4ccc(F)c(C(F)(F)F)c4)C3(Cl)Cl)ccc2Cl)c1F] | 25 |
| F1883 | 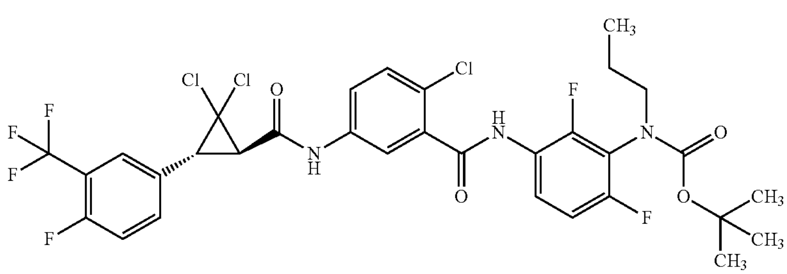 [SMILES: CCCN(C(=O)OC(C)(C)C)c1c(F)ccc(NC(=O)c2cc(NC(=O)[C@H]3[C@H](c4ccc(F)c(C(F)(F)F)c4)C3(Cl)Cl)ccc2Cl)c1F] | 25 |
| F2001 | 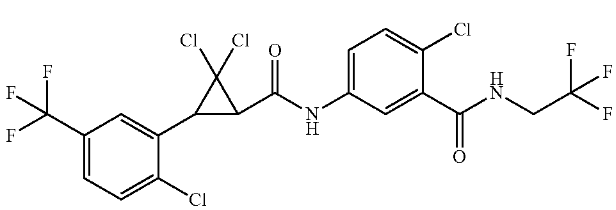 [SMILES: O=C(NCC(F)(F)F)c1cc(NC(=O)C2C(c3cc(C(F)(F)F)ccc3Cl)C2(Cl)Cl)ccc1Cl] | 20 |

TABLE 2-continued
Structure and preparation method for F Series molecules
| No. | Structure | Prep.* |
|---|---|---|
| F2002 | 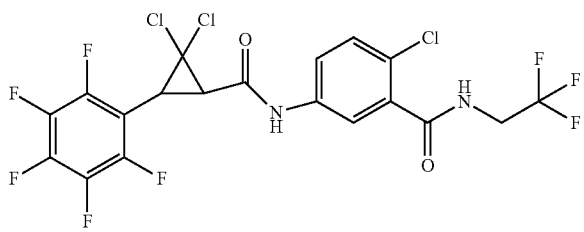 [SMILES: O=C(NCC(F)(F)F)c1cc(NC(=O)C2C(c3c(F)c(F)c(F)c(F)c3F)C2(Cl)Cl)ccc1Cl] | 20 |
| F2003 | 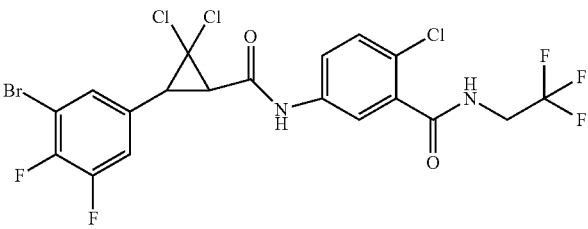 | 20 |
| F2004 | 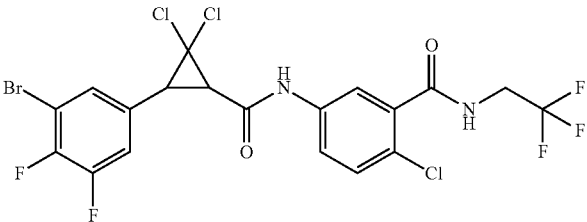 [SMILES: O=C(NCC(F)(F)F)c1cc(NC(=O)C2C(c3cc(F)c(F)c(Br)c3)C2(Cl)Cl)ccc1Cl] | 20 |
| F2005 | 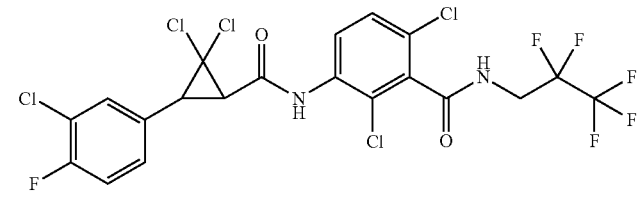 | 20 |
| F2006 | 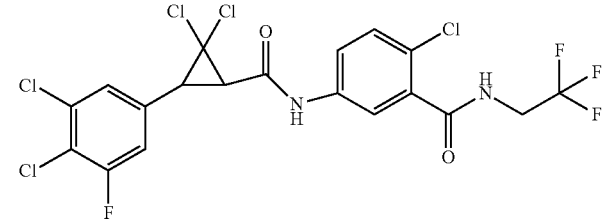 [SMILES: O=C(NCC(F)(F)F)c1cc(NC(=O)C2C(c3cc(F)c(Cl)c(Cl)c3)C2(Cl)Cl)ccc1Cl] | 20 |
| F2007 | 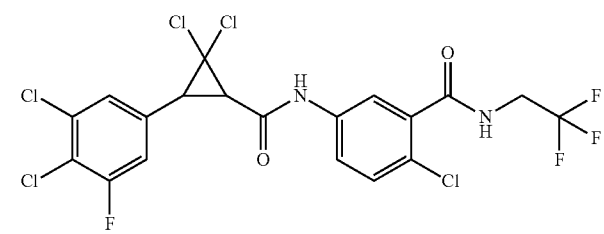 [SMILES: O=C(NCC(F)(F)F)c1cc(NC(=O)C2C(c3cc(F)c(Cl)c(Cl)c3)C2(Cl)Cl)ccc1Cl] | 20 |

TABLE 2-continued

Structure and preparation method for F Series molecules

| No. | Structure | Prep.* |
|---|---|---|
| F2008 | 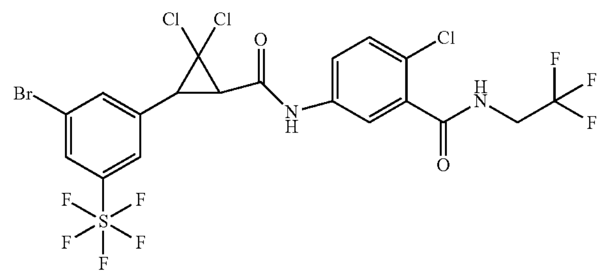 [SMILES: O=C(NCC(F)(F)F)c1cc(NC(=O)C2C(c3cc(Br)cc(S(F)(F)(F)(F)F)c3)C2(Cl)Cl)ccc1Cl] | 20 |
| F2009 | 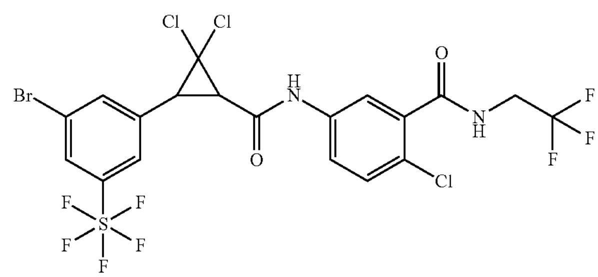 [SMILES: O=C(NCC(F)(F)F)c1cc(NC(=O)C2C(c3cc(Br)cc(S(F)(F)(F)(F)F)c3)C2(Cl)Cl)ccc1Cl] | 20 |
| F2010 | 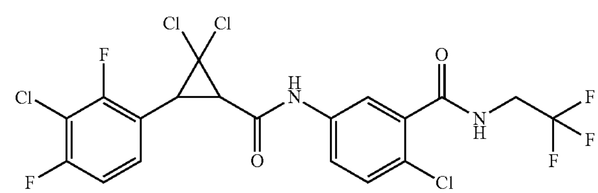 [SMILES: O=C(NCC(F)(F)F)c1cc(NC(=O)C2C(c3ccc(F)c(Cl)c3F)C2(Cl)Cl)ccc1Cl] | 20 |
| F2011 | 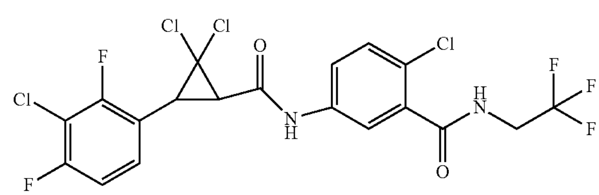 [SMILES: O=C(NCC(F)(F)F)c1cc(NC(=O)C2C(c3ccc(F)c(Cl)c3F)C2(Cl)Cl)ccc1Cl] | 20 |
| F2012 | 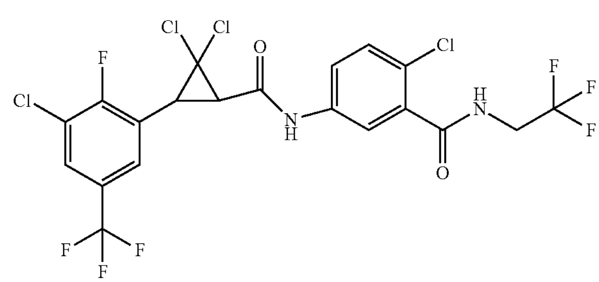 [SMILES: O=C(NCC(F)(F)F)c1cc(NC(=O)C2C(c3cc(C(F)(F)F)cc(Cl)c3F)C2(Cl)Cl)ccc1Cl] | 20 |
| F2013 | 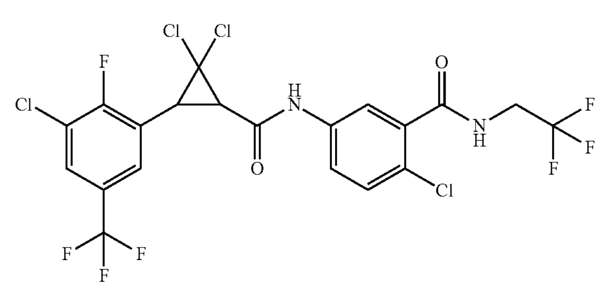 [SMILES: O=C(NCC(F)(F)F)c1cc(NC(=O)C2C(c3cc(C(F)(F)F)cc(Cl)c3F)C2(Cl)Cl)ccc1Cl] | 20 |

TABLE 2-continued

Structure and preparation method for F Series molecules

| No. | Structure | Prep.* |
|---|---|---|
| F2016 | 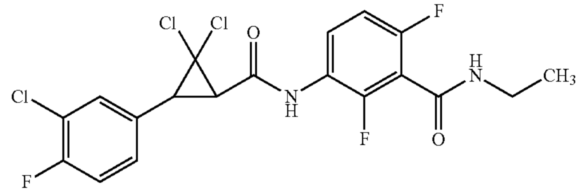 | 20 |
| F2017 | 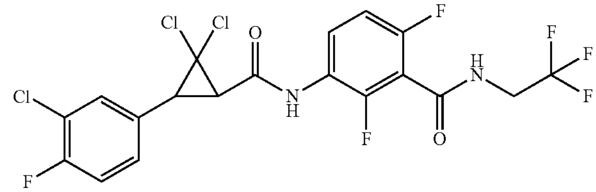 | 20 |
| F2018 | 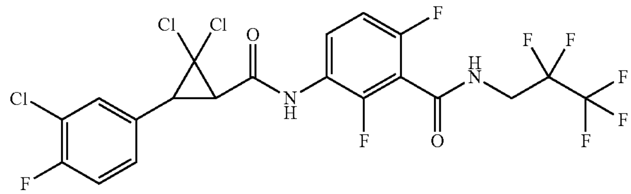 [SMILES: O=C(NCC(F)(F)C(F)(F)F)c1c(F)ccc(NC(=O)C2C(c3ccc(F)c(Cl)c3)C2(Cl)Cl)c1F] | 20 |
| F2019 | 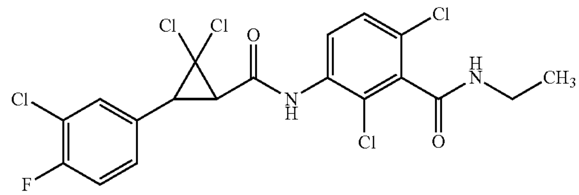 | 20 |
| F2020 | 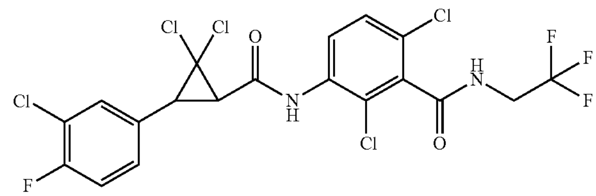 [SMILES: O=C(NCC(F)(F)F)c1c(Cl)ccc(NC(=O)C2C(c3ccc(F)c(Cl)c3)C2(Cl)Cl)c1Cl] | 20 |
| F2021 | 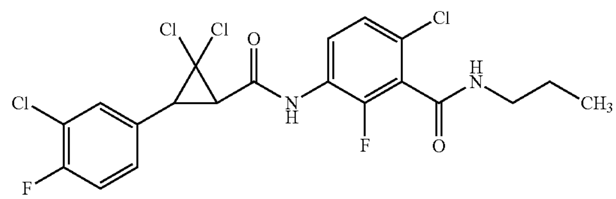 [SMILES: CCCNC(=O)c1c(Cl)ccc(NC(=O)C2C(c3ccc(F)c(Cl)c3)C2(Cl)Cl)c1F] | 20 |
| F2022 | 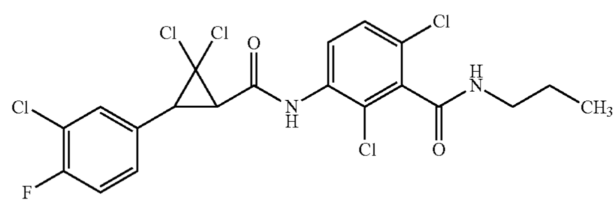 [SMILES: CCCNC(=O)c1c(Cl)ccc(NC(=O)C2C(c3ccc(F)c(Cl)c3)C2(Cl)Cl)c1Cl] | 20 |

TABLE 2-continued

Structure and preparation method for F Series molecules

| No. | Structure | Prep.* |
|---|---|---|
| F2023 | 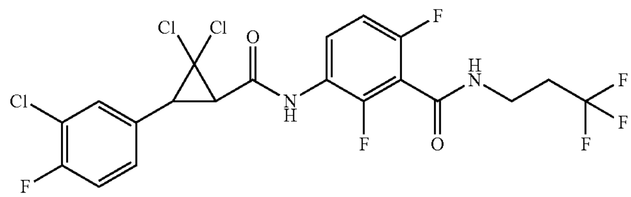 [SMILES: O=C(NCCC(F)(F)F)c1c(F)ccc(NC(=O)C2C(c3ccc(F)c(Cl)c3)C2(Cl)Cl)c1F] | 20 |
| F2024 | 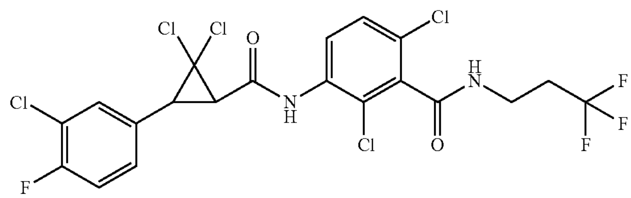 [SMILES: O=C(NCCC(F)(F)F)c1c(Cl)ccc(NC(=O)C2C(c3ccc(F)c(Cl)c3)C2(Cl)Cl)c1Cl] | 20 |
| F2025 | 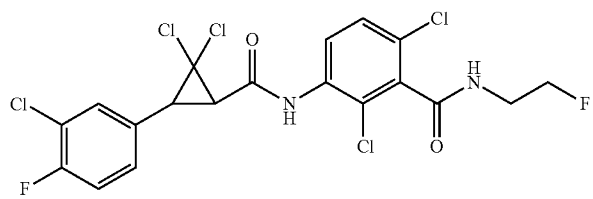 [SMILES: O=C(NCCF)c1c(Cl)ccc(NC(=O)C2C(c3ccc(F)c(Cl)c3)C2(Cl)Cl)c1Cl] | 20 |
| F2026 | 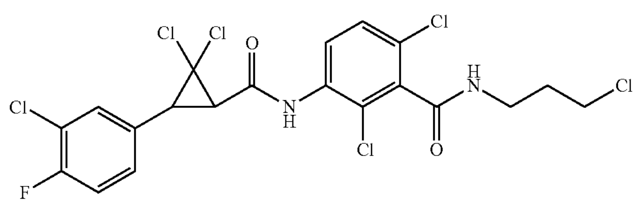 [SMILES: O=C(NCCCCl)c1c(Cl)ccc(NC(=O)C2C(c3ccc(F)c(Cl)c3)C2(Cl)Cl)c1Cl] | 20 |
| F2027 | 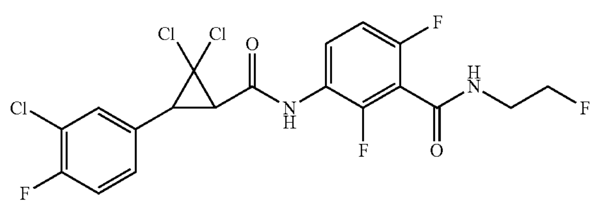 [SMILES: O=C(NCCF)c1c(F)ccc(NC(=O)C2C(c3ccc(F)c(Cl)c3)C2(Cl)Cl)c1F] | 20 |
| F2028 | 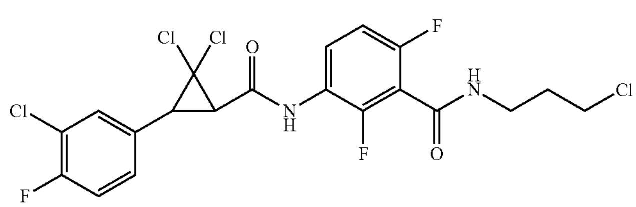 [SMILES: O=C(NCCCCl)c1c(F)ccc(NC(=O)C2C(c3ccc(F)c(Cl)c3)C2(Cl)Cl)c1F] | 20 |
| F2029 | 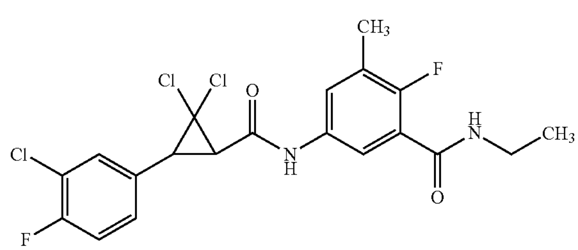 [SMILES: CCNC(=O)c1cc(NC(=O)C2C(c3ccc(F)c(Cl)c3)C2(Cl)Cl)cc(C)c1F] | 25 |

TABLE 2-continued

Structure and preparation method for F Series molecules

| No. | Structure | Prep.* |
|---|---|---|
| F2030 | 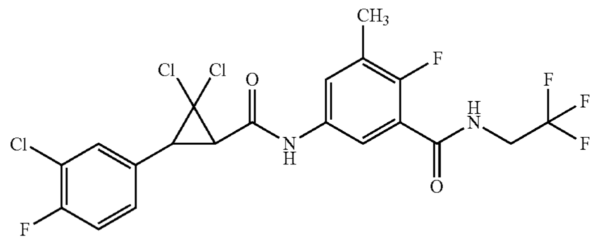 [SMILES: Cc1cc(NC(=O)C2C(c3ccc(F)c(Cl)c3)C2(Cl)Cl)cc(C(=O)NCC(F)(F)F)c1F] | 25 |
| F2031 | 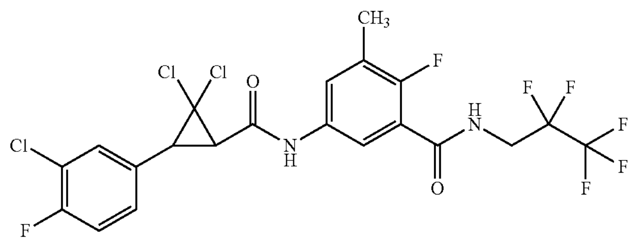 [SMILES: Cc1cc(NC(=O)C2C(c3ccc(F)c(Cl)c3)C2(Cl)Cl)cc(C(=O)NCC(F)(F)C(F)(F)F)c1F] | 25 |
| F2032 | 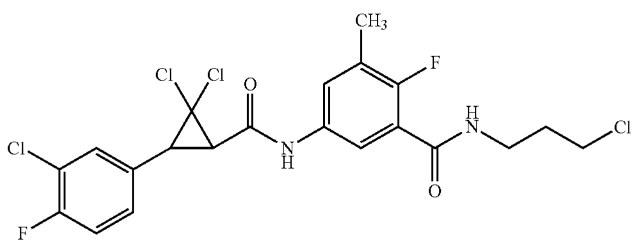 [SMILES: Cc1cc(NC(=O)C2C(c3ccc(F)c(Cl)c3)C2(Cl)Cl)cc(C(=O)NCCCCl)c1F] | 25 |
| F2033 | 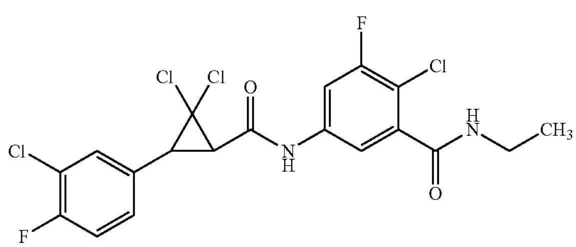 | 25 |
| F2034 | 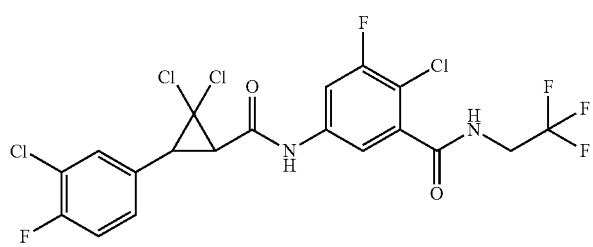 [SMILES: O=C(NCC(F)(F)F)c1cc(NC(=O)C2C(c3ccc(F)c(Cl)c3)C2(Cl)Cl)cc(F)c1Cl] | 25 |
| F2035 | 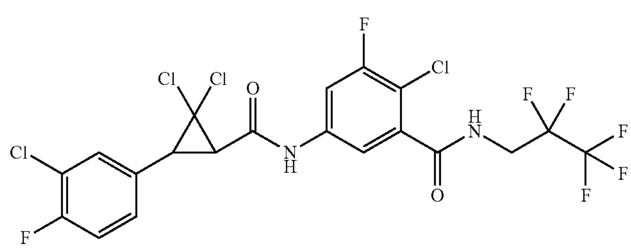 [SMILES: O=C(NCC(F)(F)C(F)(F)F)c1cc(NC(=O)C2C(c3ccc(F)c(Cl)c3)C2(Cl)Cl)cc(F)c1Cl] | 25 |

TABLE 2-continued

Structure and preparation method for F Series molecules

| No. | Structure | Prep.* |
|---|---|---|
| F2036 | 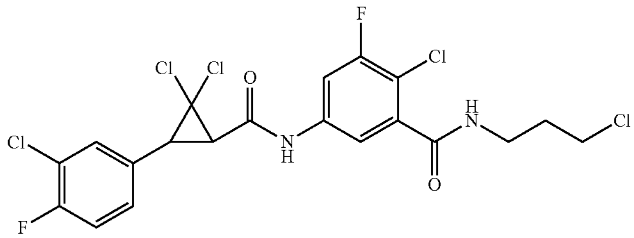 [SMILES: O=C(NCCCCl)c1cc(NC(=O)C2C(c3ccc(F)c(Cl)c3)C2(Cl)Cl)cc(F)c1Cl] | 25 |
| F2037 | 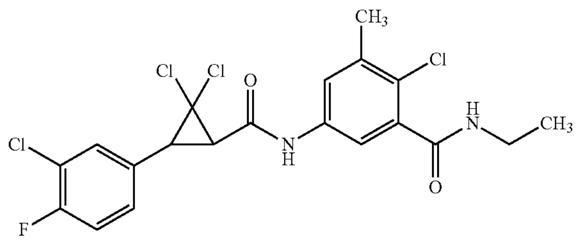 [SMILES: CCNC(=O)c1cc(NC(=O)C2C(c3ccc(F)c(Cl)c3)C2(Cl)Cl)cc(C)c1Cl] | 25 |
| F2038 | 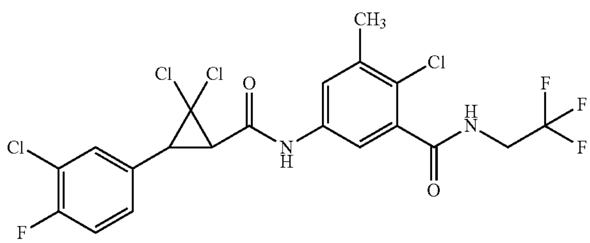 | 25 |
| F2039 | 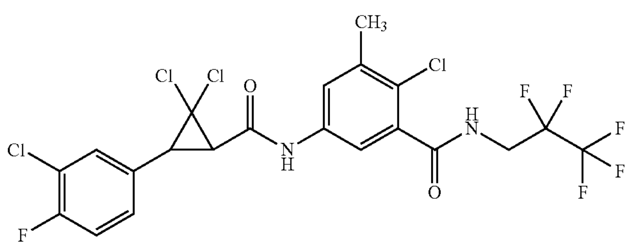 | 25 |
| F2040 | 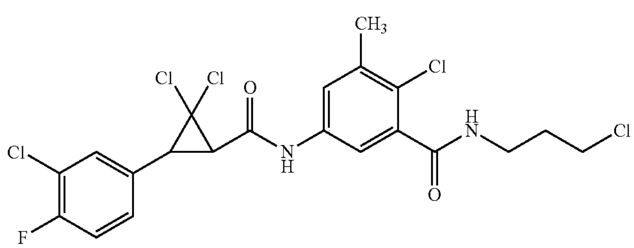 | 25 |
| F2041 | 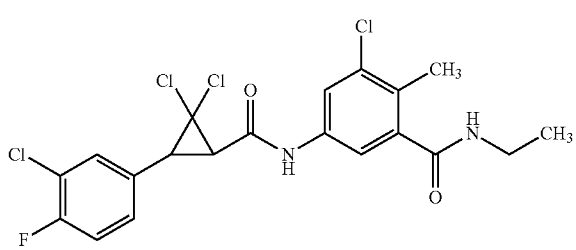 [SMILES: CCNC(=O)c1cc(NC(=O)C2C(c3ccc(F)c(Cl)c3)C2(Cl)Cl)cc(Cl)c1C] | 25 |

TABLE 2-continued

Structure and preparation method for F Series molecules

| No. | Structure | Prep.* |
|---|---|---|
| F2042 | 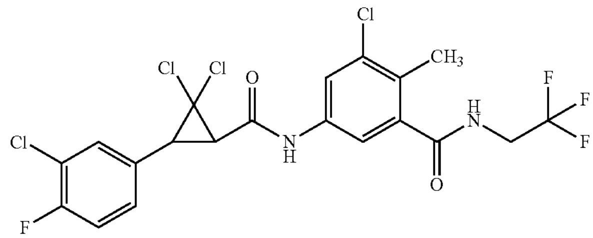 | 25 |
| F2043 | 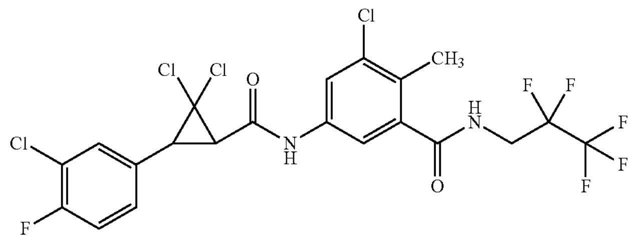 [SMILES: Cc1c(Cl)cc(NC(=O)C2C(c3ccc(F)c(Cl)c3)C2(Cl)Cl)cc1C(=O)NCC(F)(F)C(F)(F)F] | 25 |
| F2044 | 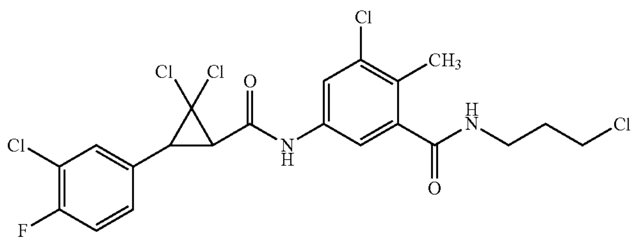 | 25 |
| F2045 | 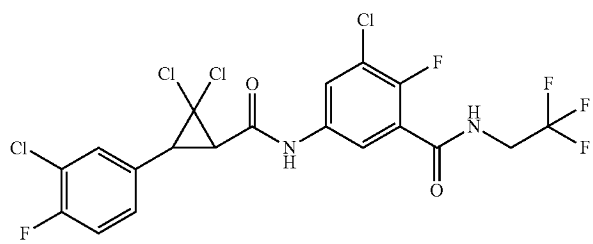 | 25 |
| F2046 | 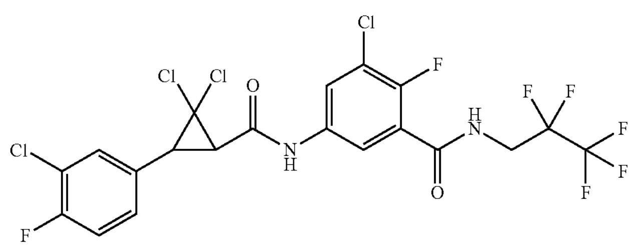 | 25 |
| F2047 | 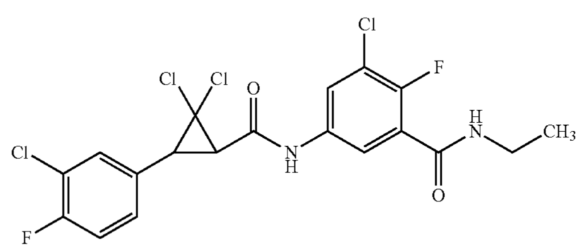 | 25 |

TABLE 2-continued

Structure and preparation method for F Series molecules

| No. | Structure | Prep.* |
|---|---|---|
| F2048 | 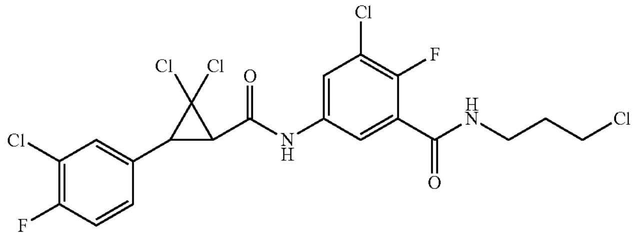 | 25 |
| F2049 | 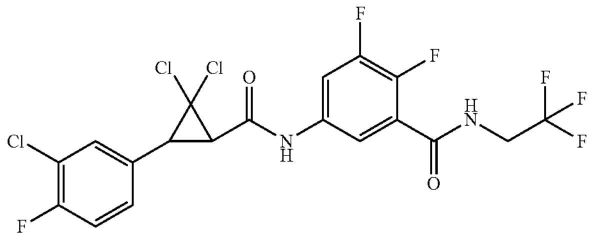 [SMILES: O=C(NCC(F)(F)F)c1cc(NC(=O)C2C(c3ccc(F)c(Cl)c3)C2(Cl)Cl)cc(F)c1F] | 25 |
| F2050 | 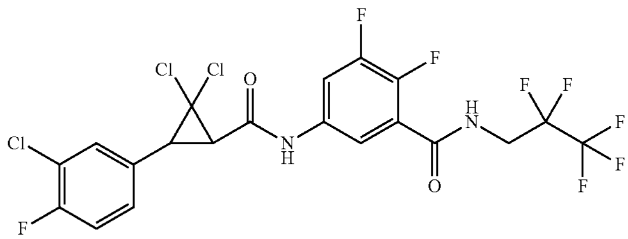 | 25 |
| F2051 | 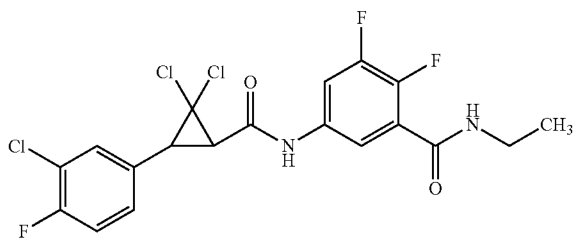 [SMILES: CCNC(=O)c1cc(NC(=O)C2C(c3ccc(F)c(Cl)c3)C2(Cl)Cl)cc(F)c1F] | 25 |
| F2052 | 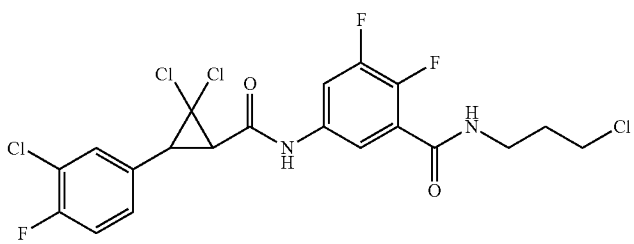 [SMILES: O=C(NCCCCl)c1cc(NC(=O)C2C(c3ccc(F)c(Cl)c3)C2(Cl)Cl)cc(F)c1F] | 25 |
| F2053 | 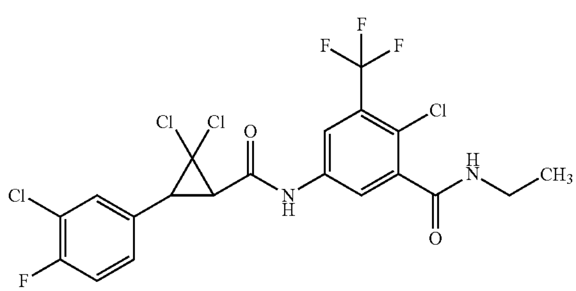 [SMILES: CCNC(=O)c1cc(NC(=O)C2C(c3ccc(F)c(Cl)c3)C2(Cl)Cl)cc(C(F)(F)F)c1Cl] | 25 |

TABLE 2-continued

Structure and preparation method for F Series molecules

| No. | Structure | Prep.* |
|---|---|---|
| F2054 | 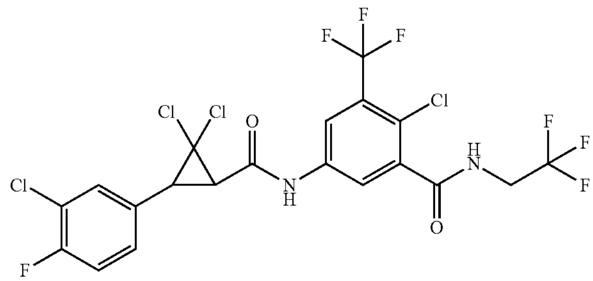 [SMILES: O=C(NCC(F)(F)F)c1cc(NC(=O)C2C(c3ccc(F)c(Cl)c3)C2(Cl)Cl)cc(C(F)(F)F)c1Cl] | 25 |
| F2055 | 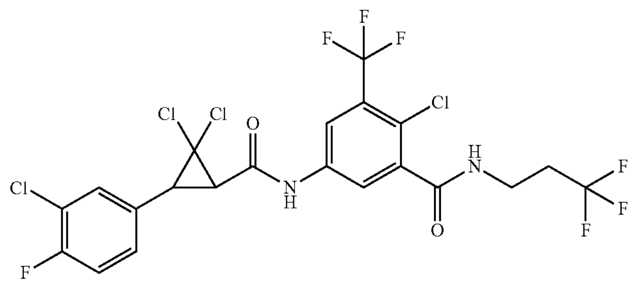 [SMILES: O=C(NCCC(F)(F)F)c1cc(NC(=O)C2C(c3ccc(F)c(Cl)c3)C2(Cl)Cl)cc(C(F)(F)F)c1Cl] | 25 |
| F2056 | 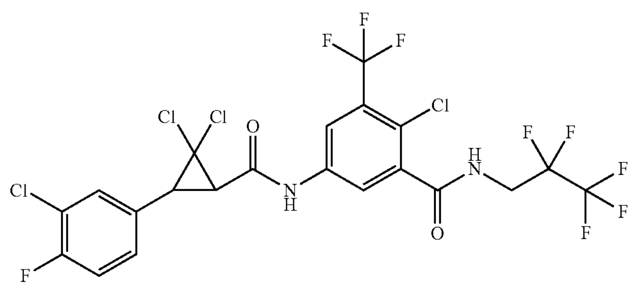 [SMILES: O=C(NCC(F)(F)C(F)(F)F)c1cc(NC(=O)C2C(c3ccc(F)c(Cl)c3)C2(Cl)Cl)cc(C(F)(F)F)c1Cl] | 25 |
| F2057 | 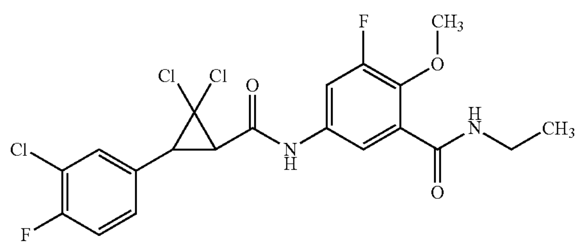 [SMILES: CCNC(=O)c1cc(NC(=O)C2C(c3ccc(F)c(Cl)c3)C2(Cl)Cl)cc(F)c1OC] | 25 |
| F2058 | 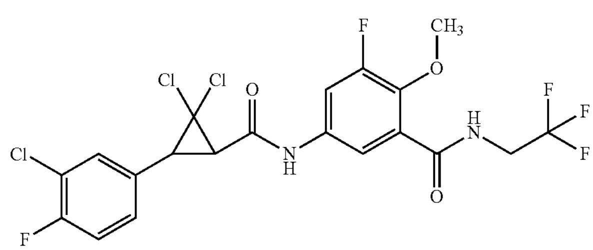 [SMILES: COc1c(F)cc(NC(=O)C2C(c3ccc(F)c(Cl)c3)C2(Cl)Cl)cc1C(=O)NCC(F)(F)F] | 25 |

TABLE 2-continued
Structure and preparation method for F Series molecules
| No. | Structure | Prep.* |
|---|---|---|
| F2059 | 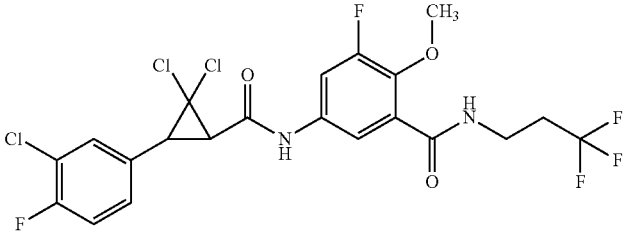 [SMILES: COc1c(F)cc(NC(=O)C2C(c3ccc(F)c(Cl)c3)C2(Cl)Cl)cc1C(=O)NCCC(F)(F)F] | 25 |
| F2060 | 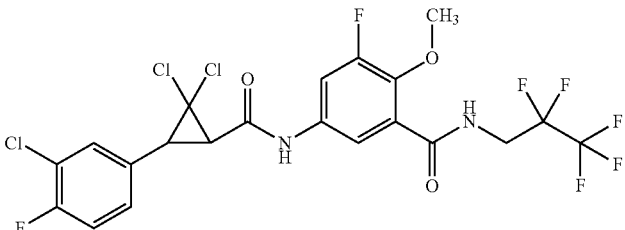 | 25 |
| F2061 | 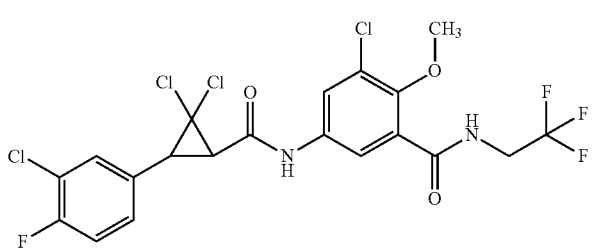 [SMILES: COc1c(Cl)cc(NC(=O)C2C(c3ccc(F)c(Cl)c3)C2(Cl)Cl)cc1C(=O)NCC(F)(F)F] | 25 |
| F2062 | 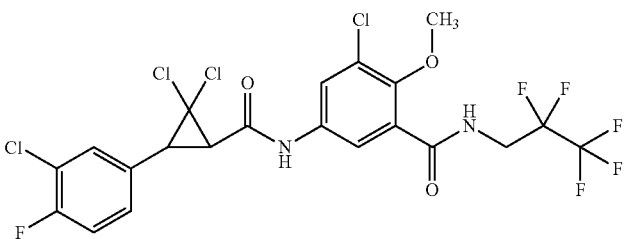 [SMILES: COc1c(Cl)cc(NC(=O)C2C(c3ccc(F)c(Cl)c3)C2(Cl)Cl)cc1C(=O)NCC(F)(F)C(F)(F)F] | 25 |
| F2063 | 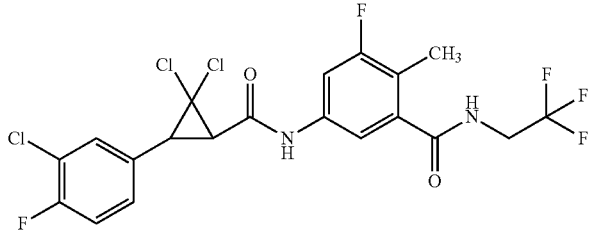 | 25 |
| F2064 | 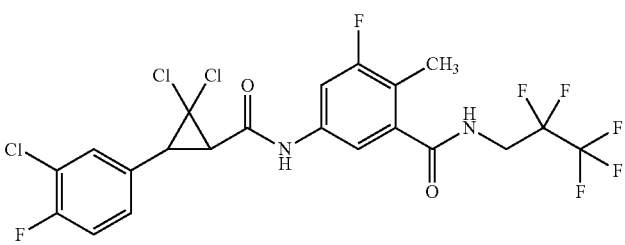 [SMILES: Cc1c(F)cc(NC(=O)C2C(c3ccc(F)c(Cl)c3)C2(Cl)Cl)cc1C(=O)NCC(F)(F)C(F)(F)F] | 25 |

TABLE 2-continued

Structure and preparation method for F Series molecules

| No. | Structure | Prep.* |
|---|---|---|
| F2066 | 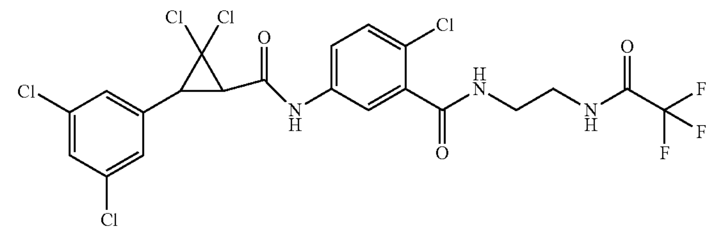 [SMILES: O=C(NCCNC(=O)C(F)(F)F)c1cc(NC(=O)C2C(c3cc(Cl)cc(Cl)c3)C2(Cl)Cl)ccc1Cl] | 20 |
| F2067 | 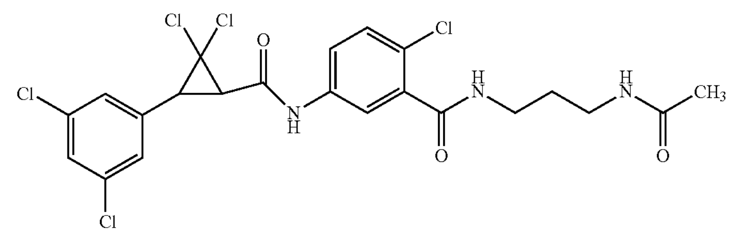 [SMILES: CC(=O)NCCCNC(=O)c1cc(NC(=O)C2C(c3cc(Cl)cc(Cl)c3)C2(Cl)Cl)ccc1Cl] | 20 |
| F2068 | 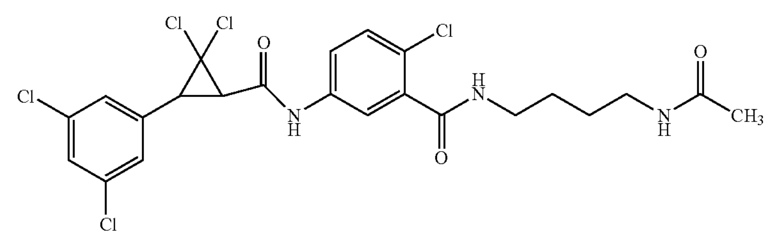 [SMILES: CC(=O)NCCCCNC(=O)c1cc(NC(=O)C2C(c3cc(Cl)cc(Cl)c3)C2(Cl)Cl)ccc1Cl] | 20 |
| F2069 | 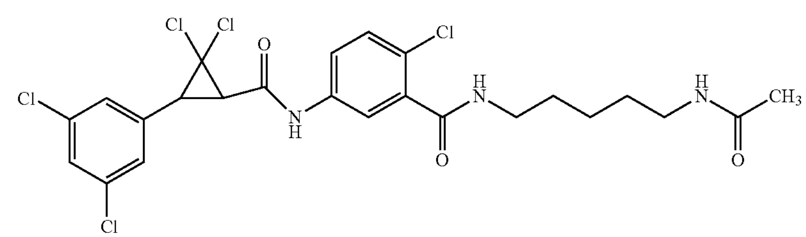 [SMILES: CC(=O)NCCCCCNC(=O)c1cc(NC(=O)C2C(c3cc(Cl)cc(Cl)c3)C2(Cl)Cl)ccc1Cl] | 20 |
| F2070 | 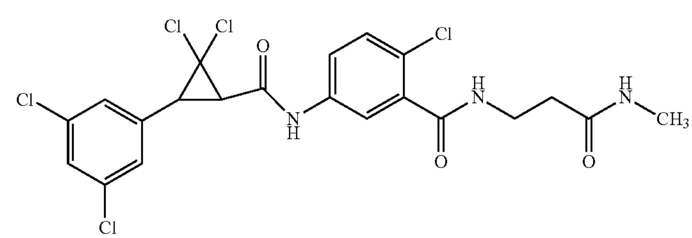 [SMILES: CNC(=O)CCNC(=O)c1cc(NC(=O)C2C(c3cc(Cl)cc(Cl)c3)C2(Cl)Cl)ccc1Cl] | 20 |
| F2071 | 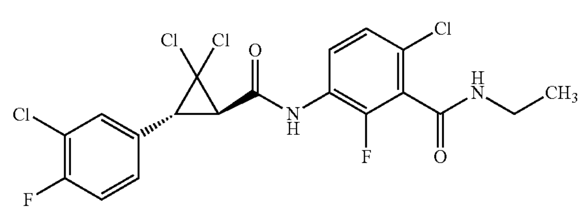 [SMILES: CCNC(=O)c1c(Cl)ccc(NC(=O)[C@H]2[C@H](c3ccc(F)c(Cl)c3)C2(Cl)Cl)c1F] | 83 |

TABLE 2-continued

Structure and preparation method for F Series molecules

| No. | Structure | Prep.* |
|---|---|---|
| F2072 | 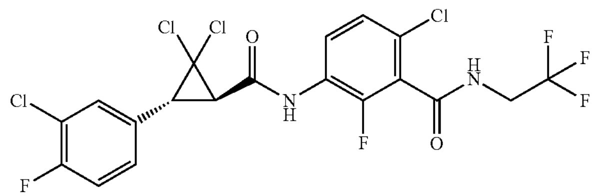 [SMILES: O=C(NCC(F)(F)F)c1c(Cl)ccc(NC(=O)[C@H]2[C@H](c3ccc(F)c(Cl)c3)C2(Cl)Cl)c1F] | 83 |
| F2073 | 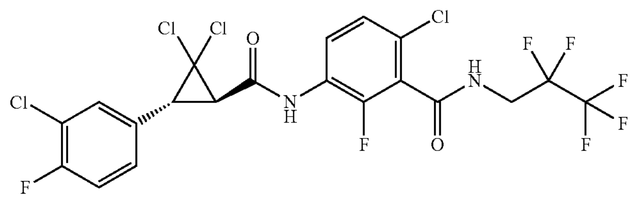 [SMILES: O=C(NCC(F)(F)C(F)(F)F)c1c(Cl)ccc(NC(=O)[C@H]2[C@H](c3ccc(F)c(Cl)c3)C2(Cl)Cl)c1F] | 83 |
| F2074 | 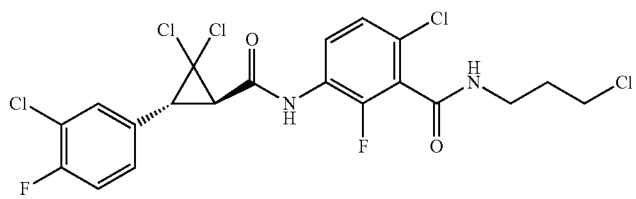 [SMILES: O=C(NCCCCl)c1c(Cl)ccc(NC(=O)[C@H]2[C@H](c3ccc(F)c(Cl)c3)C2(Cl)Cl)c1F] | 83 |
| F2075 | 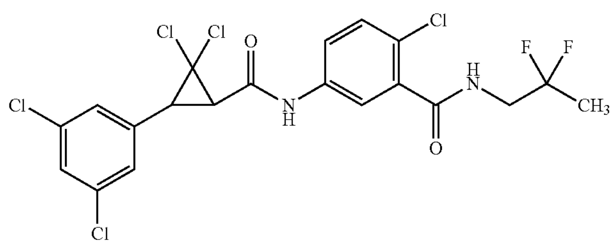 [SMILES: CC(F)(F)CNC(=O)c1cc(NC(=O)C2C(c3cc(Cl)cc(Cl)c3)C2(Cl)Cl)ccc1Cl] | 20 |
| F2076 | 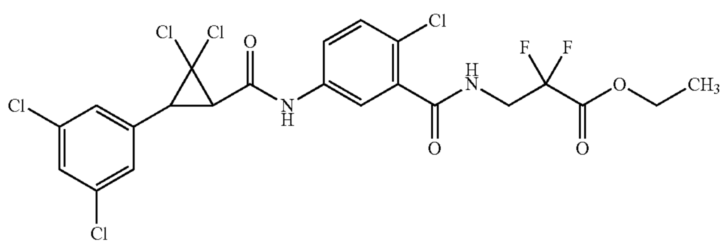 [SMILES: CCOC(=O)C(F)(F)CNC(=O)c1cc(NC(=O)C2C(c3cc(Cl)cc(Cl)c3)C2(Cl)Cl)ccc1Cl] | 20 |
| F2077 | 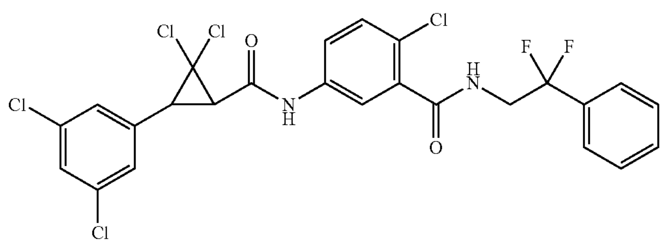 [SMILES: O=C(NCC(F)(F)c1ccccc1)c1cc(NC(=O)C2C(c3cc(Cl)cc(Cl)c3)C2(Cl)Cl)ccc1Cl] | 20 |

TABLE 2-continued
Structure and preparation method for F Series molecules
| No. | Structure | Prep.* |
|---|---|---|
| F2078 | 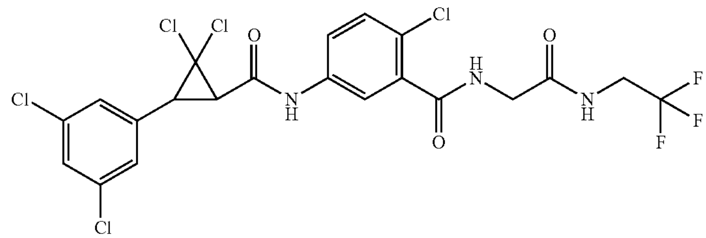 [SMILES: O=C(CNC(=O)c1cc(NC(=O)C2C(c3cc(Cl)cc(Cl)c3)C2(Cl)Cl)ccc1Cl)NCC(F)(F)F] | 20 |
| F2079 | 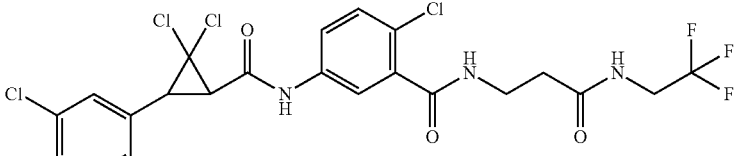 | 20 |
| F2080 | 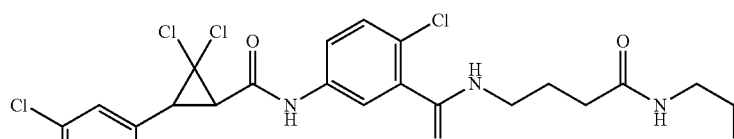 | 20 |
| F2081 | 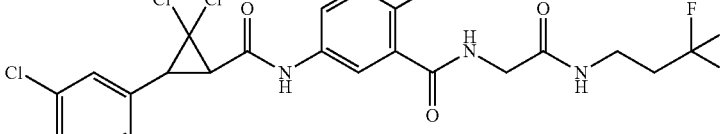 | 20 |
| F2082 | 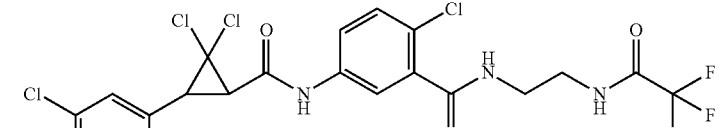 | 20 |
| F2083 | 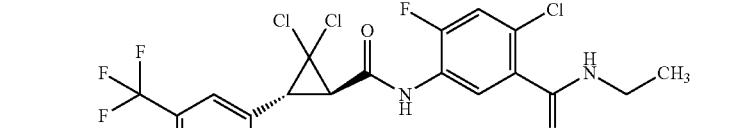 | 25 |

TABLE 2-continued

Structure and preparation method for F Series molecules

| No. | Structure | Prep.* |
|---|---|---|
| F2084 | 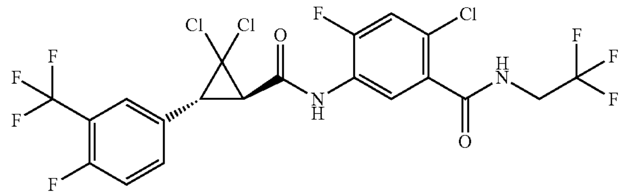 [SMILES: O=C(NCC(F)(F)F)c1cc(NC(=O)[C@H]2[C@H](c3ccc(F)c(C(F)(F)F)c3)C2(Cl)Cl)c(F)cc1Cl] | 25 |
| F2085 | 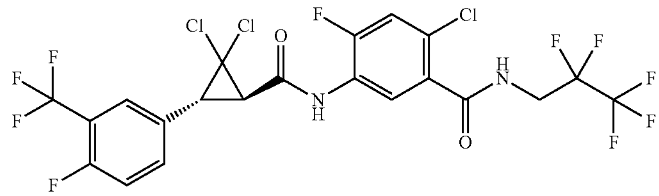 [SMILES: O=C(NCC(F)(F)C(F)(F)F)c1cc(NC(=O)[C@H]2[C@H](c3ccc(F)c(C(F)(F)F)c3)C2(Cl)Cl)c(F)cc1Cl] | 25 |
| F2086 | 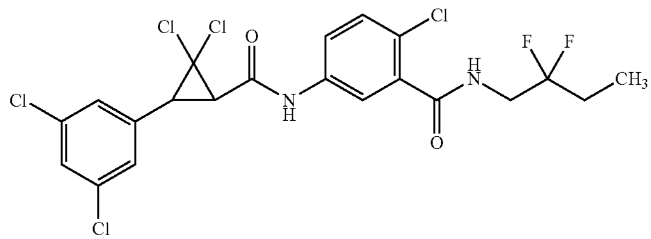 [SMILES: CCC(F)(F)CNC(=O)c1cc(NC(=O)C2C(c3cc(Cl)cc(Cl)c3)C2(Cl)Cl)ccc1Cl] | 20 |
| F2087 | 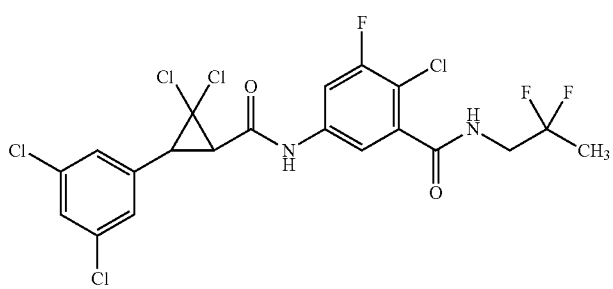 [SMILES: CC(F)(F)CNC(=O)c1cc(NC(=O)C2C(c3cc(Cl)cc(Cl)c3)C2(Cl)Cl)cc(F)c1Cl] | 20 |
| F2088 | 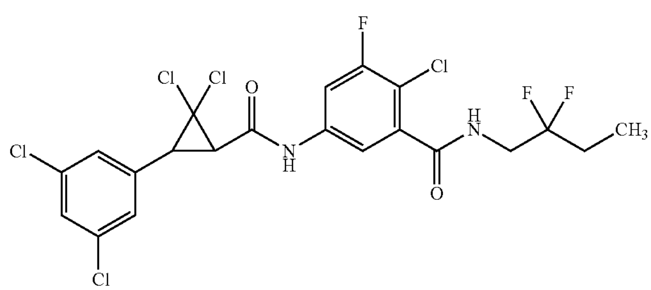 [SMILES: CCC(F)(F)CNC(=O)c1cc(NC(=O)C2C(c3cc(Cl)cc(Cl)c3)C2(Cl)Cl)cc(F)c1Cl] | 20 |
| F2089 | 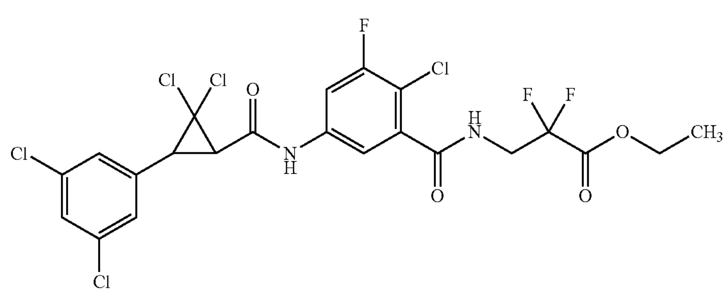 [SMILES: CCOC(=O)C(F)(F)CNC(=O)c1cc(NC(=O)C2C(c3cc(Cl)cc(Cl)c3)C2(Cl)Cl)cc(F)c1Cl] | 20 |

TABLE 2-continued

Structure and preparation method for F Series molecules

| No. | Structure | Prep.* |
|---|---|---|
| F2091 | 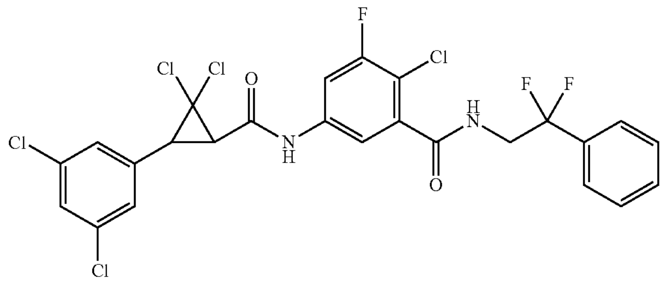 [SMILES: O=C(NCC(F)(F)c1ccccc1)c1cc(NC(=O)C2C(c3cc(Cl)cc(Cl)c3)C2(Cl)Cl)cc(F)c1Cl] | 20 |
| F2092 | 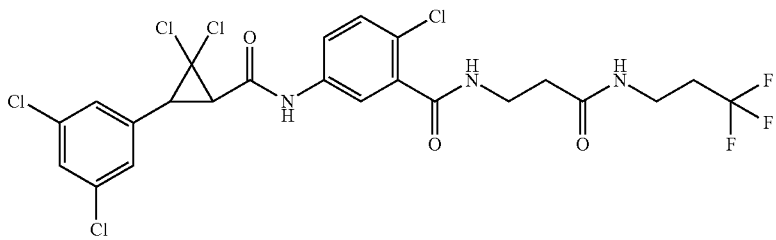 [SMILES: O=C(CCNC(=O)c1cc(NC(=O)C2C(c3cc(Cl)cc(Cl)c3)C2(Cl)Cl)ccc1Cl)NCCC(F)(F)F] | 20 |
| F2093 | 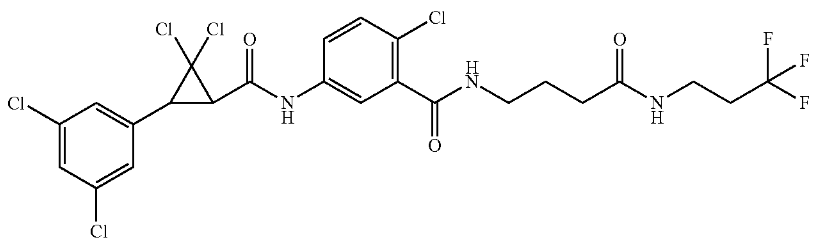 [SMILES: O=C(CCCNC(=O)c1cc(NC(=O)C2C(c3cc(Cl)cc(Cl)c3)C2(Cl)Cl)ccc1Cl)NCCC(F)(F)F] | 20 |
| F2094 | 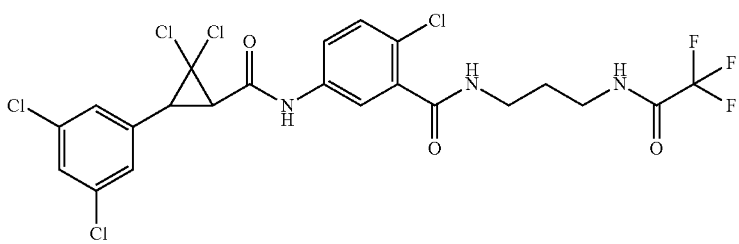 [SMILES: O=C(NCCCNC(=O)C(F)(F)F)c1cc(NC(=O)C2C(c3cc(Cl)cc(Cl)c3)C2(Cl)Cl)ccc1Cl] | 20 |
| F2095 | 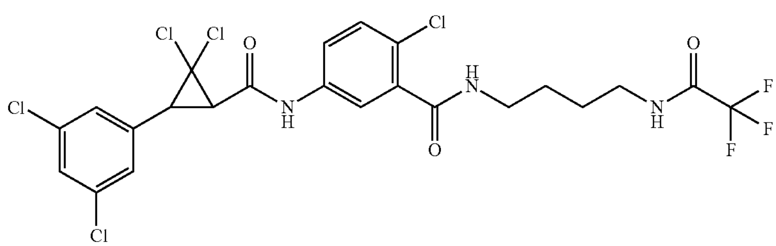 [SMILES: O=C(NCCCCNC(=O)C(F)(F)F)c1cc(NC(=O)C2C(c3cc(Cl)cc(Cl)c3)C2(Cl)Cl)ccc1Cl] | 20 |
| F2096 | 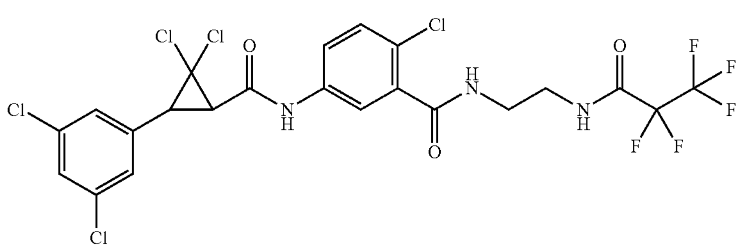 [SMILES: O=C(NCCNC(=O)C(F)(F)C(F)(F)F)c1cc(NC(=O)C2C(c3cc(Cl)cc(Cl)c3)C2(Cl)Cl)ccc1Cl] | 20 |

TABLE 2-continued

Structure and preparation method for F Series molecules

| No. | Structure | Prep.* |
|---|---|---|
| F2097 | 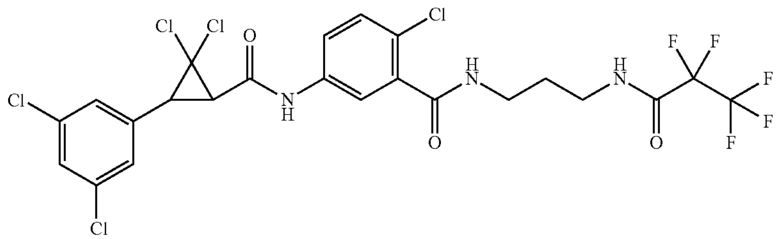 [SMILES: O=C(NCCCNC(=O)C(F)(F)C(F)(F)F)c1cc(NC(=O)C2C(c3cc(Cl)cc(Cl)c3)C2(Cl)Cl)ccc1Cl] | 20 |
| F2098 | 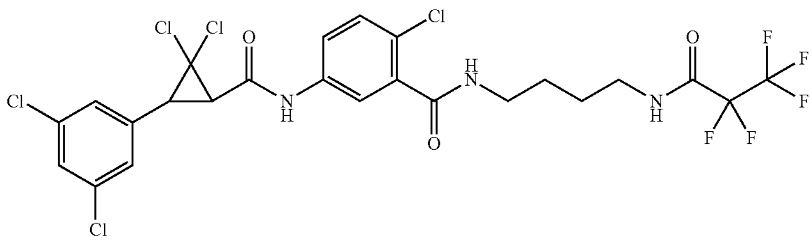 [SMILES: O=C(NCCCCNC(=O)C(F)(F)C(F)(F)F)c1cc(NC(=O)C2C(c3cc(Cl)cc(Cl)c3)C2(Cl)Cl)ccc1Cl] | 20 |
| F2099 | 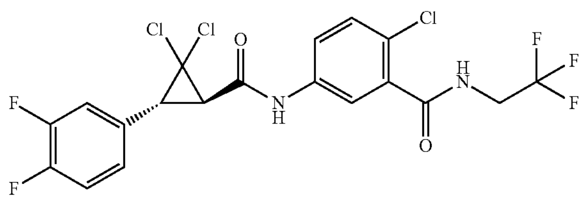 [SMILES: O=C(NCC(F)(F)F)c1cc(NC(=O)[C@H]2[C@H](c3ccc(F)c(F)c3)C2(Cl)Cl)ccc1Cl] | 20 |
| F2100 | 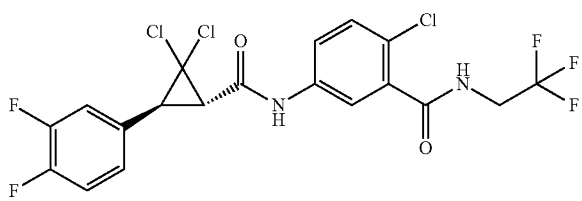 [SMILES: O=C(NCC(F)(F)F)c1cc(NC(=O)[C@@H]2[C@@H](c3ccc(F)c(F)c3)C2(Cl)Cl)ccc1Cl] | 20 |
| F2501 | 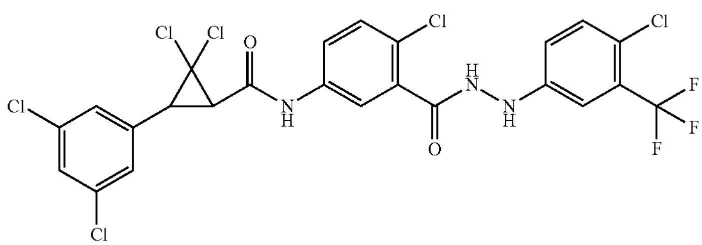 [SMILES: O=C(NNc1ccc(Cl)c(C(F)(F)F)c1)c1cc(NC(=O)C2C(c3cc(Cl)cc(Cl)c3)C2(Cl)Cl)ccc1Cl] | 28 |
| F2502 | 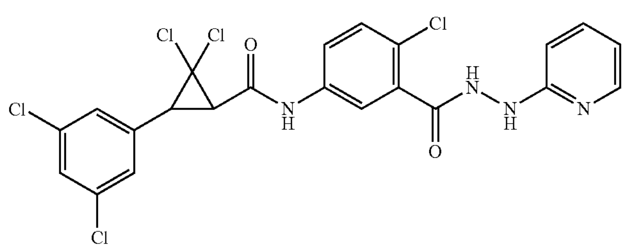 [SMILES: O=C(NNc1ccccn1)c1cc(NC(=O)C2C(c3cc(Cl)cc(Cl)c3)C2(Cl)Cl)ccc1Cl] | 28 |

TABLE 2-continued

Structure and preparation method for F Series molecules

| No. | Structure | Prep.* |
|---|---|---|
| F2503 | 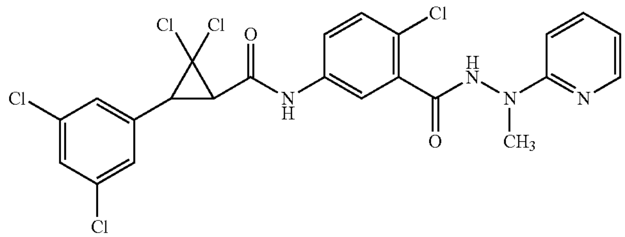 [SMILES: CN(NC(=O)c1cc(NC(=O)C2C(c3cc(Cl)cc(Cl)c3)C2(Cl)Cl)ccc1Cl)c1ccccn1] | 28 |
| F2504 | 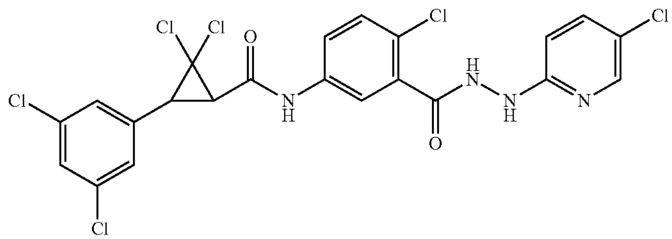 [SMILES: O=C(NNc1ccc(Cl)cn1)c1cc(NC(=O)C2C(c3cc(Cl)cc(Cl)c3)C2(Cl)Cl)ccc1Cl] | 28 |
| F2505 | 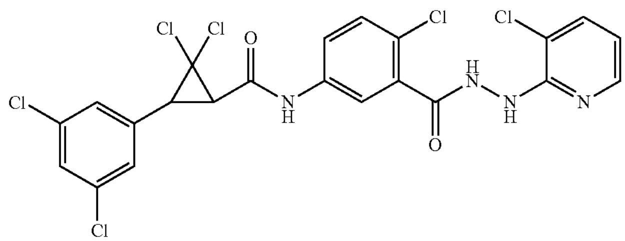 [SMILES: O=C(NNc1ncccc1Cl)c1cc(NC(=O)C2C(c3cc(Cl)cc(Cl)c3)C2(Cl)Cl)ccc1Cl] | 28 |
| F2506 | 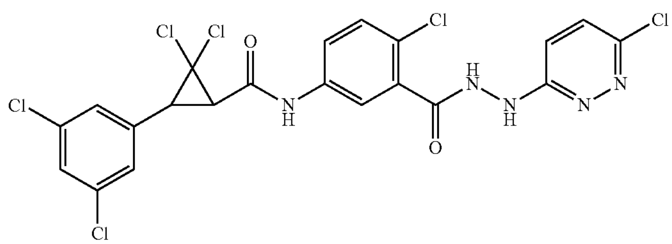 [SMILES: O=C(NNc1ccc(Cl)nn1)c1cc(NC(=O)C2C(c3cc(Cl)cc(Cl)c3)C2(Cl)Cl)ccc1Cl] | 28 |
| F2507 | 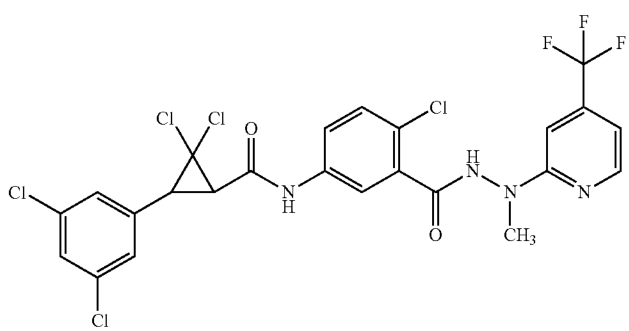 [SMILES: CN(NC(=O)c1cc(NC(=O)C2C(c3cc(Cl)cc(Cl)c3)C2(Cl)Cl)ccc1Cl)c1cc(C(F)(F)F)ccn1] | 28 |
| F2508 | 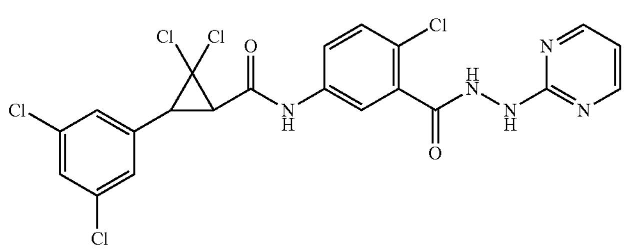 [SMILES: O=C(NNc1ncccn1)c1cc(NC(=O)C2C(c3cc(Cl)cc(Cl)c3)C2(Cl)Cl)ccc1Cl] | 28 |

TABLE 2-continued

Structure and preparation method for F Series molecules

| No. | Structure | Prep.* |
|---|---|---|
| F2509 | 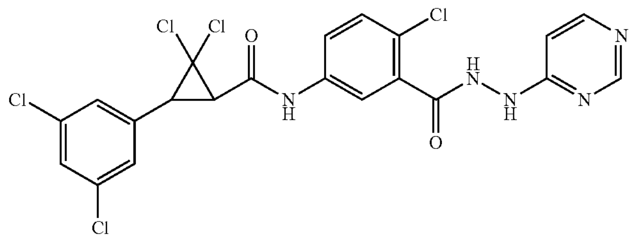 [SMILES: O=C(NNc1ccncn1)c1cc(NC(=O)C2C(c3cc(Cl)cc(Cl)c3)C2(Cl)Cl)ccc1Cl] | 28 |
| F2510 | 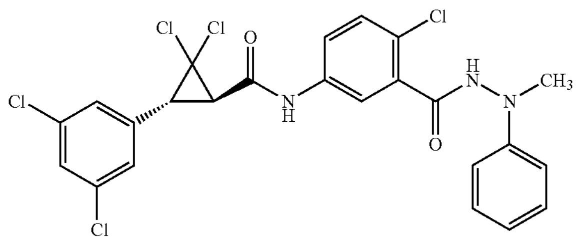 [SMILES: CN(NC(=O)c1cc(NC(=O)[C@H]2[C@H](c3cc(Cl)cc(Cl)c3)C2(Cl)Cl)ccc1Cl)c1ccccc1] | 28 |
| F2511 | 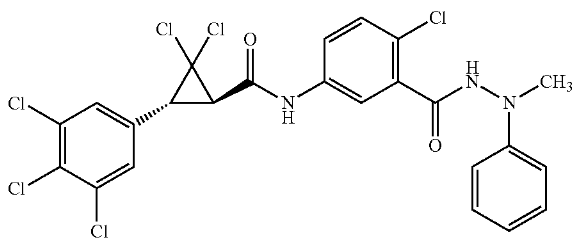 [SMILES: CN(NC(=O)c1cc(NC(=O)[C@H]2[C@H](c3cc(Cl)c(Cl)c(Cl)c3)C2(Cl)Cl)ccc1Cl)c1ccccc1] | 28 |
| F2512 | 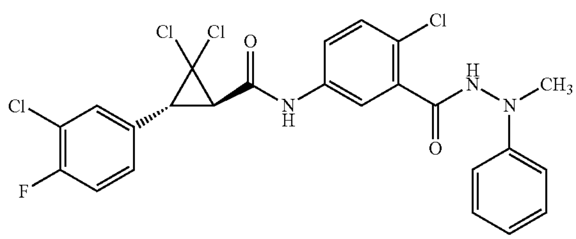 [SMILES: CN(NC(=O)c1cc(NC(=O)[C@H]2[C@H](c3ccc(F)c(Cl)c3)C2(Cl)Cl)ccc1Cl)c1ccccc1] | 28 |
| F2513 | 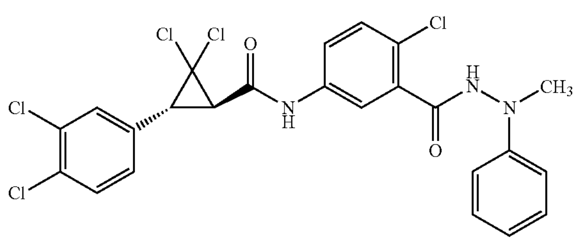 [SMILES: CN(NC(=O)c1cc(NC(=O)[C@H]2[C@H](c3ccc(Cl)c(Cl)c3)C2(Cl)Cl)ccc1Cl)c1ccccc1] | 28 |
| F2514 | 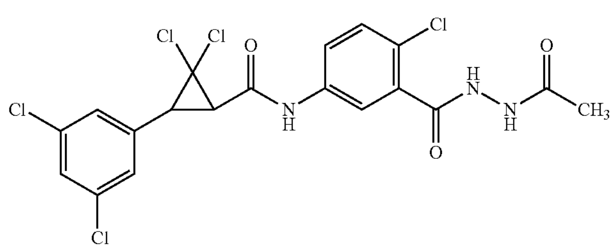 [SMILES: CC(=O)NNC(=O)c1cc(NC(=O)C2C(c3cc(Cl)cc(Cl)c3)C2(Cl)Cl)ccc1Cl] | 29 |

TABLE 2-continued

Structure and preparation method for F Series molecules

| No. | Structure | Prep.* |
|---|---|---|
| F2515 | 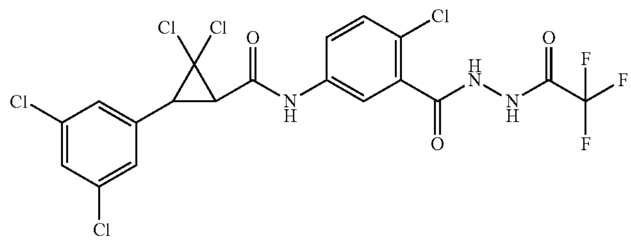 [SMILES: O=C(NNC(=O)C(F)(F)F)c1cc(NC(=O)C2C(c3cc(Cl)cc(Cl)c3)C2(Cl)Cl)ccc1Cl] | 29 |
| F2516 | 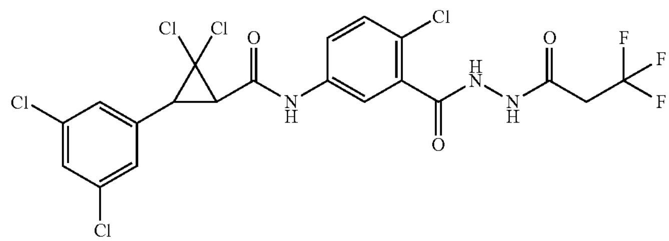 [SMILES: O=C(CC(F)(F)F)NNC(=O)c1cc(NC(=O)C2C(c3cc(Cl)cc(Cl)c3)C2(Cl)Cl)ccc1Cl] | 29 |
| F2517 | 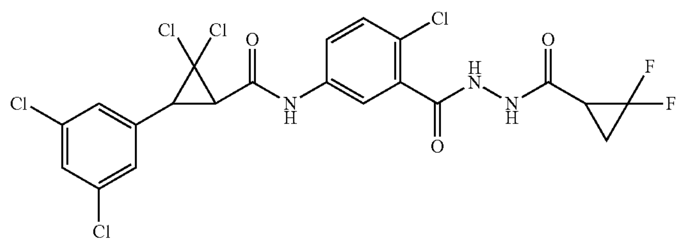 [SMILES: O=C(NNC(=O)C1CC1(F)F)c1cc(NC(=O)C2C(c3cc(Cl)cc(Cl)c3)C2(Cl)Cl)ccc1Cl] | 29 |
| F2518 | 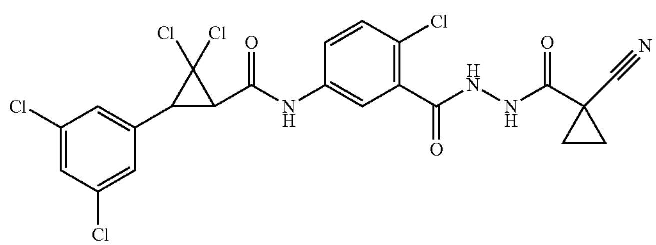 [SMILES: N#CC1(C(=O)NNC(=O)c2cc(NC(=O)C3C(c4cc(Cl)cc(Cl)c4)C3(Cl)Cl)ccc2Cl)CC1] | 29 |
| F2519 | 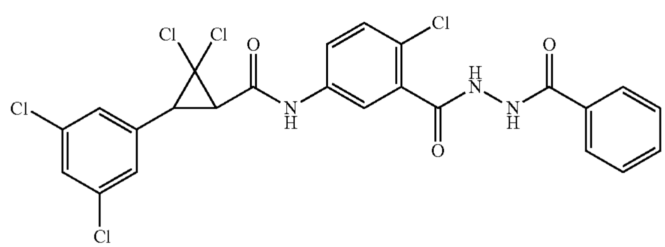 [SMILES: O=C(NNC(=O)c1cc(NC(=O)C2C(c3cc(Cl)cc(Cl)c3)C2(Cl)Cl)ccc1Cl)c1ccccc1] | 29 |
| F2520 | 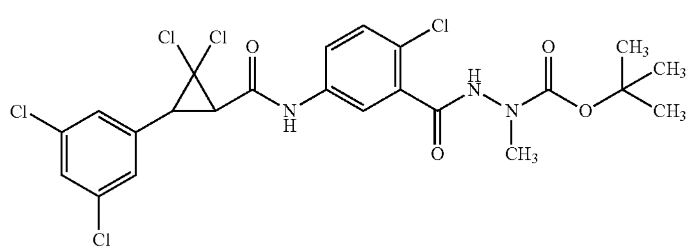 [SMILES: CN(NC(=O)c1cc(NC(=O)C2C(c3cc(Cl)cc(Cl)c3)C2(Cl)Cl)ccc1Cl)C(=O)OC(C)(C)C] | 29 |

TABLE 2-continued

Structure and preparation method for F Series molecules

| No. | Structure | Prep.* |
|---|---|---|
| F2521 | 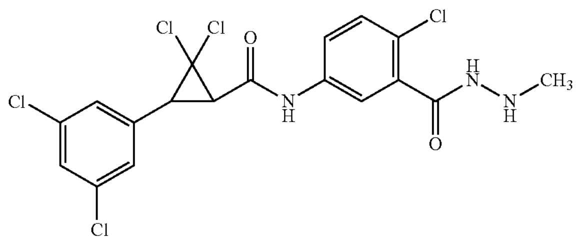 [SMILES: CNNC(=O)c1cc(NC(=O)C2C(c3cc(Cl)cc(Cl)c3)C2(Cl)Cl)ccc1Cl] | 29 |
| F2522 | 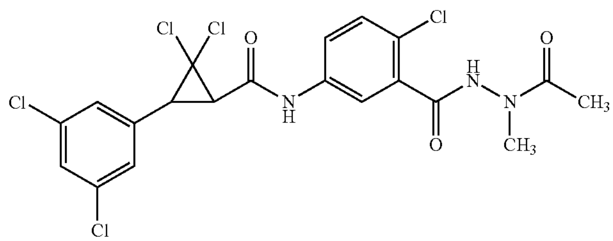 [SMILES: CC(=O)N(C)NC(=O)c1cc(NC(=O)C2C(c3cc(Cl)cc(Cl)c3)C2(Cl)Cl)ccc1Cl] | 29 |
| F2523 | 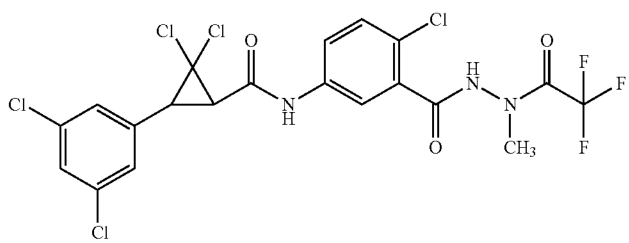 [SMILES: CN(NC(=O)c1cc(NC(=O)C2C(c3cc(Cl)cc(Cl)c3)C2(Cl)Cl)ccc1Cl)C(=O)C(F)(F)F] | 29 |
| F2524 | 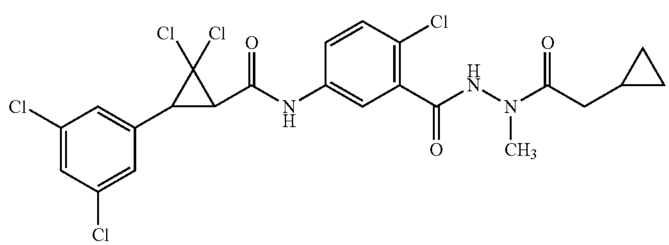 [SMILES: CN(NC(=O)c1cc(NC(=O)C2C(c3cc(Cl)cc(Cl)c3)C2(Cl)Cl)ccc1Cl)C(=O)CC1CC1] | 29 |
| F2525 | 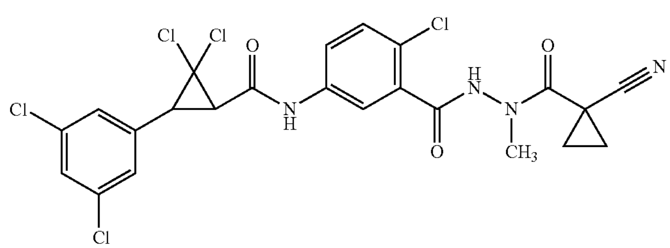 [SMILES: CN(NC(=O)c1cc(NC(=O)C2C(c3cc(Cl)cc(Cl)c3)C2(Cl)Cl)ccc1Cl)C(=O)C1(C#N)CC1] | 29 |
| F2526 | 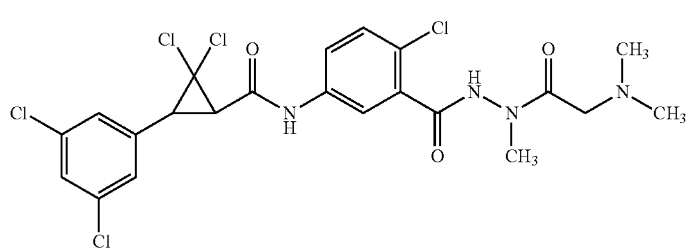 [SMILES: CN(C)CC(=O)N(C)NC(=O)c1cc(NC(=O)C2C(c3cc(Cl)cc(Cl)c3)C2(Cl)Cl)ccc1Cl] | 29 |

TABLE 2-continued

Structure and preparation method for F Series molecules

| No. | Structure | Prep.* |
|---|---|---|
| F2527 | 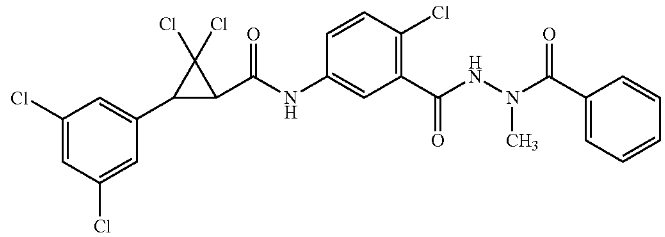 [SMILES: CN(NC(=O)c1cc(NC(=O)C2C(c3cc(Cl)cc(Cl)c3)C2(Cl)Cl)ccc1Cl)C(=O)c1ccccc1] | 29 |
| F2528 | 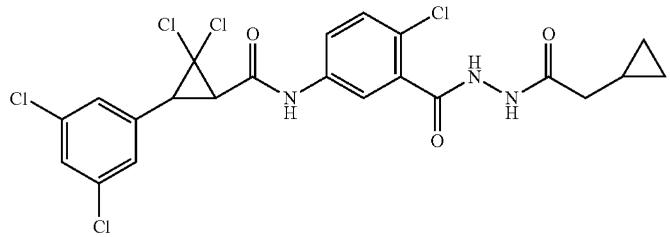 [SMILES: O=C(CC1CC1)NNC(=O)c1cc(NC(=O)C2C(c3cc(Cl)cc(Cl)c3)C2(Cl)Cl)ccc1Cl] | 29 |
| F2529 | 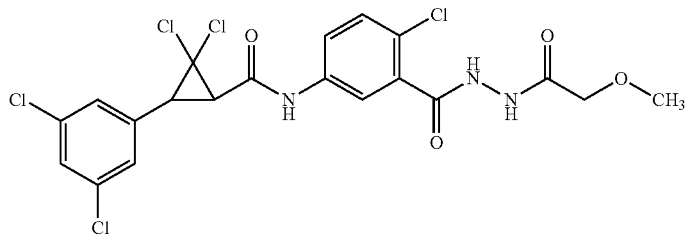 [SMILES: COCC(=O)NNC(=O)c1cc(NC(=O)C2C(c3cc(Cl)cc(Cl)c3)C2(Cl)Cl)ccc1Cl] | 29 |
| F2530 | 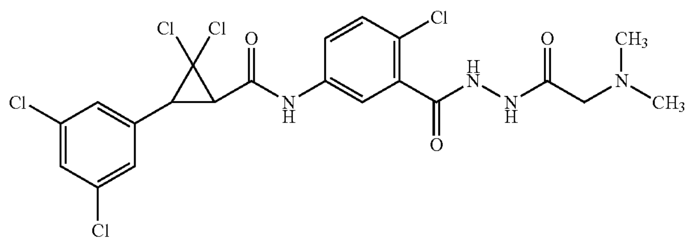 [SMILES: CN(C)CC(=O)NNC(=O)c1cc(NC(=O)C2C(c3cc(Cl)cc(Cl)c3)C2(Cl)Cl)ccc1Cl] | 29 |
| F2531 | 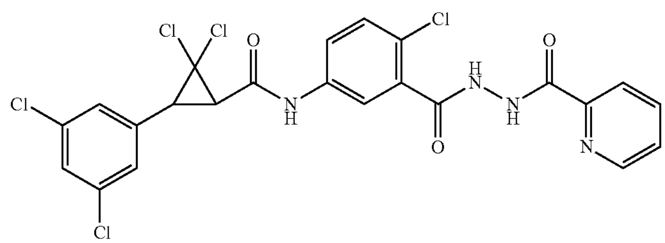 [SMILES: O=C(NNC(=O)c1cc(NC(=O)C2C(c3cc(Cl)cc(Cl)c3)C2(Cl)Cl)ccc1Cl)c1ccccn1] | 29 |
| F2532 | 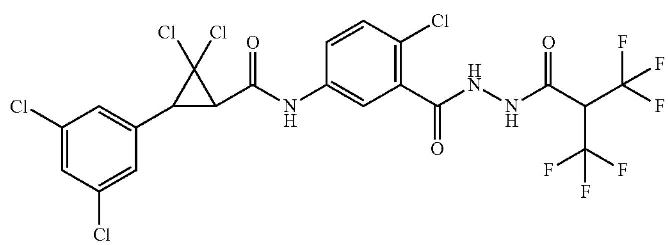 [SMILES: O=C(NNC(=O)C(C(F)(F)F)C(F)(F)F)c1cc(NC(=O)C2C(c3cc(Cl)cc(Cl)c3)C2(Cl)Cl)ccc1Cl] | 29 |

TABLE 2-continued
Structure and preparation method for F Series molecules
| No. | Structure | Prep.* |
|---|---|---|
| F2533 | 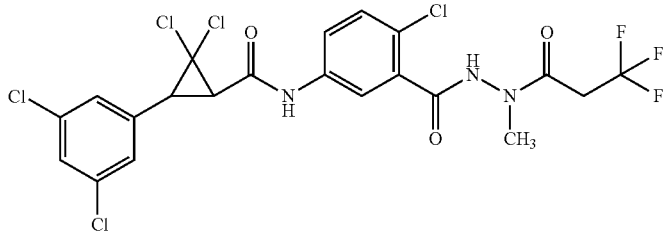 [SMILES: CN(NC(=O)c1cc(NC(=O)C2C(c3cc(Cl)cc(Cl)c3)C2(Cl)Cl)ccc1Cl)C(=O)CC(F)(F)F] | 29 |
| F2534 | 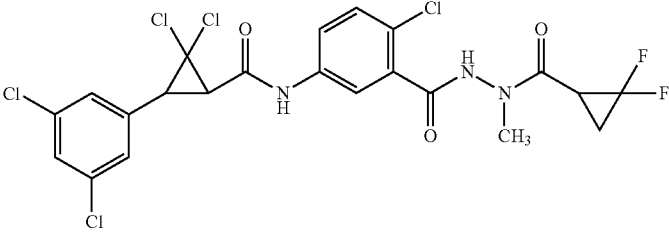 [SMILES: CN(NC(=O)c1cc(NC(=O)C2C(c3cc(Cl)cc(Cl)c3)C2(Cl)Cl)ccc1Cl)C(=O)C1CC1(F)F] | 29 |
| F2535 | 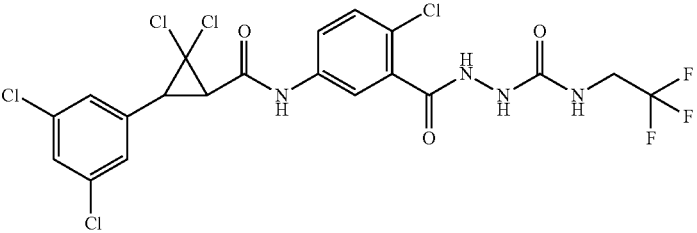 [SMILES: O=C(NCC(F)(F)F)NNC(=O)c1cc(NC(=O)C2C(c3cc(Cl)cc(Cl)c3)C2(Cl)Cl)ccc1Cl] | 30 |
| F2536 | 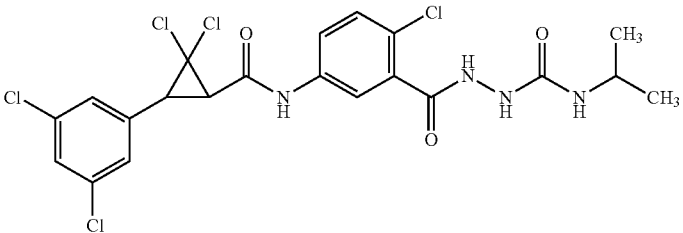 [SMILES: CC(C)NC(=O)NNC(=O)c1cc(NC(=O)C2C(c3cc(Cl)cc(Cl)c3)C2(Cl)Cl)ccc1Cl] | 30 |
| F2537 | 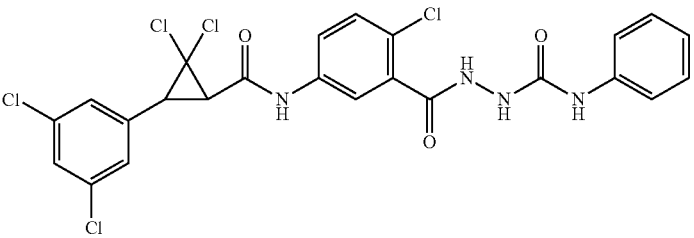 [SMILES: O=C(NNC(=O)c1cc(NC(=O)C2C(c3cc(Cl)cc(Cl)c3)C2(Cl)Cl)ccc1Cl)Nc1ccccc1] | 30 |
| F2538 | 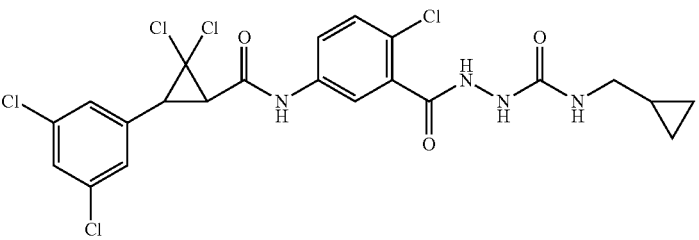 [SMILES: O=C(NCC1CC1)NNC(=O)c1cc(NC(=O)C2C(c3cc(Cl)cc(Cl)c3)C2(Cl)Cl)ccc1Cl] | 30 |

TABLE 2-continued

Structure and preparation method for F Series molecules

| No. | Structure | Prep.* |
|---|---|---|
| F2539 | 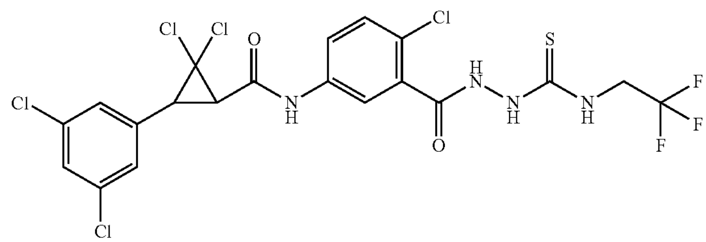 | 31 |
| F2540 | 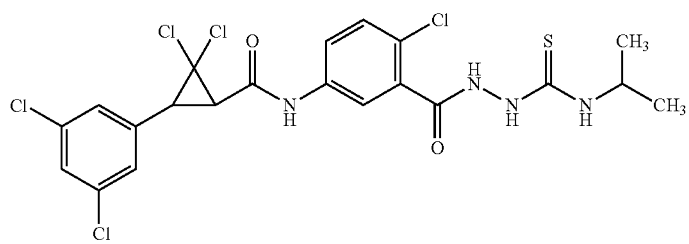 [SMILES: CC(C)NC(=S)NNC(=O)c1cc(NC(=O)C2C(c3cc(Cl)cc(Cl)c3)C2(Cl)Cl)ccc1Cl] | 31 |
| F2541 | 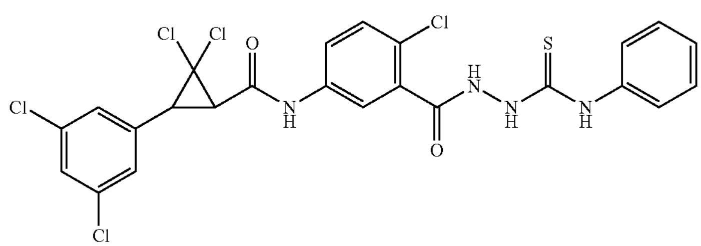 | 31 |
| F2542 | 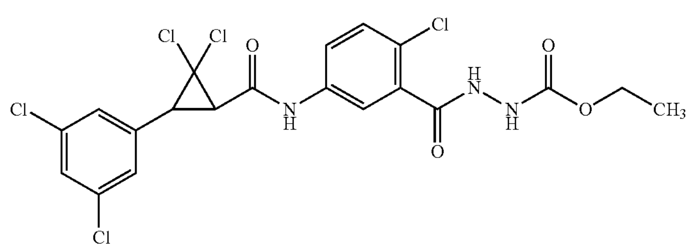 [SMILES: CCOC(=O)NNC(=O)c1cc(NC(=O)C2C(c3cc(Cl)cc(Cl)c3)C2(Cl)Cl)ccc1Cl] | 32 |
| F2543 | 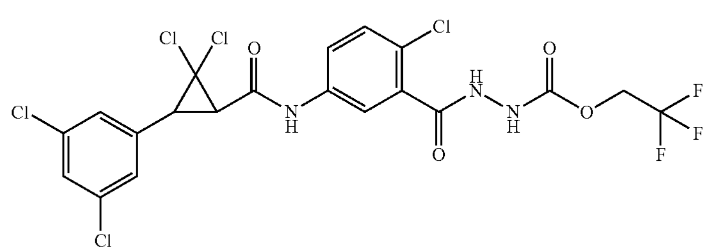 [SMILES: O=C(NNC(=O)c1cc(NC(=O)C2C(c3cc(Cl)cc(Cl)c3)C2(Cl)Cl)ccc1Cl)OCC(F)(F)F] | 32 |
| F2544 | 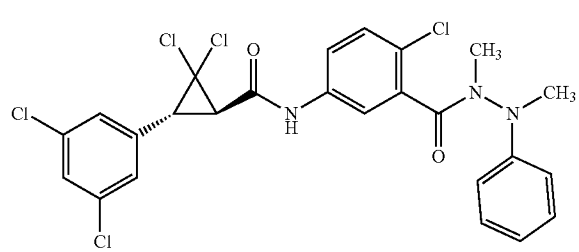 [SMILES: CN(C(=O)c1cc(NC(=O)[C@H]2[C@H](c3cc(Cl)cc(Cl)c3)C2(Cl)Cl)ccc1Cl)N(C)c1ccccc1] | 18 |

TABLE 2-continued

Structure and preparation method for F Series molecules

| No. | Structure | Prep.* |
|---|---|---|
| F2545 | 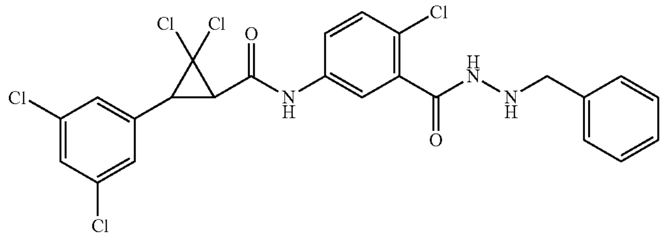 [SMILES: O=C(NNCc1ccccc1)c1cc(NC(=O)C2C(c3cc(Cl)cc(Cl)c3)C2(Cl)Cl)ccc1Cl] | 34 |
| F2546 | 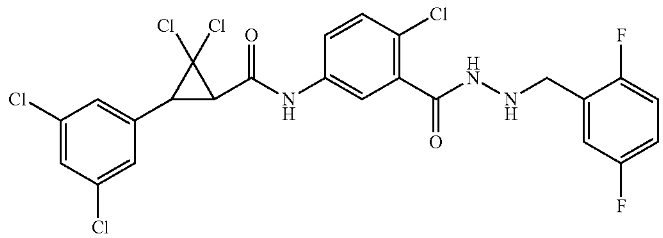 [SMILES: O=C(NNCc1cc(F)ccc1F)c1cc(NC(=O)C2C(c3cc(Cl)cc(Cl)c3)C2(Cl)Cl)ccc1Cl] | 34 |
| F2547 | 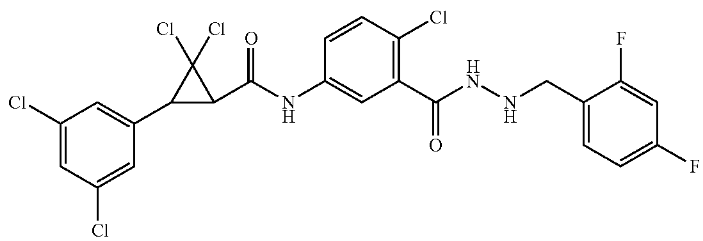 [SMILES: O=C(NNCc1ccc(F)cc1F)c1cc(NC(=O)C2C(c3cc(Cl)cc(Cl)c3)C2(Cl)Cl)ccc1Cl] | 34 |
| F2548 | 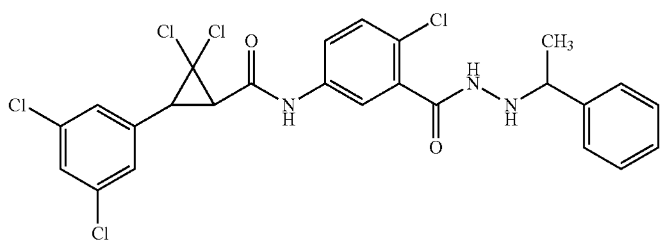 [SMILES: CC(NNC(=O)c1cc(NC(=O)C2C(c3cc(Cl)cc(Cl)c3)C2(Cl)Cl)ccc1Cl)c1ccccc1] | 34 |
| F2549 | 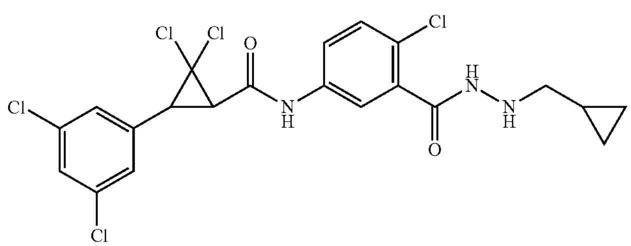 [SMILES: O=C(NNCC1CC1)c1cc(NC(=O)C2C(c3cc(Cl)cc(Cl)c3)C2(Cl)Cl)ccc1Cl] | 34 |
| F2550 | 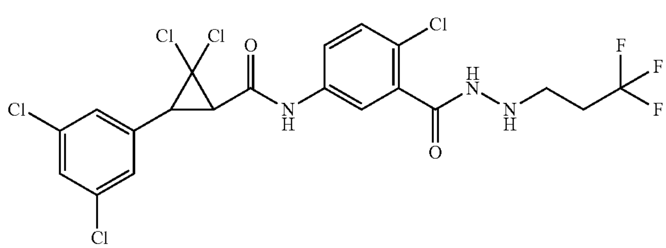 [SMILES: O=C(NNCCC(F)(F)F)c1cc(NC(=O)C2C(c3cc(Cl)cc(Cl)c3)C2(Cl)Cl)ccc1Cl] | 34 |

TABLE 2-continued

Structure and preparation method for F Series molecules

| No. | Structure | Prep.* |
|---|---|---|
| F2551 | 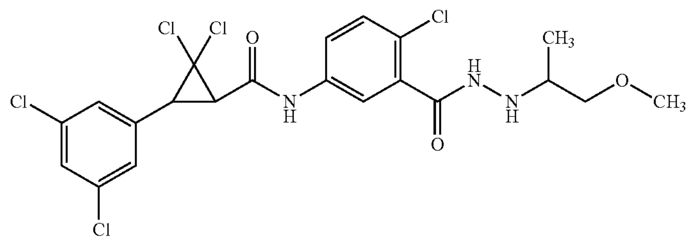 [SMILES: COCC(C)NNC(=O)c1cc(NC(=O)C2C(c3cc(Cl)cc(Cl)c3)C2(Cl)Cl)ccc1Cl] | 34 |
| F2552 | 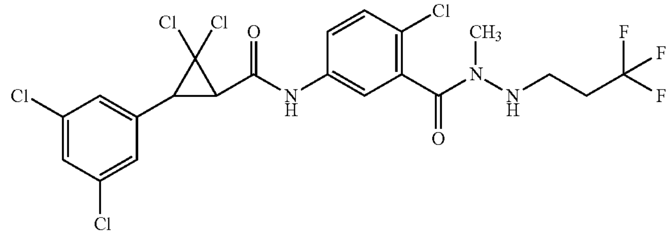 [SMILES: CN(NCCC(F)(F)F)C(=O)c1cc(NC(=O)C2C(c3cc(Cl)cc(Cl)c3)C2(Cl)Cl)ccc1Cl] | 34 |
| F2553 | 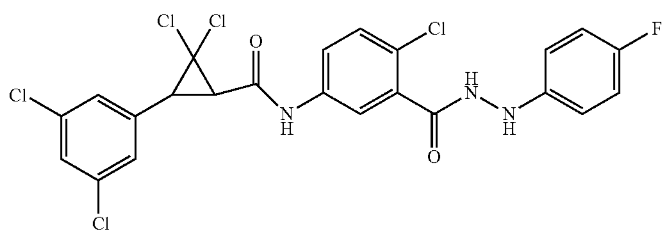 [SMILES: O=C(NNc1ccc(F)cc1)c1cc(NC(=O)C2C(c3cc(Cl)cc(Cl)c3)C2(Cl)Cl)ccc1Cl] | 28 |
| F2554 | 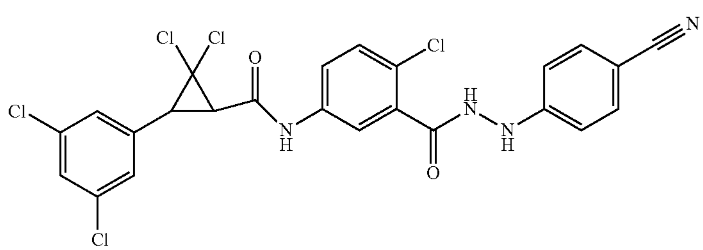 [SMILES: N#Cc1ccc(NNC(=O)c2cc(NC(=O)C3C(c4cc(Cl)cc(Cl)c4)C3(Cl)Cl)ccc2Cl)cc1] | 28 |
| F2555 | 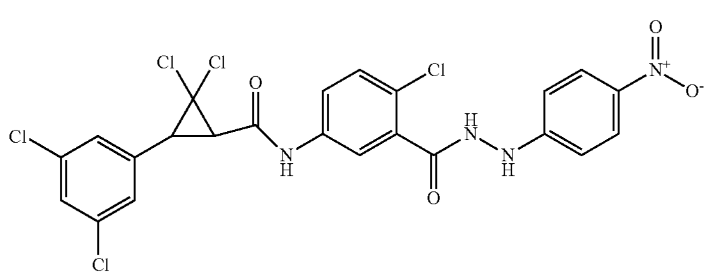 [SMILES: O=C(NNc1ccc([N+](=O)[O-])cc1)c1cc(NC(=O)C2C(c3cc(Cl)cc(Cl)c3)C2(Cl)Cl)ccc1Cl] | 28 |
| F2556 | 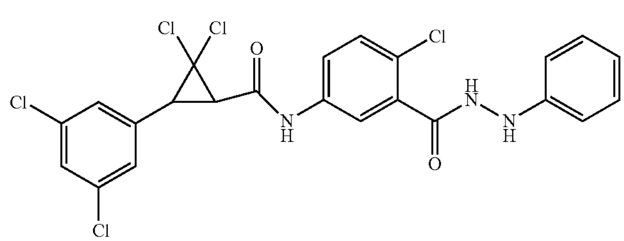 [SMILES: O=C(NNc1ccccc1)c1cc(NC(=O)C2C(c3cc(Cl)cc(Cl)c3)C2(Cl)Cl)ccc1Cl] | 28 |

TABLE 2-continued

Structure and preparation method for F Series molecules

| No. | Structure | Prep.* |
|---|---|---|
| F2557 | 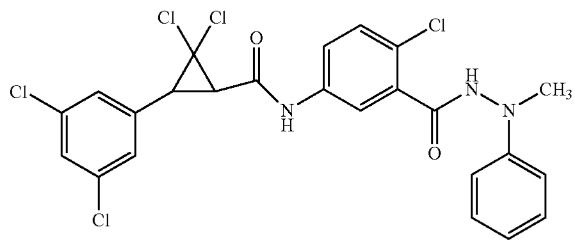 [SMILES: CN(NC(=O)c1cc(NC(=O)C2C(c3cc(Cl)cc(Cl)c3)C2(Cl)Cl)ccc1Cl)c1ccccc1] | 28 |
| F2558 | 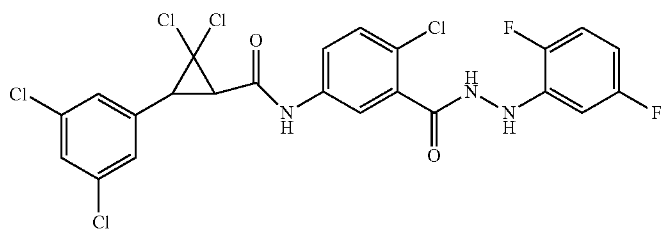 [SMILES: O=C(NNc1cc(F)ccc1F)c1cc(NC(=O)C2C(c3cc(Cl)cc(Cl)c3)C2(Cl)Cl)ccc1Cl] | 28 |
| F2559 | 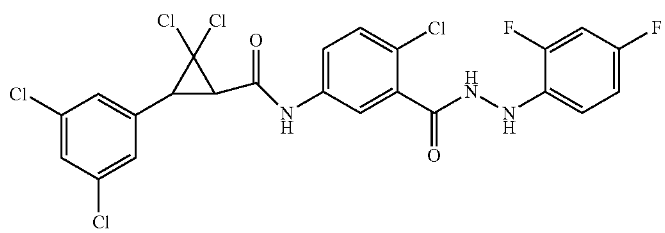 [SMILES: O=C(NNc1ccc(F)cc1F)c1cc(NC(=O)C2C(c3cc(Cl)cc(Cl)c3)C2(Cl)Cl)ccc1Cl] | 28 |
| F2560 | 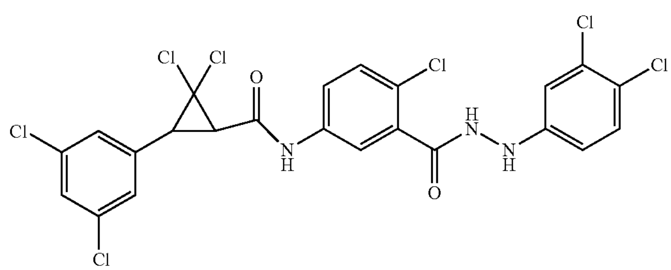 [SMILES: O=C(NNc1ccc(Cl)c(Cl)c1)c1cc(NC(=O)C2C(c3cc(Cl)cc(Cl)c3)C2(Cl)Cl)ccc1Cl] | 28 |
| F2561 | 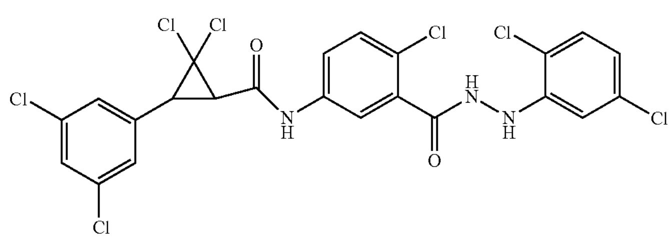 [SMILES: O=C(NNc1cc(Cl)ccc1Cl)c1cc(NC(=O)C2C(c3cc(Cl)cc(Cl)c3)C2(Cl)Cl)ccc1Cl] | 28 |
| F2562 | 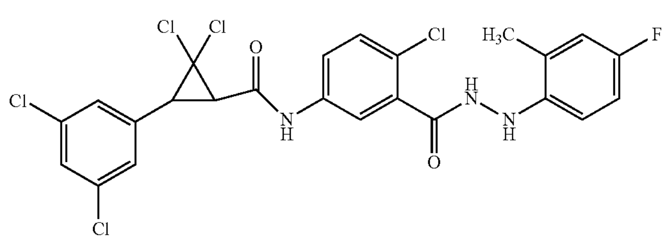 [SMILES: Cc1cc(F)ccc1NNC(=O)c1cc(NC(=O)C2C(c3cc(Cl)cc(Cl)c3)C2(Cl)Cl)ccc1Cl] | 28 |

TABLE 2-continued

Structure and preparation method for F Series molecules

| No. | Structure | Prep.* |
|---|---|---|
| F2563 | 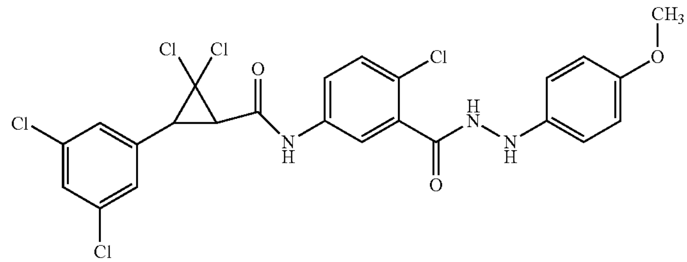 [SMILES: COc1ccc(NNC(=O)c2cc(NC(=O)C3C(c4cc(Cl)cc(Cl)c4)C3(Cl)Cl)ccc2Cl)cc1] | 28 |
| F2564 | 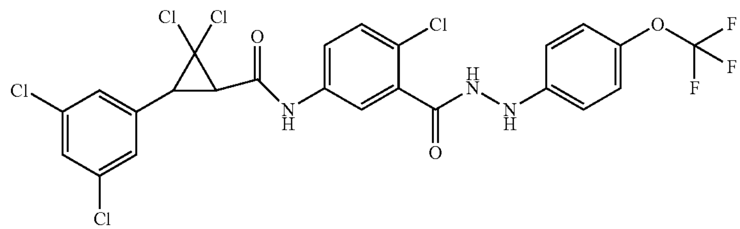 [SMILES: O=C(NNc1ccc(OC(F)(F)F)cc1)c1cc(NC(=O)C2C(c3cc(Cl)cc(Cl)c3)C2(Cl)Cl)ccc1Cl] | 28 |
| F2565 | 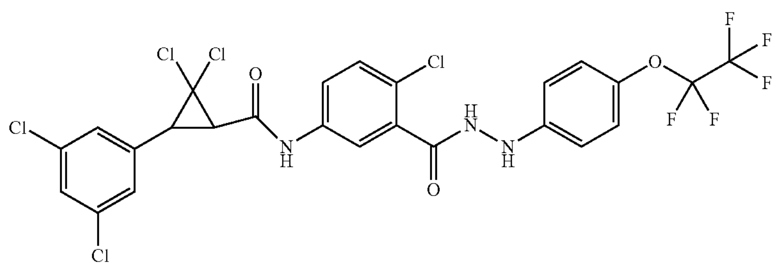 [SMILES: O=C(NNc1ccc(OC(F)(F)C(F)(F)F)cc1)c1cc(NC(=O)C2C(c3cc(Cl)cc(Cl)c3)C2(Cl)Cl)ccc1Cl] | 28 |
| F2566 | 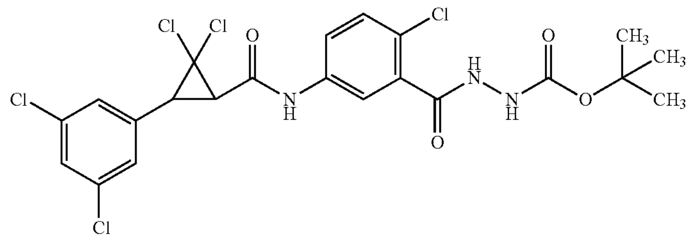 [SMILES: CC(C)(C)OC(=O)NNC(=O)c1cc(NC(=O)C2C(c3cc(Cl)cc(Cl)c3)C2(Cl)Cl)ccc1Cl] | 38 |
| F2567 | 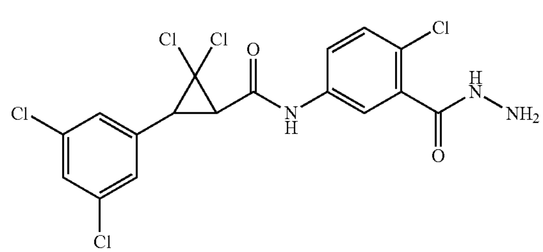 [SMILES: NNC(=O)c1cc(NC(=O)C2C(c3cc(Cl)cc(Cl)c3)C2(Cl)Cl)ccc1Cl] | 37 |
| F2569 | 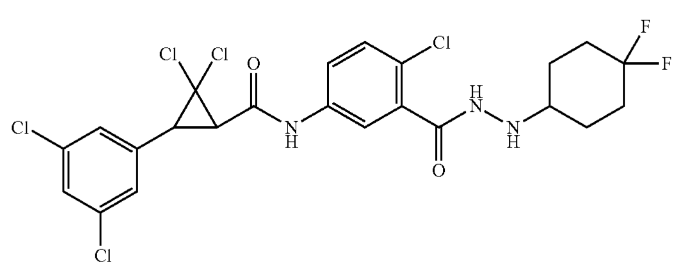 [SMILES: O=C(NNC1CCC(F)(F)CC1)c1cc(NC(=O)C2C(c3cc(Cl)cc(Cl)c3)C2(Cl)Cl)ccc1Cl] | 33 |

TABLE 2-continued

Structure and preparation method for F Series molecules

| No. | Structure | Prep.* |
|---|---|---|
| F2570 | 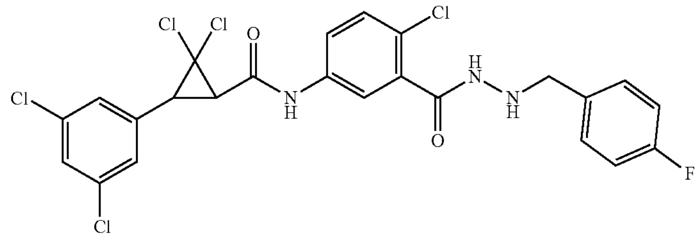 [SMILES: O=C(NNCc1ccc(F)cc1)c1cc(NC(=O)C2C(c3cc(Cl)cc(Cl)c3)C2(Cl)Cl)ccc1Cl] | 33 |
| F2571 | 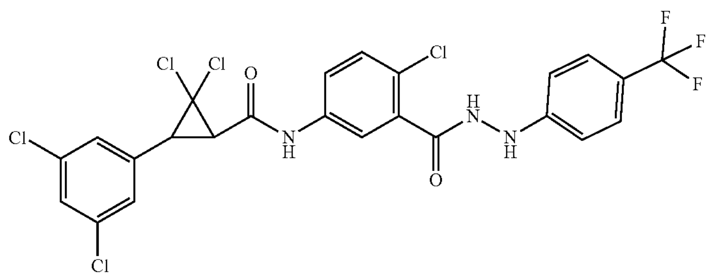 [SMILES: O=C(NNc1ccc(C(F)(F)F)cc1)c1cc(NC(=O)C2C(c3cc(Cl)cc(Cl)c3)C2(Cl)Cl)ccc1Cl] | 28 |
| F2572 | 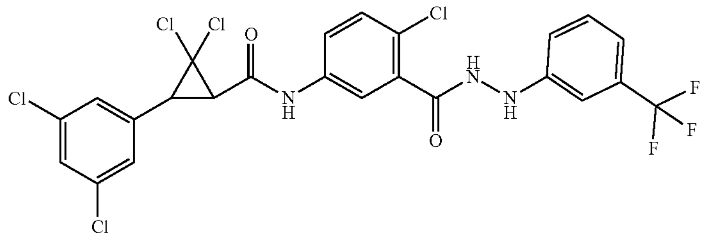 [SMILES: O=C(NNc1cccc(C(F)(F)F)c1)c1cc(NC(=O)C2C(c3cc(Cl)cc(Cl)c3)C2(Cl)Cl)ccc1Cl] | 28 |
| F2573 | 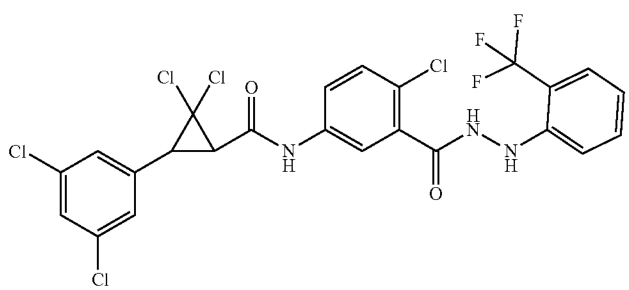 [SMILES: O=C(NNc1ccccc1C(F)(F)F)c1cc(NC(=O)C2C(c3cc(Cl)cc(Cl)c3)C2(Cl)Cl)ccc1Cl] | 28 |
| F2574 | 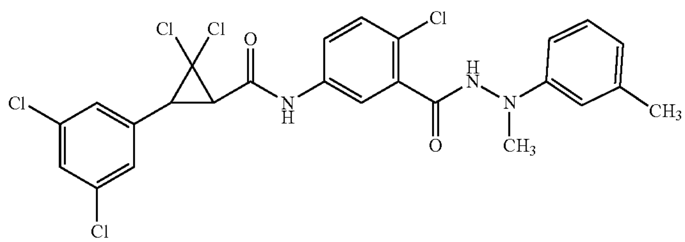 [SMILES: Cc1cccc(N(C)NC(=O)c2cc(NC(=O)C3C(c4cc(Cl)cc(Cl)c4)C3(Cl)Cl)ccc2Cl)c1] | 28 |
| F2575 | 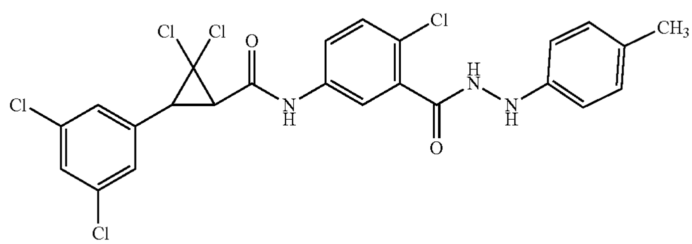 [SMILES: Cc1ccc(NNC(=O)c2cc(NC(=O)C3C(c4cc(Cl)cc(Cl)c4)C3(Cl)Cl)ccc2Cl)cc1] | 28 |

TABLE 2-continued

Structure and preparation method for F Series molecules

| No. | Structure | Prep.* |
|---|---|---|
| F2576 | 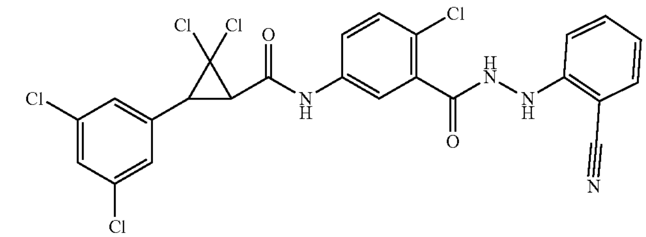 [SMILES: N#Cc1ccccc1NNC(=O)c1cc(NC(=O)C2C(c3cc(Cl)cc(Cl)c3)C2(Cl)Cl)ccc1Cl] | 28 |
| F3001 | 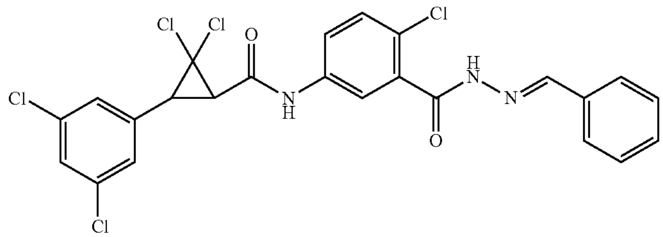 [SMILES: O=C(N/N=C/c1ccccc1)c1cc(NC(=O)C2C(c3cc(Cl)cc(Cl)c3)C2(Cl)Cl)ccc1Cl] | 35 |
| F3002 | 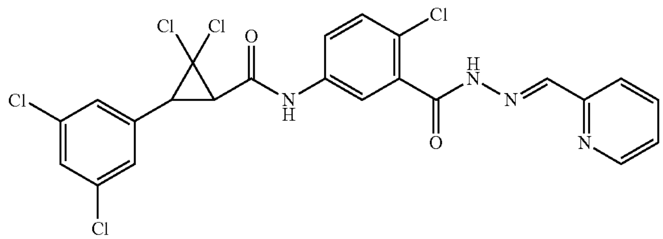 [SMILES: O=C(N/N=C/c1ccccn1)c1cc(NC(=O)C2C(c3cc(Cl)cc(Cl)c3)C2(Cl)Cl)ccc1Cl] | 35 |
| F3003 | 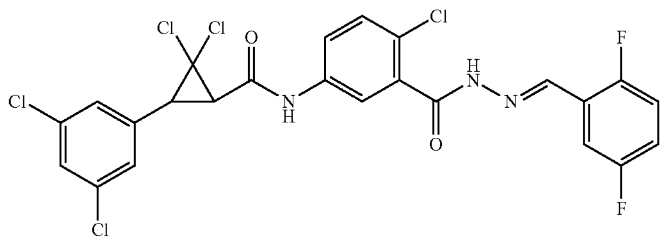 [SMILES: O=C(N/N=C/c1cc(F)ccc1F)c1cc(NC(=O)C2C(c3cc(Cl)cc(Cl)c3)C2(Cl)Cl)ccc1Cl] | 35 |
| F3004 | 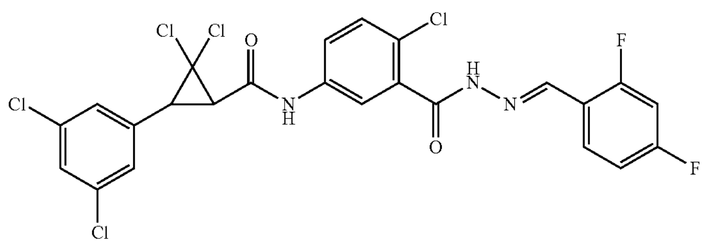 [SMILES: O=C(N/N=C/c1ccc(F)cc1F)c1cc(NC(=O)C2C(c3cc(Cl)cc(Cl)c3)C2(Cl)Cl)ccc1Cl] | 35 |
| F3005 | 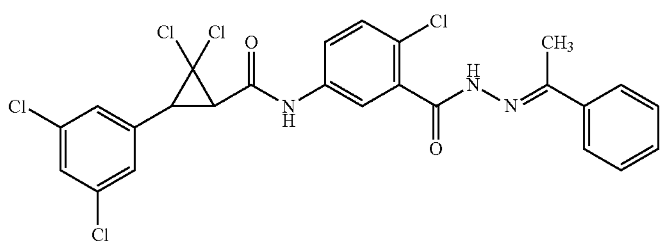 [SMILES: C/C(=N\NC(=O)c1cc(NC(=O)C2C(c3cc(Cl)cc(Cl)c3)C2(Cl)Cl)ccc1Cl)c1ccccc1] | 35 |

TABLE 2-continued

Structure and preparation method for F Series molecules

| No. | Structure | Prep.* |
|---|---|---|
| F3006 | 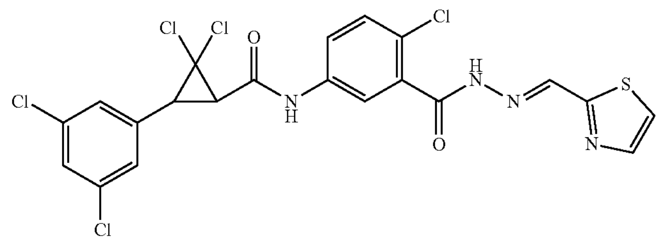 [SMILES: O=C(N/N=C/c1nccs1)c1cc(NC(=O)C2C(c3cc(Cl)cc(Cl)c3)C2(Cl)Cl)ccc1Cl] | 35 |
| F3007 | 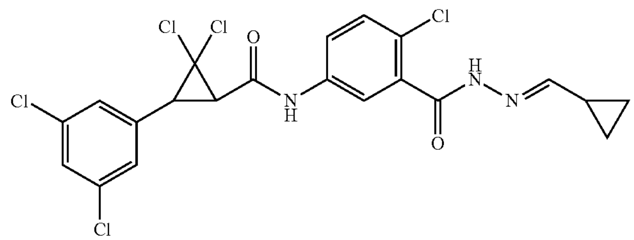 [SMILES: O=C(N/N=C/C1CC1)c1cc(NC(=O)C2C(c3cc(Cl)cc(Cl)c3)C2(Cl)Cl)ccc1Cl] | 35 |
| F3008 | 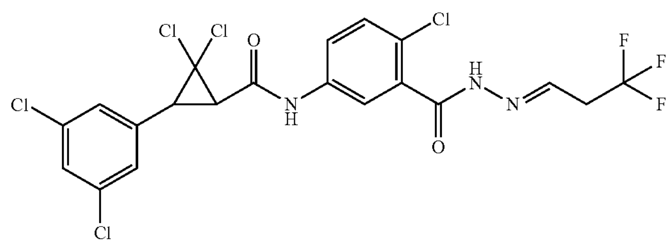 [SMILES: O=C(N/N=C/CC(F)(F)F)c1cc(NC(=O)C2C(c3cc(Cl)cc(Cl)c3)C2(Cl)Cl)ccc1Cl] | 35 |
| F3009 | 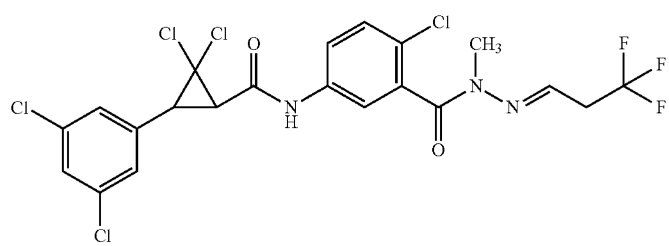 [SMILES: CN(/N=C/CC(F)(F)F)C(=O)c1cc(NC(=O)C2C(c3cc(Cl)cc(Cl)c3)C2(Cl)Cl)ccc1Cl] | 35 |
| F3010 | 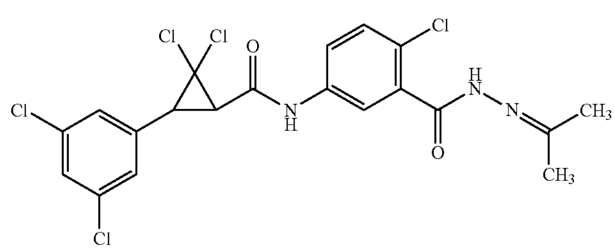 [SMILES: CC(C)=NNC(=O)c1cc(NC(=O)C2C(c3cc(Cl)cc(Cl)c3)C2(Cl)Cl)ccc1Cl] | 35 |

*prepared according to example number

TABLE 3

Structure and preparation method for DP Series molecules

| No. | Structure | Prep.* |
|---|---|---|
| DP1 | 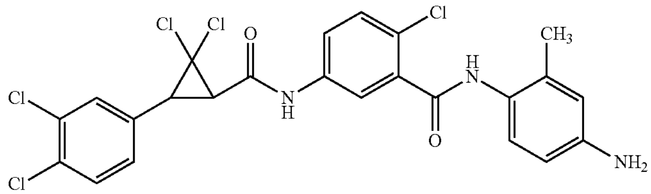 [SMILES: Cc1cc(N)ccc1NC(=O)c1cc(NC(=O)C2C(c3ccc(Cl)c(Cl)c3)C2(Cl)Cl)ccc1Cl] | 27 |
| DP2 | 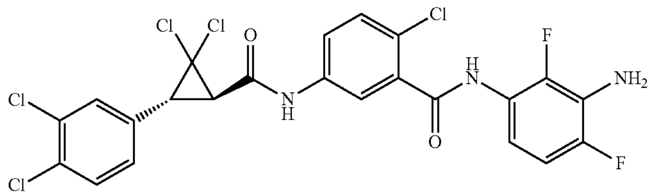 | 13 |
| DP3 | 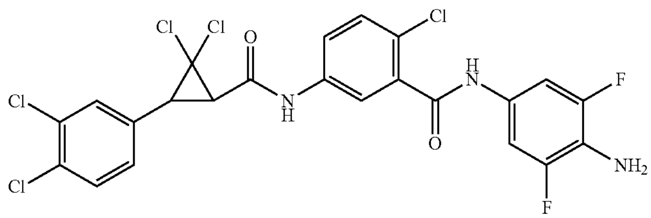 [SMILES: Nc1c(F)cc(NC(=O)c2cc(NC(=O)C3C(c4ccc(Cl)c(Cl)c4)C3(Cl)Cl)ccc2Cl)cc1F] | 13 |
| DP4 | 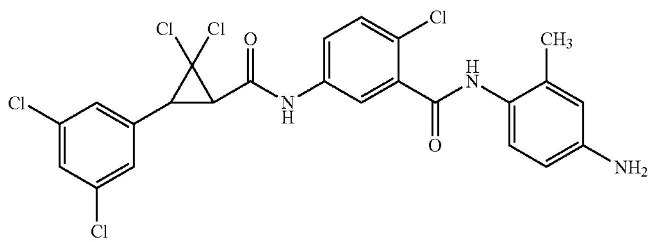 [SMILES: Cc1cc(N)ccc1NC(=O)c1cc(NC(=O)C2C(c3cc(Cl)cc(Cl)c3)C2(Cl)Cl)ccc1Cl] | 13 |
| DP5 | 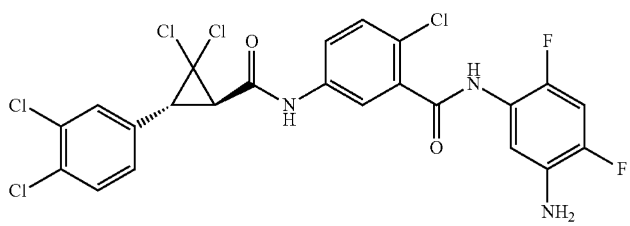 [SMILES: Nc1cc(NC(=O)c2cc(NC(=O)[C@H]3[C@H](c4ccc(Cl)c(Cl)c4)C3(Cl)Cl)ccc2Cl)c(F)cc1F] | 13 |
| DP6 | 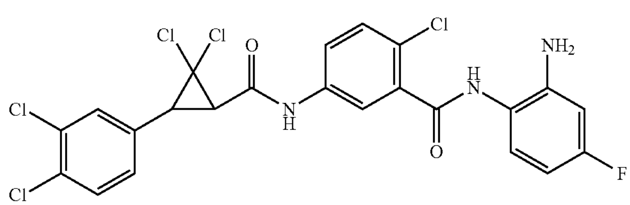 [SMILES: Nc1cc(F)ccc1NC(=O)c1cc(NC(=O)C2C(c3ccc(Cl)c(Cl)c3)C2(Cl)Cl)ccc1Cl] | 14 |

TABLE 3-continued

Structure and preparation method for DP Series molecules

| No. | Structure | Prep.* |
|---|---|---|
| DP7 | 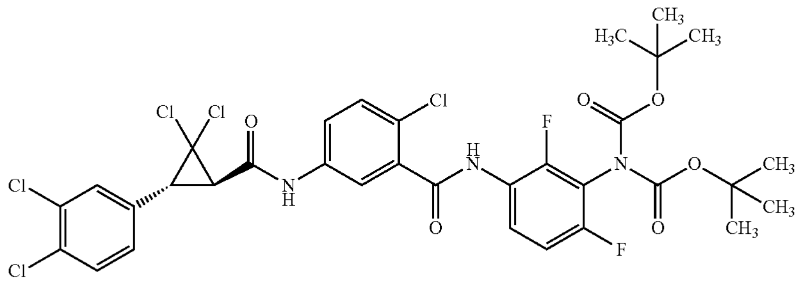 [SMILES: CC(C)(C)OC(=O)N(C(=O)OC(C)(C)C)c1c(F)ccc(NC(=O)c2cc(NC(=O)[C@H]3[C@H](c4ccc(Cl)c(Cl)c4)C3(Cl)Cl)ccc2Cl)c1F] | 18 |
| DP8 | 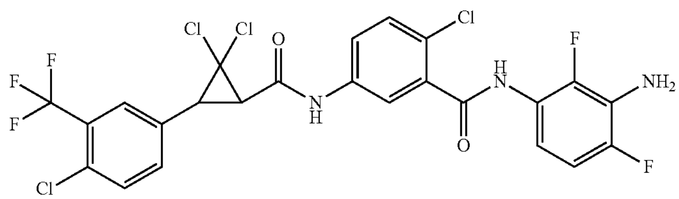 [SMILES: Nc1c(F)ccc(NC(=O)c2cc(NC(=O)C3C(c4ccc(Cl)c(C(F)(F)F)c4)C3(Cl)Cl)ccc2Cl)c1F] | 21 |
| DP9 | 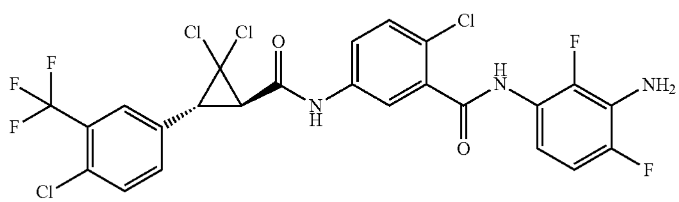 [SMILES: Nc1c(F)ccc(NC(=O)c2cc(NC(=O)[C@H]3[C@H](c4ccc(Cl)c(C(F)(F)F)c4)C3(Cl)Cl)ccc2Cl)c1F] | 21 |
| DP10 | 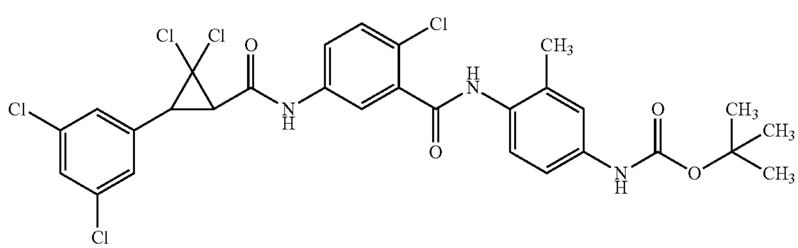 [SMILES: Cc1cc(NC(=O)OC(C)(C)C)ccc1NC(=O)c1cc(NC(=O)C2C(c3cc(Cl)cc(Cl)c3)C2(Cl)Cl)ccc1Cl] | 24 |
| DP11 | 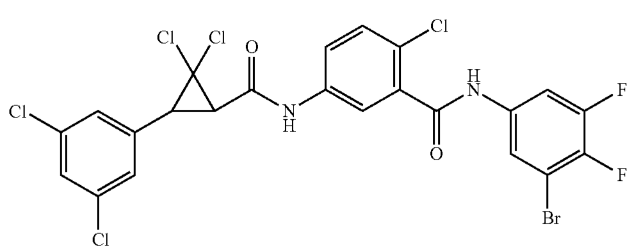 [SMILES: O=C(Nc1cc(F)c(F)c(Br)c1)c1cc(NC(=O)C2C(c3cc(Cl)cc(Cl)c3)C2(Cl)Cl)ccc1Cl] | 25 |
| DP12 | 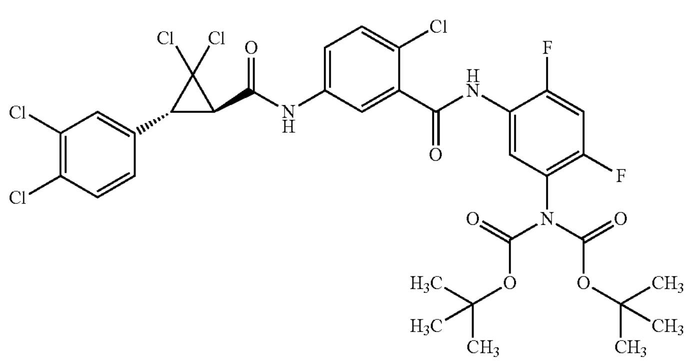 [SMILES: CC(C)(C)OC(=O)N(C(=O)OC(C)(C)C)c1cc(NC(=O)c2cc(NC(=O)[C@H]3[C@H](c4ccc(Cl)c(Cl)c4)C3(Cl)Cl)ccc2Cl)c(F)cc1F] | 25 |

TABLE 3-continued

Structure and preparation method for DP Series molecules

| No. | Structure | Prep.* |
|---|---|---|
| DP13 | 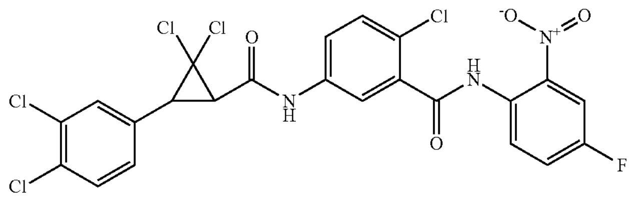 | 25 |
| DP14 | 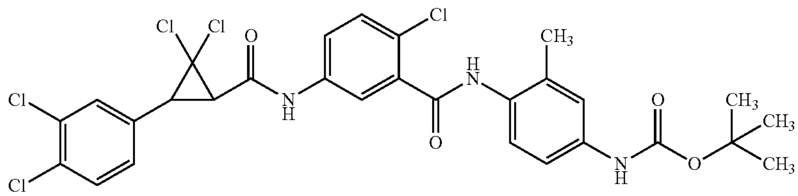 [SMILES: Cc1cc(NC(=O)OC(C)(C)C)ccc1NC(=O)c1cc(NC(=O)C2C(c3ccc(Cl)c(Cl)c3)C2(Cl)Cl)ccc1Cl] | |

*prepared according to example number

TABLE 4

Structure and preparation method for C and CF series molecules

| No. | Structure | Prep* |
|---|---|---|
| C1 | 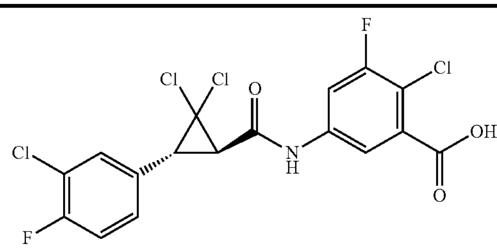 | 39 |
| C2 | 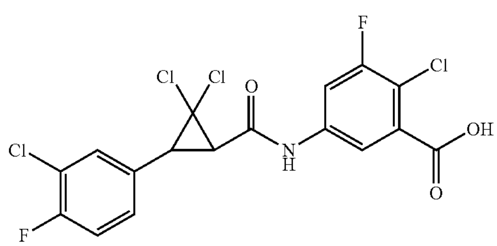 [SMILES: O=C(O)c1cc(NC(=O)C2C(c3ccc(F)c(Cl)c3)C2(Cl)Cl)cc(F)c1Cl] | 39 |
| C3 | 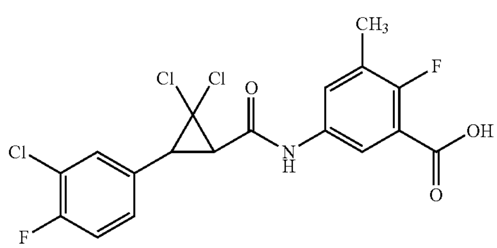 [SMILES: Cc1cc(NC(=O)C2C(c3ccc(F)c(Cl)c3)C2(Cl)Cl)cc(C(=O)O)c1F] | 39 |
| C4 | 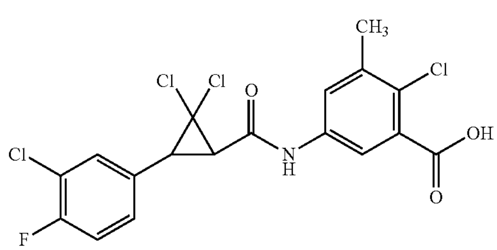 [SMILES: Cc1cc(NC(=O)C2C(c3ccc(F)c(Cl)c3)C2(Cl)Cl)cc(C(=O)O)c1Cl] | 39 |

TABLE 4-continued

Structure and preparation method for C and CF series molecules

| No. | Structure | Prep* |
|---|---|---|
| C5 | 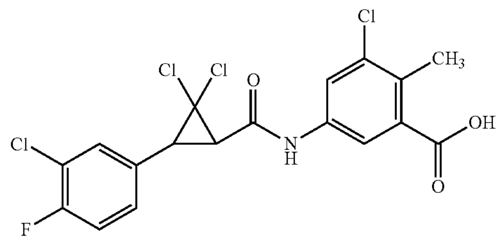 | 39 |
| C6 | 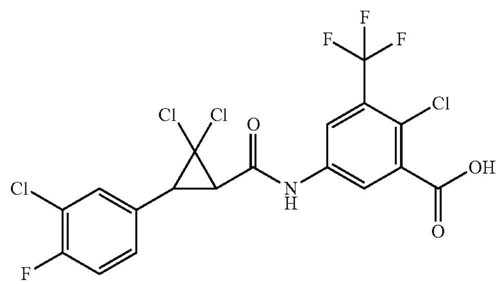 [SMILES: O=C(O)c1cc(NC(=O)C2C(c3ccc(F)c(Cl)c3)C2(Cl)Cl)cc(C(F)(F)F)c1Cl] | 39 |
| C7 | 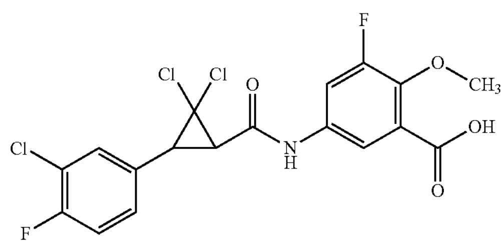 | 39 |
| C8 | 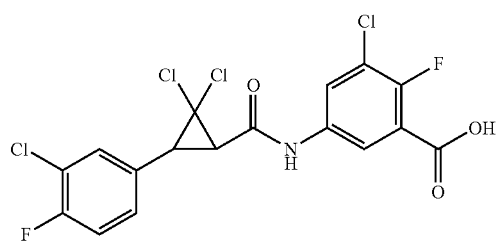 | 39 |
| C9 | 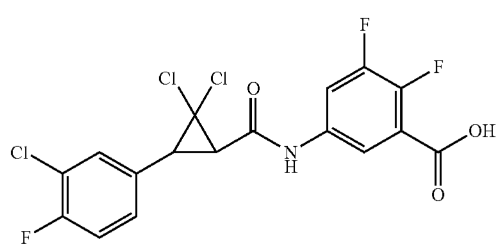 [SMILES: O=C(O)c1cc(NC(=O)C2C(c3ccc(F)c(Cl)c3)C2(Cl)Cl)cc(F)c1F] | 39 |
| C10 | 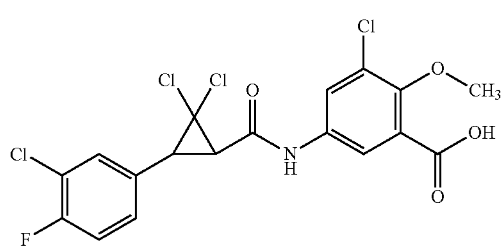 | 39 |

TABLE 4-continued

Structure and preparation method for C and CF series molecules

| No. | Structure | Prep* |
|-----|-----------|-------|
| C11 | 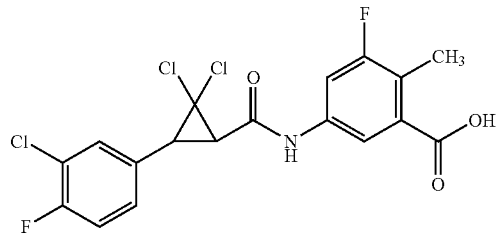 [SMILES: Cc1c(F)cc(NC(=O)C2C(c3ccc(F)c(Cl)c3)C2(Cl)Cl)cc1C(=O)O] | 39 |
| C12 | 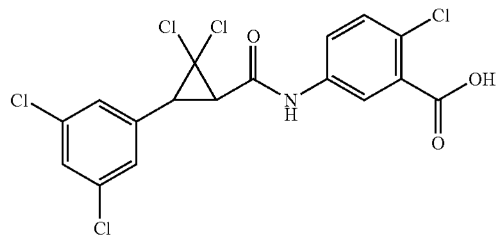 [SMILES: O=C(O)c1cc(NC(=O)C2C(c3cc(Cl)cc(Cl)c3)C2(Cl)Cl)ccc1Cl] | 39 |
| C13 | 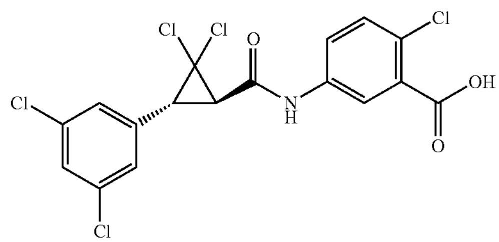 [SMILES: O=C(O)c1cc(NC(=O)[C@H]2[C@H](c3cc(Cl)cc(Cl)c3)C2(Cl)Cl)ccc1Cl] | 39 |
| C14 | 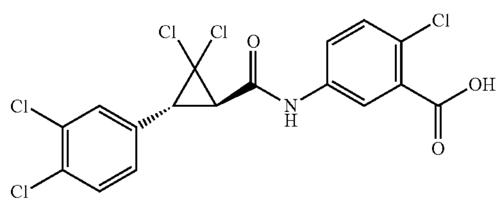 [SMILES: O=C(O)c1cc(NC(=O)[C@H]2[C@H](c3ccc(Cl)c(Cl)c3)C2(Cl)Cl)ccc1Cl] | 39 |
| C15 | 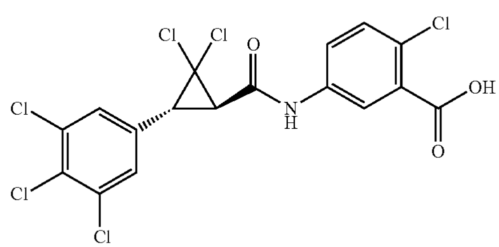 [SMILES: O=C(O)c1cc(NC(=O)[C@H]2[C@H](c3cc(Cl)c(Cl)c(Cl)c3)C2(Cl)Cl)ccc1Cl] | 39 |
| C16 | 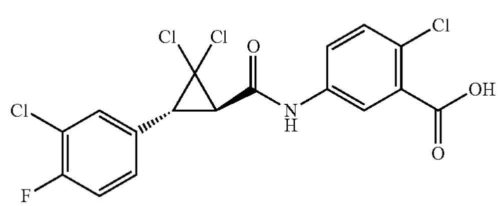 | 39 |

TABLE 4-continued

Structure and preparation method for C and CF series molecules

| No. | Structure | Prep* |
|---|---|---|
| C17 | 3-bromo-4,5-difluorophenyl 2,2-dichlorocyclopropanecarboxylic acid | 40 |
| C18 | 3,4-dichloro-5-fluorophenyl 2,2-dichlorocyclopropanecarboxylic acid | 40 |
| C19 | 3-bromo-5-(pentafluorosulfanyl)phenyl 2,2-dichlorocyclopropanecarboxylic acid | 40 |
| C20 | 3-chloro-2,4-difluorophenyl 2,2-dichlorocyclopropanecarboxylic acid | 40 |
| C21 | 3-chloro-2-fluoro-5-(trifluoromethyl)phenyl 2,2-dichlorocyclopropanecarboxylic acid | 40 |
| C22 | 3-(trifluoromethyl)-4-fluoro-5-methylphenyl 2,2-dichlorocyclopropanecarboxylic acid | 40 |

TABLE 4-continued
Structure and preparation method for C and CF series molecules
| No. | Structure | Prep* |
|---|---|---|
| C23 | 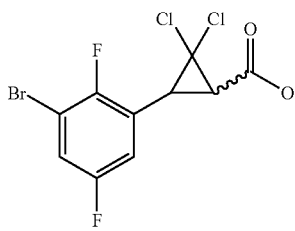 | 40 |
| C24 | 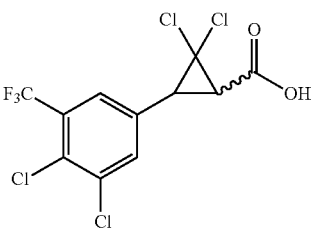 [SMILES: O=C(O)C1C(c2cc(Cl)c(Cl)c(C(F)(F)F)c2)C1(Cl)Cl] | 40 |
| C25 | 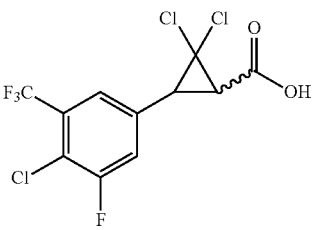 [SMILES: O=C(O)C1C(c2cc(F)c(Cl)c(C(F)(F)F)c2)C1(Cl)Cl] | 40 |
| C26 | 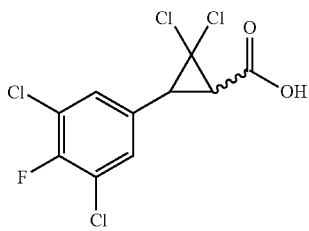 [SMILES: O=C(O)C1C(c2cc(Cl)c(F)c(Cl)c2)C1(Cl)Cl] | 40 |
| C27 | 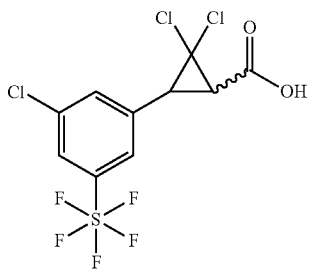 [SMILES: O=C(O)C1C(c2cc(Cl)cc(S(F)(F)(F)(F)F)c2)C1(Cl)Cl] | 40 |
| C28 | 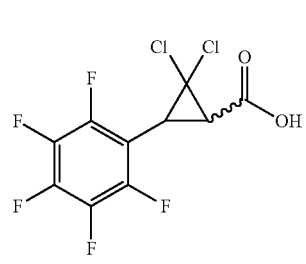 [SMILES: O=C(O)C1C(c2c(F)c(F)c(F)c(F)c2F)C1(Cl)Cl] | 40 |

TABLE 4-continued

Structure and preparation method for C and CF series molecules

| No. | Structure | Prep* |
|---|---|---|
| C29 | 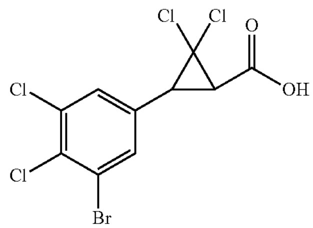 [SMILES: O=C(O)C1C(c2cc(Cl)c(Cl)c(Br)c2)C1(Cl)Cl] | 40 |
| C30 | 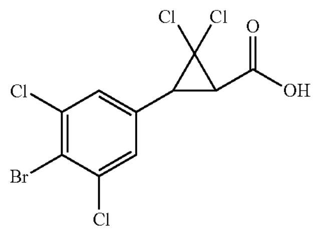 | 40 |
| C31 | 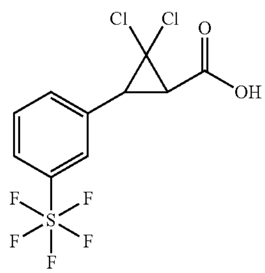 [SMILES: O=C(O)C1C(c2cccc(S(F)(F)(F)(F)F)c2)C1(Cl)Cl] | 41 |
| C32 | 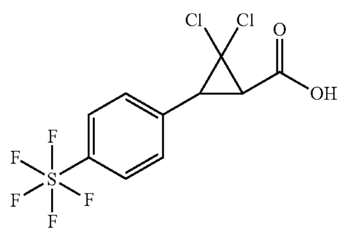 [SMILES: O=C(O)C1C(c2ccc(S(F)(F)(F)(F)F)cc2)C1(Cl)Cl] | 41 |
| C33 | 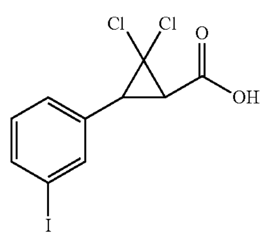 [SMILES: O=C(O)C1C(c2cccc(I)c2)C1(Cl)Cl] | 41 |
| C34 | 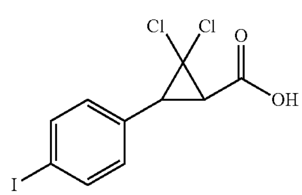 [SMILES: O=C(O)C1C(c2ccc(I)cc2)C1(Cl)Cl] | 41 |

TABLE 4-continued
Structure and preparation method for C and CF series molecules
| No. | Structure | Prep* |
|---|---|---|
| C35 | 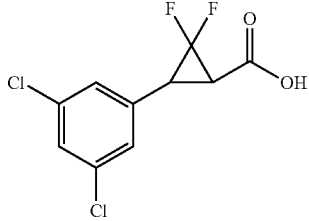 [SMILES: O=C(O)C1C(c2cc(Cl)cc(Cl)c2)C1(F)F] | 41 |
| C36 | 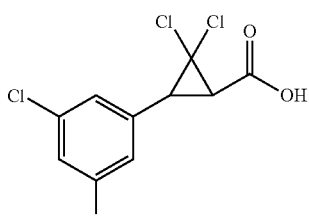 | 42 |
| C37 | 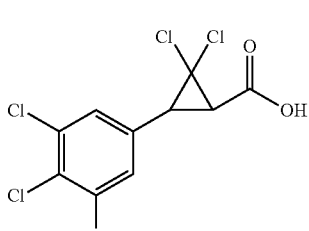 | 42 |
| C38 | 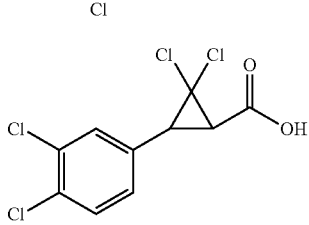 | 42 |
| C39 | 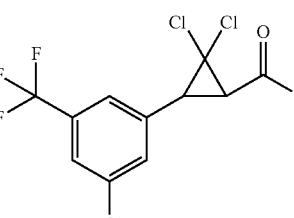 | 42 |
| C40 | 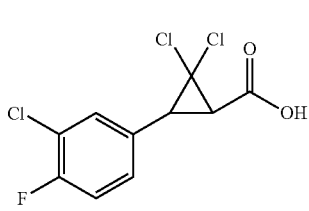 [SMILES: O=C(O)C1C(c2ccc(F)c(Cl)c2)C1(Cl)Cl] | 42 |
| C41 | 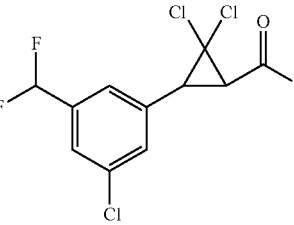 | 42 |

TABLE 4-continued

Structure and preparation method for C and CF series molecules

| No. | Structure | Prep* |
|-----|-----------|-------|
| C42 | 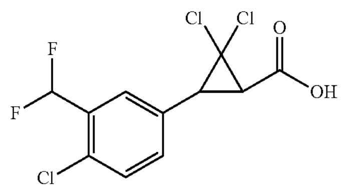 [SMILES: O=C(O)C1C(c2ccc(Cl)c(C(F)F)c2)C1(Cl)Cl] | 42 |
| C43 | 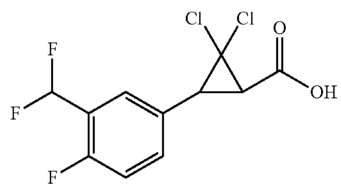 [SMILES: O=C(O)C1C(c2ccc(F)c(C(F)F)c2)C1(Cl)Cl] | 42 |
| C44 | 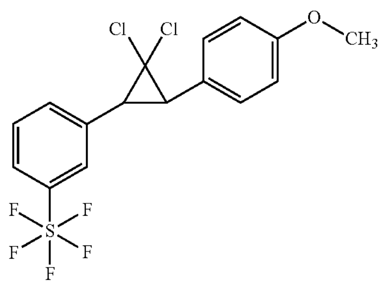 [SMILES: COc1ccc(C2C(c3cccc(S(F)(F)(F)(F)F)c3)C2(Cl)Cl)cc1] | 43 |
| C45 | 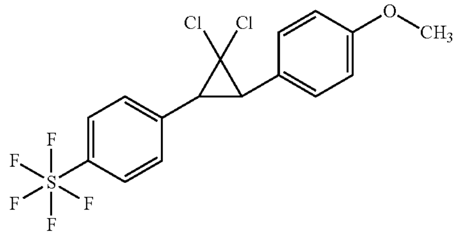 [SMILES: COc1ccc(C2C(c3ccc(S(F)(F)(F)(F)F)cc3)C2(Cl)Cl)cc1] | 43 |
| C46 | 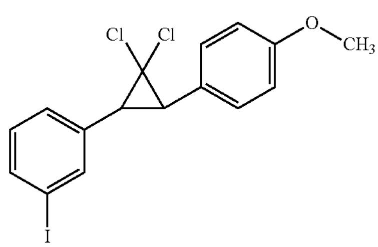 [SMILES: COc1ccc(C2C(c3cccc(I)c3)C2(Cl)Cl)cc1] | 43 |
| C47 | 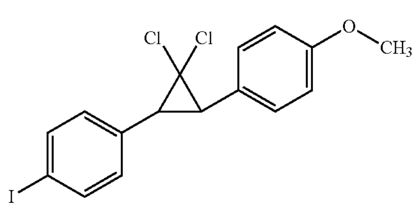 [SMILES: COc1ccc(C2C(c3ccc(I)cc3)C2(Cl)Cl)cc1] | 43 |

TABLE 4-continued

Structure and preparation method for C and CF series molecules

| No. | Structure | Prep* |
|---|---|---|
| C48 | 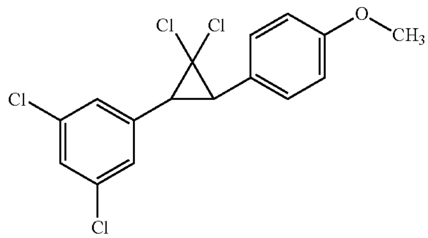 [SMILES: COc1ccc(C2C(c3cc(Cl)cc(Cl)c3)C2(Cl)Cl)cc1] | 44 |
| C49 | 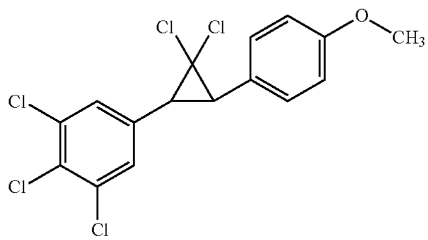 [SMILES: COc1ccc(C2C(c3cc(Cl)c(Cl)c(Cl)c3)C2(Cl)Cl)cc1] | 44 |
| C50 | 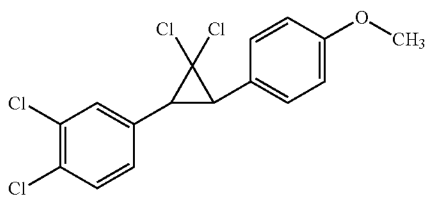 [SMILES: COc1ccc(C2C(c3ccc(Cl)c(Cl)c3)C2(Cl)Cl)cc1] | 44 |
| C51 | 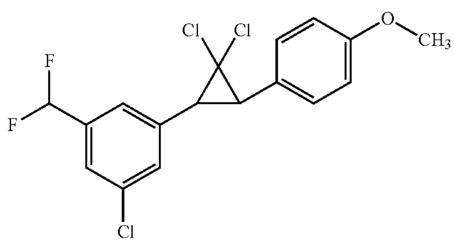 [SMILES: COc1ccc(C2C(c3cc(Cl)cc(C(F)F)c3)C2(Cl)Cl)cc1] | 44 |
| C52 | 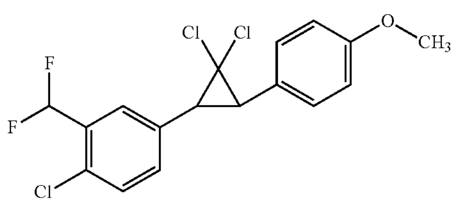 [SMILES: COc1ccc(C2C(c3ccc(Cl)c(C(F)F)c3)C2(Cl)Cl)cc1] | 44 |
| C53 | 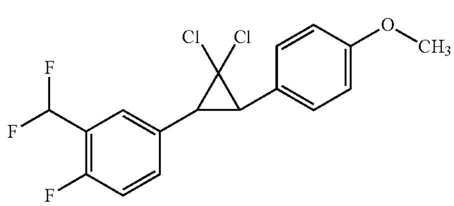 | 44 |

TABLE 4-continued

Structure and preparation method for C and CF series molecules

| No. | Structure | Prep* |
|---|---|---|
| C54 | 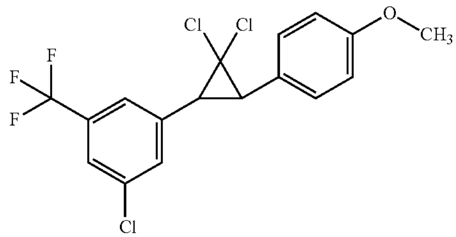 [SMILES: COc1ccc(C2C(c3cc(Cl)cc(C(F)(F)F)c3)C2(Cl)Cl)cc1] | 44 |
| C55 | 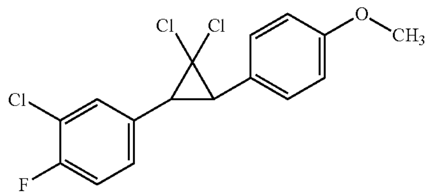 [SMILES: COc1ccc(C2C(c3ccc(F)c(Cl)c3)C2(Cl)Cl)cc1] | 44 |
| C56 | 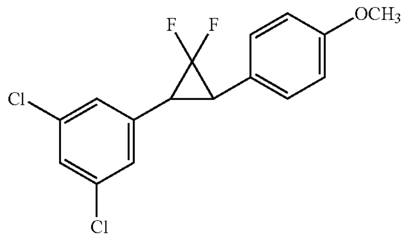 [SMILES: COc1ccc(C2C(c3cc(Cl)cc(Cl)c3)C2(F)F)cc1] | 45 |
| C57 | 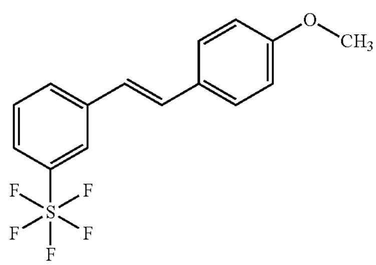 [SMILES: COc1ccc(/C=C/c2cccc(S(F)(F)(F)(F)F)c2)cc1] | 46 |
| C58 | 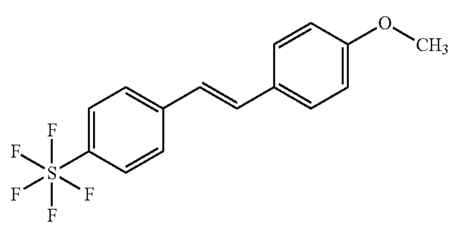 [SMILES: COc1ccc(/C=C/c2ccc(S(F)(F)(F)(F)F)cc2)cc1] | 46 |
| C59 | 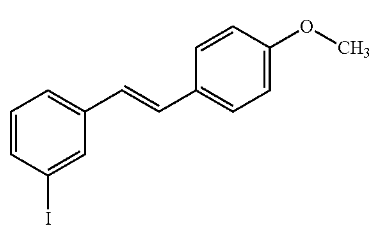 [SMILES: COc1ccc(/C=C/c2cccc(I)c2)cc1] | 46 |

TABLE 4-continued

Structure and preparation method for C and CF series molecules

| No. | Structure | Prep* |
|---|---|---|
| C60 | 4-iodophenyl-CH=CH-4-methoxyphenyl | 46 |
| C61 | 3,5-dichlorophenyl-CH=CH-4-methoxyphenyl | 47 |
| C62 | 3,4,5-trichlorophenyl-CH=CH-4-methoxyphenyl | 47 |
| C63 | 3,4-dichlorophenyl-CH=CH-4-methoxyphenyl | 47 |
| C64 | 3-trifluoromethyl-5-chlorophenyl-CH=CH-4-methoxyphenyl | 47 |
| C65 | 3,5-dichloro-4-bromophenyl-CH=CH-4-methoxyphenyl | 47 |
| C66 | 3-chloro-4-fluorophenyl-CH=CH-4-methoxyphenyl | 47 |

TABLE 4-continued
Structure and preparation method for C and CF series molecules
| No. | Structure | Prep* |
|-----|-----------|-------|
| C67 | 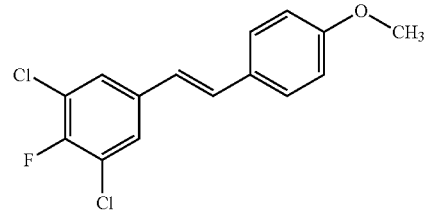 | 48 |
| C68 | 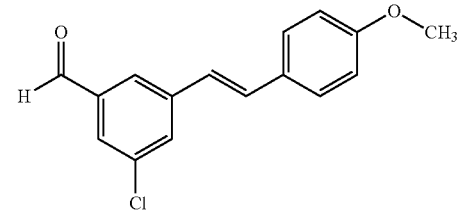 [SMILES: COc1ccc(/C=C/c2cc(Cl)cc(C(F)F)c2)cc1] | 49 |
| C69 | 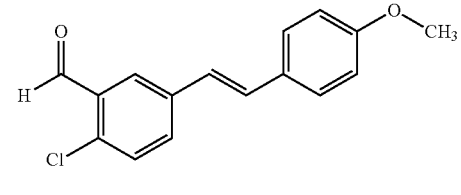 [SMILES: COc1ccc(/C=C/c2ccc(Cl)c(C(F)F)c2)cc1] | 49 |
| C70 | 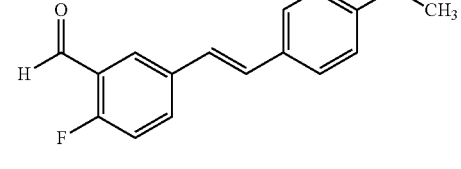 | 49 |
| C71 | 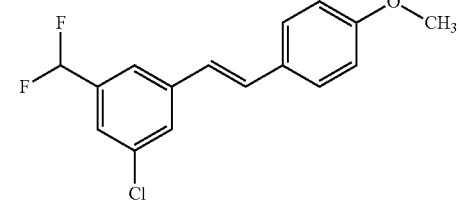 | 50 |
| C72 | 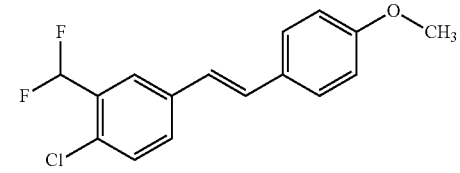 | 50 |
| C73 | 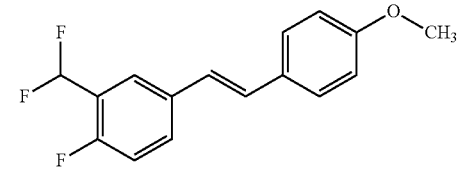 | 50 |

TABLE 4-continued

Structure and preparation method for C and CF series molecules

| No. | Structure | Prep* |
|---|---|---|
| C74 | 2,2-dichloro-3-(4-bromo-3-(trifluoromethyl)phenyl)cyclopropanecarboxylic acid | 51 |
| C75 | 2,2-dichloro-3-(4-chloro-3-(trifluoromethyl)phenyl)cyclopropanecarboxylic acid | 51 |
| C76 | 2,2-dichloro-3-(4-fluoro-3-(trifluoromethyl)phenyl)cyclopropanecarboxylic acid | 51 |
| C77 | 2,2-dichloro-3-(3-fluoro-5-(trifluoromethyl)phenyl)cyclopropanecarboxylic acid | 51 |
| C78 | 2,2-dichloro-3-(3-bromo-5-(trifluoromethyl)phenyl)cyclopropanecarboxylic acid | 51 |
| C79 | 2,2-dichloro-3-(3,5-dichlorophenyl)cyclopropanecarbaldehyde | 52 |
| C80 | 2,2-dichloro-3-(3,4-dichlorophenyl)cyclopropanecarbaldehyde | 52 |

TABLE 4-continued
Structure and preparation method for C and CF series molecules
| No. | Structure | Prep* |
|---|---|---|
| C81 | 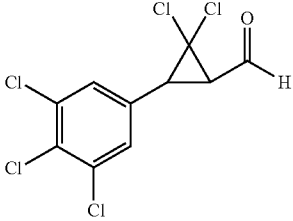 [SMILES: O=CC1C(c2cc(Cl)c(Cl)c(Cl)c2)C1(Cl)Cl] | 52 |
| C82 | 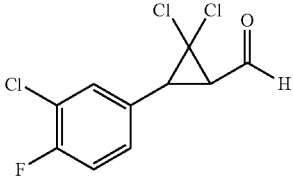 [SMILES: O=CC1C(c2ccc(F)c(Cl)c2)C1(Cl)Cl] | 52 |
| C83 | 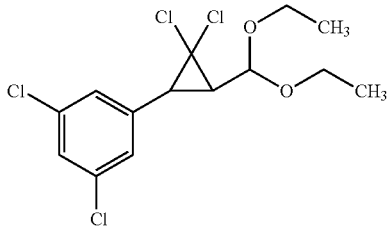 [SMILES: CCOC(OCC)C1C(c2cc(Cl)cc(Cl)c2)C1(Cl)Cl] | 53 |
| C84 | 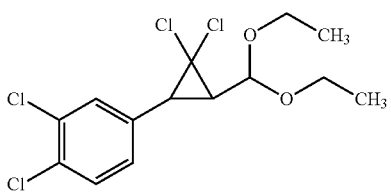 [SMILES: CCOC(OCC)C1C(c2ccc(Cl)c(Cl)c2)C1(Cl)Cl] | 53 |
| C85 | 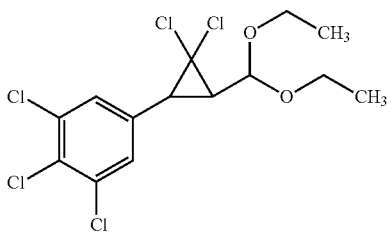 [SMILES: CCOC(OCC)C1C(c2cc(Cl)c(Cl)c(Cl)c2)C1(Cl)Cl] | 53 |
| C86 | 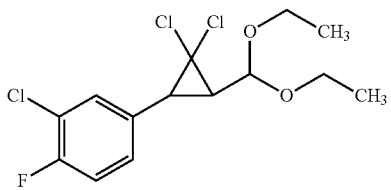 [SMILES: CCOC(OCC)C1C(c2ccc(F)c(Cl)c2)C1(Cl)Cl] | 53 |
| C87 | 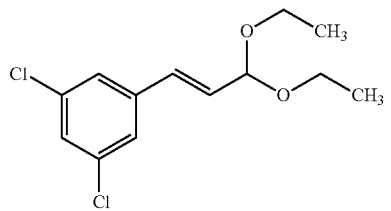 [SMILES: CCOC(/C=C/c1cc(Cl)cc(Cl)c1)OCC] | 54 |

TABLE 4-continued

Structure and preparation method for C and CF series molecules

| No. | Structure | Prep* |
|---|---|---|
| C88 | 3,4-dichlorophenyl-CH=CH-CH(OEt)$_2$ | 54 |
| C89 | 3,4,5-trichlorophenyl-CH=CH-CH(OEt)$_2$ | 54 |
| C90 | 3-chloro-4-fluorophenyl-CH=CH-CH(OEt)$_2$ | 54 |
| C91 | (R,R)-2,2-dichloro-1-(3,5-dichlorophenyl)cyclopropanecarboxylic acid | 55 |
| C92 | (R,R)-2,2-dichloro-1-(3,4-dichlorophenyl)cyclopropanecarboxylic acid | 55 |
| C93 | (R,R)-2,2-dichloro-1-(3-chloro-4-fluorophenyl)cyclopropanecarboxylic acid | 55 |
| C94 | (R,R)-2,2-dichloro-1-(3,4,5-trichlorophenyl)cyclopropanecarboxylic acid | 55 |

TABLE 4-continued

Structure and preparation method for C and CF series molecules

| No. | Structure | Prep* |
|---|---|---|
| C95 | 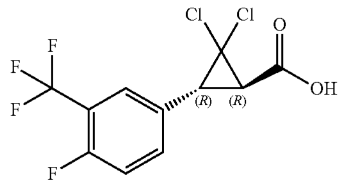 | 55 |
| C96 | 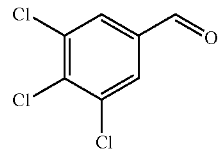 [SMILES: O=Cc1cc(Cl)c(Cl)c(Cl)c1] | 56 |
| C97 | 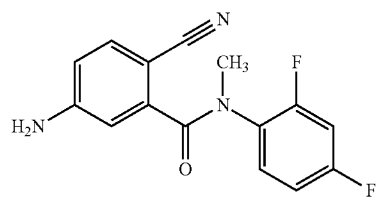 [SMILES: CN(C(=O)c1cc(N)ccc1C#N)c1ccc(F)cc1F] | 57 |
| C98 | 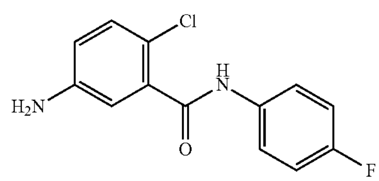 [SMILES: Nc1ccc(Cl)c(C(=O)Nc2ccc(F)cc2)c1] | 57 |
| C99 | 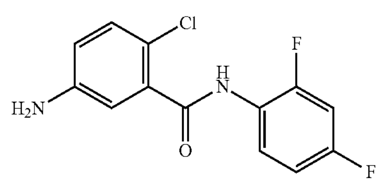 [SMILES: Nc1ccc(Cl)c(C(=O)Nc2ccc(F)cc2F)c1] | 57 |
| C100 | 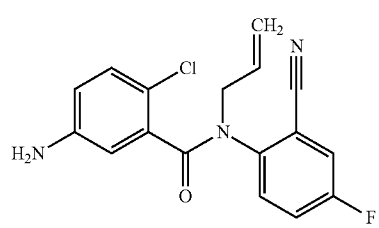 [SMILES: C=CCN(C(=O)c1cc(N)ccc1Cl)c1ccc(F)cc1C#N] | 57 |
| C101 | 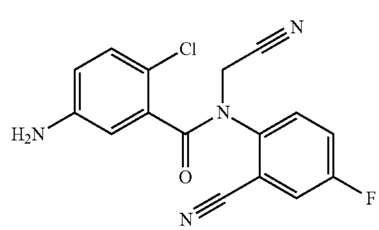 [SMILES: N#CCN(C(=O)c1cc(N)ccc1Cl)c1ccc(F)cc1C#N] | 57 |

TABLE 4-continued

Structure and preparation method for C and CF series molecules

| No. | Structure | Prep* |
|---|---|---|
| C102 | 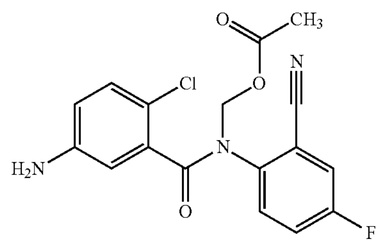 [SMILES: CC(=O)OCN(C(=O)c1cc(N)ccc1Cl)c1ccc(F)cc1C#N] | 57 |
| C103 | 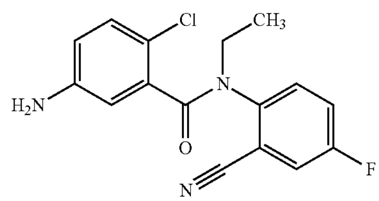 [SMILES: CCN(C(=O)c1cc(N)ccc1Cl)c1ccc(F)cc1C#N] | 57 |
| C104 | 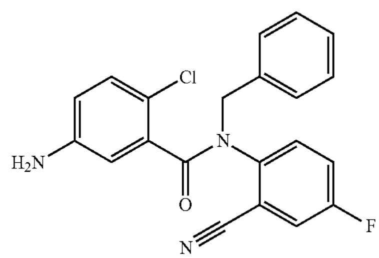 [SMILES: N#Cc1cc(F)ccc1N(Cc1ccccc1)C(=O)c1cc(N)ccc1Cl] | 57 |
| C105 | 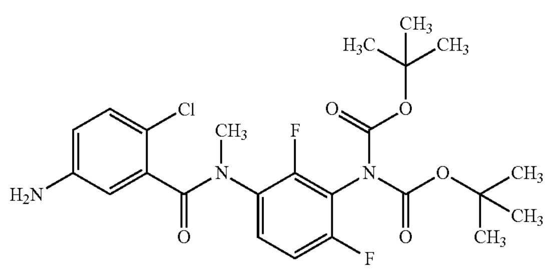 [SMILES: CN(C(=O)c1cc(N)ccc1Cl)c1ccc(F)c(N(C(=O)OC(C)(C)C)C(=O)OC(C)(C)C)c1F] | 57 |
| C106 | 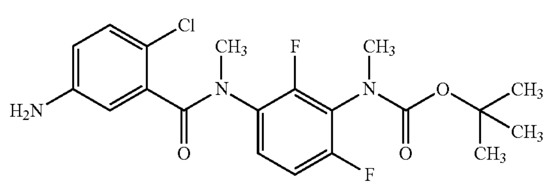 [SMILES: CN(C(=O)c1cc(N)ccc1Cl)c1ccc(F)c(N(C)C(=O)OC(C)(C)C)c1F] | 57 |
| C107 | 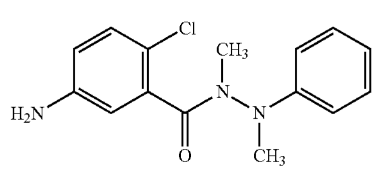 | 57 |

TABLE 4-continued

Structure and preparation method for C and CF series molecules

| No. | Structure | Prep* |
|---|---|---|
| C108 | 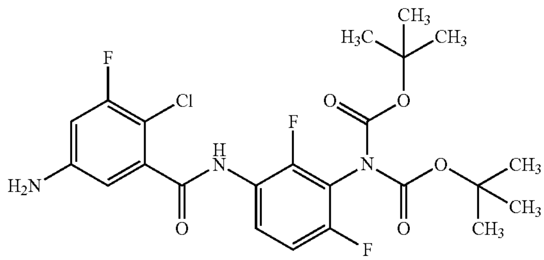 [SMILES: CC(C)(C)OC(=O)N(C(=O)OC(C)(C)C)c1c(F)ccc(NC(=O)c2cc(N)cc(F)c2Cl)c1F] | 57 |
| C109 | 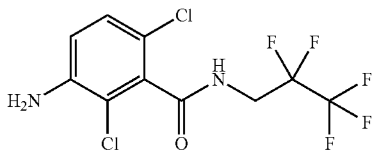 [SMILES: Nc1ccc(Cl)c(C(=O)NCC(F)(F)C(F)(F)F)c1Cl] | 57 |
| C110 | 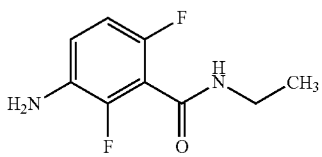 | 57 |
| C111 | 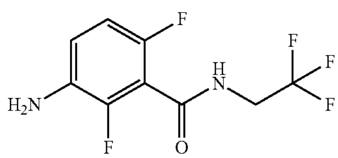 [SMILES: Nc1ccc(F)c(C(=O)NCC(F)(F)F)c1F] | 57 |
| C112 | 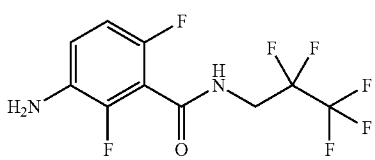 [SMILES: Nc1ccc(F)c(C(=O)NCC(F)(F)C(F)(F)F)c1F] | 57 |
| C113 | 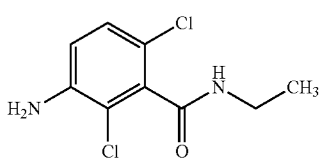 | 57 |
| C114 | 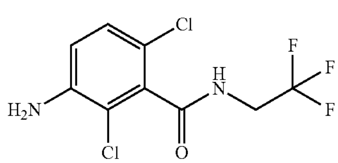 [SMILES: Nc1ccc(Cl)c(C(=O)NCC(F)(F)F)c1Cl] | 57 |
| C115 | 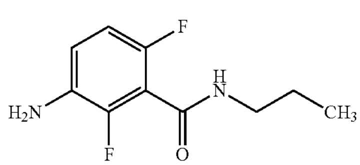 | 57 |
| C116 | 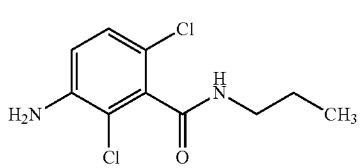 | 57 |

TABLE 4-continued

Structure and preparation method for C and CF series molecules

| No. | Structure | Prep* |
|---|---|---|
| C117 | 3-amino-2,6-difluoro-N-(3,3,3-trifluoropropyl)benzamide | 57 |
| C118 | 3-amino-2,6-dichloro-N-(3,3,3-trifluoropropyl)benzamide | 57 |
| C119 | 3-amino-2,6-dichloro-N-(2-fluoroethyl)benzamide | 57 |
| C120 | 3-amino-2,6-dichloro-N-(3-chloropropyl)benzamide | 57 |
| C121 | 3-amino-2,6-difluoro-N-(2-fluoroethyl)benzamide | 57 |
| C122 | 3-amino-2,6-difluoro-N-(3-chloropropyl)benzamide | 57 |
| C123 | 3-amino-2,6-difluoro-N-(2,4-difluorophenyl)benzamide | 57 |
| C124 | 3-amino-2,6-difluoro-N-(4-fluorophenyl)benzamide | 57 |
| C125 | 3-amino-N-(4-acetamidophenyl)-2,6-difluorobenzamide | 57 |

TABLE 4-continued

Structure and preparation method for C and CF series molecules

| No. | Structure | Prep* |
|---|---|---|
| C126 | 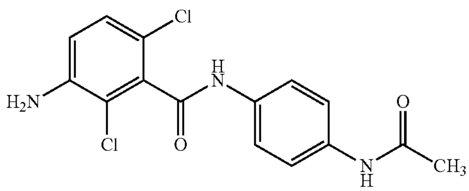 | 57 |
| C127 | 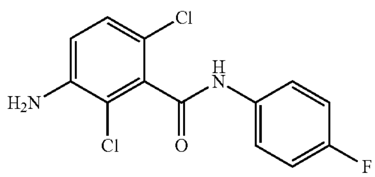 [SMILES: Nc1ccc(F)c(C(=O)Nc2ccc(F)cc2)c1F] | 57 |
| C128 | 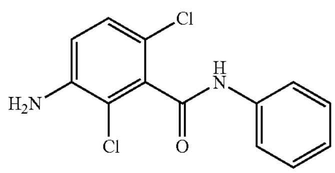 | 57 |
| C129 | 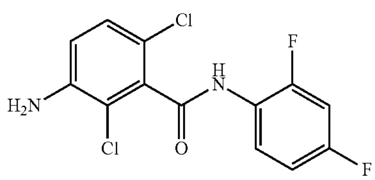 | 57 |
| C130 | 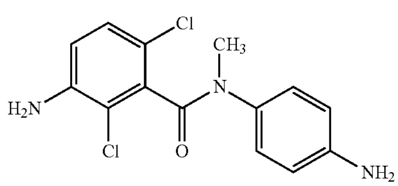 [SMILES: CN(C(=O)c1c(Cl)ccc(N)c1Cl)c1ccc(N)cc1] | 57 |
| C131 | 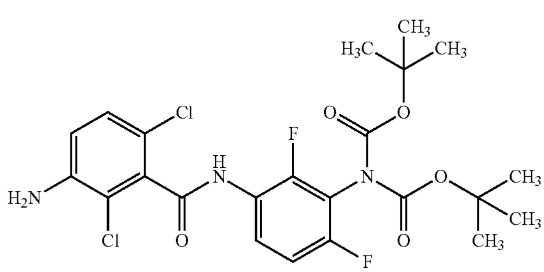 | 57 |
| C132 | 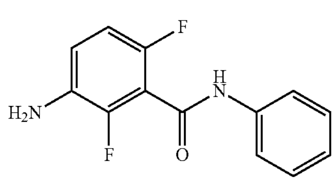 [SMILES: Nc1ccc(F)c(C(=O)Nc2ccccc2)c1F] | 57 |

TABLE 4-continued

Structure and preparation method for C and CF series molecules

| No. | Structure | Prep* |
|---|---|---|
| C133 | 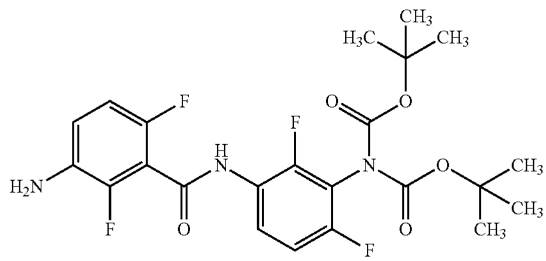 [SMILES: CC(C)(C)OC(=O)N(C(=O)OC(C)(C)C)c1c(F)ccc(NC(=O)c2c(F)ccc(N)c2F)c1F] | 57 |
| C134 | 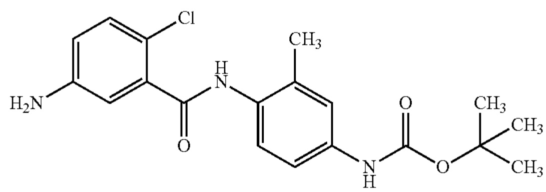 | 58 |
| C135 | 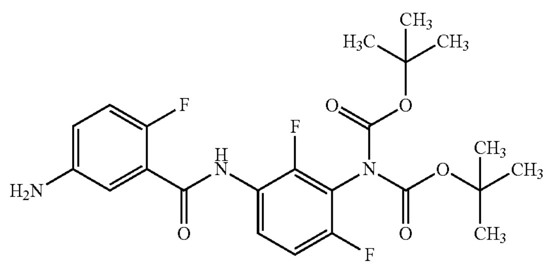 | 58 |
| C136 | 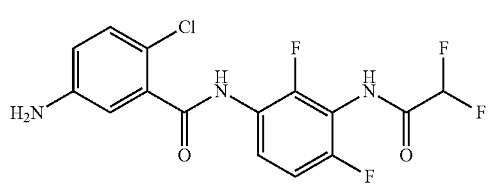 | 58 |
| C137 | 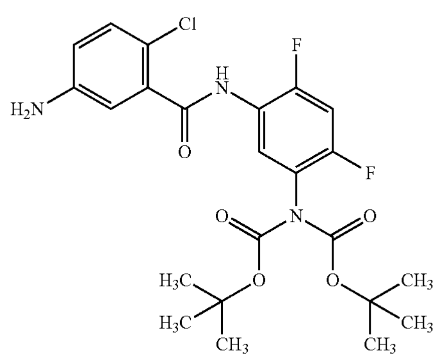 [SMILES: CC(C)(C)OC(=O)N(C(=O)OC(C)(C)C)c1cc(NC(=O)c2cc(N)ccc2Cl)c(F)cc1F] | 59 |
| C138 | 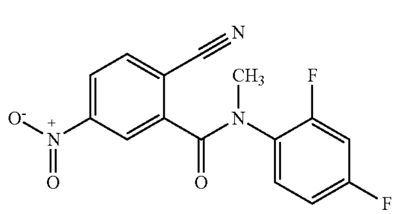 | 60 |

| No. | Structure | Prep* |
|---|---|---|
| C139 | 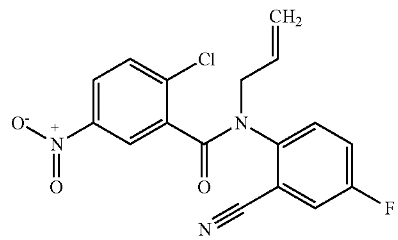 | 61 |
| C140 | 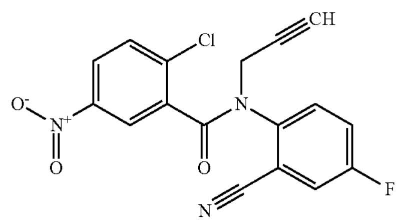 [SMILES: C#CCN(C(=O)c1cc([N+](=O)[O-])ccc1Cl)c1ccc(F)cc1C#N] | 61 |
| C141 | 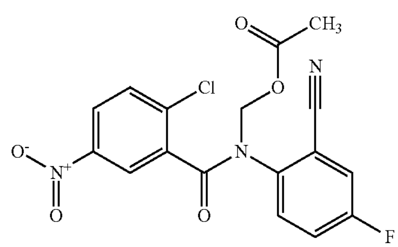 [SMILES: CC(=O)OCN(C(=O)c1cc([N+](=O)[O-])ccc1Cl)c1ccc(F)cc1C#N] | 61 |
| C142 | 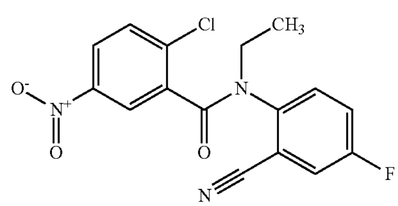 [SMILES: CCN(C(=O)c1cc([N+](=O)[O-])ccc1Cl)c1ccc(F)cc1C#N] | 61 |
| C143 | 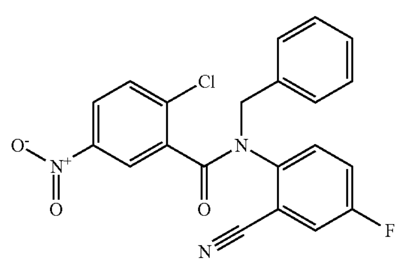 [SMILES: N#Cc1cc(F)ccc1N(Cc1ccccc1)C(=O)c1cc([N+](=O)[O-])ccc1Cl] | 61 |
| C144 | 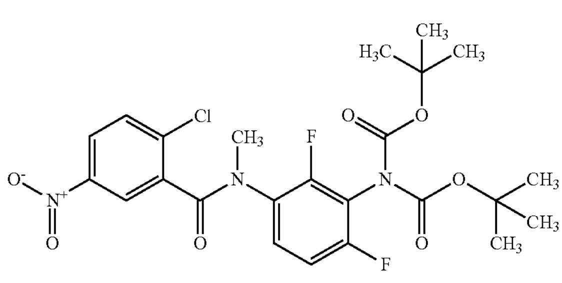 [SMILES: CN(C(=O)c1cc([N+](=O)[O-])ccc1Cl)c1ccc(F)c(N(C(=O)OC(C)(C)C)C(=O)OC(C)(C)C)c1F] | 61 |

TABLE 4-continued
Structure and preparation method for C and CF series molecules
| No. | Structure | Prep* |
|---|---|---|
| C145 | 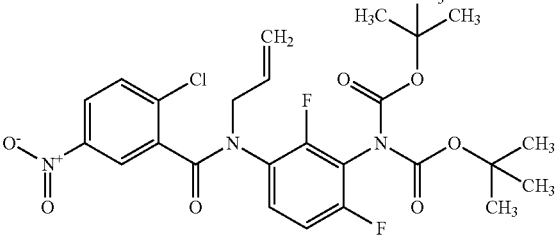 | 61 |
| C146 | 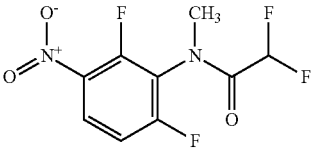 [SMILES: CN(C(=O)C(F)F)c1c(F)ccc([N+](=O)[O-])c1F] | 61 |
| C147 | 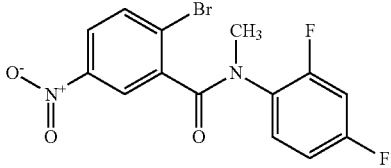 [SMILES: CN(C(=O)c1cc([N+](=O)[O-])ccc1Br)c1ccc(F)cc1F] | 61 |
| C148 | 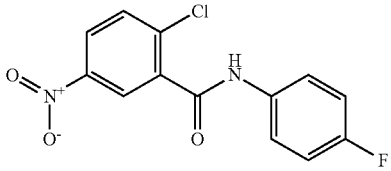 | 62 |
| C149 | 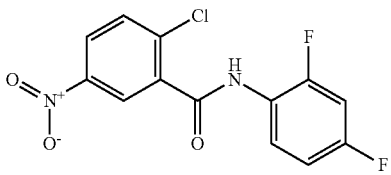 | 63 |
| C150 | 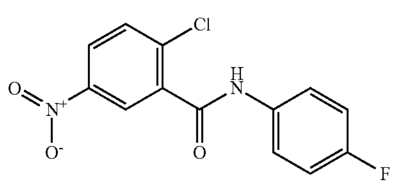 [SMILES: O=C(Nc1ccc(F)cc1)c1cc([N+](=O)[O-])ccc1Cl] | 64 |
| C151 | 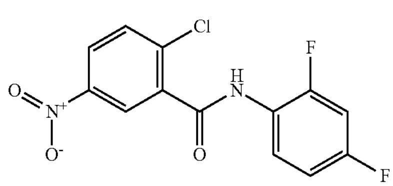 [SMILES: O=C(Nc1ccc(F)cc1F)c1cc([N+](=O)[O-])ccc1Cl] | 64 |

TABLE 4-continued

Structure and preparation method for C and CF series molecules

| No. | Structure | Prep* |
|-----|-----------|-------|
| C152 | 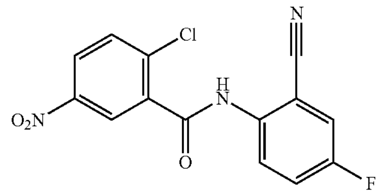 [SMILES: N#Cc1cc(F)ccc1NC(=O)c1cc([N+](=O)[O-])ccc1Cl] | 64 |
| C153 | 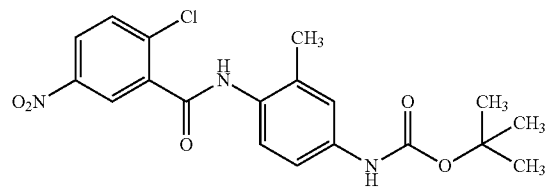 [SMILES: Cc1cc(NC(=O)OC(C)(C)C)ccc1NC(=O)c1cc([N+](=O)[O-])ccc1Cl] | 64 |
| C154 | 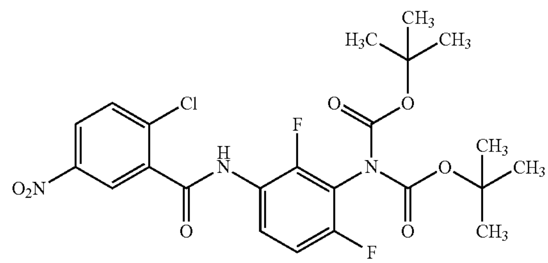 [SMILES: CC(C)(C)OC(=O)N(C(=O)OC(C)(C)C)c1c(F)ccc(NC(=O)c2cc([N+](=O)[O-])ccc2Cl)c1F] | 64 |
| C155 | 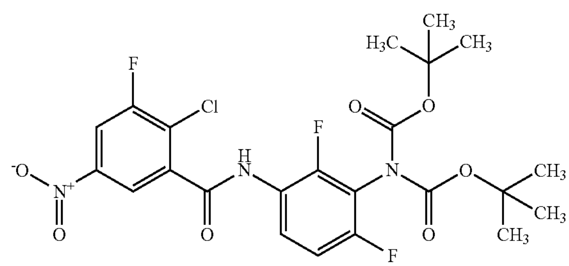 | 65 |
| C156 | 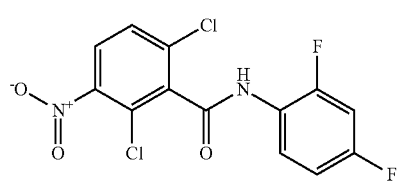 | 66 |
| C157 | 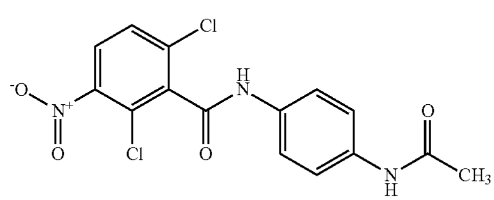 | 66 |
| C158 | 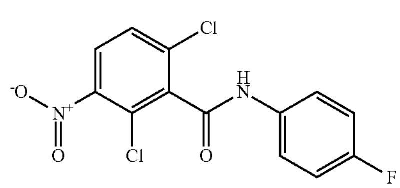 | 66 |

TABLE 4-continued

Structure and preparation method for C and CF series molecules

| No. | Structure | Prep* |
|---|---|---|
| C159 | 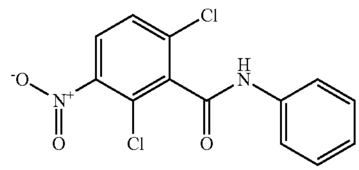 | 66 |
| C160 | 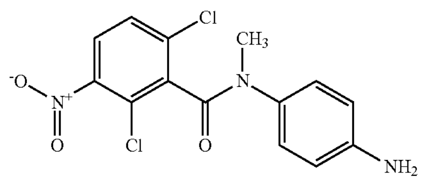 | 66 |
| C161 | 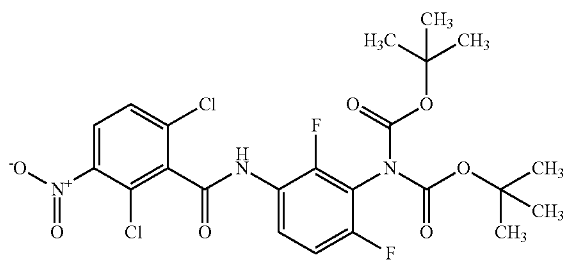 | 66 |
| C162 | 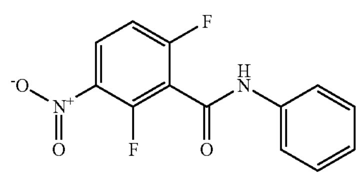 | 66 |
| C163 | 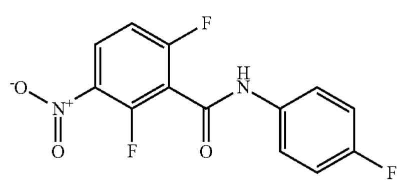 | 66 |
| C164 | 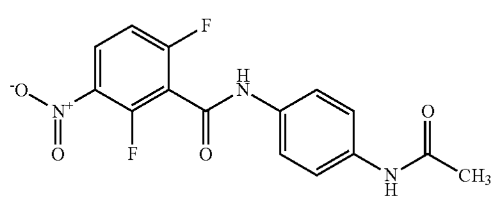 | 66 |
| C165 | 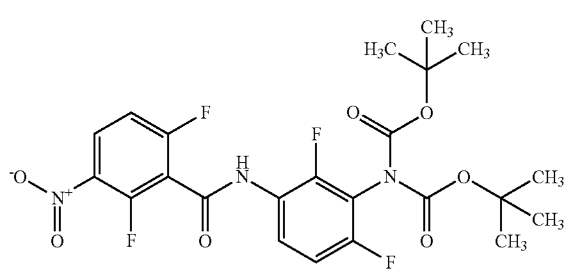 | 66 |

TABLE 4-continued

Structure and preparation method for C and CF series molecules

| No. | Structure | Prep* |
|---|---|---|
| C166 | (2,6-dichloro-3-nitro-N-(2,2,3,3,3-pentafluoropropyl)benzamide) | 66 |
| C167 | (2,6-dichloro-N-ethyl-3-nitrobenzamide) | 66 |
| C168 | (2,6-difluoro-N-ethyl-3-nitrobenzamide) | 66 |
| C169 | (2,6-dichloro-3-nitro-N-propylbenzamide) | 66 |
| C170 | (2,6-dichloro-N-(2-fluoroethyl)-3-nitrobenzamide) | 66 |
| C171 | (2,6-dichloro-3-nitro-N-(2,2,2-trifluoroethyl)benzamide) | 66 |
| C172 | (2,6-dichloro-3-nitro-N-(3,3,3-trifluoropropyl)benzamide) | 66 |
| C173 | (2,6-dichloro-N-(3-chloropropyl)-3-nitrobenzamide) | 66 |
| C174 | (2,6-difluoro-3-nitro-N-propylbenzamide) | 66 |

TABLE 4-continued

Structure and preparation method for C and CF series molecules

| No. | Structure | Prep* |
|---|---|---|
| C175 | 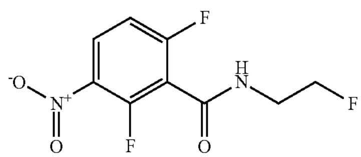 | 66 |
| C176 | 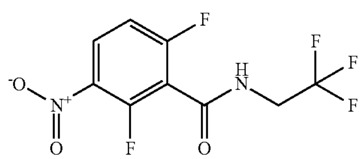 | 66 |
| C177 | 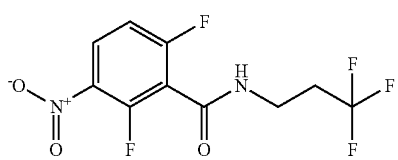 | 66 |
| C178 | 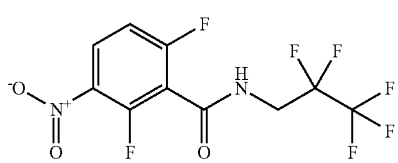 | 66 |
| C179 | 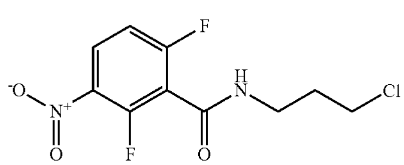 | 66 |
| C180 | 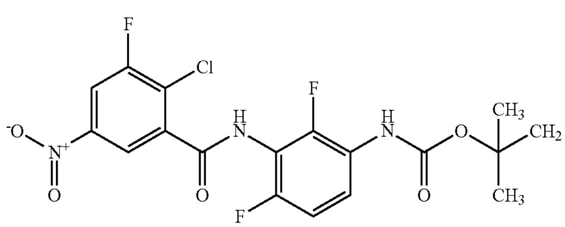 | 66 |
| C181 | 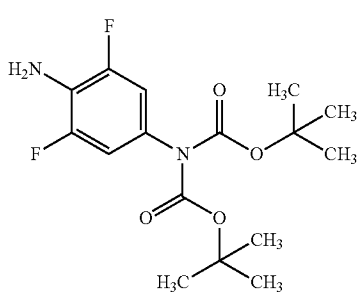 [SMILES: CC(C)(C)OC(=O)N(C(=O)OC(C)(C)C)c1cc(F)c(N)c(F)c1] | 67 |

TABLE 4-continued

Structure and preparation method for C and CF series molecules

| No. | Structure | Prep* |
|---|---|---|
| C182 | 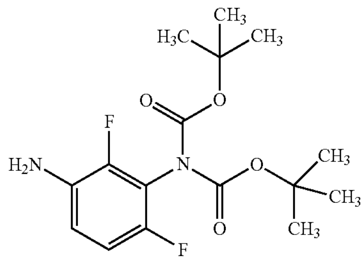 | 67 |
| C183 | 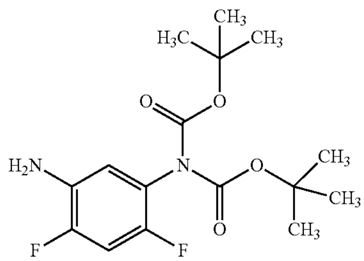 | 67 |
| C184 | 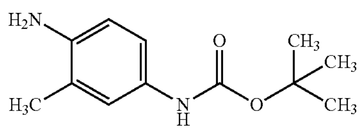 [SMILES: Cc1cc(NC(=O)OC(C)(C)C)ccc1N] | 67 |
| C185 | 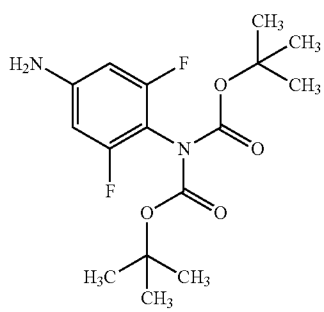 [SMILES: CC(C)(C)OC(=O)N(C(=O)OC(C)(C)C)c1c(F)cc(N)cc1F] | 67 |
| C186 | 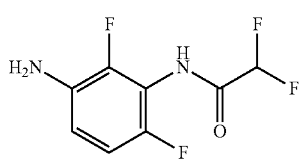 [SMILES: Nc1ccc(F)c(NC(=O)C(F)F)c1F] | 67 |
| C187 | 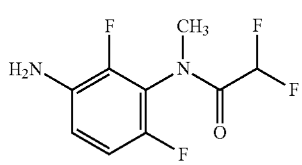 [SMILES: CN(C(=O)C(F)F)c1c(F)ccc(N)c1F] | 67 |
| C188 | 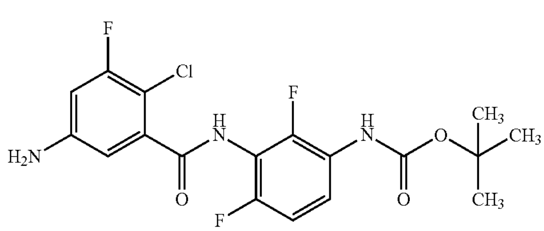 [SMILES: CC(C)(C)OC(=O)Nc1ccc(F)c(NC(=O)c2cc(N)cc(F)c2Cl)c1F] | 67 |

TABLE 4-continued

Structure and preparation method for C and CF series molecules

| No. | Structure | Prep* |
|---|---|---|
| C189 | 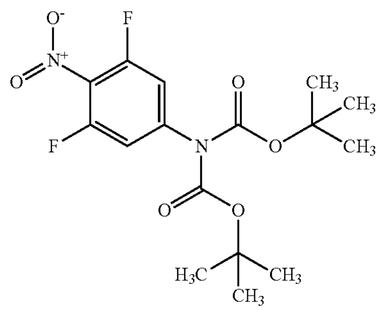 [SMILES: CC(C)(C)OC(=O)N(C(=O)OC(C)(C)C)c1cc(F)c([N+](=O)[O-])c(F)c1] | 68 |
| C190 | 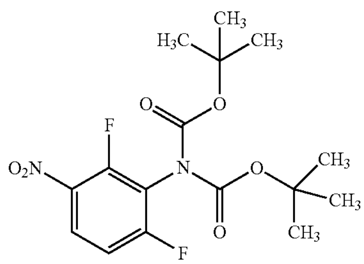 | 68 |
| C191 | 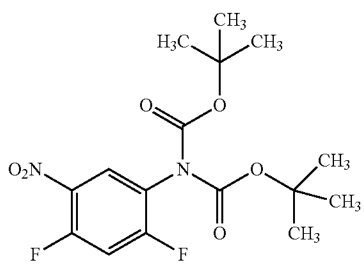 | 68 |
| C192 | 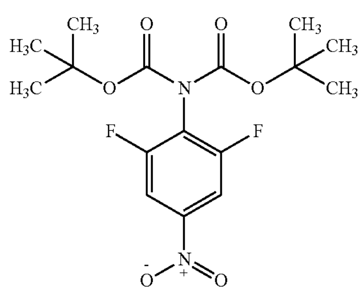 | 68 |
| C193 | 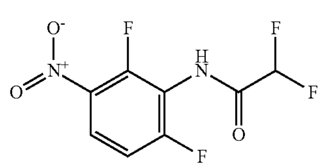 [SMILES: O=C(Nc1c(F)ccc([N+](=O)[O-])c1F)C(F)F] | 69 |
| C194 | 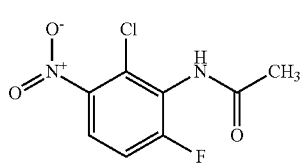 | 70 |

TABLE 4-continued

Structure and preparation method for C and CF series molecules

| No. | Structure | Prep* |
|---|---|---|
| C195 | 3-amino-2,6-difluorophenyl acetate (H$_2$N, F, O-C(=O)-CH$_3$, F) | 71 |
| C196 | 5-amino-2-chloro-3-fluorobenzoic acid | 72, 98 |
| C197 | 5-amino-2-chloro-3-(trifluoromethyl)benzoic acid | 72 |
| C198 | 5-amino-2-chloro-3-methylbenzoic acid | 72 |
| C199 | 5-amino-2,3-difluorobenzoic acid | 72 |
| C200 | 5-amino-3-chloro-2-fluorobenzoic acid | 72 |
| C201 | 5-amino-2-fluoro-3-methylbenzoic acid | 72 |

TABLE 4-continued

Structure and preparation method for C and CF series molecules

| No. | Structure | Prep* |
|---|---|---|
| C202 | 5-amino-3-chloro-2-methylbenzoic acid | 72 |
| C203 | 5-amino-3-fluoro-2-methylbenzoic acid | 72 |
| C204 | 5-amino-3-chloro-2-methoxybenzoic acid | 72 |
| C205 | 5-amino-3-fluoro-2-methoxybenzoic acid | 72 |
| C206 | 2-chloro-3-fluoro-5-nitrobenzoic acid | 73 |
| C207 | 2-chloro-5-nitro-3-(trifluoromethyl)benzoic acid | 73 |
| C208 | 2-chloro-3-methyl-5-nitrobenzoic acid | 73 |

TABLE 4-continued

Structure and preparation method for C and CF series molecules

| No. | Structure | Prep* |
|---|---|---|
| C209 | 3-nitro-5,6-difluoro-benzoic acid (nitro at 5, F at 2 and 3, COOH at 1) | 73 |
| C210 | 3-chloro-2-fluoro-5-nitrobenzoic acid | 73 |
| C211 | 2-fluoro-3-methyl-5-nitrobenzoic acid | 73 |
| C212 | 3-chloro-2-methoxy-5-nitrobenzoic acid | 73 |
| C213 | 3-fluoro-2-methoxy-5-nitrobenzoic acid | 73 |
| C214 | methyl 3-chloro-2-methyl-5-nitrobenzoate | 74 |
| C215 | methyl 3-fluoro-2-methyl-5-nitrobenzoate | 74 |

TABLE 4-continued

Structure and preparation method for C and CF series molecules

| No. | Structure | Prep* |
|---|---|---|
| C216 | 3-nitro-5-chloro-2-methylbenzoic acid | 75 |
| C217 | 3-nitro-5-fluoro-2-methylbenzoic acid | 75 |
| C218 | 2-chloro-5-nitro-N',N-dimethyl-N'-phenylbenzohydrazide | 76 |
| C219 | 2-chloro-5-nitro-N'-methyl-N'-phenylbenzohydrazide | 77 |
| C220 | N-methyl-N'-(2,2,2-trifluoroethylidene)hydrazine | 78 |
| C221 | 5-amino-2-chloro-N-(3-amino-2,4-difluorophenyl)benzamide HCl | 79 |
| C222 | 2-chloro-5-nitro-N-(3-(2,2-difluoroacetamido)-2,4-difluorophenyl)benzamide | 80 |
| C223 | tert-butyl (3-methyl-4-nitrophenyl)carbamate | 81 |

TABLE 4-continued

Structure and preparation method for C and CF series molecules

| No. | Structure | Prep* |
|---|---|---|
| C224 | 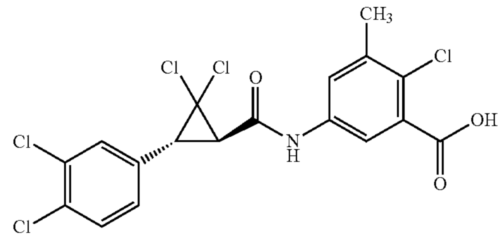 [SMILES: Cc1cc(NC(=O)[C@H]2[C@H](c3ccc(Cl)c(Cl)c3)C2(Cl)Cl)cc(C(=O)O)c1Cl] | 39 |
| C225 | 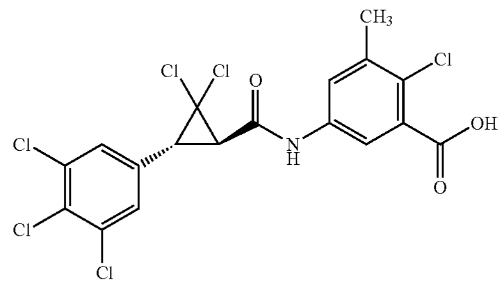 [SMILES: Cc1cc(NC(=O)[C@H]2[C@H](c3cc(Cl)c(Cl)c(Cl)c3)C2(Cl)Cl)cc(C(=O)O)c1Cl] | 39 |
| C226 | 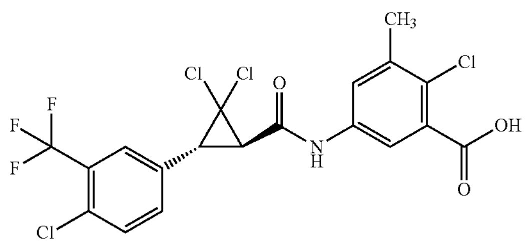 [SMILES: Cc1cc(NC(=O)[C@H]2[C@H](c3ccc(Cl)c(C(F)(F)F)c3)C2(Cl)Cl)cc(C(=O)O)c1Cl] | 39 |
| C227 | 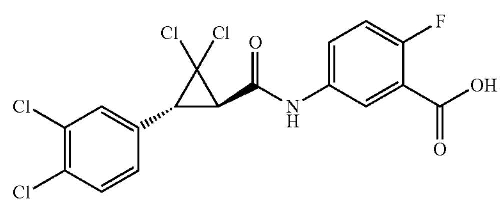 [SMILES: O=C(O)c1cc(NC(=O)[C@H]2[C@H](c3ccc(Cl)c(Cl)c3)C2(Cl)Cl)ccc1F] | 39 |
| C228 | 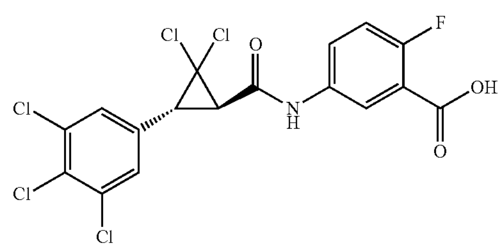 [SMILES: O=C(O)c1cc(NC(=O)[C@H]2[C@H](c3cc(Cl)c(Cl)c(Cl)c3)C2(Cl)Cl)ccc1F] | 39 |
| C229 | 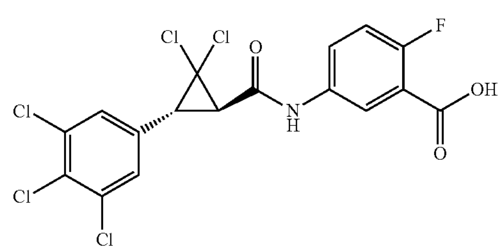 [SMILES: O=C(O)c1cc(NC(=O)[C@H]2[C@H](c3cc(Cl)c(Cl)c(Cl)c3)C2(Cl)Cl)ccc1F] | 39 |

TABLE 4-continued

Structure and preparation method for C and CF series molecules

| No. | Structure | Prep* |
|---|---|---|
| C230 | 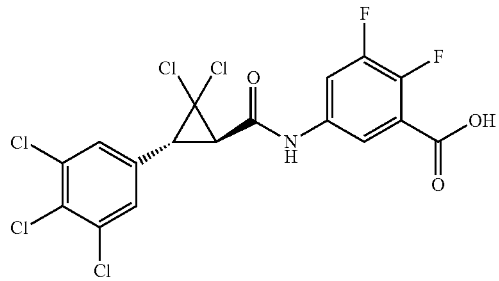 [SMILES: O=C(O)c1cc(NC(=O)[C@H]2[C@H](c3cc(Cl)c(Cl)c(Cl)c3)C2(Cl)Cl)cc(F)c1F] | 39 |
| C231 | 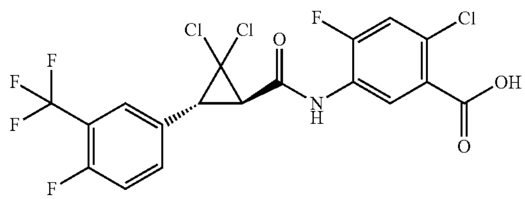 [SMILES: O=C(O)c1cc(NC(=O)[C@H]2[C@H](c3ccc(F)c(C(F)(F)F)c3)C2(Cl)Cl)c(F)cc1Cl] | 39 |
| C232 | 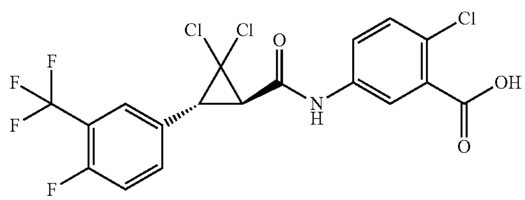 | 39 |
| C233 | 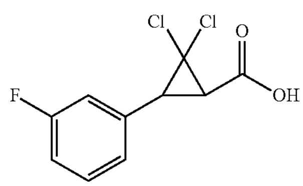 [SMILES: O=C(O)C1C(c2cccc(F)c2)C1(Cl)Cl] | 40 |
| C234 | 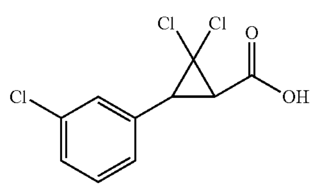 [SMILES: O=C(O)C1C(c2cccc(Cl)c2)C1(Cl)Cl] | 40 |
| C235 | 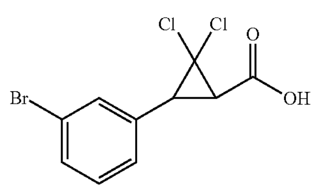 | 40 |
| C236 | 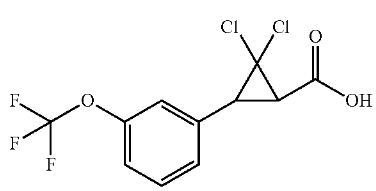 [SMILES: O=C(O)C1C(c2cccc(OC(F)(F)F)c2)C1(Cl)Cl] | 40 |

TABLE 4-continued

Structure and preparation method for C and CF series molecules

| No. | Structure | Prep* |
|---|---|---|
| C237 | 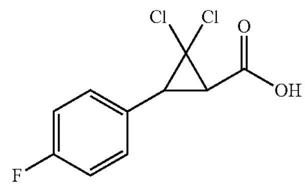 | 40 |
| C238 | 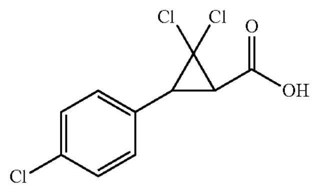 | 40 |
| C239 | 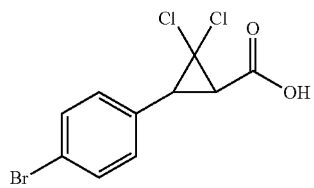 [SMILES: O=C(O)C1C(c2ccc(Cl)cc2)C1(Cl)Cl] | 40 |
| C240 | 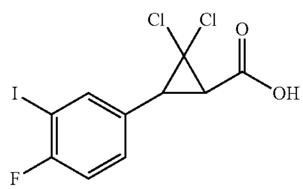 [SMILES: O=C(O)C1C(c2ccc(F)c(I)c2)C1(Cl)Cl] | 51 |
| C241 | 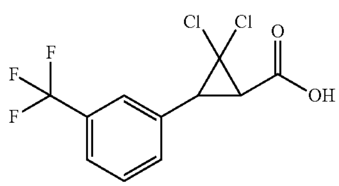 [SMILES: O=C(O)C1C(c2cccc(C(F)(F)F)c2)C1(Cl)Cl] | 51 |
| C242 | 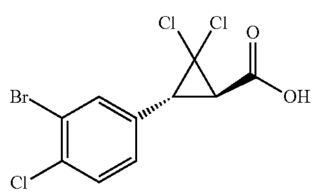 [SMILES: O=C(O)[C@H]1[C@H](c2ccc(Cl)c(Br)c2)C1(Cl)Cl] | 55 |
| C243 | 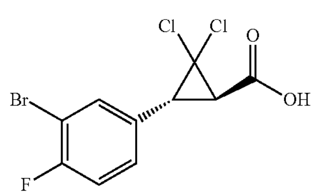 | 55 |
| C244 | 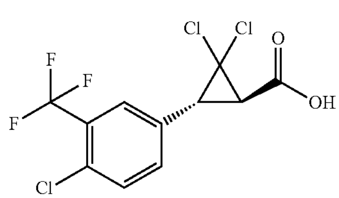 [SMILES: O=C(O)[C@H]1[C@H](c2ccc(Cl)c(C(F)(F)F)c2)C1(Cl)Cl] | 55 |

TABLE 4-continued

Structure and preparation method for C and CF series molecules

| No. | Structure | Prep* |
|---|---|---|
| C245 | 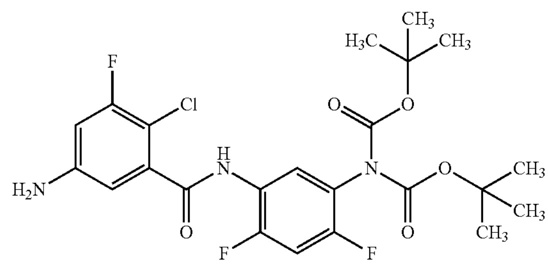 [SMILES: CC(C)(C)OC(=O)N(C(=O)OC(C)(C)C)c1cc(NC(=O)c2cc(N)cc(F)c2Cl)c(F)cc1F] | 57 |
| C246 | 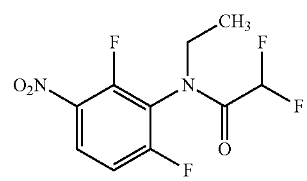 [SMILES: CCN(C(=O)C(F)F)c1c(F)ccc([N+](=O)[O-])c1F] | 61 |
| C247 | 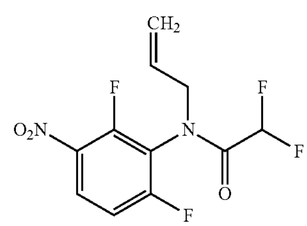 [SMILES: C=CCN(C(=O)C(F)F)c1c(F)ccc([N+](=O)[O-])c1F] | 61 |
| C248 | 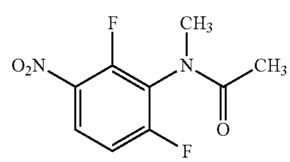 [SMILES: CC(=O)N(C)c1c(F)ccc([N+](=O)[O-])c1F] | 61 |
| C249 | 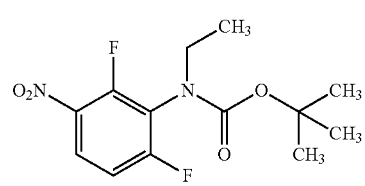 [SMILES: CCN(C(=O)OC(C)(C)C)c1c(F)ccc([N+](=O)[O-])c1F] | 61 |
| C250 | 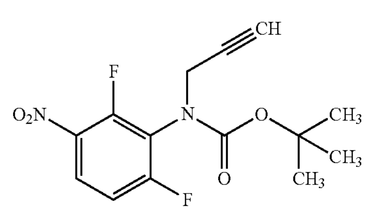 [SMILES: C#CCN(C(=O)OC(C)(C)C)c1c(F)ccc([N+](=O)[O-])c1F] | 61 |
| C251 | 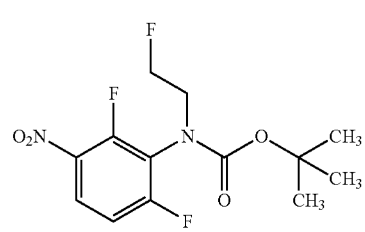 [SMILES: CC(C)(C)OC(=O)N(CCF)c1c(F)ccc([N+](=O)[O-])c1F] | 61 |

TABLE 4-continued
Structure and preparation method for C and CF series molecules
| No. | Structure | Prep* |
|-----|-----------|-------|
| C252 | 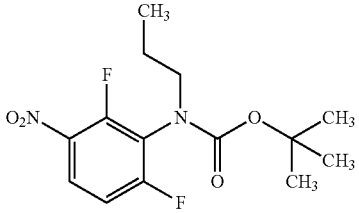 [SMILES: CCCN(C(=O)OC(C)(C)C)c1c(F)ccc([N+](=O)[O-])c1F] | 61 |
| C253 | 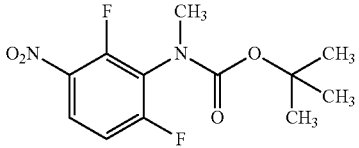 [SMILES: CN(C(=O)OC(C)(C)C)c1c(F)ccc([N+](=O)[O-])c1F] | 62 |
| C254 | 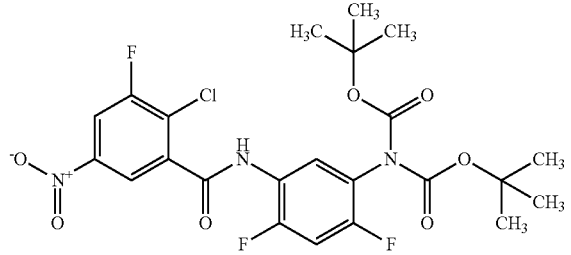 | 65 |
| C255 | 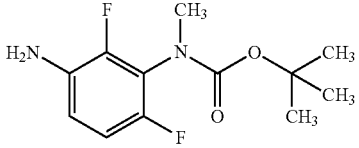 | 67 |
| C256 | 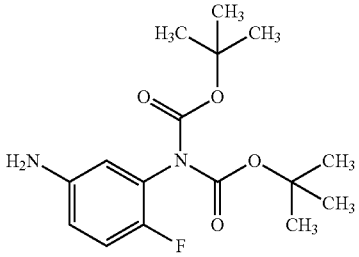 | 67 |
| C257 | 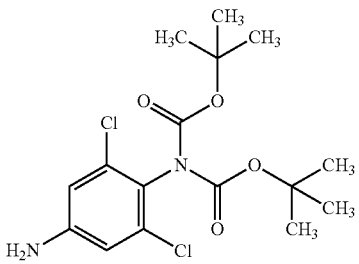 [SMILES: CC(C)(C)OC(=O)N(C(=O)OC(C)(C)C)c1c(Cl)cc(N)cc1Cl] | 67 |

TABLE 4-continued
Structure and preparation method for C and CF series molecules
| No. | Structure | Prep* |
|---|---|---|
| C258 | 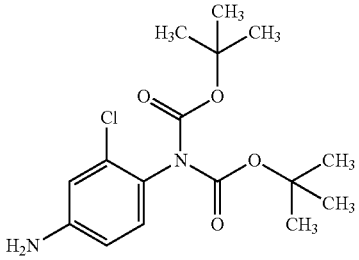 [SMILES: CC(C)(C)OC(=O)N(C(=O)OC(C)(C)C)c1ccc(N)cc1Cl] | 67 |
| C259 | 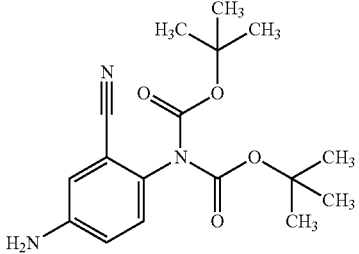 | 67 |
| C260 | 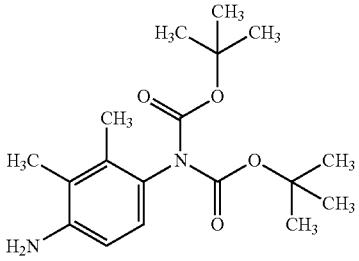 | 67 |
| C261 | 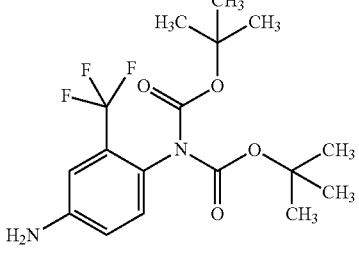 | 67 |
| C262 | 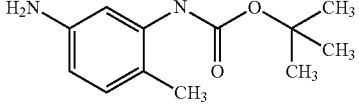 | 67 |
| C263 | 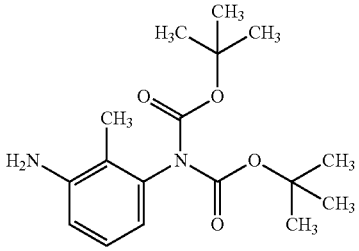 | 67 |

TABLE 4-continued

Structure and preparation method for C and CF series molecules

| No. | Structure | Prep* |
|-----|-----------|-------|
| C264 | 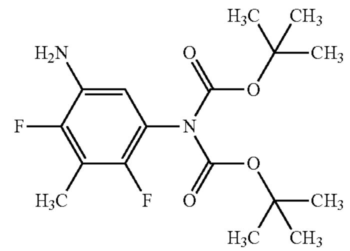 [SMILES: Cc1c(F)c(N)cc(N(C(=O)OC(C)(C)C)C(=O)OC(C)(C)C)c1F] | 67 |
| C265 | 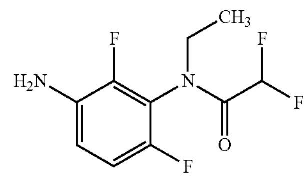 | 67 |
| C266 | 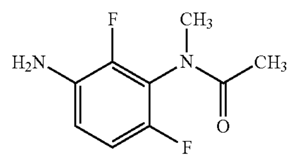 | 67 |
| C267 | 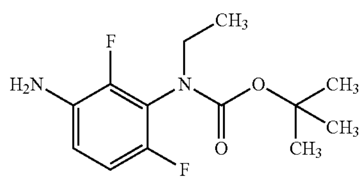 | 67 |
| C268 | 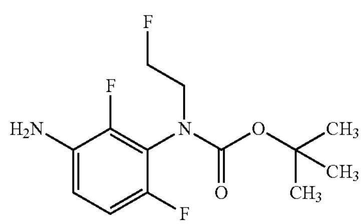 | 67 |
| C269 | 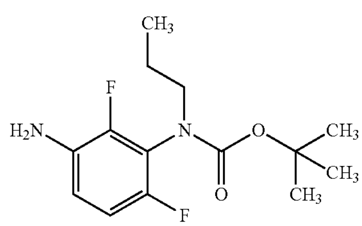 | 67 |
| C270 | 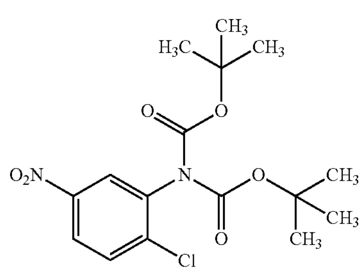 | 68 |

TABLE 4-continued

Structure and preparation method for C and CF series molecules

| No. | Structure | Prep* |
|---|---|---|
| C271 | 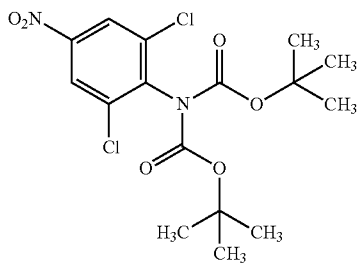 [SMILES: CC(C)(C)OC(=O)N(C(=O)OC(C)(C)C)c1c(Cl)cc([N+](=O)[O-])cc1Cl] | 68 |
| C272 | 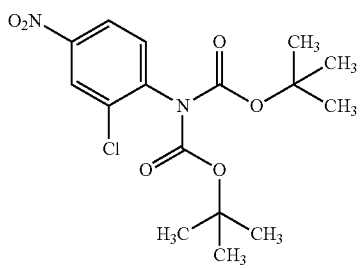 [SMILES: CC(C)(C)OC(=O)N(C(=O)OC(C)(C)C)c1ccc([N+](=O)[O-])cc1Cl] | 68 |
| C273 | 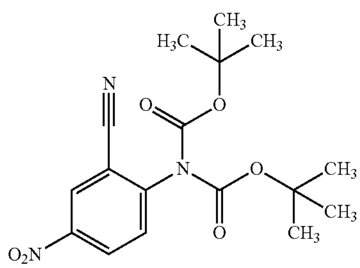 [SMILES: CC(C)(C)OC(=O)N(C(=O)OC(C)(C)C)c1ccc([N+](=O)[O-])cc1C#N] | 68 |
| C274 | 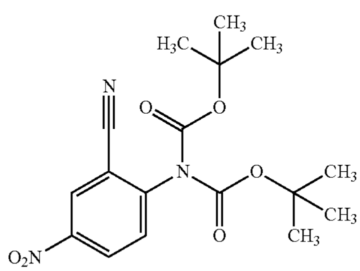 [SMILES: CC(C)(C)OC(=O)N(C(=O)OC(C)(C)C)c1ccc([N+](=O)[O-])cc1C#N] | 68 |
| C275 | 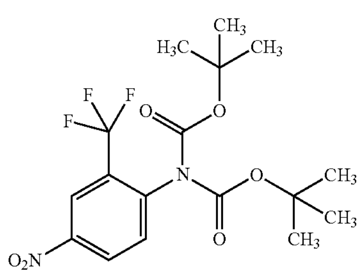 [SMILES: CC(C)(C)OC(=O)N(C(=O)OC(C)(C)C)c1ccc([N+](=O)[O-])cc1C(F)(F)F] | 68 |

TABLE 4-continued

Structure and preparation method for C and CF series molecules

| No. | Structure | Prep* |
|---|---|---|
| C276 | 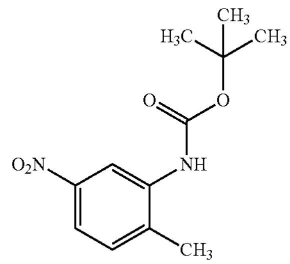 [SMILES: Cc1ccc([N+](=O)[O-])cc1NC(=O)OC(C)(C)C] | 68 |
| C277 | 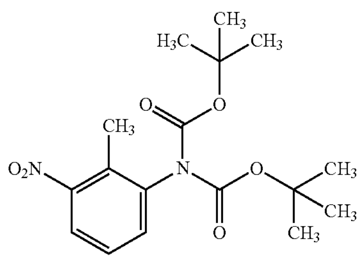 [SMILES: Cc1c(N(C(=O)OC(C)(C)C)C(=O)OC(C)(C)C)cccc1[N+](=O)[O-]] | 68 |
| C278 | 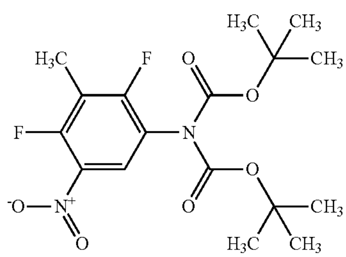 | 68 |
| C279 | 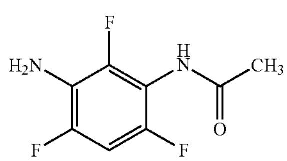 | 70 |
| C280 | 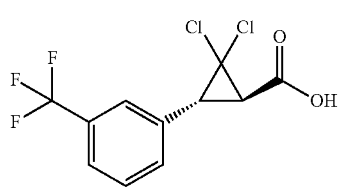 [SMILES: O=C(O)[C@H]1[C@H](c2cccc(C(F)(F)F)c2)C1(Cl)Cl] | R4 |
| C281 | 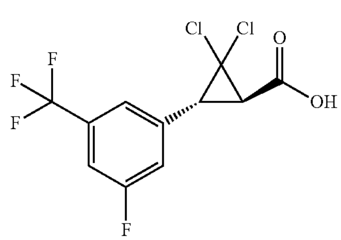 [SMILES: O=C(O)[C@H]1[C@H](c2cc(F)cc(C(F)(F)F)c2)C1(Cl)Cl] | R4 |

TABLE 4-continued

Structure and preparation method for C and CF series molecules

| No. | Structure | Prep* |
|---|---|---|
| C282 | 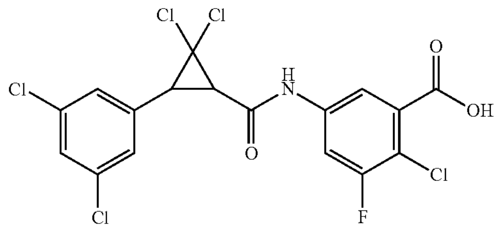 [SMILES: O=C(O)c1cc(NC(=O)C2C(c3cc(Cl)cc(Cl)c3)C2(Cl)Cl)cc(F)c1Cl] | 84 |
| C283 | 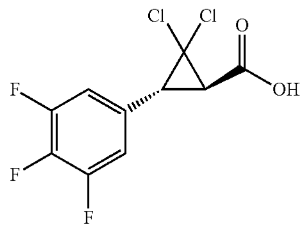 [SMILES: O=C(O)[C@H]1[C@H](c2cc(F)c(F)c(F)c2)C1(Cl)Cl] | 85 |
| C284 | 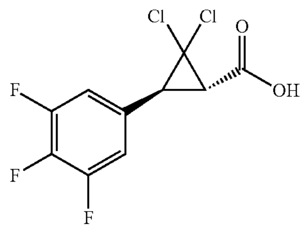 [SMILES: O=C(O)[C@@H]1[C@@H](c2cc(F)c(F)c(F)c2)C1(Cl)Cl] | 85 |
| C285 | 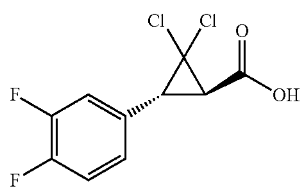 [SMILES: O=C(O)[C@H]1[C@H](c2ccc(F)c(F)c2)C1(Cl)Cl] | 85 |
| C286 | 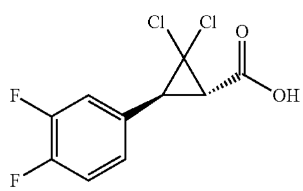 [SMILES: O=C(O)[C@@H]1[C@@H](c2ccc(F)c(F)c2)C1(Cl)Cl] | 85 |
| C287 | 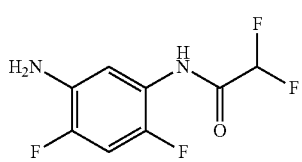 [SMILES: Nc1cc(NC(=O)C(F)F)c(F)cc1F] | 86 |
| C288 | 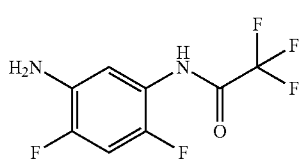 [SMILES: Nc1cc(NC(=O)C(F)(F)F)c(F)cc1F] | 86 |
| C289 | 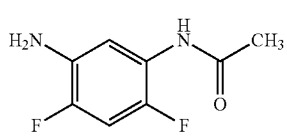 | 86 |

TABLE 4-continued

Structure and preparation method for C and CF series molecules

| No. | Structure | Prep* |
|---|---|---|
| C290 | 2-amino-3-fluoro-N-acetyl aniline | 86 |
| C291 | 2-amino-5-fluoro-N-acetyl aniline | 86 |
| C292 | 5-amino-2-fluoro-N-acetyl aniline | 86 |
| C293 | 3-amino-4-fluoro-N-acetyl aniline | 86 |
| C294 | 2-amino-3,5-difluoro-N-acetyl aniline | 86 |
| C295 | 2-amino-4,6-difluoro-N-acetyl aniline | 86 |
| C296 | 2-amino-4,5-difluoro-N-acetyl aniline | 86 |
| C297 | 2-amino-4,6-difluoro-N-trifluoroacetyl aniline | 86 |
| C298 | 2-amino-5,6-difluoro-N-trifluoroacetyl aniline | 86 |

TABLE 4-continued

Structure and preparation method for C and CF series molecules

| No. | Structure | Prep* |
|---|---|---|
| C299 | 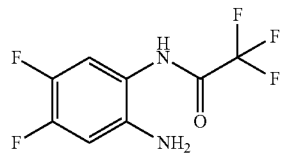 | 86 |
| C300 | 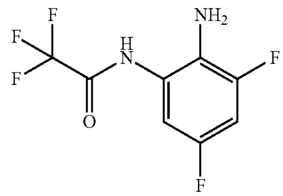 [SMILES: Nc1c(F)cc(F)cc1NC(=O)C(F)(F)F] | 86 |
| C301 | 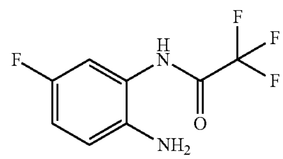 [SMILES: Nc1ccc(F)cc1NC(=O)C(F)(F)F] | 86 |
| C302 | 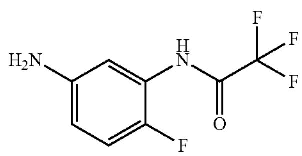 [SMILES: Nc1ccc(F)c(NC(=O)C(F)(F)F)c1] | 86 |
| C303 | 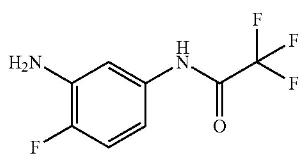 [SMILES: Nc1cc(NC(=O)C(F)(F)F)ccc1F] | 86 |
| C304 | 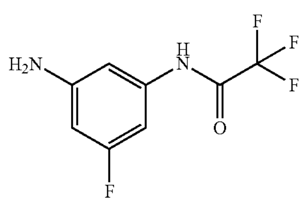 [SMILES: Nc1cc(F)cc(NC(=O)C(F)(F)F)c1] | 86 |
| C305 | 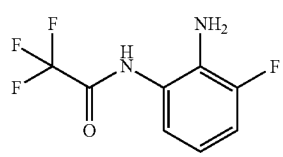 [SMILES: Nc1c(F)cccc1NC(=O)C(F)(F)F] | 86 |
| C306 | 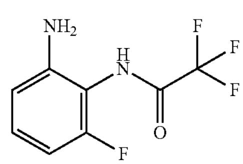 [SMILES: Nc1cccc(F)c1NC(=O)C(F)(F)F] | 86 |
| C307 | 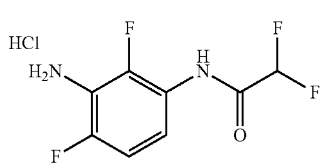 [SMILES: Cl ; Nc1c(F)ccc(NC(=O)C(F)F)c1F] | 87 |

TABLE 4-continued
Structure and preparation method for C and CF series molecules
| No. | Structure | Prep* |
|---|---|---|
| C308 | 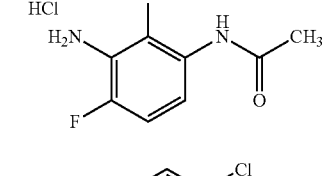 | 87 |
| C309 | 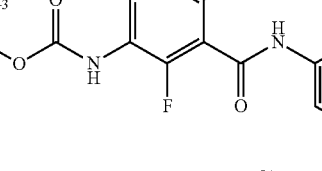 | 87 |
| C310 | 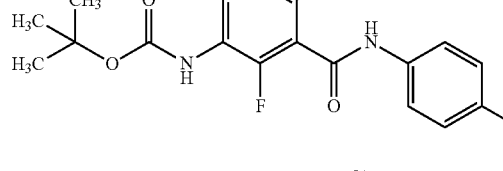 | 88 |
| C311 | 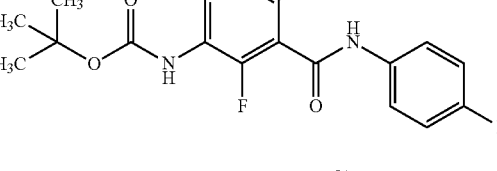 | 88 |
| C312 | 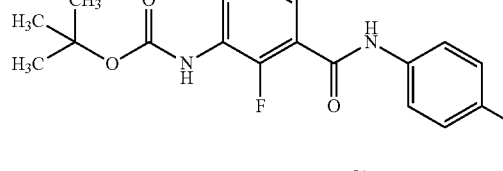 | 88 |
| C313 | 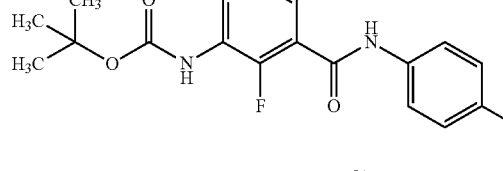 | 88 |
| C314 | 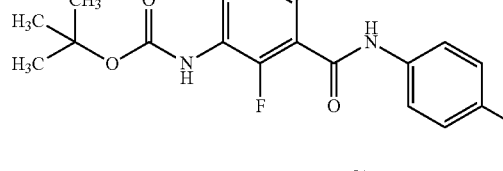 | 88 |
| C315 | 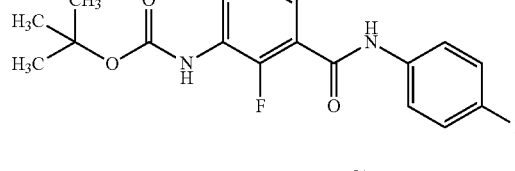 | 88 |

TABLE 4-continued
Structure and preparation method for C and CF series molecules
| No. | Structure | Prep* |
|---|---|---|
| C316 | 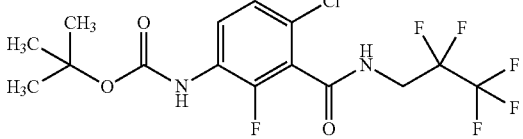 | 88 |
| C317 | 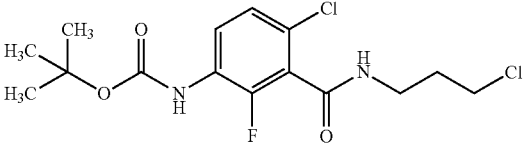 [SMILES: CC(C)(C)OC(=O)Nc1ccc(Cl)c(C(=O)NCCCCl)c1F] | 88 |
| C318 | 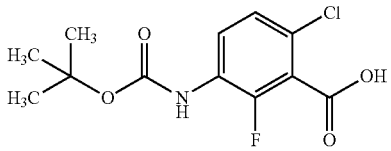 [SMILES: CC(C)(C)OC(=O)Nc1ccc(Cl)c(C(=O)O)c1F] | 89 |
| C319 | 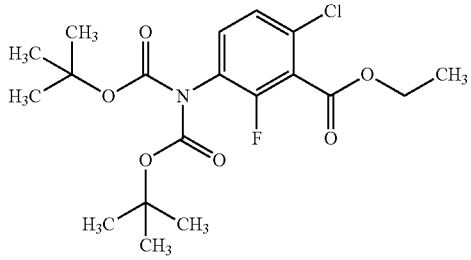 [SMILES: CCOC(=O)c1c(Cl)ccc(N(C(=O)OC(C)(C)C)C(=O)OC(C)(C)C)c1F] | 90 |
| C320 | 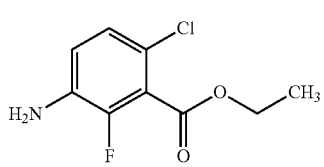 | 91 |
| C321 | 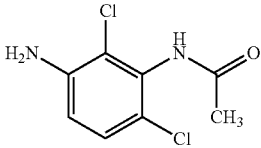 | 92 |
| C322 | 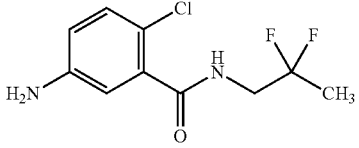 | 93 |
| C323 | 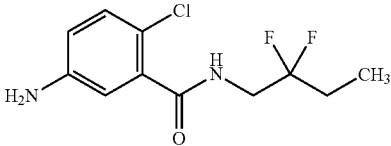 | 93 |

TABLE 4-continued
Structure and preparation method for C and CF series molecules
| No. | Structure | Prep* |
|---|---|---|
| C324 | 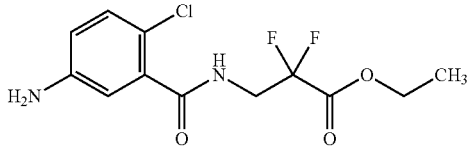 | 93 |
| C325 | 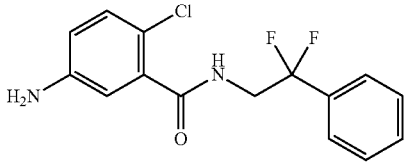 | 93 |
| C326 | 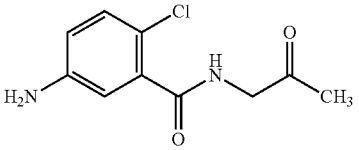 | 93 |
| C327 | 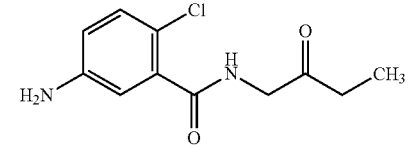 | 93 |
| C328 | 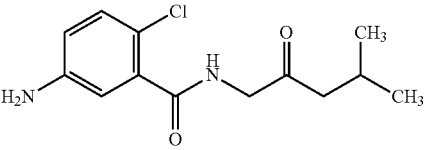 | 93 |
| C329 | 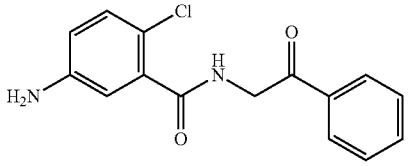 | 93 |
| C330 | 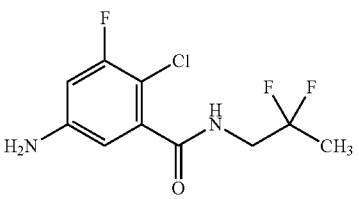 | 93 |
| C331 | 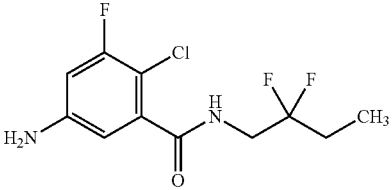 | 93 |

TABLE 4-continued

Structure and preparation method for C and CF series molecules

| No. | Structure | Prep* |
|---|---|---|
| C332 | 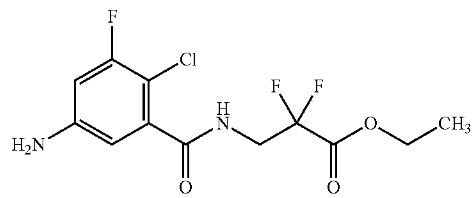 | 93 |
| C333 | 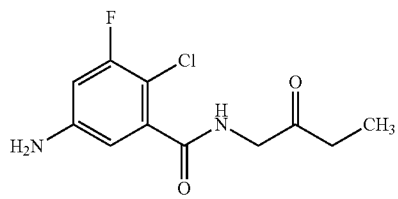 [SMILES: CCC(=O)CNC(=O)c1cc(N)cc(F)c1Cl] | 93 |
| C334 | 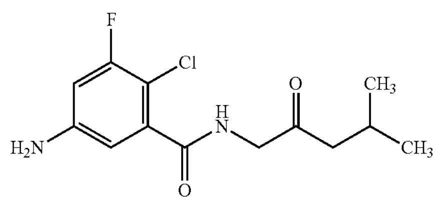 [SMILES: CC(C)CC(=O)CNC(=O)c1cc(N)cc(F)c1Cl] | 93 |
| C335 | 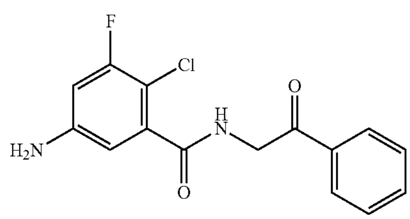 [SMILES: Nc1cc(F)c(Cl)c(C(=O)NCC(=O)c2ccccc2)c1] | 93 |
| C336 | 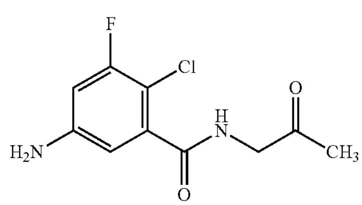 | 93 |
| C337 | 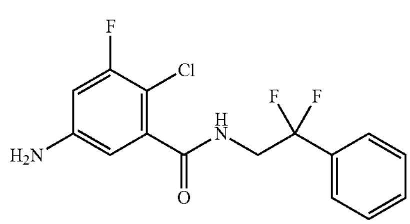 [SMILES: Nc1cc(F)c(Cl)c(C(=O)NCC(F)(F)c2ccccc2)c1] | 93 |
| C338 | 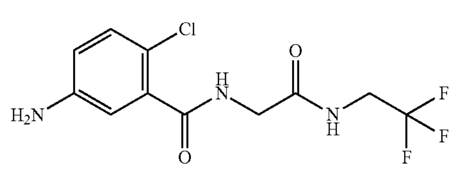 [SMILES: Nc1ccc(Cl)c(C(=O)NCC(=O)NCC(F)(F)F)c1] | 94 |

TABLE 4-continued

Structure and preparation method for C and CF series molecules

| No. | Structure | Prep* |
|---|---|---|
| C339 | 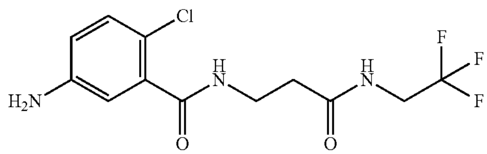 [SMILES: Nc1ccc(Cl)c(C(=O)NCCC(=O)NCC(F)(F)F)c1] | 94 |
| C340 | 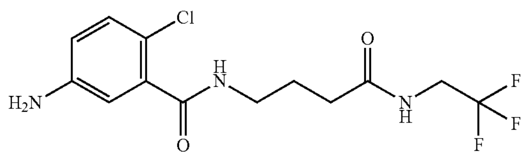 [SMILES: Nc1ccc(Cl)c(C(=O)NCCCC(=O)NCC(F)(F)F)c1] | 94 |
| C341 | 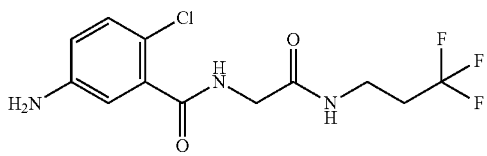 [SMILES: Nc1ccc(Cl)c(C(=O)NCC(=O)NCCC(F)(F)F)c1] | 94 |
| C342 | 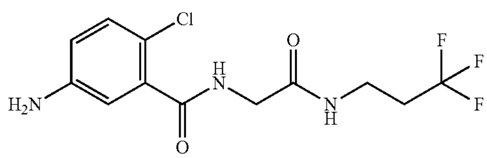 [SMILES: Nc1ccc(Cl)c(C(=O)NCC(=O)NCCC(F)(F)F)c1] | 94 |
| C343 | 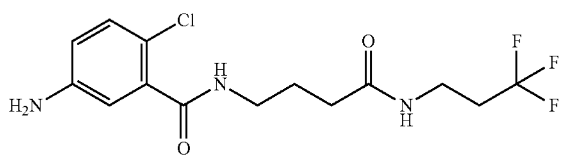 [SMILES: Nc1ccc(Cl)c(C(=O)NCCCC(=O)NCCC(F)(F)F)c1] | 94 |
| C344 | 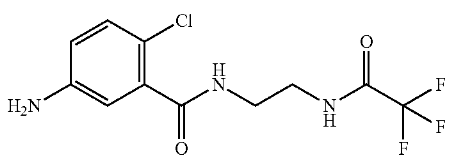 [SMILES: Nc1ccc(Cl)c(C(=O)NCCNC(=O)C(F)(F)F)c1] | 94 |
| C345 | 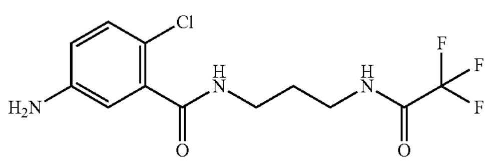 [SMILES: Nc1ccc(Cl)c(C(=O)NCCCNC(=O)C(F)(F)F)c1] | 94 |
| C346 | 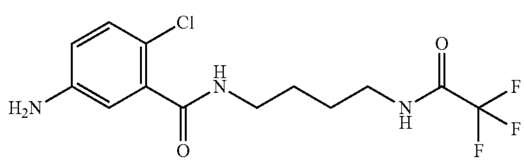 [SMILES: Nc1ccc(Cl)c(C(=O)NCCCCNC(=O)C(F)(F)F)c1] | 94 |
| C347 | 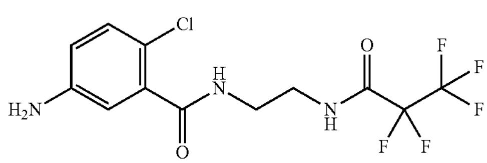 [SMILES: Nc1ccc(Cl)c(C(=O)NCCNC(=O)C(F)(F)C(F)(F)F)c1] | 94 |

TABLE 4-continued

Structure and preparation method for C and CF series molecules

| No. | Structure | Prep* |
|---|---|---|
| C348 | 5-amino-2-chloro-N-(3-(2,2,3,3,3-pentafluoropropanamido)propyl)benzamide | 94 |
| C349 | 5-amino-2-chloro-N-(4-(2,2,3,3,3-pentafluoropropanamido)butyl)benzamide | 94 |
| C350 | 2-amino-N'-(2,2,2-trifluoroethyl)acetamide · HCl | 95 |
| C351 | 3-amino-N-(2,2,2-trifluoroethyl)propanamide · HCl | 95 |
| C352 | 4-amino-N-(2,2,2-trifluoroethyl)butanamide · HCl | 95 |
| C353 | 2-amino-N-(3,3,3-trifluoropropyl)acetamide · HCl | 95 |
| C354 | 3-amino-N-(3,3,3-trifluoropropyl)propanamide · HCl | 95 |
| C355 | 4-amino-N-(3,3,3-trifluoropropyl)butanamide · HCl | 95 |
| C356 | N-(2-aminoethyl)-2,2,2-trifluoroacetamide · HCl | 95 |
| C357 | N-(3-aminopropyl)-2,2,2-trifluoroacetamide · HCl | 95 |
| C358 | N-(4-aminobutyl)-2,2,2-trifluoroacetamide · HCl | 95 |

TABLE 4-continued

Structure and preparation method for C and CF series molecules

| No. | Structure | Prep* |
|---|---|---|
| C359 | F₃C-CF₂-C(=O)-NH-CH₂CH₂-NH₂ · HCl | 95 |
| C360 | F₃C-CF₂-C(=O)-NH-(CH₂)₃-NH₂ · HCl | 95 |
| C361 | F₃C-CF₂-C(=O)-NH-(CH₂)₄-NH₂ · HCl | 95 |
| C362 | (CH₃)₃C-O-C(=O)-NH-CH₂-C(=O)-NH-CH₂CF₃ | 96 |
| C363 | (CH₃)₃C-O-C(=O)-NH-(CH₂)₂-C(=O)-NH-CH₂CF₃ | 96 |
| C364 | (CH₃)₃C-O-C(=O)-NH-(CH₂)₃-C(=O)-NH-CH₂CF₃ | 96 |
| C365 | (CH₃)₃C-O-C(=O)-NH-CH₂-C(=O)-NH-CH₂CH₂CF₃ | 96 |
| C366 | (CH₃)₃C-O-C(=O)-NH-(CH₂)₂-C(=O)-NH-CH₂CH₂CF₃ | 96 |
| C367 | (CH₃)₃C-O-C(=O)-NH-(CH₂)₃-C(=O)-NH-CH₂CH₂CF₃ | 96 |
| C368 | (CH₃)₃C-O-C(=O)-NH-CH₂CH₂-NH-C(=O)-CF₃ | 97 |
| C369 | (CH₃)₃C-O-C(=O)-NH-(CH₂)₃-NH-C(=O)-CF₃ | 97 |

TABLE 4-continued

Structure and preparation method for C and CF series molecules

| No. | Structure | Prep* |
|---|---|---|
| C370 | (structure) | 97 |
| C371 | (structure) | 97 |
| C372 | (structure) | 97 |
| C373 | (structure) | 97 |
| C375 | (structure) | 99 |
| C376 | (structure) | 99 |
| C377 | (structure) | 100 |
| C378 | (structure) | 101 |
| C379 | (structure) | 101 |

TABLE 4-continued

Structure and preparation method for C and CF series molecules

| No. | Structure | Prep* |
|---|---|---|
| C380 | 3-fluoro-2-chloro-5-nitro-N-(2-ethoxy-1,1-difluoro-2-oxoethyl... ethyl 3-(3-fluoro-2-chloro-5-nitrobenzamido)-2,2-difluoropropanoate | 101 |
| C381 | 3-fluoro-2-chloro-5-nitro-N-(2,2-difluoro-2-phenylethyl)benzamide | 101 |
| C382 | 3-fluoro-2-chloro-5-nitro-N-(2-oxopropyl)benzamide | 101 |
| C383 | 3-fluoro-2-chloro-5-nitro-N-(2-oxobutyl)benzamide | 101 |
| C384 | 3-fluoro-2-chloro-5-nitro-N-(4-methyl-2-oxopentyl)benzamide | 101 |
| C385 | 3-fluoro-2-chloro-5-nitro-N-(2-oxo-2-phenylethyl)benzamide | 101 |
| C386 | 2-chloro-5-nitro-N-(2,2-difluoropropyl)benzamide | 102 |

TABLE 4-continued

Structure and preparation method for C and CF series molecules

| No. | Structure | Prep* |
|---|---|---|
| C387 | 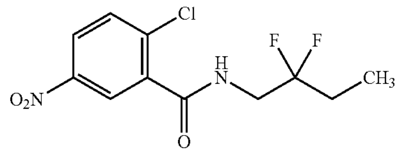 [SMILES: CCC(F)(F)CNC(=O)c1cc([N+](=O)[O-])ccc1Cl] | 102 |
| C388 | 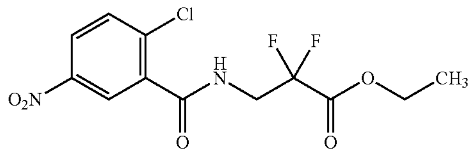 [SMILES: CCOC(=O)C(F)(F)CNC(=O)c1cc([N+](=O)[O-])ccc1Cl] | 102 |
| C389 | 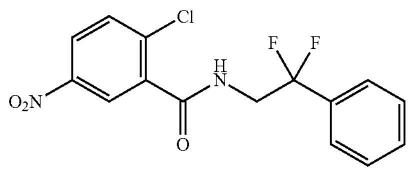 [SMILES: O=C(NCC(F)(F)c1ccccc1)c1cc([N+](=O)[O-])ccc1Cl] | 102 |
| C390 | 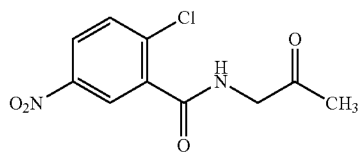 [SMILES: CC(=O)CNC(=O)c1cc([N+](=O)[O-])ccc1Cl] | 102 |
| C391 | 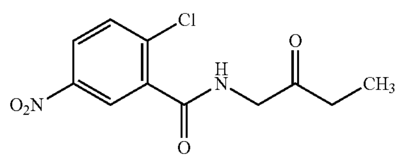 [SMILES: CCC(=O)CNC(=O)c1cc([N+](=O)[O-])ccc1Cl] | 102 |
| C392 | 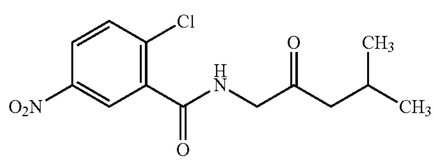 [SMILES: CC(C)CC(=O)CNC(=O)c1cc([N+](=O)[O-])ccc1Cl] | 102 |
| C393 | 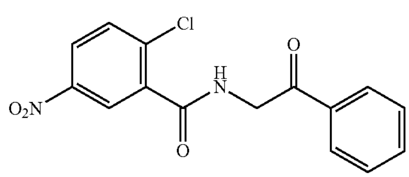 [SMILES: O=C(CNC(=O)c1cc([N+](=O)[O-])ccc1Cl)c1ccccc1] | 102 |
| CF1 | 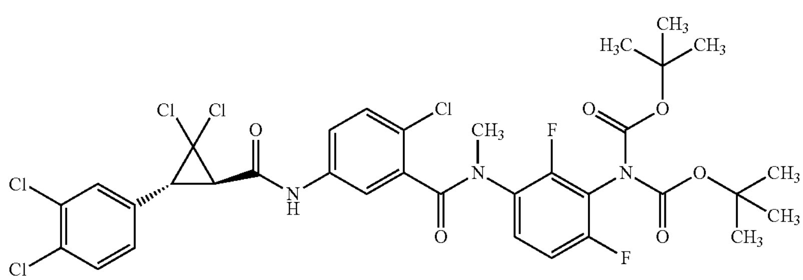 [SMILES: CN(C(=O)c1cc(NC(=O)[C@H]2[C@H](c3ccc(Cl)c(Cl)c3)C2(Cl)Cl)ccc1Cl)c1ccc(F)c(N(C(=O)OC(C)(C)C)C(=O)OC(C)(C)C)c1F] | 18 |

TABLE 4-continued

Structure and preparation method for C and CF series molecules

| No. | Structure | Prep* |
|---|---|---|
| CF2 | 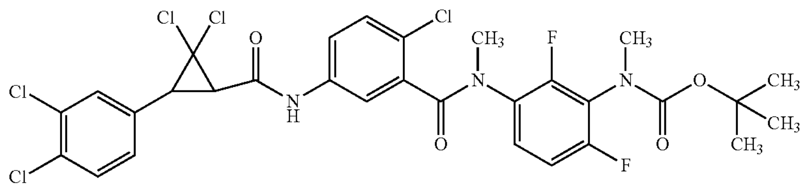 [SMILES: CN(C(=O)c1cc(NC(=O)C2C(c3ccc(Cl)c(Cl)c3)C2(Cl)Cl)ccc1Cl)c1ccc(F)c(N(C)C(=O)OC(C)(C)C)c1F] | 18 |

*prepared according to example number

---

Lengthy table referenced here

US10258045-20190416-T00001

Please refer to the end of the specification for access instructions.

Lengthy table referenced here

US10258045-20190416-T00002

Please refer to the end of the specification for access instructions.

Lengthy table referenced here

US10258045-20190416-T00003

Please refer to the end of the specification for access instructions.

Lengthy table referenced here

US10258045-20190416-T00004

Please refer to the end of the specification for access instructions.

Lengthy table referenced here

US10258045-20190416-T00005

Please refer to the end of the specification for access instructions.

Lengthy table referenced here

US10258045-20190416-T00006

Please refer to the end of the specification for access instructions.

LENGTHY TABLES

The patent contains a lengthy table section. A copy of the table is available in electronic form from the USPTO web site (http://seqdata.uspto.gov/?pageRequest=docDetail&DocID=US10258045B2). An electronic copy of the table will also be available from the USPTO upon request and payment of the fee set forth in 37 CFR 1.19(b)(3).

The invention claimed is:

1. A molecule selected from the group consisting of

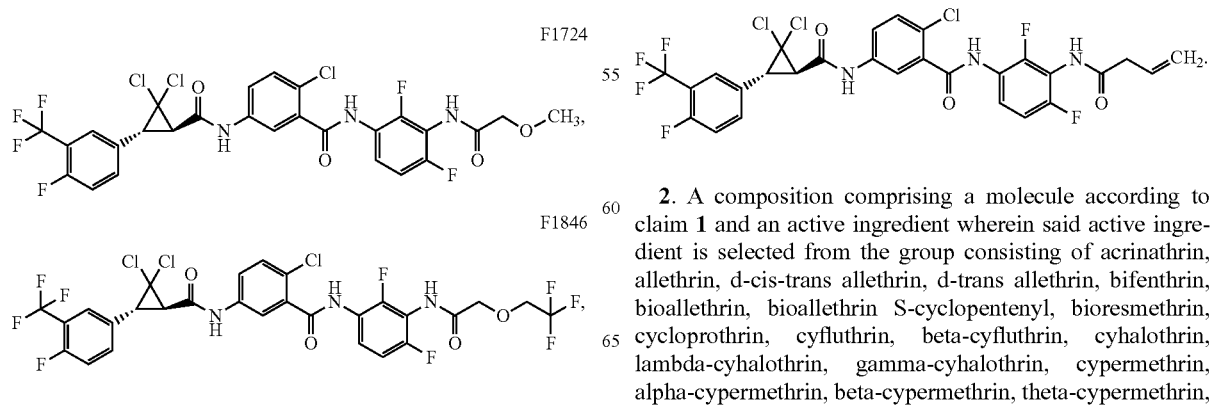

2. A composition comprising a molecule according to claim 1 and an active ingredient wherein said active ingredient is selected from the group consisting of acrinathrin, allethrin, d-cis-trans allethrin, d-trans allethrin, bifenthrin, bioallethrin, bioallethrin S-cyclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans-isomers], deltamethrin, empenthrin [(EZ)-(1R)-isomers], esfenvalerate, etofenprox, fenpropathrin, fenvalerate, flucythrinate, flumethrin, tau-fluvalinate, halfenprox, imiprothrin, kadethrin, permethrin, phenothrin [(1R)-trans-isomer], prallethrin, pyrethrins (pyrethrum), resmethrin, silafluofen, tefluthrin, tetramethrin, tetramethrin [(1R)-isomers], tralomethrin, and transfluthrin, and methoxychlor.

3. A composition according to claim 1 wherein said active ingredient is bifenthrin.

4. A composition according to claim 1 wherein said active ingredient is lambda-cyhalothrin.

5. A composition according to claim 1 wherein the weight ratio of said molecule to said active ingredient is 3:1 to 1:3.

6. A composition according to claim 3 wherein the weight ratio of said molecule to said active ingredient is 3:1 to 1:3.

7. A composition according to claim 4, wherein the weight ratio of said molecule to said active ingredient is 3:1 to 1:3.

8. A process to control a pest said process comprising applying to a locus, a pesticidally effective amount of a molecule according to claim 1.

9. A process to control a pest said process comprising applying to a locus, a pesticidally effective amount of a composition according to claim 2.

10. A process to control a pest said process comprising applying to a locus, a pesticidally effective amount of a composition according to claim 3.

11. A process to control a pest said process comprising applying to a locus, a pesticidally effective amount of a composition according to claim 4.

12. A process to control a pest said process comprising applying to a locus, a pesticidally effective amount of a composition according to claim 5.

13. A process to control a pest said process comprising applying to a locus, a pesticidally effective amount of a composition according to claim 6.

14. A process to control a pest said process comprising applying to a locus, a pesticidally effective amount of a composition according to claim 7.

15. A process according to 8 wherein said pest is selected from the group consisting of ants, aphids, bed bugs, beetles, bristletails, caterpillars, cockroaches, crickets, earwigs, fleas, flies, grasshoppers, grubs, leafhoppers, lice, locusts, maggots, mites, nematodes, planthoppers, psyllids, sawflies, scales, silverfish, slugs, snails, spiders, springtails, stink bugs, symphylans, termites, *thrips*, ticks, wasps, whiteflies, and wireworms.

16. A process according to 15 wherein said pest are stink bugs.

17. A process according to 9 wherein said pest is selected from the group consisting of *Adelges* spp., *Aulacaspis* spp., *Aphrophora* spp., *Aphis* spp., *Bemisia* spp., *Ceroplastes* spp., *Chionaspis* spp., *Chrysomphalus* spp., *Coccus* spp., *Empoasca* spp., *Euschistus* spp., *Lepidosaphes* spp., *Lagynotomus* spp., *Lygus* spp., *Macrosiphum* spp., *Nephotettix* spp., *Nezara* spp., *Nilaparvata* spp., *Philaenus* spp., *Phytocoris* spp., *Piezodorus* spp., *Planococcus* spp., *Pseudococcus* spp., *Rhopalosiphum* spp., *Saissetia* spp., *Therioaphis* spp., *Toumeyella* spp., *Toxoptera* spp., *Trialeurodes* spp., *Triatoma* spp., and *Unaspis* spp.

18. A process according to 17 wherein said pest is selected from the group consisting of *Acrosternum hilare, Acyrthosiphon pisum, Aleyrodes proletella, Aleurodicus dispersus, Aleurothrixus floccosus, Amrasca biguttula biguttula, Aonidiella aurantii, Aphis fabae, Aphis gossypii, Aphis glycines, Aphis pomi, Aulacorthum solani, Bactericera cockerelli, Bagrada hilaris, Bemisia argentifolii, Bemisia tabaci, Blissus leucopterus, Boisea trivittata, Brachycorynella asparagi, Brevennia rehi, Brevicoryne brassicae, Cacopsylla pyri, Cacopsylla pyricola, Calocoris norvegicus, Ceroplastes rubens, Cimex hemipterus, Cimex lectularius, Coccus pseudomagnoliarum, Dagbertus fasciatus, Dichelops furcatus, Diuraphis noxia, Diaphorina citri, Dysaphis plantaginea, Dysdercus suturellus, Edessa meditabunda, Empoasca vitis, Eriosoma lanigerum, Erythroneura elegantula, Eurygaster maura, Euschistus conspersus, Euschistus heros, Euschistus servus, Halyomorpha halys, Helopeltis antonii, Hyalopterus pruni, Helopeltis antonii, Helopeltis theivora, Icerya purchasi, Idioscopus nitidulus, Jacobiasca formosana, Laodelphax striatellus, Lecanium corni, Leptocorisa oratorius, Leptocorisa varicornis, Lygus hesperus, Maconellicoccus hirsutus, Macrosiphum euphorbiae, Macrosiphum granarium, Macrosiphum rosae, Macrosteles quadrilineatus, Mahanarva frimbiolata, Megacopta cribraria, Metopolophium dirhodum, Mictis longicornis, Myzus persicae, Nasonovia ribisnigri, Nephotettix cincticeps, Neurocolpus longirostris, Nezara viridula, Nilaparvata lugens, Paracoccus marginatus, Paratrioza cockerelli, Parlatoria pergandii, Parlatoria ziziphi, Peregrinus maidis, Phylloxera vitifoliae, Physokermes piceae, Phytocoris californicus, Phytocoris relativus, Piezodorus guildinii, Planococcus citri, Planococcus ficus, Poecilocapsus lineatus, Psallus vaccinicola, Pseudacysta perseae, Pseudococcus brevipes, Quadraspidiotus perniciosus, Rhopalosiphum maidis, Rhopalosiphum padi, Saissetia oleae, Scaptocoris castanea, Schizaphis graminum, Sitobion a venae, Sogatella furcifera, Trialeurodes vaporariorum, Trialeurodes abutiloneus, Unaspis yanonensis,* and *Zulia entrerriana.*

19. A process according to claim 9 wherein said locus soybeans are growing.

\* \* \* \* \*